United States Patent
Mahoney et al.

(10) Patent No.: US 11,339,144 B2
(45) Date of Patent: May 24, 2022

(54) HETEROARYL RHEB INHIBITORS AND USES THEREOF

(71) Applicant: Navitor Pharmaceuticals, Inc., Cambridge, MA (US)

(72) Inventors: Sarah Mahoney, Cambridge, MA (US); Lisa Molz, Lexington, MA (US); Sridhar Narayan, Belmont, MA (US); Eddine Saiah, Brookline, MA (US)

(73) Assignee: NAVITOR PHARMACEUTICALS, INC., Cambridge, MA (US)

( * ) Notice: Subject to any disclaimer, the term of this patent is extended or adjusted under 35 U.S.C. 154(b) by 0 days.

(21) Appl. No.: 16/604,208

(22) PCT Filed: Apr. 9, 2018

(86) PCT No.: PCT/US2018/026670
§ 371 (c)(1),
(2) Date: Oct. 10, 2019

(87) PCT Pub. No.: WO2018/191146
PCT Pub. Date: Oct. 18, 2018

(65) Prior Publication Data
US 2021/0238165 A1 Aug. 5, 2021

Related U.S. Application Data

(60) Provisional application No. 62/483,643, filed on Apr. 10, 2017.

(51) Int. Cl.
| C07D 209/42 | (2006.01) |
| C07D 403/10 | (2006.01) |
| C07D 235/12 | (2006.01) |
| C07D 401/04 | (2006.01) |
| C07D 401/12 | (2006.01) |
| C07D 403/06 | (2006.01) |
| C07D 405/12 | (2006.01) |
| C07D 413/12 | (2006.01) |
| C07D 413/14 | (2006.01) |
| C07D 471/04 | (2006.01) |
| C07D 498/04 | (2006.01) |

(52) U.S. Cl.
CPC ......... *C07D 403/10* (2013.01); *C07D 209/42* (2013.01); *C07D 235/12* (2013.01); *C07D 401/04* (2013.01); *C07D 401/12* (2013.01); *C07D 403/06* (2013.01); *C07D 405/12* (2013.01); *C07D 413/12* (2013.01); *C07D 413/14* (2013.01); *C07D 471/04* (2013.01); *C07D 498/04* (2013.01)

(58) Field of Classification Search
CPC .................................................. C07D 209/42
See application file for complete search history.

(56) References Cited

U.S. PATENT DOCUMENTS

| 5,639,600 A | 6/1997 | McGrath et al. |
| 6,441,004 B1 * | 8/2002 | Faull ...................... A61P 13/12 |
| | | 514/339 |
| 6,552,065 B2 | 4/2003 | Remiszewski et al. |
| 7,087,648 B1 | 8/2006 | McGrath |
| 7,390,799 B2 | 6/2008 | Bruncko et al. |
| 8,044,090 B2 | 10/2011 | Chen et al. |
| 8,138,347 B2 | 3/2012 | Knight et al. |
| 2006/0148830 A1 * | 7/2006 | Terakado ................ A61P 13/02 |
| | | 514/264.1 |
| 2006/0160880 A1 | 7/2006 | Kehler et al. |
| 2008/0214495 A1 | 9/2008 | Alstermark et al. |
| 2015/0376101 A1 | 12/2015 | Eisenschmid |

FOREIGN PATENT DOCUMENTS

| WO | 2000059880 A1 | 10/2000 |
| WO | WO-2001042246 A2 | 6/2001 |
| WO | 2002031511 A2 | 4/2002 |

(Continued)

OTHER PUBLICATIONS

Bronner (Org. Lett. 2009, vol. 11 (4), p. 1007-1010).*
CAS Registry STN as of Sep. 2010.*
Awad et al., "Altered TFEB-mediated lysosomal biogenesis in Gaucher disease IPSC-derived neuronal cells," Human Molecular Genetics, vol. 24, No. 20, Oct. 2015 (pp. 5775-5788).
Berge et al., "Pharmaceutical Salts," Journal of Pharmaceutical Sciences, vol. 66, No. 1, No Month Listed 1977 (pp. 1-19).

(Continued)

*Primary Examiner* — Valerie Rodriguez-Garcia
(74) *Attorney, Agent, or Firm* — Andrea L. C. Reid; Todd K. Macklin; Dechert LLP

(57) ABSTRACT

The present invention provides compounds of general Formula I and I':

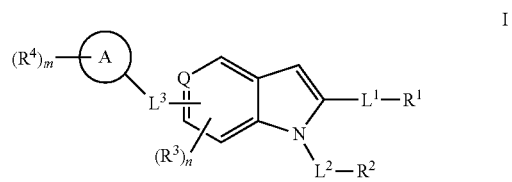

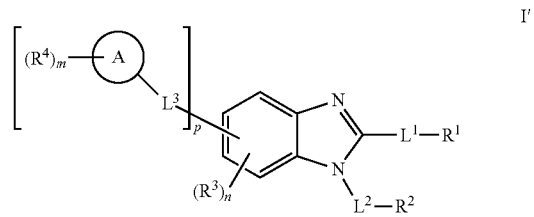

compositions thereof, and methods of using same to treat Rheb-mediated disorders.

7 Claims, 23 Drawing Sheets

(56) References Cited

FOREIGN PATENT DOCUMENTS

| WO | WO 2002/30895 | * | 4/2002 |
|----|----|----|----|
| WO | WO-2002088112 A1 | | 11/2002 |
| WO | WO-2003063794 A2 | | 8/2003 |
| WO | WO-2004019973 A1 | | 3/2004 |
| WO | WO-2004089925 A1 | | 10/2004 |
| WO | WO-2004106328 A1 | | 12/2004 |
| WO | WO-2005007623 A2 | | 1/2005 |
| WO | WO-2005113554 A2 | | 12/2005 |
| WO | WO-2006078846 A1 | | 7/2006 |
| WO | WO-2006122806 A2 | | 11/2006 |
| WO | WO-2007016176 A2 | | 2/2007 |
| WO | WO-2007044729 A2 | | 4/2007 |
| WO | WO-2007053452 A1 | | 5/2007 |
| WO | WO-2007070514 A1 | | 6/2007 |
| WO | WO-2007084786 A1 | | 7/2007 |
| WO | WO-2007129161 A2 | | 11/2007 |
| WO | WO-2008039218 A2 | | 4/2008 |
| WO | WO-2008109943 A1 | | 9/2008 |
| WO | WO-2008118802 A1 | | 10/2008 |
| WO | WO-2009114512 A1 | | 9/2009 |
| WO | WO-2015116904 A1 | | 8/2015 |

OTHER PUBLICATIONS

Bonne and Quijano-Roy, "Emery-Dreifuss muscular dystrophy, laminopathies, and other nuclear envelopathies," Handbook of Clinical Neurology, vol. 113, No Month Listed 2013 (pp. 1367-1376).

Chen et al., "Rapamycin ameliorates kidney fibrosis by inhibiting the activation of mTOR signaling in interstitial macrophages and myofibroblasts," PLoS One, vol. 7, No. 3, Mar. 2012 (p. E33626).

Cortes et al., "Polyglutamine-expanded androgen receptor interferes with TFEB to elicit autophagy defects in SBMA," Nature Neuroscience, vol. 17, No. 9, Sep. 2014 (pp. 1180-1189).

Decressac et al., "TFEB-mediated autophagy rescues midbrain dopamine neurons from ?-synuclein toxicity," Proceedings of the National Academy of Sciences, USA, vol. 110, No. 19, May 2013 (pp. E1817-1826).

Ding et al., "Farnesyltransferase inhibitor tipifarnib inhibits Rheb prenylation and stabilizes Bax in acute myelogenous leukemia cells," Haematologica, vol. 99, No. 1, Jan. 2014 (pp. 60-69).

Fok et al., "Combined treatment of rapamycin and dietary restriction has a larger effect on the transcriptome and metabolome of liver," Aging Cell, vol. 13, No. 2, Apr. 2014 (pp. 311-319).

Franz and Weiss, "Molecular therapies for tuberous sclerosis and neurofibromatosis," Currently Neurology and Neuroscience Reports, vol. 12, No. 3, Jun. 2012 (pp. 294-301).

Hua et al., "Rapamycin inhibition of eosinophil differentiation attenuates allergic airway inflammation in mice," Respirology, vol. 20, No. 7, Oct. 2015 (pp. 1055-1065).

Huang et al., "miRNA-15a/16: as tumor suppressors and more," Future Oncology, vol. 11, No. 16, No Month Listed 2015 (pp. 2351-2363).

Ilagen et al., "Emerging role of mTOR in the response to cancer therapeutics," Trends Cancer, vol. 2, No. 5, May 2016 (pp. 241-251).

International Search Report and Written Opinion issued by the United States Patent and Trademark Office as International Searching Authority for International Patent Application No. PCT/US2018/026670, dated Jul. 27, 2018 (12 pages).

Iqbal et al., "Coronary stents: historical development, current status and future directions," British Medical Bulletin, vol. 106, No Month Listed 2013 (pp. 193-211).

Jahrling and Laberge, "Age-Related Neurodegeneration Prevention Through mTOR Inhibition: Potential Mechanisms and Remaining Questions," Current Topics in Medicinal Chemistry, vol. 15, No. 21, No Month Listed 2015 (2139-2151).

Jiang et al., "Rheb/mTORC1 Signaling Promotes Kidney Fibroblast Activation and Fibrosis," Journal of the American Society of Nephrology, vol. 24, No. 7, Jun. 2013 (pp. 1114-1126).

Johnson et al., "MTOR inhibition alleviates mitochondrial disease in a mouse model of Leigh syndrome," Science, vol. 342, No. 6165, 2013 (pp. 1524-1528).

Kaeberlein, "mTOR Inhibition: From Aging to Autism and Beyond," Scientifica, vol. 2013, Oct. 2013 (17 pages).

Kaplan et al., "Strategies for the management of adverse events associated with mTOR inhibitors," Transplantation Reviews, vol. 28, No Month Listed 2014 (pp. 126-133).

Laberge et al., "MTOR regulates the pro-tumorigenic senescence-associated secretory phenotype by promoting IL1A translation," Nature Cell Biology, vol. 17, No. 8, Aug. 2015 (pp. 1049-1061).

Lamming et al., "Rapamycin-induced insulin resistance is mediated by mTORC2 loss and uncoupled from longevity," Science, vol. 335, Mar. 2012 (pp. 1638-1643).

LaPlante and Sabatini, "mTOR Signaling in Growth Control and Disease," Cell, vol. 149, No. 2, Apr. 2012 (pp. 274-293).

Liu et al., "Rapamycin reduces renal hypoxia, interstitial inflammation and fibrosis in a rat model of unilateral ureteral obstruction," Clinical and Investigative Medicine, vol. 37, No. 3, Jun. 2014 (pp. E142-E153).

Long et al., "Rheb Binds and Regulates the mTOR Kinase," Current Biology, vol. 15, No. 8, Apr. 2005 (pp. 702-713).

MacDonald, "Use of mTOR inhibitors in human organ transplantation," Expert Review of Clinical Immunology, vol. 3, No. 3, Jan. 2007 (pp. 423-436).

Medina et al., "Transcriptional Activation of Lysosomal Exocytosis Promotes Cellular Clearance," Developmental Cell, vol. 21, No. 3, Sep. 2011 (pp. 421-430).

Meng et al., "Role of the mTOR signaling pathway in epilepsy," Journal of the Neurological Sciences, vol. 332, No. 1-2, Sep. 2013 (pp. 4-15).

Mercer et al., "Exploration of a potent PI3 kinase/mTOR inhibitor as a novel anti-fibrotic agent in IPF," Thorax, vol. 71, No. 8, Aug. 2016 (pp. 701-711).

Mitra et al., "Dual mTOR Inhibition Is Required to Prevent TGF-?-Mediated Fibrosis: Implications for Scleroderma," Journal of Investigative Dermatology, vol. 135, No. 11, Nov. 2015 (pp. 2873-2876).

Nacarelli et al., "Mitochondrial stress induces cellular senescence in an mTORCl-dependent manner," Free Radical Biology and Medicine, vol. 95, Jun. 2016 (pp. 133-154).

Neuman and Henske, "Non-canonical functions of the tuberous sclerosis complex-Rheb signalling axis," EMBO Molecular Medicine, vol. 3, No. 4, Apr. 2011 (pp. 189-200).

Nie et al., "Tsc2-Rheb signaling regulates EphA-mediated axon guidance," Nature Neuroscience, vol. 13, No. 2, Feb. 2010 (pp. 163-172).

Pastore et al, "Gene transfer of master autophagy regulator TFEB results in clearance of toxic protein and correction of hepatic disease in alpha-1-anti-trypsin deficiency," EMBO Molecular Medicine, vol. 5, No. 3, Mar. 2013 (pp. 397-412).

Patel et al., "Autophagy in Idiopathic Pulmonary Fibrosis," PLoS One, vol. 7, No. 7, Jul. 2012 (pp. E41394).

Perl, "Activation of mTOR (mechanistic target of rapamycin) in rheumatic diseases," Nature Reviews Rheumatology, vol. 12, No. 3, Mar. 2016 (pp. 169-182).

Polito et al., "Selective clearance of aberrant tau proteins and rescue of neurotoxicity by transcription factor EB," EMBO Molecular Medicine, vol. 6, No. 9, Sep. 2014 (pp. 1142-1160).

Puri and Chandra, "Autophagy modulation as a potential therapeutic target for liver diseases," Journal of Clinical and Experimental Hepatology, vol. 4, No. 1, Mar. 2014 (pp. 51-59).

Ramos et al., "Rapamycin Reverses Elevated mTORCI Signaling in Lamin A/C-Deficient Mice, Rescues Cardiac and Skeletal Muscle Function, and Extends Survival," Science Translational Medicine, vol. 4, No. 144, Jul. 2012 (pp. 144ra103).

Sancak et al., "PRAS40 is an insulin-regulated inhibitor of the mTORCI protein kinase," Molecular Cell, vol. 25, No. 6, Mar. 2007 (pp. 903-915).

Sarbassov et al., "Prolonged rapamycin treatment inhibits mTORC2 assembly and Akt/PKB," Molecular Cell, vol. 22, No. 2, Apr. 2006 (pp. 159-168).

Sardiello, "Transcription factor EB: from master coordinator of lysosomal pathways to candidate therapeutic target in degenerative

(56) References Cited

OTHER PUBLICATIONS storage diseases," Annals of The New York Academy of Sciences, vol. 1371, No. 1, May 2016 (pp. 3-14).
Sato et al., "Characterization of the Rheb-mTOR Signaling Pathway in Mammalian Cells: Constitutive Active Mutants of Rheb and mTOR," Methods in Enzymology, vol. 438, No Month Listed 2008 (pp. 307-320).
Settembre et al., "Signals from the lysosome: a control centre for cellular clearance and energy metabolism," Nature Reviews Molecular Cell Biology, vol. 14, No. 5, May 2013 (pp. 283-296).
Shum et al., "Pharmacological inhibition of S6K1 increases glucose metabolism and Akt signalling in vitro and in diet-induced obese mice," Diabetologia, vol. 59, No. 3, Mar. 2016 (pp. 592-603).
Smethurst, "A pharmacologic perspective on newly emerging T-cell manipulation technologies," British Journal of Clinical Pharmacology, vo. 76, No. 2, Aug. 2013 (pp. 173-187).
Spampanato et al., "Transcription factor EB (TFEB) is a new therapeutic target for Pompe disease," EMBO Molecular Medicine, vol. 5, No. 5, May 2013 (pp. 691-706).
Syed et al., "Keloid disease can be inhibited by antagonizing excessive mTOR signaling with a novel dual TORC1/2 inhibitor," American Journal of Pathology, vol. 181, No. 5, Nov. 2012 (pp. 1642-1658).
Taveira-DaSilva et al., "Clinical features, epidemiology, and therapy of lymphangioleiomyomatosis," Journal of Clinical Epidemiology, vol. 7, Apr. 2015 (pp. 249-257).
Tsunemi et al., "PGC-1a rescues Huntington's disease proteotoxicity by preventing oxidative sliess and promoting TFEB function," Science Translational Medicine, vol. 4, No. 142, Jul. 2012 (pp. 142ra97).
Varin et al., "Dual mTORC1/2 inhibition induces anti-proliferative effect in NF1-associated plexiform neurofibroma and malignant peripheral nerve sheath tumor cells," Oncotarget, vol. 7, No. 24, Jan. 2016 (pp. 35753-35767).
Wander et al., "Next-generation mTOR inhibitors in clinical oncology: how pathway complexity informs therapeutic strategy," The Journal of Clinical Investigation, vol. 121, Apr. 2011 (pp. 1231-1241).
Wu et al., "Rapamycin attenuates unilateral ureteral obstruction-induced renal fibrosis," Kidney International, vol. 69, No. 11, Jun. 2006 (pp. 2029-2036).
Yano et al., "Clinical impact of myocardial mTORC1 activation in nonischemic dilated cardiomyopathy," Journal of Molecular and Cellular Cardiology, vol. 91, Feb. 2016 (pp. 6-9).
Yu et al., "Rapamycin and Dietary Restriction Induce Metabolically Distinctive Changes in Mouse Liver," The Journals of Gerontology: Series A, vol. 70, No. 4, Apr. 2015 (pp. 410-420).
Allen, "Synthesis of Indole-2-Carboxylic Acid Esters," Synthetic Communications. 1999;29(3):447-455.
Gogoi et al., "Role of TBATB in nano indium oxide catalyzed C-S bond formation," Sci Rep. 2015;5:13873.

\* cited by examiner

HETEROARYL RHEB INHIBITORS AND USES THEREOF

CROSS-REFERENCE TO RELATED APPLICATIONS

This application is a § 371 national stage filing of International Application No. PCT/US2018/026670, filed Apr. 9, 2018, which claims the benefit of U.S. Provisional Application No. 62/483,643, filed Apr. 10, 2017, the content of each of which is hereby incorporated by reference.

TECHNICAL FIELD OF THE INVENTION

The present invention relates to compounds and methods useful for modulating Ras homologue enriched in brain (Rheb) activity. The invention also provides pharmaceutically acceptable compositions comprising provided compounds of the present invention and methods of using such compositions in the treatment of various disorders.

BACKGROUND OF THE INVENTION

The mechanistic target of rapamycin complex 1 (mTORC1) acts as a central regulator of metabolic pathways that drive cellular growth, proliferation and survival. mTORC1 carries out this function by integrating diverse inputs such as nutrients, growth factors and energy. The functional output of mTORC1 signaling impacts an array of cellular processes such as protein synthesis and degradation, cell proliferation, and autophagy (Laplante, et al. 2012. Cell). mTOR exists in two protein complexes that have distinct cellular functions. mTOR complex 1 (mTORC1) regulates cell growth and proliferation by promoting anabolic processes, including biosynthesis of proteins, lipids and organelles, and limiting catabolic processes, such as autophagy. mTORC1 is comprised of mTOR, the catalytic subunit of the complex, and four additional subunits (Raptor, PRAS40, mLST8 and Deptor) that regulate its activity and access to substrates. mTOR complex 2 (mTORC2) is less well understood but is activated by growth factors and important for cell survival, proliferation and cytoskeleton organization. mTORC2 is comprised of mTOR, RICTOR, mLST8, Protor, Deptor and mSIN1 (Laplante, et al. 2012. Cell).

Discoveries that have been made over the last decade show that the mTOR pathway is dysregulated in numerous human disease states, including cancer (Laplante), obesity (Laplante), diabetes (Laplante), fibrosis, autoimmune disorders (lupus, rheumatoid arthritis and others) (Perl, 2015, Nature Reviews Rheumatology), epilepsy (Meng, 2013, J Neurol Sci), lysosomal storage disorders (Settembre, et al., 2013, Nature Reviews Molecular Cell Biology), neurodegenerative diseases (Parkinson's Disease, Alzheimer's Disease) (Jahrling, et al., 2015, Curr Top Med Chem) and immunological disorders (Smethurst, 2013, Br J Clin Pharmacol) can't find a good review for this yet . . . ). There is broad evidence that mTORC1 hyperactivation and the consequent metabolic changes are critical for the maintaining disease states. For this reason, there is extensive scientific and clinical interest in targeting mTORC1 in human disease. This is highlighted by the growing use of allosteric mTORC1 inhibitors [rapamycin and its analogues (rapalogues)] in pathological settings, including the treatment of solid tumors (Huang, 2015, Future Oncol), organ transplantation (Macdonald, 2007, Expert Rev Clin Immunol), coronary restenosis (Iqbal, et al., 2013, Br Med Bull) and rheumatoid arthritis (Perl, 2015, Nature Reviews Rheumatology).

Rapamycin was initially considered to be a selective inhibitor of mTORC1, but recent experiments show that prolonged exposure to rapamycin inhibits mTORC2 (Sarbassov, et al., Mol Cel. 2006), potentially resulting in serious adverse effects such as insulin resistance (Lamming, et al Science 2012). In addition to metabolic effects, some rapalogues in the clinic have been reported to cause adverse effects in wound healing, renal function, and hypertension (Kaplan, et al 2014). Therefore, a selective mTORC1 inhibitor with a mechanism of action distinct from rapamycin would have significant clinical utility.

Growth factor signaling into mTORC1 is negatively regulated by the heterotrimeric tuberous sclerosis complex (TSC), which acts as a GTPase-activating protein (GAP) toward the Ras homologue enriched in brain (Rheb), a small membrane-bound GTPase (Laplante, et al., FIG. 1). GTP-loaded Rheb activates mTORC1 via direct interaction with the mTOR kinase domain (Long, et al. Curr Biol. 2005) at the lysosomal membrane; it does not impact mTORC2 signaling (Sato, et al., 2009, Methods Enzymol). Given its key role in mTORC1 signaling, Rheb is an important molecular target for the selective inhibition of mTORC1 without impacting mTORC2. Several groups have tried to target Rheb indirectly by inhibiting farnesyltransferases (Basso, et al. JBC 2005, Ding, et al, Haematologica 2014), which are involved in the prenylation and subsequent targeting of Rheb to lysosomal membranes. To date, no small molecules have been reported that directly bind Rheb and inhibit its function.

SUMMARY OF THE INVENTION

It has now been found that compounds of this invention, and pharmaceutically acceptable compositions thereof, are effective as Rheb inhibitors. Such compounds have the general Formula I:

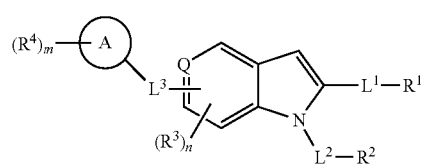

or a pharmaceutically acceptable salt thereof, wherein each variable is as defined and described herein.

Additionally it has been found that certain compounds of this invention, and pharmaceutically acceptable compositions thereof, effective as Rheb inhibitors have the general Formula I':

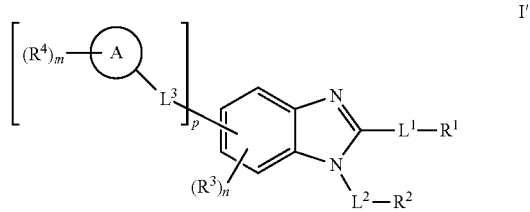

or a pharmaceutically acceptable salt thereof, wherein each variable is as defined and described herein.

Compounds of the present invention, and pharmaceutically acceptable compositions thereof, are useful for treating a variety of diseases, disorders or conditions, associated with Rheb. Such diseases, disorders, or conditions include those described herein.

DETAILED DESCRIPTION OF CERTAIN EMBODIMENTS

Figure 1:
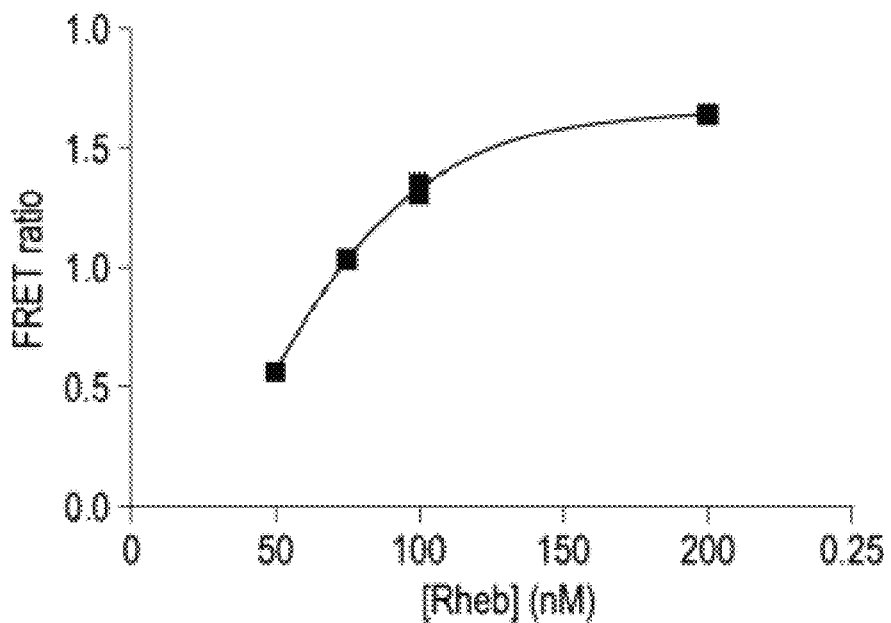
FIG. 1 shows the optimization of the Rheb-IVK protocol for Rheb and mTORC1.
Figure 1:
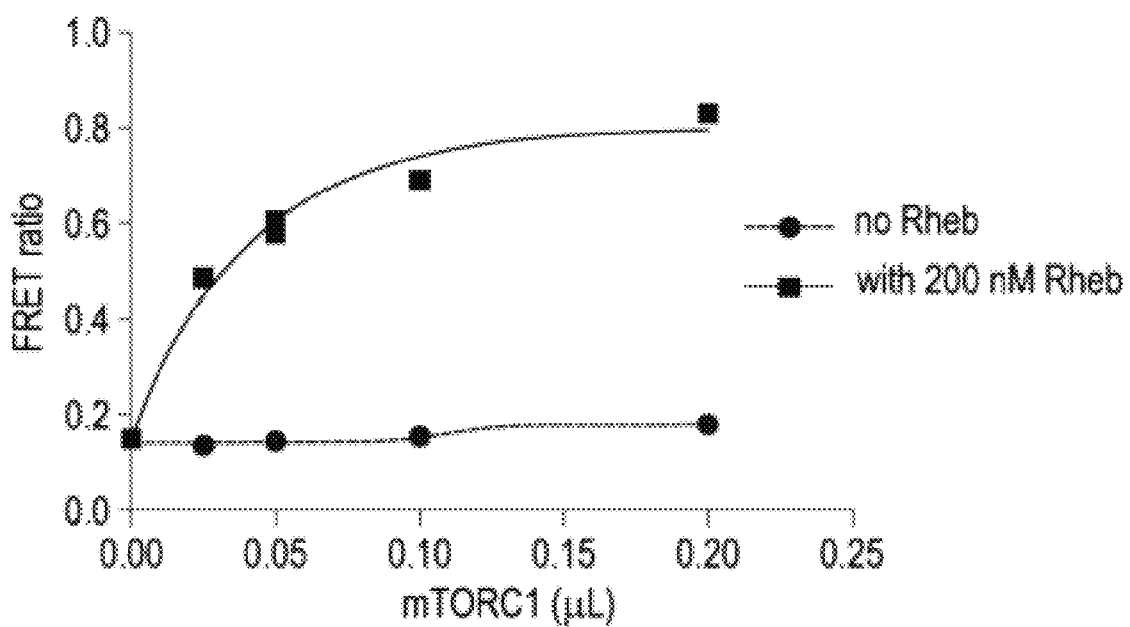

1. General Description of Certain Embodiments of the Invention

In certain embodiments, the present invention provides a compound of Formula I:

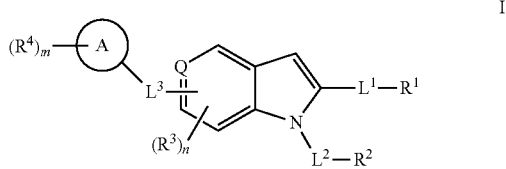

or a pharmaceutically acceptable salt thereof, wherein:

Q is CH, CR$^3$, or N;

L$^1$ is a covalent bond or a C$_{1-6}$ bivalent hydrocarbon chain wherein one, two, or three methylene units of the chain are optionally and independently replaced by -Cy$^1$-, —N(R)—, —O—, —C(O)—, —OC(O)—, —C(O)O—, —C(O)N(R)—, —N(R)C(O)—, —S(O)—, or —S(O)$_2$—;

each R is independently hydrogen, or an optionally substituted group selected from C$_{1-6}$ aliphatic, a 3-8 membered saturated or partially unsaturated monocyclic carbocyclic ring, phenyl, 4-7 membered saturated or partially unsaturated heterocyclic ring having 1-2 heteroatoms independently selected from nitrogen, oxygen, or sulfur, or 5-6 membered heteroaryl ring having 1-4 heteroatoms independently selected from nitrogen, oxygen, or sulfur, or:
  two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, or sulfur;

each -Cy$^1$- is independently an optionally substituted bivalent ring selected from phenylene, 3-7 membered saturated or partially unsaturated carbocyclylene, 4-7 membered saturated or partially unsaturated heterocyclylene having 1-2 heteroatoms independently selected from nitrogen, oxygen, or sulfur, or 5-6 membered heteroarylene having 1-4 heteroatoms independently selected from nitrogen, oxygen, or sulfur;

R$^1$ is hydrogen, halogen, —CN, —NO$_2$ or an optionally substituted group selected from C$_{1-6}$ aliphatic, a 3-8 membered saturated or partially unsaturated monocyclic carbocyclic ring, phenyl, a 4-7 membered saturated or partially unsaturated heterocyclic ring having 1-2 heteroatoms independently selected from nitrogen, oxygen, or sulfur, or a 5-6 membered heteroaryl ring having 1-4 heteroatoms independently selected from nitrogen, oxygen, or sulfur;

$L^2$ is a covalent bond or a $C_{1-6}$ bivalent hydrocarbon chain wherein one, two, or three methylene units of the chain are optionally and independently replaced by $-Cy^2-$, —C(O)—, —CH(R)—, —N(R)—, —C(O)N(R)—, —N(R)C(O)—, —O—, —C(O)O—, —OC(O)—, or —S(O)$_2$—;

each $-Cy^2-$ is independently an optionally substituted bivalent ring selected from phenylene, 4-7 membered saturated or partially unsaturated heterocyclylene having 1-2 heteroatoms independently selected from nitrogen, oxygen, or sulfur, or 5-6 membered heteroarylene having 1-4 heteroatoms independently selected from nitrogen, oxygen, or sulfur;

$R^2$ is hydrogen, halogen, —CN, —NO$_2$ or an optionally substituted group selected from $C_{1-6}$ aliphatic, a 3-8 membered saturated or partially unsaturated monocyclic carbocyclic ring, phenyl, a 4-7 membered saturated or partially unsaturated heterocyclic ring having 1-2 heteroatoms independently selected from nitrogen, oxygen, or sulfur, or a 5-6 membered heteroaryl ring having 1-4 heteroatoms independently selected from nitrogen, oxygen, or sulfur;

$L^3$ is a covalent bond or a $C_{1-6}$ bivalent hydrocarbon chain wherein one or two methylene units of the chain are optionally and independently replaced by —O—, —C(O)—, —S—, —S(O)—, —S(O)$_2$— or —N(R)—;

Ring A is phenyl, a 3-8 membered saturated or partially unsaturated carbocyclic ring, a 4-7 membered saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, or an 8-10 membered bicyclic ring having 0-3 heteroatoms independently selected from nitrogen, oxygen, or sulfur, wherein Ring A is substituted with m occurrences of $R^4$;

each $R^3$ is independently an optionally substituted $C_{1-6}$ aliphatic, phenyl, halogen, —CN, —SR, or two $R^3$ groups are optionally taken together to form a 5-8 membered partially unsaturated or aryl fused ring having 0-2 heteroatoms independently selected from nitrogen, oxygen, or sulfur;

n is 0, 1, 2, or 3;

each $R^4$ is independently an optionally substituted $C_{1-6}$ aliphatic, halogen, or —OR; and m is 0, 1, 2, 3, 4, or 5.

In certain embodiments, the present invention provides a compound of Formula I':

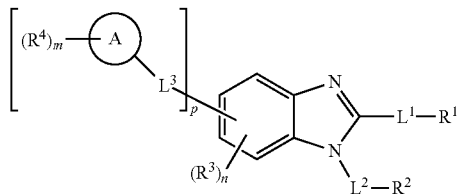

or a pharmaceutically acceptable salt thereof, wherein:

$L^1$ is a covalent bond or a $C_{1-6}$ bivalent hydrocarbon chain wherein one or two methylene units of the chain are optionally and independently replaced by $-Cy^1-$, —N(R)—, —O—, —C(O)—, —OC(O)—, —C(O)O—, —C(O)N(R)—, —N(R)C(O)—, —S(O)—, or —S(O)$_2$—; or $L^1$ and $L^2$ are optionally taken together with their intervening atoms to form a 5-8 membered partially unsaturated fused ring having 0-2 heteroatoms independently selected from nitrogen, oxygen or sulfur;

each R is independently hydrogen, or an optionally substituted group selected from $C_{1-6}$ aliphatic, a 3-8 membered saturated or partially unsaturated monocyclic carbocyclic ring, phenyl, 4-7 membered saturated or partially unsaturated heterocyclic ring having 1-2 heteroatoms independently selected from nitrogen, oxygen, or sulfur, 5-6 membered heteroaryl ring having 1-4 heteroatoms independently selected from nitrogen, oxygen, or sulfur, or an 8-10 membered bicyclic ring having 0-3 heteroatoms independently selected from nitrogen, oxygen, or sulfur;

each $-Cy^1-$ is independently an optionally substituted bivalent ring selected from phenylene, 4-7 membered saturated or partially unsaturated heterocyclylene having 1-2 heteroatoms independently selected from nitrogen, oxygen, or sulfur, or 5-6 membered heteroarylene having 1-4 heteroatoms independently selected from nitrogen, oxygen, or sulfur;

$R^1$ is hydrogen, or an optionally substituted group selected from $C_{1-6}$ aliphatic, a 3-8 membered saturated or partially unsaturated monocyclic carbocyclic ring, phenyl, 4-7 membered saturated or partially unsaturated heterocyclic ring having 1-2 heteroatoms independently selected from nitrogen, oxygen, or sulfur, 5-6 membered heteroaryl ring having 1-4 heteroatoms independently selected from nitrogen, oxygen, or sulfur, or an 8-10 membered bicyclic ring having 0-3 heteroatoms independently selected from nitrogen, oxygen, or sulfur;

$L^2$ is a covalent bond or a $C_{1-6}$ bivalent hydrocarbon chain wherein one or two methylene units of the chain are optionally and independently replaced by $-Cy^2-$;

each $-Cy^2-$ is independently an optionally substituted bivalent ring selected from phenylene or 5-6 membered heteroarylene having 1-4 heteroatoms independently selected from nitrogen, oxygen, or sulfur;

$R^2$ is hydrogen, or an optionally substituted group selected from $C_{1-6}$ aliphatic, a 3-8 membered saturated or partially unsaturated monocyclic carbocyclic ring, phenyl, 4-7 membered saturated or partially unsaturated heterocyclic ring having 1-2 heteroatoms independently selected from nitrogen, oxygen, or sulfur, 5-6 membered heteroaryl ring having 1-4 heteroatoms independently selected from nitrogen, oxygen, or sulfur, or an 8-10 membered bicyclic ring having 0-3 heteroatoms independently selected from nitrogen, oxygen, or sulfur;

$L^3$ is a covalent bond or a $C_{1-6}$ bivalent hydrocarbon chain wherein one or two methylene units of the chain are optionally and independently replaced by —O—, —S—, —S(O)—, —S(O)$_2$—, —C(O)—, or —N(R)—;

Ring A is phenyl, a 3-8 membered saturated or partially unsaturated carbocyclic ring, a 4-7 membered saturated or partially unsaturated heterocyclic ring having 1-2 heteroatoms independently selected from nitrogen, oxygen, or sulfur, or a 5-6 membered heteroaryl ring having 1-4 heteroatoms independently selected from nitrogen, oxygen, or sulfur;

each $R^3$ is halogen, —CN, —NO$_2$, or an optionally substituted $C_{1-6}$ aliphatic group;

n is 0, 1, 2, or 3;

p is 0 or 1;

or when p is 0 then $L^1$ is a covalent bond and $R^1$ is an optionally substituted group selected from phenyl, a 5-6 membered heteroaryl ring having 1-4 heteroatoms independently selected from nitrogen, oxygen, or sulfur, or an 8-10 membered bicyclic ring having 0-3 heteroatoms independently selected from nitrogen, oxygen, or sulfur;

each $R^4$ is independently halogen, —CN, —NO$_2$, —NHR, —NR$_2$, or —OR; or two $R^4$ on the same carbon are optionally taken together to form =O;

m is 0, 1, 2, 3, 4, or 5; and wherein -L$^1$-R$^1$ and -L$^2$-R$^2$ are not simultaneously hydrogen.

2. Compounds and Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH=CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR—, SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°2; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —S(O)(NR°)R°; —S(O)$_2$N=C(NR°$_2$)$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; —SiR°$_3$; —(C$_{1-4}$ straight or branched alkylene)O—N(R°)$_2$; or —(C$_{1-4}$ straight or branched alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R•, -(haloR•), —(CH$_2$)$_{0-2}$OH, —(CH$_2$)$_{0-2}$OR•, —(CH$_2$)$_{0-2}$CH(OR•)$_2$; —O(haloR•), —CN, —N$_3$, —(CH$_2$)$_{0-2}$C(O)R•, —(CH$_2$)$_{0-2}$C(O)OH, —(CH$_2$)$_{0-2}$C(O)OR•, —(CH$_2$)$_{0-2}$SR•, —(CH$_2$)$_{0-2}$SH, —(CH$_2$)$_{0-2}$NH$_2$, —(CH$_2$)$_{0-2}$NHR•, —(CH$_2$)$_{0-2}$NR•$_2$, —NO$_2$, —SiR•$_3$, —OSiR•$_3$, —C(O)SR•, —(C$_{1-4}$ straight or branched alkylene)C(O)OR•, or —SSR• wherein each R• is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR•$_2$, =NNHC(O)R•, =NNHC(O)OR•, =NNHS(O)$_2$R•, =NR•, =NOR•, —O(C(R•$_2$))$_{2-3}$O—, or —S(C(R•$_2$))$_{2-3}$S—, wherein each independent occurrence of R• is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR•$_2$)$_{2-3}$O—, wherein each independent occurrence of R• is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R• include halogen, —R•, -(haloR•), —OH, —OR•, —O(haloR•), —CN, —C(O)OH, —C(O)OR•, —NH$_2$, —NHR•, —NR•$_2$, or —NO$_2$, wherein each R• is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R†, —NR†₂, —C(O)R†, —C(O)OR†, —C(O)C(O)R†, —C(O)CH₂C(O)R†, —S(O)₂R†, —S(O)₂NR†₂, —C(S)NR†₂, —C(NH)NR†₂, or —N(R†)S(O)₂R†; wherein each R† is independently hydrogen, C₁₋₆ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R† are independently halogen, —R•, -(haloR•), —OH, —OR•, —O(haloR•), —CN, —C(O)OH, —C(O)OR•, —NH₂, —NHR•, —NR•₂, or —NO₂, wherein each R• is unsubstituted or where preceded by "halo" is substituted only with one or more halogens, and is independently C₁₋₄ aliphatic, —CH₂Ph, —O(CH₂)₀₋₁Ph, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and N⁺(C₁₋₄alkyl)₄ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a ¹³C- or ¹⁴C-enriched carbon are within the scope of this invention. Such compounds are useful, for example, as analytical tools, as probes in biological assays, or as therapeutic agents in accordance with the present invention.

The terms "measurable affinity" and "measurably inhibit," as used herein, means a measurable change in Rheb activity between a sample comprising a compound of the present invention, or composition thereof, and Rheb, and an equivalent sample comprising Rheb in the absence of said compound, or composition thereof.

3. Description of Exemplary Embodiments

As described above, in certain embodiments, the present invention provides a compound of Formula I:

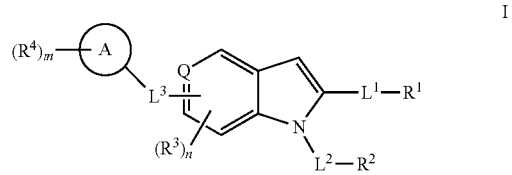

or a pharmaceutically acceptable salt thereof, wherein:
Q is CH, CR³, or N;
L¹ is a covalent bond or a C₁₋₆ bivalent hydrocarbon chain wherein one, two, or three methylene units of the chain are optionally and independently replaced by -Cy¹-, —N(R)—, —O—, —C(O)—, —OC(O)—, —C(O)O—, —C(O)N(R)—, —N(R)C(O)—, —S(O)—, or —S(O)₂—;
each R is independently hydrogen, or an optionally substituted group selected from C₁₋₆ aliphatic, a 3-8 membered saturated or partially unsaturated monocyclic carbocyclic ring, phenyl, 4-7 membered saturated or partially unsaturated heterocyclic ring having 1-2 heteroatoms independently selected from nitrogen, oxygen, or sulfur, or 5-6 membered heteroaryl ring having 1-4 heteroatoms independently selected from nitrogen, oxygen, or sulfur, or:
two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, or sulfur;
each -Cy¹- is independently an optionally substituted bivalent ring selected from phenylene, 3-7 membered saturated or partially unsaturated carbocyclylene, 4-7 membered saturated or partially unsaturated heterocyclylene having 1-2 heteroatoms independently selected from nitrogen, oxygen, or sulfur, or 5-6 membered heteroarylene having 1-4 heteroatoms independently selected from nitrogen, oxygen, or sulfur;

$R^1$ is hydrogen, halogen, —CN, —NO2 or an optionally substituted group selected from $C_{1-6}$ aliphatic, a 3-8 membered saturated or partially unsaturated monocyclic carbocyclic ring, phenyl, a 4-7 membered saturated or partially unsaturated heterocyclic ring having 1-2 heteroatoms independently selected from nitrogen, oxygen, or sulfur, or a 5-6 membered heteroaryl ring having 1-4 heteroatoms independently selected from nitrogen, oxygen, or sulfur;

$L^2$ is a covalent bond or a $C_{1-6}$ bivalent hydrocarbon chain wherein one, two, or three methylene units of the chain are optionally and independently replaced by -$Cy^2$-, —C(O)—, —CH(R)—, —N(R)—, —C(O)N(R)—, —N(R)C(O)—, —O—, —C(O)O—, —OC(O)—, or —S(O)$_2$—;

each -$Cy^2$- is independently an optionally substituted bivalent ring selected from phenylene, 4-7 membered saturated or partially unsaturated heterocyclylene having 1-2 heteroatoms independently selected from nitrogen, oxygen, or sulfur, or 5-6 membered heteroarylene having 1-4 heteroatoms independently selected from nitrogen, oxygen, or sulfur;

$R^2$ is hydrogen, halogen, —CN, —NO$_2$ or an optionally substituted group selected from $C_{1-6}$ aliphatic, a 3-8 membered saturated or partially unsaturated monocyclic carbocyclic ring, phenyl, a 4-7 membered saturated or partially unsaturated heterocyclic ring having 1-2 heteroatoms independently selected from nitrogen, oxygen, or sulfur, or a 5-6 membered heteroaryl ring having 1-4 heteroatoms independently selected from nitrogen, oxygen, or sulfur;

$L^3$ is a covalent bond or a $C_{1-6}$ bivalent hydrocarbon chain wherein one or two methylene units of the chain are optionally and independently replaced by —O—, —C(O)—, —S—, —S(O)—, —S(O)$_2$— or —N(R)—;

Ring A is phenyl, a 3-8 membered saturated or partially unsaturated carbocyclic ring, a 4-7 membered saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, or an 8-10 membered bicyclic ring having 0-3 heteroatoms independently selected from nitrogen, oxygen, or sulfur, wherein Ring A is substituted with m occurrences of $R^4$;

each $R^3$ is independently an optionally substituted $C_{1-6}$ aliphatic, phenyl, halogen, —CN, —SR, or two $R^3$ groups are optionally taken together to form a 5-8 membered partially unsaturated or aryl fused ring having 0-2 heteroatoms independently selected from nitrogen, oxygen, or sulfur;

n is 0, 1, 2, or 3;

each $R^4$ is independently an optionally substituted $C_{1-6}$ aliphatic, halogen, or —OR; and m is 0, 1, 2, 3, 4, or 5.

In certain embodiments, the present invention provides a compound of Formula I':

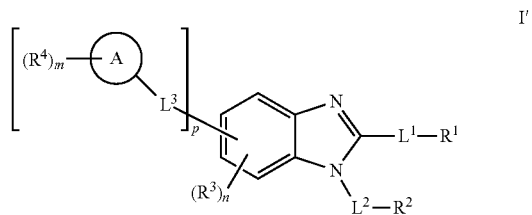

I' or a pharmaceutically acceptable salt thereof, wherein:

$L^1$ is a covalent bond or a $C_{1-6}$ bivalent hydrocarbon chain wherein one or two methylene units of the chain are optionally and independently replaced by -$Cy^1$-, —N(R)—, —O—, —C(O)—, —OC(O)—, —C(O)O—, —C(O)N(R)—, —N(R)C(O)—, —S(O)—, or —S(O)$_2$—; or $L^1$ and $L^2$ are optionally taken together with their intervening atoms to form a 5-8 membered partially unsaturated fused ring having 0-2 heteroatoms independently selected from nitrogen, oxygen or sulfur;

each R is independently hydrogen, or an optionally substituted group selected from $C_{1-6}$ aliphatic, a 3-8 membered saturated or partially unsaturated monocyclic carbocyclic ring, phenyl, 4-7 membered saturated or partially unsaturated heterocyclic ring having 1-2 heteroatoms independently selected from nitrogen, oxygen, or sulfur, 5-6 membered heteroaryl ring having 1-4 heteroatoms independently selected from nitrogen, oxygen, or sulfur, or an 8-10 membered bicyclic ring having 0-3 heteroatoms independently selected from nitrogen, oxygen, or sulfur;

each -$Cy^1$- is independently an optionally substituted bivalent ring selected from phenylene, 4-7 membered saturated or partially unsaturated heterocyclylene having 1-2 heteroatoms independently selected from nitrogen, oxygen, or sulfur, or 5-6 membered heteroarylene having 1-4 heteroatoms independently selected from nitrogen, oxygen, or sulfur;

$R^1$ is hydrogen, or an optionally substituted group selected from $C_{1-6}$ aliphatic, a 3-8 membered saturated or partially unsaturated monocyclic carbocyclic ring, phenyl, 4-7 membered saturated or partially unsaturated heterocyclic ring having 1-2 heteroatoms independently selected from nitrogen, oxygen, or sulfur, 5-6 membered heteroaryl ring having 1-4 heteroatoms independently selected from nitrogen, oxygen, or sulfur, or an 8-10 membered bicyclic ring having 0-3 heteroatoms independently selected from nitrogen, oxygen, or sulfur;

$L^2$ is a covalent bond or a $C_{1-6}$ bivalent hydrocarbon chain wherein one or two methylene units of the chain are optionally and independently replaced by -$Cy^2$-;

each -$Cy^2$- is independently an optionally substituted bivalent ring selected from phenylene or 5-6 membered heteroarylene having 1-4 heteroatoms independently selected from nitrogen, oxygen, or sulfur;

$R^2$ is hydrogen, or an optionally substituted group selected from $C_{1-6}$ aliphatic, a 3-8 membered saturated or partially unsaturated monocyclic carbocyclic ring, phenyl, 4-7 membered saturated or partially unsaturated heterocyclic ring having 1-2 heteroatoms independently selected from nitrogen, oxygen, or sulfur, 5-6 membered heteroaryl ring having 1-4 heteroatoms independently selected from nitrogen, oxygen, or sulfur, or an 8-10 membered bicyclic ring having 0-3 heteroatoms independently selected from nitrogen, oxygen, or sulfur;

L³ is a covalent bond or a C₁₋₆ bivalent hydrocarbon chain wherein one or two methylene units of the chain are optionally and independently replaced by —O—, —S—, —S(O)—, —S(O)₂—, —C(O)—, or —N(R)—;

Ring A is phenyl, a 3-8 membered saturated or partially unsaturated carbocyclic ring, a 4-7 membered saturated or partially unsaturated heterocyclic ring having 1-2 heteroatoms independently selected from nitrogen, oxygen, or sulfur, or a 5-6 membered heteroaryl ring having 1-4 heteroatoms independently selected from nitrogen, oxygen, or sulfur;

each R³ is halogen, —CN, —NO₂, or an optionally substituted C₁₋₆ aliphatic group;

n is 0, 1, 2, or 3;

p is 0 or 1;

or when p is 0 then L¹ is a covalent bond and R¹ is an optionally substituted group selected from phenyl, a 5-6 membered heteroaryl ring having 1-4 heteroatoms independently selected from nitrogen, oxygen, or sulfur, or an 8-10 membered bicyclic ring having 0-3 heteroatoms independently selected from nitrogen, oxygen, or sulfur;

each R⁴ is independently halogen, —CN, —NO₂, —NHR, —NR₂, or —OR; or two R⁴ on the same carbon are optionally taken together to form =O;

m is 0, 1, 2, 3, 4, or 5; and wherein -L¹-R¹ and -L²-R² are not simultaneously hydrogen.

As defined above and described herein, Q is CH, CR³, or N. In some embodiments, Q is CH. In some embodiments, Q is CR³. In some embodiments, Q is N. In some embodiments, Q is CR³, where R³ is

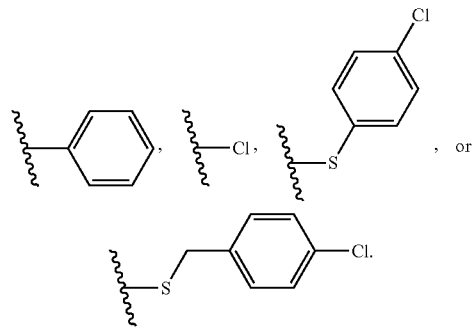

In some embodiments, Q is selected from those depicted in Table 1, below.

As defined above and described herein, L¹ is a covalent bond or a C₁₋₆ bivalent hydrocarbon chain wherein one, two, or three methylene units of the chain are optionally and independently replaced by -Cy¹-, —N(R)—, —O—, —C(O)—, —OC(O)—, —C(O)O—, —C(O)N(R)—, —N(R)C(O)—, —S(O)—, or —S(O)₂—.

In some embodiments, L¹ is a covalent bond. In some embodiments, L¹ is —C(O)O—. In some embodiments, L¹ is —C(O)N(R)—. In some embodiments, L¹ is —C(O)NH—. In some embodiments, L¹ is —C(O)NHCH₂—. In some embodiments, L¹ is —C(O)NHCH₂CH₂—. In some embodiments, L¹ is —C(O)—. In some embodiments, L¹ is —CH₂—. In some embodiments, L¹ is —CH₂CH₂—. In some embodiments, L¹ is —CH₂CH₂CH₂—.

In some embodiments, L¹ is

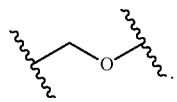 [SMILES: *CO*]

In some embodiments, L¹ is

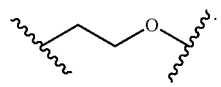 [SMILES: *CCO*]

In some embodiments, L¹ is

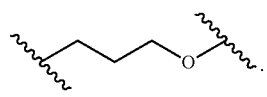 [SMILES: *CCCO*]

In some embodiments, L¹ is

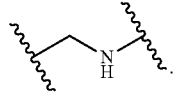

In some embodiments, L¹ is

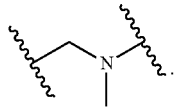

In some embodiments, L¹ is

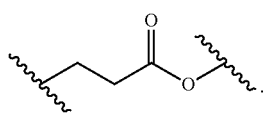 [SMILES: *CCC(=O)O*]

In some embodiments, L¹ is

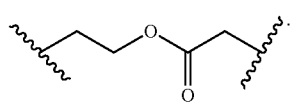 [SMILES: *CCOC(=O)C*]

In some embodiments, L¹ is

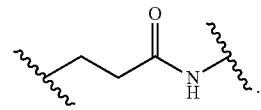 [SMILES: *CCC(=O)N*]

In some embodiments, L¹ is
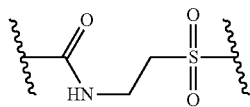 [SMILES: *C(=O)NCCS(*)(=O)=O]
In some embodiments, L¹ is
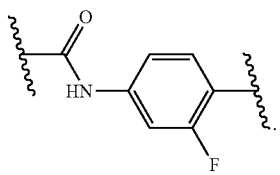 [SMILES: *C(=O)Nc1ccc(*)c(F)c1]
In some embodiments, L¹ is
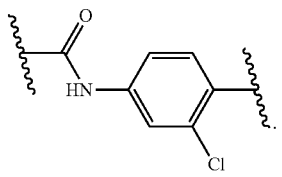 [SMILES: *C(=O)Nc1ccc(*)c(Cl)c1]
In some embodiments, L¹ is
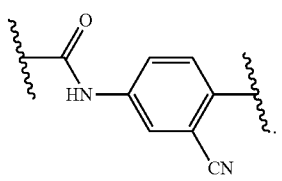 [SMILES: *C(=O)Nc1ccc(*)c(C#N)c1]
In some embodiments, L¹ is
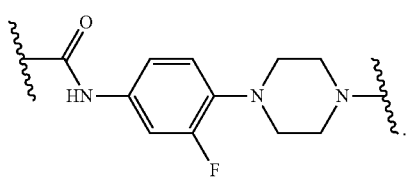 [SMILES: *C(=O)Nc1ccc(N2CCN(*)CC2)c(F)c1]
In some embodiments, L¹ is
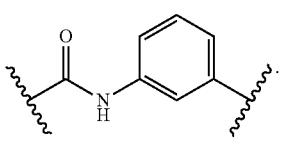 [SMILES: *C(=O)Nc1cccc(*)c1]
In some embodiments, L¹ is
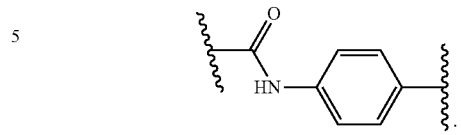
In some embodiments, L¹ is
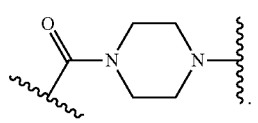
In some embodiments, L¹ is
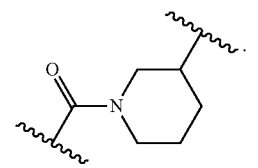 [SMILES: *C(=O)N1CCCC(*)C1]
In some embodiments, L¹ is
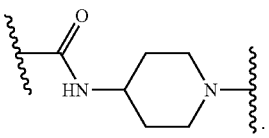 [SMILES: *C(=O)NC1CCN(*)CC1]
In some embodiments, L¹ is
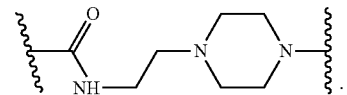
In some embodiments, L¹ is
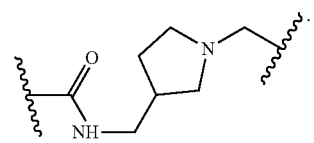 [SMILES: *CN1CCC(CNC(*)=O)C1]
In some embodiments, L¹ is
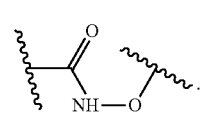

In some embodiments, L¹ is
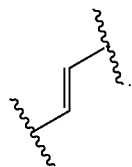
In some embodiments, L¹ is
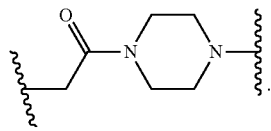 [SMILES: *CC(=O)N1CCN(*)CC1]
In some embodiments, L¹ is
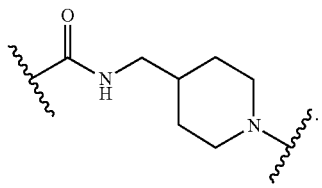 [SMILES: *C(=O)NCC1CCN(*)CC1]
In some embodiments, L¹ is
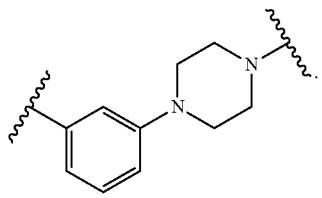 [SMILES: *c1cccc(N2CCN(*)CC2)c1]
In some embodiments, L¹ is
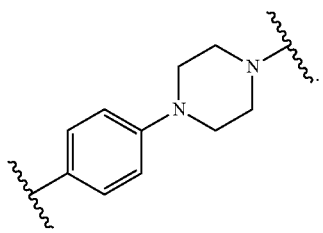 [SMILES: *c1ccc(N2CCN(*)CC2)cc1]
In some embodiments, L¹ is
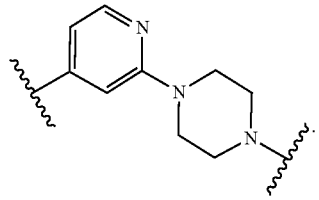 [SMILES: *c1ccnc(N2CCN(*)CC2)c1]
In some embodiments, L¹ is
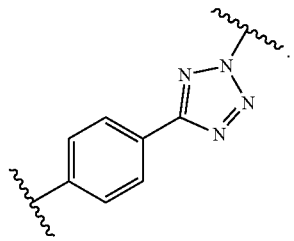 [SMILES: *c1ccc(-c2nnn(*)n2)cc1]
In some embodiments, L¹ is
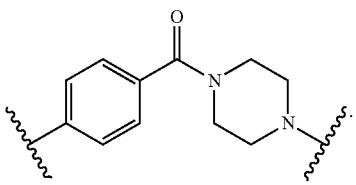 [SMILES: *c1ccc(C(=O)N2CCN(*)CC2)cc1]
In some embodiments, L¹ is
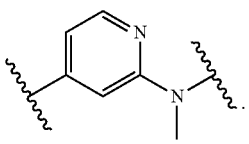 [SMILES: *c1ccnc(N(*)C)c1]
In some embodiments, L¹ is
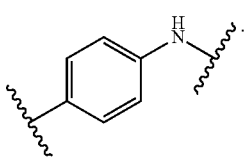 [SMILES: *Nc1ccc(*)cc1]

In some embodiments, $L^1$ is

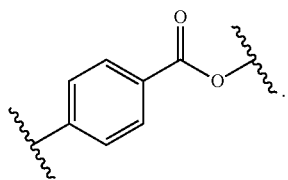 [SMILES: *OC(=O)c1ccc(*)cc1]

In some embodiments, $L^1$ is

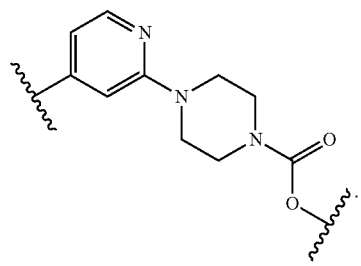 [SMILES: *OC(=O)N1CCN(c2cc(*)ccn2)CC1]

In some embodiments, $L^1$ is

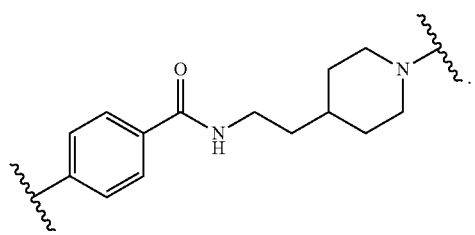 [SMILES: *c1ccc(C(=O)NCCC2CCN(*)CC2)cc1]

In some embodiments, $L^1$ is

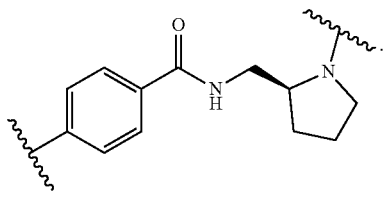 [SMILES: *c1ccc(C(=O)NC[C@@H]2CCCN2*)cc1]

In some embodiments, $L^1$ is

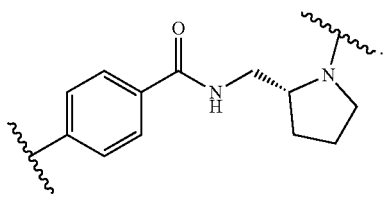 [SMILES: *c1ccc(C(=O)NC[C@H]2CCCN2*)cc1]

As defined above and described herein, $L^1$ and $L^2$ are optionally taken together with their intervening atoms to form a 5-8 membered partially unsaturated fused ring having 0-2 heteroatoms independently selected from nitrogen, oxygen or sulfur.

In some embodiments, $L^1$ and $L^2$ are taken together with their intervening atoms to form a 5-8 membered partially unsaturated fused ring having 0-2 heteroatoms independently selected from nitrogen, oxygen or sulfur. In some embodiments, $L^1$ and $L^2$ are taken together with their intervening atoms to form a 5 membered partially unsaturated fused ring having 2 heteroatoms independently selected from nitrogen, oxygen or sulfur.

In some embodiments, $L^1$ and $L^2$ are taken together with their intervening atoms to form

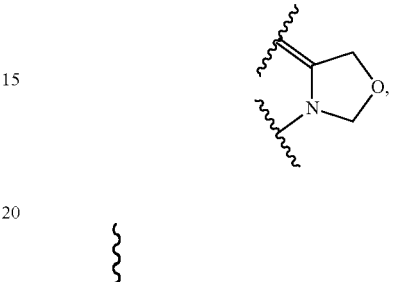

where $\xi$ indicates the site of fusion to the ring system.

In some embodiments, $L^1$ is selected from those depicted in Tables 1 and 3, below.

As defined above and described herein, $R^1$ is hydrogen, halogen, —CN, —NO$_2$ or an optionally substituted group selected from $C_{1-6}$ aliphatic, a 3-8 membered saturated or partially unsaturated monocyclic carbocyclic ring, phenyl, a 4-7 membered saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, or an 8-10 membered bicyclic ring having 0-3 heteroatoms independently selected from nitrogen, oxygen, or sulfur. In some embodiments, $R^1$ is hydrogen. In some embodiments, $R^1$ is halogen. In some embodiments, $R^1$ is —CN. In some embodiments, $R^1$ is —NO$_2$. In some embodiments, $R^1$ is an optionally substituted group selected from $C_{1-6}$ aliphatic. In some embodiments, $R^1$ is a 3-8 membered saturated or partially unsaturated monocyclic carbocyclic ring. In some embodiments, $R^1$ is phenyl. In some embodiments, $R^1$ is a 4-7 membered saturated or partially unsaturated heterocyclic ring having 1-2 heteroatoms independently selected from nitrogen, oxygen, or sulfur. In some embodiments, $R^1$ is a 5-6 membered heteroaryl ring having 1-4 heteroatoms independently selected from nitrogen, oxygen, or sulfur. In some embodiments, $R^1$ is an 8-10 membered bicyclic ring having 0-3 heteroatoms independently selected from nitrogen, oxygen, or sulfur.

In some embodiments, $R^1$ is methyl. In some embodiments, $R^1$ is ethyl. In some embodiments, $R^1$ is —CO$_2$H. In some embodiments, $R^1$ is —CH$_2$OH. In some embodiments, $R^1$ is —C(O)NH$_2$. In some embodiments, $R^1$ is —C(O)NHOH. In some embodiments, $R^1$ is —CH$_2$NH$_2$. In some embodiments, $R^1$ is —CH$_2$NHCH$_3$. In some embodiments, $R^1$ is —CH$_2$N(CH$_3$)$_2$.

In some embodiments, $R^1$ is

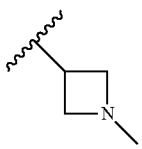

In some embodiments, R¹ is
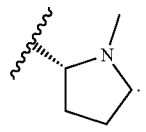
In some embodiments, R¹ is
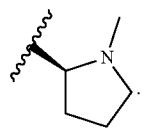
In some embodiments, R¹ is
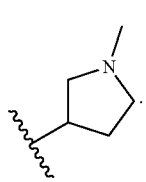 [SMILES: *C1CCN(C)C1]
In some embodiments, R¹ is
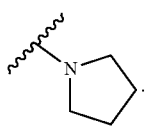
In some embodiments, R¹ is
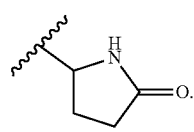 [SMILES: *C1CCC(=O)N1]
In some embodiments, R¹ is
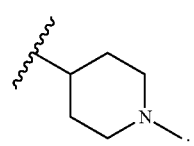 [SMILES: *C1CCN(C)CC1]
In some embodiments, R¹ is
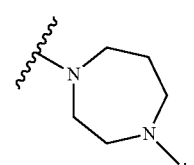 [SMILES: *N1CCCN(C)CC1]
In some embodiments, R¹ is
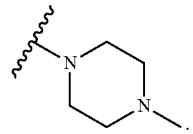 [SMILES: *N1CCN(C)CC1]
In some embodiments, R¹ is
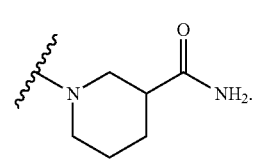 [SMILES: *N1CCCC(C(N)=O)C1]
In some embodiments, R¹ is
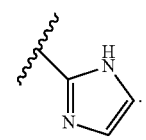 [SMILES: *c1ncc[nH]1]
In some embodiments, R¹ is
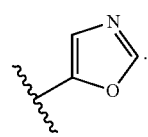 [SMILES: *c1cnco1]
In some embodiments, R¹ is
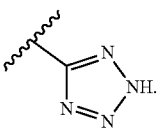 [SMILES: *c1nn[nH]n1]
In some embodiments, R¹ is
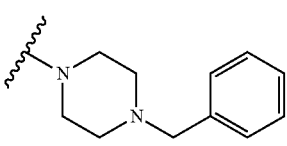 [SMILES: *N1CCN(Cc2ccccc2)CC1]
In some embodiments, R¹ is
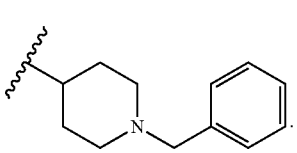 [SMILES: *C1CCN(Cc2ccccc2)CC1]

In some embodiments, R¹ is
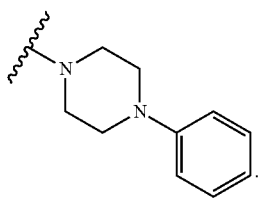 [SMILES: *N1CCN(c2ccccc2)CC1]
In some embodiments, R¹ is
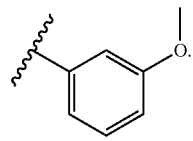
In some embodiments, R¹ is
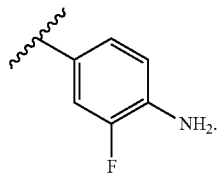 [SMILES: *c1ccc(N)c(F)c1]
In some embodiments, R¹ is
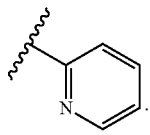 [SMILES: *c1ccccn1]
In some embodiments, R¹ is
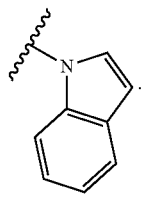
In some embodiments, R¹ is
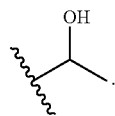
In some embodiments, R¹ is
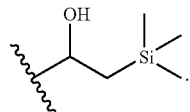 [SMILES: *C(O)C[Si](C)(C)C]
In some embodiments, R¹ is
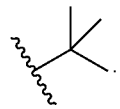
In some embodiments, R¹ is
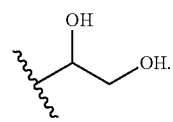
In some embodiments, R¹ is
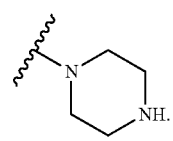
In some embodiments, R¹ is
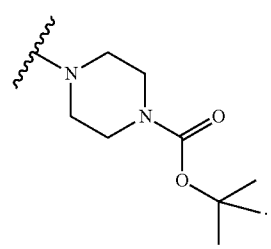 [SMILES: *N1CCN(C(=O)OC(C)(C)C)CC1]
In some embodiments, R¹ is
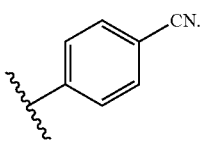 [SMILES: *c1ccc(C#N)cc1]
In some embodiments, R¹ is
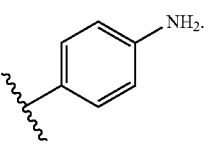 [SMILES: *c1ccc(N)cc1]

In some embodiments, R¹ is

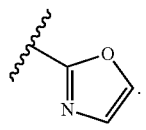

In some embodiments R¹ is

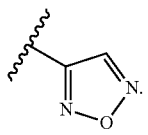

In some embodiments, R¹ is

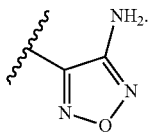 [SMILES: *c1nonc1N]

In some embodiments, R¹ is

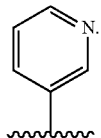

In some embodiments, R¹ is

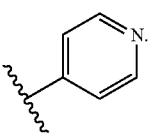 [SMILES: *c1ccncc1]

In some embodiments, R¹ is

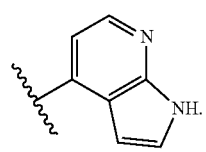 [SMILES: *c1ccnc2[nH]ccc12]

In some embodiments, R¹ is

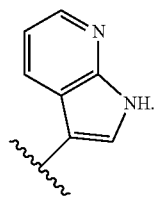 [SMILES: *c1c[nH]c2ncccc12]

In some embodiments, R¹ is

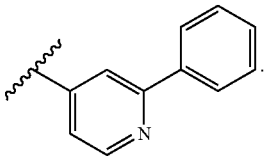 [SMILES: *c1ccnc(-c2ccccc2)c1]

In some embodiments, R¹ is

In some embodiments, R¹ is

In some embodiments, R¹ is selected from those depicted in Tables 1 and 3, below.

As defined above and described herein, $L^2$ is a covalent bond or a $C_{1-6}$ bivalent hydrocarbon chain wherein one, two, or three methylene units of the chain are optionally and independently replaced by -Cy²-, —C(O)—, —CH(R)—, —N(R)—, —C(O)N(R)—, —N(R)C(O)—, —O—, —C(O)O—, —OC(O)—, or —S(O)₂—.

In some embodiments, $L^2$ is a covalent bond. In some embodiments, $L^2$ is a $C_{1-6}$ bivalent hydrocarbon chain wherein one, two, or three methylene units of the chain are optionally and independently replaced by -Cy²-, —C(O)—, —CH(R)—, —N(R)—, —C(O)N(R)—, —N(R)C(O)—, —O—, —C(O)O—, —OC(O)—, or —S(O)₂—.

In some embodiments, $L^2$ is —CH₂—. In some embodiments, $L^2$ is —CH(CH₃)—. In some embodiments, $L^2$ is —CH₂CH₂—. In some embodiments, $L^2$ is —SO₂—. In some embodiments, $L^2$ is —CH₂CH₂NH—.

In some embodiments, $L^2$ is

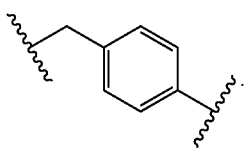 [SMILES: *Cc1ccc(*)cc1]

In some embodiments, $L^2$ is

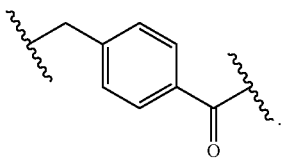 [SMILES: *Cc1ccc(C(*)=O)cc1]

In some embodiments, $L^2$ is

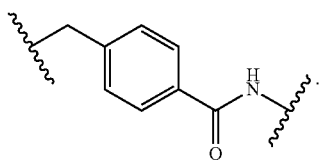 [SMILES: *Cc1ccc(C(=O)N*)cc1]

In some embodiments, $L^2$ is

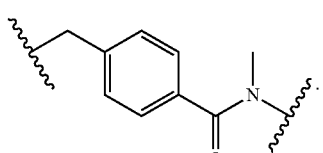

In some embodiments, $L^2$ is selected from those depicted in Tables 1 and 3, below.

As defined above and described herein, $R^2$ is hydrogen, halogen, —CN, —NO$_2$ or an optionally substituted group selected from $C_{1-6}$ aliphatic, a 3-8 membered saturated or partially unsaturated monocyclic carbocyclic ring, phenyl, a 4-7 membered saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, or an 8-10 membered bicyclic ring having 0-3 heteroatoms independently selected from nitrogen, oxygen, or sulfur.

In some embodiments, $R^2$ is hydrogen. In some embodiments, $R^2$ is halogen. In some embodiments, $R^2$ is —CN. In some embodiments, $R^2$ is —NO$_2$. In some embodiments, $R^2$ is an optionally substituted group selected from $C_{1-6}$ aliphatic. In some embodiments, $R^2$ is a 3-8 membered saturated or partially unsaturated monocyclic carbocyclic ring. In some embodiments, $R^2$ is phenyl. In some embodiments, $R^2$ is a 4-7 membered saturated or partially unsaturated heterocyclic ring having 1-2 heteroatoms independently selected from nitrogen, oxygen, or sulfur. In some embodiments, $R^2$ is a 5-6 membered heteroaryl ring having 1-4 heteroatoms independently selected from nitrogen, oxygen, or sulfur. In some embodiments, $R^2$ is an 8-10 membered bicyclic ring having 0-3 heteroatoms independently selected from nitrogen, oxygen, or sulfur.

In some embodiments, $R^2$ is methyl. In some embodiments, $R^2$ is —CO$_2$H. In some embodiments, $R^2$ is —CH$_2$NH$_2$.

In some embodiments, $R^2$ is

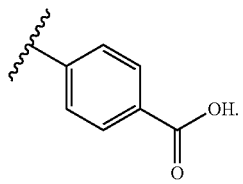 [SMILES: *c1ccc(C(=O)O)cc1]

In some embodiments, $R^2$ is

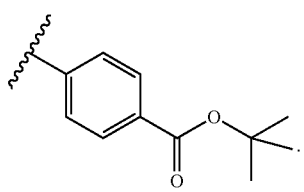 [SMILES: *c1ccc(C(=O)OC(C)(C)C)cc1]

In some embodiments, $R^2$ is

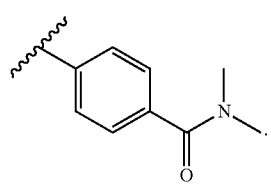 [SMILES: *c1ccc(C(=O)N(C)C)cc1]

In some embodiments, $R^2$ is

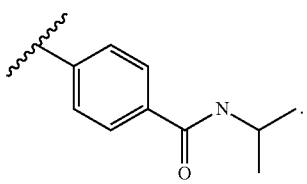 [SMILES: *c1ccc(C(=O)NC(C)C)cc1]

In some embodiments, $R^2$ is

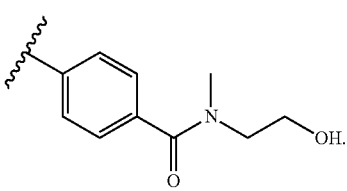 [SMILES: *c1ccc(C(=O)N(C)CCO)cc1]

In some embodiments, R² is
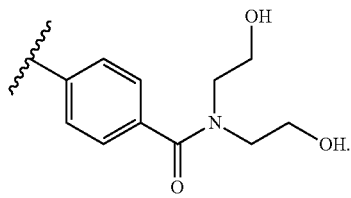 [SMILES: *c1ccc(C(=O)N(CCO)CCO)cc1]
In some embodiments, R² is
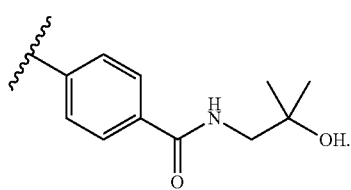 [SMILES: *c1ccc(C(=O)NCC(C)(C)O)cc1]
In some embodiments, R² is
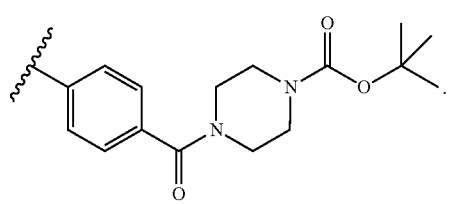 [SMILES: *c1ccc(C(=O)N2CCN(C(=O)OC(C)(C)C)CC2)cc1]
In some embodiments, R² is
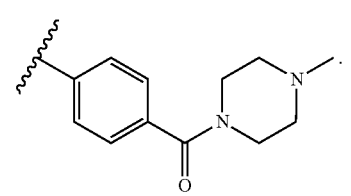 [SMILES: *c1ccc(C(=O)N2CCN(C)CC2)cc1]
In some embodiments, R² is
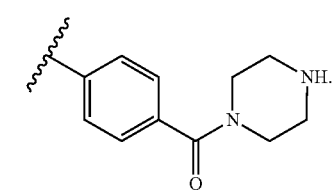 [SMILES: *c1ccc(C(=O)N2CCNCC2)cc1]
In some embodiments, R² is
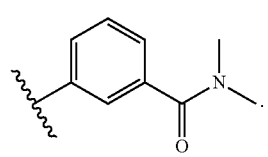 [SMILES: *c1cccc(C(=O)N(C)C)c1]
In some embodiments, R² is
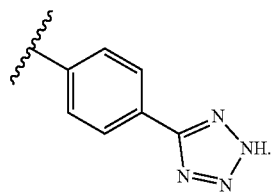 [SMILES: *c1ccc(-c2nn[nH]n2)cc1]
In some embodiments, R² is
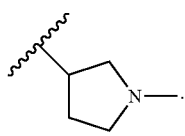 [SMILES: *C1CCN(C)C1]
In some embodiments, R² is
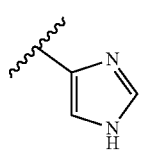 [SMILES: *c1c[nH]cn1]
In some embodiments, R² is
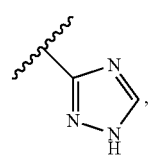 [SMILES: *c1nc[nH]n1]
In some embodiments, R² is
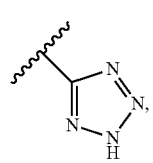 [SMILES: *c1nn[nH]n1]
In some embodiments, R² is
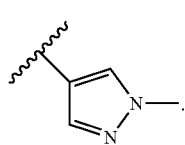 [SMILES: *c1cnn(C)c1]
In some embodiments, R² is
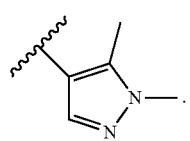 [SMILES: *c1cnn(C)c1C]

In some embodiments, R² is

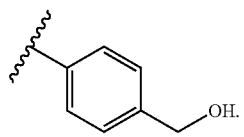 [SMILES: *c1ccc(CO)cc1]

In some embodiments, R² is

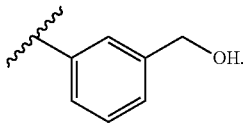 [SMILES: *c1cccc(CO)c1]

In some embodiments, R² is

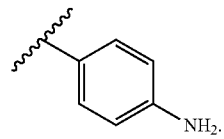 [SMILES: *c1ccc(N)cc1]

In some embodiments, R² is

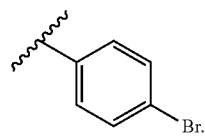 [SMILES: *c1ccc(Br)cc1]

In some embodiments, R² is

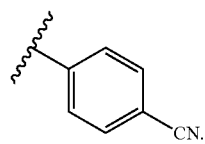 [SMILES: *c1ccc(C#N)cc1]

In some embodiments, R² is

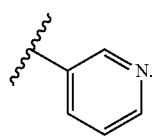

In some embodiments, R² is

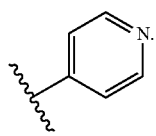 [SMILES: *c1ccncc1]

In some embodiments, R² is —CH₂CH₃. In some embodiments, R² is —CH₂CO₂H. In some embodiments, R² is —CH₂C(O)NH₂. In some embodiments, R² is —CH₂CH₂CH₃.

In some embodiments, R² is

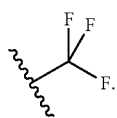 [SMILES: *C(F)(F)F]

In some embodiments, R² is

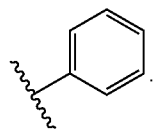 [SMILES: *c1ccccc1]

In some embodiments, R² is

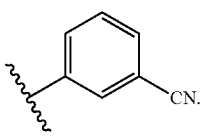

In some embodiments, R² is

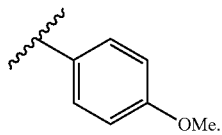 [SMILES: *c1ccc(OC)cc1]

In some embodiments, R² is

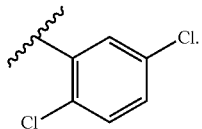 [SMILES: *c1cc(Cl)ccc1Cl]

In some embodiments, R² is

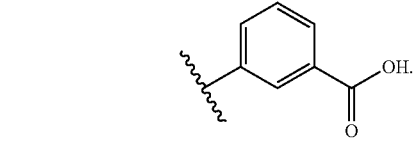 [SMILES: *c1cccc(C(=O)O)c1]

In some embodiments, $R^2$ is

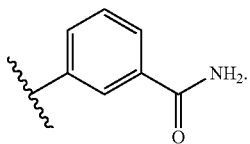 [SMILES: *c1cccc(C(N)=O)c1]

In some embodiments, $R^2$ is

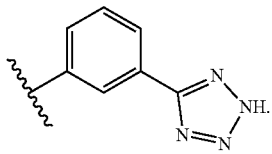 [SMILES: *c1cccc(-c2nn[nH]n2)c1]

In some embodiments, $R^2$ is

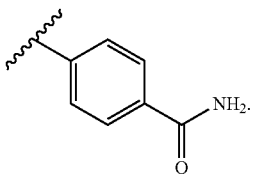 [SMILES: *c1ccc(C(N)=O)cc1]

In some embodiments, $R^2$ is selected from those depicted in Tables 1 and 3, below.

As defined above and described herein, $L^3$ is a covalent bond or a $C_{1-6}$ bivalent hydrocarbon chain wherein one or two methylene units of the chain are optionally and independently replaced by —O—, —C(O)—, —S—, —S(O)—, —S(O)$_2$— or —N(R)—.

In some embodiments, $L^3$ is a covalent bond. In some embodiments, $L^3$ is a $C_{1-6}$ bivalent hydrocarbon chain wherein one or two methylene units of the chain are optionally and independently replaced by —O—, —C(O)—, —S—, —S(O)—, —S(O)$_2$— or —N(R)—. In some embodiments, $L^3$ is —S—. In some embodiments, $L^3$ is —SCH$_2$—. In some embodiments, $L^3$ is —SCH$_2$CH$_2$—. In some embodiments, $L^3$ is —S(O)—. In some embodiments, $L^3$ is —S(O)$_2$—. In some embodiments, $L^3$ is —O—. In some embodiments, $L^3$ is —OCH$_2$—. In some embodiments, $L^3$ is —OCH$_2$CH$_2$—. In some embodiments, $L^3$ is —OCH$_2$CH$_2$CH$_2$—. In some embodiments, $L^3$ is —CH$_2$—. In some embodiments, $L^3$ is —C(O)—. In some embodiments, $L^3$ is —NH—.

In some embodiments, $L^3$ is selected from those depicted in Tables 1 and 3, below.

As defined above and described herein, Ring A is phenyl, a 3-8 membered saturated or partially unsaturated carbocyclic ring, a 4-7 membered saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, or an 8-10 membered bicyclic ring having 0-3 heteroatoms independently selected from nitrogen, oxygen, or sulfur, wherein Ring A is substituted with m occurrences of $R^4$.

In some embodiments, Ring A is phenyl substituted with m occurrences of $R^4$. In some embodiments, Ring A is a 3-8 membered saturated or partially unsaturated carbocyclic ring substituted with m occurrences of $R^4$. In some embodiments, Ring A is a 4-7 membered saturated or partially unsaturated heterocyclic ring having 1-2 heteroatoms independently selected from nitrogen, oxygen, or sulfur substituted with m occurrences of $R^4$. In some embodiments, Ring A is a 5-6 membered heteroaryl ring having 1-4 heteroatoms independently selected from nitrogen, oxygen, or sulfur substituted with m occurrences of $R^4$. In some embodiments, Ring A is an 8-10 membered bicyclic ring having 0-3 heteroatoms independently selected from nitrogen, oxygen, or sulfur substituted with m occurrences of $R^4$.

In some embodiments, Ring A is

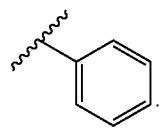

In some embodiments, Ring A is

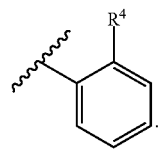

In some embodiments, Ring A is

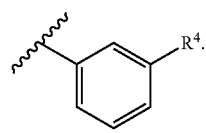

In some embodiments, Ring A is

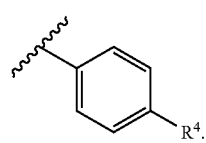

In some embodiments, Ring A is

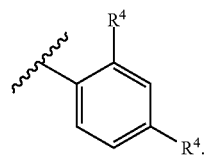

In some embodiments, Ring A is

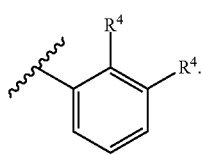

In some embodiments, Ring A is

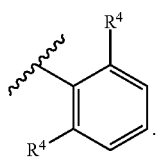

In some embodiments, Ring A is

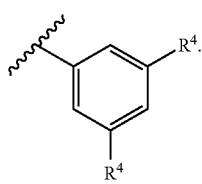

In some embodiments, Ring A is

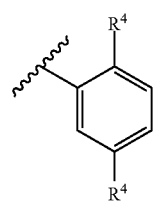

In some embodiments, Ring A

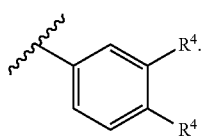

In some embodiments, Ring A is

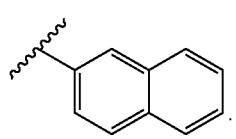 [SMILES: *c1ccc2ccccc2c1]

In some embodiments, Ring A is

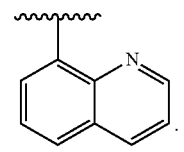

In some embodiments, Ring A is

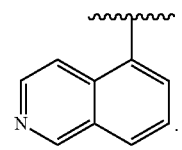

In some embodiments, Ring A is

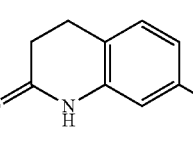

In some embodiments, Ring A is

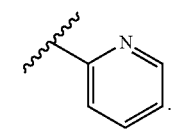 [SMILES: *c1ccccn1]

In some embodiments, Ring A is

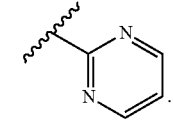 [SMILES: *c1ncccn1]

In some embodiments, Ring A is

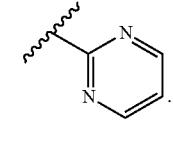

In some embodiments, Ring A is

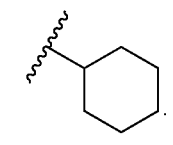

In some embodiments, Ring A is

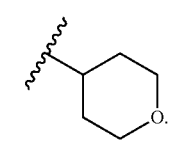 [SMILES: *C1CCOCC1]

In some embodiments, Ring A is

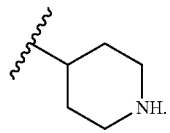 [SMILES: *C1CCNCC1]

In some embodiments, Ring A is

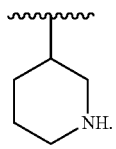

In some embodiments, Ring A is

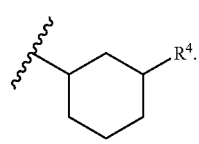

In some embodiments, Ring A is


In some embodiments, Ring A is


some embodiments, Ring A is

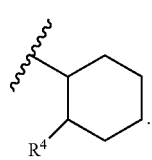

In some embodiments, Ring A is

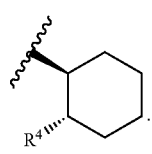

In some embodiments, Ring A is

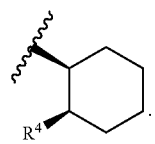

In some embodiments, Ring A is

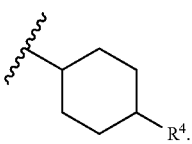

In some embodiments, Ring A is

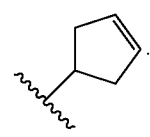

In some embodiments, Ring A is

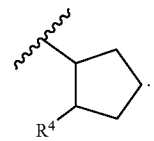

In some embodiments, Ring A is

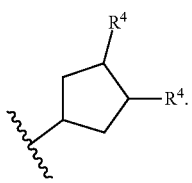

In some embodiments, Ring A is

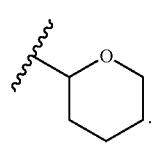

In some embodiments, Ring A is

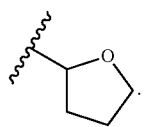 [SMILES: *C1CCCO1]

In some embodiments, Ring A is

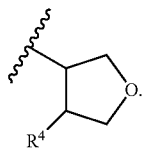

In some embodiments, Ring A is

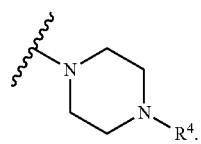

In some embodiments, Ring A is

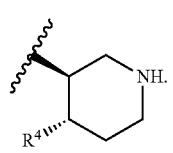

In some embodiments, Ring A is

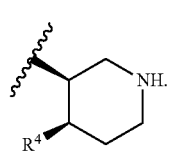

In some embodiments, Ring A is

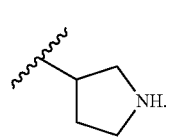

In some embodiments, Ring A is

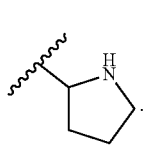

In some embodiments, Ring A is

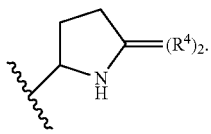

In some embodiments, Ring A is

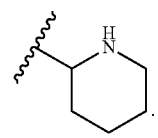 [SMILES: *C1CCCCN1]

In some embodiments, Ring A is

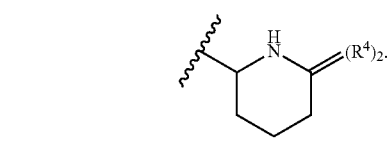

In some embodiments, Ring A is

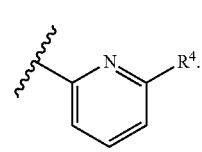

In some embodiments, Ring A is

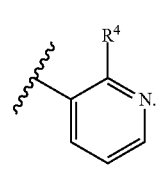

In some embodiments, Ring A is

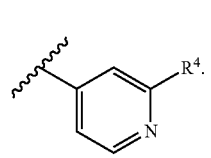

In some embodiments, Ring A is

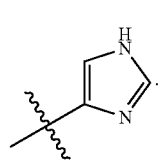

In some embodiments, Ring A is

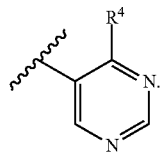

In some embodiments, Ring A is

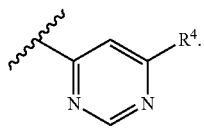

In some embodiments, Ring A is

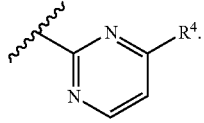

In some embodiments, Ring A is

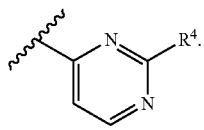

In some embodiments, Ring A is selected from those depicted in Tables 1 and 3, below.

As defined above and described herein, each $R^3$ is independently an optionally substituted $C_{1-6}$ aliphatic, phenyl, halogen, —CN, —SR, or two $R^3$ groups are optionally taken together to form a 5-8 membered partially unsaturated or aryl fused ring having 0-2 heteroatoms independently selected from nitrogen, oxygen, or sulfur.

In some embodiments, $R^3$ is an optionally substituted $C_{1-6}$ aliphatic. In some embodiments, $R^3$ is phenyl. In some embodiments, $R^3$ is halogen. In some embodiments, $R^3$ is —CN. In some embodiments, $R^3$ is —SR. In some embodiments, two $R^3$ groups are taken together to form a 5-8 membered partially unsaturated or aryl fused ring having 0-2 heteroatoms independently selected from nitrogen, oxygen, or sulfur.

In some embodiments, $R^3$ is fluoro. In some embodiments, $R^3$ is chloro. In some embodiments, $R^3$ is bromo. In some embodiments, $R^3$ is methyl. In some embodiments, $R^3$ is cyclopropyl. In some embodiments, $R^3$ is cyclohexyl.

In some embodiments, $R^3$ is

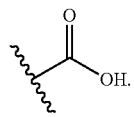

In some embodiments, $R^3$ is

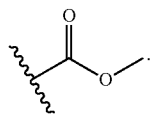

In some embodiments, $R^3$ is

In some embodiments, $R^3$ is

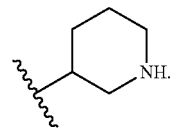

In some embodiments, $R^3$ is

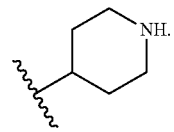 [SMILES: *C1CCNCC1]

In some embodiments, $R^3$ is

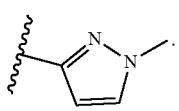 [SMILES: *c1ccn(C)n1]

In some embodiments, $R^3$ is

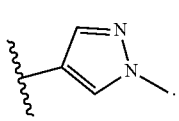 [SMILES: *c1cnn(C)c1]

In some embodiments, $R^3$ is

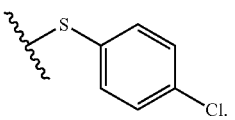 [SMILES: *Sc1ccc(Cl)cc1]

In some embodiments, $R^3$ is

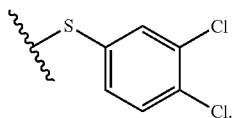 [SMILES: *Sc1ccc(Cl)c(Cl)c1]

In some embodiments, $R^3$ is

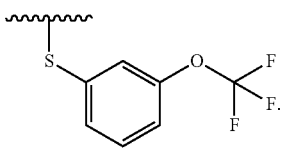 [SMILES: *Sc1cccc(OC(F)(F)F)c1]

In some embodiments, $R^3$ is

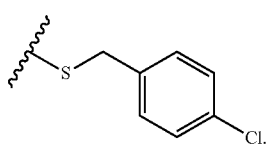 [SMILES: *SCc1ccc(Cl)cc1]

In some embodiments, $R^3$ is

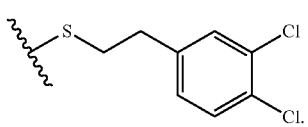 [SMILES: *SCCc1ccc(Cl)c(Cl)c1]

In some embodiments, two $R^3$ groups are taken together to form

wherein ⟩ represents the portion of the ring fused to the indole ring.

In some embodiments, $R^3$ is selected from those depicted in Tables 1 and 3, below.

As defined above and described herein, n is 0, 1, 2, or 3. In some embodiments, n is 0. In some embodiments, n is 1. In some embodiments, n is 2. In some embodiments, n is 3.

In some embodiments, n is selected from those depicted in Tables 1 and 3, below.

As defined above and described herein, $R^4$ is an optionally substituted $C_{1-6}$ aliphatic, halogen, or —OR. As defined above and described herein, $R^4$ is —CN, —$NO_2$, —NHR, or —$NR_2$; or two $R^4$ on the same carbon are optionally taken together to form =O.

In some embodiments, $R^4$ is an optionally substituted $C_{1-6}$ aliphatic. In some embodiments, $R^4$ is halogen. In some embodiments, $R^4$ is —OR.

In some embodiments, $R^4$ is fluoro. In some embodiments, $R^4$ is chloro. In some embodiments, $R^4$ is bromo. In some embodiments, $R^4$ is methyl. In some embodiments, $R^4$ is cyclohexyl. In some embodiments, $R^4$ is —$CF_3$. In some embodiments, $R^4$ is —$OCF_3$. In some embodiments, $R^4$ is —$OCH_3$. In some embodiments, $R^4$ is tert-butyl.

In some embodiments, $R^4$ is

In some embodiments, $R^4$ is

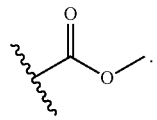 [SMILES: *C(=O)OC]

In some embodiments, $R^4$ is

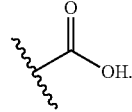

In some embodiments, $R^4$ is

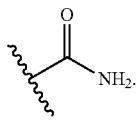

In some embodiments, $R^4$ is

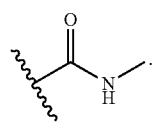 [SMILES: *C(=O)NC]

In some embodiments, $R^4$ is

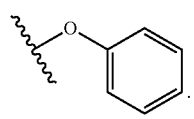

In some embodiments, $R^4$ is —OH. In some embodiments, $R^4$ is —$NO_2$. In some embodiments, $R^4$ is —$NH_2$. In some embodiments, $R^4$ is —CN. In some embodiments, $R^4$ is —$NHC(O)CH_3$. In some embodiments, $R^4$ is

In some embodiments, $R^4$ is selected from those depicted in Tables 1 and 3, below.

As defined above and described herein, m is 0, 1, 2, 3, 4, or 5. In some embodiments, m is 0. In some embodiments, m is 1. In some embodiments, m is 2. In some embodiments, m is 3. In some embodiments, m is 4. In some embodiments, m is 5.

In some embodiments, m is selected from those depicted in Tables 1 and 3, below.

As defined above and described herein, p is 0 or 1. In some embodiments, p is 0. In some embodiments, p is 1.

In some embodiments, p is selected from those depicted in Tables 1 and 3, below.

In certain embodiments, the present invention provides a compound of Formula I-a:

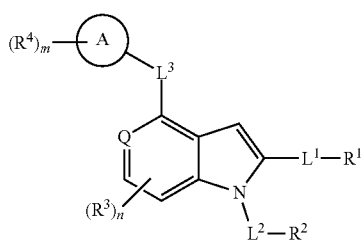

I-a or a pharmaceutically acceptable salt thereof, wherein each of Q, $L^1$, $R^1$, $L^2$, $R^2$, $R^3$, L, Ring A, $R^4$, m and n is as defined above and in embodiments herein, both singly and in combination.

In certain embodiments, the present invention provides a compound of Formula I-b:

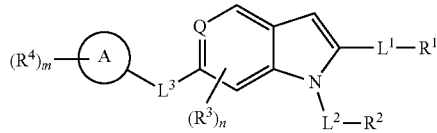

I-b or a pharmaceutically acceptable salt thereof, wherein each of Q, $L^1$, $R^1$, $L^2$, $R^2$, $L^3$, $R^3$, Ring A, $R^4$, n, and m is as defined above and in embodiments herein, both singly and in combination.

In certain embodiments, the present invention provides a compound of Formula I'-a:

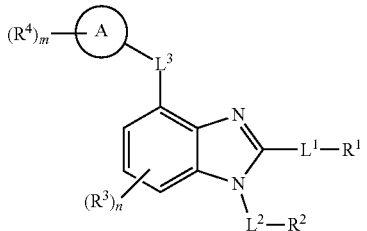

I'-a or a pharmaceutically acceptable salt thereof, wherein each of $L^1$, $R^1$, $L^2$, $R^2$, $R^3$, $L^3$, Ring A, $R^4$, m and n is as defined above and in embodiments herein, both singly and in combination.

In certain embodiments, the present invention provides a compound of Formula I'-b:

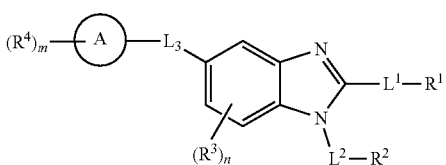

I'-b or a pharmaceutically acceptable salt thereof, wherein each of $L^1$, $R^1$, $L^2$, $R^2$, $L^3$, $R^3$, Ring A, $R^4$, n, and m is as defined above and in embodiments herein, both singly and in combination.

Exemplary compounds of the invention are set forth in Table 1, below.

TABLE 1

Exemplary Compounds

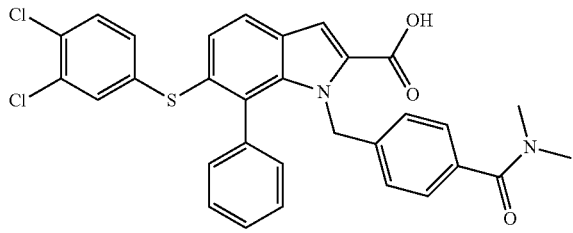 [SMILES: CN(C)C(=O)c1ccc(Cn2c(C(=O)O)cc3ccc(Sc4ccc(Cl)c(Cl)c4)c(-c4ccccc4)c32)cc1]

I-1

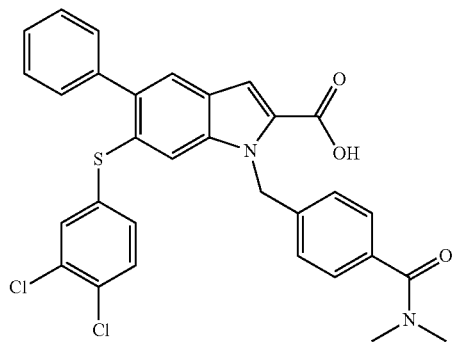 [SMILES: CN(C)C(=O)c1ccc(Cn2c(C(=O)O)cc3cc(-c4ccccc4)c(Sc4ccc(Cl)c(Cl)c4)cc32)cc1]

I-2

TABLE 1-continued
Exemplary Compounds
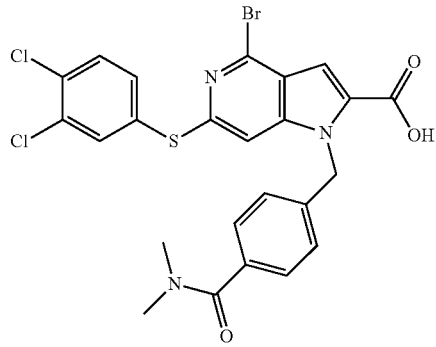 [SMILES: CN(C)C(=O)c1ccc(Cn2c(C(=O)O)cc3c(Br)nc(Sc4ccc(Cl)c(Cl)c4)cc32)cc1]
I-3
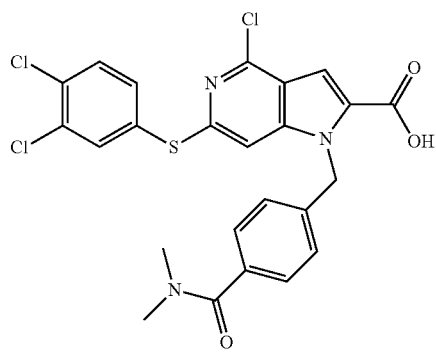 [SMILES: CN(C)C(=O)c1ccc(Cn2c(C(=O)O)cc3c(Cl)nc(Sc4ccc(Cl)c(Cl)c4)cc32)cc1]
I-4
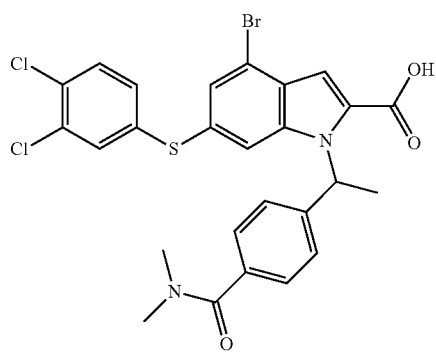 [SMILES: CC(c1ccc(C(=O)N(C)C)cc1)n1c(C(=O)O)cc2c(Br)cc(Sc3ccc(Cl)c(Cl)c3)cc21]
I-5
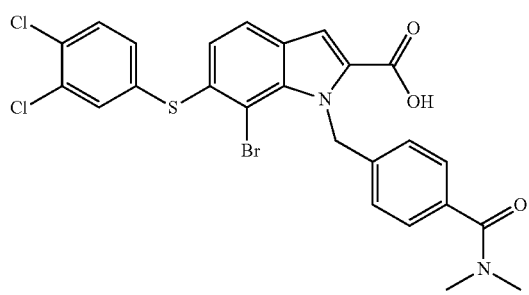 [SMILES: CN(C)C(=O)c1ccc(Cn2c(C(=O)O)cc3ccc(Sc4ccc(Cl)c(Cl)c4)c(Br)c32)cc1]
I-6

TABLE 1-continued

Exemplary Compounds

I-7

I-8

I-9

I-10

TABLE 1-continued
Exemplary Compounds
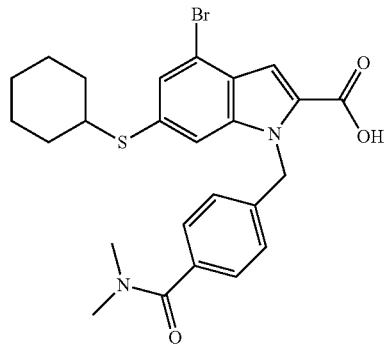 [SMILES: CN(C)C(=O)c1ccc(Cn2c(C(=O)O)cc3c(Br)cc(SC4CCCCC4)cc32)cc1]
I-11
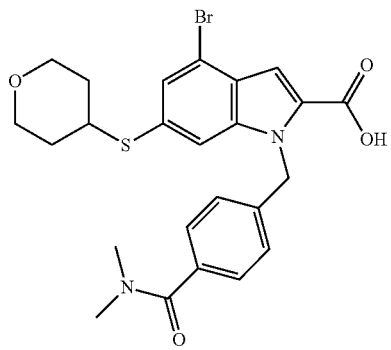 [SMILES: CN(C)C(=O)c1ccc(Cn2c(C(=O)O)cc3c(Br)cc(SC4CCOCC4)cc32)cc1]
I-12
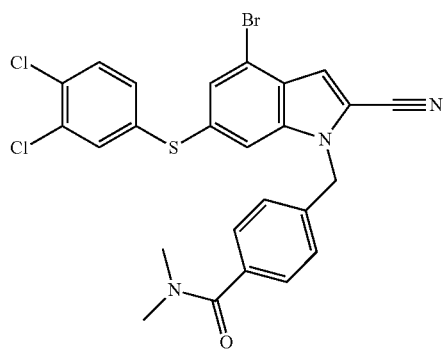 [SMILES: CN(C)C(=O)c1ccc(Cn2c(C#N)cc3c(Br)cc(Sc4ccc(Cl)c(Cl)c4)cc32)cc1]
I-13
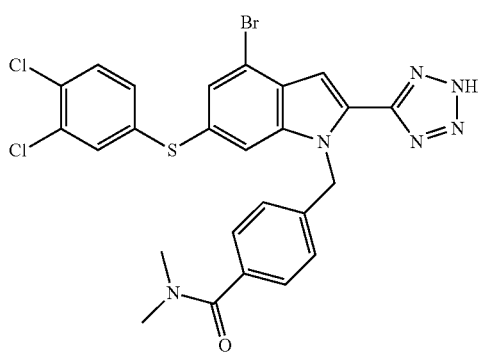 [SMILES: CN(C)C(=O)c1ccc(Cn2c(-c3nn[nH]n3)cc3c(Br)cc(Sc4ccc(Cl)c(Cl)c4)cc32)cc1]
I-14

TABLE 1-continued
Exemplary Compounds
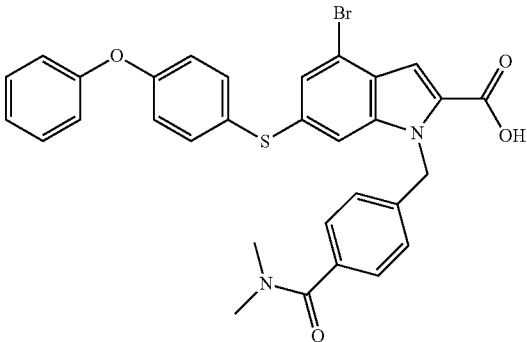 [SMILES: CN(C)C(=O)c1ccc(Cn2c(C(=O)O)cc3c(Br)cc(Sc4ccc(Oc5ccccc5)cc4)cc32)cc1]
I-15
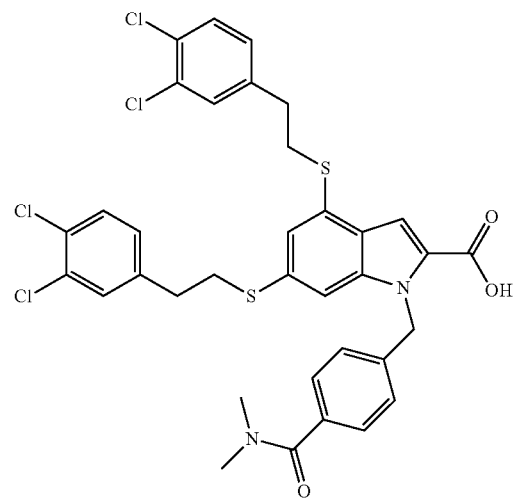 [SMILES: CN(C)C(=O)c1ccc(Cn2c(C(=O)O)cc3c(SCCc4ccc(Cl)c(Cl)c4)cc(SCCc4ccc(Cl)c(Cl)c4)cc32)cc1]
I-16
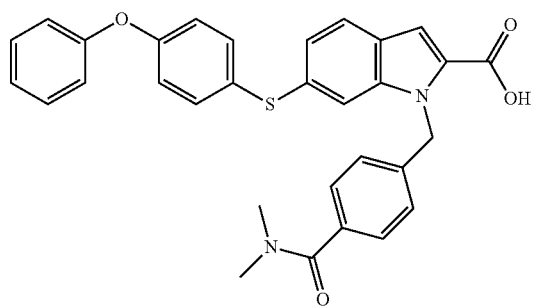 [SMILES: CN(C)C(=O)c1ccc(Cn2c(C(=O)O)cc3ccc(Sc4ccc(Oc5ccccc5)cc4)cc32)cc1]
I-17
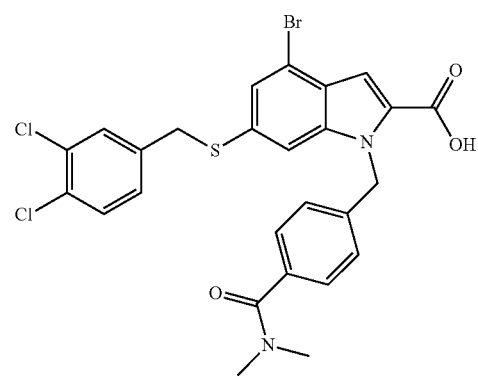 [SMILES: CN(C)C(=O)c1ccc(Cn2c(C(=O)O)cc3c(Br)cc(SCc4ccc(Cl)c(Cl)c4)cc32)cc1]
I-18

TABLE 1-continued
Exemplary Compounds
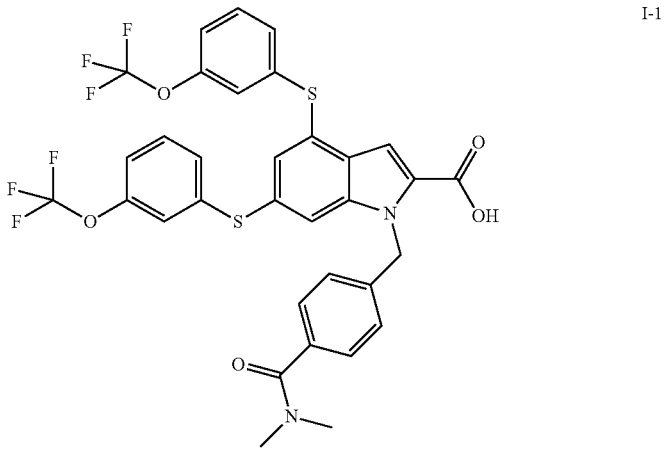
I-19
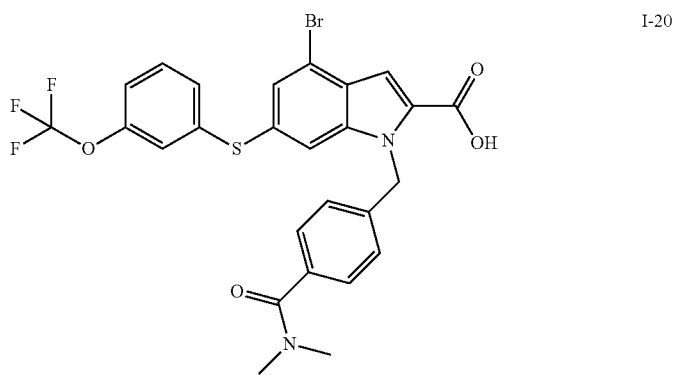
I-20
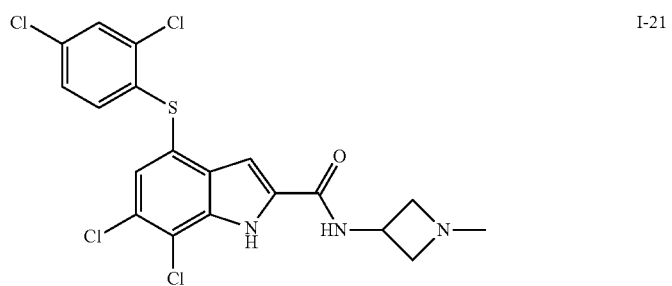
I-21
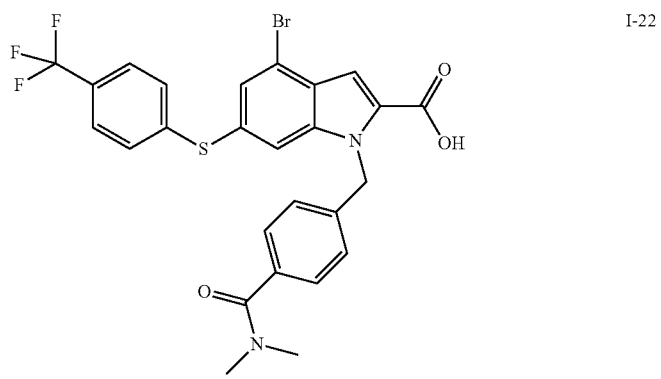
I-22

TABLE 1-continued
Exemplary Compounds
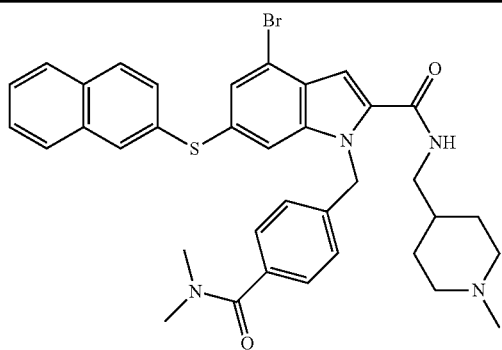
I-23
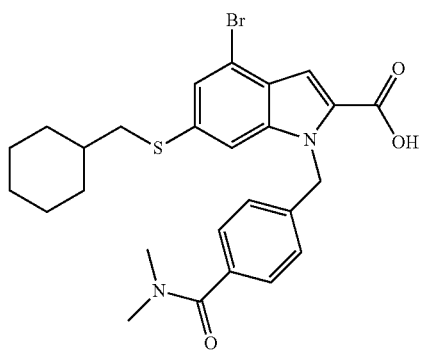 [SMILES: CN(C)C(=O)c1ccc(Cn2c(C(=O)O)cc3c(Br)cc(SCC4CCCCC4)cc32)cc1]
I-24
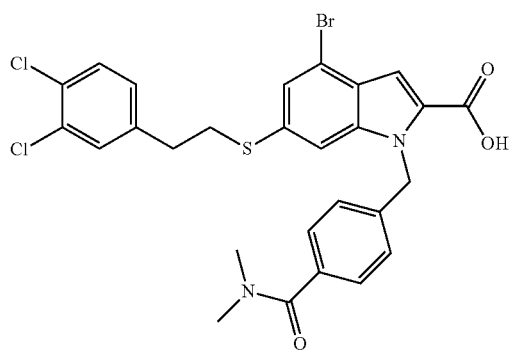 [SMILES: CN(C)C(=O)c1ccc(Cn2c(C(=O)O)cc3c(Br)cc(SCCc4ccc(Cl)c(Cl)c4)cc32)cc1]
I-25
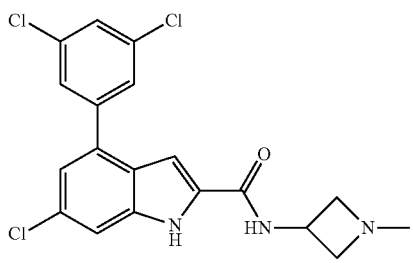 [SMILES: CN1CC(NC(=O)c2cc3c(-c4cc(Cl)cc(Cl)c4)cc(Cl)cc3[nH]2)C1]
I-26
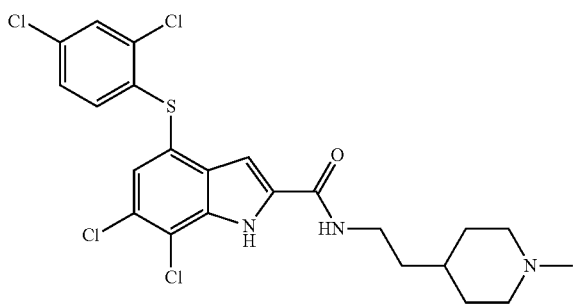 [SMILES: CN1CCC(CCNC(=O)c2cc3c(Sc4ccc(Cl)cc4Cl)cc(Cl)c(Cl)c3[nH]2)CC1]
I-27

TABLE 1-continued

Exemplary Compounds

I-28

I-29

I-30

I-31

I-32

TABLE 1-continued
Exemplary Compounds
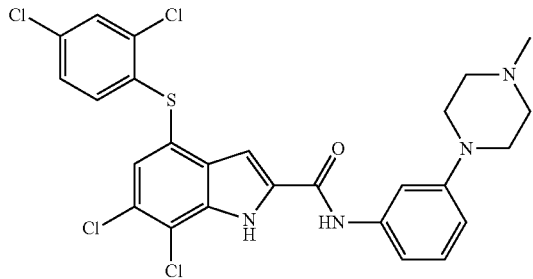 [SMILES: CN1CCN(c2cccc(NC(=O)c3cc4c(Sc5ccc(Cl)cc5Cl)cc(Cl)c(Cl)c4[nH]3)c2)CC1]
I-33
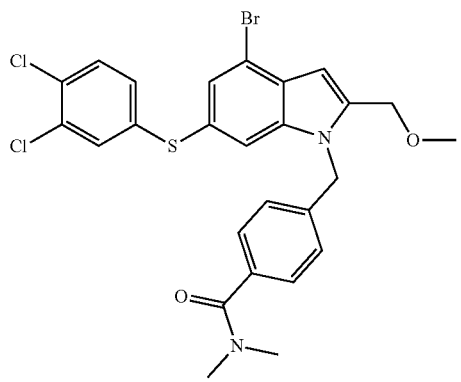 [SMILES: COCc1cc2c(Br)cc(Sc3ccc(Cl)c(Cl)c3)cc2n1Cc1ccc(C(=O)N(C)C)cc1]
I-34
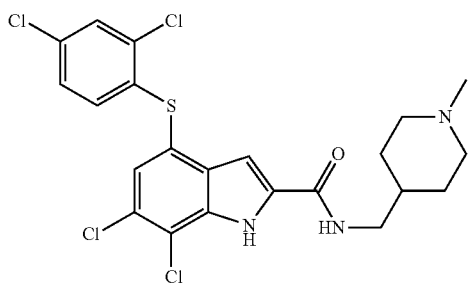 [SMILES: CN1CCC(CNC(=O)c2cc3c(Sc4ccc(Cl)cc4Cl)cc(Cl)c(Cl)c3[nH]2)CC1]
I-35
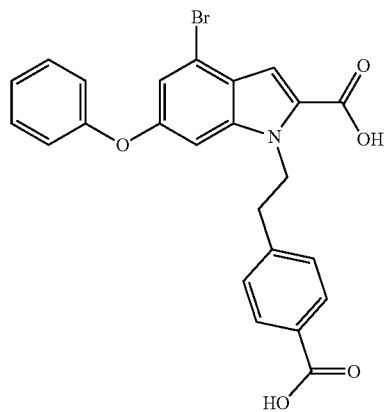 [SMILES: O=C(O)c1ccc(CCn2c(C(=O)O)cc3c(Br)cc(Oc4ccccc4)cc32)cc1]
I-36

TABLE 1-continued
Exemplary Compounds
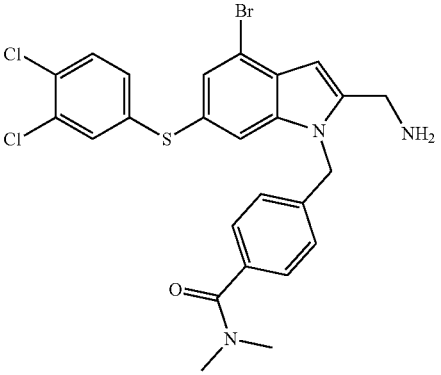 [SMILES: CN(C)C(=O)c1ccc(Cn2c(CN)cc3c(Br)cc(Sc4ccc(Cl)c(Cl)c4)cc32)cc1]
I-37
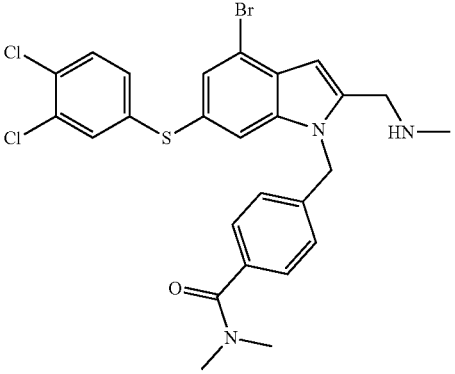 [SMILES: CNCc1cc2c(Br)cc(Sc3ccc(Cl)c(Cl)c3)cc2n1Cc1ccc(C(=O)N(C)C)cc1]
I-38
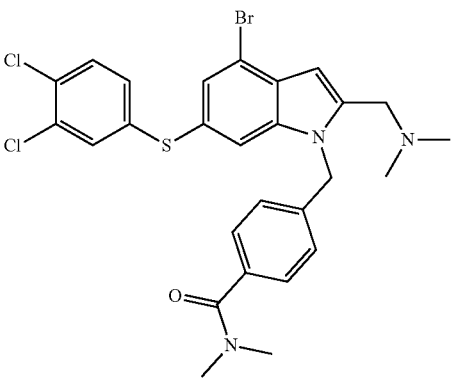 [SMILES: CN(C)Cc1cc2c(Br)cc(Sc3ccc(Cl)c(Cl)c3)cc2n1Cc1ccc(C(=O)N(C)C)cc1]
I-39
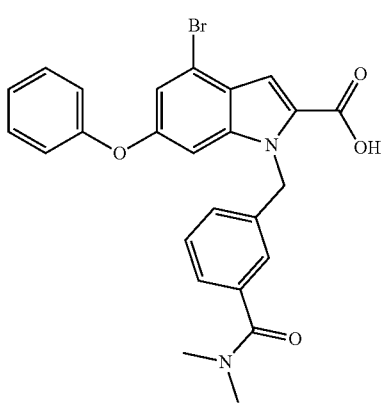 [SMILES: CN(C)C(=O)c1cccc(Cn2c(C(=O)O)cc3c(Br)cc(Oc4ccccc4)cc32)c1]
I-40

TABLE 1-continued
Exemplary Compounds
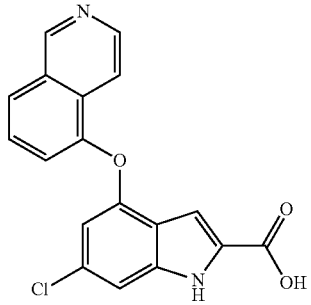 [SMILES: O=C(O)c1cc2c(Oc3cccc4cnccc34)cc(Cl)cc2[nH]1]
I-41
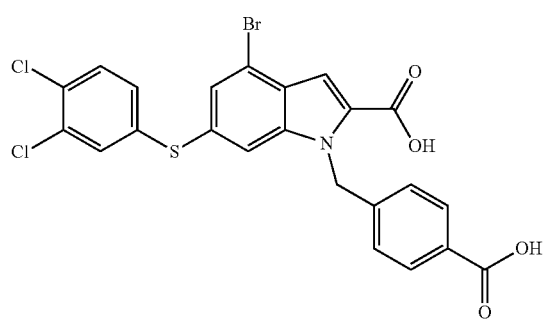 [SMILES: O=C(O)c1ccc(Cn2c(C(=O)O)cc3c(Br)cc(Sc4ccc(Cl)c(Cl)c4)cc32)cc1]
I-42
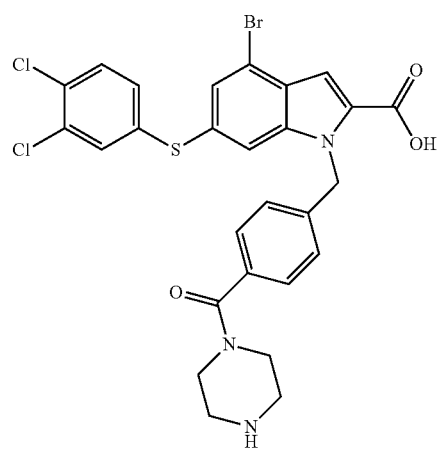 [SMILES: O=C(O)c1cc2c(Br)cc(Sc3ccc(Cl)c(Cl)c3)cc2n1Cc1ccc(C(=O)N2CCNCC2)cc1]
I-43
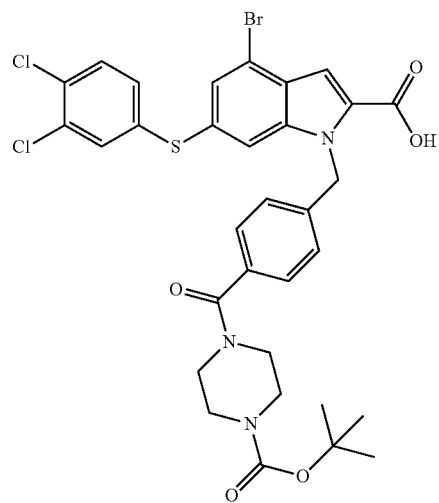 [SMILES: CC(C)(C)OC(=O)N1CCN(C(=O)c2ccc(Cn3c(C(=O)O)cc4c(Br)cc(Sc5ccc(Cl)c(Cl)c5)cc43)cc2)CC1]
I-44

TABLE 1-continued
Exemplary Compounds
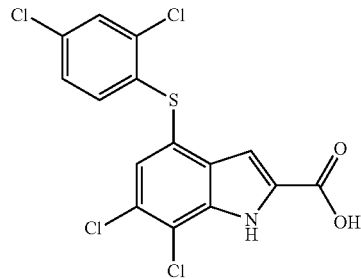 [SMILES: O=C(O)c1cc2c(Sc3ccc(Cl)cc3Cl)cc(Cl)c(Cl)c2[nH]1]
I-45
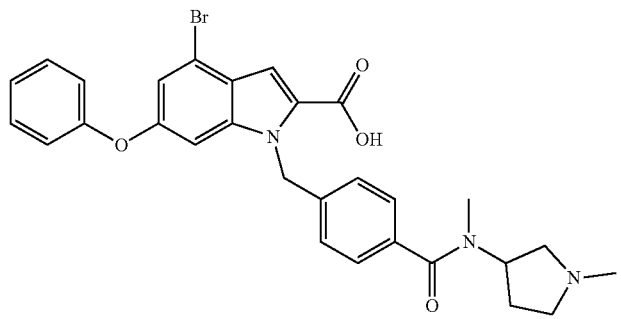 [SMILES: CN1CCC(N(C)C(=O)c2ccc(Cn3c(C(=O)O)cc4c(Br)cc(Oc5ccccc5)cc43)cc2)C1]
I-46
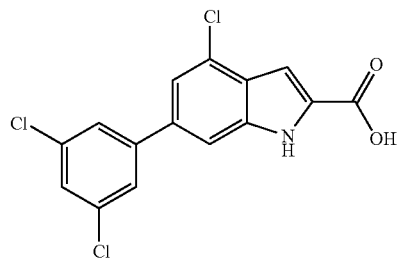 [SMILES: O=C(O)c1cc2c(Cl)cc(-c3cc(Cl)cc(Cl)c3)cc2[nH]1]
I-47
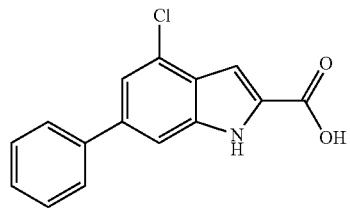 [SMILES: O=C(O)c1cc2c(Cl)cc(-c3ccccc3)cc2[nH]1]
I-48
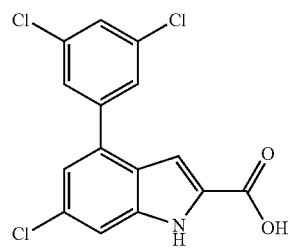 [SMILES: O=C(O)c1cc2c(-c3cc(Cl)cc(Cl)c3)cc(Cl)cc2[nH]1]
I-49

TABLE 1-continued
Exemplary Compounds
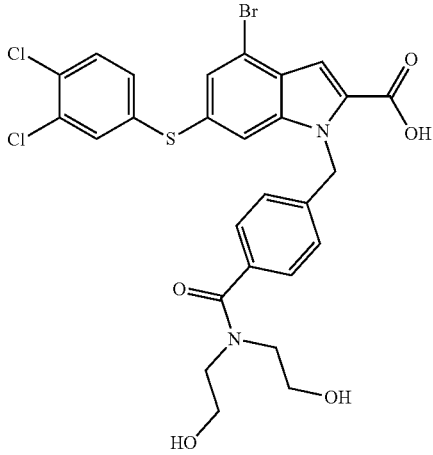 [SMILES: O=C(O)c1cc2c(Br)cc(Sc3ccc(Cl)c(Cl)c3)cc2n1Cc1ccc(C(=O)N(CCO)CCO)cc1]
I-50
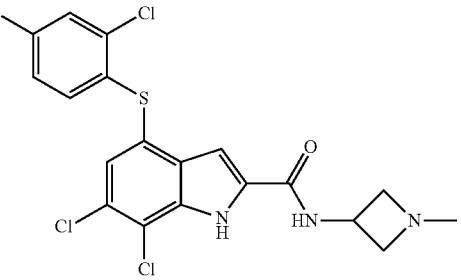
I-51
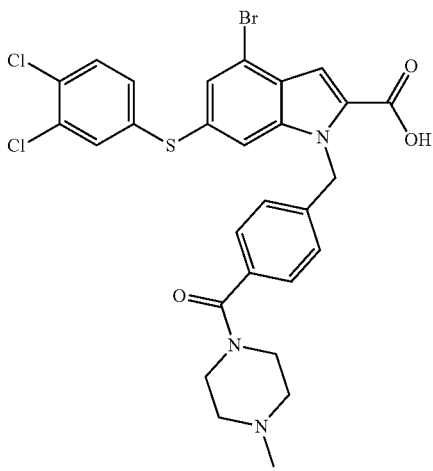 [SMILES: CN1CCN(C(=O)c2ccc(Cn3c(C(=O)O)cc4c(Br)cc(Sc5ccc(Cl)c(Cl)c5)cc43)cc2)CC1]
I-52
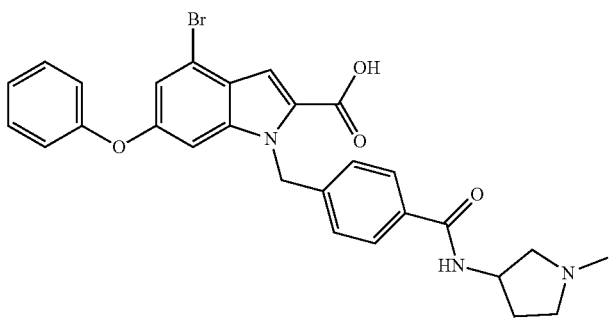 [SMILES: CN1CCC(NC(=O)c2ccc(Cn3c(C(=O)O)cc4c(Br)cc(Oc5ccccc5)cc43)cc2)C1]
I-53

TABLE 1-continued
Exemplary Compounds
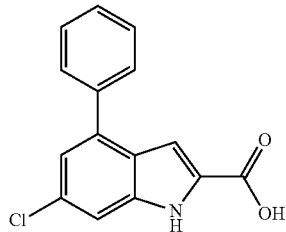 [SMILES: O=C(O)c1cc2c(-c3ccccc3)cc(Cl)cc2[nH]1]
I-54
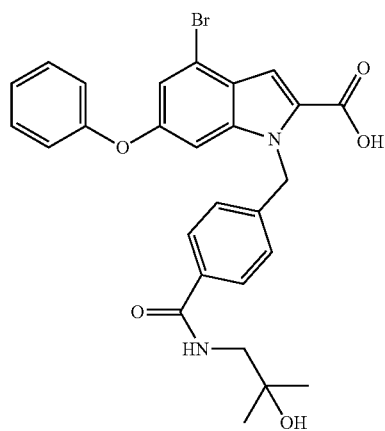 [SMILES: CC(C)(O)CNC(=O)c1ccc(Cn2c(C(=O)O)cc3c(Br)cc(Oc4ccccc4)cc32)cc1]
I-55
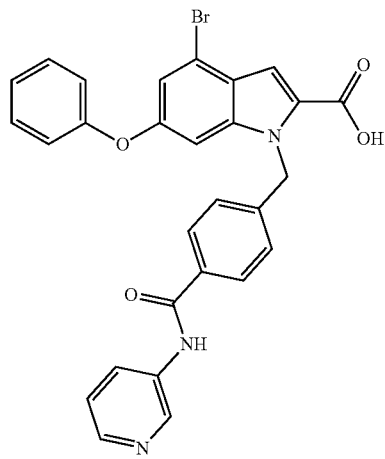 [SMILES: O=C(Nc1cccnc1)c1ccc(Cn2c(C(=O)O)cc3c(Br)cc(Oc4ccccc4)cc32)cc1]
I-56
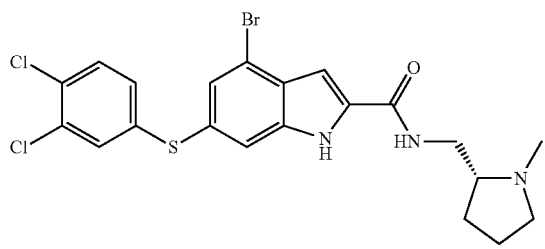 [SMILES: CN1CCC[C@@H]1CNC(=O)c1cc2c(Br)cc(Sc3ccc(Cl)c(Cl)c3)cc2[nH]1]
I-57

TABLE 1-continued
Exemplary Compounds
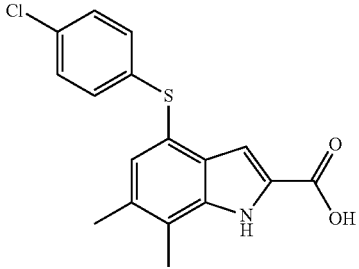 [SMILES: Cc1cc(Sc2ccc(Cl)cc2)c2cc(C(=O)O)[nH]c2c1C]
I-58
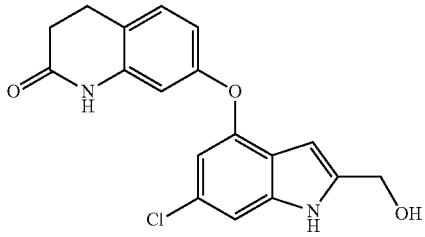 [SMILES: O=C1CCc2ccc(Oc3cc(Cl)cc4[nH]c(CO)cc34)cc2N1]
I-59
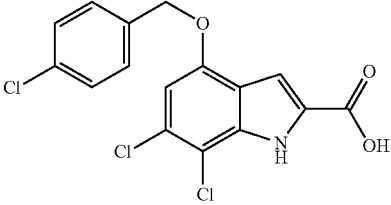 [SMILES: O=C(O)c1cc2c(OCc3ccc(Cl)cc3)cc(Cl)c(Cl)c2[nH]1]
I-60
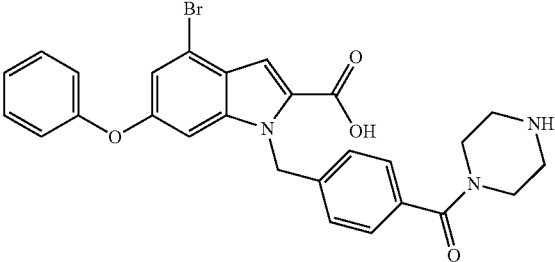 [SMILES: O=C(O)c1cc2c(Br)cc(Oc3ccccc3)cc2n1Cc1ccc(C(=O)N2CCNCC2)cc1]
I-61
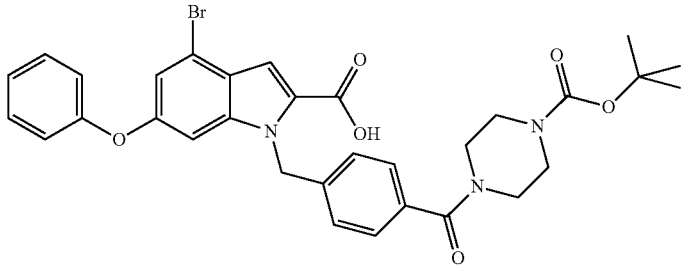 [SMILES: CC(C)(C)OC(=O)N1CCN(C(=O)c2ccc(Cn3c(C(=O)O)cc4c(Br)cc(Oc5ccccc5)cc43)cc2)CC1]
I-62
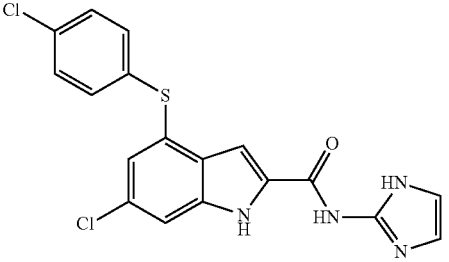 [SMILES: O=C(Nc1ncc[nH]1)c1cc2c(Sc3ccc(Cl)cc3)cc(Cl)cc2[nH]1]
I-63

TABLE 1-continued

Exemplary Compounds

I-64

I-65

I-66

I-67

I-68

TABLE 1-continued
Exemplary Compounds
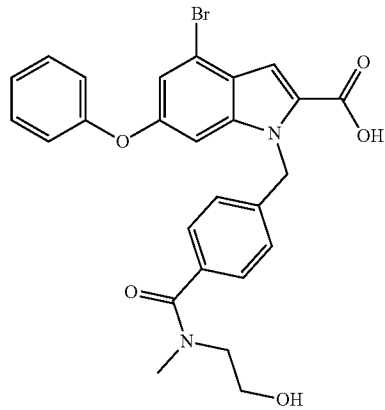 [SMILES: CN(CCO)C(=O)c1ccc(Cn2c(C(=O)O)cc3c(Br)cc(Oc4ccccc4)cc32)cc1]
I-69
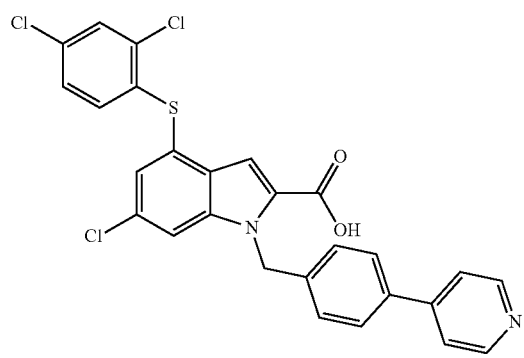 [SMILES: O=C(O)c1cc2c(Sc3ccc(Cl)cc3Cl)cc(Cl)cc2n1Cc1ccc(-c2ccncc2)cc1]
I-70
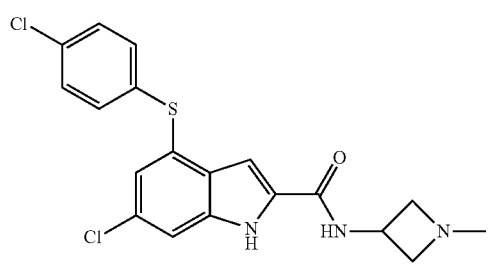 [SMILES: CN1CC(NC(=O)c2cc3c(Sc4ccc(Cl)cc4)cc(Cl)cc3[nH]2)C1]
I-71
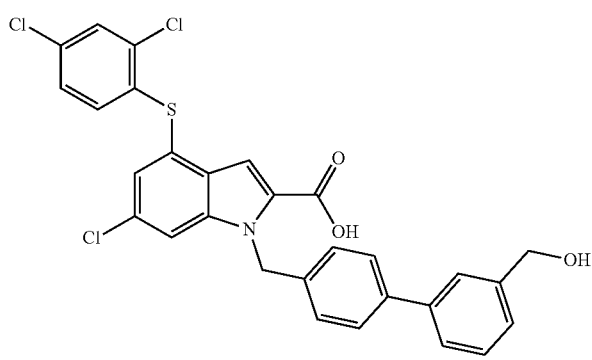 [SMILES: O=C(O)c1cc2c(Sc3ccc(Cl)cc3Cl)cc(Cl)cc2n1Cc1ccc(-c2cccc(CO)c2)cc1]
I-72

TABLE 1-continued

Exemplary Compounds

I-73, I-74, I-75, I-76, I-77

TABLE 1-continued
Exemplary Compounds
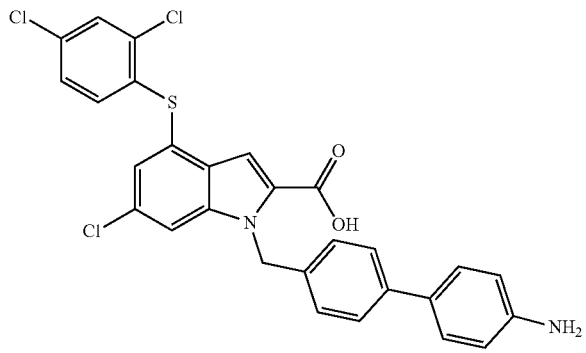 [SMILES: Nc1ccc(-c2ccc(Cn3c(C(=O)O)cc4c(Sc5ccc(Cl)cc5Cl)cc(Cl)cc43)cc2)cc1]
I-78
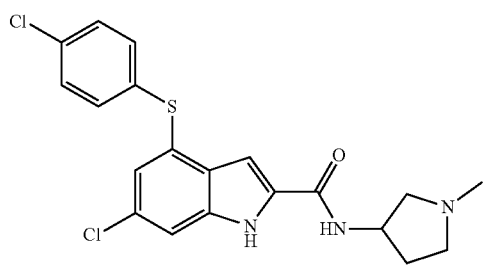 [SMILES: CN1CCC(NC(=O)c2cc3c(Sc4ccc(Cl)cc4)cc(Cl)cc3[nH]2)C1]
I-79
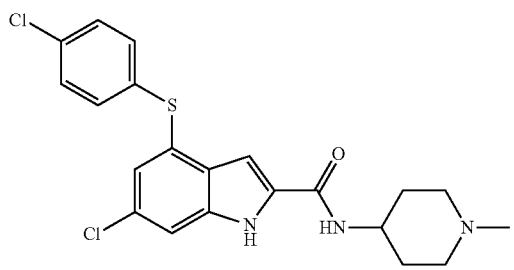 [SMILES: CN1CCC(NC(=O)c2cc3c(Sc4ccc(Cl)cc4)cc(Cl)cc3[nH]2)CC1]
I-80
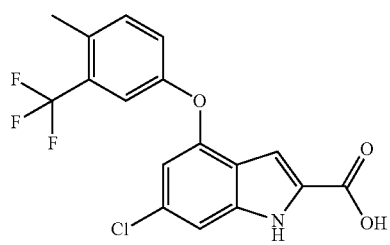 [SMILES: Cc1ccc(Oc2cc(Cl)cc3[nH]c(C(=O)O)cc23)cc1C(F)(F)F]
I-81
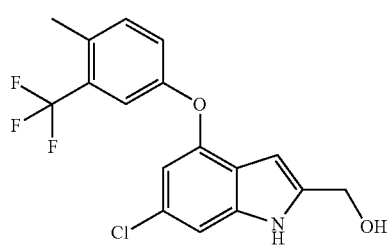 [SMILES: Cc1ccc(Oc2cc(Cl)cc3[nH]c(CO)cc23)cc1C(F)(F)F]
I-82

TABLE 1-continued

Exemplary Compounds

I-83

I-84

I-85

I-86

I-87

I-88

TABLE 1-continued
Exemplary Compounds
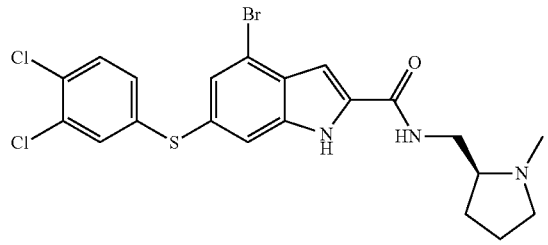 [SMILES: CN1CCC[C@H]1CNC(=O)c1cc2c(Br)cc(Sc3ccc(Cl)c(Cl)c3)cc2[nH]1]
I-89
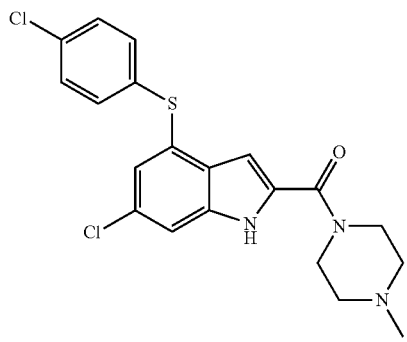 [SMILES: CN1CCN(C(=O)c2cc3c(Sc4ccc(Cl)cc4)cc(Cl)cc3[nH]2)CC1]
I-90
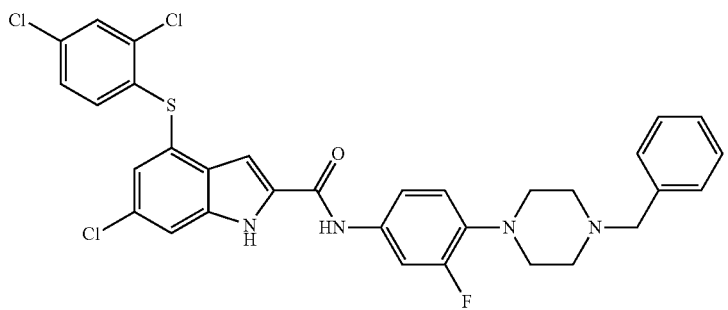 [SMILES: O=C(Nc1ccc(N2CCN(Cc3ccccc3)CC2)c(F)c1)c1cc2c(Sc3ccc(Cl)cc3Cl)cc(Cl)cc2[nH]1]
I-91
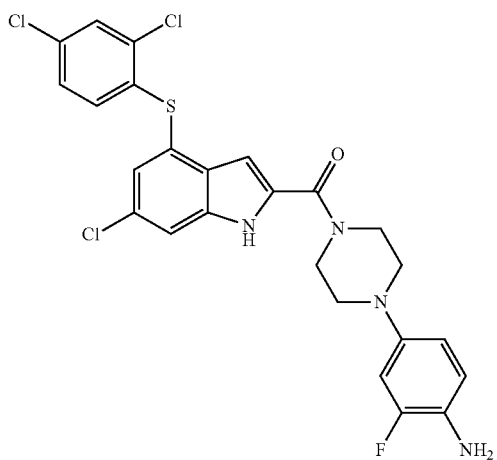 [SMILES: Nc1ccc(N2CCN(C(=O)c3cc4c(Sc5ccc(Cl)cc5Cl)cc(Cl)cc4[nH]3)CC2)cc1F]
I-92

TABLE 1-continued
Exemplary Compounds
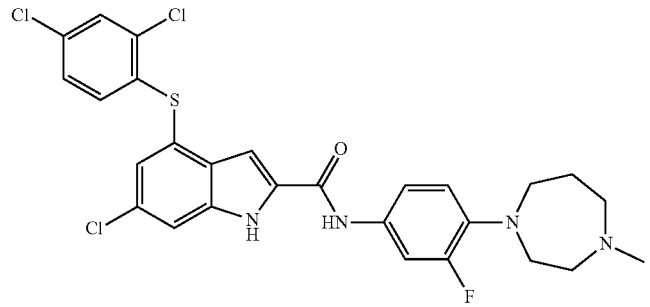 [SMILES: CN1CCCN(c2ccc(NC(=O)c3cc4c(Sc5ccc(Cl)cc5Cl)cc(Cl)cc4[nH]3)cc2F)CC1]
I-93
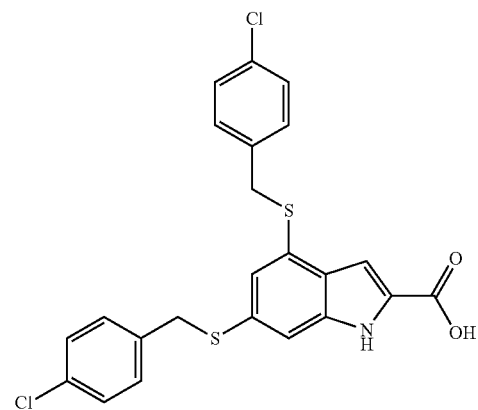 [SMILES: O=C(O)c1cc2c(SCc3ccc(Cl)cc3)cc(SCc3ccc(Cl)cc3)cc2[nH]1]
I-94
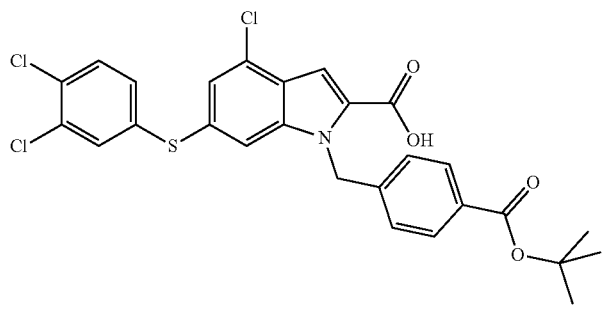 [SMILES: CC(C)(C)OC(=O)c1ccc(Cn2c(C(=O)O)cc3c(Cl)cc(Sc4ccc(Cl)c(Cl)c4)cc32)cc1]
I-95
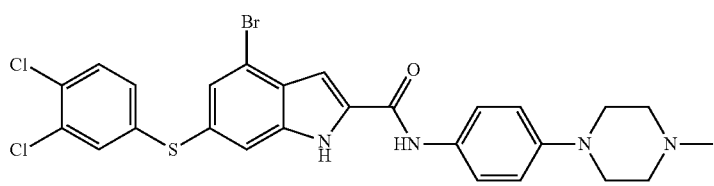 [SMILES: CN1CCN(c2ccc(NC(=O)c3cc4c(Br)cc(Sc5ccc(Cl)c(Cl)c5)cc4[nH]3)cc2)CC1]
I-96
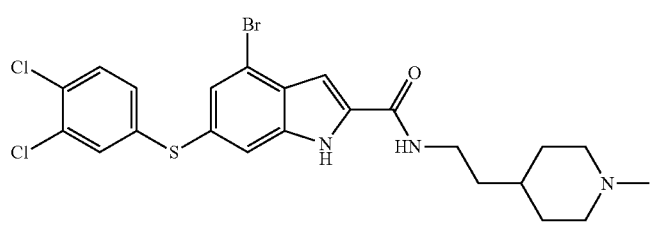 [SMILES: CN1CCC(CCNC(=O)c2cc3c(Br)cc(Sc4ccc(Cl)c(Cl)c4)cc3[nH]2)CC1]
I-97

TABLE 1-continued
Exemplary Compounds
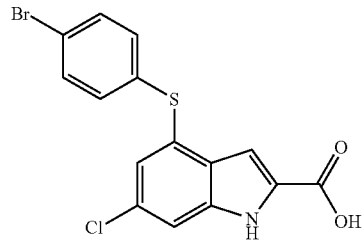
I-98
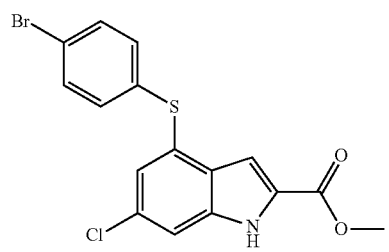 [SMILES: COC(=O)c1cc2c(Sc3ccc(Br)cc3)cc(Cl)cc2[nH]1]
I-99
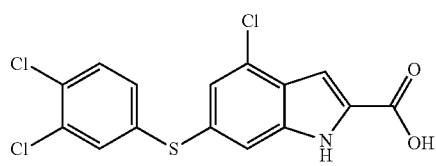 [SMILES: O=C(O)c1cc2c(Cl)cc(Sc3ccc(Cl)c(Cl)c3)cc2[nH]1]
I-100
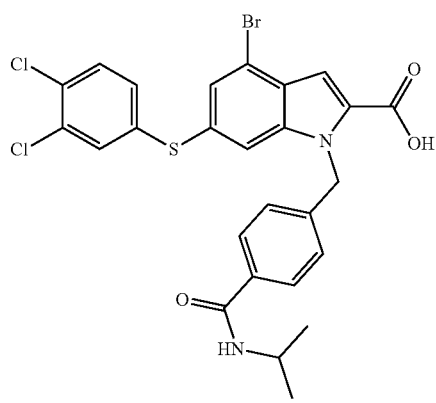 [SMILES: CC(C)NC(=O)c1ccc(Cn2c(C(=O)O)cc3c(Br)cc(Sc4ccc(Cl)c(Cl)c4)cc32)cc1]
I-101
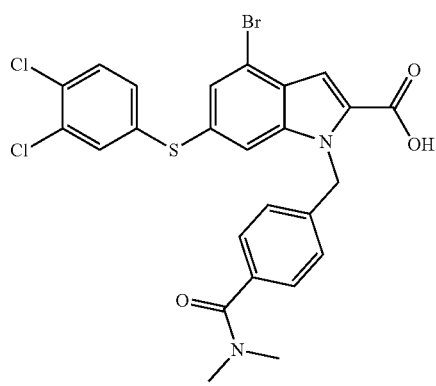 [SMILES: CN(C)C(=O)c1ccc(Cn2c(C(=O)O)cc3c(Br)cc(Sc4ccc(Cl)c(Cl)c4)cc32)cc1]
I-102

TABLE 1-continued
Exemplary Compounds
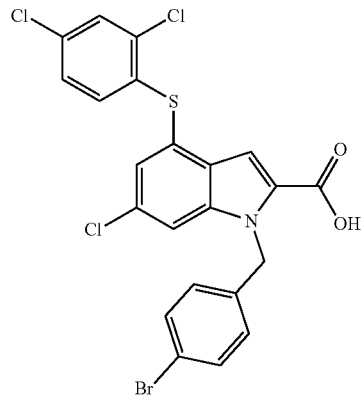 [SMILES: O=C(O)c1cc2c(Sc3ccc(Cl)cc3Cl)cc(Cl)cc2n1Cc1ccc(Br)cc1]
I-103
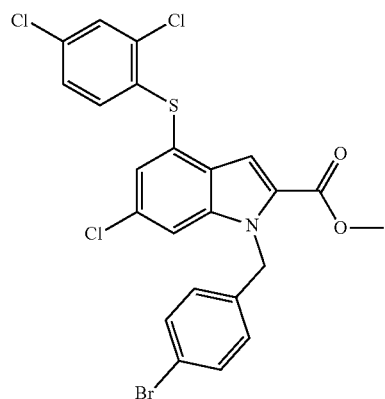 [SMILES: COC(=O)c1cc2c(Sc3ccc(Cl)cc3Cl)cc(Cl)cc2n1Cc1ccc(Br)cc1]
I-104
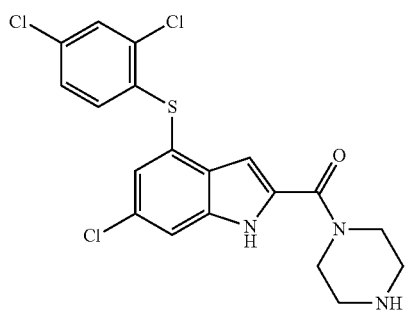 [SMILES: O=C(c1cc2c(Sc3ccc(Cl)cc3Cl)cc(Cl)cc2[nH]1)N1CCNCC1]
I-105
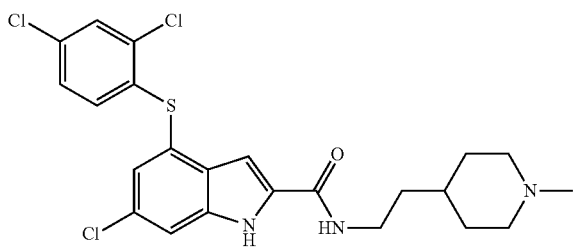 [SMILES: CN1CCC(CCNC(=O)c2cc3c(Sc4ccc(Cl)cc4Cl)cc(Cl)cc3[nH]2)CC1]
I-106

TABLE 1-continued
Exemplary Compounds
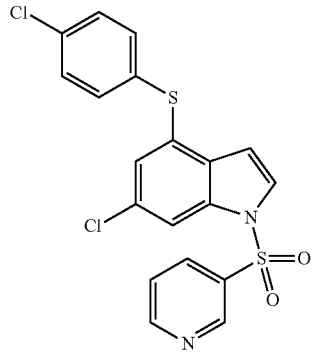 [SMILES: O=S(=O)(c1cccnc1)n1ccc2c(Sc3ccc(Cl)cc3)cc(Cl)cc21]
I-107
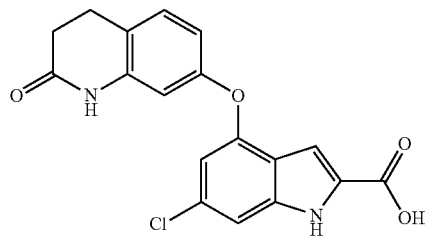 [SMILES: O=C1CCc2ccc(Oc3cc(Cl)cc4[nH]c(C(=O)O)cc34)cc2N1]
I-108
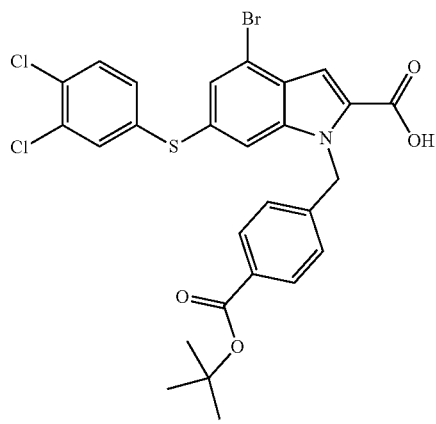 [SMILES: CC(C)(C)OC(=O)c1ccc(Cn2c(C(=O)O)cc3c(Br)cc(Sc4ccc(Cl)c(Cl)c4)cc32)cc1]
I-109
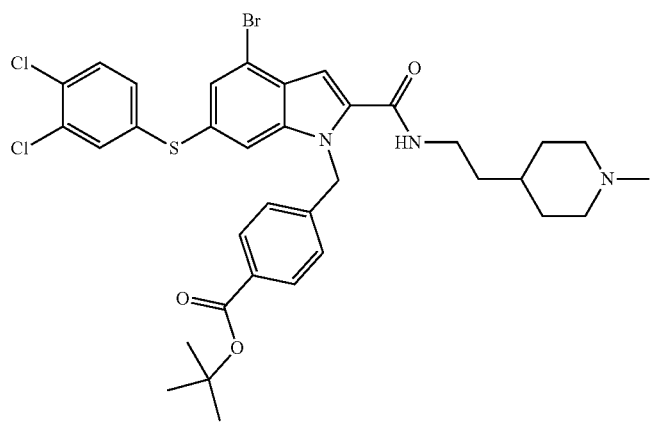 [SMILES: CN1CCC(CCNC(=O)c2cc3c(Br)cc(Sc4ccc(Cl)c(Cl)c4)cc3n2Cc2ccc(C(=O)OC(C)(C)C)cc2)CC1]
I-110

TABLE 1-continued

Exemplary Compounds

I-111: 4-(2,4-dichlorophenylthio)-6-chloro-N-(3-chloro-4-(4-methylpiperazin-1-yl)phenyl)-1H-indole-2-carboxamide I-112: 4-(2,4-dichlorophenylthio)-6-chloro-N-(3-cyano-4-(4-methylpiperazin-1-yl)phenyl)-1H-indole-2-carboxamide I-113: 4-(2,4-dichlorophenylthio)-6-chloro-N-(3-fluoro-4-(4-methylpiperazin-1-yl)phenyl)-1H-indole-2-carboxamide I-114: 4-(2,4-dichlorophenylthio)-6-chloro-N-(1-methylpiperidin-4-yl)-1H-indole-2-carboxamide I-115: 4-(2,4-dichlorophenylthio)-6-chloro-N-(2-(dimethylamino)ethyl)-1H-indole-2-carboxamide TABLE 1-continued Exemplary Compounds

I-116

I-117

I-118

I-119

I-120

I-121

TABLE 1-continued
Exemplary Compounds
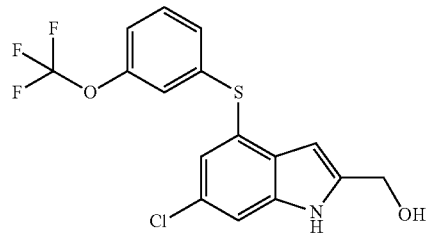 [SMILES: OCc1cc2c(Sc3cccc(OC(F)(F)F)c3)cc(Cl)cc2[nH]1]
I-122
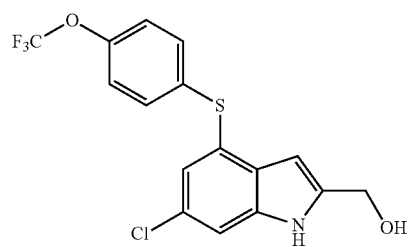 [SMILES: OCc1cc2c(Sc3ccc(OC(F)(F)F)cc3)cc(Cl)cc2[nH]1]
I-123
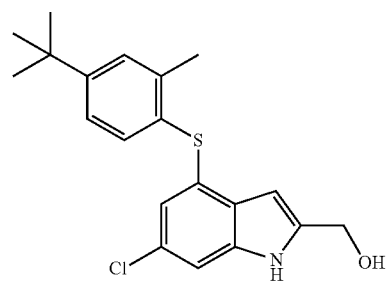 [SMILES: Cc1cc(C(C)(C)C)ccc1Sc1cc(Cl)cc2[nH]c(CO)cc12]
I-124
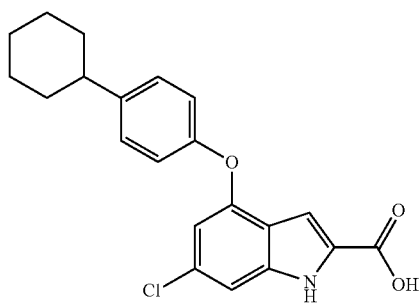 [SMILES: O=C(O)c1cc2c(Oc3ccc(C4CCCCC4)cc3)cc(Cl)cc2[nH]1]
I-125
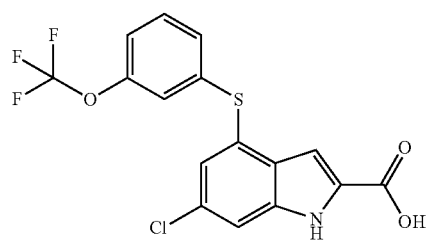 [SMILES: O=C(O)c1cc2c(Sc3cccc(OC(F)(F)F)c3)cc(Cl)cc2[nH]1]
I-126

TABLE 1-continued
Exemplary Compounds
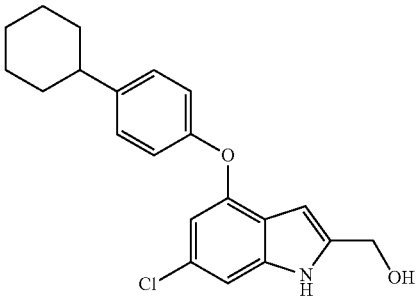 [SMILES: OCc1cc2c(Oc3ccc(C4CCCCC4)cc3)cc(Cl)cc2[nH]1]
I-127
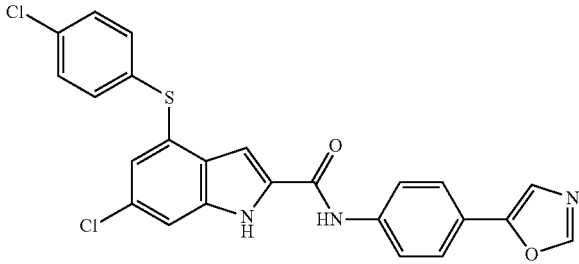 [SMILES: O=C(Nc1ccc(-c2cnco2)cc1)c1cc2c(Sc3ccc(Cl)cc3)cc(Cl)cc2[nH]1]
I-128
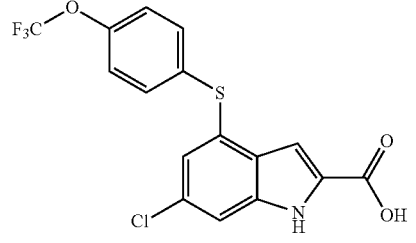 [SMILES: O=C(O)c1cc2c(Sc3ccc(OC(F)(F)F)cc3)cc(Cl)cc2[nH]1]
I-129
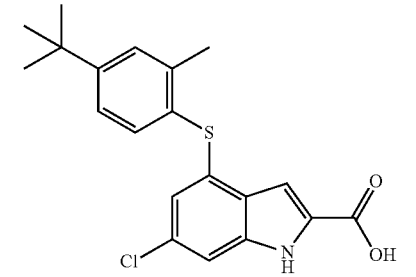 [SMILES: Cc1cc(C(C)(C)C)ccc1Sc1cc(Cl)cc2[nH]c(C(=O)O)cc12]
I-130
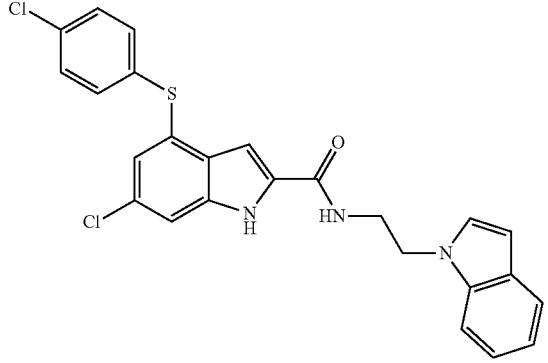 [SMILES: O=C(NCCn1ccc2ccccc21)c1cc2c(Sc3ccc(Cl)cc3)cc(Cl)cc2[nH]1]
I-131

TABLE 1-continued
Exemplary Compounds
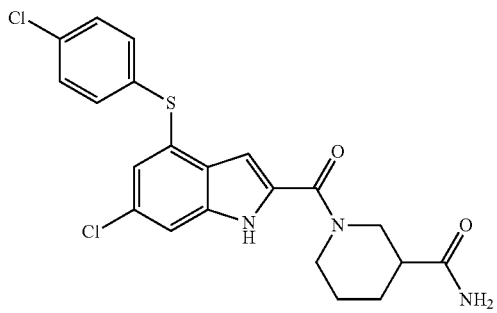 [SMILES: NC(=O)C1CCCN(C(=O)c2cc3c(Sc4ccc(Cl)cc4)cc(Cl)cc3[nH]2)C1]
I-132
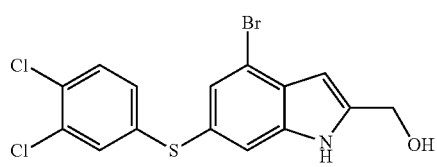 [SMILES: OCc1cc2c(Br)cc(Sc3ccc(Cl)c(Cl)c3)cc2[nH]1]
I-133
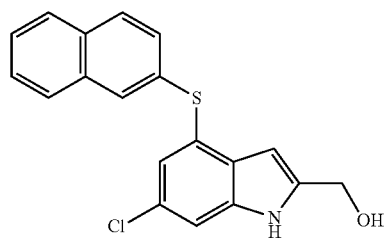 [SMILES: OCc1cc2c(Sc3ccc4ccccc4c3)cc(Cl)cc2[nH]1]
I-134
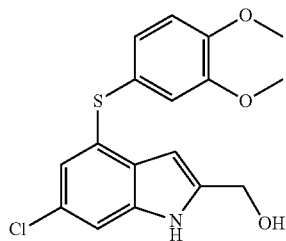 [SMILES: COc1ccc(Sc2cc(Cl)cc3[nH]c(CO)cc23)cc1OC]
I-135
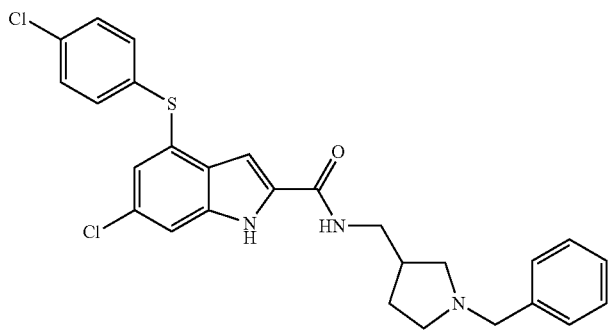 [SMILES: O=C(NCC1CCN(Cc2ccccc2)C1)c1cc2c(Sc3ccc(Cl)cc3)cc(Cl)cc2[nH]1]
I-136
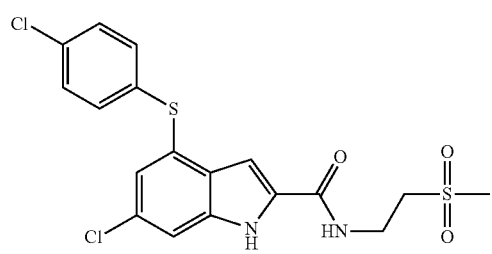 [SMILES: CS(=O)(=O)CCNC(=O)c1cc2c(Sc3ccc(Cl)cc3)cc(Cl)cc2[nH]1]
I-137

TABLE 1-continued
Exemplary Compounds
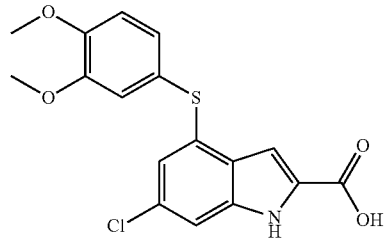 [SMILES: COc1ccc(Sc2cc(Cl)cc3[nH]c(C(=O)O)cc23)cc1OC]
I-138
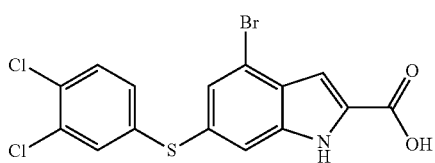
I-139
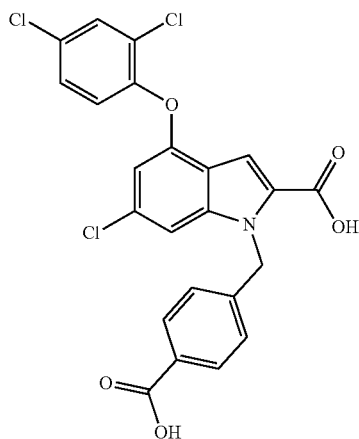 [SMILES: O=C(O)c1ccc(Cn2c(C(=O)O)cc3c(Oc4ccc(Cl)cc4Cl)cc(Cl)cc32)cc1]
I-140
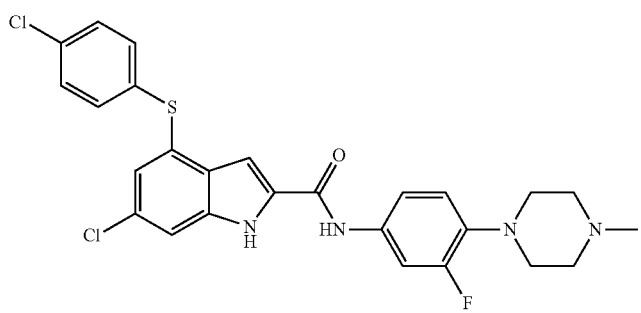 [SMILES: CN1CCN(c2ccc(NC(=O)c3cc4c(Sc5ccc(Cl)cc5)cc(Cl)cc4[nH]3)cc2F)CC1]
I-141
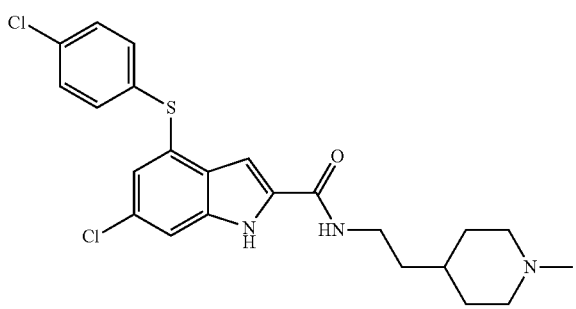 [SMILES: CN1CCC(CCNC(=O)c2cc3c(Sc4ccc(Cl)cc4)cc(Cl)cc3[nH]2)CC1]
I-142

TABLE 1-continued
Exemplary Compounds
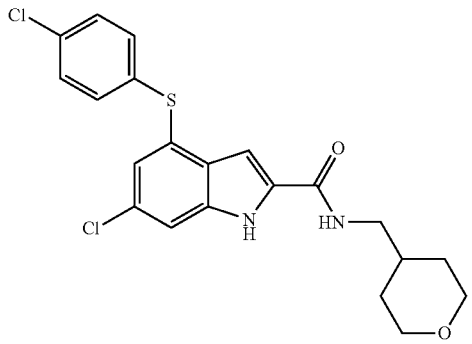 [SMILES: O=C(NCC1CCOCC1)c1cc2c(Sc3ccc(Cl)cc3)cc(Cl)cc2[nH]1]
I-143
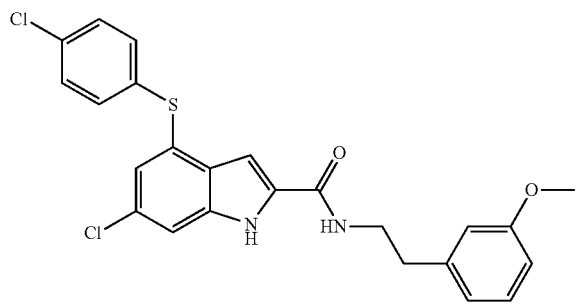 [SMILES: COc1cccc(CCNC(=O)c2cc3c(Sc4ccc(Cl)cc4)cc(Cl)cc3[nH]2)c1]
I-144
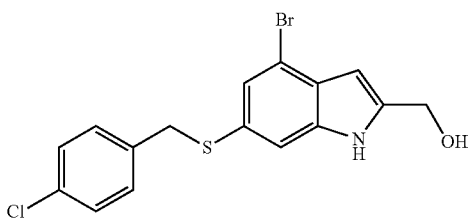 [SMILES: OCc1cc2c(Br)cc(SCc3ccc(Cl)cc3)cc2[nH]1]
I-145
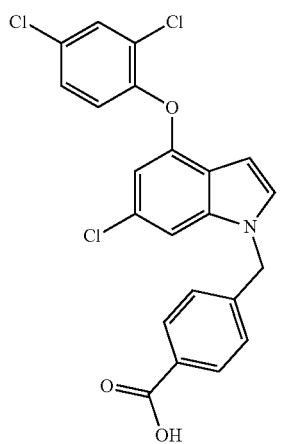 [SMILES: O=C(O)c1ccc(Cn2ccc3c(Oc4ccc(Cl)cc4Cl)cc(Cl)cc32)cc1]
I-146

TABLE 1-continued
Exemplary Compounds
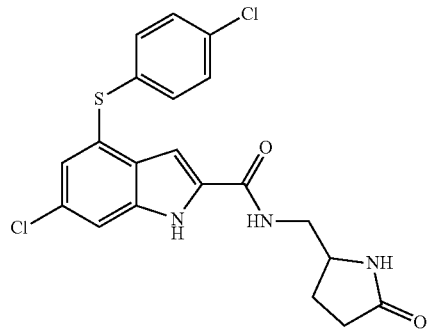 [SMILES: O=C1CCC(CNC(=O)c2cc3c(Sc4ccc(Cl)cc4)cc(Cl)cc3[nH]2)N1] I-147
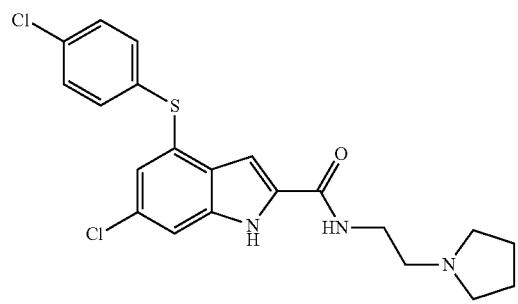 [SMILES: O=C(NCCN1CCCC1)c1cc2c(Sc3ccc(Cl)cc3)cc(Cl)cc2[nH]1] I-148
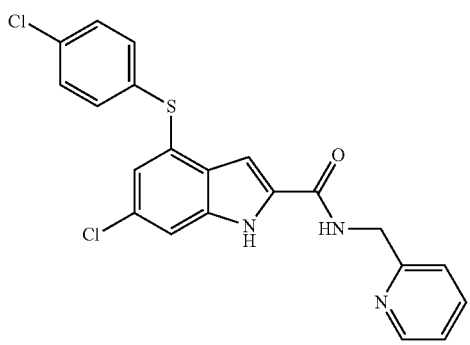 [SMILES: O=C(NCc1ccccn1)c1cc2c(Sc3ccc(Cl)cc3)cc(Cl)cc2[nH]1] I-149
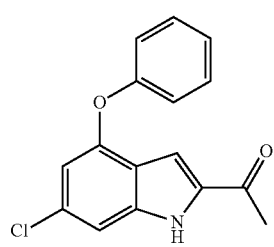 [SMILES: CC(=O)c1cc2c(Oc3ccccc3)cc(Cl)cc2[nH]1] I-150

TABLE 1-continued
Exemplary Compounds
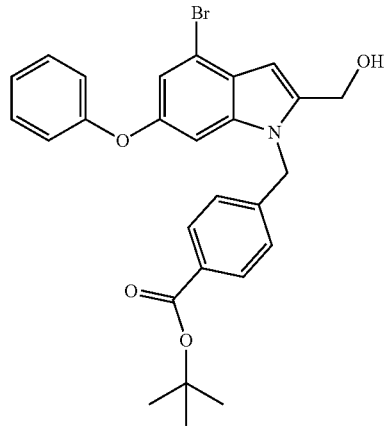 [SMILES: CC(C)(C)OC(=O)c1ccc(Cn2c(CO)cc3c(Br)cc(Oc4ccccc4)cc32)cc1]
I-151
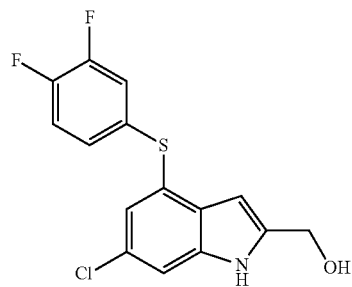 [SMILES: OCc1cc2c(Sc3ccc(F)c(F)c3)cc(Cl)cc2[nH]1]
I-152
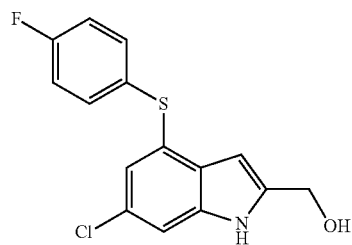 [SMILES: OCc1cc2c(Sc3ccc(F)cc3)cc(Cl)cc2[nH]1]
I-153
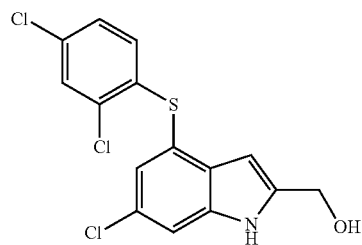 [SMILES: OCc1cc2c(Sc3ccc(Cl)cc3Cl)cc(Cl)cc2[nH]1]
I-154
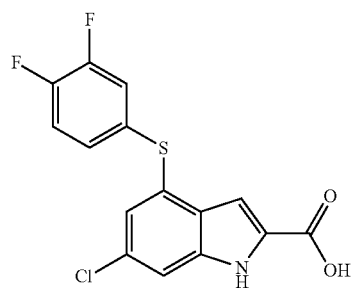 [SMILES: O=C(O)c1cc2c(Sc3ccc(F)c(F)c3)cc(Cl)cc2[nH]1]
I-155

TABLE 1-continued
Exemplary Compounds
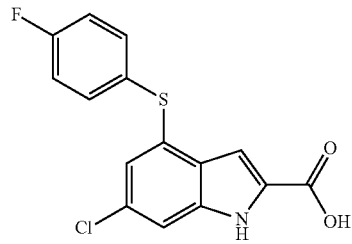 [SMILES: O=C(O)c1cc2c(Sc3ccc(F)cc3)cc(Cl)cc2[nH]1]
I-156
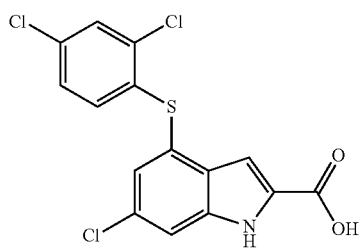 [SMILES: O=C(O)c1cc2c(Sc3ccc(Cl)cc3Cl)cc(Cl)cc2[nH]1]
I-157
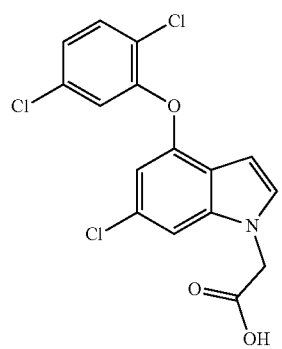 [SMILES: O=C(O)Cn1ccc2c(Oc3cc(Cl)ccc3Cl)cc(Cl)cc21]
I-158
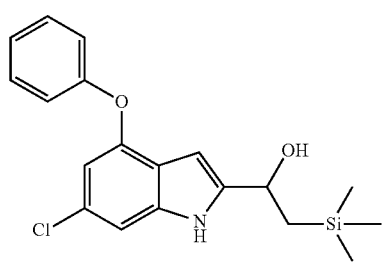 [SMILES: C[Si](C)(C)CC(O)c1cc2c(Oc3ccccc3)cc(Cl)cc2[nH]1]
I-159
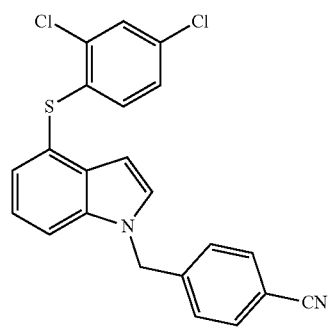 [SMILES: N#Cc1ccc(Cn2ccc3c(Sc4ccc(Cl)cc4Cl)cccc32)cc1]
I-160

TABLE 1-continued
Exemplary Compounds
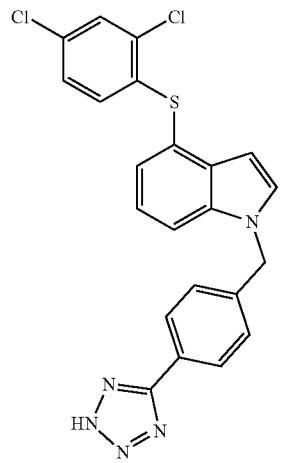 [SMILES: Clc1ccc(Sc2cccc3c2ccn3Cc2ccc(-c3nn[nH]n3)cc2)c(Cl)c1]
I-161
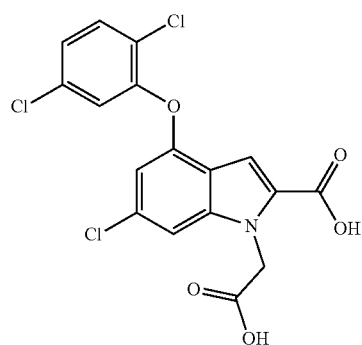 [SMILES: O=C(O)Cn1c(C(=O)O)cc2c(Oc3cc(Cl)ccc3Cl)cc(Cl)cc21]
I-162
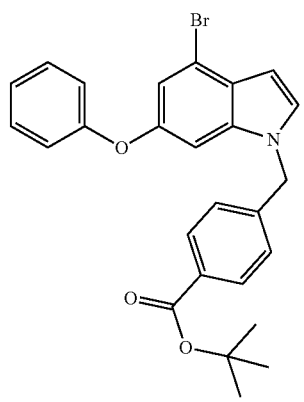 [SMILES: CC(C)(C)OC(=O)c1ccc(Cn2ccc3c(Br)cc(Oc4ccccc4)cc32)cc1]
I-163
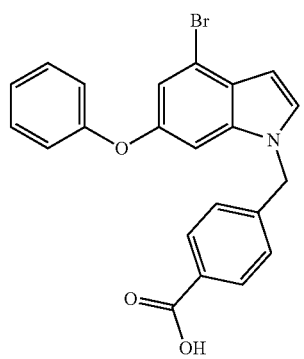 [SMILES: O=C(O)c1ccc(Cn2ccc3c(Br)cc(Oc4ccccc4)cc32)cc1]
I-164

TABLE 1-continued
Exemplary Compounds
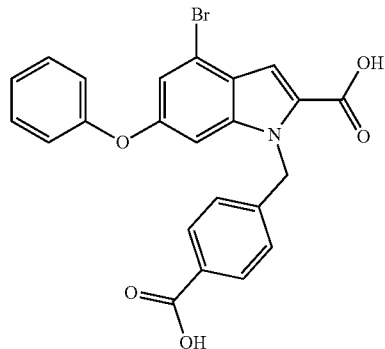 [SMILES: O=C(O)c1ccc(Cn2c(C(=O)O)cc3c(Br)cc(Oc4ccccc4)cc32)cc1]
I-165
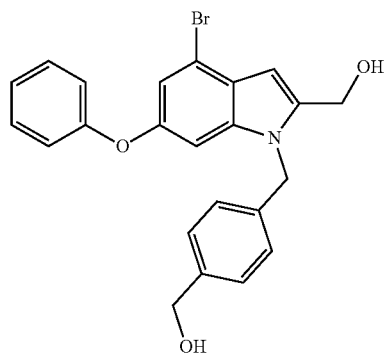 [SMILES: OCc1ccc(Cn2c(CO)cc3c(Br)cc(Oc4ccccc4)cc32)cc1]
I-166
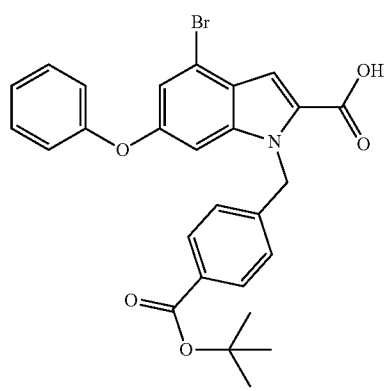 [SMILES: CC(C)(C)OC(=O)c1ccc(Cn2c(C(=O)O)cc3c(Br)cc(Oc4ccccc4)cc32)cc1]
I-167
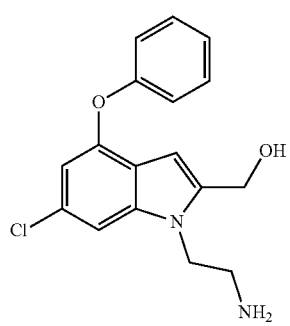 [SMILES: NCCn1c(CO)cc2c(Oc3ccccc3)cc(Cl)cc21]
I-168

TABLE 1-continued
Exemplary Compounds
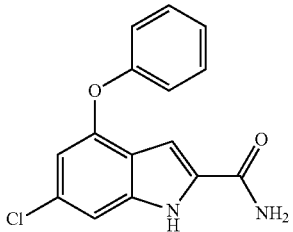 [SMILES: NC(=O)c1cc2c(Oc3ccccc3)cc(Cl)cc2[nH]1]
I-169
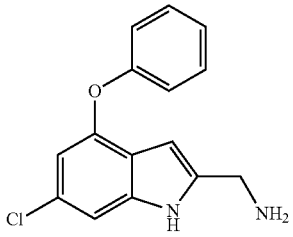 [SMILES: NCc1cc2c(Oc3ccccc3)cc(Cl)cc2[nH]1]
I-170
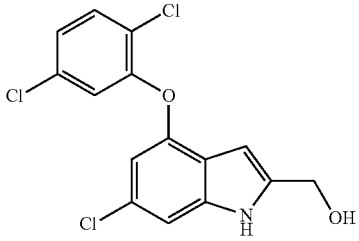 [SMILES: OCc1cc2c(Oc3cc(Cl)ccc3Cl)cc(Cl)cc2[nH]1]
I-171
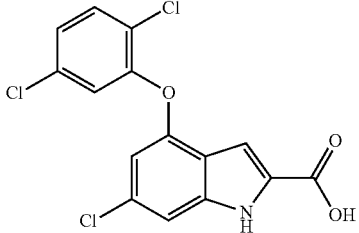 [SMILES: O=C(O)c1cc2c(Oc3cc(Cl)ccc3Cl)cc(Cl)cc2[nH]1]
I-172
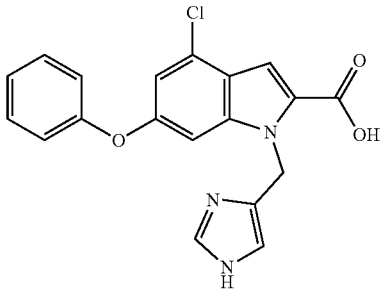 [SMILES: O=C(O)c1cc2c(Cl)cc(Oc3ccccc3)cc2n1Cc1c[nH]cn1]
I-173
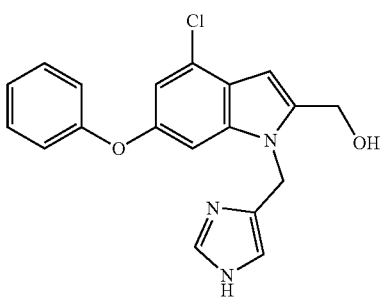
I-174

TABLE 1-continued
Exemplary Compounds
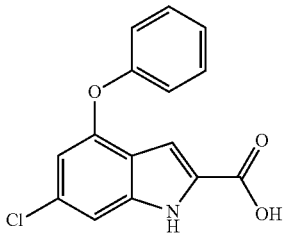 [SMILES: O=C(O)c1cc2c(Oc3ccccc3)cc(Cl)cc2[nH]1] I-175
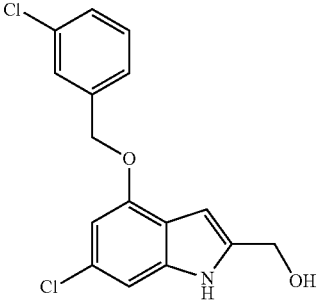 [SMILES: OCc1cc2c(OCc3cccc(Cl)c3)cc(Cl)cc2[nH]1] I-176
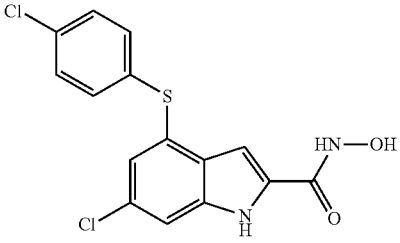 [SMILES: O=C(NO)c1cc2c(Sc3ccc(Cl)cc3)cc(Cl)cc2[nH]1] I-177
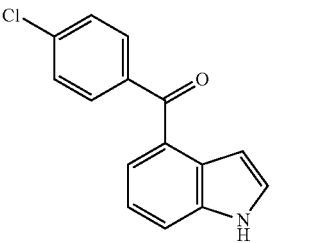 [SMILES: O=C(c1ccc(Cl)cc1)c1cccc2[nH]ccc12] I-178
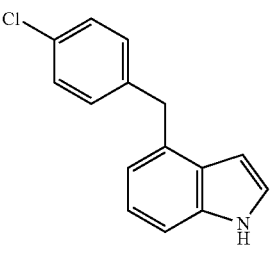 [SMILES: Clc1ccc(Cc2cccc3[nH]ccc23)cc1] I-179
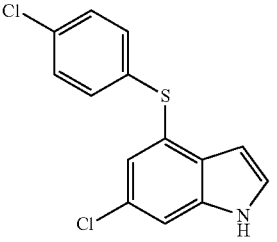 [SMILES: Clc1ccc(Sc2cc(Cl)cc3[nH]ccc23)cc1] I-180

TABLE 1-continued
Exemplary Compounds
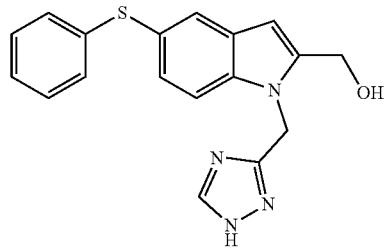 [SMILES: OCc1cc2cc(Sc3ccccc3)ccc2n1Cc1nc[nH]n1]
I-181
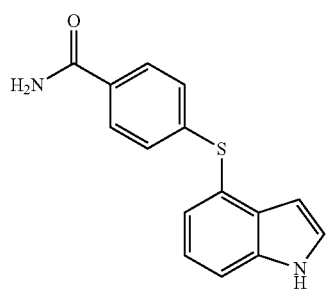 [SMILES: NC(=O)c1ccc(Sc2cccc3[nH]ccc23)cc1]
I-182
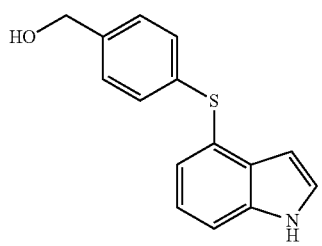 [SMILES: OCc1ccc(Sc2cccc3[nH]ccc23)cc1]
I-183
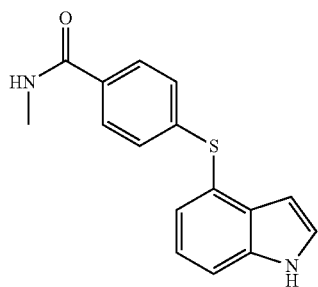 [SMILES: CNC(=O)c1ccc(Sc2cccc3[nH]ccc23)cc1]
I-184
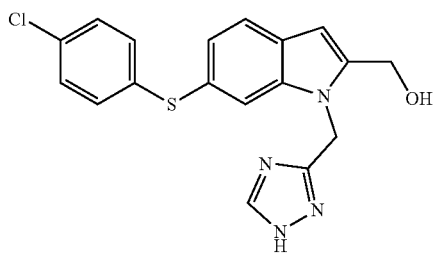 [SMILES: OCc1cc2ccc(Sc3ccc(Cl)cc3)cc2n1Cc1nc[nH]n1]
I-185
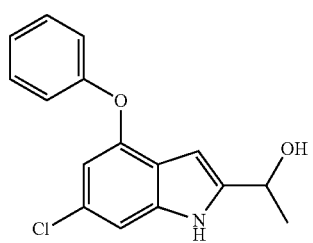 [SMILES: CC(O)c1cc2c(Oc3ccccc3)cc(Cl)cc2[nH]1]
I-186

TABLE 1-continued
Exemplary Compounds
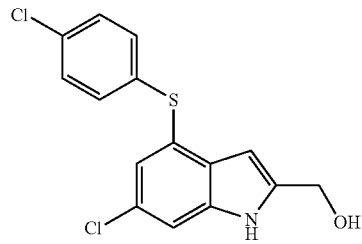 [SMILES: OCc1cc2c(Sc3ccc(Cl)cc3)cc(Cl)cc2[nH]1]
I-187
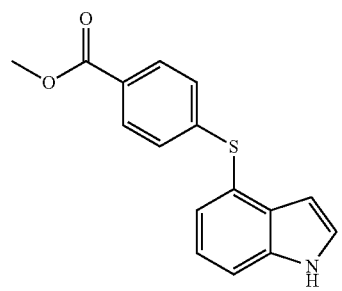 [SMILES: COC(=O)c1ccc(Sc2cccc3[nH]ccc23)cc1]
I-188
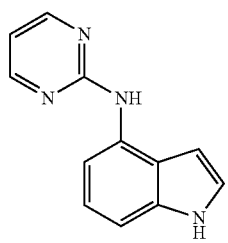 [SMILES: c1cnc(Nc2cccc3[nH]ccc23)nc1]
I-189
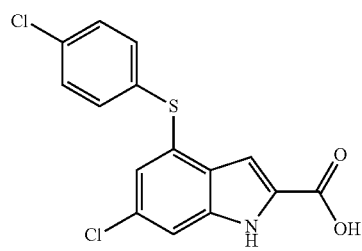 [SMILES: O=C(O)c1cc2c(Sc3ccc(Cl)cc3)cc(Cl)cc2[nH]1]
I-190
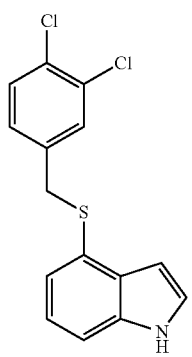 [SMILES: Clc1ccc(CSc2cccc3[nH]ccc23)cc1Cl]
I-191

TABLE 1-continued
Exemplary Compounds
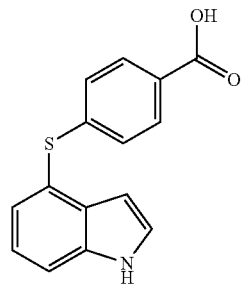 [SMILES: O=C(O)c1ccc(Sc2cccc3[nH]ccc23)cc1]
I-192
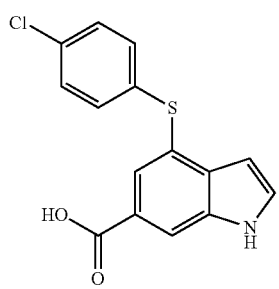 [SMILES: O=C(O)c1cc(Sc2ccc(Cl)cc2)c2cc[nH]c2c1]
I-193
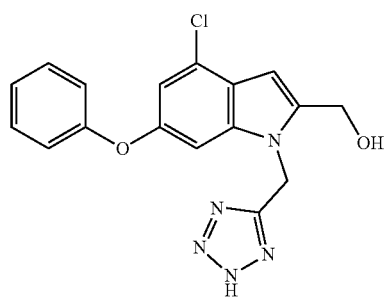 [SMILES: OCc1cc2c(Cl)cc(Oc3ccccc3)cc2n1Cc1nn[nH]n1]
I-194
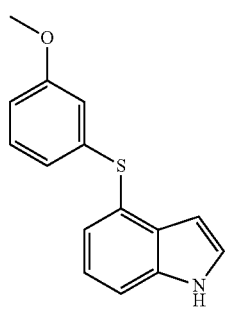 [SMILES: COc1cccc(Sc2cccc3[nH]ccc23)c1]
I-195
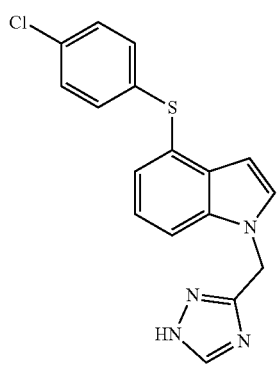 [SMILES: Clc1ccc(Sc2cccc3c2ccn3Cc2nc[nH]n2)cc1]
I-196

TABLE 1-continued
Exemplary Compounds
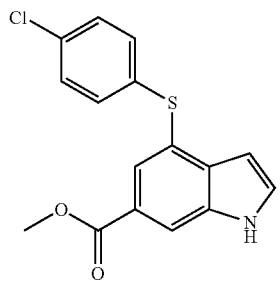 [SMILES: COC(=O)c1cc(Sc2ccc(Cl)cc2)c2cc[nH]c2c1]
I-197
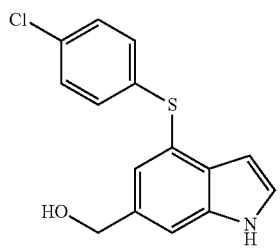 [SMILES: OCc1cc(Sc2ccc(Cl)cc2)c2cc[nH]c2c1]
I-198
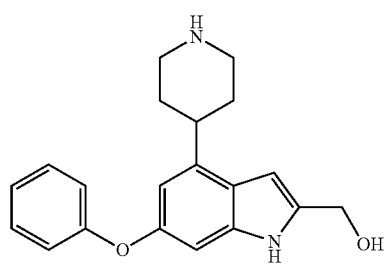 [SMILES: OCc1cc2c(C3CCNCC3)cc(Oc3ccccc3)cc2[nH]1]
I-199
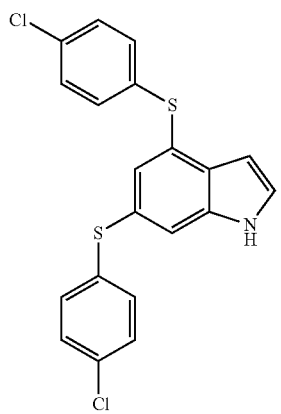 [SMILES: Clc1ccc(Sc2cc(Sc3ccc(Cl)cc3)c3cc[nH]c3c2)cc1]
I-200
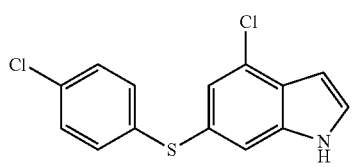 [SMILES: Clc1ccc(Sc2cc(Cl)c3cc[nH]c3c2)cc1]
I-201

TABLE 1-continued
| Exemplary Compounds | |
|---|---|
| 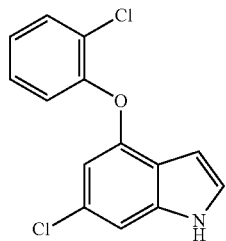 [SMILES: Clc1cc(Oc2ccccc2Cl)c2cc[nH]c2c1] | I-202 |
| 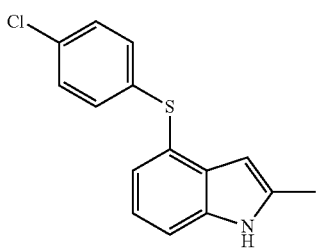 [SMILES: Cc1cc2c(Sc3ccc(Cl)cc3)cccc2[nH]1] | I-203 |
| 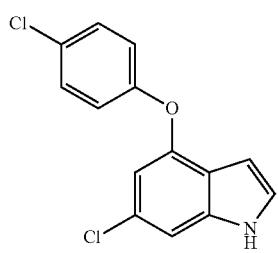 [SMILES: Clc1ccc(Oc2cc(Cl)cc3[nH]ccc23)cc1] | I-204 |
| 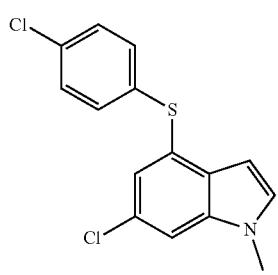 [SMILES: Cn1ccc2c(Sc3ccc(Cl)cc3)cc(Cl)cc21] | I-205 |
| 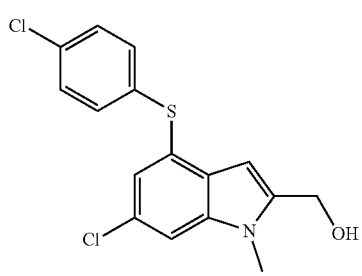 [SMILES: Cn1c(CO)cc2c(Sc3ccc(Cl)cc3)cc(Cl)cc21] | I-206 |
| 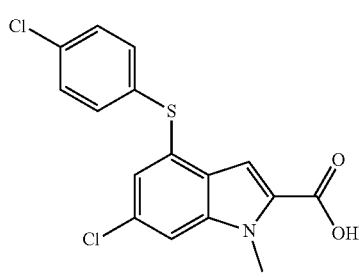 [SMILES: Cn1c(C(=O)O)cc2c(Sc3ccc(Cl)cc3)cc(Cl)cc21] | I-207 |

TABLE 1-continued
Exemplary Compounds
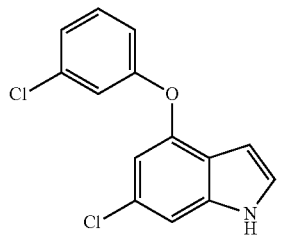 [SMILES: Clc1cccc(Oc2cc(Cl)cc3[nH]ccc23)c1]
I-208
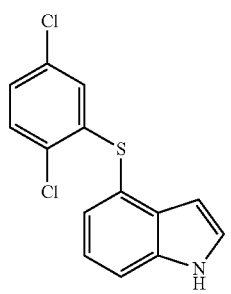 [SMILES: Clc1ccc(Cl)c(Sc2cccc3[nH]ccc23)c1]
I-209
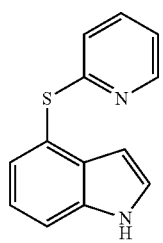 [SMILES: c1ccc(Sc2cccc3[nH]ccc23)nc1]
I-210
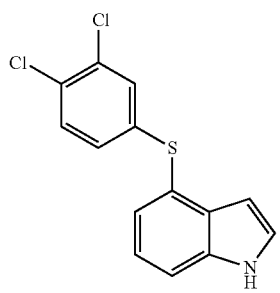 [SMILES: Clc1ccc(Sc2cccc3[nH]ccc23)cc1Cl]
I-211
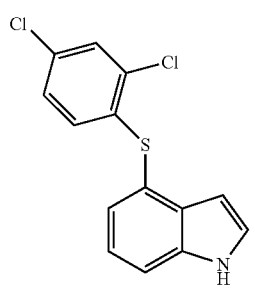 [SMILES: Clc1ccc(Sc2cccc3[nH]ccc23)c(Cl)c1]
I-212

TABLE 1-continued
Exemplary Compounds
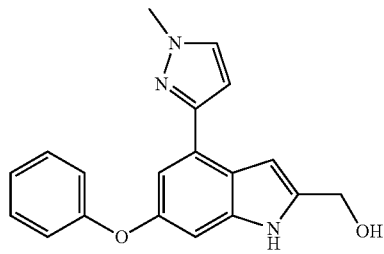 [SMILES: Cn1ccc(-c2cc(Oc3ccccc3)cc3[nH]c(CO)cc23)n1]
I-213
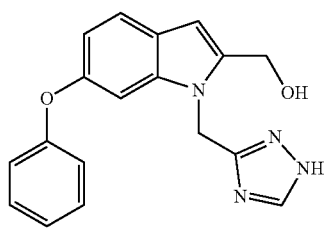 [SMILES: OCc1cc2ccc(Oc3ccccc3)cc2n1Cc1nc[nH]n1]
I-214
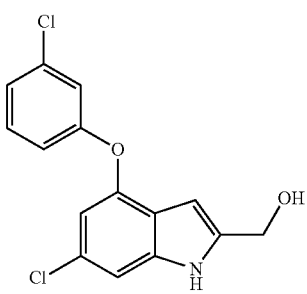 [SMILES: OCc1cc2c(Oc3cccc(Cl)c3)cc(Cl)cc2[nH]1]
I-215
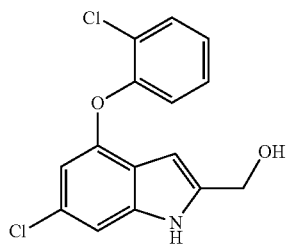 [SMILES: OCc1cc2c(Oc3ccccc3Cl)cc(Cl)cc2[nH]1]
I-216
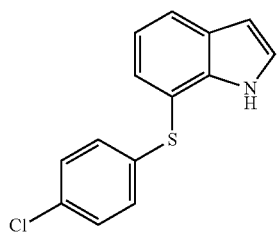 [SMILES: Clc1ccc(Sc2cccc3cc[nH]c23)cc1]
I-217
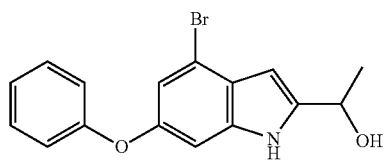 [SMILES: CC(O)c1cc2c(Br)cc(Oc3ccccc3)cc2[nH]1]
I-218

TABLE 1-continued
Exemplary Compounds
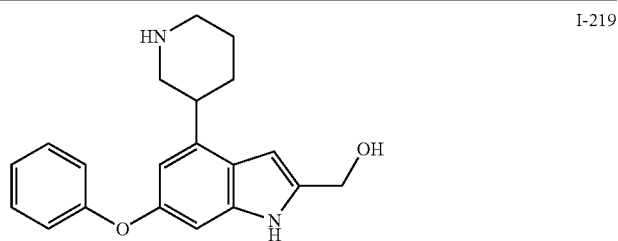 I-219
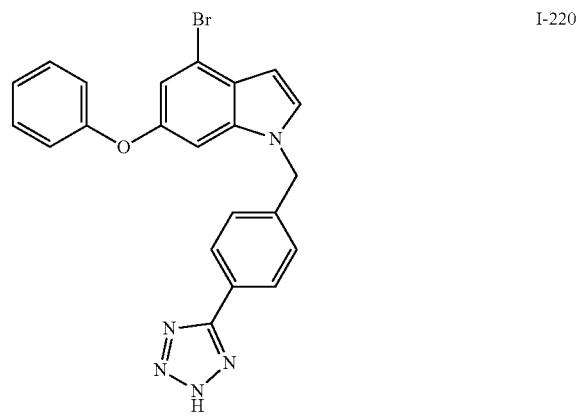 I-220
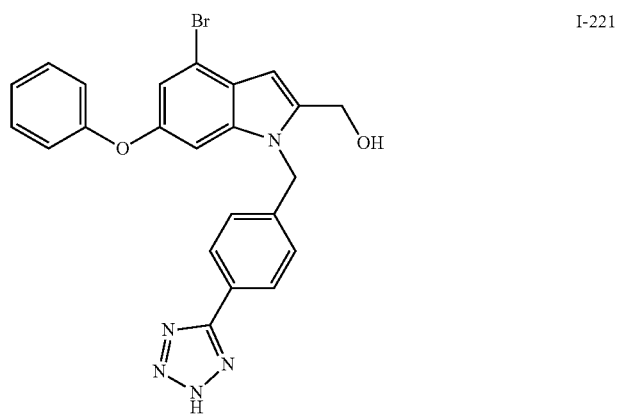 I-221
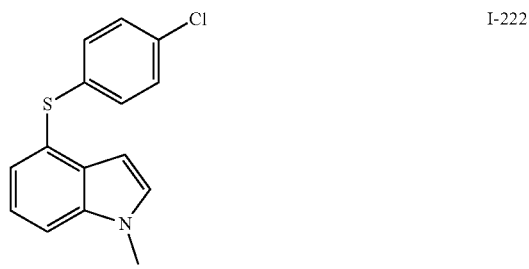 I-222
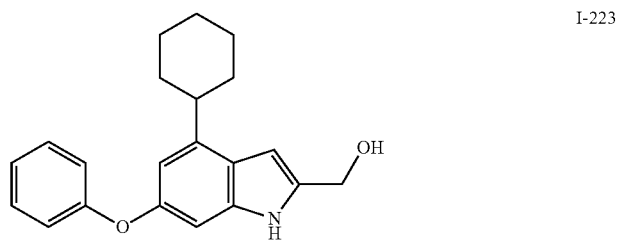 I-223

TABLE 1-continued
Exemplary Compounds
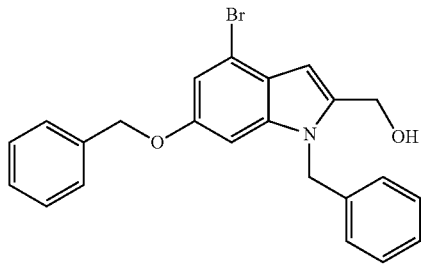 [SMILES: OCc1cc2c(Br)cc(OCc3ccccc3)cc2n1Cc1ccccc1] I-224
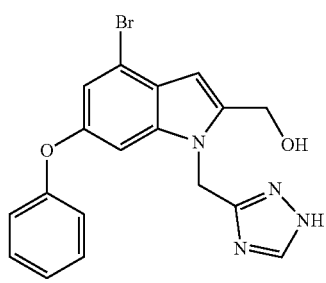 [SMILES: OCc1cc2c(Br)cc(Oc3ccccc3)cc2n1Cc1nc[nH]n1] I-225
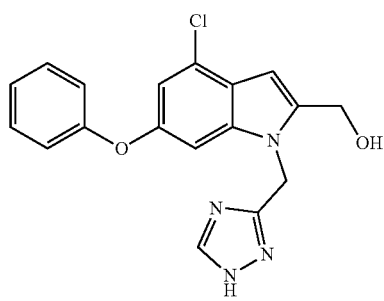 [SMILES: OCc1cc2c(Cl)cc(Oc3ccccc3)cc2n1Cc1nc[nH]n1] I-226
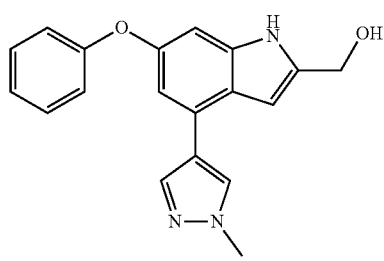 [SMILES: Cn1cc(-c2cc(Oc3ccccc3)cc3[nH]c(CO)cc23)cn1] I-227
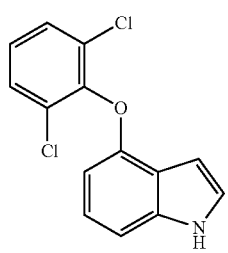 [SMILES: Clc1cccc(Cl)c1Oc1cccc2[nH]ccc12] I-228
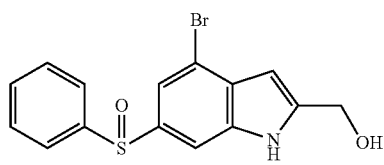 [SMILES: O=S(c1ccccc1)c1cc(Br)c2cc(CO)[nH]c2c1] I-229

TABLE 1-continued
Exemplary Compounds
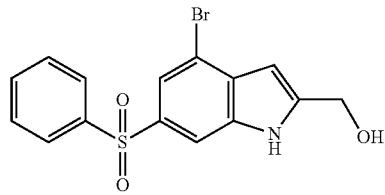 [SMILES: O=S(=O)(c1ccccc1)c1cc(Br)c2cc(CO)[nH]c2c1]
I-230
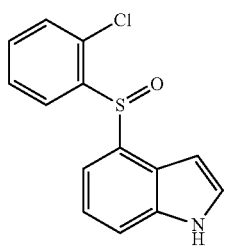 [SMILES: O=S(c1ccccc1Cl)c1cccc2[nH]ccc12]
I-231
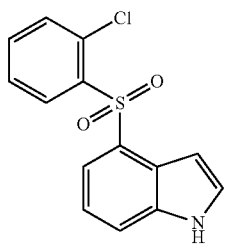 [SMILES: O=S(=O)(c1ccccc1Cl)c1cccc2[nH]ccc12]
I-232
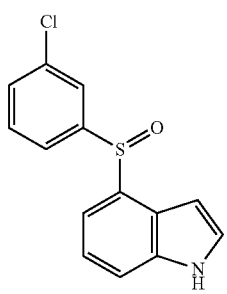 [SMILES: O=S(c1cccc(Cl)c1)c1cccc2[nH]ccc12]
I-233
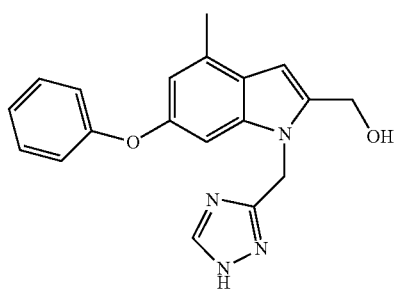 [SMILES: Cc1cc(Oc2ccccc2)cc2c1cc(CO)n2Cc1nc[nH]n1]
I-234
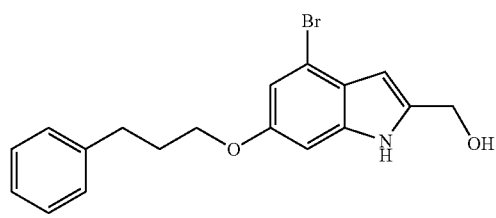 [SMILES: OCc1cc2c(Br)cc(OCCCc3ccccc3)cc2[nH]1]
I-235

TABLE 1-continued
Exemplary Compounds
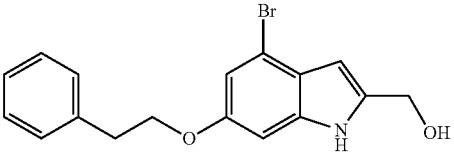 [SMILES: OCc1cc2c(Br)cc(OCCc3ccccc3)cc2[nH]1] I-236
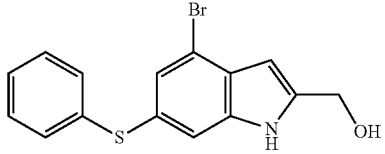 [SMILES: OCc1cc2c(Br)cc(Sc3ccccc3)cc2[nH]1] I-237
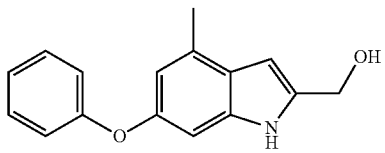 [SMILES: Cc1cc(Oc2ccccc2)cc2[nH]c(CO)cc12] I-238
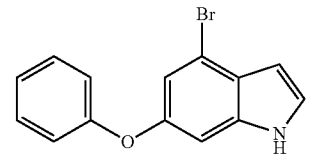 [SMILES: Brc1cc(Oc2ccccc2)cc2[nH]ccc12] I-239
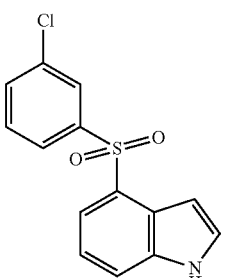 I-240
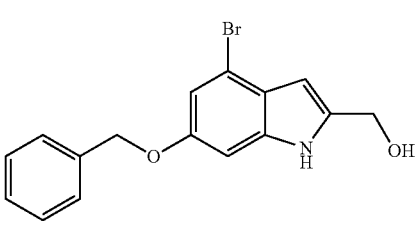 [SMILES: OCc1cc2c(Br)cc(OCc3ccccc3)cc2[nH]1] I-241
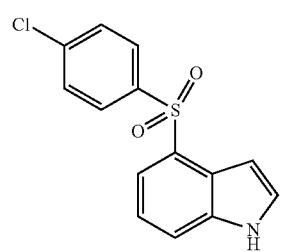 [SMILES: O=S(=O)(c1ccc(Cl)cc1)c1cccc2[nH]ccc12] I-242

TABLE 1-continued
Exemplary Compounds
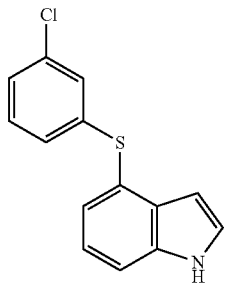 [SMILES: Clc1cccc(Sc2cccc3[nH]ccc23)c1]
I-243
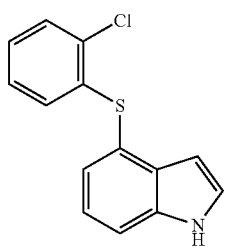 [SMILES: Clc1ccccc1Sc1cccc2[nH]ccc12]
I-244
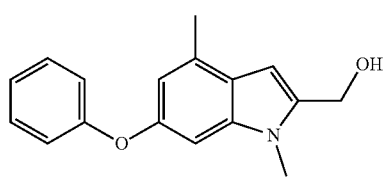 [SMILES: Cc1cc(Oc2ccccc2)cc2c1cc(CO)n2C]
I-245
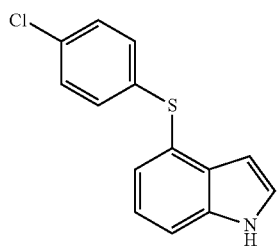 [SMILES: Clc1ccc(Sc2cccc3[nH]ccc23)cc1]
I-246
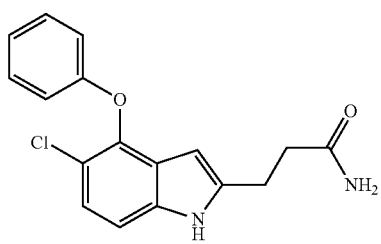 [SMILES: NC(=O)CCc1cc2c(Oc3ccccc3)c(Cl)ccc2[nH]1]
I-247
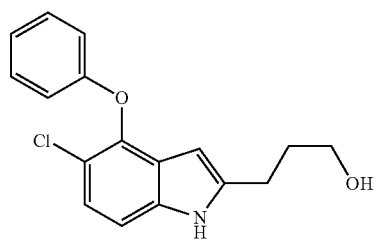 [SMILES: OCCCc1cc2c(Oc3ccccc3)c(Cl)ccc2[nH]1]
I-248

TABLE 1-continued
Exemplary Compounds
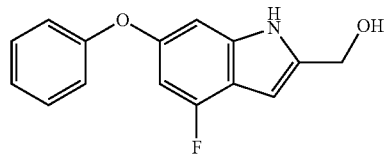 [SMILES: OCc1cc2c(F)cc(Oc3ccccc3)cc2[nH]1] I-249
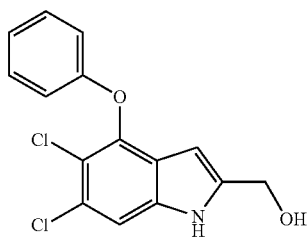 [SMILES: OCc1cc2c(Oc3ccccc3)c(Cl)c(Cl)cc2[nH]1] I-250
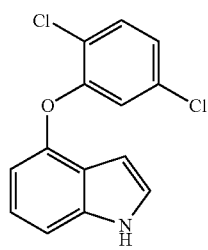 [SMILES: Clc1ccc(Cl)c(Oc2cccc3[nH]ccc23)c1] I-251
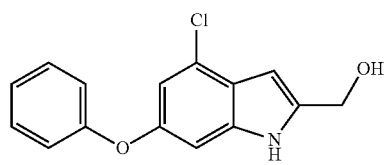 I-252
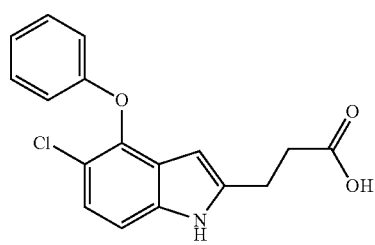 [SMILES: O=C(O)CCc1cc2c(Oc3ccccc3)c(Cl)ccc2[nH]1] I-253
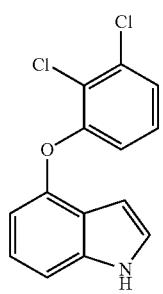 [SMILES: Clc1cccc(Oc2cccc3[nH]ccc23)c1Cl] I-254

TABLE 1-continued
Exemplary Compounds
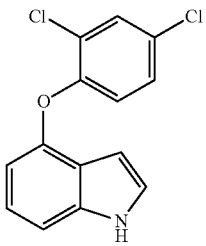 [SMILES: Clc1ccc(Oc2cccc3[nH]ccc23)c(Cl)c1]
I-255
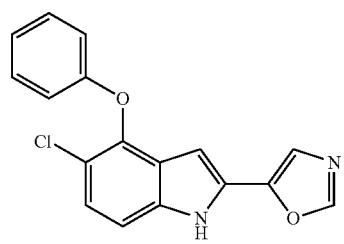 [SMILES: Clc1ccc2[nH]c(-c3cnco3)cc2c1Oc1ccccc1]
I-256
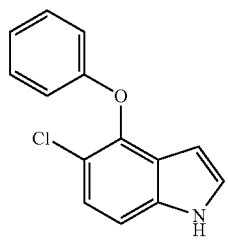 [SMILES: Clc1ccc2[nH]ccc2c1Oc1ccccc1]
I-257
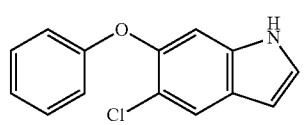 [SMILES: Clc1cc2cc[nH]c2cc1Oc1ccccc1]
I-258
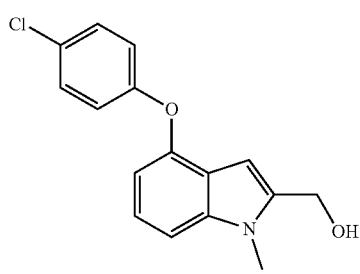 [SMILES: Cn1c(CO)cc2c(Oc3ccc(Cl)cc3)cccc21]
I-259
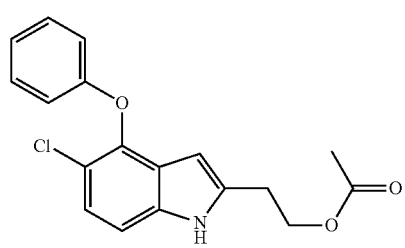 [SMILES: CC(=O)OCCc1cc2c(Oc3ccccc3)c(Cl)ccc2[nH]1]
I-260

TABLE 1-continued
Exemplary Compounds
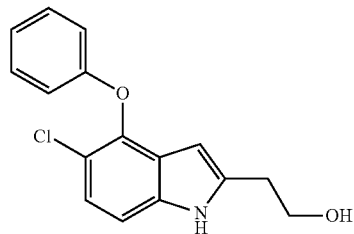 [SMILES: OCCc1cc2c(Oc3ccccc3)c(Cl)ccc2[nH]1]
I-261
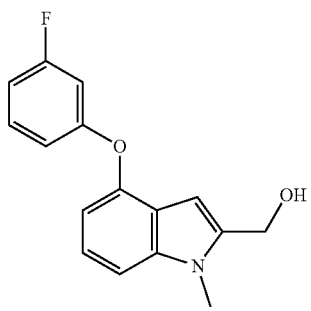 [SMILES: Cn1c(CO)cc2c(Oc3cccc(F)c3)cccc21]
I-262
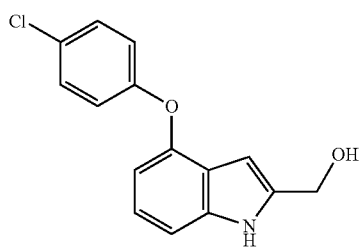 [SMILES: OCc1cc2c(Oc3ccc(Cl)cc3)cccc2[nH]1]
I-263
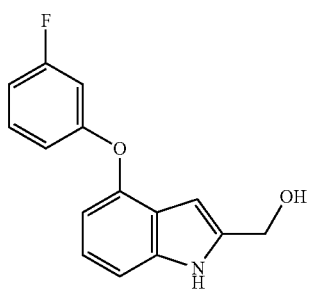 [SMILES: OCc1cc2c(Oc3cccc(F)c3)cccc2[nH]1]
I-264
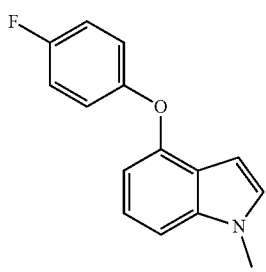 [SMILES: Cn1ccc2c(Oc3ccc(F)cc3)cccc21]
I-265

TABLE 1-continued
Exemplary Compounds
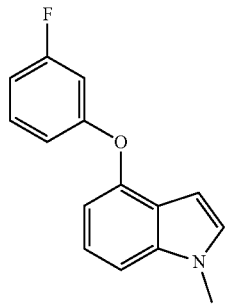 [SMILES: Cn1ccc2c(Oc3cccc(F)c3)cccc21]
I-266
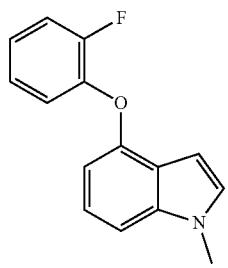 [SMILES: Cn1ccc2c(Oc3ccccc3F)cccc21]
I-267
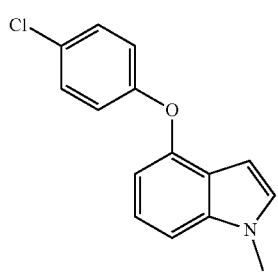 [SMILES: Cn1ccc2c(Oc3ccc(Cl)cc3)cccc21]
I-268
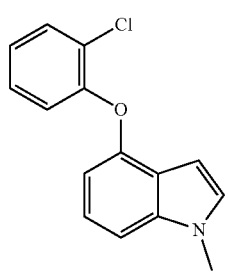
I-269
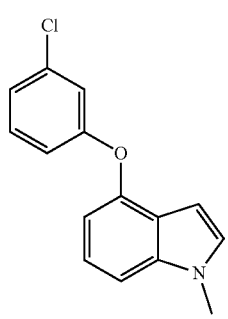 [SMILES: Cn1ccc2c(Oc3cccc(Cl)c3)cccc21]
I-270

TABLE 1-continued
Exemplary Compounds
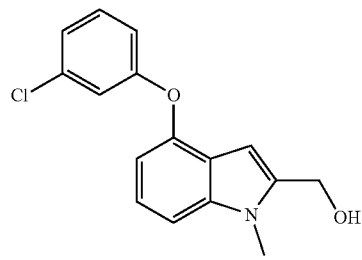 [SMILES: Cn1c(CO)cc2c(Oc3cccc(Cl)c3)cccc21]
I-271
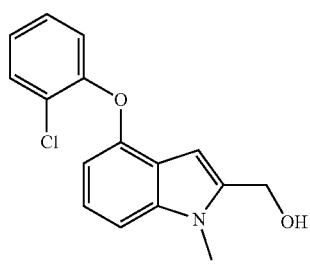 [SMILES: Cn1c(CO)cc2c(Oc3ccccc3Cl)cccc21]
I-272
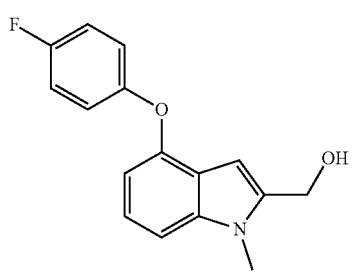 [SMILES: Cn1c(CO)cc2c(Oc3ccc(F)cc3)cccc21]
I-273
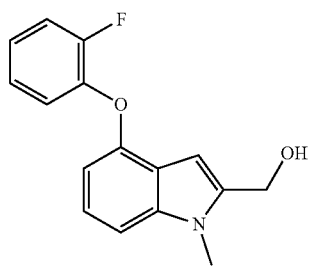 [SMILES: Cn1c(CO)cc2c(Oc3ccccc3F)cccc21]
I-274
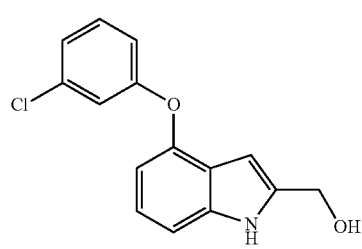 [SMILES: OCc1cc2c(Oc3cccc(Cl)c3)cccc2[nH]1]
I-275
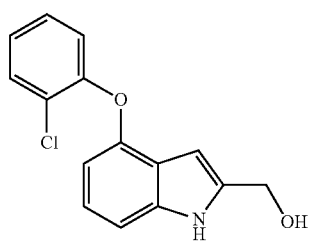 [SMILES: OCc1cc2c(Oc3ccccc3Cl)cccc2[nH]1]
I-276

TABLE 1-continued
Exemplary Compounds
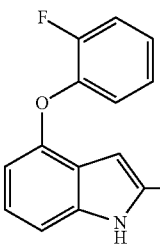
I-277
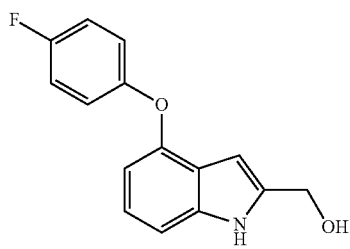 [SMILES: OCc1cc2c(Oc3ccc(F)cc3)cccc2[nH]1]
I-278
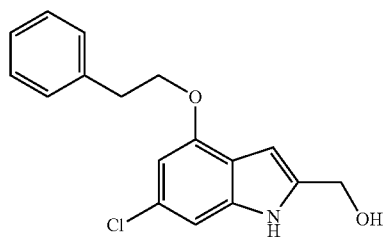 [SMILES: OCc1cc2c(OCCc3ccccc3)cc(Cl)cc2[nH]1]
I-279
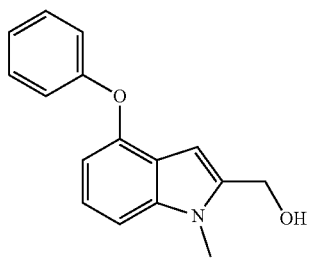 [SMILES: Cn1c(CO)cc2c(Oc3ccccc3)cccc21]
I-280
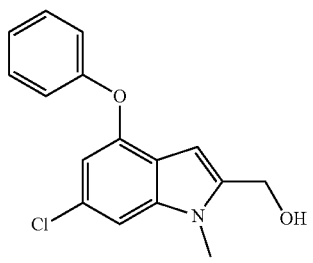 [SMILES: Cn1c(CO)cc2c(Oc3ccccc3)cc(Cl)cc21]
I-281
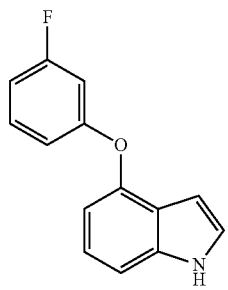 [SMILES: Fc1cccc(Oc2cccc3[nH]ccc23)c1]
I-282

TABLE 1-continued

Exemplary Compounds

| | |
|---|---|
| 4-(4-chlorophenoxy)-1H-indole | I-283 |
| 4-(3-chlorophenoxy)-1H-indole | I-284 |
| 4-(2-chlorophenoxy)-1H-indole | I-285 |
| (6-phenoxy-1H-indol-2-yl)methanol | I-286 |
| (4-phenoxy-1H-indol-2-yl)methanol | I-287 |
| 4-(2-fluorophenoxy)-1H-indole | I-288 |
| (5-chloro-1-methyl-4-phenoxy-1H-indol-2-yl)methanol | I-289 |

TABLE 1-continued
Exemplary Compounds
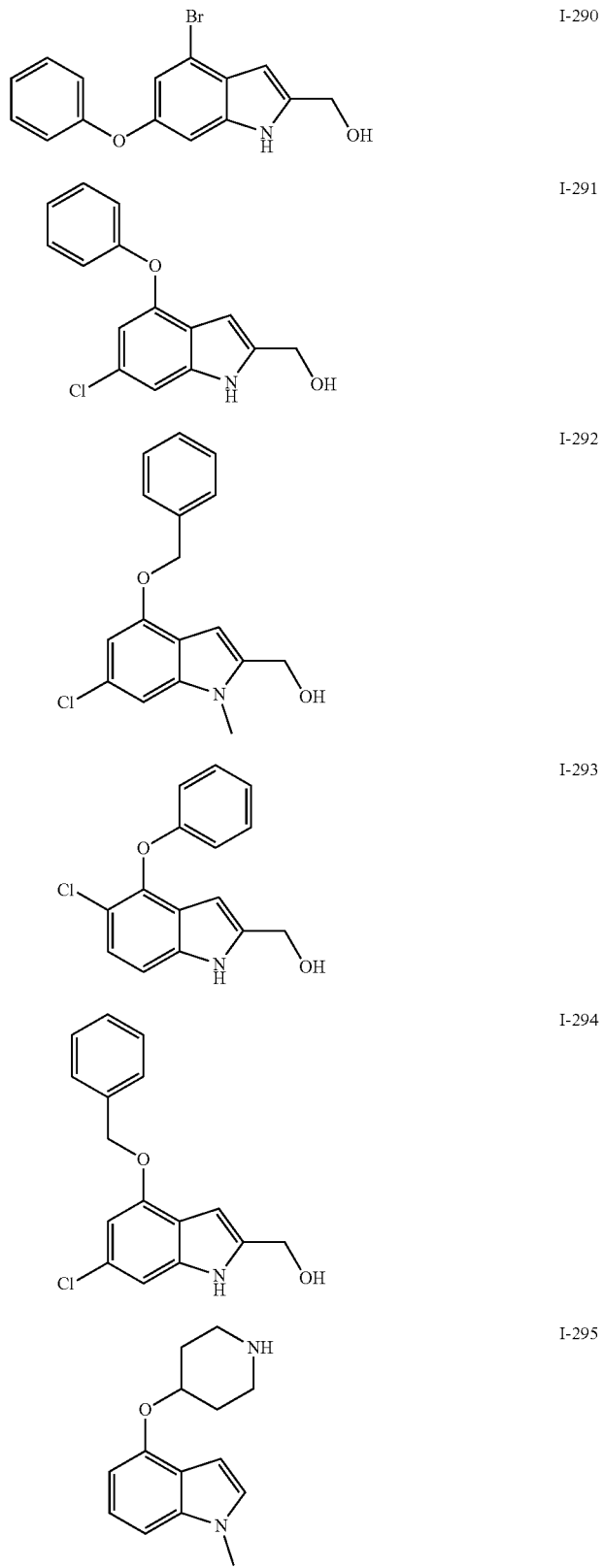
I-290
I-291
I-292
I-293
I-294
I-295

TABLE 1-continued
Exemplary Compounds
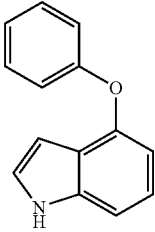 [SMILES: c1ccc(Oc2cccc3[nH]ccc23)cc1]
I-296
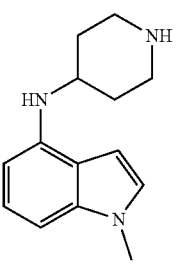 [SMILES: Cn1ccc2c(NC3CCNCC3)cccc21]
I-297
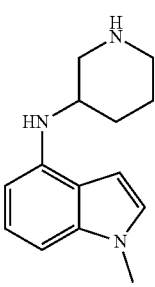 [SMILES: Cn1ccc2c(NC3CCCNC3)cccc21]
I-298
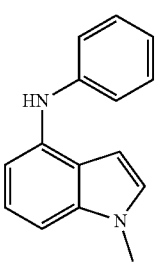 [SMILES: Cn1ccc2c(Nc3ccccc3)cccc21]
I-299
In some embodiments, the present invention provides a compound set forth in Table 1, above, or a pharmaceutically acceptable salt thereof.
Additional compounds are set forth in Table 2, below.
TABLE 2
Compounds
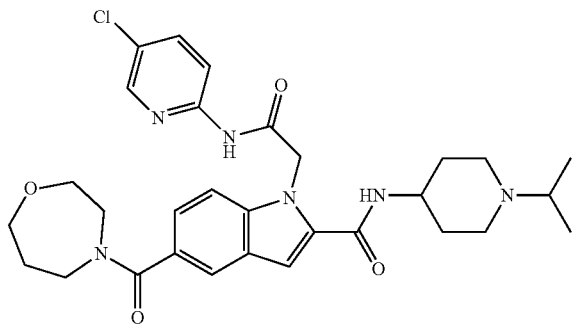 [SMILES: CC(C)N1CCC(NC(=O)c2cc3cc(C(=O)N4CCCOCC4)ccc3n2CC(=O)Nc2ccc(Cl)cn2)CC1]
I-300

TABLE 2-continued
Compounds
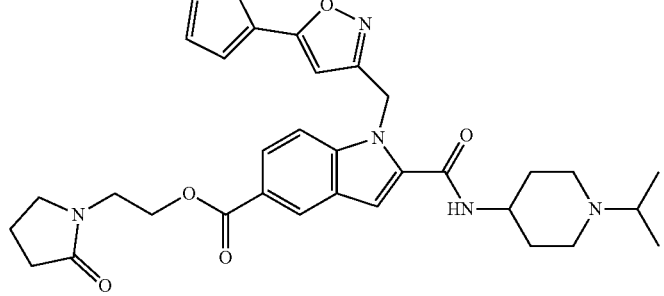
I-301
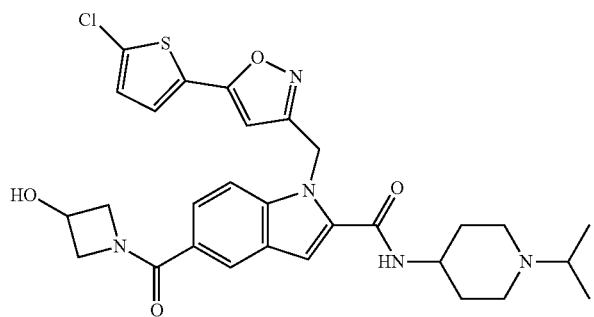 [SMILES: CC(C)N1CCC(NC(=O)c2cc3cc(C(=O)N4CC(O)C4)ccc3n2Cc2cc(-c3ccc(Cl)s3)on2)CC1]
I-302
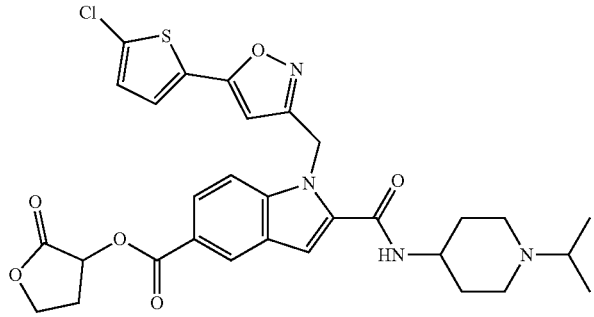 [SMILES: CC(C)N1CCC(NC(=O)c2cc3cc(C(=O)OC4CCOC4=O)ccc3n2Cc2cc(-c3ccc(Cl)s3)on2)CC1]
I-303
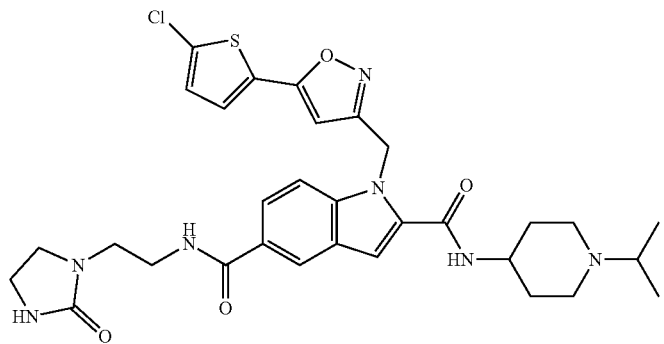 [SMILES: CC(C)N1CCC(NC(=O)c2cc3cc(C(=O)OCCN4CCNC4=O)ccc3n2Cc2cc(-c3ccc(Cl)s3)on2)CC1]
I-304

TABLE 2-continued
Compounds
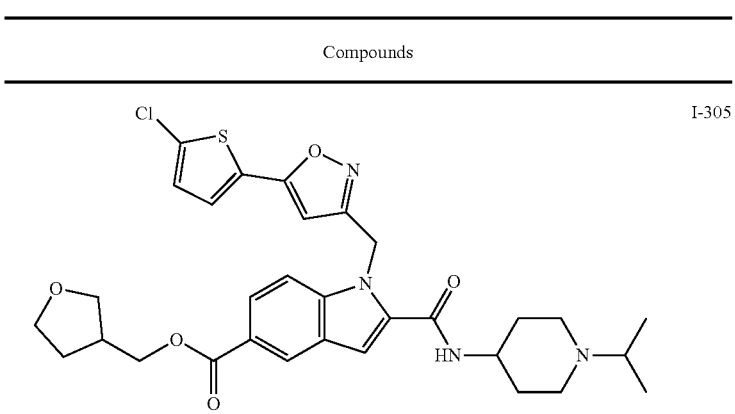
I-305
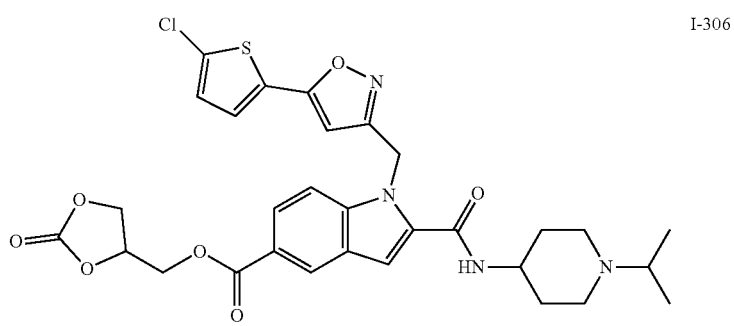
I-306
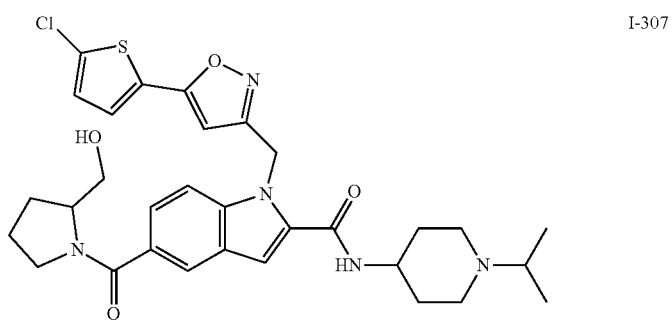
I-307
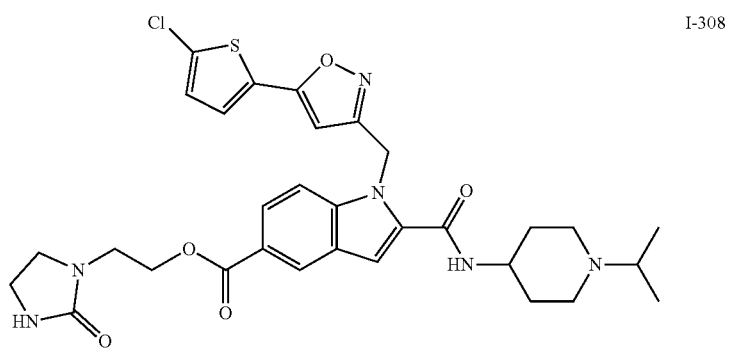
I-308

TABLE 2-continued
Compounds
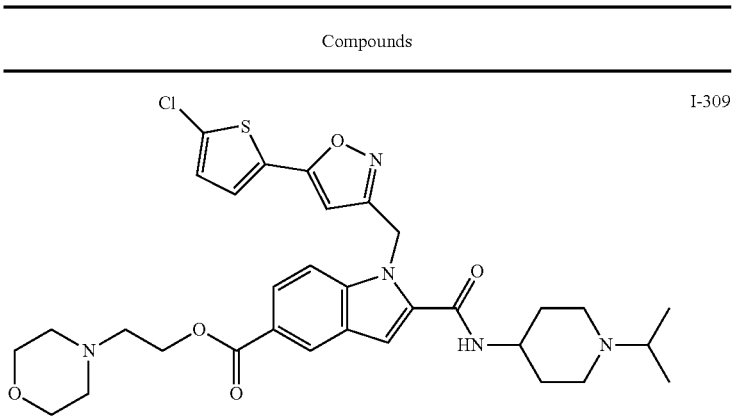
I-309
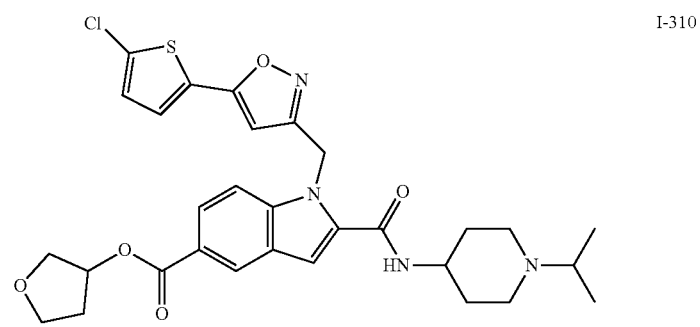
I-310
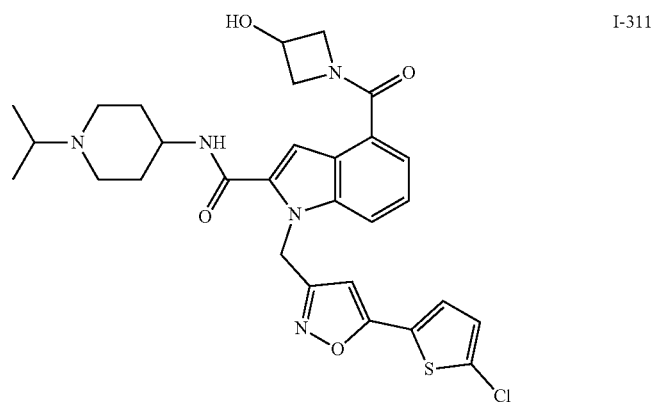
I-311
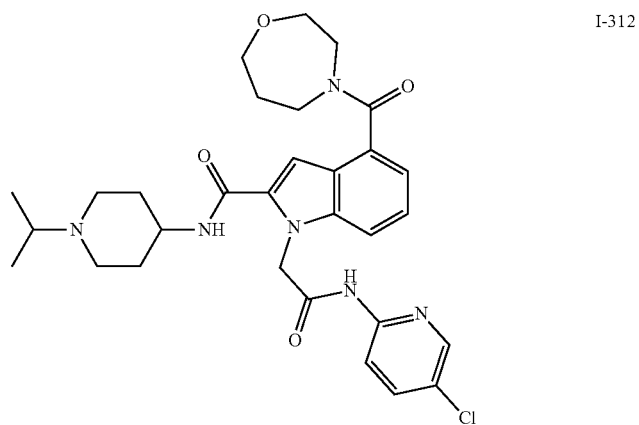
I-312

TABLE 2-continued

| Compounds | |
|---|---|
| [structure] | I-313 |
| [structure] | I-314 |
| [structure] | I-315 |
| [structure] | I-316 |

TABLE 2-continued

| Compounds | |
|---|---|
| [Structure of I-317] | I-317 |
| [Structure of I-318] | I-318 |
| [Structure of I-319] | I-319 |

In some embodiments, the present invention provides a compound other than a compound set forth in Table 2.

Exemplary compounds of the invention are set forth in Table 3, below.

TABLE 3

| Exemplary Compounds | |
|---|---|
| [Structure of I-320] | I-320 |

TABLE 3-continued
Exemplary Compounds
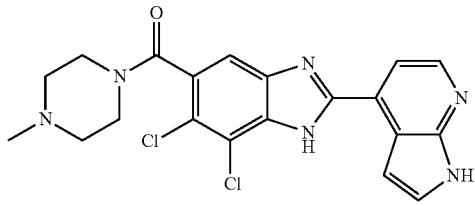 [SMILES: CN1CCN(C(=O)c2cc3nc(-c4ccnc5[nH]ccc45)[nH]c3c(Cl)c2Cl)CC1]
I-321
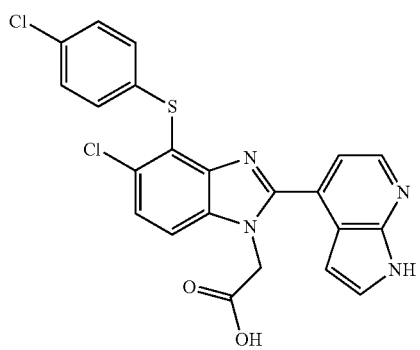 [SMILES: O=C(O)Cn1c(-c2ccnc3[nH]ccc23)nc2c(Sc3ccc(Cl)cc3)c(Cl)ccc21]
I-322
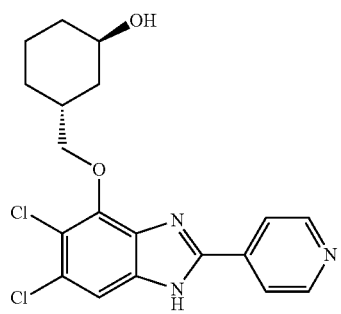 [SMILES: O[C@@H]1CCC[C@@H](COc2c(Cl)c(Cl)cc3[nH]c(-c4ccncc4)nc23)C1]
I-323
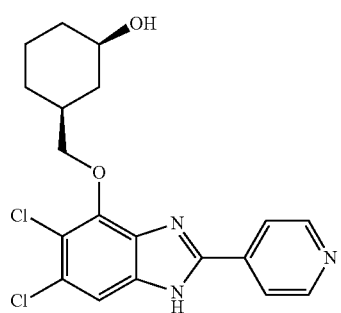 [SMILES: O[C@@H]1CCC[C@H](COc2c(Cl)c(Cl)cc3[nH]c(-c4ccncc4)nc23)C1]
I-324
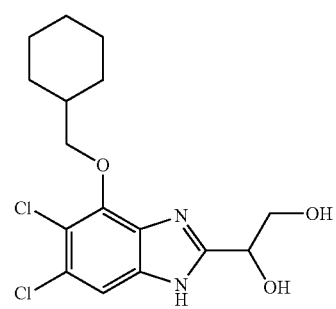 [SMILES: OCC(O)c1nc2c(OCC3CCCCC3)c(Cl)c(Cl)cc2[nH]1]
I-325

TABLE 3-continued
Exemplary Compounds
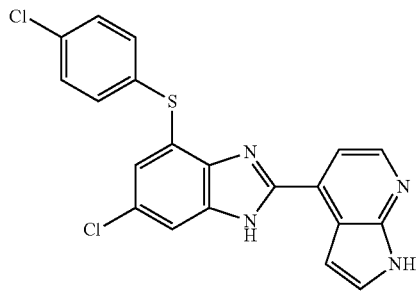 [SMILES: Clc1ccc(Sc2cc(Cl)cc3[nH]c(-c4ccnc5[nH]ccc45)nc23)cc1]
I-326
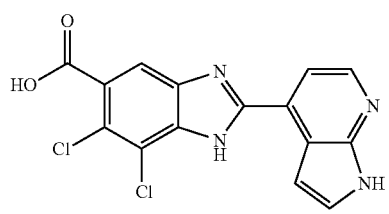 [SMILES: O=C(O)c1cc2nc(-c3ccnc4[nH]ccc34)[nH]c2c(Cl)c1Cl]
I-327
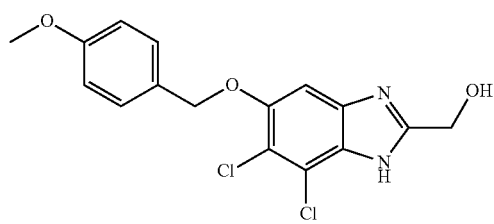 [SMILES: COc1ccc(COc2cc3nc(CO)[nH]c3c(Cl)c2Cl)cc1]
I-328
I-329
I-330
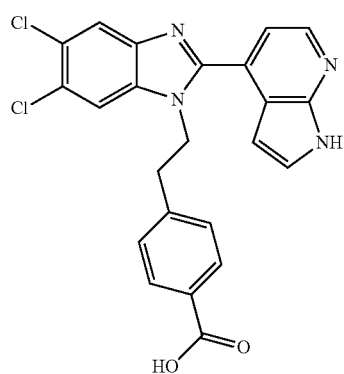 [SMILES: O=C(O)c1ccc(CCn2c(-c3ccnc4[nH]ccc34)nc3cc(Cl)c(Cl)cc32)cc1]
I-331

TABLE 3-continued

Exemplary Compounds

I-332

I-333

I-334

I-335

I-336

I-337

TABLE 3-continued
Exemplary Compounds
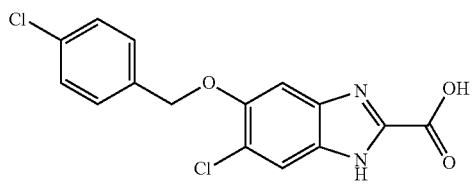 [SMILES: O=C(O)c1nc2cc(OCc3ccc(Cl)cc3)c(Cl)cc2[nH]1]
I-338
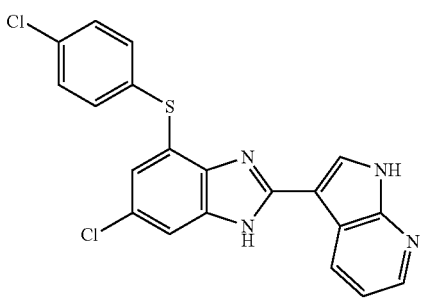 [SMILES: Clc1ccc(Sc2cc(Cl)cc3[nH]c(-c4c[nH]c5ncccc45)nc23)cc1]
I-339
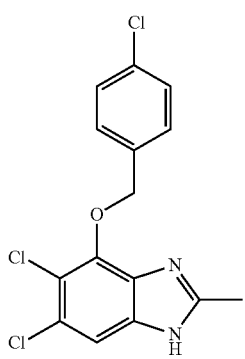 [SMILES: Cc1nc2c(OCc3ccc(Cl)cc3)c(Cl)c(Cl)cc2[nH]1]
I-340
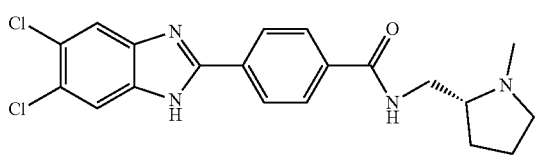 [SMILES: CN1CCC[C@@H]1CNC(=O)c1ccc(-c2nc3cc(Cl)c(Cl)cc3[nH]2)cc1]
I-341
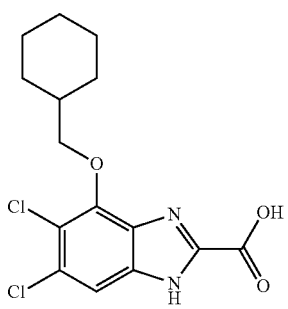 [SMILES: O=C(O)c1nc2c(OCC3CCCCC3)c(Cl)c(Cl)cc2[nH]1]
I-342
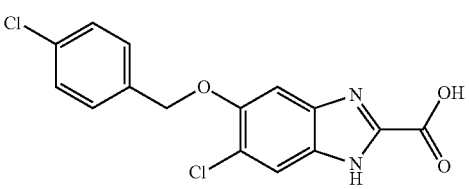
I-343

TABLE 3-continued
Exemplary Compounds
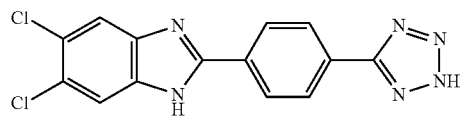 I-344
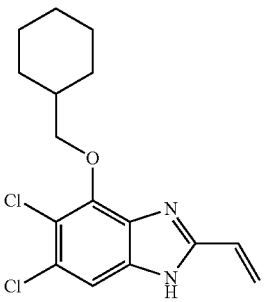 [SMILES: C=Cc1nc2c(OCC3CCCCC3)c(Cl)c(Cl)cc2[nH]1] I-345
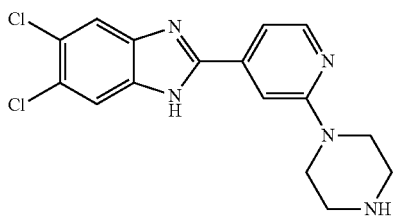 [SMILES: Clc1cc2nc(-c3ccnc(N4CCNCC4)c3)[nH]c2cc1Cl] I-346
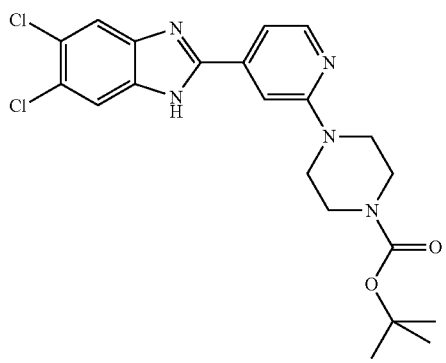 [SMILES: CC(C)(C)OC(=O)N1CCN(c2cc(-c3nc4cc(Cl)c(Cl)cc4[nH]3)ccn2)CC1] I-347
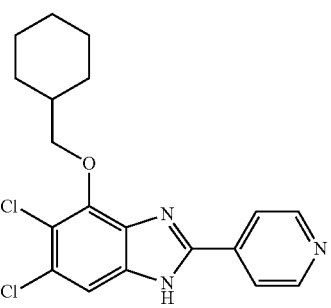 [SMILES: Clc1cc2[nH]c(-c3ccncc3)nc2c(OCC2CCCCC2)c1Cl] I-348
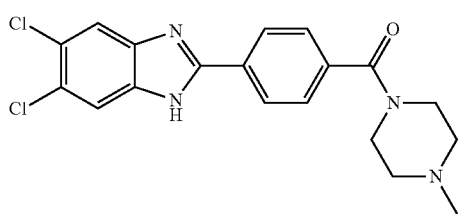 [SMILES: CN1CCN(C(=O)c2ccc(-c3nc4cc(Cl)c(Cl)cc4[nH]3)cc2)CC1] I-349

TABLE 3-continued
Exemplary Compounds
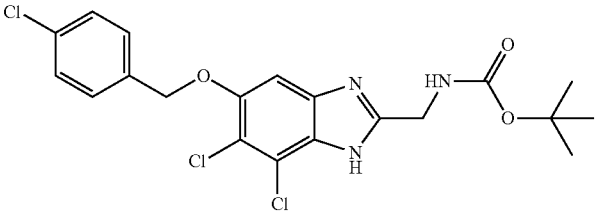 [SMILES: CC(C)(C)OC(=O)NCc1nc2cc(OCc3ccc(Cl)cc3)c(Cl)c(Cl)c2[nH]1] I-350
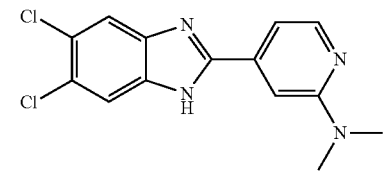 [SMILES: CN(C)c1cc(-c2nc3cc(Cl)c(Cl)cc3[nH]2)ccn1] I-351
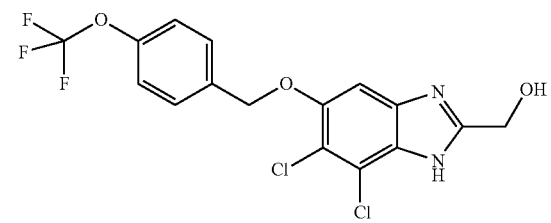 [SMILES: OCc1nc2cc(OCc3ccc(OC(F)(F)F)cc3)c(Cl)c(Cl)c2[nH]1] I-352
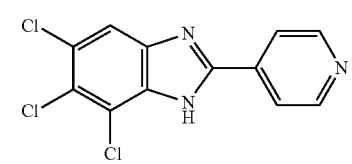 [SMILES: Clc1cc2nc(-c3ccncc3)[nH]c2c(Cl)c1Cl] I-353
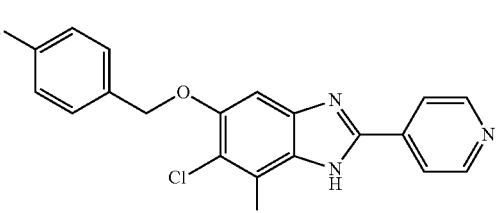 I-354
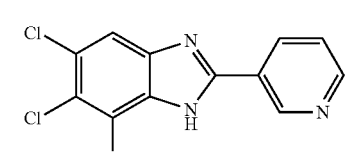 I-355
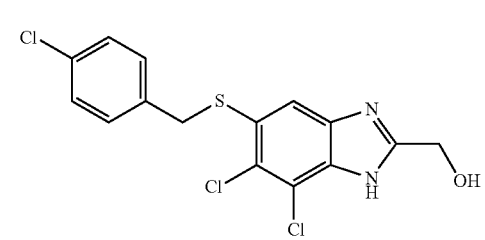 [SMILES: OCc1nc2cc(SCc3ccc(Cl)cc3)c(Cl)c(Cl)c2[nH]1] I-356
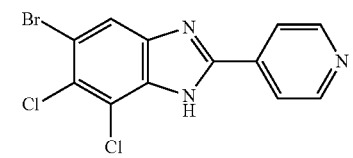 [SMILES: Clc1c(Br)cc2nc(-c3ccncc3)[nH]c2c1Cl] I-357

TABLE 3-continued
Exemplary Compounds
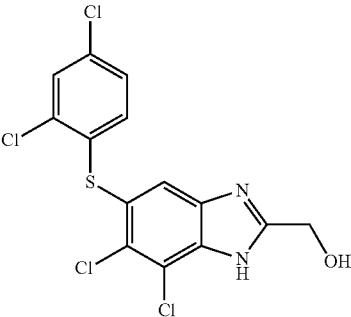 [SMILES: OCc1nc2cc(Sc3ccc(Cl)cc3Cl)c(Cl)c(Cl)c2[nH]1]
I-358
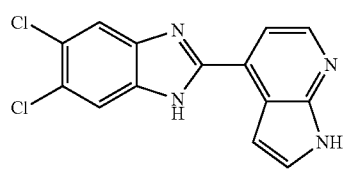 [SMILES: Clc1cc2nc(-c3ccnc4[nH]ccc34)[nH]c2cc1Cl]
I-359
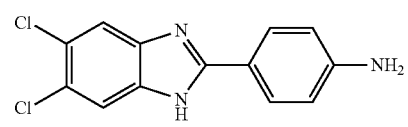 [SMILES: Nc1ccc(-c2nc3cc(Cl)c(Cl)cc3[nH]2)cc1]
I-360
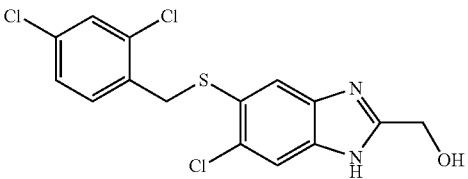 [SMILES: OCc1nc2cc(SCc3ccc(Cl)cc3Cl)c(Cl)cc2[nH]1]
I-361
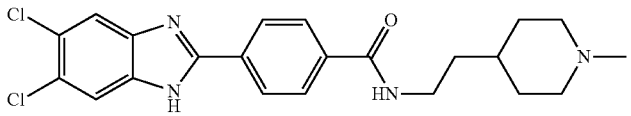
I-362
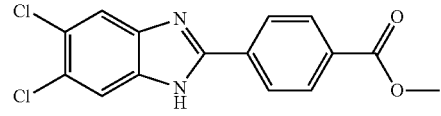 [SMILES: COC(=O)c1ccc(-c2nc3cc(Cl)c(Cl)cc3[nH]2)cc1]
I-363
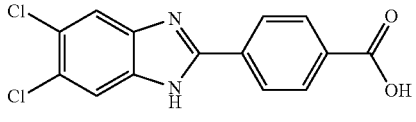 [SMILES: O=C(O)c1ccc(-c2nc3cc(Cl)c(Cl)cc3[nH]2)cc1]
I-364
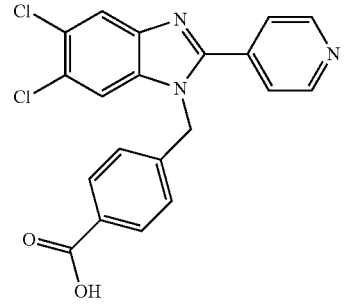 [SMILES: O=C(O)c1ccc(Cn2c(-c3ccncc3)nc3cc(Cl)c(Cl)cc32)cc1]
I-365

TABLE 3-continued
Exemplary Compounds
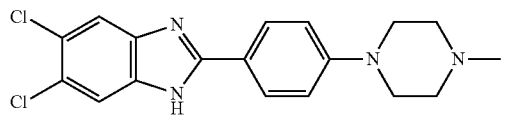 [SMILES: CN1CCN(c2ccc(-c3nc4cc(Cl)c(Cl)cc4[nH]3)cc2)CC1]
I-366
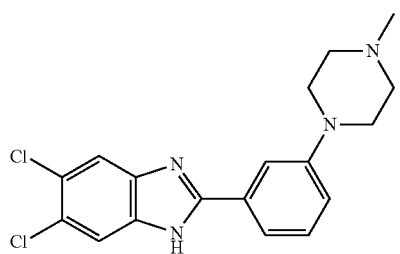 [SMILES: CN1CCN(c2cccc(-c3nc4cc(Cl)c(Cl)cc4[nH]3)c2)CC1]
I-367
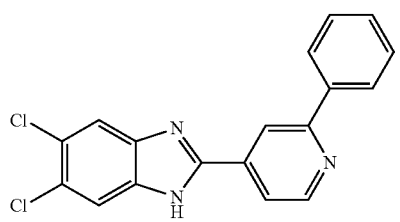 [SMILES: Clc1cc2nc(-c3ccnc(-c4ccccc4)c3)[nH]c2cc1Cl]
I-368
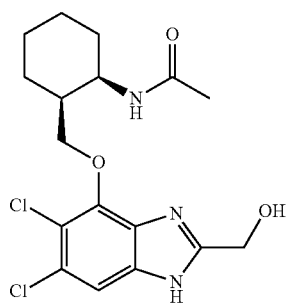 [SMILES: CC(=O)N[C@@H]1CCCC[C@@H]1COc1c(Cl)c(Cl)cc2[nH]c(CO)nc12]
I-369
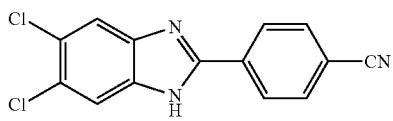
I-370
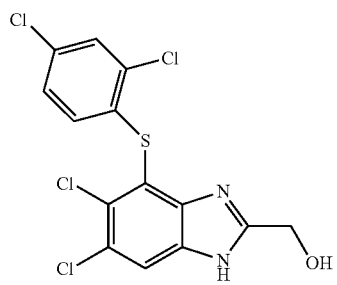 [SMILES: OCc1nc2c(Sc3ccc(Cl)cc3Cl)c(Cl)c(Cl)cc2[nH]1]
I-371
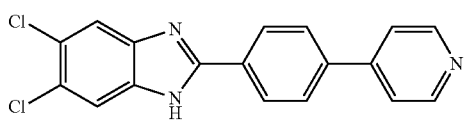 [SMILES: Clc1cc2nc(-c3ccc(-c4ccncc4)cc3)[nH]c2cc1Cl]
I-372

TABLE 3-continued
| Exemplary Compounds | |
|---|---|
| 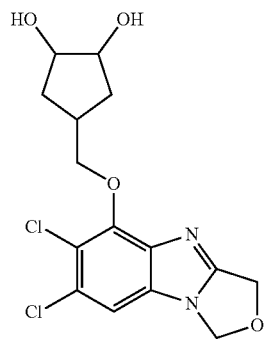 | I-373 |
| 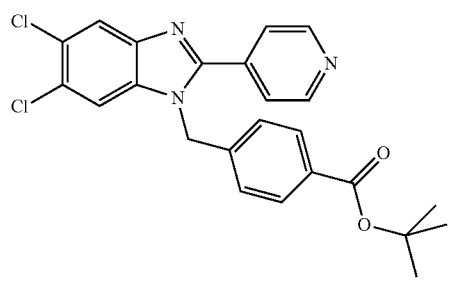 [SMILES: CC(C)(C)OC(=O)c1ccc(Cn2c(-c3ccncc3)nc3cc(Cl)c(Cl)cc32)cc1] | I-374 |
| 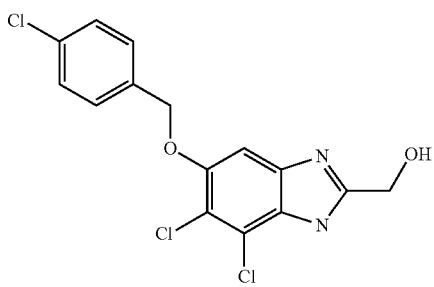 [SMILES: OCc1nc2cc(OCc3ccc(Cl)cc3)c(Cl)c(Cl)c2[nH]1] | I-375 |
| 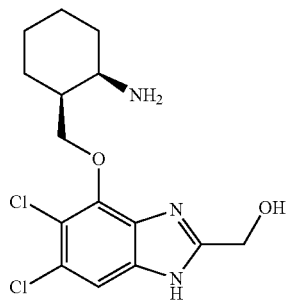 [SMILES: N[C@@H]1CCCC[C@@H]1COc1c(Cl)c(Cl)cc2[nH]c(CO)nc12] | I-376 |
| 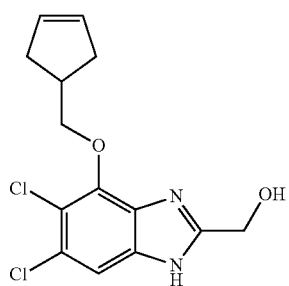 [SMILES: OCc1nc2c(OCC3CC=CC3)c(Cl)c(Cl)cc2[nH]1] | I-377 |

TABLE 3-continued
Exemplary Compounds
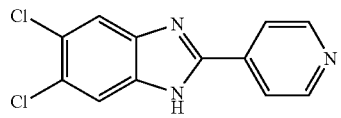 [SMILES: Clc1cc2nc(-c3ccncc3)[nH]c2cc1Cl] I-378
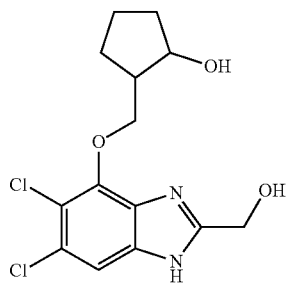 [SMILES: OCc1nc2c(OCC3CCCC3O)c(Cl)c(Cl)cc2[nH]1] I-379
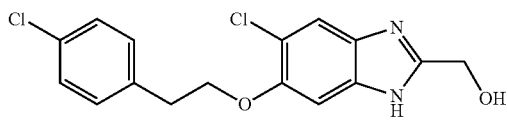 [SMILES: OCc1nc2cc(Cl)c(OCCc3ccc(Cl)cc3)cc2[nH]1] I-380
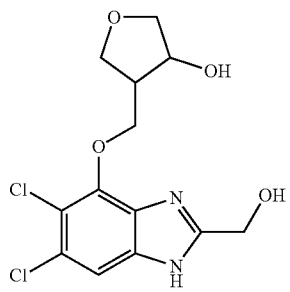 [SMILES: OCc1nc2c(OCC3COCC3O)c(Cl)c(Cl)cc2[nH]1] I-381
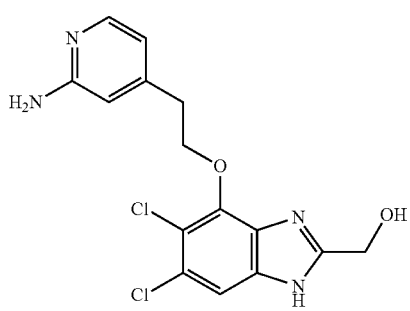 [SMILES: Nc1cc(CCOc2c(Cl)c(Cl)cc3[nH]c(CO)nc23)ccn1] I-382
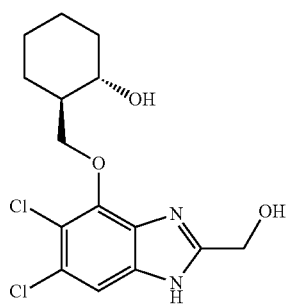 [SMILES: OCc1nc2c(OC[C@H]3CCCC[C@@H]3O)c(Cl)c(Cl)cc2[nH]1] I-383

TABLE 3-continued
Exemplary Compounds
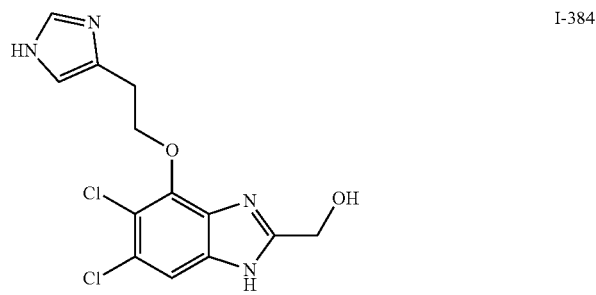 I-384
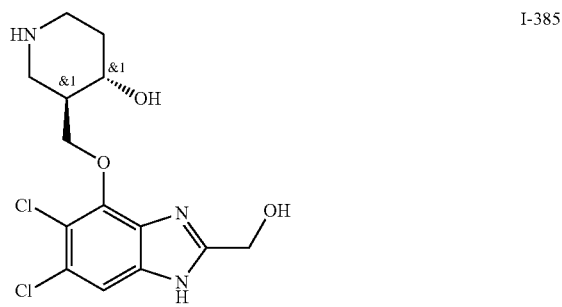 I-385
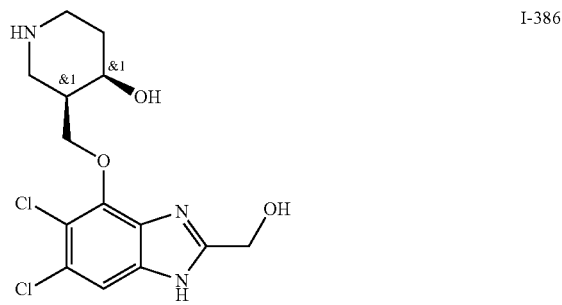 I-386
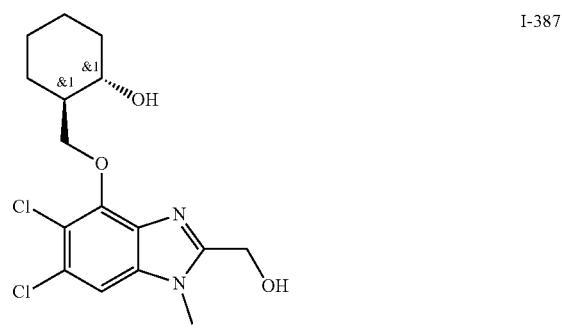 I-387
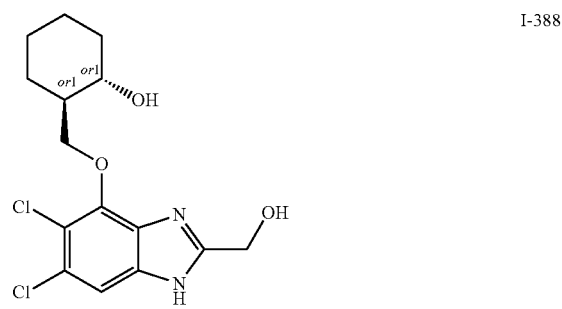 I-388

TABLE 3-continued
Exemplary Compounds
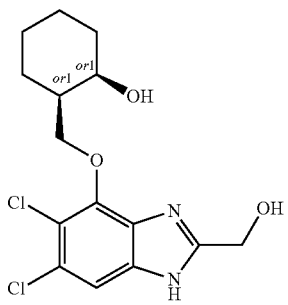 [SMILES: OCc1nc2c(OC[C@H]3CCCC[C@H]3O)c(Cl)c(Cl)cc2[nH]1]
I-389
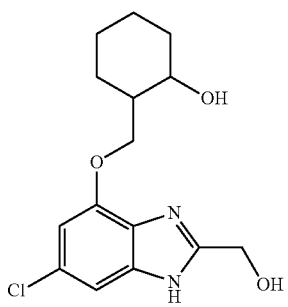 [SMILES: OCc1nc2c(OCC3CCCCC3O)cc(Cl)cc2[nH]1]
I-390
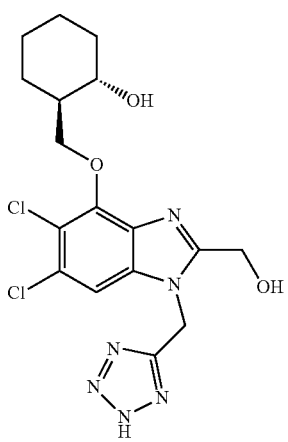 [SMILES: OCc1nc2c(OC[C@H]3CCCC[C@@H]3O)c(Cl)c(Cl)cc2n1Cc1nn[nH]n1]
I-391
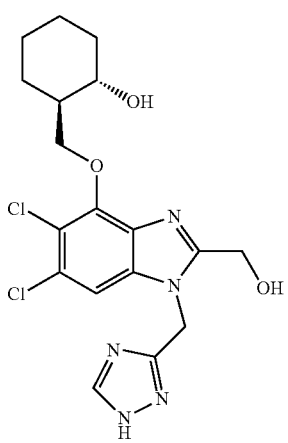 [SMILES: OCc1nc2c(OC[C@H]3CCCC[C@@H]3O)c(Cl)c(Cl)cc2n1Cc1nc[nH]n1]
I-392

TABLE 3-continued
Exemplary Compounds
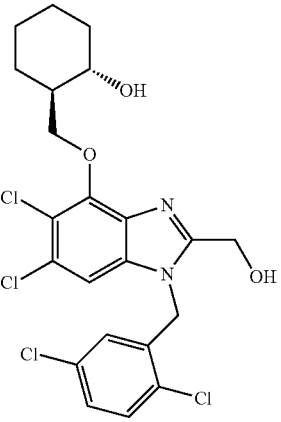 [SMILES: OCc1nc2c(OC[C@H]3CCCC[C@@H]3O)c(Cl)c(Cl)cc2n1Cc1cc(Cl)ccc1Cl]
I-393
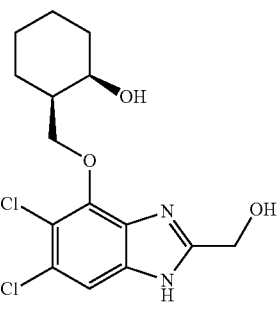 [SMILES: OCc1nc2c(OC[C@H]3CCCC[C@H]3O)c(Cl)c(Cl)cc2[nH]1]
I-394
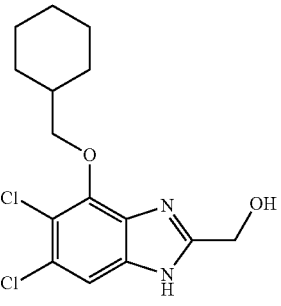 [SMILES: OCc1nc2c(OCC3CCCCC3)c(Cl)c(Cl)cc2[nH]1]
I-395
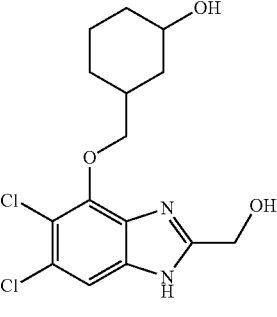 [SMILES: OCc1nc2c(OCC3CCCC(O)C3)c(Cl)c(Cl)cc2[nH]1]
I-396
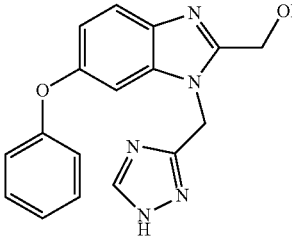
I-397

TABLE 3-continued
Exemplary Compounds
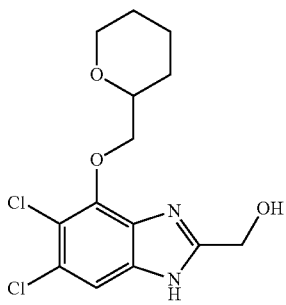 [SMILES: OCc1nc2c(OCC3CCCCO3)c(Cl)c(Cl)cc2[nH]1]
I-398
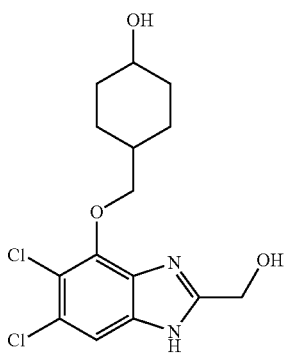 [SMILES: OCc1nc2c(OCC3CCC(O)CC3)c(Cl)c(Cl)cc2[nH]1]
I-399
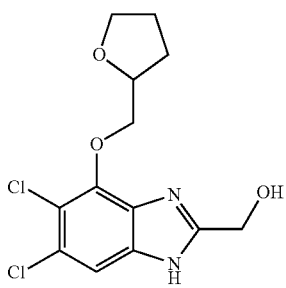 [SMILES: OCc1nc2c(OCC3CCCO3)c(Cl)c(Cl)cc2[nH]1]
I-400
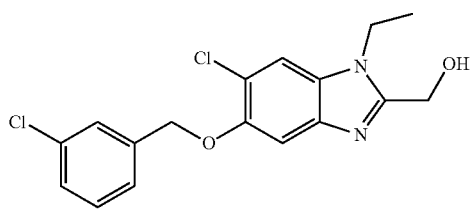 [SMILES: CCn1c(CO)nc2cc(OCc3cccc(Cl)c3)c(Cl)cc21]
I-401
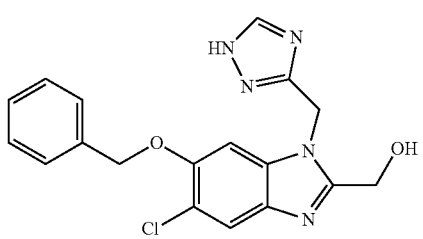 [SMILES: OCc1nc2cc(Cl)c(OCc3ccccc3)cc2n1Cc1nc[nH]n1]
I-402

TABLE 3-continued
Exemplary Compounds
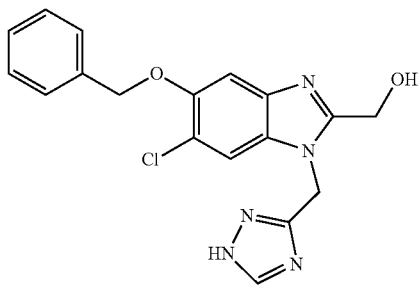 [SMILES: OCc1nc2cc(OCc3ccccc3)c(Cl)cc2n1Cc1nc[nH]n1]
I-403
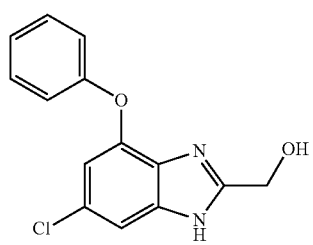 [SMILES: OCc1nc2c(Oc3ccccc3)cc(Cl)cc2[nH]1]
I-404
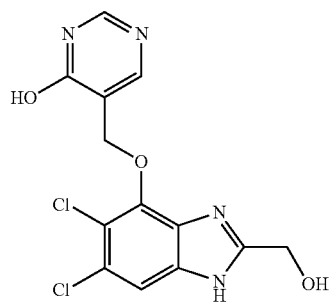 [SMILES: OCc1nc2c(OCc3cncnc3O)c(Cl)c(Cl)cc2[nH]1]
I-405
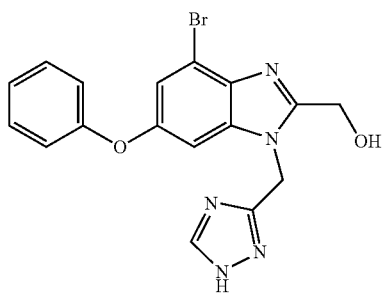 [SMILES: OCc1nc2c(Br)cc(Oc3ccccc3)cc2n1Cc1nc[nH]n1]
I-406
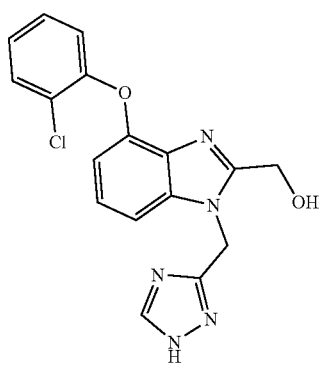 [SMILES: OCc1nc2c(Oc3ccccc3Cl)cccc2n1Cc1nc[nH]n1]
I-407

TABLE 3-continued
Exemplary Compounds
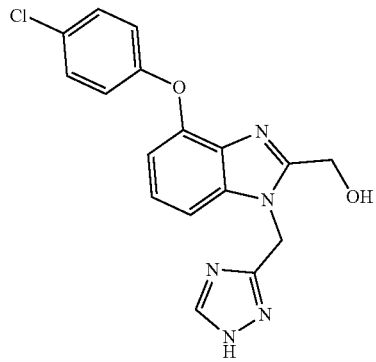 [SMILES: OCc1nc2c(Oc3ccc(Cl)cc3)cccc2n1Cc1nc[nH]n1]
I-408
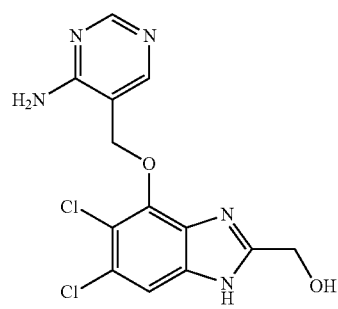 [SMILES: Nc1ncncc1COc1c(Cl)c(Cl)cc2[nH]c(CO)nc12]
I-409
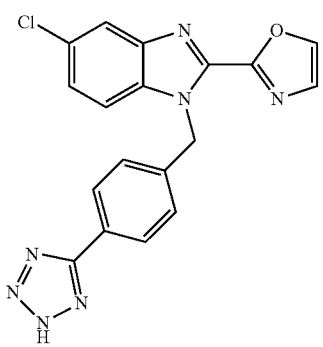 [SMILES: Clc1ccc2c(c1)nc(-c1ncco1)n2Cc1ccc(-c2nn[nH]n2)cc1]
I-410
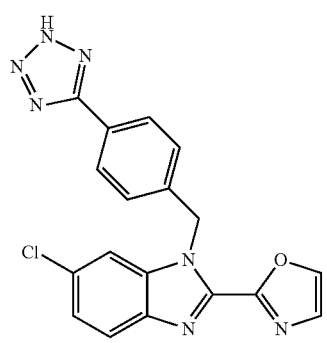 [SMILES: Clc1ccc2nc(-c3ncco3)n(Cc3ccc(-c4nn[nH]n4)cc3)c2c1]
I-411

TABLE 3-continued
Exemplary Compounds
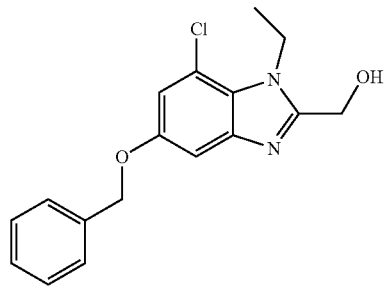 [SMILES: CCn1c(CO)nc2cc(OCc3ccccc3)cc(Cl)c21] I-412
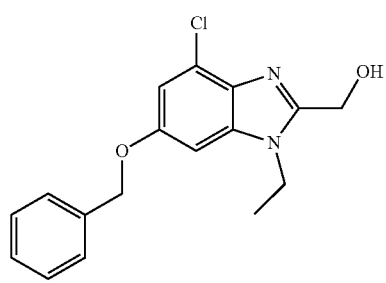 [SMILES: CCn1c(CO)nc2c(Cl)cc(OCc3ccccc3)cc21] I-413
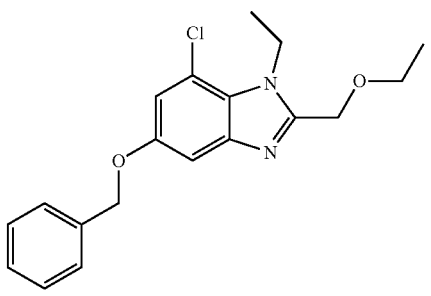 [SMILES: CCOCc1nc2cc(OCc3ccccc3)cc(Cl)c2n1CC] I-414
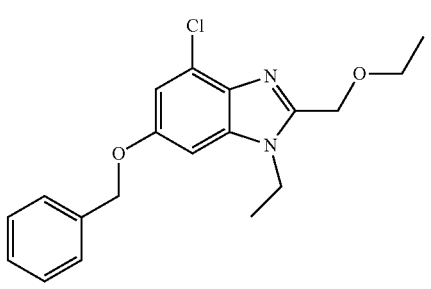 [SMILES: CCOCc1nc2c(Cl)cc(OCc3ccccc3)cc2n1CC] I-415
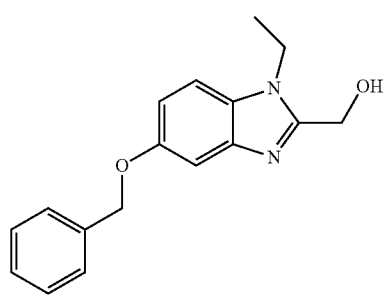 [SMILES: CCn1c(CO)nc2cc(OCc3ccccc3)ccc21] I-416

TABLE 3-continued

Exemplary Compounds

I-417

I-418

I-419

I-420

I-421

TABLE 3-continued
Exemplary Compounds
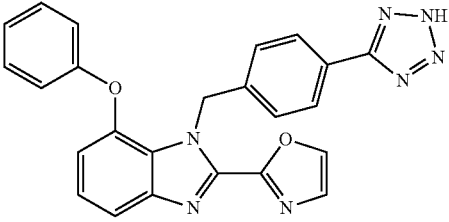 [SMILES: c1ccc(Oc2cccc3nc(-c4ncco4)n(Cc4ccc(-c5nn[nH]n5)cc4)c23)cc1] I-422
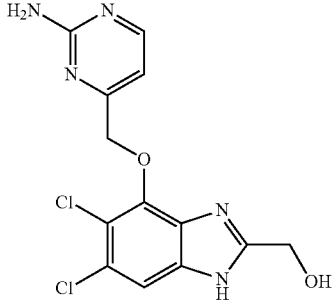 [SMILES: Nc1nccc(COc2c(Cl)c(Cl)cc3[nH]c(CO)nc23)n1] I-423
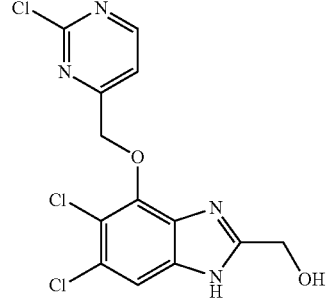 [SMILES: OCc1nc2c(OCc3ccnc(Cl)n3)c(Cl)c(Cl)cc2[nH]1] I-424
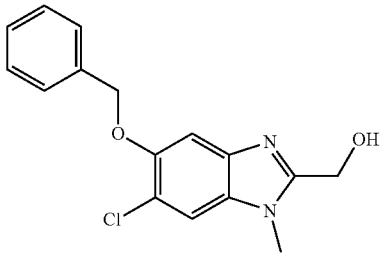 [SMILES: Cn1c(CO)nc2cc(OCc3ccccc3)c(Cl)cc21] I-425
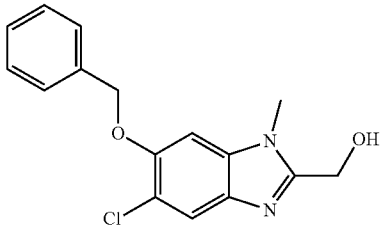 [SMILES: Cn1c(CO)nc2cc(Cl)c(OCc3ccccc3)cc21] I-426
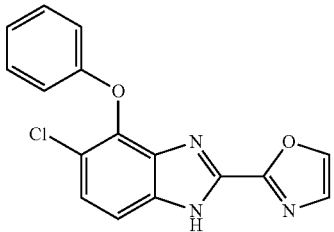 [SMILES: Clc1ccc2[nH]c(-c3ncco3)nc2c1Oc1ccccc1] I-427

TABLE 3-continued
Exemplary Compounds
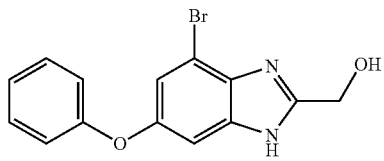 [SMILES: OCc1nc2c(Br)cc(Oc3ccccc3)cc2[nH]1] I-428
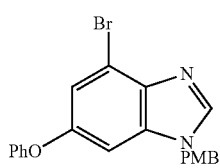 I-429
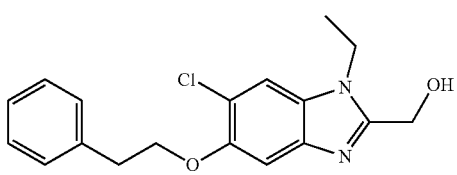 [SMILES: CCn1c(CO)nc2cc(OCCc3ccccc3)c(Cl)cc21] I-430
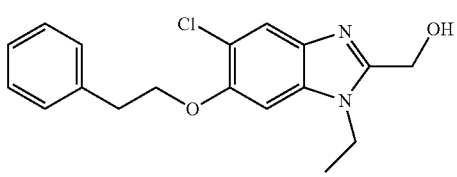 [SMILES: CCn1c(CO)nc2cc(Cl)c(OCCc3ccccc3)cc21] I-431
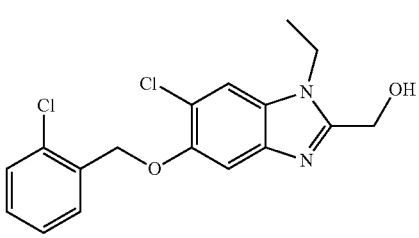 [SMILES: CCn1c(CO)nc2cc(OCc3ccccc3Cl)c(Cl)cc21] I-432
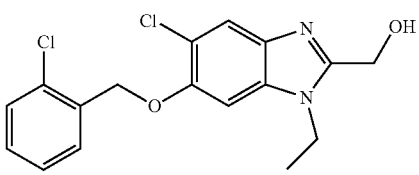 [SMILES: CCn1c(CO)nc2cc(Cl)c(OCc3ccccc3Cl)cc21] I-433
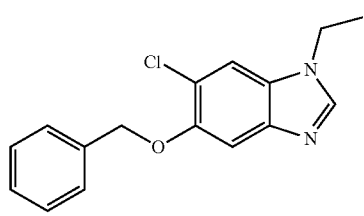 [SMILES: CCn1cnc2cc(OCc3ccccc3)c(Cl)cc21] I-434
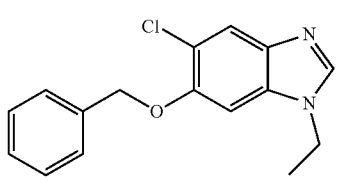 [SMILES: CCn1cnc2cc(Cl)c(OCc3ccccc3)cc21] I-435

TABLE 3-continued
| Exemplary Compounds | |
|---|---|
| 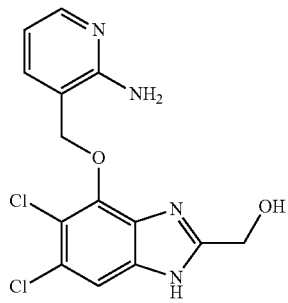 [SMILES: Nc1ncccc1COc1c(Cl)c(Cl)cc2[nH]c(CO)nc12] | I-436 |
| 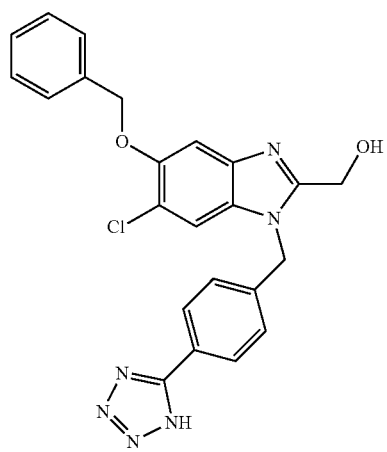 [SMILES: OCc1nc2cc(OCc3ccccc3)c(Cl)cc2n1Cc1ccc(-c2nnn[nH]2)cc1] | I-437 |
| 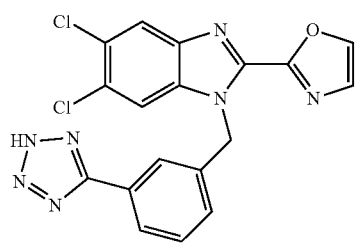 [SMILES: Clc1cc2nc(-c3ncco3)n(Cc3cccc(-c4nn[nH]n4)c3)c2cc1Cl] | I-438 |
| 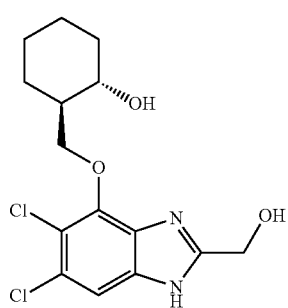 [SMILES: OCc1nc2c(OC[C@H]3CCCC[C@@H]3O)c(Cl)c(Cl)cc2[nH]1] | I-439 |

TABLE 3-continued
Exemplary Compounds
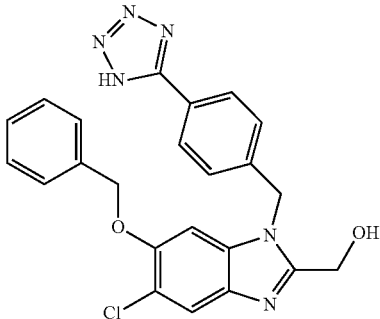 [SMILES: OCc1nc2cc(Cl)c(OCc3ccccc3)cc2n1Cc1ccc(-c2nnn[nH]2)cc1]
I-440
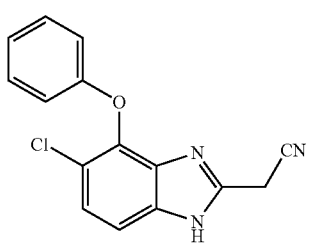 [SMILES: N#CCc1nc2c(Oc3ccccc3)c(Cl)ccc2[nH]1]
I-441
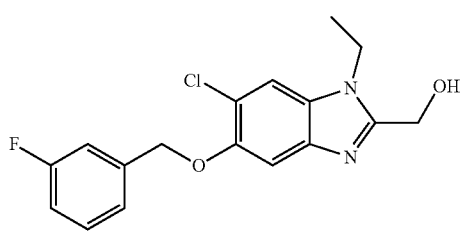 [SMILES: CCn1c(CO)nc2cc(OCc3cccc(F)c3)c(Cl)cc21]
I-442
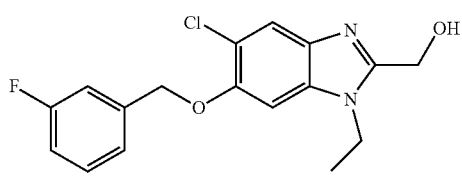 [SMILES: CCn1c(CO)nc2cc(Cl)c(OCc3cccc(F)c3)cc21]
I-443
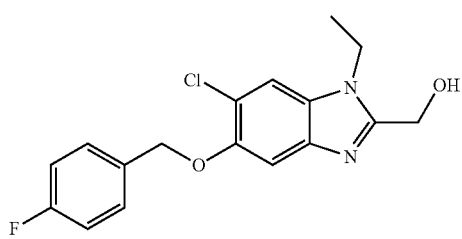 [SMILES: CCn1c(CO)nc2cc(OCc3ccc(F)cc3)c(Cl)cc21]
I-444
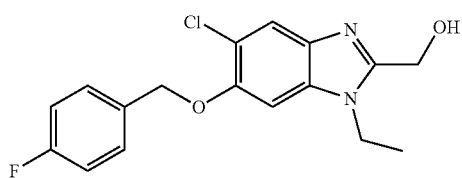 [SMILES: CCn1c(CO)nc2cc(Cl)c(OCc3ccc(F)cc3)cc21]
I-445

TABLE 3-continued
Exemplary Compounds
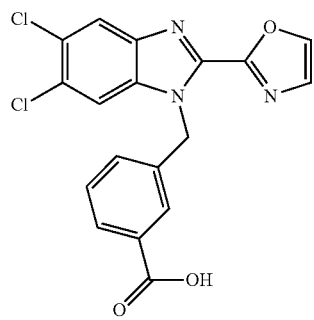 [SMILES: O=C(O)c1cccc(Cn2c(-c3ncco3)nc3cc(Cl)c(Cl)cc32)c1] I-446
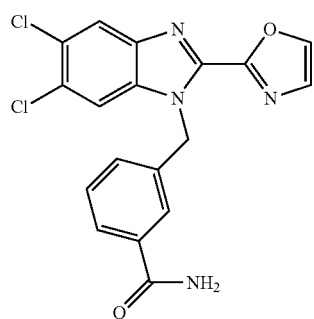 I-447
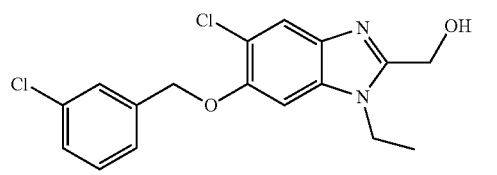 [SMILES: CCn1c(CO)nc2cc(Cl)c(OCc3cccc(Cl)c3)cc21] I-448
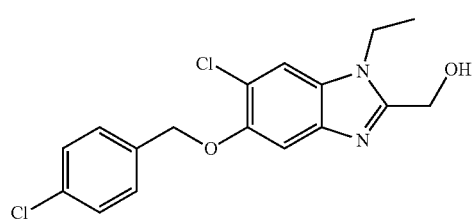 [SMILES: CCn1c(CO)nc2cc(OCc3ccc(Cl)cc3)c(Cl)cc21] I-449
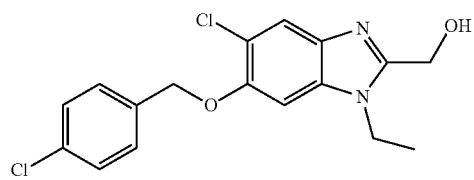 [SMILES: CCn1c(CO)nc2cc(Cl)c(OCc3ccc(Cl)cc3)cc21] I-450
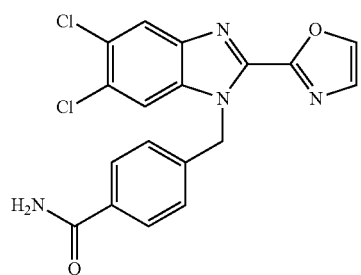 [SMILES: NC(=O)c1ccc(Cn2c(-c3ncco3)nc3cc(Cl)c(Cl)cc32)cc1] I-451

223
224
TABLE 3-continued
Exemplary Compounds
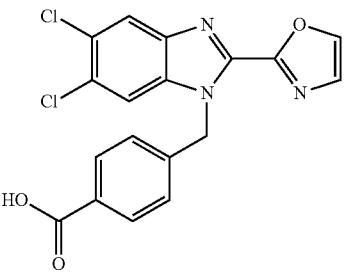 [SMILES: O=C(O)c1ccc(Cn2c(-c3ncco3)nc3cc(Cl)c(Cl)cc32)cc1] I-452
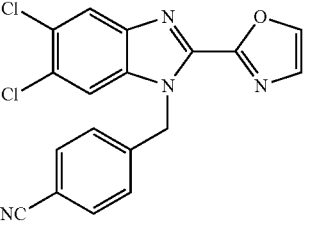 [SMILES: N#Cc1ccc(Cn2c(-c3ncco3)nc3cc(Cl)c(Cl)cc32)cc1] I-453
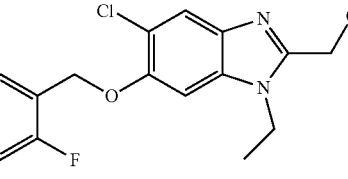 I-454
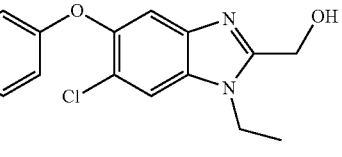 I-455
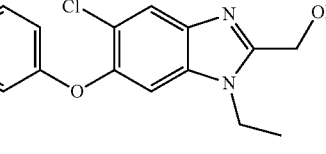 I-456
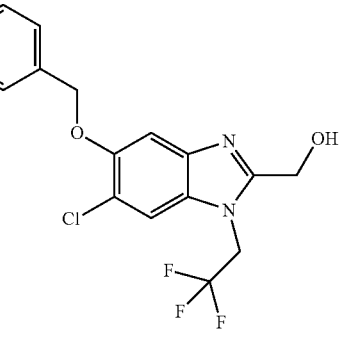 I-457
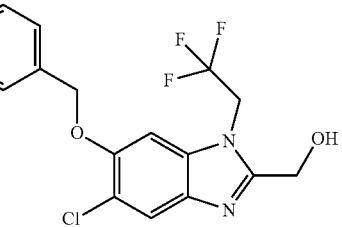 I-458

TABLE 3-continued
Exemplary Compounds
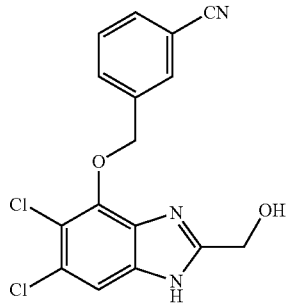 [SMILES: N#Cc1cccc(COc2c(Cl)c(Cl)cc3[nH]c(CO)nc23)c1]
I-459
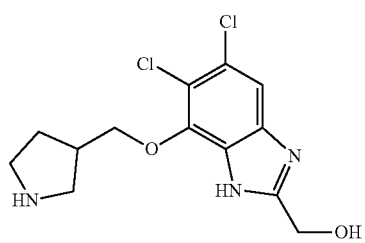 [SMILES: OCc1nc2cc(Cl)c(Cl)c(OCC3CCNC3)c2[nH]1]
I-460
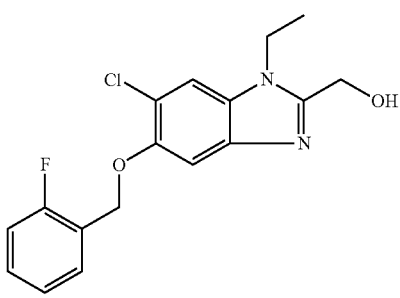 [SMILES: CCn1c(CO)nc2cc(OCc3ccccc3F)c(Cl)cc21]
I-461
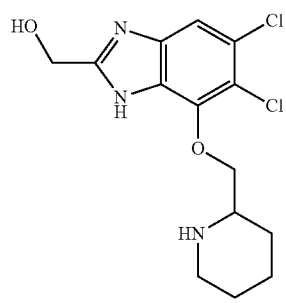 [SMILES: OCc1nc2cc(Cl)c(Cl)c(OCC3CCCCN3)c2[nH]1]
I-462
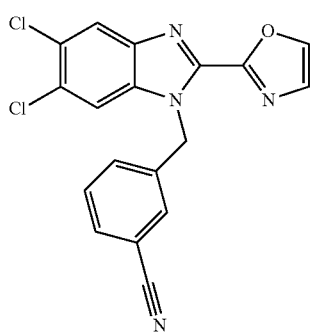 [SMILES: N#Cc1cccc(Cn2c(-c3ncco3)nc3cc(Cl)c(Cl)cc32)c1]
I-463

TABLE 3-continued
Exemplary Compounds
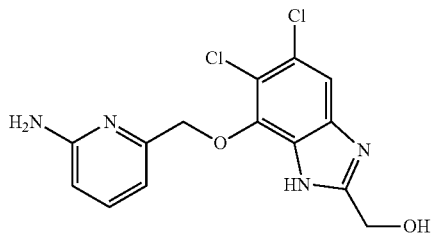 [SMILES: Nc1cccc(COc2c(Cl)c(Cl)cc3nc(CO)[nH]c23)n1]
I-464
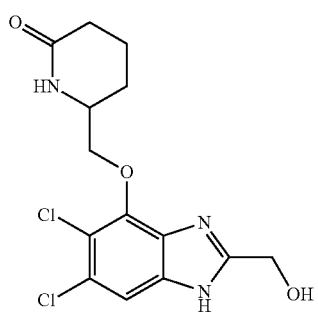 [SMILES: O=C1CCCC(COc2c(Cl)c(Cl)cc3[nH]c(CO)nc23)N1]
I-465
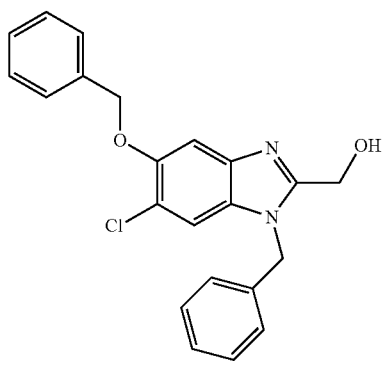 [SMILES: OCc1nc2cc(OCc3ccccc3)c(Cl)cc2n1Cc1ccccc1]
I-466
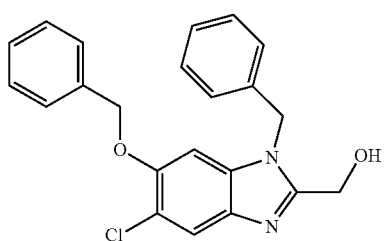 [SMILES: OCc1nc2cc(Cl)c(OCc3ccccc3)cc2n1Cc1ccccc1]
I-467
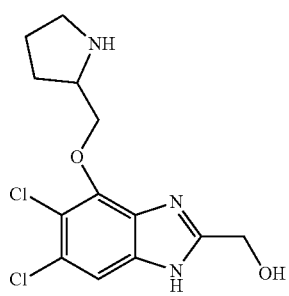 [SMILES: OCc1nc2c(OCC3CCCN3)c(Cl)c(Cl)cc2[nH]1]
I-468

TABLE 3-continued
Exemplary Compounds
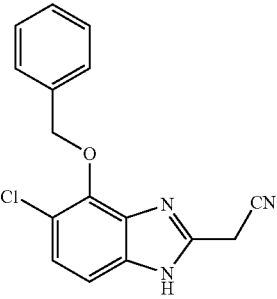 [SMILES: N#CCc1nc2c(OCc3ccccc3)c(Cl)ccc2[nH]1]
I-469
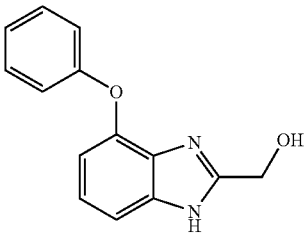 [SMILES: OCc1nc2c(Oc3ccccc3)cccc2[nH]1]
I-470
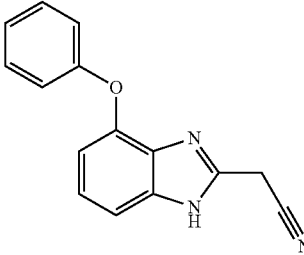
I-471
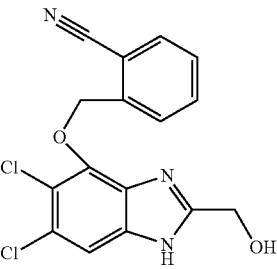 [SMILES: N#Cc1ccccc1COc1c(Cl)c(Cl)cc2[nH]c(CO)nc12]
I-472
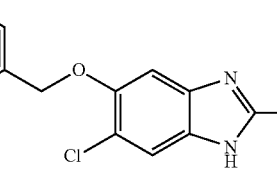
I-473
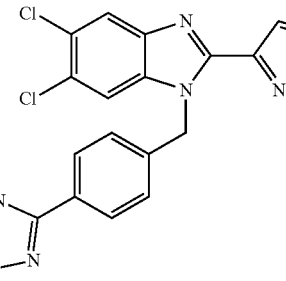
I-474

TABLE 3-continued
Exemplary Compounds
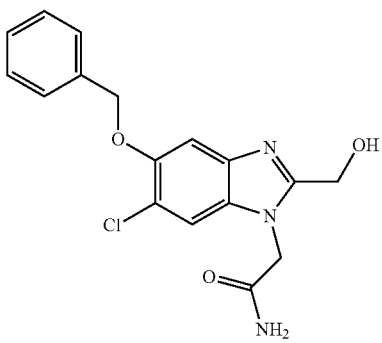 [SMILES: NC(=O)Cn1c(CO)nc2cc(OCc3ccccc3)c(Cl)cc21]
I-475
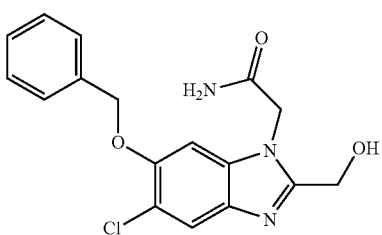 [SMILES: NC(=O)Cn1c(CO)nc2cc(Cl)c(OCc3ccccc3)cc21]
I-476
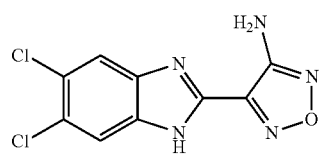 [SMILES: Nc1nonc1-c1nc2cc(Cl)c(Cl)cc2[nH]1]
I-477
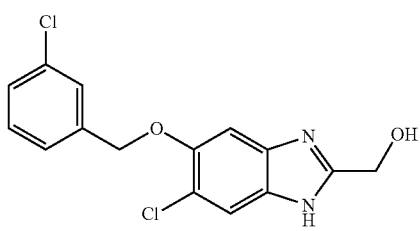 [SMILES: OCc1nc2cc(OCc3cccc(Cl)c3)c(Cl)cc2[nH]1]
I-478
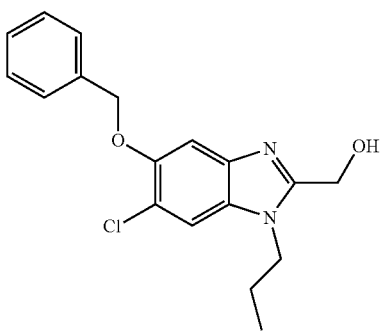 [SMILES: CCCn1c(CO)nc2cc(OCc3ccccc3)c(Cl)cc21]
I-479
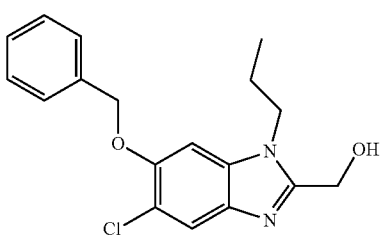 [SMILES: CCCn1c(CO)nc2cc(Cl)c(OCc3ccccc3)cc21]
I-480

TABLE 3-continued

Exemplary Compounds

I-481

I-482

I-483

I-484

I-485

I-486

TABLE 3-continued
Exemplary Compounds
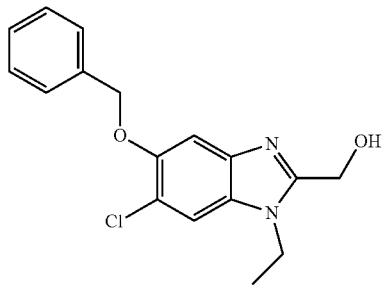 [SMILES: CCn1c(CO)nc2cc(OCc3ccccc3)c(Cl)cc21]
I-487
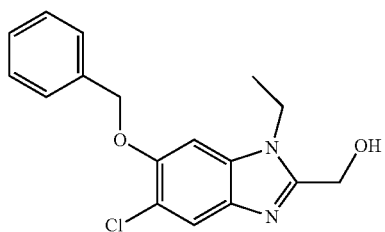 [SMILES: CCn1c(CO)nc2cc(Cl)c(OCc3ccccc3)cc21]
I-488
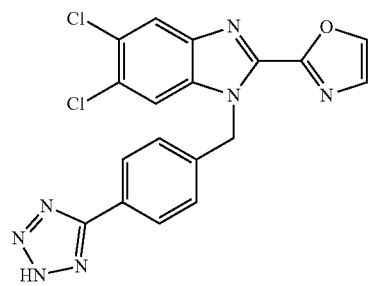 [SMILES: Clc1cc2nc(-c3ncco3)n(Cc3ccc(-c4nn[nH]n4)cc3)c2cc1Cl]
I-489
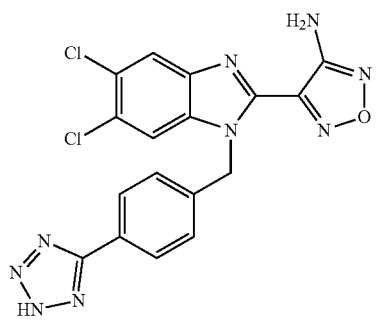 [SMILES: Nc1nonc1-c1nc2cc(Cl)c(Cl)cc2n1Cc1ccc(-c2nn[nH]n2)cc1]
I-490
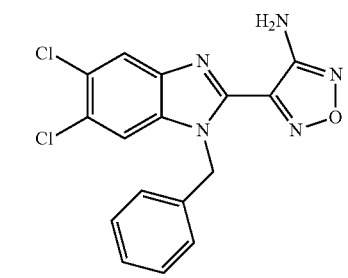 [SMILES: Nc1nonc1-c1nc2cc(Cl)c(Cl)cc2n1Cc1ccccc1]
I-491

TABLE 3-continued
Exemplary Compounds
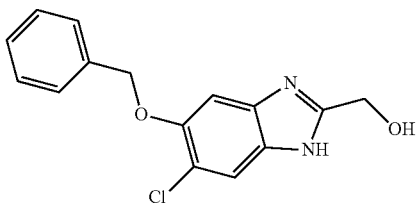 [SMILES: OCc1nc2cc(OCc3ccccc3)c(Cl)cc2[nH]1]
I-492
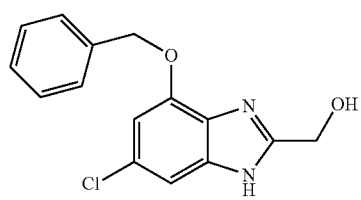 [SMILES: OCc1nc2c(OCc3ccccc3)cc(Cl)cc2[nH]1]
I-493
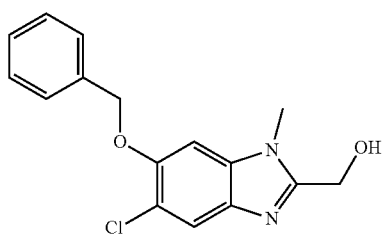 [SMILES: Cn1c(CO)nc2cc(Cl)c(OCc3ccccc3)cc21]
I-692
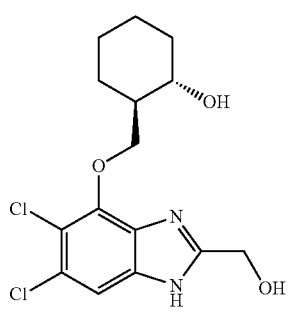 [SMILES: OCc1nc2c(OC[C@H]3CCCC[C@@H]3O)c(Cl)c(Cl)cc2[nH]1]
I-693
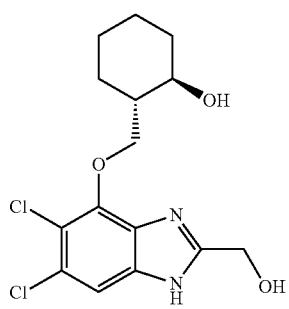 [SMILES: OCc1nc2c(OC[C@@H]3CCCC[C@H]3O)c(Cl)c(Cl)cc2[nH]1]
I-694

In some embodiments, the present invention provides a compound set forth in Table 3, above, or a pharmaceutically acceptable salt thereof.
Additional compounds are set forth in Table 4, below.
TABLE 4
Compounds
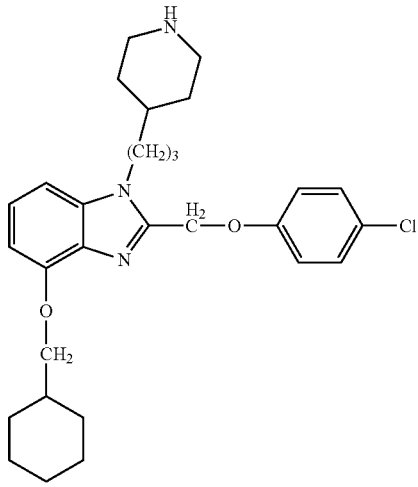
I-494
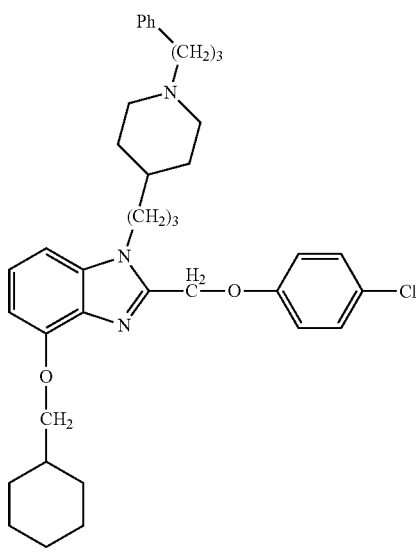
I-495
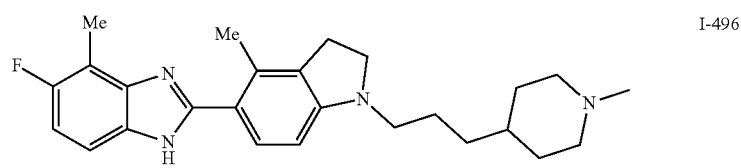
I-496

TABLE 4-continued
Compounds
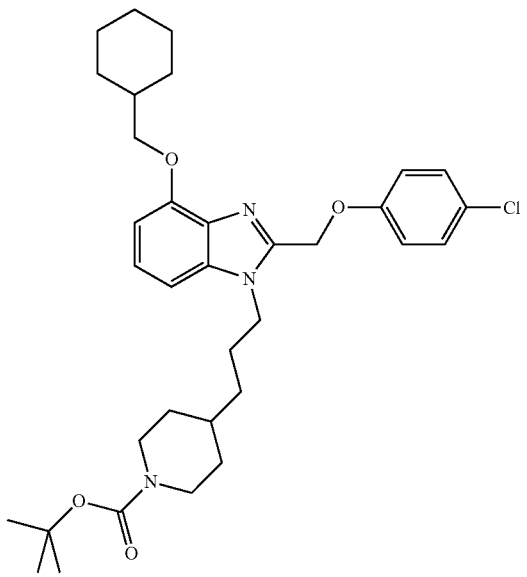 [SMILES: CC(C)(C)OC(=O)N1CCC(CCCn2c(COc3ccc(Cl)cc3)nc3c(OCC4CCCCC4)cccc32)CC1]
I-497
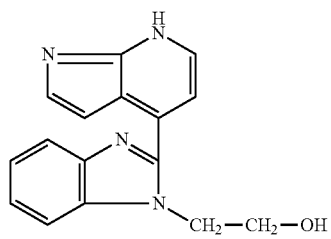 [SMILES: OCCn1c(-c2cc[nH]c3nccc2-3)nc2ccccc21]
I-498
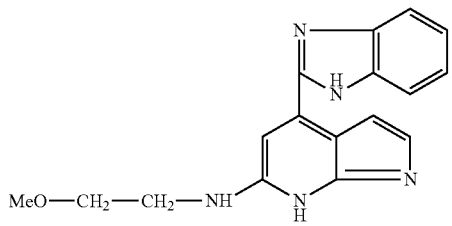 [SMILES: COCCNc1cc(-c2nc3ccccc3[nH]2)c2ccnc-2[nH]1]
I-499
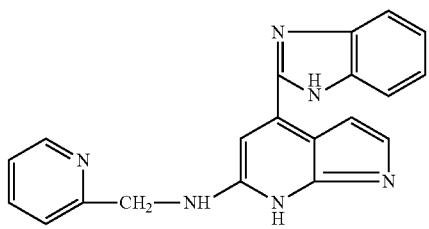 [SMILES: c1ccc(CNc2cc(-c3nc4ccccc4[nH]3)c3ccnc-3[nH]2)nc1]
I-500
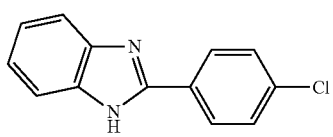 [SMILES: Clc1ccc(-c2nc3ccccc3[nH]2)cc1]
I-501
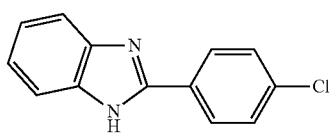 [SMILES: Clc1ccc(-c2nc3ccccc3[nH]2)cc1]
I-502

TABLE 4-continued
| Compounds | |
|---|---|
| 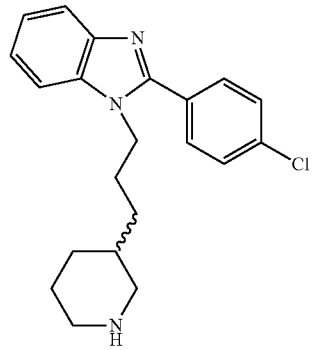 [SMILES: Clc1ccc(-c2nc3ccccc3n2CCCC2CCCNC2)cc1] | I-503 |
| 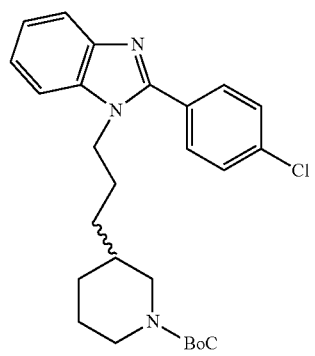 | I-504 |
| 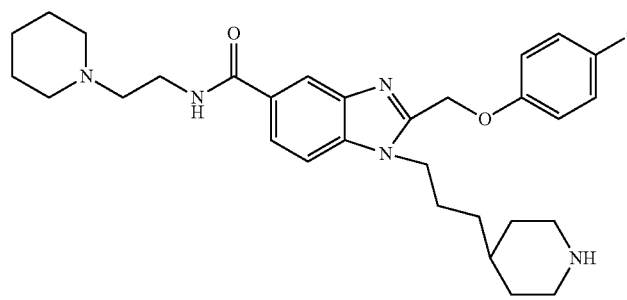 | I-505 |

TABLE 4-continued
Compounds
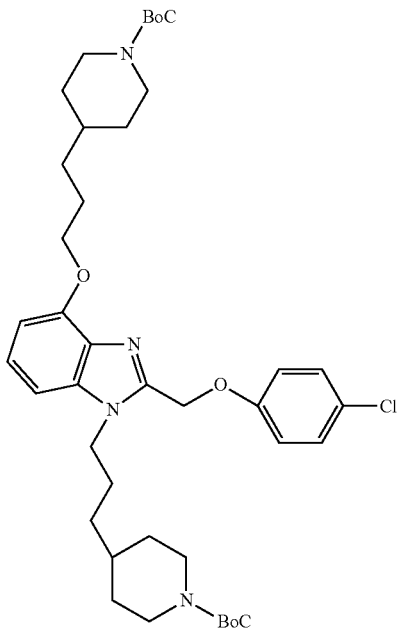
I-506
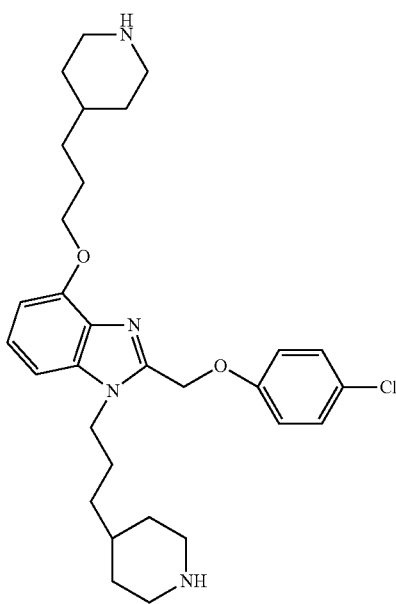 [SMILES: Clc1ccc(OCc2nc3c(OCCCC4CCNCC4)cccc3n2CCCC2CCNCC2)cc1]
I-507

TABLE 4-continued
Compounds
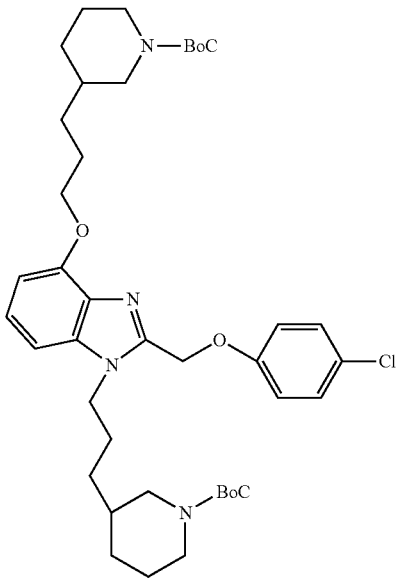
I-508
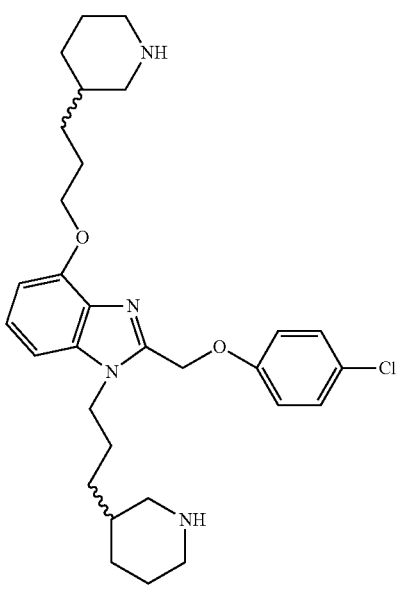 [SMILES: Clc1ccc(OCc2nc3c(OCCCC4CCCNC4)cccc3n2CCCC2CCCNC2)cc1]
I-509

TABLE 4-continued
Compounds
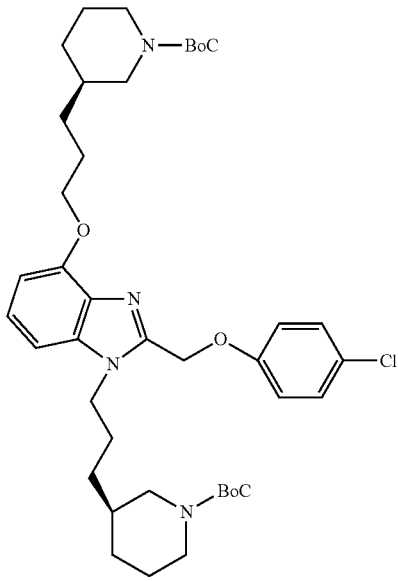
I-510
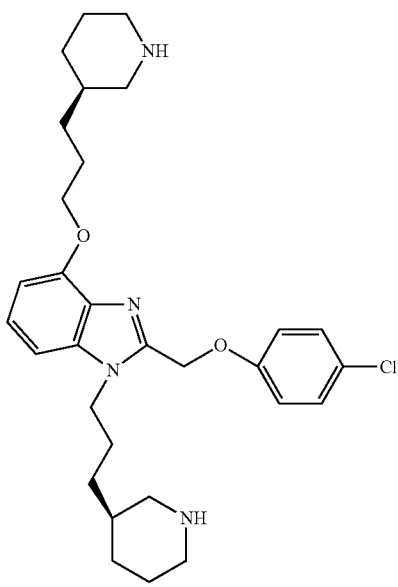 [SMILES: Clc1ccc(OCc2nc3c(OCCC[C@H]4CCCNC4)cccc3n2CCC[C@@H]2CCCNC2)cc1]
I-511

TABLE 4-continued
Compounds
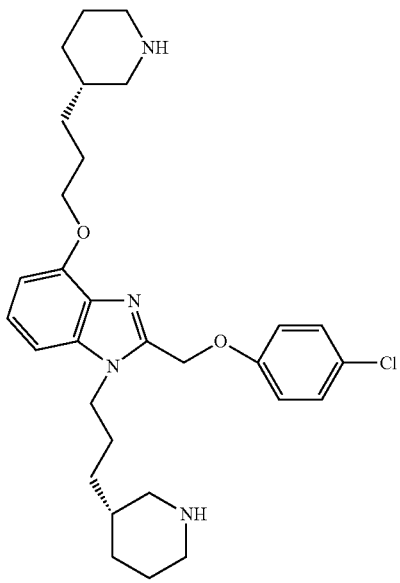 [SMILES: Clc1ccc(OCc2nc3c(OCCC[C@@H]4CCCNC4)cccc3n2CCC[C@H]2CCCNC2)cc1]
I-512
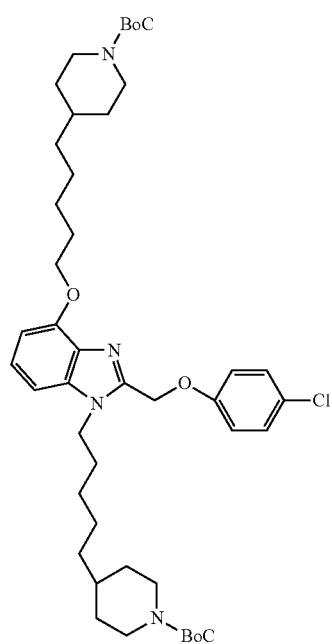
I-513

TABLE 4-continued
| Compounds | |
|---|---|
| 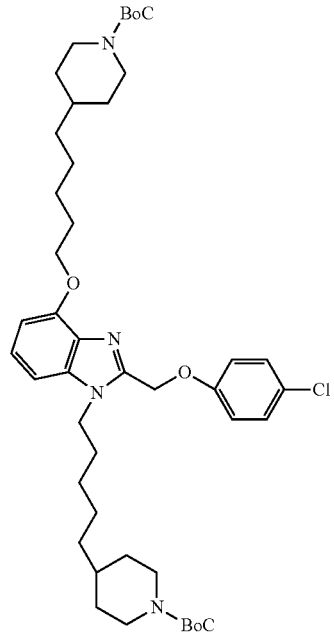 | I-514 |
| 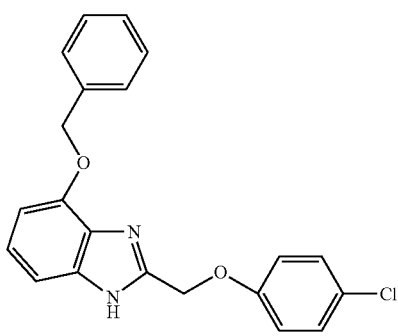 [SMILES: Clc1ccc(OCc2nc3c(OCc4ccccc4)cccc3[nH]2)cc1] | I-515 |
| 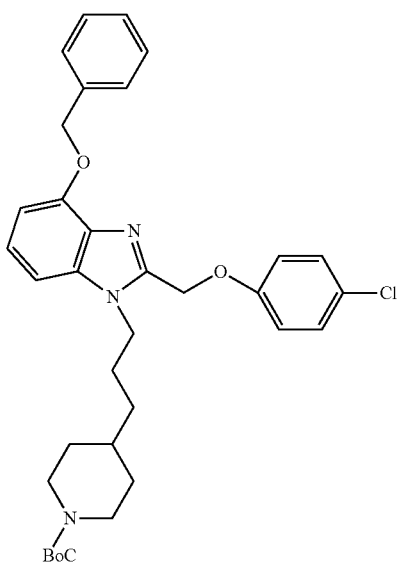 | I-516 |

TABLE 4-continued

Compounds

I-517

I-518

I-519

TABLE 4-continued
Compounds
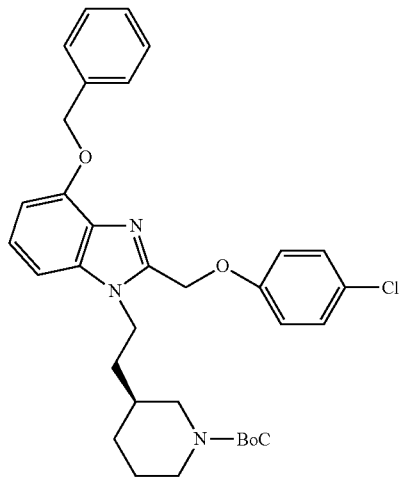
I-520
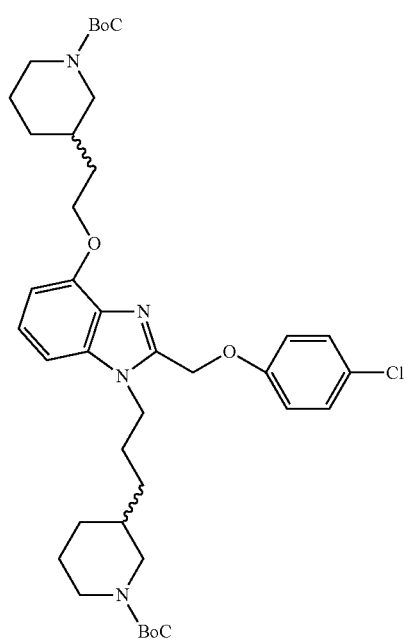
I-521

TABLE 4-continued
| Compounds | |
|---|---|
| 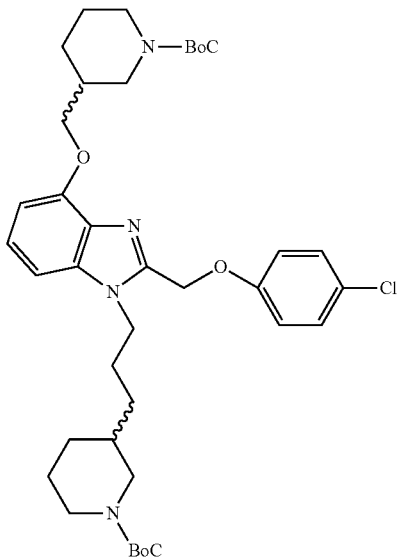 | I-522 |
| 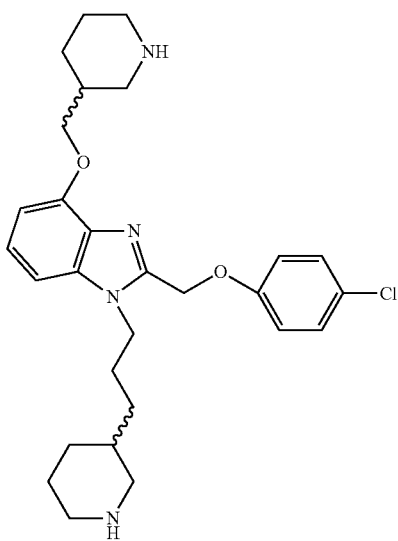 [SMILES: Clc1ccc(OCc2nc3c(OCC4CCCNC4)cccc3n2CCCC2CCCNC2)cc1] | I-523 |

TABLE 4-continued
Compounds
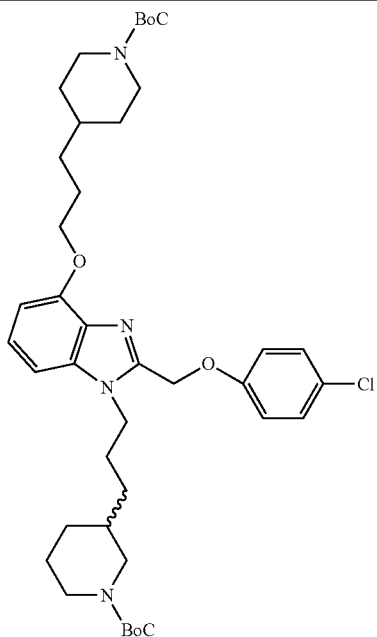
I-524
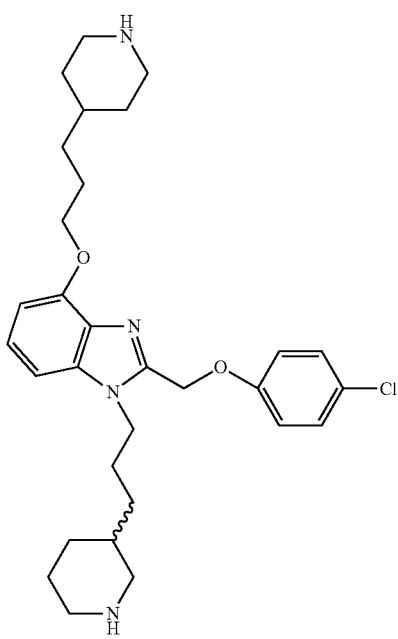 [SMILES: Clc1ccc(OCc2nc3c(OCCCC4CCNCC4)cccc3n2CCCC2CCCNC2)cc1]
I-525

TABLE 4-continued
| Compounds | |
|---|---|
| 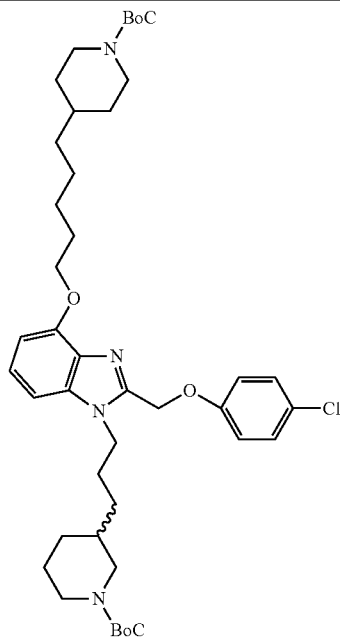 | I-526 |
| 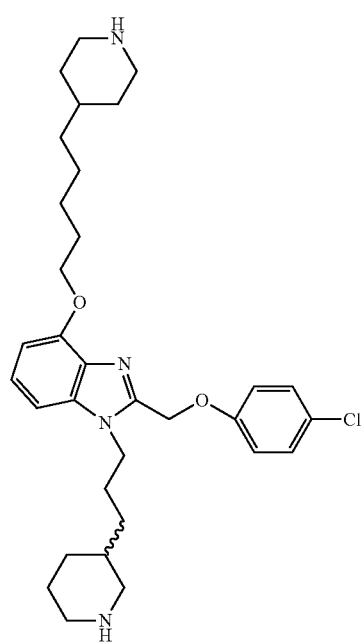 [SMILES: Clc1ccc(OCc2nc3c(OCCCCCC4CCNCC4)cccc3n2CCCC2CCCNC2)cc1] | I-527 |

TABLE 4-continued

| Compounds | |
|---|---|
| (structure of compound with benzimidazole core bearing 4-O-(pentyl)-linked N-Boc-piperidine, 2-(4-chlorophenoxymethyl), and N1-propyl-linked N-Boc-piperidine substituent) | I-528 |
| (structure of compound with benzimidazole core bearing 4-O-(pentyl)-linked N-Boc-piperidine, 2-(4-chlorophenoxymethyl), and N1-propyl-linked N-Boc-piperidine substituent) | I-529 |
| (structure of 4-benzyloxy-2-((4-methylphenoxy)methyl)-1H-benzimidazole) | I-530 |

TABLE 4-continued
| Compounds | |
|---|---|
| 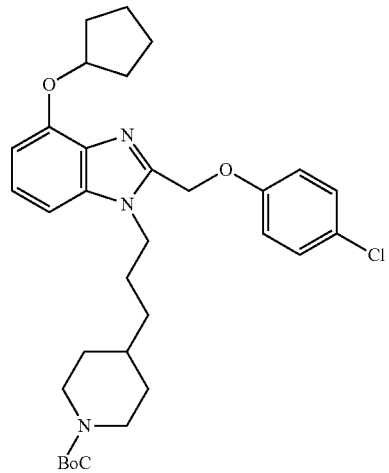 | I-531 |
| 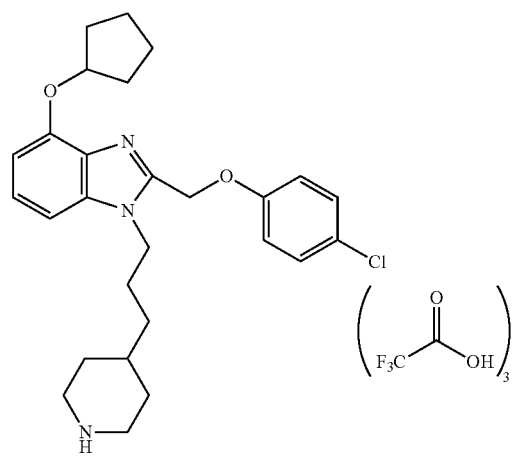 | I-532 |
| 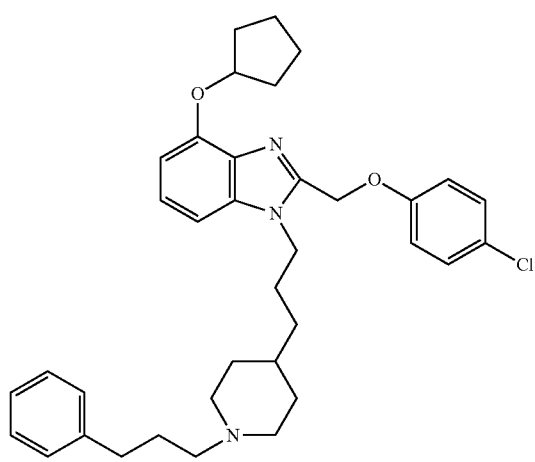 [SMILES: Clc1ccc(OCc2nc3c(OC4CCCC4)cccc3n2CCCC2CCN(CCCc3ccccc3)CC2)cc1] | I-533 |

TABLE 4-continued

Compounds

I-534

I-535

I-536

TABLE 4-continued
| Compounds |
|---|
| 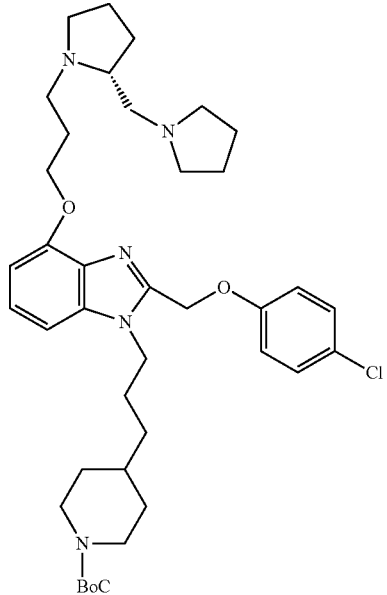 I-537 |
| 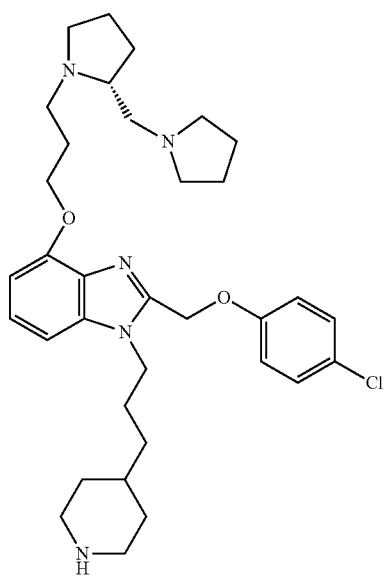 [SMILES: Clc1ccc(OCc2nc3c(OCCCN4CCC[C@@H]4CN4CCCC4)cccc3n2CCCC2CCNCC2)cc1] I-538 |

TABLE 4-continued
Compounds
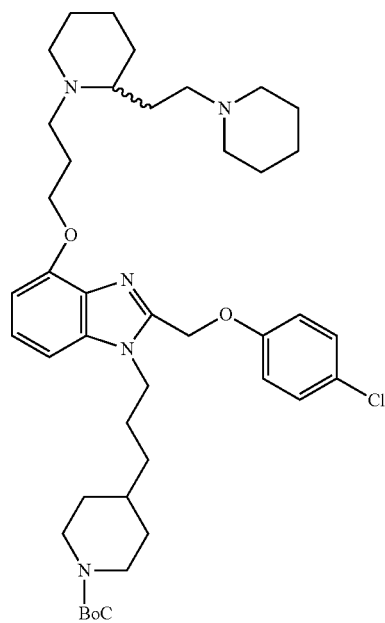
I-539
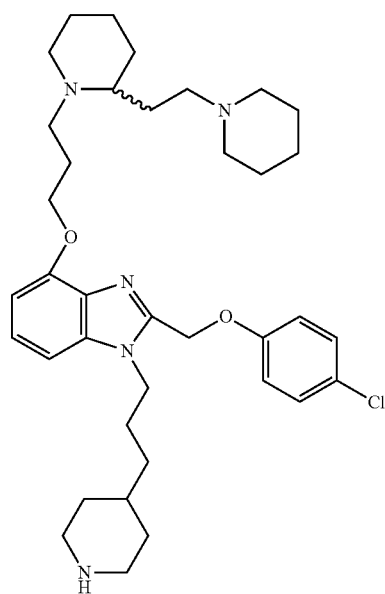 [SMILES: Clc1ccc(OCc2nc3c(OCCCN4CCCCC4CCN4CCCCC4)cccc3n2CCCC2CCNCC2)cc1]
I-540

TABLE 4-continued
| Compounds | |
|---|---|
| 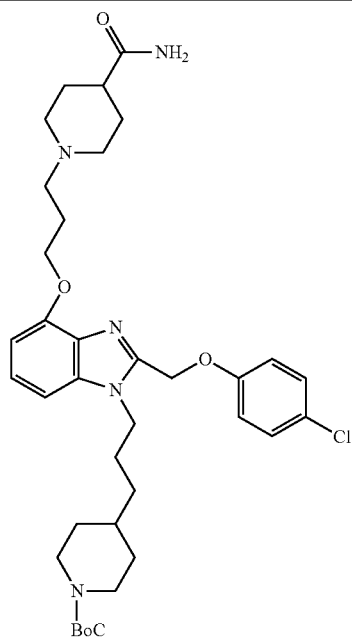 | I-541 |
| 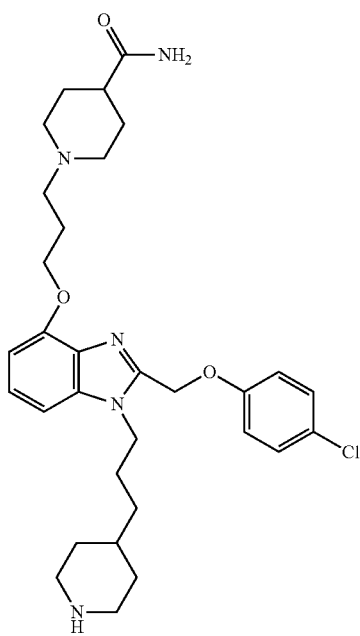 [SMILES: NC(=O)C1CCN(CCCOc2cccc3c2nc(COc2ccc(Cl)cc2)n3CCCC2CCNCC2)CC1] | I-542 |

TABLE 4-continued
Compounds
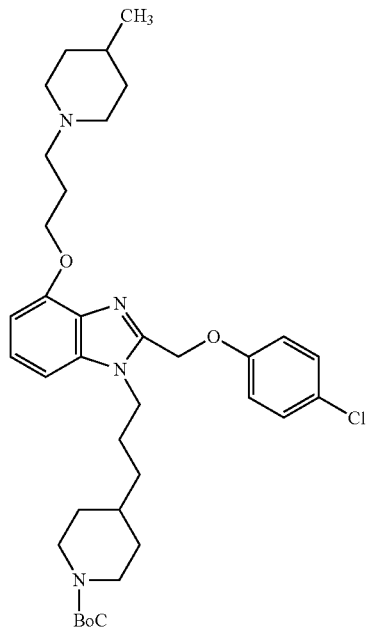
I-543
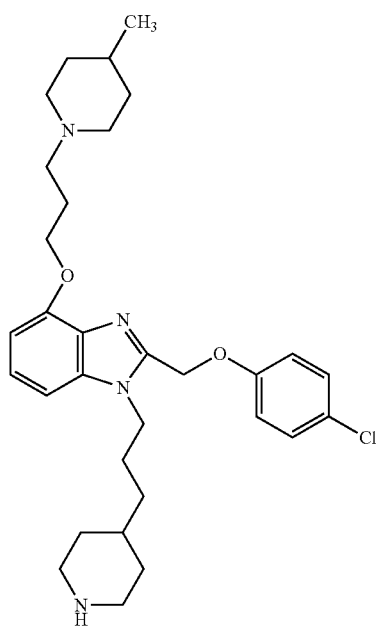 [SMILES: CC1CCN(CCCOc2cccc3c2nc(COc2ccc(Cl)cc2)n3CCCC2CCNCC2)CC1]
I-544

TABLE 4-continued
Compounds
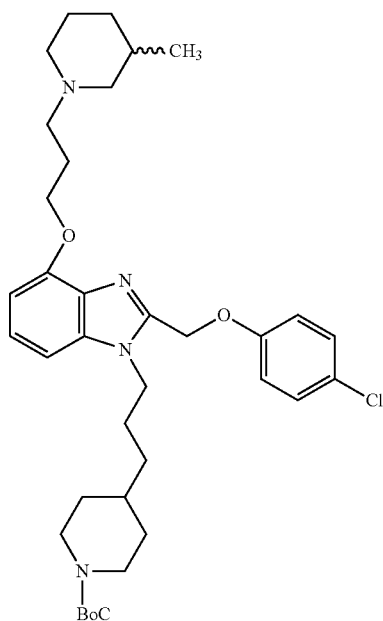
I-545
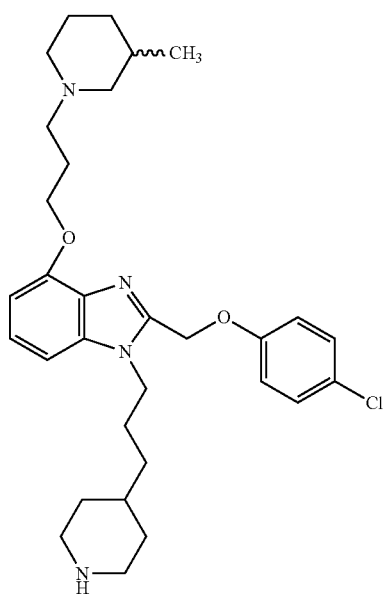 [SMILES: CC1CCCN(CCCOc2cccc3c2nc(COc2ccc(Cl)cc2)n3CCCC2CCNCC2)C1]
I-546

TABLE 4-continued
Compounds
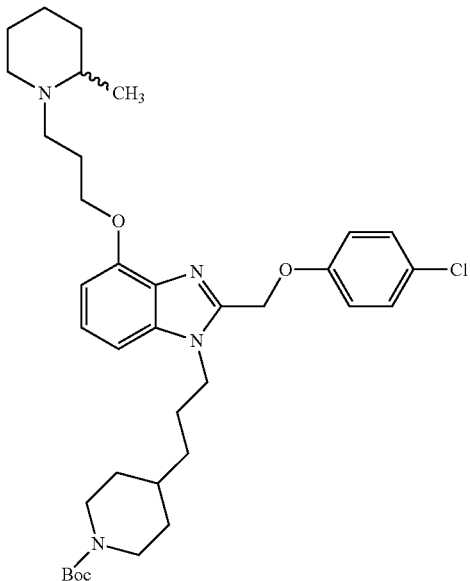 [SMILES: CC1CCCCN1CCCOc1cccc2c1nc(COc1ccc(Cl)cc1)n2CCCC1CCN(C(=O)OC(C)(C)C)CC1]
I-547
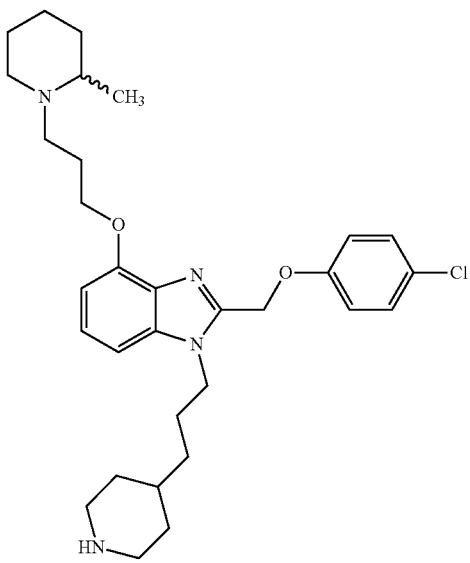 [SMILES: CC1CCCCN1CCCOc1cccc2c1nc(COc1ccc(Cl)cc1)n2CCCC1CCNCC1]
I-548
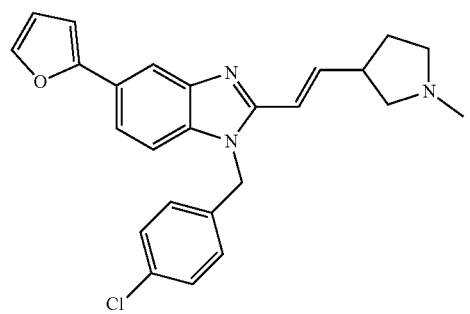 [SMILES: CN1CCC(/C=C/c2nc3cc(-c4ccco4)ccc3n2Cc2ccc(Cl)cc2)C1]
I-549

TABLE 4-continued
| Compounds | |
|---|---|
| 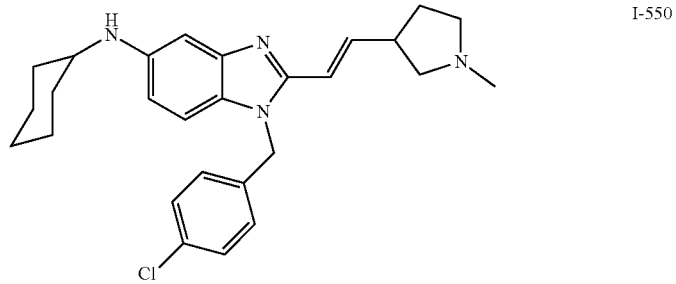 | I-550 |
| 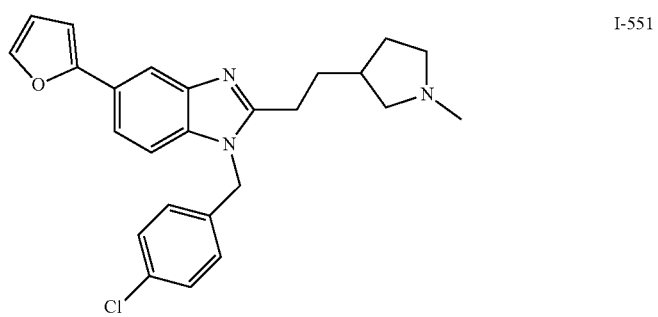 | I-551 |
| 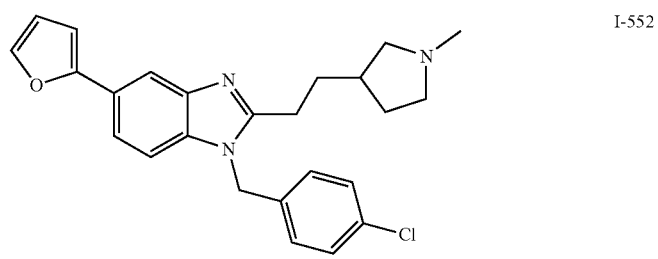 | I-552 |
| 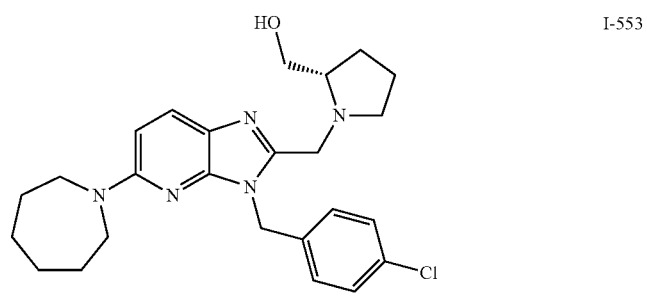 | I-553 |
| 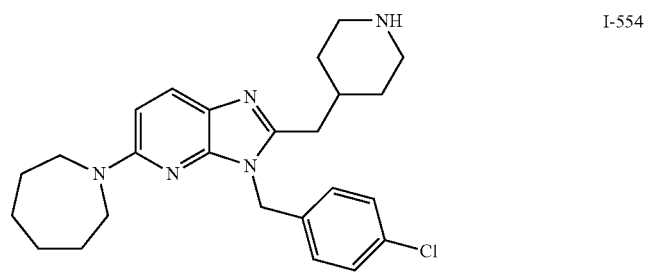 | I-554 |

TABLE 4-continued
| Compounds | |
|---|---|
| 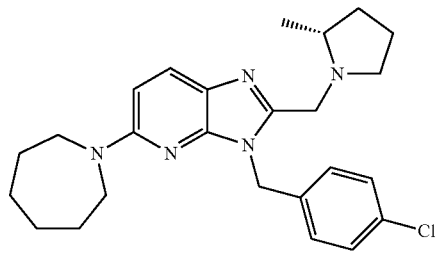 [SMILES: C[C@@H]1CCCN1Cc1nc2ccc(N3CCCCCC3)nc2n1Cc1ccc(Cl)cc1] | I-555 |
| 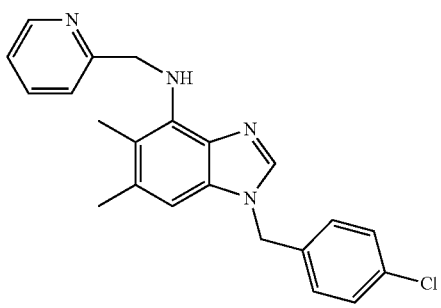 [SMILES: Cc1cc2c(ncn2Cc2ccc(Cl)cc2)c(NCc2ccccn2)c1C] | I-556 |
| 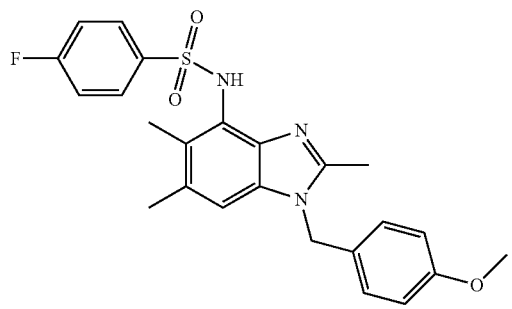 [SMILES: COc1ccc(Cn2c(C)nc3c(NS(=O)(=O)c4ccc(F)cc4)c(C)c(C)cc32)cc1] | I-557 |
| 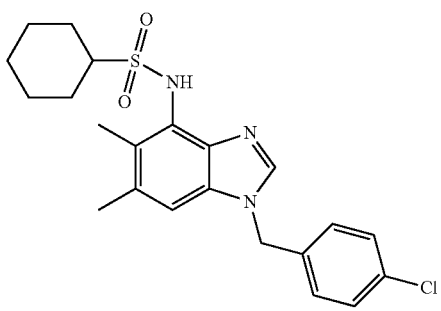 [SMILES: Cc1cc2c(ncn2Cc2ccc(Cl)cc2)c(NS(=O)(=O)C2CCCCC2)c1C] | I-558 |
| 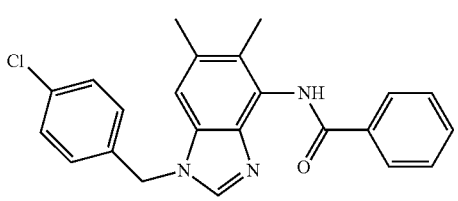 [SMILES: Cc1cc2c(ncn2Cc2ccc(Cl)cc2)c(NC(=O)c2ccccc2)c1C] | I-559 |

TABLE 4-continued
| Compounds | |
|---|---|
| 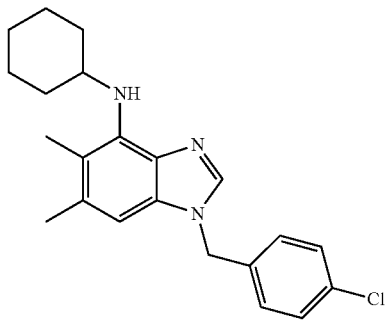 [SMILES: Cc1cc2c(ncn2Cc2ccc(Cl)cc2)c(NC2CCCCC2)c1C] | I-560 |
| 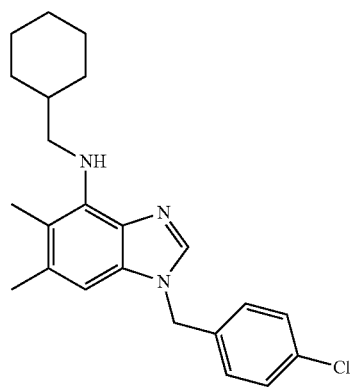 [SMILES: Cc1cc2c(ncn2Cc2ccc(Cl)cc2)c(NCC2CCCCC2)c1C] | I-561 |
| 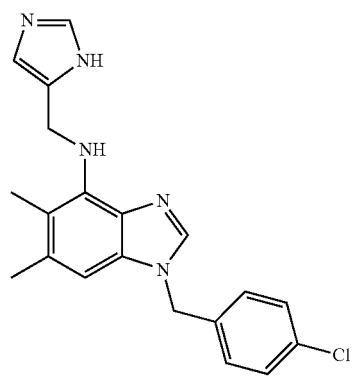 [SMILES: Cc1cc2c(ncn2Cc2ccc(Cl)cc2)c(NCc2cnc[nH]2)c1C] | I-562 |
| 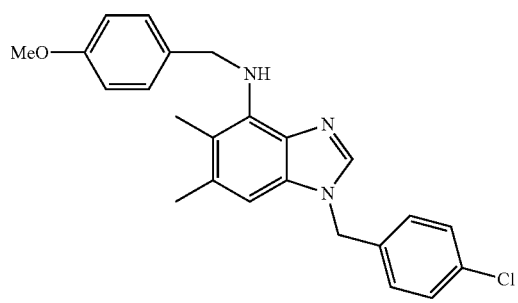 [SMILES: COc1ccc(CNc2c(C)c(C)cc3c2ncn3Cc2ccc(Cl)cc2)cc1] | I-563 |

TABLE 4-continued

| Compounds | |
|---|---|
| (structure: 4-phenyl-1-pentyl-1H-benzimidazol-2-amine) | I-564 |
| (structure: 4-benzyl-1-pentyl-1H-benzimidazol-2-amine) | I-565 |
| (structure: 4-(benzyloxy)-1-pentyl-1H-benzimidazol-2-amine) | I-566 |
| (structure: 5-fluoro-4-methyl-2-[4-methyl-1-(3-(1-methylpiperidin-4-yl)propyl)-2,3-dihydro-1H-indol-5-yl]-1H-benzimidazole) | I-567 |
| (structure: 4,5-dimethyl-2-[4-methyl-1-(3-(1-methylpiperidin-4-yl)propyl)-2,3-dihydro-1H-indol-5-yl]-1H-benzimidazole) | I-568 |
| (structure: 2-[4-chloro-1-(3-(1-methylpiperidin-4-yl)propyl)-2,3-dihydro-1H-indol-5-yl]-4,6-dimethyl-1H-benzimidazole) | I-569 |
| (structure: 2-[4-chloro-1-(3-(1-methylpiperidin-4-yl)propyl)-2,3-dihydro-1H-indol-5-yl]-5-fluoro-4-methyl-1H-benzimidazole) | I-570 |

TABLE 4-continued

Compounds

I-571

I-572

I-573

I-574

I-575

I-576

I-577

I-578

I-579

TABLE 4-continued
| Compounds | |
|---|---|
| 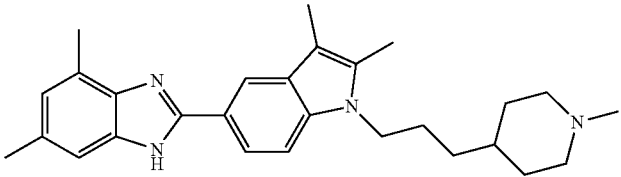 | I-580 |
| 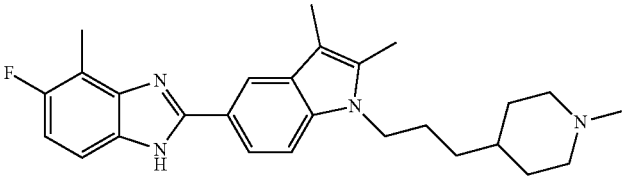 [SMILES: Cc1c(C)n(CCCC2CCN(C)CC2)c2ccc(-c3nc4c(C)c(F)ccc4[nH]3)cc12] | I-581 |
| 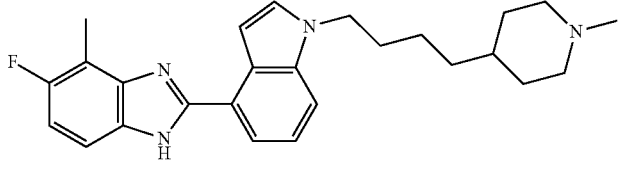 [SMILES: Cc1c(F)ccc2[nH]c(-c3cccc4c3ccn4CCCCC3CCN(C)CC3)nc12] | I-582 |
| 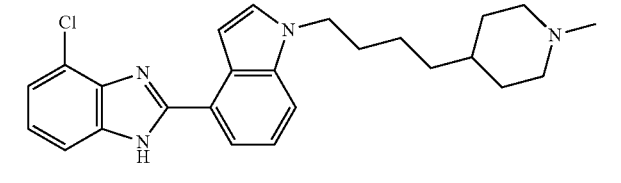 [SMILES: CN1CCC(CCCCn2ccc3c(-c4nc5c(Cl)cccc5[nH]4)cccc32)CC1] | I-583 |
| 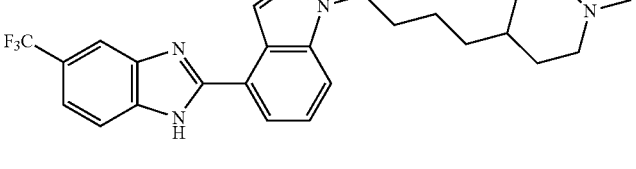 | I-584 |
| 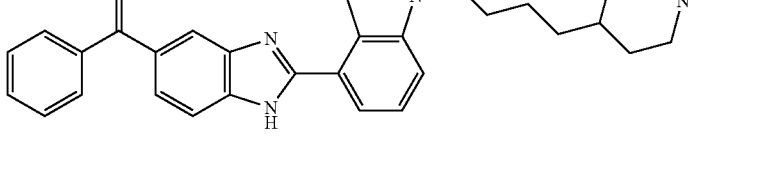 | I-585 |
| 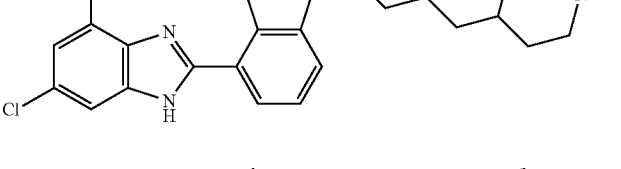 | I-586 |
| 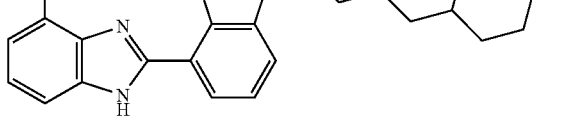 | I-587 |

TABLE 4-continued

Compounds

I-588

I-589

I-590

I-591

I-592

I-593

I-594

TABLE 4-continued
| Compounds | |
|---|---|
| 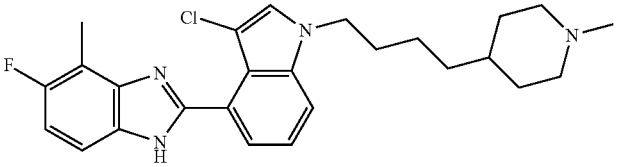 [SMILES: Cc1c(F)ccc2[nH]c(-c3cccc4c3c(Cl)cn4CCCCC3CCN(C)CC3)nc12] | I-595 |
| 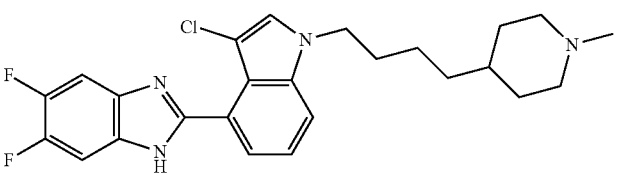 [SMILES: CN1CCC(CCCCn2cc(Cl)c3c(-c4nc5cc(F)c(F)cc5[nH]4)cccc32)CC1] | I-596 |
| 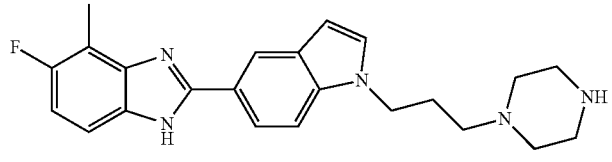 [SMILES: Cc1c(F)ccc2[nH]c(-c3ccc4c(ccn4CCCN4CCNCC4)c3)nc12] | I-597 |
| 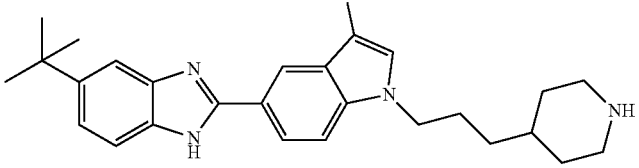 | I-598 |
| 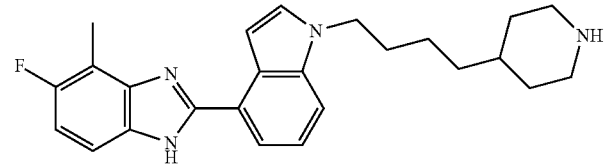 | I-599 |
| 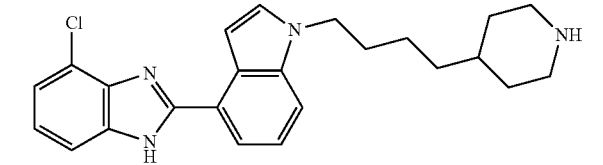 [SMILES: Clc1cccc2[nH]c(-c3cccc4c3ccn4CCCCC3CCNCC3)nc12] | I-600 |
| 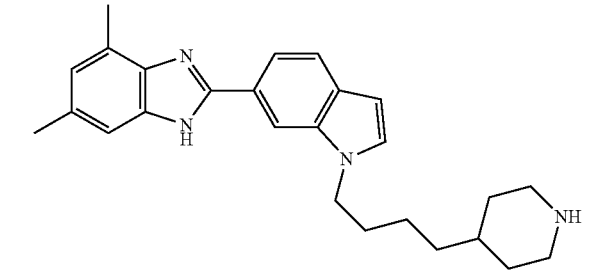 [SMILES: Cc1cc(C)c2nc(-c3ccc4ccn(CCCCC5CCNCC5)c4c3)[nH]c2c1] | I-601 |

TABLE 4-continued
Compounds
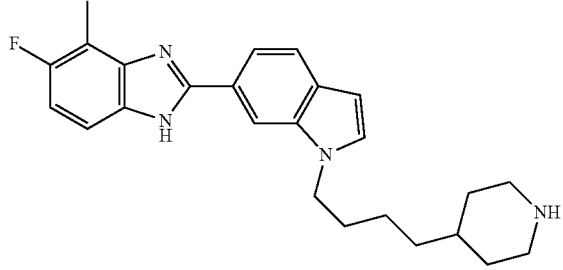 [SMILES: Cc1c(F)ccc2[nH]c(-c3ccc4ccn(CCCCC5CCNCC5)c4c3)nc12]
I-602
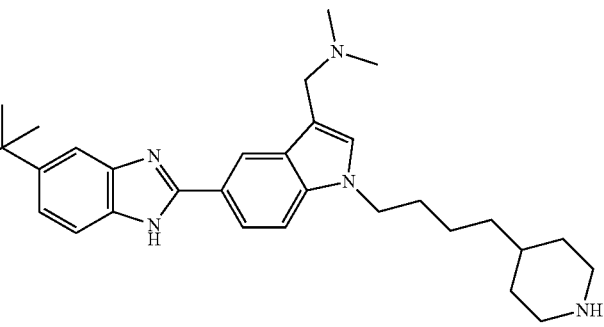
I-603
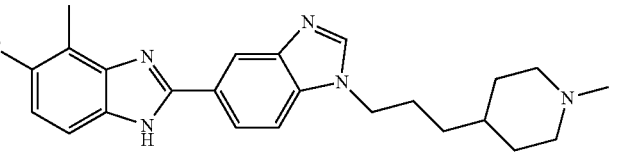
I-604
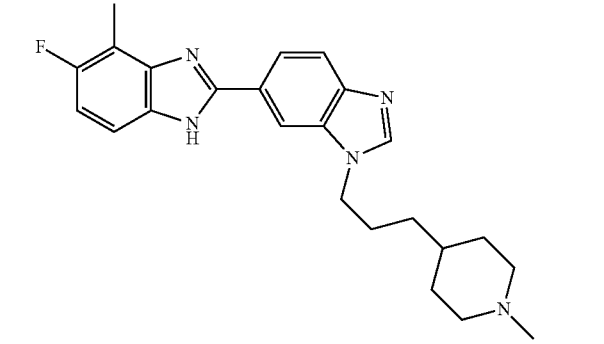 [SMILES: Cc1c(F)ccc2[nH]c(-c3ccc4ncn(CCCC5CCN(C)CC5)c4c3)nc12]
I-605
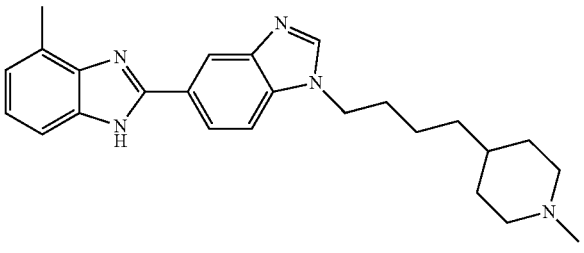 [SMILES: Cc1cccc2[nH]c(-c3ccc4c(c3)ncn4CCCCC3CCN(C)CC3)nc12]
I-606

TABLE 4-continued

Compounds

I-607

I-608

I-609

I-610

I-611

I-612

I-613

TABLE 4-continued
| Compounds | |
|---|---|
| 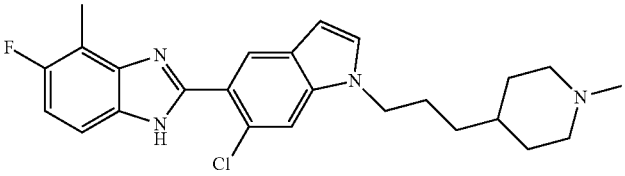 [SMILES: Cc1c(F)ccc2[nH]c(-c3cc4ccn(CCCC5CCN(C)CC5)c4cc3Cl)nc12] | I-614 |
| 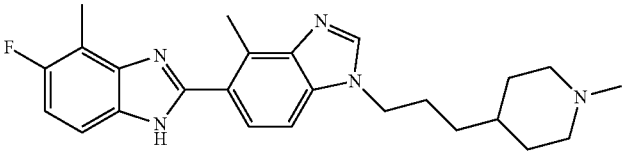 [SMILES: Cc1c(F)ccc2[nH]c(-c3ccc4c(ncn4CCCC4CCN(C)CC4)c3C)nc12] | I-615 |
| 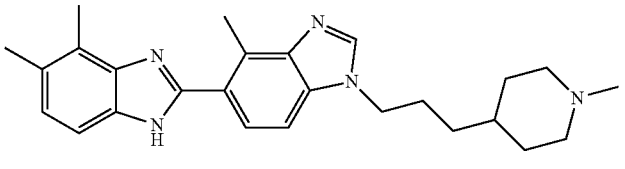 | I-616 |
| 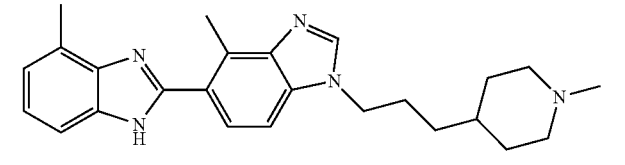 [SMILES: Cc1cccc2[nH]c(-c3ccc4c(ncn4CCCC4CCN(C)CC4)c3C)nc12] | I-617 |
| 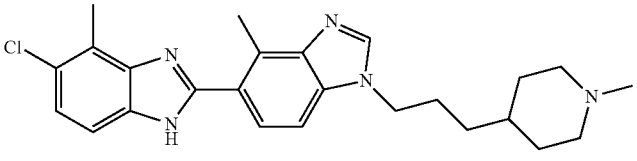 [SMILES: Cc1c(Cl)ccc2[nH]c(-c3ccc4c(ncn4CCCC4CCN(C)CC4)c3C)nc12] | I-618 |
| 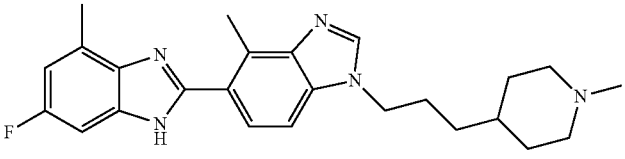 [SMILES: Cc1cc(F)cc2[nH]c(-c3ccc4c(ncn4CCCC4CCN(C)CC4)c3C)nc12] | I-619 |
| 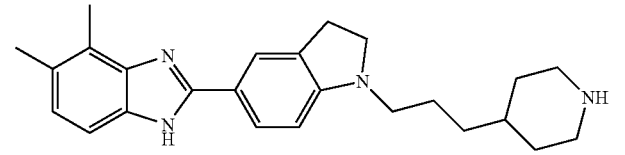 [SMILES: Cc1ccc2[nH]c(-c3ccc4c(c3)CCN4CCCC3CCNCC3)nc2c1C] | I-620 |
| 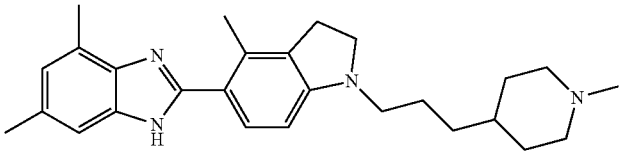 | I-621 |
| 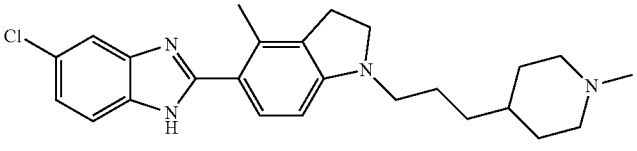 [SMILES: Cc1c(-c2nc3cc(Cl)ccc3[nH]2)ccc2c1CCN2CCCC1CCN(C)CC1] | I-622 |

TABLE 4-continued

| Compounds | |
|---|---|
| (structure) | I-623 |
| (structure) | I-624 |
| (structure) | I-625 |
| (structure) | I-626 |
| (structure) | I-627 |
| (structure) | I-628 |
| (structure) | I-629 |
| (structure) | I-630 |
| (structure) | I-631 |

TABLE 4-continued
| Compounds | |
|---|---|
| 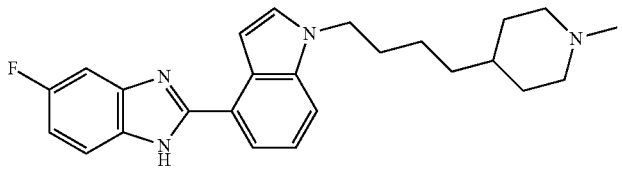 [SMILES: CN1CCC(CCCCn2ccc3c(-c4nc5cc(F)ccc5[nH]4)cccc32)CC1] | I-632 |
| 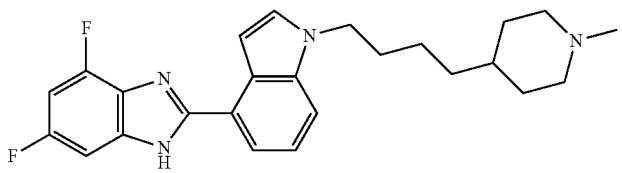 [SMILES: CN1CCC(CCCCn2ccc3c(-c4nc5c(F)cc(F)cc5[nH]4)cccc32)CC1] | I-633 |
| 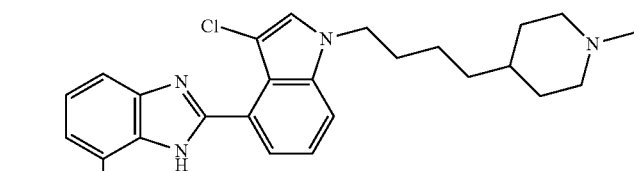 | I-634 |
| 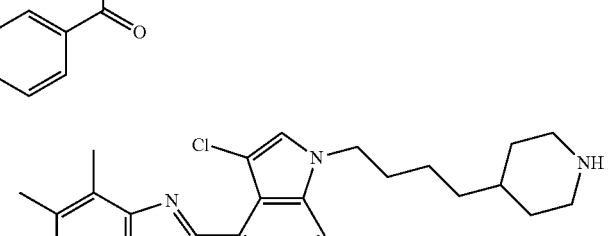 | I-635 |
| 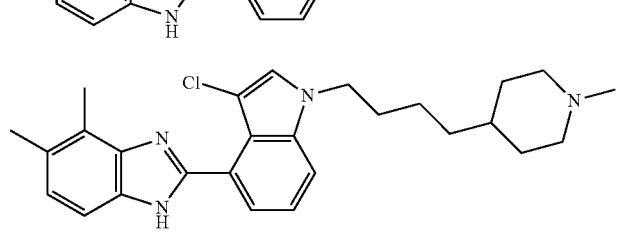 | I-636 |
| 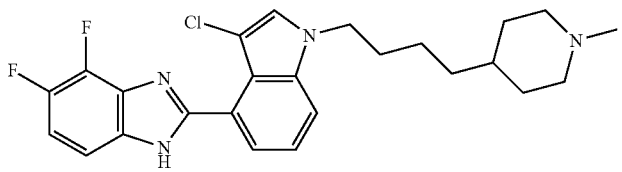 [SMILES: CN1CCC(CCCCn2cc(Cl)c3c(-c4nc5c(F)c(F)ccc5[nH]4)cccc32)CC1] | I-637 |
| 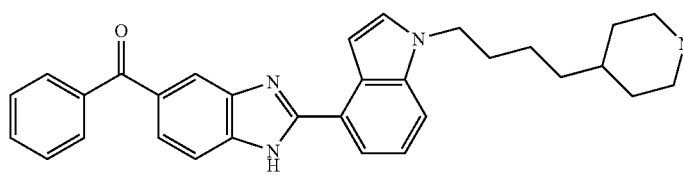 | I-638 |
| 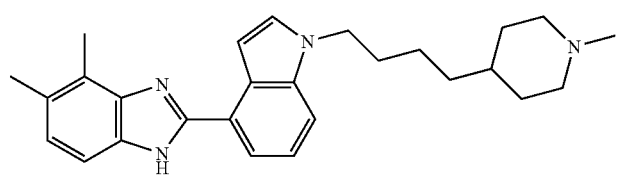 | I-639 |

TABLE 4-continued
Compounds
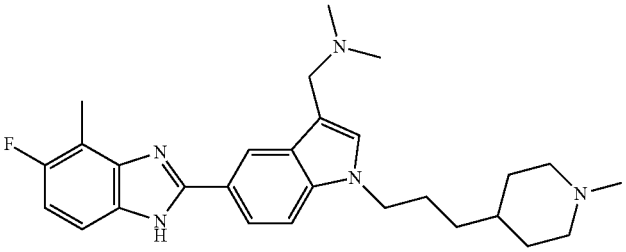 [SMILES: Cc1c(F)ccc2[nH]c(-c3ccc4c(c3)c(CN(C)C)cn4CCCC3CCN(C)CC3)nc12]
I-640
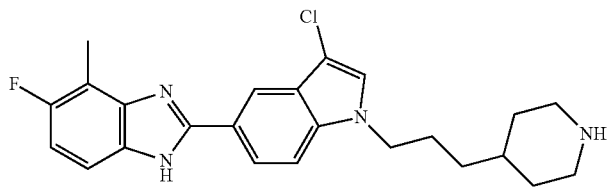 [SMILES: Cc1c(F)ccc2[nH]c(-c3ccc4c(c3)c(Cl)cn4CCCC3CCNCC3)nc12]
I-641
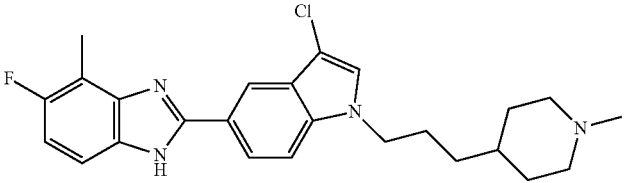 [SMILES: Cc1c(F)ccc2[nH]c(-c3ccc4c(c3)c(Cl)cn4CCCC3CCN(C)CC3)nc12]
I-642
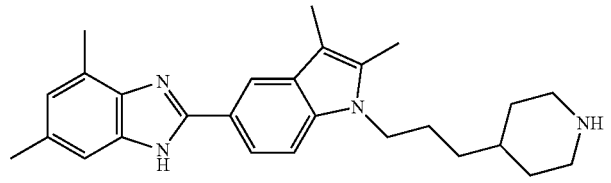 [SMILES: Cc1cc(C)c2nc(-c3ccc4c(c3)c(C)c(C)n4CCCC3CCNCC3)[nH]c2c1]
I-643
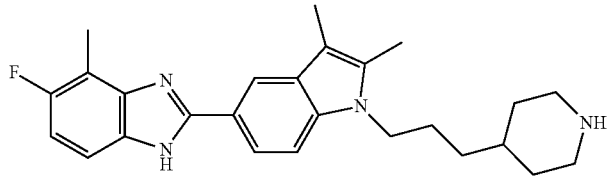 [SMILES: Cc1c(C)n(CCCC2CCNCC2)c2ccc(-c3nc4c(C)c(F)ccc4[nH]3)cc12]
I-644
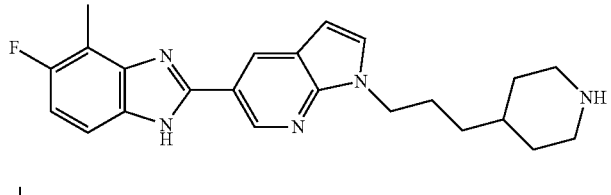
I-645
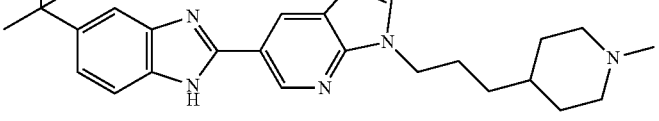
I-646
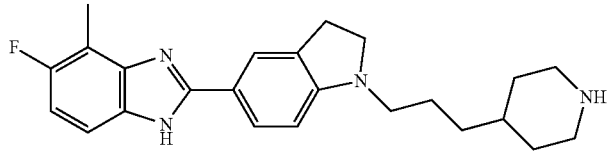 [SMILES: Cc1c(F)ccc2[nH]c(-c3ccc4c(c3)CCN4CCCC3CCNCC3)nc12]
I-647

TABLE 4-continued

| Compounds | |
|---|---|
| (structure) | I-648 |
| (structure) | I-649 |
| (structure) | I-650 |
| (structure) | I-651 |
| (structure) | I-652 |
| (structure) | I-653 |
| (structure) | I-654 |
| (structure) | I-655 |
| (structure) | I-656 |

TABLE 4-continued

| Compounds | |
|---|---|
| (structure) | I-657 |
| (structure) | I-658 |
| (structure) | I-659 |
| (structure) | I-660 |
| (structure) | I-661 |
| (structure) | I-662 |
| (structure) | I-663 |

TABLE 4-continued
| Compounds | |
|---|---|
| 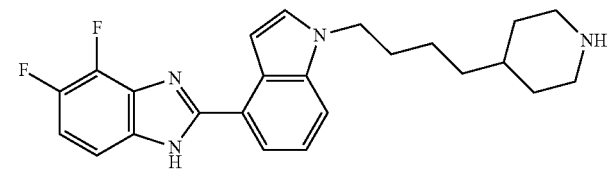 [SMILES: Fc1ccc2[nH]c(-c3cccc4c3ccn4CCCCC3CCNCC3)nc2c1F] | I-664 |
| 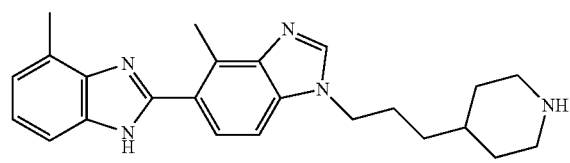 [SMILES: Cc1cccc2[nH]c(-c3ccc4c(ncn4CCCC4CCNCC4)c3C)nc12] | I-665 |
| 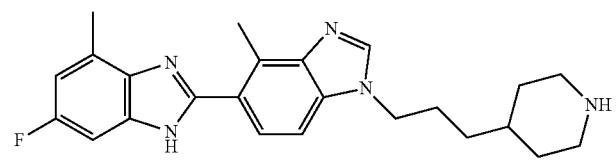 [SMILES: Cc1cc(F)cc2[nH]c(-c3ccc4c(ncn4CCCC4CCNCC4)c3C)nc12] | I-666 |
| 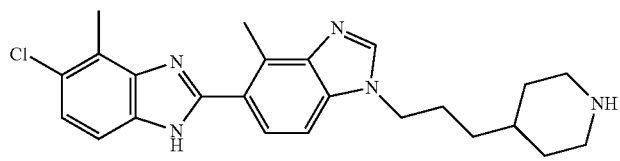 [SMILES: Cc1c(Cl)ccc2[nH]c(-c3ccc4c(ncn4CCCC4CCNCC4)c3C)nc12] | I-667 |
| 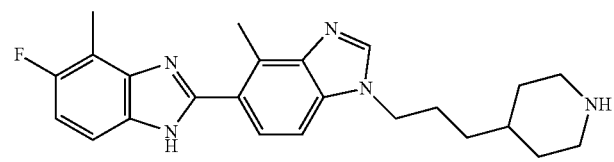 [SMILES: Cc1c(F)ccc2[nH]c(-c3ccc4c(ncn4CCCC4CCNCC4)c3C)nc12] | I-668 |
| 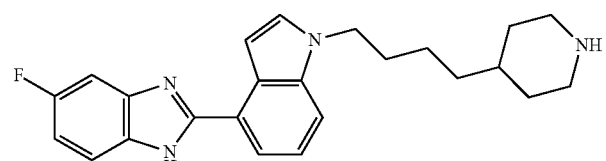 | I-669 |
| 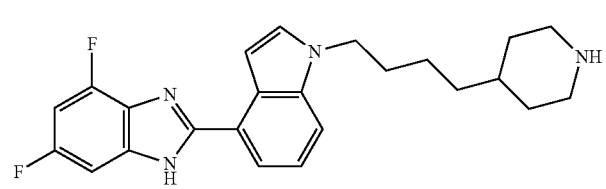 [SMILES: Fc1cc(F)c2nc(-c3cccc4c3ccn4CCCCC3CCNCC3)[nH]c2c1] | I-670 |
| 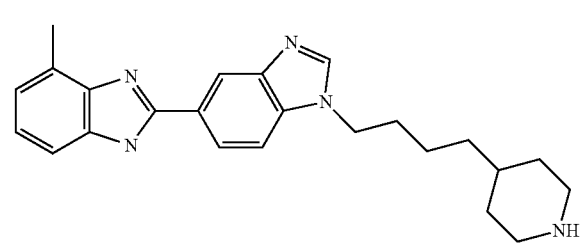 [SMILES: Cc1cccc2[nH]c(-c3ccc4c(c3)ncn4CCCCC3CCNCC3)nc12] | I-671 |

TABLE 4-continued

| Compounds | |
|---|---|
| | I-672 |
| | I-673 |
| | I-674 |
| | I-675 |
| | I-676 |
| | I-677 |

TABLE 4-continued
| Compounds | |
|---|---|
| 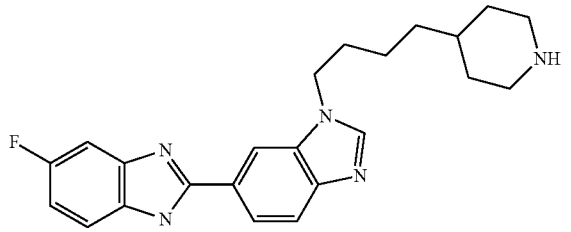 [SMILES: Fc1ccc2[nH]c(-c3ccc4ncn(CCCCC5CCNCC5)c4c3)nc2c1] | I-678 |
| 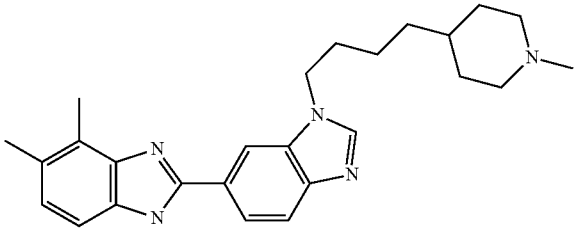 | I-679 |
| 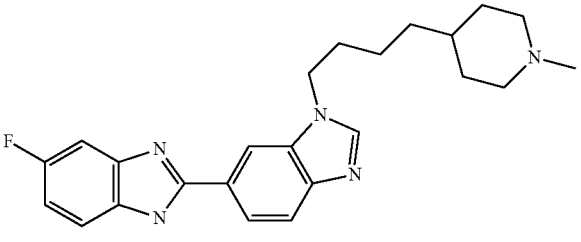 [SMILES: CN1CCC(CCCCn2cnc3ccc(-c4nc5cc(F)ccc5[nH]4)cc32)CC1] | I-680 |
| 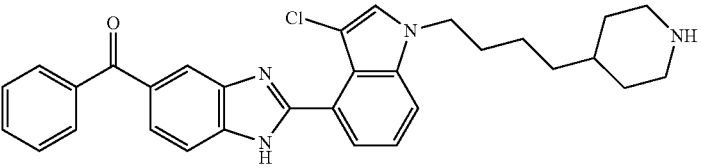 [SMILES: O=C(c1ccccc1)c1ccc2[nH]c(-c3cccc4c3c(Cl)cn4CCCCC3CCNCC3)nc2c1] | I-681 |
| 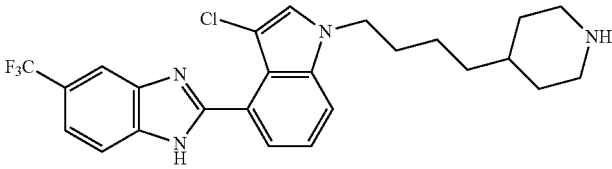 [SMILES: FC(F)(F)c1ccc2[nH]c(-c3cccc4c3c(Cl)cn4CCCCC3CCNCC3)nc2c1] | I-682 |
| 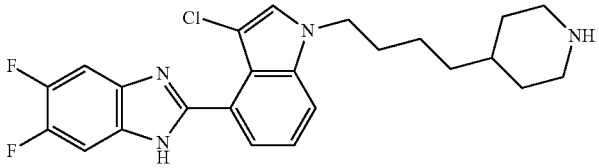 [SMILES: Fc1cc2nc(-c3cccc4c3c(Cl)cn4CCCCC3CCNCC3)[nH]c2cc1F] | I-683 |
| 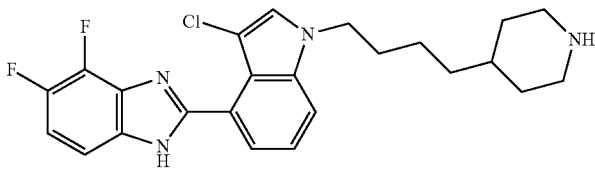 [SMILES: Fc1ccc2[nH]c(-c3cccc4c3c(Cl)cn4CCCCC3CCNCC3)nc2c1F] | I-684 |

TABLE 4-continued

Compounds

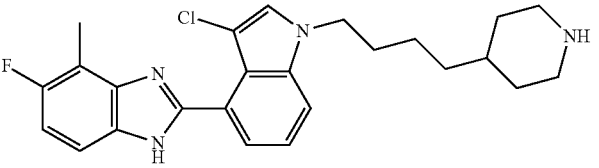 I-685

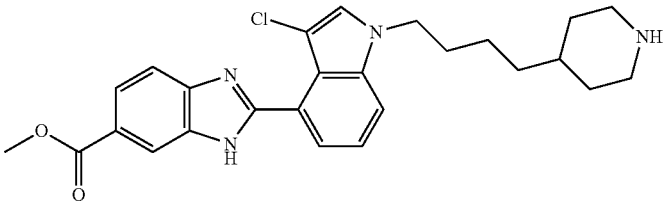 [SMILES: COC(=O)c1ccc2nc(-c3cccc4c3c(Cl)cn4CCCCC3CCNCC3)[nH]c2c1] I-686

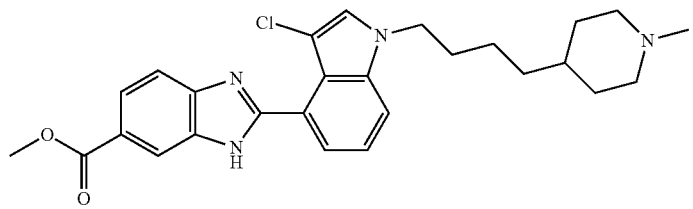 I-687

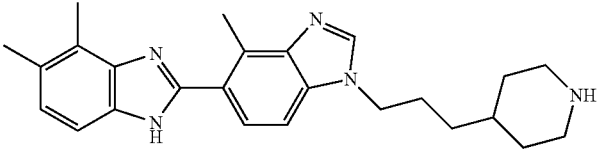 [SMILES: Cc1ccc2[nH]c(-c3ccc4c(ncn4CCCC4CCNCC4)c3C)nc2c1C] I-688

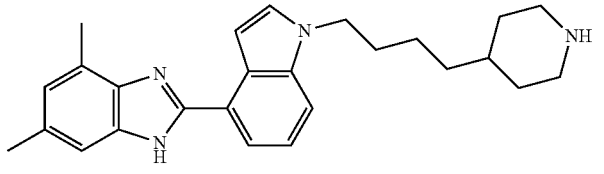 [SMILES: Cc1cc(C)c2nc(-c3cccc4c3ccn4CCCCC3CCNCC3)[nH]c2c1] I-689

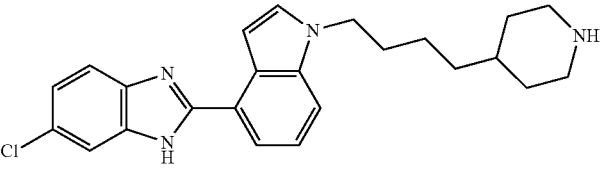 [SMILES: Clc1ccc2nc(-c3cccc4c3ccn4CCCCC3CCNCC3)[nH]c2c1] I-690

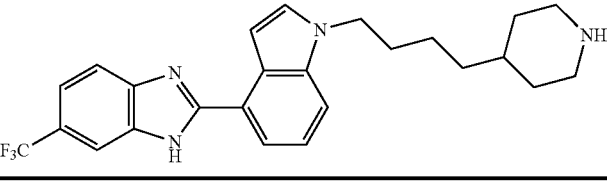 I-691

In some embodiments, the present invention provides a compound other than a compound set forth in Table 4.

5. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit Rheb, in a biological sample or in a patient. In certain embodiments, the amount of compound in compositions of this invention is such that is effective to measurably inhibit Rheb, in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Compounds and compositions described herein are generally useful for the inhibition of Rheb.

The activity of a compound utilized in this invention as an inhibitor of Rheb, may be assayed in vitro, in vivo or in a cell line. In vitro assays include assays that determine the inhibition of Rheb. Detailed conditions for assaying a compound utilized in this invention as an inhibitor of Rheb are well known to one of ordinary skill in the art. Such methods are described in detail by Sancak et al. (Sancak et al. 2007, Mol Cell.)

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Provided compounds are inhibitors of Rheb and are therefore useful for treating one or more disorders associated with activity of Rheb. Thus, in certain embodiments, the present invention provides a method for treating an Rheb-mediated disorder comprising the step of administering to a patient in need thereof a compound of the present invention, or pharmaceutically acceptable composition thereof.

As used herein, the terms "Rheb-mediated" disorders, diseases, and/or conditions as used herein means any disease or other deleterious condition in which Rheb is known to play a role. Accordingly, another embodiment of the present invention relates to treating or lessening the severity of one or more diseases in which the Rheb axis is known to play a role. In certain embodiments, a Rheb inhibitor is useful for the treatment of an mTORC1-mediated disorder, disease, and/or condition selected from those described by Matt Kaeberlin, *Scientifica*, vol. 2013, Article ID 849186.

The methods described herein include methods for the treatment of cancer in a subject. As used in this context, to "treat" means to ameliorate or improve at least one symptom or clinical parameter of the cancer. For example, a treatment can result in a reduction in tumor size or growth rate. A treatment need not cure the cancer or cause remission 100% of the time, in all subjects.

As used herein, the term "cancer" refers to cells having the capacity for autonomous growth, i.e., an abnormal state or condition characterized by rapidly proliferating cell growth. The term is meant to include all types of cancerous growths or oncogenic processes, metastatic tissues or malignantly transformed cells, tissues, or organs, irrespective of histopathologic type or stage of invasiveness. The term "tumor" as used herein refers to cancerous cells, e.g., a mass of cancer cells.

Cancers that can be treated or diagnoses using the methods described herein include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

In some embodiments, the methods described herein are used for treating or diagnosing a carcinoma in a subject. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. In some embodiments, the cancer is renal carcinoma or melanoma. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation.

In some embodiments, the cancers that are treated by the methods described herein are cancers that have increased levels of Rheb or an increased expression or activity of a Rheb relative to normal tissues or to other cancers of the same tissues; methods known in the art and described herein can be used to identify those cancers. In some embodiments, the methods include obtaining a sample comprising cells of the cancer, determining the Rheb activity in the sample, and administering a treatment as described herein (e.g., a provided inhibitor of Rheb). In some embodiments, the cancer is one that is shown herein to have increased levels of Rheb activity In some embodiments, the present invention provides a method for treating one or more disorders, diseases, and/or conditions wherein the disorder, disease, or condition includes, but is not limited to, a cellular proliferative disorder.

Cellular Proliferative Disorders

The present invention features methods and compositions for the diagnosis and prognosis of cellular proliferative disorders (e.g., cancer) and the treatment of these disorders by inhibiting Rheb activity. Cellular proliferative disorders described herein include, e.g., cancer, obesity, and proliferation-dependent diseases. Such disorders may be diagnosed using methods known in the art.

Cancer

Cancers include, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (e.g., Hodgkin's disease or non-Hodgkin's disease), Waldenstrom's macroglobulinemia, multiple myeloma, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, schwannoma, meningioma, melanoma, neuroblastoma, and retinoblastoma). In some embodiments, the cancer is melanoma or breast cancer.

Other Proliferative Diseases

Other proliferative diseases include, e.g., obesity, benign prostatic hyperplasia, psoriasis, abnormal keratinization, lymphoproliferative disorders (e.g., a disorder in which there is abnormal proliferation of cells of the lymphatic system), chronic rheumatoid arthritis, arteriosclerosis, restenosis, and diabetic retinopathy. Proliferative diseases that are hereby incorporated by reference include those described in U.S. Pat. Nos. 5,639,600 and 7,087,648.

Fibrotic Diseases

Idiopathic Pulmonary Fibrosis (IPF). The PI3K pathway is activated in fibrotic foci, the cardinal lesions in IPF. mTOR kinase inhibitor GSK2126458 reduces PI3K pathway signaling and functional responses in IPF-derived lung fibroblasts and mTOR inhibition reduces collagen expression in models of IPF patients. In the bleomycin model of pulmonary fibrosis, rapamycin treatment is antifibrotic, and rapamycin also decreases expression of α-smooth muscle actin and fibronectin by fibroblasts in vitro.

In some embodiments, the method of inhibiting mTORC1 activity via Rheb inhibition is used to treat idiopathic pulmonary fibrosis (IPF). (See Thorax. 2016, 71(8), pp. 701-11; PLoS One. 2012, 7(7)). Accordingly, in some embodiments, the present invention provides a method of treating idiopathic pulmonary fibrosis (IPF), in a patient in need thereof, comprising the step of administering to said patient a provided compound or pharmaceutically acceptable salt thereof.

Kidney Fibrosis. mTORC1 is activated in myofibroblasts, a major pathogenic cell type in kidney fibrosis. Inhibition of mTOR with rapamycin in a murine model of kidney fibrosis (UUO), attenuated expression of markers of fibrosis and tubulointerstitial damage.

In some embodiments, the method of inhibiting mTORC1 activity via Rheb inhibition is used to treat kidney fibrosis. (See J Am Soc Nephrol 2013, 24, pp. 1114-1126; Kidney International 2006, 69, pp. 2029-2036; PLoS 2012, 7, Issue 3, e33626; Clin Invest Med 2014, Vol 37, no 3, E142). Accordingly, in some embodiments, the present invention provides a method of treating kidney fibrosis, in a patient in need thereof, comprising the step of administering to said patient a provided compound or pharmaceutically acceptable salt thereof.

In some embodiments, the method of inhibiting mTORC1 activity via Rheb inhibition is used to treat scleroderma. (See J Invest Dermatol. 2015 November; 135(11): 2873-6). Accordingly, in some embodiments, the present invention provides a method of treating scleroderma, in a patient in need thereof, comprising the step of administering to said patient a provided compound or pharmaceutically acceptable salt thereof.

In some embodiments, the method of inhibiting mTORC1 activity via Rheb inhibition is used to treat hypertrophic scarring and keloid disease. (See Am J Pathol. 2012 November; 181(5): 1642-58). Accordingly, in some embodiments, the present invention provides a method of treating hypertrophic scarring and keloid disease, in a patient in need thereof, comprising the step of administering to said patient a provided compound or pharmaceutically acceptable salt thereof.

In some embodiments, the method of inhibiting mTORC1 activity via Rheb inhibition is used to treat cardiac fibrosis. (See J Mol Cell Cardiol. 2016 February; 91: 6-9). Accordingly, in some embodiments, the present invention provides a method of treating cardiac fibrosis, in a patient in need thereof, comprising the step of administering to said patient a provided compound or pharmaceutically acceptable salt thereof.

Other Disorders

Other disorders include lysosomal storage diseases, including but not limited to Pompe disease, Gaucher disease, mucopolysaccharidosis, multiple sulfatase deficiency; neurodegenerative diseases such as Parkinson's disease, Alzheimer's disease, Huntington's disease, alpha1-antitrypsin deficiency, and spinal bulbar muscular atrophy. The present invention provides compounds that were shown to cause translocation of TFEB to the nucleus. TFEB translocation to the nucleus promotes exocytosis and/or cellular clearance of accumulating substrates in the above-mentioned diseases.

In some embodiments, the method of inhibiting mTORC1 activity via Rheb inhibition is used to treat asthma. (See Respirology 2015 October; 20(7): 1055-65). Accordingly, in some embodiments, the present invention provides a method of treating asthma, in a patient in need thereof, comprising the step of administering to said patient a provided compound or pharmaceutically acceptable salt thereof.

In some embodiments, the method of inhibiting mTORC1 activity via Rheb inhibition is used to treat a lysosomal storage disease. (See Annals of the New York Academy of Sciences, 2016, Volume 1371, Issue 1, pp. 3-14; Hum Mol Genet. 2015, 24(20), pp. 5775-88; EMBO Mol Med. 2013, 5(5), pp. 691-706; Medina, D. L., et al., Dev Cell. 2011 Sep. 13, 21(3), pp. 421-30). Accordingly, in some embodiments, the present invention provides a method of treating a lysosomal storage disease, in a patient in need thereof, comprising the step of administering to said patient a provided compound or pharmaceutically acceptable salt thereof.

In some embodiments, the method of inhibiting mTORC1 activity via Rheb inhibition is used to treat Parkinson's disease. (See Proc Natl Acad Sci USA. 2013, 110(19): E1817-26). Accordingly, in some embodiments, the present invention provides a method of treating Parkinson's disease, in a patient in need thereof, comprising the step of administering to said patient a provided compound or pharmaceutically acceptable salt thereof.

In some embodiments, the method of inhibiting mTORC1 activity via Rheb inhibition is used to treat Alzheimer's disease. (See EMBO Mol Med. 2014, 6(9), pp. 1142-60). Accordingly, in some embodiments, the present invention provides a method of treating Alzheimer's disease, in a patient in need thereof, comprising the step of administering to said patient a provided compound or pharmaceutically acceptable salt thereof.

In some embodiments, the method of inhibiting mTORC1 activity via Rheb inhibition is used to treat Huntington's disease. (See Sci Transl Med. 2012, 4(142):142ra97). Accordingly, in some embodiments, the present invention provides a method of treating Huntington's disease, in a patient in need thereof, comprising the step of administering to said patient a provided compound or pharmaceutically acceptable salt thereof.

In some embodiments, the method of inhibiting mTORC1 activity via Rheb inhibition is used to treat alpha1-anti-trypsin deficiency. (See EMBO Mol Med. 2013, 5(3), pp. 397-412). Accordingly, in some embodiments, the present invention provides a method of treating alpha1-anti-trypsin deficiency, in a patient in need thereof, comprising the step of administering to said patient a provided compound or pharmaceutically acceptable salt thereof.

In some embodiments, the method of inhibiting mTORC1 activity via Rheb inhibition is used to treat spinal bulbar muscular atrophy. (See Nat Neurosci. 2014, 17(9), pp. 1180-9). Accordingly, in some embodiments, the present invention provides a method of treating spinal bulbar muscular atrophy, in a patient in need thereof, comprising the step of administering to said patient a provided compound or pharmaceutically acceptable salt thereof.

The present invention provides compounds that are inhibitors Rheb and of mTORC1 activity and were shown to selectively inhibit mTORC1 over mTORC2 as measured by pS6K inhibition (a measure of mTORC1 activity) and pAKT activation (a measure of mTORC2 activity). In some embodiments, a provided compound inhibits mTORC1 selectively over mTORC2. In some embodiments, a provided compound does not measurably inhibit mTORC2. In some embodiments, a provided compound has a pAKT activation $IC_{50}$ of >10 µM. In some embodiments, a provided compound inhibits mTORC1 with >10-fold selectivity over mTORC2. In some embodiments, a provided compound inhibits mTORC1 with >20-fold selectivity over mTORC2. In some embodiments, a provided compound inhibits mTORC1 with >50-fold selectivity over mTORC2. In some embodiments, a provided compound inhibits mTORC1 with >100-fold selectivity over mTORC2. In some embodiments, a provided compound inhibits mTORC1 with >150-fold selectivity over mTORC2. In some embodiments, a provided compound inhibits mTORC1 with >200-fold selectivity over mTORC2. In some embodiments, a provided compound inhibits mTORC1 with >500-fold selectivity over mTORC2. In some embodiments, a provided compound inhibits mTORC1 with >1,000-fold selectivity over mTORC2. Accordingly, in some embodiments, the present invention provides a method of treating a disorder associate with mTORC1 comprising administering to patient a compound that inhibits mTORC1 wherein said compound does not inhibit mTORC2. Such compounds may be employed for indications where rapamycin and rapalogs demonstrated a benefit either in animal models or in a human disease setting. Such indications include:

Treatment of Metabolic Disease (Obesity and Insulin Resistance in Type 2 Diabetes). Inhibition of mTORC1 pathway leads to extension of life span in yeast, fly and mouse, and caloric restriction improves longevity and insulin sensitivity. The underlying mechanism has been proposed to function by regulation of mTORC1 activation. Rapamycin-induced insulin resistance has been shown to be mediated by inhibition of mTORC2 and a selective mTORC1 inhibitor is predicted to improve insulin sensitivity and glucose homeostasis.

In some embodiments, the method of inhibiting mTORC1 activity via Rheb inhibition is used to treat metabolic disease (obesity and insulin resistance in type 2 diabetes). (See J Gerontol A Biol Sci Med Sci 2015, 70 (4), pp. 410-20; Aging Cell 2014, 13 (2), pp. 311-9; Diabetologia 2016, 59(3), pp. 592-603; Science 2012, 335, pp. 1638-1643). Accordingly, in some embodiments, the present invention provides a method of treating metabolic disease (obesity and insulin resistance in type 2 diabetes), in a patient in need thereof, comprising the step of administering to said patient a provided compound or pharmaceutically acceptable salt thereof.

Neurofibromatosis. Neurofibromatosis type 1 (NF1) is caused by mutations in the NF1 gene. Its protein product, neurofibromin, functions as a tumor suppressor and ultimately produces constitutive upregulation of mTOR. mTOR inhibitors have been shown to reduce tumor size and induce anti-proliferative effect in NF1-associated plexiform neurofibroma.

In some embodiments, the method of inhibiting mTORC1 activity via Rheb inhibition is used to treat neurofibromatosis. (See Curr Neurol Neurosci Rep. 2012 Jun. 12(3), pp. 294-301; Oncotarget. 2016 Jan. 31). Accordingly, in some embodiments, the present invention provides a method of treating neurofibromatosis, in a patient in need thereof, comprising the step of administering to said patient a provided compound or pharmaceutically acceptable salt thereof.

Cardiomyopathy and skeletal muscle dystrophy, Emery-Dreifuss muscular dystrophy model ($LMNA^{-/-}$). Mutations in LMNA result in several human diseases including limb-girdle muscular dystrophy (LGMD1B), Emery-Dreifuss muscular dystrophy (EDMD2/3), dilated cardiomyopathy (DCM) and conduction-system disease (CMD1A), lipodystrophy, Charcot-Marie-Tooth disease, and Hutchinson-Gilford progeria syndrome (HGPS). $Lmna^{-/-}$ mice have elevated mTORC1 activity and short-term treatment with rapamycin in $Lmna^{-/-}$ mice results in reduced mTORC1 signaling, improved cardiac and skeletal muscle function and enhanced survival by ~50%.

In some embodiments, the method of inhibiting mTORC1 activity via Rheb inhibition is used to treat cardiomyopathy and skeletal muscle dystrophy. (See Sci Transl Med. 2012, 4(144):144ra103; Handb Clin Neurol. 2013, 113, pp. 1367-76). Accordingly, in some embodiments, the present invention provides a method of treating cardiomyopathy and skeletal muscle dystrophy, in a patient in need thereof, comprising the step of administering to said patient a provided compound or pharmaceutically acceptable salt thereof.

Leigh syndrome. Ndufs4 knockout (KO) mice are used as a model of Leigh syndrome and exhibit hyperactivation of mTORC1 and metabolic defects. Treatment of Ndufs4 KO mice with rapamycin extended lifespan, improve metabolic and neurological defect associated with this disease.

In some embodiments, the method of inhibiting mTORC1 activity via Rheb inhibition is used to treat Leigh syndrome. (See Science 2013, 342(6165), pp. 1524-8). Accordingly, in some embodiments, the present invention provides a method of treating Leigh syndrome, in a patient in need thereof, comprising the step of administering to said patient a provided compound or pharmaceutically acceptable salt thereof.

Oncology. Inhibition of mTOR with rapalogs has been shown to have antitumor activity in murine cancer models and in cancer patients. Examples of sensitive cancer types include, but are not limited to, hepatocellular carcinoma, breast cancers, mantle cell lymphomas, lung carcinoma, tuberous sclerosis and lymphangioleiomyomatosis.

In some embodiments, the method of inhibiting mTORC1 activity via Rheb inhibition is used to treat cancer and oncologic disorders. (See Trends Cancer 2016; In press). Accordingly, in some embodiments, the present invention provides a method of treating cancer and oncologic disorders, in a patient in need thereof, comprising the step of administering to said patient a provided compound or pharmaceutically acceptable salt thereof.

Non-alcoholic steatohepatitis (NASH). The present invention provides inhibitors that induce autophagy to clear degraded cytoplasmic proteins, and NASH disease is characterized by lipid deposits, inflammation and fibrosis in the liver. The inhibition of the mTORC1 pathway via Rheb inhibition induces autophagy and down regulate SREBP-1 to decrease lipid biosynthesis to reduce lipid storage.

In some embodiments, the method of inhibiting mTORC1 activity via Rheb inhibition is used to treat non-alcoholic steatohepatitis (NASH). (See J Clin Exp Hepatol 2014; 4(1), pp. 51-9). Accordingly, in some embodiments, the present invention provides a method of treating non-alcoholic steatohepatitis (NASH), in a patient in need thereof, comprising the step of administering to said patient a provided compound or pharmaceutically acceptable salt thereof.

Tuberous sclerosis (TSC) and lymphangioleiomyomatosis (LAM). Failure in the regulation of mTOR is critical to the pathogenesis of the inherited disorder tuberous sclerosis complex (TSC) and the related lung disease, lymphangioleiomyomatosis (LAM). Both diseases are caused by mutations of TSC1 or TSC2 leading to inappropriate activity of signaling downstream of mTORC1. TSC patients develop nonmalignant tumors in many organs, including the brain, while LAM patients, mostly women, accumulate abnormal, muscle-like cells in certain organs or tissues, especially the lungs, lymph nodes, and kidneys. The rapalogs, Everolimus and Sirolimus, are currently approved for the treatment of both TSC and LAM, respectively, by the US FDA.

In some embodiments, the method of inhibiting mTORC1 activity via Rheb inhibition is used to treat tuberous sclerosis and lymphangioleiomyomatosis. (See J. Clin. Invest. 2011, 121, pp. 1231-1241; J. Clin Epidemiol. 2015, 7, pp. 249-57). Accordingly, in some embodiments, the present invention provides a method of treating tuberous sclerosis and lymphangioleiomyomatosis, in a patient in need thereof, comprising the step of administering to said patient a provided compound or pharmaceutically acceptable salt thereof.

Senescence and diseases of aging. Rapamycin suppresses the mammalian TORC1 complex, which regulates translation, and extends lifespan in diverse species, including mice. Rapamycin was shown to inhibit the pro-inflammatory phenotype of senescent cells. As senescent cells accumulate with age, the senescence-associated secretory phenotype (SASP) can disrupt tissues and contribute to age-related pathologies, including cancer. Inhibition of mTOR suppressed the secretion of inflammatory cytokines by senescent cells. Rapamycin reduced cytokine levels including IL6 and suppressed translation of the membrane-bound cytokine IL1A. Reduced IL1A diminishes NF-κB transcriptional activity, which controls the SASP. Thus, Rheb or mTORC1 inhibitors might ameliorate age-related pathologies, including late-life cancer, by suppressing senescence-associated inflammation.

In some embodiments, the method of inhibiting mTORC1 activity via Rheb inhibition is used to treat senescence and diseases of aging. (See Nature Cell Biology 17, 2015, pp. 1049-1061; Free Radic Biol Med. 2016 June; 95:133-54). Accordingly, in some embodiments, the present invention provides a method of treating senescence and diseases of aging, in a patient in need thereof, comprising the step of administering to said patient a provided compound or pharmaceutically acceptable salt thereof.

Additional therapeutic indications where mTORC inhibition may be beneficial are: cardiovascular disease (acute coronary syndrome), coronary occlusions with eluting stents, renal cyst pathologies (e.g. autosomal dominant polycystic kidney disease, see EMBO Mol Med. 2011 April; 3(4): 189-200), polycystic kidney disease, neurofibromatosis, epilepsy assoc. with TSC1 and/or TSC2 mutations, polycystic liver, pachyonychia congenital, fragile x syndrome, Friedrich ataxia, Peutz-Jeghers syndrome, eye disease including neovascular age-related macular degeneration, uveitis, diabetic macular edema, diabetic nephropathy (See J Am Soc Nephrol. 2013 Jun. 28; 24(7): 1114-1126), fibroblast growth including pulmonary fibrosis, renal insufficiency/fibrosis, metabolic syndrome, diseases of the immune system including immune senescence, lupus nephritis, chronic immune thrombocytopenia, multiple sclerosis, cancer including lymphoma, tumors associated with TSC1/2 mutations, angiomyolipoma assoc. with TSC1/2 mutations, breast cancer, hepatocellular cancer, leukemia, glioma, adenoid cystic carcinoma, senescence, and vascular rheumatoid arthritis.

In some embodiments, the method of inhibiting mTORC1 activity via Rheb inhibition is used to treat cardiovascular disease (acute coronary syndrome), coronary occlusions with eluting stents, renal cyst pathologies, polycystic kidney disease, autosomal dominant polycystic kidney disease, neurofibromatosis, epilepsy assoc. with TSC1 and/or TSC2 mutations, polycystic liver, pachyonychia congenital, fragile x syndrome, Friedrich ataxia, Peutz-Jeghers syndrome, eye disease including neovascular age-related macular degeneration, uveitis, diabetic macular edema, diabetic nephropathy, fibroblast growth including pulmonary fibrosis, renal insufficiency/fibrosis, metabolic syndrome, diseases of the immune system including immune senescence, lupus nephritis, chronic immune thrombocytopenia, multiple sclerosis, cancer including lymphoma, tumors associated with TSC1/2 mutations, angiomyolipoma assoc. with TSC1/2 mutations, breast cancer, hepatocellular cancer, leukemia, glioma, adenoid cystic carcinoma, senescence, and vascular rheumatoid arthritis. Accordingly, in some embodiments, the present invention provides a method of treating cardiovascular disease (acute coronary syndrome), coronary occlusions with eluting stents, renal cyst pathologies, polycystic kidney disease, autosomal dominant polycystic kidney disease, neurofibromatosis, epilepsy assoc. with TSC1 and/or TSC2 mutations, polycystic liver, pachyonychia congenital, fragile x syndrome, Friedrich ataxia, Peutz-Jeghers syndrome, eye disease including neovascular age-related macular degeneration, uveitis, diabetic macular edema, diabetic nephropathy, fibroblast growth including pulmonary fibrosis, renal insufficiency/fibrosis, metabolic syndrome, diseases of the immune system including immune senescence, lupus nephritis, chronic immune thrombocytopenia, multiple sclerosis, cancer including lymphoma, tumors associated with TSC1/2 mutations, angiomyolipoma assoc. with TSC1/2 mutations, breast cancer, hepatocellular cancer, leukemia, glioma, adenoid cystic carcinoma, senescence, and vascular rheumatoid arthritis, in a patient in need thereof, comprising the step of administering to said patient a provided compound or pharmaceutically acceptable salt thereof.

Dysregulation of axon growth and guidance plays a significant role in the pathogenesis of epilepsy, autism and intellectual disabilities. Deficient axonal growth has been associated with cerebral dysgenesis and intellectual disability while excessive growth of neuronal processes has been associated with epilepsy. The role of neuronal connectivity has also become apparent in autism (See Nat Neurosci. 2010 February; 13(2): 163-172).

In some embodiments, the method of inhibiting Rheb activity is used to treat epilepsy, autism and intellectual disabilities. Accordingly, in some embodiments, the present invention provides a method of treating epilepsy, autism and intellectual disabilities, in a patient in need thereof, comprising the step of administering to said patient a provided compound or pharmaceutically acceptable salt thereof.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The term "biological sample", as used herein, includes, without limitation, cell cultures or extracts thereof; biopsied material obtained from a mammal or extracts thereof, and blood, saliva, urine, feces, semen, tears, or other body fluids or extracts thereof.

In other embodiments, the present invention provides a method for treating a disorder mediated by Rheb in a patient in need thereof, comprising the step of administering to said patient a compound according to the present invention or pharmaceutically acceptable composition thereof. Such disorders are described in detail herein.

Depending upon the particular condition, or disease, to be treated, additional therapeutic agents that are normally administered to treat that condition, may also be present in the compositions of this invention. As used herein, additional therapeutic agents that are normally administered to treat a particular disease, or condition, are known as "appropriate for the disease, or condition, being treated."

A compound of the current invention may also be used to advantage in combination with other antiproliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics; temozolomide (Temodal®); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, AZD6244 from AstraZeneca, PD181461 from Pfizer and leucovorin. The term "aromatase inhibitor" as used herein relates to a compound which inhibits estrogen production, for instance, the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. Exemestane is marketed under the trade name Aromasin™. Formestane is marketed under the trade name Lentaron™. Fadrozole is marketed under the trade name Afema™. Anastrozole is marketed under the trade name Arimidex™. Letrozole is marketed under the trade names Femara™ or Femar™. Aminoglutethimide is marketed under the trade name Orimeten™. A combination of the invention comprising a chemotherapeutic agent which is an aromatase inhibitor is particularly useful for the treatment of hormone receptor positive tumors, such as breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen is marketed under the trade name Nolvadex™. Raloxifene hydrochloride is marketed under the trade name Evista™. Fulvestrant can be administered under the trade name Faslodex™. A combination of the invention comprising a chemotherapeutic agent which is an antiestrogen is particularly useful for the treatment of estrogen receptor positive tumors, such as breast tumors.

The term "anti-androgen" as used herein relates to any substance which is capable of inhibiting the biological effects of androgenic hormones and includes, but is not limited to, bicalutamide (Casodex™). The term "gonadorelin agonist" as used herein includes, but is not limited to abarelix, goserelin and goserelin acetate. Goserelin can be administered under the trade name Zoladex™.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148. Irinotecan can be administered, e.g. in the form as it is marketed, e.g. under the trademark Camptosar™. Topotecan is marketed under the trade name Hycamptin™.

The term "topoisomerase II inhibitor" as used herein includes, but is not limited to the anthracyclines such as doxorubicin (including liposomal formulation, such as Caelyx™), daunorubicin, epirubicin, idarubicin and nemorubicin, the anthraquinones mitoxantrone and losoxantrone, and the podophillotoxines etoposide and teniposide. Etoposide is marketed under the trade name Etopophos™. Teniposide is marketed under the trade name VM 26-Bristol Doxorubicin is marketed under the trade name Acriblastin™ or Adriamycin™. Epirubicin is marketed under the trade name Farmorubicin™. Idarubicin is marketed. under the trade name Zavedos™. Mitoxantrone is marketed under the trade name Novantron.

The term "microtubule active agent" relates to microtubule stabilizing, microtubule destabilizing compounds and microtublin polymerization inhibitors including, but not limited to taxanes, such as paclitaxel and docetaxel; vinca alkaloids, such as vinblastine or vinblastine sulfate, vincristine or vincristine sulfate, and vinorelbine; discodermolides; cochicine and epothilones and derivatives thereof. Paclitaxel is marketed under the trade name Taxol™. Docetaxel is marketed under the trade name Taxotere™. Vinblastine sulfate is marketed under the trade name Vinblastin R.P™. Vincristine sulfate is marketed under the trade name Farmistin™.

The term "alkylating agent" as used herein includes, but is not limited to, cyclophosphamide, ifosfamide, melphalan or nitrosourea (BCNU or Gliadel). Cyclophosphamide is marketed under the trade name Cyclostin™. Ifosfamide is marketed under the trade name Holoxan™.

The term "histone deacetylase inhibitors" or "HDAC inhibitors" relates to compounds which inhibit the histone deacetylase and which possess antiproliferative activity. This includes, but is not limited to, suberoylanilide hydroxamic acid (SAHA).

The term "antineoplastic antimetabolite" includes, but is not limited to, 5-fluorouracil or 5-FU, capecitabine, gemcitabine, DNA demethylating compounds, such as 5-azacytidine and decitabine, methotrexate and edatrexate, and folic acid antagonists such as pemetrexed. Capecitabine is marketed under the trade name Xeloda™. Gemcitabine is marketed under the trade name Gemzar™.

The term "platin compound" as used herein includes, but is not limited to, carboplatin, cis-platin, cisplatinum and oxaliplatin. Carboplatin can be administered, e.g., in the form as it is marketed, e.g. under the trademark Carboplat™. Oxaliplatin can be administered, e.g., in the form as it is marketed, e.g. under the trademark Eloxatin™.

The term "compounds targeting/decreasing a protein or lipid kinase activity; or a protein or lipid phosphatase activity; or further anti-angiogenic compounds" as used herein includes, but is not limited to, protein tyrosine kinase and/or serine and/or threonine kinase inhibitors or lipid kinase inhibitors, such as a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, such as an N-phenyl-2-pyrimidine-amine derivative, such as imatinib, SU101, SU6668 and GFB-111; b) compounds targeting, decreasing or inhibiting the activity of the fibroblast growth factor-receptors (FGFR); c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, or antibodies that target the extracellular domain of IGF-I receptor or its growth factors; d) compounds targeting, decreasing or inhibiting the activity of the Trk receptor tyrosine kinase family, or ephrin B4 inhibitors; e) compounds targeting, decreasing or inhibiting the activity of the AxI receptor tyrosine kinase family; f) compounds targeting, decreasing or inhibiting the activity of the Ret receptor tyrosine kinase; g) compounds targeting, decreasing or inhibiting the activity of the Kit/SCFR receptor tyrosine kinase, such as imatinib; h) compounds targeting, decreasing or inhibiting the activity of the C-kit receptor tyrosine kinases, which are part of the PDGFR family, such as compounds which target, decrease or inhibit the activity of the c-Kit receptor tyrosine kinase family, especially compounds which inhibit the c-Kit receptor, such as imatinib; i) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, such as an N-phenyl-2-pyrimidine-amine derivative, such as imatinib or nilotinib (AMN107); PD180970; AG957; NSC 680410; PD173955 from ParkeDavis; or dasatinib (BMS-354825); j) compounds targeting, decreasing or inhibiting the activity of members of the protein kinase C (PKC) and Raf family of serine/threonine kinases, members of the MEK, SRC, JAK/pan-JAK, FAK, PDK1, PKB/Akt, Ras/MAPK, PI3K, SYK, TYK2, BTK and TEC family, and/or members of the cyclin-dependent kinase family (CDK) including staurosporine derivatives, such as midostaurin; examples of further compounds include UCN-01, safingol, BAY 43-9006, Bryostatin 1, Perifosine; Ilmofosine; RO 318220 and RO 320432; GO 6976; Isis 3521; LY333531/LY379196; isochinoline compounds; FTIs; PD184352 or QAN697 (a PI3K inhibitor) or AT7519 (CDK inhibitor); k) compounds targeting, decreasing or inhibiting the activity of protein-tyrosine kinase inhibitors, such as compounds which target, decrease or inhibit the activity of protein-tyrosine kinase inhibitors include imatinib mesylate (Gleevec™) or tyrphostin such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); 1) compounds targeting, decreasing or inhibiting the activity of the epidermal growth factor family of receptor tyrosine kinases (EGFR$_1$ ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, such as EGF receptor, ErbB2, ErbB3 and ErbB4 or bind to EGF or EGF related ligands, CP 358774, ZD 1839, ZM 105180; trastuzumab (Herceptin™), cetuximab (Erbitux™), Iressa, Tarceva, OSI-774, C1-1033, EKB-569, GW-2016, E1.1, E2.4, E2.5, E6.2, E6.4, E2.11, E6.3 or E7.6.3, and 7H-pyrrolo-[2,3-d]pyrimidine derivatives; m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF, n) compounds targeting, decreasing or inhibiting the kinase activity of one or more JAK family members (JAK1/JAK2/JAK3/TYK2 and/or pan-JAK), including but not limited to PRT-062070, SB-1578, baricitinib, pacritinib, momelotinib, VX-509, AZD-1480, TG-101348, tofacitinib, and ruxolitinib; o) compounds targeting, decreasing or inhibiting the kinase activity of PI3 kinase (PI3K) including but not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib; and; and q) compounds targeting, decreasing or inhibiting the signaling effects of hedgehog protein (Hh) or smoothened receptor (SMO) pathways, including but not limited to cyclopamine, vismodegib, itraconazole, erismodegib, and IPI-926 (saridegib).

The term "PI3K inhibitor" as used herein includes, but is not limited to compounds having inhibitory activity against one or more enzymes in the phosphatidylinositol-3-kinase family, including, but not limited to PI3Kα, PI3Kγ, PI3Kδ, PI3Kβ, PI3K-C2α, PI3K-C2β, PI3K-C2γ, Vps34, p110-α, p110-β, p110-γ, p110-δ, p85-α, p85-β, p55-γ, p150, p101, and p87. Examples of PI3K inhibitors useful in this invention include but are not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib.

The term "Bcl-2 inhibitor" as used herein includes, but is not limited to compounds having inhibitory activity against B-cell lymphoma 2 protein (Bcl-2), including but not limited to ABT-199, ABT-731, ABT-737, apogossypol, Ascenta's pan-Bcl-2 inhibitors, curcumin (and analogs thereof), dual Bcl-2/Bcl-xL inhibitors (Infinity Pharmaceuticals/Novartis Pharmaceuticals), Genasense (G3139), HA14-1 (and analogs thereof; see WO2008118802), navitoclax (and analogs thereof, see U.S. Pat. No. 7,390,799), NH-1 (Shenayng Pharmaceutical University), obatoclax (and analogs thereof, see WO2004106328), S-001 (Gloria Pharmaceuticals), TW series compounds (Univ. of Michigan), and venetoclax. In some embodiments the Bcl-2 inhibitor is a small molecule therapeutic. In some embodiments the Bcl-2 inhibitor is a peptidomimetic.

The term "BTK inhibitor" as used herein includes, but is not limited to compounds having inhibitory activity against Bruton's Tyrosine Kinase (BTK), including, but not limited to AVL-292 and ibrutinib.

The term "SYK inhibitor" as used herein includes, but is not limited to compounds having inhibitory activity against spleen tyrosine kinase (SYK), including but not limited to PRT-062070, R-343, R-333, Excellair, PRT-062607, and fostamatinib Further examples of BTK inhibitory compounds, and conditions treatable by such compounds in combination with compounds of this invention can be found in WO2008039218 and WO2011090760, the entirety of which are incorporated herein by reference.

Further examples of SYK inhibitory compounds, and conditions treatable by such compounds in combination with compounds of this invention can be found in WO2003063794, WO2005007623, and WO2006078846, the entirety of which are incorporated herein by reference.

Further examples of PI3K inhibitory compounds, and conditions treatable by such compounds in combination with compounds of this invention can be found in WO2004019973, WO2004089925, WO2007016176, U.S. Pat. No. 8,138,347, WO2002088112, WO2007084786, WO2007129161, WO2006122806, WO2005113554, and WO2007044729 the entirety of which are incorporated herein by reference.

Further examples of JAK inhibitory compounds, and conditions treatable by such compounds in combination with compounds of this invention can be found in WO2009114512, WO2008109943, WO2007053452, WO2000142246, and WO2007070514, the entirety of which are incorporated herein by reference.

Further anti-angiogenic compounds include compounds having another mechanism for their activity, e.g. unrelated to protein or lipid kinase inhibition e.g. thalidomide (Thalomid™) and TNP-470.

Examples of proteasome inhibitors useful for use in combination with compounds of the invention include, but are not limited to bortezomib, disulfiram, epigallocatechin-3-gallate (EGCG), salinosporamide A, carfilzomib, ONX-0912, CEP-18770, and MLN9708.

Compounds which target, decrease or inhibit the activity of a protein or lipid phosphatase are e.g. inhibitors of phosphatase 1, phosphatase 2A, or CDC25, such as okadaic acid or a derivative thereof.

Compounds which induce cell differentiation processes include, but are not limited to, retinoic acid, α- γ- or δ-tocopherol or α- γ- or δ-tocotrienol.

The term cyclooxygenase inhibitor as used herein includes, but is not limited to, Cox-2 inhibitors, 5-alkyl substituted 2-arylaminophenylacetic acid and derivatives, such as celecoxib (Celebrex™), rofecoxib (Vioxx™), etoricoxib, valdecoxib or a 5-alkyl-2- arylaminophenylacetic acid, such as 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. Etridonic acid is marketed under the trade name Didronel™. Clodronic acid is marketed under the trade name Bonefos™. Tiludronic acid is marketed under the trade name Skelid™. Pamidronic acid is marketed under the trade name Aredia™. Alendronic acid is marketed under the trade name Fosamax™. Ibandronic acid is marketed under the trade name Bondranat™. Risedronic acid is marketed under the trade name Actonel™. Zoledronic acid is marketed under the trade name Zometa™. The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88. The term "biological response modifier" as used herein refers to a lymphokine or interferons.

The term "inhibitor of Ras oncogenic isoforms", such as H-Ras, K-Ras, or N-Ras, as used herein refers to compounds which target, decrease or inhibit the oncogenic activity of Ras; for example, a "farnesyl transferase inhibitor" such as L-744832, DK8G557 or R115777 (Zamestra™). The term "telomerase inhibitor" as used herein refers to compounds which target, decrease or inhibit the activity of telomerase. Compounds which target, decrease or inhibit the activity of telomerase are especially compounds which inhibit the telomerase receptor, such as telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase include, but are not limited to, bengamide or a derivative thereof.

The term "proteasome inhibitor" as used herein refers to compounds which target, decrease or inhibit the activity of the proteasome. Compounds which target, decrease or inhibit the activity of the proteasome include, but are not limited to, Bortezomib (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors, which are compounds targeting, decreasing or inhibiting the activity of FMS-like tyrosine kinase receptors (Flt-3R); interferon, 1-β-D-arabinofuransylcytosine (ara-c) and bisulfan; and ALK inhibitors, which are compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, such as PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino, 17-demethoxygeldanamycin (17AAG), a geldanamycin derivative; other geldanamycin related compounds; radicicol and HDAC inhibitors.

The term "antiproliferative antibodies" as used herein includes, but is not limited to, trastuzumab (Herceptin™), Trastuzumab-DM1, erbitux, bevacizumab (Avastin™), rituximab (Rituxan®), PRO64553 (anti-CD40) and 2C4 Antibody. By antibodies is meant intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the current invention can be used in combination with standard leukemia therapies, especially in combination with therapies used for the treatment of AML. In particular, compounds of the current invention can be administered in combination with, for example, farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

Other anti-leukemic compounds include, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065 including, but not limited to, N-hydroxy-3-[4-[[[2-(2-methyl-1H-indol-3-yl)-ethyl]-amino]methyl]phenyl]-2E-2-propenamide, or a pharmaceutically acceptable salt thereof and N-hydroxy-3-[4-[(2-hydroxyethyl){2-(1H-indol-3-yl)ethyl]-amino]methyl]phenyl]-2E-2-propenamide, or a pharmaceutically acceptable salt thereof, especially the lactate salt. Somatostatin receptor antagonists as used herein refer to compounds which target, treat or inhibit the somatostatin receptor such as octreotide, and SOM230. Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in Principles and Practice of Oncology, Devita et al., Eds., 4$^{th}$ Edition, Vol. 1, pp. 248-275 (1993).

Also included are EDG binders and ribonucleotide reductase inhibitors. The term "EDG binders" as used herein refers to a class of immunosuppressants that modulates lymphocyte recirculation, such as FTY720. The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives.

Also included are in particular those compounds, proteins or monoclonal antibodies of VEGF such as 1-(4-chloroanilino)-4-(4-pyridylmethyl)phthalazine or a pharmaceutically acceptable salt thereof, 1-(4-chloroanilino)-4-(4-pyridylmethyl)phthalazine succinate; Angiostatin™; Endostatin™; anthranilic acid amides; ZD4190; ZD6474; SU5416; SU6668; bevacizumab; or anti-VEGF antibodies or anti-VEGF receptor antibodies, such as rhuMAb and RHUFab, VEGF aptamer such as Macugon; FLT-4 inhibitors, FLT-3 inhibitors, VEGFR-2 IgGI antibody, Angiozyme (RPI 4610) and Bevacizumab (Avastin™).

Photodynamic therapy as used herein refers to therapy which uses certain chemicals known as photosensitizing compounds to treat or prevent cancers. Examples of photodynamic therapy include treatment with compounds, such as Visudyne™ and porfimer sodium.

Angiostatic steroids as used herein refers to compounds which block or inhibit angiogenesis, such as, e.g., anecortave, triamcinolone, hydrocortisone, 11-α-epihydrocotisol, cortexolone, 17α-hydroxyprogesterone, corticosterone, desoxycorticosterone, testosterone, estrone and dexamethasone.

Implants containing corticosteroids refers to compounds, such as fluocinolone and dexamethasone.

Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The structure of the active compounds identified by code numbers, generic or trade names may be taken from the actual edition of the standard compendium "The Merck Index" or from databases, e.g. Patents International (e.g. IMS World Publications).

A compound of the current invention may also be used in combination with known therapeutic processes, for example, the administration of hormones or radiation. In certain embodiments, a provided compound is used as a radiosensitizer, especially for the treatment of tumors which exhibit poor sensitivity to radiotherapy.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. A compound of the current invention can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the current invention, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-1,000 µg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Implantable devices coated with a compound of this invention are another embodiment of the present invention.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

List of common abbreviations used in the experimental section.

AcOH: acetic acid
aq: aqueous
Boc: tert-butoxycarbonyl
$(Boc)_2O$: di-tert-butyl dicarbonate
BrettPhos: 2-(Dicyclohexylphosphino)3,6-dimethoxy-2', 4',6'-triisopropyl-1,1'-biphenyl
n-BuOH: n-butanol
t-BuLi: tert-butyllithium
t-BuOK: potassium tert-butoxide
t-BuONa: sodium tert-butoxide
chiral-HPLC: chiral high performance liquid chromatography
Conc.: concentrated
d: days
dba: dibenzylideneacetone
DCM: dichloromethane
DIAD: diisopropyl azodicarboxylate
DIPEA: N,N-diisopropylethylamine
DMA: N,N-dimethylacetamide
DMAP: 4-dimethylaminopyridine
DMF: N,N-dimethylformamide
DMG: dimethylglyoxime
DMSO: dimethyl sulfoxide
DPE-Phos: (Oxydi-2,1-phenylene)bis(diphenylphosphine)
dppf: 1,1'-bis(diphenylphosphino)ferrocene
EA: ethyl acetate
EDCI: 1-(3-dimethylaminopropyl)-3-ethylcarbodiimide hydrochloride
EDTA: ethylenediaminetetraacetic acid
ee: enantiomeric excess
ESI: electrospray ionization
$Et_3N$: triethylamine
$Et_2O$: diethyl ether
EtOAc: ethyl acetate
EtOH: ethanol
EtONa: sodium ethoxide
$Fe(OTf)_2$: iron(II) trifluoromethanesulfonate
h: hours
HATU: N,N,N',N'-tetramethyl-O-(7-azabenzotriazol-1-yl)uranium hexafluorophosphate
HCl: hydrochloric acid
HCl(con): concentrated hydrochloric acid
HOBT: Hydroxybenzotriazole
HPLC: high performance liquid chromatography
IBX: 2-iodoxybenzoic acid
LAH: lithium aluminum hydride
LDA: lithium diisopropylamide
M: molar
Me: methyl
MeCN: acetonitrile Me₄t-BuXphos: 2-di-tert-butylphosphino-3,4,5,6-tetramethyl-2',4',6'-triisopropyl-1,1'-biphenyl
MeOH: methanol
min: minutes
mL: milliliters
mM: millimolar
mmol: millimoles
MsCl: Mesyl Chloride
MW: microwave
n: normal
n-BuLi: n-butyl lithium
NBS: N-bromosuccinimide
NIS: N-iodosuccinimide
NMO: 4-methylmorpholine N-oxide
NMP: N-methyl-2-pyrrolidone
NMR: Nuclear Magnetic Resonance
° C.: degrees Celsius
Pd/C: palladium on carbon
Pd₂(dba)₃: tris(dibenzylideneacetone)dipalladium(0)
Pd(PPh₃)₄: tetrakis(triphenylphosphine)palladium(0)
PE: petroleum ether
PPh₃: triphenylphosphine
Ph: phenyl
prep-HPLC: preparative high performance liquid chromatography
rel: relative
rt: room temperature
sat: saturated
SEM-Cl: 2-(trimethylsilyl)ethoxymethyl chloride
SFC: supercritical fluid chromatography
SGC: silica gel chromatography
t: tertiary
TBAB: Tetra-n-butylammonium bromide
TBAF: Tetra-n-butylammonium fluoride
TCCA: trichloroisocyanuric acid
TEA: triethylamine
Tf: trifluoromethanesulfonate
TFA: trifluoroacetic acid
TLC: thin layer chromatography
THF: tetrahydrofuran
TMSBr: trimethylsilyl bromide
Trt: triphenylmethyl
pTSA: para-toluenesulfonic acid
TsCH₂CN: toluenesulfonylmethyl isocyanide
TsCl: 4-toluenesulfonyl chloride
TosCl: 4-toluenesulfonyl chloride
XantPhos: 4,5-bis(diphenylphosphino)-9,9-dimethylxanthene
XPhos: 2-dicyclohexylphosphino-2',4',6'-triisopropylbiphenyl LCMS Methods Method 1: '1-POS-3MIN.
  Method Info: Column: SUNFIRE C18 4.6×50 mm, 3.5 um
  Mobile phase: H₂O (0.01% TFA) (A)/ACN (0.01% TFA) (B)
  Elution program: Gradient from 5 to 95% of B in 1.4 min at 2.0 ml/min
  Temperature: 50° C.
  Detection: UV (214, 4 nm) and MS (ESI, POS mode, 113 to 1200 amu)

Method 2: '1-POS-MON-1'
  Method Info: Column: Xbridge C18(2) (4.6×50 mm, 3.5 um)
  Mobile phase: H₂O (10 mmol NH₄HCO3) (A)/ACN(B)
  Elution program: Gradient from 10 to 95% of B in 1.5 min at 1.8 ml/min
  Temperature: 50° C.
  Detection: UV (214, 4 nm) and MS (ESI, Pos mode, 103 to 800 amu)

Example 1: 4-Bromo-6-(3,4-dichlorophenylthio)-1-(4-(dimethylcarbamoyl)benzyl)-1H-indole-2-carboxylic acid, I-102

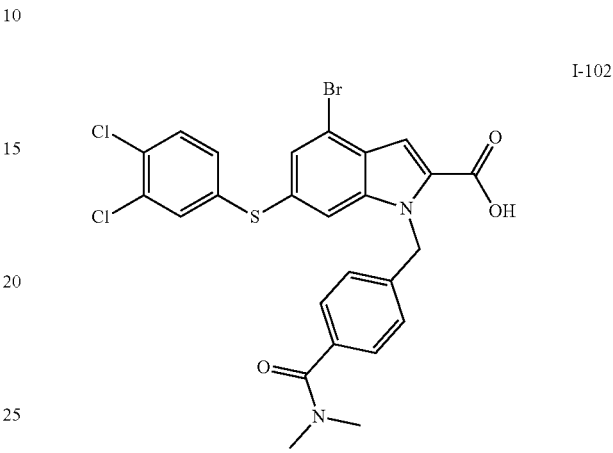

Synthetic Scheme:

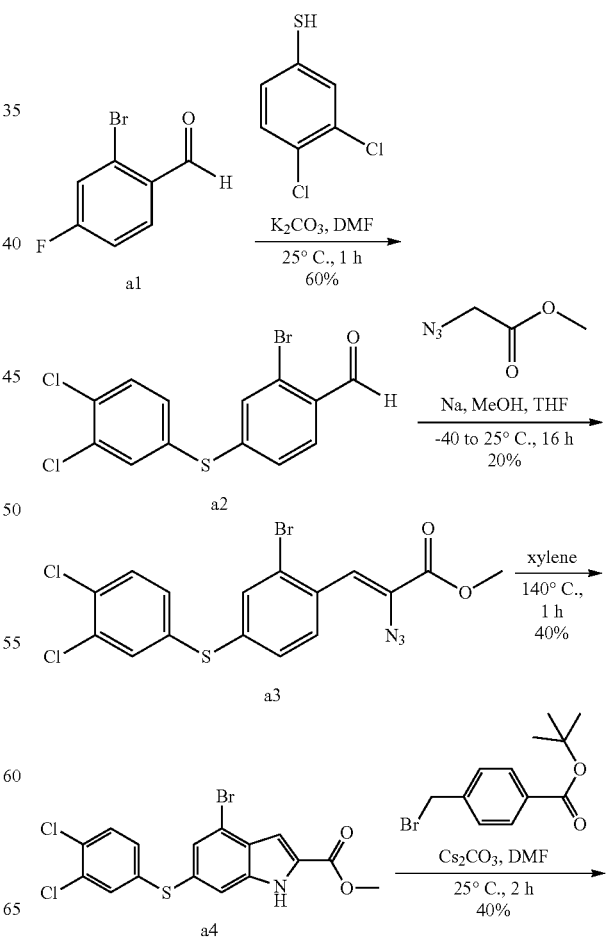

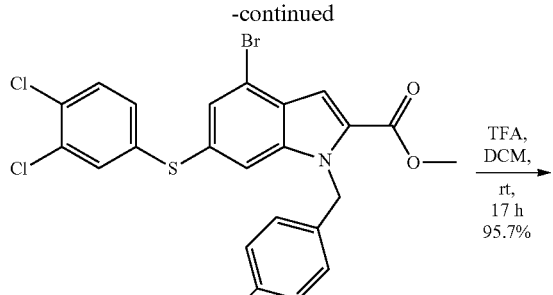

a5

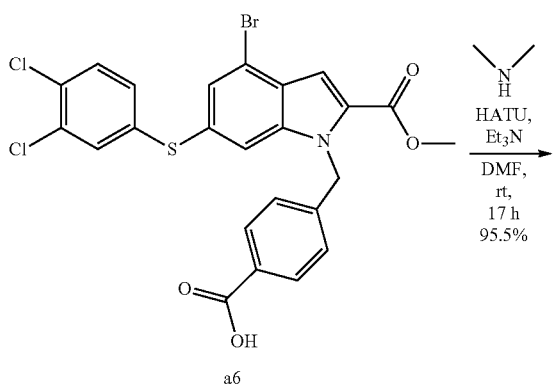

a6

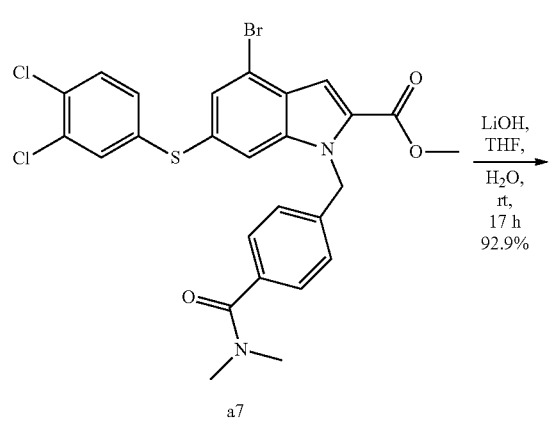

a7

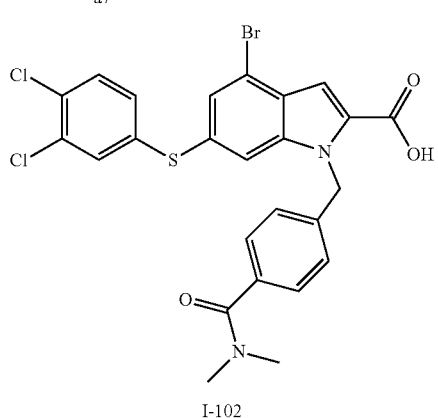

I-102

Procedures and Characterization:

Step 1: 2-bromo-4-(3,4-dichlorophenylthio)benzaldehyde

A mixture of 2-bromo-4-fluorobenzaldehyde (7.45 g, 36.9 mmol), 3,4-dichlorobenzenethiol (6.89 mg, 38.7 mmol) and K$_2$CO$_3$ (6.1 g, 44.3 mmol) in DMF (120 mL) was stirred for 1 h at 25° C. The reaction was quenched with water (250 mL) and extracted with ethyl acetate (300 mL). The organic phase was washed water (80 mL×2), and brine (80 mL), dried (Na$_2$SO$_4$), filtered and concentrated in vacuo and the residue was purified by chromatography (silica, ethyl acetate/petroleum ether=1/20) to afford 2-bromo-4-(3,4-dichlorophenylthio)benzaldehyde (9 g, 25 mmol, 60%) as a white solid. $^1$H NMR (500 MHz, CDCl$_3$) δ 10.26 (s, 1H), 7.79 (d, J=10 Hz, 1H), 7.61 (d, J=2.5 Hz, 1H), 7.51 (d, J=10 Hz, 1H), 7.38 (d, J=2 Hz, 1H), 7.34 (dd, J=10 Hz, J=2.5 Hz, 1H), 7.15 (dd, J=10 Hz, J=1 Hz, 1H).

Step 2: (Z)-methyl 2-azido-3-(2-bromo-4-(3,4-dichlorophenylthio)phenyl)acrylate

Metal Na (184 mg, 8 mmol) was dissolved in dry MeOH (20 mL). A mixture of was 2-bromo-4-(3,4-dichlorophenylthio)benzaldehyde (720 mg, 2 mmol) and methyl 2-azidoacetate (920 mg, 8 mmol) in dry THF (3 mL) was added at −40° C. The reaction was stirred for 1 h at −40° C. and for 16 h at 25° C. under N$_2$ atmosphere. The reaction was filtered. The cake was dried in vacuo to afford (Z)-methyl 2-azido-3-(2-bromo-4-(3,4-dichlorophenylthio)phenyl) acrylate (283 mg, 0.6 mmol, 20%) as an off-white solid. ESI-MS (EI+, m/z): 430.0 [M-27]$^-$.

Step 3: methyl 4-bromo-6-(3,4-dichlorophenylthio)-1H-indole-2-carboxylate

A mixture of (Z)-methyl 2-azido-3-(2-bromo-4-(3,4-dichlorophenylthio)phenyl)acrylate (250 mg, 0.55 mmol) in xylene (10 mL) was stirred for 1 h at 140° C. The reaction was filtered. The cake was dried in vacuo to afford methyl 4-bromo-6-(3,4-dichlorophenylthio)-1H-indole-2-carboxylate (120 mg, 0.28 mmol, 40%) as a light yellow solid. ESI-MS (EI+, m/z): 427.9 [M−H]$^-$. $^1$H NMR (500 MHz, CDCl$_3$) δ 9.06 (s, 1H), 7.43 (s, 1H), 7.36 (s, 2H), 7.35 (s, 1H), 7.11 (dd, J=10.5 Hz, J=2 Hz, 1H), 3.97 (s, 3H).

Step 4: methyl 4-bromo-1-(4-(tert-butoxycarbonyl)benzyl)-6-(3,4-dichlorophenylthio)-1H-indole-2-carboxylate A mixture of methyl 4-bromo-6-(3,4-dichlorophenylthio)-1H-indole-2-carboxylate (120 mg, 0.28 mmol), tert-butyl 4-(bromomethyl)benzoate (91 mg, 0.34 mmol) and Cs$_2$CO$_3$ (184 mg, 0.56 mmol) in DMF (5 mL) was stirred for 2 h at 25° C. The reaction was quenched with water (10 mL) and extracted with ethyl acetate (30 mL). The organic phase was washed water (10 mL×2), and brine (10 mL), dried (Na$_2$SO$_4$), filtered and concentrated in vacuo and the residue was purified by chromatography (silica, ethyl acetate/petroleum ether=1/5) to afford methyl 4-bromo-1-(4-(tert-butoxycarbonyl)benzyl)-6-(3,4-dichlorophenylthio)-1H-indole-2-carboxylate (100 mg, 0.16 mmol, 40%) as a white solid. ESI-MS (EI+, m/z): 641.9 [M+Na]$^+$.

Step 5: 4-((4-Bromo-6-(3,4-dichlorophenylthio)-2-(methoxycarbonyl)-1H-indol-1-yl)methyl)benzoic acid To a solution of methyl 4-bromo-1-(4-(tert-butoxycarbonyl)benzyl)-6-(3,4-dichlorophenylthio)-1H-indole-2-carboxylate (230 mg, 0.37 mmol) in DCM (8 mL) and TFA (4 mL). The mixture was stirred at rt for 17 h. Filtered and concentrated in vacuo to afford 4-((4-bromo-6-(3,4-dichlorophenylthio)-2-(methoxycarbonyl)-1H-indol-1-yl)methyl)benzoic acid (200 mg, 95.7%) as a yellow solid which was used directly in the next step without further purification. ESI-MS (EI⁺, m/z): 563.8 [M−H]⁺.

Step 6: Methyl 4-bromo-6-(3,4-dichlorophenylthio)-1-(4-(dimethylcarbamoyl)benzyl)-1H-indole-2-carboxylate To a solution of 4-((4-bromo-6-(3,4-dichlorophenylthio)-2-(methoxycarbonyl)-1H-indol-1-yl)methyl)benzoic acid (130 mg, 0.23 mmol) in DMF (8 ml) was added dimethylamine (40.7 mg, 0.69 mmol) and Et₃N (69.7 mg, 0.69 mmol) and HATU (262.2 mg, 0.69 mmol). The mixture was stirred at rt for 17 h. Concentrated and purified by prep-HPLC to afford methyl 4-bromo-6-(3,4-dichlorophenylthio)-1-(4-(dimethylcarbamoyl)benzyl)-1H-indole-2-carboxylate (130 mg, 95.5%) as a white solid. MS (EI+, m/z): 593.0 [M+H]⁺.

Step 7: 4-bromo-6-(3,4-dichlorophenylthio)-1-(4-(dimethylcarbamoyl)benzyl)-1H-indole-2-carboxylic acid, I-102

To a solution of methyl 4-bromo-6-(3,4-dichlorophenylthio)-1-(4-(dimethylcarbamoyl)benzyl)-1H-indole-2-carboxylate (130 mg, 0.22 mmol) in THF/H₂O (4 mL: 4 mL) was added LiOH.H₂O (18.5 mg, 0.44 mmol), then stirred at rt for 17 h. The reaction was quenched with ice-water, adjust pH to 5 with 1N HCl aqueous solution, extracted with EtOAc, washed with brine, dried over sodium sulfate. Concentrated and purified by prep-HPLC to afford 4-bromo-6-(3,4-dichlorophenylthio)-1-(4-(dimethylcarbamoyl)benzyl)-1H-indole-2-carboxylic acid, I-102 (118 mg, 92.9%) as a white solid. MS (EI+, m/z): 576.8 [M−H]⁺. ¹H NMR (500 MHz, DMSO) δ 13.49 (s, 1H), 7.86 (s, 1H), 7.60-7.41 (m, 3H), 7.30 (d, J=8.1 Hz, 2H), 7.23 (s, 1H), 7.12 (dd, J=8.5, 2.1 Hz, 1H), 7.03 (d, J=8.1 Hz, 2H), 5.94 (s, 2H), 2.89 (d, J=54.0 Hz, 6H).

Example 2: 4-bromo-6-(3,4-dichlorophenylthio)-1-(4-(4-methylpiperazine-1-carbonyl)benzyl)-1H-indole-2-carboxylic acid, I-52

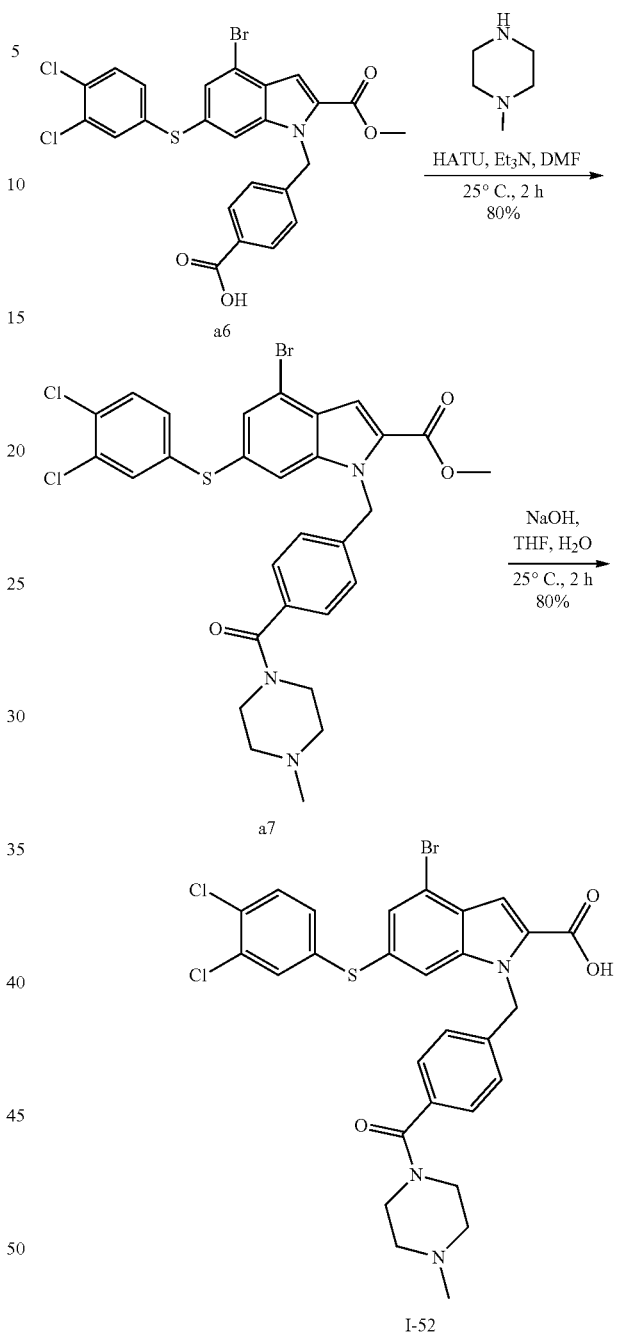

Procedures and Characterization:

Step 1: methyl 4-bromo-6-(3,4-dichlorophenylthio)-1-(4-(4-methylpiperazine-1-carbonyl)benzyl)-1H-indole-2-carboxylate The same procedure used to prepare methyl 4-bromo-6-(3,4-dichlorophenylthio)-1-(4-(dimethylcarbamoyl)benzyl)-1H-indole-2-carboxylate (a7) afforded methyl 4-bromo-6-(3,4-dichlorophenylthio)-1-(4-(4-methylpiperazine-1-carbonyl)benzyl)-1H-indole-2-carboxylate (120 mg, 0.18 mmol, 80%) as a white solid. The reaction time was 1 h. ESI-MS (EI+, m/z): 646.0 [M+H]⁺.

Step 2: 4-bromo-6-(3,4-dichlorophenylthio)-1-(4-(4-methylpiperazine-1-carbonyl)benzyl)-1H-indole-2-carboxylic acid, I-52

A mixture of methyl 4-bromo-6-(3,4-dichlorophenylthio)-1-(4-(4-methylpiperazine-1-carbonyl)benzyl)-1H-indole-2-carboxylate (120 mg, 0.18 mmol), NaOH (44 mg, 1.1 mmol) in THF (2 mL) and H$_2$O (2 mL) was stirred for 2 h at 25° C. The reaction was neutralized with 2 N HCl to pH 6 and extracted with ethyl acetate (20 mL). The organic phase was dried (Na$_2$SO$_4$), filtered and concentrated in vacuo and the residue was purified by prep-HPLC (0.01% TFA) to afford 4-bromo-6-(3,4-dichlorophenylthio)-1-(4-(4-methylpiperazine-1-carbonyl)benzyl)-1H-indole-2-carboxylic acid (FA salt), I-52 (103.2 mg, 0.15 mmol, 80%) as a white solid. ESI-MS (EI+, m/z): 631.9 [M+H]$^+$. $^1$H NMR (500 MHz, DMSO) δ 8.15 (s, 1H), 7.85 (s, 1H), 7.55 (d, J=11 Hz, 1H), 7.47 (d, J=3 Hz, 1H), 7.42 (s, 1H), 7.29 (d, J=10 Hz, 1H), 7.16 (s, 1H), 7.09 (dd, J=11 Hz, J=3 Hz, 1H), 7.05 (d, J=10 Hz, 1H), 5.98 (s, 2H), 3.60 (s, 2H), 3.26 (s, 2H), 2.45 (s, 4H), 2.29 (s, 3H).

Example 3: 4-bromo-6-(3,4-dichlorophenylthio)-1-(4-((2-hydroxyethyl)(methyl)carbamoyl)benzyl)-1H-indole-2-carboxylic acid, I-51

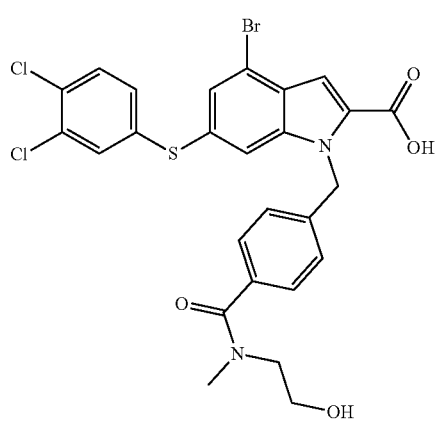

I-51

Synthetic Scheme:

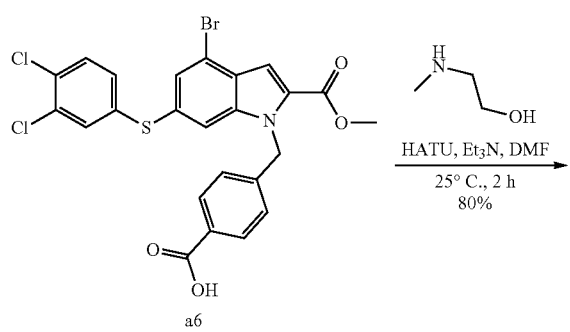

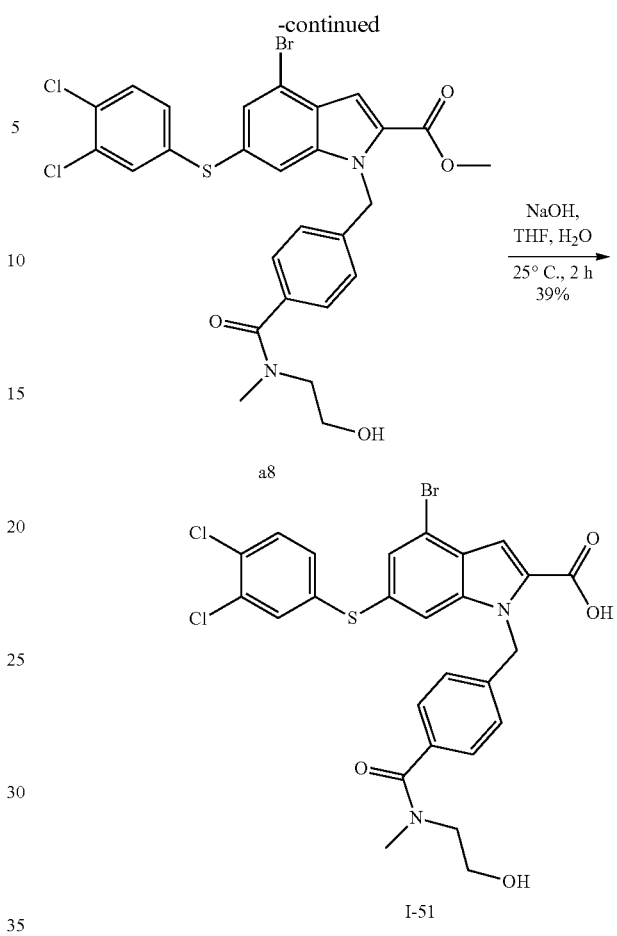

Procedures and Characterization:

Step 1: methyl 4-bromo-6-(3,4-dichlorophenylthio)-1-(4-((2-hydroxyethyl) (methyl) carbamoyl)benzyl)-1H-indole-2-carboxylate The same procedure used to prepare methyl 4-bromo-6-(3,4-dichlorophenylthio)-1-(4-(dimethylcarbamoyl)benzyl)-1H-indole-2-carboxylate (a7) afforded methyl 4-bromo-6-(3,4-dichlorophenylthio)-1-(4-((2-hydroxyethyl)(methyl)carbamoyl)benzyl)-1H-indole-2-carboxylate (90 mg, 0.15 mmol, 85%) as a white solid. The reaction time was 2 h. ESI-MS (EI+, m/z): 621.0 [M+H]$^+$.

Step 2: 4-bromo-6-(3,4-dichlorophenylthio)-1-(4-((2-hydroxyethyl)(methyl)carbamoyl) benzyl)-1H-indole-2-carboxylic acid, I-51

The same procedure that was used to prepare I-52 afforded 4-bromo-6-(3,4-dichlorophenylthio)-1-(4-((2-hydroxyethyl) (methyl)carbamoyl)benzyl)-1H-indole-2-carboxylic acid, I-51 (35.4 mg, 0.06 mmol, 39%) as a white solid. ESI-MS (EI+, m/z): 606.9 [M+H]$^+$. $^1$H NMR (500 MHz, DMSO) δ 13.5 (s, 1H), 7.87 (d, J=10 Hz, 1H), 7.57 (d, J=6 Hz, 1H), 7.51 (s, 1H), 7.44 (s, 1H), 7.30 (d, J=10 Hz, 1H), 7.23 (s, 1H), 7.13 (dd, J=11 Hz, J=3 Hz, 1H), 7.02 (d, J=8 Hz, 2H), 5.93 (s, 2H), 4.78 (s, 1H), 3.45 (t, J=6 Hz, 2H), 3.34 (s, 1H), 3.21 (s, 1H), 2.92 (s, 2H), 2.88 (s, 1H).

353

Example 4: 4-bromo-6-(3,4-dichlorophenylthio)-1-(4-((2-hydroxyethyl)(methyl)carbamoyl)benzyl)-1H-indole-2-carboxylic acid, I-50

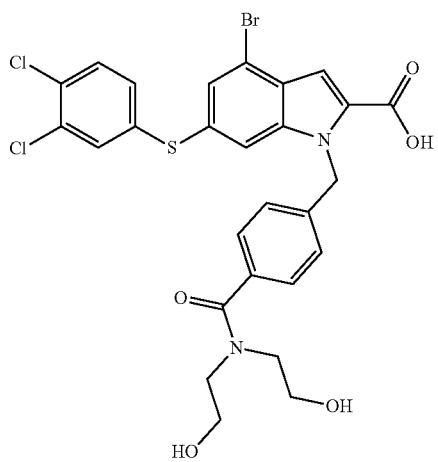
I-50

Synthetic Scheme:

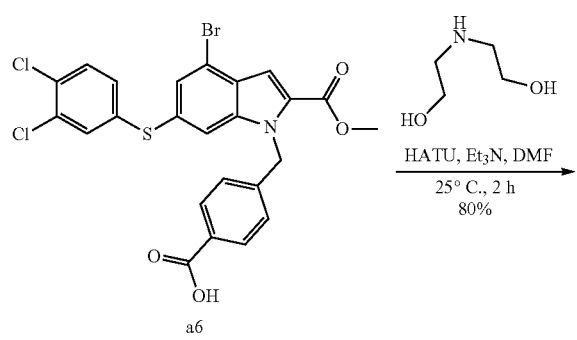

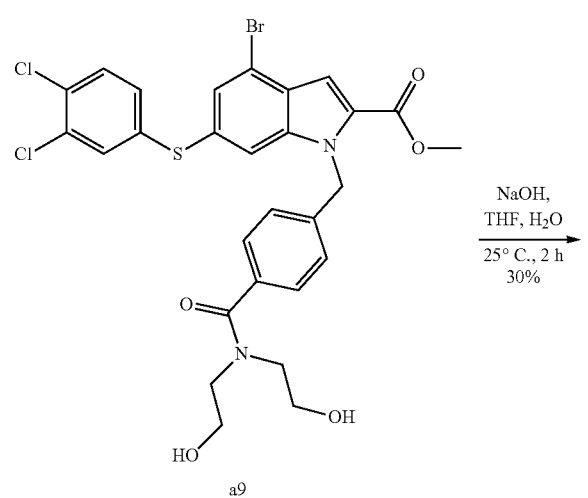

354

-continued

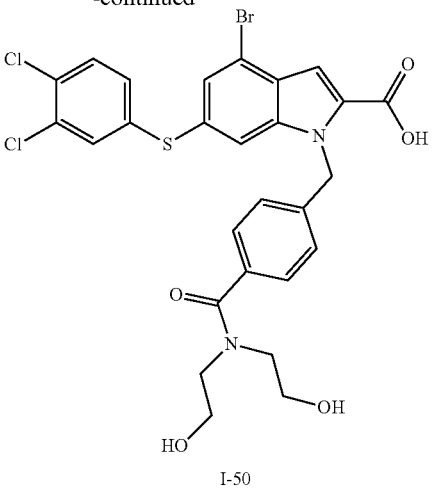
I-50

Procedures and Characterization:

Step 1: methyl 1-(4-(bis(2-hydroxyethyl)carbamoyl)benzyl)-4-bromo-6-(3,4-dichlorophenyl thio)-1H-indole-2-carboxylate The same procedure used to prepare methyl 4-bromo-6-(3,4-dichlorophenylthio)-1-(4-(dimethylcarbamoyl)benzyl)-1H-indole-2-carboxylate (a7) afforded methyl 1-(4-(bis(2-hydroxyethyl)carbamoyl)benzyl)-4-bromo-6-(3,4-dichlorophenylthio)-1H-indole-2-carboxylate (80 mg, 0.12 mmol, 80%) as a white solid. The reaction time was 2 h. ESI-MS (EI+, m/z): 651.0 [M+H]+.

Step 2: 1-(4-(bis(2-hydroxyethyl)carbamoyl)benzyl)-4-bromo-6-(3,4-dichlorophenylthio)-1H-indole-2-carboxylic acid, I-50

The same procedure used to prepare I-52 afforded 1-(4-(bis(2-hydroxyethyl)carbamoyl)benzyl)-4-bromo-6-(3,4-dichloro phenyl thio)-1H-indole-2-carboxylic acid I-50 (34.2 mg, 0.05 mmol, 30%) as a white solid. ESI-MS (EI+, m/z): 637.0 [M+H]+. 1H NMR (500 MHz, DMSO) δ 13.53 (s, 1H), 7.88 (s, 1H), 7.57 (d, J=10.5 Hz, 1H), 7.51 (d, J=2 Hz, 1H), 7.43 (s, 11H), 7.30 (d, J=9.5 Hz, 2H), 7.22 (s, 1H), 7.12 (dd, J=10.5 Hz, J=8 Hz, 11H), 7.02 (d, J=10 Hz, 1H), 5.93 (s, 2H), 4.80 (t, J=8 Hz, 2H), 3.57 (s, 2H), 3.48 (s, 2H), 3.41 (s, 2H), 3.25 (s, 2H).

Example 5: 4-bromo-6-(3,4-dichlorophenylthio)-1-(1-(4-(dimethylcarbamoyl)phenyl)ethyl)-1H-indole-2-carboxylic acid, I-5

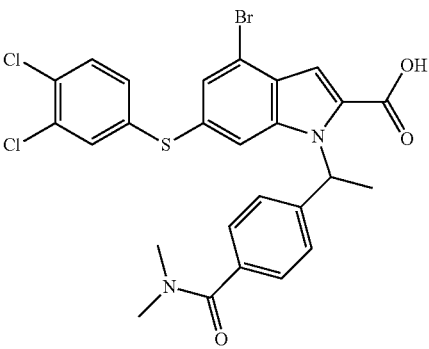
I-5

Synthetic Scheme:

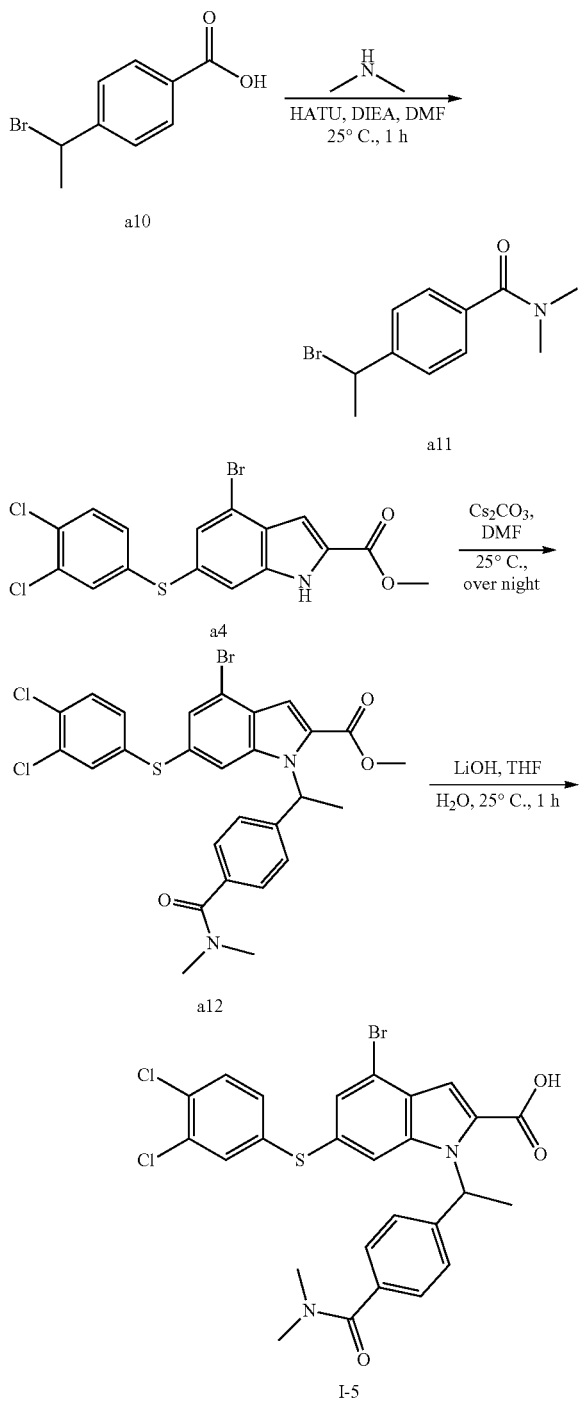

Procedures and Characterization:

Step 1: 4-(1-bromoethyl)-N,N-dimethylbenzamide

To a solution of 4-(1-bromoethyl)benzoic acid (350.00 mg, 1.53 mmol) in DMF (15.00 mL) was added HATU (865.83 mg, 2.30 mmol), DIEA (395.47 mg, 3.06 mmol, 534.42 μL) and N-methylmethanamine (75.87 mg, 1.68 mmol). Then the reaction mixture was stirred at room temperature for 1 h. Then the reaction mixture was treated with water (100 mL) and extracted with EtOAc (30 mL×3). The combined organic layers were washed with brine (30 mL), dried over $Na_2SO_4$ and concentrated in vacuo. The crude product was purified by prep-TLC to give 4-(1-bromoethyl)-N,N-dimethyl-benzamide (15.00 mg, 58.56 μmol, 3.83% yield) and most of a by-product. ESI-MS (EI+, m/z): 256.1 $[M+H]^+$.

Step 2: methyl 4-bromo-6-(3,4-dichlorophenylthio)-1-(1-(4-(dimethylcarbamoyl)phenyl)ethyl)-1H-indole-2-carboxylate The same procedure used to prepare methyl 4-bromo-1-(4-(tert-butoxycarbonyl)benzyl)-6-(3,4-dichlorophenylthio)-1H-indole-2-carboxylate (a5) afforded methyl 4-bromo-6-(3,4-dichlorophenylthio)-1-(1-(4-(dimethylcarbamoyl)phenyl)ethyl)-1H-indole-2-carboxylate (45.00 mg, crude) as an off-white solid which was used directly in the next step. The reaction time was over night. ESI-MS (EI+, m/z): 606.9 $[M+H]^+$.

Step 3: 4-bromo-6-(3,4-dichlorophenylthio)-1-(1-(4-(dimethylcarbamoyl)phenyl)ethyl)-1H-indole-2-carboxylic acid, I-5

The same procedure used to prepare I-102 afforded 4-bromo-6-(3,4-dichlorophenylthio)-1-(1-(4-(dimethylcarbamoyl)phenyl)ethyl)-1H-indole-2-carboxylic acid I-5 (15.40 mg, 26.00 μmol, 35.03% yield) as a white solid. The reaction time was 1 h. ESI-MS (EI+, m/z): 593.0 $[M+H]^+$. $^1$H NMR (400 MHz, DMSO) δ 7.46 (1H, s), 7.40 (2H, m), 7.33 (1H, d, J=8.4 Hz), 7.26 (1H, s), 7.17 (1H, d, J=1.6 Hz), 7.13 (2H, m), 7.02 (1H, m), 6.89 (1H, dd, J=8.4 Hz, 2.4 Hz), 6.86 (1H, s), 3.15 (3H, s), 2.89 (3H, s), 1.92 (3H, d, J=6.8 Hz).

Example 6: 4-cyclopropyl-6-(3,4-dichlorophenylthio)-1-(4-(dimethylcarbamoyl)benzyl)-1H-indole-2-carboxylic acid, I-10

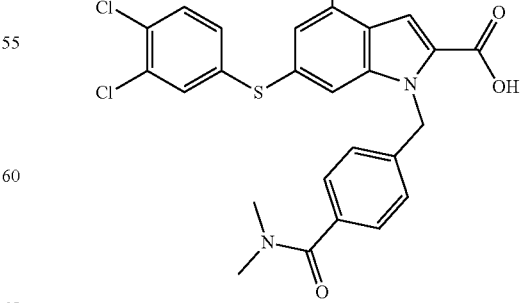

I-10

Synthetic Scheme:

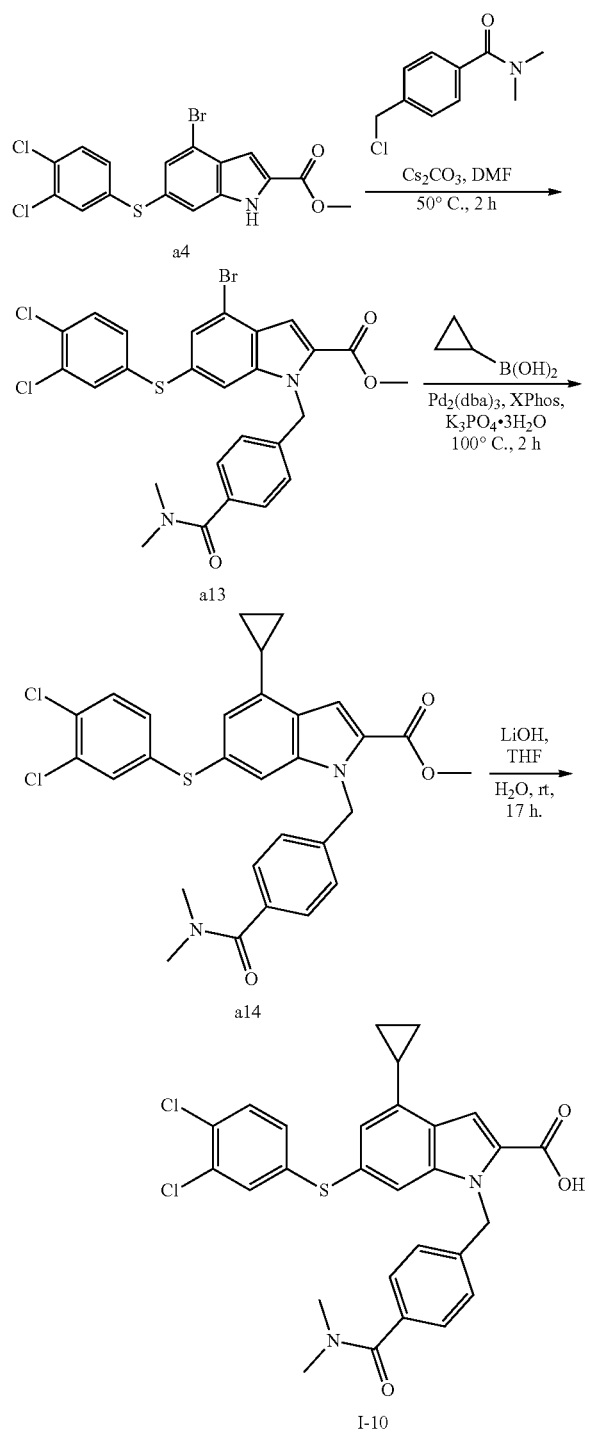

Procedures and Characterization:

Step 1: methyl 4-bromo-6-(3,4-dichlorophenylthio)-1-(4-(dimethylcarbamoyl)benzyl)-1H-indole-2-carboxylate The same procedure used to prepare methyl 4-bromo-1-(4-(tert-butoxycarbonyl)benzyl)-6-(3,4-dichlorophenylthio)-1H-indole-2-carboxylate (a5) except that temperature was 50° C. afforded methyl 4-bromo-6-(3,4-dichlorophenylthio)-1-(4-(dimethylcarbamoyl)benzyl)-1H-indole-2-carboxylate (263.00 mg, 444.01 µmol, 95.71% yield) as a yellow solid. ESI-MS (EI+, m/z): 592.9 [M+H]+.

Step 2: methyl 4-cyclopropyl-6-(3,4-dichlorophenylthio)-1-(4-(dimethylcarbamoyl)benzyl)-1H-indole-2-carboxylate To a mixture of methyl 4-bromo-6-(3,4-dichlorophenylthio)-1-(4-(dimethylcarbamoyl)benzyl)-1H-indole-2-carboxylate (80.00 mg, 135.06 µmol) and cyclopropylboronic acid (17.74 mg, 175.58 µmol) in toluene (4.00 mL) and $H_2O$ (399.96 L) was added $Pd_2(dba)_3$ (12.37 mg, 13.51 µmol), XPhos (12.86 mg, 27.01 µmol) and $K_3PO_4 \cdot 3H_2O$ (71.85 mg, 270.12 µmol). Then the reaction mixture was heated to 100° C. for 2 h. LCMS showed the reaction worked well. Then the mixture was cooled to room temperature and water (10 mL) was added and extracted with EtOAc (10 mL×2). The combined organic layers were washed with brine (10 mL), dried over $Na_2SO_4$ and concentrated in vacuo to give methyl 4-cyclopropyl-6-(3,4-dichlorophenylthio)-1-(4-(dimethylcarbamoyl)benzyl)-1H-indole-2-carboxylate (118.00 mg, crude) as a brown solid which was used directly in the next step. ESI-MS (EI+, m/z): 553.1 [M+H]$^+$.

Step 3: 4-cyclopropyl-6-(3,4-dichlorophenylthio)-1-(4-(dimethylcarbamoyl)benzyl)-1H-indole-2-carboxylic acid, I-10

The same procedure used to prepare I-102 afforded 4-cyclopropyl-6-(3,4-dichlorophenylthio)-1-(4-(dimethylcarbamoyl)benzyl)-1H-indole-2-carboxylic acid, I-10 (18.10 mg, 33.55 µmol, 15.74% yield) as a white solid. ESI-MS (EI+, m/z): 539.0 [M+H]$^+$. $^1$H NMR (400 MHz, DMSO) δ 7.32 (3H, m), 7.31 (3H, m), 7.06 (3H, m), 6.73 (1H, s), 5.96 (2H, s), 2.94 (3H, s), 2.84 (3H, s), 2.36 (1H, m), 1.03 (2H, m), 0.80 (2H, m).

Example 7: 6-(3,4-dichlorophenylthio)-1-(4-(dimethylcarbamoyl)benzyl)-4-phenyl-1H-indole-2-carboxylic acid, I-8

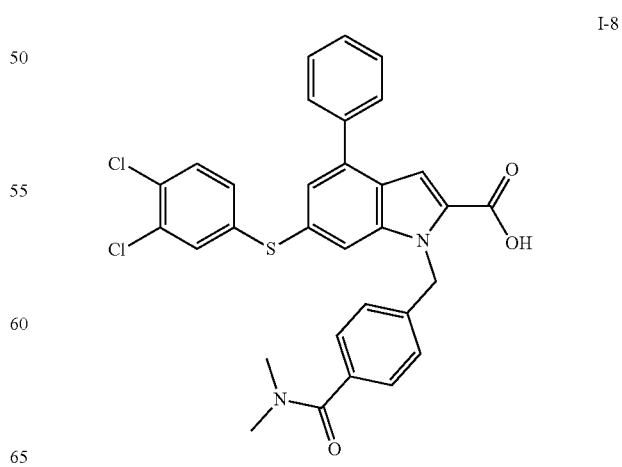

I-8

Synthetic Scheme:

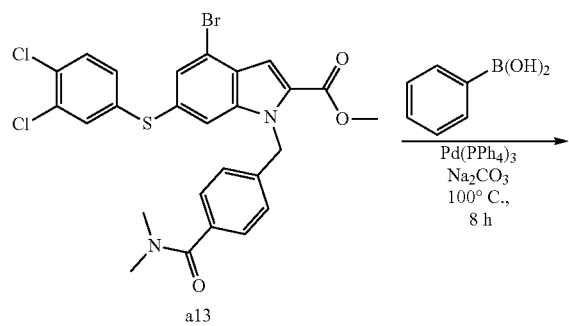

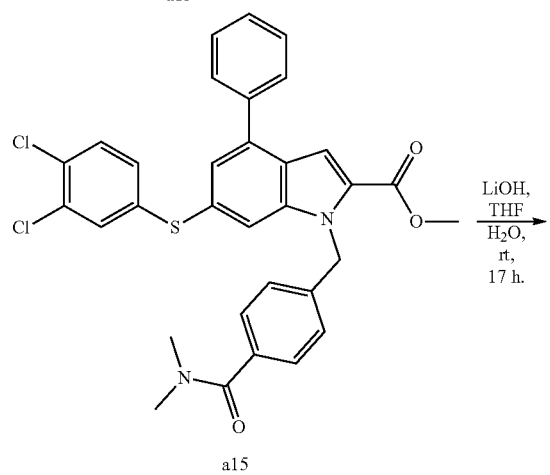

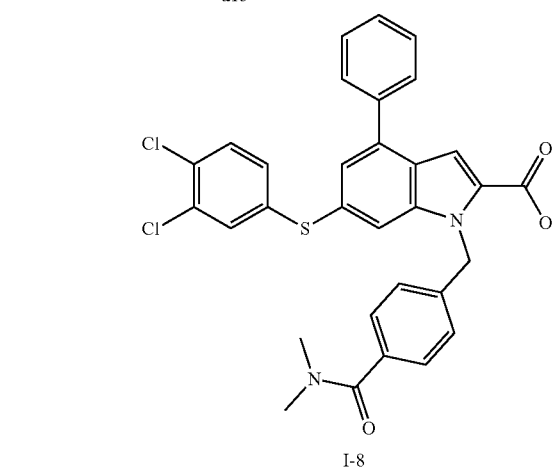

Procedures and Characterization:

Step 1: methyl 6-(3,4-dichlorophenylthio)-1-(4-(dimethylcarbamoyl)benzyl)-4-phenyl-1H-indole-2-carboxylate To a solution of methyl 4-bromo-6-(3,4-dichlorophenyl) sulfanyl-1-[[4-(dimethylcarbamoyl)phenyl]methyl]indole-2-carboxylate (100.00 mg, 168.82 μmol) and phenylboronic acid (24.70 mg, 202.58 μmol) in dioxane (4.00 mL) and H$_2$O (1.00 mL) was added Pd(PPh$_3$)$_4$ (31.81 mg, 25.32 μmol) and Na$_2$CO$_3$ (35.79 mg, 337.64 μmol). Then the reaction mixture was heated to 100° C. under N$_2$ for 8 h. LCMS showed the reaction was complete. The reaction was cooled to room temperature and water (20 mL) was added. The reaction mixture was extracted with EtOAc (10 mL×2) and the combined organic layers were washed with brine (10 mL). The organic layers were dried over Na$_2$SO$_4$ and concentrated in vacuo to give methyl 6-(3,4-dichlorophenylthio)-1-(4-(dimethylcarbamoyl)benzyl)-4-phenyl-1H-indole-2-carboxylate (138.00 mg, crude) as a brown solid which was used directly in the next step. ESI-MS (EI+, m/z): 589.0 [M+H]$^+$.

Step 2: 6-(3,4-dichlorophenylthio)-1-(4-(dimethylcarbamoyl)benzyl)-4-phenyl-1H-indole-2-carboxylic acid, I-8

The same procedure used to prepare I-102 afforded 6-(3,4-dichlorophenylthio)-1-(4-(dimethylcarbamoyl)benzyl)-4-phenyl-1H-indole-2-carboxylic acid, I-8 (27.50 mg, 47.78 μmol, 20.41% yield) as a white solid. ESI-MS (EI+, m/z): 575.0 [M+H]$^+$. $^1$H NMR (400 MHz, DMSO) δ 7.80 (1H, s), 7.67 (2H, m), 7.56 (3H, m), 7.47 (2H, m), 7.33 (3H, m), 7.27 (1H, d, J=0.8 Hz), 7.13 (1H, dd, J=8.8 Hz, 2.4 Hz), 7.11 (2H, m), 6.01 (2H, s), 2.95 (3H, s), 2.85 (3H, s).

Example 8: 4-cyano-6-(3,4-dichlorophenylthio)-1-(4-(dimethylcarbamoyl)benzyl)-1H-indole-2-carboxylic acid, I-7

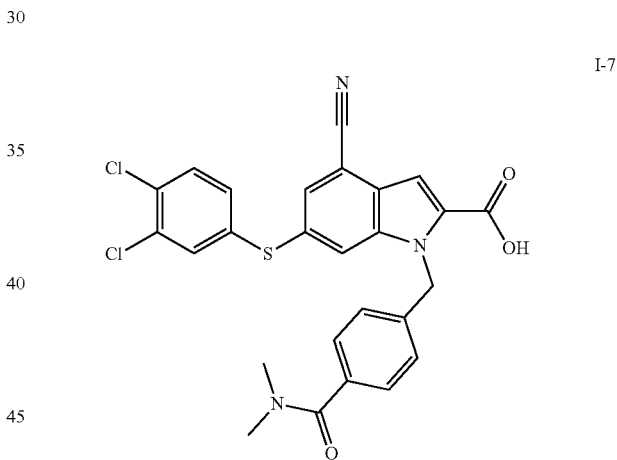

Synthetic Scheme:

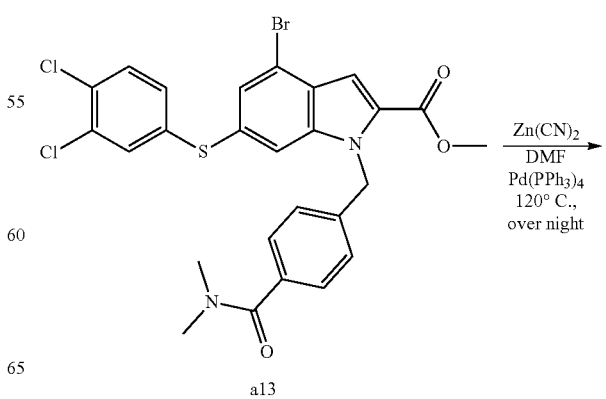

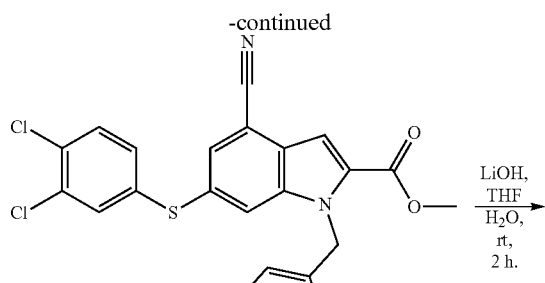

(3K, m), 7.35 (1H, d, J=2.0 Hz), 7.08 (1H, dd, J=8.8 Hz, 2.4 Hz), 7.03 (2H, m), 5.86 (2H, s), 3.15 (3H, s), 2.98 (3H, s).

Example 9: 4-bromo-1-(4-carboxybenzyl)-6-(3,4-dichlorophenylthio)-1H-indole-2-carboxylic acid, I-42

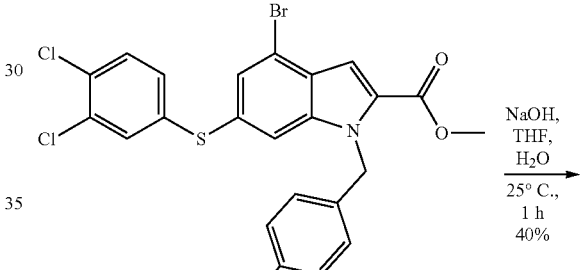

Synthetic Scheme:

Procedures and Characterization:

Step 1: methyl 4-cyano-6-(3,4-dichlorophenylthio)-1-(4-(dimethylcarbamoyl)benzyl)-1H-indole-2-carboxylate To a solution of methyl 4-bromo-6-(3,4-dichlorophenyl)sulfanyl-1-[[4-(dimethylcarbamoyl)phenyl]methyl]indole-2-carboxylate (150.00 mg, 253.24 μmol) in DMF (15.00 mL) was added Zn(CN)₂ (148.15 mg, 1.27 mmol) and Pd(PPh₃)₄ (159.03 mg, 126.62 μmol). The reaction mixture was heated to 120° C. overnight under N₂. LCMS showed the reaction worked well. The reaction mixture was treated with water (100 mL) and extracted with EtOAc (30 mL×2). The combined organic layers were washed with brine (50 mL), dried over Na₂SO₄ and concentrated in vacuo. The crude product was purified by prep-TLC to give methyl 4-cyano-6-(3,4-dichlorophenylthio)-1-(4-(dimethylcarbamoyl)benzyl)-1H-indole-2-carboxylate (85.00 mg, crude) as a brown solid which was used directly in the next step. ESI-MS (EI+, m/z): 538.0 [M+H]⁺.

Step 2: 4-cyano-6-(3,4-dichlorophenylthio)-1-(4-(dimethylcarbamoyl)benzyl)-1H-indole-2-carboxylic acid, I-7

The same procedure used to prepare I-102 afforded 4-cyano-6-(3,4-dichlorophenylthio)-1-(4-(dimethylcarbamoyl)benzyl)-1H-indole-2-carboxylic acid I-7 (12.70 mg, 24.22 μmol, 15.34% yield) as an off-white solid. The reaction time was 2 h. ESI-MS (EI+, m/z): 524.0 [M+H]⁺. ¹H NMR (400 MHz, DMSO) δ 7.58 (2H, s), 7.51 (1H, s), 7.38

Procedures and Characterization:

Step 1: 4-bromo-1-(4-carboxybenzyl)-6-(3,4-dichlorophenylthio)-1H-indole-2-carboxylic acid, I-42

The same procedure used to prepare I-52 afforded 1-(4-(bis(2-hydroxyethyl)carbamoyl)benzyl)-4-bromo-6-(3,4-dichlorophenylthio)-1H-indole-2-carboxylic acid I-42 (34.7 mg, 0.06 mmol, 40%) as a white solid. ESI-MS (EI+, m/z): 547.9 [M−H]⁻. ¹H NMR (500 MHz, DMSO) δ 13.53 (s, 1H), 7.83 (t, J=8.5 Hz, 3H), 7.53 (d, J=10.5 Hz, 1H), 7.44 (d, J=6 Hz, 2H), 7.20 (s, 1H), 7.12 (dd, J=10.5 Hz, J=8.5 Hz, 1H), 7.07 (d, J=10 Hz, 2H), 6.00 (s, 2H).

Example 10: 4-Bromo-1-(4-(tert-butoxycarbonyl)benzyl)-6-(3,4-dichlorophenylthio)-1H-indole-2-carboxylic acid, I-109

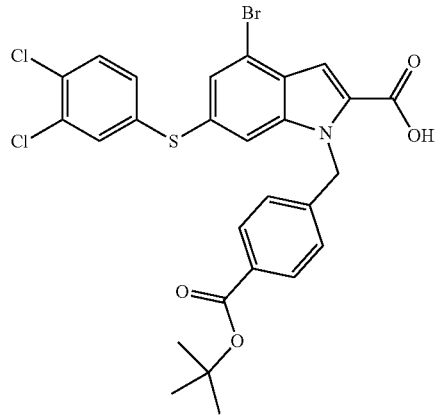

I-109

Synthetic Scheme:

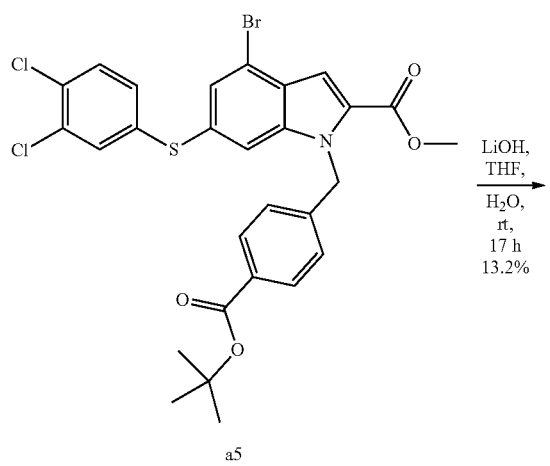

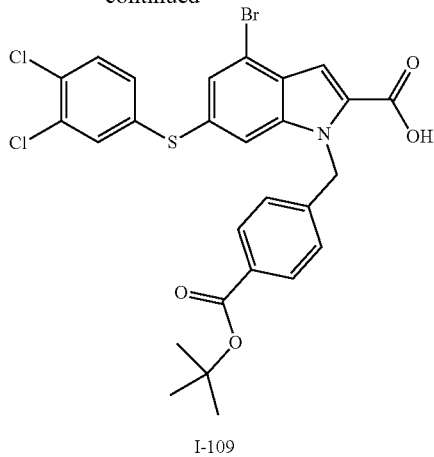

I-109

Step 1: 4-Bromo-1-(4-(tert-butoxycarbonyl)benzyl)-6-(3,4-dichlorophenylthio)-1H-indole-2-carboxylic acid, I-109

The same procedure used to prepare I-102 afforded 4-bromo-1-(4-(tert-butoxycarbonyl)benzyl)-6-(3,4-dichlorophenylthio)-1H-indole-2-carboxylic acid I-109 (36 mg, 13.2%) as a white solid. MS (EI+, m/z): 605.8 [M+H]$^+$. $^1$H NMR (500 MHz, DMSO) δ 13.50 (s, 1H), 7.90-7.70 (m, 3H), 7.60-7.39 (m, 3H), 7.27-7.13 (m, 2H), 7.06 (d, J=8.2 Hz, 2H), 5.97 (s, 2H), 1.51 (s, 9H).

Example 11: 1-(4-(tert-butoxycarbonyl)benzyl)-4-chloro-6-(3,4-dichlorophenylthio)-1H-indole-2-carboxylic acid, I-95

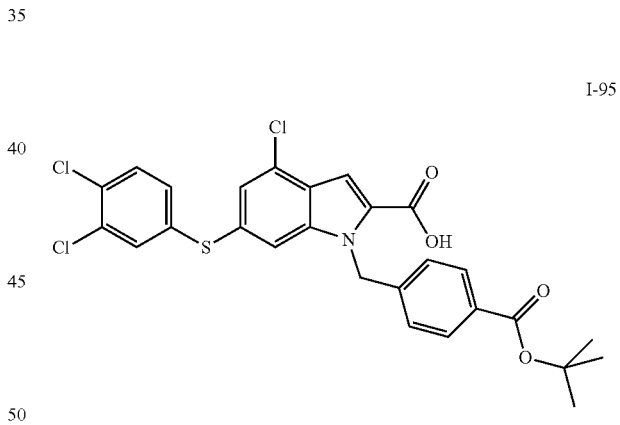

I-95

Synthetic Scheme:

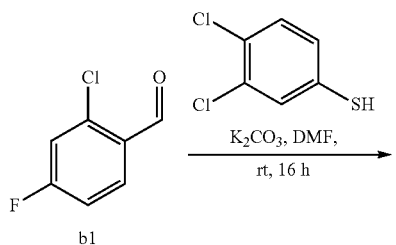

b1

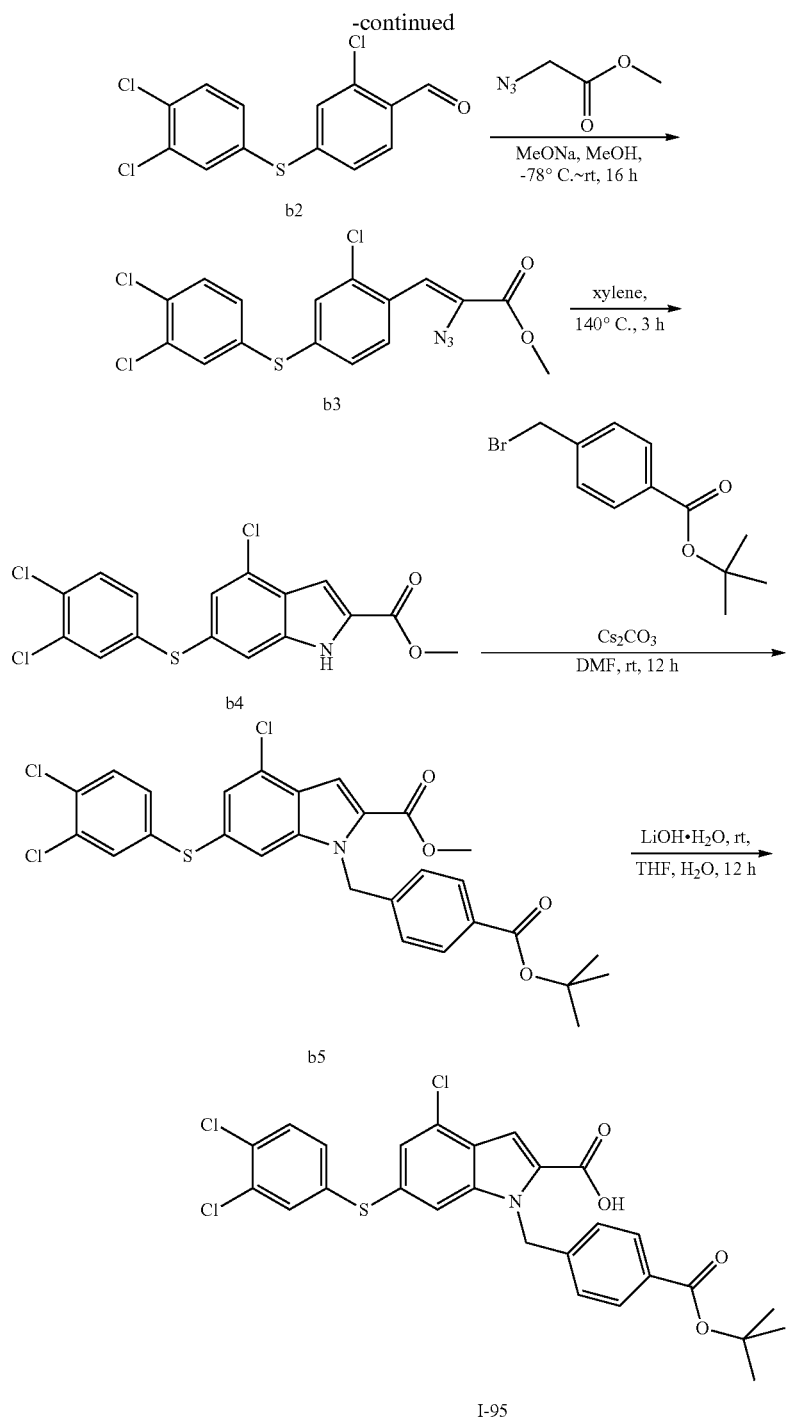

Procedures and Characterization:

Step 1: 2-chloro-4-(3,4-dichlorophenylthio)benzaldehyde

The same procedure used to prepare 2-bromo-4-(3,4-dichlorophenylthio)benzaldehyde (a2) afforded 2-chloro-4-(3,4-dichlorophenylthio)benzaldehyde (3 g, 65% yield) as a white solid. ESI-MS (EI+, m/z): no MS. $^1$H NMR (500 MHz, CDCl$_3$) δ 10.38 (s, 1H), 7.81 (d, J=8.0 Hz, 1H), 7.61 (d, J=2.0 Hz, 1H), 7.51 (d, J=8.5 Hz, 1H), 7.35-7.33 (m, 1H), 7.18 (d, J=2.0 Hz, 1H), 7.12 (dd, J=1.0 Hz, J=4.0 Hz, 1H).

Step 2: (Z)-methyl 2-azido-3-(2-chloro-4-(3,4-dichlorophenylthio)phenyl)acrylate MeONa (2 g, 38 mmol) was added to a suspension of 2-chloro-4-(3,4-dichlorophenylthio)benzaldehyde (3 g, 9.5 mmol) in MeOH (30 ml) at −78° C. and stirred at −78° C. for 1 h. methyl 2-azidoacetate (4.37 g, 38 mmol) was added to the reaction mixture as dropwise and stirred at −78° C.~ rt for 20 h. The reaction mixture was cooled to 0° C., quenched with water, extracted with EtOAc, washed with water and brine, dried, concentrated, washed with EtOAc and PE to afford (Z)-methyl 2-azido-3-(2-chloro-4-(3,4-dichlorophenylthio)phenyl)acrylate (2.6 g, 65% yield) as solid. ESI-MS (EI⁺, m/z): no MS.

¹H NMR (500 MHz, DMSO) δ 8.20 (d, J=8.5 Hz, 1H), 7.73 (d, J=2.5 Hz, 1H), 7.69 (d, J=8.5 Hz, 1H), 7.49 (d, J=1.5 Hz, 1H), 7.40 (dd, J=2.0 Hz, J=4.25 Hz, 1H), 7.32, 7.31 (dd, J=1.5 Hz, J=4.25 Hz, 1H), 7.06 (s, 1H), 3.87 (s, 3H).

Step 3: methyl 4-chloro-6-(3,4-dichlorophenylthio)-1H-indole-2-carboxylate

The same procedure used to prepare methyl 4-bromo-6-(3,4-dichlorophenylthio)-1H-indole-2-carboxylate (a4) afforded methyl 4-chloro-6-(3,4-dichlorophenylthio)-1H-indole-2-carboxylate (1.7 g, 73% yield). ESI-MS (EI⁻, m/z): 383.9 [M−H]⁻.

¹H NMR (500 MHz, DMSO) δ 12.51 (s, 1H), 7.60 (d, J=8.5 Hz, 1H), 7.54 (d, J=2.5 Hz, 1H), 7.52 (s, 1H), 7.24 (d, J=1.0 Hz, 1H), 7.20 (dd, J=2.0 Hz, J=4.25 Hz, 1H), 7.14 (s, 1H), 3.90 (s, 3H).

Step 4: methyl 1-(4-(tert-butoxycarbonyl)benzyl)-4-chloro-6-(3,4-dichlorophenylthio)-1H-indole-2-carboxylate The same procedure used to prepare methyl 4-bromo-1-(4-(tert-butoxycarbonyl)benzyl)-6-(3,4-dichlorophenylthio)-1H-indole-2-carboxylate (a5) afforded methyl 1-(4-(tert-butoxycarbonyl)benzyl)-4-chloro-6-(3,4-dichlorophenylthio)-1H-indole-2-carboxylate (155 mg, 34% yield) as a white solid. The reaction time is 12 h.

ESI-MS (EI⁺, m/z): no MS.

¹H NMR (500 MHz, DMSO) δ 7.78 (t, J=7.5 Hz, 3H), 7.55 (d, J=8.5 Hz, 1H), 7.47 (d, J=2.5 Hz, 1H), 7.37 (s, 1H), 7.32 (s, 1H), 7.19, 7.18 (dd, J=2.0 Hz, 4.0 Hz, 1H), 7.07 (d, J=8.5 Hz, 2H), 5.95 (s, 2H), 3.85 (s, 3H), 1.51 (s, 9H).

Step 5: 1-(4-(tert-butoxycarbonyl)benzyl)-4-chloro-6-(3,4-dichlorophenylthio)-1H-indole-2-carboxylic acid, I-95

The same procedure used to prepare I-102 afforded 1-(4-(tert-butoxycarbonyl)benzyl)-4-chloro-6-(3,4-dichlorophenylthio)-1H-indole-2-carboxylic acid I-95 (50 mg, 68.5% yield). ESI-MS (EI⁺, m/z): 559.9 [M−H]⁻.

¹H NMR (500 MHz, DMSO) δ 13.51 (s, 1H), 7.79 (d, J=8.0 Hz, 2H), 7.71 (s, 1H), 7.53 (d, J=8.5 Hz, 1H), 7.43 (d, J=2.0 Hz, 1H), 7.30 (s, 2H), 7.15 (dd, J=2.0 Hz, 4.25 Hz, 1H), 7.06 (d, J=8.5 Hz, 2H), 5.98 (s, 2H), 1.51 (s, 9H).

Example 12: 4-chloro-6-(3,4-dichlorophenylthio)-1-(4-(dimethylcarbamoyl)benzyl)-1H-indole-2-carboxylic acid, I-75

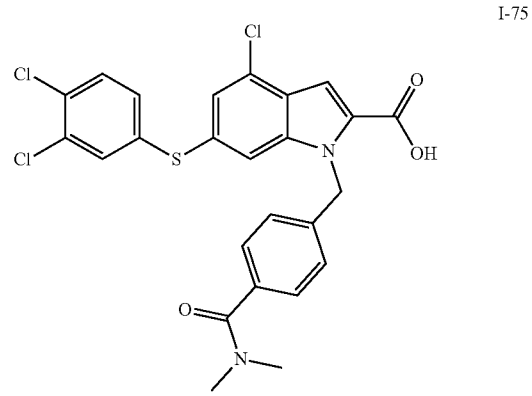 [SMILES: CN(C)C(=O)c1ccc(Cn2c(C(=O)O)cc3c(Cl)cc(Sc4ccc(Cl)c(Cl)c4)cc32)cc1]

I-75

Synthetic Scheme:

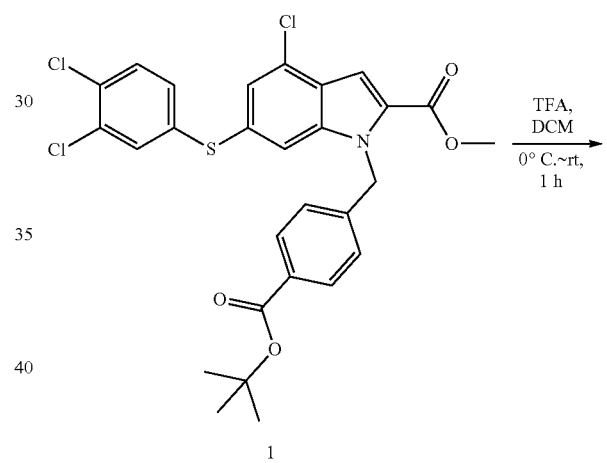

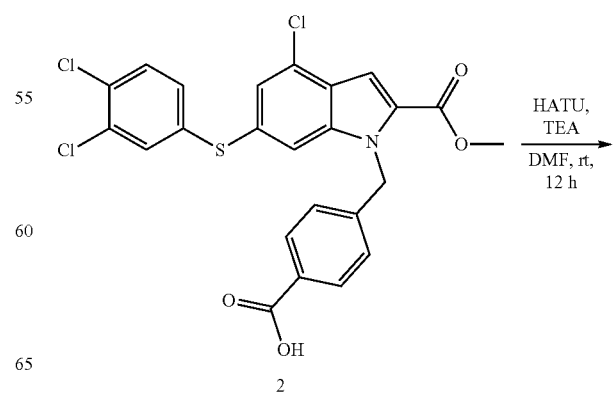

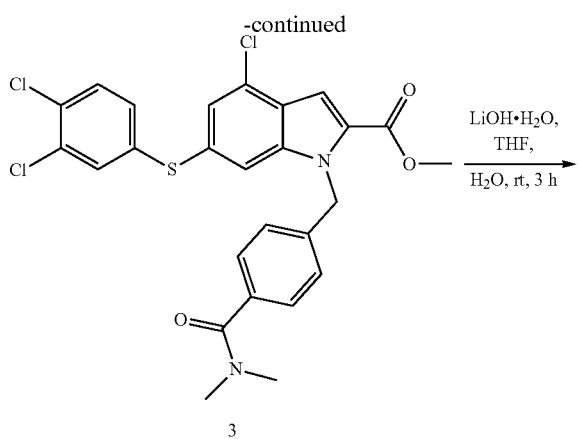

```
           LiOH·H₂O,
           THF,
           H₂O, rt, 3 h
```

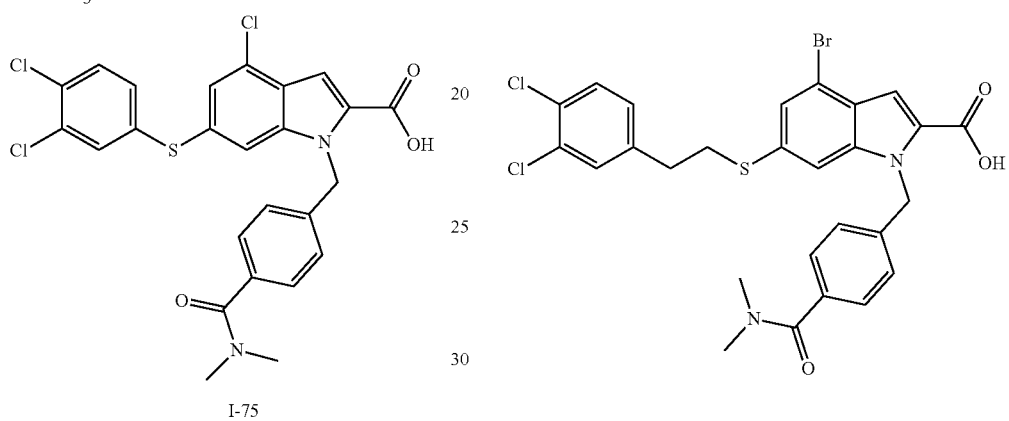

oyl)benzyl)-1H-indole-2-carboxylic acid I-75 (69.6 mg, 55% yield). The reaction time was 3 h. ESI-MS (EI⁺, m/z): 533.0 [M+H]⁺.

¹H NMR (500 MHz, DMSO) δ 13.50 (s, 1H), 7.82 (s, 1H), 7.56 (d, J=11.0 Hz, 1H), 7.49 (d, J=2.5 Hz, 1H), 7.30 (t, J=4.75 Hz, 4H), 7.12 (d, J=10.5 Hz, 1H), 7.02 (d, J=10.0 Hz, 2H), 5.94 (s, 2H), 2.94 (s, 3H), 2.83 (s, 3H).

Example 13: 4-bromo-6-(3,4-dichlorophenethylthio)-1-(4-(dimethyl carbamoyl) benzyl)-1H-indole-2-carboxylic acid, I-25

I-25

Step 1: 4-((4-chloro-6-(3,4-dichlorophenylthio)-2-(methoxycarbonyl)-1H-indol-1-yl)methyl)benzoic acid TFA (25 mL) was added to a solution of methyl 1-(4-(tert-butoxycarbonyl)benzyl)-4-chloro-6-(3,4-dichlorophenylthio)-1H-indole-2-carboxylate (250 mg, 0.43 mmol) in DCM (7.5 ml) at 0° C. and stirred at 0° C.~rt for 1 h. NaHCO₃ (aq.) was added to the reaction mixture to pH~6, extracted with EtOAc, washed with brine, dried, concentrated to afford 4-((4-chloro-6-(3,4-dichlorophenylthio)-2-(methoxycarbonyl)-1H-indol-1-yl)methyl)benzoic acid (280 mg, crude), used for the next step.

ESI-MS (EI⁺, m/z): 520.0 [M+H]⁺.

Step 2: methyl 4-chloro-6-(3,4-dichlorophenylthio)-1-(4-(dimethylcarbamoyl)benzyl)-1H-indole-2-carboxylate The same procedure used to prepare methyl 4-bromo-6-(3,4-dichlorophenylthio)-1-(4-(dimethylcarbamoyl)benzyl)-1H-indole-2-carboxylate (a7) afforded methyl 4-chloro-6-(3,4-dichlorophenylthio)-1-(4-(dimethylcarbamoyl)benzyl)-1H-indole-2-carboxylate (150 mg, crude). ESI-MS (EI⁺, m/z): 549.0 [M+H]⁺.

Step 3: 4-chloro-6-(3,4-dichlorophenylthio)-1-(4-(dimethylcarbamoyl)benzyl)-1H-indole-2-carboxylic acid, I-75

The same procedure used to prepare I-102 afforded 4-chloro-6-(3,4-dichlorophenylthio)-1-(4-(dimethylcarbam- Synthetic Scheme:

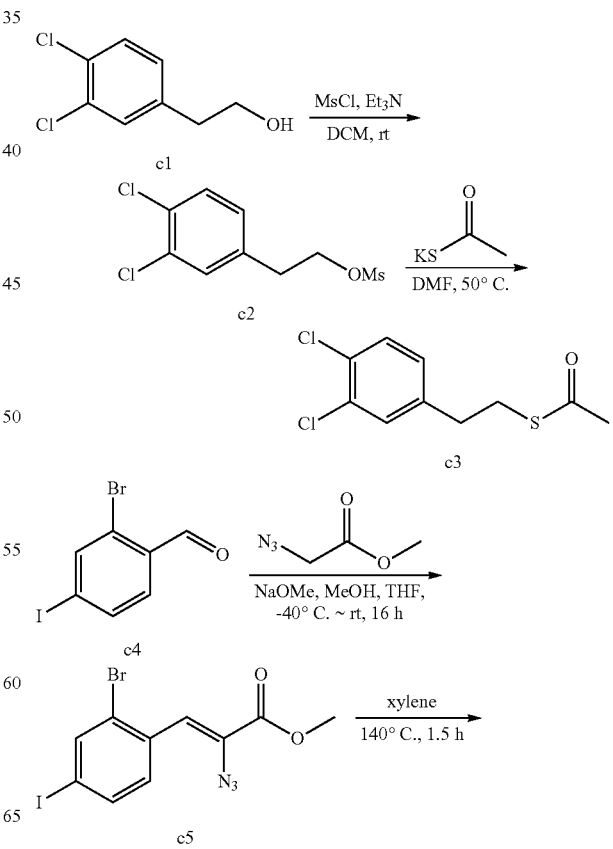

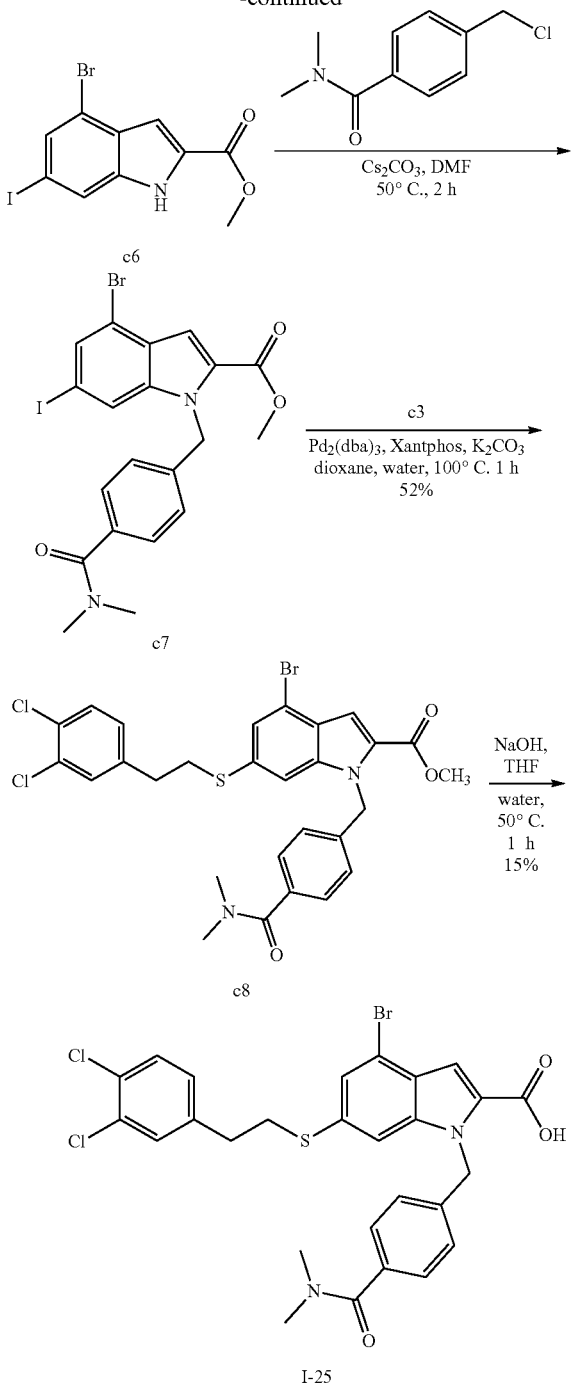

Step 2: S-3,4-dichlorophenethyl ethanethioate

A solution of 2-(3,4-dichlorophenyl)ethyl methanesulfonate (1.42 g, 5.28 mmol) and potassium ethanethioate (903.87 mg, 7.91 mmol) in DMF (10.00 mL) was stirred at 50° C. for 1 h under $N_2$ atmosphere. It was monitored by LC-MS. After completed, it was diluted with ethyl acetate, washed with brine, the organic layer was dried over magnesium sulfate, filtrated, concentrated to yield the crude product. It was purified by SGC to give S-[2-(3,4-dichlorophenyl)ethyl] ethanethioate (1.22 g, 4.90 mmol, 92.74%) as a yellow oil. ESI-MS (EI+, m/z): 249 [M+H]$^+$. $^1$H NMR (500 MHz, CDCl$_3$) δ 7.39 (d, 1H, J=10.5 Hz), 7.33 (s, 1H), 7.07 (d, 1H, J=10.5 Hz), 3.08-3.12 (t, 2H, J=9 Hz), 2.83-2.86 (t, 2H, J=9 Hz), 2.36 (s, 3H).

Step 3: (Z)-methyl 2-azido-3-(2-bromo-4-iodophenyl)acrylate

The same procedure used to prepare (Z)-methyl 2-azido-3-(2-chloro-4-(3,4-dichlorophenylthio)phenyl)acrylate (b3) afforded (Z)-methyl 2-azido-3-(2-bromo-4-iodophenyl)acrylate.

Step 4: methyl 4-bromo-6-iodo-1H-indole-2-carboxylate

The procedure for methyl 4-bromo-6-iodo-1H-indole-2-carboxylate was the same as methyl 4-bromo-6-(3,4-dichlorophenylthio)-1H-indole-2-carboxylate (a4).
ESI-MS (EI+, m/z): 378, 380 [M+H]$^+$.

Step 5: methyl 4-bromo-1-[[4-(dimethylcarbamoyl)phenyl]methyl]-6-iodo-indole-2-carboxylate A mixture of methyl 4-bromo-6-iodo-1H-indole-2-carboxylate (1.13 g, 2.97 mmol), 4-(chloromethyl)-N,N-dimethyl-benzamide (704.46 mg, 3.56 mmol) and Cs$_2$CO$_3$ (1.25 g, 3.86 mmol) in DMF (20.00 mL) was stirred at 50° C. for 2 h. TLC showed the reaction was complete. The reaction was quenched with water (10 mL) and extracted with ethyl acetate (30 mL). The organic layer was washed with water, dried, concentrated and purified by silica gel chromatography to give methyl 4-bromo-1-[[4-(dimethylcarbamoyl)phenyl]methyl]-6-iodo-indole-2-carboxylate (1.20 g, 2.17 mmol, 73.17% yield, 98% purity) as a white solid.
ESI-MS (EI+, m/z): 541, 543 [M+H]$^+$.

Step 6: methyl 4-bromo-6-(3,4-dichlorophenethylthio)-1-(4-(dimethylcarbamoyl)benzyl)-1H-indole-2-carboxylate A solution of methyl 4-bromo-1-[[4-(dimethylcarbamoyl)phenyl]methyl]-6-iodo-indole-2-carboxylate (100.00 mg, 0.18 mmol), S-3,4-dichlorophenethyl ethanethioate (68.74 mg, 0.28 mmol), Xantphos (21.40 mg, 0.04 mmol), K$_2$CO$_3$ (51.00 mg, 0.37 mmol) and Pd$_2$(dba)$_3$ (16.93 mg, 0.02 mmol) in 1.0 mL of a mixture of dioxane (1.60 mL) and water (0.40 mL) was stirred at 100° C. for 1 h under $N_2$ atmosphere by microwave. It was monitored by LC-MS. After completed, it was diluted with EtOAc, washed with brine, the organic layer was dried over magnesium sulfate, filtrated, concentrated to yield the crude product. It was purified by TLC to yield methyl 4-bromo-6-[2-(3,4-dichlorophenyl)ethylsulfanyl]-1-[[4-(dimethylcarbamoyl) phenyl]

Procedures and Characterization:

Step 1: 3,4-dichlorophenethyl methanesulfonate

MsCl (2.40 g, 20.92 mmol) was added to a solution of 2-(3,4-dichlorophenyl)ethanol (1.00 g, 5.23 mmol) and TEA (1.59 g, 15.69 mmol, 2.17 mL) in dry DCM (10.00 mL) dropwise under $N_2$ atmosphere for 5 minutes. It was stirred at 0 to 20° C. for 0.6 h. The solution was diluted with water and extracted with ethyl acetate. The organic phase was washed with water (100 mL×2) and brine (100 mL), dried (Na$_2$SO$_4$), filtered and concentrated in vacuo to yield the crude product. It was used for the next step directly.

methyl]indole-2-carboxylate (60.00 mg, 96.71 μmol, 52.34% yield) as a yellow solid.

Step 7: 4-bromo-6-(3,4-dichlorophenethylthio)-1-(4-(dimethyl carbamoyl) benzyl)-1H-indole-2-carboxylic acid, I-25

To a solution of methyl 4-bromo-6-[2-(3,4-dichlorophenyl)ethylsulfanyl]-1-[[4-(dimethylcarbamoyl)phenyl]methyl]indole-2-carboxylate (60.00 mg, 0.01 mmol) in 5 mL of a mixture of THF (2.50 mL) and water (2.50 mL) was added NaOH (19.34 mg, 0.48 mmol) It was stirred at 50° C. for 2 h and monitored by LC-MS. After completed, it was diluted with ethyl acetate (15 mL) and adjusted pH to 6 with 1N HCl at 0° C., then the organic layer was washed with brine (10 mL), dried over magnesium sulfate, filtered and concentrated to afford the crude product. It was purified by prep-HPLC to yield 4-bromo-6-[2-(3,4-dichlorophenyl)ethyl-sulfanyl]-1-[[4-(dimethylcarbamoyl)phenyl]methyl]indole-2-carboxylic acid I-25 as a white solid (9.00 mg, 14.84 μmol, 15.35%). ESI-MS (EI+, m/z): 603 [M−H]−. $^1$H NMR (500 MHz, MeOD) δ 7.31-7.37 (m, 7H), 7.14 (d, 2H, J=10 Hz), 7.03 (d, 1H, J=10 Hz), 5.97 (s, 2H), 3.19-3.23 (t, 2H, J=9 Hz), 3.06 (s, 3H), 2.91 (s, 3H), 2.82-2.86 (t, 2H, J=9 Hz).

Example 14: 4-bromo-6-(cyclohexylmethylthio)-1-(4-(dimethylcarbamoyl) benzyl)-1H-indole-2-carboxylic acid, I-24

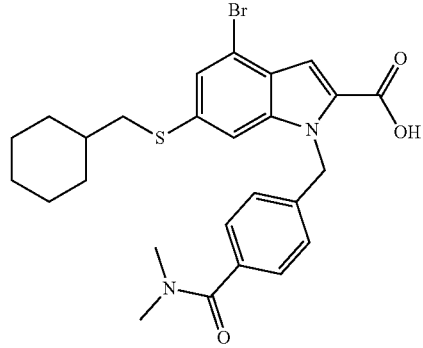

I-24

Synthetic Scheme:

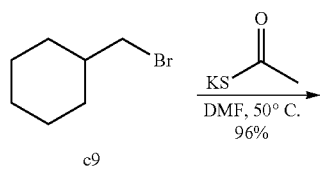

c9

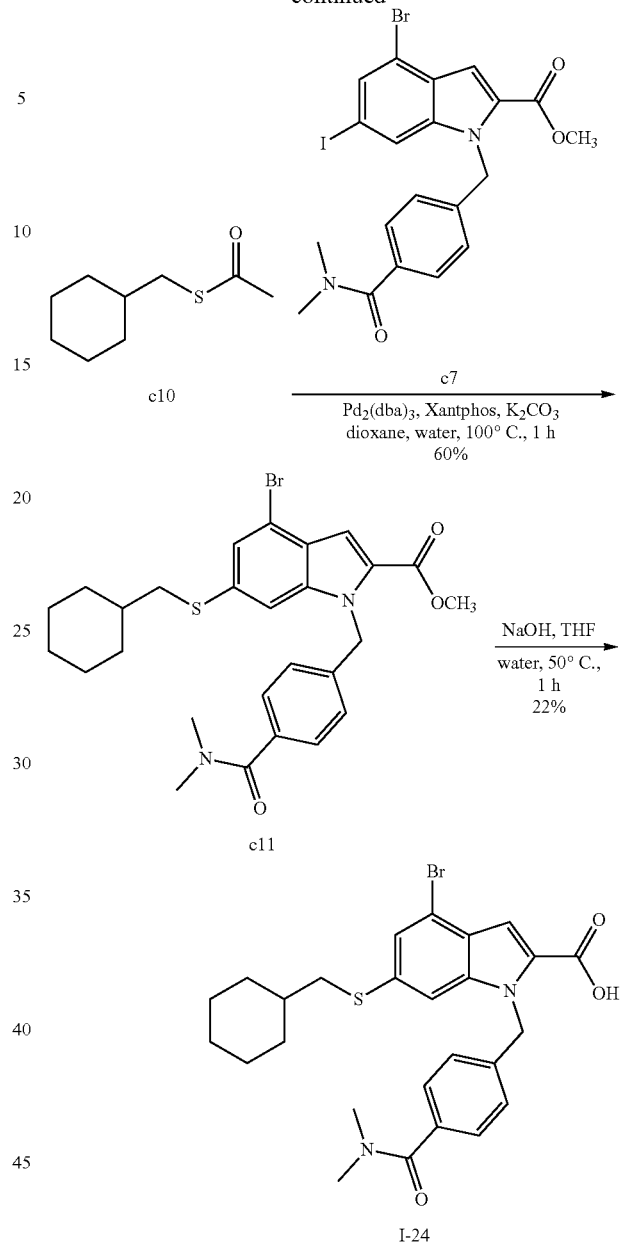

Procedures and Characterization:

Step 1: S-cyclohexylmethyl ethanethioate

A solution of bromomethylcyclohexane (2.00 g, 11.29 mmol) and potassium ethanethioate (1.93 g, 16.93 mmol) in DMF (20.00 mL) was stirred at 50° C. for 1 h under N$_2$ atmosphere. It was monitored by LC-MS. After completed, it was diluted with EtOAc, washed with brine, the organic layer was dried over magnesium sulfate, filtrated, concentrated to yield the crude product. It was purified by SGC to give S-(cyclohexylmethyl) ethanethioate (1.90 g, 11.03 mmol, 97.68%) as a yellow oil. ESI-MS (EI+, m/z): 173 [M+H]+. $^1$H NMR (500 MHz, CDCl$_3$) δ 2.79 (d, 2H, J=9 Hz), 2.34 (s, 3H), 1.64-1.80 (m, 5H), 1.40-1.48 (m, 1H), 1.12-1.17 (m, 3H), 0.91-1.00 (m, 2H).

Step 2: methyl 4-bromo-6-(cyclohexylmethylthio)-1-(4-(dimethylcarbamoyl)benzyl)-1H-indole-2-carboxylate A solution of methyl 4-bromo-1-[[4-(dimethylcarbamoyl) phenyl]methyl]-6-iodo-indole-2-carboxylate (60.00 mg, 0.11 mmol), S-cyclohexylmethyl ethanethioate (28.65 mg, 0.17 mmol), Xantphos (12.84 mg, 0.03 mmol), $K_2CO_3$ (30.60 mg, 0.22 mmol) and $Pd_2(dba)_3$ (10.16 mg, 0.02 mmol) in 1.0 mL of a 4:1 mixture of dioxane (0.80 mL) and water (0.20 mL) was stirred at 100° C. for 0.5 h under $N_2$ atmosphere by microwave. It was monitored by LC-MS. After completed, it was diluted with ethyl acetate, washed with brine, the organic layer was dried over magnesium sulfate, filtrated, concentrated to yield the crude product. It was purified by TLC to yield methyl 4-bromo-6-(cyclohexylmethylsulfanyl)-1-[[4-(dimethylcarbamoyl) phenyl] methyl]indole-2-carboxylate (36.00 mg, 0.07 mmol, 59.74%) as a yellow oil.

Step 3: 4-bromo-6-(cyclohexylmethylthio)-1-(4-(dimethylcarbamoyl) benzyl)-1H-indole-2-carboxylic acid, I-24

The same procedure used to prepare I-25 is to yield 4-bromo-6-(cyclohexylmethylsulfanyl)-1-[[4-(dimethylcarbamoyl) phenyl]methyl]indole-2-carboxylic acid I-24 (13.80 mg, 0.03 mmol, 44%) as a light yellow solid. ESI-MS (EI+, m/z): 529 [M+H]+. 1H NMR (500 MHz, MeOD) δ 7.36 (s, 1H), 7.34 (s, 2H), 7.30 (d, 2H, J=10 Hz), 7.13 (d, 2H, J=9 Hz), 5.96 (s, 2H), 3.08 (s, 3H), 2.83 (d, 2H, J=8.5 Hz), 1.64-1.87 (m, 5H), 1.42-1.51 (m, 1H), 1.13-1.25 (m, 2H), 0.95-1.04 (m, 2H).

Example 15: 1-(4-(dimethylcarbamoyl)benzyl)-6-(4-phenoxyphenylthio)-1H-indole-2-carboxylic acid, I-17

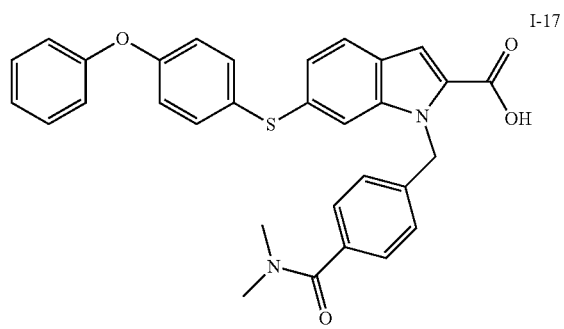 [SMILES: CN(C)C(=O)c1ccc(Cn2c(C(=O)O)cc3ccc(Sc4ccc(Oc5ccccc5)cc4)cc32)cc1]

Synthetic Scheme:

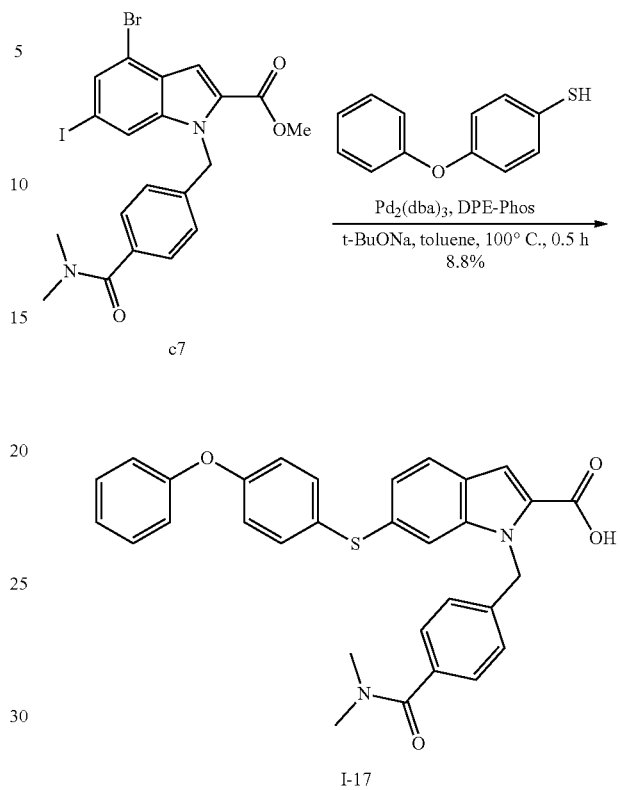

Procedures and Characterization:

Step 1: methyl 4-bromo-1-[[4-(dimethylcarbamoyl) phenyl]methyl]-6-iodo-indole-2-carboxylate The same procedure used to prepare I-25 afforded methyl 4-bromo-1-[[4-(dimethylcarbamoyl)phenyl]methyl]-6-iodo-indole-2-carboxylate.

Step 2: 1-(4-(dimethylcarbamoyl)benzyl)-6-(4-phenoxyphenylthio)-1H-indole-2-carboxylic acid, I-17

A solution of methyl 4-bromo-1-[[4-(dimethylcarbamoyl) phenyl]methyl]-6-iodo-indole-2-carboxylate (140.00 mg, 0.26 mmol), 4-phenoxybenzenethiol (78.49 mg, 0.39 mmol), t-BuONa (29.80 mg, 0.31 mmol), DPE-Phos (13.92 mg, 0.03 mmol) and $Pd_2(dba)_3$ (11.85 mg, 0.02 mmol) in toluene (5.00 mL) was stirred at 100° C. for 0.5 h under $N_2$ atmosphere. It was monitored by LC-MS. After completed, it was diluted with ethyl acetate, washed with brine, the organic layer was dried over magnesium sulfate, filtrated, concentrated to yield the crude product. It was purified by prep-HPLC to yield 1-[[4-(dimethylcarbamoyl)phenyl] methyl]-6-(4-phenoxy phenyl)sulfanyl-indole-2-carboxylic acid I-17 as a yellow oil (11.90 mg, 22.77 μmol, 8.80%). ESI-MS (EI+, m/z): 523 [M+H]+. 1H NMR (500 MHz, MeOD) δ 7.62 (d, 1H, J=10.5 Hz), 7.31-7.47 (t, 3H, J=10.5 Hz), 7.28-7.34 (m, 5H), 7.24 (s, 1H), 7.14-7.18 (t, 1H, J=9.5 Hz), 7.07-7.10 (m, 3H), 7.03 (d, 2H, J=10.0 Hz), 6.93 (d, 2H, J=11.0 Hz), 5.92 (s, 2H), 3.06 (s, 3H), 2.92 (s, 3H).

Example 16: 4-bromo-1-(4-(dimethylcarbamoyl) benzyl)-6-(4-phenoxy phenyl-thio)-1H-indole-2-carboxylic acid, I-15

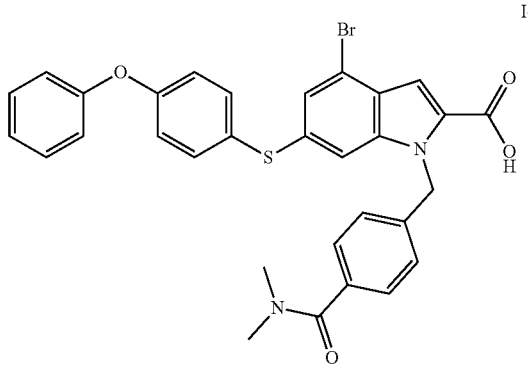

Synthetic Scheme:

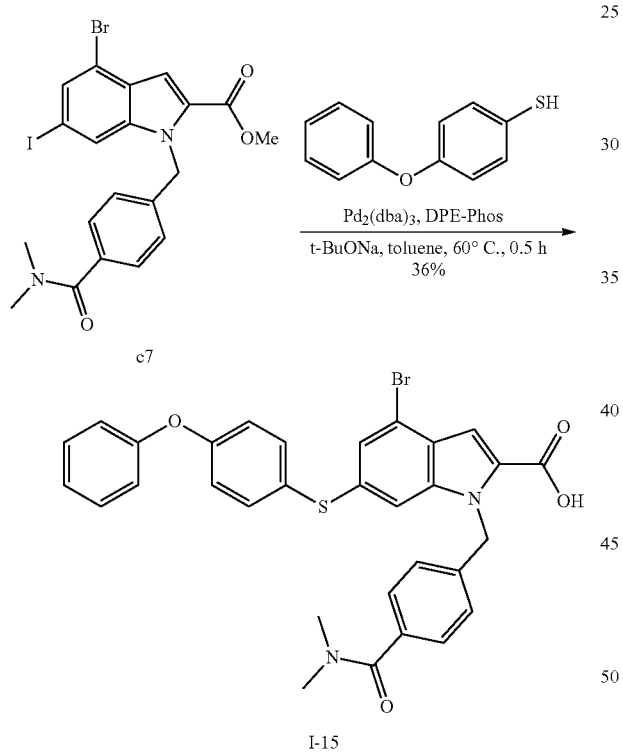

Procedures and Characterization:

Step 1: 4-bromo-1-(4-(dimethylcarbamoyl)benzyl)-6-(4-phenoxy phenyl-thio)-1H-indole-2-carboxylic acid, I-15

The same procedure used to prepare I-17 is to yield 4-bromo-1-(4-(dimethylcarbamoyl)benzyl)-6-(4-phenoxy-phenyl-thio)-1H-indole-2-carboxylic acid I-15 as a yellow oil (19.90 mg, 0.04 mmol, 36%). The temperature of the reaction was 60° C. ESI-MS (EI+, m/z): 601 [M+H]$^+$. $^1$H NMR (500 MHz, MeOD) δ 7.35-7.43 (m, 4H), 7.31 (d, 2H, J=9.5 Hz), 7.17-7.22 (m, 4H), 7.05-7.09 (t, 41H, J=10 Hz), 6.98 (d, 2H, J=11.0 Hz), 5.89 (s, 2H), 3.07 (s, 3H), 2.93 (s, 3H).

Example 17: 4-bromo-1-(4-(dimethylcarbamoyl) benzyl)-6-(3-(trifluoromethoxy)phenylthio)-1H-indole-2-carboxylic acid, I-20, and 1-(4-(dimethylcarbamoyl)benzyl)-4,6-bis(3-(trifluoromethoxy) phenylthio)-1H-indole-2-carboxylic acid, I-19

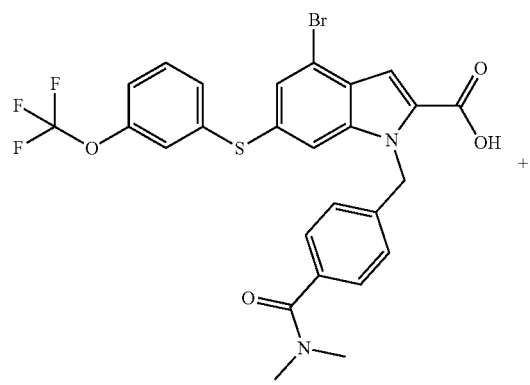

+

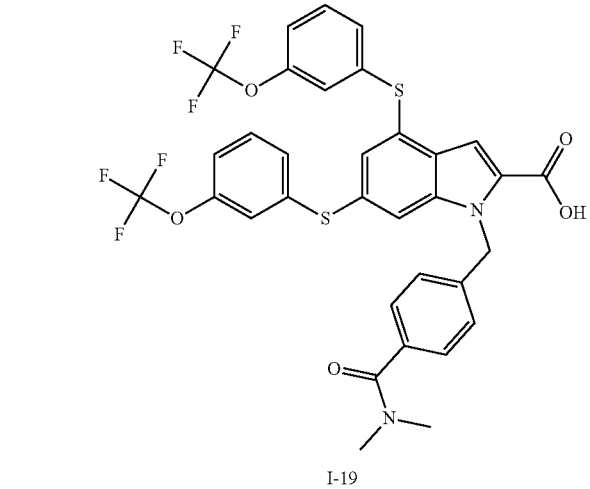

Synthetic Scheme:

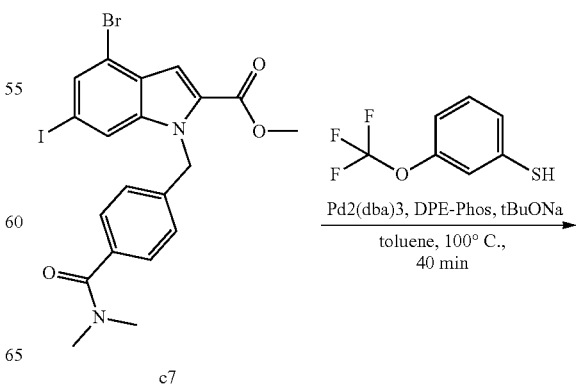

-continued

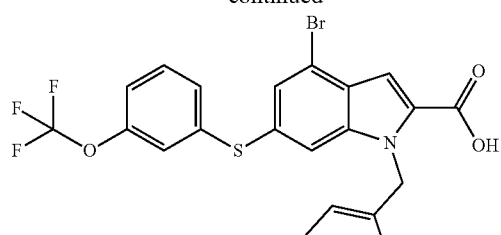

I-20

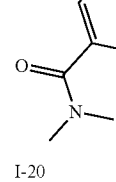
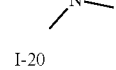

I-19

Procedures and Characterization:

The same procedure used to prepare I-17 afforded 4-bromo-1-[[4-(dimethylcarbamoyl)phenyl]methyl]-6-[3-(trifluoromethoxy)phenyl]sulfanyl-indole-2-carboxylic acid I-20 (10.20 mg, 17.19 μmol, 8.61% yield, 100% purity) as a white solid ESI-MS (EI+, m/z): 593.0 [M+H]+. $^1$H NMR (400 MHz, MeOD) δ 7.55 (s, 1H), 7.37-7.34 (m, 5H), 7.14-7.18 (m, 5H), 5.95 (d, J=2.5 Hz, 2H), 3.06 (s, 3H), 2.94 (s, 3H). and 1-[[4-(dimethylcarbamoyl)phenyl]methyl]-4,6-bis[[3-(trifluoromethoxy)phenyl]sulfanyl]indole-2-carboxylic acid I-19 (9.60 mg, 13.58 μmol, 6.81% yield, 100% purity) as a white solid. ESI-MS (EI+, m/z): 707.0 [M+H]+. $^1$H NMR (400 MHz, MeOD) δ 7.61 (s, 1H), 7.37-7.31 (m, 4H), 7.26 (d, J=9.0 Hz, 2H), 7.17-7.08 (m, 6H), 7.03 (d, J=16.0 Hz, 2H), 5.97 (s, 2H), 3.07 (s, 3H), 2.94 (s, 3H).

Example 18: 4-bromo-1-(4-(dimethylcarbamoyl)benzyl)-6-(4-phenoxy phenyl-thio)-1H-indole-2-carboxylic acid, I-16

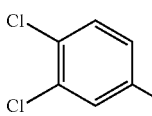

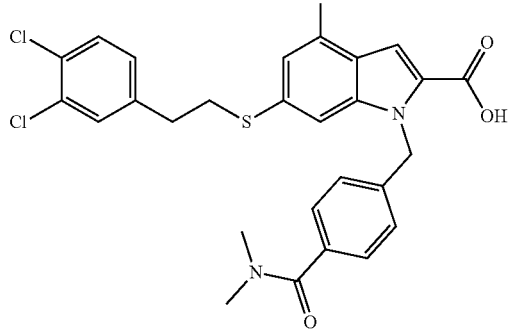

I-16

Synthetic Scheme:

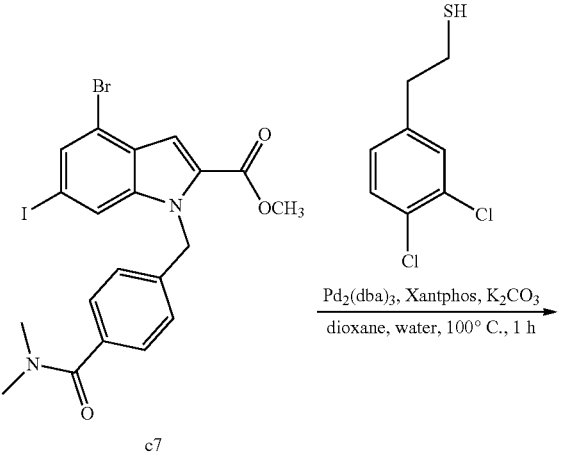

c7

381

-continued

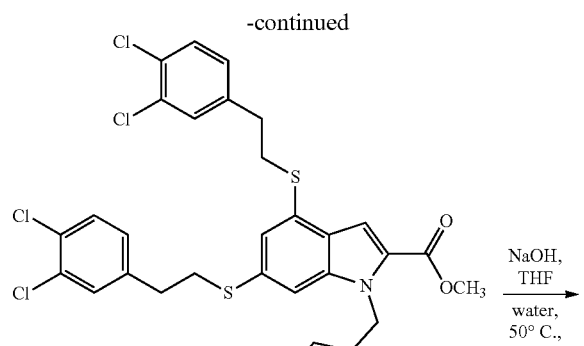

I-16

Procedures and Characterization:

Step 1: 4,6-bis(3,4-dichlorophenethylthio)-1-(4-(dimethylcarbamoyl)benzyl)-1H-indole-2-carboxylic acid A solution of methyl 4-bromo-1-[[4-(dimethylcarbamoyl)phenyl]methyl]-6-iodo-indole-2-carboxylate (100.00 mg, 0.18 mmol), S-3,4-dichlorophenethyl ethanethioate (114.56 mg, 0.46 mmol), Xantphos (21.40 mg, 0.04 mmol), K$_2$CO$_3$ (51.00 mg, 0.37 mmol) and Pd$_2$(dba)$_3$ (16.93 mg, 0.02 mmol) in 2.0 mL of a mixture of dioxane (1.60 mL) and water (0.40 mL) was stirred at 100° C. for 1 h under N2 atmosphere by microwave. It was monitored by LC-MS. It showed that the ratio of methyl 4-bromo-6-[2-(3,4-dichlorophenyl)ethylsulfanyl]-1-[[4-(dimethyl carbamoyl)phenyl]methyl]indole-2-carboxylate and methyl 4,6-bis[2-(3,4-dichlorophenyl)ethyl sulfanyl]-1-[[4-(dimethylcarbamoyl)phenyl]methyl]indole-2-carboxylate was about 1:2.36. After completed, it was diluted with ethyl acetate, washed with brine, the organic layer was dried over magnesium sulfate, filtered, concentrated to yield the crude product. It was purified by TLC and used for the next step directly.

382

Step 2: 4-bromo-1-(4-(dimethylcarbamoyl)benzyl)-6-(4-phenoxy phenyl-thio)-1H-indole-2-carboxylic acid, I-16

The same procedure used to prepare I-25 is to yield 4-bromo-1-(4-(dimethylcarbamoyl)benzyl)-6-(4-phenoxy phenyl-thio)-1H-indole-2-carboxylic acid I-16 (5.20 mg, 7.10 μmol, 7.57%) as a yellow oil. $^1$H NMR (500 MHz, MeOD) δ 7.30-7.37 (m, 7H), 7.23 (s, 1H), 7.11-7.15 (t, 3H, J=10.5 Hz), 7.06 (s, 1H), 7.02 (d, 11H, J=10.5 Hz), 5.96 (s, 2H), 3.33 (s, 3H), 3.17-3.21 (t, 2H, J=9.5 Hz), 3.06 (s, 3H), 2.93-2.96 (t, 2H, J=9.5 Hz), 2.91 (s, 3H).

Example 19: 4-bromo-1-(4-(dimethylcarbamoyl)benzyl)-6-(tetrahydro-2H-pyran-4-ylthio)-1H-indole-2-carboxylic acid, I-12

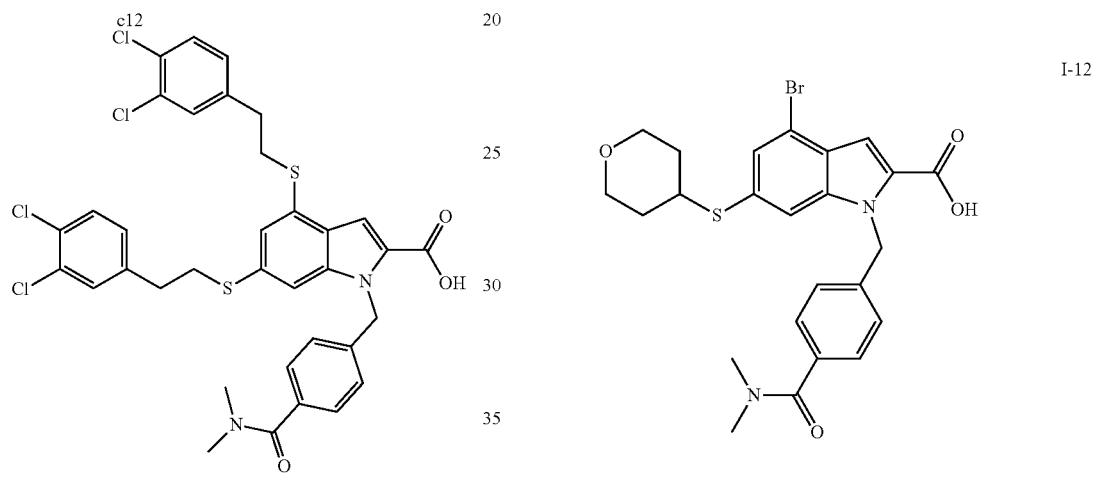

I-12

Synthetic Scheme:

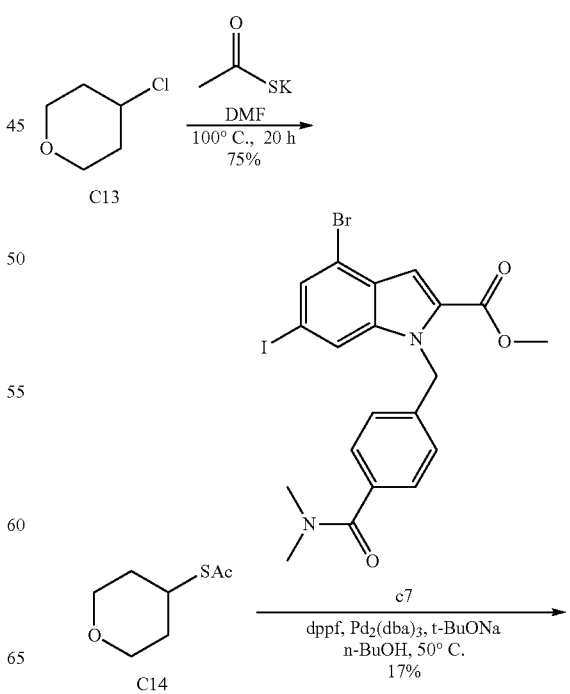

383
-continued

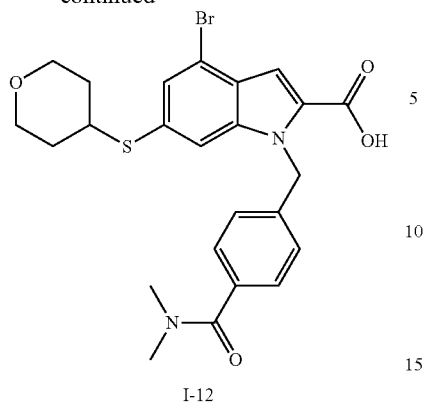

I-12

Procedures and Characterization:

Step 1: S-tetrahydro-2H-pyran-4-yl ethanethioate

A solution of 4-chlorotetrahydropyran (1.36 g, 11.28 mmol) and potassium ethanethioate (1.93 g, 16.92 mmol) in DMF (15.00 mL) was stirred at 100° C. for 20 h at N2 atmosphere. It was monitored by LC-MS. After completed, it was diluted with ethyl acetate, washed with brine, the organic layer was dried over magnesium sulfate, filtered, and concentrated to yield the crude product. It was purified by SGC to yield S-tetrahydropyran-4-yl ethanethioate (1.36 g, 8.49 mmol, 75%) as a red oil.

Step 2: 4-bromo-1-(4-(dimethylcarbamoyl)benzyl)-6-(tetrahydro-2H-pyran-4-ylthio)-1H-indole-2-carboxylic acid, I-12

A solution of methyl 4-bromo-1-[[4-(dimethylcarbamoyl)phenyl]methyl]-6-iodo-indole-2-carboxylate (340.00 mg, 0.63 mmol), S-tetrahydro-2H-pyran-4-yl ethanethioate (151.00 mg, 0.94 mmol), sodium 2-methylpropan-2-olate (181.13 mg, 1.88 mmol), dppf (34.81 mg, 0.07 mmol) and Pd$_2$(dba)$_3$ (57.55 mg, 0.06 mmol) in 2-methylpropan-2-ol (4.00 mL) was stirred at 50° C. for 0.5 h at N$_2$ atmosphere. It was monitored by LC-MS. After completed, it was diluted with ethyl acetate, washed with brine, the organic layer was dried over magnesium sulfate, filtrated, concentrated to yield the crude product. It was purified by prep-HPLC to yield 4-bromo-1-(4-(dimethylcarbamoyl)benzyl)-6-(tetrahydro-2H-pyran-4-ylthio)-1H-indole-2-carboxylic acid I-12 (56.8 mg, 0.11 mmol, 17%) as a white solid. ESI-MS (EI+, m/z): 517 [M+H]$^+$. $^1$H NMR (500 MHz, DMSO) δ 7.60 (s, 1H), 7.37 (s, 1H), 7.30-7.32 (d, 1H, J=10.5), 7.08-7.11 (m, 3H), 7.06 (s, 1H), 6.00 (s, 2H), 3.79 (d, 2H, J=10.5 Hz), 3.47-3.52 (m, 1H) 3.31 (d, 2H, J=16 Hz), 3.06 (s, 3H), 2.94 (s, 3H), 2.84 (s, 3H), 1.73 (d, 2H, J=16 Hz), 1.36 (d, 2H, J=10.5 Hz).

384

Example 20: 5-(3,4-dichlorophenylthio)-3-(4-(dimethylcarbamoyl)benzyl)-3H-benzo[e]indole-2-carboxylic acid, I-9

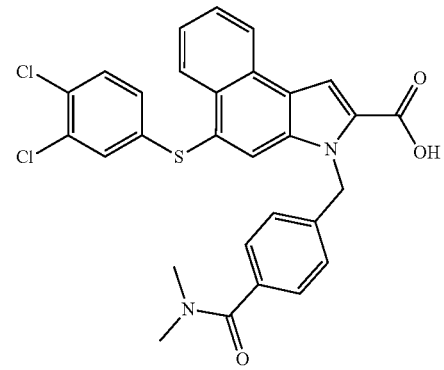

I-9

Synthetic Scheme:

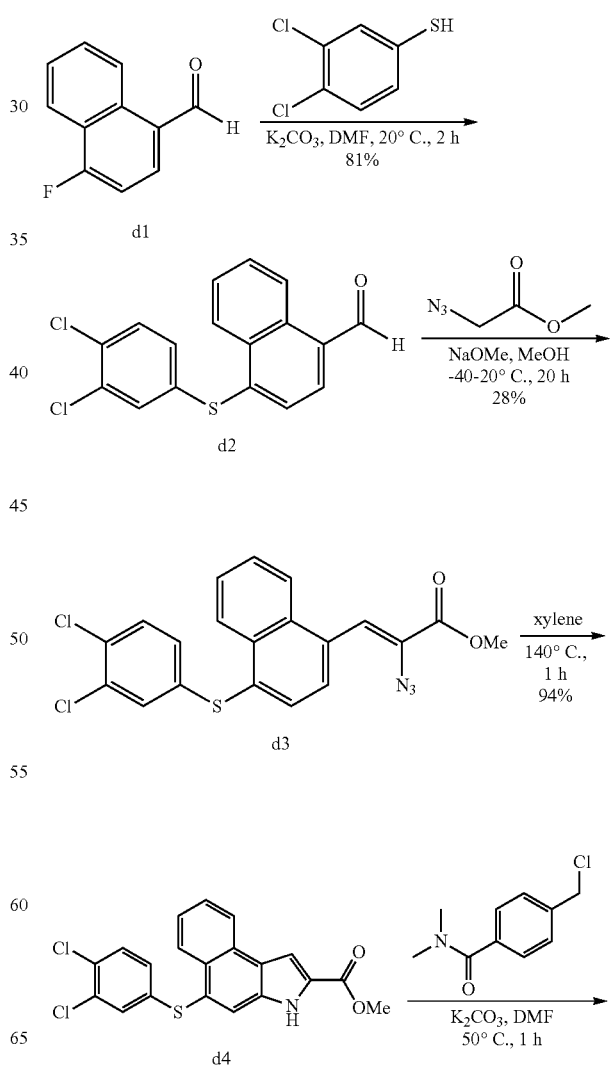

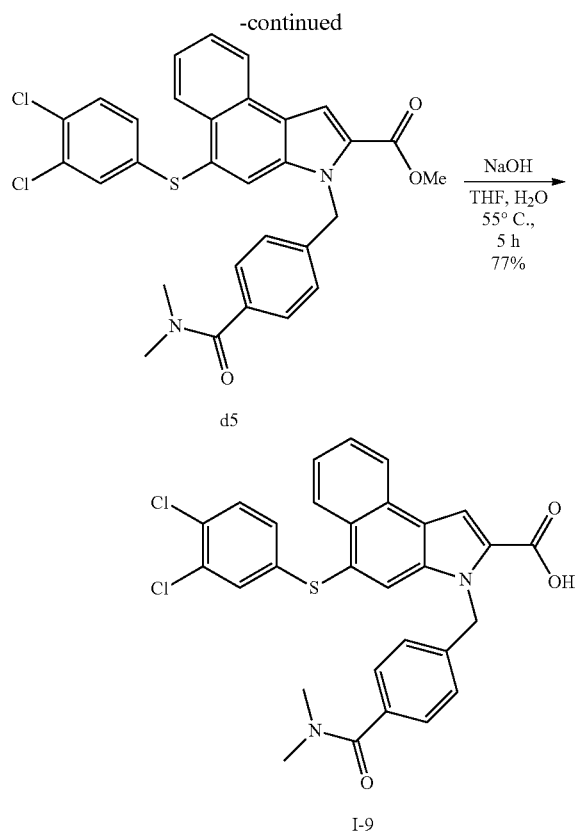

Procedures and Characterization:

Step 1: 4-(3,4-dichlorophenylthio)-1-naphthaldehyde

The procedure for 4-(3,4-dichlorophenylthio)-1-naphthaldehyde was the same as a2. (81.26%) as a yellow solid. ESI-MS (EI+, m/z): 333 [M+H]+.

Step 2: (Z)-methyl 2-azido-3-(4-(3,4-dichlorophenylthio)naphthalen-1-yl)acrylate The procedure for (Z)-methyl 2-azido-3-(4-(3,4-dichlorophenylthio)naphthalen-1-yl)acrylate was the same as b3.

Step 3: methyl 5-(3,4-dichlorophenylthio)-3H-benzo[e]indole-2-carboxylate

The procedure for 5-(3,4-dichlorophenyl)sulfanyl-3H-benzo[e]indole-2-carboxylate was the same as a4 (94%) as a white solid. ESI-MS (EI+, m/z): 402 [M+H]+.

Step 4: methyl 5-(3,4-dichlorophenylthio)-3-(4-(dimethylcarbamoyl)benzyl)-3H-benzo[e]indole-2-carboxylate A solution of methyl 5-(3,4-dichlorophenyl)sulfanyl-3H-benzo[e]indole-2-carboxy-late (150.00 mg, 0.37 mmol), 4-(chloromethyl)-N,N-dimethylbenzamide (110.55 mg, 0.56 mmol) and K$_2$CO$_3$ (103.07 mg, 0.74 mmol) was stirred at 50° C. for 1 h under N$_2$ atmosphere. It was monitored by LC-MS. After completed, it was diluted with ethyl acetate, washed with brine, the organic layer was dried over magnesium sulfate, filtrated, and concentrated to yield the crude product. It was used directly for the next step. ESI-MS (EI+, m/z): 563 [M+H]+.

Step 5: 5-(3,4-dichlorophenylthio)-3-(4-(dimethylcarbamoyl)benzyl)-3H-benzo[e]indole-2-carboxylic acid, I-9

The same procedure used to prepare I-25 afforded 5-(3,4-dichlorophenyl)sulfanyl-3-[[4-(dimethylcarbamoyl)phenyl]methyl]benzo[e]indole-2-carboxylic acid I-9 (226.40 mg, 0.41 mmol, 77%) as a white solid. ESI-MS (EI+, m/z): 549 [M+H]+. $^1$H NMR (400 MHz, DMSO) δ 8.54 (d, 1H, J=10 Hz), 8.25-8.27 (t, 2H, J=5 Hz), 8.08 (s, 1H), 7.67-7.70 (t, 1H, J=10 Hz), 7.53-7.56 (t, 1H, J=9 Hz), 7.46 (d, 1H, J=10.5 Hz), 7.30-7.35 (m, 3H), 7.30-7.32 (d, 1H, J=10.5 Hz), 7.08-7.11 (m, 3H), 7.04 (d, 1H, J=10.5 Hz), 6.93 (dd, 1H, J=3, 10.5 Hz), 6.11 (s, 2H), 3.79 (d, 2H, J=10.5 Hz), 3.47-3.52 (m, 1H) 3.31 (d, 2H, J=16 Hz), 3.06 (s, 3H), 2.94 (s, 3H), 2.83 (s, 3H).

Example 21: 7-bromo-6-(3,4-dichlorophenylthio)-1-(4-(dimethylcarbamoyl) benzyl)-1H-indole-2-carboxylic acid, I-6

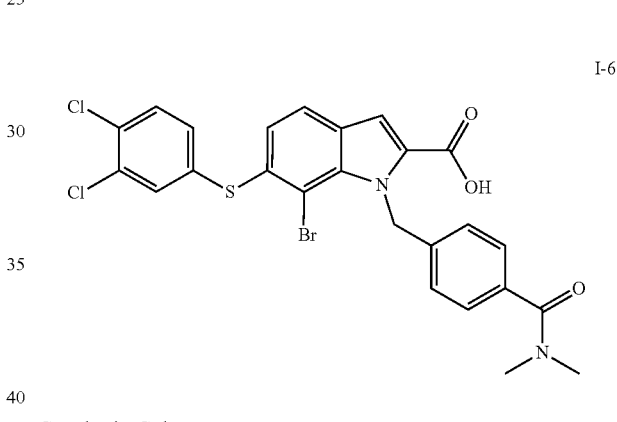

Synthetic Scheme:

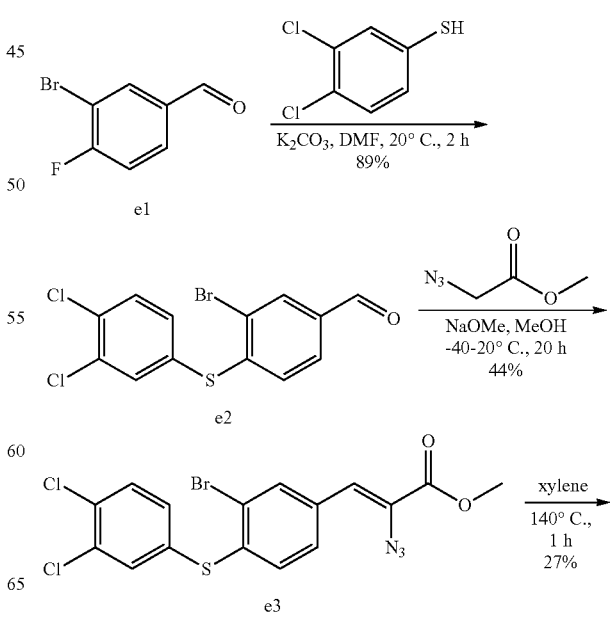

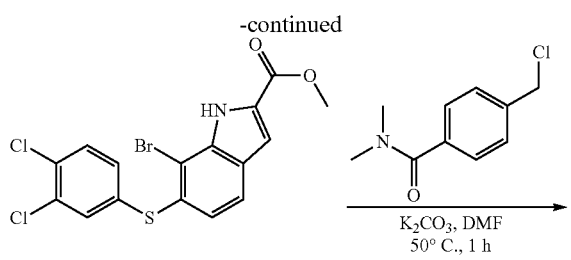

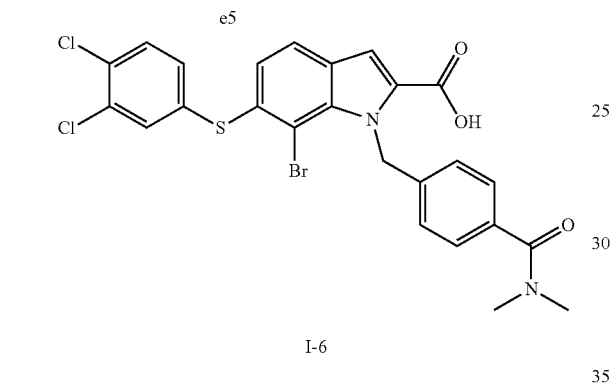

Procedures and Characterization:

Step 1: 3-bromo-4-(3,4-dichlorophenylthio)benzaldehyde

The procedure for 3-bromo-4-(3,4-dichlorophenylthio) benzaldehyde was the same as a2. Afforded 3-bromo-4-(3, 4-dichlorophenylthio)benzaldehyde (89%) as a light yellow solid. ESI-MS (EI+, m/z): 361 [M+H]$^+$.

Step 2: (Z)-methyl 2-azido-3-(3-bromo-4-(3,4-dichlorophenylthio)phenyl)acrylate

The procedure for methyl (Z)-2-azido-3-[3-bromo-4-(3, 4-dichlorophenyl)sulfanyl-phenyl]prop-2-enoate was the same as b3 (44%) and afforded a yellow solid. H NMR (400 MHz, CDCl$_3$) δ 8.08 (d, J=1.5 Hz, 1H), 7.61 (dd, J=8.4, 1.5 Hz, 1H), 7.54 (d, J=2.0 Hz, 1H), 7.47 (d, J=8.3 Hz, 1H), 7.29 (d, J=2.0 Hz, 1H), 6.93 (d, J=8.3 Hz, 1H), 6.75 (s, 11H), 3.91 (s, 3H).

Step 3: methyl 7-bromo-6-(3,4-dichlorophenylthio)-1H-indole-2-carboxylate

The procedure for methyl 7-bromo-6-(3,4-dichlorophenyl)sulfanyl-1H-indole-2-carboxylate was the same as a4 (27%) and afforded a light-yellow solid. H NMR (400 MHz, DMSO) δ 12.07 (s, 1H), 7.75 (d, J=8.3 Hz, 1H), 7.59 (d, J=8.5 Hz, 1H), 7.44 (d, J=2.2 Hz, 11H), 7.35 (s, 1H), 7.19 (d, J=8.3 Hz, 11H), 7.12 (dd, J=8.5, 2.2 Hz, 1H).

Step 4: methyl 7-bromo-6-(3,4-dichlorophenylthio)-1-(4-(dimethylcarbamoyl)benzyl)-1H-indole-2-carboxylate The procedure for methyl 7-bromo-6-(3,4-dichlorophenylthio)-1-(4-(dimethylcarbamoyl)benzyl)-1H-indole-2-carboxylate was the same as d5 ESI-MS (EI+, m/z): 590 [M+H]$^-$.

Step 5: 7-bromo-6-(3,4-dichlorophenylthio)-1-(4-(dimethylcarbamoyl) benzyl)-1H-indole-2-carboxylic acid, I-6

The same procedure used to prepare I-25 afforded 7-bromo-6-(3,4-dichlorophenyl)sulfanyl-1-[[4-(dimethylcarbamoyl)phenyl]methyl]indole-2-carboxylic acid I-6 (119.10 mg, 0.21 mmol, 31%) as a white solid. ESI-MS (EI+, m/z): 577 [M+H]$^+$. $^1$H NMR (400 MHz, DMSO) δ 13.40 (s, 1H), 8.19 (s, 1H), 7.77 (s, 1H), 7.57 (d, J=8.5 Hz, 1H), 7.40 (d, J=2.2 Hz, 1H), 7.33 (s, 11H), 7.29 (d, J=8.1 Hz, 2H), 7.04 (dd, J=8.5, 2.2 Hz, 1H), 6.98 (d, J=8.1 Hz, 2H), 5.89 (s, 2H), 2.92 (d, J=17.4 Hz, 3H), 2.83 (s, 3H).

Example 22: 4,6-bis(4-chlorobenzylthio)-1H-indole-2-carboxylic acid, I-28

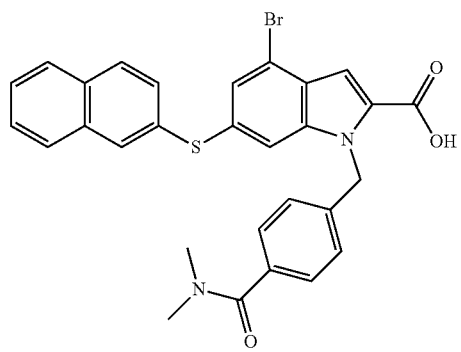

Synthetic Scheme:

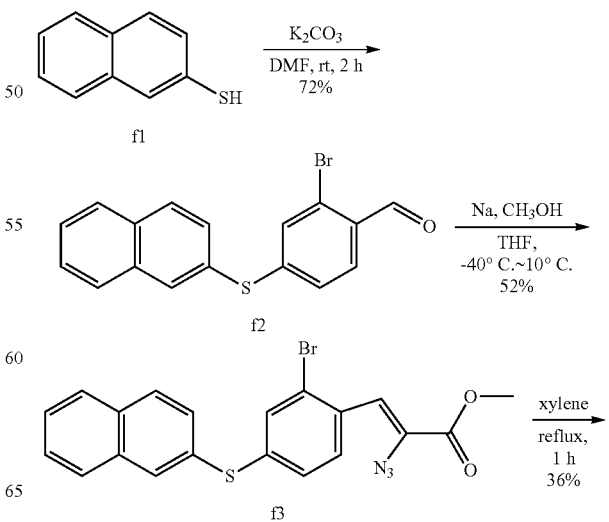

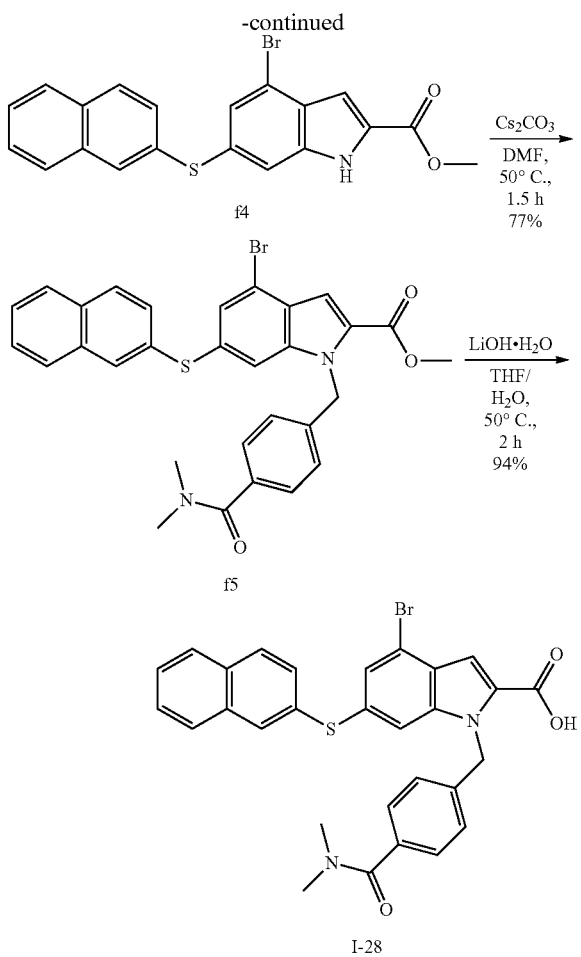

Procedures and Characterization:

Step 1: 2-bromo-4-(naphthalen-2-ylthio)benzaldehyde

The procedure for 2-bromo-4-(2-naphthylsulfanyl)benzaldehyde was the same as a2 (72.47% yield) and afforded a yellow solid. ESI-MS (EI+, m/z): 364.9 [M+Na]+.

Step 2: (Z)-methyl 2-azido-3-(2-bromo-4-(naphthalen-2-ylthio)phenyl)acrylate The procedure for methyl (Z)-2-azido-3-[2-bromo-4-(2-naphthylsulfanyl)phenyl]prop-2-enoate was the same as a3 (52.48% yield) and afforded a white solid. ESI-MS (EI+, m/z): 462.0 [M+Na]−.

1H NMR (400 MHz, DMSO-d6) δ 8.18 (s, 1H), 8.13 (d, J=8.5 Hz, 1H), 8.03-7.95 (m, 3H), 7.63-7.56 (m, 2H), 7.55-7.48 (m, 2H), 7.27 (dd, J=8.4, 1.5 Hz, 1H), 7.03 (s, 1H), 3.83 (d, J=29.6 Hz, 3H).

Step 3: methyl 4-bromo-6-(naphthalen-2-ylthio)-1H-indole-2-carboxylate

The procedure for methyl 4-bromo-6-(naphthalen-2-ylthio)-1H-indole-2-carboxylate was the same as a4 (36% yield) and afforded a yellow solid. 1H NMR (400 MHz, DMSO-d6) δ 8.00 (s, 1H), 7.97-7.88 (m, 3H), 7.59-7.51 (m, 2H), 7.46-7.39 (m, 2H), 7.32 (s, 1H), 7.04 (s, 1H), 4.09 (d, J=22.7 Hz, 1H), 3.88 (s, 3H).

Step 4: methyl 4-bromo-1-(4-(dimethylcarbamoyl)benzyl)-6-(naphthalen-2-ylthio)-1H-indole-2-carboxylate A mixture of methyl 4-bromo-6-(2-naphthylsulfanyl)-1H-indole-2-carboxylate (150.00 mg, 363.81 μmol), 4-(chloromethyl)-N,N-dimethyl-benzamide (79.10 mg, 400.19 μmol) Cs2CO3 (236.48 mg, 727.62 μmol) and DMF (8.00 mL) was kept stirring at 50° C. for 1.5 h. The mixture was poured into water (80 mL), then extracted with ethyl acetate (30 mL×3), washed with water (20 mL×2), brine (20 mL). The organic layer was dried over Na2SO4 for 20 min, filtered and concentrated in vacuo. The residue was purified by CombiFlash (silica gel, 254 nm, ethyl acetate/petroleum ether from 0%~25%) to afford methyl 4-bromo-1-[[4-(dimethylcarbamoyl)phenyl]methyl]-6-(2-naphthylsulfanyl)indole-2-carboxylate (160.00 mg, 278.99 μmol, 76.69% yield) as a yellow solid. ESI-MS (EI+, m/z): 575.1 [M+H]+

Step 5: 4-bromo-1-(4-(dimethylcarbamoyl)benzyl)-6-(naphthalen-2-ylthio)-1H-indole-2-carboxylic acid, I-28

A mixture of methyl 4-bromo-1-[[4-(dimethylcarbamoyl)phenyl]methyl]-6-(2-naphthylsulfanyl)indole-2-carboxylate (112.00 mg, 195.29 μmol), LiOH.H2O (28.06 mg, 1.17 mmol), THF (15.00 mL) and water (4.00 mL) was kept stirring at 50° C. for 1 h. The mixture was adjusted pH=4 with 1N HCl, extracted with ethyl acetate (20 mL×3). The organic layer was removed in vacuo and the residue was purified by prep-HPLC (NH4HCO3) to give 4-bromo-1-[[4-(dimethylcarbamoyl)phenyl]methyl]-6-(2-naphthylsulfanyl)indole-2-carboxylic acid I-28 (103.00 mg, 184.10 μmol, 94.27% yield) as a white solid. ESI-MS (EI+, m/z): 557.0 [M−H]+

1H NMR (400 MHz, DMSO-d6) δ 13.44 (s, 1H), 7.95-7.79 (m, 4H), 7.71 (s, 1H), 7.57-7.44 (m, 2H), 7.33 (d, J=4.5 Hz, 2H), 7.26-7.13 (m, 3H), 6.98 (d, J=7.9 Hz, 2H), 5.90 (s, 2H), 2.95 (s, 3H), 2.81 (s, 3H).

Example 23: 1-((4'-aminobiphenyl-4-yl)methyl)-6-chloro-4-(2,4-dichlorophenylthio)-1H-indole-2-carboxylic acid, I-78

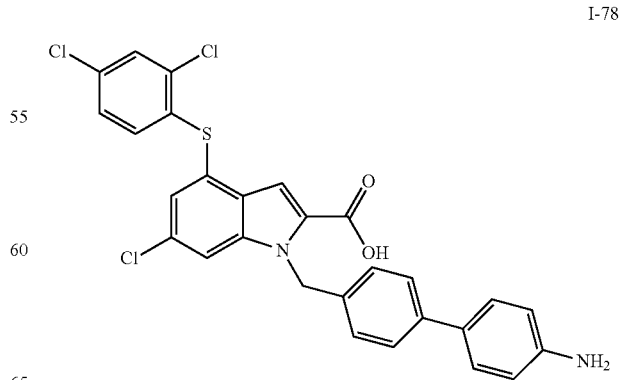

Synthetic Scheme:

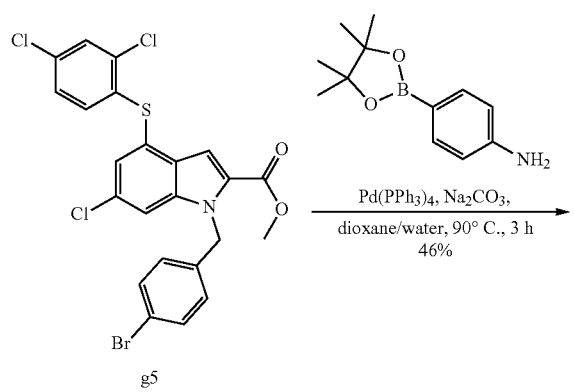

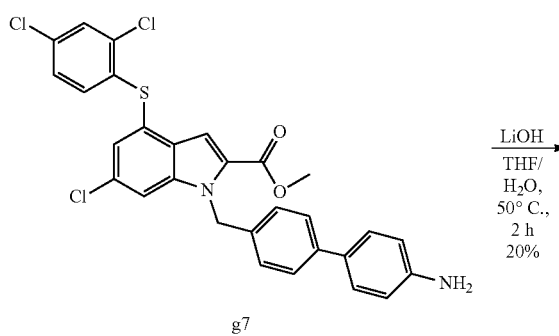

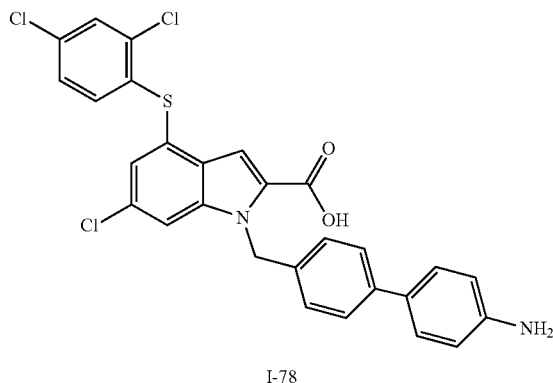

Procedures and Characterization:

Step 1: 1-((4'-aminobiphenyl-4-yl)methyl)-6-chloro-4-(2,4-dichlorophenylthio)-1H-indole-2-carboxylic acid, I-78

The procedure for 1-((4'-aminobiphenyl-4-yl)methyl)-6-chloro-4-(2,4-dichlorophenylthio)-1H-indole-2-carboxylic acid I-78 was the same as I-28.

ESI-MS (EI⁺, m/z): 550.8 [M−H]⁺. ¹H NMR (500 MHz, DMSO-d6) δ 7.89 (s, 1H), 7.78 (d, J=2.1 Hz, 1H), 7.44 (d, J=8.2 Hz, 2H), 7.33 (dd, J=8.6, 2.1 Hz, 1H), 7.29 (d, J=8.5 Hz, 2H), 7.23 (d, J=1.3 Hz, 1H), 7.06 (d, J=8.1 Hz, 2H), 7.00 (s, 1H), 6.92 (d, J=8.6 Hz, 1H), 6.60 (d, J=8.4 Hz, 2H), 5.93 (s, 2H).

Example 24: 6-chloro-4-(2,4-dichlorophenylthio)-1-(4-(1,5-dimethyl-1H-pyrazol-4-yl)benzyl)-1H-indole-2-carboxylic acid, I-77

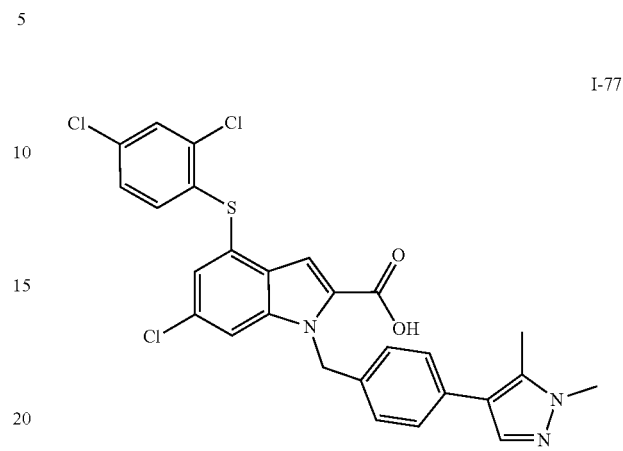

Synthetic Scheme:

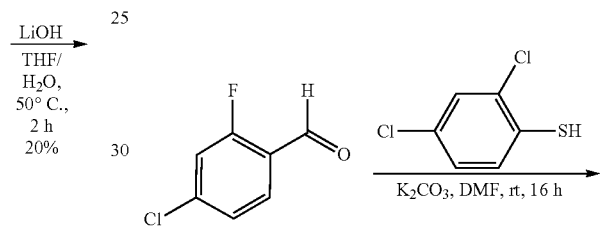

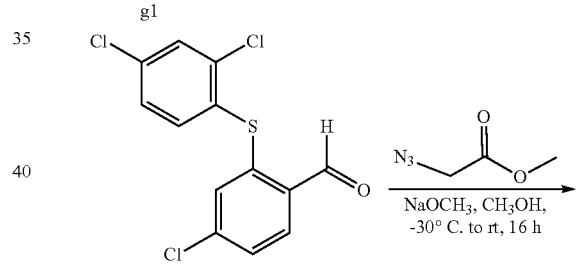

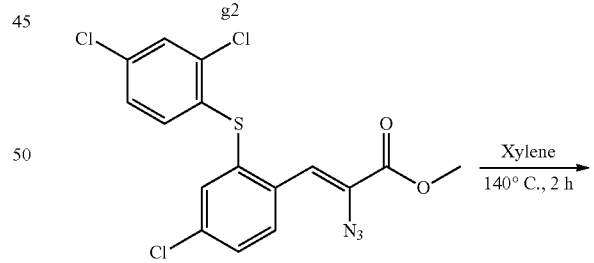

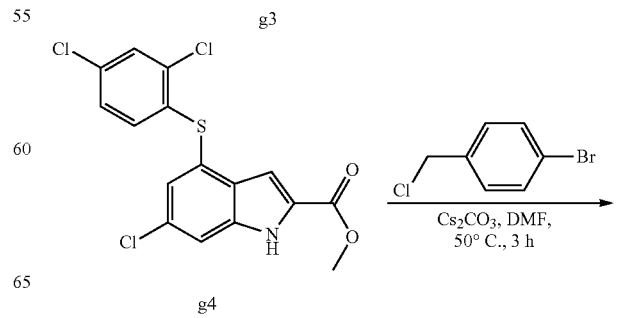

-continued

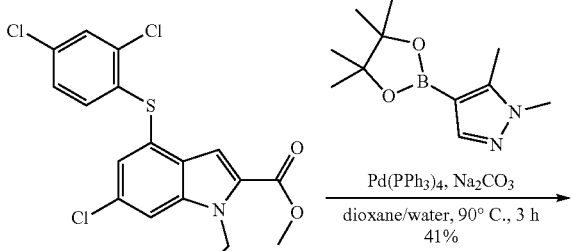

g5

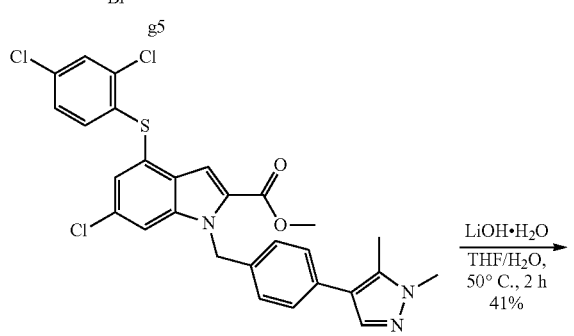

g6

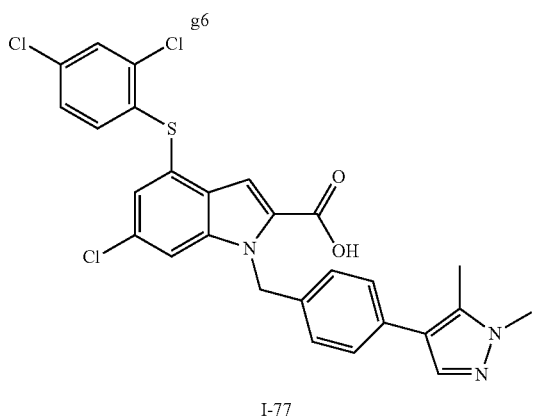

I-77

Procedures and Characterization:

Step 1: methyl 6-chloro-4-(2,4-dichlorophenylthio)-1-(4-(1,5-dimethyl-1H-pyrazol-4-yl)benzyl)-1H-indole-2-carboxylate A mixture of methyl 1-(4-bromobenzyl)-6-chloro-4-(2,4-dichlorophenylthio)-1H-indole-2-carboxylate (100 mg, 0.18 mmol), 1,5-dimethyl-4-(4,4,5,5-tetramethyl-1,3,2-dioxaborolan-2-yl)-1H-pyrazole (80 mg, 0.36 mmol), Na$_2$CO$_3$ (76 mg, 0.72 mmol), dioxane (30 mL) and water (7 mL) was degassed for 3 min. Pd(PPh$_3$)$_4$ (21 mg, 0.018 mmol) was added into above mixture, the resulting mixture was degassed for 3 min again, and kept stirring at 90° C. for 3 h under N$_2$ atmosphere. The mixture was filtered and concentrated in vacuo. The residue was purified by prep-TLC (silica gel, 254 nm, acetate/petroleum ether=5/1) to afford methyl 6-chloro-4-(2,4-dichlorophenylthio)-1-((3'-(hydroxymethyl)biphenyl-4-yl)methyl)-1H-indole-2-carboxylate (42 mg, 72 μmol, 41% yield) as a white solid. ESI-MS (EI+, m/z): 572.1 [M+H]$^+$ Step 2: 6-chloro-4-(2,4-dichlorophenylthio)-1-(4-(1,5-dimethyl-1H-pyrazol-4-yl)benzyl)-1H-indole-2-carboxylic acid, I-77

A mixture of methyl 6-chloro-4-(2,4-dichlorophenylthio)-1-(4-(1,5-dimethyl-1H-pyrazol-4-yl)benzyl)-1H-indole-2-carboxylate (42 mg, 0.074 mmol), LiOH.H$_2$O (32 mg, 0.74 mmol), THF (10 mL) and water (3 mL) was kept stirring at 50° C. for 2 h. The mixture was cooled down to 10° C. and adjusted pH 4 with 1N HCl, then removed the solvent by vacuum. The residue was purified by prep-HPLC (NH$_4$HCO$_3$) to afford 6-chloro-4-(2,4-dichlorophenylthio)-1-(4-(1,5-dimethyl-1H-pyrazol-4-yl)benzyl)-1H-indole-2-carboxylic acid I-77 (20 mg, 36 μmol, 41% yield) as a white solid. ESI-MS (EI+, m/z): 553.8 [M–H]$^+$ $^1$H NMR (500 MHz, DMSO-d6) δ 13.39 (s, 11H), 7.95 (s, 1H), 7.79 (d, J=1.9 Hz, 11H), 7.51 (s, 11H), 7.36-7.27 (m, 3H), 7.24 (s, 11H), 7.10-7.01 (m, 3H), 6.96 (d, J=8.6 Hz, 1H), 5.91 (s, 2H), 3.75 (s, 3H), 2.32 (s, 3H).

Example 25: 6-chloro-4-(2,4-dichlorophenylthio)-1-(4-(pyridin-4-yl)benzyl)-1H-indole-2-carboxylic acid, I-70

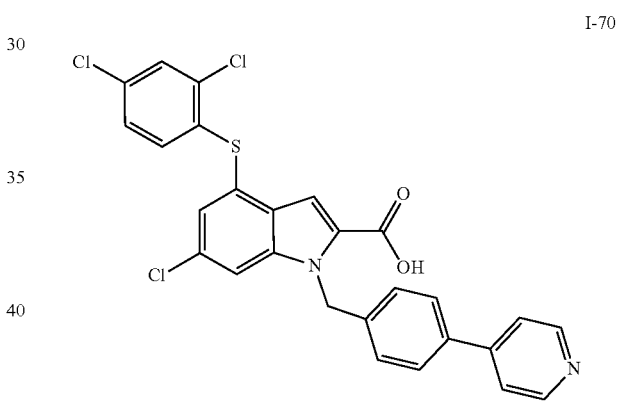

I-70

Synthetic Scheme:

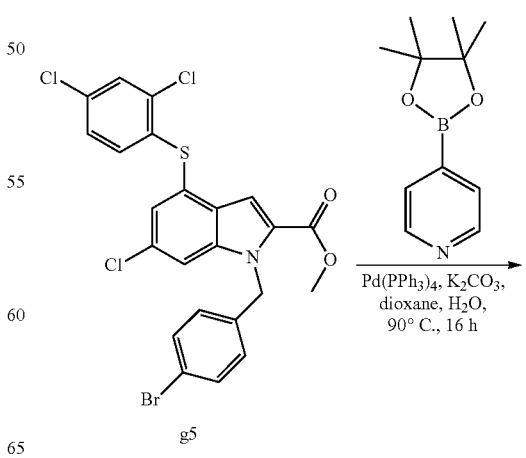

g5

395
-continued

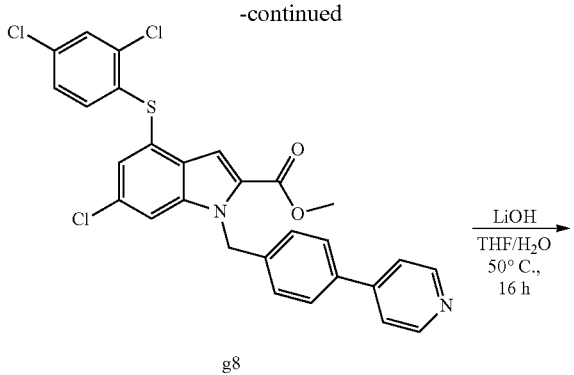

g8

396

Step 2: 6-chloro-4-(2,4-dichlorophenylthio)-1-(4-(pyridin-4-yl)benzyl)-1H-indole-2-carboxylic acid, I-70

The procedure for 6-chloro-4-(2,4-dichlorophenylthio)-1-(4-(pyridin-4-yl)benzyl)-1H-indole-2-carboxylic acid, I-70 was same as example I-77. ESI-MS (EI+, m/z): 539, 541. $^1$H NMR (400 MHz, DMSO-$d_6$) δ 8.77 (d, J=4.8 Hz, 2H), 7.98 (d, J=4.4 Hz, 2H), 7.95 (s, 1H), 7.85 (d, J=6.8 Hz, 2H), 7.80 (d, J=2.0 Hz, 1H), 7.35 (d, d, J=4.8 Hz, J=1.6 Hz, 1H), 7.25 (d, J=1.2 Hz, 1H), 7.20 (d, J=6.8 Hz, 2H), 7.11 (s, 1H), 6.98 (d, J=6.8 Hz, 1H), 6.00 (s, 2H).

Example 26: 6-chloro-4-(2,4-dichlorophenylthio)-1-((3'-(hydroxymethyl)biphenyl-4-yl)methyl)-1H-indole-2-carboxylic acid, I-72

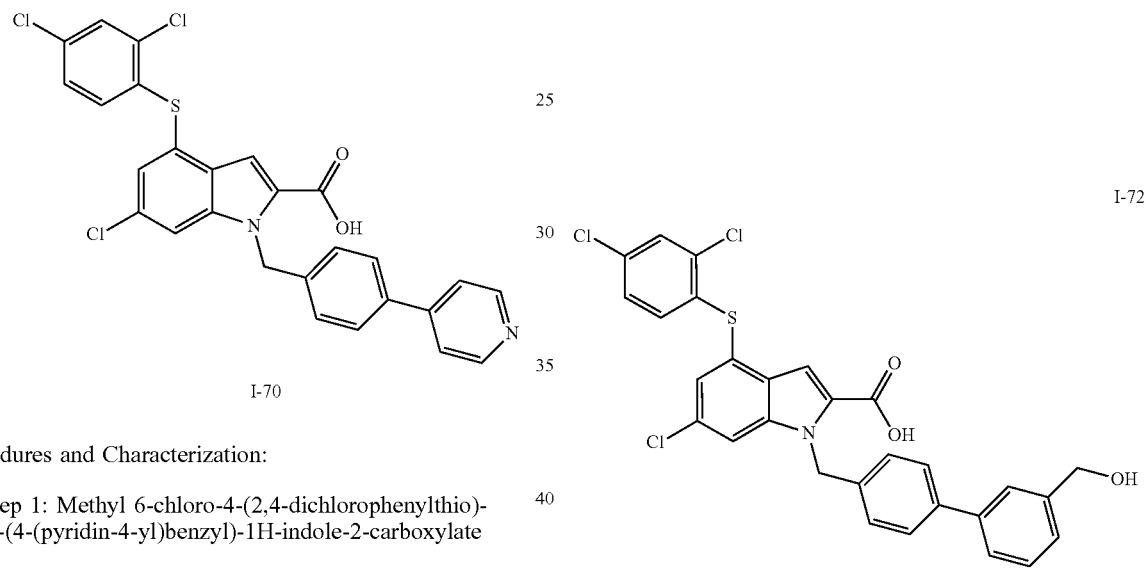

I-70

Procedures and Characterization:

Step 1: Methyl 6-chloro-4-(2,4-dichlorophenylthio)-1-(4-(pyridin-4-yl)benzyl)-1H-indole-2-carboxylate The procedure for methyl 6-chloro-4-(2,4-dichlorophenylthio)-1-(4-(pyridin-4-yl)benzyl)-1H-indole-2-carboxylate was same as g6. The base was $K_2CO_3$. ESI-MS (EI+, m/z): 553, 555.

Synthetic Scheme:

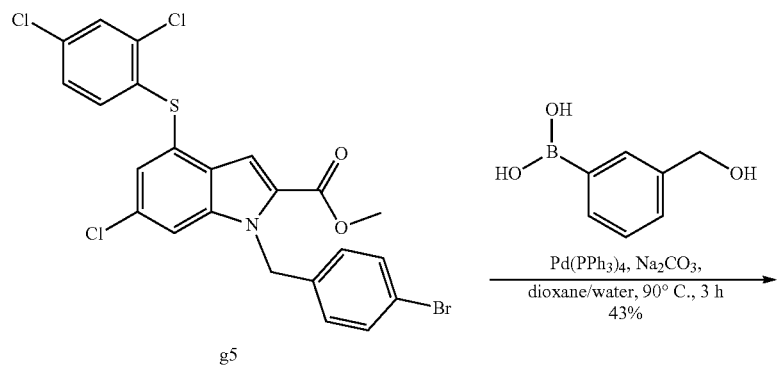

g5

-continued

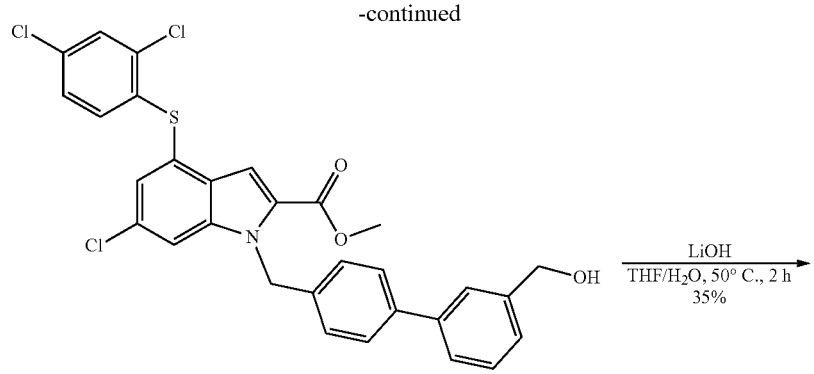

g9

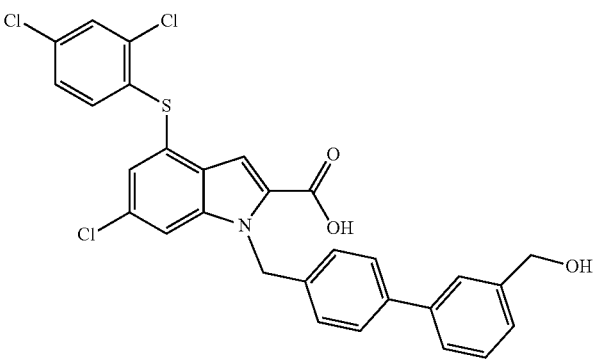

I-72

Procedures and Characterization:

The procedure was the same as I-77 to give 6-chloro-4-(2,4-dichlorophenylthio)-1-((3'-(hydroxymethyl)biphenyl-4-yl)methyl)-1H-indole-2-carboxylic acid, I-72:

ESI-MS (EI$^+$, m/z): 567.9 [M−H]$^+$. $^1$H NMR (400 MHz, DMSO-d6) δ 7.92 (s, 1H), 7.79 (s, 1H), 7.61-7.53 (m, 3H), 7.47 (d, J=7.7 Hz, 1H), 7.42-7.32 (m, 2H), 7.30 (d, J=7.6 Hz, 1H), 7.23 (s, 1H), 7.12 (d, J=9.2 Hz, 3H), 6.99 (d, J=8.6 Hz, 1H), 5.95 (s, 2H), 4.54 (s, 2H).

Example 27: 4-chloro-6-(3,4-dichlorophenylthio)-1-(4-(dimethylcarbamoyl)benzyl)-1H-pyrrolo[3,2-c]pyridine-2-carboxylic acid, I-4

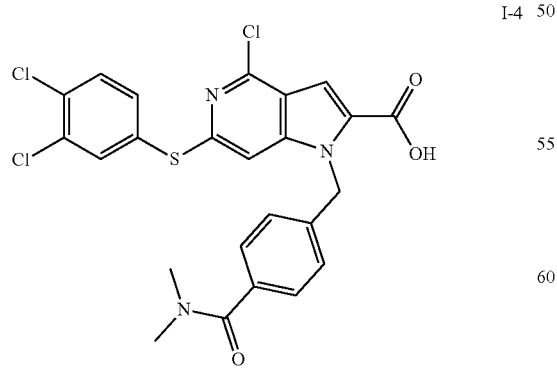

I-4

Synthetic Scheme:
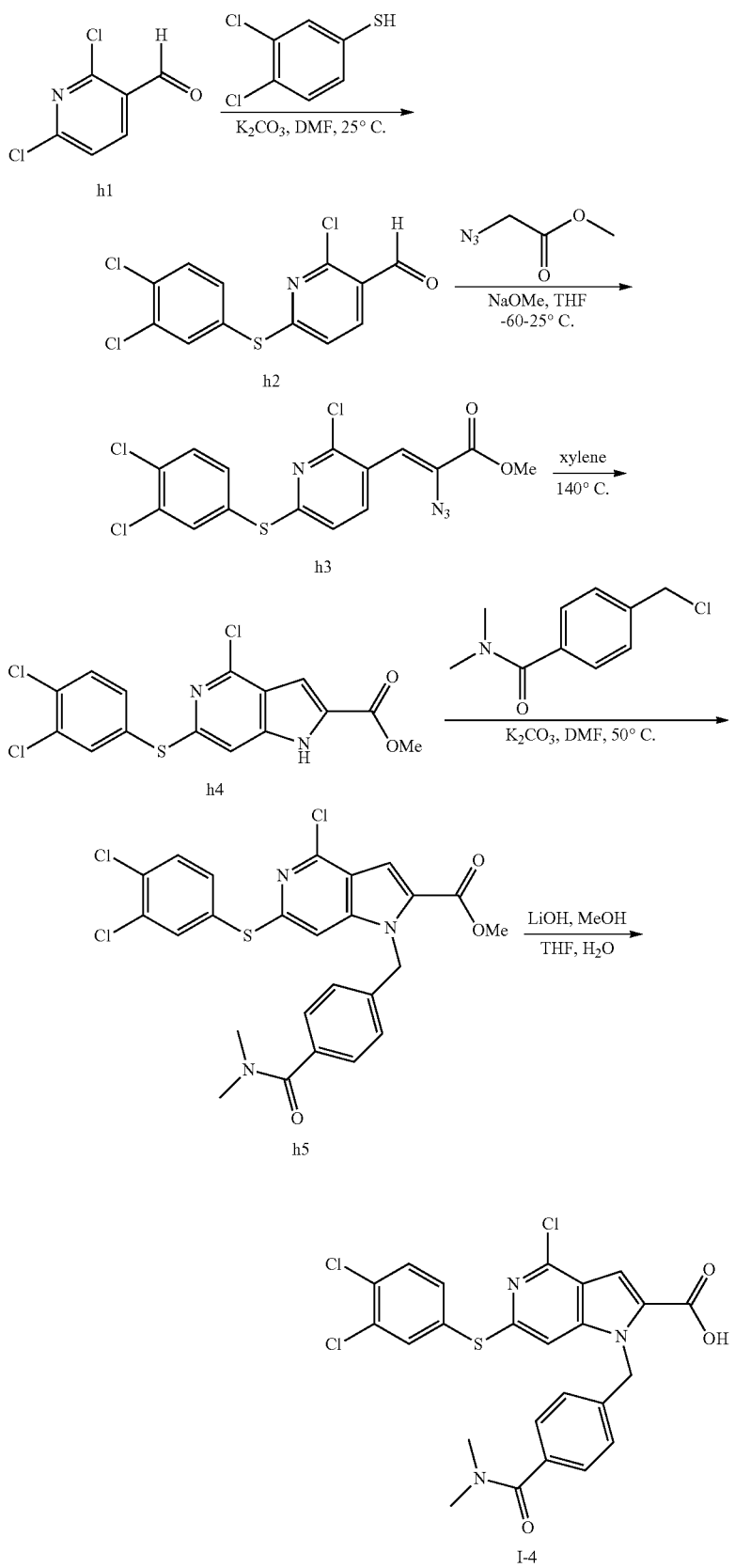

Procedures and Characterization:

Step 3: methyl 4-chloro-6-(3,4-dichlorophenylthio)-1H-pyrrolo[3,2-c]pyridine-2-carboxylate The procedure for methyl 4-chloro-6-(3,4-dichlorophenylthio)-1H-pyrrolo[3,2-c]pyridine-2-carboxylate (h4) was the same as a4. ESI-MS (EI+, m/z): 387, 389[M+H]+.

Step 4: methyl 4-chloro-6-(3,4-dichlorophenylthio)-1-(4-(dimethylcarbamoyl)benzyl)-1H-pyrrolo[3,2-c]pyridine-2-carboxylate The mixture of methyl 4-chloro-6-(3,4-dichlorophenyl)sulfanyl-1H-pyrrolo[3,2-c]pyridine-2-carboxylate (400.00 mg, 515.90 μmol), 4-(chloromethyl)-N,N-dimethylbenzamide (122.37 mg, 619.08 μmol), K₂CO₃ (213.91 mg, 1.55 mmol) and DMF (3.00 mL) was heated to 50° C. for 4 h, LCMS showed desired MS, The mixture was cooled down and extracted with H₂O (10 mL), and EtOAc (50 mL×2). The combined organics were washed with H₂O (10 mL×5), and dried over Na₂SO₄, filtered, and concentrated in vacuo to afford the residue (300 mg) as a yellow oil. The residue was purified by prep-TLC (EtOAc/petroleum ether=1/1, Rf~0.4, UV, 254 nm) to afford the product (0.15 g) as an off-white solid (yield: 52.97%).
ESI-MS (EI+, m/z): 548 [M+H]+.

Step 5: 4-chloro-6-(3,4-dichlorophenylthio)-1-(4-(dimethylcarbamoyl)benzyl)-1H-pyrrolo[3,2-c]pyridine-2-carboxylic acid, I-4

To the solution of methyl 4-chloro-6-(3,4-dichlorophenyl)sulfanyl-1-[[4-(dimethylcarbamoyl)phenyl]methyl]pyrrolo[3,2-c]pyridine-2-carboxylate (150.00 mg, 273.29 μmol) in THF (3.00 mL), MeOH (3.00 mL) and H₂O (1.50 mL) was added LiOH (32.73 mg, 1.37 mmol). The resulting reaction mixture was heated to 50° C. and stirred for 1 hour. The reaction was cooled down and neutralized to pH=7 with saturated NH₄Cl aqueous solution. The mixture was concentrated in vacuo to afford the residue (200 mg) as a yellow oil. The residue was purified by prep-HPLC (formic acid system) to afford the product 4-chloro-6-(3,4-dichlorophenyl)sulfanyl-1-[[4-(dimethylcarbamoyl)phenyl]methyl]pyrrolo[3,2-c]pyridine-2-carboxylic acid I-4 (35.00 mg, 65.44 μmol, 23.95% yield) as an off-white solid. ESI-MS (EI+, m/z): 534,536 [M+H]+. ¹H NMR (500 MHz, MeOD-d4) δ 8.23 (s, 1H), 7.61 (s, 1H), 7.55 (d, J=10 Hz, 1H), 7.32 (m, 4H), 7.20 (s, 1H), 7.20 (d, J=10 Hz, 1H), 5.96 (s, 2H), 3.09 (s, 3H), 2.97 (s, 3H).

Example 28: 4-bromo-6-(3,4-dichlorophenylthio)-1-(4-(dimethyl carbamoyl)benzyl)-1H-pyrrolo[3,2-c]pyridine-2-carboxylic acid, I-3

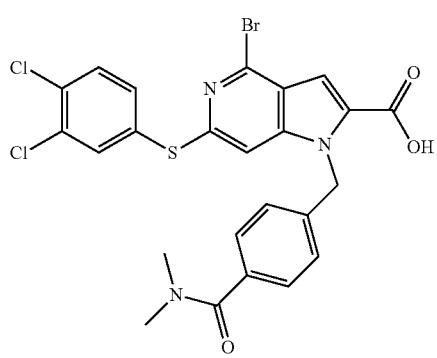

I-3

Synthetic Scheme:

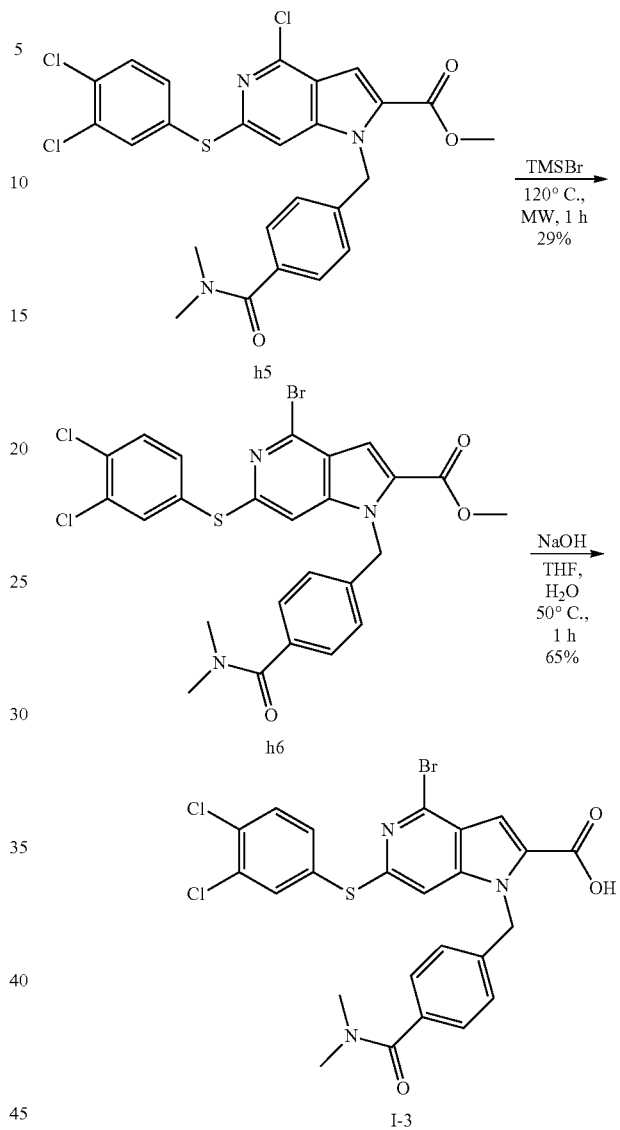

Procedures and Characterization:

Step 1: methyl 4-bromo-6-(3,4-dichlorophenylthio)-1-(4-(dimethylcarbamoyl)benzyl)-1H-pyrrolo[3,2-c]pyridine-2-carboxylate A solution of methyl 4-chloro-6-(3,4-dichlorophenyl)sulfanyl-1-[[4-(dimethyl carbamoyl)phenyl]methyl]pyrrolo[3,2-c]pyridine-2-carboxylate (500.00 mg, 0.91 mmol) and TMSBr (278.75 mg, 1.82 mmol) in propionitrile (5.00 mL) was stirred at 120° C. for 1 h by microwave. It was monitored by LC-MS. After the reaction was complete, it was diluted with ethyl acetate, washed with brine, the organic layer was dried over magnesium sulfate, filtered, and concentrated to yield the crude product. It was purified by TLC to yield methyl 4-bromo-6-(3,4-dichlorophenyl)sulfanyl-1-[[4-(dimethylcarbamoyl)phenyl]methyl]pyrrolo[3,2-c]pyridine-2-carboxylate (156.00 mg, 0.26 mmol, 29%) as a red oil. ESI-MS (EI+, m/z): 592 [M+H]+.

Step 2: 4-bromo-6-(3,4-dichlorophenylthio)-1-(4-(dimethyl carbamoyl)benzyl)-1H-pyrrolo[3,2-c]pyridine-2-carboxylic acid, I-3

A solution of methyl 4-bromo-6-(3,4-dichlorophenyl)sulfanyl-1-[[4-(dimethyl carbamoyl)phenyl]methyl]pyrrolo[3,2-c]pyridine-2-carboxylate (103.00 mg, 0.17 mmol) and NaOH (34.72 mg, 0.87 mmol) in a mixture of THF (4.00 mL) and water (2.00 mL) was stirred at 50° C. for 1 h. It was monitored by LC-MS. After completed, it was diluted with ethyl acetate, adjusted pH to 6, washed with brine, the organic layer was dried over magnesium sulfate, filtrated, concentrated to yield the crude product. It was purified by prep-HPLC to yield 4-bromo-6-(3,4-dichlorophenyl)sulfanyl-1-[[4-(dimethylcarbamoyl)phenyl]methyl]pyrrolo[3,2-c]pyridine-2-carboxylic acid I-3 (65.30 mg, 0.13 mmol, 65%) as a white solid. ESI-MS (EI+, m/z): 578 [M+H]$^+$. H NMR (400 MHz, DMSO) δ 13.54 (s, 1H), 7.75 (d, J=1.7 Hz, 1H), 7.72-7.56 (m, 2H), 7.37 (dd, J=8.4, 1.9 Hz, 1H), 7.31 (d, J=8.0 Hz, 2H), 7.21 (s, 1H), 7.04 (d, J=7.9 Hz, 2H), 5.86 (s, 2H), 2.95 (s, 3H), 2.85 (s, 3H).

Example 29: methyl 6-(4-chloro-3-methylphenylthio)-1-(4-(dimethylcarbamoyl)benzyl)-5-phenyl-1H-indole-2-carboxylate, I-2, and methyl 6-(3,4-dichloro phenylthio)-1-(4-(dimethylcarbamoyl) benzyl)-7-phenyl-1H-indole-2-carboxylate, I-1

Synthetic Scheme:

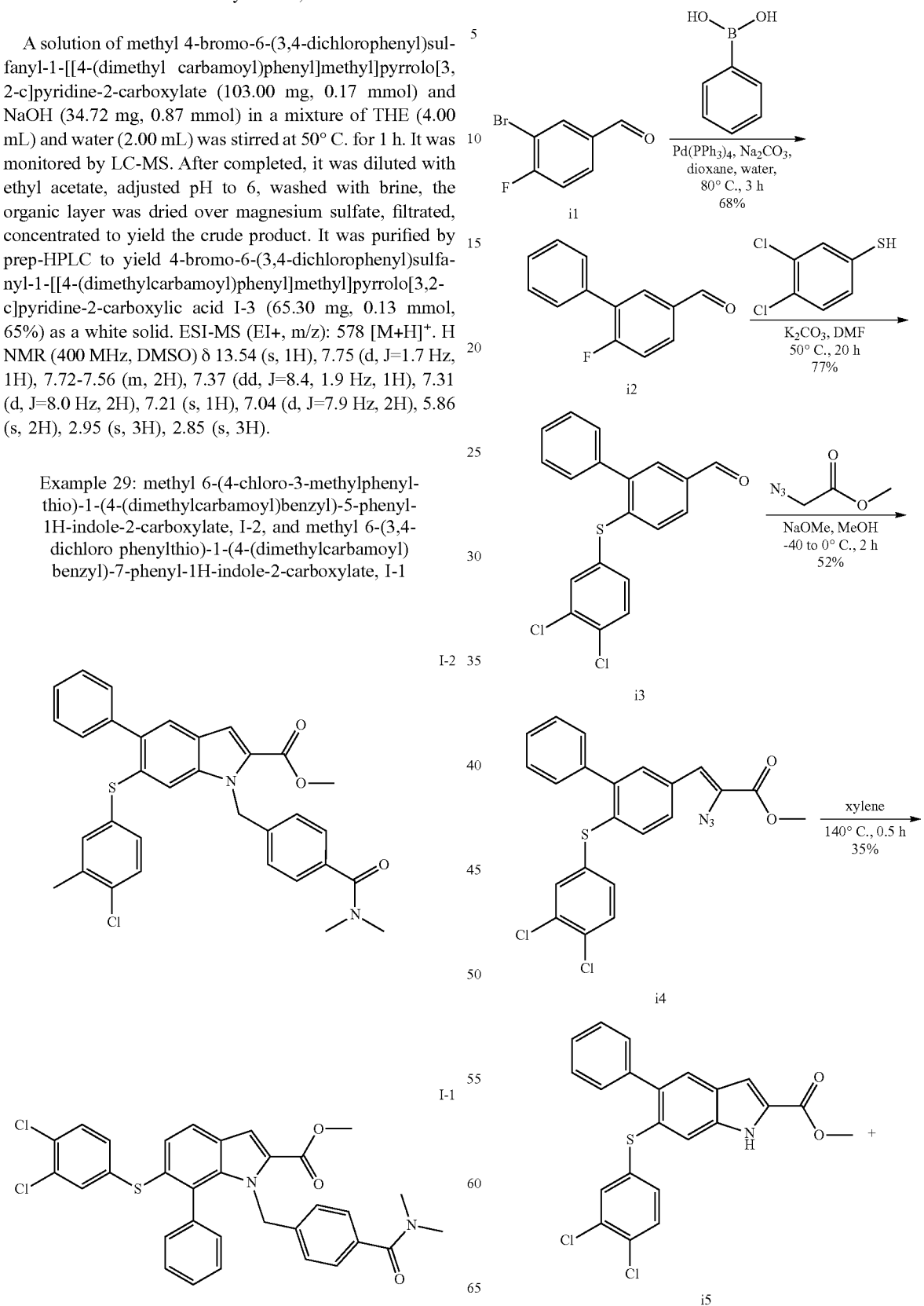

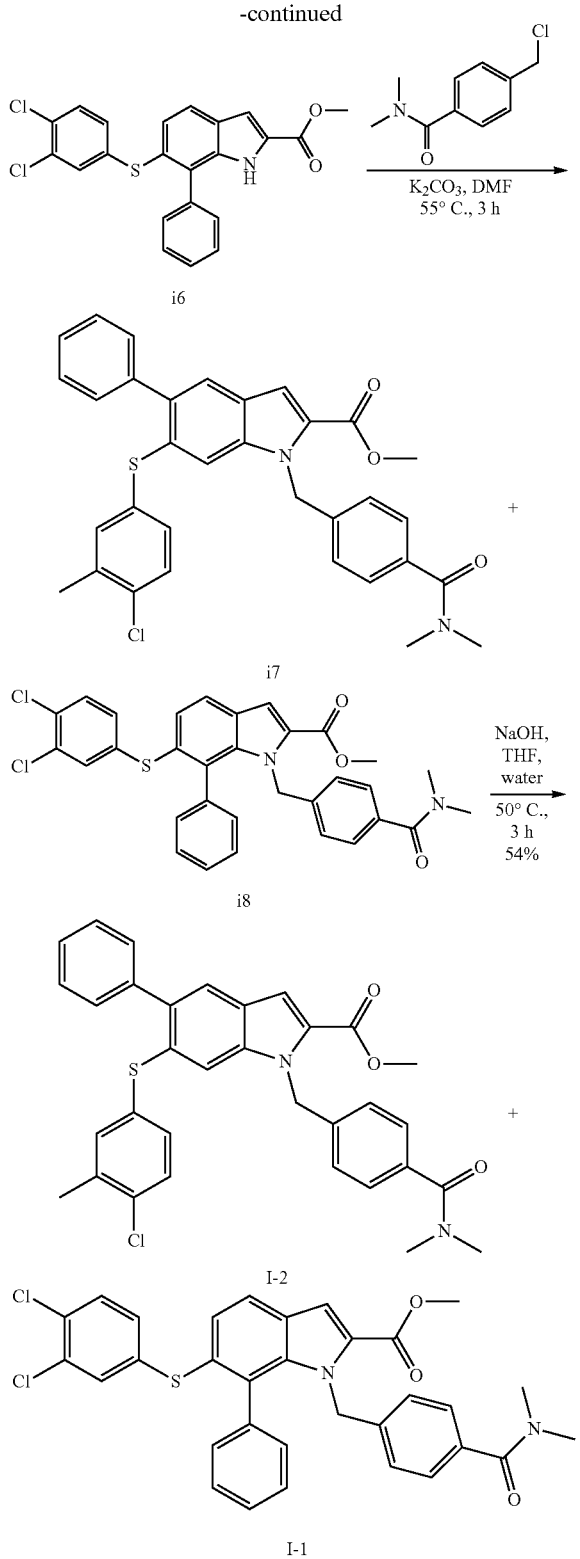

Procedures and Characterization:

Step 1: 6-fluorobiphenyl-3-carbaldehyde

A solution of 3-bromo-4-fluoro-benzaldehyde (3.00 g, 14.78 mmol), phenylboronic acid (3.60 g, 29.56 mmol), $K_2CO_3$ (4.08 g, 29.56 mmol) and PdTPh$_3$)$_4$ (3.42 g, 2.96 mmol) in a mixture of dioxane (30.00 mL) and water (10.00 mL) was stirred at 80° C. for 3 h under $N_2$ atmosphere. It was monitored by LC-MS. After completion, it was filtrated with diatomite, diluted with ethyl acetate, washed with brine, the organic layer was dried over magnesium sulfate, filtered and concentrated to yield the crude product. It was purified by SGC to yield 4-fluoro-3-phenyl-benzaldehyde (2.00 g, 9.99 mmol, 68%) as a yellow oil.

Step 2: 6-(3,4-dichlorophenylthio)biphenyl-3-carbaldehyde

A solution of 4-fluoro-3-phenyl-benzaldehyde (1.60 g, 7.99 mmol), 3,4-dichloro benzenethiol (1.50 g, 8.39 mmol) and $K_2CO_3$ (2.21 g, 15.98 mmol) in DMF (16.00 mL) was stirred at 50° C. for 20 h. It was monitored by LC-MS. After completed, it was diluted with ethyl acetate, washed with brine, the organic layer was dried over magnesium sulfate, filtrated, concentrated to yield the crude product. It was purified by SGC to yield 4-(3,4-dichlorophenyl) sulfanyl-3-phenyl-benzaldehyde (2.20 g, 6.12 mmol, 77%) as a red oil.

Step 3: (Z)-methyl 2-azido-3-(6-(3,4-dichlorophenylthio)biphenyl-3-yl)acrylate

The procedure of methyl (Z)-2-azido-3-[4-(3,4-dichlorophenyl)sulfanyl-3-phenyl-phenyl]prop-2-enoate was the same as a3 (2.29 g, 5.02 mmol, 52%) as a light yellow solid.

Step 4: (methyl 6-(3,4-dichlorophenylthio)-5-phenyl-1H-indole-2-carboxylate and methyl 6-(3,4-dichlorophenylthio)-7-phenyl-1H-indole-2-carboxylate The procedure of methyl 6-(3,4-dichlorophenyl)sulfanyl-5-phenyl-1H-indole-2-carboxylate (348.00 mg, 0.81 mmol, 31%) and methyl 6-(3,4-dichloro phenyl)sulfanyl-7-phenyl-1H-indole-2-carboxylate (397.00 mg, 0.93 mmol, 35%) as a light-yellow oil was the same as a4.

Step 5: methyl 6-(3,4-dichlorophenylthio)-1-(4-(dimethylcarbamoyl)benzyl)-5-phenyl-1H-indole-2-carboxylate and methyl 6-(3,4-dichlorophenylthio)-1-(4-(dimethylcarbamoyl)benzyl)-7-phenyl-1H-indole-2-carboxylate A solution of methyl 6-(3,4-dichlorophenyl)sulfanyl-7-phenyl-1H-indole-2-carboxylate (180.00 mg, 0.42 mmol), methyl 6-(3,4-dichlorophenyl)sulfanyl-5-phenyl-1H-indole-2-carboxylate (205.20 mg, 0.48 mmol), 4-(chloromethyl)-N,N-dimethylbenzamide (99.68 mg, 0.50 mmol) and $K_2CO_3$ (173.98 mg, 1.26 mmol) in DMF (8.00 mL) was stirred at 55° C. for 3 h. It was monitored by LC-MS. After completed, it was diluted with ethyl acetate, washed with brine, the organic layer was dried over magnesium sulfate, and filtered to afford the crude product. It was used directly in the next step. ESI-MS (EI+, m/z): 589 [M+H]$^+$.

Step 5: methyl 6-(4-chloro-3-methylphenylthio)-1-(4-(dimethylcarbamoyl)benzyl)-5-phenyl-1H-indole-2-carboxylate, I-2, and methyl 6-(3,4-dichloro phenylthio)-1-(4-(dimethylcarbamoyl)benzyl)-7-phenyl-1H-indole-2-carboxylate, I-1

The same procedure as prepared I-25 afforded methyl 6-(4-chloro-3-methylphenylthio)-1-(4-(dimethylcarbamoyl)

benzyl)-5-phenyl-1H-indole-2-carboxylate, I-2, (74.10 mg, 0.13 mmol, 54%) and methyl 6-(3,4-dichloro phenylthio)-1-(4-(dimethylcarbamoyl)benzyl)-7-phenyl-1H-indole-2-carboxylate I-1 (63.30 mg, 0.11 mmol, 46%) as white solids. ESI-MS (EI+, m/z): 575 [M+H]⁻. ¹H NMR (400 MHz, DMSO) δ 7.74 (d, J=7.3 Hz, 2H), 7.40 (d, J=9.0 Hz, 2H), 7.11 (s, 1H), 7.04 (d, J=6.2 Hz, 2H), 6.82 (d, J=8.6 Hz, 1H), 5.96 (s, 2H), 2.95 (s, 3H), 2.84 (s, 3H).

¹H NMR (400 MHz, DMSO) δ 7.80 (d, J=9.0 Hz, 1H), 7.45 (d, J=7.0 Hz, 1H), 7.35 (s, 1H), 7.33-7.24 (m, 2H), 7.22 (d, J=6.7 Hz, 2H), 7.10 (s, 5H), 6.89 (d, J=8.9 Hz, 2H), 6.24 (d, J=6.9 Hz, 2H), 2.93 (s, 3H), 2.85 (s, 3H).

Example 30: 6-chloro-4-(4-chlorophenylthio)-1-methyl-1H-indole-2-carboxylic acid, I-207

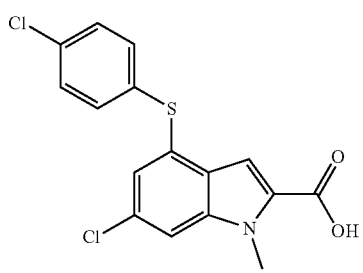

I-207

Synthetic Scheme:

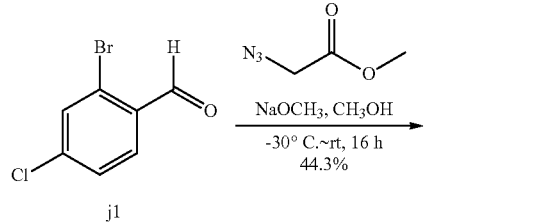

j1

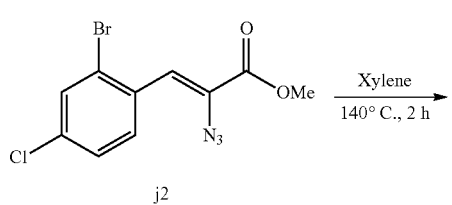

j2

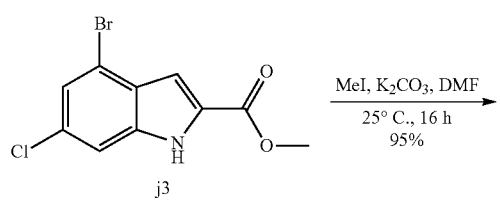

j3

-continued

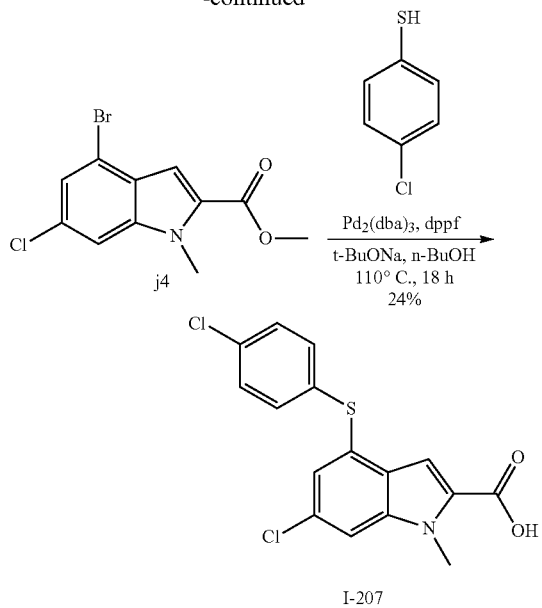

I-207

Procedures and Characterization:

Step 1: (Z)-Methyl 2-azido-3-(2-bromo-4-chlorophenyl)acrylate

The same procedure used to prepare b3 afforded (Z)-methyl 2-azido-3-(2-bromo-4-chlorophenyl)acrylate (4.3 g, 35.0%) as a yellow oil. MS (EI+, m/z): No mass.

Step 2: Methyl 4-bromo-6-chloro-1H-indole-2-carboxylate

The same procedure used to prepare a4 afforded methyl 4-bromo-6-chloro-1H-indole-2-carboxylate (2.3 g, 60.0%) as a yellow solid. MS (EI+, m/z): No mass.

Step 3: methyl 4-bromo-6-chloro-1-methyl-1H-indole-2-carboxylate

A mixture of methyl 4-bromo-6-chloro-1H-indole-2-carboxylate (100 mg, 0.35 mmol), MeI (100 mg, 0.7 mmol) and K₂CO₃ (121 mg, 0.88 mmol) in dry DMF (4 mL) was stirred for 16 h at rt. The reaction was quenched with water (10 mL) and extracted with ethyl acetate (20 mL). The organic phase was washed water (10 mL×2), and brine (10 mL), dried (Na₂SO₄), filtered and concentrated in vacuo and the residue was purified by chromatography (silica, ethyl acetate/petroleum ether=1/5) to afford methyl 4-bromo-6-chloro-1-methyl-1H-indole-2-carboxylate (100 mg, 0.33 mmol, 95%) as a white solid. ESI-MS (EI+, m/z): 302.0 [M+H]⁺.

Step 4: 6-chloro-4-(4-chlorophenylthio)-1-methyl-1H-indole-2-carboxylic acid, I-207

A mixture of methyl 4-bromo-6-chloro-1-methyl-1H-indole-2-carboxylate (20 mg, 0.066 mmol), 4-chlorobenzenethiol (19 mg, 0.13 mmol), dppf (4 mg, 0.0066 mmol), Pd₂(dba)₃ (3 mg, 0.04 mmol) and t-BuONa (19 mg, 0.2 mmol) in n-BuOH (2 mL) was stirred for 18 h at 110° C. under N₂ atmosphere. The reaction was quenched with water (10 mL) and extracted with ethyl acetate (20 mL). The organic phase was washed with water (10 mL×2), and brine (10 mL), dried (Na$_2$SO$_4$), filtered and concentrated in vacuo, the crude product was purified by prep-HPLC (0.01% TFA) to afford 6-chloro-4-(4-chlorophenylthio)-1-methyl-1H-indole-2-carboxylic acid I-207 (5.6 mg, 0.016 mmol, 24%) as a white solid. ESI-MS (EI+, m/z): 350.0 [M−H]$^-$. H NMR (500 MHz, DMSO) δ 7.39 (s, 1H), 7.18 (d, J=8.5 Hz, 2H), 7.13 (d, J=8.5 Hz, 2H), 6.94 (d, J=1 Hz, 1H), 6.89 (s, 1H), 3.94 (s, 3H).

Example 31: 4-bromo-1-(4-((2-hydroxyethyl)(methyl)carbamoyl)benzyl)-6-phenoxy-1H-indole-2-carboxylic acid, I-69

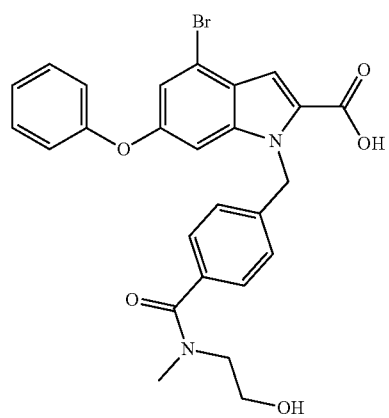

Synthetic Scheme:

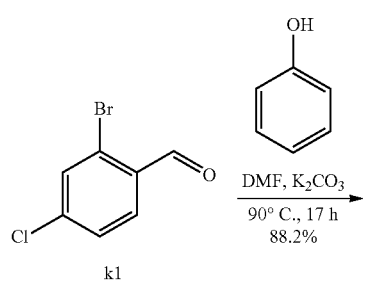

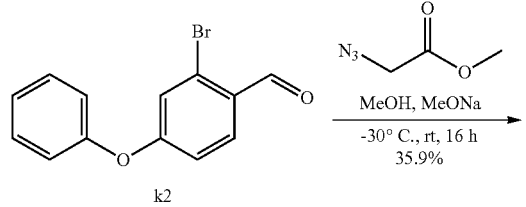

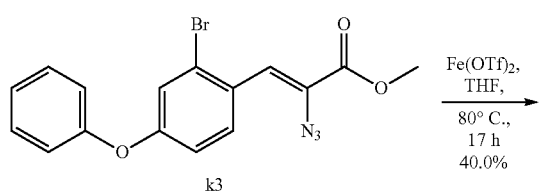

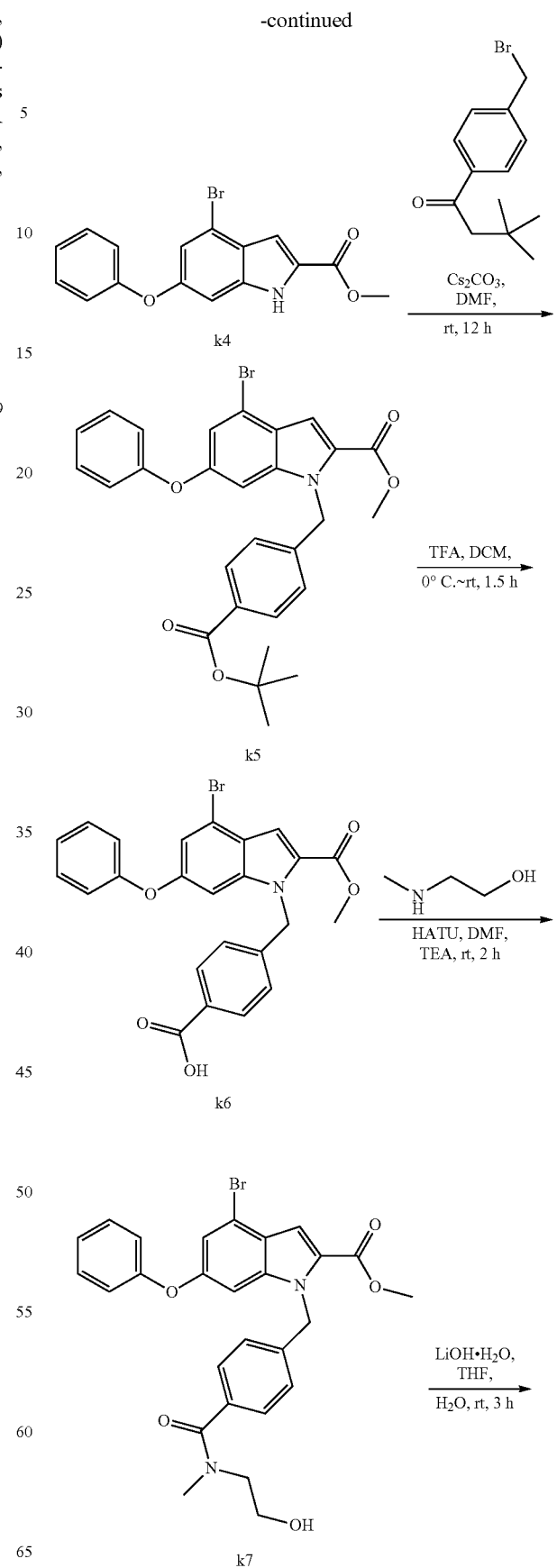

-continued

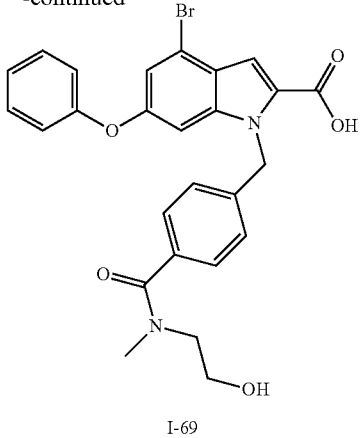

I-69

Procedures and Characterization:

Step 1: 2-bromo-4-phenoxybenzaldehyde

To a solution of 2-bromo-4-chlorobenzaldehyde (15 g, 68.5 mmol) in DMF (200 mL) under $N_2$ was added phenol (9.5 g, 82.2 mmol) and $K_2CO_3$ (28.4 g, 205.5 mmol). The mixture was stirred at 90° C. for 17 h. Concentrated and purified by chromatography (silica, DCM/petroleum ether=1/2) to afford k2 (6.1 g, 38.6%) as a white solid. ESI-MS (EI$^+$, m/z): 233.0 [M+H]$^+$.

Step 2: (Z)-methyl 2-azido-3-(2-bromo-4-phenoxyphenyl)acrylate

To a solution of k2 (6.1 g, 26.3 mmol) and MeONa (14.2 g, 263.0 mmol) in MeOH (80 m L), cooled to –30° C., was added methyl 2-azidoacetate (12.1 g, 105.2 mmol), this mixture was stirred at –30° C., then stirred at rt, for 16 h. The reaction was quenched with saturated $NH_4Cl$ solution, concentrated to remove MeOH, extracted with EtOAc, washed with brine, dried over sodium sulfate and concentrated to afford crude product, purified by column chromatography on silica gel with PE:DCM=4:1 to afford k3 (1.8 g, 20.9%) as a yellow oil. MS (EI+, m/z): No mass Step 3: methyl 4-bromo-6-phenoxy-1H-indole-2-carboxylate To the solution of k3 (1.8 g, 5.5 mmol) and Fe(OTf)$_2$ (584.1 mg, 1.65 mmol) in THF (20 mL). The mixture was stirred at 80° C. for 17 h. The reaction was quenched with ice-water, extracted with EtOAc, washed with brine, dried over sodium sulfate. Concentrated and purified by column chromatography on silica gel with PE:EtOAc=6:1 to afford k4 (640 mg, 40.0%) as a white solid. ESI-MS (EI$^+$, m/z): 302.0 [M+H]$^+$.

Step 4: methyl 4-bromo-1-(4-(tert-butoxycarbonyl)benzyl)-6-phenoxy-1H-indole-2-carboxylate A suspension of methyl 4-bromo-6-phenoxy-1H-indole-2-carboxylate (300 mg, 0.87 mmol), tert-butyl 4-(bromomethyl)benzoate (282 mg, 1.04 mmol) and $Cs_2CO_3$ (567 mg, 1.674 mmol) in DMF (8 ml) was stirred at room temperature for 12 h. The reaction mixture was extracted with EtOAc, washed with water and brine, dried, concentrated, purified by SGC (PE:EtOAc=40:1) to afford methyl 4-bromo-1-(4-(tert-butoxycarbonyl)benzyl)-6-phenoxy-1H-indole-2-carboxylate (350 mg, 75% yield) as a white solid. SI-MS (EI+, m/z): 536.2 [M+H]$^+$.

Step 5: 4-((4-bromo-2-(methoxycarbonyl)-6-phenoxy-1H-indol-1-yl)methyl)benzoic acid TFA (9 mL) was added to a solution of methyl 4-bromo-1-(4-(tert-butoxycarbonyl)benzyl)-6-phenoxy-1H-indole-2-carboxylate (720 mg, 01.35 mmol) in DCM (27 ml) at 0° C. and stirred at 0° C.~rt for 1.5 h. NaHCO$_3$ (aq.) was added to the reaction mixture to pH~6, extracted with EtOAc, washed with brine, dried, concentrated to afford 4-((4-bromo-2-(methoxycarbonyl)-6-phenoxy-1H-indol-1-yl)methyl)benzoic acid (700 mg, crude), used for next step.

ESI-MS (EI$^+$, m/z): 480.0 [M+H]$^+$.

Step 6: methyl 4-bromo-1-(4-((2-hydroxyethyl)(methyl)carbamoyl)benzyl)-6-phenoxy-1H-indole-2-carboxylate A solution of 4-((4-bromo-2-(methoxycarbonyl)-6-phenoxy-1H-indol-1-yl)methyl)benzoic acid (144 mg, 0.3 mmol), 2-(methylamino)ethanol (45 mg, 0.6 mmol), HATU (171 mg, 0.45 mmol) and TEA (91 mg, 0.9 mmol) in DMF (5 mL) was stirred at room temperature for 2 h. The reaction mixture was extracted with EtOAc, washed with brine, dried, concentrated to afford methyl 4-bromo-1-(4-((2-hydroxyethyl)(methyl)carbamoyl)benzyl)-6-phenoxy-1H-indole-2-carboxylate (180 mg, crude), used for next step. ESI-MS (EI, m/z): 537.0 [M+H]$^+$.

Step 7: 4-bromo-1-(4-((2-hydroxyethyl)(methyl)carbamoyl)benzyl)-6-phenoxy-1H-indole-2-carboxylic acid, I-69

LiOH.H$_2$O (121 mg, 0.9 mmol) was added to a solution of 4-bromo-1-(4-((2-hydroxyethyl)(methyl)carbamoyl)benzyl)-6-phenoxy-1H-indole-2-carboxylate (155 mg, 0.29 mmol) in THF (5 ml) and H$_2$O (5 ml) at room temperature and stirred for 3 h. 1 N HCl was added to the reaction mixture to pH~6, extracted with EtOAc, washed with brine, dried, concentrated, purified by prep-HPLC to afford 4-bromo-1-(4-((2-hydroxyethyl)(methyl) carbamoyl)benzyl)-6-phenoxy-1H-indole-2-carboxylic acid I-69 (50.4 mg, 33% yield).

ESI-MS (EI$^+$, m/z): 525.0 [M+H]$^+$.

$^1$H NMR (500 MHz, DMSO) δ 13.27-13.24 (m, 1H), 7.38-7.29 (m, 5H), 7.25 (s, 1H), 7.16-7.07 (m, 2H), 6.99 (t, J=9.25 Hz, 4H), 5.85 (s, 2H), 4.78 (s, 1H), 3.58 (s, 1H), 3.45 (s, 2H), 3.21 (s, 1H), 2.88 (s, 3H).

Example 32: 4-bromo-1-(4-(2-hydroxy-2-methyl-propylcarbamoyl)benzyl)-6-phenoxy-1H-indole-2-carboxylic acid, I-55

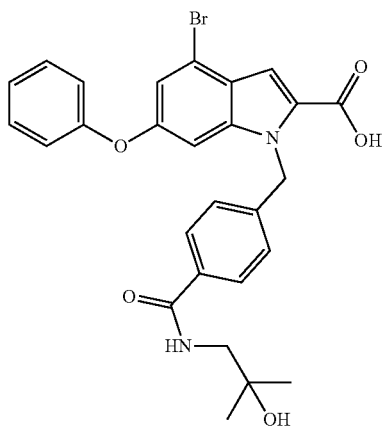

I-55

Synthetic Scheme:

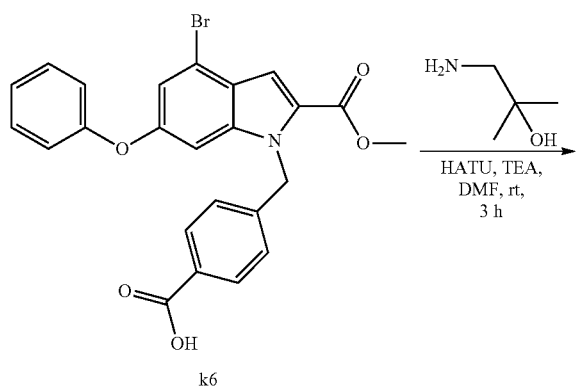

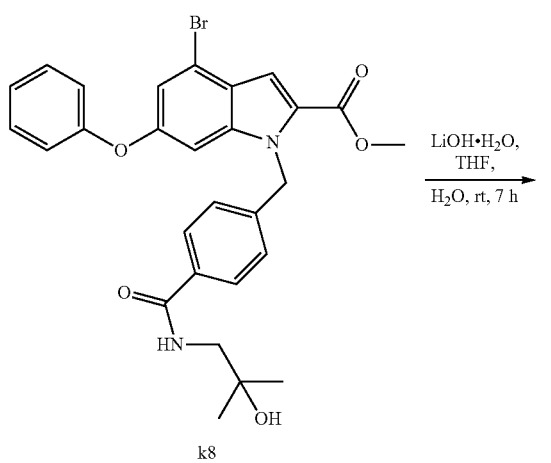

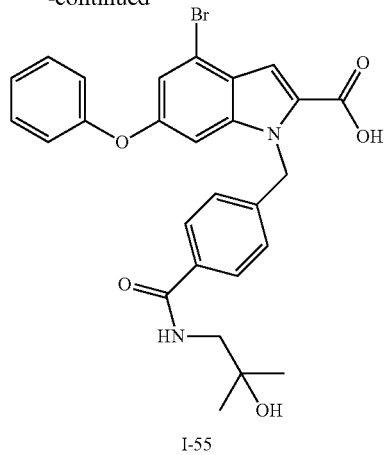

I-55

Procedures and Characterization:

Step 1: methyl 4-bromo-1-(4-(2-hydroxy-2-methylpropylcarbamoyl)benzyl)-6-phenoxy-1H-indole-2-carboxylate The same procedure used to prepare a7 afforded methyl 4-bromo-1-(4-(2-hydroxy-2-methylpropylcarbamoyl)benzyl)-6-phenoxy-1H-indole-2-carboxylate (200 mg, crude), used for next step. ESI-MS (EI$^+$, m/z): 551.0 [M+H]$^-$.

Step 2: 4-bromo-1-(4-(2-hydroxy-2-methylpropylcarbamoyl)benzyl)-6-phenoxy-1H-indole-2-carboxylic acid, I-55

The same procedure used to prepare I-102 afforded 4-bromo-1-(4-(2-hydroxy-2-methylpropylcarbamoyl)benzyl)-6-phenoxy-1H-indole-2-carboxylic acid I-55 (12.6 mg, 7% yield).

ESI-MS (EI$^+$, m/z): 537.0 [M+H]$^+$.

$^1$H NMR (500 MHz, DMSO) δ 13.27 (s, 1H), 8.17 (t, J=7.5 Hz, 1H), 7.74 (d, J=5.0 Hz, 2H), 7.37 (t, J=10.0 Hz, 2H), 7.31 (s, 1H), 7.21 (s, 1H), 7.14 (t, J=9.25 Hz, 1H), 7.10 (d, J=2.0 Hz, 1H), 7.05 (d, J=5.25 Hz, 2H), 6.98 (d, J=5.0 Hz, 2H), 5.88 (s, 2H), 4.51 (s, 1H), 3.30 (s, 1H), 3.22 (d, J=3.5 Hz, 2H), 1.07 (s, 6H).

Example 33: 1-(4-(bis(2-hydroxyethyl)carbamoyl)benzyl)-4-bromo-6-phenoxy-1H-indole-2-carboxylic acid, I-67

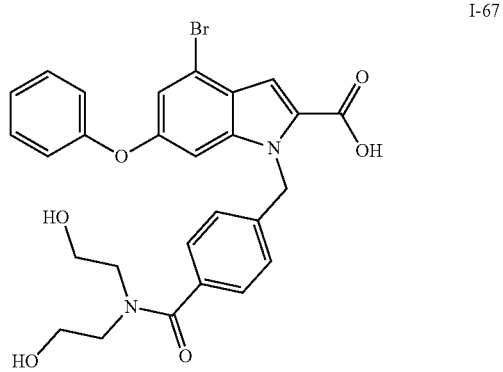 [SMILES: O=C(O)c1cc2c(Br)cc(Oc3ccccc3)cc2n1Cc1ccc(C(=O)N(CCO)CCO)cc1]

I-67

Synthetic Scheme:

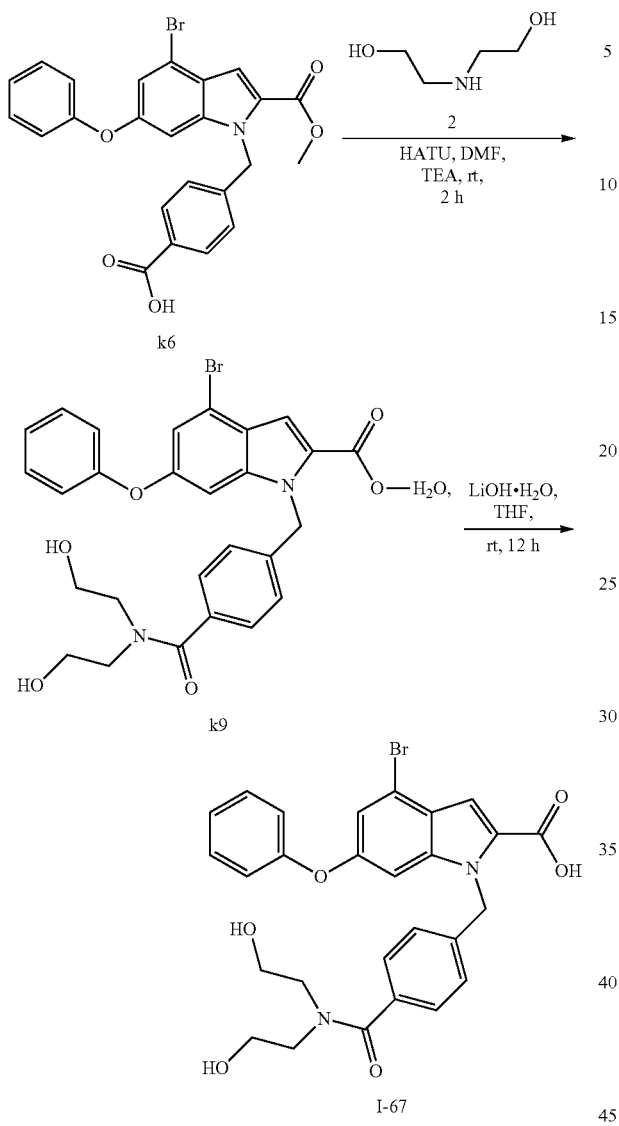

Procedures and Characterization:

Step 1: methyl 1-(4-(bis(2-hydroxyethyl)carbamoyl)benzyl)-4-bromo-6-phenoxy-1H-indole-2-carboxylate The same procedure used to prepare a7 afforded methyl 1-(4-(bis(2-hydroxyethyl)carbamoyl)benzyl)-4-bromo-6-phenoxy-1H-indole-2-carboxylate (190 mg, crude), which was used in the next step.
ESI-MS (EI⁺, m/z): 567.1 [M+H]⁺.

Step 2: 1-(4-(bis(2-hydroxyethyl)carbamoyl)benzyl)-4-bromo-6-phenoxy-1H-indole-2-carboxylic acid, I-67

The same procedure used to prepare I-102 afforded 1-(4-(bis(2-hydroxyethyl)carbamoyl)benzyl)-4-bromo-6-phenoxy-1H-indole-2-carboxylic acid I-67 (23.9 mg, 13% yield). ESI-MS (EI⁺, m/z): 553.2 [M+H]⁺.
$^1$H NMR (500 MHz, DMSO) δ 13.20 (s, 1H), 7.40-7.38 (m, 2H), 7.31 (d, J=6.5 Hz, 2H), 7.28 (s, 1H), 7.20 (s, 1H), 7.14 (t, J=9.25 Hz, 1H), 7.10 (d, J=2.5 Hz, 1H), 7.03-6.97 (m, 4H), 5.85 (s, 2H), 4.77 (s, 2H), 3.57 (s, 2H), 3.48 (s, 2H), 3.42 (d, J=2.0 Hz, 2H), 3.27 (d, J=9.5 Hz, 2H).

Example 34: 4-bromo-6-phenoxy-1-(4-(pyridin-3-ylcarbamoyl)benzyl)-1H-indole-2-carboxylic acid, I-56

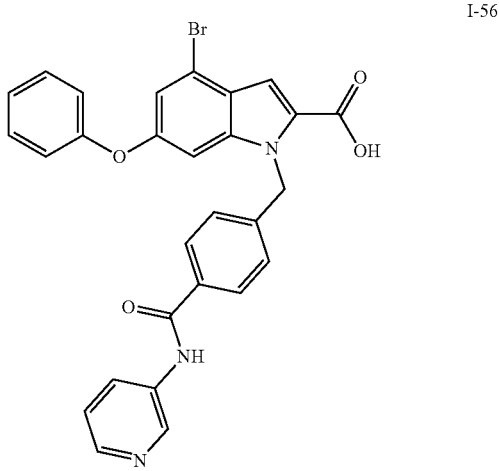 [SMILES: O=C(Nc1cccnc1)c1ccc(Cn2c(C(=O)O)cc3c(Br)cc(Oc4ccccc4)cc32)cc1]

Synthetic Scheme:

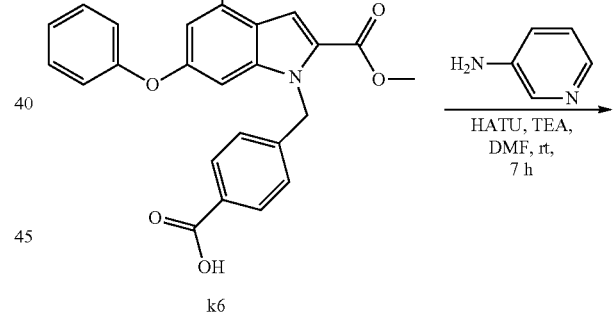

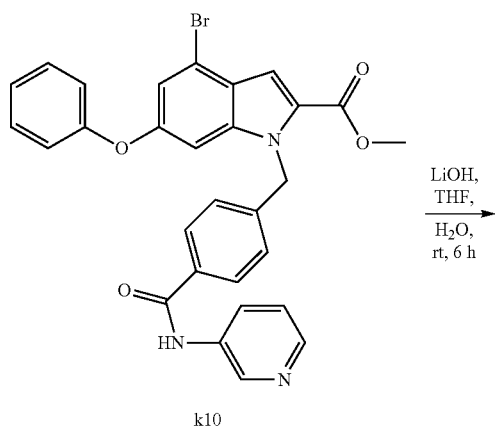

-continued

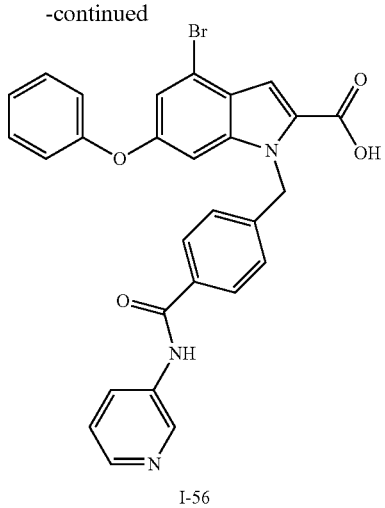

I-56

Synthetic Scheme:

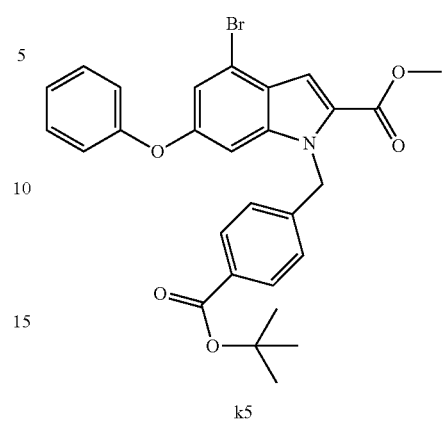

k5

LiOH·H₂O,
THF/Water
50° C., 2 h
95%

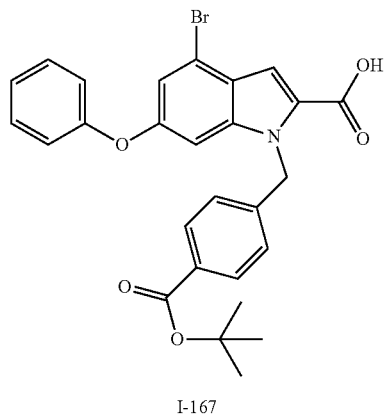

I-167

Step 1: methyl 4-bromo-6-phenoxy-1-(4-(pyridin-3-ylcarbamoyl)benzyl)-1H-indole-2-carboxylate The same procedure used to prepare a7 afforded methyl 4-bromo-6-phenoxy-1-(4-(pyridin-3-ylcarbamoyl)benzyl)-1H-indole-2-carboxylate (200 mg, crude), used in the next step. ESI-MS (EI⁺, m/z): 556.0 [M+H]⁺.

Step 2: 4-bromo-6-phenoxy-1-(4-(pyridin-3-ylcarbamoyl)benzyl)-1H-indole-2-carboxylic acid, I-56

The same procedure used to prepare I-102 afforded 4-bromo-6-phenoxy-1-(4-(pyridin-3-ylcarbamoyl)benzyl)-1H-indole-2-carboxylic acid I-56 (27 mg, 16% yield).
ESI-MS (EI⁺, m/z): 542.0 [M+H]⁺.
$^1$H NMR (500 MHz, DMSO) δ13.29 (s, 1H), 10.39 (s, 1H), 8.89 (s, 1H), 8.30 (d, J=5.5 Hz, 1H), 8.15 (d, J=5.25 Hz, 1H), 7.85 (d, J=5.0 Hz, 2H), 7.40-7.35 (m, 4H), 7.22 (s, 1H), 7.16-7.11 (m, 4H), 7.00 (d, J=4.75 Hz, 2H), 5.92 (s, 2H).

Example 35: 4-bromo-1-(4-(tert-butoxycarbonyl)benzyl)-6-phenoxy-1H-indole-2-carboxylic acid, I-167

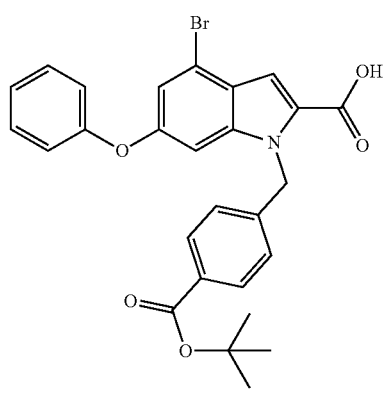

I-167

Procedures and Characterization:

Step 1: 4-bromo-1-(4-(tert-butoxycarbonyl)benzyl)-6-phenoxy-1H-indole-2-carboxylic acid, I-167

To a solution of methyl 4-bromo-1-(4-(tert-butoxycarbonyl)benzyl)-6-phenoxy-1H-indole-2-carboxylate (100 mg, 0.187 mmol) in a mixture of THF (2.00 mL) and water (2.00 mL) was added lithium hydroxide monohydrate (31 mg, 0.748 mmol) and stirred for 2 h at 50° C. The mixture was adjusted to pH 4-5 and extracted with ethyl acetate. The organic phase was washed with water (100 mL×2), and brine (100 mL), dried (Na₂SO₄), filtered and concentrated in vacuo, the crude product was purified by prep-HPLC to afford 4-bromo-1-(4-(tert-butoxy carbonyl)benzyl)-6-phenoxy-1H-indole-2-carboxylic acid I-167 as a white solid (20.6 mg, 0.04 mmol, 21%). ESI-MS (EI+, m/z): 522 [M+H]⁺. $^1$H NMR (500 MHz, CDCl₃) δ 7.90 (d, 2H, J=8.5 Hz), 7.55 (s, 1H), 7.34-7.37 (t, 2H, J=8 Hz), 7.14-7.16 (m, 2H), 7.04 (d, 2H, J=8 Hz), 6.99 (d, 2H, J=8 Hz), 6.84 (s, 1H), 5.77 (s, 2H), 1.58 (s, 9H).

Example 36: 4-bromo-1-(4-carboxybenzyl)-6-phenoxy-1H-indole-2-carboxylic acid, I-165

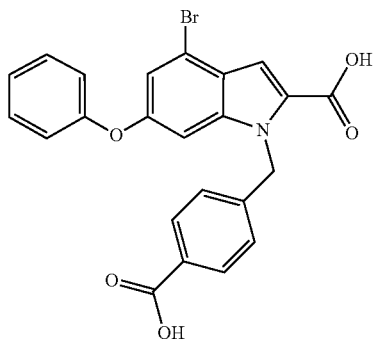

I-165

Synthetic Scheme:

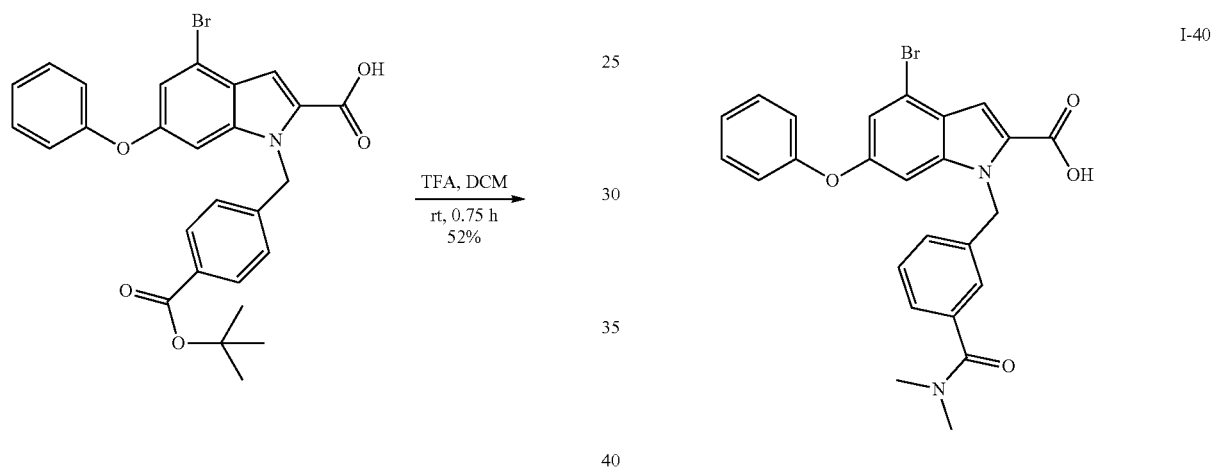

Procedures and Characterization:

Step 1: 4-bromo-1-(4-carboxybenzyl)-6-phenoxy-1H-indole-2-carboxylic acid, I-165

To a solution of 4-bromo-1-(4-(tert-butoxycarbonyl)benzyl)-6-phenoxy-1H-indole-2-carboxylic acid (160 mg, 0.31 mmol) in DCM (6 mL) was added TFA (3 mL) under 0° C. and stirred at rt for 0.75 h. The solution was diluted with water (50 mL) and extracted with DCM (100 mL). The organic phase was washed with water (25 mL×2), and brine (50 mL), dried (Na$_2$SO$_4$), filtered and concentrated in vacuo, the crude product was purified by prep-HPLC to afford 4-bromo-1-(4-carboxybenzyl)-6-phenoxy-1H-indole-2-carboxylic acid I-165 as a white solid (73.7 mg, 0.16 mml, 52%). ESI-MS (EI+, m/z): 466 [M+H]$^+$. $^1$H NMR (500 MHz, DMSO) δ 13.04 (br s, 2H), 7.85 (d, 2H, J=8.5 Hz), 7.35-7.38 (t, 2H, J=8 Hz), 7.30 (s, 1H), 7.22 (s, 1H), 7.13-7.16 (t, 2H, J=7.5 Hz), 7.10 (s, 1H), 7.08 (d, 1H, J=8 Hz), 6.98 (d, 1H, J=8 Hz), 5.90 (s, 2H).

Example 37: 4-bromo-1-(3-(dimethylcarbamoyl)benzyl)-6-phenoxy-1H-indole-2-carboxylic acid, I-40

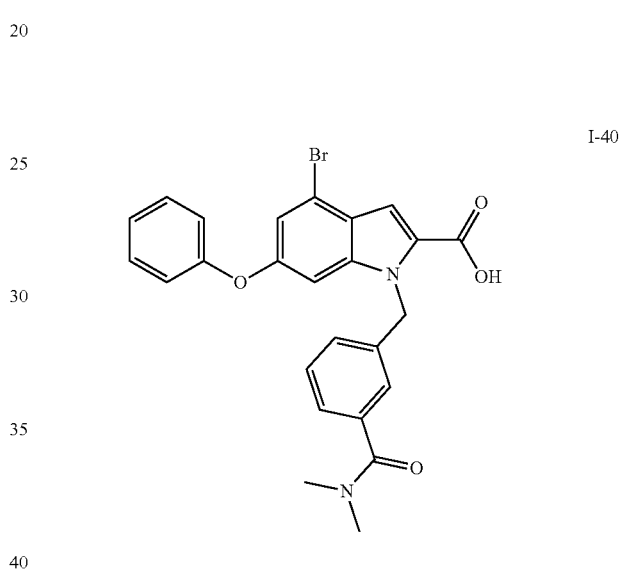

I-40

Synthetic Scheme:

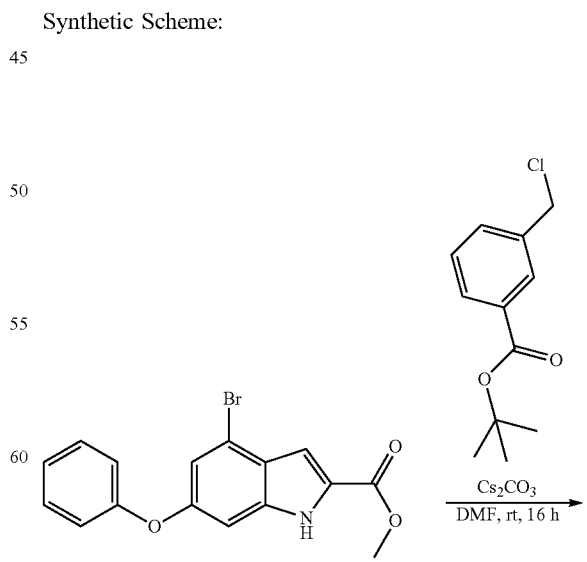

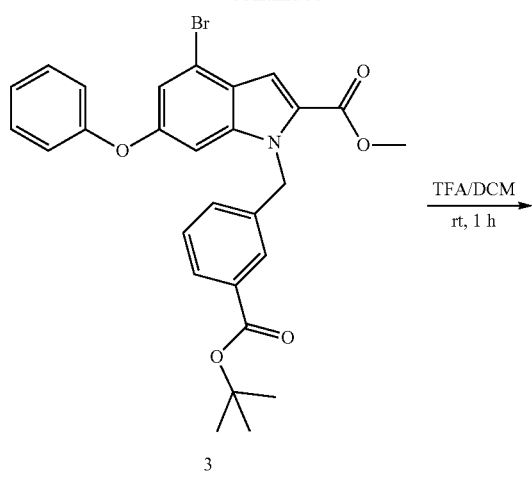
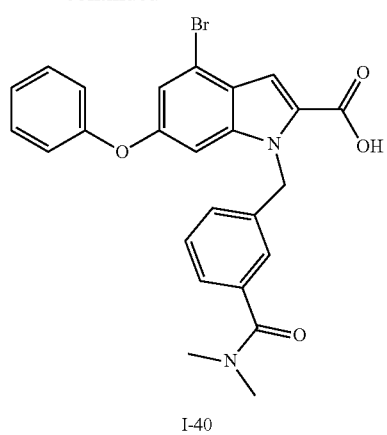
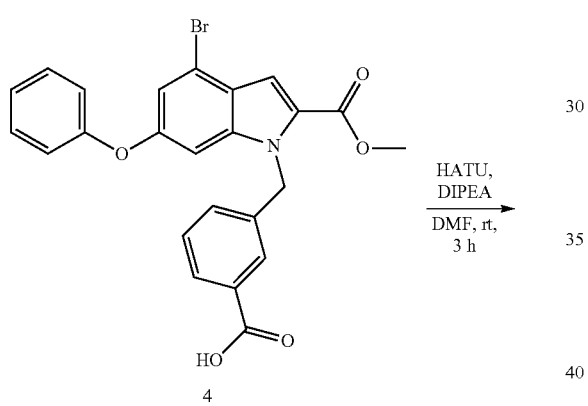
Procedures and Characterization:
The same procedure used to prepare I-65 afforded 4-bromo-1-(3-(dimethylcarbamoyl)benzyl)-6-phenoxy-1H-indole-2-carboxylic acid I-40. ESI-MS (EI⁺, m/z): 493. ¹H NMR (400 MHz, DMSO-d₆) δ 13.25 (br s, 1H), 7.34 (m, 4H), 7.24 (d, J=3.6 Hz, 1H), 7.08 (m, 5H), 6.96 (d, J=2.0 Hz, 1H), 7.35 (d, d, J=8.0 Hz, 2H), 5.89 (s, 2H), 2.93 (s, 3H), 2.77 (s, 3H).
Example 38: 1-(4-carboxybenzyl)-6-chloro-4-(3,4-dichlorophenoxy)-1H-indole-2-carboxylic acid, I-140
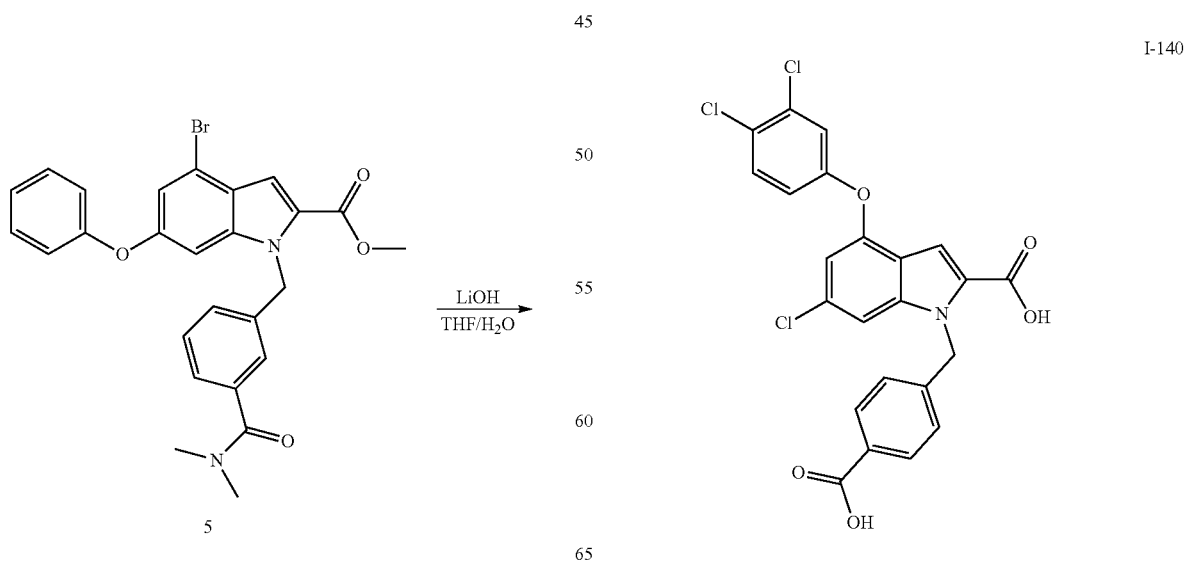

Synthetic Scheme:

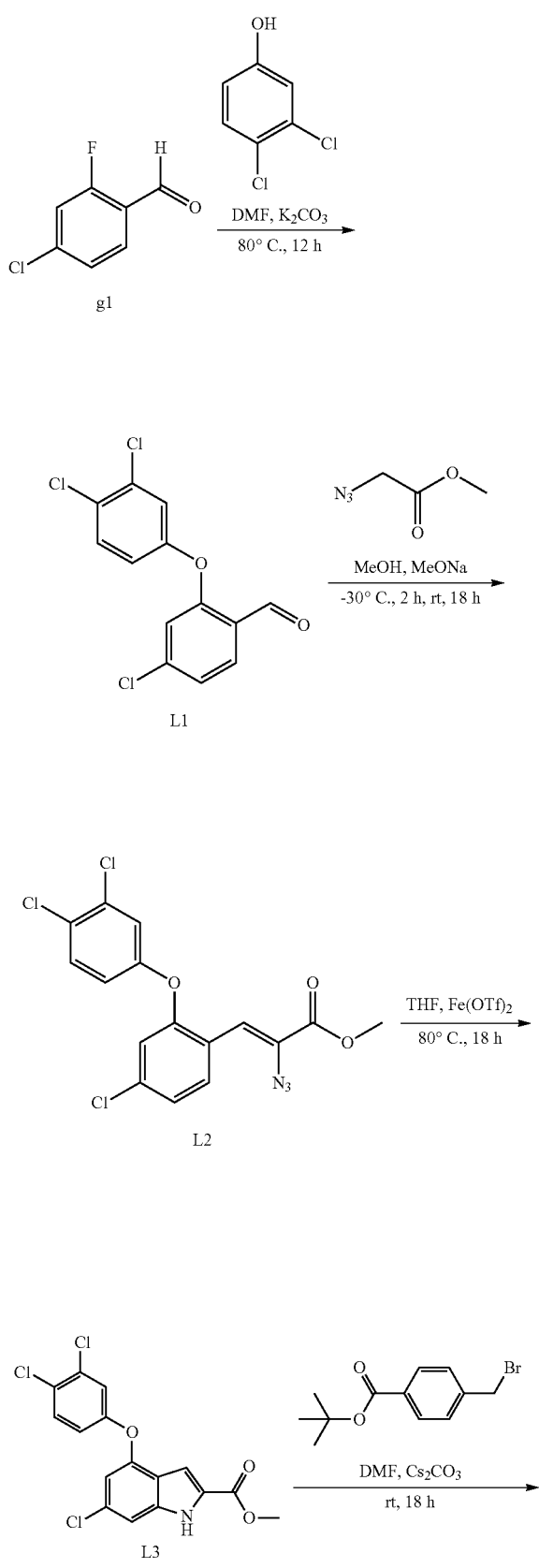

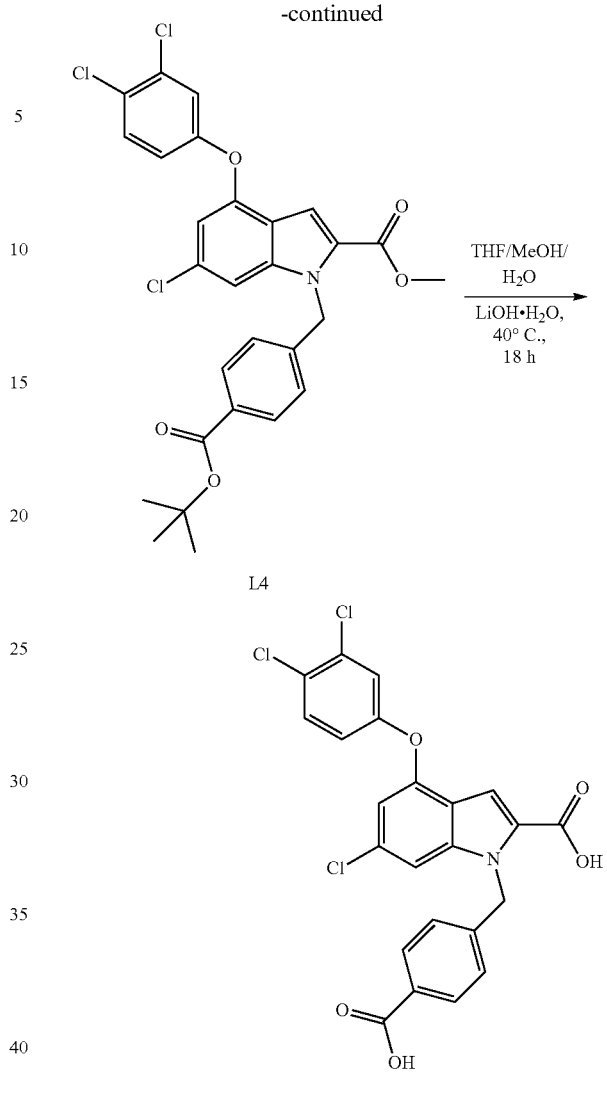

Procedures and Characterization:

Step 1:
4-chloro-2-(3,4-dichlorophenoxy)benzaldehyde

To a solution of 4-chloro-2-fluorobenzaldehyde (5.0 g, 31.53 mmol) and 3,4-dichlorophenol (5.65 g, 34.69 mmol) in DMF (50 mL), was added $K_2CO_3$ (5.67 g, 40.99 mmol), this mixture was stirred at 80° C. for 18 h. Then reaction solution was cooled to rt and extracted with EtOAc, washed with brine and concentrated to afford the crude product. Purification by column chromatography on silica gel with PE:EtOAc=1:0 afforded 4-chloro-2-(3,4-dichlorophenoxy)benzaldehyde (3.94 g, 13.06 mmol, purity: 100%, yield: 42.06%) as a yellow solid. ESI-MS (EI+, m/z): 303.0 $[M+H]^+$.

Step 2 (Z)-methyl 2-azido-3-(4-chloro-2-(3,4-dichlorophenoxy)phenyl)acrylate

The same procedure used to prepare k3 afforded (Z)-methyl 2-azido-3-(4-chloro-2-(3,4-dichlorophenoxy)phenyl)acrylate (2.48 g, 6.25 mmol, purity: 95.0%, yield: 45.45%) as a yellow solid. No MS.

Step 3: methyl 6-chloro-4-(3,4-dichlorophenoxy)-1H-indole-2-carboxylate

The same procedure used to prepare k4 afforded methyl 6-chloro-4-(3,4-dichlorophenoxy)-1H-indole-2-carboxylate as a yellow solid (1.132 g, yield: 49.0%). ESI-MS (EI+, m/z): 392.3[M+Na]+.

Step 4: methyl 1-(4-(tert-butoxycarbonyl)benzyl)-6-chloro-4-(3,4-dichlorophenoxy)-1H-indole-2-carboxylate The same procedure used to prepare a5 afforded methyl 1-(4-(tert-butoxycarbonyl)benzyl)-6-chloro-4-(3,4-dichlorophenoxy)-1H-indole-2-carboxylate (1.17 g, purity: 100%, yield: 82.8%). ESI-MS (EI+, m/z): 584.0 [M+Na]+.

Step 5: 1-(4-carboxybenzyl)-6-chloro-4-(3,4-dichlorophenoxy)-1H-indole-2-carboxylic acid, I-140

To a solution of methyl 1-(4-(tert-butoxycarbonyl)benzyl)-6-chloro-4-(3,4-dichlorophenoxy)-1H-indole-2-carboxylate (1.17 g, 2.08 mmol) in THF/MeOH/H$_2$O (1:1:1, 18 mL), was added LiOH.H$_2$O (0.699 g, 16.7 mmol), this mixture was stirred at 40° C. for 18 h. The reaction was quenched with ice-water, adjust to pH 5 with 1N HCl solution, extracted with EtOAc, dried and concentrated to afford 1-(4-carboxybenzyl)-6-chloro-4-(3,4-dichlorophenoxy)-1H-indole-2-carboxylic acid I-140 (800 mg, purity: 100%, yield: 78%). ESI-MS (EI+, m/z): 492.9 [M+H]+.

$^1$H NMR (500 MHz, DMSO) δ 7.90-7.83 (m, 3H), 7.56 (s, 1H), 7.48 (dd, J=8.7, 2.5 Hz, 1H), 7.29 (d, J=8.8 Hz, 1H), 7.17 (s, 1H), 7.12 (d, J=8.2 Hz, 2H), 6.51 (d, J=1.3 Hz, 1H), 5.96 (s, 2H).

Example 39: 1-(Carboxymethyl)-6-chloro-4-(2,5-dichlorophenoxy)-1H-indole-2-carboxylic acid, I-162

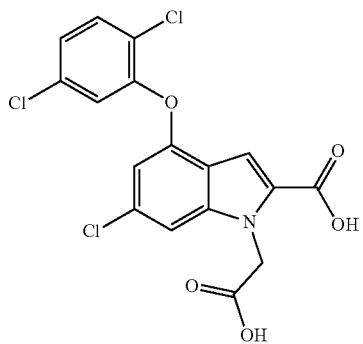

I-162

Synthetic Scheme:

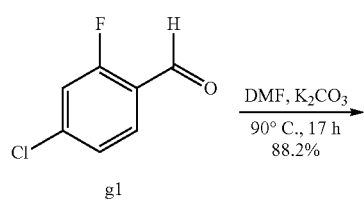

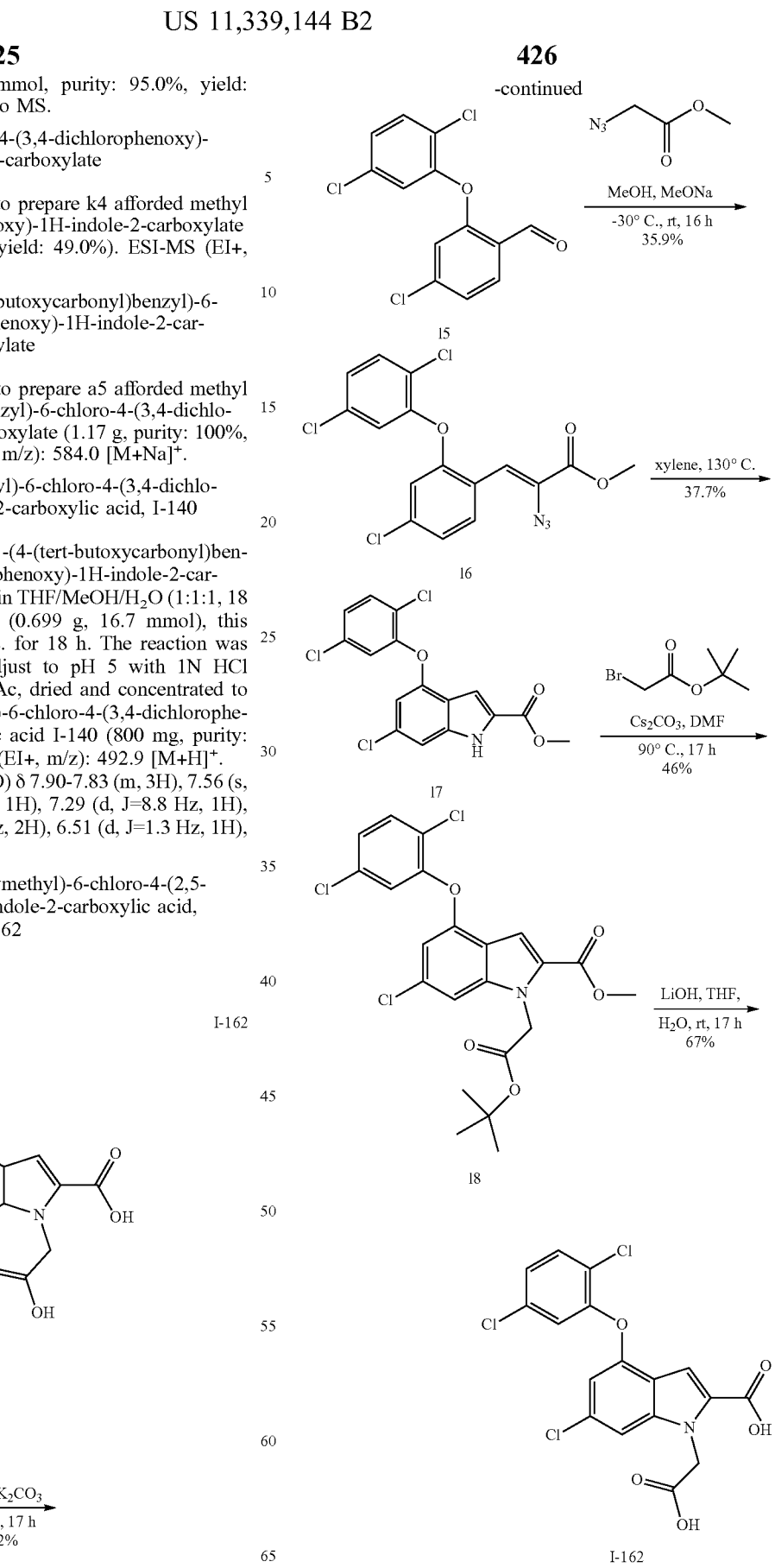

Procedures and Characterization:

Step 1: 4-Chloro-2-(2,5-dichlorophenoxy)benzaldehyde

The same procedure used to prepare II afforded 4-chloro-2-(2,5-dichlorophenoxy)benzaldehyde (30 g, 88.2%) as a yellow solid. ESI-MS (EI$^+$, m/z): 303.0 [M+H]$^+$.

Step 2: (Z)-Methyl 2-azido-3-(4-chloro-2-(2,5-dichlorophenoxy)phenyl)acrylate The same procedure used to prepare k3 afforded (Z)-methyl 2-azido-3-(4-chloro-2-(2,5-dichlorophenoxy)phenyl)acrylate (14 g, 35.9%) as a yellow solid. MS (EI+, m/z): No mass Step 3: Methyl 6-chloro-4-(2,5-dichlorophenoxy)-1H-indole-2-carboxylate:

The same procedure used to prepare a4 is afford methyl 6-chloro-4-(2,5-dichlorophenoxy)-1H-indole-2-carboxylate (4.9 g, 37.7%) as a white solid. MS (EI+, m/z): No mass

Step 4: Methyl 1-(2-tert-butoxy-2-oxoethyl)-6-chloro-4-(2,5-dichlorophenoxy)-1H-indole-2-carboxylate To a solution of methyl 6-chloro-4-(2,5-dichlorophenoxy)-1H-indole-2-carboxylate (2 g, 5.4 mmol), tert-butyl 2-bromoacetate (1.3 g, 6.48 mmol), Cs$_2$CO$_3$ (5.3 g, 16.2 mmol) in DMF (30 mL) under N$_2$. The mixture was stirred at 90° C. for 17 h. The reaction was quenched with ice-water, extracted with EtOAc, washed with brine, dried over sodium sulfate, and concentrated. Purification by chromatography (silica, DCM/petroleum ether=1/1) afforded methyl 1-(2-tert-butoxy-2-oxoethyl)-6-chloro-4-(2,5-dichlorophenoxy)-1H-indole-2-carboxylate (1.2 g, 46%) as a white solid. ESI-MS (EI+, m/z): No mass

Step 5: 1-(Carboxymethyl)-6-chloro-4-(2,5-dichlorophenoxy)-1H-indole-2-carboxylic acid, I-162

The same procedure used to prepare I-102 afforded 1-(carboxymethyl)-6-chloro-4-(2,5-dichlorophenoxy)-1H-indole-2-carboxylic acid I-162 (230 mg, 67%) as a white solid. MS (EI+, m/z): 413.9 [M–H]$^+$. $^1$H NMR (500 MHz, DMSO) δ 13.17 (s, 2H), 7.77-7.62 (m, 2H), 7.45-7.22 (m, 2H), 7.04 (s, 1H), 6.55 (d, J=1.3 Hz, 1H), 5.31 (s, 2H).

Example 40: 1-((1H-imidazol-4-yl)methyl)-4-chloro-6-phenoxy-1H-indole-2-carboxylic acid, I-173

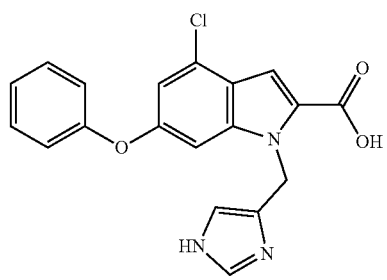

I-173

Synthetic Scheme:

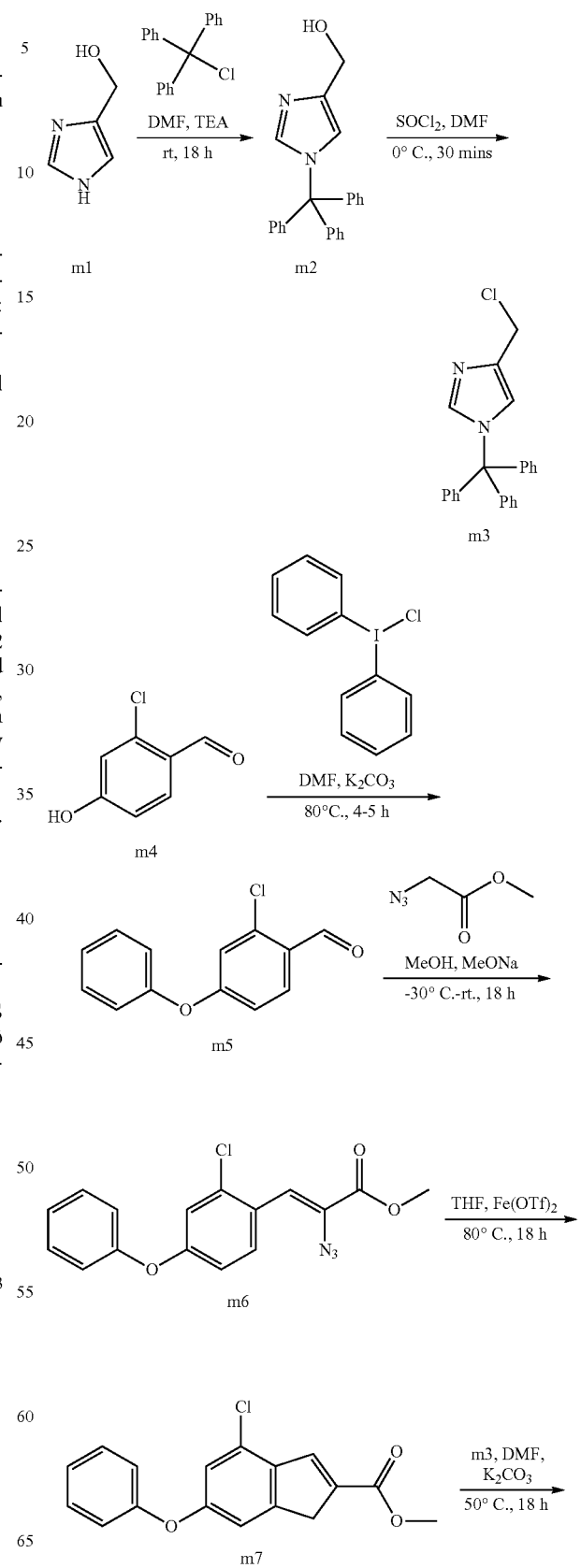

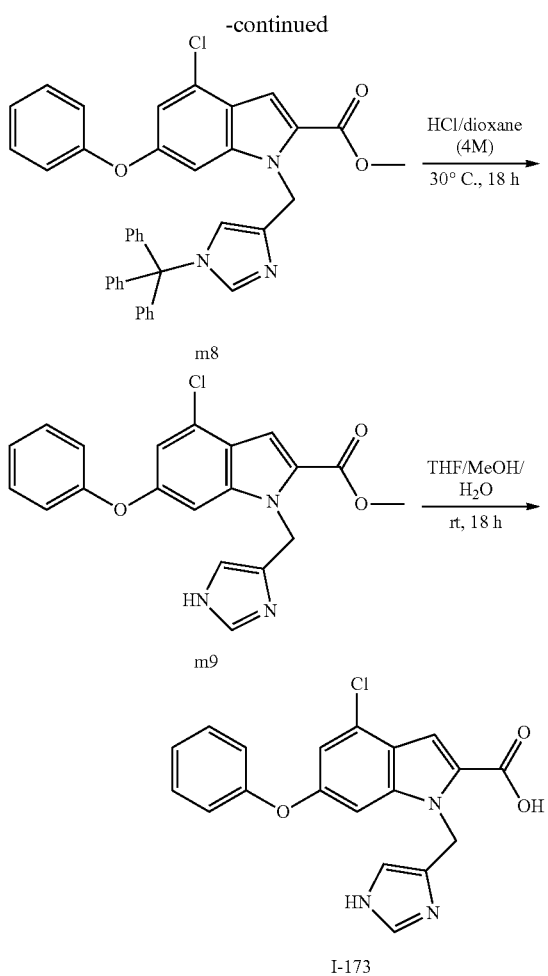

Procedures and Characterization:

Step 1: -(1-trityl-1H-imidazol-4-yl)methanol

To a solution of (1H-imidazol-4-yl)methanol (2.0 g, 20.39 mmol) in DMF (30 mL), was added and TrtCl (8.52 g, 30.58 mmol) and TEA (4.13 g, 40.77 mmol), this mixture was stirred at rt for 18 h. The reaction solution was quenched with ice-water, filtered and triturated with PE to afford a white solid (5.5 g, purity: 70%, yield: 55.4%). ESI-MS (EI+, m/z): no MS was detected.

Step 2: 4-(chloromethyl)-1-trityl-1H-imidazole

A solution of (1-trityl-1H-imidazol-4-yl)methanol (1.50 g, 4.41 mmol) in DCM (15 mL) was cooled to 0° C. before adding $SOCl_2$ (786.34 mg, 6.61 mmol). DMF (483.12 mg, 6.61 mmol) was added and the reaction mixture was stirred at rt for 30 mins. The mixture was quenched with saturated $NaHCO_3$ solution, extracted with EtOAc, washed with brine, dried over sodium sulfate, and concentrated to afford the crude product as a yellow solid (1.5 g) which was used directly in the next step. No MS was detected.

Step 3: 2-chloro-4-phenoxybenzaldehyde

To a solution of 2-chloro-4-hydroxybenzaldehyde (8.0 g, 51.10 mmol) and compound 2 (17.79 g, 56.21 mmol) in DMF (100 mL), was added $K_2CO_3$ (21.19 g, 153.29 mmol) and the reaction mixture was stirred at 80° C. for 12 h. Then reaction solution was cooled to rt and extracted with EtOAc, washed with brine and concentrated to afford the crude product. Purification by chromatography (silica, ethyl acetate/petroleum ether=1/5) afforded 2-chloro-4-phenoxybenzaldehyde (6 g, 25.8 mmol, purity: 85%, yield: 72.8%) as a yellow oil. ESI-MS (EI+, m/z): 233.1 $[M+H]^+$.

Step 4: (Z)-methyl 2-azido-3-(2-chloro-4-phenoxyphenyl)acrylate

To a solution of MeONa (2.44 g, 45.13 mmol) was added 2-chloro-4-phenoxybenzaldehyde (3.0 g, 12.89 mmol) in MeOH (40 mL), cooled to −30° C., added methyl 2-azidoacetate (5.19 g, 45.13 mmol). The mixture was stirred at −30° C. for 3 h, then stirred at rt for 18 h. The resulting solution was quenched with ice-water, concentrated to remove MeOH, extracted with EtOAc (30 mL*2), the organic phase was combined and washed with brine and dried over sodium sulfate, and concentrated to afford the crude product. Purified by chromatography (silica, ethyl acetate/petroleum ether=1/30) to afford (Z)-methyl 2-azido-3-(2-chloro-4-phenoxyphenyl)acrylate (1.39 g, 4.2 mmol, purity: 70%, yield: 22.9%) as a yellow solid. No MS, Step 5: methyl 4-chloro-6-phenoxy-1H-indole-2-carboxylate To a solution of (Z)-methyl 2-azido-3-(2-chloro-4-phenoxyphenyl)acrylate (500 mg, 1.52 mmol) in THE (5 mL), was added $Fe(OTf)_2$ (536.76 mg, 1.52 mmol), this mixture was stirred at 80° C. for 18 h. The resulting solution was extracted with EtOAc (5 mL*2), the organic phase was combined and washed with brine, dried over sodium sulfate, and concentrated to afford crude product. Purified by column chromatography on silica gel (PE:EtOAc=5:1) to afford a yellow solid (600 mg, purity: 89%, yield: 84.76%). ESI-MS (EI+, m/z): 302.1$[M+H]^+$.

Step 6: methyl 4-chloro-6-phenoxy-1-((1-trityl-1H-imidazol-4-yl)methyl)-1H-indole-2-carboxylate To a solution of methyl 4-chloro-6-phenoxy-1H-indole-2-carboxylate (350 mg, 1.16 mmol) and 4-(chloromethyl)-1-trityl-1H-imidazole (541.17 mg, 1.51 mmol) in DMF (5 mL), was added $Cs_2CO_3$ (568.68 mg, 1.74 mmol), and stirred at rt, for 18 h. extracted with EtOAc, washed with brine, dried over sodium sulfate, concentrated to afford crude product, and purified by column chromatography on silica gel with PE:EtOAc=3:1 to afford a white solid (600 mg, yield: 82.9%). No ms was detected.

Step 7: methyl 1-((1H-imidazol-4-yl)methyl)-4-chloro-6-phenoxy-1H-indole-2-carboxylate A solution of methyl 4-chloro-6-phenoxy-1-((1-trityl-1H-imidazol-4-yl)methyl)-1H-indole-2-carboxylate (678 mg, 1.69 mmol) in HCl/dioxane (5 mL, 4 mol/L) was stirred at 30° C. for 18 h.

Concentrated to afford the HCl salt (400 mg). ESI-MS (EI+, m/z): 382.1 $[M+H]^+$.

Step 8: 1-((1H-imidazol-4-yl)methyl)-4-chloro-6-phenoxy-1H-indole-2-carboxylic acid, I-173

To a solution of methyl 1-((1H-imidazol-4-yl)methyl)-4-chloro-6-phenoxy-1H-indole-2-carboxylate (100 mg, 0.262 mmol) in THF/MeOH/H$_2$O (2/2/2 mL), was added LiOH.H$_2$O (32.97 mg, 0.785 mmol), and stirred at rt for 18 h. The reaction was adjusted to pH=4-5 with 5% citric acid solution, extracted with EtOAc, dried over sodium sulfate, and concentrated to afford crude product. Purification by prep-HPLC afforded 1-((1H-imidazol-4-yl)methyl)-4-chloro-6-phenoxy-1H-indole-2-carboxylic acid I-173 (42.6 mg, yield: 44.2%). ESI-MS (EI+, m/z): 368.1 [M+H]$^+$.

$^1$H NMR (500 MHz, DMSO) δ 13.87 (s, 1H), 7.46 (d, J=0.9 Hz, 1H), 7.40 (dd, J=8.5, 7.5 Hz, 2H), 7.29-7.24 (m, 2H), 7.16 (t, J=7.4 Hz, 1H), 7.02 (dd, J=8.6, 0.9 Hz, 2H), 6.98 (d, J=1.8 Hz, 1H), 5.84 (s, 2H).

Example 41: 6-chloro-4-(2,4-dichlorophenylthio)-1H-indole-2-carboxylic acid, I-157

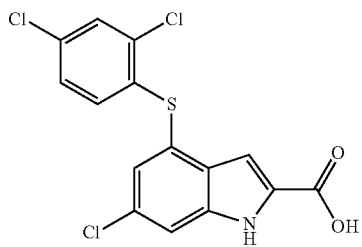

I-157

Synthetic Scheme:

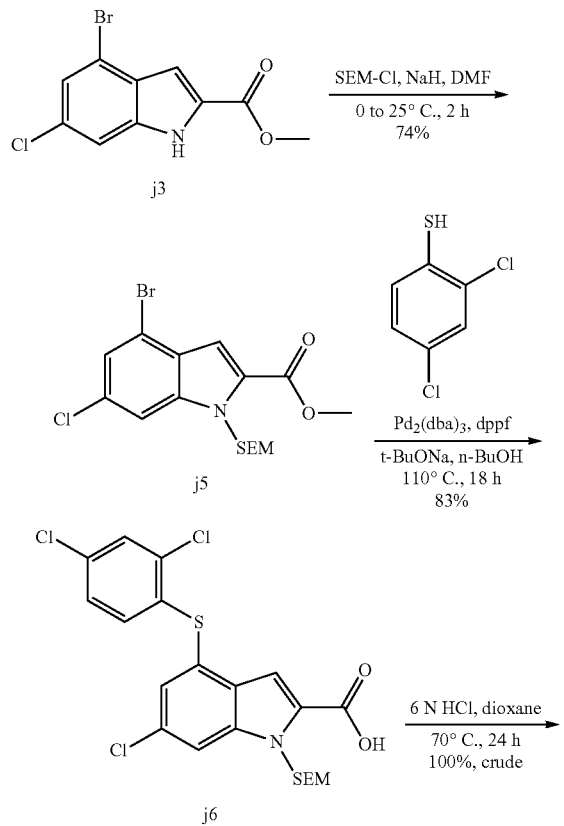

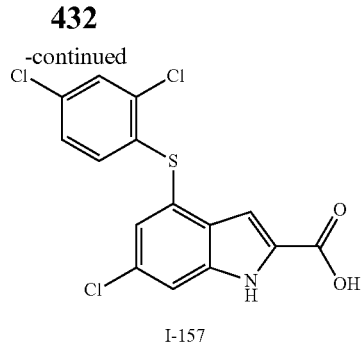

I-157

Procedures and Characterization:

Step 1: methyl 4-bromo-6-chloro-1-((2-(trimethylsilyl)ethoxy)methyl)-1H-indole-2-carboxylate To a solution of methyl 4-bromo-6-chloro-1H-indole-2-carboxylate (550 mg, 1.92 mmol) in dry DMF (10 mL) was added 60% NaH in mineral oil (100 mg, 2.5 mmol) at 0° C. and stirred at 0° C. for 30 min under a N2 atmosphere. SEM-Cl (418 mg, 2.5 mmol) was added to the mixture and stirred for 2 h at rt. The reaction was quenched with aq NH$_4$Cl (20 mL) and extracted with ethyl acetate (30 mL). The organic phase was washed with water (10 mL×2), and brine (10 mL), dried (Na$_2$SO$_4$), filtered and concentrated in vacuo, the crude product was purified by chromatography (silica, ethyl acetate/petroleum ether=1/5) to afford methyl 4-bromo-6-chloro-1-((2-(trimethylsilyl)ethoxy)methyl)-1H-indole-2-carboxylate (600 mg, 1.44 mmol, 74%) as a light yellow solid. ESI-MS (EI+, m/z): 440.02 [M+Na]$^+$ Step 2: 6-chloro-4-(2,4-dichlorophenylthio)-1-((2-(trimethylsilyl)ethoxy)methyl)-1H-indole-2-carboxylic acid A mixture of methyl 4-bromo-6-chloro-1-((2-(trimethylsilyl)ethoxy)methyl)-1H-indole-2-carboxylate (2 g, 4.8 mmol), 2,4-dichlorobenzenethiol (2.15 g, 12 mmol), dppf (266 mg, 0.48 mmol), Pd$_2$(dba)$_3$ (440 mg, 0.48 mmol) and t-BuONa (1.38 g, 14.4 mmol) in n-BuOH (50 mL) was stirred for 18 h at 110° C. under N$_2$ atmosphere. The reaction was quenched with water (50 mL) and extracted with ethyl acetate (100 mL). The organic phase was washed with water (30 mL×2), and brine (20 mL), dried (Na$_2$SO$_4$), filtered and concentrated in vacuo, the crude product was purified by chromatography (silica, ethyl acetate/petroleum ether=1/1) to afford 6-chloro-4-(2,4-dichlorophenylthio)-1-((2-(trimethylsilyl)ethoxy)methyl)-1H-indole-2-carboxylic acid (2 g, 4 mmol, 83%) as a brown solid. ESI-MS (EI+, m/z): 499.9 [M–H]$^-$.

Step 3: 6-chloro-4-(2,4-dichlorophenylthio)-1H-indole-2-carboxylic acid, I-157

A mixture of 6-chloro-4-(2,4-dichlorophenylthio)-1-((2-(trimethylsilyl)ethoxy)methyl)-1H-indole-2-carboxylic acid (1.4 g, 2.8 mmol) in aq 6 N HCl (60 mL) and dioxane (120 mL) was stirred for 24 h at 70° C. The reaction was diluted with water (100 mL), neutralized with Na$_2$CO$_3$ to pH 5 and extracted with ethyl acetate (200 mL). The organic phase was washed with water (50 mL×2), and brine (50 mL), dried (Na$_2$SO$_4$), filtered and concentrated in vacuo to afford crude 6-chloro-4-(2,4-dichlorophenylthio)-1H-indole-2-carboxylic acid I-157 (1.04 g, 2.8 mmol, 100%) as a brown solid. ESI-MS (EI+, m/z): 371.8 [M–H]$^-$. $^1$H NMR (500 MHz, DMSO) δ 13.40 (s, 1H), 12.30 (s, 1H), 7.76 (d, J=2 Hz, 1H), 7.55 (s, 1H), 7.30 (dd, J=8.5 Hz, J=2 Hz, 1H), 7.24 (d, J=1.5 Hz, 1H), 6.87 (d, J=8.5 Hz, 1H), 6.83 (d, J=2 Hz, 1H).

Example 42: 6-chloro-4-(4-chlorophenylthio)-1H-indole-2-carboxylic acid, I-190

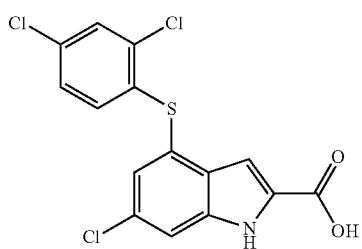

Synthetic Scheme:

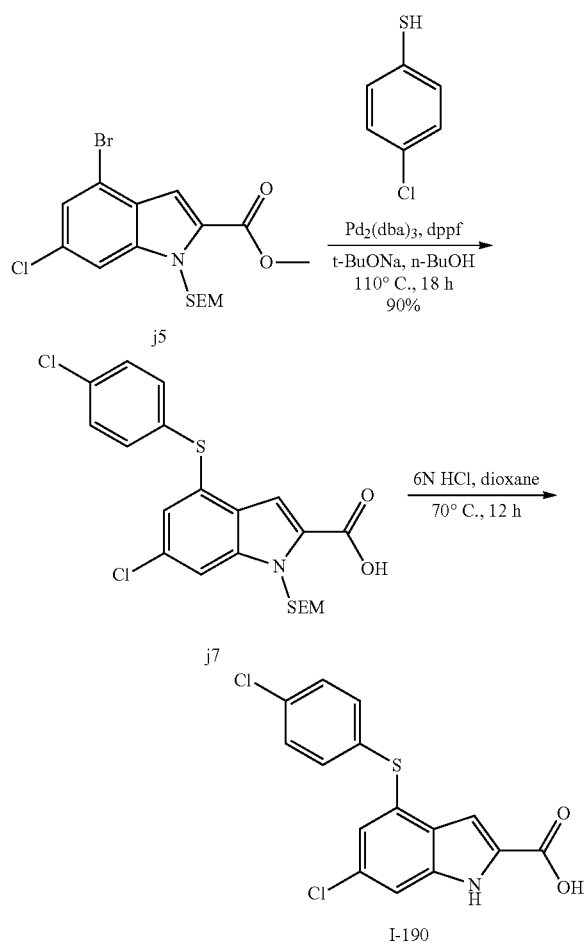

Procedures and Characterization:

The same procedure used to prepare I-157 afforded 6-chloro-4-(4-chlorophenylthio)-1H-indole-2-carboxylic acid I-190 (yield 70%) as a light brown solid. ESI-MS (EI+, m/z): 336.0 [M−H]⁻. ¹H NMR (500 MHz, DMSO) δ 13.28 (s, 1H), 12.23 (s, 1H), 7.46 (dd, J=2 Hz, J=1 Hz, 1H), 7.44-7.42 (m, 2H), 7.35-7.32 (m, 2H), 7.06 (d, J=1 Hz, 1H), 6.87 (d, J=2.5 Hz, J=1 Hz, 1H).

Example 43: 4-(3-tert-butylphenylthio)-6-chloro-1H-indole-2-carboxylic acid, I-65

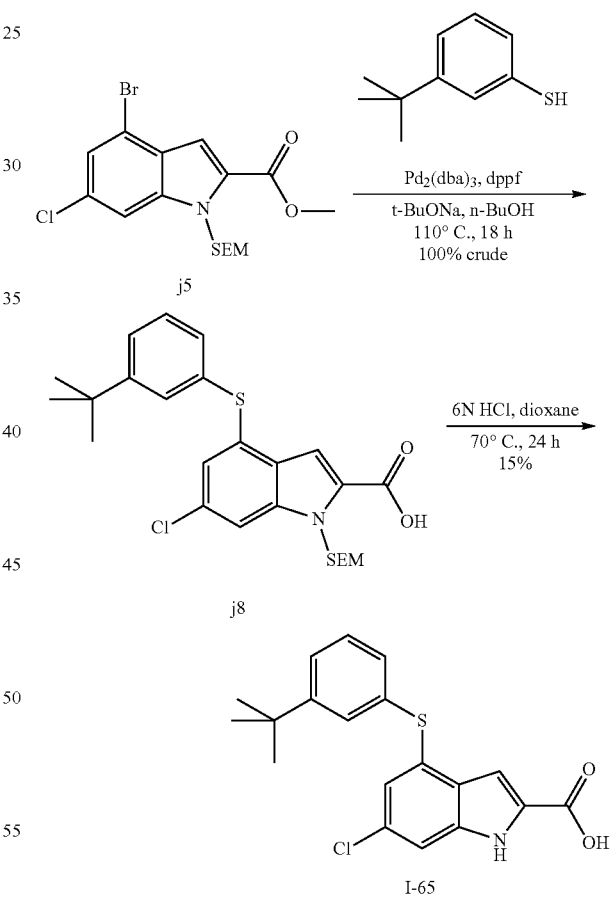

Synthetic Scheme:

Procedures and Characterization:

The same procedure used to prepare I-157 afforded 4-(3-tert-butylphenylthio)-6-chloro-1H-indole-2-carboxylic acid I-65 (15%) as a brown solid. ESI-MS (EI+, m/z): 358.0 [M−H]⁻. ¹H NMR (500 MHz, MeOD) δ 7.44 (s, 1H), 7.37 (s, 2H), 7.29 (t, J=9.5 Hz, 1H), 7.17 (d, J=9.5 Hz, 1H), 7.03 (s, 1H), 6.85 (s, 1H).

Example 44: 6-chloro-4-(quinolin-8-ylthio)-1H-indole-2-carboxylic acid, I-87

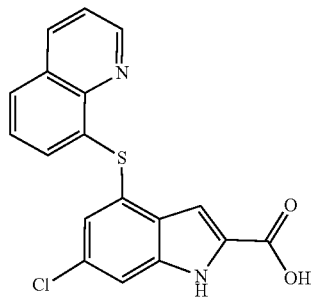

Synthetic Scheme:

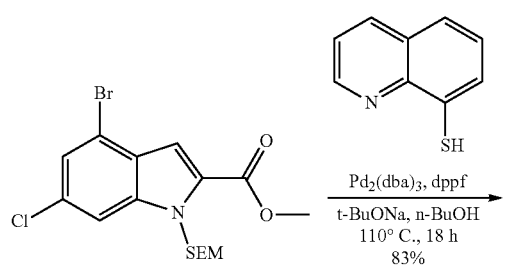

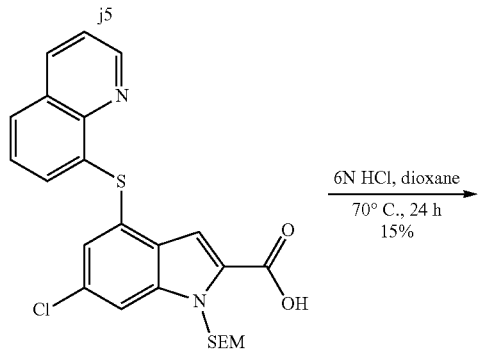

Procedures and Characterization:

The same procedure used to prepare I-157 afforded 6-chloro-4-(quinolin-8-ylthio)-1H-indole-2-carboxylic acid I-87 (yield 13%) as a white solid. ESI-MS (EI+, m/z): 355.0 [M+H]$^+$. $^1$H NMR (500 MHz, MeOD) δ 8.91 (dd, J=4 Hz, J=1.5 Hz, 1H), 8.34 (dd, J=8.5 Hz, J=2 Hz, 1H), 7.68 (dd, J=8 Hz, J=1 Hz, 1H), 7.61-7.58 (m, 2H), 7.30 (dd, J=8.5 Hz, J=7 Hz, 2H), 6.95 (dd, J=7.5 Hz, J=1 Hz, 1H), 6.89 (s, 1H).

Example 45: 6-chloro-4-(4-(4-chlorophenoxy)phenylthio)-1H-indole-2-carboxylic acid, I-84

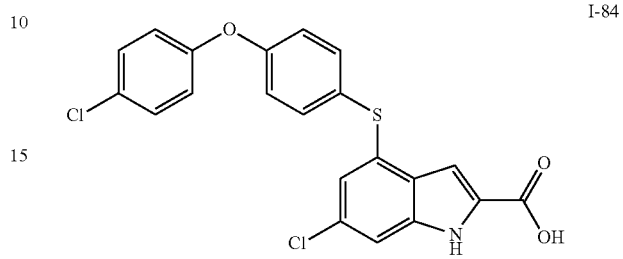

Synthetic Scheme:

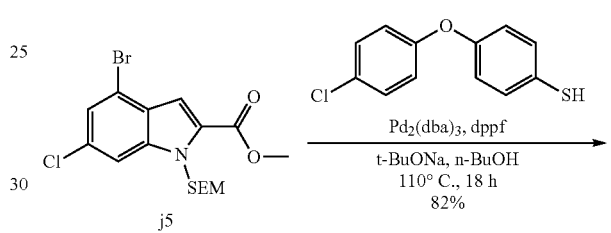

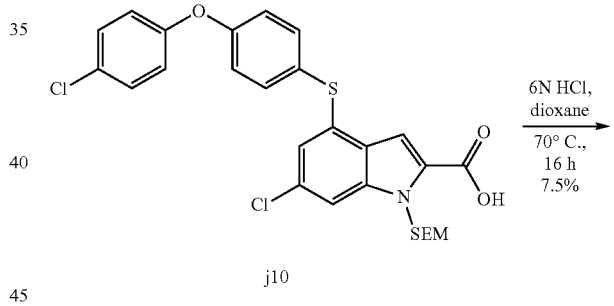

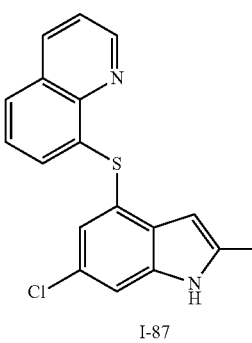

Procedures and Characterization:

The same procedure used to prepare I-157 afforded 6-chloro-4-(4-(4-chlorophenoxy)phenylthio)-1H-indole-2-carboxylic acid I-84 (yield 6.5%) as a white solid. ESI-MS (EI+, m/z): 427.9 [M−H]$^−$. $^1$H NMR (500 MHz, MeOD) δ 7.41 (s, 1H), 7.38 (d, J=4 Hz, 2H), 7.36 (s, 2H), 7.02 (d, J=9 Hz, 2H), 6.97 (t, J=8.5 Hz, 3H), 6.87 (d, J=1 Hz, 1H).

Example 46: 6-chloro-4-(4-(trifluoromethoxy)phenylthio)-1H-indole-2-carboxylic acid, I-129

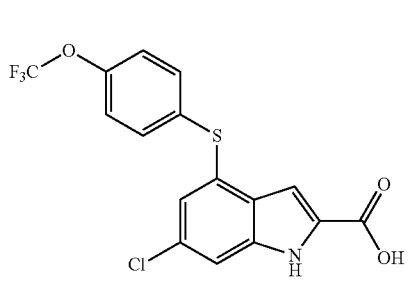

Synthetic Scheme:

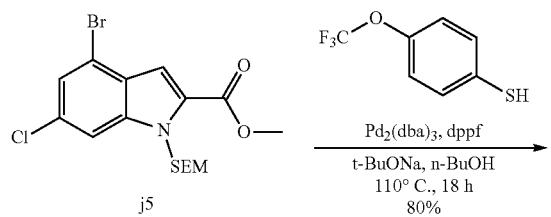

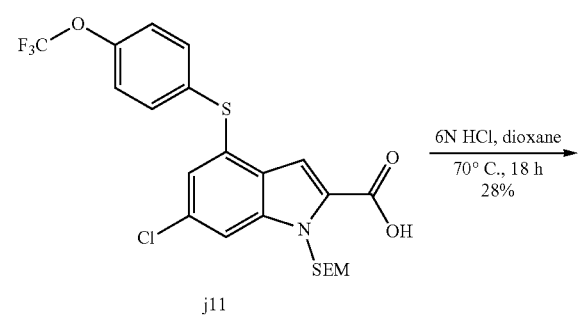

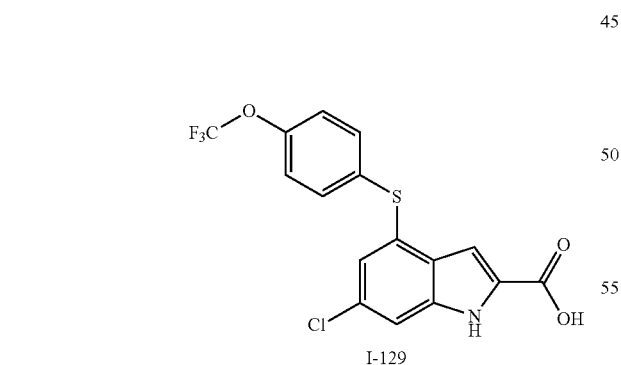

Procedures and Characterization:

The same procedure used to prepare I-157 afforded 6-chloro-4-(4-(trifluoromethoxy)phenylthio)-1H-indole-2-carboxylic acid I-129 (yield 28%) as a white solid. ESI-MS (EI+, m/z): 386.1 [M−H]⁻. ¹H NMR (500 MHz, DMSO) δ 13.28 (s, 1H), 12.24 (s, 1H), 7.48 (s, 1H), 7.41 (dd, J=7 Hz, J=5 Hz, 2H), 7.36 (d, J=8 Hz, 2H), 7.11 (d, J=2 Hz, 1H), 6.89 (d, J=1.5 Hz, 1H).

Example 47: 4-(4-tert-butylphenylthio)-6-chloro-1H-indole-2-carboxylic acid, I-130

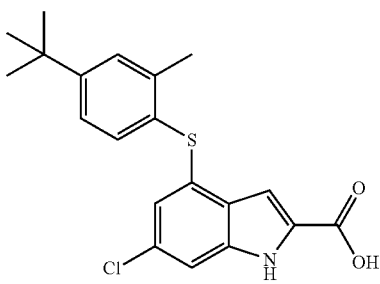

Synthetic Scheme:

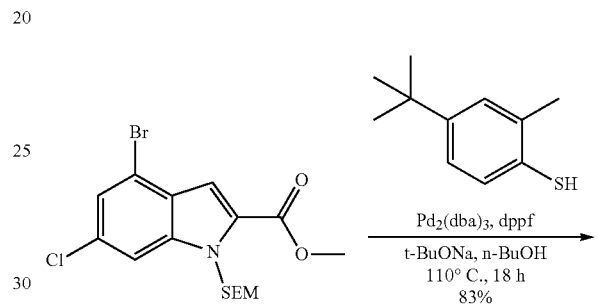

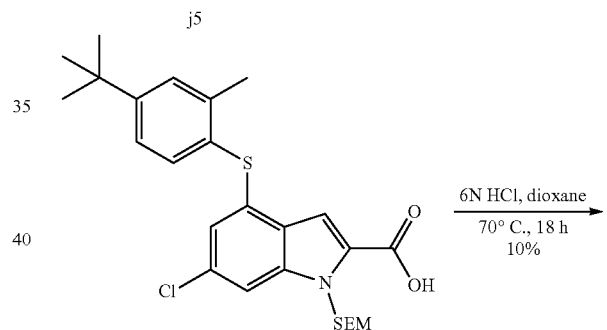

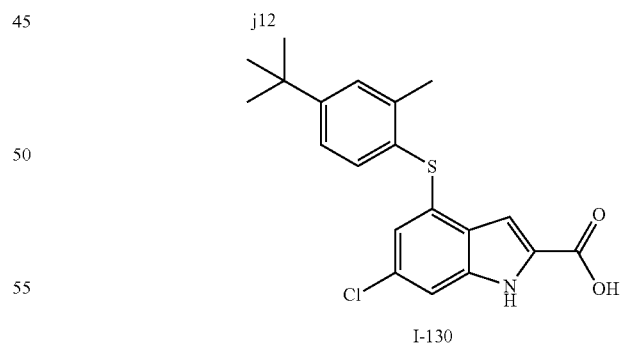

Procedures and Characterization:

The same procedure used to prepare I-157 to afford 4-(4-tert-butylphenylthio)-6-chloro-1H-indole-2-carboxylic acid I-130 (14.8 mg, 0.04 mmol, 10%) as a white solid. ESI-MS (EI+, m/z): 372.0 [M−H]⁻. ¹H NMR (500 MHz, MeOD) δ 7.31 (d, J=1.5 Hz, 1H), 7.23 (d, J=2 Hz, 1H), 7.21 (s, 1H), 7.16 (d, J=2.5 Hz, 1H), 6.95 (s, 11H), 6.47 (d, J=2 Hz, 1H), 2.23 (s, 3H), 1.14 (s, 9H).

Example 48: 4-(4-tert-butylphenylthio)-6-chloro-1H-indole-2-carboxylic acid, I-156

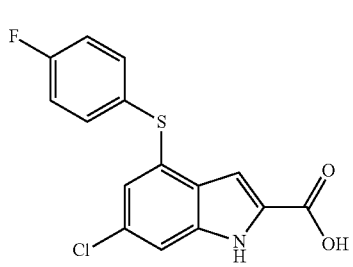

Synthetic Scheme:

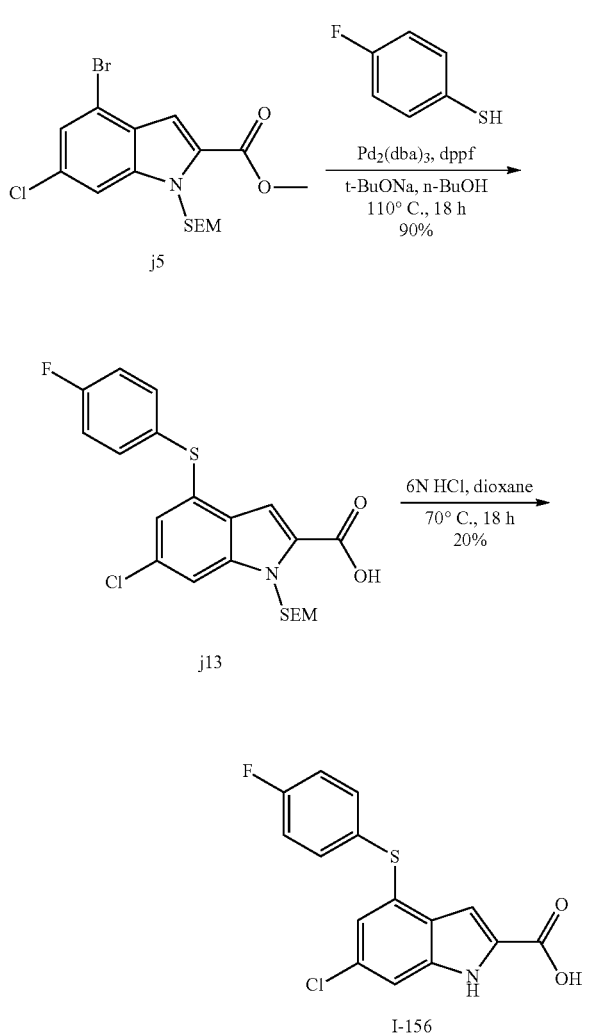

Example 49: 6-chloro-4-(3,4-difluorophenylthio)-1H-indole-2-carboxylic acid, I-155

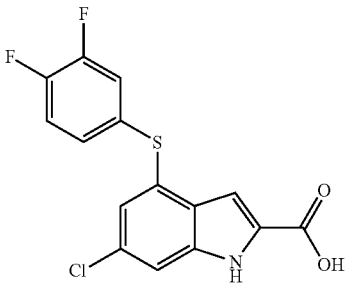

Synthetic Scheme:

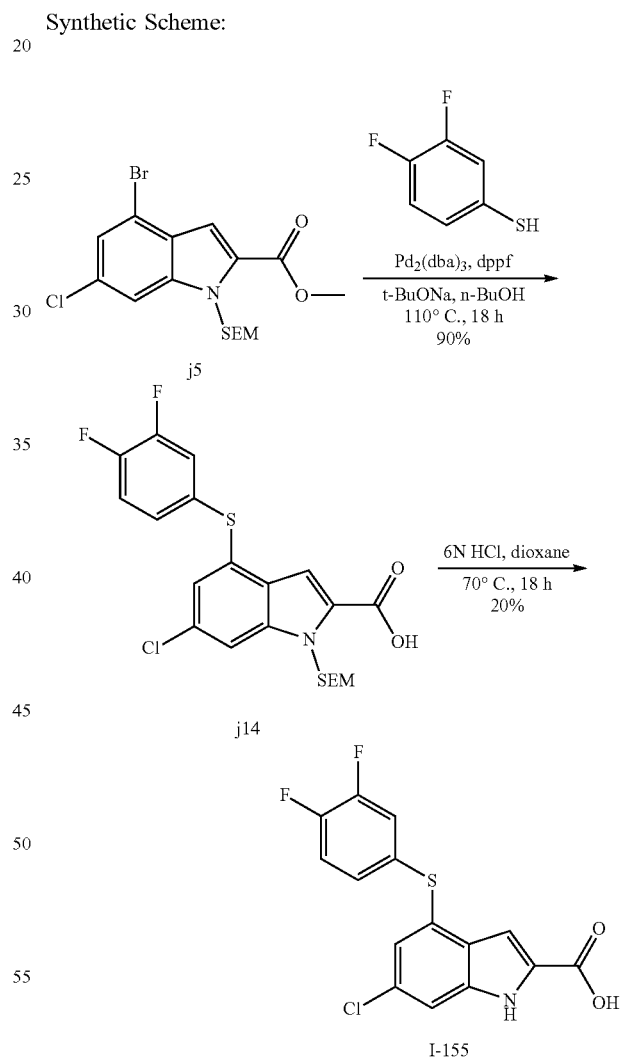

Procedures and Characterization:

The same procedure used to prepare I-157 afforded 6-chloro-4-(4-fluorophenylthio)-1H-indole-2-carboxylic acid I-156 (yield 20%) as a white solid. ESI-MS (EI+, m/z): 320.0 [M−H]⁻. $^1$H NMR (500 MHz, DMSO) δ 13.26 (s, 1H), 12.19 (s, 1H), 7.50-7.47 (m, 2H), 7.39 (s, 1H), 7.27 (t, J=8.5 Hz, 2H), 6.92 (d, J=1.5 Hz, 11H), 6.86 (d, J=1.5 Hz, 1H).

Procedures and Characterization:

The same procedure used to prepare I-157 to afford 6-chloro-4-(3,4-difluorophenylthio)-1H-indole-2-carboxylic acid I-155 (yield 20%) as a white solid. ESI-MS (EI+, m/z): 320.0 [M−H]⁻. $^1$H NMR (500 MHz, DMSO) δ 13.41 (s, 1H), 12.23 (s, 1H), 7.52-7.44 (m, 3H), 7.19-7.16 (m, 1H), 7.07 (d, J=1.5 Hz, 1H), 6.90 (s, 1H).

Example 50: 6-chloro-4-(3,4-dimethoxyphenylthio)-1H-indole-2-carboxylic acid, I-138

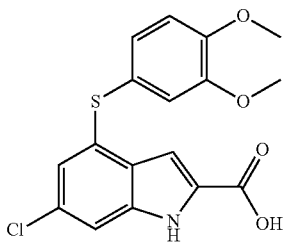
I-138

Synthetic Scheme:

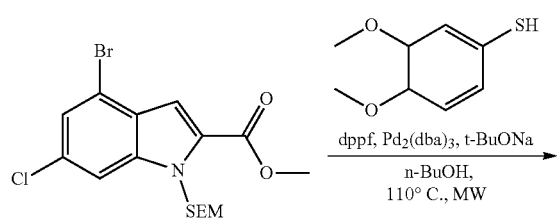

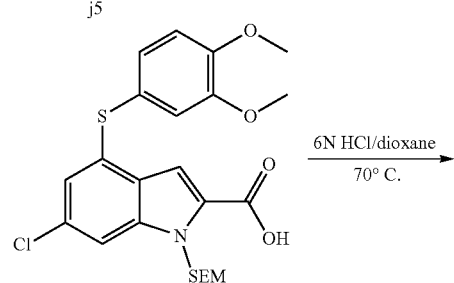

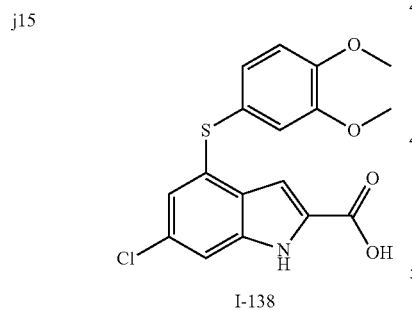
I-138

Procedures and Characterization:

Step 1: 6-chloro-4-(3,4-dimethoxyphenylthio)-1-((2-(trimethylsilyl)ethoxy)methyl)-1H-indole-2-carboxylic acid To a solution of methyl 4-bromo-6-chloro-1-((2-(trimethylsilyl)ethoxy)methyl)-1H-indole-2-carboxylate (250 mg, 0.60 mmol) in 1-butanol (13 mL) was added 1,1'-bis(diphenyl phosphino)ferrocene (34 mg, 0.06 mmol), sodium tert-butoxide (173 mg, 1.8 mmol) and 3,4-dimethoxycyclohexa-1,5-dienethiol (204 mg, 1.2 mmol) followed by tris (dibenzylidene ace-tone)dipalladium(0) (27 mg, 0.03 mmol) under N2 atmosphere. It was stirred at 110° C. by microwave for 1 h. The solution was filtered, diluted with water (50 mL) and extracted with ethyl acetate (100 mL×2). The organic phase was washed with water (50 mL×2), and brine (50 mL), dried (Na₂SO₄), filtered and concentrated in vacuo, the crude product was purified by chromatography (silica methanol/dcm=1/15) to afford 6-chloro-4-(3,4-dimethoxyphenylthio)-1-((2-(trimethylsilyl)ethoxy)methyl)-1H-indole-2-carboxylic acid (405 mg, 0.82 mmol) as a brown oil. ESI-MS (EI+, m/z): 492 [M−H]⁻.

Step 2: 6-chloro-4-(3,4-dimethoxyphenylthio)-1H-indole-2-carboxylic acid, I-138

The same procedure used to prepare I-157 afforded 6-chloro-4-(3,4-dimethoxyphenylthio)-1H-indole-2-carboxylic acid I-138 as a white solid (12.2 mg, 0.04 mmol, 6%). ESI-MS (EI+, m/z): 462 [M−H]⁻. ¹H NMR (500 MHz, DMSO) δ 13.23 (br s, 1H), 12.12 (s, 1H), 7:29 (S, 1H), 7.05-7.12 (m, 3H), 7.04 (d, 2H, J=8 Hz), 6.99 (s, 1H), 6.59 (s, 1H), 3.80 (s, 3H), 3.74 (s, 3H).

Example 51: 6-chloro-4-(3-(trifluoromethoxy)phenylthio)-1H-indole-2-carboxylic acid, I-126

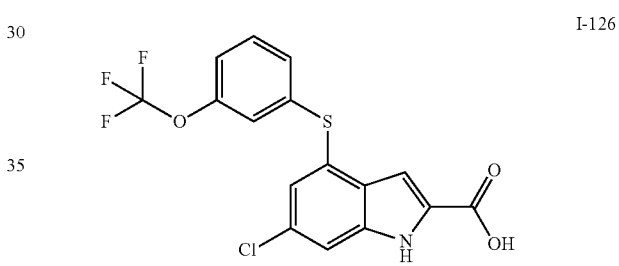
I-126

Synthetic Scheme:

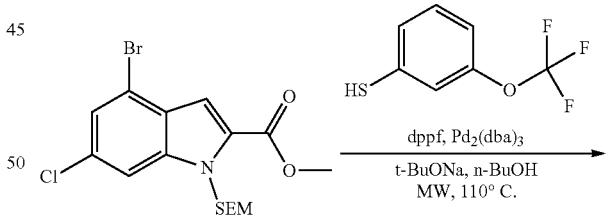

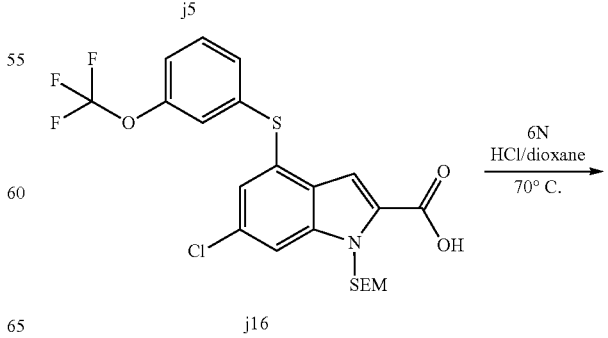

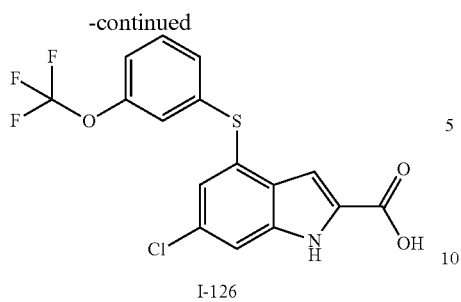

I-126

Procedures and Characterization:

Step 1: 6-chloro-4-(3-(trifluoromethoxy)phenyl-thio)-1-((2-(trimethylsilyl)ethoxy)methyl)-1H-indole-2-carboxylic acid The same procedure used to prepare 6-chloro-4-(3,4-difluorophenylthio)-1-((2-(trimethylsilyl)ethoxy)methyl)-1H-indole-2-carboxylic acid (j15) afforded 6-chloro-4-(3-(trifluoromethoxy) phenylthio)-1-((2-(trimethylsilyl) ethoxy)methyl)-1H-indole-2-carboxylic acid (632 mg, 1.22 mmol) as a brown oil. ESI-MS (EI+, m/z): 516 [M−H]⁻.

Step 2: 6-chloro-4-(3-(trifluoromethoxy)phenyl-thio)-1H-indole-2-carboxylic acid, I-126

The same procedure used to prepare I-157 afforded 6-chloro-4-(3-(trifluoromethoxy)phenylthio)-1H-indole-2-carboxylic acid, I-126 as a white solid (400 mg, 1.02 mmol). ESI-MS (EI+, m/z): 386 [M−H]⁻. $^1$H NMR (500 MHz, DMSO) δ 13.29 (br s, 1H), 12.26 (s, 1H), 7.52 (s, 1H), 7.46-7.49 (t, 1H, J=7.5 Hz), 7.26-7.29 (m, 2H), 7.24 (s, 1H), 7.20 (s, 1H), 6.85 (s, 1H).

Example 52: 6-chloro-4-(4-(trifluoromethyl)phenyl-thio)-1H-indole-2-carboxylic acid, I-86

I-86

Synthetic Scheme:

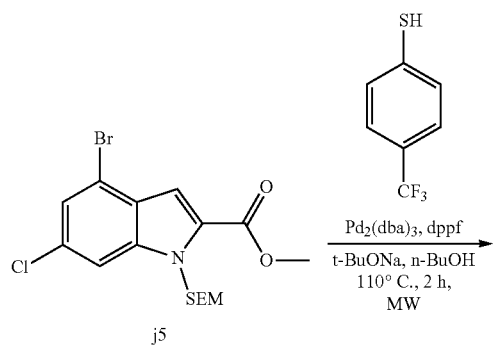

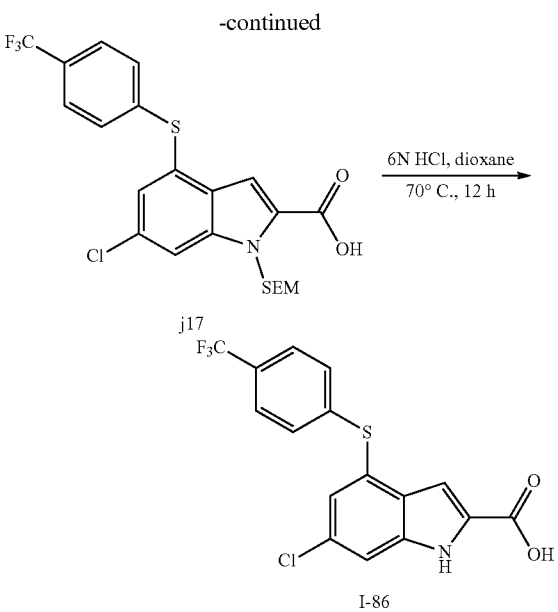

Procedures and Characterization:

Step 1: 6-chloro-4-(4-(trifluoromethyl)phenylthio)-1-((2-(trimethylsilyl)ethoxy)methyl)-1H-indole-2-carboxylic acid The same procedure used to prepare 6-chloro-4-(3,4-difluorophenylthio)-1-((2-(trimethylsilyl)ethoxy)methyl)-1H-indole-2-carboxylic acid (j15) afforded 6-chloro-4-(4-(trifluoromethyl)phenylthio)-1-((2-(trimethylsilyl)ethoxy) methyl)-1H-indole-2-carboxylic acid (60 mg, 25% yield) as a brown oil. ESI-MS (EI⁺, m/z): 500 [M−H]⁻.

Step 2: 6-chloro-4-(4-(trifluoromethyl)phenylthio)-1H-indole-2-carboxylic acid, I-86

The same procedure used to prepare I-157 afforded 6-chloro-4-(4-(trifluoromethyl)phenylthio)-1H-indole-2-carboxylic acid I-86 (5.1 mg, 69% yield). ESI-MS (EI⁺, m/z): 326.2 [M-COOH—H]⁻.

$^1$H NMR (500 MHz, MeOD) δ 7.55 (d, J=8.5 Hz, 3H), 7.32 (d, J=8.0 Hz, 2H), 7.27 (d, J=2.0 Hz, 12H), 6.98 (d, J=1.0 Hz, 1H).

Example 53: 6-chloro-4-(4-phenoxyphenylthio)-1H-indole-2-carboxylic acid, I-118

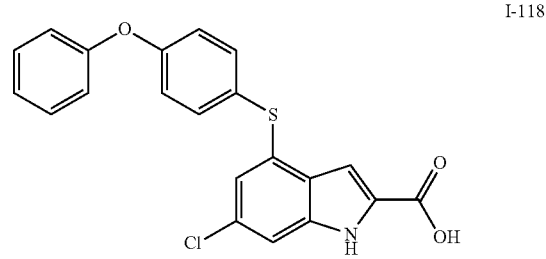 [SMILES: O=C(O)c1cc2c(Sc3ccc(Oc4ccccc4)cc3)cc(Cl)cc2[nH]1]

I-118

Synthetic Scheme:

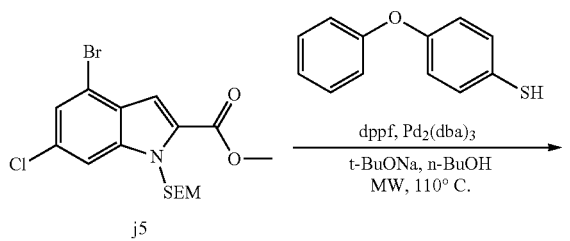

j5

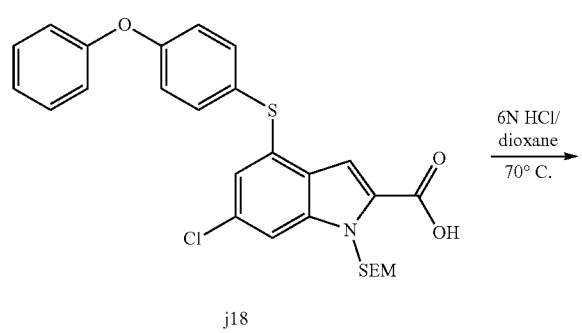

j18

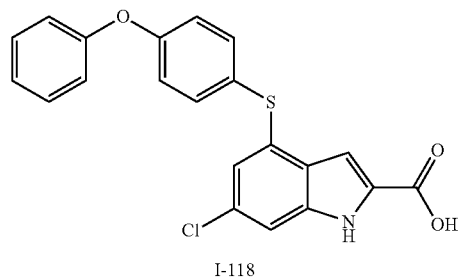

I-118

Procedures and Characterization:

Step 1: 6-chloro-4-(4-phenoxyphenylthio)-1-((2-(trimethylsilyl)ethoxy)methyl)-1H-indole-2-carboxylic acid The same procedure used to prepare 6-chloro-4-(3,4-difluorophenylthio)-1-((2-(trimethylsilyl)ethoxy)methyl)-1H-indole-2-carboxylic acid (j15) afforded 6-chloro-4-(4-phenoxyphenylthio)-1-((2-(trimethylsilyl)ethoxy)methyl)-1H-indole-2-carboxylic acid (490 mg, 0.93 mmol) as a brown oil. ESI-MS (EI+, m/z): 524 [M−H]⁻

Step 2: 6-chloro-4-(4-phenoxyphenylthio)-1H-indole-2-carboxylic acid

The same procedure used to prepare I-157 afforded 6-chloro-4-(4-phenoxyphenylthio)-1H-indole-2-carboxylic acid I-118 as a white solid (295 mg, 0.75 mmol). ESI-MS (EI+, m/z): 396 [M+H]⁺. $^1$H NMR (500 MHz, DMSO) δ 13.27 (s, 1H), 12.18 (s, 1H), 7.48 (d, 2H, J=9 Hz), 7.41-7.44 (t, 2H, J=7.5 Hz), 7.36 (s, 1H), 7.18-7.21 (t, 1H, J=7.5 Hz), 7.08 (d, 1H, J=7.5 Hz), 7.05 (d, 1H, J=8.5 Hz) 6.92 (s, 1H), 6.81 (s, 1H).

Example 54: 6-chloro-5-(4-chlorobenzylthio)-1H-indole-2-carboxylic acid, I-85

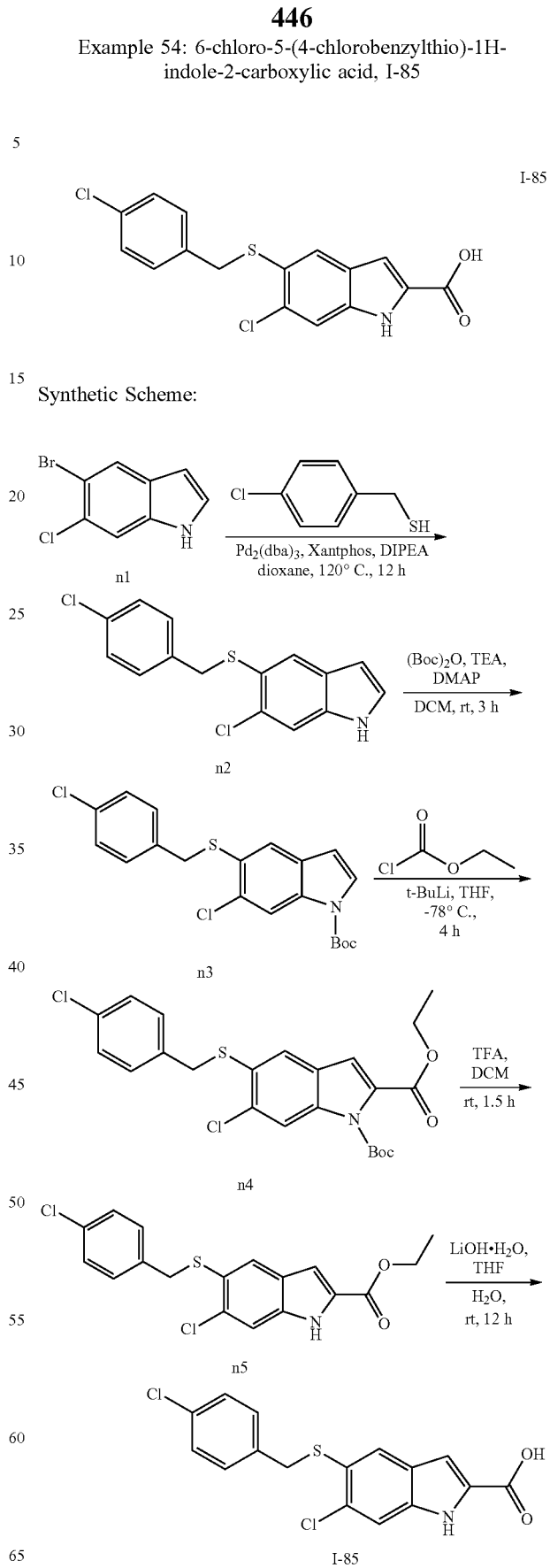

Synthetic Scheme:

Procedures and Characterization:

Step 1: 6-chloro-5-(4-chlorobenzylthio)-1H-indole

A suspension of 5-bromo-6-chloro-1H-indole (3.45 g, 15 mmol), (4-chlorophenyl)methanethiol (2.6 g, 16.5 mmol), Pd$_2$(dba)$_3$ (1.37 g, 1.5 mmol), Xantphos (1.74 g, 3 mmol) and DIPEA (3.87 g, 30 mmol) in dioxane (30 ml) was stirred at 120° C. for 12 h under N$_2$. The reaction mixture was cooled to room temperature, extracted with EtOAc, washed with brine, dried, concentrated, and purified by SGC and prep-HPLC to afford 6-chloro-5-(4-chlorobenzylthio)-1H-indole (2.1 g, 34% yield).

ESI-MS (EI$^+$, m/z): 306.0 [M−H]$^-$.

Step 2: tert-butyl 6-chloro-5-(4-chlorobenzylthio)-1H-indole-1-carboxylate

DMAP (36 mg, 0.295 mmol) and TEA (894 mg, 8.85 mmol) was added to a solution of 6-chloro-5-(4-chlorobenzylthio)-1H-indole (1.2 g, 2.95 mmol) and (Boc)$_2$O (764 mg, 3.54 mmol) in DCM (15 ml) and the reaction mixture was stirred at room temperature for 1.5 h. The reaction mixture was extracted with EtOAc, washed with brine, dried, concentrated, and purified by SGC (PE:EtOAc=20:1) to afford tert-butyl 6-chloro-5-(4-chlorobenzylthio)-1H-indole-1-carboxylate (1.6 g, overnight) as an oil.

ESI-MS (EI$^+$, m/z): 430 [M+Na]$^+$.

Step 3: 1-tert-butyl 2-ethyl 6-chloro-5-(4-chlorobenzylthio)-1H-indole-1,2-dicarboxylate 1.5N tBuLi (6.4 ml) was added to a solution of tert-butyl 6-chloro-5-(4-chlorobenzylthio)-1H-indole-1-carboxylate (1.3 g, 3.2 mmol) in THF (20 ml) at −78° C. and stirred for 1 h. ethyl carbonochloridate (1.03 g, 9.6 mmol) in THF (2 ml) was added to the reaction mixture and stirred at −78° C. for 4 h. The reaction mixture was quenched with NH$_4$Cl (aq.), extracted with EtOAc, washed with brine and water, dried, concentrated, and purified by SGC (PE:EtOAc=60:1) to afford 1-tert-butyl 2-ethyl 6-chloro-5-(4-chlorobenzylthio)-1H-indole-1,2-dicarboxylate (160 mg, 10.5% yield). ESI-MS (EI$^+$, m/z): 502.0 [M+Na]$^+$.

Step 4: ethyl 6-chloro-5-(4-chlorobenzylthio)-1H-indole-2-carboxylate

TFA (5 ml) was added to a solution of 1-tert-butyl 2-ethyl 6-chloro-5-(4-chlorobenzylthio)-1H-indole-1,2-dicarboxylate (160 mg, 0.334 mmol) in DCM (15 ml) at 0° C. and stirred at rt for 1.5 h. NaHCO$_3$ (aq.) was added to the reaction mixture to pH-7, extracted with EtOAc, washed with brine, dried, and concentrated to afford ethyl 6-chloro-5-(4-chlorobenzylthio)-1H-indole-2-carboxylate (115 mg, 91% yield), used for the next step. ESI-MS (EI$^+$, m/z): 377.9 [M−H]$^-$.

Step 5: 6-chloro-5-(4-chlorobenzylthio)-1H-indole-2-carboxylic acid, I-85

LiOH.H$_2$O (24 mg, 0.64 mmol) was added to a solution of ethyl 6-chloro-5-(4-chlorobenzylthio)-1H-indole-2-carboxylate (55 mg, 0.16 mmol) in THF (3 ml) and H$_2$O (3 ml) and stirred at room temperature for 12 h. 1 N HCl was added to the reaction mixture to adjust to pH-6, extracted with EtOAc, washed with brine, dried, concentrated, and purified by prep-HPLC to afford 6-chloro-5-(4-chlorobenzylthio)-1H-indole-2-carboxylic acid I-85 (16.4 mg, 29% yield) as a white solid.

ESI-MS (EI$^+$, m/z): 350 [M−H]$^-$.

1H NMR (500 MHz, MeOD) δ 7.56 (s, 1H), 7.52 (s, 1H), 7.19 (d, J=8.5 Hz, 2H), 7.14 (d, J=8.5 Hz, 2H), 6.81 (s, 1H), 4.04 (s, 2H),

Example 55: 6,7-dichloro-4-(2,4-dichlorophenylthio)-1H-indole-2-carboxylic acid, I-45

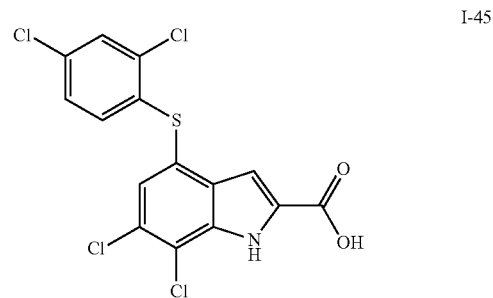 [SMILES: O=C(O)c1cc2c(Sc3ccc(Cl)cc3Cl)cc(Cl)c(Cl)c2[nH]1]

Synthetic Scheme:

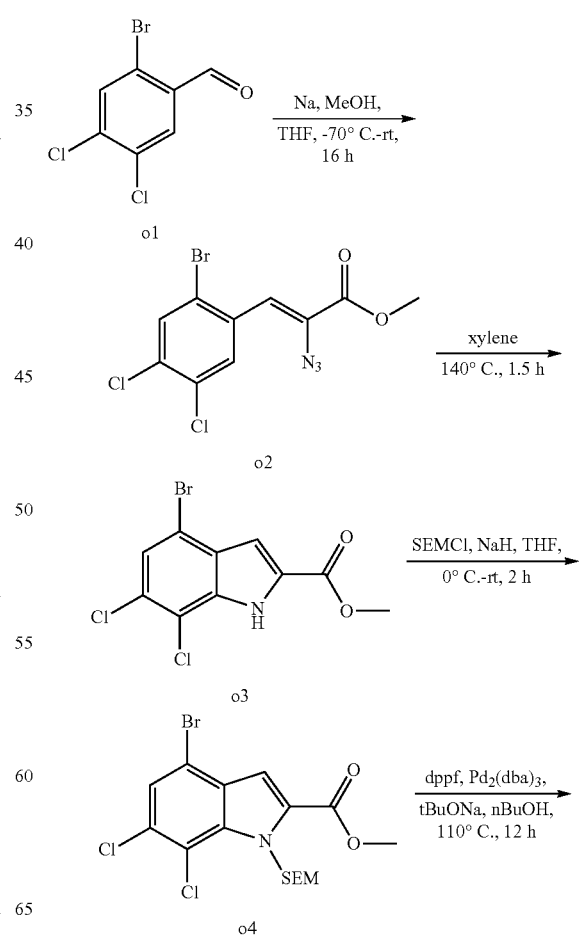

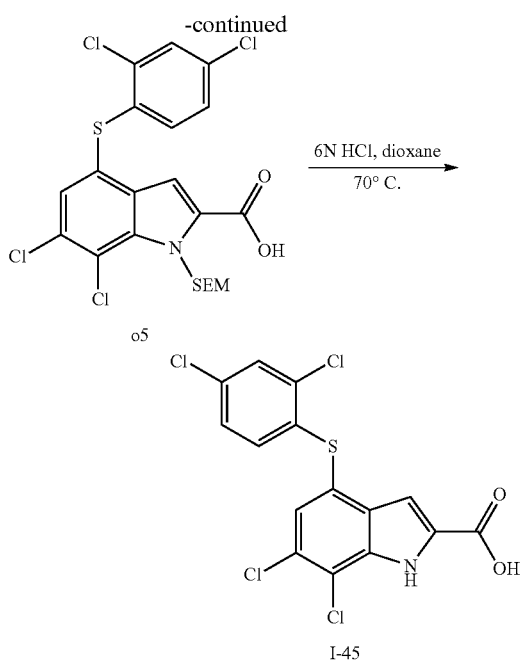

o5

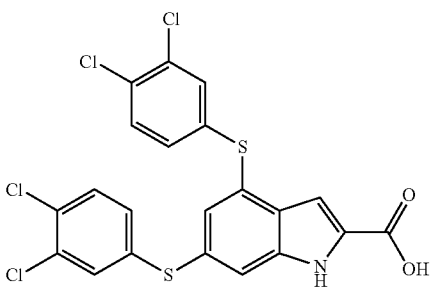

I-45

Procedures and Characterization:

Step 1: (Z)-methyl 2-azido-3-(2-bromo-4,5-dichlorophenyl)acrylate

The same procedure used to prepare a3 afforded (Z)-methyl 2-azido-3-(2-bromo-4,5-dichlorophenyl)acrylate (550 mg, 31% yield). ESI-MS (EI+, m/z): no MS.

Step 2: methyl 4-bromo-6,7-dichloro-1H-indole-2-carboxylate

The same procedure used to prepare a4 afforded methyl 4-bromo-6,7-dichloro-1H-indole-2-carboxylate (350 mg, 31% yield).
ESI-MS (EI+, m/z): 319.9 [M−H]−.

Step 3: methyl 4-bromo-6,7-dichloro-1-((2-(trimethylsilyl)ethoxy)methyl)-1H-indole-2-carboxylate The same procedure used to prepare a5 afforded methyl 4-bromo-6,7-dichloro-1-((2-(trimethylsilyl)ethoxy)methyl)-1H-indole-2-carboxylate (350 mg, 89% yield).
ESI-MS (EI+, m/z): no MS.

Step 4: 6,7-dichloro-4-(2,4-dichlorophenylthio)-1-((2-(trimethylsilyl)ethoxy)methyl)-1H-indole-2-carboxylic acid The same procedure used to prepare j6 afforded 6,7-dichloro-4-(2,4-dichlorophenylthio)-1-((2-(trimethylsilyl)ethoxy)methyl)-1H-indole-2-carboxylic acid (380 mg, 100% yield).
ESI-MS (EI+, m/z): 536.0 [M−H]−.

Step 5: 6,7-dichloro-4-(2,4-dichlorophenylthio)-1H-indole-2-carboxylic acid, I-45

The same procedure used to prepare I-157 afforded 6,7-dichloro-4-(2,4-dichlorophenylthio)-1H-indole-2-carboxylic acid I-45 (22 mg, 25% yield). ESI-MS (EI+, m/z): 405.9 [M+H]+.

$^1$H NMR (500 MHz, DMSO) δ 13.0 (s, 1H), 12.63 (s, 1H), 7.77 (d, J=3.0 Hz, 1H), 7.48 (s, 1H), 7.29, 7.28 (dd, J=3.0 Hz, 5.5 Hz, 1H), 6.88 (s, 1H), 6.86 (d, J=5.25 Hz, 1H).

Example 56: 4,6-bis(3,4-dichlorophenylthio)-1H-indole-2-carboxylic acid, I-88

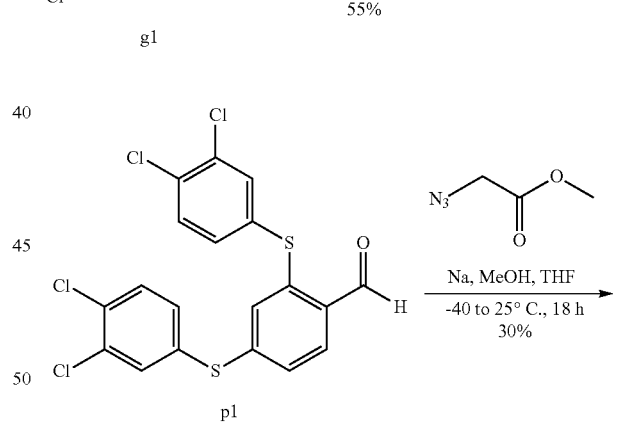

Synthetic Scheme:

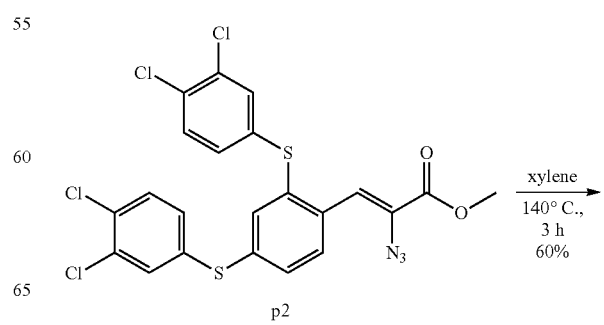

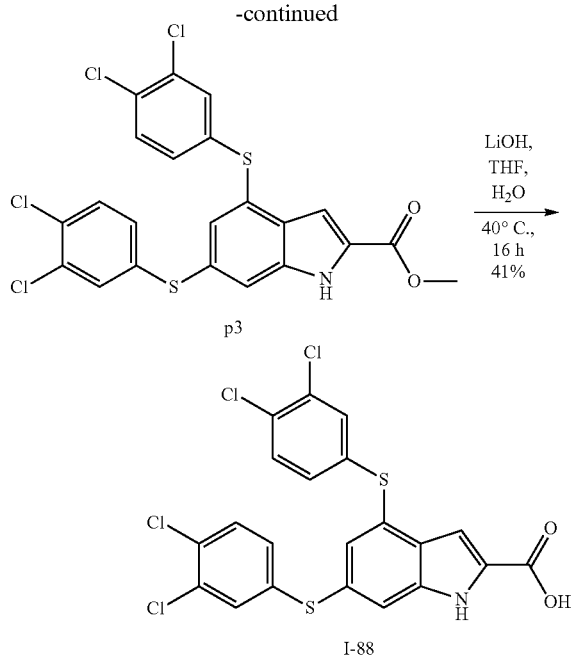

mg, 1.5 mmol) in THF (5 mL) and H₂O (2 mL) was stirred for 16 h at 40° C. The reaction was neutralized with 2 N HCl to pH 6 and extracted with ethyl acetate (20 mL). The organic phase was dried (Na₂SO₄), filtered and concentrated in vacuo and the residue was purified by prep-HPLC (0.01% TFA) to afford 4,6-bis(3,4-dichlorophenylthio)-1H-indole-2-carboxylic acid I-88 (31.9 mg, 0.06 mmol, 41%) as a white solid. ESI-MS (EI+, m/z): 511.9 [M−H]⁻. H NMR (500 MHz, MeOD) δ 7.63 (s, 1H), 7.40 (t, J=13.5 Hz, J=8.5 Hz, 2H), 7.31 (t, J=2 Hz, 2H), 7.12-7.10 (m, 3H), 7.06 (s, 1H).

Procedures and Characterization:

Step 1: 2,4-bis(3,4-dichlorophenylthio)benzaldehyde

A mixture of 4-chloro-2-fluorobenzaldehyde (2 g, 12.7 mmol), 3,4-dichlorobenzenethiol (5 g, 27.8 mmol) and K₂Cd₃ (8.74 g, 63.3 mmol) in DMF (50 mL) was stirred for 18 h at 110° C. The reaction was quenched with water (100 mL) and extracted with ethyl acetate (160 mL). The organic phase was washed water (40 mL×2), and brine (40 mL), dried (Na₂SO4), filtered and concentrated in vacuo and the residue was purified by chromatography (silica, ethyl acetate/petroleum ether =1/20) to afford 2,4-bis(3,4-dichlorophenylthio)benzaldehyde (3.2 g, 7 mmol, 55%) as a light yellow solid. ¹H NMR (500 MHz, CDCl₃) δ 10.17 (s, 1H), 7.74 (d, ==8.5 Hz, 1H), 7.47 (dd, J=12.5 Hz, J=2.5 Hz, 2H), 7.41 (t, J=8.5 Hz, 2H), 7.21-7.16 (m, 2H), 7.11 (dd, J=8.5 Hz, J=1.5 Hz, 1H), 6.51 (d, J=1.5 Hz, 1H).

Step 2: (Z)-methyl 2-azido-3-(2,4-bis(3,4-dichlorophenylthio)phenyl)acrylate

The same procedure used to prepare compound a3 afforded (Z)-methyl 2-azido-3-(2,4-bis(3,4-dichlorophenylthio)phenyl)acrylate (370 mg, 0.67 mmol, 30%) as a light yellow solid. 1H NMR (500 MHz, CDCl₃) δ 8.10 (d, J=8.5 Hz, 1H), 7.44 (d, J=1.5 Hz, 1H), 7.38 (d, J=8 Hz, 1H), 7.33-7.28 (m, 3H), 7.23-7.15 (m, 3H), 7.00 (dd, J=8.5 Hz, J=2 Hz, 1H), 3.90 (s, 3H).

Step 3: methyl 4,6-bis(3,4-dichlorophenylthio)-1H-indole-2-carboxylate

The same procedure used to prepare compound a4 afforded methyl 4,6-bis(3,4-dichlorophenylthio)-1H-indole-2-carboxylate (180 mg, 0.34 mmol, 61%) as an off-white solid. ESI-MS (EI+, m/z): 526.0 [M−H]⁻.

Step 4: 4,6-bis(3,4-dichlorophenylthio)-1H-indole-2-carboxylic acid, I-88

A mixture of methyl 4,6-bis(3,4-dichlorophenylthio)-1H-indole-2-carboxylate (80 mg, 0.15 mmol), LiOH·H₂O (64

Example 57: 4,6-bis(4-chlorobenzylthio)-1H-indole-2-carboxylic acid, I-94

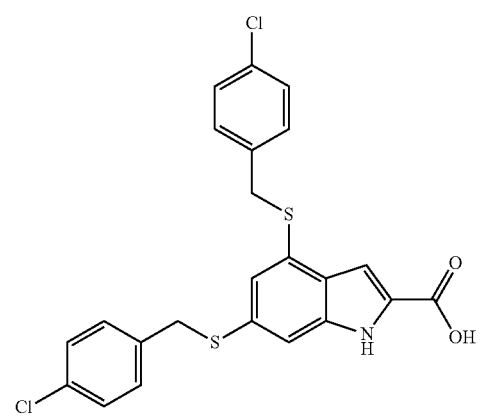

Synthetic Scheme:

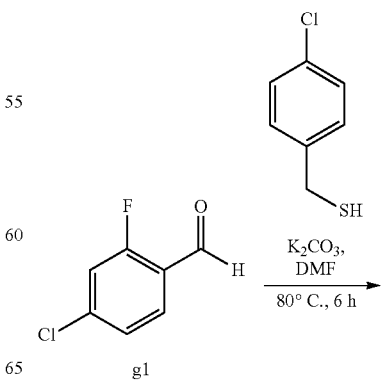

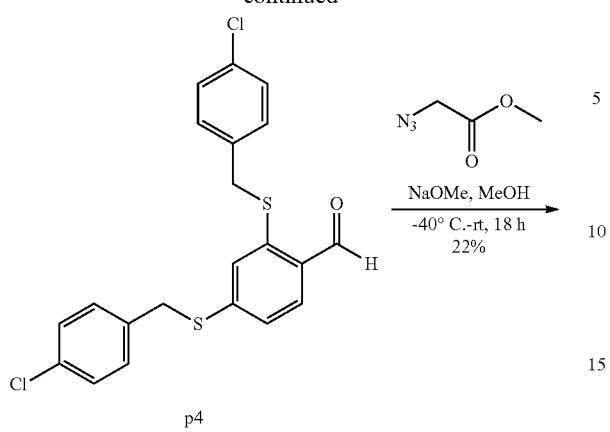
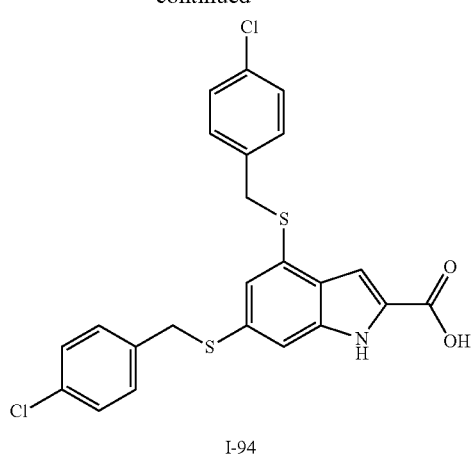
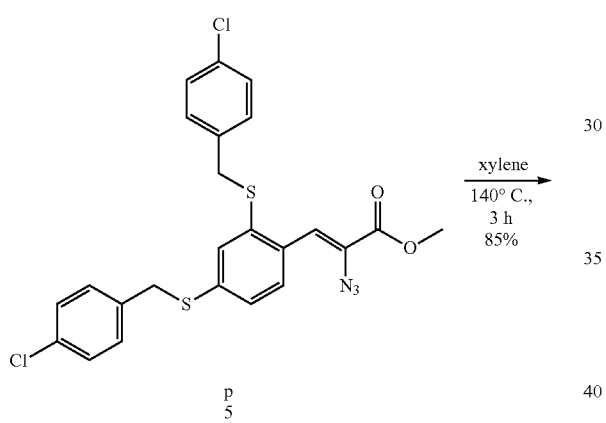
Procedures and Characterization:
The same procedure used to prepare I-88 afforded 2-(4-(5-(4,6-bis(4-chlorobenzylthio)-1H-indole-2-carboxylic acid, I-94:
ESI-MS (EI+, m/z): 471.9 [M−H]+. $^1$H NMR (500 MHz, DMSO-d6) δ 13.05 (s, 1H), 11.90 (s, 1H), 7.39-7.28 (m, 6H), 7.23 (d, J=8.4 Hz, 2H), 7.15 (s, 1H), 6.97 (d, J=6.7 Hz, 2H), 4.30 (s, 2H), 4.16 (s, 2H).
Example 58: 7-chloro-6-(3,4-dichlorophenylthio)-4-fluoro-1H-indole-2-carboxylic acid, I-66
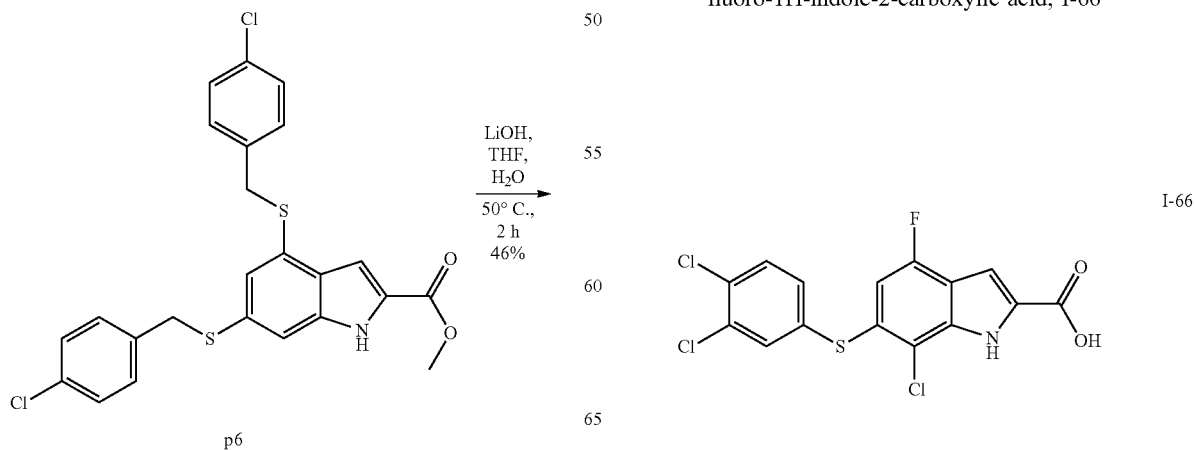

Synthetic Scheme:

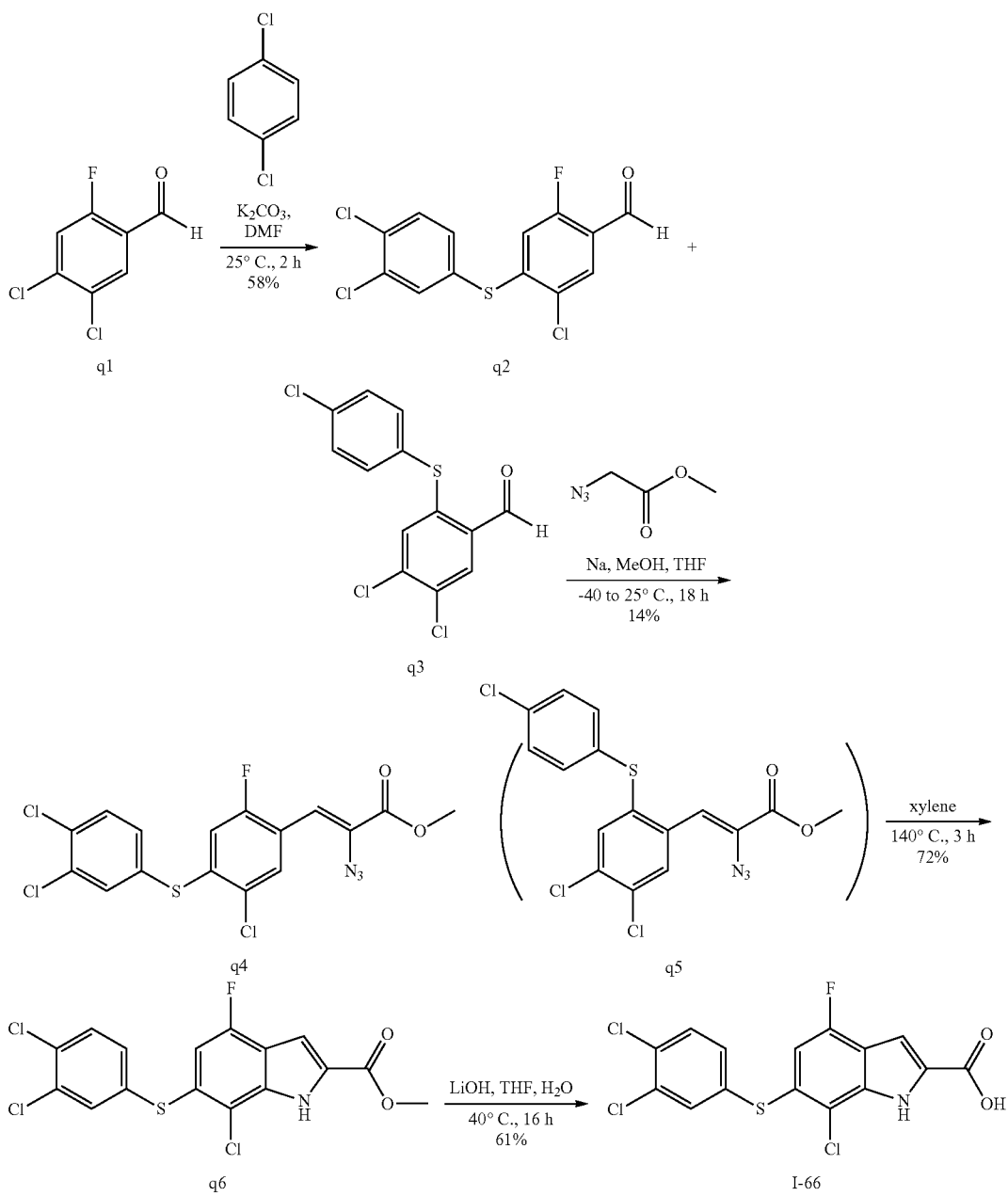

Procedures and Characterization:

Step 1: 5-chloro-4-(3,4-dichlorophenylthio)-2-fluorobenzaldehyde

A mixture of 4,5-dichloro-2-fluorobenzaldehyde (1.5 g, 7.81 mmol), 4-chlorobenzenethiol (1.13 g, 7.81 mmol) and Na$_2$CO$_3$ (1.65 g, 15.6 mmol) in DMF (30 mL) was stirred for 2 h at 25° C. The reaction was quenched with water (60 mL) and extracted with ethyl acetate (150 mL). The organic phase was washed water (30 mL×2), and brine (30 mL), dried (Na$_2$SO$_4$), filtered, concentrated in vacuo and the residue was purified by chromatography (silica, ethyl acetate/petroleum ether=1/20) to afford a mixture of 4,5-dichloro-2-(4-chlorophenylthio) benzaldehyde and 5-chloro-4-(3,4-dichlorophenylthio)-2-fluorobenzaldehyde (1.5 g, 4.75 mmol, 61%) as white solids. ESI-MS (EI+, m/z): 317.0 [M+H]$^+$ and 301.0 [M+H]$^+$.

Step 2: (Z)-methyl 2-azido-3-(5-chloro-4-(3,4-dichlorophenylthio)-2-fluorophenyl) acrylate Metal Na (204 mg, 8.86 mmol) was dissolved in dry MeOH (15 mL). A mixture of 4,5-dichloro-2-(4-chlorophenylthio) benzaldehyde and 5-chloro-4-(3,4-dichlorophenylthio)-2-fluorobenzaldehyde (700 mg, 2.22 mmol), methyl 2-azidoacetate (1.02 g, 8.86 mmol) in dry THF (3 mL) was added at −40° C. The reaction was stirred for 1 h at −40° C. and then for 16 h at 25° C. under N$_2$ atmosphere. The reaction was filtered. The cake was dried to afford (Z)-methyl 2-azido-3-(5-chloro-4-(3,4-dichlorophenylthio)-2-fluorophenyl)acrylate (300 mg, 0.7 mmol, 31%) as a light yellow solid. The filtrate was concentrated in vacuo and the residue was purified by chromatography (silica, ethyl acetate/petroleum ether=1/10) to afford (Z)-methyl 2-azido-3-(4,5-dichloro-2-(4-chlorophenylthio)phenyl)acrylate (170 mg, 0.41 mmol, 19%) as a light yellow solid.

Step 3: methyl 7-chloro-6-(3,4-dichlorophenylthio)-4-fluoro-1H-indole-2-carboxylate The same procedure used to prepare a4 afforded methyl 7-chloro-6-(3,4-dichlorophenylthio)-4-fluoro-1H-indole-2-carboxylate (180 mg, 0.45 mmol, 72%) as an off-white solid. ESI-MS (EI+, m/z): 367.9 [M−H]⁻.

Step 4: 7-chloro-6-(3,4-dichlorophenylthio)-4-fluoro-1H-indole-2-carboxylic acid, I-66

A mixture of methyl 7-chloro-6-(3,4-dichlorophenylthio)-4-fluoro-1H-indole-2-carboxylate (100 mg, 0.27 mmol), LiOH.H$_2$O (33 mg, 1.35 mmol) in THF (5 mL) and H$_2$O (2 mL) was stirred for 16 h at 40° C. The reaction was neutralized with 2 N HCl to pH 6 and extracted with ethyl acetate (20 mL). The organic phase was dried (Na$_2$SO$_4$), filtered and concentrated in vacuo and the residue was purified by prep-HPLC (0.01% TFA) to afford 7-chloro-6-(3,4-dichloro phenylthio)-4-fluoro-1H-indole-2-carboxylic acid I-66 (58.6 mg, 0.15 mmol, 61%) as a white solid. ESI-MS (EI+, m/z): 354.0 [M−H]⁻. ¹H NMR (500 MHz, MeOD) δ 7.39 (d, J=10.5 Hz, 2H), 7.32 (d, J=10 Hz, 2H), 7.24 (s, 1H), 6.68 (d, J=12.5 Hz, 1H).

Example 59: 6,7-dichloro-4-(4-chlorophenylthio)-1H-indole-2-carboxylic acid, I-73

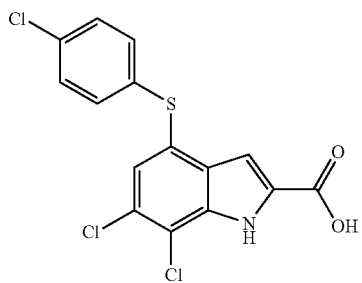

I-73

Synthetic Scheme:

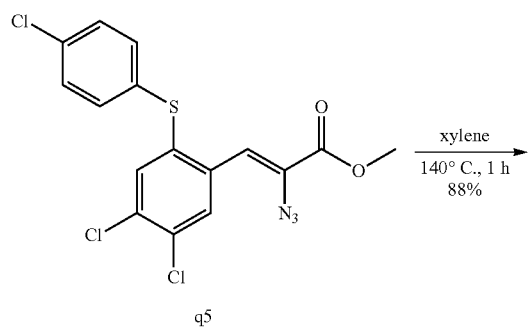

q5

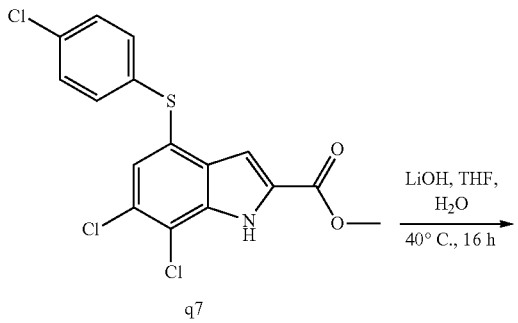

q7

LiOH, THF, H$_2$O
40° C., 16 h

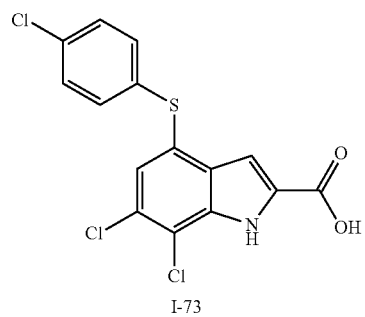

I-73

Procedures and Characterization:

The same procedure used to prepare I-88 afforded 6,7-dichloro-4-(4-chlorophenylthio)-1H-indole-2-carboxylic acid I-73 (yield 15%) as a white solid. ESI-MS (EI+, m/z): 370.0 [M−H]⁻. 1H NMR (500 MHz, DMSO) δ 7.37 (q, J=10.5 Hz, 4H), 7.20 (s, 1H), 7.13 (s, 1H).

Example 60: 7-bromo-4-(4-chlorophenylthio)-6-methyl-1H-indole-2-carboxylic acid, I-64

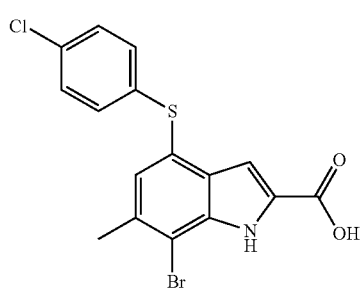

I-64

Synthetic Scheme:

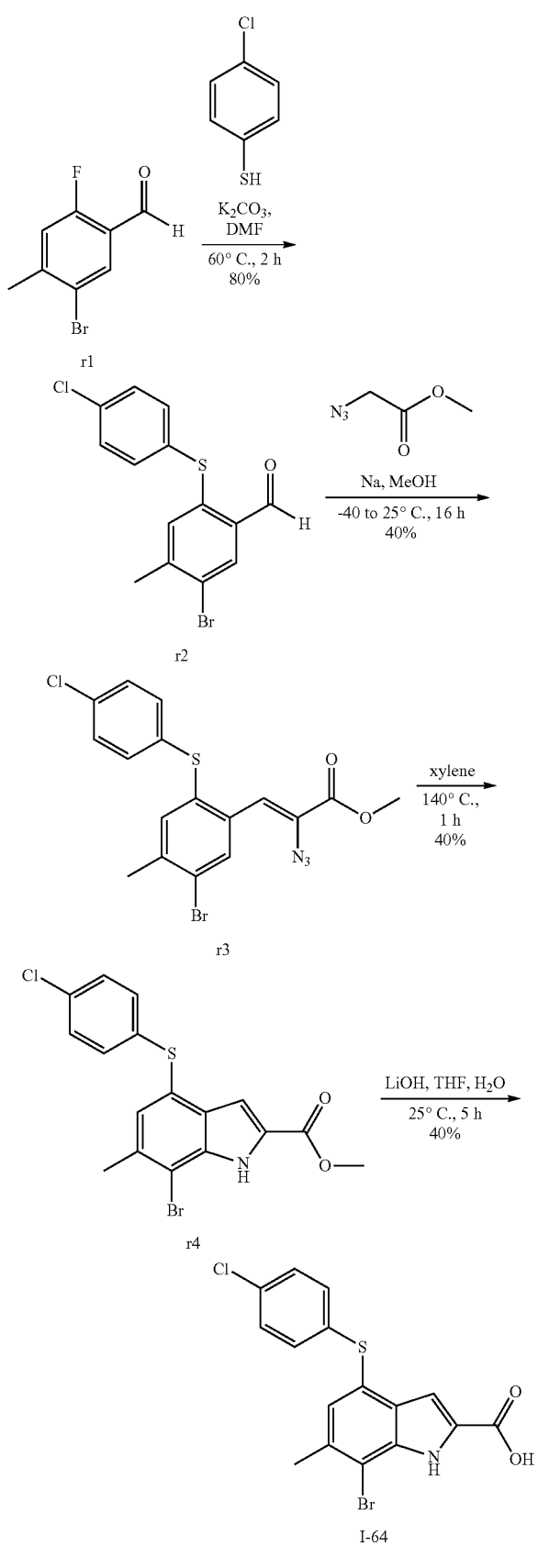

Procedures and Characterization:

The same procedure used to prepare I-88 afforded 7-bromo-4-(4-chlorophenylthio)-6-methyl-1H-indole-2-carboxylic acid I-64 (50.5 mg, 0.13 mmol, 40%) as a white solid. The temperature for the 1st step was 60° C. The temperature for the last step was 25° C. ESI-MS (EI+, m/z): 395.9 [M+H]$^+$. $^1$H NMR (500 MHz, DMSO) δ 13.18 (t, J=3 Hz, 1H), 11.83 (s, 1H), 7.36 (d, J=11 Hz, 2H), 7.28 (s, 1H), 7.19 (d, J=11 Hz, 2H), 6.92 (s, 1H), 2.46 (s, 3H).

Example 61: 7-bromo-4-(4-chlorophenylthio)-6-methyl-1H-indole-2-carboxylic acid, I-58

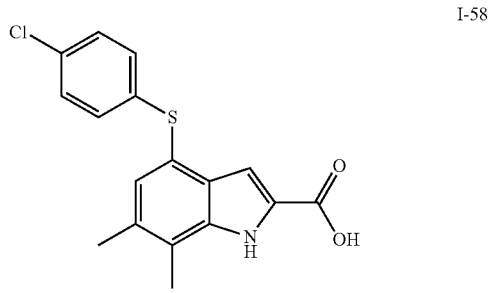 [SMILES: Cc1cc(Sc2ccc(Cl)cc2)c2cc(C(=O)O)[nH]c2c1C]

Synthetic Scheme:

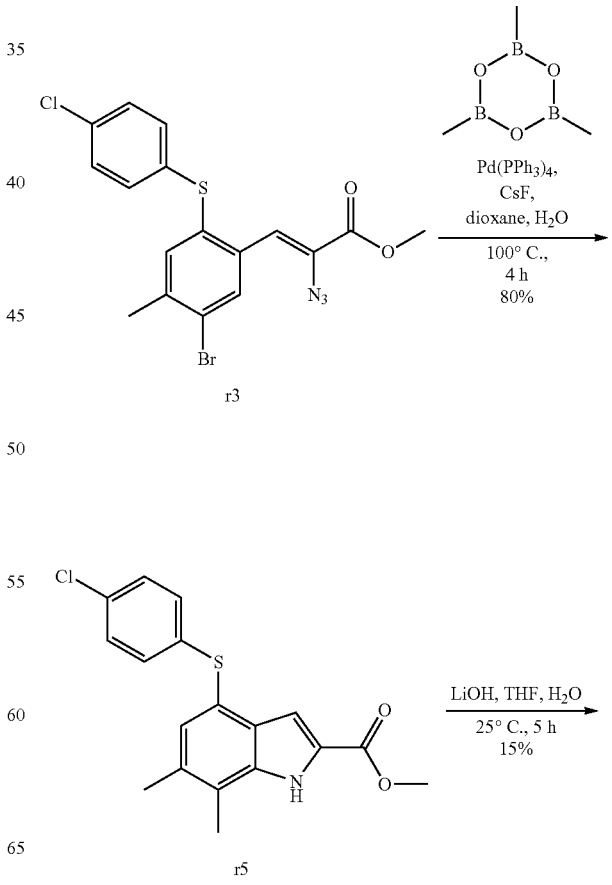

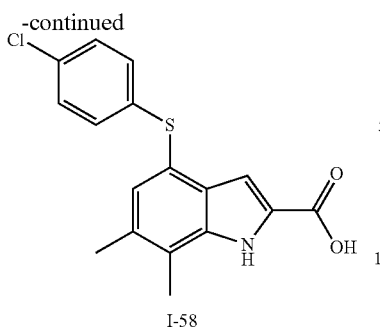

I-58

Procedures and Characterization:

Step 1: methyl 4-(4-chlorophenylthio)-6,7-dimethyl-1H-indole-2-carboxylate

A mixture of methyl 7-bromo-4-(4-chlorophenylthio)-6-methyl-1H-indole-2-carboxylate (150 mg, 0.37 mmol), 2,4,6-trimethyl-1,3,5,2,4,6-trioxatriborinane (69 mg, 0.55 mmol), Pd(PPh$_3$)$_4$ (86 mg, 0.08 mmol) and CsF (169 mg, 1.1 mmol) in dioxane (9 mL) and H$_2$O (1 mL) was stirred for 4 h at 100° C. under N$_2$ atmosphere. The reaction was quenched with water (20 mL) and extracted with ethyl acetate (30 mL). The organic phase was washed water (10 mL×2), and brine (40 mL), dried (Na$_2$SO$_4$), filtered and concentrated in vacuo and the residue was purified by chromatography (silica, ethyl acetate/petroleum ether=1/5) to afford methyl 4-(4-chlorophenylthio)-6,7-dimethyl-1H-indole-2-carboxylate (102 mg, 0.3 mmol, 80%) as a light brown solid. ESI-MS (EI+, m/z): 346.0 [M+H]$^+$.

Step 2: 4-(4-chlorophenylthio)-6,7-dimethyl-1H-indole-2-carboxylic acid, I-58

The same procedure used to prepare I-102 afforded 4-(4-chlorophenylthio)-6,7-dimethyl-1H-indole-2-carboxylic acid I-58 (37.8 mg, 0.11 mmol, 15%) as a white solid. ESI-MS (EI+, m/z): 332.1 [M+H]$^+$. $^1$H NMR (500 MHz, MeOD) δ 7.19 (d, J=11 Hz, 2H), 7.14 (s, 1H), 7.07 (d, J=11 Hz, 2H), 6.98 (s, 1H), 2.48 (s, 3H), 2.39 (s, 3H).

Example 62: 4-chloro-6-(3,4-dichlorophenylthio)-1H-indole-2-carboxylic acid, I-100

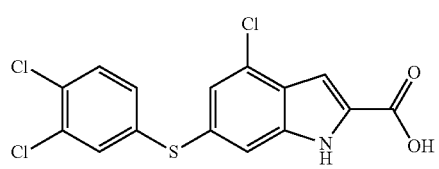

I-100

Synthetic Scheme:

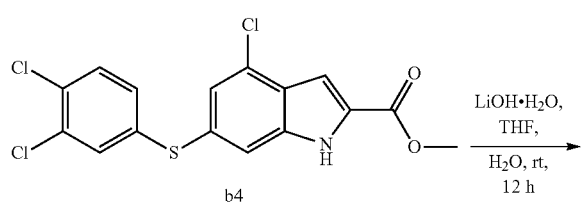

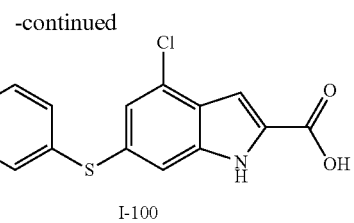

I-100

Procedures and Characterization:

Step 1: 4-chloro-6-(3,4-dichlorophenylthio)-1H-indole-2-carboxylic acid, I-100

The same procedure used to prepare I-102 afforded 4-chloro-6-(3,4-dichlorophenylthio)-1H-indole-2-carboxylic acid I-100 (10 mg, 9% yield).
ESI-MS (EI$^+$, m/z): 371.9 [M−H]$^-$. $^1$H NMR (500 MHz, MeOD) δ 7.54 (s, 1H), 7.45 (d, J=4.5 Hz, 1H), 7.36 (d, J=2.0 Hz, 1H), 7.20 (s, 1H), 7.17 (d, J=1.0 Hz, 1H), 7.14 (dd, J=2.0 Hz, J=4.25 Hz, 1H).

Example 63: 4-bromo-6-(3,4-dichlorophenylthio)-1H-indole-2-carboxylic acid, I-139

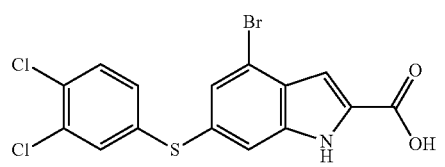

I-139

Synthetic Scheme:

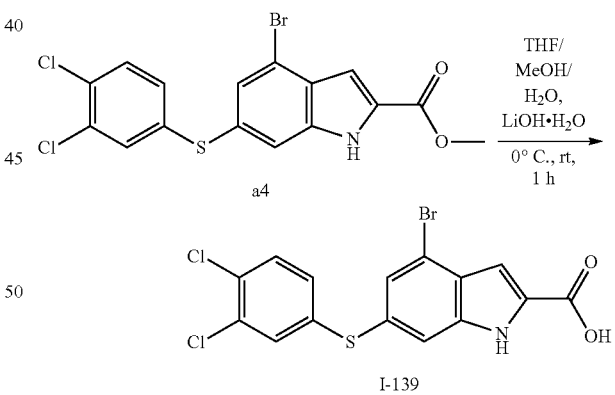

Procedures and Characterization:

Step 1: 4-bromo-6-(3,4-dichlorophenylthio)-1H-indole-2-carboxylic acid, I-139

To a solution of methyl 1-(4-(tert-butoxycarbonyl)benzyl)-6-chloro-4-(3,4-dichlorophenoxy)-1H-indole-2-carboxylate (1.17 g, 2.08 mmol) in THF/MeOH/H$_2$O (1:1:1, 18 mL), was added LiOH.H$_2$O (0.699 g, 16.7 mmol), this mixture was stirred at 40° C. for 18 h, The reaction was quenched with ice-water, adjust to pH 5 with 1N HCl solution, extracted with EtOAc, dried and concentrated to afford 1-(4-carboxybenzyl)-6-chloro-4-(3,4-dichlorophenoxy)-1H-indole-2-carboxylic acid I-139 (800 mg, purity: 100%, yield: 78%). No MS was detected.

¹H NMR (500 MHz, DMSO) δ 12.66 (s, 1H), 8.07 (d, J=1.5 Hz, 1H), 7.92 (s, 1H), 7.83 (d, J=8.4 Hz, 1H), 7.75 (d, J=8.2 Hz, 1H), 7.64 (s, 1H), 7.02 (s, 1H).

Example 64: 4-(4-bromophenylthio)-6-chloro-1H-indole-2-carboxylic acid, I-98

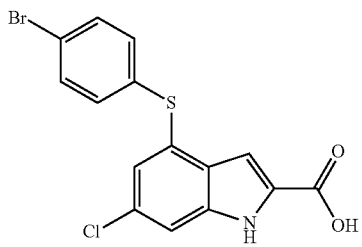

Synthetic Scheme:

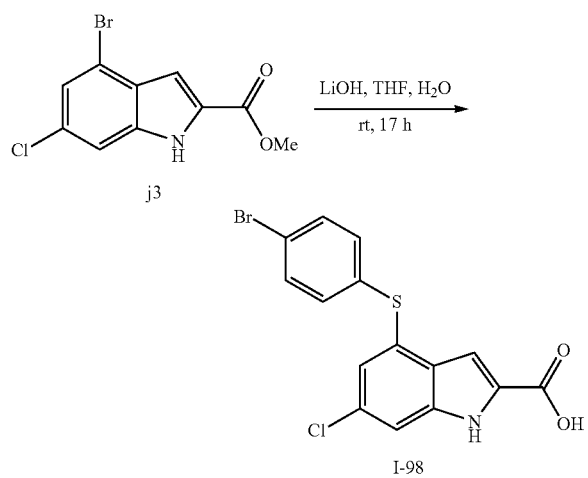

Procedures and Characterization:

The procedure for 4-(4-bromophenylthio)-6-chloro-1H-indole-2-carboxylic acid, I-98 was same as example 1, I-102. ¹H NMR (400 MHz, DMSO-$d_6$) δ 7.50 (d, J=6.8 Hz, 2H), 7.42 (s, 1H), 7.16 (d, J=6.8 Hz, 2H), 7.00 (s, 1H), 6.40 (s, 1H).

Example 65: 6-chloro-4-phenyl-1H-indole-2-carboxylic acid, I-54

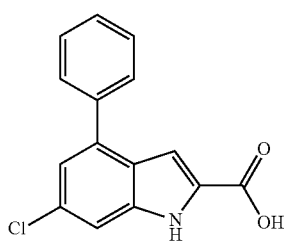

Synthetic Scheme:

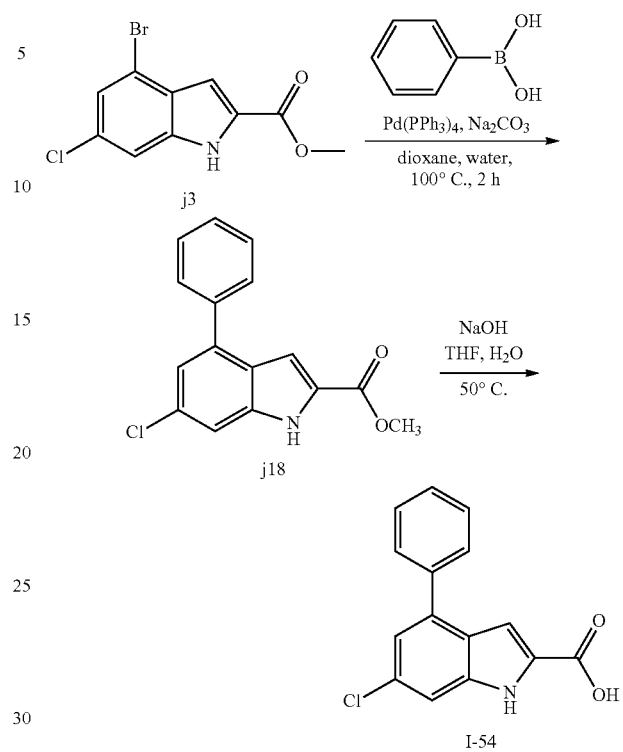

Procedures and Characterization:

Step 1: methyl 6-chloro-4-phenyl-1H-indole-2-carboxylate

To a solution of methyl 4-bromo-6-chloro-1H-indole-2-carboxylate (200 mg, 0.70 mmol) in a mixture of dioxane (6.00 mL) and water (1.20 mL) was added phenylboronic acid (110 mg, 0.91 mmol) and sodium carbonate decahydrate (149 mg, 1.4 mmol) followed by tetrakis(triphenylphosphine)platinum (162 mg, 0.14 mmol) under N2 atmosphere and stirred for 2 h at 100° C. The solution was diluted with water (200 mL) and extracted with ethyl acetate (100 mL). The organic phase was washed with water (100 mL×2), and brine (100 mL), dried (Na₂SO₄), filtered and concentrated in vacuo, the crude product was purified by chromatography (silica, ethyl acetate/petroleum ether=1/5) to afford methyl 6-chloro-4-phenyl-1H-indole-2-carboxylate (140 mg, 0.49 mmol, 70%) as a brown oil. ESI-MS (m/z): 286 [M+H]⁺.

Step 2: 6-chloro-4-phenyl-1H-indole-2-carboxylic acid, I-54

To a solution of methyl 6-chloro-4-phenyl-1H-indole-2-carboxylate (70 mg, 0.25 mmol) in a mixture of THF (5.00 mL) and water (5.00 mL) was added NaOH (50 mg, 1.25 mmol) and stirred for 2 h at 50° C. The solution was adjusted to pH 4-5 and extracted with ethyl acetate (100 mL). The organic phase was washed with water (100 mL×2), and brine (100 mL), dried (Na₂SO₄), filtered and concentrated in vacuo. The crude product was purified by prep-HPLC to afford 6-chloro-4-phenyl-1H-indole-2-carboxylic acid I-54 as a white solid (30 mg, 0.11 mmol, 49%). ESI-MS (EI+, m/z): 272 [M+H]$^+$. $^1$H NMR (500 MHz, MeOD) δ 7.66 (d, 1H, J=9.5 Hz), 7.51-7.55 (t, 2H, J=9.5 Hz), 7.47 (s, 1H), 7.44 (d, 11H, J=9 Hz), 7.24 (s, 1H), 7.14 (s, 1H).

Example 66: 6-chloro-4-(3,5-dichlorophenyl)-1H-indole-2-carboxylic acid, I-49

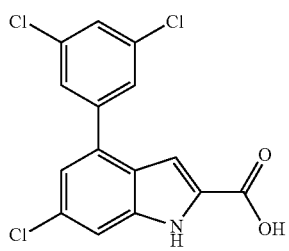

Synthetic Scheme:

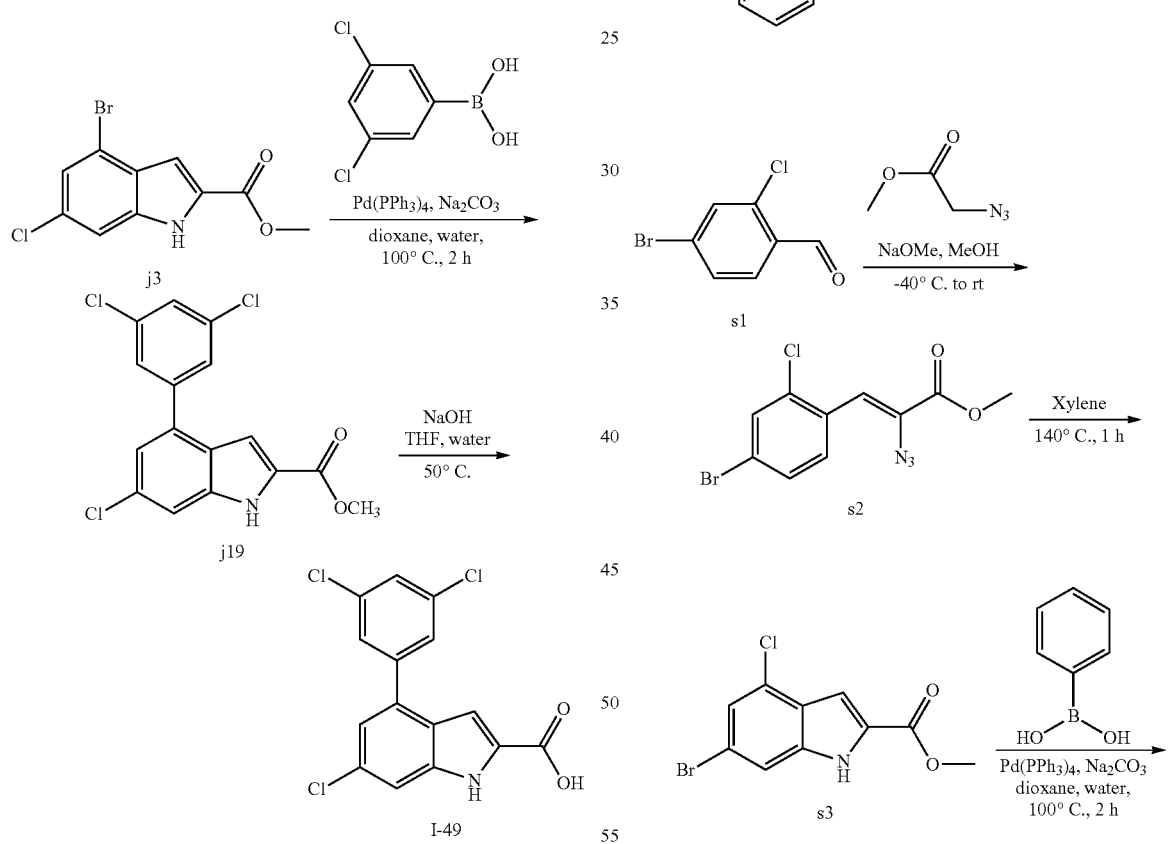

Procedures and Characterization:

Step 1: methyl 6-chloro-4-(3,5-dichlorophenyl)-1H-indole-2-carboxylate

The same procedure used to prepare methyl 6-chloro-4-phenyl-1H-indole-2-carboxylate (j18) afforded methyl 6-chloro-4-(3,5-dichlorophenyl)-1H-indole-2-carboxylate (200 mg, 0.49 mmol, 82%) as a brown oil. ESI-MS (EI+, m/z): 354 [M+H]$^+$.

Step 2: 6-chloro-4-(3,5-dichlorophenyl)-1H-indole-2-carboxylic acid, I-49

The same procedure used to prepare I-54 afforded to afford 6-chloro-4-(3,5-dichlorophenyl)-1H-indole-2-carboxylic acid I-49 as a white solid (21.8 mg, 0.07 mmol, 20%). $^1$H NMR (500 MHz, MeOD) δ 7.61 (s, 2H), 7.54 (s, 2H), 7.18 (s, 2H).

Example 67: 4-chloro-6-phenyl-1H-indole-2-carboxylic acid, I-48

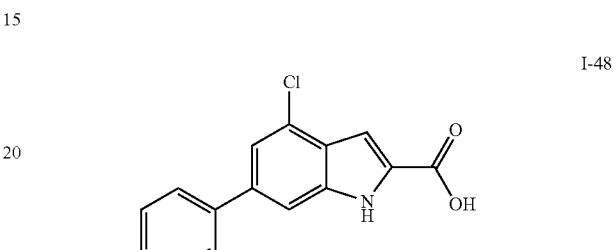

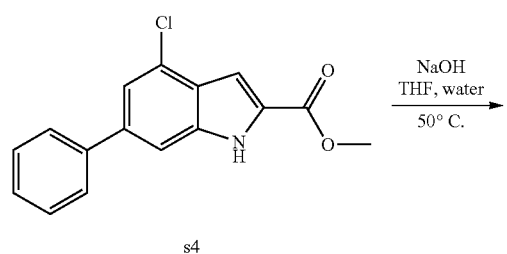

-continued

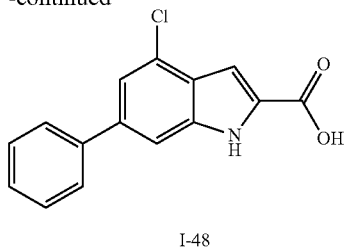

I-48

Procedures and Characterization:

Step 1: (Z)-methyl 2-azido-3-(4-bromo-2-chloro-phenyl)acrylate

The same procedure used to prepare b3 afforded (Z)-methyl 2-azido-3-(4-bromo-2-chlorophenyl)acrylate (5.8 g, 18 mmol, 67%) as a white solid. ESI-MS (EI+, m/z).

Step 2: methyl 6-bromo-4-chloro-1H-indole-2-carboxylate

The same procedure used to prepare a4 to afford to afford methyl 6-bromo-4-chloro-1H-indole-2-carboxylate as a white solid (44%). ESI-MS (EI+, m/z): 287 [M+H]$^+$.

Step 3: methyl 4-chloro-6-phenyl-1H-indole-2-carboxylate

The same procedure used to prepare methyl 6-chloro-4-phenyl-1H-indole-2-carboxylate (j18) afforded the crude product (160 mg), which was used directly for the next step without further purification. ESI-MS (m/z): 286 [M+H]$^+$.

Step 4: 4-chloro-6-phenyl-1H-indole-2-carboxylic acid, I-48

The same procedure used to prepare I-54 afforded 4-chloro-6-phenyl-1H-indole-2-carboxylic acid I-48 as a white solid (9.3 mg, 0.04 mmol, 14%). ESI-MS (EI+, m/z): 272 [M+H]$^+$. $^1$H NMR (500 MHz, MeOD) δ 7.67 (d, 2H, J=9.5 Hz), 7.64 (s, 1H), 7.45-7.49 (t, 2H, J=9.5 Hz), 7.42 (s, 1H), 7.35-7.39 (t, 1H, J=9 Hz), 7 7.20 (s, 1H).

Example 68: 4-chloro-6-(3,5-dichlorophenyl)-1H-indole-2-carboxylic acid, I-47

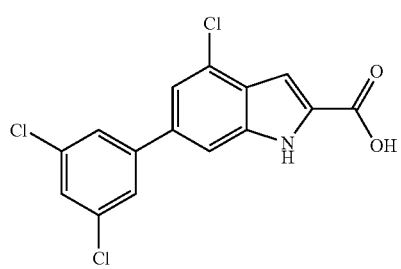

I-47

Synthetic Scheme:

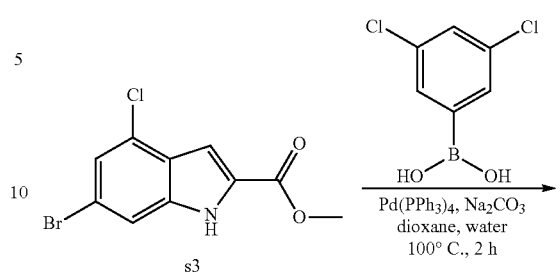

Procedures and Characterization:

Step 1: methyl 4-chloro-6-(3,5-dichlorophenyl)-1H-indole-2-carboxylate

The same procedure used to prepare methyl 6-chloro-4-phenyl-1H-indole-2-carboxylate (j18) afforded the crude product (160 mg), which was used directly for the next step without further purification.

Step 2: 4-chloro-6-(3,5-dichlorophenyl)-1H-indole-2-carboxylic acid, I-47

The same procedure used to prepare I-54 afforded 4-chloro-6-(3,5-dichlorophenyl)-1H-indole-2-carboxylic acid I-47 as a white solid (4.6 mg, 0.02 mmol, 9%). $^1$H NMR (500 MHz, DMSO) δ 12.18 (br, 1H), 7.75 (s, 2H), 7.62 (s, 2H), 7.53 (s, 1H), 7.00 (s, 1H).

Example 69: 6-chloro-4-(4-cyclohexylphenoxy)-1H-indole-2-carboxylic acid, I-125

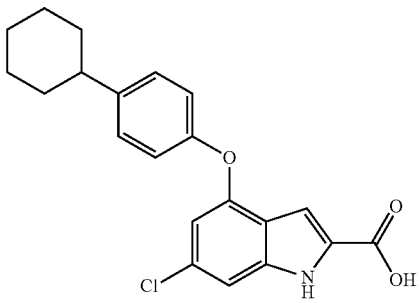

Synthetic Scheme:

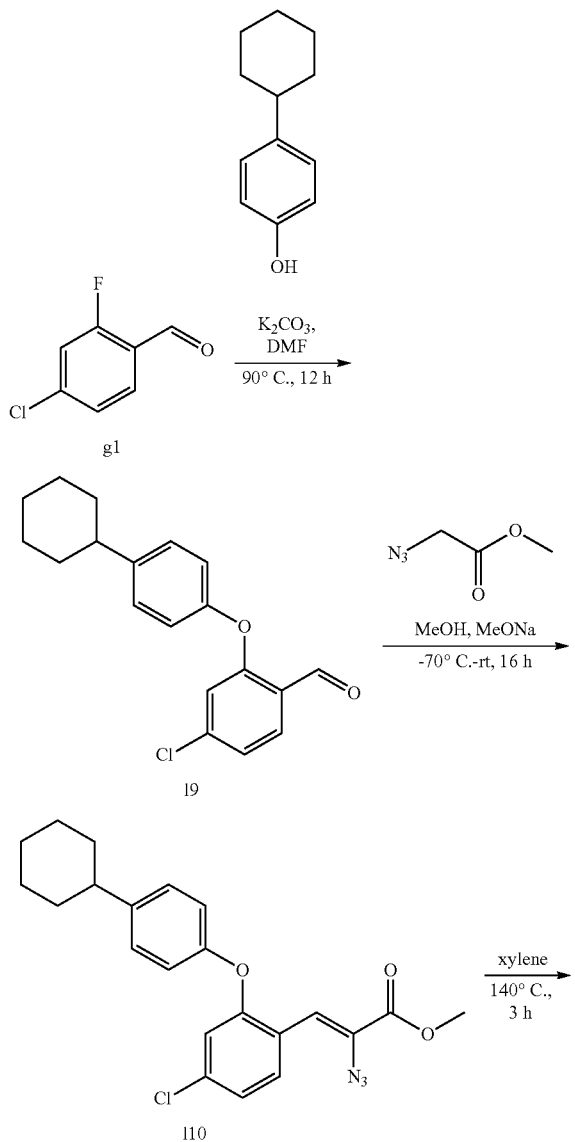

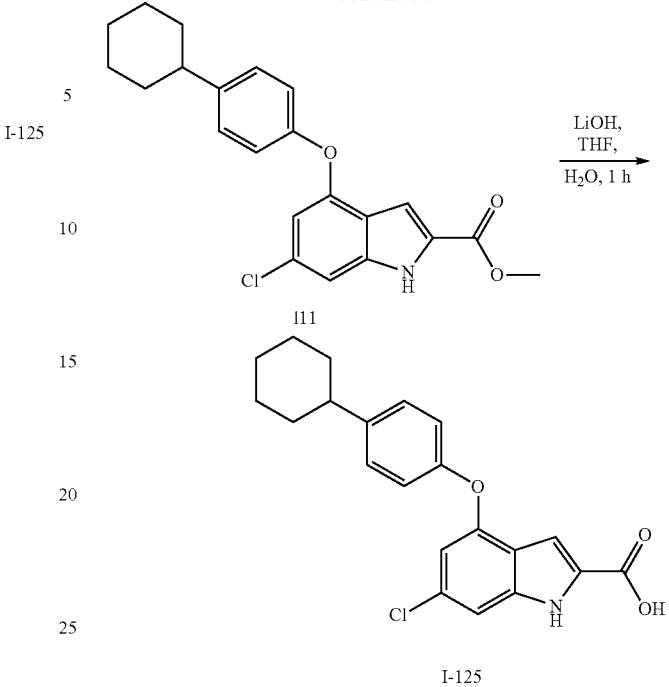

Procedures and Characterization:

Step 1: 4-chloro-2-(4-cyclohexylphenoxy)benzaldehyde

To a solution of 4-chloro-2-fluorobenzaldehyde (2.0 g, 12.66 mmol) and 4-cyclohexylphenol (2.23 g, 12.66 mmol) in DMF (20 mL) was added $K_2CO_3$ (3.5 g, 25.32 mmol). The mixture was stirred at 90° C. for 12 h. The reaction was diluted with water (100 ml), extracted by EtOAc (200 ml). The organic layer was dried, concentrated to give the crude product, purified by SGC (eluting with 0-50% EtOAc in PE) to afford 4-chloro-2-(4-cyclohexylphenoxy)benzaldehyde (3.2 g, 80%) as a white solid. ESI-MS (EI$^+$, m/z): 315.0[M+H]$^+$.

Step 2: (Z)-methyl 2-azido-3-(4-chloro-2-(4-cyclohexylphenoxy)phenyl)acrylate To a solution of 4-chloro-2-(4-cyclohexylphenoxy)benzaldehyde (928 mg, 2.95 mmol) and MeONa (795 mg, 14.73 mmol) in MeOH (15 mL) was added methyl 2-azidoacetate (1.36 g, 11.8 mmol) at −70° C., then stirred at rt for 16 h. The reaction was quenched with saturated $NH_4Cl$ solution, concentrated to remove MeOH, extracted with EtOAc, washed with brine, dried over sodium sulfate and concentrated to afford the crude product which was purified by SGC (eluting with 0-5% EtOAc in PE) to afford (Z)-methyl 2-azido-3-(4-chloro-2-(4-cyclohexylphenoxy)phenyl)acrylate (0.8 g, 66%) as a yellow solid.

MS (EI+, m/z): 434.0[M+Na]$^+$.

Step 3: methyl 6-chloro-4-(4-cyclohexylphenoxy)-1H-indole-2-carboxylate

A solution of (Z)-methyl 2-azido-3-(4-chloro-2-(4-cyclohexylphenoxy)phenyl)acrylate (0.7 g, 1.7 mmol) in xylene (20 mL) was stirred at 140° C. for 3 h, the reaction solution was cooled to rt, filtered and triturated with PE to afford methyl 6-chloro-4-(4-cyclohexylphenoxy)-1H-indole-2-carboxylate (0.45 g, 60%) as a yellow solid.

MS (EI+, m/z): 406.0[M+Na]+.

Step 4: 6-chloro-4-(4-cyclohexylphenoxy)-1H-indole-2-carboxylic acid, I-125

To a solution of methyl 6-chloro-4-(4-cyclohexylphenoxy)-1H-indole-2-carboxylate (100 mg, 0.261 mmol) in THF/H$_2$O (6 mL, 2:1) was added LiOH.H$_2$O (23 mg, 0.522 mmol) at 0° C. The reaction was allowed to rt and stirred for 1 h. The reaction was quenched with ice-water, the pH adjusted to 5 with 1N HCl aqueous solution, extracted with EtOAc, washed with brine, dried over Na$_2$SO$_4$, and purified by prep-HPLC to afford 6-chloro-4-(4-cyclohexylphenoxy)-1H-indole-2-carboxylic acid I-125 (67 mg) as a white solid.

MS (EI+, m/z): 370.0[M+H]+.

$^1$H NMR (500 MHz, MeOD) δ 13.1 (s, 1H), 12.1 (s, 1H), 7.27 (d, J=8.5 Hz, 2H), 7.19 (s, 1H), 7.03 (d, J=8.5 Hz, 2H), 6.83 (d, J=1.5 Hz, 2H), 6.45 (d, J=1.5 Hz, 2H), 1.79-1.69 (m, 5H), 1.41-1.35 (m, 4H), 1.24-1.22 (m, 1H).

Example 70: 6-chloro-4-(2-oxo-1,2,3,4-tetrahydroquinolin-7-yloxy)-1H-indole-2-carboxylic acid, I-108

I-108

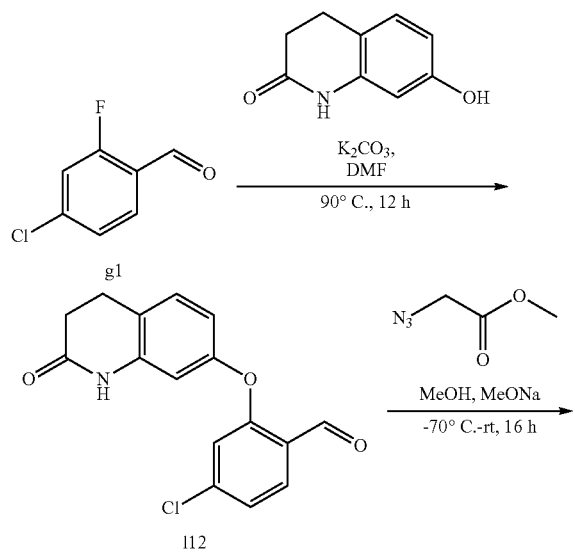

Synthetic Scheme:

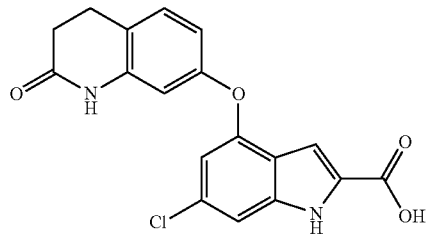

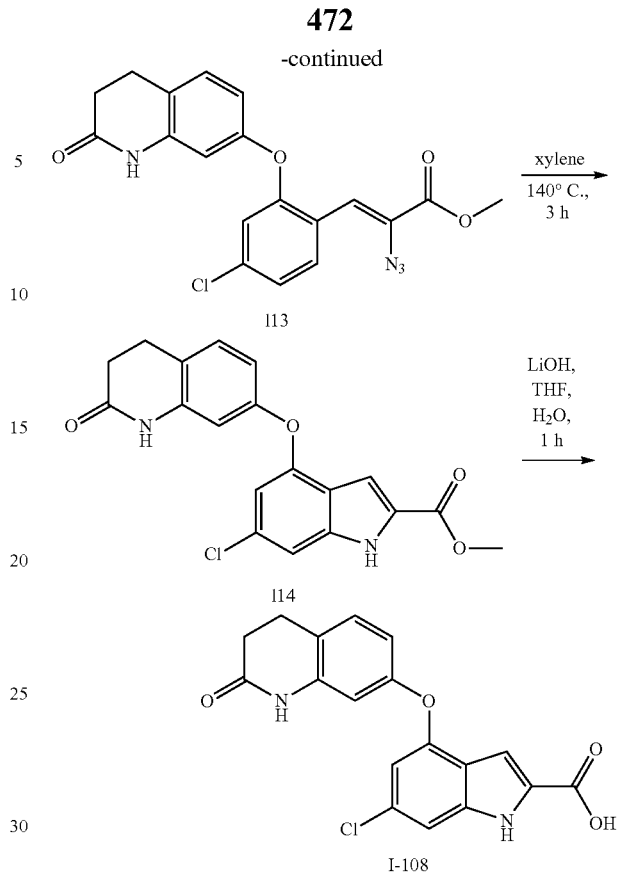

Procedures and Characterization:

Step 1: 4-chloro-2-(2-oxo-1,2,3,4-tetrahydroquinolin-7-yloxy)benzaldehyde

The same procedure used to prepare 4-chloro-2-(4-cyclohexylphenoxy)benzaldehyde (19) afforded 4-chloro-2-(2-oxo-1,2,3,4-tetrahydroquinolin-7-yloxy)benzaldehyde (1.5 g, 40%) as a white solid. ESI-MS (EI+, m/z): 302.0[M+H]+.

Step 2: (Z)-methyl 2-azido-3-(4-chloro-2-(2-oxo-1,2,3,4-tetrahydroquinolin-7-yloxy)phenyl)acrylate The same procedure used to prepare (Z)-methyl 2-azido-3-(4-chloro-2-(4-cyclohexylphenoxy)phenyl)acrylate (110) afforded (Z)-methyl 2-azido-3-(4-chloro-2-(2-oxo-1,2,3,4-tetrahydroquinolin-7-yloxy)phenyl)acrylate (32%) as a yellow solid. MS (EI+, m/z): 421.0[M+Na]+.

Step 3: methyl 6-chloro-4-(2-oxo-1,2,3,4-tetrahydroquinolin-7-yloxy)-1H-indole-2-carboxylate The same procedure used to prepare (methyl 6-chloro-4-(4-cyclohexylphenoxy)-1H-indole-2-carboxylate (111) afforded methyl 6-chloro-4-(2-oxo-1,2,3,4-tetrahydroquinolin-7-yloxy)-1H-indole-2-carboxylate (0.12 g, 59%) as a yellow solid.

MS (EI+, m/z): 371.0[M+H]+.

Step 4: 6-chloro-4-(2-oxo-1,2,3,4-tetrahydroquinolin-7-yloxy)-1H-indole-2-carboxylic acid, I-108

The same procedure used to prepare I-125 afforded 6-chloro-4-(2-oxo-1,2,3,4-tetrahydroquinolin-7-yloxy)-1H-indole-2-carboxylic acid I-108 (26 mg) as a white solid.

MS (EI+, m/z): 357.0[M+H]+.

¹H NMR (500 MHz, DMSO) δ 12.1 (s, 1H), 10.0 (s, 1H), 7.21 (t, J=10 Hz, 2H), 6.86 (d, J=1.5 Hz, 11H), 6.68 (dd, J1=2.5 Hz, J2=2.5 Hz 1H), 6.58 (d, J=2.5 Hz, 1H), 6.53 (d, J=2.5 Hz, 1H), 2.88-2.85 (m, 2H), 2.49-2.45 (m, 2H).

Example 71: 6-chloro-4-(4-methyl-3-(trifluoromethyl)phenoxy)-1H-indole-2-carboxylic acid, I-81

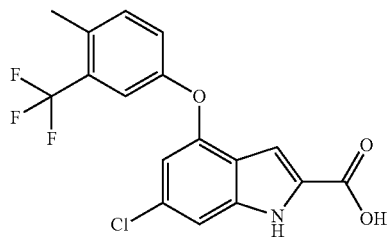

Synthetic Scheme:

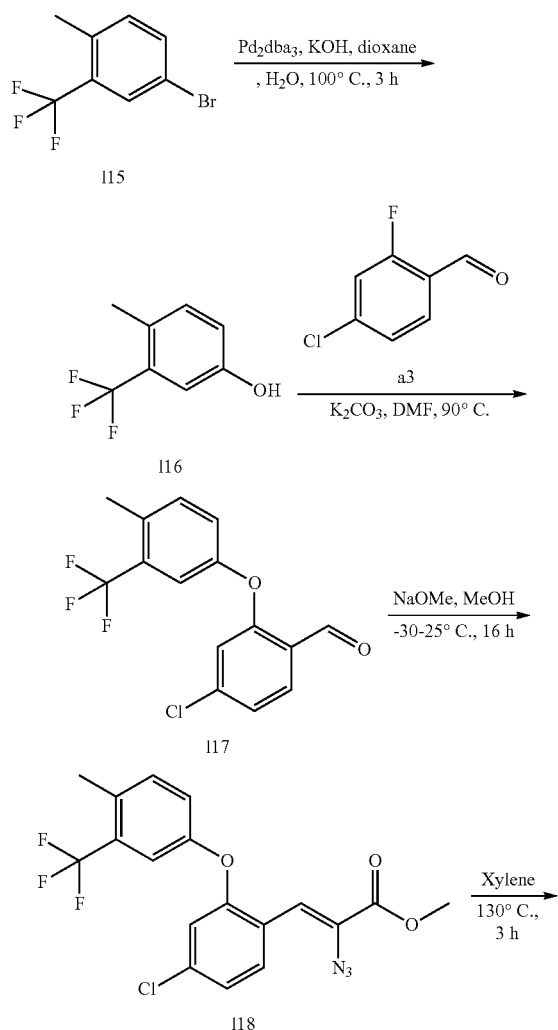

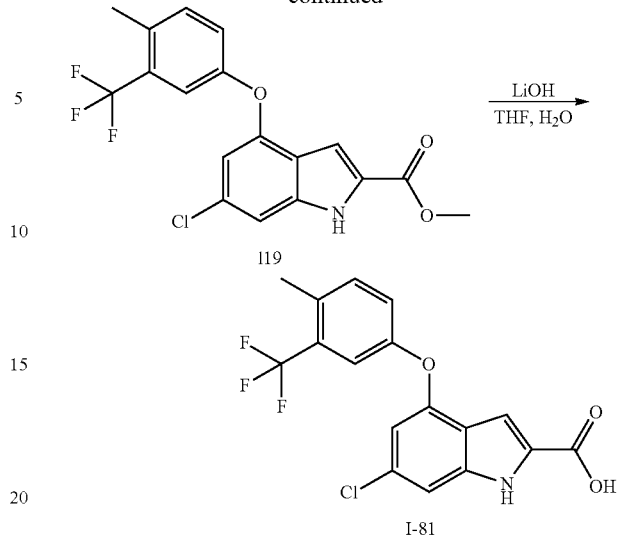

Procedures and Characterization:

Step 1: 4-Methyl-3-(trifluoromethyl)phenol

To a solution of 4-bromo-1-methyl-2-(trifluoromethyl)benzene (6 g, 25.1 mmol), 2-Di-t-butylphosphino-2',4',6'-tri-1-propyl-1,1'-biphenyl (848 mg, 2.0 mmol), Pd₂dba₃ (4.6 g, 5.0 mmol) and KOH (4.2 g, 75.3 mmol) in dioxane (40 mL) and water (40 mL) under N₂. The mixture was stirred at 100° C. for 2.5 h. The reaction was quenched with ice-water, the pH adjusted to 5 with 1N HCl aqueous solution, extracted with EtOAc, washed with brine, dried over sodium sulfate, concentrated and purified by chromatography (silica, DCM/petroleum ether=1/2) to afford 4-methyl-3-(trifluoromethyl)phenol (3.5 g, 79%) as a white solid. ESI-MS (EI⁺, m/z): No mass Step 2: 4-Chloro-2-(4-methyl-3-(trifluoromethyl)phenoxy)benzaldehyde The same procedure used to prepare 4-chloro-2-(4-cyclohexylphenoxy)benzaldehyde (19) afforded 4-chloro-2-(4-methyl-3-(trifluoromethyl)phenoxy)benzaldehyde (2.9 g, 46.8%) as a yellow solid. ESI-MS (EI⁺, m/z): 315.0 [M+H]⁺.

Step 3: (Z)-Methyl 2-azido-3-(4-chloro-2-(4-methyl-3-(trifluoromethyl)phenoxy)phenyl)acrylate The same procedure used to prepare 4-chloro-2-(4-cyclohexylphenoxy)benzaldehyde (110) to afford (Z)-methyl 2-azido-3-(4-chloro-2-(4-methyl-3-(trifluoromethyl)phenoxy)phenyl)acrylate (1.5 g, 39.4%) as a yellow solid. MS (EI+, m/z): 434.0[M+Na]⁺.

Step 4: Methyl 6-chloro-4-(4-methyl-3-(trifluoromethyl)phenoxy)-1H-indole-2-carboxylate The same procedure used to prepare 4-chloro-2-(4-cyclohexylphenoxy)benzaldehyde (19) afforded methyl 6-chloro-4-(4-methyl-3-(trifluoromethyl)phenoxy)-1H-indole-2-carboxylat (1.1 g, 78.5%) as a white solid. MS (EI+, m/z): 384.0 [M+H]⁺.

Step 5: 6-Chloro-4-(4-methyl-3-(trifluoromethyl) phenoxy)-1H-indole-2-carboxylic acid, I-81

The same procedure used to prepare I-125 afforded 6-chloro-4-(4-methyl-3-(trifluoromethyl)phenoxy)-1H-indole-2-carboxylic acid I-81 (61 mg, 22.7%) as a white solid. The reaction time was 17 h. MS (EI+, m/z): 368.0 [M−H]+. 1H NMR (500 MHz, MeOD-d4) δ 7.36 (d, J=8.4 Hz, 1H), 7.33-7.22 (m, 2H), 7.19-7.07 (m, 1H), 6.75 (s, 1H), 6.57 (d, J=1.4 Hz, 1H), 2.47 (s, 3H).

Example 72: 6-chloro-4-(isoquinolin-5-yloxy)-1H-indole-2-carboxylic acid, I-41

I-41

Synthetic Scheme:

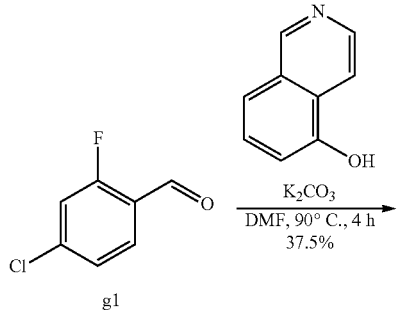

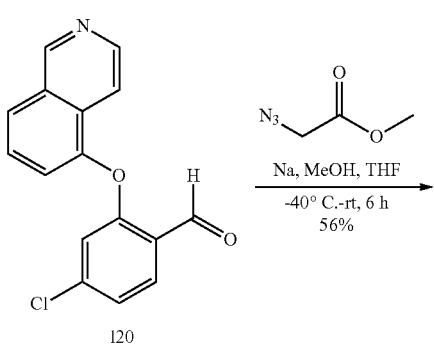

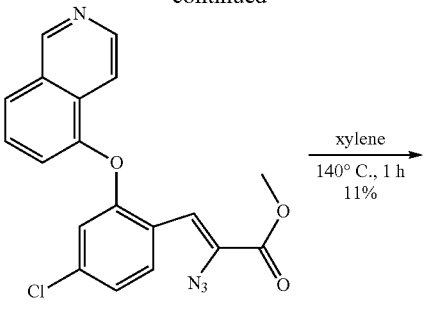

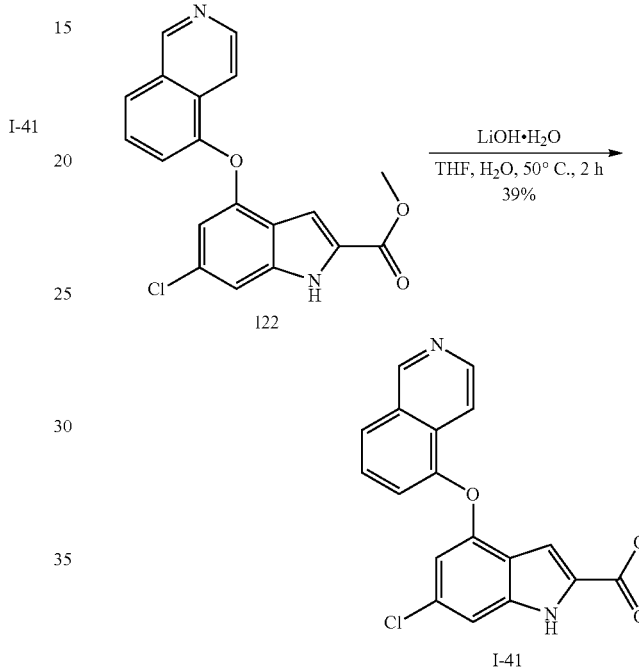

Procedures and Characterization:

Step 1:
4-chloro-2-(isoquinolin-5-yloxy)benzaldehyde

The same procedure used to prepare 4-chloro-2-(4-cyclohexylphenoxy)benzaldehyde (19) afforded 4-chloro-2-(isoquinolin-5-yloxy)benzaldehyde (1.35 g, 4.8 mmol, 37.5% yield) as a yellow solid. ESI-MS (EI+, m/z): 284.1 [M+H]−.

Step 2: (Z)-methyl 2-azido-3-(4-chloro-2-(isoquinolin-5-yloxy)phenyl)acrylate

Na (0.438 g, 19.03 mmol) was dissolved in dry MeOH (40 mL). A mixture of 4-chloro-2-(isoquinolin-5-yloxy)benzaldehyde (1.35 g, 4.76 mmol) and methyl 2-azidoacetate (2.19 g, 19.03 mmol) in dry THF (5 mL) was added at −40° C. The reaction was stirred at −40° C. for 30 min, then stirred at 10° C. for 1 h under N2 atmosphere. The suspension was filtrated, and the cake was washed with MeOH (3 mL), then dried in vacuo to afford (Z)-methyl 2-azido-3-(4-chloro-2-(isoquinolin-5-yloxy)phenyl)acrylate (1.01 g, 2.6 mmol, 56% yield) as a white solid. ESI-MS (EI+, m/z): 381.0 [M+H]−

Step 3: methyl 6-chloro-4-(isoquinolin-5-yloxy)-1H-indole-2-carboxylate

The same procedure used to prepare a4 is to afford methyl 6-chloro-4-(isoquinolin-5-yloxy)-1H-indole-2-carboxylate (60 mg, 0.17 mmol, 11% yield) as a white solid. ESI-MS (EI+, m/z): 353.0 [M+H]+

Step 4: 6-chloro-4-(isoquinolin-5-yloxy)-1H-indole-2-carboxylic acid, I-41

A mixture of methyl 6-chloro-4-(isoquinolin-5-yloxy)-1H-indole-2-carboxylate (55 mg, 0.156 mmol), LiOH.H$_2$O (67 mg, 1.56 mmol), THF (8 mL) and H$_2$O (2 mL) was kept stirring at 50° C. for 2 h. The mixture was removed the solvent. The residue was dissolved in H$_2$O (15 mL), adjusted pH to 4 with 1N HCl, extracted with EtOAc (15 mL×2). The organic layer was concentrated, the residue was purified by prep-HPLC to afford 6-chloro-4-(isoquinolin-5-yloxy)-1H-indole-2-carboxylic acid I-41 (20 mg, 0.06 mmol, 39% yield) as a white solid. ESI-MS (EI+, m/z): 339.1 [M+H]+

$^1$H NMR (400 MHz, DMSO-d6) δ 11.56 (s, 1H), 9.41 (s, 1H), 8.57 (d, J=5.8 Hz, 1H), 7.96 (dd, J=19.1, 7.1 Hz, 2H), 7.61 (t, J=7.9 Hz, 1H), 7.30-7.15 (m, 2H), 6.60 (d, J=1.4 Hz, 1H), 6.33 (s, 1H).

Example 73: 6-chloro-4-phenoxy-1H-indole-2-carboxylic acid, I-175

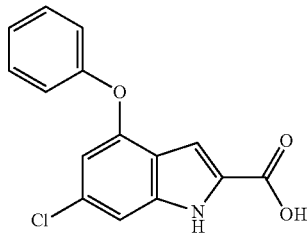

I-175

Synthetic Scheme:

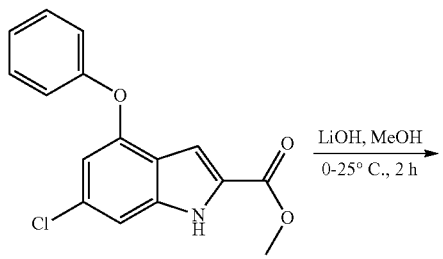

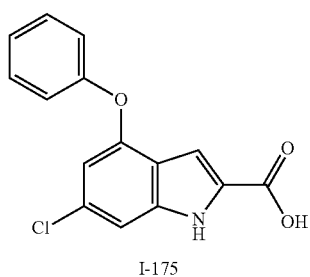

I-175

Procedures and Characterization:

The same as prepared I-41 afforded 6-chloro-4-phenoxy-1H-indole-2-carboxylic acid I-175 as a white solid. ESI-MS (EI+, m/z): 288, $^1$H NMR (500 MHz, DMSO-d$_6$) δ 13.18 (s, 1H), 12.10 (s, 1H), 7.47-7.38 (m, 2H), 7.24-7.18 (m, 2H), 7.15-7.06 (m, 2H), 6.80 (d, J=1.5 Hz, 1H), 6.51 (d, J=1.6 Hz, 1H).

Example 74: 6-Chloro-4-(2,5-dichlorophenoxy)-1H-indole-2-carboxylic acid, I-172

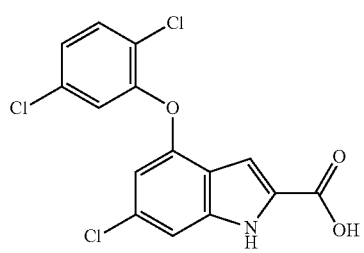

I-172

Synthetic Scheme:

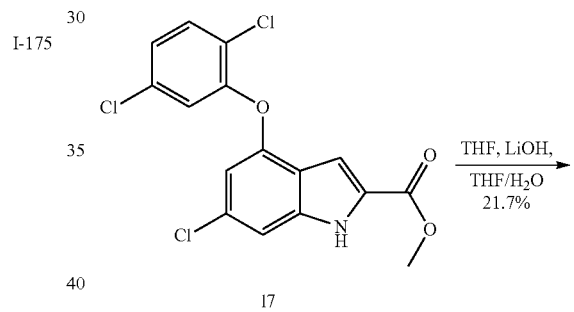

I7

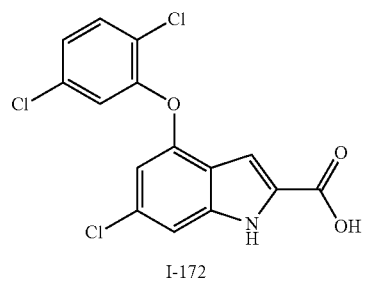

I-172

Procedures and Characterization:

Step 1: 6-Chloro-4-(2,5-dichlorophenoxy)-1H-indole-2-carboxylic acid, I-172

The same as prepared I-102 afforded 6-chloro-4-(2,5-dichlorophenoxy)-1H-indole-2-carboxylic acid I-172 (73 mg, 21.7%) as a white solid. MS (EI+, m/z): No mass $^1$H NMR (500 MHz, DMSO) δ 7.67 (d, J=8.6 Hz, 1H), 7.36-7.26 (m, 2H), 7.05 (d, J=2.0 Hz, 1H), 6.60 (d, J=1.4 Hz, 1H), 6.35 (s, 1H).

Example 75: 6,7-dichloro-4-(4-chlorobenzyloxy)-1H-indole-2-carboxylic acid, I-60

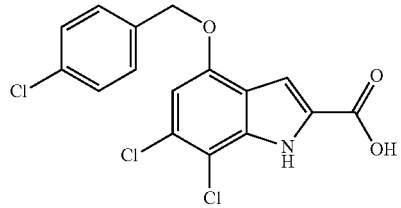

I-60

Synthetic Scheme:

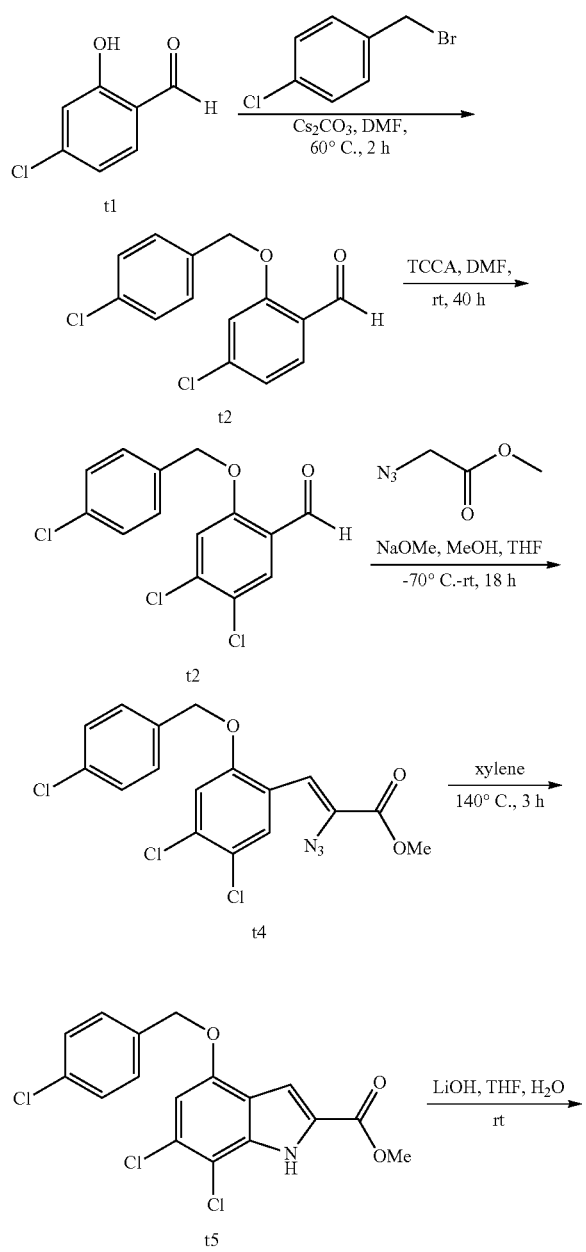

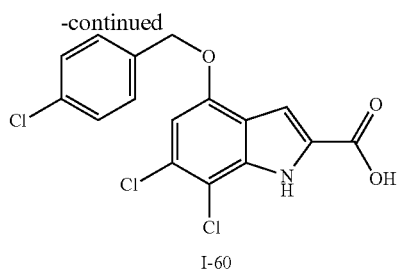

I-60

Procedures and Characterization:

Step 1: 4-chloro-2-(4-chlorobenzyloxy)benzaldehyde $Cs_2CO_3$ (1.96 g, 6 mmol) was added to a solution of 4-chloro-2-hydroxybenzaldehyde (468 mg, 3 mmol) and 1-(bromomethyl)-4-chlorobenzene (800 mg, 3.9 mmol) in DMF (5 ml) was stirred at 60° C. for 2 h. The reaction mixture was cooled, extracted with EtOAc, washed with water and brine, dried, concentrated, purified by SGC (PE:EtOAc=50:1) to afford 4-chloro-2-(4-chlorobenzyloxy)benzaldehyde (800 mg, 96% yield) as a white solid.

ESI-MS (EI$^+$, m/z): no MS.

$^1$H NMR (500 MHz, CDCl$_3$) δ 10.43 (s, 1H), 7.80 (d, J=5.25 Hz, 1H), 7.41-7.36 (m, 4H), 7.05 (d, J=5.0 Hz, 2H), 5.14 (s, 2H).

Step 2: 4,5-dichloro-2-(4-chlorobenzyloxy)benzaldehyde

TCCA (302 mg, 1.3 mmol) was added to a solution of 4-chloro-2-(4-chlorobenzyloxy) benzaldehyde (520 mg, 1.86 mmol) in DMF (4 ml) at room temperature and stirred for 40 h. The reaction mixture was extracted with EtOAc, washed with brine, dried, concentrated, purified by SGC (PE:EtOAc=40:1) to afford 4,5-dichloro-2-(4-chlorobenzyloxy)benzaldehyde (480 mg, 82% yield).

ESI-MS (EI$^+$, m/z): 336.9 [M+Na]$^+$.

$^1$H NMR (500 MHz, DMSO) δ 10.38 (s, 1H), 7.90 (s, 1H), 7.41-7.35 (m, 4H), 7.16 (s, 1H), 5.13 (s, 2H).

Step 3: (Z)-methyl 2-azido-3-(4,5-dichloro-2-(4-chlorobenzyloxy)phenyl)acrylate The same as prepared a3 afforded (Z)-methyl 2-azido-3-(4,5-dichloro-2-(4-chlorobenzyloxy)phenyl)acrylate (350 mg, 56% yield), used for next step.

ESI-MS (EI$^+$, m/z): no MS.

$^1$H NMR (500 MHz, DMSO) δ 8.31 (d, J=6.25 Hz, 1H), 7.48 (t, J=8.75 Hz, 5H), 7.10 (d, J=3.75 Hz, 1H), 5.26 (d, J=3.5 Hz, 2H), 3.85 (t, J=3.75 Hz, 3H).

Step 4: methyl 6,7-dichloro-4-(4-chlorobenzyloxy)-1H-indole-2-carboxylate

The same as prepared a4 afforded methyl 6,7-dichloro-4-(4-chlorobenzyloxy)-1H-indole-2-carboxylate (200 mg, 67% yield). ESI-MS (EI$^+$, m/z): 382.0 [M−H]$^-$.

Step 5: 6,7-dichloro-4-(4-chlorobenzyloxy)-1H-indole-2-carboxylic acid, I-60

The same as prepared I-102 afforded 6,7-dichloro-4-(4-chlorobenzyloxy)-1H-indole-2-carboxylic acid I-60 (25.7 mg, 27% yield). ESI-MS (EI+, m/z): 368.0 [M–H]−. H NMR (500 MHz, DMSO) δ13.22 (s, 1H), 12.21 (s, 1H), 7.54 (d, J=5.25 Hz, 2H), 7.48 (d, J=5.25 Hz, 2H), 7.17 (s, 1H), 6.90 (s, 1H), 5.28 (s, 2H).

Example 76: 6-chloro-4-phenoxy-1H-indole-2-carboxamide, I-169

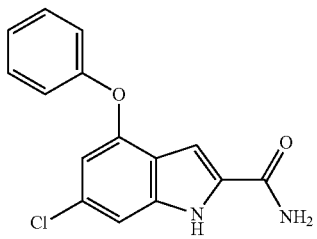

Synthetic Scheme:

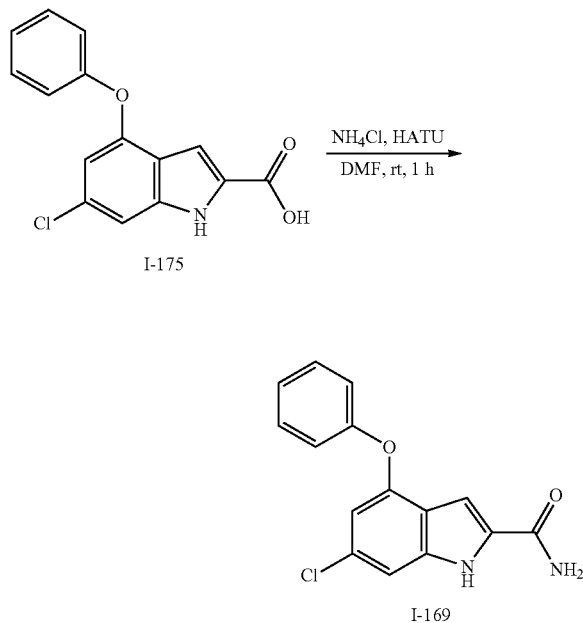

Procedures and Characterization:

Step 1: 6-chloro-4-phenoxy-1H-indole-2-carboxamide, I-169

The solution of 6-chloro-4-phenoxy-1H-indole-2-carboxylic acid, I-175, (100 mg, 0.35 mmol), NH₄Cl (37.3 mg, 0.7 mmol), HATU (146 mg, 0.385 mmol) and DIPEA (0.2 mL, 1.05 mmol) in DMF (2.0 mL) was stirred at rt for 1 h, then filtered and purified by prep-HPLC to obtain I-169 as a white solid. ESI-MS (EI+, m/z): 287, ¹H NMR (500 MHz, DMSO-d₆) δ 11.87 (s, 1H), 8.00 (s, 1H), 7.49-7.35 (m, 3H), 7.29-7.01 (m, 5H), 6.44 (d, J=1.6 Hz, 1H).

Example 77: 6-chloro-4-(2,4-dichlorophenylthio)-N-(3-fluoro-4-(4-methyl-1,4-diazepan-1-yl)phenyl)-1H-indole-2-carboxamide, I-93

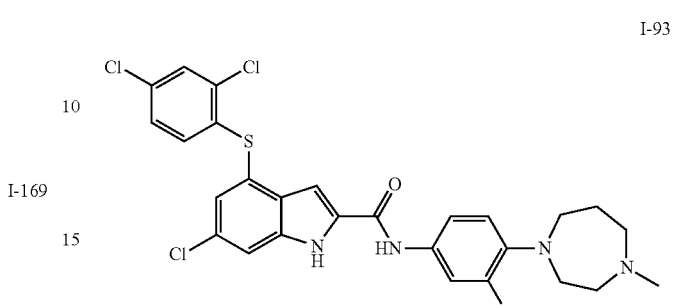

Synthetic Scheme:

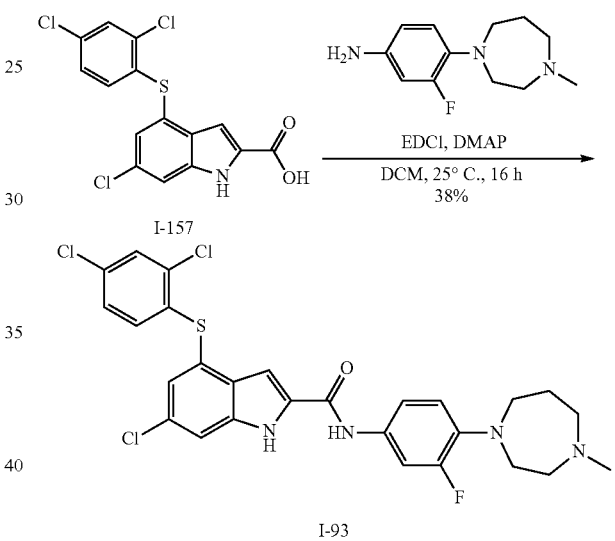

Procedures and Characterization:

Step 1: 6-chloro-4-(2,4-dichlorophenylthio)-N-(3-fluoro-4-(4-methyl-1,4-diazepan-1-yl)phenyl)-1H-indole-2-carboxamide, I-93

A mixture of crude 6-chloro-4-(2,4-dichlorophenylthio)-1H-indole-2-carboxylic acid, I-157, (100 mg, 0.27 mmol), 3-fluoro-4-(4-methyl-1,4-diazepan-1-yl)benzenamine (120 mg, 0.54 mmol), EDCI (110 mg, 0.54 mmol), DMAP (70 mg, 0.54 mmol) in DCM (10 mL) was stirred for 16 h at rt. The reaction was quenched with water (20 mL) and extracted with DCM (20 mL). The organic phase was washed with brine (30 mL), dried (Na₂SO₄), filtered and concentrated in vacuo, purified by prep-HPLC (0.01% TFA) to afford 6-chloro-4-(2,4-dichlorophenylthio)-N-(3-fluoro-4-(4-methyl-1,4-diazepan-1-yl)phenyl)-1H-indole-2-carboxamide (TFA salt) I-93 (58.6 mg, 0.085 mmol, 16%) as a white solid. ESI-MS (EI+, m/z): 577.2 [M+H]−. ¹H NMR (500 MHz, DMSO) δ 12.29 (s, 1H), 10.35 (s, 1H), 9.64 (s, 1H1), 7.77 (d, J=2.5 Hz, 1H), 7.69 (dd, J=15 Hz, J=2 Hz, 1H), 7.62 (s, 2H), 7.43 (dd, J=10.5 Hz, J=1.5 Hz, 1H), 7.4

(s, 1H), 7.30-7.28 (m, 2H), 7.01 (q, J=5.5 Hz, 1H), 6.70 (d, J=9 Hz, 1H), 3.57-3.19 (m, 8H), 2.89 (d, J=3.5 Hz, 3H), 2.18-2.13 (m, 2H).

Example 78: 6-chloro-N-(3-chloro-4-(piperazin-1-yl)phenyl)-4-(2,4-dichlorophenylthio)-1H-indole-2-carboxamide, I-105

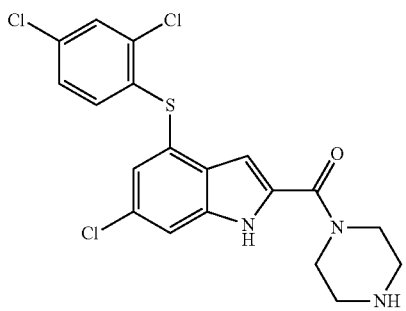

Synthetic Scheme:

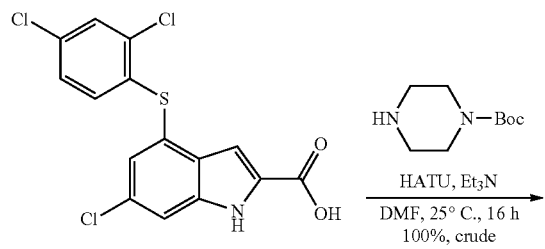

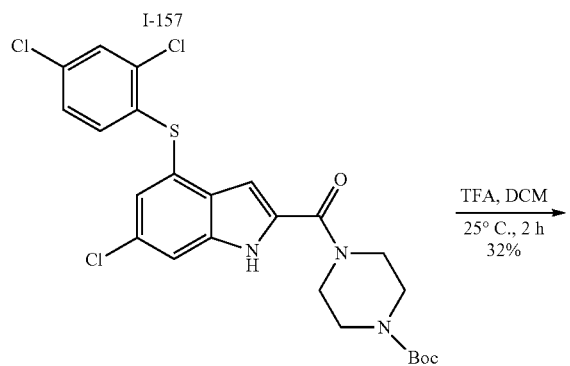

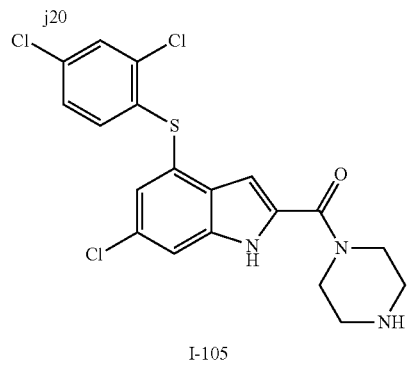

Procedures and Characterization:

Step 1: 6-chloro-4-(2,4-dichlorophenylthio)-1H-indole-2-carboxylic acid

A mixture of 6-chloro-4-(2,4-dichlorophenylthio)-1H-indole-2-carboxylic acid (150 mg, 0.4 mmol), tert-butyl piperazine-1-carboxylate (149 mg, 0.8 mmol), HATU (304 mg, 0.8 mmol), Et₃N (202 mg, 2 mmol) in DMF (5 mL) was stirred for 16 h at rt. The reaction was quenched with water (10 mL) and extracted with ethyl acetate (20 mL). The organic phase was washed water (10 mL×2), and brine (10 mL), dried (Na₂SO₄), filtered and concentrated in vacuo to afford crude tert-butyl 4-(6-chloro-4-(2,4-dichlorophenylthio)-1H-indole-2-carbonyl)piperazine-1-carboxylate (216 mg, 0.4 mmol, 100%) as a brown oil. ESI-MS (EI+, m/z): 440.1 [M-100+H]⁺.

Step 2: (6-chloro-4-(2,4-dichlorophenylthio)-1H-indol-2-yl)(piperazin-1-yl)methanone, I-105

A mixture of crude tert-butyl 4-(6-chloro-4-(2,4-dichlorophenylthio)-1H-indole-2-carbonyl)piperazine-1-carboxylate (216 mg, 0.4 mmol) in TFA (10 mL) and DCM (10 mL) was stirred for 2 h at rt. The reaction was concentrated and the residue was purified by prep-HPLC (0.01% TFA) to afford (6-chloro-4-(2,4-dichlorophenylthio)-1H-indol-2-yl)(piperazin-1-yl)methanone (TFA salt) I-105 (71.7 mg, 0.13 mmol, 32%) as a white solid. ESI-MS (EI+, m/z): 440.0 [M+H]⁺. ¹H NMR (500 MHz, DMSO) δ 12.19 (s, 1H), 9.00 (s, 1H), 7.76 (d, J=2.5 Hz, 1H), 7.57 (s, 1H), 7.32 (dd, J=8 Hz, J=2 Hz, 1H), 7.19 (d, J=1.5 Hz, 1H), 6.89 (d, J=9 Hz, 1H), 6.71 (s, 1H), 3.87 (s, 4H), 3.19 (t, J=5 Hz, 4H).

Example 79: 6-chloro-N-(3-chloro-4-(4-methylpiperazin-1-yl)phenyl)-4-(2,4-dichlorophenylthio)-1H-indole-2-carboxamide, I-111

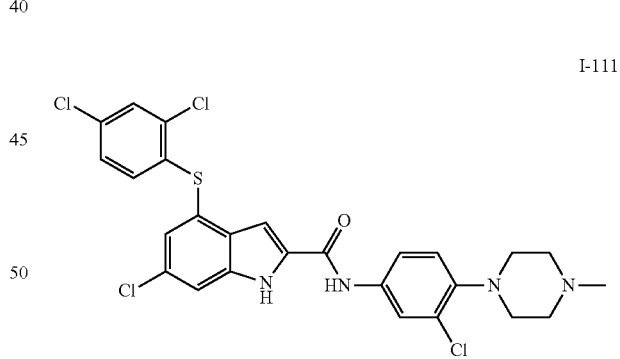

Synthetic Scheme:

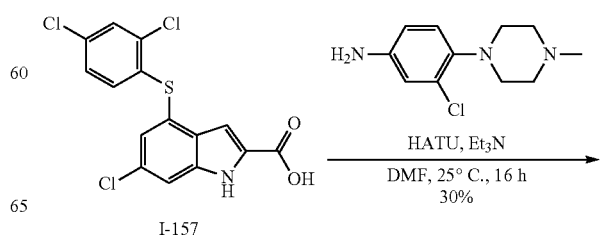

-continued

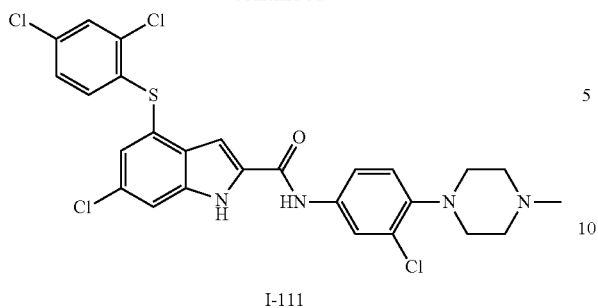

I-111

Procedures and Characterization:

Step 1: 6-chloro-N-(3-chloro-4-(4-methylpiperazin-1-yl)phenyl)-4-(2,4-dichlorophenylthio)-1H-indole-2-carboxamide, I-111

A mixture of 6-chloro-4-(2,4-dichlorophenylthio)-1H-indole-2-carboxylic acid (100 mg, 0.27 mmol), 3-chloro-4-(4-methylpiperazin-1-yl)benzenamine (122 mg, 0.54 mmol), HATU (156 mg, 0.41 mmol), Et$_3$N (136 mg, 1.35 mmol) in DMF (5 mL) was stirred for 16 h at rt. The reaction was quenched with water (10 mL) and extracted with ethyl acetate (20 mL). The organic phase was washed water (10 mL×2), and brine (10 mL), dried (Na$_2$SO$_4$), filtered and concentrated in vacuo and the residue was purified by prep-HPLC (0.01% TFA) to afford 6-chloro-N-(3-chloro-4-(4-methylpiperazin-1-yl)phenyl)-4-(2,4-dichlorophenylthio)-1H-indole-2-carboxamide (TFA salt) I-111 (56.0 mg, 0.08 mmol, 30%) as a white solid. ESI-MS (EI+, m/z): 581.0 [M+H]$^+$. $^1$H NMR (500 MHz, DMSO) δ 12.32 (d, J=1.5 Hz, 1H), 10.41 (s, 1H), 9.86 (s, 1H), 7.96 (d, J=2.5 Hz, 1H), 7.77 (d, J=2.5 Hz, 1H), 7.71 (dd, J=8.5 Hz, J=2 Hz, 1H), 7.63 (s, 1H), 7.31-7.25 (m, 3H), 6.72 (d, J=8.5 Hz, 1H), 3.52 (s, 2H), 3.49 (s, 2H), 3.24 (s, 2H), 3.00 (s, 2H), 2.88 (s, 3H).

Example 80: 6-chloro-N-(3-cyano-4-(4-methylpiperazin-1-yl)phenyl)-4-(2,4-dichlorophenylthio)-1H-indole-2-carboxamide, I-112

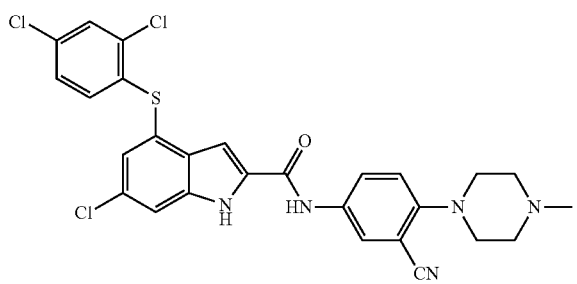

I-112

Synthetic Scheme:

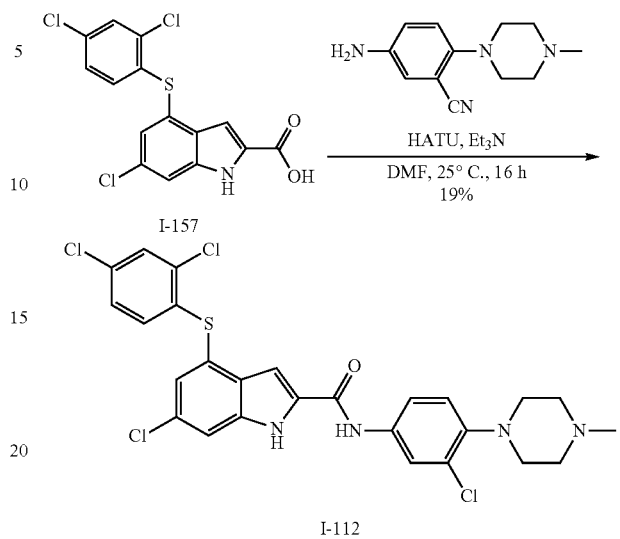

Procedures and Characterization:

The same procedure used to prepare I-111 afforded 6-chloro-N-(3-cyano-4-(4-methylpiperazin-1-yl)phenyl)-4-(2,4-dichlorophenylthio)-1H-indole-2-carboxamide (TFA salt) I-112 (yield 19%) as a white solid. ESI-MS (EI+, m/z): 570.7 [M+H]$^+$. $^1$H NMR (500 MHz, DMSO) δ 12.35 (d, J=2 Hz, 1H), 10.53 (s, 1H), 8.16 (d, J=3 Hz, 1H), 7.96 (dd, J=9 Hz, J=2.5 Hz, 1H), 7.77 (d, J=2 Hz, 1H), 7.63 (s, 1H), 7.43 (d, J=1.5 Hz, 1H), 7.33-7.28 (m, 3H), 6.71 (d, J=8.5 Hz, 1H), 3.55 (s, 4H), 3.24 (s, 2H), 3.13 (s, 2H), 2.90 (s, 3H).

Example 81: 6-chloro-4-(2,4-dichlorophenylthio)-N-(3-fluoro-4-(4-methylpiperazin-1-yl)phenyl)-1H-indole-2-carboxamide, I-113

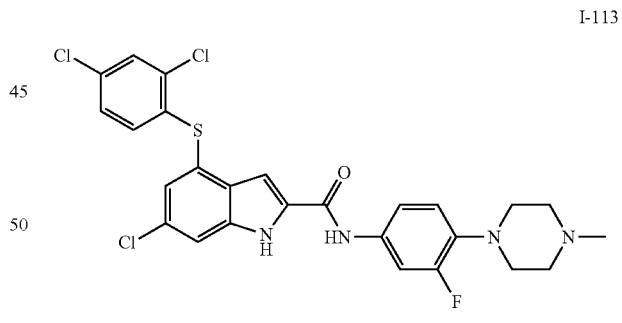

I-113

Synthetic Scheme:

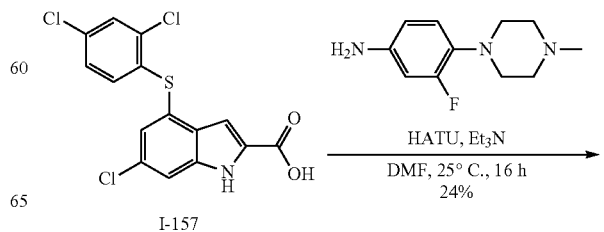

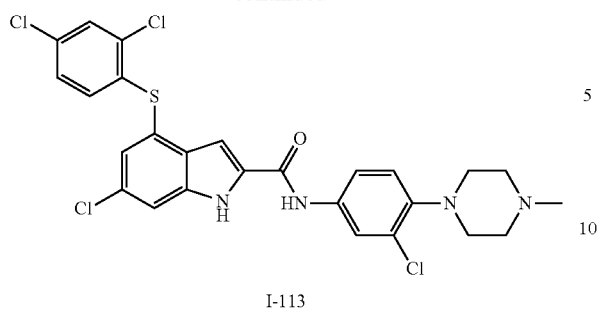

I-113

Procedures and Characterization:

The same procedure used to prepare I-111 afforded 6-chloro-4-(2,4-dichlorophenylthio)-N-(3-fluoro-4-(4-methylpiperazin-1-yl)phenyl)-1H-indole-2-carboxamide (TFA salt) I-113 (yield 24%) as a white solid. ESI-MS (EI+, m/z): 563.1 [M+H]$^+$. $^1$H NMR (500 MHz, DMSO) δ 12.32 (d, J=1.5 Hz, 1H), 10.41 (s, 1H), 9.85 (s, 1H), 7.77 (d, J=2 Hz, 2H), 7.74 (dd, J=15 Hz, J=2.5 Hz, 1H), 7.62 (d, J=1 Hz, 1H), 7.49 (dd, J=8.5 Hz, J=1.5 Hz, 1H), 7.42 (d, J=2 Hz, 1H), 7.37-7.27 (m, 2H), 7.14 (t, J=4.5 Hz, 1H), 6.71 (d, J=9 Hz, 1H), 3.49 (s, 4H), 3.23 (s, 2H), 3.00 (s, 2H), 2.87 (s, 3H).

Example 82: 6-chloro-4-(2,4-dichlorophenylthio)-N-(2-(dimethylamino)ethyl)-1H-indole-2-carboxamide, I-115

I-115

Procedures and Characterization:

The same procedure used to prepare I-111 afforded 6-chloro-4-(2,4-dichlorophenylthio)-N-(2-(dimethylamino)ethyl)-1H-indole-2-carboxamide (TFA salt) I-115 (yield 33%) as a white solid. ESI-MS (EI+, m/z): 442.0 [M+H]$^+$. $^1$H NMR (500 MHz, DMSO) δ 12.23 (d, J=1 Hz, 1H), 9.41 (s, 1H), 8.15 (t, J=6 Hz, 1H), 7.76 (d, J=2 Hz, 1H), 7.61 (s, 1H), 7.29-7.27 (m, 2H), 7.08 (d, J=1.5 Hz, 1H), 6.66 (d, J=9 Hz, 1H), 3.60 (q, J=12 Hz, J=5.5 Hz, 2H), 3.24 (d, J=5 Hz, 2H), 2.83 (d, J=3 Hz, 6H).

Example 83: 6-chloro-4-(2,4-dichlorophenylthio)-N-(3-(4-methylpiperazin-1-yl)phenyl)-1H-indole-2-carboxamide, I-121

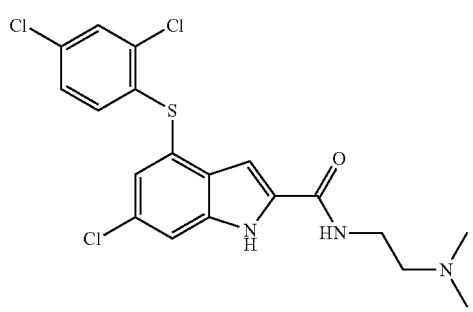

I-115

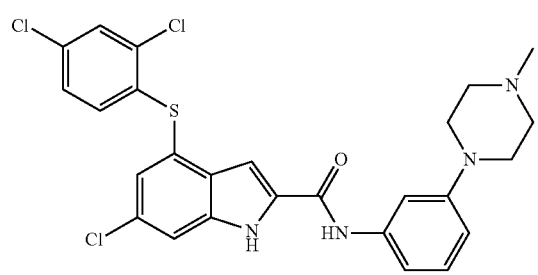

I-121

Synthetic Scheme:

Synthetic Scheme:

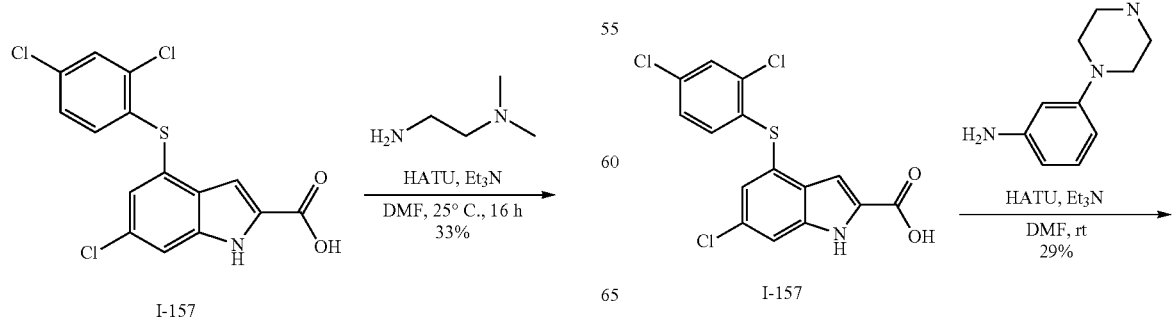

-continued

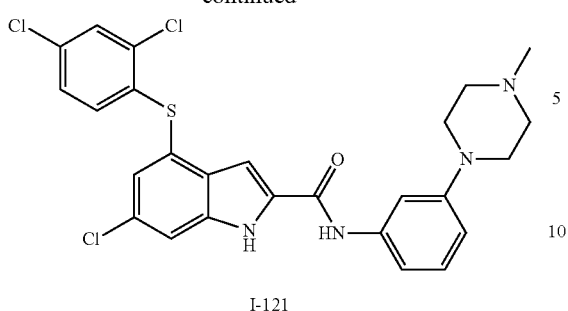

I-121

Procedures and Characterization:

Step 1: (6-chloro-4-(3-(trifluoromethoxy)phenyl-thio)-1H-indol-2-yl)methanol

The same procedure used to prepare I-111 afforded (6-chloro-4-(3-(trifluoromethoxy)phenylthio)-1H-indol-2-yl)methanol I-121 as a white solid (42.5 mg, 0.06 mmol, 29%). ESI-MS (EI+, m/z): 545 [M+H]$^+$. $^1$H NMR (500 MHz, DMSO) δ 12.28 (s, 1H), 10.24 (s, 1H), 9.86 (br s, 1H), 7.77 (s, 1H), 7.64 (s, 1H), 7.44 (s, 1H), 7.39 (d, 1H, J=8.5 Hz), 7.36 (s, 1H), 7.24-7.31 (m, 3H), 7.03 (d, 1H, J=8 Hz), 6.79 (d, 1H, J=8.5 Hz), 6.72 (d, 1H, J=8.5 Hz), 3.79 (s, 2H), 3.54 (s, 2H), 3.18 (s, 2H), 2.99 (s, 2H), 2.87 (s, 3H)

Example 84: 6-chloro-4-(2,4-dichlorophenylthio)-N-(3-(4-methylpiperazin-1-yl)phenyl)-1H-indole-2-carboxamide, I-120

-continued

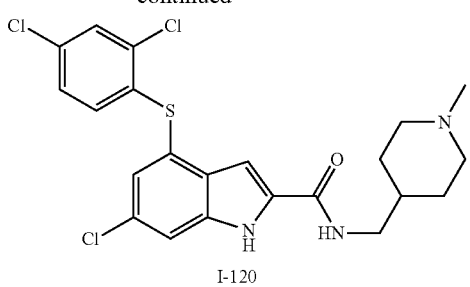

I-120

Procedures and Characterization:

Step 1: 6-chloro-4-(2,4-dichlorophenylthio)-N-((1-methylpiperidin-4-yl)methyl)-1H-indole-2-carboxamide The same procedure used to prepare I-111 afforded 6-chloro-4-(2,4-dichlorophenylthio)-N-((1-methylpiperidin-4-yl)methyl)-1H-indole-2-carboxamide I-120 as a white solid (14.9 mg, 0.04 mmol, 11%). ESI-MS (EI+, m/z): 482 [M+H]$^+$. $^1$H NMR (500 MHz, DMSO) δ 12.13 (s, 1H), 9.14 (br s, 1H), 8.72 (t, 1H, J=5.5 Hz), 7.76 (s, 1H), 7.60 (s, 1H), 7.26-7.31 (m, 2H), 7.14 (s, 11H), 6.68 (d, 1H, J=8.5 Hz), 3.42 (s, 2H), 3.18 (t, 1H, J=6.5 Hz), 2.85-2.92 (m, 2H), 2.87 (s, 3H), 2.74 (d, 1H, J=4.5 Hz), 1.86 (d, 2H, J=9 Hz), 1.76 (s, 1H), 1.30-1.38 (m, 2H).

Example 85: 6-chloro-4-(2,4-dichlorophenylthio)-N-(2-(1-methylpiperidin-4-yl)ethyl)-1H-indole-2-carboxamide, I-106

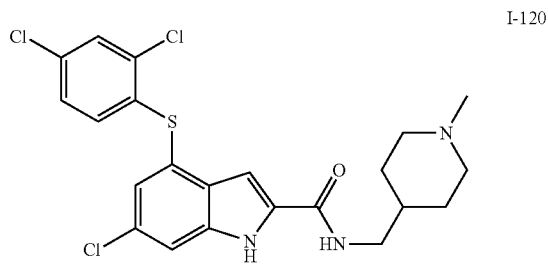 [SMILES: CN1CCC(CNC(=O)c2cc3c(Sc4ccc(Cl)cc4Cl)cc(Cl)cc3[nH]2)CC1]

I-120

Synthetic Scheme:

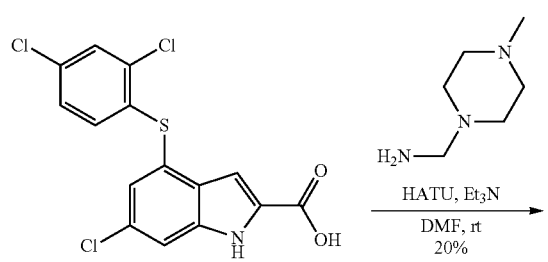

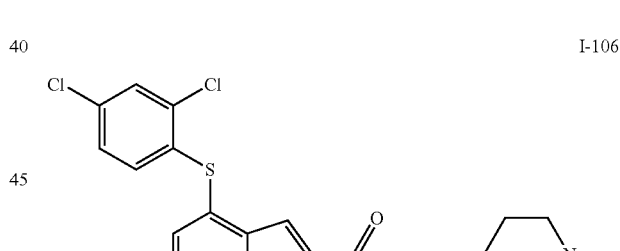

I-106

Synthetic Scheme:

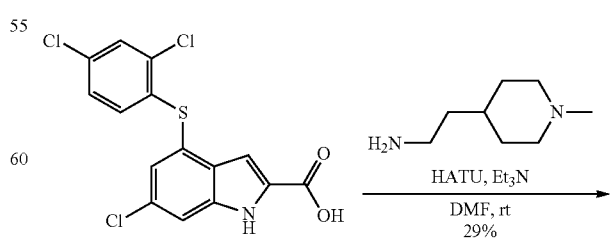

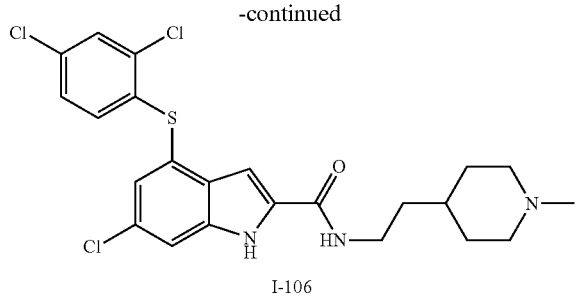

I-106

Procedures and Characterization:

Step 1: 6-chloro-4-(2,4-dichlorophenylthio)-N-(2-(1-methylpiperidin-4-yl)ethyl)-1H-indole-2-carboxamide The same procedure used to prepare I-111 afforded 6-chloro-4-(2,4-dichlorophenylthio)-N-(2-(1-methylpiperidin-4-yl)ethyl)-1H-indole-2-carboxamide I-106 as a white solid (26.4 mg, 0.04 mmol, 20%). ESI-MS (EI+, m/z): 496 [M+H]$^+$. $^1$H NMR (500 MHz, DMSO) δ 12.12 (s, 1H), 9.18 (br s, 1H), 7.76 (s, 1H), 7.60 (s, 1H), 7.26-7.30 (m, 2H), 7.10 (s, 1H), 6.67 (d, 1H, J=8.5 Hz), 3.44-3.66 (m, 5H), 2.84-2.91 (m, 2H), 2.73 (s, 3H), 1.93 (s, 1H), 1.90 (s, 1H), 2.87 (s, 3H), 1.44-1.51 (m, 3H), 1.24-1.33 (m, 2H).

Example 86: (4-(4-amino-3-fluorophenyl)piperazin-1-yl)(6-chloro-4-(2,4-dichlorophenylthio)-1H-indol-2-yl)methanone, I-92

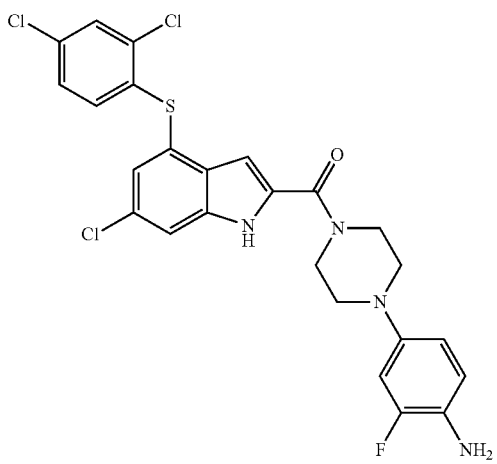

I-92

Synthetic Scheme:

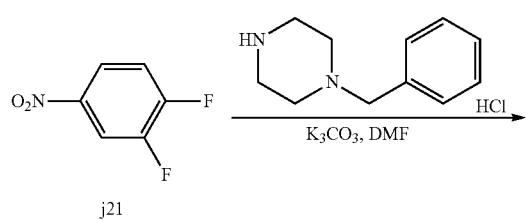

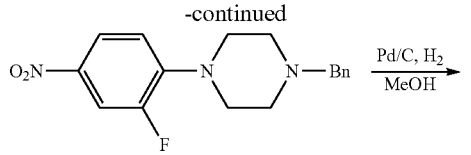

j22

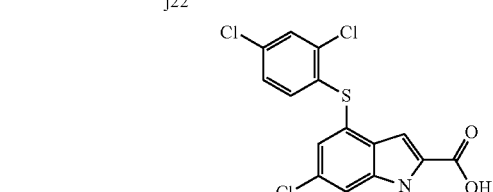

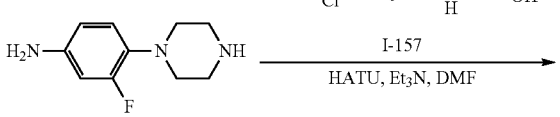

j23

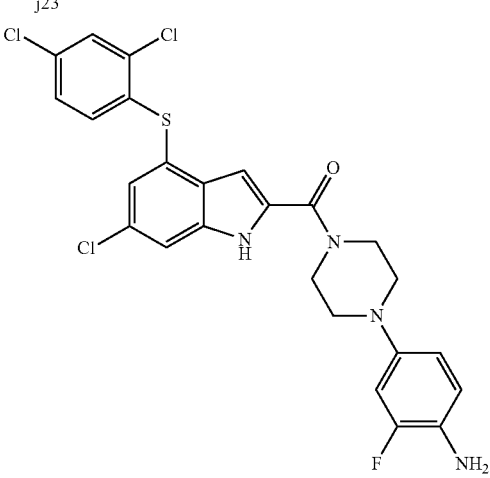

I-92

Procedures and Characterization:

Step 1:
1-benzyl-4-(2-fluoro-4-nitrophenyl)piperazine

To a solution of 1,2-difluoro-4-nitrobenzene (2.0 g, 12.57 mmol) and 1-benzyl-piperazine hydrochloride in DMF (30.00 mL) was added potassium cesium carbonate (5.6 g, 17.23 mmol) and stirred for 20 h at 110° C. The mixture was adjusted pH to 8, extracted with ethyl acetate. The organic phase was washed with water (100 mL×2), and brine (100 mL), dried (Na$_2$SO$_4$), filtered and concentrated in vacuo, the crude product (2.4 g) was used directly for the next step without further purification. ESI-MS (EI+, m/z): 316 [M+H]$^+$.

Step 2: 3-fluoro-4-(piperazin-1-yl)benzenamine

To a solution of 1-benzyl-4-(2-fluoro-4-nitrophenyl)piperazine (500 mg) in methanol (20.00 mL) was added Pd/C (100 mg) under H$_2$ atmosphere and stirred for 1 h at rt. It was filtered and concentrated in vacuo, the crude product (300 mg) was used directly for the next step without further purification.

Step 3: (4-(4-amino-3-fluorophenyl)piperazin-1-yl)(6-chloro-4-(2,4-dichlorophenylthio)-1H-indol-2-yl)methanone, I-92

The same procedure used to prepare I-111 afforded (4-(4-amino-3-fluorophenyl)piperazin-1-yl)(6-chloro-4-(2,4-dichlorophenylthio)-1H-indol-2-yl)methanone I-92 as a white solid (10.2 mg, 0.02 mmol). ESI-MS (EI+, m/z): 549 [M+H]−. $^1$H NMR (500 MHz, DMSO) δ 12.17 (s, 1H), 7.77 (s, 1H), 7.55 (s, 1H), 7.32 (d, 1H, J=8.5 Hz), 7.22 (s, 1H), 6.93 (d, 1H, J=8.5 Hz), 6.77-6.80 (t, 1H, J=9 Hz), 6.54 (s, 1H), 6.30-6.37 (m, 2H).

Example 87: N-(4-(4-benzylpiperazin-1-yl)-3-fluorophenyl)-6-chloro-4-(2,4-dichlorophenylthio)-1H-indole-2-carboxamide, I-91

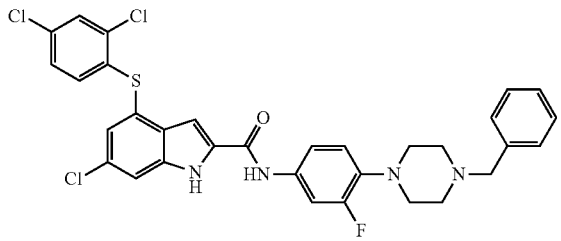

I-91

Synthetic Scheme:

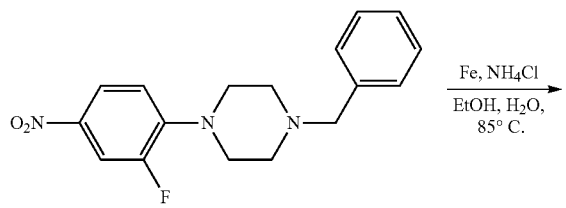

j22

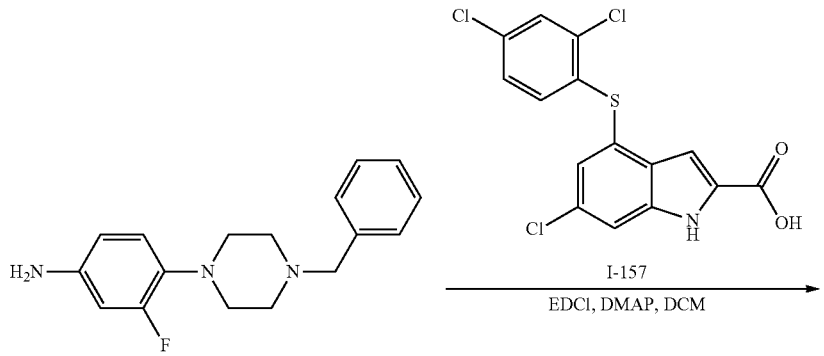

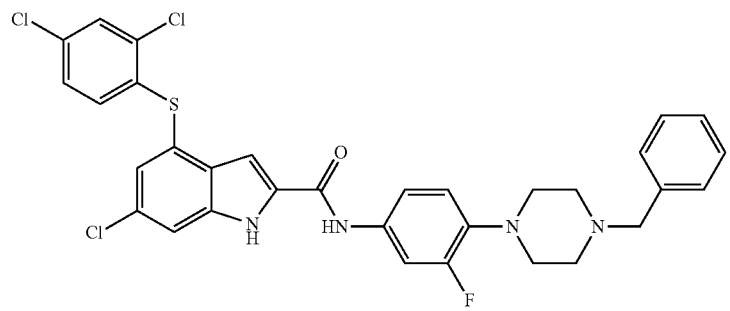

I-91

Procedures and Characterization:

Step 1: 4-(4-benzylpiperazin-1-yl)-3-fluorobenzenamine

To a solution of 1-benzyl-4-(2-fluoro-4-nitrophenyl)piperazine (630 mg) in a mix of ethanol (30.00 mL) and water (6.00 mL) was added Fe (1.2 g, 20 mmol) and ammonium chloride (1.07 g, 20 mmol) and stirred for 4 h at 80° C. The solution was filtrated by Celite, diluted with ethyl acetate. The organic phase was washed with water (100 mL×2), and brine (100 mL), dried ($Na_2SO_4$), filtered and concentrated in vacuo, the crude product was purified by prep-HPLC to afford 4-(4-benzylpiperazin-1-yl)-3-fluorobenzenamine as a white solid (150 mg, 0.53 mmol). ESI-MS (EI+, m/z): 286[M+H]$^+$.

Step 2: N-(4-(4-benzylpiperazin-1-yl)-3-fluorophenyl)-6-chloro-4-(2,4-dichlorophenylthio)-1H-indole-2-carboxamide, I-91

The same procedure used to prepare I-93 afforded N-(4-(4-benzylpiperazin-1-yl)-3-fluorophenyl)-6-chloro-4-(2,4-dichlorophenylthio)-1H-indole-2-carboxamide I-91 as a white solid (25.6 mg, 0.04 mmol, 10%). $^1$H NMR (500 MHz, DMSO) δ 12.33 (s, 1H), 10.42 (s, 1H), 9.96 (br, 1H), 7.77 (s, 1H), 7.73 (d, 1H, J=15 Hz), 7.62 (s, 1H), 7.48-7.54 (m, 6H), 7.42 (s, 1H), 7.27-7.31 (m, 2H), 7.10-7.14 (t, 1H, J=9 Hz), 6.7 (d, 1H, J=8.5 Hz), 6.30-6.37 (m, 2H), 4.43 (s, 2H), 3.42-3.45 (m, 6H), 3.0-3.06 (t, 1H, J=11.5 Hz).

Example 88: 6-chloro-4-(4-chlorophenylthio)-N-(2-(1-methylpiperidin-4-yl)ethyl)-1H-indole-2-carboxamide, I-142

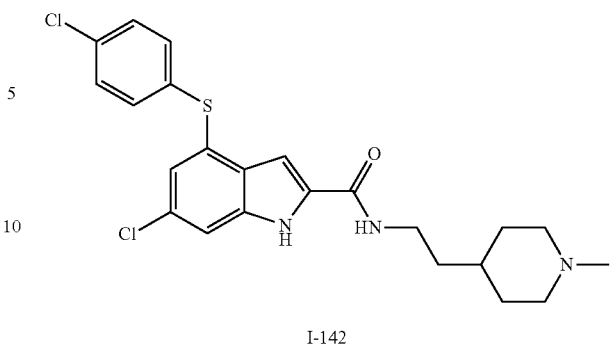

Procedures and Characterization:

The same procedure used to prepare I-111 to afford 6-chloro-4-(4-chlorophenylthio)-N-(2-(1-methylpiperidin-4-yl)ethyl)-1H-indole-2-carboxamide (TFA salt) I-142 (yield 21%) as a white solid. ESI-MS (EI+, m/z): 462.1 [M+H]$^+$. $^1$H NMR (500 MHz, DMSO) δ 12.02 (s, 1H), 9.13 (s, 1H), 8.62 (t, J=6 Hz, 1H), 7.47 (s, 1H), 7.42 (d, J=8.5 Hz, 2H), 7.20 (d, J=8.5 Hz, 2H), 7.15 (d, J=1.5 Hz, 1H), 7.03 (d, J=1.5 Hz, 1H), 3.40 (d, J=12 Hz, 2H), 3.33-3.30 (m, 2H), 2.88 (q, J=6 Hz, 2H), 2.73 (d, J=4.5 Hz, 3H), 1.92 (d, J=13 Hz, 2H), 1.52-1.46 (m, 3H), 1.32 (q, J=11 Hz, 2H).

Example 89: 6-chloro-4-(4-chlorophenylthio)-N-(3-fluoro-4-(4-methylpiperazin-1-yl)phenyl)-1H-indole-2-carboxamide, I-141

Synthetic Scheme:

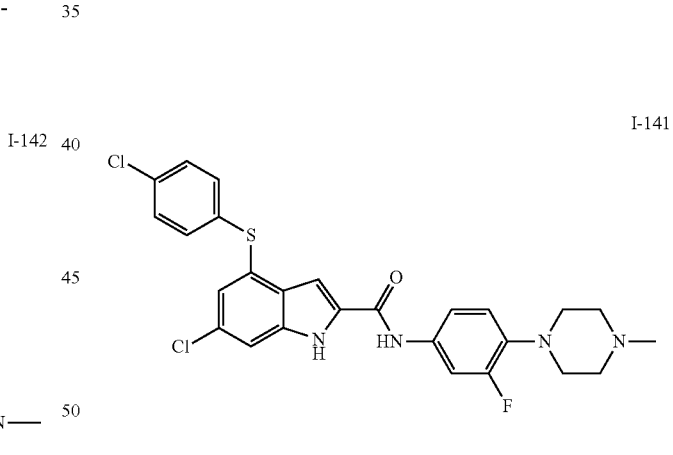

Synthetic Scheme:

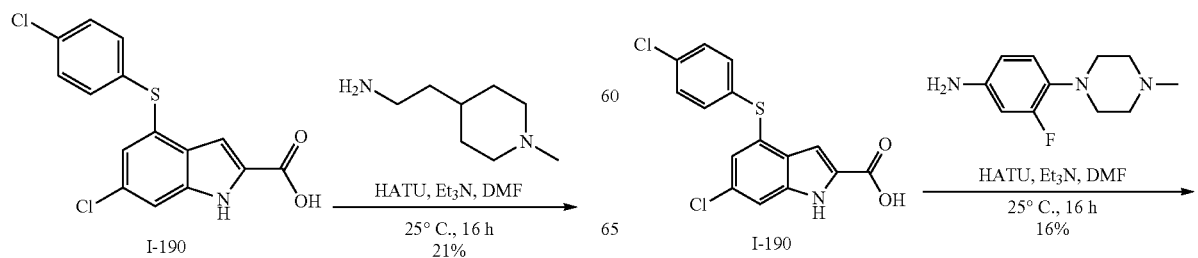

497
-continued

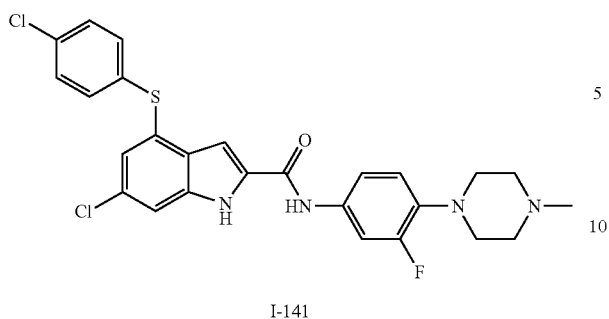

I-141

Procedures and Characterization:

The same procedure used to prepare I-111 to afford 6-chloro-4-(4-chlorophenylthio)-N-(3-fluoro-4-(4-methylpiperazin-1-yl)phenyl)-1H-indole-2-carboxamide (TFA salt) I-141 (yield 16%) as a white solid. ESI-MS (EI+, m/z): 529.2 [M+H]+. $^1$H NMR (500 MHz, DMSO) δ 12.20 (s, 1H), 10.42 (s, 1H), 9.7 (s, 1H), 7.45 (dd, J=14.5 Hz, J=2 Hz, 1H), 7.51-7.43 (m, 5H), 7.30 (d, J=8.5 Hz, 1H), 7.14 (t, J=9 Hz, 1H), 7.04 (d, J=1.5 Hz, 1H), 3.53-3.42 (m, 4H), 3.26 (t, J=7 Hz, 2H), 2.99 (q, J=10 Hz, 2H), 2.87 (s, 3H).

Example 90: 6-chloro-4-(4-chlorophenylthio)-N-(pyridin-2-ylmethyl)-1H-indole-2-carboxamide, I-149

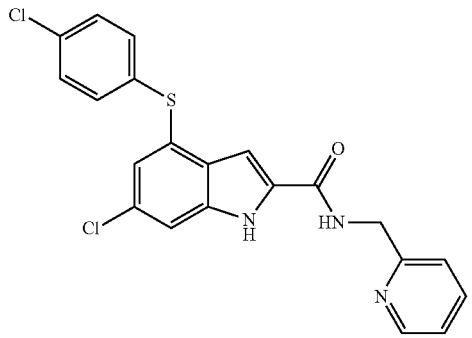

I-149

Synthetic Scheme:

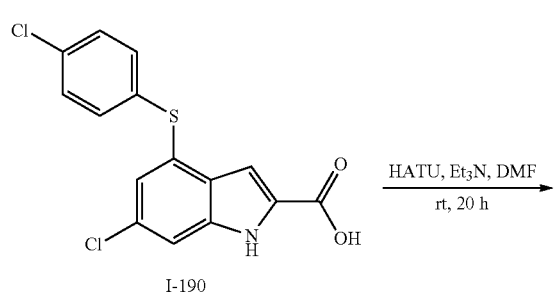

498
-continued

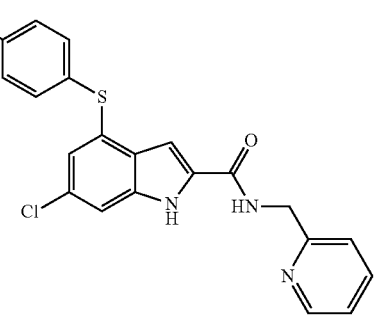

I-149

Procedures and Characterization:

Step 1: 6-chloro-4-(4-chlorophenylthio)-N-(pyridin-2-ylmethyl)-1H-indole-2-carboxamide The same procedure used to prepare I-111 afforded 6-chloro-4-(4-chlorophenylthio)-N-(pyridin-2-ylmethyl)-1H-indole-2-carboxamide I-149 as a white solid (5 mg, 0.01 mml, 4%). ESI-MS (EI+, m/z): 428 [M+H]+. $^1$H NMR (500 MHz, DMSO) δ 12.08 (br s, 1H), 9.27-9.29 (t, 1H, J=6.0 Hz), 8.52 (d, 1H, J=4.5 Hz), 7.65 (d, 1H, J=3.5 Hz) 7.75-7.78 (m, 1H), 7.49 (s, 1H), 7.42-7.44 (m, 2H), 7.27-7.34 (m, 5H), 7.05 (s, 1H), 4.57 (d, 2H, J=6 Hz).

Example 91: 6-chloro-4-(4-chlorophenylthio)-N-(2-(pyrrolidin-1-yl)ethyl)-1H-indole-2-carboxamide, I-148

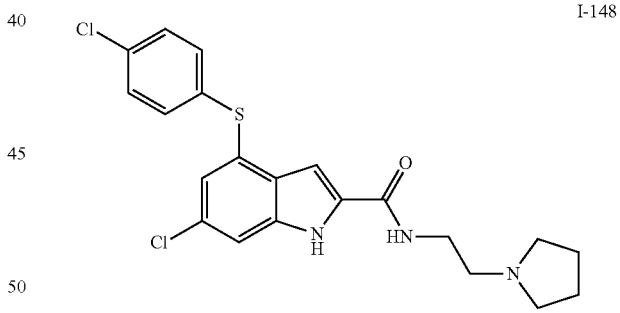

Synthetic Scheme:

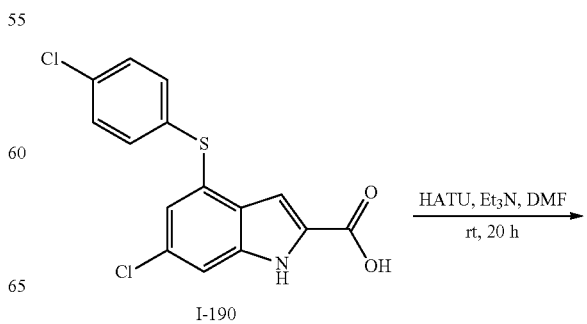

-continued

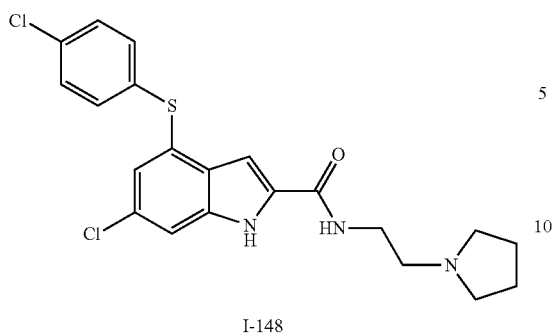

I-148

Procedures and Characterization:

Step 1: 6-chloro-4-(4-chlorophenylthio)-N-(2-(pyrrolidin-1-yl)ethyl)-1H-indole-2-carboxamide, I-148

The same procedure used to prepare I-111 afforded 6-chloro-4-(4-chlorophenylthio)-N-(2-(pyrrolidin-1-yl)ethyl)-1H-indole-2-carboxamide I-148 as a white solid (6.8 mg, 0.01 mml, 5%). ESI-MS (EI+, m/z): 434 [M+H]$^+$. $^1$H NMR (500 MHz, DMSO) δ 12.14 (s, 1H), 9.48 (br s, 1H), 8.85 (t, 1H, J=5.5 Hz), 7.50 (s, 1H), 7.43 (d, 2H, J=7 Hz), 7.26 (d, 2H, J=8.5 Hz), 7.15 (s, 1H), 7.07 (s, 1H).

Example 92: 6-chloro-4-(4-chlorophenylthio)-N-(1-methylpyrrolidin-3-yl)-1H-indole-2-carboxamide, I-79

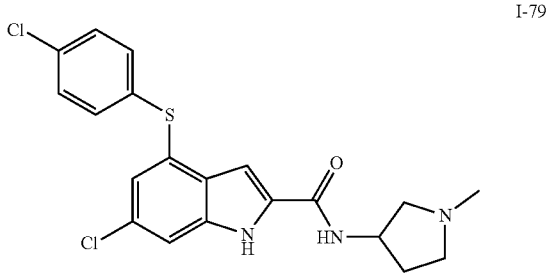 [SMILES: CN1CCC(NC(=O)c2cc3c(Sc4ccc(Cl)cc4)cc(Cl)cc3[nH]2)C1]

I-79

Synthetic Scheme:

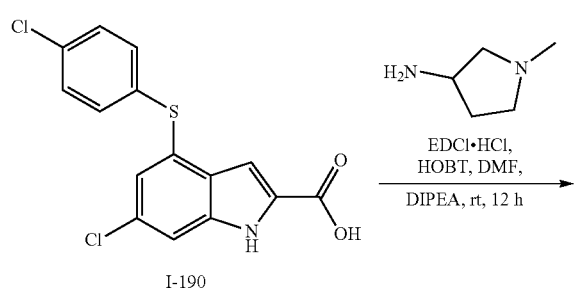

-continued

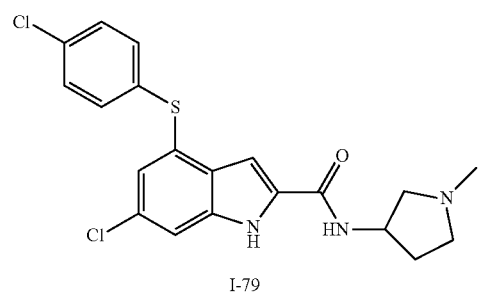

I-79

Procedures and Characterization:

EDCI.HCl (69 mg, 0.36 mmol) was added to a solution of 6-chloro-4-(4-chlorophenylthio)-1H-indole-2-carboxylic acid (100 mg, 0.3 mmol) and 1-methylpyrrolidin-3-amine (60 mg, 0.6 mmol), HOBT (49 mg, 0.36 mmol) and DIPEA (77 mg, 0.6 mmol) in DMF (4 ml) and stirred at room temperature for 12 h. The reaction mixture was extracted with EtOAc, washed with brine, dried, concentrated, purified by prep-HPLC to afford 6-chloro-4-(4-chlorophenylthio)-N-(1-methylpyrrolidin-3-yl)-1H-indole-2-carboxamide I-79 (30.8 mg, 25% yield) as a white solid.

ESI-MS (EI$^+$, m/z): 419.9 [M+H]$^+$.

$^1$H NMR (500 MHz, MeOD) δ 7.49 (s, 1H), 7.31 (d, J=11 Hz, 2H), 7.22 (d, J=11 Hz, 2H), 7.15 (s, 1H), 7.07 (d, J=1.0 Hz, 1H), 4.69-4.50 (m, 1H), 3.93-3.68 (m, 2H), 3.48-3.35 (m, 1H), 3.24-3.10 (m, 1H), 2.99 (s, 3H), 2.65-2.42 (m, 1H), 2.30-2.20 (m, 1H).

Example 93: 6-chloro-4-(4-chlorophenylthio)-N-(4-(oxazol-5-yl)phenyl)-1H-indole-2-carboxamide, I-128

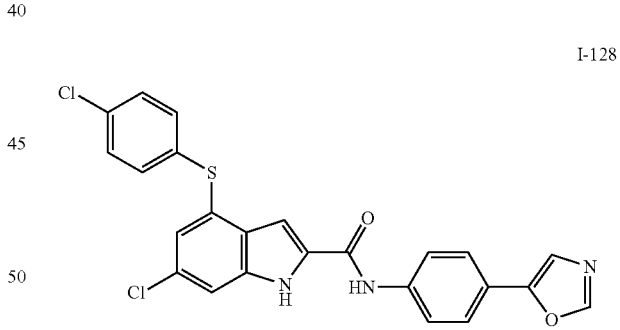

Synthetic Scheme:

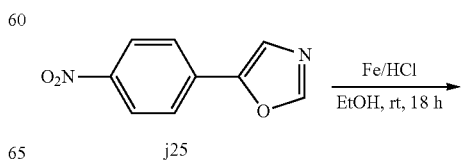

-continued

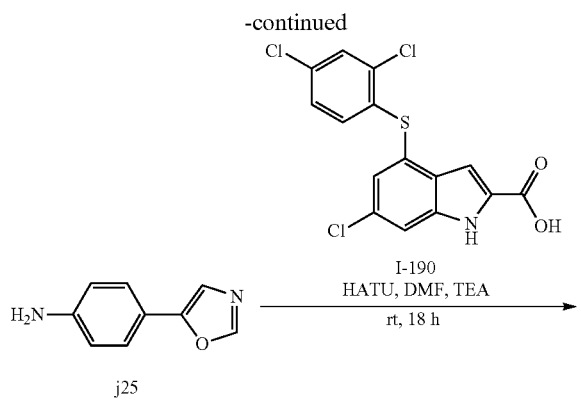

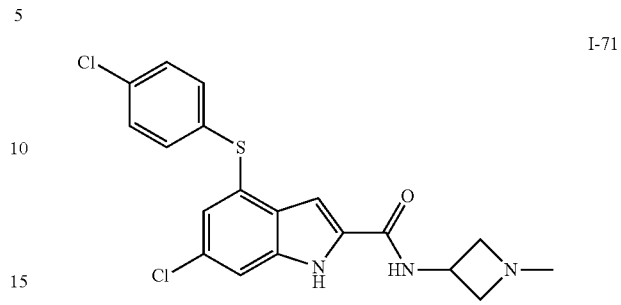

Example 94: 6-chloro-4-(4-chlorophenylthio)-N-(1-methylazetidin-3-yl)-1H-indole-2-carboxamide, I-71

Synthetic Scheme:

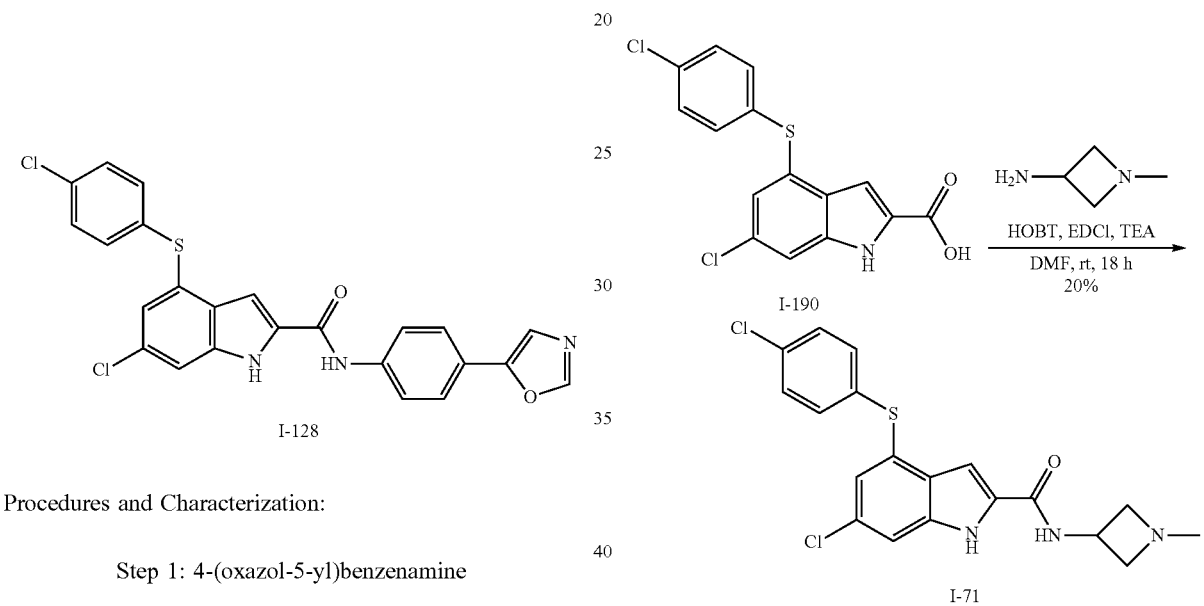

Procedures and Characterization:

Step 1: 4-(oxazol-5-yl)benzenamine

To a solution of 5-(4-nitrophenyl)oxazole (400 mg, 2.10 mmol) in EtOH (5 mL) was added Fe (62 mg, 11 mmol) and HCl (2 ml, 6N) at 0° C. The reaction was stirred at 0° C. for 1 h and then at 25° C. for 16 h. The solution was diluted with DCM (20 mL) and neutralized with NaHCO₃ to pH 7 (10 mL×2), dried (Na₂SO₄), filtered and concentrated in vacuo, the crude product was purified by chromatography (silica, ethyl acetate/petroleum ether=1/1) to afford 4-(oxazol-5-yl)benzenamine (300 mg, 1.87 mmol, 89%) as a yellow solid. ESI-MS (EI+, m/z): 161.2 [M+H]⁺.

Step 2: 6-chloro-4-(4-chlorophenylthio)-N-(4-(oxazol-5-yl)phenyl)-1H-indole-2-carboxamide The same procedure used to prepare I-111 is to 6-chloro-4-(4-chlorophenylthio)-N-(4-(oxazol-5-yl)phenyl)-1H-indole-2-carboxamide I-128 (6.2 mg, 0.012 mmol, 1.7%) as a white solid. (15 mg, 0.61 mmol, 61%). ESI-MS (EI+, m/z): 480.0 [M+H]⁺. ¹H NMR (500 MHz, DMSO) δ 12.2 (s, 1H), 10.44 (s, 1H), 8.58 (s, 1H), 8.46 (s, 1H), 7.85-7.88 (m, 2H), 7.79-7.81 (m, 2H), 7.52-7.53 (m, 2H), 7.45-7.46 (m, 2H), 7.43-7.44 (m, 2H), 7.04 (s, 1H).

Procedures and Characterization:

Step 1: 6-chloro-4-(4-chlorophenylthio)-N-(1-methylazetidin-3-yl)-1H-indole-2-carboxamide, I-71

A mixture of 6-chloro-4-(4-chlorophenylthio)-1H-indole-2-carboxylic acid (100 mg, 0.296 mmol), 1-methylazetidin-3-amine (51 mg, 0.592 mmol), HOBT (60 mg, 0.44 mmol), EDCI (86 mg, 0.44 mmol), TEA (0.16 mL, 1.184 mmol) in DMF (5 mL) was kept stirring at 10° C. for 18 h. The mixture was poured into water (30 mL), extracted with ethyl acetate (25 mL×3). The combined organic layer was washed with sat. NaHCO₃ (30 mL), brine (30 mL), then removed the solvent. The residue was purified by prep-HPLC (NH₄HCO₃) to afford 6-chloro-4-(4-chlorophenylthio)-N-(1-methylazetidin-3-yl)-1H-indole-2-carboxamide I-71 (25 mg, 61.7 μmol, 20% yield) as a white solid. ESI-MS (EI+, m/z): 405.9 [M+H]⁻ ¹H NMR (500 MHz, MeOD) δ 7.52 (s, 1H), 7.34 (d, J=8.5 Hz, 2H), 7.25 (d, J=7.7 Hz, 2H), 7.16 (s, 1H), 7.10 (s, 1H), 4.86-4.77 (m, 1H), 4.69-4.55 (m, 2H), 4.33 (t, J=9.7 Hz, 1H), 4.24 (t, J=9.5 Hz, 1H), 3.08-2.97 (m, 3H).

Example 95: 6-chloro-4-(4-chlorophenylthio)-N-hydroxy-1H-indole-2-carboxamide, I-177

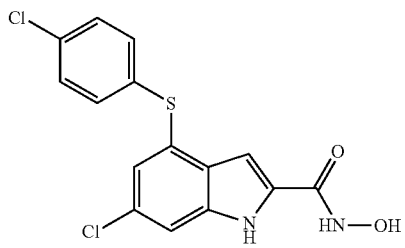

I-177

Synthetic Scheme:

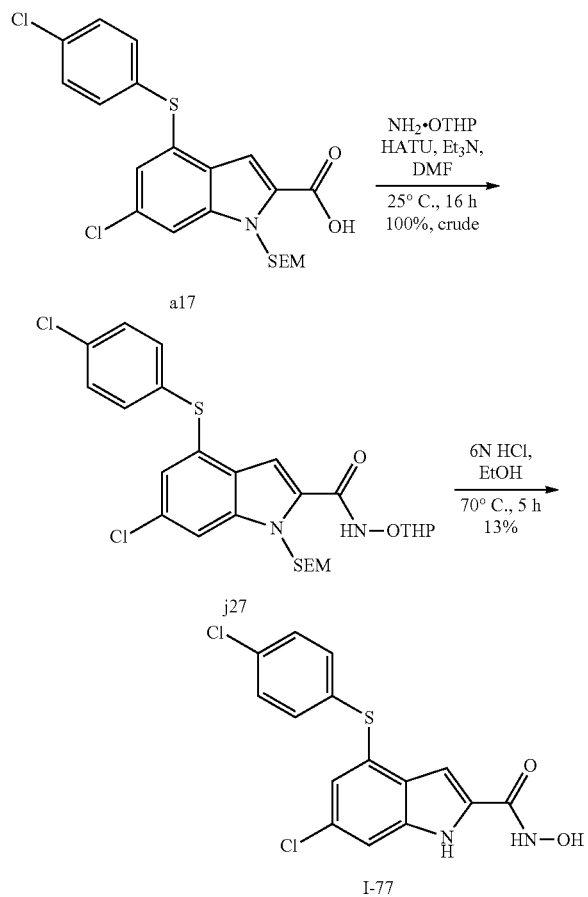

Procedures and Characterization:

Step 1: 6-chloro-4-(4-chlorophenylthio)-N-(tetrahydro-2H-pyran-2-yloxy)-1-((2-(trimethylsilyl)ethoxy)methyl)-1H-indole-2-carboxamide A mixture of 6-chloro-4-(4-chlorophenylthio)-1-((2-(trimethylsilyl)ethoxy)methyl)-1H-indole-2-carboxylic acid (234 mg, 0.5 mmol), O-(tetrahydro-2H-pyran-2-yl)hydroxylamine (117 mg, 1 mmol), HATU (290 mg, 0.75 mmol), $Et_3N$ (150 mg, 1.5 mmol) in DMF (6 mL) was stirred for 16 h at 25° C. The reaction was quenched with water (10 mL) and extracted with ethyl acetate (20 mL). The organic phase was washed water (10 mL×2), and brine (10 mL), dried ($Na_2SO_4$), filtered and concentrated in vacuo to afford crude 6-chloro-4-(4-chlorophenylthio)-N-(tetrahydro-2H-pyran-2-yloxy)-1-((2-(trimethylsilyl)ethoxy)methyl)-1H-indole-2-carboxamide (283 mg, 0.24 mmol, 100%) as a brown oil, which was used in next step directly. ESI-MS (EI+, m/z): 567.0 $[M+H]^+$.

Step 2: 6 6-chloro-4-(4-chlorophenylthio)-N-hydroxy-1H-indole-2-carboxamide, I-177

A mixture of 6-chloro-4-(4-chlorophenylthio)-N-(tetrahydro-2H-pyran-2-yloxy)-1-((2-(trimethylsilyl)ethoxy)methyl)-1H-indole-2-carboxamide (250 mg, 0.44 mmol) in aq 6 N HCl (5 mL) and EtOH (10 mL) was stirred for 5 h at 70° C. The reaction was diluted with water (30 mL), neutralized with $Na_2CO_3$ to pH 5 and extracted with ethyl acetate (50 mL). The organic phase was washed with water (20 mL×2), and brine (20 mL), dried ($Na_2SO_4$), filtered and concentrated, the crude product was purified by prep-HPLC (0.01% TFA) to afford 6-chloro-4-(4-chlorophenylthio)-N-hydroxy-1H-indole-2-carboxamide I-177 (20 mg, 0.06 mmol, 13%) as a white solid. ESI-MS (EI+, m/z): 353.0 $[M+H]^+$. $^1$H NMR (500 MHz, MeOD) δ 7.49 (d, J=0.5 Hz, 1H), 7.34-7.32 (m, 2H), 7.28-7.26 (m, 2H), 7.06 (d, J=1.5 Hz, 1H), 6.97 (s, 1H).

Example 96: 4-bromo-6-(3,4-dichlorophenylthio)-N-(4-(4-methylpiperazin-1-yl)phenyl)-1H-indole-2-carboxamide, I-96

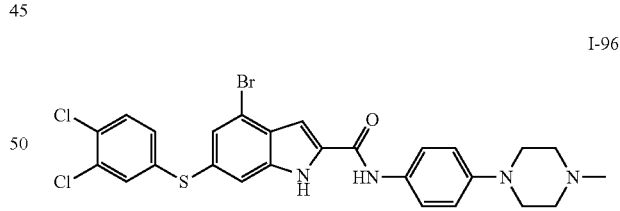

I-96

Synthetic Scheme:

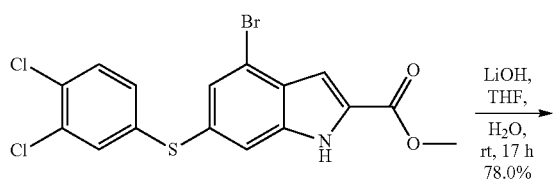

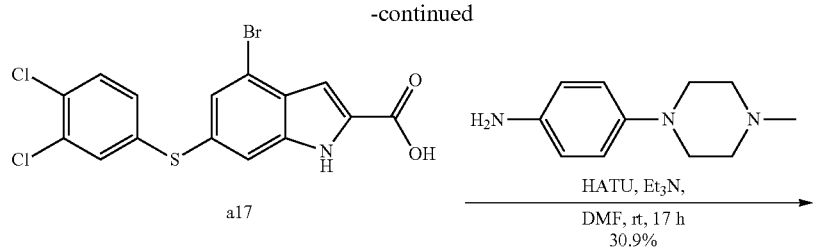

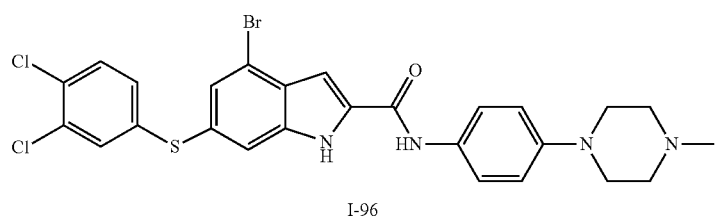

Procedures and Characterization:

Step 1: 4-Bromo-6-(3,4-dichlorophenylthio)-1H-indole-2-carboxylic acid

To a solution of methyl 4-bromo-6-(3,4-dichlorophenyl-thio)-1H-indole-2-carboxylate (500 mug, 1.2 mmol) in THF/H$_2$O (8 mL: 8 mL) was added LiOH.H$_2$O (101 mg, 2.4 mmol), then stirred at rt for 17 h. The reaction was quenched with ice-water, adjusted to pH 5 with 1N HCl aqueous solution, extracted with EtOAc, washed with brine, dried over sodium sulfate, and concentrated to afford crude product 4-bromo-6-(3,4-dichlorophenylthio)-1H-indole-2-carboxylic acid (380 mg, 78.0%) as a yellow solid which was used directly in the next step without further purification. ESI-MS (EI$^+$, m/z): 415.8 [M+H]$^+$.

Step 3: 4-Bromo-6-(3,4-dichlorophenylthio)-N-(4-(4-methylpiperazin-1-yl)phenyl)-1H-indole-2-carboxamide The same procedure used to prepare I-111 afforded 4-bromo-6-(3,4-dichlorophenylthio)-N-(4-(4-methylpiperazin-1-yl)phenyl)-1H-indole-2-carboxamide I-96 (35 mg, 30.9%) as a white solid. MS (EI+, m/z): 590.9 M−H]$^+$. $^1$H NMR (500 MHz, DMSO) δ 12.28 (s, 1H), 10.34 (s, 1H), 9.73 (s, 1H), 7.71 (d, J=8.9 Hz, 2H), 7.66-7.55 (m, 2H), 7.51 (s, 2H), 7.39 (s, 1H), 7.17 (dd, J=8.5, 2.1 Hz, 1H), 7.05 (d, J=9.0 Hz, 2H), 3.88 (d, J=70.0 Hz, 2H), 3.52 (s, 2H), 3.18 (s, 2H), 2.91 (d, J=40.5 Hz, 5H).

Example 97: 6,7-dichloro-4-(2,4-dichlorophenyl)sulfanyl-N-[3-fluoro-4-(4-methyl-1,4-diazepan-1-yl)phenyl]-1H-indole-2-carboxamide, I-32

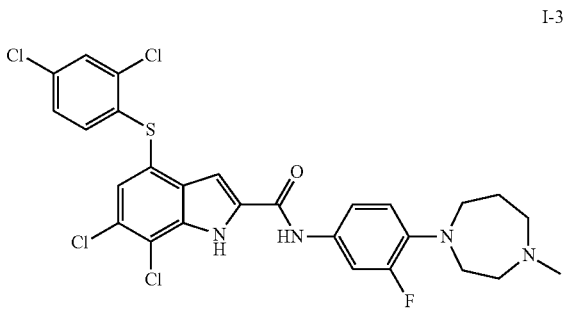

Synthetic Scheme:

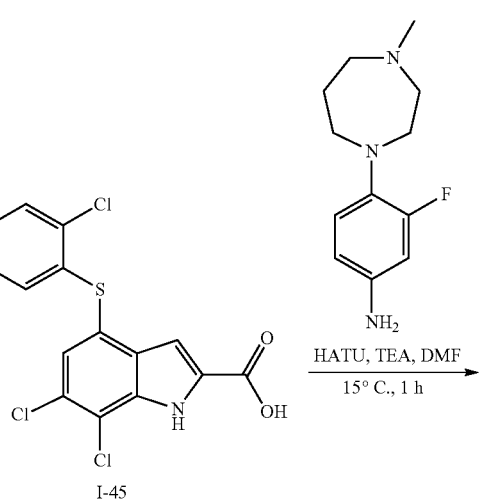

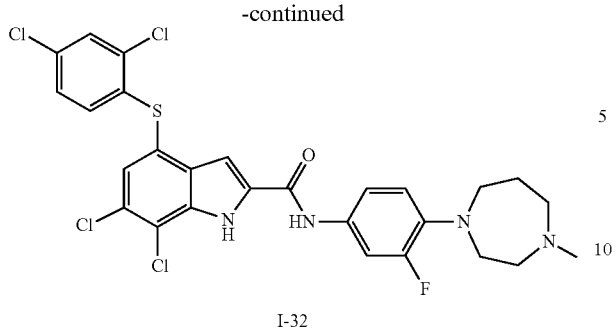

I-32

I-33

Procedures and Characterization:

The same procedure used to prepare I-111 afforded 6,7-dichloro-4-(2,4-dichlorophenyl)sulfanyl-N-[3-fluoro-4-(4-methyl-1,4-diazepan-1-yl)phenyl]-1H-indole-2-carboxamide I-32 (11.70 mg, 19.11 μmol, 11.11% yield) as a white solid. The reaction time was 1 h, ESI-MS (EI⁺, m/z): 613.0 [M+H]⁺.

¹H NMR (500 MHz, DMSO) δ 12.51 (s, 1H), 10.36 (s, 1H), 7.77 (s, 1H), 7.66 (d, J=9.75 Hz, 1H), 7.49 (s, 1H), 7.41-7.37 (m, 2H), 7.28 (d, J=5.5 Hz, 1H), 6.98 (t, J=4.0 Hz, 1H), 6.75 (d, J=5.25 Hz, 1H), 3.85-3.70 (m, 2H), 3.45-3.39 (m, 2H), 3.11-3.01 (m, 4H), 2.62 (s, 3H), 2.04 (d, J=3.5 Hz, 2H).

Example 98: 6,7-dichloro-4-(2,4-dichlorophenyl-thio)-N-(3-(4-methylpiperazin-1-yl)phenyl)-1H-indole-2-carboxamide, I-33

Procedures and Characterization:

The same procedure used to prepare I-111 afforded 6,7-dichloro-4-(2,4-dichlorophenyl)sulfanyl-N-[3-(4-methylpiperazin-1-yl)phenyl]-1H-indole-2-carboxamide I-33 (21.20 mg, 35.98 μmol, 18.31% yield, 98.51% purity) as a white solid. The reaction time was 1.5 h. ESI-MS (EI⁺, m/z): 581.0 [M+H]⁺.

¹H NMR (500 MHz, DMSO) δ 13.0 (s, 1H), 10.22 (s, 1H), 7.76 (d, J=2.0 Hz, 1H), 7.48 (s, 1H), 7.40 (s, 1H), 7.36 (s, 1H), 7.30-7.27 (m, 2H), 7.21 (t, J=15.0 Hz, 1H), 6.77 (d, J=10.5 Hz, 1H), 6.74 (d, J=9.5 Hz, 1H), 3.18 (s, 4H), 2.62 (s, 4H), 2.34 (s, 3H).

Example 99: 6,7-dichloro-4-(2,4-dichlorophenyl-thio)-N-((1-methylpiperidin-4-yl)methyl)-1H-indole-2-carboxamide, I-35

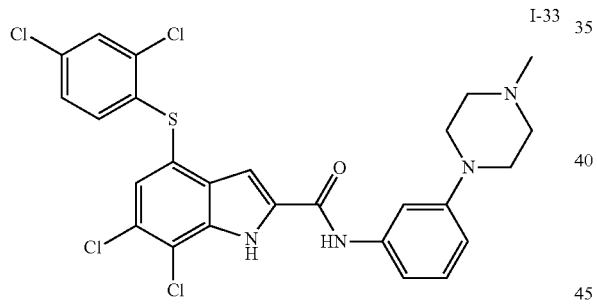

I-33

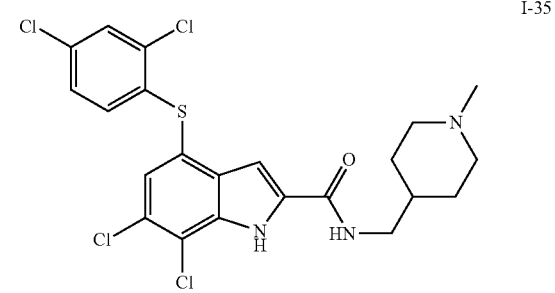 [SMILES: CN1CCC(CNC(=O)c2cc3c(Sc4ccc(Cl)cc4Cl)cc(Cl)c(Cl)c3[nH]2)CC1]

I-35

Synthetic Scheme:

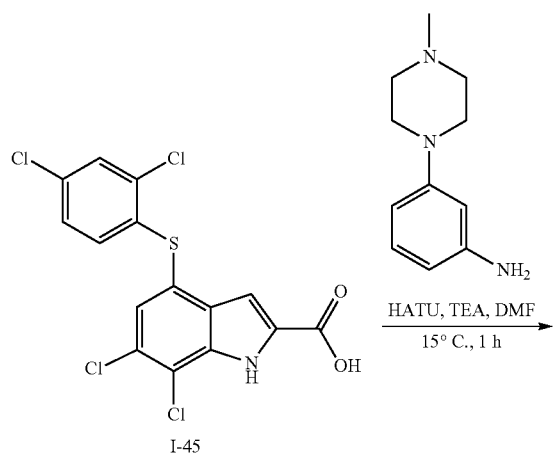

Synthetic Scheme:

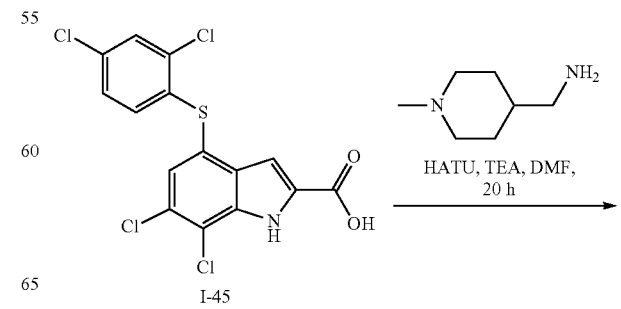

-continued

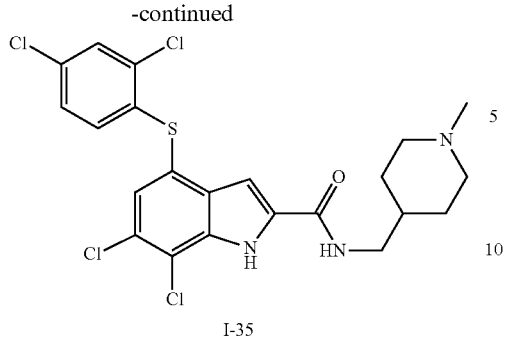
I-35

Procedures and Characterization:

The same procedure used to prepare I-111 afforded 6,7-dichloro-4-(2,4-dichlorophenylthio)-N-((1-methylpiperidin-4-yl)methyl)-1H-indole-2-carboxamide I-35 (9.2 mg, 7% yield).

ESI-MS (EI+, m/z): 518.0 [M+H]+.

$^1$H NMR (500 MHz, DMSO) δ 12.36 (s, 1H), 8.71 (d, J=5.0 Hz, 1H), 7.77 (s, 1H), 7.48 (s, 1H), 7.27 (d, J=9.0 Hz, 1H), 7.13 (s, 1H), 6.72 (d, J=5.0 Hz, 1H), 3.27-3.17 (m, 5H), 2.32-2.27 (m, 3H), 2.22-2.15 (m, 1H), 1.77 (d, J=8.25 Hz, 2H), 1.67-1.65 (m, 1H), 1.32-1.29 (m, 2H).

Example 100: 6-chloro-4-(3,5-dichlorophenyl)-N-(3-(4-methylpiperazin-1-yl)phenyl)-1H-indole-2-carboxamide, I-30

-continued

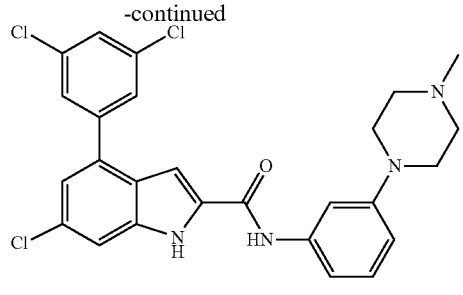
I-30

Procedures and Characterization:

Step 1: 6-chloro-4-(3,5-dichlorophenyl)-N-(3-(4-methylpiperazin-1-yl)phenyl)-1H-indole-2-carboxamide, I-30

The same procedure used to prepare I-111 except that the reaction was stirred at 20° C. for 1 h afforded 6-chloro-4-(3,5-dichlorophenyl)-N-[3-(4-methylpiperazin-1-yl)phenyl]-1H-indole-2-carboxamide I-30 as a light yellow solid (38.90 mg, 75.70 μmol, 28.65%). ESI-MS (EI+, m/z): 513 [M+H]+. $^1$H NMR (500 MHz, MeOD) δ 7.67 (s, 2H), 7.58 (s, 2H), 7.55 (s, 1H), 7.51 (s, 1H), 7.28-7.32 (t, 1H, J=10 Hz), 7.20-7.23 (m, 2H), 6.85 (d, 1H), 3.90 (d, 2H, J=17 Hz), 3.63 (d, 2H, J=15.5 Hz), 3.28 (s, 2H), 3.08 (t, 2H, J=15.5 Hz).

Example 101: 6-chloro-4-(3,5-dichlorophenyl)-N-(3-(4-methylpiperazin-1-yl)phenyl)-1H-indole-2-carboxamide, I-29

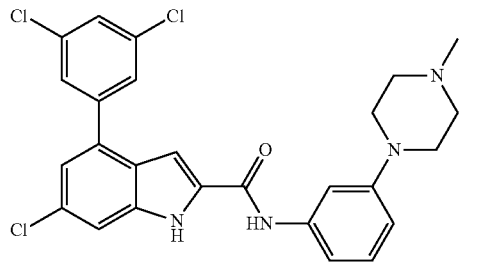
I-30

Synthetic Scheme:

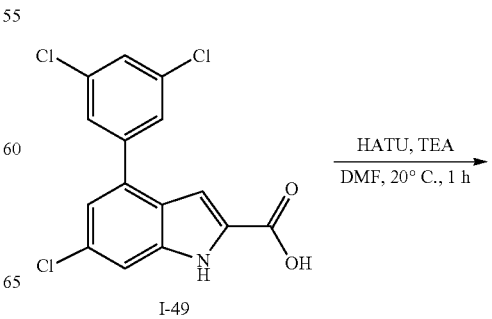

Synthetic Scheme:

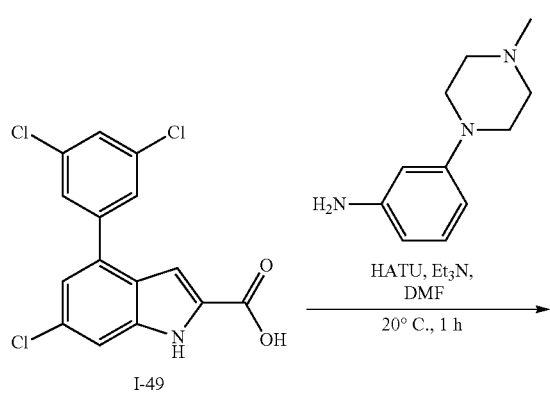

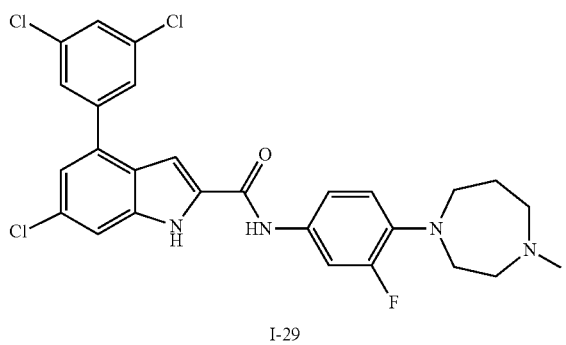

I-29

Procedures and Characterization:

Step 1: 6-chloro-4-(3,5-dichlorophenyl)-N-(3-(4-methylpiperazin-1-yl)phenyl)-1H-indole-2-carboxamide The same procedure used to prepare I-111 except that the reaction was stirred at 20° C. for 1 h afforded 6-chloro-4-(3,5-dichlorophenyl)-N-(3-(4-methylpiperazin-1-yl)phenyl)-1H-indole-2-carboxamide I-29 as a yellow solid (27.00 mg, 49.46 μmol, 16.85%). ESI-MS (EI+, m/z): 545 [M+H]+. 1H NMR (500 MHz, DMSO) δ 12.17 (s, 1H), 10.23 (s, 1H), 8.21 (s, 1H), 7.74 (s, 3H), 7.63 (d, 1H, J=20 Hz), 7.53 (d, 2H, J=9 Hz), 7.38 (d, 1H, J=11 Hz), 7.23 (s, 1H), 6.93-6.98 (t, 1H, J=12 Hz), 3.90 (d, 2H, J=17 Hz), 3.63 (d, 2H, J=15.5 Hz), 3.31-3.35 (m, 3H), 2.73 (s, 2H), 2.63-2.65 (t, 2H, J=6 Hz), 2.34 (s, 1H), 1.92-1.94 (m, 2H).

Example 102: 3-(5-chloro-4-phenoxy-1H-indol-2-yl)propanamide, I-247

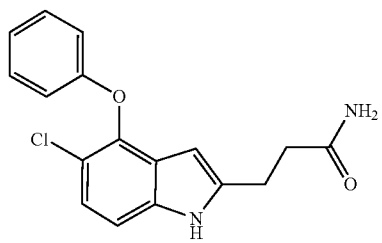

I-247

Synthetic Scheme:

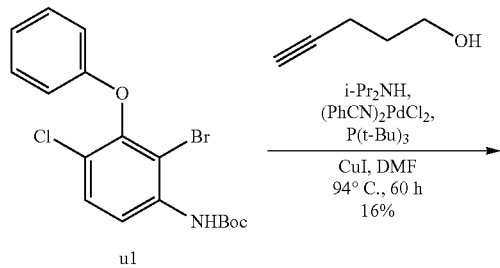

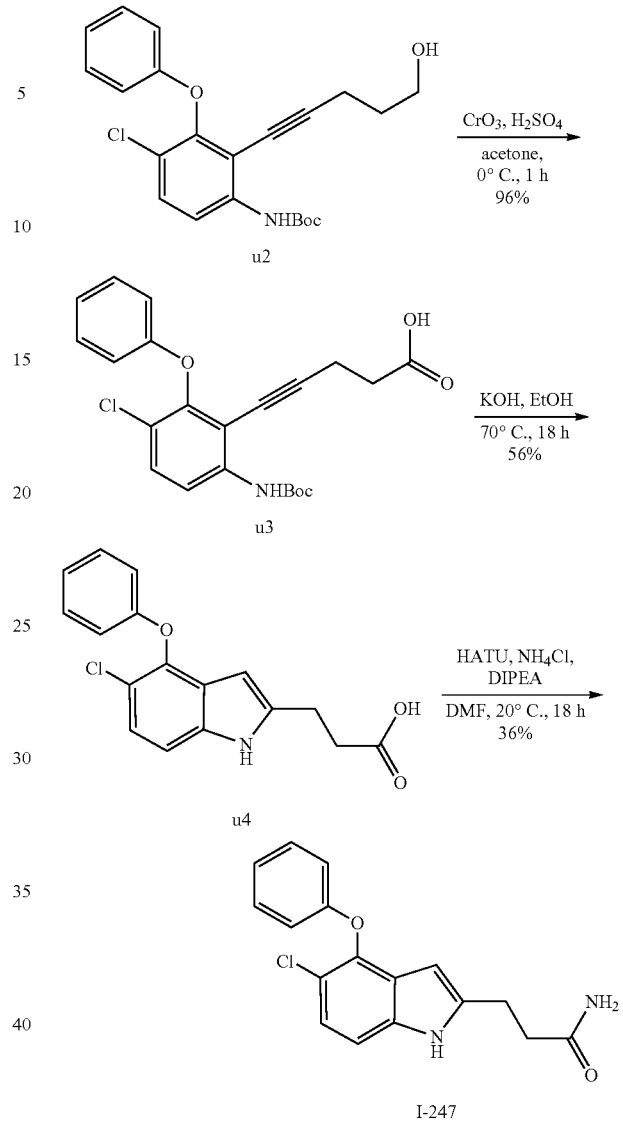

Procedures and Characterization:

Step 1: tert-butyl 4-chloro-2-(5-hydroxypent-1-ynyl)-3-phenoxyphenylcarbamate

To solution of tert-butyl 2-bromo-4-chloro-3-phenoxyphenylcarbamate (500 mg, 1.25 mmol), pent-4-yn-1-ol (315 mg, 3.75 mmol), PdCl₂(CH₃CN)₂ (14 mg, 0.05 mmol) and tri(tert-butyl)phosphine (20 mg, 0.1 mmol) in DMF (10 mL) under N₂ were added CuI (10 mg, 0.05 mmol) and diisopropylamine (500 mg, 5 mmol). After stirring for 20 h at 94° C., the reaction mixture was added into ice-water (50 mL), extracted by EtOAc (50 mL×2). The combined organics was washed by water (50 mL×2), brine (50 mL×2), dried (Na₂SO₄) and filtered. The filtrate was concentrated in vacuo and the residue was purified by column chromatography (SiO₂, petrol ether/EtOAc 75:25) to give tert-butyl 4-chloro-2-(5-hydroxypent-1-ynyl)-3-phenoxyphenylcarbamate: (80 mg, 0.199 mmol, 16%) as a light-tan solid. ESI-MS (EI+, m/z): 424.2[M+Na]+.

Step 2: 5-(6-(tert-butoxycarbonylamino)-3-chloro-2-phenoxyphenyl)pent-4-ynoic acid To solution of tert-butyl 4-chloro-2-(5-hydroxypent-1-ynyl)-3-phenoxyphenylcarbamate (80 mg, 0.199 mmol) in acetone (5 mL) was added Jones reagent (2.7M, 0.2 mL, 0.54 mmol) at 0° C. carefully. After stirring for 1 h at 0° C., the reaction mixture was quenched by i-PrOH (0.2 mL) dropwise at 0° C. The reaction mixture was stirred at 0° C. for another 30 mins before filtered and diluted with EtOAc (20 mL), washed by water (50 mL×2), brine (50 mL×2), dried (Na$_2$SO$_4$) and filtered. The filtrate was concentrated in vacuo to give crude 5-(6-(tert-butoxycarbonylamino)-3-chloro-2-phenoxyphenyl)pent-4-ynoic acid: (80 mg, 0.192 mmol, 96%) as a light-green solid. ESI-MS (EI+, m/z): 438.0[M+Na]$^+$.

Step 3: 3-(5-chloro-4-phenoxy-1H-indol-2-yl)propanoic acid

To solution of 5-(6-(tert-butoxycarbonylamino)-3-chloro-2-phenoxyphenyl)pent-4-ynoic acid (70 mg, 0.168 mmol) in EtOH (4 mL) was added KOH (38 mg, 0.67 mmol) at 20° C. After stirring for 18 h at 70° C., the reaction mixture was quenched by sat NH$_4$Cl (2 mL) at 20° C. The reaction mixture was diluted with EtOAc (20 mL), washed by brine (20 mL), dried (Na$_2$SO$_4$) and filtered. The filtrate was concentrated in vacuo. The residue was purified by prep-HPLC using 10 mM NH$_4$HCO3 buffer to give 3-(5-chloro-4-phenoxy-1H-indol-2-yl)propanoic acid: (30 mg, 0.095 mmol, 56%) as a white solid. ESI-MS (EI+, m/z): 316.1 [M+H]$^+$.

Step 4: 3-(5-chloro-4-phenoxy-1H-indol-2-yl)propanamide, I-247

To a mixture of 3-(5-chloro-4-phenoxy-1H-indol-2-yl) propanoic acid (30 mg, 0.095 mmol), NH$_4$Cl (16 mg, 0.29 mmol), HATU 32 mg, 0.114 mmol) in DMF (2 mL) was added DIPEA (61 mg, 0.475 mmol) at 0° C. The reaction mixture was stirred at 0° C. for 18 h. The reaction mixture was added into ice-water (10 mL), extracted by EtOAc (10 mL×2). The combined organics was washed by water (10 mL×2), brine (10 mL×2), dried (Na$_2$SO$_4$) and filtered. The filtrate was concentrated in vacuo and the residue was purified by prep-HPLC using 10 mM NH$_4$HCO$_3$ buffer to provide 3-(5-chloro-4-phenoxy-1H-indol-2-yl)propanamide 1-247 (11 mg, 0.035 mmol, 36%) as a white solid. ESI-MS (EI+, m/z): 315.1[M+H]$^+$.

$^1$H NMR (500 MHz, CDCl$_3$) δ 9.27 (s, 1H), 7.29-7.23 (m, 2H), 7.16 (d, J=8.6 Hz, 1H), 7.12 (d, J=8.8 Hz, 1H), 7.01 (t, J=7.3 Hz, 1H), 6.90 (d, J=7.8 Hz, 2H), 5.95 (s, 1H), 5.43 (d, J=21.9 Hz, 2H), 3.01-2.96 (m, 2H), 2.62-2.57 (m, 2H).

Example 103: 5-(5-chloro-4-phenoxy-1H-indol-2-yl)oxazole, 1-256

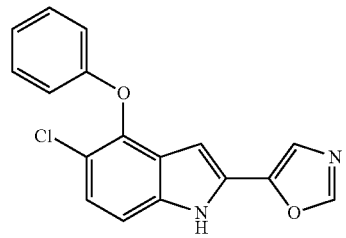

I-256

Synthetic Scheme:

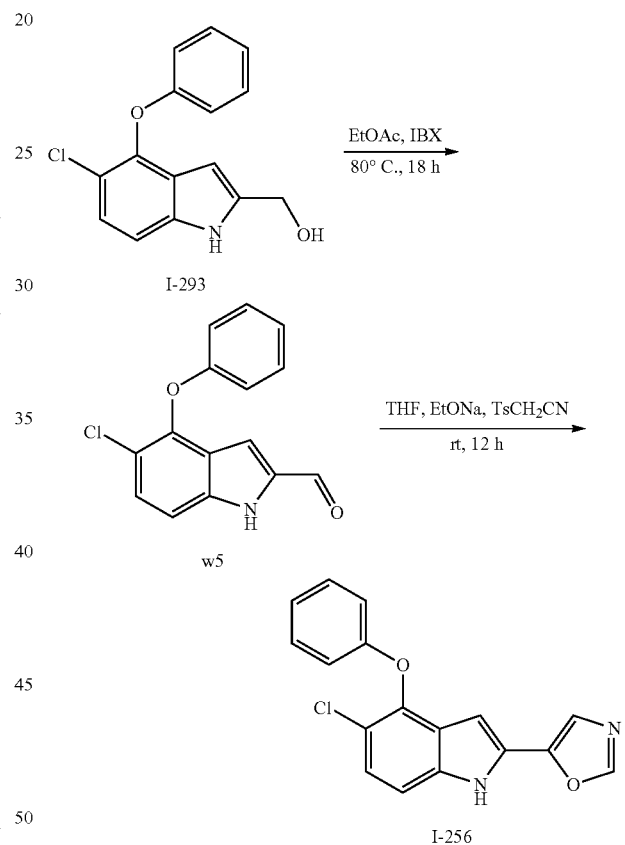

Procedures and Characterization:

Step 1: 5-chloro-4-phenoxy-1H-indole-2-carbaldehyde

To a solution of (5-chloro-4-phenoxy-1H-indol-2-yl) methanol (790 mg, 2.89 mmol) and IBX (2.42 g, 8.66 mmol) in EtOAc (20 m L), and stirred at 80° C. for 18 h. Then filtered and concentrated to afford the crude product. Purified by chromatography (silica, ethyl acetate/petroleum ether=10/1) to afford 5-chloro-4-phenoxy-1H-indole-2-carbaldehyde (700 mg, 2.58 mmol, purity: 95%, yield: 88.9%) as a white solid. ESI-MS (EI+, m/z): 272.74 [M+H]$^+$.

Step 2: 5-(5-chloro-4-phenoxy-1H-indol-2-yl)oxazole, I-256

A solution of 5-chloro-4-phenoxy-1H-indole-2-carbaldehyde (500 mg, 1.84 mmol) and EtONa (150.28 mg, 2.21 mmol) were dissolved in THE (5 mL) and TsCH₂CN (359.29 mg, 1.84 mmol) was added. The mixture was stirred at rt for 12 h. The resulting solution was extracted with EtOAc (30 mL*2), the organic phase was combined and washed with brine, dried over sodium sulfate, and concentrated to afford the crude product which was purified by prep-HPLC to afford 5-(5-chloro-4-phenoxy-1H-indol-2-yl)oxazole I-256 (90 mg, purity: 100%, yield: 15.6%) as a yellow solid. ESI-MS (EI+, m/z): 311.1 [M+H]⁺. ¹H NMR (500 MHz, DMSO) δ 8.47 (s, 1H), 8.13 (d, J=19.9 Hz, 2H), 7.75 (d, J=12.2 Hz, 2H), 7.59 (s, 1H), 7.51 (t, J=7.7 Hz, 1H), 7.44 (d, J=7.9 Hz, 1H), 6.14 (s, 2H).

Example 104: (6-chloro-4-(4-chlorophenylthio)-1H-indol-2-yl)methanol, I-187

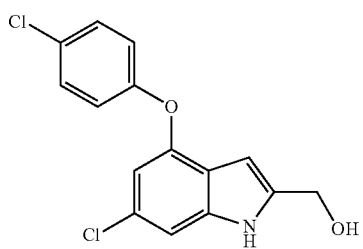

I-187

Synthetic Scheme:

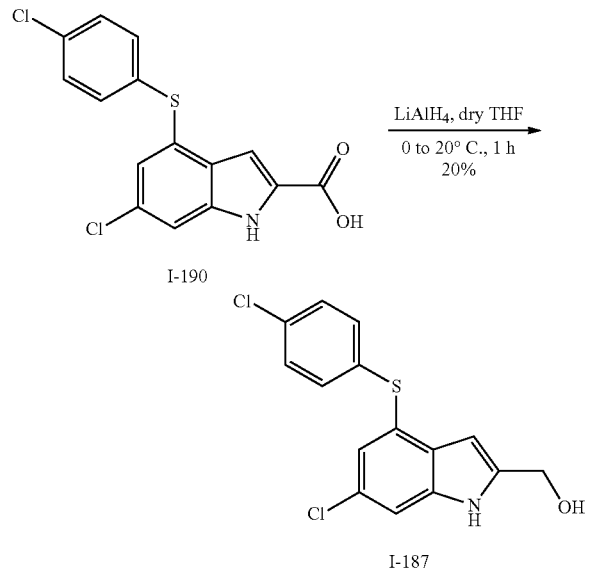

Procedures and Characterization:

Step 1: (6-chloro-4-(4-chlorophenylthio)-1H-indol-2-yl)methanol

To a solution of 6-chloro-4-(4-chlorophenylthio)-1H-indole-2-carboxylic acid (120 mg, 0.36 mmol) in dry THE (5 mL) was added 1 M LiAlH₄ in THE (0.72 mL, 0.72 mmol) at 0° C. The reaction was stirred for 1 h at 20° C. under N₂ atmosphere. The reaction was quenched with Na₂SO₄.10H₂O and filtered. The filtrate was concentrated in vacuo and the crude product was purified by prep-HPLC (0.01% TFA) to afford (6-chloro-4-(4-chlorophenylthio)-1H-indol-2-yl)methanol I-187 (22.5 mg, 0.07 mmol, 20%) as a white solid. ESI-MS (EI+, m/z): 324.0 [M+H]⁺. ¹H NMR (500 MHz, MeOD) δ 7.40 (d, J=1 Hz, 1H), 7.27 (d, J=8.5 Hz, 2H), 7.18 (d, J=8.5 Hz, 2H), 7.07 (d, J=2.5 Hz, 1H), 6.29 (s, 1H), 4.69 (s, 2H).

Example 105: (6-chloro-4-(2,4-dichlorophenylthio)-1H-indol-2-yl)methanol, I-154

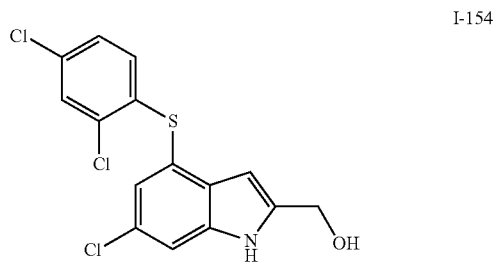 [SMILES: OCc1cc2c(Sc3ccc(Cl)cc3Cl)cc(Cl)cc2[nH]1]

I-154

Synthetic Scheme:

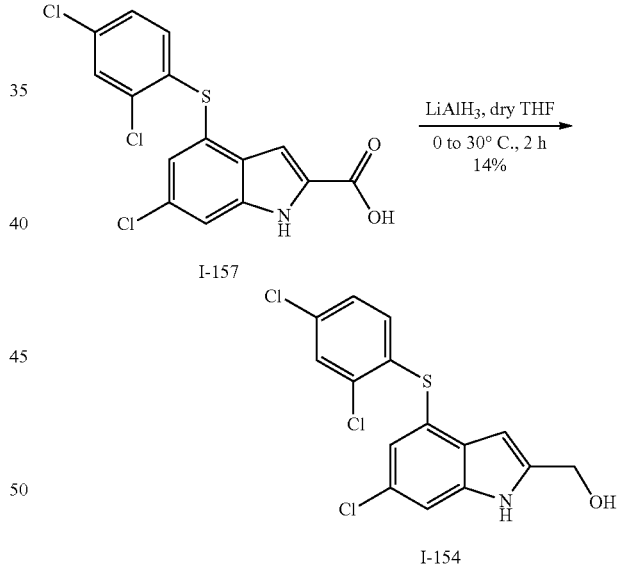

Procedures and Characterization:

Step 1: (6-chloro-4-(2,4-dichlorophenylthio)-1H-indol-2-yl)methanol, I-154

To a solution of 6-chloro-4-(2,4-dichlorophenylthio)-1H-indole-2-carboxylic acid (320 mg, 0.86 mmol) in dry THF (6 mL) was added 1 M LiAlH₄ in THF (2.5 mL, 2.5 mmol) at 0° C. The reaction was stirred for 2 h at 30° C. under N₂ atmosphere. The reaction was quenched with Na₂SO₄.10H₂O and filtered. The filtrate was concentrated in vacuo and the crude product was purified by prep-HPLC (0.01% TFA) to afford (6-chloro-4-(2,4-dichlorophenylthio)-1H-indol-2-yl)methanol I-154 (41.1 mg, 0.12 mmol, 14%) as a white solid. ESI-MS (EI+, m/z): 324.0 [M+H]+. 1H NMR (500 MHz, CDCl3) δ 8.59 (s, 1H), 7.40 (dd, J=7 Hz, J=5 Hz, 2H), 7.26 (d, J=2 Hz, 1H), 6.98 (dd, J=8.5 Hz, J=2 Hz, 1H), 6.68 (d, J=8.5 Hz, 1H), 6.32 (d, J=1 Hz, 1H), 4.81 (s, 2H).

Example 106: (6-chloro-4-(quinolin-8-ylthio)-1H-indol-2-yl)methanol, I-74

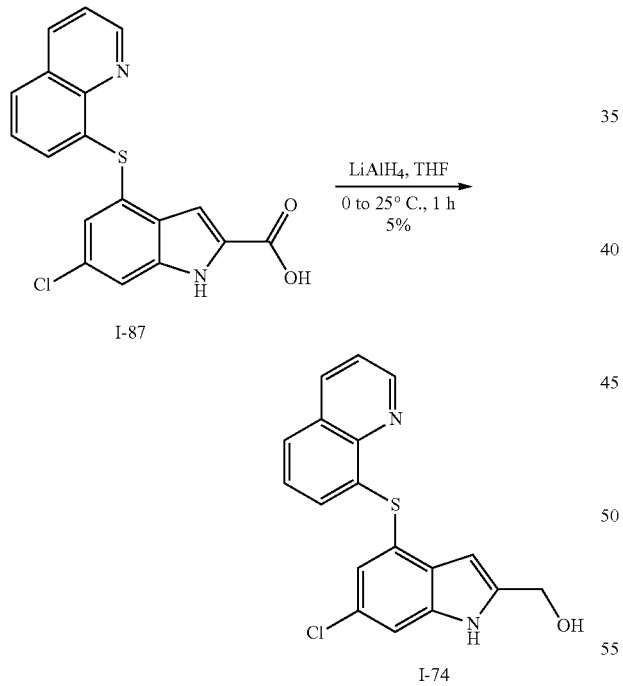

Synthetic Scheme:

Procedures and Characterization:

The same procedure used to prepare I-187 afforded (6-chloro-4-(quinolin-8-ylthio)-1H-indol-2-yl)methanol I-74 (6.5 mg, 0.02 mmol, 5%) as a white solid. ESI-MS (EI+, m/z): 339.0 [M−H]−. 1H NMR (500 MHz, MeOD) δ 8.92 (s, 1H), 8.36 (d, J=11 Hz, 1H), 7.67 (d, J=9.5 Hz, 1H), 7.62 (s, 1H), 7.53 (s, 1H), 7.29 (t, J=9 Hz, 2H), 6.89 (d, J=9 Hz, 1H), 6.28 (s, 1H), 4.67 (s, 2H).

Example 107: (6-chloro-4-(naphthalen-2-ylthio)-1H-indol-2-yl)methanol, I-134

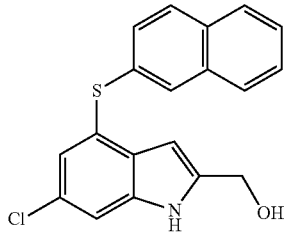

Synthetic Scheme:

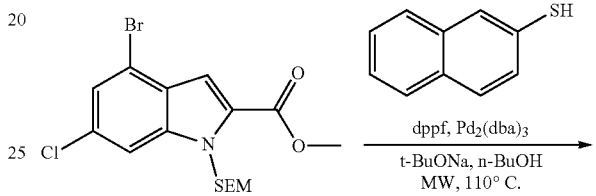

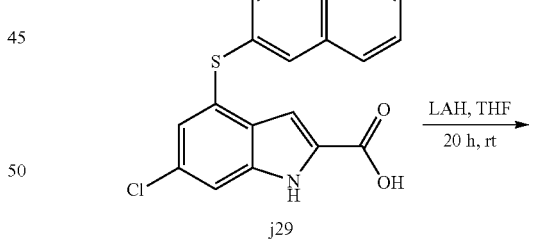

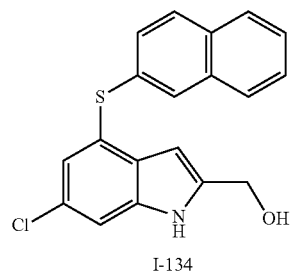

Procedures and Characterization:

Step 1: 6-chloro-4-(naphthalen-2-ylthio)-1-((2-(trimethylsilyl)ethoxy)methyl)-1H-indole-2-carboxylic acid To a solution of methyl 4-bromo-6-chloro-1-((2-(trimethylsilyl)ethoxy)methyl)-1H-indole-2-carboxylate (400 mg, 0.96 mmol) in 1-butanol (16 mL) was added 1,1'-bis(diphenyl phosphino)ferrocene (54 mg, 0.1 mmol), sodium tert-butoxide (338 mg, 3.52 mmol) and naphthalene-2-thiol (460 mg, 2.88 mmol) followed by tris(dibenzylideneacetone)dipalladium(0) (92 mg, 0.1 mmol) under $N_2$ atmosphere. It was stirred at 110° C. by microwave for 1 h. The solution was filtrated, diluted with water (50 mL) and extracted with ethyl acetate (100 mL×2). The organic phase was washed with water (50 mL×2), and brine (50 mL), dried ($Na_2SO_4$), filtered and concentrated in vacuo, the crude product was purified by chromatography (silica methanol/dcm=1/15) to afford 6-chloro-4-(naphthalen-2-ylthio)-1-((2-(trimethylsilyl) ethoxy) methyl)-1H-indole-2-carboxylic acid (700 mg) as a brown oil. ESI-MS (EI+, m/z): 482 [M−H]⁻.

Step 2: 6-chloro-4-(naphthalen-2-ylthio)-1H-indole-2-carboxylic acid

To a solution of 6-chloro-4-(naphthalen-2-ylthio)-1H-indole-2-carboxylic acid (700 mg, 1.45 mmol) in dioxane (46.00 mL) was added 6N hydrochloric acid (23.00 mL) and stirred for 20 h at 70° C. The mixture was adjusted to pH 7 and extracted with ethyl acetate. The organic phase was washed with water (100 mL×2), and brine (100 mL), dried ($Na_2SO_4$), filtered and concentrated in vacuo, the crude product was purified by prep-HPLC to afford 6-chloro-4-(naphthalen-2-ylthio)-1H-indole-2-carboxylic acid (550 mg, 1.55 mmol) as a yellow solid. ESI-MS (EI+, m/z): 354 [M+H]⁺. ¹H NMR (500 MHz, DMSO) δ 13.26 (br s, 1H), 12.20 (s, 1H), 8.03 (s, 1H), 7.87-7.94 (m, 3H), 7.54-7.56 (m, 2H), 7.39-7.44 (m, 2H), 6.99 (s, 1H), 6.93 (s, 1H).

Step 3: (6-chloro-4-(naphthalen-2-ylthio)-1H-indol-2-yl)methanol, I-134

To a solution of 6-chloro-4-(naphthalen-2-ylthio)-1H-indole-2-carboxylic acid (550 mg, 1.55 mmol) in THF (20 mL) was added lithium aluminium hydride (350 mg, 9.20 mmol) and stirred for 20 h at rt. The mixture was quenched with sodium sulfate decahydrate, filtered and concentrated in vacuo, the crude product was purified by prep-HPLC to afford (6-chloro-4-(naphthalen-2-ylthio)-1H-indol-2-yl)methanol I-134 as a white solid (9.8 mg, 0.03 mmol). ESI-MS (EI+, m/z): 338 [M−H]⁻. ¹H NMR (500 MHz, DMSO) δ 11.47 (s, 1H), 7.83-7.90 (m, 4H), 7.49-7.54 (m, 2H), 7.41 (s, 1H), 7.33 (d, 1H, J=8 Hz), 7.0 (s, 1H), 6.22 (s, 1H), 5.33 (t, 1H, J=5.5 Hz), 4.56 (d, 2H, J=5.5 Hz).

Example 108: (6-chloro-4-(4-(trifluoromethoxy)phenylthio)-1H-indol-2-yl)methanol, I-123

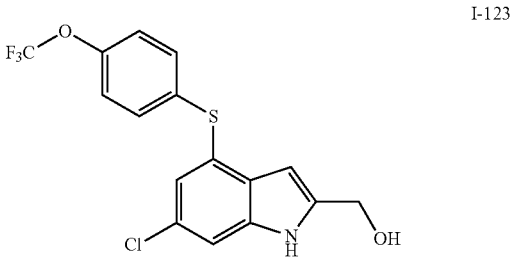 [SMILES: OCc1cc2c(Sc3ccc(OC(F)(F)F)cc3)cc(Cl)cc2[nH]1]

Synthetic Scheme:

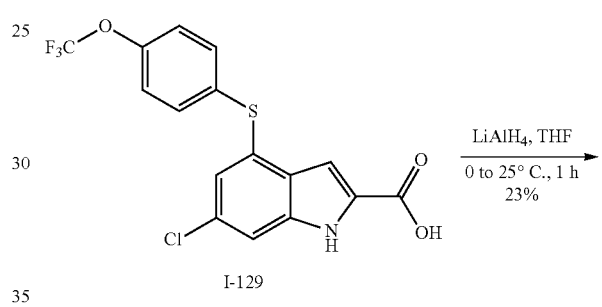

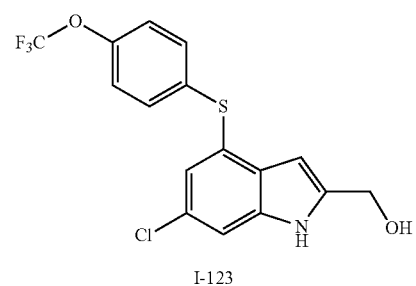

Procedures and Characterization:

The same procedure used to prepare I-187 afforded (6-chloro-4-(4-(trifluoromethoxy) phenylthio)-1H-indol-2-yl)methanol I-123 (56.2 mg, 0.15 mmol, 23%) as a white solid. ESI-MS (EI+, m/z): 372.0 [M−H]⁻. ¹H NMR (500 MHz, MeOD) δ 7.30 (d, J=0.5 Hz, 1H), 7.15 (dd, J=7 Hz, J=2 Hz, 2H), 7.05 (d, J=7.5 Hz, 2H), 6.99 (d, J=1.5 Hz, 1H), 6.20 (s, 1H), 4.57 (s, 2H).

Example 109: (4-(4-tert-butylphenylthio)-6-chloro-1H-indol-2-yl)methanol, I-124

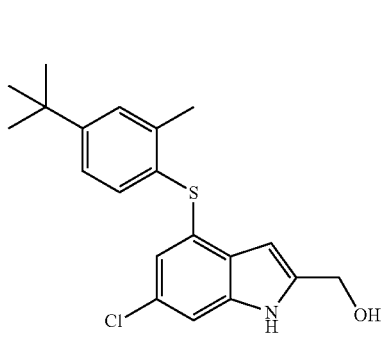

Synthetic Scheme:

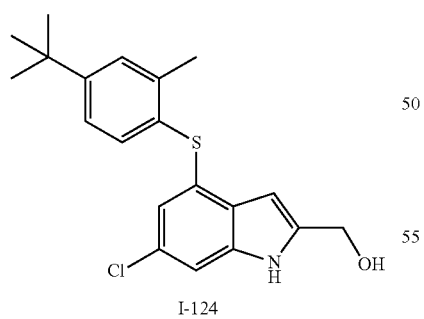

Procedures and Characterization:

The same procedure used to prepare I-187 afforded (4-(4-tert-butylphenylthio)-6-chloro-1H-indol-2-yl)methanol I-124 (25.7 mg, 0.07 mmol, 11%) as a white solid. ESI-MS (EI+, m/z): 358.2 [M−H]−. $^{1}$H NMR (500 MHz, MeOD) δ 7.31-7.27 (m, 3H), 7.22 (d, J=8 Hz, 1H), 6.63 (d, J=2 Hz, 1H), 6.33 (s, 1H), 4.70 (s, 2H), 2.33 (s, 3H), 1.22 (s, 9H).

Example 110: (6-chloro-4-(4-fluorophenylthio)-1H-indol-2-yl)methanol, I-153

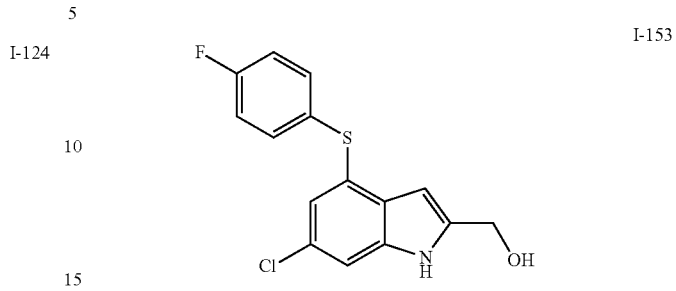

Synthetic Scheme:

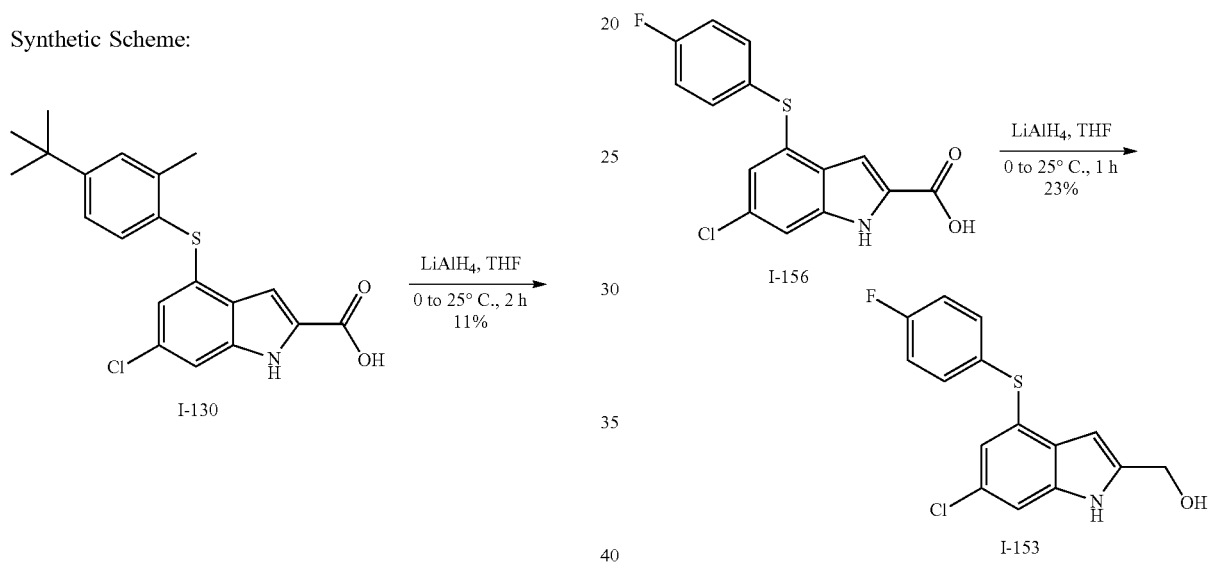

Procedures and Characterization:

The same procedure used to prepare I-187 afforded (6-chloro-4-(4-fluorophenylthio)-1H-indol-2-yl)methanol I-153 (40.0 mg, 0.13 mmol, 23%) as a white solid. ESI-MS (EI+, m/z): 306.0 [M−H]−. $^{1}$H NMR (500 MHz, CDCl$_3$) δ 8.48 (s, 1H), 7.34-7.31 (m, 2H), 7.27 (s, 1H), 7.01-6.98 (m, 3H), 6.37 (d, J=1 Hz, 1H), 4.81 (s, 2H).

Example 111: (6-chloro-4-(3,4-difluorophenylthio)-1H-indol-2-yl)methanol, I-152

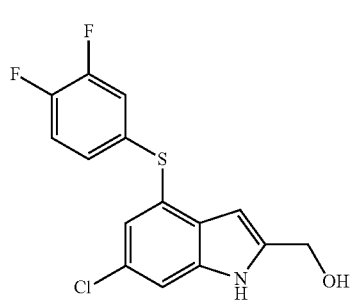

Synthetic Scheme:

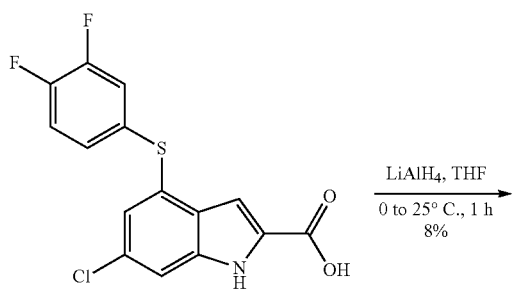

Procedures and Characterization:

The same procedure used to prepare I-187 afforded (6-chloro-4-(3,4-difluorophenylthio)-1H-indol-2-yl)methanol I-152 (11.5 mg, 0.04 mmol, 8%) as a white solid. ESI-MS (EI+, m/z): 324.0 [M−H]⁻. ¹H NMR (500 MHz, CDCl₃) δ 8.69 (s, 1H), 7.32 (s, 1H), 7.13 (d, J=1 Hz, 1H), 7.06-6.99 (m, 3H), 6.32 (s, 1H), 4.79 (s, 2H).

Example 112: (6-chloro-4-(3-(trifluoromethoxy)phenylthio)-1H-indol-2-yl)methanol, I-122

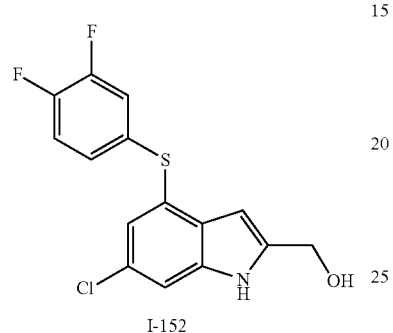

Synthetic Scheme:

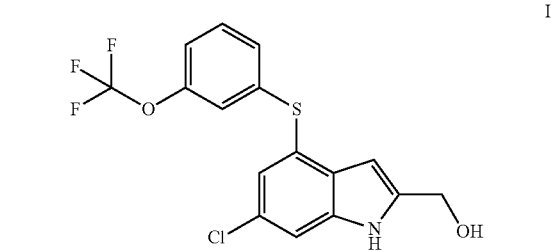

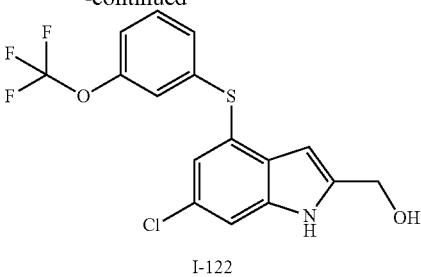

Procedures and Characterization:

Step 1: (6-chloro-4-(3-(trifluoromethoxy)phenyl-thio)-1H-indol-2-yl)methanol

The same procedure used to prepare I-187 afforded (6-chloro-4-(naphthalen-2-ylthio)-1H-indol-2-yl)methanol I-122 as a white solid (25.6 mg, 0.07 mmol). ESI-MS (EI+, m/z): 372 [M−H]⁻. ¹H NMR (500 MHz, CDCl₃) δ 8.65 (s, 1H), 7.40 (s, 2H), 7.25-7.28 (m, 2H), 7.14 (d, 1H, J=8 Hz), 7.05 (s, 1H), 7.03 (d, 1H, J=8 Hz), 6.34 (s, 1H), 4.82 (s, 2H).

Example 113: (6-chloro-4-(4-phenoxyphenylthio)-1H-indol-2-yl)methanol, I-116

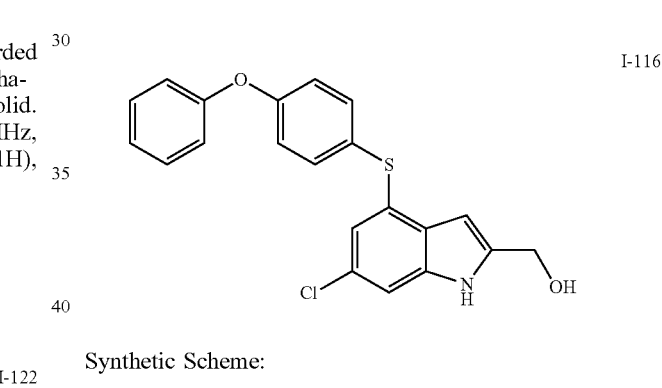

Synthetic Scheme:

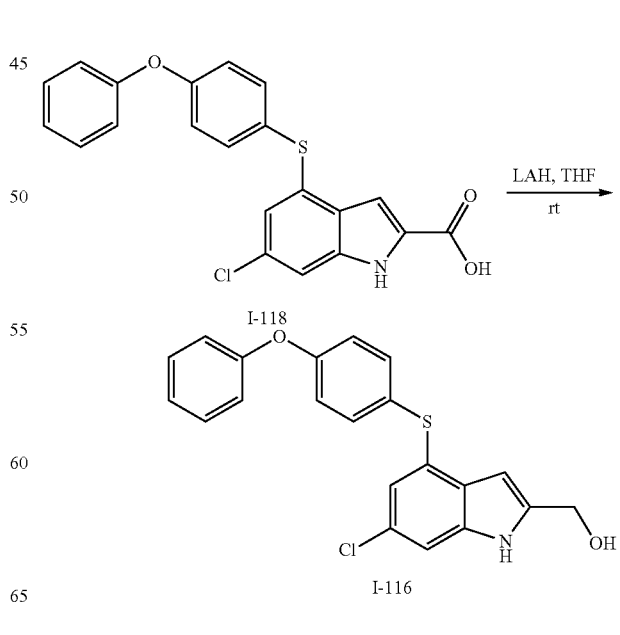

Procedures and Characterization:

Step 1: (6-chloro-4-(4-phenoxyphenylthio)-1H-indol-2-yl)methanol

The same procedure used to prepare I-187 afforded 6-chloro-4-(4-phenoxyphenylthio)-1H-indol-2-yl)methanol I-116 as a white solid (21.8 mg, 0.06 mmol). ESI-MS (EI+, m/z): 380 [M−H]⁻. ¹H NMR (500 MHz, DMSO) δ 11.46 (s, 1H), 7.40-7.43 (t, 2H, J=8 Hz), 7.37 (d, 2H, J=9 Hz), 7.33 (s, 1H), 7.16-7.19 (t, 1H, J=7.5 Hz), 7.06 (d, 2H, J=8 Hz), 7.01 (d, 2H, J=8.5 Hz), 6.82 (s, 1H), 6.25 (s, 1H), 5.36-5.38 (t, 1H, J=5.5 Hz), 4.59 (d, 2H, J=5.5 Hz).

Example 114: (4-bromo-6-(phenylthio)-1H-indol-2-yl)methanol, I-237

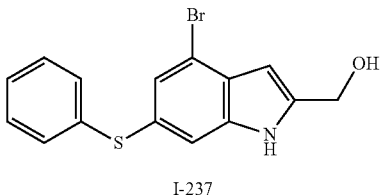

Synthetic Scheme:

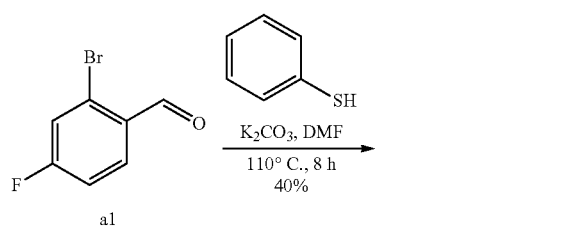

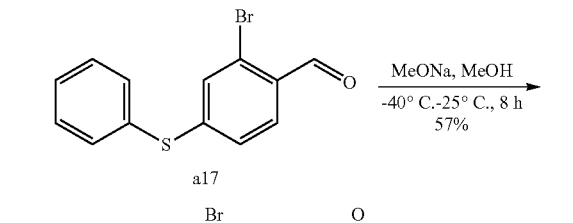

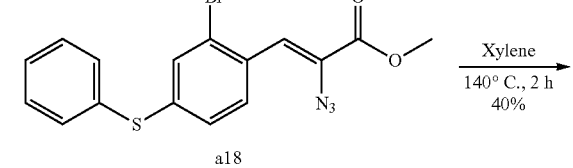

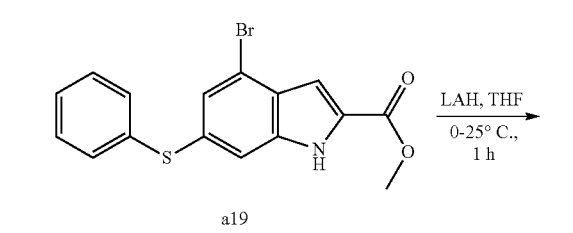

-continued

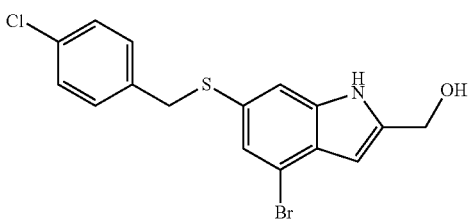

Procedures and Characterization:

Methyl 4-bromo-6-(phenylthio)-1H-indole-2-carboxylate was prepared as L7. The same procedure for the last as prepared I-187 afforded (4-bromo-6-(phenylthio)-1H-indol-2-yl)methanol I-237: ESI-MS (EI⁺, m/z): 335 [M+H]⁺. ¹H NMR (500 MHz, DMSO-d₆) δ 11.61 (d, J=20.2 Hz, 1H), 7.44 (d, J=28.2 Hz, 1H), 7.32 (t, J=7.6 Hz, 2H), 7.20 (dd, J=17.5, 6.6 Hz, 4H), 6.30 (s, 1H), 5.42 (t, J=5.6 Hz, 1H), 4.65 (t, J=9.1 Hz, 2H).

Example 115: (4-bromo-6-(4-chlorobenzylthio-1H-indol-2-yl)methanol, I-145

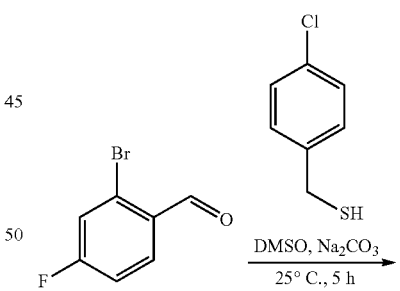

Synthetic Scheme:

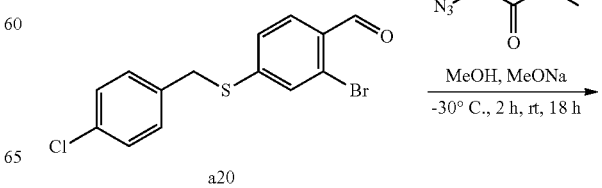

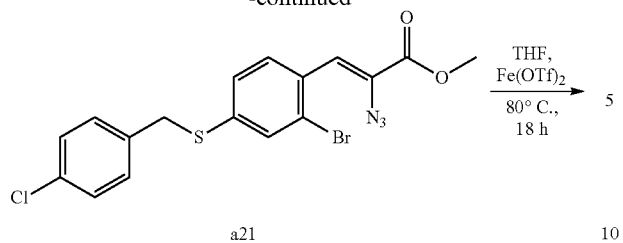

a21

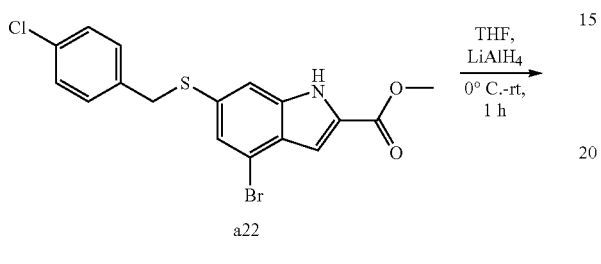

a22

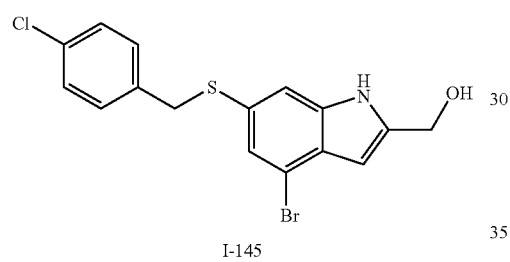

I-145

Procedures and Characterization:

Step 1:
2-bromo-4-(4-chlorobenzylthio)benzaldehyde

To a solution of 2-bromo-4-fluorobenzaldehyde (2.0 g, 9.85 mmol) and compound 2(4-chlorophenyl)methanethiol (1.56 g, 9.85 mmol) in DMSO (20 mL), was added Na$_2$CO$_3$ (1.57 g, 14.78 mmol) and stirred at 25° C. for 5 h. Then reaction solution was cooled to rt and extracted with EtOAc, washed with brine and concentrated to afford crude product. Purified by chromatography (silica, ethyl acetate/petroleum ether=0/1) to afford 2-bromo-4-(4-chlorobenzylthio)benzaldehyde (3.066 g, 8.97 mmol, yield: 82.7%) as a white solid. ESI-MS (EI+, m/z): 343.0 [M+H]$^+$.

Step 4: (4-bromo-6-(4-chlorobenzylthio)-1H-indol-2-yl)methanol, I-145

The same procedure was prepared as I-252 afforded (4-bromo-6-(4-chlorobenzylthio)-1H-indol-2-yl)methanol, I-145 as a yellow solid (39.6 mg, purity: 100%, yield: 42.4%). ESI-MS (EI+, m/z): 384.0[M+H]$^+$.

$^1$H NMR (500 MHz, DMSO) δ 11.41 (s, 1H), 7.32 (d, J=8.4 Hz, 2H), 7.29-7.23 (m, 3H), 7.18 (d, J=1.1 Hz, 1H), 6.21 (s, 1H), 5.35 (t, J=5.6 Hz, 1H), 4.59 (d, J=5.6 Hz, 2H), 4.16 (s, 2H).

Example 116: (6-chloro-5-(4-chlorobenzylthio)-1H-indol-2-yl)methanol, I-76

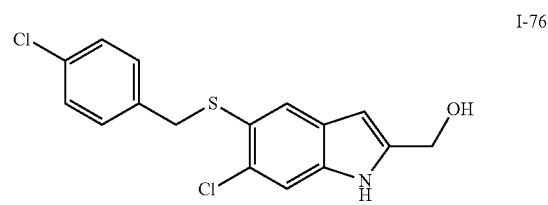 [SMILES: OCc1cc2cc(SCc3ccc(Cl)cc3)c(Cl)cc2[nH]1]

Synthetic Scheme:

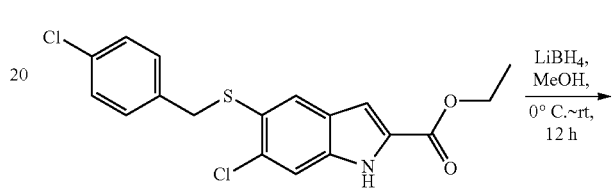

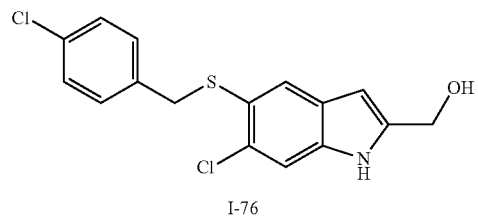

I-76

LiBH$_4$ (18 mg, 0.8 mmol) was added to a solution of ethyl 6-chloro-5-(4-chlorobenzylthio)-1H-indole-2-carboxylate (30 mg, 0.08 mmol) in THF (3 mL) and MeOH (0.3 mL) at 0° C. and stirred at 0° C.~rt for 16 h. The reaction mixture was cooled to 0° C., quenched with NH$_4$Cl (aq.), extracted with EtOAc, brine, dried, concentrated, purified by prep-HPLC to afford (6-chloro-5-(4-chlorobenzylthio)-1H-indol-2-yl)methanol I-76 (10 mg, 37% yield) as a white solid.

ESI-MS (EI$^+$, m/z): 319.9 [M-OH]$^+$.

$^1$H NMR (500 MHz, CDCl$_3$) δ 8.44 (s, 1H), 7.50 (s, 1H), 7.44 (s, 1H), 7.18 (d, J=10.5 Hz, 2H), 7.12 (d, J=10 Hz, 2H), 6.27 (s, 1H), 4.81 (s, 2H), 4.03 (s, 2H).

Example 117: (4-bromo-6-(3,4-dichlorophenylthio)-1H-indol-2-yl)methanol, I-133

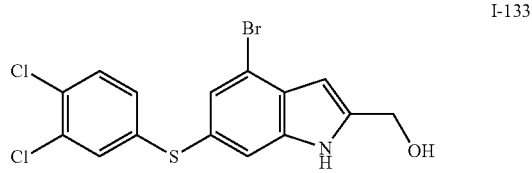 [SMILES: OCc1cc2c(Br)cc(Sc3ccc(Cl)c(Cl)c3)cc2[nH]1]

Synthetic Scheme:

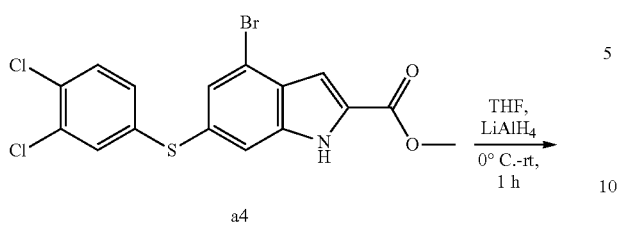

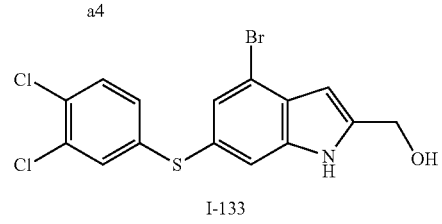

Procedures and Characterization:

Step 1: (4-bromo-6-(3,4-dichlorophenylthio)-1H-indol-2-yl)methanol, I-133

To a solution of methyl 4-bromo-6-(3,4-dichlorophenyl-thio)-1H-indole-2-carboxylate (120 mg, 0.278 mmol) in THF (2 mL), was added LiAlH$_4$ (32.45 mg, 0.885 mmol), this mixture was stirred at 0° C. for 2 h. The reaction was quenched with ice-water and extracted with EtOAc, dried and concentrated and purified by prep-HPLC to afford (4-bromo-6-(3,4-dichlorophenylthio)-1H-indol-2-yl)methanol I-133 (15.6 mg, purity: 100%, yield: 13.9%).

$^1$H NMR (500 MHz, DMSO) δ 11.70 (s, 1H), 7.54 (d, J=7.9 Hz, 2H), 7.33 (d, J=20.3 Hz, 2H), 7.04 (d, J=8.3 Hz, 1H), 6.33 (s, 1H), 5.47 (s, 1H), 4.66 (s, 2H).

Example 118:
(5-chloro-4-phenoxy-1H-indol-2-yl)methanol, I-293

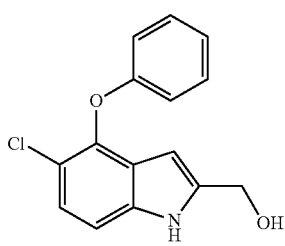

Synthetic Scheme:

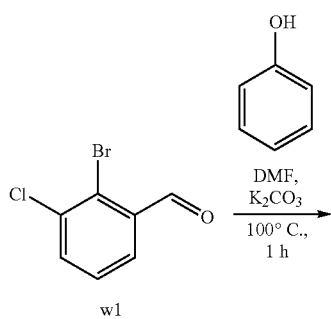

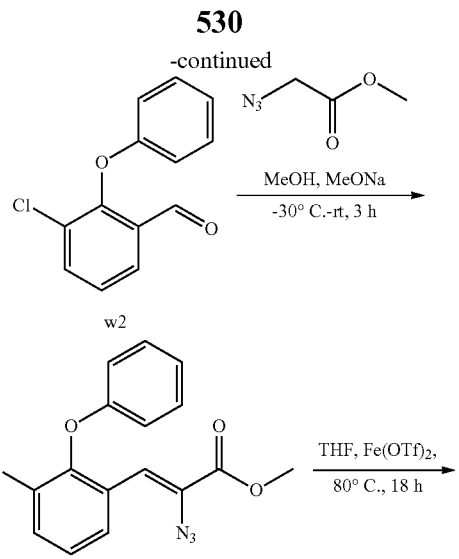

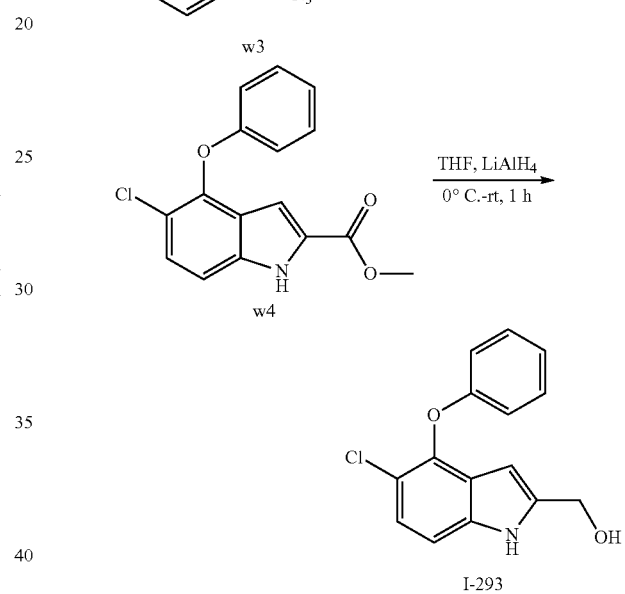

Procedures and Characterization:

Step 1: 3-chloro-2-phenoxybenzaldehyde

To a solution of 2-bromo-3-chlorobenzaldehyde (500 mg, 2.28 mmol) and phenol (225.13 mg, 2.39 mmol) in DMF (5 mL), was added K$_2$CO$_3$ (944.62 mg, 26.83 mmol) and stirred at 100° C. for 1 h. Then filtered and extracted with EtOAc, washed with brine and concentrated to afford crude product. Purified by chromatography (silica, ethyl acetate/petroleum ether=1/5) afforded 3-chloro-2-phenoxybenzaldehyde (286 mg, 1.23 mmol, purity: 85%, yield: 45.86%) as a yellow solid ESI-MS (EI+, m/z): 233.1 [M+H]$^+$.

Step 2: (Z)-methyl 2-azido-3-(3-chloro-2-phenoxyphenyl)acrylate

A solution of MeONa (248.92 mg, 4.61 mmol) was added 3-chloro-2-phenoxybenzaldehyde (268 mg, 1.15 mmol) in MeOH (3 mL), cooled to −30° C., added methyl azidoacetate (530.28 mg, 4.61 mmol). The mixture was stirred at −30° C. for 3 h, then stirred at rt for 18 h. The resulting solution was quenched with ice-water, concentrated to remove MeOH, extracted with EtOAc (30 mL*2), the organic phase was combined and washed with brine and dried over sodium sulfate, concentrated to afford crude product (128 mg, purity: 100%, yield: 33.7%) as a yellow solid. No MS, $^1$H NMR (500 MHz, DMSO) δ 8.30 (dd, J=8.0, 1.2 Hz, 1H), 7.65 (dd, J=8.0, 1.4 Hz, 1H), 7.42 (t, J=8.1 Hz, 1H), 7.34 (dd, J=8.6, 7.5 Hz, 2H), 7.07 (q, J=7.0 Hz, 1H), 6.86 (s, 1H), 6.77 (d, J=7.9 Hz, 2H), 3.75 (s, 3H).

Step 3: methyl 5-chloro-4-phenoxy-1H-indole-2-carboxylate

To a solution of (Z)-methyl 2-azido-3-(3-chloro-2-phenoxyphenyl)acrylate (128 mg, 0.388 mmol) in THF (5 mL), was added Fe(OTf)$_2$ (41.22 mg, 0.116 mmol), this mixture was stirred at 80° C. for 18 h. The resulting solution was extracted with EtOAc (5 mL*2), the organic phase was combined and washed with brine and dried over sodium sulfate, concentrated to afford crude product, purified by column chromatography on silica gel to afford white solid (86 mg, yield: 73.4%). ESI-MS (EI+, m/z): 302.0[M+H]$^+$.

Step 4: (5-chloro-4-phenoxy-1H-indol-2-yl)methanol, I-293

To a solution of methyl 5-chloro-4-phenoxy-1H-indole-2-carboxylate (80 mg, 0.285 mmol) in THF (3 mL), was added LiAlH$_4$ (32.45 mg, 0.885 mmol), this mixture was stirred at 0° C. for 2 h, The reaction was quenched with ice-water and extracted with EtOAc, dried and concentrated and purified by prep-HPLC to afford (5-chloro-4-phenoxy-1H-indol-2-yl)methanol I-293 (23 mg, purity: 100%, yield: 29.5%). ESI-MS (EI+, m/z): 274.1[M+H]$^+$.

$^1$H NMR (500 MHz, DMSO) δ 11.43 (s, 1H), 7.30 (t, J=7.7 Hz, 2H), 7.17 (d, J=8.6 Hz, 1H), 7.03 (t, J=6.9 Hz, 1H), 6.82 (d, J=7.9 Hz, 2H), 5.92 (s, 1H), 5.28 (s, 1H), 4.52 (s, 2H).

Example 119: (4-chloro-6-phenoxy-1H-indol-2-yl)methanol, I-252

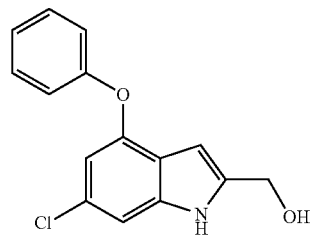

Synthetic Scheme:

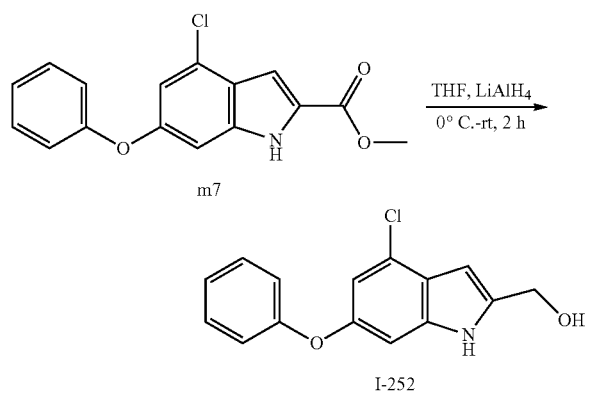

Procedures and Characterization:

Step 4: (4-chloro-6-phenoxy-1H-indol-2-yl)methanol

The same procedure used to prepare I-187 afforded (4-chloro-6-phenoxy-1H-indol-2-yl)methanol I-252 (76.6 mg, purity: 100%, yield: 42.2%). ESI-MS (EI+, m/z): 274.1 [M+H]$^+$. H NMR (500 MHz, DMSO) δ 11.34 (s, 1H), 7.37 (dd, J=8.4, 7.5 Hz, 2H), 7.11 (t, J=7.4 Hz, 1H), 7.02-6.96 (m, 2H), 6.93 (d, J=1.1 Hz, 1H), 6.81 (d, J=1.9 Hz, 1H), 6.30 (s, 1H), 5.33 (t, J=5.6 Hz, 1H), 4.59 (d, J=5.6 Hz, 2H).

Example 120: Synthesis of (6-Chloro-4-phenoxy-1H-indol-2-yl)methanol, I-291 and (4-Bromo-6-phenoxy-1H-indol-2-yl)methanol, I-290

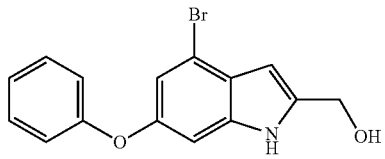

Synthetic Scheme:

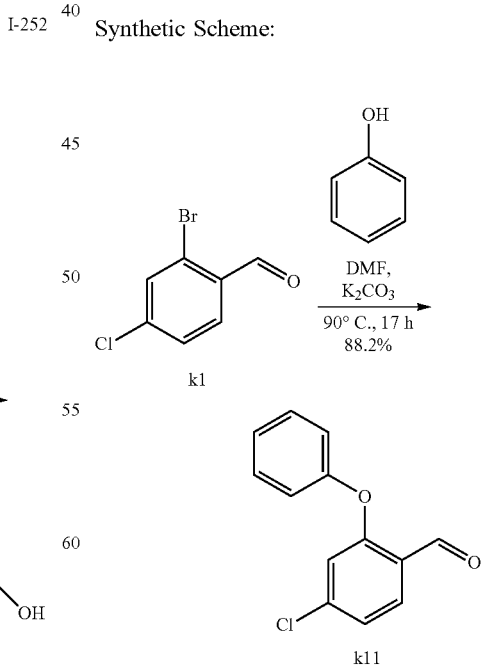

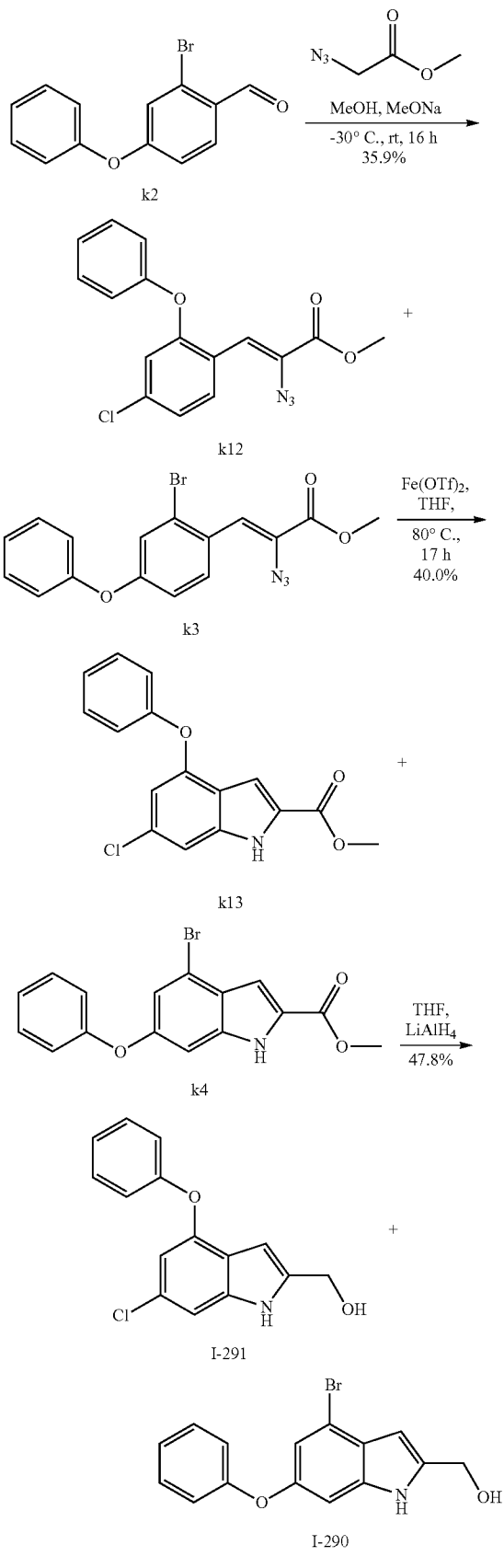

Procedures and Characterization:

Step 1: 4-chloro-2-phenoxybenzaldehyde and 2-bromo-4-phenoxybenzaldehyde

The same temperature as prepared w2 afforded the mixture of 4-chloro-2-phenoxybenzaldehyde and 2-bromo-4-phenoxybenzaldehyde (6.1 g, 38.6%) as a white solid. ESI-MS (EI+, m/z): 233.0 [M+H]+.

Step 2: (Z)-methyl 2-azido-3-(4-chloro-2-phenoxyphenyl)acrylate and (Z)-methyl 2-azido-3-(2-bromo-4-phenoxyphenyl)acrylate The same temperature as prepared w2 afforded (Z)-methyl 2-azido-3-(4-chloro-2-phenoxyphenyl)acrylate and (Z)-methyl 2-azido-3-(2-bromo-4-phenoxyphenyl)acrylate (1.8 g, 20.9%) as a yellow oil. MS (EI+, m/z): No mass Step 3: methyl 6-chloro-4-phenoxy-1H-indole-2-carboxylate and methyl 4-bromo-6-phenoxy-1H-indole-2-carboxylate:

The same temperature as prepared w2 afforded methyl 6-chloro-4-phenoxy-1H-indole-2-carboxylate and methyl 4-bromo-6-phenoxy-1H-indole-2-carboxylate (640 mg, 40.0%) as a white solid. ESI-MS (EI−, m/z): 302.0 [M+H]+.

Step 4: (6-chloro-4-phenoxy-1H-indol-2-yl)methanol, I-291, and 4-bromo-6-phenoxy-1H-indol-2-yl)methanol, I-290

The same procedure used to prepare I-187 afforded (6-chloro-4-phenoxy-1H-indol-2-yl)methanol I-291 (63 mg) MS (EI+, m/z): 274.1 [M+H]+ 1H NMR (500 MHz, DMSO) δ 11.38 (s, 1H), 7.47-7.30 (m, 2H), 7.24-7.09 (m, 2H), 7.01 (d, J=7.8 Hz, 2H), 6.53 (d, J=1.6 Hz, 1H), 6.04 (s, 1H), 5.30 (t, J=5.4 Hz, 1H), 4.54 (d, J=5.1 Hz, 2H). 4-bromo-6-phenoxy-1H-indol-2-yl)methanol I-290 (100 mg) MS (EI+, m/z): 318.0 [M−H]+ 1H NMR (500 MHz, DMSO) δ 11.38 (s, 1H), 7.37 (t, J=7.9 Hz, 2H), 7.11 (t, J=7.4 Hz, 1H), 7.03-6.76 (m, 4H), 6.24 (s, 1H), 5.35 (s, 1H), 4.59 (s, 2H).

Example 121: (6-Phenoxy-1H-indol-2-yl)methanol, I-286

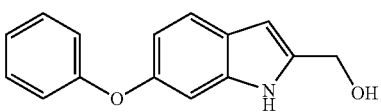

Synthetic Scheme:

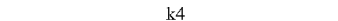

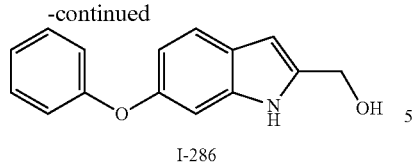

I-286

Procedures and Characterization:

Step 1: methyl 6-phenoxy-1H-indole-2-carboxylate

To a solution of methyl 4-bromo-6-phenoxy-1H-indole-2-carboxylate (240 mg, 0.79 mmol) in MeOH (10 mL), was added Pd/C (48 mg, 10%), and stirred at rt with $H_2$ balloon for 17 h. The Pd/C was removed by filtration to afford the crude product (137 mg, yield: 64.5%). ESI-MS (EI$^+$, m/z): 268.1 [M+H]$^+$.

Step 2: (6-phenoxy-1H-indol-2-yl)methanol, I-286

The same procedure used to prepare I-187 afforded (6-phenoxy-1H-indol-2-yl)methanol I-286 (20 mg, 16.4%) MS (EI+, m/z): 274.1 [M+H]$^+$ and SP-0015080-031-A (100 mg) MS (EI+, m/z): 240.1 [M+H]$^+$ $^1$H NMR (500 MHz, DMSO) δ 10.99 (s, 1H), 7.45 (d, J=8.5 Hz, 1H), 7.37-7.22 (m, 2H), 7.04 (t, J=7.4 Hz, 1H), 6.98-6.85 (m, 3H), 6.71 (dd, J=8.5, 2.2 Hz, 1H), 6.26 (d, J=0.9 Hz, 1H), 5.25 (t, J=5.2 Hz, 1H), 4.57 (d, J=4.6 Hz, 2H).

Example 122: (4-fluoro-6-phenoxy-1H-indol-2-yl)methanol, I-249

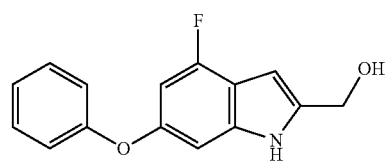

I-249

Synthetic Scheme:

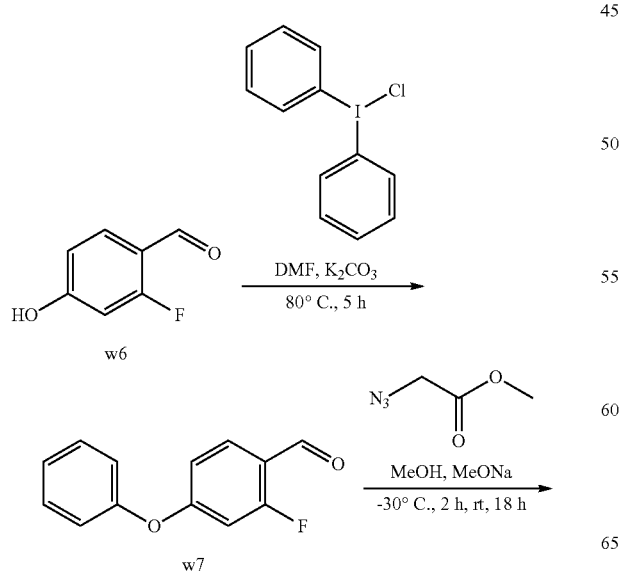

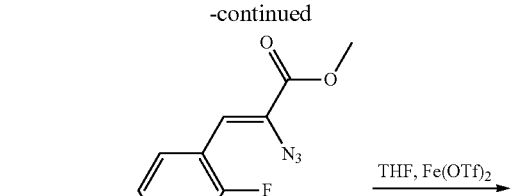

w8

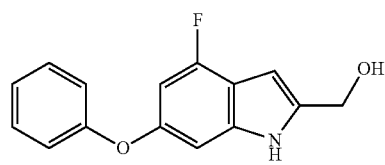

w9

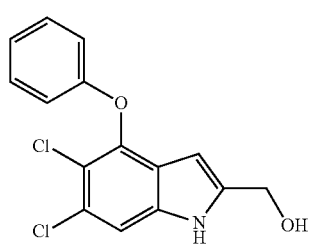

I-249

Procedures and Characterization:

The same procedure was prepared as I-252 afforded (4-fluoro-6-phenoxy-1H-indol-2-yl)methanol I-249 (76.6 mg, purity: 100%, yield: 31.58%). ESI-MS (EI+, m/z): 258.1 [M+H]$^-$. $^1$H NMR (500 MHz, DMSO) δ 11.29 (s, 1H), 7.37 (t, J=8.0 Hz, 2H), 7.11 (t, J=7.4 Hz, 1H), 7.00 (d, J=7.8 Hz, 2H), 6.78 (d, J=1.1 Hz, 1H), 6.56 (dd, J=11.2, 1.8 Hz, 1H), 6.31 (s, 1H), 5.30 (t, J=5.5 Hz, 1H), 4.58 (d, J=5.5 Hz, 2H).

Example 123: (5,6-Dichloro-4-phenoxy-1H-indol-2-yl)methanol, I-250

I-250

Synthetic Scheme:

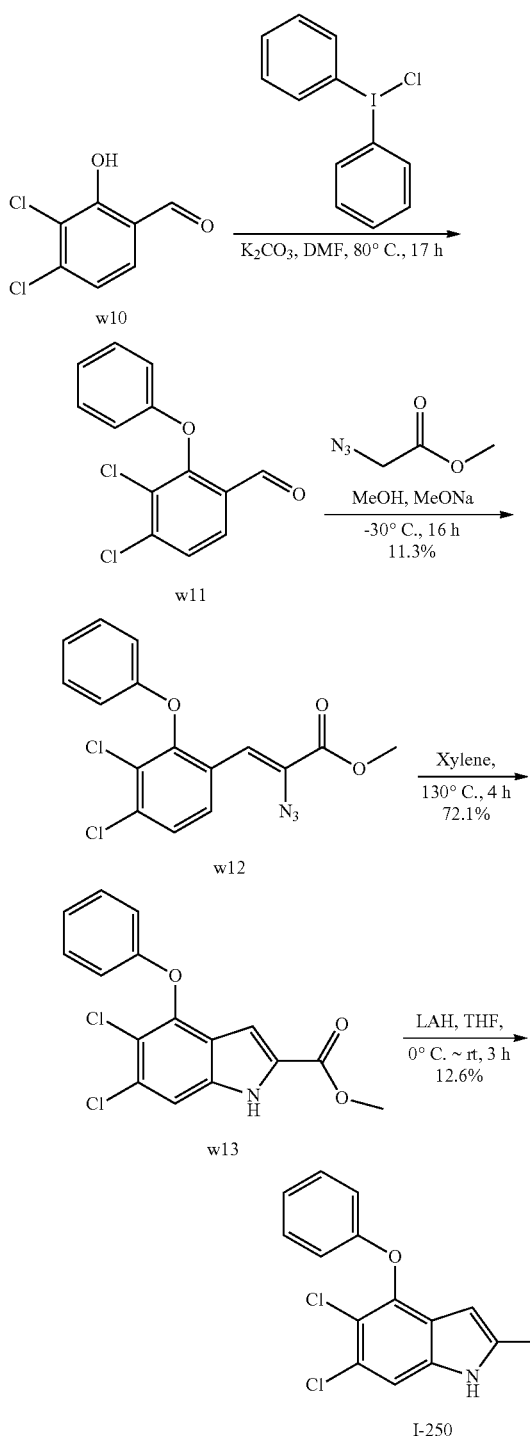

Procedures and Characterization:

Step 1: 3,4-Dichloro-2-phenoxybenzaldehyde

The same procedure was prepared as m5 afforded 3,4-dichloro-2-phenoxybenzaldehyde (3.0 g, 42.8%) as a white solid. ESI-MS (EI+, m/z): No mass

Step 2: (Z)-Methyl 2-azido-3-(3,4-dichloro-2-phenoxyphenyl)acrylate

The same procedure was prepared as b3 afforded (Z)-methyl 2-azido-3-(3,4-dichloro-2-phenoxyphenyl)acrylate (0.6 g, 14.6%) as a yellow solid. MS (EI+, m/z): No mass

Step 3: Methyl 5,6-dichloro-4-phenoxy-1H-indole-2-carboxylate

The same procedure was prepared as a4 afforded methyl 5,6-dichloro-4-phenoxy-1H-indole-2-carboxylate (400 mg, 72.1%) as a yellow solid. MS (EI+, m/z): No mass

Step 4: (5,6-Dichloro-4-phenoxy-1H-indol-2-yl)methanol

The same procedure used to prepare I-187 afforded 5,6-dichloro-4-phenoxy-1H-indol-2-yl)methanol I-250 (15 mg, 12.6%) as a white solid. ESI-MS (EI+, m/z): 308.1 [M–H]$^+$. $^1$H NMR (500 MHz, CDCl$_3$) δ 8.62 (s, 1H), 7.29 (dd, J=29.6, 22.0 Hz, 3H), 7.04 (t, J=7.4 Hz, 1H), 6.89 (d, J=8.1 Hz, 2H), 6.05 (s, 1H), 4.72 (s, 2H), 2.28-1.77 (m, 1H).

Example 124: (6-(Benzyloxy)-4-bromo-1H-indol-2-yl)methanol, I-241

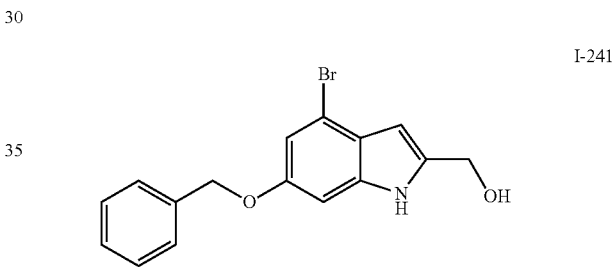

Synthetic Scheme:

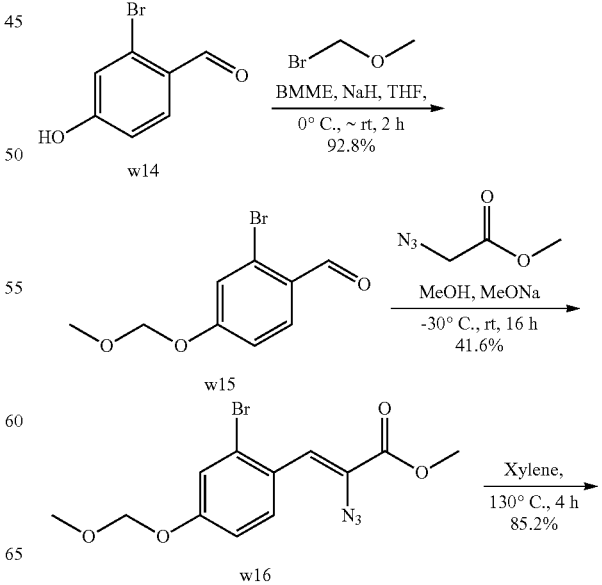

539

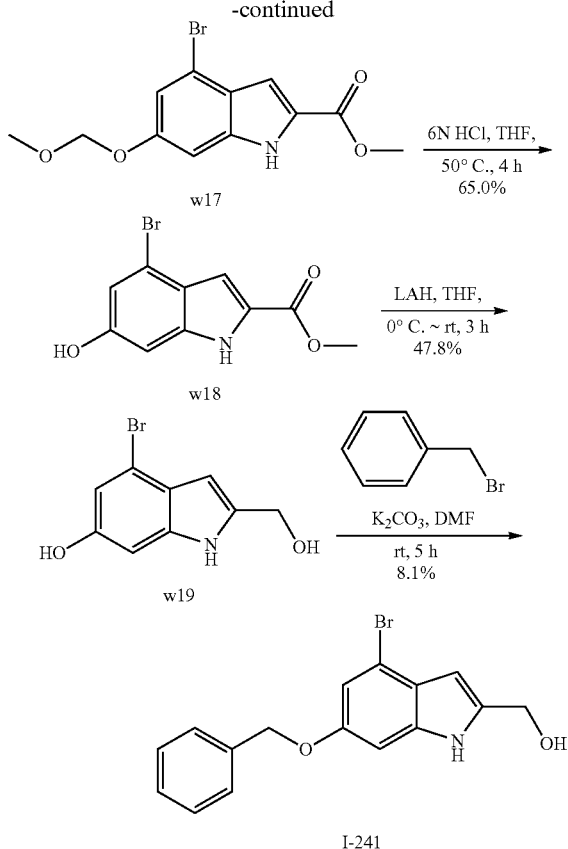

Procedures and Characterization:

Step 1: 2-Bromo-4-(methoxymethoxy)benzaldehyde

To a stirred solution of NaH (2.7 g, 68.7 mmol, 60%) in THF (50 mL) under $N_2$ at 0° C. was added 2-bromo-4-hydroxybenzaldehyde (4.6 g, 22.9 mmol), bromo(methoxy)methane (4.3 g, 34.3 mmol), the mixture was stirred at rt for 2 h. The reaction mixture was added dropwise slowly to a cold saturated aqueous NaCl solution at 0° C. The mixture was extracted with EtOAc (20 mL×3), and the organic layers were washed with water, brine, dried and concentrated, purified by silica gel column chromatography (PE/EtOAc=4/1) to give 2-bromo-4-(methoxymethoxy)benzaldehyde (5.2 g, 92.8%) as a yellow solid. MS (EI+, m/z): No mass $^1$H NMR (500 MHz, DMSO) δ 10.10 (s, 1H), 7.84 (d, J=8.7 Hz, 1H), 7.42 (d, J=2.4 Hz, 1H), 7.20 (dd, J=8.7, 2.3 Hz, 1H), 5.35 (s, 2H), 3.40 (s, 3H).

Step 2: (E)-Methyl 2-azido-3-(2-bromo-4-(methoxymethoxy)phenyl)acrylate

The same procedure was prepared as b3 afforded (E)-methyl 2-azido-3-(2-bromo-4-(methoxymethoxy)phenyl)acrylate (3 g, 41.6%) as a yellow solid. MS (EI+, m/z): No mass Step 3: Methyl 4-bromo-6-(methoxymethoxy)-1H-indole-2-carboxylate The same procedure was prepared as a4 afforded methyl 4-bromo-6-(methoxymethoxy)-1H-indole-2-carboxylate (2.3 g, 85.2%) as a yellow solid. MS (EI+, m/z): 314.0 $[M-H]^+$.

540

Step 4: Methyl 4-bromo-6-hydroxy-1H-indole-2-carboxylate

To the solution of methyl 4-bromo-6-(methoxymethoxy)-1H-indole-2-carboxylate (2.3 g, 7.3 mmol) in THF (15 mL) was added 6N HCl (15 mL). The mixture was stirred at 50° C. for 4 h. The reaction was extracted with EtOAc, washed with $NaHCO_3$ (aq) and brine, dried over sodium sulfate, concentrated to afford methyl 4-bromo-6-hydroxy-1H-indole-2-carboxylate (1.3 g, 65.0%) as a yellow solid. MS (EI+, m/z): 272.0 $[M+H]^+$.

Step 5: 4-Bromo-2-(hydroxymethyl)-1H-indol-6-ol

The same procedure used to prepare I-187 afforded 4-bromo-2-(hydroxymethyl)-1H-indol-6-ol (582 mg, 47.8%) as a white solid. MS (EI+, m/z): 242.0 $[M-H]^+$.

Step 6: (6-(Benzyloxy)-4-bromo-1H-indol-2-yl)methanol, I-241

To a solution of 4-bromo-2-(hydroxymethyl)-1H-indol-6-ol (90 mg, 0.37 mmol) in DMF (10 mL) under $N_2$ was added (bromomethyl)benzene (63.3 mg, 0.37 mmol) and $K_2CO_3$ (153.2 mg, 1.11 mmol). The mixture was stirred at rt for 5 h. Concentrated and purified by prep-HPLC to afford (6-(benzyloxy)-4-bromo-1H-indol-2-yl)methanol I-241 (10 mg, 8.1%) as a yellow solid. ESI-MS (EI+, m/z): 334.0 $[M+H]^+$. $^1$H NMR (500 MHz, DMSO) δ 11.18 (s, 1H), 7.38 (ddd, J=33.8, 21.0, 7.3 Hz, 5H), 7.00-6.86 (m, 2H), 6.15 (s, 1H), 5.32 (t, J=5.6 Hz, 1H), 5.11 (s, 2H), 4.55 (d, J=5.5 Hz, 2H).

Example 125: (4-Bromo-6-phenethoxy-1H-indol-2-yl)methanol, I-236

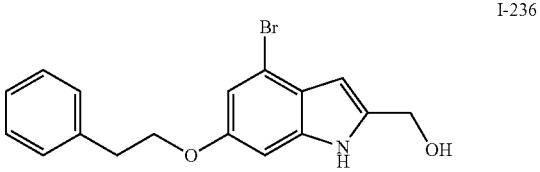 [SMILES: OCc1cc2c(Br)cc(OCCc3ccccc3)cc2[nH]1]

Synthetic Scheme:

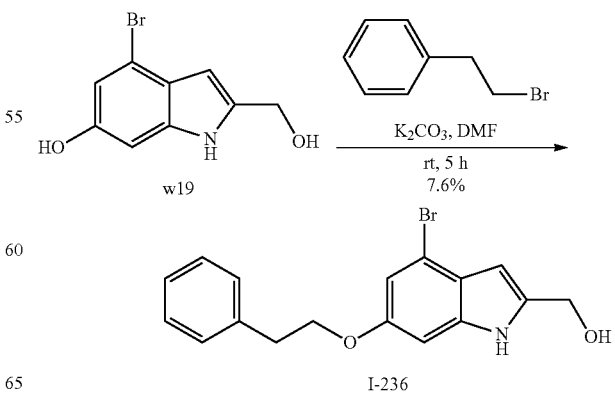

Procedures and Characterization:

(4-bromo-6-phenethoxy-1H-indol-2-yl)methanol

To a solution of 4-bromo-2-(hydroxymethyl)-1H-indol-6-ol (120 mg, 0.49 mmol) in DMF (10 mL) under $N_2$ was added (2-bromoethyl)benzene (90.6 mg, 0.49 mmol) and $K_2CO_3$ (202.9 mg, 1.47 mmol). The mixture was stirred at rt for 5 h. Concentrated and purified by prep-HPLC to afford (4-bromo-6-phenethoxy-1H-indol-2-yl)methanol I-236 (13 mg, 7.6%) as a yellow solid. ESI-MS (EI$^+$, m/z): 348.0 [M+H]$^+$. $^1$H NMR (500 MHz, CDCl$_3$) δ 8.39 (s, 1H), 7.36-7.23 (m, 5H), 6.97 (s, 1H), 6.75 (s, 1H), 6.35 (s, 1H), 4.76 (s, 2H), 4.16 (t, J=7.0 Hz, 2H), 3.10 (t, J=7.0 Hz, 2H), 1.83 (d, J=114.4 Hz, 1H).

Example 126: (4-Bromo-6-(3-phenylpropoxy)-1H-indol-2-yl)methanol, I-235

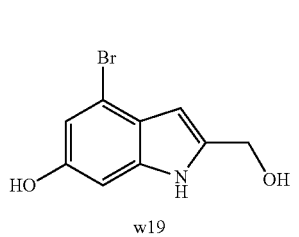

I-235

Synthetic Scheme:

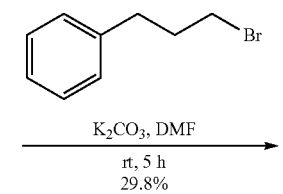

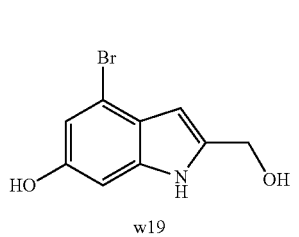

I-235

Procedures and Characterization:

(4-bromo-6-(3-phenylpropoxy)-1H-indol-2-yl)methanol

To a solution of 4-bromo-2-(hydroxymethyl)-1H-indol-6-ol (120 mg, 0.49 mmol) in DMF (10 mL) under $N_2$ was added 3-(3-bromopropyl)benzene-1-ylium (97.5 mg, 0.49 mmol) and $K_2CO_3$ (202.9 mg, 1.47 mmol). The mixture was stirred at rt for 5 h. Concentrated and purified by prep-HPLC to afford (4-bromo-6-(3-phenylpropoxy)-1H-indol-2-yl)methanol I-235 (53 mg, 29.8%) as a yellow solid. ESI-MS (EI$^+$, m/z): 360.0 [M−H]$^+$. $^1$H NMR (500 MHz, CDCl$_3$) δ 8.42 (d, J=41.8 Hz, 1H), 7.33-7.11 (m, 5H), 6.97 (d, J=1.8 Hz, 1H), 6.68 (s, 1H), 6.34 (s, 1H), 4.73 (s, 2H), 3.91 (t, J=6.2 Hz, 2H), 2.80 (t, J=7.6 Hz, 2H), 2.21 (d, J=34.1 Hz, 1H), 2.09 (hept, J=21.1 Hz, 2H).

Example 127: 1-(4-bromo-6-phenoxy-1H-indol-2-yl)ethanol, I-218

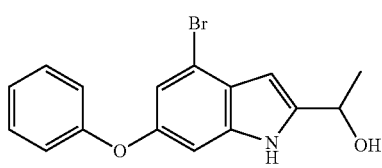

Synthetic Scheme:

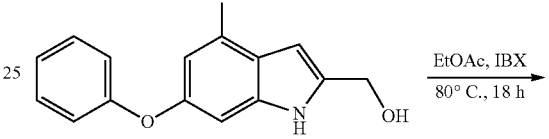

I-290

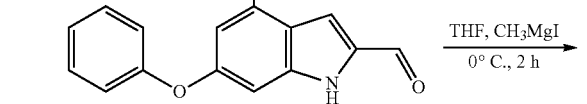

k15

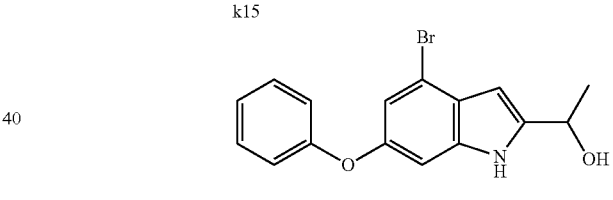

I-218

Procedures and Characterization:

Step 1:
4-bromo-6-phenoxy-1H-indole-2-carbaldehyde

To a solution of (4-bromo-6-phenoxy-1H-indol-2-yl)methanol (500 mg, 1.57 mmol) in EtOAc (5 mL), was added IBX (1.32 g, 4.71 mmol), this mixture was stirred at 80° C. for 18 h. Filtered off solid to afford the filtrate which was concentrated to afford crude product, purified by column chromatography on silica gel with PE:EtOAc=10:1 to afford a yellow solid (208 mg, purity: 95%, yield: 41.8%). ESI-MS (EI+, m/z): 319.0[M+H]$^+$.

Step 2:
1-(4-bromo-6-phenoxy-1H-indol-2-yl)ethanol

To a solution of 4-bromo-6-phenoxy-1H-indole-2-carbaldehyde (170 mg, 0.537 mmol) in THF (4 mL), cooled to 0° C., was added CH$_3$MgI (893.93 mg, 5.38 mmol). The mixture was stirred at 0° C. for 2 h. The reaction was quenched with ice-water, extracted with EtOAc, washed with brine, dried over sodium sulfate, concentrated to afford yellow solid, and purified by prep-HPLC to afford 1-(4-bromo-6-phenoxy-1H-indol-2-yl)ethanol I-218 (25.2 mg, yield: 14.1%) as a yellow oil.

ESI-MS (EI+, m/z): 332.1[M+H]$^+$.

$^1$H NMR (500 MHz, DMSO) δ 11.30 (s, 1H), 7.37 (t, J=7.9 Hz, 2H), 7.10 (t, J=7.3 Hz, 1H), 6.98 (d, J=8.6 Hz, 3H), 6.93 (d, J=1.6 Hz, 1H), 6.19 (s, 1H), 5.40 (d, J=4.9 Hz, 1H), 4.92-4.80 (m, 1H), 1.45 (d, J=6.4 Hz, 3H).

Example 128: 1-(6-Chloro-4-phenoxy-1H-indol-2-yl)ethanol, I-186

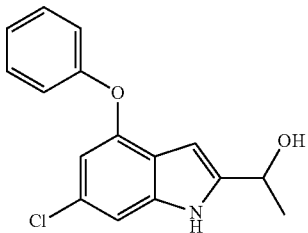

Synthetic Scheme:

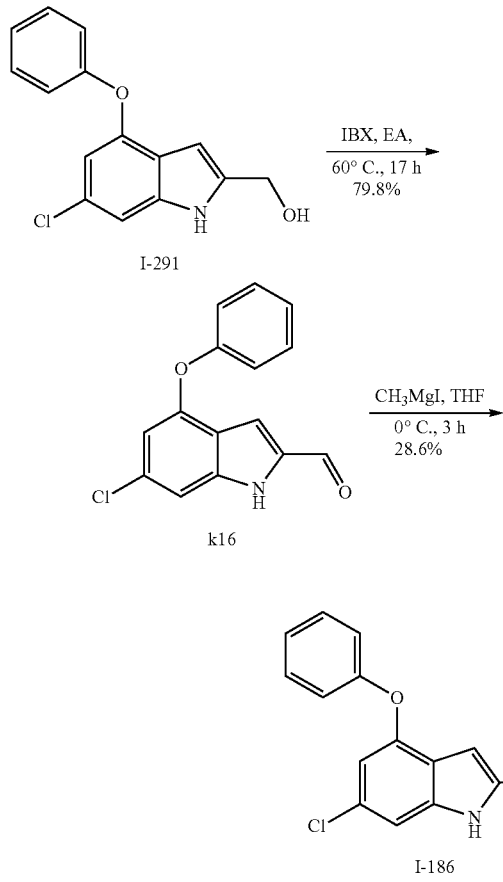

Procedures and Characterization:

Step 1:
6-Chloro-4-phenoxy-1H-indole-2-carbaldehyde

The same procedure used to prepare k15 afforded 6-chloro-4-phenoxy-1H-indole-2-carbaldehyde (380 mg, 79.8%) as a yellow solid. ESI-MS (EI$^+$, m/z): 272.0 [M+H]$^+$.

Step 2:
1-(6-Chloro-4-phenoxy-1H-indol-2-yl)ethanol

The same procedure used to prepare I-218 afforded 1-(6-chloro-4-phenoxy-1H-indol-2-yl)ethanol I-186 (115 mg, 28.6%) as a white solid. ESI-MS (EI, m/z): 288.1 [M+H]$^+$.

$^1$H NMR (500 MHz, DMSO) δ 11.30 (s, 1H), 7.47-7.30 (m, 2H), 7.25-7.05 (m, 2H), 7.07-6.88 (m, 2H), 6.49 (d, J=1.6 Hz, 1H), 6.03 (d, J=0.9 Hz, 1H), 5.36 (d, J=4.9 Hz, 1H), 4.90-4.72 (m, 1H), 1.41 (d, J=6.5 Hz, 3H).

Example 129: (6-Chloro-4-(2,5-dichlorophenoxy)-1H-indol-2-yl)methanol, I-171

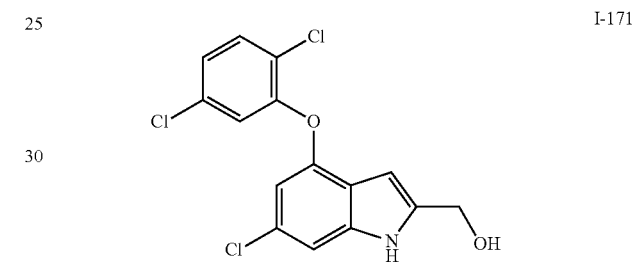

Synthetic Scheme:

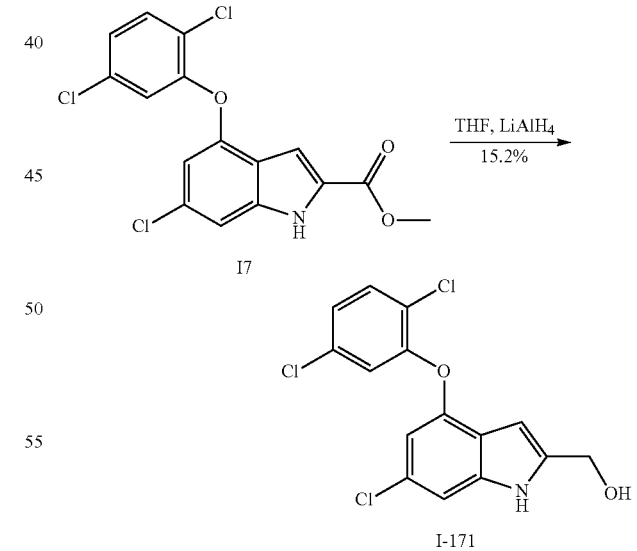

Procedures and Characterization:

Step 1: (6-Chloro-4-(2,5-dichlorophenoxy)-1H-indol-2-yl)methanol

The same procedure used to prepare I-187 afforded (6-chloro-4-(2,5-dichlorophenoxy)-1H-indol-2-yl)methanol I-171 (49 mg, 15.2%) as a white solid. MS (EI+, m/z): 342.0 [M−H]⁻. ¹H NMR (500 MHz, DMSO) δ 11.49 (s, 1H), 7.66 (d, J=8.6 Hz, 1H), 7.42-7.09 (m, 2H), 6.98 (s, 1H), 6.61 (s, 1H), 6.04 (s, 1H), 5.33 (t, J=5.4 Hz, 1H), 4.56 (d, J=5.4 Hz, 2H).

Example 130: (1-((1H-1,2,3-triazol-4-yl)methyl)-4-chloro-6-phenoxy-1H-indol-2-yl)methanol, I-194

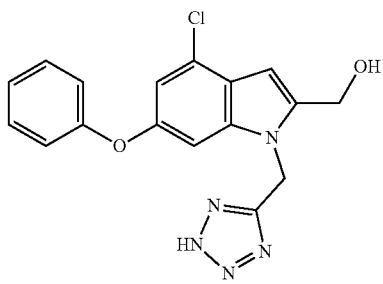

I-194

Synthetic Scheme:

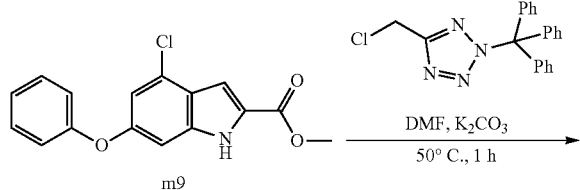

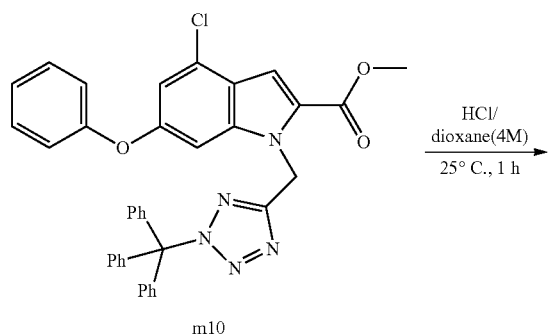

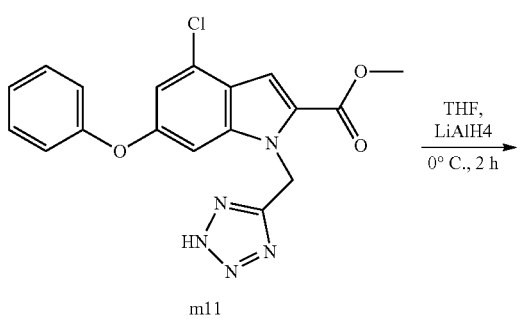

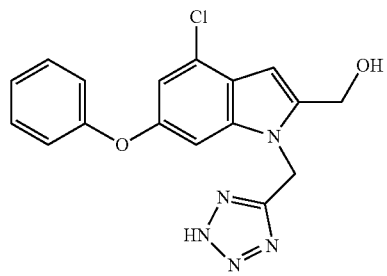

I-194

Procedures and Characterization:

Step 1: methyl 4-chloro-6-phenoxy-1-((2-trityl-2H-tetrazol-5-yl)methyl)-1H-indole-2-carboxylate To a solution of methyl 4-chloro-6-phenoxy-1H-indole-2-carboxylate (200 mg, 0.662 mmol) and 5-(chloromethyl)-2-trityl-2H-tetrazole (286.24 mg, 0.795 mmol) in DMF (5 mL), was added K₂CO₃ (274.8 mg, 1.99 mmol), this mixture was stirred at 50° C. for 12 h. The reaction was quenched with ice-water and extracted with EtOAc, dried and concentrated and purified by column chromatography on silica gel (PE:EtOAc=10:1) to afford methyl 4-chloro-6-phenoxy-1-((2-trityl-2H-tetrazol-5-yl)methyl)-1H-indole-2-carboxylate as a yellow solid (319 mg, purity: 100%, yield: 77.0%).

Step 2: methyl 1-((2H-tetrazol-5-yl)methyl)-4-chloro-6-phenoxy-1H-indole-2-carboxylate To a solution of methyl 4-chloro-6-phenoxy-1-((2-trityl-2H-tetrazol-5-yl)methyl)-1H-indole-2-carboxylate (319 mg, 0.509 mmol) in 3 mL of HCl/dioxane (4M), stirred at rt, for 2 h. Concentrated to afford crude product (195 mg), which was used directly in the next step.

Step 3: (1-((2H-tetrazol-5-yl)methyl)-4-chloro-6-phenoxy-1H-indol-2-yl)methanol, I-194

To a solution of methyl 1-((2H-tetrazol-5-yl)methyl)-4-chloro-6-phenoxy-1H-indole-2-carboxylate (195.54 mg, 0.509 mmol) in THF (3 mL), was added LiAlH₄ (19.34 mg, 0.509 mmol), this mixture was stirred at 0° C. for 2 h, The reaction was quenched with ice-water and extracted with EtOAc, dried and concentrated and purified by prep-HPLC to afford (1-((2H-tetrazol-5-yl)methyl)-4-chloro-6-phenoxy-1H-indol-2-yl)methanol I-194 (31.0 mg, purity: 100%, yield: 17.5%). ESI-MS (EI+, m/z): 378.2[M+Na]⁺.

¹H NMR (500 MHz, DMSO) δ 7.36 (t, J=7.9 Hz, 2H), 7.30 (s, 1H), 7.09 (d, J=7.3 Hz, 1H), 6.97 (d, J=8.0 Hz, 2H), 6.81 (d, J=1.3 Hz, 1H), 6.43 (s, 1H), 5.57 (s, 2H), 4.77 (s, 2H), 3.51 (s, 1H).

Example 131: (6-chloro-4-(4-cyclohexylphenoxy)-1H-indol-2-yl)methanol, I-127

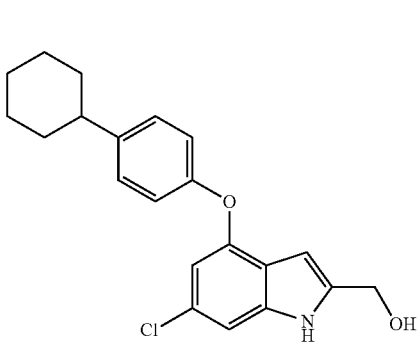

Synthetic Scheme:

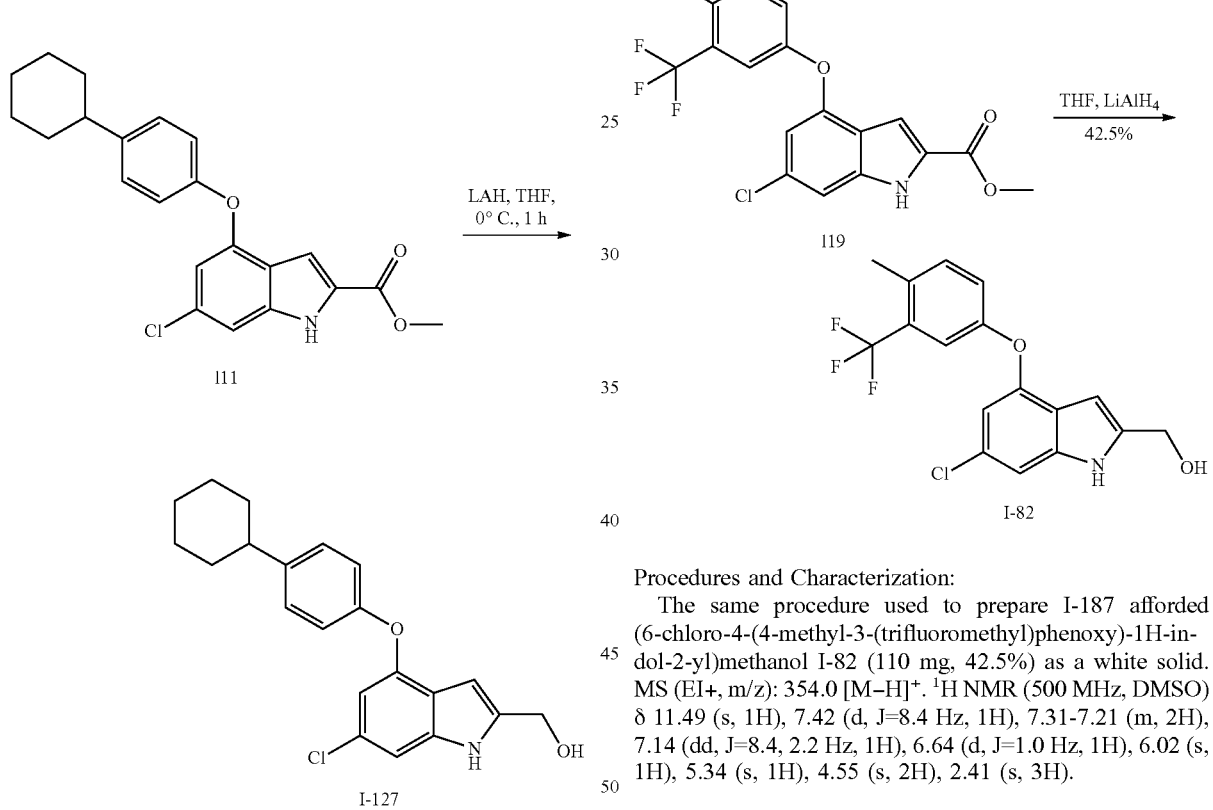

Procedures and Characterization:

Step 4: (6-chloro-4-(4-cyclohexylphenoxy)-1H-indol-2-yl)methanol

The same procedure used to prepare I-194 afforded (6-chloro-4-(4-cyclohexylphenoxy)-1H-indol-2-yl)methanol I-127 (56 mg) as a white solid. MS (EI+, m/z): 356.0 [M+H]$^+$.

$^1$H NMR (500 MHz, DMSO) δ 11.3 (s, 1H), 7.22 (d, J=8.5 Hz, 2H), 7.16 (s, 1H), 6.93 (d, J=8.5 Hz, 2H), 6.46 (d, J=1.5 Hz, 1H), 6.08 (s, 1H), 5.29 (t, J=6.0 Hz, 1H), 4.55 (d, J=5.0 Hz, 2H), 1.79-1.68 (m, 5H), 1.61-1.38 (m, 5H).

Example 132: (6-Chloro-4-(4-methyl-3-(trifluoromethyl)phenoxy)-1H-indol-2-yl)methanol, I-82

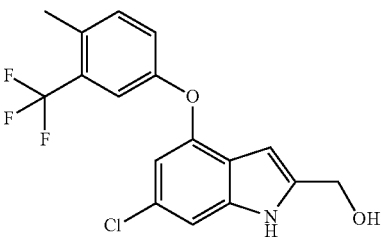

Synthetic Scheme:

Procedures and Characterization:

The same procedure used to prepare I-187 afforded (6-chloro-4-(4-methyl-3-(trifluoromethyl)phenoxy)-1H-indol-2-yl)methanol I-82 (110 mg, 42.5%) as a white solid. MS (EI+, m/z): 354.0 [M−H]$^+$. $^1$H NMR (500 MHz, DMSO) δ 11.49 (s, 1H), 7.42 (d, J=8.4 Hz, 1H), 7.31-7.21 (m, 2H), 7.14 (dd, J=8.4, 2.2 Hz, 1H), 6.64 (d, J=1.0 Hz, 1H), 6.02 (s, 1H), 5.34 (s, 1H), 4.55 (s, 2H), 2.41 (s, 3H).

Example 133: (4-(2-chlorophenoxy)-1H-indol-2-yl)methanol, I-276

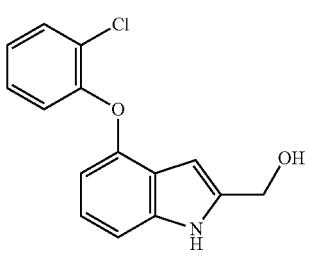

Synthetic Scheme:

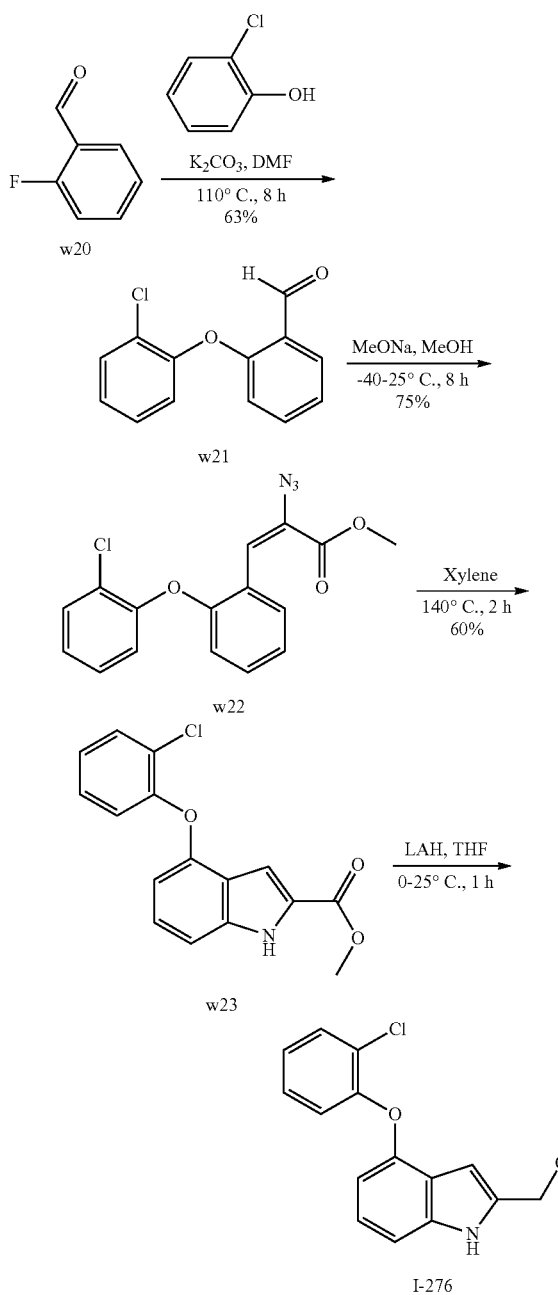

Procedures and Characterization:

Step 1: 2-(2-chlorophenoxy)benzaldehyde

The mixture of 2-fluorobenzaldehyde (1.11 g, 8.93 mmol, 1 eq), 2-chlorophenol (1.14 g, 8.93 mmol, 1 eq) and K$_2$CO$_3$ (1.85 g, 13.4 mmol, 1.5 eq) in 5 ml DMF was stirred at 110° C. for 8 h. Cooled down and quenched with water. Extracted with EtOAc (50 ml*2) and washed with water (100 ml*2), brine (100 ml). Combined the EtOAc layer and dried over Na$_2$SO$_4$. Filtered and concentrated. Purified by SGC (PE: EtOAc=9:1) to obtain 2-(3-fluorophenoxy)benzaldehyde (1.3 g, 63%) as a yellow oil. ESI-MS (EI$^+$, m/z): 233 [M+H]$^+$.

Step 2: (E)-methyl 2-azido-3-(2-(2-chlorophenoxy)phenyl)acrylate

The same procedure used to prepare b3 to obtain (E)-methyl 2-azido-3-(2-(3-fluorophenoxy)phenyl)acrylate (690 mg, 75%) as a yellow solid. ESI-MS (EI$^+$, m/z): 330 [M+H]$^+$.

Step 3: methyl 4-(2-chlorophenoxy)-1H-indole-2-carboxylate

The same procedure used to prepare a4 is to obtain methyl 4-(3-fluorophenoxy)-1H-indole-2-carboxylate (370 mg, 60%) as a yellow solid. ESI-MS (EI$^+$, m/z): 302[M+H]$^+$.

Step 4: (4-(2-chlorophenoxy)-1H-indol-2-yl)methanol, I-276

The same procedure used to prepare I-187 afforded (4-(2-chlorophenoxy)-1H-indol-2-yl)methanol I-276. ESI-MS (EI$^+$, m/z): 274 [M+H]$^+$. $^1$H-NMR (500 MHz, CDCl$_3$): δ 8.4 (s, 1H), 7.5 (s, 1H), 7.00-7.20 (m, 5H), 6.60 (m, 1H), 6.33 (s, 1H), 4.8 (s, 2H).

Example 134: (4-(3-chlorophenoxy)-1H-indol-2-yl)methanol, I-275

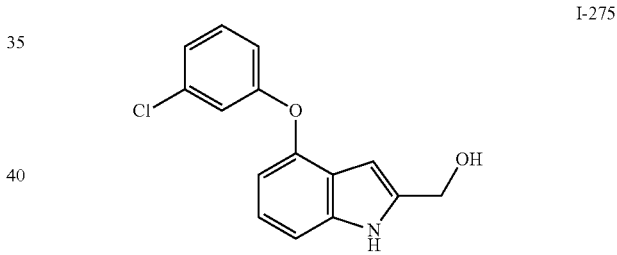

Synthetic Scheme:

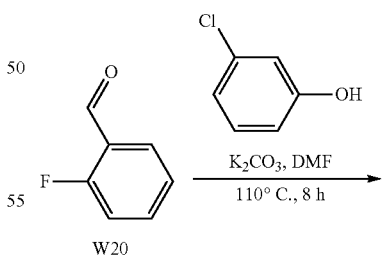

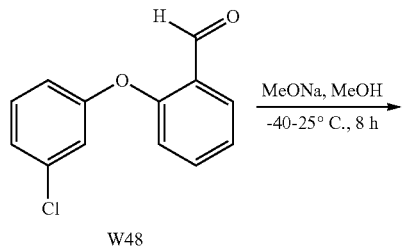

-continued

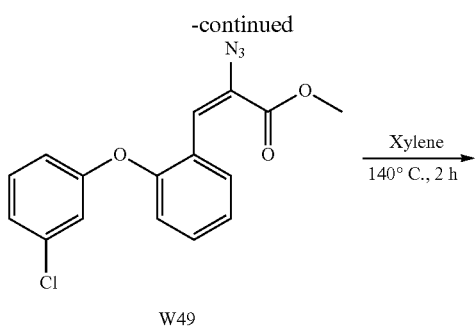

W49

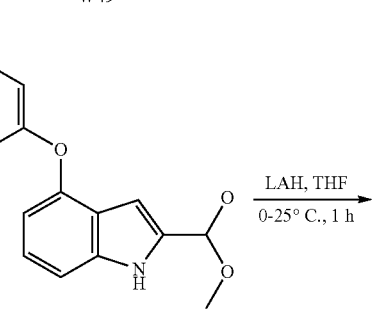

W50

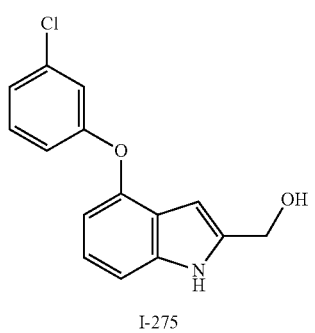

I-275

Procedures and Characterization:

The procedure was the same as I-276.

(4-(3-chlorophenoxy)-1H-indol-2-yl)methanol I-275: ESI-MS (EI⁺, m/z): 274 [M+H]⁺. ¹H NMR (500 MHz, CDCl₃) δ 8.48 (s, 1H), 7.24-7.18 (m, 2H), 7.14 (t, J=7.9 Hz, 1H), 7.02 (d, J=7.9 Hz, 1H), 6.98 (d, J=2.1 Hz, 1H), 6.90 (d, J=8.3 Hz, 1H), 6.73 (d, J=7.6 Hz, 1H), 6.25 (s, 1H), 4.80 (s, 2H).

Example 135: (4-(4-chlorophenoxy)-1H-indol-2-yl)methanol, I-263

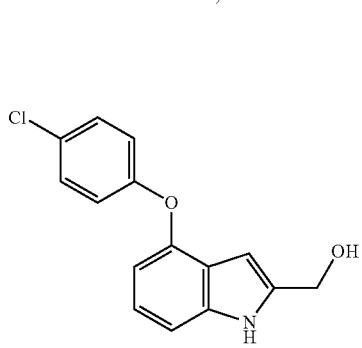

I-263

Synthetic Scheme:

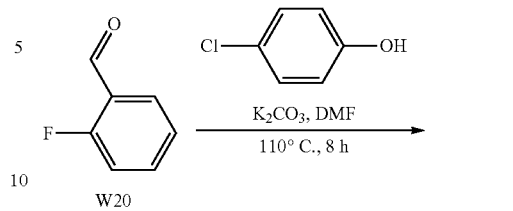

W20

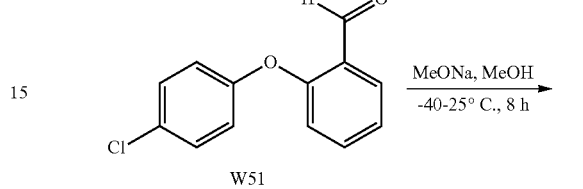

W51

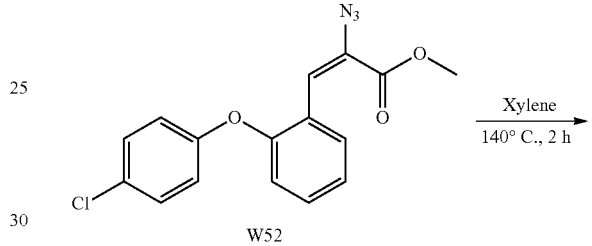

W52

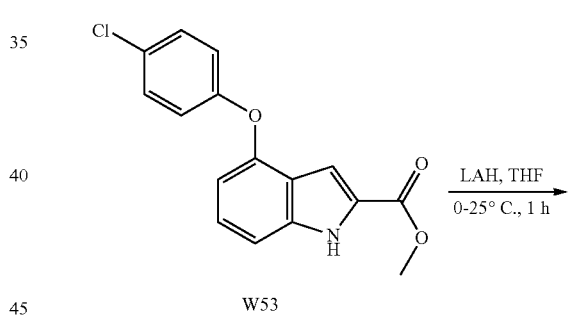

W53

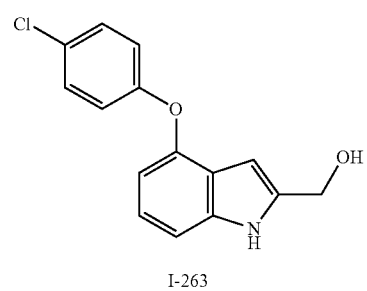

I-263

Procedures and Characterization:

The procedure was the same as I-276.

(4-(4-chlorophenoxy)-1H-indol-2-yl)methanol I-263: ESI-MS (EI⁺, m/z): 274 [M+H]⁺. ¹H-NMR (500 MHz, DMSO-d₆): δ 11.27 (s, 1H), 7.37 (m, 2H), 7.20 (m, 11H), 7.04 (m, 1H), 6.93 (m, 2H), 6.63 (s, 1H), 5.97 (s, 1H), 5.25 (s, 1H), 4.54 (s, 2H).

Example 136: (6-chloro-4-(2-chlorophenoxy)-1H-indol-2-yl)methanol, I-216
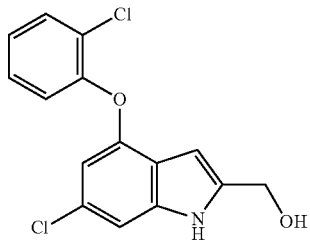
Synthetic Scheme:
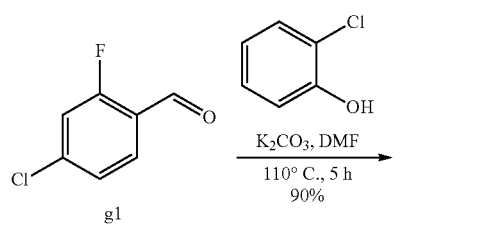
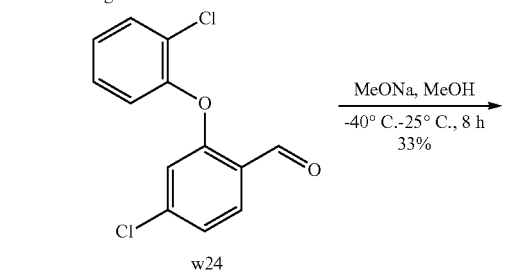
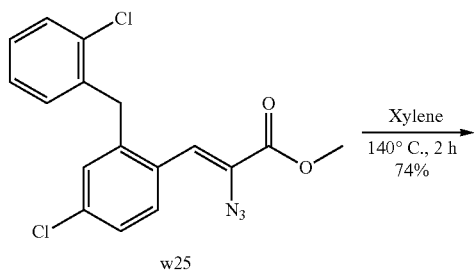
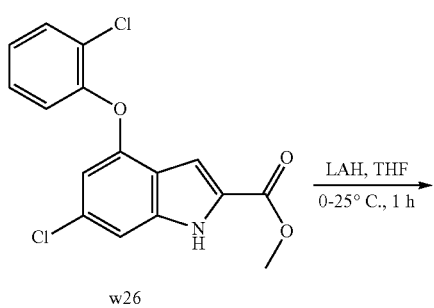
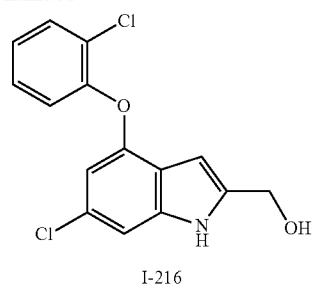
I-216
Procedures and Characterization:
The procedure was same as I-276.
(6-chloro-4-(2-chlorophenoxy)-1H-indol-2-yl)methanol I-216: ESI-MS (EI+, m/z): 308 $^1$H NMR (500 MHz, DMSO-$d_6$) δ 11.43 (s, 1H), 7.63 (d, J=7.8 Hz, 1H), 7.34 (t, J=7.7 Hz, 1H), 7.27-7.17 (m, 2H), 7.04 (d, J=8.3 Hz, 1H), 6.43 (s, 1H), 6.07 (s, 1H), 5.32 (t, J=5.5 Hz, 1H), 4.55 (d, J=5.6 Hz, 2H).
Example 137: (6-chloro-4-(3-chlorophenoxy)-1H-indol-2-yl)methanol, I-215
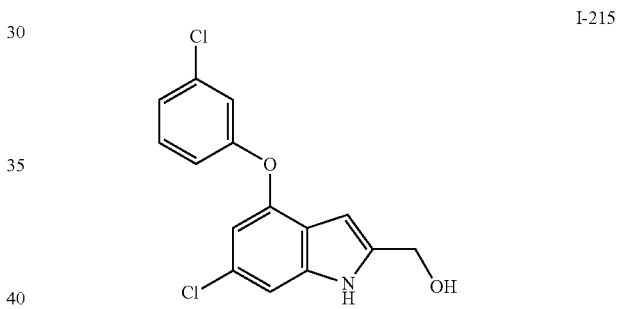
Synthetic Scheme:
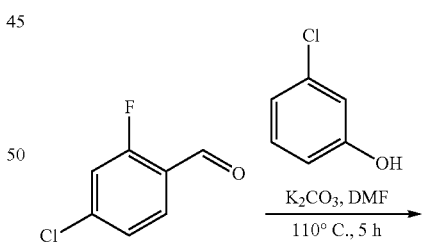
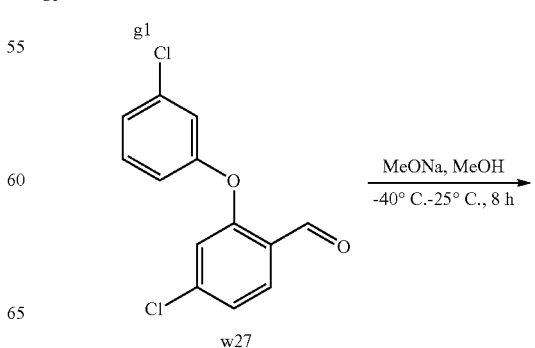

555
-continued

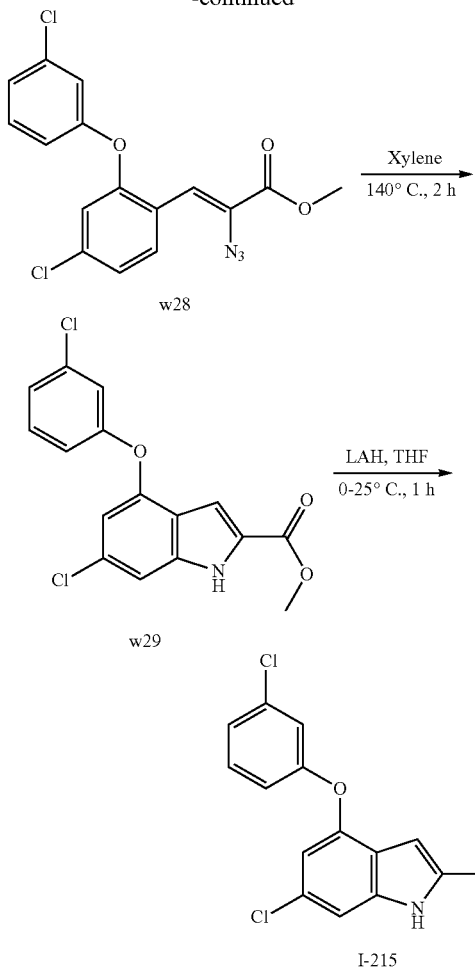

Procedures and Characterization:

The procedure was same as example I-276.

(6-chloro-4-(3-chlorophenoxy)-1H-indol-2-yl)methanol I-215: ESI-MS (EI+, m/z): 308 $^1$H NMR (500 MHz, DMSO-d6) δ 11.45 (s, 1H), 7.39 (t, J=8.2 Hz, 1H), 7.26 (s, 1H), 7.18 (d, J=8.0 Hz, 1H), 7.04 (s, 1H), 6.95 (dd, J=8.3, 2.1 Hz, 1H), 6.69 (s, 1H), 6.02 (s, 1H), 5.32 (t, J=5.6 Hz, 1H), 4.55 (d, J=5.6 Hz, 2H).

Example 138: (4-(2-fluorophenoxy)-1H-indol-2-yl)methanol, I-277

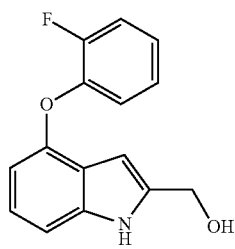

I-277

556

Synthetic Scheme:

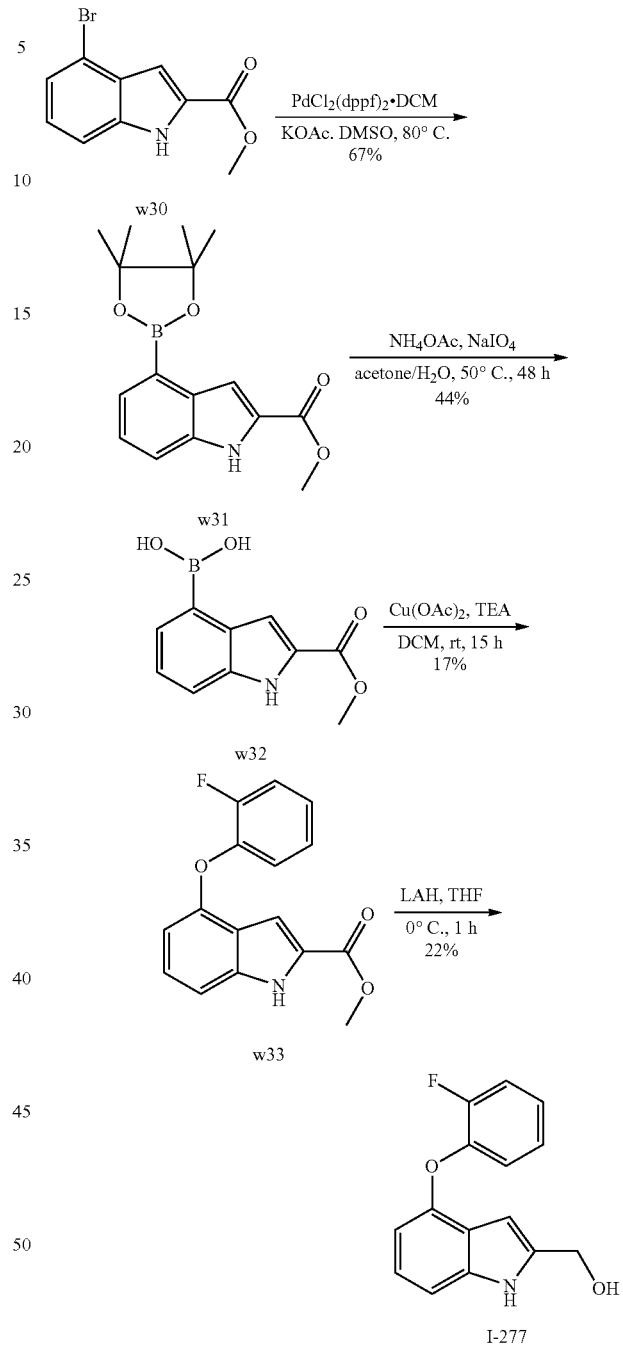

Procedures and Characterization:

Step 1: methyl 4-(4,4,5,5-tetramethyl-1,3,2-dioxaborolan-2-yl)-1H-indole-2-carboxylate The solution of methyl 4-bromo-1H-indole-2-carboxylate (2.0 g, 7.87 mmol), PdCl$_2$(dppf)$_2$·DCM (318 mg, 0.39 mmol), KOAc (2.47 g, 25.18 mmol) and 4,4,4',4',5,5,5',5'-octamethyl-2,2'-bi(1,3,2-dioxaborolane) (3.0 g, 11.8 mmol) in DMSO (20 mL) was stirred at 80° C. for 18 h. Then quenched by ice-water and EtOAc, filtered, the organic layer was washed with brine, dried over Na$_2$SO$_4$, filtered and concentrated, purified by SGC to obtain a light yellow solid. ESI-MS (EI$^+$, m/z): 302 [M+H]$^+$.

Step 2: 2-(methoxycarbonyl)-1H-indol-4-ylboronic acid

To a solution of methyl 4-(4,4,5,5-tetramethyl-1,3,2-dioxaborolan-2-yl)-1H-indole-2-carboxylate (1.0 g, 3.32 mmol) in acetone (25 mL) was added a mixture of NH$_4$OAc (256 mg, 6.64 mmol), NaIO$_4$ (2.13 g, 9.96 mmol) in water (5 mL) and stirred at 50° C. for 48 h. Then cool down and quenched with EtOAc and water, filtered and the organic layer was dried over Na$_2$SO$_4$, filtered and concentrated, purified by reverse-phase biotage to obtain a light brown solid. ESI-MS (EI$^+$, m/z): 220 [M+H]$^+$.

Step 3: methyl 4-(2-fluorophenoxy)-1H-indole-2-carboxylate

To a solution of 2-(methoxycarbonyl)-1H-indol-4-ylboronic acid (440 mg, 2.0 mmol), 2-fluorophenol (336 mg, 3.0 mmol), Cu(OAc)$_2$ (366 mg, 2.0 mmol) in DCM (10 mL) was added TEA (1.4 mL) at rt and stirred at rt under O$_2$ for 18 h, then filtered and concentrated. The crude was purified by reverse-phase Biotage to obtain a brown solid. MS (EI$^+$, m/z): 286 [M+H]$^+$. $^1$H NMR (500 MHz, DMSO-d6) δ 12.18 (s, 1H), 7.36-7.04 (m, 6H), 6.95 (s, 1H), 6.48 (d, J=7.2 Hz, 1H), 3.86 (s, 3H).

Step 4: (4-(2-fluorophenoxy)-1H-indol-2-yl)methanol, I-277

To a solution of methyl 4-(2-fluorophenoxy)-1H-indole-2-carboxylate (60 mg, 0.21 mmol) in THF (5 mL) was added LAH (0.21 mL, 1.0 M in THF) at 0° C. and stirred at this temperature for 1 h, then quenched by Na$_2$SO$_{4101}$H$_2$O and filtered, concentrated. The crude was purified by reverse-phase Biotage to obtain (4-(2-fluorophenoxy)-1H-indol-2-yl)methanol I-277 as a white solid. MS (EI$^+$, m/z): 258 [M+H]$^+$. $^1$H NMR (500 MHz, DMSO-d$_6$) δ 11.25 (s, 1H), 7.43-7.29 (m, 1H), 7.22-7.07 (m, 3H), 7.03-6.89 (m, 2H), 6.48 (d, J=7.6 Hz, 1H), 6.08 (s, 1H), 5.28 (d, J=38.6 Hz, 1H), 4.56 (d, J=3.3 Hz, 2H).

Example 139: (4-(4-fluorophenoxy)-1H-indol-2-yl)methanol, I-278

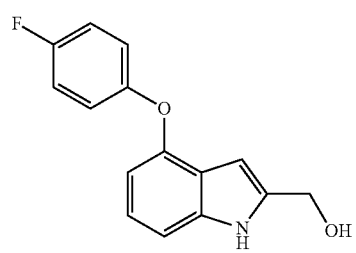

I-278

Synthetic Scheme:

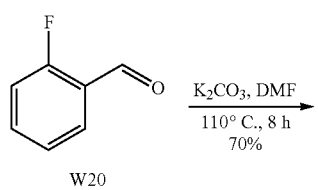

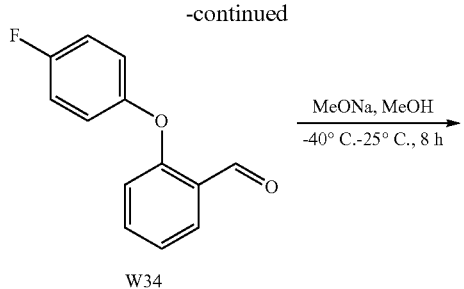

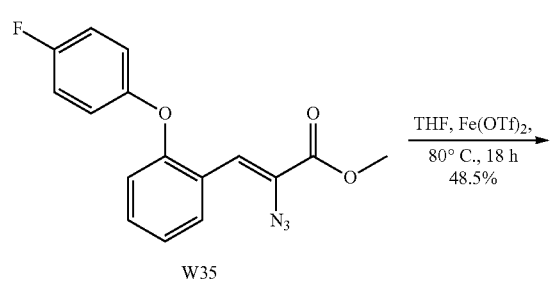

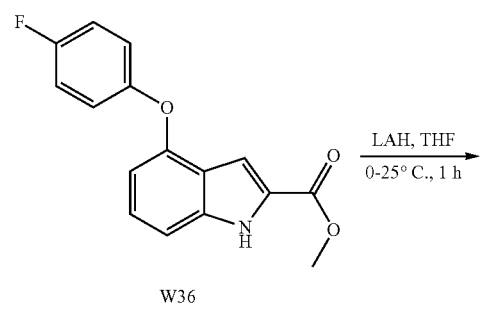

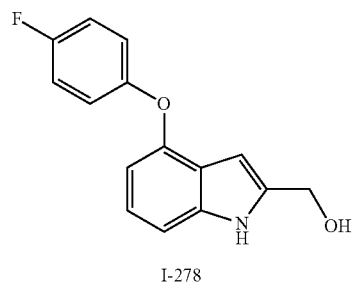

I-278

Procedures and Characterization:

(4-(4-fluorophenoxy)-1H-indol-2-yl)methanol

The procedure was same as example I-276. The 3$^{rd}$ step was the same as k4 (4-(4-fluorophenoxy)-1H-indol-2-yl) methanol I-278: ESI-MS (EI$^+$, m/z): 258.1 [M+H]$^+$. $^1$H NMR (500 MHz, DMSO-d$_6$) δ 11.22 (s, 1H), 7.16 (t, J=7.1 Hz, 3H), 7.05-6.91 (m, 3H), 6.55 (d, J=7.7 Hz, 1H), 6.01 (s, 1H), 5.22 (t, J=5.4 Hz, 1H), 4.54 (d, J=5.2 Hz, 2H).

Example 140: (6-chloro-4-(3-chlorobenzyloxy)-1H-indol-2-yl)methanol, I-176

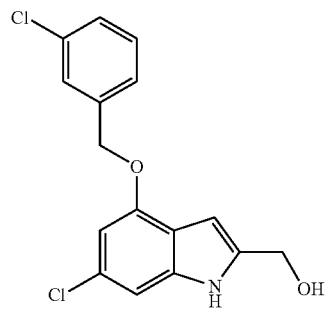

I-176

Synthetic Scheme:

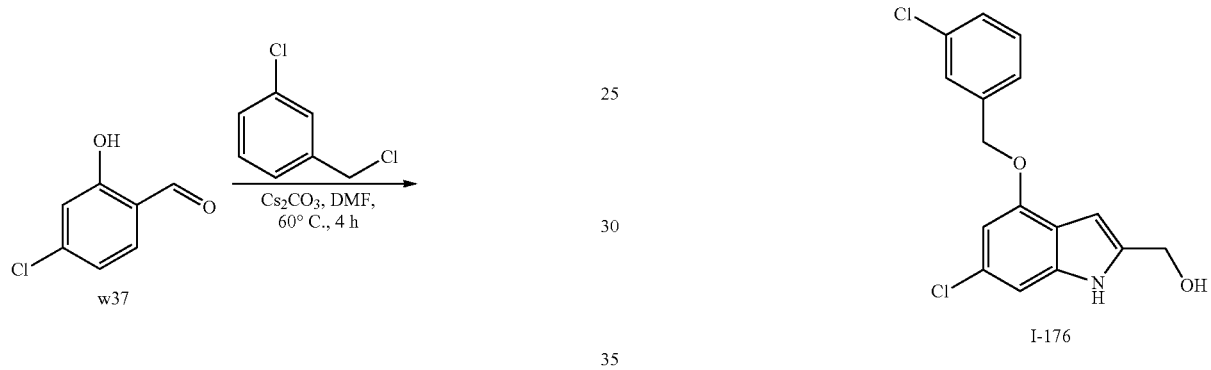

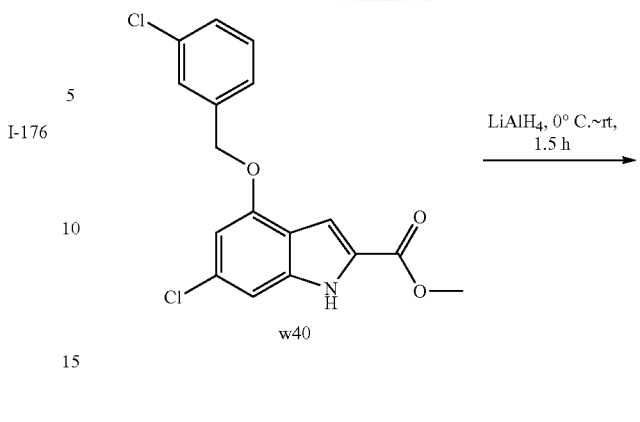

Procedures and Characterization:

(6-chloro-4-(3-chlorobenzyloxy)-1H-indol-2-yl)methanol

The procedure was the same as example I-276. The 1$^{st}$ step used $Cs_2CO_3$ as base, and the temperature was 60° C. (6-chloro-4-(3-chlorobenzyloxy)-1H-indol-2-yl)methanol I-176: ESI-MS (EI$^+$, m/z): 322,324 [M+H]$^+$. $^1$H NMR (500 MHz, CDCl$_3$) δ 8.30 (s, 1H), 7.48 (s, 1H), 7.33 (m, 3H), 7.02 (s, 1H), 6.53 (m, 2H), 5.14 (s, 2H), 4.81 (s, 2H).

Example 141: 2-(5-chloro-4-phenoxy-1H-indol-2-yl)ethanol, I-261

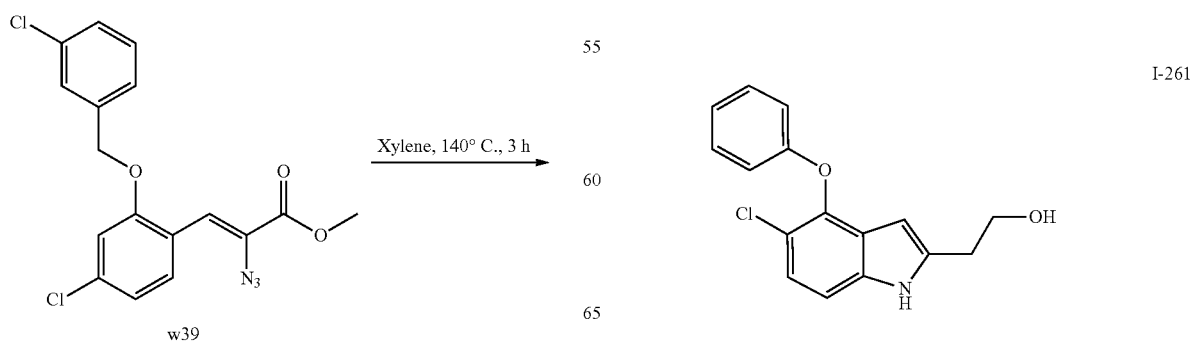

Synthetic Scheme:

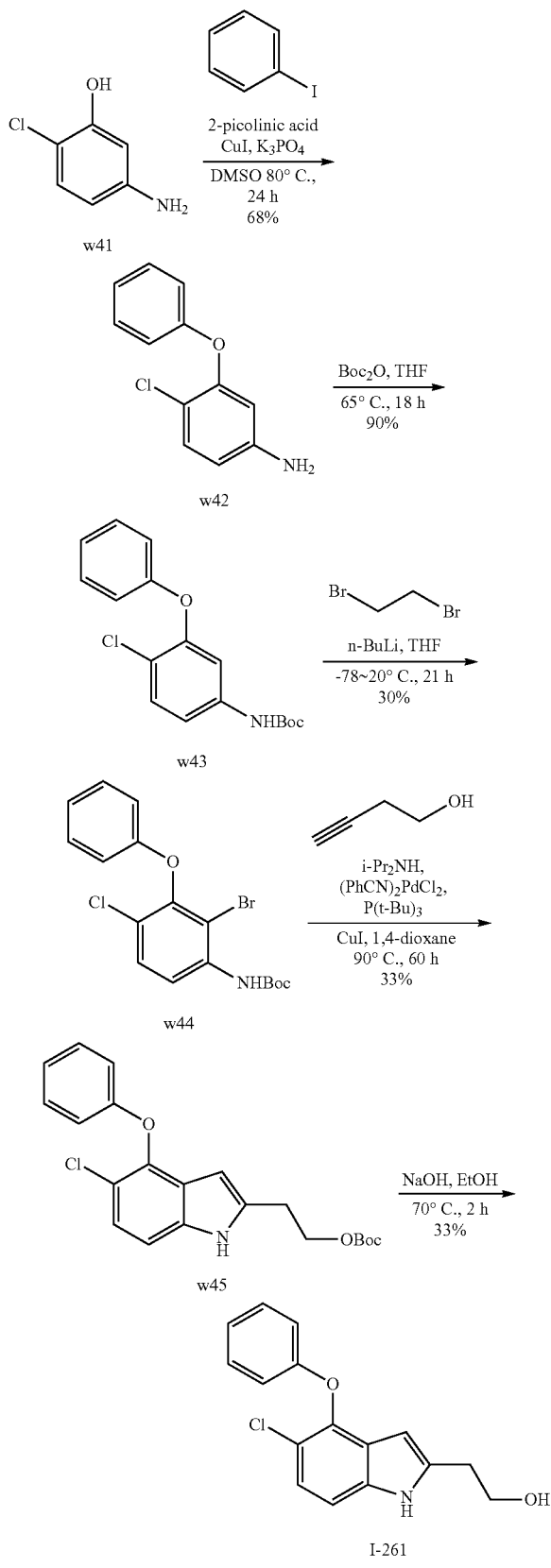

Procedures and Characterization:

Step 1: 4-chloro-3-phenoxybenzenamine

To a mixture of copper(I) iodide (0.96 g, 5 mmol), 2-picolinic acid (1.23 g, 10 mmol), iodobenzene (10.2 g, 50 mmol), 5-amino-2-chlorophenol (10.2 g, 70 mmol) and $K_3PO_4$ (21.2 g, 100 mmol), DMSO (150 mL) was added under nitrogen. The reaction mixture was stirred vigorously for 24 h at 80° C. The reaction mixture was cooled to room temperature. Ethyl acetate (500 mL) and $H_2O$ (300 mL) were added. The organic layer was separated and the aqueous layer was extracted twice more with ethyl acetate (200 mL). Combined organic layers were dried over anhydrous $Na_2SO_4$ and concentrated in vacuo. The crude product was purified by column chromatography ($SiO_2$, petrol ether/EtOAc 70:30) to give the title compound 4-chloro-3-phenoxybenzenamine (7.5 g, 34 mmol, 68%) as a white solid. ESI-MS (EI+, m/z): 220.2[M+H]$^+$.

Step 2: tert-butyl 4-chloro-3-phenoxyphenylcarbamate

To a solution of 4-chloro-3-phenoxybenzenamine (7.5 g, 34 mmol) in THE (100 mL) was added di-tert-butyl dicarbonate (7.9 g, 36 mmol). The reaction was heated at reflux for 16 h, at which time it was allowed to cool to room temperature. The solvent was removed in vacuo and the residue diluted with ether (300 mL) and washed with 1 M citric acid (2*200 mL). The aqueous washings were extracted with ether (150 mL) and the combined organics washed with brine (300 mL), dried ($MgSO_4$). and concentrated. The resultant brown solid was triturated with hexanes and dried in vacuo to give tert-butyl 4-chloro-3-phenoxyphenylcarbamate (9.8 g, 30.6 mmol, 90%) as a white solid. ESI-MS (EI+, m/z): 342.2[M+Na]$^+$.

Step 3: tert-butyl 2-bromo-4-chloro-3-phenoxyphenylcarbamate

To solution of tert-butyl 4-chloro-3-phenoxyphenylcarbamate (640 mg, 2.0 mmol) in tetrahydrofuran (20 mL) at −78° C. was added n-butyl lithium (2.5M, 4.4 mmol). The solution was allowed to warm to 0° C. and stirred for 3 h. Ethylene dibromide (9.9 g, 5 mmol) was added and the solution was stirred for 18 h before being quenched with ammonium chloride (saturated solution, 10 mL) and extracted with ethyl ether (2×20 mL). The combined extracts were washed with brine, dried (sodium sulfate) and concentrated. The residue was purified by column chromatography ($SiO_2$, petrol ether/EtOAc 90:10) to give tert-butyl 2-bromo-4-chloro-3-phenoxyphenylcarbamate (250 mg, 0.61 mmol, 30%) as a tan solid.

$^1$H NMR (500 MHz, CDCl$_3$) δ 8.09 (d, J=9.1 Hz, 1H), 7.40 (d, J=9.1 Hz, 1H), 7.32-7.27 (m, 2H), 7.10-7.03 (m, 2H), 6.81 (d, J=7.9 Hz, 2H), 1.54 (s, 9H).

Step 4: tert-butyl 2-(5-chloro-4-phenoxy-1H-indol-2-yl)ethyl carbonate

To solution of tert-butyl 2-bromo-4-chloro-3-phenoxyphenylcarbamate (400 mg, 1.0 mmol), but-3-yn-1-ol (210 mg, 3.0 mmol), PdCl$_2$(CH$_3$CN)$_2$ (11 mg, 0.04 mmol) and tri(tert-butyl)phosphine (16 mg, 0.08 mmol) in 1,4-dioxane (10 mL) under N$_2$ were added CuI (8 mg, 0.04 mmol) and diisopropylamine (400 mg, 4 mmol). After stirring for 60 h at 90° C., the reaction mixture was diluted with Et$_2$O and filtered through a pad of Celite. The filtrate was concentrated in vacuo and the residue was purified by column chromatography (SiO₂, petrol ether/EtOAc 85:15) to give tert-butyl 2-(5-chloro-4-phenoxy-1H-indol-2-yl)ethyl carbonate: (130 mg, 0.33 mmol, 33%) as a white solid. ESI-MS (EI+, m/z): 388.1[M+H]⁺ ¹H NMR (500 MHz, CDCl₃) δ 8.37 (s, 1H), 7.28-7.24 (m, 2H), 7.19 (d, J=8.6 Hz, 1H), 7.14 (d, J=8.6 Hz, 1H), 7.01 (t, J=7.4 Hz, 1H), 6.90 (d, J=7.9 Hz, 2H), 6.03 (s, 1H), 4.30 (t, J=6.3 Hz, 2H), 3.03 (t, J=6.2 Hz, 2H), 1.48 (s, 9H).

Step 5: 2-(5-chloro-4-phenoxy-1H-indol-2-yl)ethanol, I-261

To a solution of tert-butyl 2-(5-chloro-4-phenoxy-1H-indol-2-yl)ethyl carbonate (110 mg, 0.28 mmol) in EtOH (4 mL) was added NaOH (34 mg, 0.84 mmol). The resulting mixture was stirred at 70° C. for 2 h before cooled to 20° C. and then treated with saturated aqueous NH₄Cl (20 mL). The reaction mixture was extracted by EtOAc (20 mL), washed with brine (10 mL), dried (Na₂SO₄), filtered and concentrated in vacuo, the crude product was purified by prep-HPLC using 10 mM NH₄HCO₃ buffer to afford 2-(5-chloro-4-phenoxy-1H-indol-2-yl)ethanol I-261 as a white solid (27 mg, 0.094 mmol, 33%). ESI-MS (EI+, m/z): 288.1[M+H]⁺.

¹H NMR (500 MHz, CDCl₃) δ 8.74 (s, 1H), 7.27 (t, J=8.0 Hz, 2H), 7.18 (d, J=8.6 Hz, 1H), 7.13 (d, J=8.6 Hz, 1H), 7.01 (t, J=7.4 Hz, 1H), 6.91 (d, J=7.9 Hz, 2H), 6.00 (s, 1H), 3.94 (t, J=5.6 Hz, 2H), 2.93 (t, J=5.6 Hz, 2H).

Example 142: 3-(5-chloro-4-phenoxy-1H-indol-2-yl)propan-1-ol, I-248

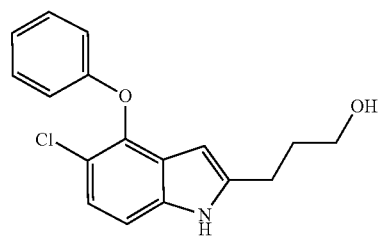

Synthetic Scheme:

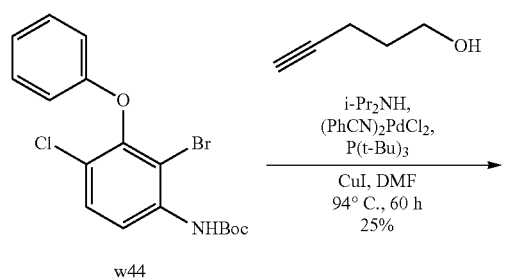

-continued

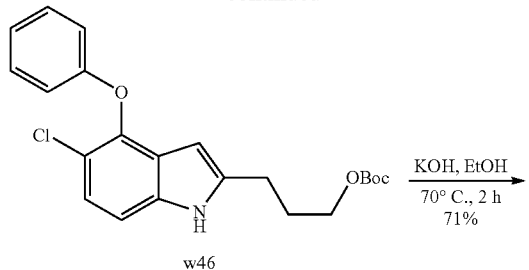

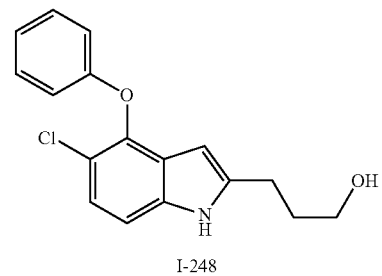

Procedures and Characterization:

Step 1: tert-butyl 3-(5-chloro-4-phenoxy-1H-indol-2-yl)propyl carbonate

Using a similar procedure as I-261 step 4 (solvent DMF, reaction temperature 94° C., 20 h), from tert-butyl 2-bromo-4-chloro-3-phenoxyphenylcarbamate (540 mg, 1.36 mmol) and pent-4-yn-1-ol (340 mg, 4.0 mmol) to provide tert-butyl 3-(5-chloro-4-phenoxy-1H-indol-2-yl)propyl carbonate (140 mg, 0.35 mmol, 25%) as a white solid. ESI-MS (EI+, m/z): 402.2[M+H]⁺ ¹H NMR (500 MHz, CDCl₃) δ 8.40 (s, 1H), 7.28-7.25 (m, 2H), 7.18 (d, J=8.6 Hz, 1H), 7.13 (d, J=8.6 Hz, 1H), 7.02 (t, J=7.4 Hz, 1H), 6.90 (d, J=7.9 Hz, 2H), 5.98 (s, 1H), 4.13 (t, J=6.1 Hz, 2H), 2.77 (t, J=7.3 Hz, 2H), 2.02-1.97 (m, 2H), 1.49 (s, 9H).

Step 2: 3-(5-chloro-4-phenoxy-1H-indol-2-yl)propan-1-ol, I-248

Using a similar procedure as I-261 step 5, from tert-butyl 3-(5-chloro-4-phenoxy-1H-indol-2-yl)propyl carbonate (120 mg, 0.299 mmol) and KOH (51 mg, 0.9 mmol) to provide 3-(5-chloro-4-phenoxy-1H-indol-2-yl)propan-1-ol I-248 (65 mg, 0.214 mmol, 71%) as a white solid. ESI-MS (EI+, m/z): 302.1 [M+H]⁺.

¹H NMR (500 MHz, CDCl₃) δ 8.48 (s, 1H), 7.30-7.24 (m, 2H), 7.16 (d, J=8.5 Hz, 1H), 7.12-7.08 (m, 1H), 7.01 (t, J=7.3 Hz, 1H), 6.90 (dd, J=8.7, 0.8 Hz, 2H), 5.98 (d, J=1.2 Hz, 1H), 3.72 (t, J=6.0 Hz, 2H), 2.82 (t, J=7.2 Hz, 2H), 1.94-1.87 (m, 2H).

Example 143: 1-(6-chloro-4-phenoxy-1H-indol-2-yl)-2-(trimethylsilyl)ethanol, I-159

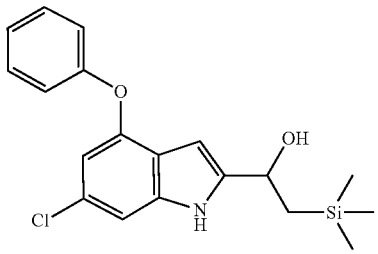

I-159

Synthetic Scheme:

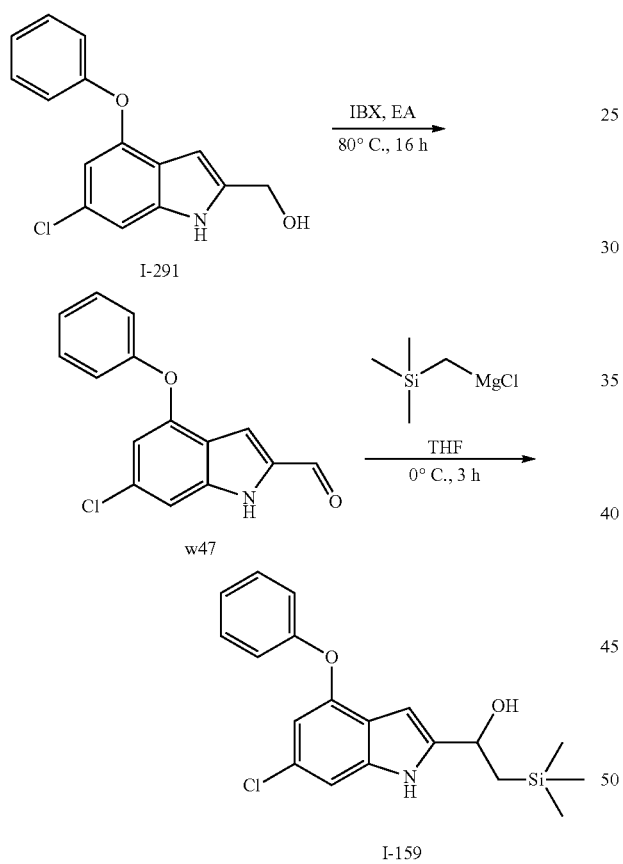

Procedures and Characterization:

Step 1: 6-chloro-4-phenoxy-1H-indole-2-carbaldehyde

To a solution of (6-chloro-4-phenoxy-1H-indol-2-yl)methanol (60 mg, 0.22 mmol) in EtOAc was added IBX (185 mg, 0.66 mmol) and heated at reflux for 16 h, cool down and filtered, washed with sat. NaHCO₃, brine, dried over Na₂SO₄, filtered and concentrated to obtain the target compound as a yellow solid (55 mg).

Step 2: 1-(6-chloro-4-phenoxy-1H-indol-2-yl)-2-(trimethylsilyl)ethanol, I-159

To a solution of 6-chloro-4-phenoxy-1H-indole-2-carbaldehyde (400 mg, 1.48 mmol) in THF (5 mL) was added ((trimethylsilyl)methyl)magnesium chloride (7.38 mL, 1M) at 0° C. and then stirred at rt for 3 h, quenched by NH₄Cl solution, extracted with EtOAc and concentrated. The crude was purified by prep-TLC to obtain 1-(6-chloro-4-phenoxy-1H-indol-2-yl)-2-(trimethylsilyl)ethanol I-159 as a yellow solid (530 mg, 92%). $^1$H NMR (500 MHz, CDCl₃) δ 8.40 (s, 1H), 7.36 (t, J=8.0 Hz, 2H), 7.15-7.06 (m, 4H), 6.65 (s, 1H), 6.25 (s, 1H), 5.05-5.00 (m, 1H), 1.35-1.26 (m, 2H), 0.09 (s, 9H).

Example 144: (6-chloro-4-phenoxy-1H-indol-2-yl)methanamine, I-170

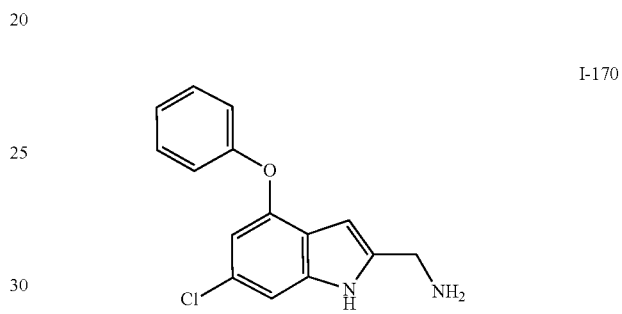

I-170

Synthetic Scheme:

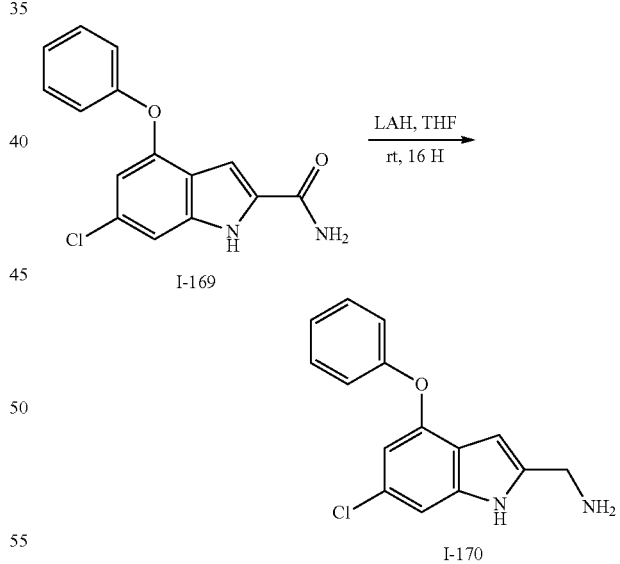

Procedures and Characterization:

Step 1: (6-chloro-4-phenoxy-1H-indol-2-yl)methanamine

To a solution of 6-chloro-4-phenoxy-1H-indole-2-carboxamide (290 mg, 1.01 mmol) in THF (6.0 mL) was added LAH (0.47 mL, 1M in THF) at 0° C. and stirred at rt for 16 h, quenched by Na₂SO₄. 10H₂O and purified by prep-HPLC to obtain (6-chloro-4-phenoxy-1H-indol-2-yl)methanamine I-170 as a white solid. ESI-MS (EI+, m/z): 273, ¹H NMR (500 MHz, DMSO-d6) δ 11.29 (s, 1H), 7.38 (t, J=8.0 Hz, 2H), 7.23-7.08 (m, 2H), 7.01 (d, J=7.9 Hz, 2H), 6.51 (d, J=1.6 Hz, 1H), 6.04 (s, 1H), 3.78 (s, 2H).

Example 145:
6-chloro-4-(4-chlorophenylthio)-1H-indole, I-180

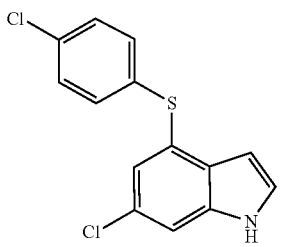

Synthetic Scheme:

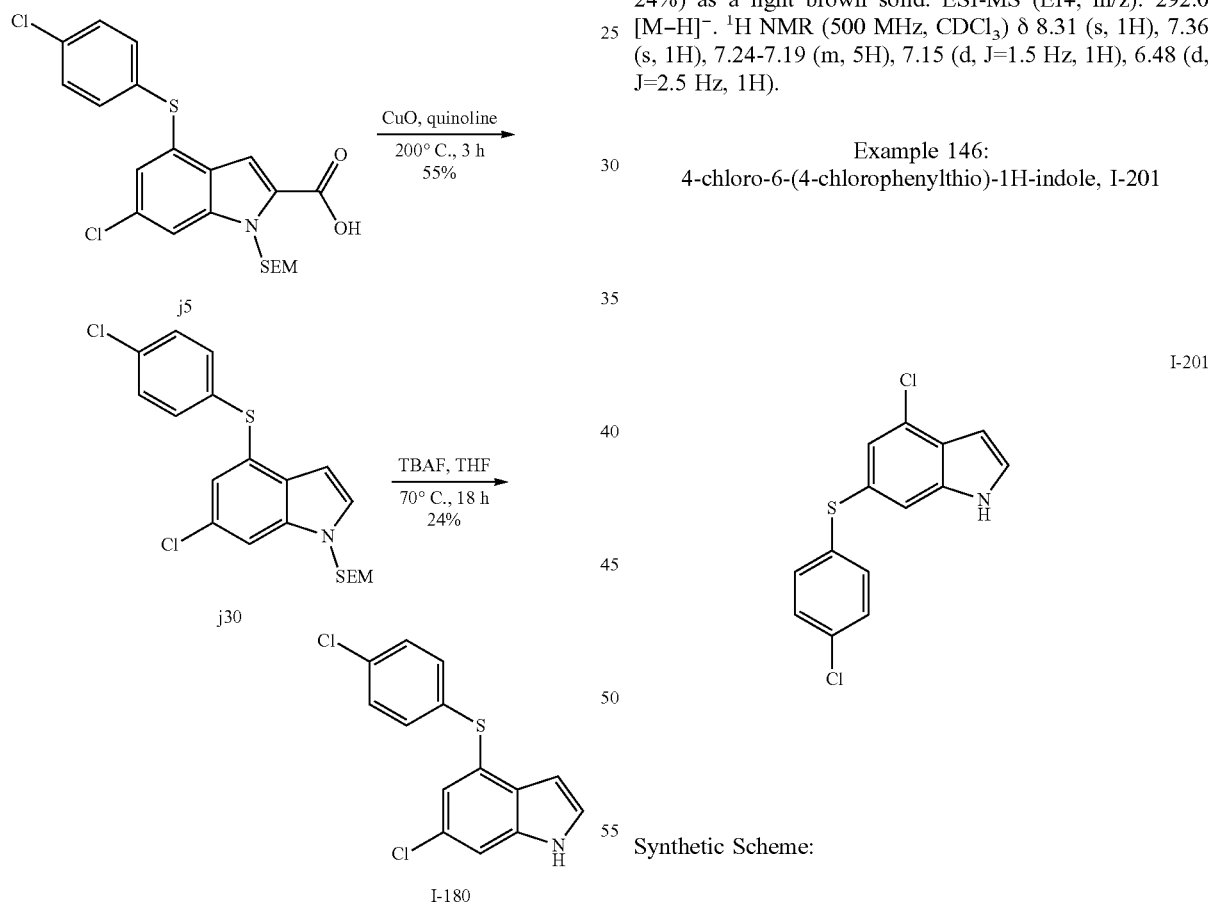

Procedures and Characterization:

Step 1: 6-chloro-4-(4-chlorophenylthio)-1-((2-(trimethylsilyl)ethoxy)methyl)-1H-indole A mixture of 6-chloro-4-(4-chlorophenylthio)-1-((2-(trimethylsilyl)ethoxy)methyl)-1H-indole-2-carboxylic acid (200 mg, 0.43 mmol) and CuO (1.7 g, 21 mmol) in quinoline (10 mL) was stirred for 3 h at 200° C. under N₂ atmosphere. The reaction was diluted with ethyl acetate (100 mL) and washed with aq 1 N HCl (20 mL×5), and brine (20 mL), dried (Na₂SO₄), filtered and concentrated in vacuo, the crude product was purified by chromatography (silica, ethyl acetate/petroleum ether=1/5) to afford 6-chloro-4-(4-chlorophenylthio)-1-((2-(trimethylsilyl)ethoxy)methyl)-1H-indole (100 mg, 0.24 mmol, 55%) as a light brown solid. ESI-MS (EI+, m/z): 424.0 [M+H]+.

Step 2: 6-chloro-4-(4-chlorophenylthio)-1H-indole, I-180

A mixture of 6-chloro-4-(4-chlorophenylthio)-1-((2-(trimethylsilyl)ethoxy)methyl)-1H-indole (200 mg, 0.47 mmol) and TBAF (1.24 g, 4.73 mmol) in THF (10 mL) was stirred for 18 h at 70° C. The reaction was diluted with EtOAc (50 mL) and washed with water (20 mL×2), dried (Na₂SO₄), filtered and concentrated, the crude product was purified by prep-HPLC (0.01% TFA) to afford 6-chloro-4-(4-chlorophenylthio)-1H-indole I-180 (32.5 mg, 0.11 mmol, 24%) as a light brown solid. ESI-MS (EI+, m/z): 292.0 [M−H]−. ¹H NMR (500 MHz, CDCl₃) δ 8.31 (s, 1H), 7.36 (s, 1H), 7.24-7.19 (m, 5H), 7.15 (d, J=1.5 Hz, 1H), 6.48 (d, J=2.5 Hz, 1H).

Example 146:
4-chloro-6-(4-chlorophenylthio)-1H-indole, I-201

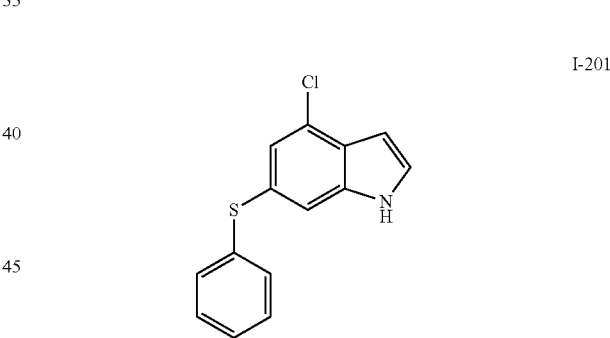

Synthetic Scheme:

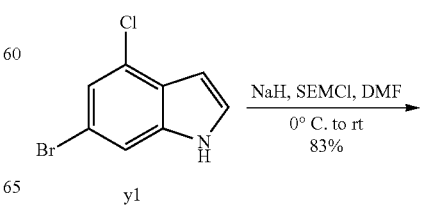

-continued

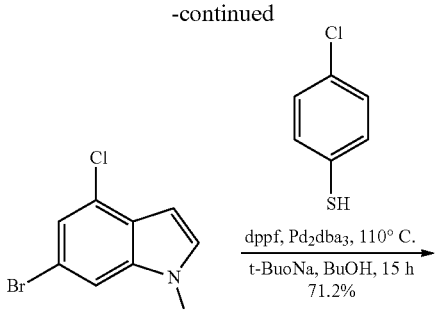

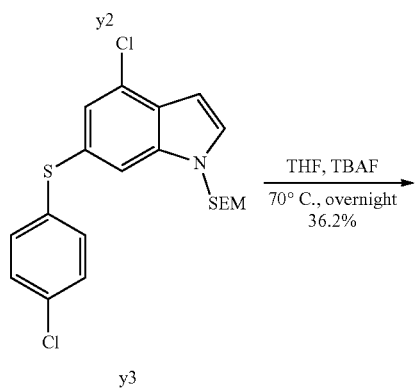

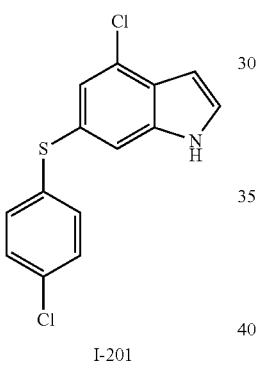

I-201

Procedures and Characterization:

Step 1: 6-bromo-4-chloro-1-((2-(trimethylsilyl)ethoxy)methyl)-1H-indole

To a solution of 6-bromo-4-chloro-1H-indole (200 mg, 0.868 mmol) in 5 mL of DMF was added Na (45.81 mg, 1.91 mmol) at 0° C. and the mixture was stirred at 0 BC for 1 h. SEMCl (0.2 mL, 0.6 mmol) was added dropwise slowly at 0° C. and stirred at rt for 12 h. The reaction mixture was added dropwise slowly to a cold saturated aqueous NaHCO$_3$ solution at 0° C. The mixture was extracted with EtOAc (20 mL×2), and the organic layers were washed with water, brine, dried and concentrated. The crude was purified by SGC (PE/EtOAc=100:1) to give 6-bromo-4-chloro-1H-indole (260 mg, 83%) as a yellow oil. MS (EI+, m/z): 361[M]$^+$.

Step 2: 4-chloro-6-(4-chlorophenylthio)-1-((2-(trimethylsilyl)ethoxy)methyl)-1H-indole To the mixture of 6-bromo-4-chloro-1-((2-(trimethylsilyl)ethoxy)methyl)-1H-indole (160 mg, 0.444 mmol) and 4-chlorobenzenethiol (77 mg, 0.532 mmol), dppf (50 mg, 0.089 mmol), Pd$_2$dba$_3$ (41 mg, 0.044 mmol), t-BuONa (149.2 mg, 1.77 mmol) was added n-BuOH (5 mL). This mixture was stirred at 110° C. for 15 h under N$_2$ protection. The mixture was extracted with EtOAc/H$_2$O (20 ml/20 ml), the organic phase was dried over anhydrous Na$_2$SO$_4$, and concentrated in vacuo. The residue was purified by SG column (petroleum ether/ethyl acetate=0~10%) to afford 4-chloro-6-(4-chlorophenylthio)-1-((2-(trimethylsilyl)ethoxy)methyl)-1H-indole (134 mg, 71.2%). MS (EI+, m/z): 425 [M]$^+$.

Step 3: 4-chloro-6-(4-chlorophenylthio)-1H-indole, I-201

A mixture of 4-chloro-6-(4-chlorophenylthio)-1-((2-(trimethyl silyl) ethoxy)methyl)-1H-indole (100 mg, 0.236 mmol) and TBAF (462 mg, 1.77 mmol) in THF (7 mL) was stirred at 70° C. for overnight. Diluted with EtOAc (30 mL), the mixture was washed with water and brine, dried over Na$_2$SO$_4$, concentrated under reduced pressure. The crude was purified by prep-HPLC to give 4-chloro-6-(4-chlorophenylthio)-1H-indole I-201 (25 mg, 36.2%); ESI-MS (EI+, m/z): 293 [M+H]$^+$. $^1$H NMR (500 MHz, DMSO-d$_6$) δ 11.62 (s, 1H), 7.56 (s, 1H), 7.51 (s, 1H), 7.38 (d, J=8.6 Hz, 2H), 7.20 (d, J=8.6 Hz, 2H), 7.14 (d, J=1.3 Hz, 1H).

Example 147: 4-(2-chlorophenylthio)-1H-indole, I-244

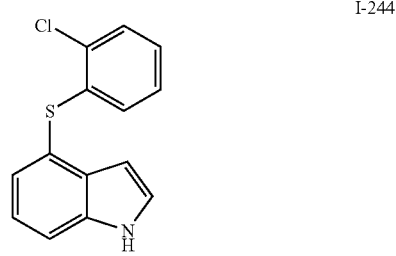 [SMILES: Clc1ccccc1Sc1cccc2[nH]ccc12]

Synthetic Scheme:

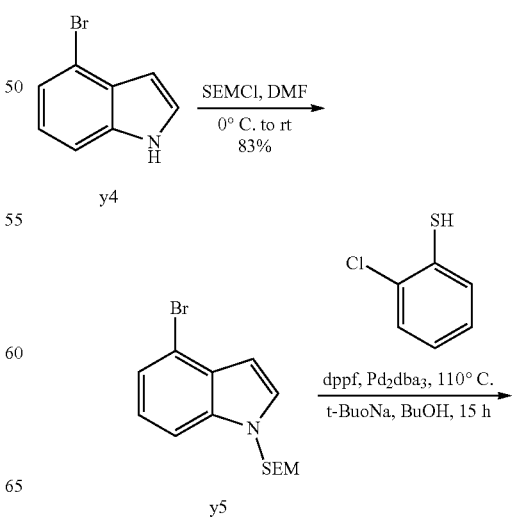

571

-continued

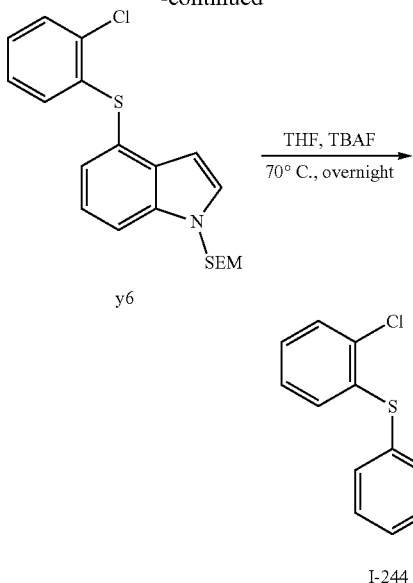

Procedures and Characterization:

Step 1: 4-bromo-1-((2-(trimethylsilyl)ethoxy)methyl)-1H-indole

Using a similar procedure as I-201 step 1, from 4-bromo-1H-indole (5.25 g, 26.78 mmol) and SEMCl (5.2 mL, 29.41 mmol) to provide 4-bromo-1-((2-(trimethylsilyl)ethoxy)methyl)-1H-indole as a yellow oil. ESI-MS (EI+, m/z): 326 [M+H]+.

Step 2: 4-bromo-1-((2-(trimethylsilyl)ethoxy)methyl)-1H-indole

The same procedure used to prepare y3 afforded 4-(2-chlorophenylthio)-1-((2-(trimethylsilyl)ethoxy)methyl)-1H-indole (210 mg, 41%) as a yellow oil. MS (EI+, m/z): 390 [M+H]+.

Step 3: 4-(2-chlorophenylthio)-1H-indole, I-244

The same procedure used to prepare I-201 afforded 4-(2-chlorophenylthio)-1H-indole I-244 (26 mg, 22%); ESI-MS (EI+, m/z): 260 [M+H]+.
$^1$H NMR (500 MHz, DMSO-$d_6$) δ 11.45 (s, 1H), 7.57 (d, J=8.0 Hz, 1H), 7.49 (d, J=3.0 Hz, 1H), 7.42 (d, J=1.5 Hz, 1H), 7.23-7.20 (m, 2H), 7.19-7.15 (m, 1H), 7.14-7.06 (m, 1H), 6.60 (d, J=1.0 Hz, 1H), 6.26 (s, 1H).

Example 148: 4-(4-chlorophenylthio)-1H-indole, I-246

572

Synthetic Scheme:

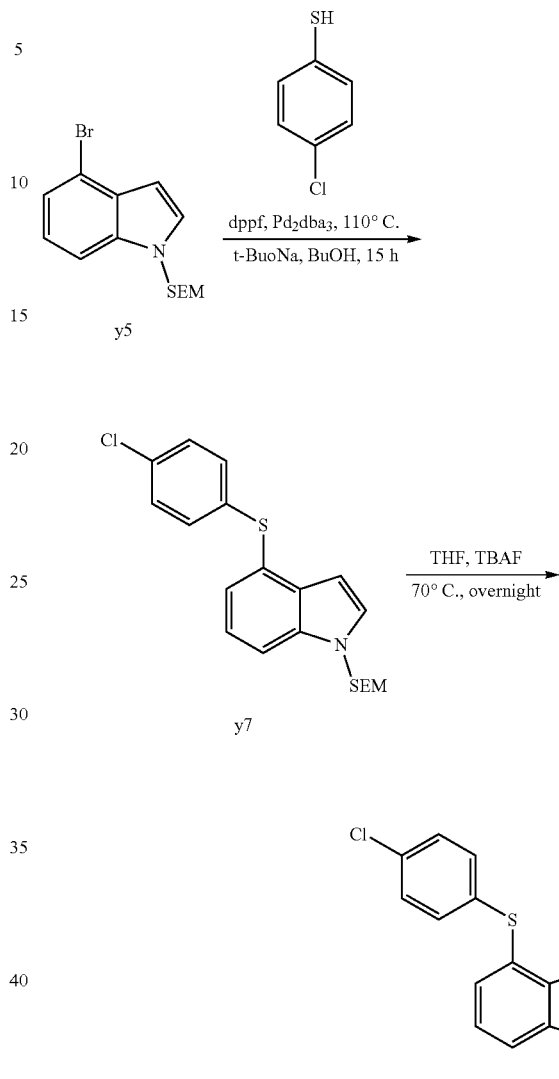

Procedures and Characterization:

Step 1: 4-(4-chlorophenylthio)-1-((2-(trimethylsilyl)ethoxy)methyl)-1H-indole

The same procedure used to prepare y3 afforded 4-(4-chlorophenylthio)-1-((2-(trimethylsilyl)ethoxy)methyl)-1H-indole (210 mg, 41%) as a yellow oil. MS (EI+, m/z): 390 [M+H]+.

Step 2: give 4-(4-chlorophenylthio)-1H-indole, I-246

The same procedure used to prepare I-201 afforded 4-(4-chlorophenylthio)-1H-indole I-246 (26 mg, 22%); ESI-MS (EI+, m/z): 260 [M+H]+.
$^1$H NMR (500 MHz, DMSO-d6) δ 11.39 (s, 1H), 7.50 (d, J=8.0 Hz, 1H), 7.39 (t, J=3.0 Hz, 1H), 7.32 (d, J=8.5 Hz, 21H), 7.17-7.11 (m, 4H), 6.27 (s, 1H).

Example 149: 4-(3-chlorophenylthio)-1H-indole, I-243

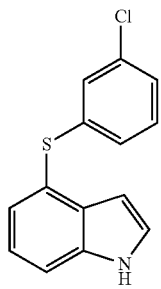

I-243

Synthetic Scheme:

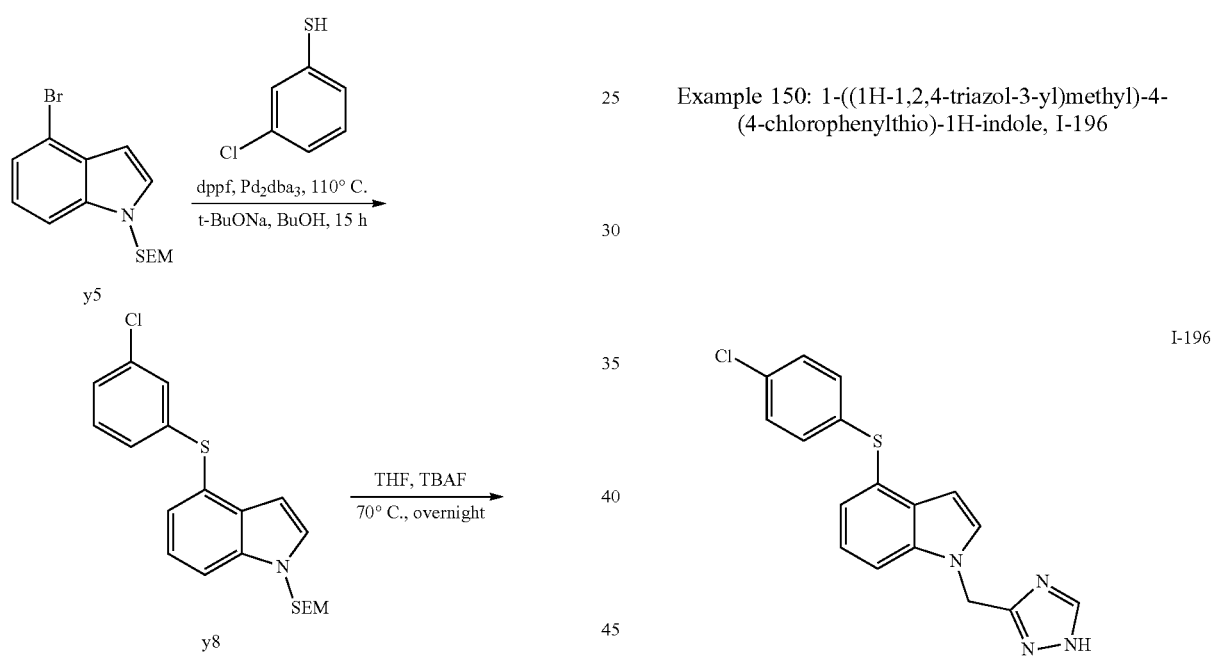

Procedures and Characterization:

Step 1: 4-(3-chlorophenylthio)-1-((2-(trimethylsilyl)ethoxy)methyl)-1H-indole

The same procedure used to prepare y3 afforded 4-(3-chlorophenylthio)-1-((2-(trimethylsilyl)ethoxy)methyl)-1H-indole (210 mg, 41%) as a yellow oil. MS (EI+, m/z): 390 [M+H]+.

Step 2: 4-(3-chlorophenylthio)-1H-indole, I-243

The same procedure used to prepare I-201 afforded 4-(3-chlorophenylthio)-1H-indole I-243 (26 mg, 22%); ESI-MS (EI+, m/z): 260 [M+H]+. 1H NMR (500 MHz, DMSO-d6) δ 11.44 (s, 1H), 7.55 (d, J=8.0 Hz, 2H), 7.42 (t, J=2.5 Hz, 1H), 7.29-7.26 (m, 1H), 7.23-7.16 (m, 3H), 7.07-7.16 (m, 2H), 6.29 (s, 1H).

Example 150: 1-((1H-1,2,4-triazol-3-yl)methyl)-4-(4-chlorophenylthio)-1H-indole, I-196

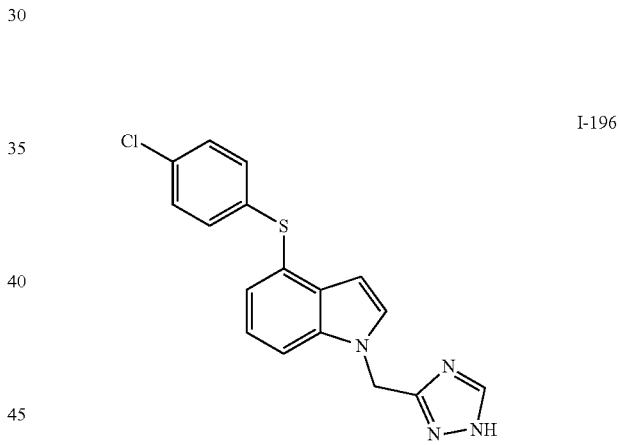

Synthetic Scheme:

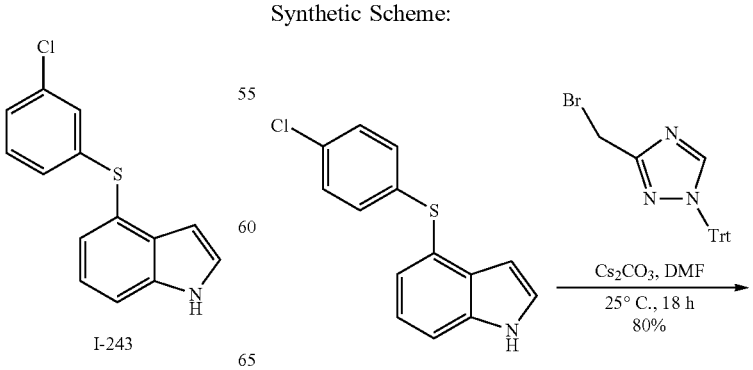

-continued

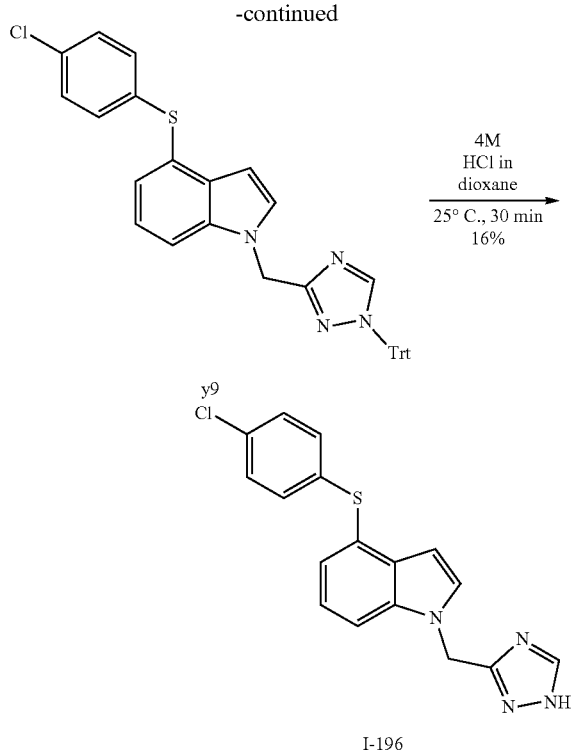

I-196

Procedures and Characterization:

Step 1: 4-(4-chlorophenylthio)-1-((1-trityl-1H-1,2,4-triazol-3-yl)methyl)-1H-indole A mixture of 4-(4-chlorophenylthio)-1H-indole (120 mg, 0.46 mmol), 3-(bromomethyl)-1-trityl-1H-1,2,4-triazole (224 mg, 0.56 mmol) and Cs$_2$CO$_3$ (226 mg, 0.7 mmol) in DMF (5 mL) was stirred for 18 h at 25° C. The reaction was quenched with water (10 mL) and extracted with ethyl acetate (30 mL). The organic phase was washed water (10 mL×2), and brine (10 mL), dried (Na$_2$SO$_4$), filtered and concentrated in vacuo and the residue was purified by chromatography (silica, ethyl acetate/petroleum ether=1/5) to afford 4-(4-chlorophenylthio)-1-((1-trityl-1H-1,2,4-triazol-3-yl)methyl)-1H-indole (270 mg, 0.44 mmol, 80%) as a light yellow solid. ESI-MS (EI+, m/z): 605.2 [M+Na]$^+$.

Step 2: 1-((1H-1,2,4-triazol-3-yl)methyl)-4-(4-chlorophenylthio)-1H-indole, I-196

A mixture of 4-(4-chlorophenylthio)-1-((1-trityl-1H-1,2,4-triazol-3-yl)methyl)-1H-indole (230 mg, 0.4 mmol) in 4 M HCl in dioxane (4 mL) was stirred for 30 min at 25° C. The reaction was diluted with water (50 mL), neutralized with Na$_2$CO$_3$ to pH 5 and extracted with ethyl acetate (100 mL). The organic phase was washed with water (30 mL×2), and brine (30 mL), dried (Na$_2$SO$_4$), filtered and concentrated in vacuo and the residue was purified by prep-HPLC (0.01% TFA) to afford 1-((1H-1,2,4-triazol-3-yl)methyl)-4-(4-chlorophenylthio)-1H-indole I-196 (22.4 mg, 0.07 mmol, 16%) as a white solid. ESI-MS (EI+, m/z): 320.0 [M–H]$^-$. $^1$H NMR (500 MHz, CDCl$_3$) δ 8.12 (s, 1H), 7.37 (d, J=7.5 Hz, 1H), 7.19-7.13 (m, 7H), 6.51 (d, J=3 Hz, 1H), 5.46 (s, 2H).

Example 151: 1-(4-(1H-tetrazol-5-1)benzyl)-4-(2,4-dichlorophenylthio)-1H-indole, I-161

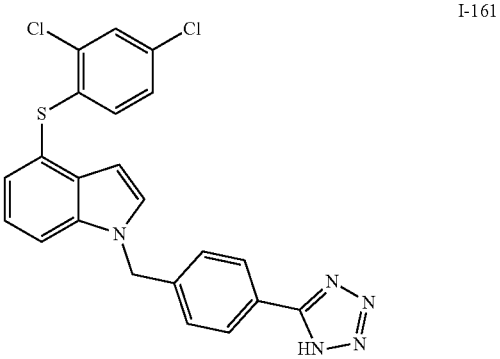 [SMILES: Clc1ccc(Sc2cccc3c2ccn3Cc2ccc(-c3nnn[nH]3)cc2)c(Cl)c1]

Synthetic Scheme:

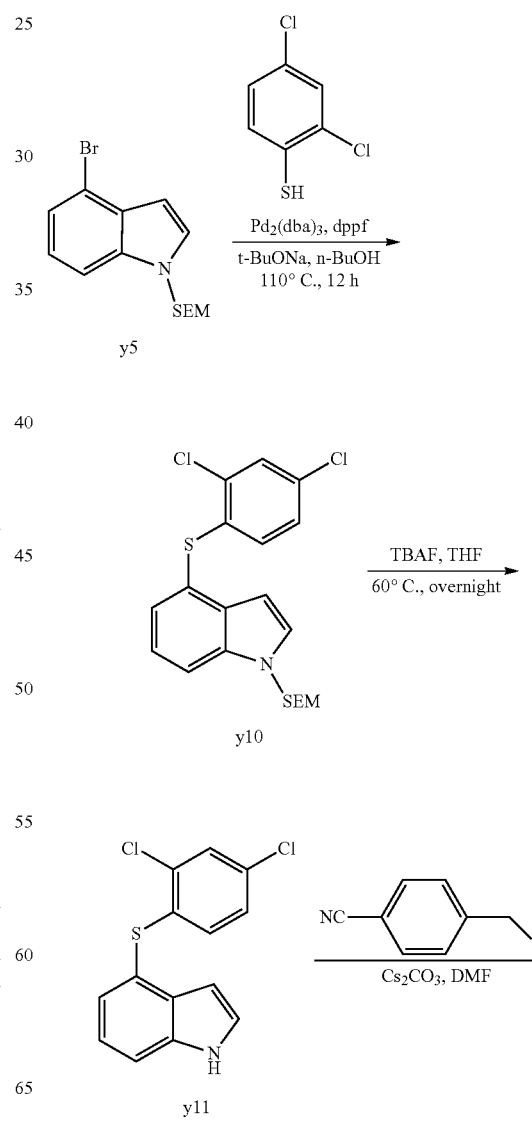

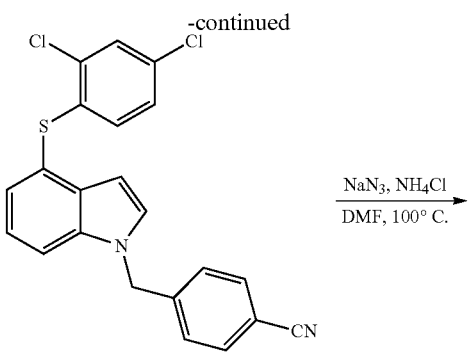

y12

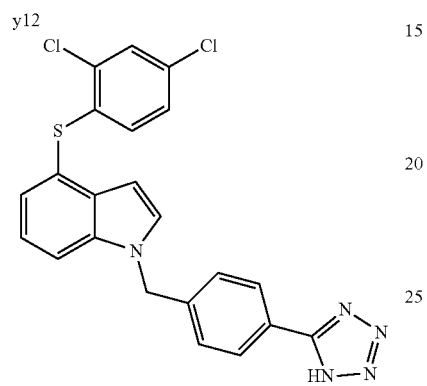

I-161

Procedures and Characterization:

Step 1: 4-(2,4-dichlorophenylthio)-1-((2-(trimethylsilyl)ethoxy)methyl)-1H-indole The same procedure used to prepare y3 afforded a red oil, which was purified by SGC to give 4-(2,4-dichlorophenylthio)-1-((2-(trimethylsilyl)ethoxy)methyl)-1H-indole as a yellow oil. (225 mg, 35.5%). ESI-MS (EI+, m/z): 424[M+H]$^+$.

Step 2: 4-(2,4-dichlorophenylthio)-1H-indole

The same procedure used to prepare I-201 afforded 4-(2,4-dichlorophenylthio)-1H-indole as a white solid. (10 mg, 9.8%). ESI-MS (EI+, m/z): 293[M+H]$^+$. 1H-NMR (500 MHz, DMSO-d6): δ 11.58 (s, 1H), 7.96-7.95 (m, J=5.5 Hz, 3H), 7.67-7.59 (m, 4H), 6.35 (m, 1H) Step 3: 4-((4-(2,4-dichlorophenylthio)-1H-indol-1-yl)methyl)benzonitrile:

The mixture of 4-(2,4-dichlorophenylthio)-1H-indole (500 mg, 1.18 mmol), TBAF (1.54 g, 5.91 mmol) in THF (30 mL) was stirred at 60° C. overnight. Concentrated, the crude was purified by combiflash (ISCO, 4 g silica gel, EtOAc/PE=50%) to afford the product (300 mg, 86.96%) as a yellow solid. ESI-MS (EI$^+$, m/z): 410.9[M+H+2]$^-$. $^1$H NMR (500 MHz, CDCl$_3$) δ 7.53 (d, J=8.2 Hz, 2H), 7.31 (d, J=2.2 Hz, 1H), 7.25 (d, J=7.1 Hz, 1H), 7.20-7.17 (m, 1H), 7.15-7.06 (m, 4H), 6.87 (dd, J=8.6, 2.2 Hz, 1H), 6.57 (d, J=8.6 Hz, 1H), 6.49 (d, J=3.0 Hz, 1H), 5.33 (s, 2H).

Step 4: 1-(4-(1H-tetrazol-5-yl)benzyl)-4-(2,4-dichlorophenylthio)-1H-indole, I-161

The mixture of 4-((4-(2,4-dichlorophenylthio)-1H-indol-1-yl)methyl)benzonitrile (40 mg, 0.1 mmol), NaN$_3$ (32 mg, 0.5 mmol), NH$_4$Cl (26 mg, 0.5 mmol) in DMF (4 mL) was stirred at 100° C. overnight. 10 mL of water was added, extracted with EtOAc (20 mL*2). Concentrated, the crude was purified by prep-HPLC to afford the product I-161 (22 mg, 24.44%) as a white solid. ESI-MS (EI+, m/z). 452[M+H]$^+$. $^1$H NMR (400 MHz, DMSO-d$_6$) δ 7.95 (d, J=8.2 Hz, 2H), 7.76-7.63 (m, 3H), 7.34 (d, J=8.2 Hz, 2H), 7.30-7.20 (m, 3H), 6.58 (d, J=8.6 Hz, 1H), 6.35 (d, J=3.1 Hz, 1H), 5.53 (s, 2H).

Example 152: 4-(2,5-dichlorophenylthio)-1H-indole, I-209

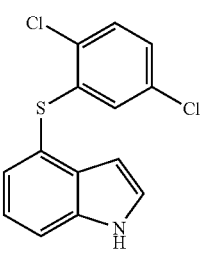

I-209

Synthetic Scheme:

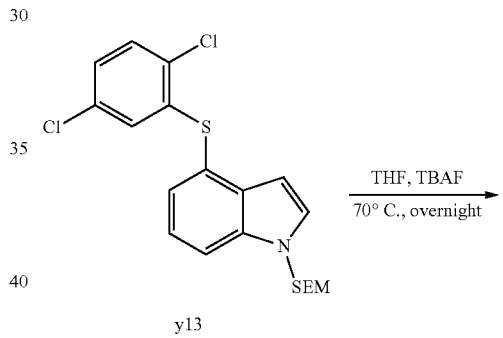

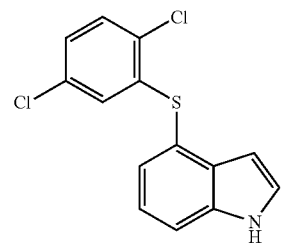

I-209

Procedures and Characterization:

Step 1: 4-(2,5-dichlorophenylthio)-1H-indole, I-209

The same procedure used to prepare I-201 afforded 4-(2,5-dichlorophenylthio)-1H-indole 1-209 (25 mg, 36%); ESI-MS (EI$^+$, m/z): 294 [M+H]$^+$.

$^1$H NMR (500 MHz, DMSO-d$_6$) δ 11.51 (s, 1H), 7.63 (d, J=7.5 Hz, 1H), 7.53 (d, J=7.5 Hz, 1H), 7.47 (t, J=3.0 Hz, 1H), 7.31-7.18 (m, 3H), 6.39 (d, J=2.0 Hz, 11H), 6.29 (d, J=2.5 Hz, 1H).

Example 153: (4-(4-chlorophenylthio)-1H-indol-6-yl)methanol, I-198

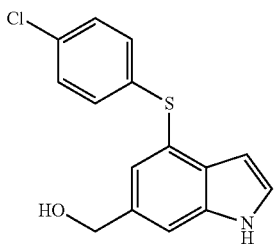

Synthetic Scheme:

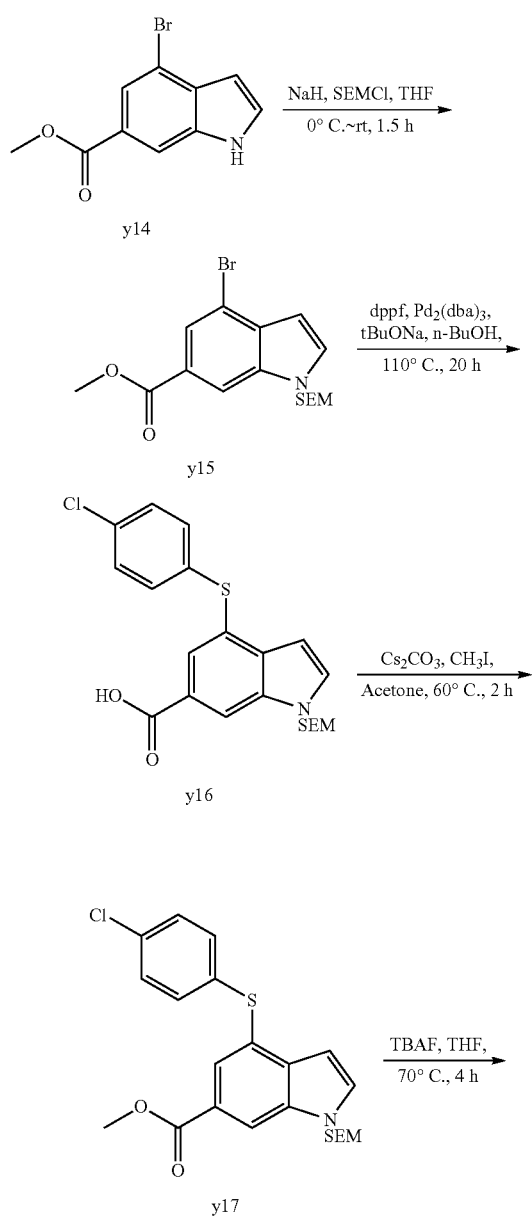

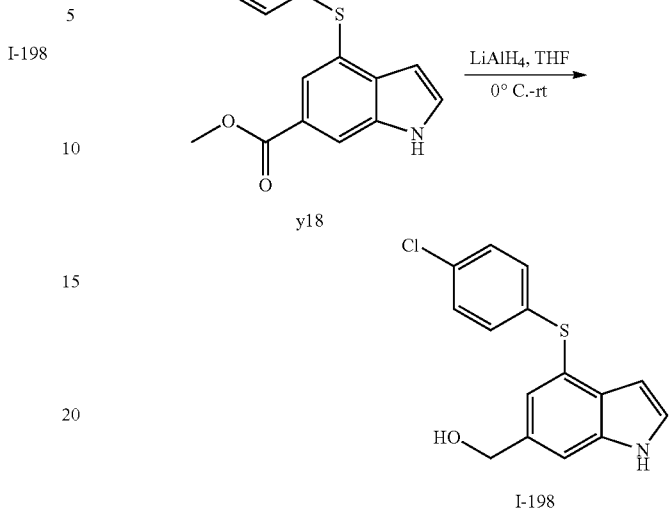

Procedures and Characterization:

(4-(4-chlorophenylthio)-1H-indol-6-yl)methanol

The procedures for 1$^{st}$, 2$^{nd}$ and 4$^{th}$ step are the same as I-201.

Step 3: methyl 4-(4-chlorophenylthio)-1-((2-(trimethylsilyl)ethoxy)methyl)-1H-indole-6-carboxylate The mixture of 4-(4-chlorophenylthio)-1-((2-(trimethylsilyl)ethoxy)methyl)-1H-indole-6-carboxylic acid (1.0 g, 2.35 mmol), $Cs_2CO_3$ (3.0 g, 0.94 mmol), and MeI (3.33 g, 23.5 mmol), acetone (30 mL) was heated to 60° C. and stirred for 2 h. The reaction was quenched by adding $H_2O$ (20 mL), and then extracted with EtOAc (100 mL×2). The combined organics were dried over $Na_2SO_4$, filtered, concentrated in vacuo to afford the residue. The residue was purified by column to afford methyl 4-(4-chlorophenylthio)-1-((2-(trimethylsilyl)ethoxy)methyl)-1H-indole-6-carboxylate (1.0 g). ESI-MS (EI+, m/z): 448.0 [M+H]$^+$.

Step 5: (4-(4-chlorophenylthio)-1H-indol-6-yl)methanol, I-198

The same procedure used to prepare I-187 afforded (4-(4-chlorophenylthio)-1H-indol-6-yl)methanol I-198. ESI-MS (EI+, m/z): 290 [M+H]$^+$. $^1$H NMR (500 MHz, CDCl$_3$) δ 8.33 (s, 1H), 7.43 (s, 1H), 7.23 (s, 1H), 7.21 (t, J=3.0 Hz, 1H), 7.17-7.13 (m, 4H), 6.48 (br s, 1H), 4.76 (s, 2H).

Example 154: 4-bromo-6-phenoxy-1H-indole, I-239

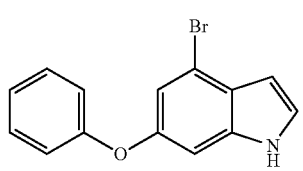

Synthetic Scheme:

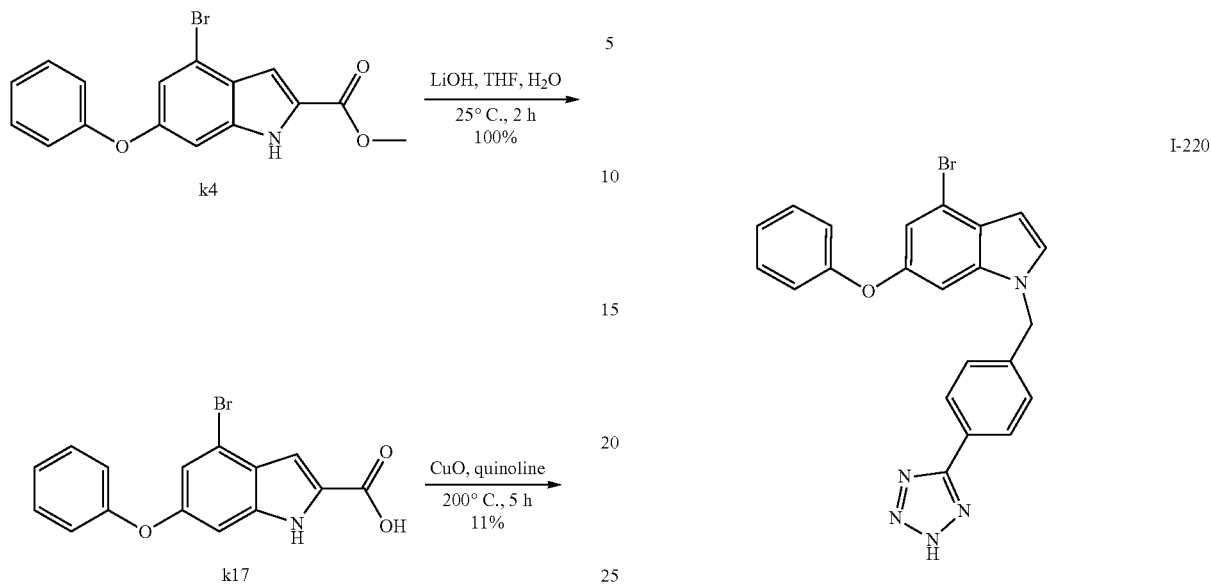

Example 155: 1-(4-(2H-tetrazol-5-yl)benzyl)-4-bromo-6-phenoxy-1H-indole, I-220

Procedures and Characterization:

Step 1: 4-bromo-6-phenoxy-1H-indole-2-carboxylic acid

A mixture of methyl 4-bromo-6-phenoxy-1H-indole-2-carboxylate (150 mg, 0.44 mmol), LiOH.H$_2$O (55 mg, 1.3 mmol) in THF (2 mL), MeOH (2 mL) and H$_2$O (2 mL) was stirred for 2 h at 25° C. The reaction was neutralized with 2 N HCl to pH 6 and extracted with ethyl acetate (20 mL). The organic phase was dried (Na$_2$SO$_4$), filtered and concentrated in vacuo to afford crude 4-bromo-6-phenoxy-1H-indole-2-carboxylic acid (144 mg, 1.3 mmol, 100%) as a white solid. ESI-MS (EI+, m/z): 332.0 [M+H]$^+$.

Step 2: 4-bromo-6-phenoxy-1H-indole, I-239

The same procedure used to prepare j30 afforded 4-bromo-6-phenoxy-1H-indole I-239 (13.6 mg, 0.05 mmol, 11%) as a light brown solid. ESI-MS (EI+, m/z): 288.0 [M+H]$^+$. $^1$H NMR (500 MHz, CDCl$_3$) δ 8.24 (s, 1H), 7.32 (t, J=7.5 Hz, 2H), 7.22 (t, J=3 Hz, 1H), 7.10-7.07 (m, 2H), 7.01-6.99 (m, 3H), 6.58 (s, 1H).

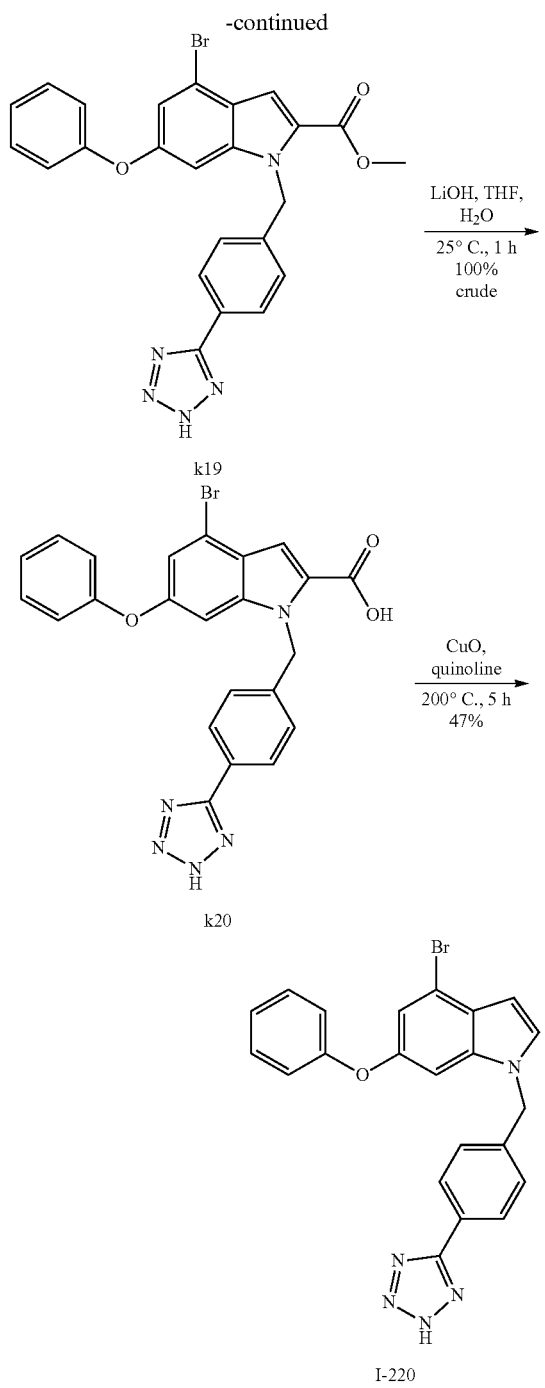

purified by chromatography (silica, ethyl acetate/petroleum ether=1/5) to afford methyl 4-bromo-1-(4-cyanobenzyl)-6-phenoxy-1H-indole-2-carboxylate (600 mg, 1.3 mmol, 90%) as a white solid. ESI-MS (EI+, m/z): 461.0 [M+H]$^+$.

Step 2: methyl 1-(4-(2H-tetrazol-5-yl)benzyl)-4-bromo-6-phenoxy-1H-indole-2-carboxylate A mixture of methyl 4-bromo-1-(4-cyanobenzyl)-6-phenoxy-1H-indole-2-carboxylate (630 mg, 1.37 mmol), NaN$_3$ (445 mg, 6.85 mmol) and NH$_4$Cl (364 mg, 6.85 mmol) in dry DMF (10 mL) was stirred for 16 h at 100° C. under N$_2$ atmosphere. The reaction was quenched with water (20 mL) and extracted with ethyl acetate (60 mL). The organic phase was washed with water (20 mL×2), and brine (20 mL), dried (Na$_2$SO$_4$), filtered and concentrated in vacuo and the residue was purified by chromatography (silica, ethyl acetate/petroleum ether=1/5) to afford methyl 1-(4-(2H-tetrazol-5-yl)benzyl)-4-bromo-6-phenoxy-1H-indole-2-carboxylate (550 mg, 1.1 mmol, 80%) as a white solid. ESI-MS (EI+, m/z): 504.0 [M+H]$^+$.

Step 3: 1-(4-(2H-tetrazol-5-yl)benzyl)-4-bromo-6-phenoxy-1H-indole-2-carboxylic acid A mixture of methyl 1-(4-(2H-tetrazol-5-yl)benzyl)-4-bromo-6-phenoxy-1H-indole-2-carboxylate (200 mg, 0.4 mmol), LiOH.H$_2$O (36 mg, 1.5 mmol) in THF (3 mL) and H$_2$O (3 mL) was stirred for 1 h at 25° C. The reaction was neutralized with 2 N HCl to pH 6 and extracted with ethyl acetate (20 mL). The organic phase was dried (Na$_2$SO$_4$), filtered and concentrated in vacuo to afford crude 1-(4-(2H-tetrazol-5-yl)benzyl)-4-bromo-6-phenoxy-1H-indole-2-carboxylic acid (194 mg, 0.4 mmol, 100%) as a white solid. ESI-MS (EI+, m/z): 490.0 [M+H]$^+$.

Step 4: 1-(4-(2H-tetrazol-5-yl)benzyl)-4-bromo-6-phenoxy-1H-indole, I-220

The same procedure used to prepare j30 afforded 1-(4-(2H-tetrazol-5-yl)benzyl)-4-bromo-6-phenoxy-1H-indole 1-220 (106.4 mg, 0.24 mmol, 47%) as a white solid. ESI-MS (EI+, m/z): 446.0 [M+H]$^+$. $^1$H NMR (500 MHz, DMSO) δ 7.98 (d, J=8 Hz, 2H), 7.68 (d, J=3.5 Hz, 1H), 7.38 (d, J=8.5 Hz, 2H), 7.33 (dd, J=16 Hz, J=8.5 Hz, 3H), 7.08 (t, J=8 Hz, 1H), 6.99 (d, J=1.5 Hz, 1H), 6.93 (d, J=8 Hz, 2H), 6.49 (d, J=3 Hz, 1H), 5.52 (s, 2H).

Example 156: 4-((4-bromo-6-phenoxy-1H-indol-1-yl)methyl)benzoic acid, I-164

Procedures and Characterization:

Step 1: methyl 4-bromo-1-(4-cyanobenzyl)-6-phenoxy-1H-indole-2-carboxylate

A mixture of methyl 4-bromo-6-phenoxy-1H-indole-2-carboxylate (500 mg, 1.45 mmol), 4-(bromomethyl)benzonitrile (341 mg, 1.74 mmol) and Cs$_2$CO$_3$ (707 mg, 2.18 mmol) in DMF (10 mL) was stirred for 16 h at 25° C. The reaction was quenched with water (20 mL) and extracted with ethyl acetate (60 mL). The organic phase was washed water (20 mL×2), and brine (20 mL), dried (Na$_2$SO$_4$), filtered and concentrated in vacuum and the residue was

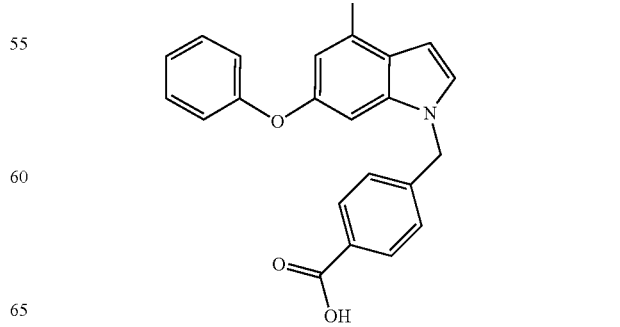

I-164

Synthetic Scheme:

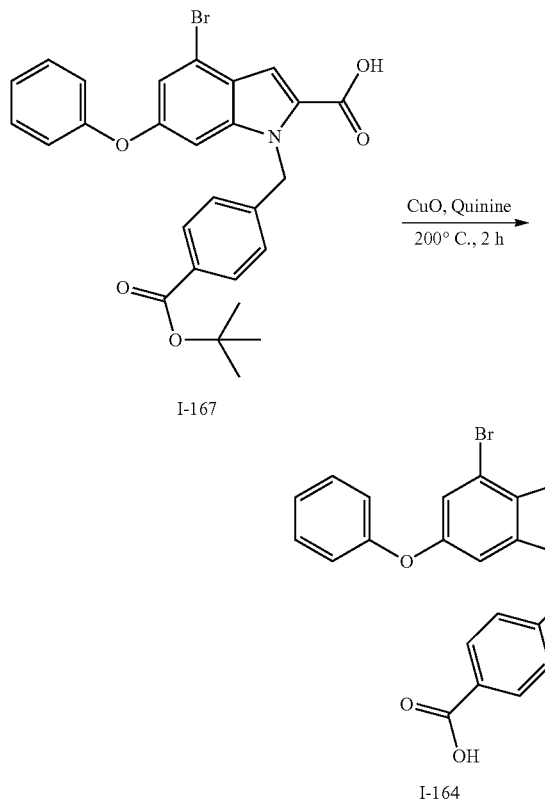

Procedures and Characterization:

Step 1: 4-((4-bromo-6-phenoxy-1H-indol-1-yl)methyl)benzoic acid, I-164

The same procedure used to prepare j30 afforded 4-((4-bromo-6-phenoxy-1H-indol-1-yl)methyl)benzoic acid I-164 as a white solid (57.1 mg, 0.14 mml, 14%). ESI-MS (EI+, m/z): 422 [M+H]$^+$. $^1$H NMR (500 MHz, DMSO) δ 12.93 (br s, 1H), 7.88 (d, 2H, J=8.0 Hz), 7.65 (d, 1H, J=3.5 Hz) 7.32-7.35 (t, 2H, J=7.5 Hz), 7.21-7.25 (m, 3H), 7.08-7.11 (t, 2H, J=7.5 Hz), 6.99 (d, 1H, J=7.5 Hz), 6.93 (d, 2H, J=8 Hz), 6.48 (d, 1H, J=3.5 Hz), 5.49 (s, 2H).

Example 157:
6-chloro-4-(2-chlorophenoxy)-1H-indole, I-202

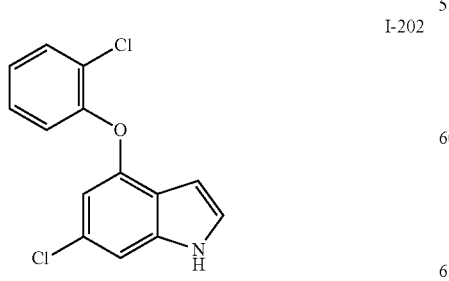

Synthetic Scheme:

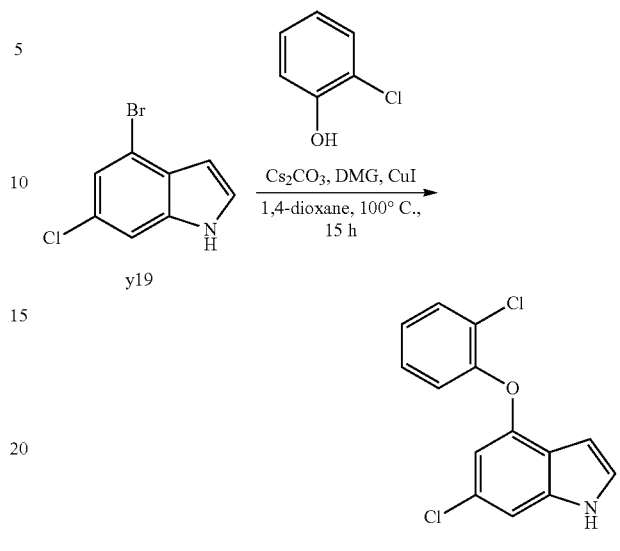

Procedures and Characterization:

Step 1: 6-chloro-4-(2-chlorophenoxy)-1H-indole, I-202

The solution of 4-bromo-6-chloro-1H-indole (400 mg, 1.74 mmol), 2-chlorophenol (267 mg, 2.09 mmol), Cs$_2$CO$_3$ (856 mg, 2.61 mmol), CuI (333 mg, 1.74 mmol) and DMG (146 mg, 1.04 mmol) in 1,4-dioxane (10 mL) was stirred at 100° C. for 15 h under nitrogen. Then cool down and filtered and washed with water, EtOAc, the organic layer was dried, filtered and concentrated. The crude was purified by reverse-phase Biotage (10 mmol NH$_4$HCO$_3$ in water/CH$_3$CN) to obtain 6-chloro-4-(2-chlorophenoxy)-1H-indole I-202 (12 mg, 2.5%) as a white solid. ESI-MS (EI$^-$, m/z): 276 [M–H]$^-$. $^1$H NMR (500 MHz, DMSO-d$_6$) δ 11.45 (s, 1H), 7.64 (dd, J=8.0, 1.5 Hz, 1H), 7.36 (td, J=7.5, 1.6 Hz, 2H), 7.28-7.19 (m, 2H), 7.11 (dd, J=8.1, 1.4 Hz, 1H), 6.38 (d, J=1.6 Hz, 1H), 6.27 (d, J=2.9 Hz, 1H).

Example 158:
6-chloro-4-(3-chlorophenoxy)-1H-indole, I-208

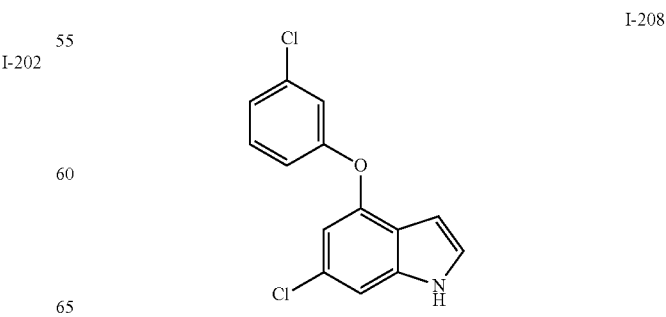

Synthetic Scheme:

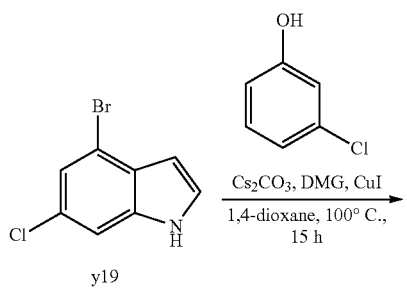

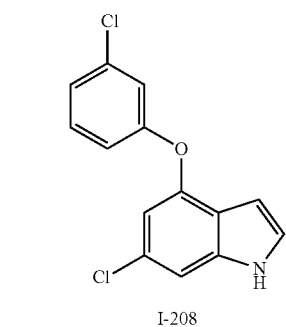

Procedures and Characterization:
The procedure was same as example I-202.
6-chloro-4-(3-chlorophenoxy)-1H-indole, I-208: ESI-MS (EI−, m/z): 276 [M−H]−. ¹H NMR (500 MHz, DMSO-d₆) δ 11.47 (s, 1H), 7.41 (t, J=8.1 Hz, 1H), 7.38-7.36 (m, 1H), 7.33 (s, 1H), 7.22-7.20 (m, 1H), 7.09 (t, J=2.2 Hz, 1H), 6.99 (dd, J=8.3, 1.7 Hz, 1H), 6.66 (d, J=1.6 Hz, 1H), 6.20 (s, 1H).

Example 159:
6-chloro-4-(4-chlorophenoxy)-1H-indole, I-204

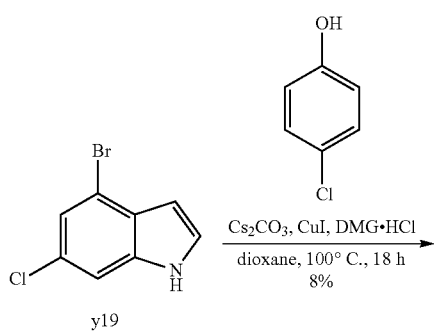

Synthetic Scheme:

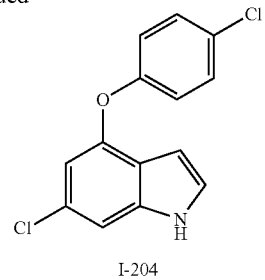

Step 1: 6-chloro-4-(4-chlorophenoxy)-1H-indole, I-204

The same procedure used to prepare I-202 afforded 6-chloro-4-(4-chlorophenoxy)-1H-indole I-204 (21.4 mg, 0.08 mmol, 8%) as a light brown solid. ESI-MS (EI+, m/z): 276.1 [M−H]−. ¹H NMR (500 MHz, CDCl₃) δ 8.23 (s, 1H), 7.31-7.28 (m, 2H), 7.19 (d, J=1 Hz, 1H), 7.13 (dd, J=3 Hz, J=2.5 Hz, 1H), 7.01-6.98 (m, 2H), 6.63 (d, J=1.5 Hz, 1H), 6.42-6.41 (m, 1H).

Example 160: 4-(4-chlorophenoxy)-1H-indole, I-283

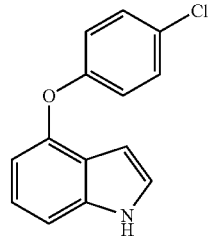

Synthetic Scheme:

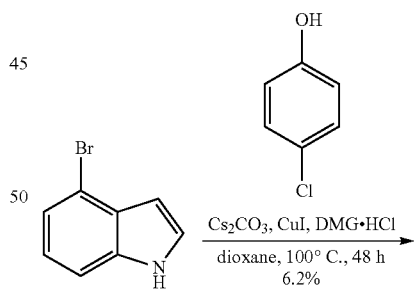

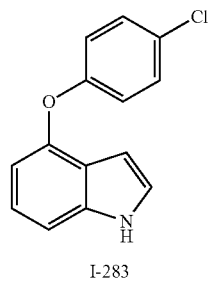

Procedures and Characterization:

Step 1: 4-(4-chlorophenoxy)-1H-indole

The same procedure used to prepare I-202 afforded 4-(4-chlorophenoxy)-1H-indole I-283 (30.5 mg, 0.13 mmol, 8%) as a brown solid. ESI-MS (EI+, m/z): 244.0 [M+H]⁺. ¹H NMR (500 MHz, CDCl₃) δ 8.23 (s, 1H), 7.24 (d, J=8.5 Hz, 2H), 7.20 (d, J=8.5 Hz, 1H), 7.13 (d, J=8 Hz, 1H), 7.11 (s, 1H), 6.95 (d, J=9 Hz, 2H), 6.69 (d, J=7.5 Hz, 1H), 6.40 (s, 1H).

Example 161: 4-(3-chlorophenoxy)-1H-indole, I-284

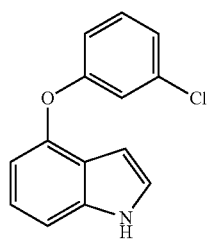

Synthetic Scheme:

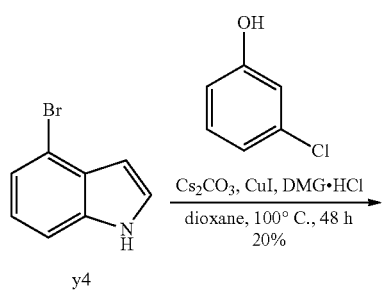

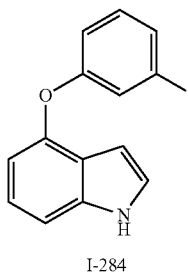

Procedures and Characterization:

Step 1: 4-(3-chlorophenoxy)-1H-indole

The same procedure used to prepare I-202 afforded 4-(3-chlorophenoxy)-1H-indole I-284 (98.6 mg, 0.4 mmol, 20%) as a brown solid. ESI-MS (EI+, m/z): 244.0 [M+H]⁺. ¹H NMR (500 MHz, CDCl₃) δ 8.23 (s, 1H), 7.31-7.28 (m, 2H), 7.19 (d, J=1 Hz, 1H), 7.13 (dd, J=3 Hz, J=2.5 Hz, 1H), 7.01-6.98 (m, 2H), 6.63 (d, J=1.5 Hz, 1H), 6.41 (dd, J=3 Hz, J=1 Hz, 1H).

Example 162: 4-(3-fluorophenoxy)-1H-indole, I-282

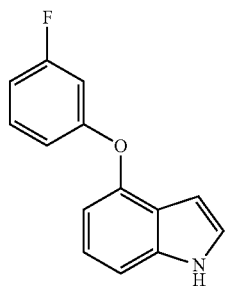

Synthetic Scheme:

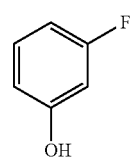

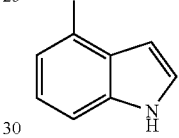

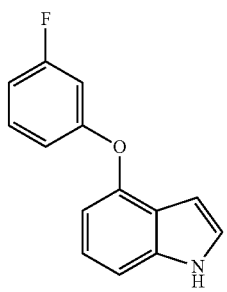

Procedures and Characterization:

Step 1: 4-(3-fluorophenoxy)-1H-indole

The same procedure used to prepare I-202 afforded 4-(3-fluorophenoxy)-1H-indole I-282 as a white solid. ESI-MS (EI⁻, m/z): 228.1 [M+H]⁺. ¹H NMR (500 MHz, DMSO-d₆) δ 11.34 (s, 1H), 7.40-7.24 (m, 3H), 7.10 (t, J=7.9 Hz, 1H), 6.94-6.86 (m, 1H), 6.78 (dd, J=7.5, 5.3 Hz, 2H), 6.68 (d, J=7.6 Hz, 1H), 6.16 (s, 1H).

Example 163: 4-(2-fluorophenoxy)-1H-indole, I-288

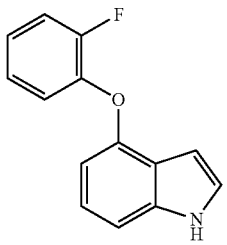

I-288

Synthetic Scheme:

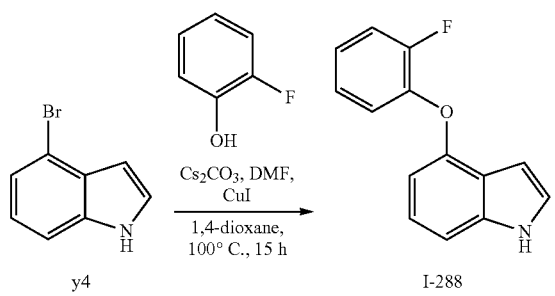

Procedures and Characterization:

The procedure was same as example I-282.

4-(2-fluorophenoxy)-1H-indole I-288: ESI-MS (EI+, m/z): 228.1 [M+H]+. $^1$H NMR (500 MHz, DMSO-$d_6$) δ 11.31 (s, 1H), 7.41-7.33 (m, 1H), 7.31 (d, J=2.4 Hz, 1H), 7.24-7.10 (m, 3H), 7.09-6.96 (m, 2H), 6.45 (d, J=7.7 Hz, 1H), 6.27 (s, 1H), 6.05 (s, 1H).

Example 164: 5-chloro-4-phenoxy-1H-indole, I-257

I-257

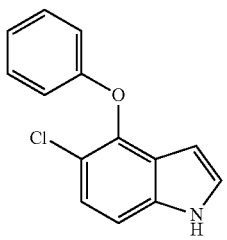

Synthetic Scheme:

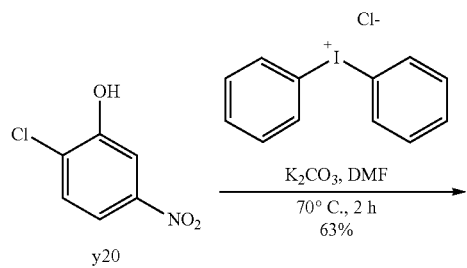

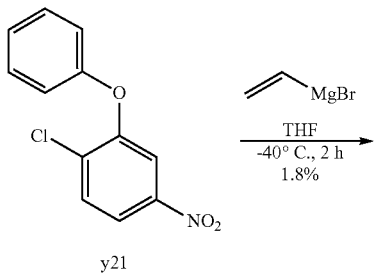

Procedures and Characterization:

Step 1: 1-chloro-4-nitro-2-phenoxybenzene

To a mixture of 2-chloro-5-nitrophenol (1.73 g, 10 mmol) and $K_2CO_3$ (2.77 g, 20 mmol) in DMF (20 mL) was added diphenyliodonium chloride (3.8 g, 12 mmol) and stirred at 70° C. for 2 h. The mixture was added into ice-water (100 mL) and extracted with EtOAc (100 mL). The organic phase was washed with water (100 mL×2), and brine (100 mL), dried ($Na_2SO_4$), filtered and concentrated in vacuo, the crude product was purified by chromatography (silica, petroleum ether to ethyl acetate/petroleum ether=1/10) to afford 1-chloro-4-nitro-2-phenoxybenzene (1.58 g, 6.3 mmol, 63%) as a colorless oil. $^1$H NMR (500 MHz, CDCl$_3$) δ 7.92 (dd, J=8.8, 2.5 Hz, 1H), 7.72 (d, J=2.5 Hz, 1H), 7.63 (d, J=8.7 Hz, 1H), 7.43 (dd, J=8.4, 7.6 Hz, 2H), 7.26-7.23 (m, 1H), 7.08-7.04 (m, 2H).

Step 2: 5-chloro-4-phenoxy-1H-indole, I-257

To a solution of 1-chloro-4-nitro-2-phenoxybenzene (1.0 g, 4.0 mmol) in THF (20 mL) at −40° C. (dry ice-acetonitrile) was added slowly a solution of vinylmagnesium bromide (1.0 M in THF, 12 mL, 12 mmol). The resulting mixture was stirred at −40° C. for 2 h, then was then treated with saturated aqueous NH$_4$Cl (50 mL) and stirred at room temperature for 1 h. HCl (1M) was added to adjust the pH to 7. EtOAc (100 mL) was added and the organic phase was separated, washed with water (100 mL×2), and brine (100 mL), dried (Na$_2$SO$_4$), filtered and concentrated in vacuo, the crude product was purified by chromatography twice (silica, petroleum ether to ethyl acetate/petroleum ether=1/10) to afford 5-chloro-4-phenoxy-1H-indole I-257 as a white solid (18 mg, 0.073 mmol, 1.8%). ESI-MS (EI+, m/z): 244.1[M+H]+. $^1$H NMR (500 MHz, CDCl$_3$) δ 8.28 (bs, 1H), 7.33-7.19 (m, 4H), 7.13 (t, J=2.7 Hz, 1H), 7.03 (t, J=7.3 Hz, 1H), 6.92 (d, J=7.9 Hz, 2H), 6.27 (s, 1H).

Example 165: 4-(2,4-Dichlorophenoxy)-1H-indole, I-255

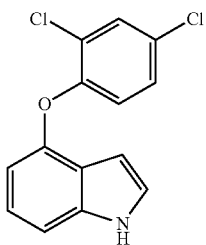

Synthetic Scheme:

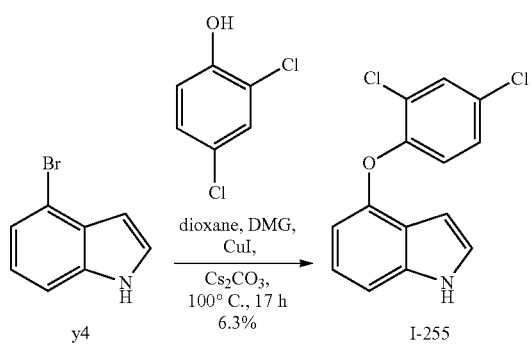 [SMILES: Brc1cccc2[nH]ccc12 ; Oc1ccc(Cl)cc1Cl ; Clc1ccc(Oc2cccc3[nH]ccc23)c(Cl)c1]

Step 1: 4-(2,4-Dichlorophenoxy)-1H-indole

The same procedure used to prepare I-202 afforded 4-(2,4-dichlorophenoxy)-1H-indole I-255 (18 mg, 6.3%) MS (EI+, m/z): 278.0 [M−H]+ 1H NMR (500 MHz, CDCl3) δ 8.27 (s, 1H), 7.48 (d, J=2.5 Hz, 1H), 7.21 (d, J=8.2 Hz, 1H), 7.17-7.06 (m, 3H), 6.82 (dd, J=12.2, 6.1 Hz, 1H), 6.63 (d, J=7.6 Hz, 1H), 6.45 (dd, J=3.7, 1.5 Hz, 1H).

Example 166: 4-(2,3-Dichlorophenoxy)-1H-indole, I-254

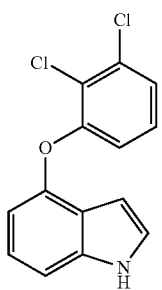

Synthetic Scheme:

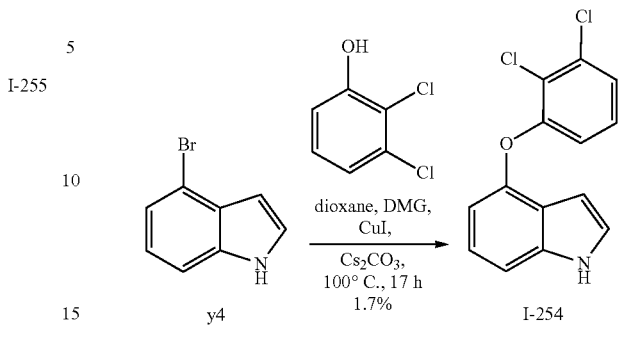

Procedures and Characterization:

Step: 4-(2,3-Dichlorophenoxy)-1H-indole

The same procedure used to prepare I-202 afforded 4-(2,3-Dichlorophenoxy)-1H-indole I-254.
MS (EI+, m/z): 278.0 [M−H]+ 1H NMR (500 MHz, CDCl3) δ 8.29 (s, 1H), 7.25-7.11 (m, 4H), 7.06 (t, J=8.2 Hz, 1H), 6.80 (dd, J=8.3, 1.3 Hz, 1H), 6.66 (d, J=7.7 Hz, 1H), 6.45 (t, J1=2.2 Hz, 1H).

Example 167: 4-(2,5-Dichlorophenoxy)-1H-indole, I-251

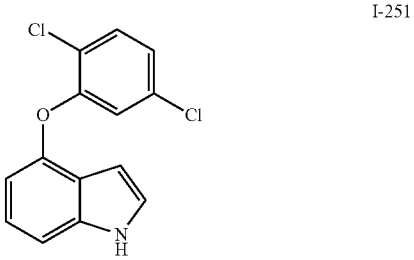 [SMILES: Clc1ccc(Cl)c(Oc2cccc3[nH]ccc23)c1]

Synthetic Scheme:

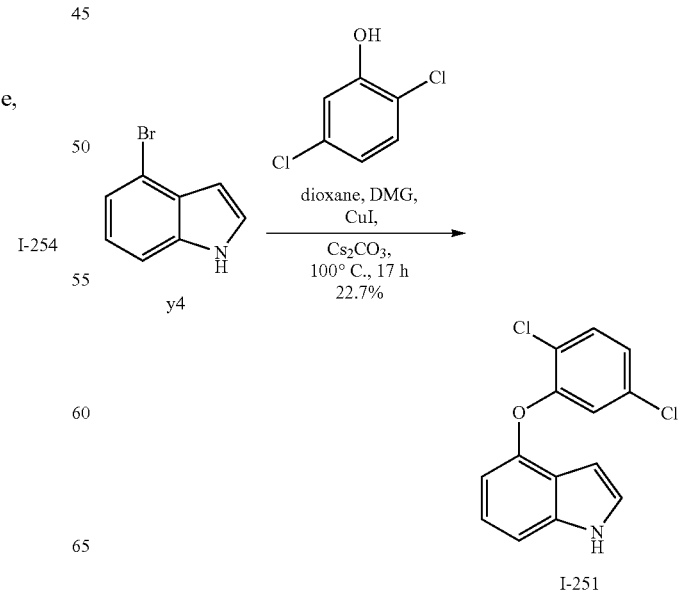

The same procedure used to prepare I-202 afforded 4-(2,5-Dichlorophenoxy)-1H-indole, I-251.

MS (EI+, m/z): 278.0 [M−H]+ 1H NMR (500 MHz, CDCl3) δ 8.28 (s, 1H), 7.39 (d, J=8.5 Hz, 1H), 7.25 (t, J=3.9 Hz, 11H), 7.19-7.10 (m, 2H), 7.01 (td, J=8.7, 2.4 Hz, 1H), 6.85 (d, J=2.3 Hz, 1H), 6.72 (dd, J=21.5, 5.4 Hz, 1H), 6.44 (d, J=2.3 Hz, 1H).

Example 168: 4-phenoxy-1H-indole, I-296

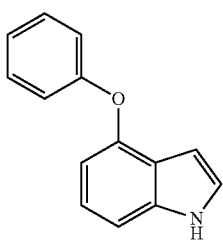

I-296

Synthetic Scheme:

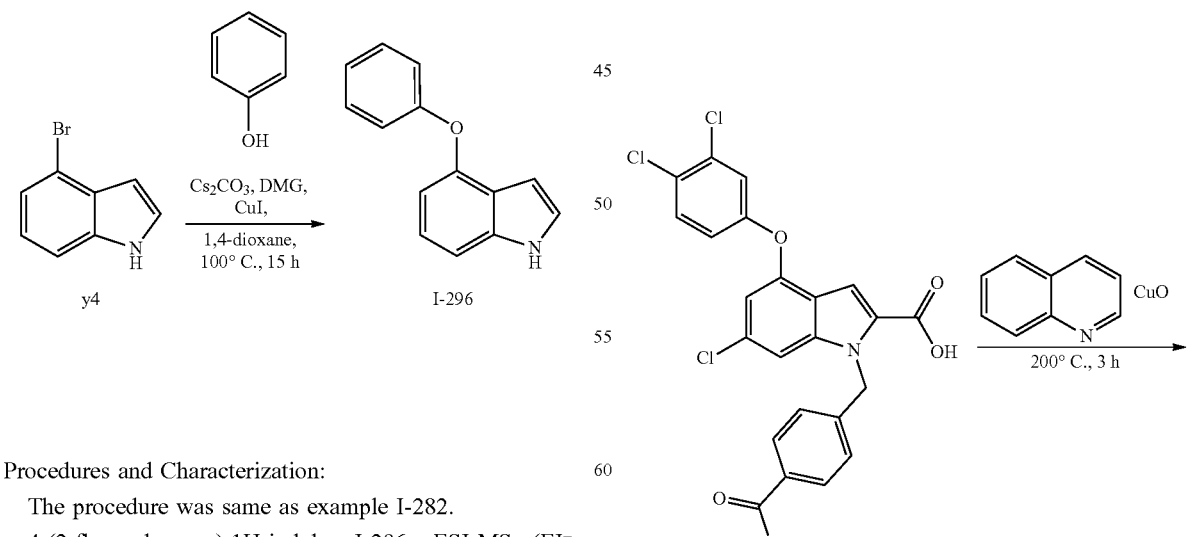

Procedures and Characterization:

The procedure was same as example I-282.

4-(2-fluorophenoxy)-1H-indole, I-296: ESI-MS (EI−, m/z): 210.1 [M+H]+. 1H NMR (500 MHz, DMSO-d6) δ 11.27 (s, 1H), 7.34 (t, J=7.9 Hz, 2H), 7.28 (t, J=2.7 Hz, 1H), 7.22 (d, J=8.1 Hz, 1H), 7.11-7.03 (m, 2H), 6.97 (d, J=7.8 Hz, 2H), 6.57 (d, J=7.6 Hz, 1H), 6.17 (s, 1H).

Example 169: 4-((6-chloro-4-(3,4-dichlorophenoxy)-1H-indol-1-yl)methyl)benzoic acid, I-146

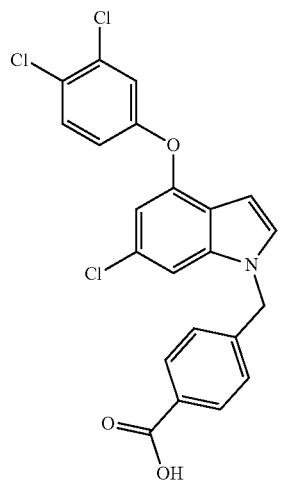

I-146

Synthetic Scheme:

597
-continued

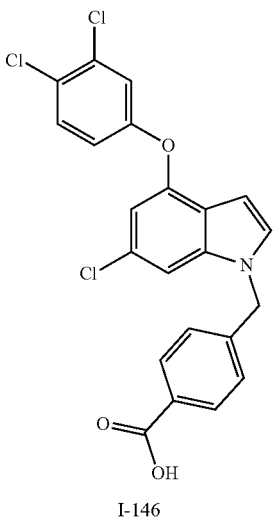

I-146

Procedures and Characterization:

Step 1: 4-((6-chloro-4-(3,4-dichlorophenoxy)-1H-indol-1-yl)methyl)benzoic acid, I-146

The same procedure used to prepare j30 afforded 4-((6-chloro-4-(3,4-dichlorophenoxy)-1H-indol-1-yl)methyl)benzoic acid I-146 as a brown-yellow solid (15.5 mg, yield: 11.35%) as a yellow oil.

$^1$H NMR (500 MHz, DMSO) δ 7.90 (d, J=8.2 Hz, 2H), 7.82 (d, J=2.5 Hz, 1H), 7.57 (d, J=3.1 Hz, 1H), 7.48-7.37 (m, 2H), 7.29 (d, J=8.1 Hz, 2H), 7.14 (d, J=8.8 Hz, 1H), 6.48 (s, 1H), 6.38 (d, J=3.1 Hz, 1H), 5.55 (s, 2H).

Example 170: 2-(6-Chloro-4-(2,5-dichlorophenoxy)-1H-indol-1-yl)acetic acid, I-158

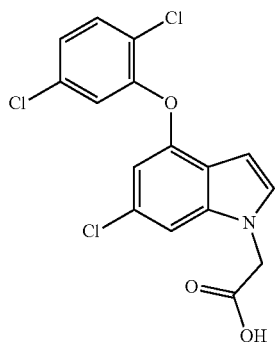

I-158

598

Synthetic Scheme:

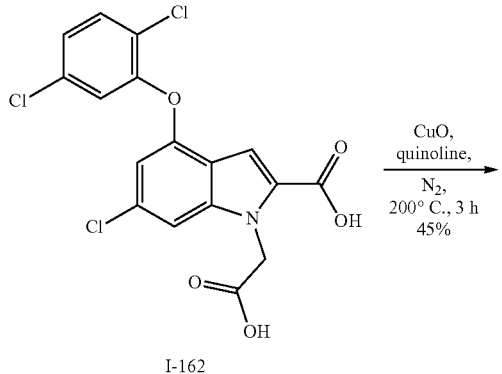

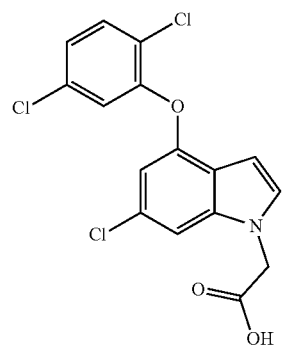

I-158

Procedures and Characterization:

Step 3: 2-(6-Chloro-4-(2,5-dichlorophenoxy)-1H-indol-1-yl)acetic acid

The same procedure used to prepare j30 afforded 2-(6-chloro-4-(2,5-dichlorophenoxy)-1H-indol-1-yl)acetic acid I-158 (86 mg, 45%) as a white solid. MS (EI+, m/z): 371.9 [M+H]$^+$. $^1$H NMR (500 MHz, DMSO) δ 13.05 (s, 1H), 7.68 (d, J=8.6 Hz, 1H), 7.47 (s, 1H), 7.41-7.28 (m, 2H), 7.14 (d, J=2.4 Hz, 1H), 6.55 (d, J=1.4 Hz, 1H), 6.29 (d, J=3.2 Hz, 1H), 5.08 (s, 2H).

Example 171: 1-methyl-N-(piperidin-4-yl)-1H-indol-4-amine, I-297

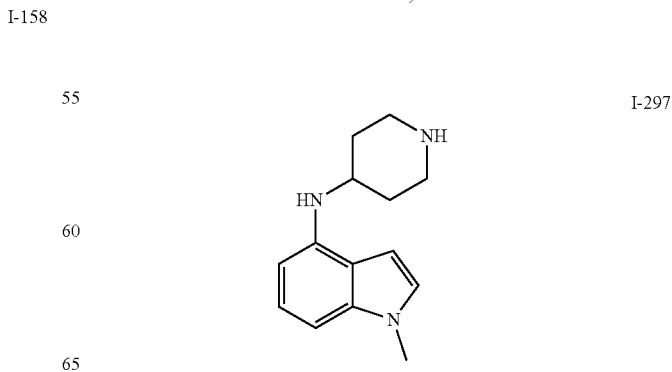

I-297

Synthetic Scheme:

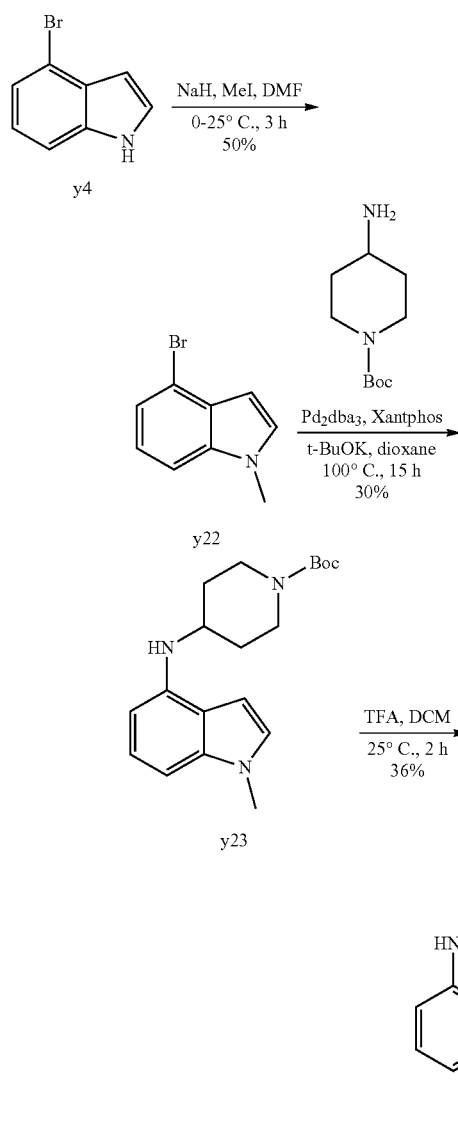

Procedures and Characterization:

Step 1: 4-bromo-1-methyl-1H-indole

To a solution of 4-bromo-1H-indole (2.0 g, 0.01 mol) in DMF (30 mL) was added NaH (0.6 g, 0.015 mol) at 0° C. The resultant solution was stirred at rt for 30 min, then MeI (1.42 g, 0.01 mol) was added and stirred at for 3 h. The reaction mixture was poured into ice-water and extracted with EtOAc, the organic phase was dried over $Na_2SO_4$, filtered and concentrated, the crude was purified by SGC to obtain 4-bromo-1-methyl-1H-indole (1.05 g, 50%) as a yellow solid.

Step 2: tert-butyl 4-(1-methyl-1H-indol-4-ylamino)piperidine-1-carboxylate

To a solution of tert-butyl 4-aminopiperidine-1-carboxylate (260 mg, 1.3 mmol), 4-bromo-1-methyl-1H-indole (210 mg, 1.0 mmol), $Pd_2dba_3$ (18 mg, 0.02 mmol), Xantphos (29 mg, 0.05 mmol) in 1,4-dioxane (5 mL) was added t-BuOK (336 mg, 3.0 mmol). The mixture was stirred at 100° C. for 15 h, then poured into water and extracted with EtOAc, the organic phase was dried over $Na_2SO_4$, filtered and concentrated, the crude was purified by prep-TLC to obtain tert-butyl 4-(1-methyl-1H-indol-4-ylamino)piperidine-1-carboxylate (80 mg, 30%) as a brown oil. ESI-MS (EI+, m/z): 330 $[M+H]^+$.

Step 3: 1-methyl-N-(piperidin-4-yl)-1H-indol-4-amine, I-297

The solution of tert-butyl 4-(1-methyl-1H-indol-4-ylamino)piperidine-1-carboxylate (80 mg, 0.243 mmol) in TFA/DCM (1 mL/4 mL) was stirred at rt for 2 h and concentrated. The crude was purified by prep-HPLC to obtain 1-methyl-N-(piperidin-4-yl)-1H-indol-4-amine I-297 (20 mg, 36%) as a white solid. ESI-MS (EI+, m/z): 230 $[M+H]^+$. $^1$H NMR (400 MHz, MeOD-$d_4$) δ 6.96-6.81 (m, 2H), 6.65 (d, J=8.2 Hz, 1H), 6.42 (d, J=3.1 Hz, 1H), 6.22 (d, J=7.6 Hz, 1H), 3.63 (s, 3H), 3.50 (td, J=10.5, 5.3 Hz, 1H), 3.08 (d, J=12.8 Hz, 2H), 2.71 (td, J=12.6, 2.5 Hz, 2H), 2.04 (d, J=11.4 Hz, 2H), 1.41 (td, J=13.7, 3.9 Hz, 2H).

Example 172: (5-chloro-6-(3-chlorobenzyloxy)-1H-benzo[d]imidazol-2-yl)methanol, I-478

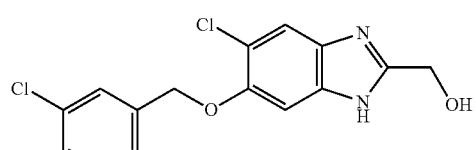

Synthetic Scheme:

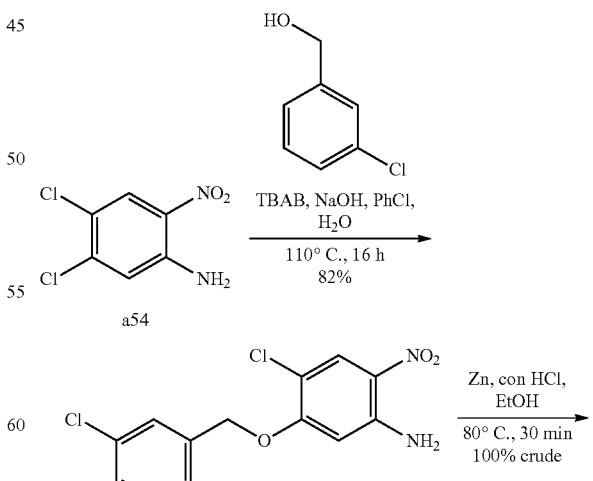

-continued

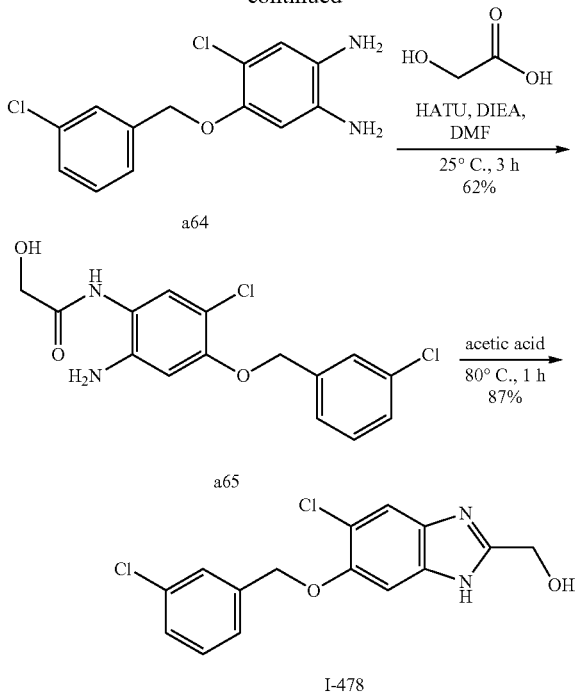

a64 a65

I-478

Procedures and Characterization:

Step 1: 4-chloro-5-(3-chlorobenzyloxy)-2-nitrobenzenamine

A mixture of 4-chloro-5-(3-chlorobenzyloxy)-2-nitrobenzenamine (3 g, 14.7 mmol), (3-chlorophenyl)methanol (2.5 g, 17.6 mmol), TBAB (397 mg, 1.23 mmol) and NaOH (1.76 g, 44.1 mmol) in PhCl (15 mL) and H$_2$O (30 mL) was stirred for 16 h at 110° C. under N2 atmosphere. The reaction was quenched with water (30 mL) and filtered. The cake was recrystallized with ethyl acetate/petroleum ether=1/2 to afford 4-chloro-5-(3-chlorobenzyloxy)-2-nitrobenzenamine (3.6 g, 11.5 mmol, 82%) as a black solid. ESI-MS (EI+, m/z): 313.0 [M+H]$^-$.

Step 2: 4-chloro-5-(3-chlorobenzyloxy)benzene-1,2-diamine

A mixture of 4-chloro-5-(3-chlorobenzyloxy)-2-nitrobenzenamine (2 g, 6.41 mmol), Zn (3.34 g, 51.3 mmol) and con. HCl (5.4 mL, 64.1 mmol) in EtOH (60 mL) was stirred for 30 min at 80° C. under N$_2$ atmosphere. The reaction was diluted with water (200 mL) and neutralized with NaHCO$_3$ to pH 6 and extracted with ethyl acetate (200 mL). The organic layer was washed with water (10 mL×2), dried (Na$_2$SO$_4$), filtered and concentrated to afford crude 4-chloro-5-(3-chlorobenzyloxy)benzene-1,2-diamine (1.81 g, 6.41 mmol, 100%) as a black solid, which was used in next step directly. ESI-MS (EI+, m/z): 283.0 [M+H]$^+$.

Step 3: N-(2-amino-5-chloro-4-(3-chlorobenzyloxy)phenyl)-2-hydroxyacetamide

A mixture of 4-chloro-5-(3-chlorobenzyloxy)benzene-1,2-diamine (1.81 g, 6.41 mmol), 2-hydroxyacetic acid (585 mg, 7.7 mmol), HATU (2.93 g, 7.7 mmol) and DIEA (1.24 g, 9.6 mmol) in DMF (20 mL) was stirred for 3 h at 25° C. The reaction was quenched with water (40 mL) and filtered. The cake was recrystallized with ethyl acetate/petroleum ether=1/2 to afford N-(2-amino-5-chloro-4-(3-chlorobenzyloxy)phenyl)-2-hydroxyacetamide (1.36 g, 4 mmol, 62%) as a brown solid. ESI-MS (EI+, m/z): 341.0 [M+H]$^-$.

Step 4: (5-chloro-6-(3-chlorobenzyloxy)-1H-benzo[d]imidazol-2-yl)methanol, I-478

A mixture of N-(2-amino-5-chloro-4-(3-chlorobenzyloxy)phenyl)-2-hydroxyacet amide (680 mg, 2 mmol) in acetic acid (7 mL) was stirred for 1 h at 80° C. The reaction was concentrated, quenched with water (50 mL) and extracted with ethyl acetate (50 mL). The organic layer was washed with water (10 mL×2), aq NaHCO$_3$ (200 mL) and dried (Na$_2$SO$_4$), filtered and concentrated in vacuo, the crude product was purified by prep-HPLC (TFA) to afford (5-chloro-6-(3-chlorobenzyloxy)-1H-benzo[d]imidazol-2-yl)methanol I-478 as a pink solid (432 mg, 1.3 mmol, 67%). ESI-MS (EI+, m/z): 323.0 [M+H]$^+$. $^1$H NMR (500 MHz, DMSO) δ 7.84 (s, 1H), 7.59 (s, 1H), 7.48-7.43 (m, 4H), 5.32 (s, 2H), 4.88 (s, 2H).

Example 173: (5-chloro-6-(3-chlorobenzyloxy)-1H-benzo[(d]imidazol-2-yl)methanol, I-485

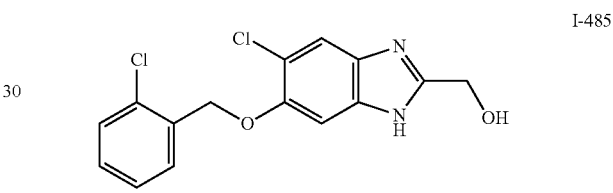

I-485

Synthetic Scheme:

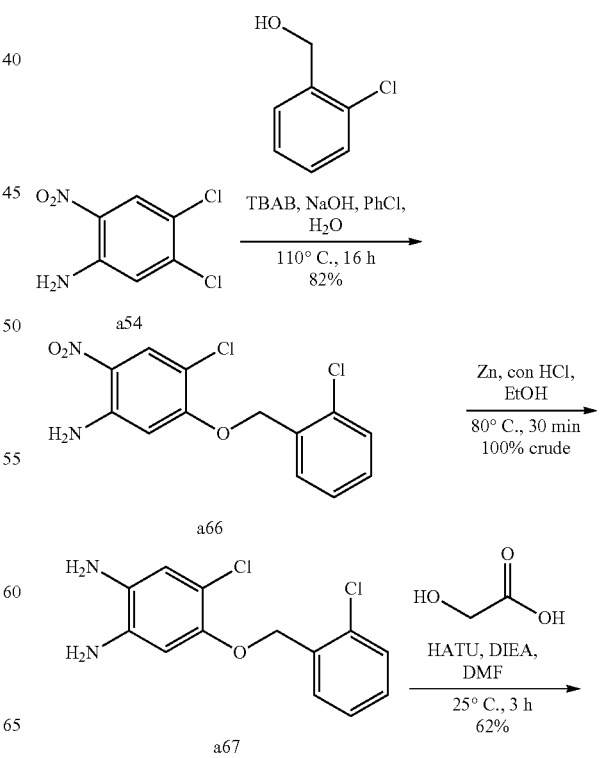

a54 a66 a67

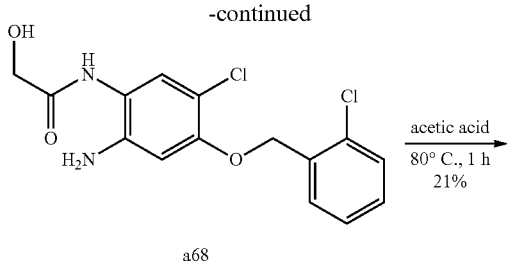

a68

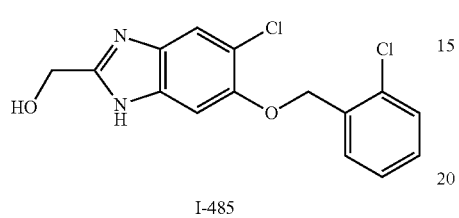

I-485

Procedures and Characterization:

Step 1:
4-chloro-5-(3-chlorobenzyloxy)-2-nitrobenzenamine

The same procedure used to prepare 4-chloro-5-(3-chlorobenzyloxy)-2-nitrobenzenamine (a63) afforded 4-chloro-5-(2-chlorobenzyloxy)-2-nitrobenzenamine (4 g, 12.8 mmol, 64%) as a yellow solid. ESI-MS (EI+, m/z): 313.0 [M+H]$^+$.

Step 2:
4-chloro-5-(2-chlorobenzyloxy)benzene-1,2-diamine

The same procedure used to prepare 4-chloro-5-(3-chlorobenzyloxy)benzene-1,2-diamine (a64) afforded crude 4-chloro-5-(2-chlorobenzyloxy)benzene-1,2-diamine (1.6 g, 5.65 mmol, 88%) as a black solid, which was used in next step directly. ESI-MS (EI+, m/z): 283.0 [M+H]$^+$ Step 3: N-(2-amino-5-chloro-4-(2-chlorobenzyloxy)phenyl)-2-hydroxyacetamide The same procedure used to prepare N-(2-amino-5-chloro-4-(3-chlorobenzyloxy)phenyl)-2-hydroxyacetamide (a65) afforded afford N-(2-amino-5-chloro-4-(2-chlorobenzyloxy)phenyl)-2-hydroxyacetamide (1.4 g, 4.1 mmol, 62%) as a brown solid. ESI-MS (EI+, m/z): 341.0 [M+H]$^+$ Step 4: (5-chloro-6-(3-chlorobenzyloxy)-1H-benzo[d]imidazol-2-yl)methanol, I-485

The same procedure used to prepare I-478 afforded (5-chloro-6-(2-chlorobenzyloxy)-1H-benzo[d]imidazol-2-yl)methanol I-485 as a pink solid (160 mg, 0.5 mmol, 21%). ESI-MS (EI+, m/z): 323.0 [M+H]$^+$. $^1$H NMR (500 MHz, DMSO) δ 12.43 (s, 1H), 7.68-7.66 (m, 1H), 7.66-7.51 (m, 2H), 7.43-7.39 (m, 2H), 7.27 (s, 1H), 5.71 (s, 1H), 5.26 (s, 2H), 4.66 (s, 2H).

Example 174: (5-chloro-4-phenoxy-1H-benzo[d]imidazol-2-yl)methanol, I-418

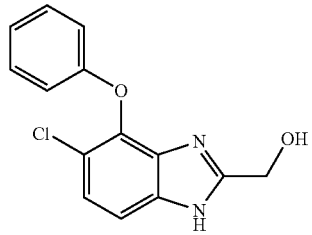

Synthetic Scheme:

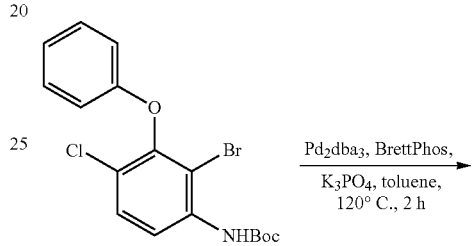

Procedures and Characterization:

Step 1: tert-butyl 4-chloro-2-(2,4-dimethoxybenzy-lamino)-3-phenoxyphenylcarbamate A mixture of tert-butyl 2-bromo-4-chloro-3-phenoxyphenylcarbamate (180 mg, 0.45 mmol) and (2,4-dimethoxyphenyl)methanamine (410 mg, 2.45 mmol), BrettPhos (140 mg, 0.26 mmol), Pd$_2$dba$_3$ (220 mg, 0.24 mmol), K$_3$PO$_4$ (350 mg, 1.65 mmol) in toluene (10 mL). This mixture was stirred under microwave at 120° C. for 2 h. The mixture was extracted with EtOAc/H$_2$O (50 mL/50 mL), the organic phase was dried over anhydrous Na$_2$SO$_4$, and concentrated in vacuo. The residue was purified by prep-HPLC to provide tert-butyl 4-chloro-2-(2,4-dimethoxybenzylamino)-3-phenoxyphenylcarbamate as a yellow solid.
ESI-MS (EI+, m/z): 485 [M+H]+.

Step 2: 4-chloro-3-phenoxybenzene-1,2-diamine

A mixture of tert-butyl 4-chloro-2-(2,4-dimethoxybenzylamino)-3-phenoxyphenylcarbamate (50 mg, 0.11 mmol) and TFA (0.5 mL in DCM (10 mL) was stirred at rt for 2 h. concentrated to provide 4-chloro-3-phenoxybenzene-1,2-diamine as a yellow solid. ESI-MS (EI+, m/z): 235 [M+H]+.

Step 3: (5-chloro-4-phenoxy-1H-benzo[d]imidazol-2-yl)methanol, I-418

4-chloro-3-phenoxybenzene-1,2-diamine (24 mg, 0.103 mmol) and 2-hydroxyacetic acid (10 mg, 0.123 mmol) in 4 M HCl (10 mL) was heated to reflux for 3 h, cool down and adjusted pH at 8-10 with aqueous NaOH solution, filtered to obtain the target as a yellow solid to provide (5-chloro-4-phenoxy-1H-benzo[d]imidazol-2-yl)methanol I-418 as a white solid.
ESI-MS (EI+, m/z): 275 [M+H]$^+$ $^1$H NMR (500 MHz, DMSO) δ 7.51 (d, J=8.5 Hz, 1H), 7.45 (d, J=9.0 Hz, 1H), 7.30 (t, J=8.0 Hz, 2H), 7.05 (t, J=8.0 Hz, 2H), 6.82 (d, J=8.0 Hz, 2H), 4.71 (s, 2H).

Example 175: (5-chloro-6-(4-chlorophenethoxy)-1H-benzo[d]imidazol-2-yl)methanol, I-380

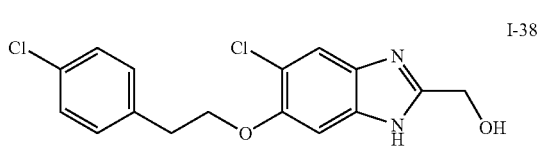

Synthetic Scheme:

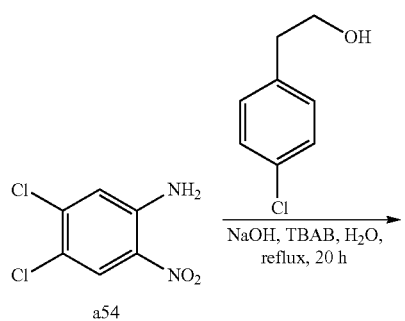

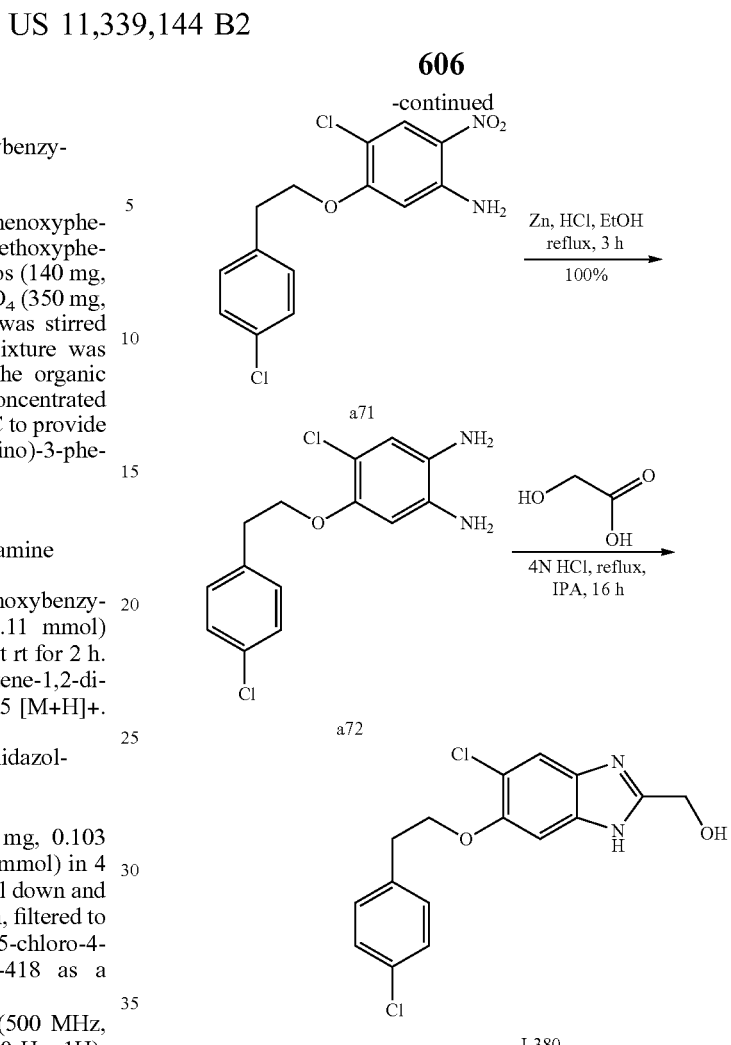

Procedures and Characterization:

Step 1: 4-chloro-5-(4-chlorophenethoxy)-2-nitroaniline

A mixture of 4,5-dichloro-2-nitroaniline (2 g, 9.7 mmol), 2-(4-chlorophenyl)ethanol (3 g, 19.3 mmol), TBAB (218 mg, 0.68 mmol) and NaOH (1.2 g, 29.1 mmol) in PhCl (40 mL) and H$_2$O (20 mL) was stirred for 16 h at 110° C. under N$_2$ atmosphere. The reaction was quenched with water (30 mL), and then extracted with EtOAc (100 mL). The organic phase was dried over Na$_2$SO$_4$, filtered, and concentrated in vacuo to give the residue. The residue was purified by silica gel column to give 4-chloro-5-(4-chlorophenethoxy)-2-nitroaniline (0.65 g, 20%) as a yellow solid. ESI-MS (EI+, m/z): 327 [M+H]$^-$.

Step 2: 4-chloro-5-(4-chlorophenethoxy)benzene-1,2-diamine

To a suspension of 4-chloro-5-(4-chlorophenethoxy)-2-nitroaniline (650 mg, 1.99 mmol), and Zn (650 mg, 10 mmol) in EtOH (13 mL) was added con. HCl (1.7 mL). The resulting reaction mixture was heated to reflux for 2 h. The reaction mixture was filtered and concentrated to give the residue (1 g) as a yellow oil. The residue was used directly in the next step. ESI-MS (EI+, m/z): 297

Step 3: (5-chloro-6-(4-chlorophenethoxy)-1H-benzo[d]imidazol-2-yl)methanol

To a solution of 4-chloro-5-(4-chlorophenethoxy)benzene-1,2-diamine (1 g, crude) in i-PrOH (10 mL) and 4M HCl (3 mL) was added 2-hydroxyacetic acid (228 mg, 3 mmol). The resulting reaction mixture was heated to reflux for 16 h. The reaction mixture was concentrated in vacuo, and then purified by prep-HPLC to give (5-chloro-6-(4-chlorophenethoxy)-1H-benzo[d]imidazol-2-yl)methanol I-380 (7 mg): ESI-MS (EI$^+$, m/z): 337 $^1$H NMR (400 MHz, DMSO-d$_6$) δ 7.73 (s, 1H), 7.40 (m, 4H), 7.26 (s, 1H), 7.30 (s, 1H), 4.83 (s, 2H), 4.30 (t, J=4.2 Hz, 2H), 3.11 (t, J=4.2 Hz, 2H).

Example 176: (6,7-dichloro-5-(4-chlorobenzyloxy)-1H-benzo[d]imidazol-2-yl)methanol, I-375

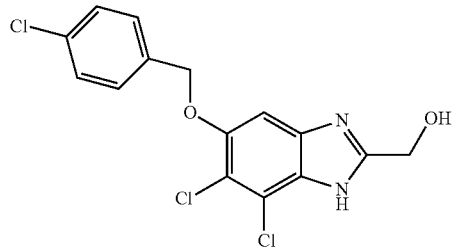

Synthetic Scheme:

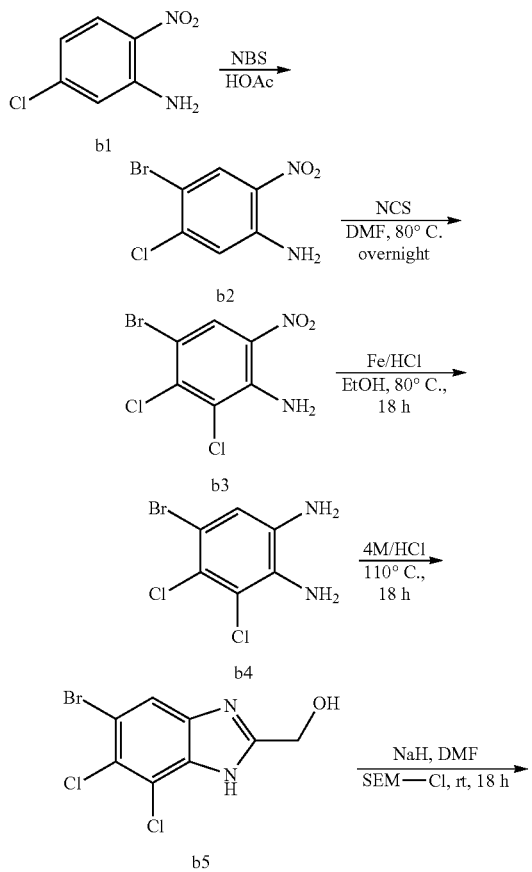

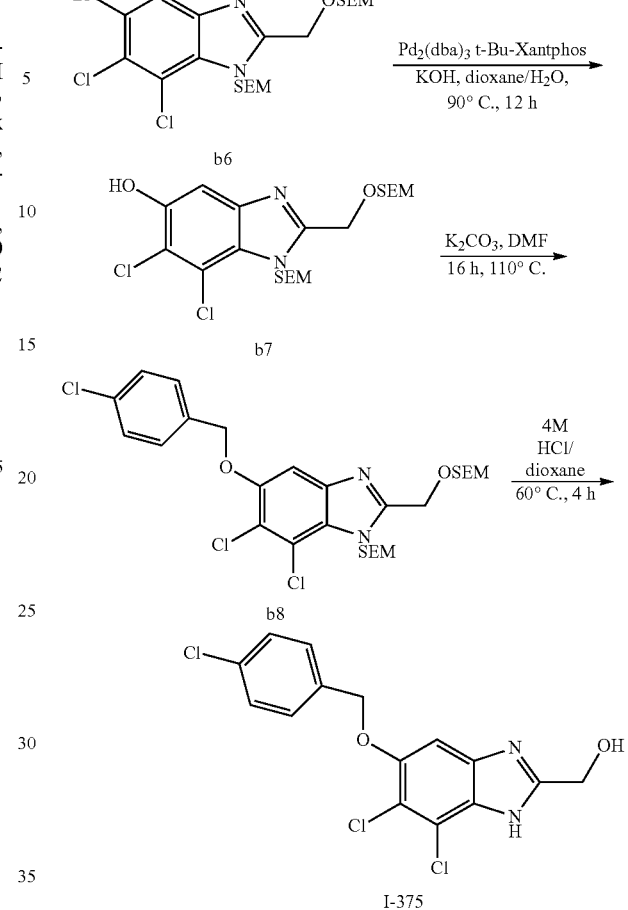

Procedures and Characterization:

Step 1: 4-bromo-5-chloro-2-nitrobenzenamine

A mixture of 5-chloro-2-nitrobenzenamine (17 g, 0.1 mol), NBS (17 g, 0.1 mol) and CH$_3$COOH (210 ml) was stirred for 16 h at 25° C. The reaction was quenched with water (100 mL) and extracted with ethyl acetate (1000 mL). The organic layer was washed with water (500 mL×2), dried (Na$_2$SO$_4$), filtered and concentrated in vacuo, the crude product was purified by chromatography (silica, ethyl acetate/petroleum ether=1/1) to afford 4-bromo-5-chloro-2-nitrobenzenamine (20 g, 0.08 mmol, 80%) as a light yellow solid ESI-MS (EI+, m/z): 251 [M+H]$^+$.

Step 2: 4-bromo-2,3-dichloro-6-nitrobenzenamine

A mixture of 4-bromo-5-chloro-2-nitrobenzenamine (20 g, 0.08 mol), NCS (10.4 g, 0.08 mol) in DMF (210 ml) was stirred for 16 h at 80° C. The reaction was quenched with water (100 mL) and extracted with ethyl acetate (1000 mL). The organic layer was washed with water (500 mL×2), dried (Na$_2$SO$_4$), filtered and concentrated in vacuo, the crude product was purified by chromatography (silica, ethyl acetate/petroleum ether=1/1) to afford 4-bromo-2,3-dichloro-6-nitrobenzenamine (20 g, 0.07 mmol, 85%) as a light yellow solid ESI-MS (EI+, m/z): 285 [M+H]$^+$.

Step 3: 5-bromo-3,4-dichlorobenzene-1,2-diamine

A mixture of 4-bromo-2,3-dichloro-6-nitrobenzenamine (20 g, 0.07 mol), Fe (22 g, 0.4 mol) in EtOH (210 ml) was added HCl (100 ml, 2N), the solution was stirred for 18 h at 80° C. The reaction was quenched with water (100 mL) and NaHCO$_3$ (100 ml, 2N) and extracted with ethyl acetate (1000 mL). The organic layer was washed with water (500 mL×2), dried (Na$_2$SO$_4$), filtered and concentrated in vacuo, the crude product was purified by chromatography (silica, ethyl acetate/petroleum ether=1/1) to afford 5-bromo-3,4-dichlorobenzene-1,2-diamine (18 g, 0.06 mol, 90%) as a light yellow solid ESI-MS (EI+, m/z): 255 [M+H]$^+$.

Step 4: (5-bromo-6,7-dichloro-1H-benzo[d]imidazol-2-yl)methanol

A mixture of 5-bromo-3,4-dichlorobenzene-1,2-diamine (18 g, 0.06 mol) and 2-hydroxyacetic acid (21 g, 0.3 mol) was added HCl (100 ml, 6N), the solution was stirred for 18 h at 110° C. The reaction was quenched with water (100 mL) and NaHCO$_3$ (100 ml, 2N) and extracted with ethyl acetate (1000 mL). The organic layer was washed with water (300 mL×2), dried (Na$_2$SO$_4$), filtered and concentrated in vacuo, the crude product was purified by chromatography (silica, ethyl acetate/petroleum ether=1/1) to afford (5-bromo-6,7-dichloro-1H-benzo[d]imidazol-2-yl)methanol (8.8 g, 0.03 mol, 50%) as a light yellow solid ESI-MS (EI+, m/z): 295 [M+H]$^+$.

Step 5: 5-bromo-6,7-dichloro-2-(trimethylsilyl) ethoxy)methoxy)methyl)-1-((2-(trimethylsilyl) ethoxy)methyl)-1H-benzo[d]imidazole To a mixture of (5-bromo-6,7-dichloro-1H-benzo[d]imidazol-2-yl)methanol (8.8 g, 0.03 mol) in DMF (100 ml) was added NaH (2.2 g, 0.08 mol) and the solution was stirred for 30 mins at 0° C. before SEM-Cl (14 g, 0.08 mol) was added. The reaction was stirred for 18 h at 25° C., quenched with water (100 mL) and NH$_4$Cl (100 ml, 2N) and extracted with ethyl acetate (1000 mL). The organic layer was washed with water (300 mL×2), dried (Na$_2$SO$_4$), filtered and concentrated in vacuo, the crude product was purified by chromatography (silica, ethyl acetate/petroleum ether=1/1) to afford 5-bromo-6,7-dichloro-2-(((2-(trimethylsilyl)ethoxy) methoxy)methyl)-1-((2-(trimethylsilyl)ethoxy)methyl)-1H-benzo[d]imidazole (11 g, 0.02 mol, 66%) as a light yellow solid ESI-MS (EI+, m/z): 555 [M+H]$^+$.

Step 6: 6,7-dichloro-2-(((2-(trimethylsilyl)ethoxy) methoxy)methyl)-1-((2-(trimethylsilyl)ethoxy) methyl)-1H-benzo[d]imidazol-5-ol A mixture of 5-bromo-6,7-dichloro-2-(((2-(trimethylsilyl) ethoxy)methoxy)methyl)-1-((2-(trimethylsilyl)ethoxy) methyl)-1H-benzo[d]imidazole (11 g, 0.02 mol) and Pd$_2$ (dba)$_3$ (3.22 g, 2 mmol), t-Bu-Xantphos (2.0 g, 2 mmol), KOH (2.24 g, 0.04 mol), H$_2$O (50 ml) in dioxane (100 ml) was stirred for 30 mins at 90° C. under N$_2$, quenched with water (100 mL) and NH$_4$Cl (80 ml, 2N) and extracted with ethyl acetate (1000 mL). The organic layer was washed with water (200 mL×2), dried (Na$_2$SO$_4$), filtered and concentrated in vacuo, the crude product was purified by chromatography (silica, ethyl acetate/petroleum ether=2/1) to afford 6,7-dichloro-2-(((2-(trimethylsilyl)ethoxy)methoxy) methyl)-1-((2-(trimethylsilyl)ethoxy)methyl)-1H-benzo[d] imidazol-5-ol (4.9, 0.01 mol, 50%) as a light yellow solid ESI-MS (EI+, m/z): 493 [M+H]$^+$.

Step 7: 6,7-dichloro-5-(4-chlorobenzyloxy)-2-(((2-(trimethylsilyl)ethoxy)methoxy)methyl)-1-((2-(trimethylsilyl)ethoxy)methyl)-1H-benzo[d]imidazole A mixture of 6,7-dichloro-2-(((2-(trimethylsilyl)ethoxy) methoxy)methyl)-1-((2-(trimethylsilyl)ethoxy)methyl)-1H-benzo[d]imidazol-5-ol (688 mg, 1.40 mmol), 1-(bromomethyl)-4-chlorobenzene (290 mg, 1.4 mmol) and K$_2$CO$_3$ (256 mg, 2.0 mmol) in dry DMF (5 mL) was stirred for 16 h at 110° C. The reaction was quenched with water (40 mL) and extracted with ethyl acetate (100 mL). The organic layer was washed with water (20 mL×2), dried (Na$_2$SO$_4$), filtered and concentrated in vacuo, the crude product was purified by chromatography (silica, ethyl acetate/petroleum ether=1/5) to afford 6,7-dichloro-5-(4-chlorobenzyloxy)-2-(((2-(trimethylsilyl)ethoxy)methoxy)methyl)-1-((2-(trimethylsilyl) ethoxy)methyl)-1H-benzo[d]imidazole (200 mg, 0.32 mmol, 30%) as a light yellow oil ESI-MS (EI+, m/z): 617 [M+H]$^+$.

Step 8: (6,7-dichloro-5-(4-chlorobenzyloxy)-1H-benzo[d]imidazol-2-yl)methanol, I-375

A solution of 6,7-dichloro-5-(4-chlorobenzyloxy)-2-(((2-(trimethylsilyl)ethoxy)methoxy)methyl)-1-((2-(trimethylsilyl)ethoxy)methyl)-1H-benzo[d]imidazole (200 mg, 0.3 mmol) in 4 M HCl/dioxane (40 mL) was stirred for 4 h at 60° C. The reaction was diluted with water (40 mL) and neutralized with NaHCO$_3$ to pH 6. and extracted with ethyl acetate (200 mL). The organic layer was washed with water (50 mL×2), dried (Na$_2$SO$_4$), filtered and concentrated in vacuo, the crude product was purified by prep-HPLC (TFA) to afford (6,7-dichloro-5-(4-chlorobenzyloxy)-1H-benzo[d] imidazol-2-yl)methanol I-375 as a white solid (18 mg, 0.05 mmol, 16%). ESI-MS (EI+, m/z): 357.0 [M+H]$^+$. $^1$H NMR (500 MHz, DMSO) δ 7.48-7.54 (m, 4H), 7.18 (s, 1H), 5.25 (s, 2H), 4.67-4.68 (m, 2H).

Example 177: (6,7-dichloro-5-(4-nitrobenzyloxy)-1H-benzo[d]imidazol-2-yl)methanol, I-329

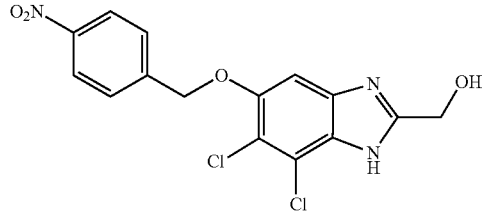

I-329

Synthetic Scheme:

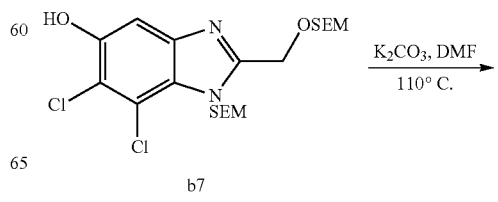

b7

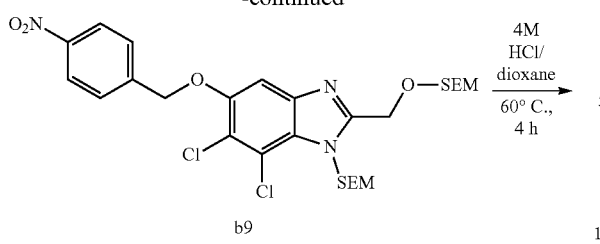

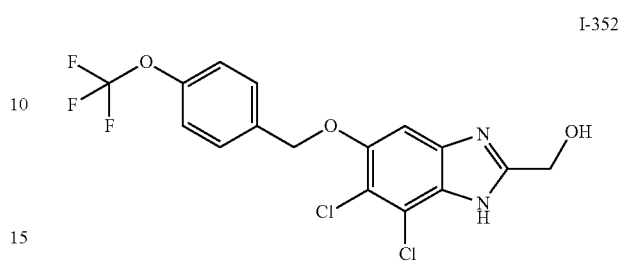

Example 178: (6,7-dichloro-5-(4-(trifluoromethoxy)benzyloxy)-1H-benzo[d]imidazol-2-yl)methanol, I-352

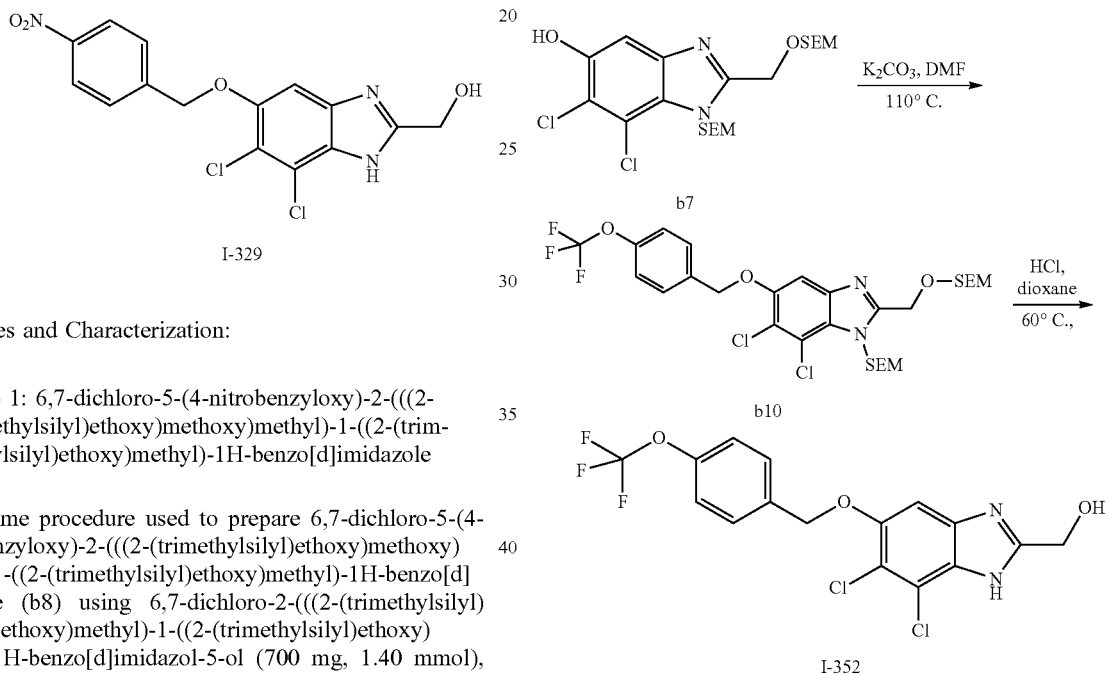

Procedures and Characterization:

Procedures and Characterization:

Step 1: 6,7-dichloro-5-(4-nitrobenzyloxy)-2-(((2-(trimethylsilyl)ethoxy)methoxy)methyl)-1-((2-(trimethylsilyl)ethoxy)methyl)-1H-benzo[d]imidazole The same procedure used to prepare 6,7-dichloro-5-(4-chlorobenzyloxy)-2-(((2-(trimethylsilyl)ethoxy)methoxy)methyl)-1-((2-(trimethylsilyl)ethoxy)methyl)-1H-benzo[d]imidazole (b8) using 6,7-dichloro-2-(((2-(trimethylsilyl)ethoxy)methoxy)methyl)-1-((2-(trimethylsilyl)ethoxy)methyl)-1H-benzo[d]imidazol-5-ol (700 mg, 1.40 mmol), 1-(chloromethyl)-4-nitrobenzene (370 mg, 1.4 mmol) and $K_2CO_3$ (210 mg, 1.2 mmol) afforded 6,7-dichloro-5-(4-nitrobenzyloxy)-2-(((2-(trimethylsilyl)ethoxy)methoxy)methyl)-1-((2-(trimethylsilyl)ethoxy)methyl)-1H-benzo[d]imidazole (200 mg, 0.34 mmol, 30%) as a light yellow oil. ESI-MS (EI+, m/z): 628 [M+H]$^+$.

Step 2: (6,7-dichloro-5-(4-nitrobenzyloxy)-1H-benzo[d]imidazol-2-yl)methanol The same procedure used to prepare I-375 using 6,7-dichloro-5-(4-nitrobenzyloxy)-2-(((2-(trimethylsilyl)ethoxy)methoxy)methyl)-1-((2-(trimethylsilyl)ethoxy)methyl)-1H-benzo[d]imidazole in 4 M HCl/dioxane (40 mL) afforded the crude product, which was purified by prep-HPLC (TFA) to afford (6,7-dichloro-5-(4-nitrobenzyloxy)-1H-benzo[d]imidazol-2-yl)methanol I-329 as a white solid (6.6 mg, 0.61 mmol, 9.1%). ESI-MS (EI+, m/z). 368.0 [M+H]$^+$. $^1$H NMR (500 MHz, DMSO) δ 12.74 (s, 1H), 8.29-8.31 (m, 2H), 7.77-7.79 (m, 2H), 7.20-7.22 (m, 1H), 5.74-5.79 (m, 1H), 5.43 (s, 2H), 4.66-4.70 (m, 2H).

Step 1:6,7-dichloro-5-(4-(trifluoromethoxy)benzyloxy)-2-(((2-(trimethylsilyl)ethoxy)methoxy)methyl)-1-((2-(trimethylsilyl)ethoxy)methyl)-1H-benzo[d]imidazole The same procedure used to prepare 6,7-dichloro-5-(4-chlorobenzyloxy)-2-(((2-(trimethylsilyl)ethoxy)methoxy)methyl)-1-((2-(trimethylsilyl)ethoxy)methyl)-1H-benzo[d]imidazole (b8) using 6,7-dichloro-2-(((2-(trimethylsilyl)ethoxy)methoxy)methyl)-1-((2-(trimethylsilyl)ethoxy)methyl)-1H-benzo[d]imidazol-5-ol (700 mg, 1.40 mmol), 1-(bromomethyl)-4-(trifluoromethoxy)benzene (370 mg, 1.4 mmol) and $K_2CO_3$ (210 mg, 1.2 mmol) in dry DMF (5 mL) afforded the crude product, which was purified by chromatography (silica, ethyl acetate/petroleum ether=1/4) to afford 6,7-dichloro-2-(((2-(trimethylsilyl)ethoxy)methoxy)methyl)-1-((2-(trimethylsilyl)ethoxy)methyl)-1H-benzo[d]imidazol-5-ol (200 mg, 0.34 mmol, 80%) as a light yellow oil ESI-MS (EI+, m/z): 667 [M+H]$^+$.

Step 2: (6,7-dichloro-5-(4-(trifluoromethoxy)benzyloxy)-1H-benzo[d]imidazol-2-yl)methanol, I-352

The same procedure used to prepare I-375 using 6,7-dichloro-5-(4-(trifluoromethoxy)benzyloxy)-2-(((2-(trimethylsilyl)ethoxy)methoxy)methyl)-1-((2-(trimethylsilyl)ethoxy)methyl)-1H-benzo[d]imidazole (200 mg, 0.24 mmol) in 4 M HCl/dioxane (40 mL) afforded the crude product, which was purified by prep-HPLC (TFA) to afford (6,7-dichloro-5-(4-(trifluoromethoxy)benzyloxy)-1H-benzo[d]imidazol-2-yl)methanol I-352 as a white solid (7.5 mg, 0.61 mmol, 9.1%). ESI-MS (EI+, m/z): 407.0 [M+H]$^+$. $^1$H NMR (500 MHz, MeOD) δ: 7.62-7.64 (m, 2H), 7.31-7.33 (m, 2H), 7.20 (s, 1H), 5.23 (s, 2H), 4.82 (m, 2H).

Example 179: [6,7-dichloro-5-[(4-phenoxyphenyl)methoxy]-1H-benzimidazol-2-yl]methanol, I-320

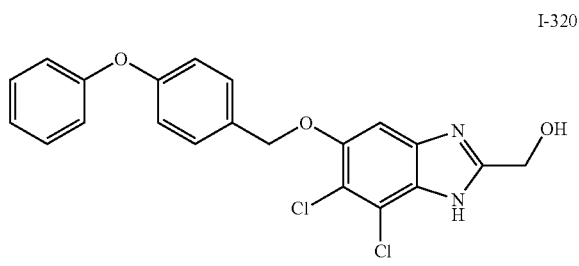 [SMILES: OCc1nc2cc(OCc3ccc(Oc4ccccc4)cc3)c(Cl)c(Cl)c2[nH]1]

Synthetic Scheme:

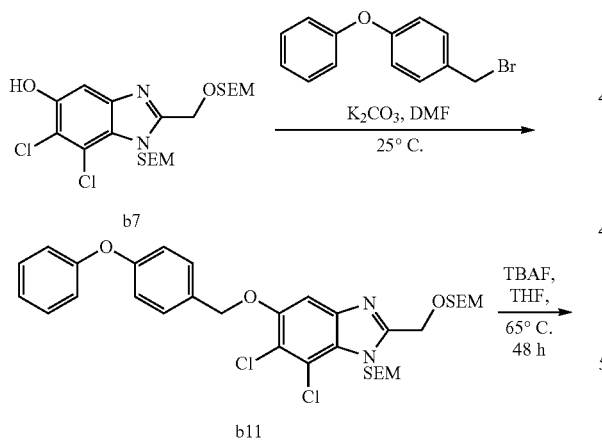

Procedures an Characterization:

Step 1: 2-[[6,7-dichloro-5-[(4-phenoxyphenyl)methoxy]-2-(2-trimethylsilylethoxymethoxymethyl)benzimidazol-1-yl]methoxy]ethyl-trimethyl-silane To a solution of 6,7-dichloro-2-(2-trimethylsilylethoxymethoxymethyl)-1-(2-trimethylsilylethoxymethyl)benzimidazol-5-ol (131.30 mg, 266.03 μmol) in DMF (2.00 mL) was added 1-(bromomethyl)-4-phenoxy-benzene (70.00 mg, 266.03 μmol) and K$_2$CO$_3$ (110.14 mg, 798.09 μmol). the solution was stirred for 18 h at rt. LCMS showed the reaction worked well. EtOAc (30 ml) was added, washed with water (10 mL×2), removed the solvent to give 2-[[6,7-dichloro-5-[(4-phenoxyphenyl)methoxy]-2-(2-trimethylsilylethoxymethoxymethyl)benzimidazol-1-yl]methoxy]ethyl-trimethyl-silane (130.00 mg, 192.37 μmol, 72.31% yield). ESI-MS (EI+, m/z): 675[M+H]$^+$.

Step 2: [6,7-dichloro-5-[(4-phenoxyphenyl)methoxy]-1H-benzimidazol-2-yl]methanol, I-320

To a solution of 2-[[6,7-dichloro-5-[(4-phenoxyphenyl)methoxy]-2-(2-trimethylsilylethoxymethoxymethyl)benzimidazol-1-yl]methoxy]ethyl-trimethyl-silane (140.00 mg, 207.16 μmol) in THF (4.00 mL) was added TBAF (541.64 mg, 2.07 mmol). The solution was stirred at 65° C. for 48 h. It was concentrated and purified by prep-HPLC to afford [6,7-dichloro-5-[(4-phenoxyphenyl)methoxy]-1H-benzimidazol-2-yl]methanol I-320 (8.60 mg, 20.71 μmol, 10.00% yield) as a white solid. MS (EI+, m/z): 415 [M+H]$^+$.

$^1$H-NMR (DMSO-d6,500 MHz): $^1$H NMR (500 MHz, DMSO) δ 12.75 (s, 1H), 7.53 (m, 2H), 7.51 (m, 2H), 7.41 (m, 1H), 7.16 (m, 1H), 7.06 (m, 4H), 5.80 (m, 1H), 5.20 (s, 2H), 4.67 (s, 2H).

Example 180: (6,7-dichloro-5-(2,4-dichlorophenylthio)-1H-benzo[d]imidazol-2-yl)methanol, I-358

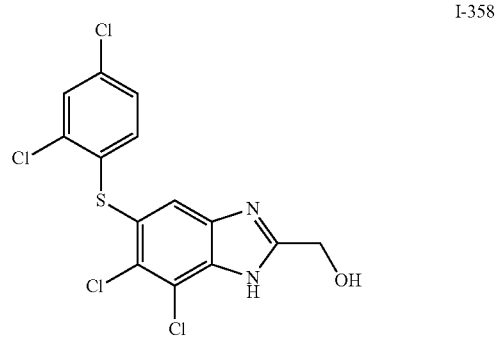 [SMILES: OCc1nc2cc(Sc3ccc(Cl)cc3Cl)c(Cl)c(Cl)c2[nH]1]

Synthetic Scheme:

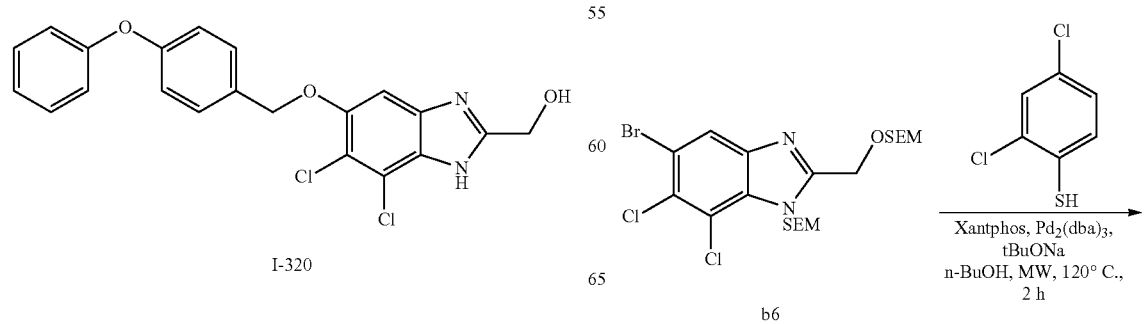

Example 181: (6,7-dichloro-5-(4-chlorobenzylthio)-1H-benzo[d]imidazol-2-yl)methanol, I-356

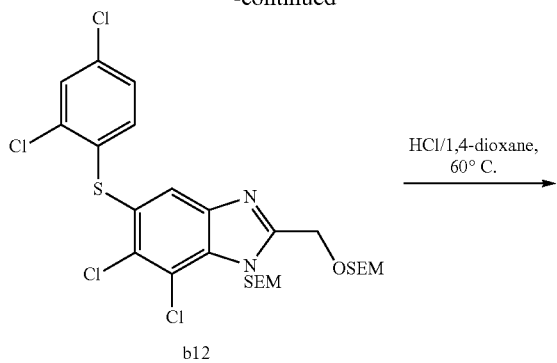

Synthetic Scheme:

Procedures and Characterization:

Step 1: 6,7-dichloro-5-(2,4-dichlorophenylthio)-2-(((2-(trimethylsilyl)ethoxy)methoxy)methyl)-1-((2-(trimethylsilyl)ethoxy)methyl)-1H-benzo[d]imidazole A solution of 5-bromo-6,7-dichloro-2-(((2-(trimethylsilyl)ethoxy)methoxy)methyl)-1-((2-(trimethylsilyl)ethoxy)methyl)-1H-benzo[d]imidazole (225 mg, 0.405 mmol) in n-BuOH (10 mL) was added 2,4-dichlorobenzenethiol (150 mg, 0.84 mmol) followed by Xantphos (90 mg, 0.155 mmol) and Pd$_2$dba$_3$ (70 mg, 0.076 mmol), tBuONa (130 mg, 1.35 mmol) and the reaction was heated by microwave (130° C., 2 h). The reaction was purified by flash chromatography and prep-HPLC to afford 6,7-dichloro-5-(2,4-dichlorophenylthio)-2-(((2-(trimethylsilyl)ethoxy)methoxy)methyl)-1-((2-(trimethylsilyl)ethoxy)methyl)-1H-benzo[d]imidazole (60 mg) as a yellow solid.

MS (EI+, m/z): 653.0[M+H]$^+$.

Step 2: (6,7-dichloro-5-(2,4-dichlorophenylthio)-1H-benzo[d]imidazol-2-yl)methanol, I-358

A solution of 6,7-dichloro-5-(2,4-dichlorophenylthio)-2-(((2-(trimethylsilyl)ethoxy)methoxy)methyl)-1-((2-(trimethylsilyl)ethoxy)methyl)-1H-benzo[d]imidazole (100 mg, 0.153 mmol) in HCl/1,4-dioxane (3 mL) was stirred at 60° C. for 3 h. The reaction was concentrated and prep-HPLC to afford 6,7-dichloro-5-(2,4-dichlorophenylthio)-1H-benzo[d]imidazol-2-yl)methanol I-358 (50 mg) as a white solid.

MS (EI+, m/z): 393.0[M+H]$^+$.

$^1$H NMR (500 MHz, DMSO) δ 7.76 (d, J2=2.5 Hz 1H), 7.63 (s, 1H), 7.35 (dd, J1=2.0 Hz, J2=2.0 Hz 1H), 6.78 (d, J=3.5 Hz, 2H), 4.75 (s, 2H).

Procedures and Characterization:

Step 1: 6,7-dichloro-5-(4-chlorobenzylthio)-2-(((2-(trimethylsilyl)ethoxy)methoxy)methyl)-1-((2-(trimethylsilyl)ethoxy)methyl)-1H-benzo[d]imidazole A solution of 5-bromo-6,7-dichloro-2-(((2-(trimethylsilyl)ethoxy)methoxy)methyl)-1-((2-(trimethylsilyl)ethoxy)methyl)-1H-benzo[d]imidazole (225 mg, 0.405 mmol) in n-BuOH (10 mL) was added (4-chlorophenyl)methanethiol (125 mg, 0.785 mmol) followed by Xantphos (90 mg, 0.155 mmol) and Pd$_2$dba$_3$ (70 mg, 0.076 mmol), tBuONa (130 mg, 1.35 mmol) and the reaction mixture was heated in a microwave (130° C., 2 h). The reaction was purified by flash chromatography and prep-HPLC to afford 6,7-dichloro-5-(4-chlorobenzylthio)-2-(((2-(trimethylsilyl)ethoxy)

methoxy)methyl)-1-((2-(trimethylsilyl)ethoxy)methyl)-1H-benzo[d]imidazole (20 mg) as a yellow solid.

MS (EI+, m/z): 633.0[M+H]+.

Step 2: (6,7-dichloro-5-(4-chlorobenzylthio)-1H-benzo[d]imidazol-2-yl)methanol, I-356

A solution of 6,7-dichloro-5-(4-chlorobenzylthio)-2-(((2-(trimethylsilyl)ethoxy)methoxy)methyl)-1-((2-(trimethylsilyl)ethoxy)methyl)-1H-benzo[d]imidazole (20 mg, 0.0316 mmol) in HCl/1,4-dioxane (1 mL) was stirred at 60° C. for 12 h. The reaction was concentrated and purified by prep-HPLC to afford (6,7-dichloro-5-(4-chlorobenzylthio)-1H-benzo[d]imidazol-2-yl)methanol I-356 (6 mg) as a white solid. MS (EI+, m/z): 373.0[M+H]+.

1H NMR (500 MHz, MeOD) δ 7.46 (s, 1H), 7.30 (d, J=3.5 Hz 2H), 7.25 (d, J=3.5 Hz, 2H), 4.92 (s, 2H), 4.23 (s, 2H).

Example 182: (4-(2-(2-aminopyridin-4-yl)ethoxy)-5,6-dichloro-1H-benzo[d]imidazol-2-yl)methanol, I-182

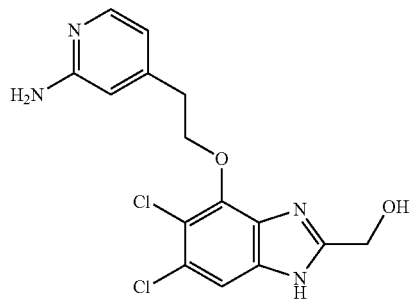

I-182

Synthetic Scheme:

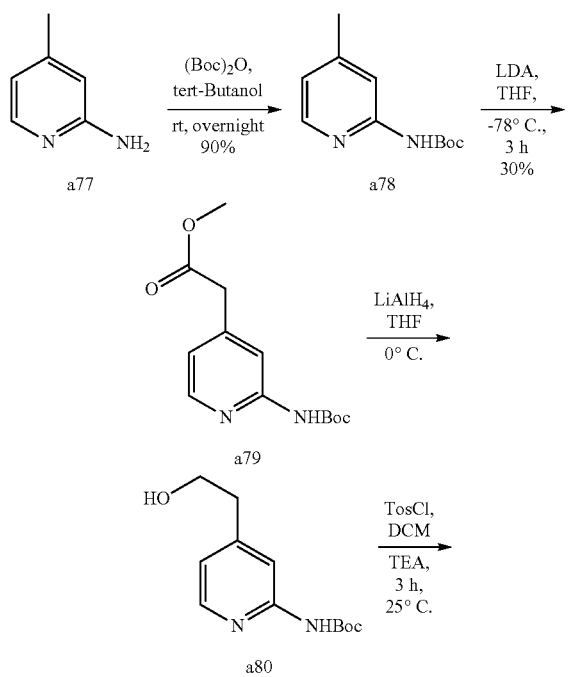

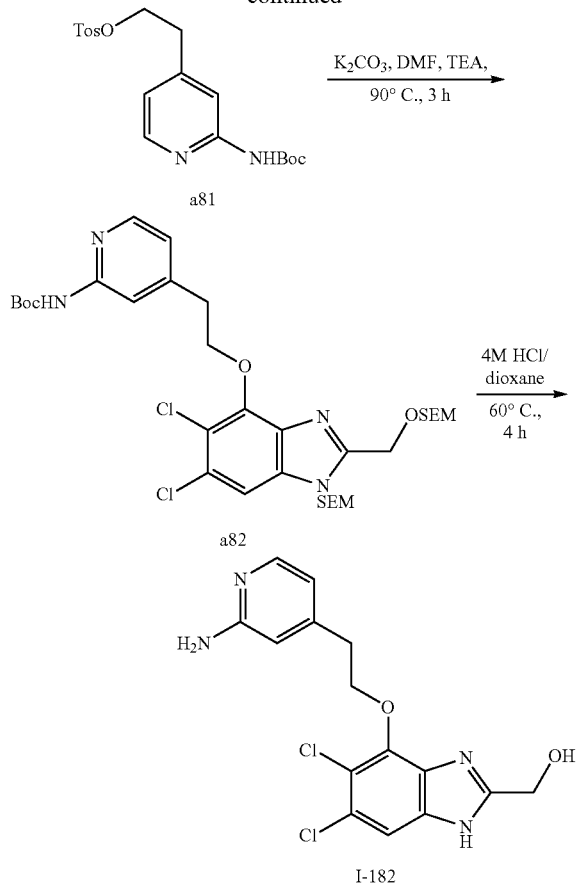

Procedures and Characterization:

Step 1: tert-butyl 4-methylpyridin-2-ylcarbamate

A mixture of 4-methylpyridin-2-amine (10.8 g, 100 mmol), tert-Butanol (100 ml), and (Boc)2O (21.8 g, 100 mmol) was stirred for 16 h at 25° C. removed the solvent to afford tert-butyl 4-methylpyridin-2-ylcarbamate (20.8 g) as a yellow solid, which was used directly in the next step. ESI-MS (EI+, m/z): 209 [M+H]+.

Step 2: methyl 2-(2-(tert-butoxycarbonylamino)pyridin-4-yl)acetate

A mixture of tert-butyl 4-methylpyridin-2-ylcarbamate (15 g, 0.07 mol) in THF (150 mL) was added LDA (35 mL, 2 mol/L) at −70° C. under N2 atmosphere. The reaction was stirred 30 mins, and the dimethyl carbonate (9.3 g, 0.1 mol) was added, stirred 2 h, diluted with water (200 mL) and neutralized with NH4Cl to pH 6 and extracted with ethyl acetate (200 mL). The organic layer was washed with water (10 mL×2), dried (Na2SO4), filtered and concentrated to afford crude methyl 2-(2-(tert-butoxycarbonylamino)pyridin-4-yl)acetate (16 g, 0.066 mol, 90%) as a black solid, which was used in next step directly. ESI-MS (EI+, m/z): 267.0 [M+H]+

Step 3: tert-butyl 4-(2-hydroxyethyl)pyridin-2-ylcarbamate

A mixture of 4 methyl 2-(2-(tert-butoxycarbonylamino)pyridin-4-yl)acetate (16 g, 0.066 mol in THF (200 mL) was added LiAlH4 (2.5 g, 0.066) at 0° C. stirred for 3 h The reaction was quenched with water (50 mL) and extracted with ethyl acetate (100 mL). The organic layer was washed with water (50 mL×2), dried (Na$_2$SO$_4$), filtered and concentrated in vacuo, the crude product was purified by chromatography (silica, ethyl acetate/petroleum ether=1/1) to afford tert-butyl 4-(2-hydroxyethyl)pyridin-2-ylcarbamate (10 g, 0.042 mol, 40%) as a brown oil. ESI-MS (EI+, m/z): 239.0 [M+H]$^+$.

Step 4:
2-(2-(tert-butoxycarbonylamino)pyridin-4-yl)ethyl 4-methylbenzenesulfonate A mixture of tert-butyl 4-(2-hydroxyethyl)pyridin-2-yl-carbamate (10 g, 0.042 mol) in DCM (100 mL) was added TosCl (7.9 g, 0.042) and TEA (11.2 g, 0.12 mol), the mixture was stirred for 3 h at 25° C. The reaction was concentrated, quenched with water (50 mL) and extracted with ethyl acetate (50 mL). The organic layer was washed with water (10 mL×2), aq NaHCO$_3$ (200 mL) and dried (Na$_2$SO$_4$), filtered and concentrated in vacuo, the crude product was chromatography (silica, ethyl acetate/petroleum ether=1/1) to afford 2-(2-(tert-butoxycarbonylamino)pyridin-4-yl)ethyl 4-methylbenzenesulfonate as a yellow solid (12 g, 0.03 mol, 75%). ESI-MS (EI+, m/z): 393.0 [M+H]$^+$.

Step 5: tert-butyl 4-(2-(5,6-dichloro-2-(((2-(trimethylsilyl)ethoxy)methoxy)methyl)-1-((2-(trimethylsilyl)ethoxy)methyl)-1H-benzo[d]imidazol-4-yloxy) ethyl)pyridin-2-ylcarbamate A mixture of 2-(2-(tert-butoxycarbonylamino)pyridin-4-yl)ethyl 4-methylbenzenesulfonate as a yellow solid (12 g, 0.03 mol) in DMF (100 mL) was added K$_2$CO$_3$ (13 g, 0.09) and TEA (11.2 g, 0.12 mol), and 5,6-dichloro-2-(((2-(trimethylsilyl)ethoxy)methoxy)methyl)-1-((2-(trimethylsilyl)ethoxy)methyl)-1H-benzo[d]imidazol-4-ol (14.7 g, 0.03 mol), the mixture was stirred for 3 h at 90° C. The reaction was concentrated, quenched with water (50 mL) and extracted with ethyl acetate (50 mL). The organic layer was washed with water (10 mL×2), aq NaHCO$_3$ (200 mL) and dried (Na$_2$SO$_4$), filtered and concentrated in vacuo, the crude product was chromatography (silica, ethyl acetate/petroleum ether=2/1) to afford tert-butyl 4-(2-(5,6-dichloro-2-(((2-(trimethylsilyl)ethoxy)methoxy)methyl)-1-((2-(trimethylsilyl)ethoxy)methyl)-1H-benzo[d]imidazol-4-yloxy) ethyl)pyridin-2-ylcarbamate (6 g, 0.03 mol, 40%). ESI-MS (EI+, m/z): 713.0 [M+H]$^+$.

Step 6: tert-butyl 4-(2-(5,6-dichloro-2-(((2-(trimethylsilyl)ethoxy)methoxy)methyl)-1-((2-(trimethylsilyl)ethoxy)methyl)-1H-benzo[d]imidazol-4-yloxy) ethyl)pyridin-2-ylcarbamate, I-182

A solution of tert-butyl 4-(2-(5,6-dichloro-2-(((2-(trimethylsilyl)ethoxy)methoxy)methyl)-1-((2-(trimethylsilyl)ethoxy)methyl)-1H-benzo[d]imidazol-4-yloxy)ethyl)pyridin-2-ylcarbamate (200 mg, 0.34 mmol) in 4 M HCl/dioxane (40 mL) was stirred for 4 h at 60° C. The reaction was diluted with water (40 mL) and neutralized with NaHCO$_3$ to pH 6. and extracted with ethyl acetate (200 mL). The organic layer was washed with water (50 mL×2), dried (Na$_2$SO$_4$), filtered and concentrated in vacuo, the crude product was purified by prep-HPLC (TFA) to afford (4-(2-(2-aminopyridin-4-yl)ethoxy)-5,6-dichloro-1H-benzo[d]imidazol-2-yl)methanol I-182 as a white solid (14.2 mg, 0.034 mmol, 10%). ESI-MS (EI+, m/z): 353.0 [M+H]$^+$. $^1$H NMR (500 MHz, DMSO) δ 8.04 (s, 2H), 7.87-7.88 (m, 1H), 7.37-7.38 (m, 1H), 6.91-6.93 (m, 2H), 4.95-4.96 (m, 2H), 4.72-4.73 (m, 2H), 3.11-3.13 (m, 2H).

Example 183: (5,6-dichloro-4-(cyclohexylmethoxy)-1H-benzo[d]imidazol-2-yl)methanol, I-395

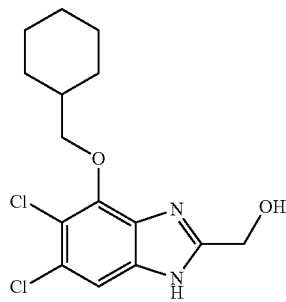

I-395

Synthetic Scheme:

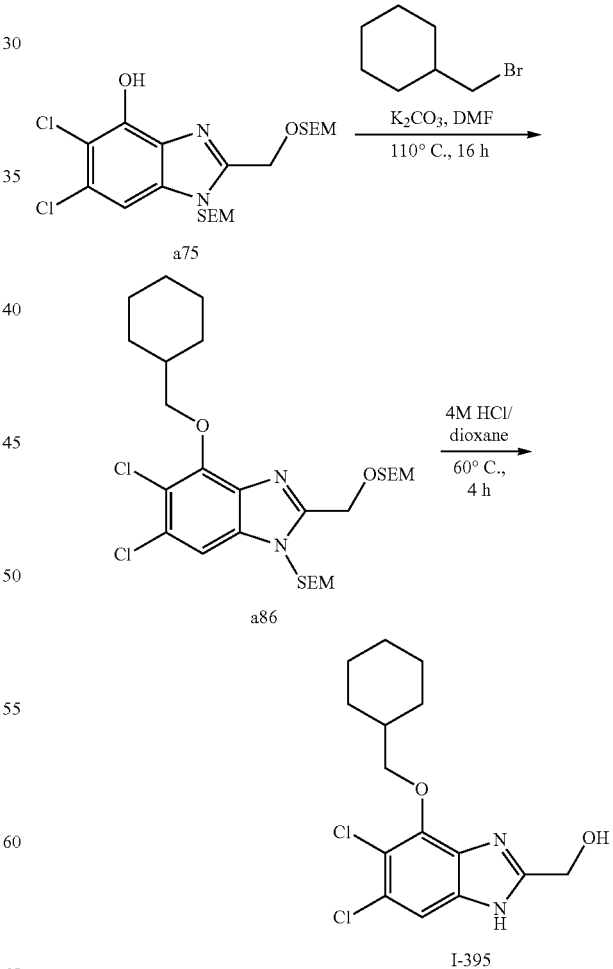

Procedures and Characterization:

Step 1: 5,6-dichloro-4-(cyclohexylmethoxy)-2-(((2-(trimethylsilyl)ethoxy)methoxy)methyl)-1-((2-(trimethylsilyl)ethoxy)methyl)-1H-benzo[d]imidazole A mixture of 5,6-dichloro-2-(((2-(trimethylsilyl)ethoxy)methoxy)methyl)-1-((2-(trimethylsilyl)ethoxy)methyl)-1H-benzo[d]imidazol-4-ol (700 mg, 1.40 mmol), (chloromethyl)cyclohexane (370 mg, 1.4 mmol) and $K_2CO_3$ (210 mg, 1.2 mmol) in dry DMF (5 mL) was stirred for 16 h at 110° C. The reaction was quenched with water (100 mL) and extracted with ethyl acetate (100 mL). The organic layer was washed with water (5 mL×2), dried ($Na_2SO_4$), filtered and concentrated in vacuum, the crude product was purified by chromatography (silica, ethyl acetate/petroleum ether=1/3) to afford 5,6-dichloro-4-(cyclohexylmethoxy)-2-(((2-(trimethylsilyl)ethoxy)methoxy)methyl)-1-((2-(trimethylsilyl)ethoxy)methyl)-1H-benzo[d]imidazole (200 mg, 0.34 mmol, 30%) as a light yellow oil ESI-MS (EI+, m/z): 589 [M+H]$^+$.

Step 2: (5,6-dichloro-4-(cyclohexylmethoxy)-1H-benzo[d]imidazol-2-yl)methanol, I-395

A solution of 5,6-dichloro-4-(cyclohexylmethoxy)-2-(((2-(trimethylsilyl)ethoxy)methoxy)methyl)-1-((2-(trimethylsilyl)ethoxy)methyl)-1H-benzo[d]imidazole (100 mg, 0.17 mmol) in 4 M HCl/dioxane (40 mL) was stirred for 4 h at 60° C. The reaction was diluted with water (40 mL) and neutralized with NaHCO3 to pH 6. and extracted with ethyl acetate (200 mL). The organic layer was washed with water (50 mL×2), dried ($Na_2SO_4$), filtered and concentrated in vacuum, the crude product was purified by prep-HPLC (TFA) to afford (5,6-dichloro-4-(cyclohexylmethoxy)-1H-benzo[d]imidazol-2-yl)methanol I-395 as a white solid (30 mg, 0.09 mmol, 55%). ESI-MS (EI+, m/z): 329.0 [M+H]$^+$. 1H NMR (500 MHz, DMSO) δ 12.64 (s, 1H), 7.30 (s, 1H), 5.77-5.79 (m, 1H), 4.55-4.69 (m, 4H), 1.63-1.87 (m, 6H), 1.06-1.09 (m, 5H).

Example 184: 4-((5,6-dichloro-2-(hydroxymethyl)-1H-benzo[d]imidazol-4-yloxy)methyl)cyclohexanol, I-399

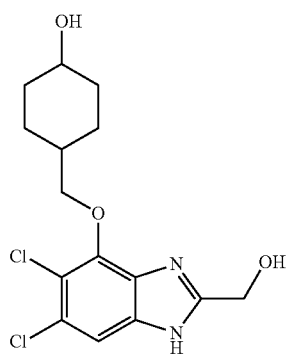

I-399

Synthetic Scheme:

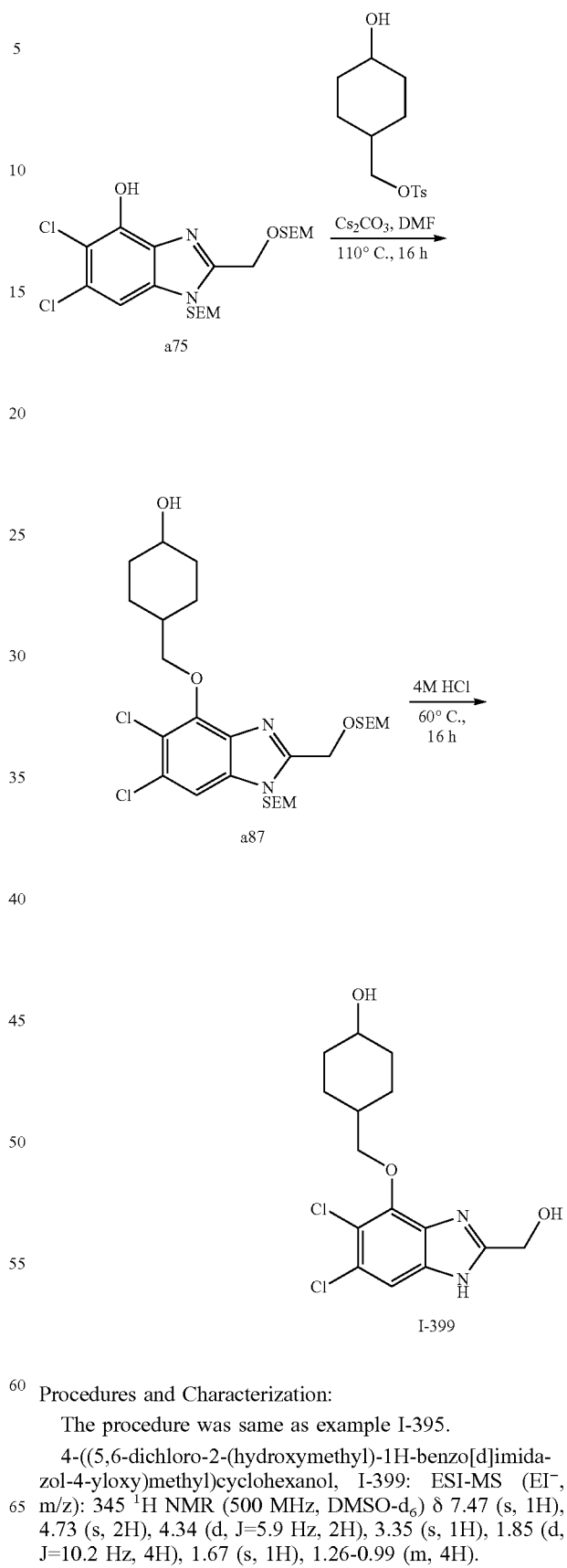

Procedures and Characterization:
The procedure was same as example I-395.
4-((5,6-dichloro-2-(hydroxymethyl)-1H-benzo[d]imidazol-4-yloxy)methyl)cyclohexanol, I-399: ESI-MS (EI$^-$, m/z): 345 $^1$H NMR (500 MHz, DMSO-$d_6$) δ 7.47 (s, 1H), 4.73 (s, 2H), 4.34 (d, J=5.9 Hz, 2H), 3.35 (s, 1H), 1.85 (d, J=10.2 Hz, 4H), 1.67 (s, 1H), 1.26-0.99 (m, 4H).

Example 185: 3-((5,6-dichloro-2-(hydroxymethyl)-1H-benzo[d]imidazol-4-yloxy)methyl)cyclohexanol, I-396

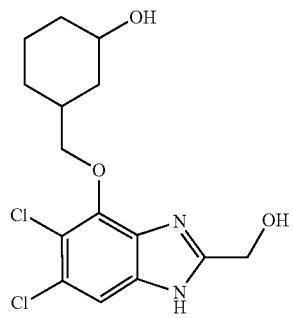

I-396

Synthetic Scheme:

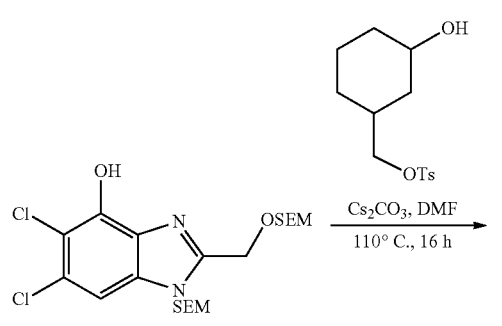

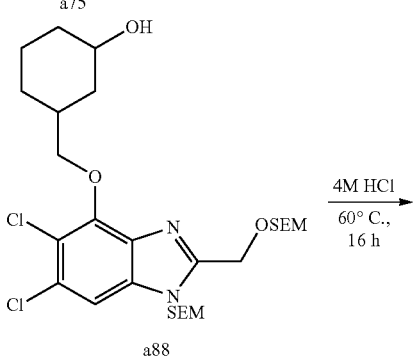

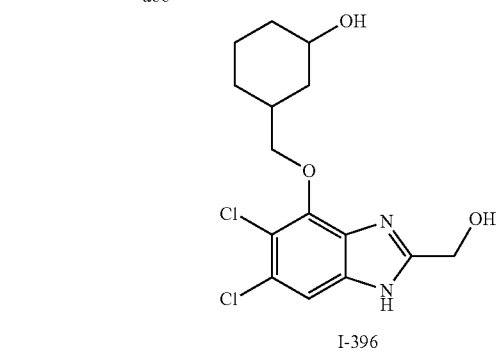

Procedures and Characterization:
The procedure was same as example I-395.
3-((5,6-dichloro-2-(hydroxymethyl)-1H-benzo[d]imidazol-4-yloxy)methyl)cyclohexanol, I-396: ESI-MS (EI+, m/z): 345 $^1$H NMR (500 MHz, DMSO) δ 12.63 (s, 1H), 7.30 (s, 1H), 4.69 (d, J=5.8 Hz, 2H), 4.55 (qd, J=9.9, 6.5 Hz, 2H), 4.32 (d, J=3.4 Hz, 1H), 3.90 (s, 1H), 2.15 (s, 1H), 1.73 (d, J=13.2 Hz, 2H), 1.67-1.50 (m, 2H), 1.38 (ddd, J=40.2, 17.9, 8.9 Hz, 3H).

Example 186: 2-((5,6-dichloro-2-(hydroxymethyl)-1H-benzo[d]imidazol-4-yloxy)methyl)cyclohexanol, I-439

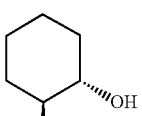

I-439

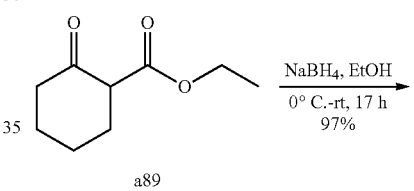

Synthetic Scheme:

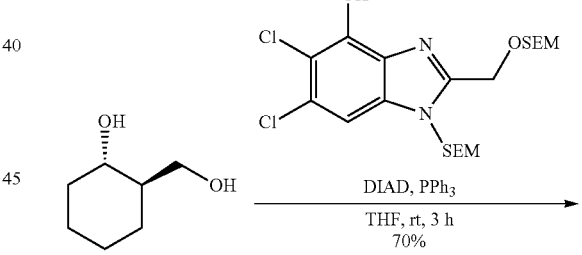

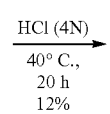

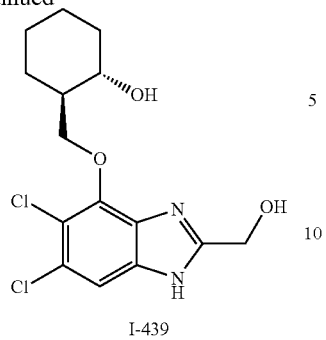

I-439

Procedures and Characterization:

Step 1: 2-(hydroxymethyl)cyclohexanol

To a suspension of ethyl 2-oxocyclohexanecarboxylate (5.1 g, 30 mmol) in EtOH (100 mL) was added NaBH₄ (5.7 g, 150 mmol) slowly at 0° C., and the resulting mixture was stirred at rt for 18 h. Thereafter the mixture was treated dropwise with HOAc. The resulting solution was concentrated under reduced pressure. The residue was treated with brine (150 mL) and extracted with EtOAc (100 mL×4). The combined organic extracts were dried (Na₂SO₄), and the solvent was removed to give crude. The residue was purified by column chromatography (PE:EtOAc=1:4) to afford 2-(hydroxymethyl)cyclohexanol (3.8 g, 29 mmol, 97%) as a colorless oil. ESI-MS (EI⁺, m/z): 153 [M+Na]⁻.

Step 2: 2-((5,6-dichloro-2-(((2-(trimethylsilyl)ethoxy)methoxy)methyl)-1-((2-(trimethylsilyl)ethoxy) methyl)-1H-benzo[d]imidazol-4-yloxy) methyl) cyclohexanol To a mixture of 5,6-dichloro-2-(((2-(trimethylsilyl)ethoxy) methoxy) methyl)-1-((2-(trimethylsilyl) ethoxy) methyl)-1H-benzo[d]imidazol-4-ol (0.5 g, 1 mmol), 2-(hydroxymethyl)cyclohexanol (0.39 g, 3 mmol) and PPh₃ (0.53 g, 2 mmol) in THF (20 mL) was added DIAD (0.41 g, 2 mmol) at room temperature. The resulting solution was sucked in vacuo and purged with nitrogen for 3 times. It was stirred for 3 h at rt. The reaction mixture was concentrated and the residue was purified by column chromatography (silica, PE:EtOAc=10:1-3:1) to afford 2-((5,6-dichloro-2-(((2-(trimethylsilyl)ethoxy) methoxy) methyl)-1-((2-(trimethylsilyl) ethoxy) methyl)-1H-benzo[d]imidazol-4-yloxy) methyl) cyclohexanol (0.42 g, 0.7 mmol, 70%) as a yellow solid. MS (EI⁺, m/z): 605 [M+H]⁺.

Step 3: 2-((5,6-dichloro-2-(hydroxymethyl)-1H-benzo[d]imidazol-4-yloxy) methyl) cyclohexanol, I-439

A solution of 2-((5,6-dichloro-2-(((2-(trimethylsilyl)ethoxy)methoxy)methyl)-1-((2-(trimethylsilyl)ethoxy)methyl)-1H-benzo[d]imidazol-4-yloxy)methyl)cyclohexanol (320 mg, 0.51 mmol) in HCl (4M in dioxane, 10 mL) was heated to 40° C. and then stirred for 20 h. It was concentrated and the crude was purified by prep-HPLC to afford 2-((5,6-dichloro-2-(hydroxymethyl)-1H-benzo[d]imidazol-4-yloxy)methyl)cyclohexanol I-439 (20.2 mg, 0.06 mmol, 12%) as a white solid. MS (EI⁺, m/z): 345 [M+H]⁺. ¹H-NMR (500 MHz, DMSO-d₆): δ 7.40 (s, 1H), 4.73 (s, 2H), 4.71 (d, J=3 Hz, 1H), 4.56 (dd, J=7 Hz, 9 Hz, 1H), 3.35-3.40 (m, 1H), 1.88-2.01 (m, 2H), 1.58-1.69 (m, 3H), 1.18-1.31 (m, 4H).

Example 187: (+,−)-cis-2-((5,6-dichloro-2-(hydroxymethyl)-1H-benzo[d]imidazol-4-yloxy)methyl)cyclohexanol, I-394

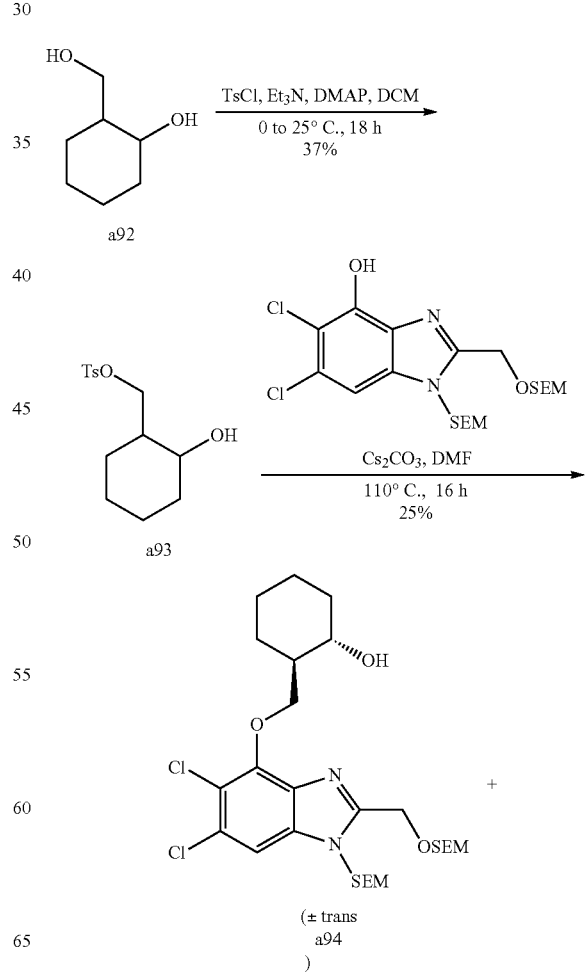

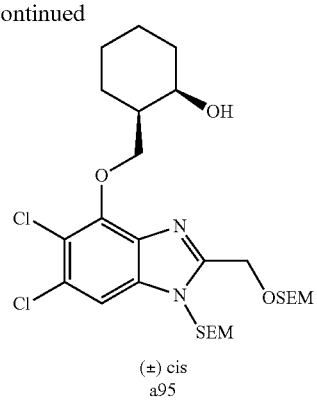

(±) cis
a95

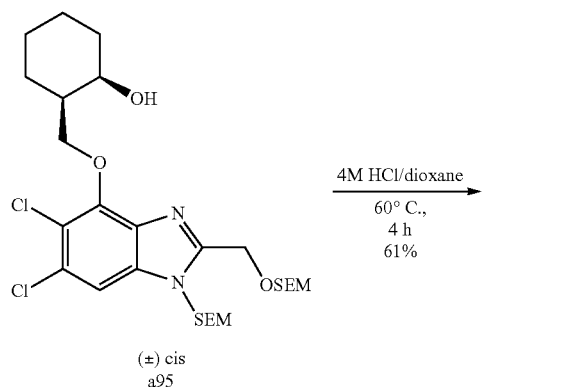

(±) cis
a95

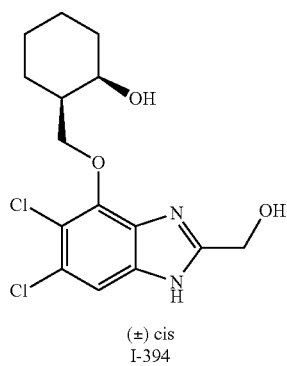 [SMILES: OCc1nc2c(OC[C@H]3CCCC[C@H]3O)c(Cl)c(Cl)cc2[nH]1]

(±) cis
I-394

Procedures and Characterization:

Step 1: (4-hydroxycyclohexyl)methyl 4-methylbenzenesulfonate

To a mixture of 2-(hydroxymethyl)cyclohexanol (500 mg, 1.97 mmol), Et$_3$N (3.33 g, 23 mmol) and DMAP (141 mg, 1.15 mmol) in dry DCM (15 mL) was added a suspension of TsCl (2.2 g, 11.9 mmol) in dry DCM (30 mL) at 0° C. The reaction was stirred at 0° C. for 1 h and then at 25° C. for 16 h. The solution was diluted with DCM (100 mL) and washed with water (30 mL×2), dried (Na$_2$SO$_4$), filtered and concentrated in vacuo, the crude product was purified by chromatography (silica, ethyl acetate/petroleum ether=1/5) to afford (4-hydroxycyclohexyl) methyl 4-methylbenzenesulfonate (1.2 g, 4.23 mmol, 37%) as a yellow oil. ESI-MS (EI+, m/z): 285.1 [M+H]$^+$.

Step 2: (1S,2R)—2-((5,6-dichloro-2-(((2-(trimethylsilyl)ethoxy)methoxy)methyl)-1-((2-(trimethylsilyl)ethoxy)methyl)-1H-benzo[d]imidazol-4-yloxy)methyl)cyclohexanol and (1R,2R)-2-((5,6-dichloro-2-(((2-(trimethylsilyl)ethoxy)methoxy)methyl)-1-((2-(trimethylsilyl)ethoxy) methyl)-1H-benzo[d]imidazol-4-yloxy)methyl)cyclohexanol A mixture of 5,6-dichloro-2-(((2-(trimethylsilyl)ethoxy)methoxy)methyl)-1-((2-(trimethylsilyl)ethoxy)methyl)-1H-benzo[d]imidazol-4-ol (2.43 g, 5 mmol), (2-hydroxycyclohexyl)methyl 4-methylbenzenesulfonate (1.71 g, 6 mmol) and Cs$_2$CO$_3$ (3.25 g, 10 mmol) in dry DMF (50 mL) was stirred for 16 h at 110° C. The reaction was quenched with water (100 mL) and extracted with ethyl acetate (200 mL). The organic layer was washed with water (50 mL×2), dried (Na$_2$SO$_4$), filtered and concentrated in vacuo, the crude product was purified by chromatography (silica, ethyl acetate/petroleum ether=1/5) to afford (1S,2R)-2-((5,6-dichloro-2-(((2-(trimethylsilyl)ethoxy)methoxy)methyl)-1-((2-(trimethylsilyl)ethoxy)methyl)-1H-benzo[d]imidazol-4-yloxy)methyl)cyclohexanol (1.18 g, 1.95 mmol, 40%) as a light yellow oil and (1R,2R)-2-((5,6-dichloro-2-(((2-(trimethylsilyl)ethoxy)methoxy)methyl)-1-((2-(trimethylsilyl)ethoxy)methyl)-1H-benzo[d]imidazol-4-yloxy)methyl)cyclohexanol (740 mg, 1.23 mmol, 25%) as a light yellow oil. ESI-MS (EI+, m/z): 605.1 [M+H]$^+$.

Step 3: (+,−)-cis-2-((5,6-dichloro-2-(hydroxymethyl)-1H-benzo[d]imidazol-4-yloxy)methyl) cyclohexanol, I-394

A solution of (1R,2R)—2-((5,6-dichloro-2-(((2-(trimethylsilyl)ethoxy)methoxy) methyl)-1-((2-(trimethylsilyl)ethoxy)methyl)-1H-benzo[d]imidazol-4-yloxy)methyl) cyclohexanol (600 mg, 1 mmol) in 4 M HCl/dioxane (40 mL) was stirred for 4 h at 60° C. The reaction was diluted with water (40 mL) and neutralized with NaHCO$_3$ to pH 6. and extracted with ethyl acetate (200 mL). The organic layer was washed with water (50 mL×2), dried (Na$_2$SO$_4$), filtered and concentrated in vacuo, the crude product was purified by prep-HPLC (TFA) to afford (+,−)-cis-2-((5,6-dichloro-2-(hydroxymethyl)-1H-benzo[d]imidazol-4-yloxy) methyl) cyclohexanol I-394 as a white solid (210 mg, 0.61 mmol, 61%). ESI-MS (EI+, m/z): 345.0 [M+H]$^+$. $^1$H NMR (500 MHz, DMSO) δ 7.40 (s, 1H), 4.73 (s, 2H), 4.60 (t, J=8 Hz, 1H), 4.36 (t, J=8.5 Hz, 1H), 4.06 (d, J=1.5 Hz, 1H), 1.87 (t, J=4 Hz, 1H), 1.72-1.58 (m, 3H), 1.51-1.35 (m, 4H), 1.22-1.12 (m, 1H).

Example 189: (+,−)-trans-2-((5,6-dichloro-2-(hydroxymethyl)-1H-benzo[d]imidazol-4-yloxy)methyl)cyclohexanol, I-383

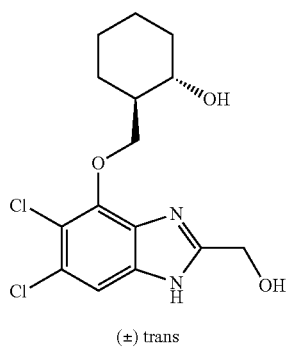

Synthetic Scheme:

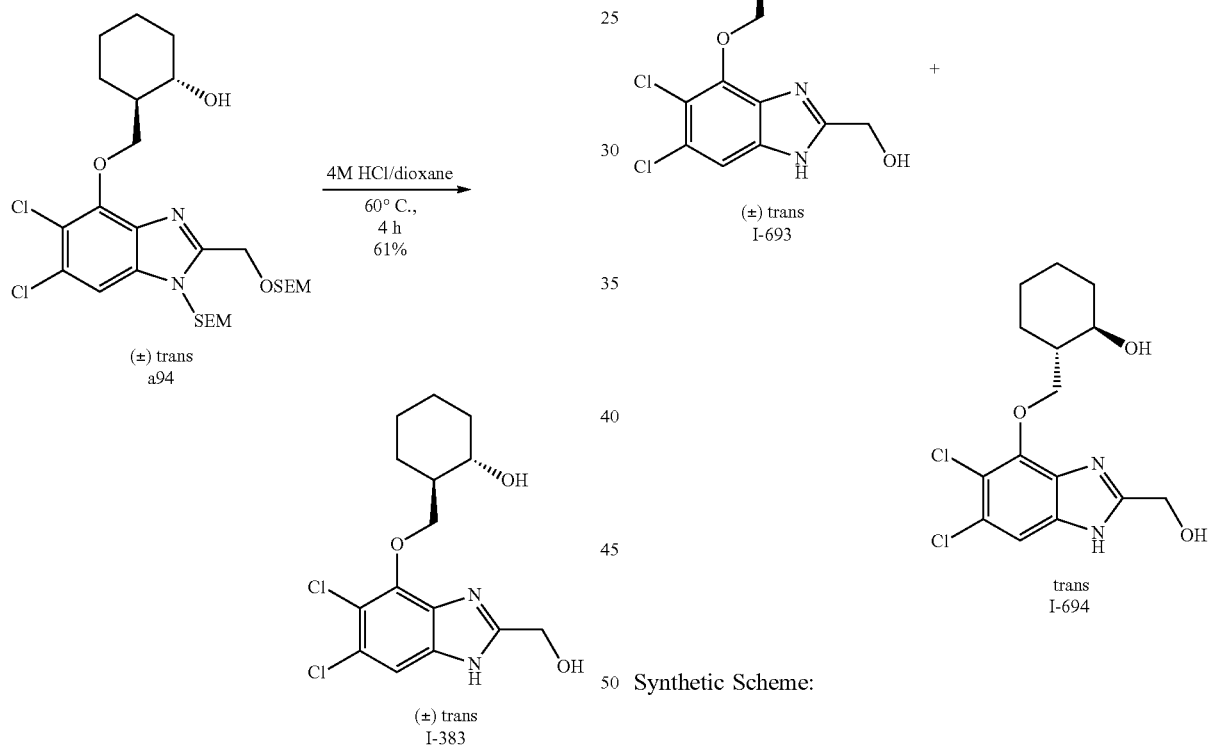

Procedures and Characterization:

Step 1: (+,−)-trans-2-((5,6-dichloro-2-(hydroxymethyl)-1H-benzo[d]imidazol-4-yloxy)methyl)cyclohexanol A solution of (+,−)-trans-2-((5,6-dichloro-2-(((2-(trimethylsilyl)ethoxy)methoxy)methyl)-1-((2-(trimethylsilyl)ethoxy)methyl)-1H-benzo[d]imidazol-4-yloxy)methyl)cyclohexanol (800 mg, 1.32 mmol) in 4 M HCl/dioxane (60 mL) was stirred for 4 h at 60° C. The reaction was diluted with water (40 mL) and neutralized with NaHCO₃ to pH 6. and extracted with ethyl acetate (200 mL). The organic layer was washed with water (50 mL×2), dried (Na₂SO₄), filtered and concentrated in vacuo, the crude product was purified by prep-HPLC (TFA) to afford (+,−)-trans-2-((5,6-dichloro-2-(hydroxymethyl)-1H-benzo[d]imidazol-4-yloxy) methyl) cyclohexanol I-383 as a white solid (278 mg, 0.81 mmol, 61%). ESI-MS (EI+, m/z): 345.0 [M+H]⁺. ¹H NMR (500 MHz, DMSO) δ 7.39 (s, 1H), 4.74 (d, J=7 Hz, 3H), 4.58 (t, J=7.5 Hz, 1H), 3.38-3.37 (m, 1H), 2.02-1.99 (m, 1H), 1.90-1.88 (m, 1H), 1.70-1.58 (m, 3H), 1.32-1.19 (m, 4H).

Example 190: (1S,2R)—2-((5,6-dichloro-2-(hydroxymethyl)-1H-benzo[d]imidazol-4-yloxy)methyl)cyclohexanol I-693 and (1R,2S)-2-((5,6-dichloro-2-(hydroxymethyl)-1H-benzo[d]imidazol-4-yloxy)methyl)cyclohexanol, I-694

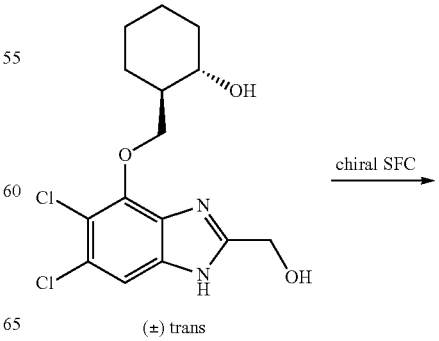

Synthetic Scheme:

631

-continued

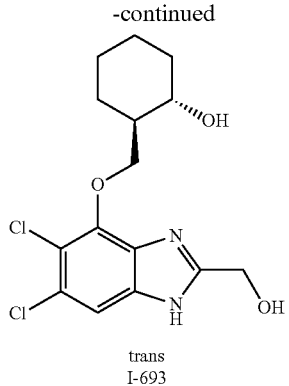

trans
I-693

+

632

Example 191: (4-(((+,−)-cis-2-aminocyclohexyl)methoxy)-5,6-dichloro-1H-benzo[d]imidazol-2-yl)methanol, I-376

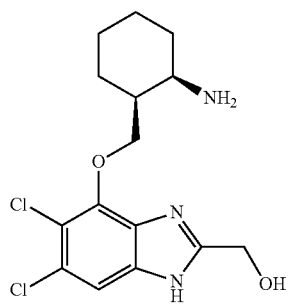

I-376

(±) trans

Synthetic Scheme:

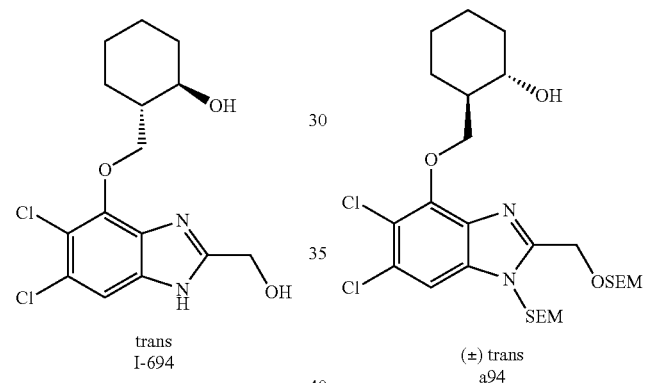

Procedures and Characterization:

Step 1: (1S,2R)—2-((5,6-dichloro-2-(hydroxymethyl)-1H-benzo[d]imidazol-4-yloxy)methyl)cyclohexanol I-693 and (1R,2S)-2-((5,6-dichloro-2-(hydroxymethyl)-1H-benzo[d]imidazol-4-yloxy)methyl)cyclohexanol I-694

(+,−)-trans-2-((5,6-dichloro-2-(hydroxymethyl)-1H-benzo[d]imidazol-4-yloxy) methyl)cyclohexanol I-383 (100 mg, 0.29 mmol) was separated by chiral SFC to afford an earlier eluting compound that was arbitrarily assigned the (1S,2R) stereochemistry, (1S,2R)—2-((5,6-dichloro-2-(hydroxymethyl)-1H-benzo[d]imidazol-4-yloxy)methyl)cyclohexanol I-693 as a white solid (24.4 mg, 0.07 mmol, 25%) and a later eluting compound that was arbitrarily assigned the (1R,2S) stereochemistry, (1R,2S)-2-((5,6-dichloro-2-(hydroxymethyl)-1H-benzo[d]imidazol-4-yloxy)methyl)cyclohexanol I-694 as a white solid (27.9 mg, 0.08 mmol, 28%). ESI-MS (EI+, m/z): 345.0 [M+H]+. $^1$H NMR (500 MHz, MeOD) δ 7.58 (s, 1H), 5.06 (s, 2H), 4.51 (dd, J=9.5 Hz, J=5 Hz, 1H), 4.37 (dd, J=9 Hz, J=2.5 Hz, 1H), 3.72-3.67 (m, 1H), 2.07 (d, J=13 Hz, 2H), 1.84-1.72 (m, 3H), 1.61-1.53 (m, 1H), 1.41-1.31 (m, 3H).

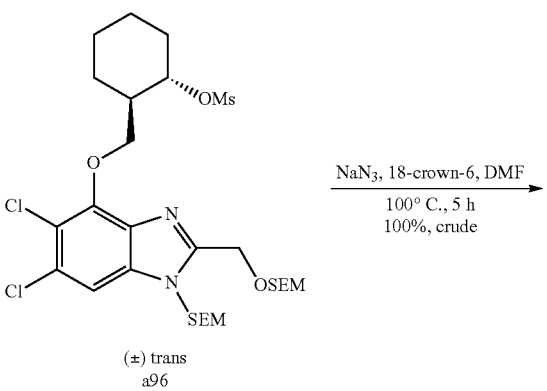

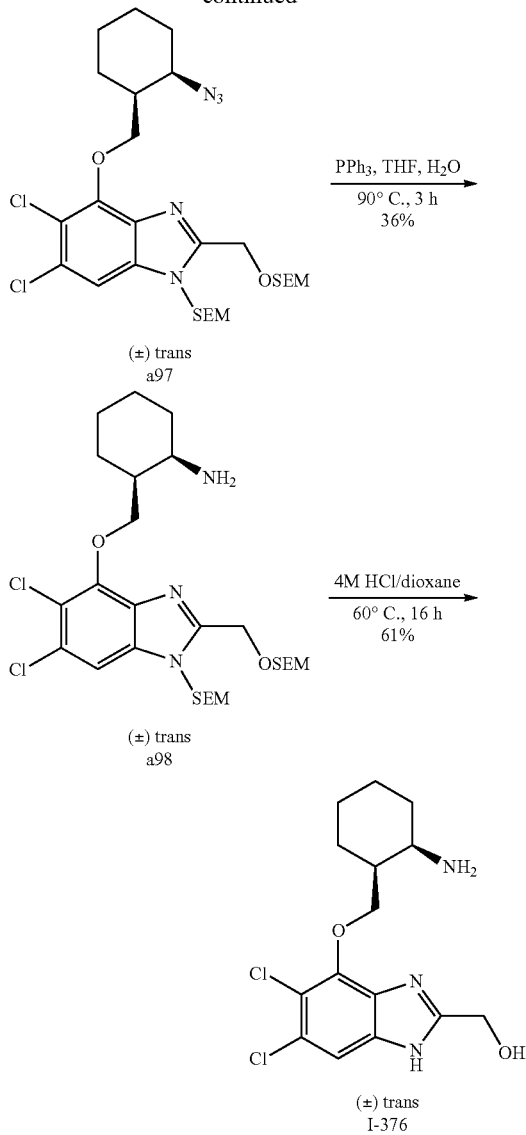

Procedures and Characterization:

Step 1: (+,−)-trans-2-((5,6-dichloro-2-(((2-(trimethylsilyl)ethoxy)methoxy)methyl)-1-((2-(trimethylsilyl)ethoxy)methyl)-1H-benzo[d]imidazol-4-yloxy)methyl)cyclohexyl methanesulfonate To a mixture of (+,−)-trans-2-((5,6-dichloro-2-(((2-(trimethylsilyl)ethoxy)methoxy) methyl)-1-((2-(trimethylsilyl)ethoxy)methyl)-1H-benzo[d]imidazol-4-yloxy)methyl)cyclohexanol (400 mg, 0.66 mmol) and Et$_3$N (335 mg, 3.31 mmol) in dry DCM (15 mL) was added methanesulfonyl chloride (151 mg, 1.32 mmol) at 0° C. The reaction was stirred for 2 h at 25° C. The reaction was quenched with water (10 mL) and extracted with DCM (30 mL). The organic phase was dried (Na$_2$SO$_4$), filtered and concentrated in vacuo to afford crude (+,−)-trans-2-((5,6-dichloro-2-(((2-(trimethylsilyl)ethoxy)methoxy)methyl)-1-((2-(trimethylsilyl) ethoxy)methyl)-1H-benzo[d]imidazol-4-yloxy)methyl) cyclohexyl methanesulfonate (450 mg, 0.66 mmol, 100%) as a light brown oil.

Step 2: 4-(((+,−)-cis)-2-azidocyclohexyl)methoxy)-5,6-dichloro-2-(((2-(trimethylsilyl)ethoxy) methoxy)methyl)-1-((2-(trimethylsilyl)ethoxy)methyl)-1H-benzo[d]imidazole A mixture of (+,−)-trans-2-((5,6-dichloro-2-(((2-(trimethylsilyl)ethoxy)methoxy) methyl)-1-((2-(trimethylsilyl)ethoxy)methyl)-1H-benzo[d]imidazol-4-yloxy)methyl)cyclohexyl methanesulfonate (600 mg, 0.88 mmol), NaN$_3$ (572 mg, 8.8 mmol) and 18-crown-6 (534 mg, 2 mmol) in dry DMF (15 mL) was stirred for 5 h at 100° C. under N$_2$ atmosphere. The reaction was quenched with water (30 mL) and extracted with ethyl acetate (60 mL). The organic phase was washed with water (20 mL×2), and brine (20 mL), dried (Na$_2$SO$_4$), filtered and concentrated in vacuo to afford crude 4-(((+,−)-cis)-2-azidocyclohexyl)methoxy)-5,6-dichloro-2-(((2-(trimethylsilyl)ethoxy)methoxy)methyl)-1-((2-(trimethylsilyl)ethoxy)methyl)-1H-benzo[d]imidazole (554 mg, 0.88 mmol, 100%) as a brown solid. ESI-MS (EI+, m/z): 630.0 [M+H]$^+$.

Step 3: (+,−)-cis-2-((5,6-dichloro-2-(((2-(trimethylsilyl)ethoxy)methoxy)methyl)-1-((2-(trimethylsilyl)ethoxy)methyl)-1H-benzo[d]imidazol-4-yloxy) methyl)cyclohexanamine A mixture of 4-(((+,−)-cis)-2-azidocyclohexyl)methoxy)-5,6-dichloro-2-(((2-(trimethylsilyl)ethoxy)methoxy) methyl)-1-((2-(trimethylsilyl)ethoxy)methyl)-1H-benzo[d] imidazole (460 mg, 0.73 mmol) and PPh$_3$ (383 mg, 1.46 mmol) in THF (15 mL) and H$_2$O (5 mL) was stirred for 3 h at 90° C. under N$_2$ atmosphere. The reaction was quenched with water (30 mL) and extracted with ethyl acetate (60 mL). The organic phase was washed with water (20 mL×2), and brine (20 mL), dried (Na$_2$SO$_4$), filtered and concentrated in vacuo, the crude product was purified by chromatography (silica, MeOH/DCM=20/1) to afford (+,−)-cis-2-((5,6-dichloro-2-(((2-(trimethylsilyl)ethoxy)methoxy)methyl)-1-((2-(trimethylsilyl)ethoxy)methyl)-1H-benzo[d]imidazol-4-yloxy)methyl)cyclohexanamine (160 mg, 0.27 mmol, 36%) as a white solid. ESI-MS (EI+, m/z): 604.2 [M+H]$^+$.

Step 4: (4-((((+,−)-cis-2-aminocyclohexyl)methoxy)-5,6-dichloro-1H-benzo[d]imidazol-2-yl)methanol, I-376

A solution of (+,−)-cis-2-((5,6-dichloro-2-(((2-(trimethylsilyl)ethoxy)methoxy) methyl)-1-((2-(trimethylsilyl)ethoxy)methyl)-1H-benzo[d]imidazol-4-yloxy)methyl) cyclohexanamine (160 mg, 0.26 mmol) in 4 M HCl/dioxane (10 mL) was stirred for 16 h at 60° C. The reaction was diluted with water (20 mL) and neutralized with NaHCO$_3$ to pH 6. and extracted with ethyl acetate (50 mL). The organic layer was washed with water (10 mL×2), dried (Na$_2$SO$_4$), filtered and concentrated in vacuo, the crude product was purified by prep-HPLC (TFA) to afford (4-((((+,−)-cis-2-aminocyclohexyl)methoxy)-5,6-dichloro-1H-benzo[d]imidazol-2-yl)methanol (TFA salt) I-376 as a white solid (28.1 mg, 0.08 mmol, 32%). ESI-MS (EI+, m/z): 344.1 [M+H]$^+$. $^1$H NMR (500 MHz, MeOD) δ 7.50 (s, 1H), 4.91 (s, 2H), 4.40 (d, J=9.5 Hz, 1H), 4.30 (dd, J=10.5 Hz, J=4 Hz, 1H), 3.82 (s, 1H), 2.5 (s, 1H), 2.02 (d, J=4.5 Hz, 1H), 1.89 (s, 1H), 1.67-1.51 (m, 6H).

Example 192: N-(((+,−)-cis-2-((5,6-dichloro-2-(hydroxymethyl)-1H-benzo[d]imidazol-4-yloxy)methyl)cyclohexyl)acetamide, I-369

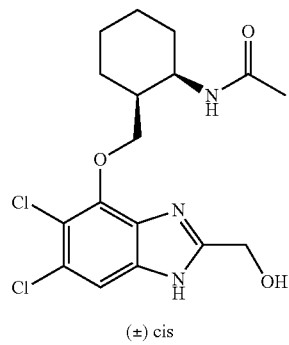

(±) cis
I-369

Synthetic Scheme:

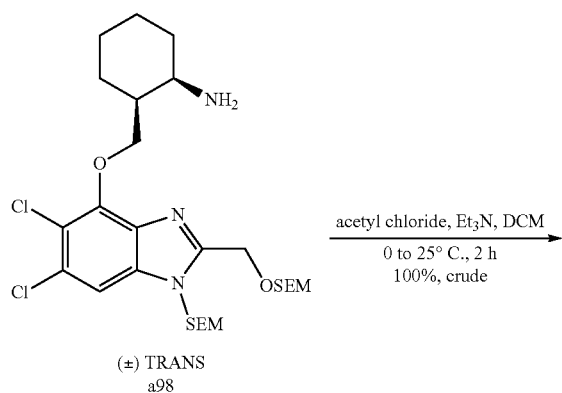

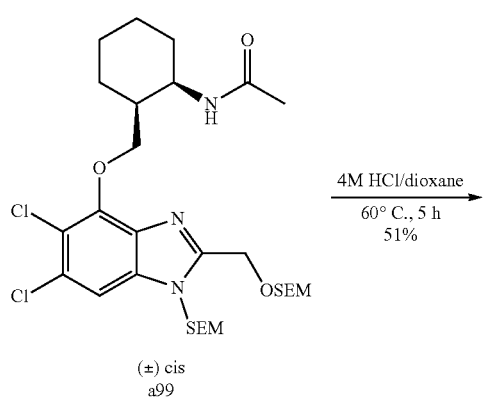

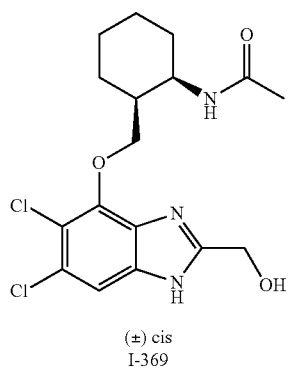

(±) cis
I-369

Procedures and Characterization:

Step 1: N-((+,−)-cis-2-((5,6-dichloro-2-(((2-(trimethylsilyl)ethoxy)methoxy)methyl)-1-((2-(trimethylsilyl)ethoxy)methyl)-1H-benzo[d]imidazol-4-yloxy)methyl)cyclohexyl)acetamide To a mixture of (4-((((+,−)-cis-2-aminocyclohexyl)methoxy)-5,6-dichloro-1H-benzo[d]imidazol-2-yl)methanol (90 mg, 0.15 mmol) and Et$_3$N (303 mg, 3 mmol) in dry DCM (10 mL) was added acetyl chloride (117 mg, 1.5 mmol) at 0° C. The reaction was stirred for 2 h at 25° C. The reaction was quenched with water (10 mL) and extracted with DCM (30 mL). The organic phase was dried (Na$_2$SO$_4$), filtered and concentrated in vacuo to afford crude N-((+,−)-cis-2-((5,6-dichloro-2-(((2-(trimethylsilyl)ethoxy)methoxy)methyl)-1-((2-(trimethylsilyl)ethoxy) methyl)-1H-benzo[d]imidazol-4-yloxy)methyl)cyclohexyl)acetamide (97 mg, 0.15 mmol, 100%) as a light brown oil. ESI-MS (EI+, m/z): 646.2 [M+H]$^+$.

Step 2: N-(((+,−)-cis-2-((5,6-dichloro-2-(hydroxymethyl)-1H-benzo[d]imidazol-4-yloxy) methyl)cyclohexyl)acetamide, I-369

A solution of N-((+,−)-cis-2-((5,6-dichloro-2-(((2-(trimethylsilyl)ethoxy)methoxy) methyl)-1-((2-(trimethylsilyl)ethoxy)methyl)-1H-benzo[d]imidazol-4-yloxy)methyl)cyclohexyl) acetamide (97 mg, 0.15 mmol) in 4 M HCl/dioxane (10 mL) was stirred for 5 h at 60° C. The reaction was diluted with water (20 mL) and neutralized with NaHCO$_3$ to pH 6. and extracted with ethyl acetate (50 mL). The organic layer was washed with water (10 mL×2), dried (Na$_2$SO$_4$), filtered and concentrated in vacuo, the crude product was purified by prep-HPLC (TFA) to afford N-(((+,−)-cis-2-((5,6-dichloro-2-(hydroxymethyl)-1H-benzo[d]imidazol-4-yloxy) methyl)cyclohexyl)acetamide (TFA salt) I-369 as a white solid (27.6 mg, 0.07 mmol, 51%). ESI-MS (EI+, m/z): 386.1 [M+H]$^+$. $^1$H NMR (500 MHz, MeOD) δ 7.61 (s, 1H), 4.99 (s, 2H), 4.45 (s, 1H), 4.22-4.17 (m, 2H), 2.32-2.30 (m, 1H), 2.00 (s, 3H), 1.82-1.74 (m, 3H), 1.65-1.45 (m, 5H).

Example 193: (5,6-dichloro-4-((tetrahydrofuran-2-yl) methoxy)-1H-benzo[d]imidazol-2-yl) methanol bis (2,2,2-trifluoroacetate), I-400

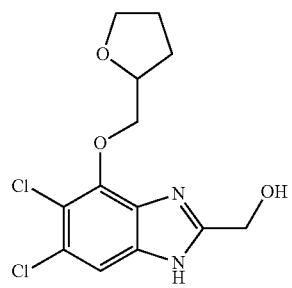

Synthetic Scheme:

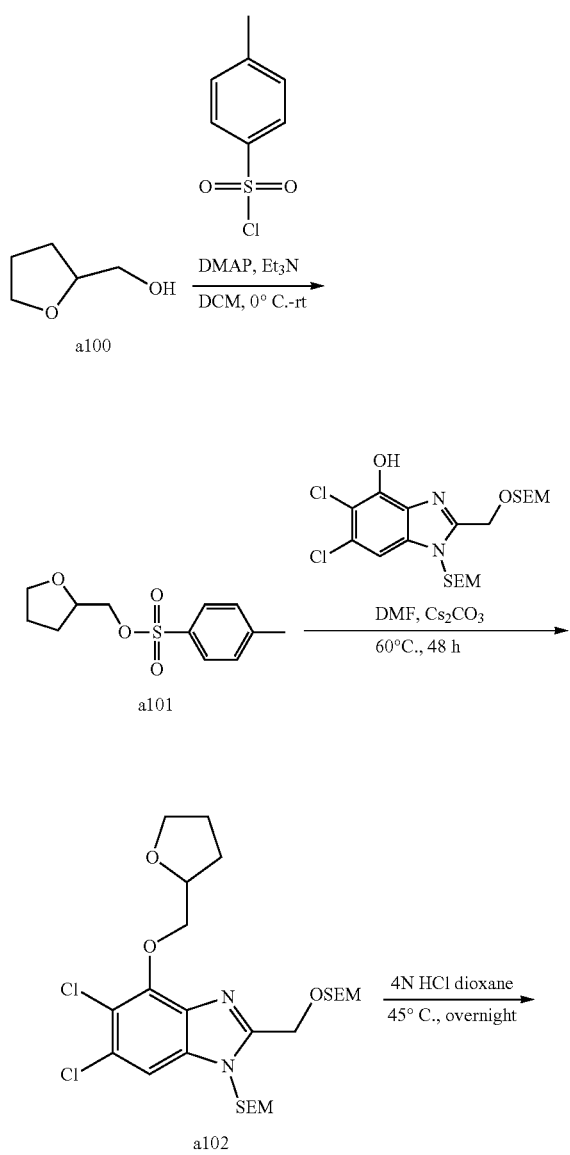

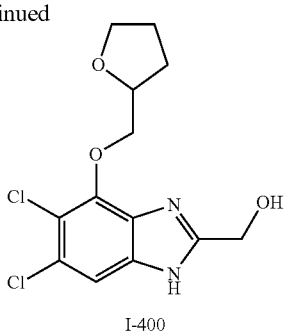

Procedures and Characterization:

Step 1: (tetrahydrofuran-2-yl)methyl 4-methylbenzenesulfonate

To the solution of (tetrahydrofuran-2-yl)methanol (200 mg, 1.96 mmol) and DMAP (12 mg, 0.098 mmol), Et$_3$N (396.3 mg, 3.92 mmol) in 5 mL CH$_2$Cl2 was added 4-methylbenzene-1-sulfonyl chloride (380.1 mg, 2 mmol) in 10 mL CH$_2$Cl$_2$ at 0° C. slowly. This mixture was stirred at rt overnight under N$_2$ protection. The mixture was extracted with EtOAc/H$_2$O (20 mL/20 mL), the organic phase was dried over anhydrous Na$_2$SO$_4$, and concentrated in vacuo. The residue was purified by SG column (petroleum ether/ ethyl acetate=0~20%) to afford (tetrahydrofuran-2-yl) methyl 4-methylbenzenesulfonate (280 mg, 56.7%). MS (EI+, m/z): 257[M+H]$^T$.

Step 2: 5,6-dichloro-4-((tetrahydrofuran-2-yl) methoxy)-2-(((2-(trimethylsilyl) ethoxy)methoxy) methyl)-1-((2-(trimethylsilyl)ethoxy)methyl)-1H-benzo[d]imidazole To the mixture of 2(tetrahydrofuran-2-yl)methyl 4-methylbenzenesulfonate (400 mg, 1.56 mmol) and 5,6-dichloro-2-(((2-(trimethylsilyl) ethoxy) methoxy) methyl)-1-((2-(trimethylsilyl) ethoxy) methyl)-1H-benzo[d]imidazol-4-ol (513.5 mg, 1.04 mmol), CS$_2$CO$_3$ (678 mg, 2.08 mmol) was added DMF (6 mL). This mixture was stirred at 60° C. for 48 h. The mixture was extracted with EtOAc/H$_2$O (50 mL/50 mL), the organic phase was dried over anhydrous Na$_2$SO$_4$, and concentrated in vacuo. The residue was purified by SG column (petroleum ether/ethyl acetate=0-20%) to afford 5,6-dichloro-4-((tetrahydrofuran-2-yl) methoxy)-2-(((2-(trimethylsilyl)ethoxy)methoxy)methyl)-1-((2-(trimethylsilyl)ethoxy)methyl)-1H-benzo[d]imidazole (523 mg, 87%). MS (EI+, m/z): 578 [M]$^+$.

Step 3: (5,6-dichloro-4-((tetrahydrofuran-2-yl) methoxy)-1H-benzo[d]imidazol-2-yl)methanol, I-400

To the 5,6-dichloro-4-((tetrahydrofuran-2-yl) methoxy)-2-(((2-(trimethylsilyl) ethoxy) methoxy) methyl)-1-((2-(trimethylsilyl) ethoxy) methyl)-1H-benzo[d]imidazole (280 mg, 0.485 mmol) was added 4N HCl dioxane (5.0 mL). This mixture was stirred at 45° C. overnight. The crude was purified by prep-HPLC to give (5,6-dichloro-4-((tetrahydrofuran-2-yl)methoxy)-1H-benzo[d]imidazol-2-yl) methanol I-400 (70 mg, 45%). MS (EI+, m/z): 317[M]$^+$.

¹H NMR (500 MHz, DMSO-d₆) δ 7.50 (s, 1H), 4.76 (s, 2H), 4.59-4.50 (m, 2H), 4.25-4.14 (m, 1H), 3.71-3.56 (m, 2H), 2.05-1.94 (m, 1H), 1.94-1.71 (m, 3H).

Example 194: 2-((5,6-dichloro-2-(hydroxymethyl)-1H-benzo[d]imidazol-4-yloxy)methyl)cyclopentanol, I-379

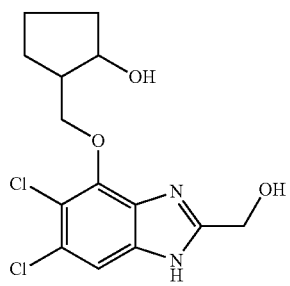

Synthetic Scheme:

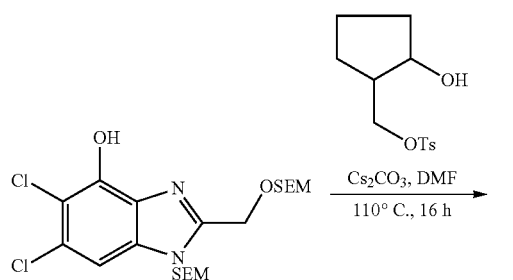

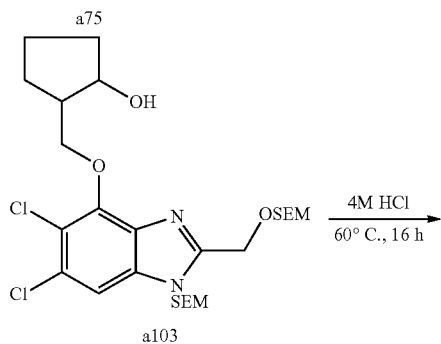

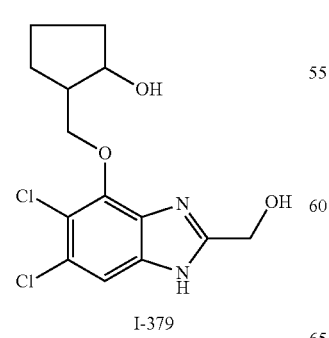

Procedures and Characterization:

The procedure was same as example I-395.

2-((5,6-dichloro-2-(hydroxymethyl)-1H-benzo[d]imidazol-4-yloxy)methyl)cyclopentanol ESI-MS (EI⁺, m/z): 331 [M+H]⁺.

¹H NMR (500 MHz, DMSO-d₆) δ 7.47 (s, 1H), 4.86 (s, 2H), 4.19 (d, J=1.5 Hz, 2H), 4.14 (d, J=5.5 Hz, 1H), 2.22-2.17 (m, 1H), 1.92-1.83 (m, 2H), 1.72-1.66 (m, 1H), 1.60-1.55 (m, 2H), 1.55-1.47 (m, 1H).

Example 195: 6-((5,6-dichloro-2-(hydroxymethyl)-1H-benzo[d]imidazol-4-yloxy)methyl)piperidin-2-one, I-465

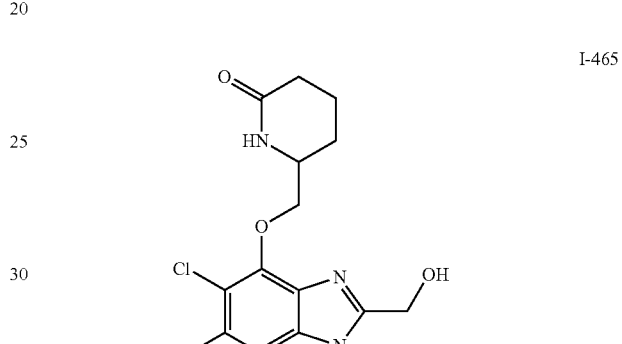

Synthetic Scheme:

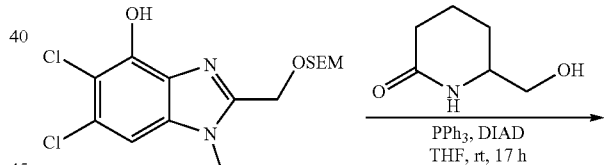

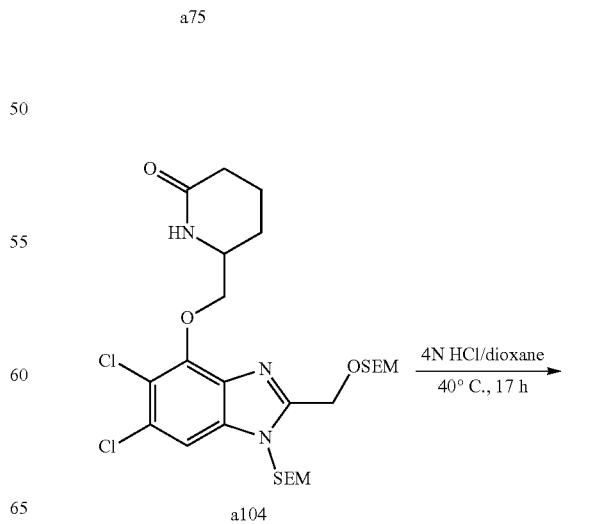

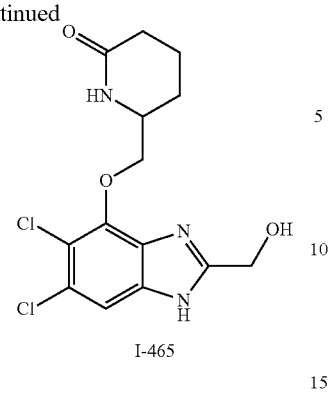

I-465

Procedures and Characterization:

Step 1: 6-((5,6-dichloro-2-(((2-(trimethylsilyl) ethoxy)methoxy)methyl)-1-((2-(trimethylsilyl) ethoxy)methyl)-1H-benzo[d]imidazol-4-yloxy) methyl)piperidin-2-one To a solution of 5,6-dichloro-2-(((2-(trimethylsilyl) ethoxy)methoxy)methyl)-1-((2-(trimethylsilyl)ethoxy) methyl)-1H-benzo[d]imidazol-4-ol (300 mg, 0.61 mmol), 6-(hydroxymethyl)piperidin-2-one (111 mg, 0.91 mmol) and PPh₃ (238 mg, 0.91 mmol), in THF (10 mL) was added DIAD (184 mg, 0.91 mmol). The solution was stirred at rt for 17 h. The solution was concentrated in vacuo and purified by chromatography (silica, ethyl acetate/petroleum ether=1/5) to afford 6-((5,6-dichloro-2-(((2-(trimethylsilyl) ethoxy)methoxy)methyl)-1-((2-(trimethylsilyl)ethoxy) methyl)-1H-benzo[d]imidazol-4-yloxy)methyl)piperidin-2-one (400 mg, 0.66 mmol, purity, 63%) as a yellow oil. ESI-MS (EI+, m/z): 604.2 [M+H]⁺.

Step 2: 6-((5,6-dichloro-2-(hydroxymethyl)-1H-benzo[d]imidazol-4-yloxy)methyl)piperidin-2-one, I-465

A solution of 6-((5,6-dichloro-2-(((2-(trimethylsilyl) ethoxy)methoxy)methyl)-1-((2-(trimethylsilyl)ethoxy) methyl)-1H-benzo[d]imidazol-4-yloxy)methyl)piperidin-2-one (400 mg, 0.66 mmol, purity, 63%) in 4M HCl/dioxane (10 mL) was stirred for 17 h at 40° C. The solution was concentrated and purified by prep-HPLC to afford 6-((5,6-dichloro-2-(hydroxymethyl)-1H-benzo[d]imidazol-4-yloxy) methyl)piperidin-2-one I-465 as a white solid (116.7 mg, 0.34 mmol, 56%, 2 steps). ESI-MS (EI+, m/z): 344.0 [M+H]⁺. ¹H NMR (500 MHz, DMSO) δ 7.55 (s, 1H), 7.45 (s, 1H), 4.75 (s, 2H), 4.58 (dd, J=10.0 Hz, J=5.5 Hz, 1H), 4.44 (dd, J=10.0 Hz, J=5.5 Hz, 1H), 3.71 (t, J=5.5 Hz, 1H), 2.16 (dd, J=11.0 Hz, J=5.5 Hz, 2H), 1.90-1.92 (m, 2H), 1.65-1.70 (m, 2H).

Example 196: (5,6-dichloro-4-(2,4-dichlorophenylthio)-1H-benzo[d]imidazol-2-yl)methanol, I-371

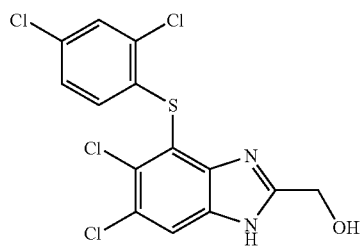

I-371

Synthetic Scheme:

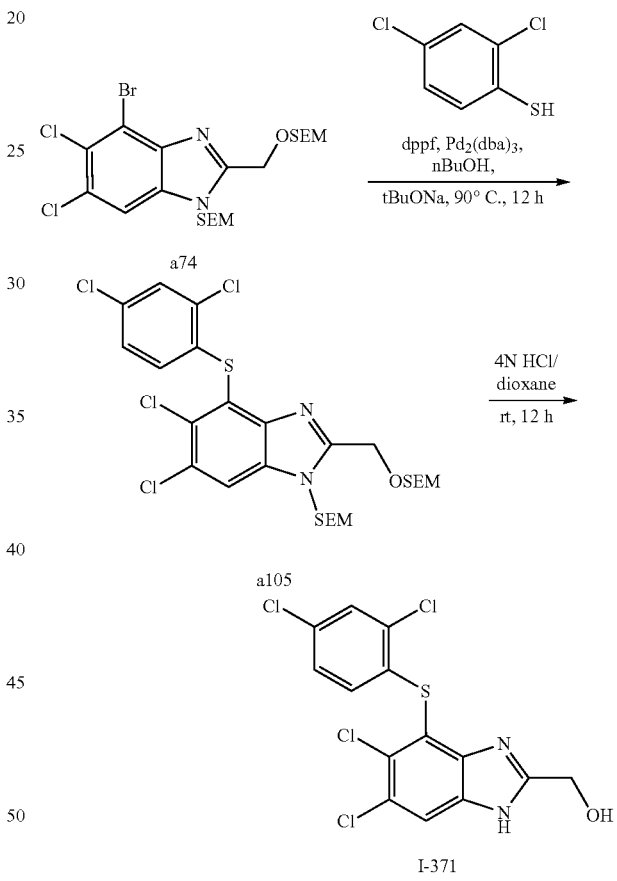

Procedures and Characterization:

Step 1: 5,6-dichloro-4-(2,4-dichlorophenylthio)-2-(((2-(trimethylsilyl)ethoxy)methoxy)methyl)-1-((2-(trimethylsilyl)ethoxy)methyl)-1H-benzo[d]imidazole A mixture of 4-bromo-5,6-dichloro-2-(((2-(trimethylsilyl) ethoxy)methoxy)methyl)-1-((2-(trimethylsilyl)ethoxy) methyl)-1H-benzo[d]imidazole (100 mg, 0.18 mmol), 2,4-dichlorobenzenethiol (39 mg, 0.22 mmol), dppf (20 mg, 0.036 mmol), Pd₂(dba)₃ (16 mg, 0.018 mmol) and tBuONa (60 mg, 0.6 mmol, 3.5 eq) in nBuOH (5 mL) was stirred at 90° C. for 12 h. It was concentrated in vacuo and purified by prep-TLC to give a crude product (0.2 g).

Step 1: (5,6-dichloro-4-(2,4-dichlorophenylthio)-1H-benzo[d]imidazol-2-yl)methanol, I-371

The crude 5,6-dichloro-4-(2,4-dichlorophenylthio)-2-(((2-(trimethylsilyl)ethoxy)methoxy)methyl)-1-((2-(trimethylsilyl)ethoxy)methyl)-1H-benzo[d]imidazole (200 mg, ~0.18 mmol) was dissolved in 4N HCl/dioxane (3 ml) and stirred at rt for 12 h. Then the reaction mixture was concentrated in vacuo to give a crude, which was purified by prep-HPLC to give (5,6-dichloro-4-(2,4-dichlorophenylthio)-1H-benzo[d]imidazol-2-yl)methanol I-371 (30 mg, 43% in two steps). ESI-MS (ESI+, m/z): 393[M+H]+.

$^1$H NMR (500 MHz, DMSO) δ 7.95 (s, 1H), 7.70 (d, J=2.0 Hz, 1H), 7.21 (m, 1H), 6.36 (d, J=9.0 Hz, 2H), 5.75 (s, 1H), 4.66 (s, 2H).

Example 197: 2-((6-chloro-2-(hydroxymethyl)-1H-benzo[d]imidazol-4-yloxy)methyl)cyclohexanol, I-390

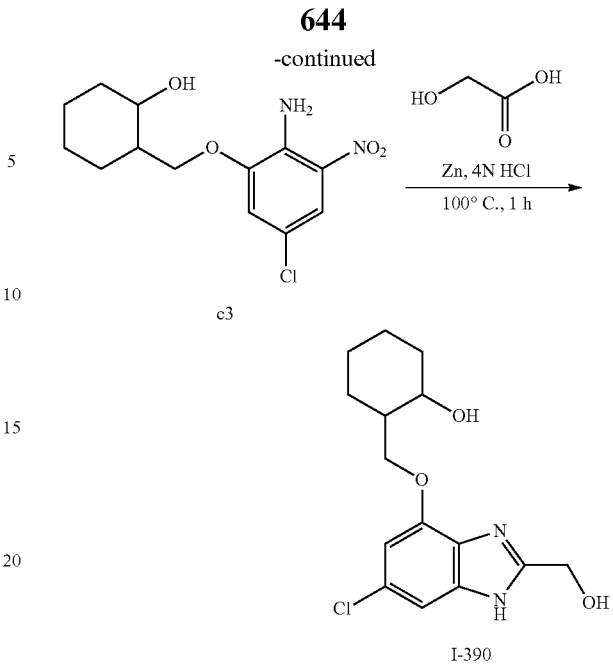

Synthetic Scheme:

Procedures and Characterization:

Step 1: 2-amino-5-chloro-3-nitrophenol

To a solution of 2-amino-3-nitrophenol (500 mg, 3.24 mmol) in Acetonitile (10 mL), was added 1-chloropyrrolidine-2,5-dione (519.84 mg, 3.89 mmol), this mixture was stirred at 80° C. for 3 h, The reaction was quenched with ice-water and extracted with EtOAc, dried and concentrated and purified by prep-HPLC to afford (4-bromo-6-(3,4-dichlorophenylthio)-1H-indol-2-yl)methanol (500 mg, purity: 100%, yield: 81.7%). ESI-MS (EI+, m/z): 189.0 [M+H]+.

Step 2: 2-((3-amino-5-chloro-2-nitrophenoxy)methyl)cyclohexanol

To a solution of 3-amino-5-chloro-2-nitrophenol (65 mg, 0.345 mmol) in DMF (2 mL), was added (2-hydroxycyclohexyl)methyl 4-methylbenzenesulfonate (117.63 mg, 0.117 mmol) and Cs$_2$CO$_3$ (168.47 mg, 0.517 mmol), this mixture was stirred at 100° C. for 18 h, The reaction was quenched with ice-water and extracted with EtOAc, dried and concentrated and purified by chromatography thinner layer with PE:EtOAc=1:1 to afford 2-((3-amino-5-chloro-2-nitrophenoxy)methyl)cyclohexanol (80 mg, purity: 100%, yield: 77.6%). ESI-MS (EI+, m/z): 301.1 [M+H]+.

Step 3: 2-((6-chloro-2-(hydroxymethyl)-1H-benzo[d]imidazol-4-yloxy)methyl)cyclohexanol, I-390

To a solution of 2-((3-amino-5-chloro-2-nitrophenoxy)methyl)cyclohexanol (50 mg, 0.166 mmol) was added Zn (108.75 mg, 1.66 mmol) and 2-hydroxyacetic acid (126.44 mg, 1.66 mmol) in HCl (4 mol/L), this mixture was stirred at 100° C. for 1 hour, The reaction was quenched with ice-water and extracted with EtOAc, dried and concentrated and purified by prep-HPLC PE:EtOAc to afford 2-((6-chloro-2-(hydroxymethyl)-1H-benzo[d]imidazol-4-yloxy)methyl)cyclohexanol I-390 (30 mg, purity: 100%, yield: 60%). ESI-MS (EI+, m/z): 311.1 [M+H]+.

$^1$H NMR (400 MHz, DMSO) δ 7.34 (s, 1H), 7.05 (s, 1H), 4.88 (d, J=5.2 Hz, 2H), 4.32 (d, J=6.7 Hz, 1H), 4.19 (dd,

J=16.8, 9.7 Hz, 1H), 4.01 (d, J=16.3 Hz, 1H), 3.42 (s, 1H), 1.93 (s, 1H), 1.68 (s, 2H), 1.47 (dd, J=30.1, 18.1 Hz, 1H), 1.23 (dd, J=20.7, 10.9 Hz, 2H).

Example 198: (5-chloro-6-(2,4-dichlorobenzylthio)-1H-benzo[d]imidazol-2-yl)methanol, I-361

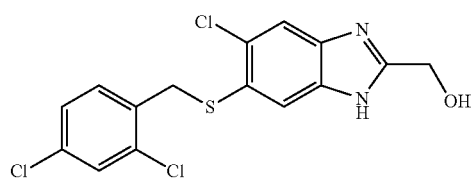

Synthetic Scheme:

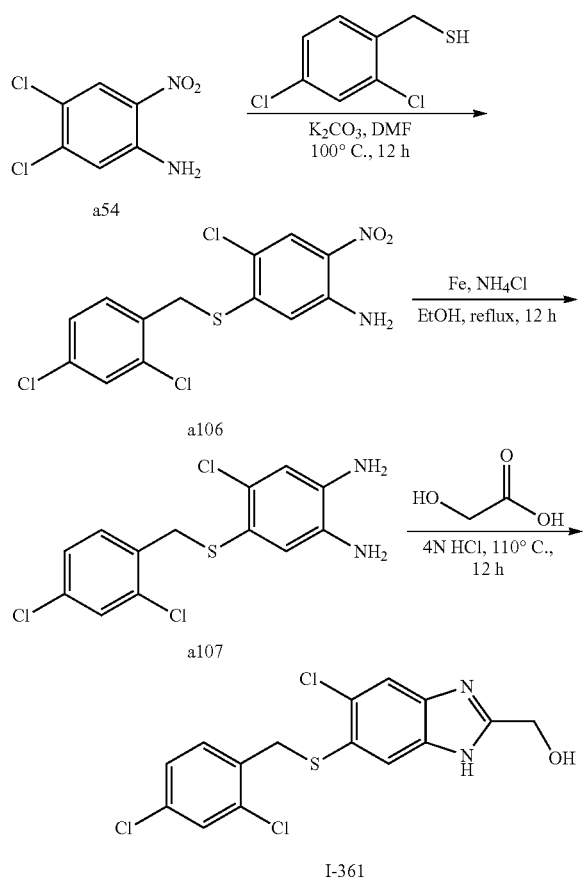 [SMILES: Nc1cc(Cl)c(Cl)cc1[N+](=O)[O-] ; SCc1ccc(Cl)cc1Cl ; Nc1cc(SCc2ccc(Cl)cc2Cl)c(Cl)cc1[N+](=O)[O-] ; Nc1cc(Cl)c(SCc2ccc(Cl)cc2Cl)cc1N ; O=C(O)CO ; OCc1nc2cc(Cl)c(SCc3ccc(Cl)cc3Cl)cc2[nH]1]

Procedures and Characterization:

Step 1:
4-chloro-5-(2,4-dichlorobenzylthio)-2-nitroaniline

To a stirred solution of 4,5-dichloro-2-nitroaniline (1.8 g, 8.7 mmol, 1.0 eq.) in DMF (20 mL) at room temperature, was added (2,4-dichlorophenyl)methanethiol (2.0 g, 10 mmol, 1.2 eq.) and K$_2$CO$_3$ (2.38 g, 25.1 mmol, 3.0 eq). The reaction mixture was stirred at 100° C. for 12 h. The mixture was filtered and extracted with EtOAc (100 ml), washed with water (100 ml*3), brine (100 ml*1), dried, filtered and concentrated to give a crude which was purified by column to give 4-chloro-5-(2,4-dichlorobenzylthio)-2-nitroaniline (1.0 g, 35 percent).

$^1$H-NMR (DMSO-d6,500 MHz): SP-0015548-165-P1A-H1-CDCl$_3$-20151201-T225

$^1$H NMR (500 MHz, DMSO) δ 8.13 (s, 1H), 7.45 (d, J=2.0 Hz, 1H), 7.40 (d, J=8.5 Hz, 1H), 7.25 (dt, J=2.5 Hz, 8.5 Hz, 1H), 6.47 (s, 1H), 6.07 (s, 1H), 4.23 (s, 2H).

Step 2: 4-chloro-5-(2,4-dichlorobenzylthio)benzene-1,2-diamine

To a stirred solution of 4-chloro-5-(2,4-dichlorobenzylthio)-2-nitroaniline (1.0 g, 2.85 mmol, 1.0 eq.) in EtOH (20 mL) and saturated aq.NH$_4$Cl (2.0 ml) was added Fe (1.0 g, 14.3 mmol, 5.0 eq) at room temperature. The reaction mixture was stirred at reflux for 2 h. The mixture was filtered and extracted with EtOAc (100 ml), washed with water (100 ml*3), brine (100 ml*1), dried, filtered and concentrated to give 4-chloro-5-(2,4-dichlorobenzylthio)benzene-1,2-diamine (0.8 g, 87 percent).

$^1$H NMR (500 MHz, CDCl$_3$) δ 7.35 (m, 1H), 7.07 (m, 1H), 6.97 (m, 1H), 6.75 (s, 1H), 6.62 (s, 1H), 4.09 (s, 2H), 3.39 (bs, 4H).

Step 3: (5-chloro-6-(2,4-dichlorobenzylthio)-1H-benzo[d]imidazol-2-yl)methanol, I-361

To a stirred solution of 4-chloro-5-(2,4-dichlorobenzylthio)benzene-1,2-diamine (200 mg, 0.72 mmol, 1.0 eq.) in 4N HCl (20 mL) at room temperature, was added 2-hydroxyacetic acid (100 mg, 0.78 mmol, 1.2 eq) and the reaction mixture was stirred at 110° C. for 12 h. It was concentrated in vacuo to give a crude which was purified by prep-HPLC to give (5-chloro-6-(2,4-dichlorobenzylthio)-1H-benzo[d]imidazol-2-yl)methanol I-361 (20 mg, 13 percent). ESI-MS (ESI$^+$, m/z): 373[M+H]$^+$.

$^1$H NMR (500 MHz, DMSO) δ 7.73 (m, 1H), 7.62 (m, 1H), 7.52 (m, 1H), 7.32 (bs, 2H), 4.76 (s, 2H), 4.29 (s, 2H).

Example 199: 2-(5-(benzyloxy)-6-chloro-2-(hydroxymethyl)-1H-benzo[d]imidazol-1-yl)acetamide, I-475

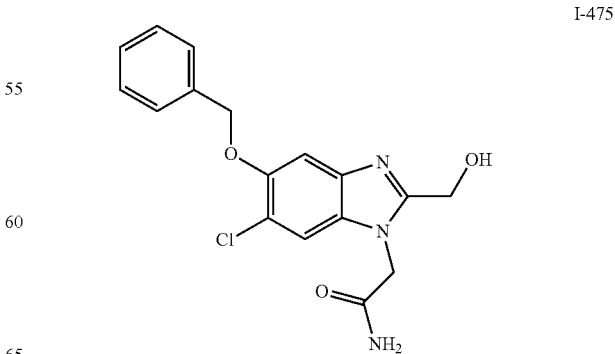

Synthetic Scheme:

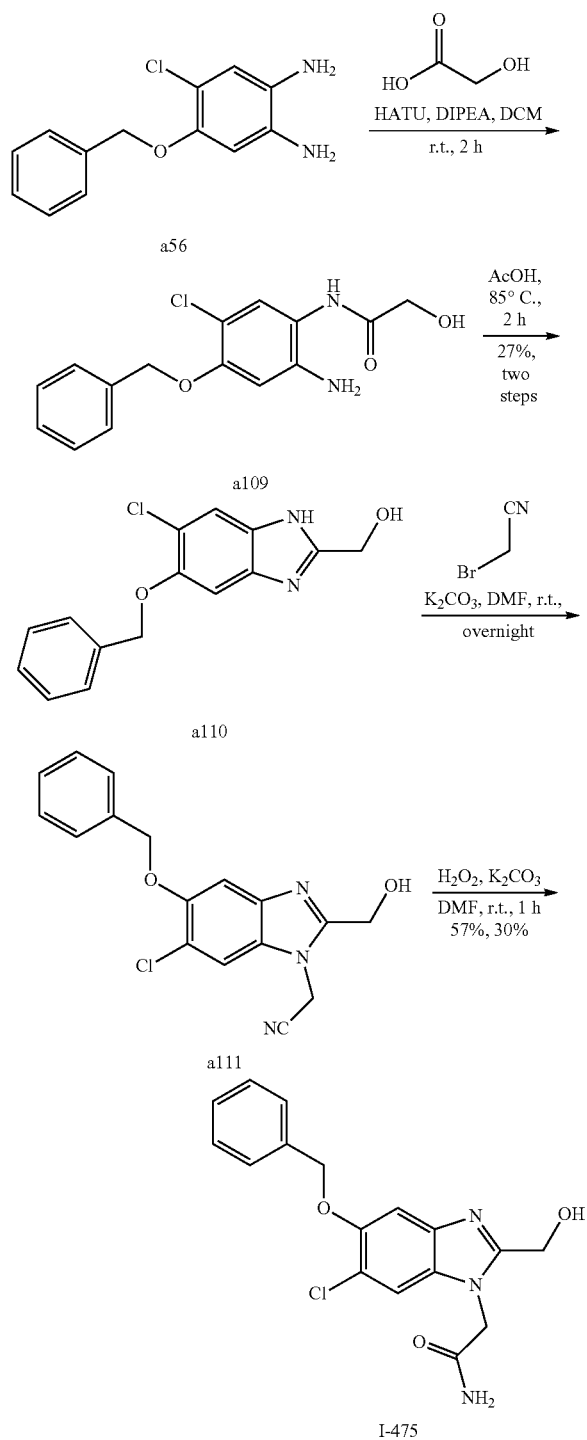

a56 a109 a110 a111

I-475

Procedures and Characterization:

Step 1: N-(2-amino-4-(benzyloxy)-5-chlorophenyl)-2-hydroxyacetamide

To a solution of 4-(benzyloxy)-5-chlorobenzene-1,2-diamine (80 mg, 0.32 mmol), 2-hydroxyacetic acid (100 mg, 1.3 mmol) and HATU (400 mg, 1.0 mmol) in DCM (5 mL) was added DIPEA (0.3 mL, 1.7 mmol) and the solution was stirred for 2 h at rt. The mixture was added water (10 mL), extracted with ethyl acetate (50 mL×2), the organic phase was dried over anhydrous $Na_2SO_4$, and concentrated in vacuo. The residue was purified by chromatography (silica, methanol/dichloromethane=5/100) to afford N-(2-amino-4-(benzyloxy)-5-chlorophenyl)-2-hydroxyacetamide (150 mg, equivalent) as a yellow solid. MS (EI+, m/z): 307.1 [M+H]⁻.

Step 2: (5-(benzyloxy)-6-chloro-1H-benzo[d]imidazol-2-yl)methanol

A mixture of (5-(benzyloxy)-6-chloro-1H-benzo[d]imidazol-2-yl)methanol (130 mg, 0.4 mmol) and AcOH (6 mL) was heated to 85° C. for 2 h. The solution was adjusted pH to 8 with ammonia water. The mixture was extracted with ethyl acetate (20 mL×3), the organic phase was dried over anhydrous $Na_2SO_4$, and concentrated in vacuo. The residue was purified by prep-HPLC (Boston C18 21*250 mm 10 μm, Mobile phase: A: 0.1% $NH_4HCO_3$; B: acetonitrile) to afford (5-(benzyloxy)-6-chloro-1H-benzo[d]imidazol-2-yl)methanol (25 mg, 0.09 mmol, 27%, two steps) as a white solid. MS (EI+, m/z): 289.0 [M+H]⁺. $^1$H-NMR (400 MHz, DMSO-$d_6$): δ 7.78 (s, 1H), 7.52-7.44 (m, 2H), 7.44-7.33 (m, 4H), 5.28 (s, 2H), 4.84 (s, 2H).

Step 3: 2-(6-(benzyloxy)-5-chloro-2-(hydroxymethyl)-1H-benzo[d]imidazol-1-yl)acetonitrile and 2-(5-(benzyloxy)-6-chloro-2-(hydroxymethyl)-1H-benzo[d]imidazol-1-yl)acetonitrile A mixture of (5-(benzyloxy)-6-chloro-1H-benzo[d]imidazol-2-yl)methanol (864 mg, 3.0 mmol), 2-bromoacetonitrile (2.1 g, 17.5 mmol) and $K_2CO_3$ (2.1 g, 15.2 mmol) in DMF (13 mL) was stirred at room temperature overnight. The mixture was purified by prep-HPLC (Boston C18 21*250 mm 10 μm, Mobile phase: A: 0.1% $NH_4HCO_3$; B: acetonitrile) to afford 2-(6-(benzyloxy)-5-chloro-2-(hydroxymethyl)-1H-benzo[d]imidazol-1-yl)acetonitrile and 2-(5-(benzyloxy)-6-chloro-2-(hydroxymethyl)-1H-benzo[d]imidazol-1-yl)acetonitrile (730 mg, 2.2 mmol, 74%) as a white solid. MS (EI+, m/z): 328.0 [M+H]⁺.

Step 4: 2-(6-(benzyloxy)-5-chloro-2-(hydroxymethyl)-1H-benzo[d]imidazol-1-yl)acetamide and 2-(5-(benzyloxy)-6-chloro-2-(hydroxymethyl)-1H-benzo[d]imidazol-1-yl)acetamide, I-475

The mixture of was 2-(6-(benzyloxy)-5-chloro-2-(hydroxymethyl)-1H-benzo[d]imidazol-1-yl) acetonitrile and 2-(5-(benzyloxy)-6-chloro-2-(hydroxymethyl)-1H-benzo[d] imidazol-1-yl) acetonitrile (730 mg, 1.93 mmol), $K_2CO_3$ (533 mg, 3.86 mmol) and $H_2O_2$ (30%, 0.4 mL, 3.86 mmol) in DMF (10 mL) was stirred at rt for 1 h, then add Con. $NH_4Cl$ (10 mL). The mixture was extracted with DCM/i-PrOH (20 mL×3). The organic layer was concentrated under pressure and purified by chiral-HPLC to afford 2-(6-(benzyloxy)-5-chloro-2-(hydroxymethyl)-1H-benzo[d]imidazol-1-yl)acetamide (380 mg, 1.1 mmol, 57%) as a white solid. MS (EI+, m/z): 346.2 [M+H]⁺. $^1$H-NMR (500 MHz, DMSO-$d_6$): δ 7.71 (s, 1H), 7.67 (s, 1H), 7.53-7.52 (m, 2H), 7.46 (s, 1H), 7.43-7.40 (m, 2H), 7.36-7.34 (m, 2H), 5.62 (t, J=6.0 Hz, 2H), 5.19 (s, 2H), 4.96 (s, 2H), 4.60 (d, J=5.5 Hz, 2H). 2-(5-(benzyloxy)-6-chloro-2-(hydroxymethyl)-1H-benzo[d]imidazol-1-yl)acetamide I-475 (201 mg, 0.58 mmol, 30%) as a white solid. MS (EI+, m/z): 346.2 [M+H]⁺. $^1$H-NMR (500 MHz, DMSO-$d_6$): δ 7.69 (s, 1H), 7.64 (s, 1H), 7.50-7.49 (m, 2H), 7.42-7.39 (m, 3H), 7.36-7.34 (m, 2H), 5.61 (t, J=6.0 Hz, 2H), 5.23 (s, 2H), 4.92 (s, 2H), 4.60 (d, J=5.5 Hz, 2H).

Example 200: (5-(benzyloxy)-6-chloro-1-methyl-1H-benzo[d]imidazol-2-yl)methanol, I-425 and (6-(benzyloxy)-5-chloro-1-methyl-1H-benzo[d]imidazol-2-yl)methanol, I-692

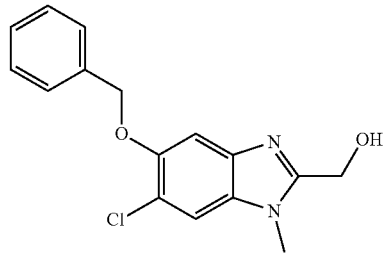

I-425

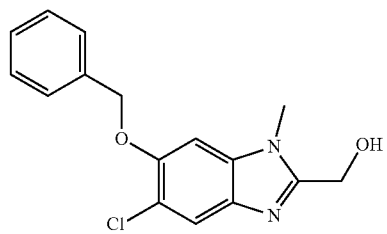

I-692

Synthetic Scheme:

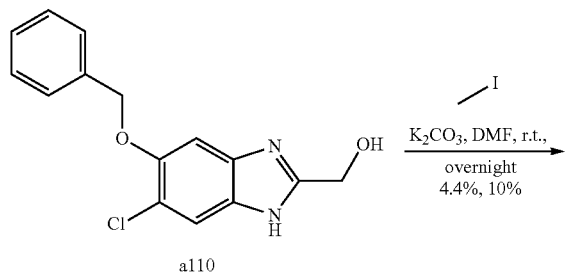

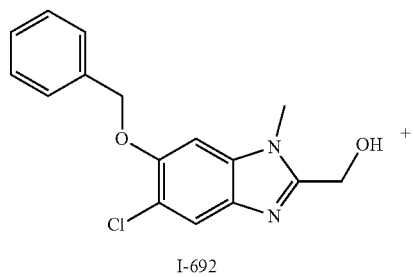

I-692

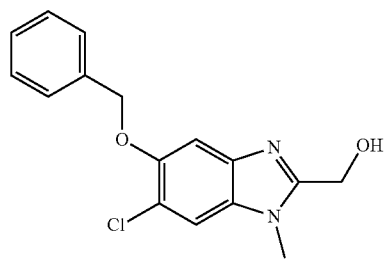

I-495

Procedures and Characterization:

Step 1: (6-(benzyloxy)-5-chloro-1-methyl-1H-benzo[d]imidazol-2-yl)methanol I-692 and (5-(benzyloxy)-6-chloro-1-methyl-1H-benzo[d]imidazol-2-yl)methanol, I-425

A mixture of (5-(benzyloxy)-6-chloro-1H-benzo[d]imidazol-2-yl)methanol (232 mg, 0.8 mmol), iodomethane (170 mg, 1.2 mmol) and $K_2CO_3$ (331 mg, 2.4 mmol) in DMF (3 mL) was stirred at room temperature overnight. The mixture was purified by chiral-HPLC to afford (6-(benzyloxy)-5-chloro-1-methyl-1H-benzo[d]imidazol-2-yl)methanol I-692 (10.7 mg, 0.035 mmol, 4.4%) as a white solid. MS (EI+, m/z): 303.1 [M+H]$^+$. H-NMR (500 MHz, MeOD-d$_4$): δ 7.64 (s, 1H), 7.56-7.54 (m, 2H), 7.43-7.40 (m, 2H), 7.36-7.33 (m, 1H), 7.28 (s, 1H), 5.25 (s, 2H), 4.83 (s, 2H) 3.89-3.88 (m, 3H); (5-(benzyloxy)-6-chloro-1-methyl-1H-benzo[d]imidazol-2-yl)methanol I-425 (25.2 mg, 0.083 mmol, 10%) as a white solid. MS (EI+, m/z): 303.1 [M+H]$^+$. $^1$H-NMR (500 MHz, MeOD-d$_4$): δ 7.54 (s, 1H), 7.41-7.40 (m, 2H), 7.29-7.26 (m, 2H), 7.22-7.20 (m, 2H), 5.10 (s, 2H), 4.72 (s, 2H) 3.77-3.76 (m, 3H).

Example 201: (1-(4-(1H-tetrazol-5-yl)benzyl)-6-(benzyloxy)-5-chloro-1H-benzo[d]imidazol-2-yl)methanol, I-440, and (1-(4-(1H-tetrazol-5-yl)benzyl)-5-(benzyloxy)-6-chloro-1H-benzo[d]imidazol-2-yl)methanol, I-437

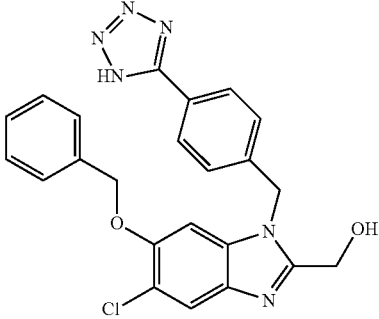

I-440

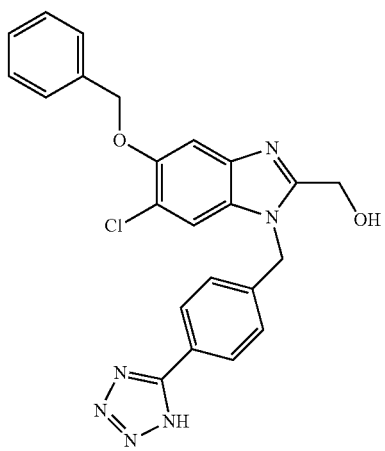

I-437

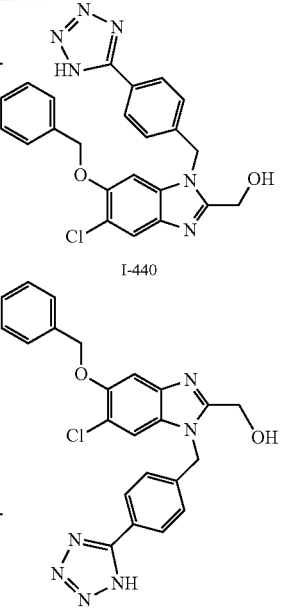

I-440

I-437

Synthetic Scheme:

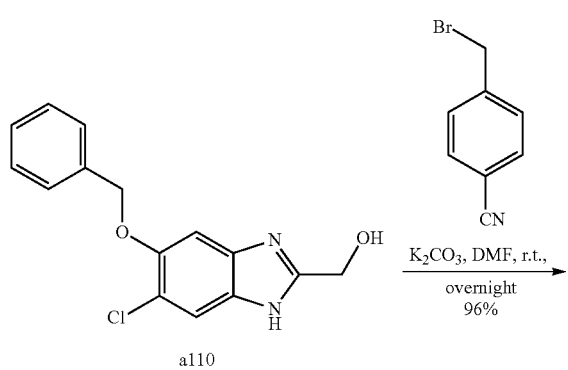

a110

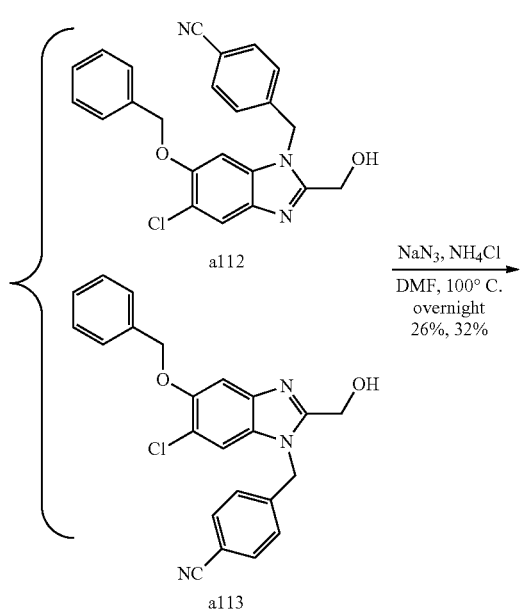

a112 a113

Procedures and Characterization:

Step 1: 4-((6-(benzyloxy)-5-chloro-2-(hydroxymethyl)-1H-benzo[d]imidazol-1-yl)methyl)benzonitrile and 4-((5-(benzyloxy)-6-chloro-2-(hydroxymethyl)-1H-benzo[d]imidazol-1-yl)methyl) benzonitrile A mixture of (5-(benzyloxy)-6-chloro-1H-benzo[d]imidazol-2-yl)methanol (432 mg, 1.5 mmol), 4-(bromomethyl) benzonitrile (441 mg, 2.25 mmol) and $K_2CO_3$ (621 mg, 4.5 mmol) in DMF (13 mL) was stirred at room temperature overnight. The mixture was purified by prep-HPLC (Boston C18 21*250 mm 10 m, Mobile phase: A: 0.1% $NH_4HCO_3$; B: acetonitrile) to afford 4-((6-(benzyloxy)-5-chloro-2-(hydroxymethyl)-1H-benzo[d]imidazol-1-yl)methyl) benzonitrile and 4-((5-(benzyloxy)-6-chloro-2-(hydroxymethyl)-1H-benzo[d]imidazol-1-yl)methyl) benzonitrile (660 mg, 1.63 mmol, 96%) as a red solid. MS (EI+, m/z): 404.1 [M+H]+.

Step 2: (1-(4-(1H-tetrazol-5-yl)benzyl)-6-(benzyloxy)-5-chloro-1H-benzo[d]imidazol-2-yl)methanol, I-440 and (1-(4-(1H-tetrazol-5-yl)benzyl)-5-(benzyloxy)-6-chloro-1H-benzo[d]imidazol-2-yl)methanol, I-437

A mixture of 4-((6-(benzyloxy)-5-chloro-2-(hydroxymethyl)-1H-benzo[d]imidazol-1-yl)methyl) benzonitrile and 4-((5-(benzyloxy)-6-chloro-2-(hydroxymethyl)-1H-benzo[d]imidazol-1-yl) methyl) benzonitrile (565 mg, 1.4 mmol), $NaN_3$ (460 mg, 7.1 mmol) and $NH_4Cl$ (400 mg, 7.5 mmol) in DMF (10 mL) was stirred at 100° C. overnight. The mixture was purified by prep-HPLC (Boston C18 21*250 mm 10 μm, Mobile phase: A: 0.1% $NH_4HCO_3$; B: acetonitrile) and chiral-HPLC to afford (1-(4-(1H-tetrazol-5-yl)benzyl)-6-(benzyloxy)-5-chloro-1H-benzo[d]imidazol-2-yl) methanol I-440 (126.2 mg, 2.8 mmol, 26%) as a white solid. MS (EI+, m/z): 447.2 [M+H]+ 1H-NMR (500 MHz, DMSO-d6): δ 7.95 (d, J=8.5 Hz, 2H), 7.71 (s, 1H), 7.43-7.26 (m, 8H), 5.61 (s, 2H), 5.17 (s, 2H), 4.67 (s, 2H); (1-(4-(1H- tetrazol-5-yl)benzyl)-5-(benzyloxy)-6-chloro-1H-benzo[d]imidazol-2-yl)methanol I-437 (155.3 mg, 0.35 mmol, 32%) as a white solid. MS (EI+, m/z): 447.2 [M+H]$^+$. $^1$H-NMR (500 MHz, DMSO-d$_6$): δ 7.91 (d, J=8.5 Hz, 2H), 7.59 (s, 1H), 7.50-7.10 (m, 8H), 5.73 (s, 1H), 5.56 (s, 2H), 5.22 (s, 2H), 4.70 (s, 2H).

Example 202: (1-((1H-1,2,4-triazol-3-yl)methyl)-5-(benzyloxy)-6-chloro-1H-benzo[d]imidazol-2-yl)methanol, I-403

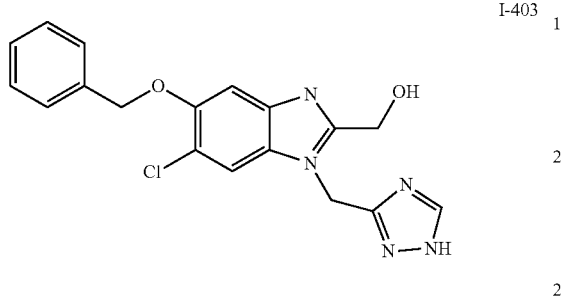

Synthetic Scheme:

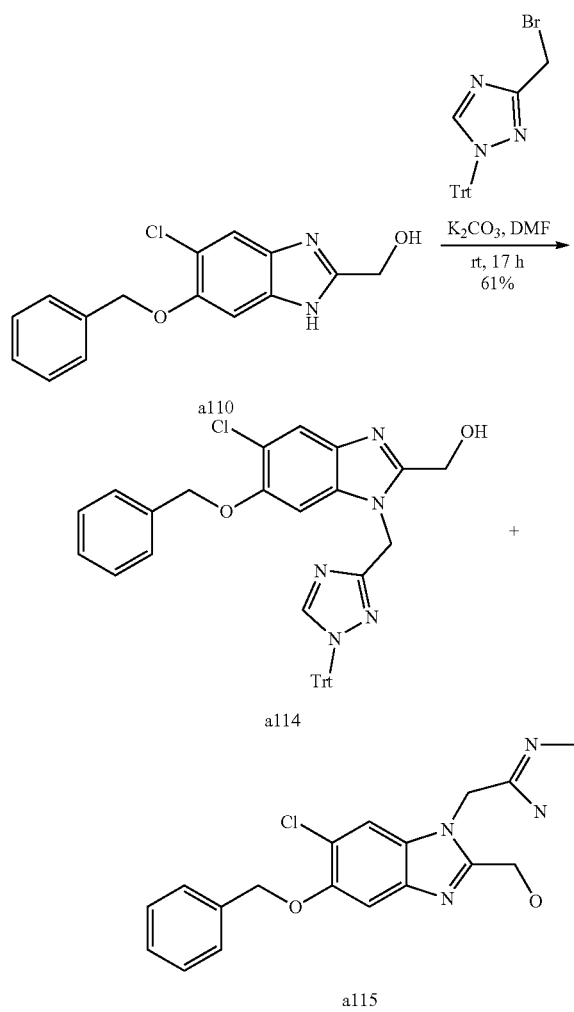

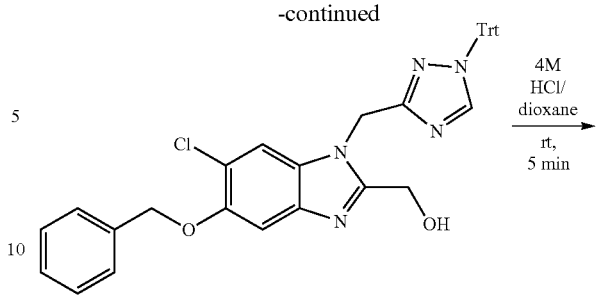

Procedures and Characterization:

Step 1: (5-(benzyloxy)-6-chloro-1-((1-trityl-1H-1,2,4-triazol-3-yl)methyl)-1H-benzo[d]imidazol-2-yl)methanol (6-(benzyloxy)-5-chloro-1H-benzo[d]imidazol-2-yl)methanol (150 mg, 0.5 mmol), 3-(bromomethyl)-1-trityl-1H-1,2,4-triazole (260 mg, 0.6 mmol) was dissolved in dry DMF (3.0 mL) and K$_2$CO$_3$ (148 mg, 1.1 mmol) was added. The reaction mixture was stirred at rt for 17 h. The mixture was partitioned between EtOAc and brine. The combined organic layers were concentrated and purified by SGC (PE:EtOAc=0~100%) to give a mixture of (6-(benzyloxy)-5-chloro-1-((1-trityl-1H-1,2,4-triazol-3-yl)methyl)-1H-benzo[d]imidazol-2-yl)methanol and (5-(benzyloxy)-6-chloro-1-((1-trityl-1H-1,2,4-triazol-3-yl)methyl)-1H-benzo[d]imidazol-2-yl)methanol (total 230 mg) which was separated by chiral-HPLC to give (6-(benzyloxy)-5-chloro-1-((1-trityl-1H-1,2,4-triazol-3-yl)methyl)-1H-benzo[d]imidazol-2-yl)methanol (100 mg, 0.16 mmol, 32%) as a yellow dope and (5-(benzyloxy)-6-chloro-1-((1-trityl-1H-1,2,4-triazol-3-yl)methyl)-1H-benzo[d]imidazol-2-yl)methanol (100 mg, 0.16 mmol, 32%) as a yellow dope. ESI-MS (EI$^+$, m/z): 612.2 [M+H]$^+$.

Step 2: (1-((1H-1,2,4-triazol-3-yl)methyl)-5-(benzyloxy)-6-chloro-1H-benzo[d]imidazol-2-yl)methanol, I-403

(5-(benzyloxy)-6-chloro-1-((1-trityl-1H-1,2,4-triazol-3-yl)methyl)-1H-benzo[d]imidazol-2-yl)methanol (100 mg, 0.16 mmol) in 4M HCl/dioxane (4.00 mL) was stirred at rt for 5 mins. The mixture was purified prep-HPLC to give (1-((1H-1,2,4-triazol-3-yl)methyl)-5-(benzyloxy)-6-chloro-1H-benzo[d]imidazol-2-yl)methanol I-403 (55 mg, 91%) as a white solid. ESI-MS (EI+, m/z): 370.1 [M+H]$^+$. $^1$H NMR (400 MHz, DMSO) δ 8.55 (s, 1H), 8.24 (s, 1H), 7.54-7.26 (m, 7H), 5.83 (s, 2H), 5.32 (d, J=16.2 Hz, 2H), 5.11 (s, 2H).

Example 203: (+,−)-trans-2-((5,6-dichloro-2-(hydroxymethyl)-1-methyl-1H-benzo[d]imidazol-4-yloxy)methyl)cyclohexanol, I-387

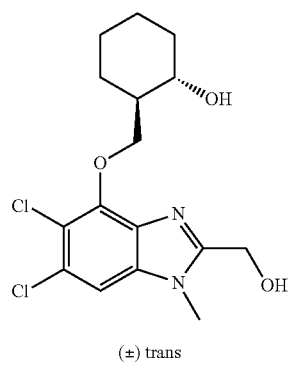

Synthetic Scheme:

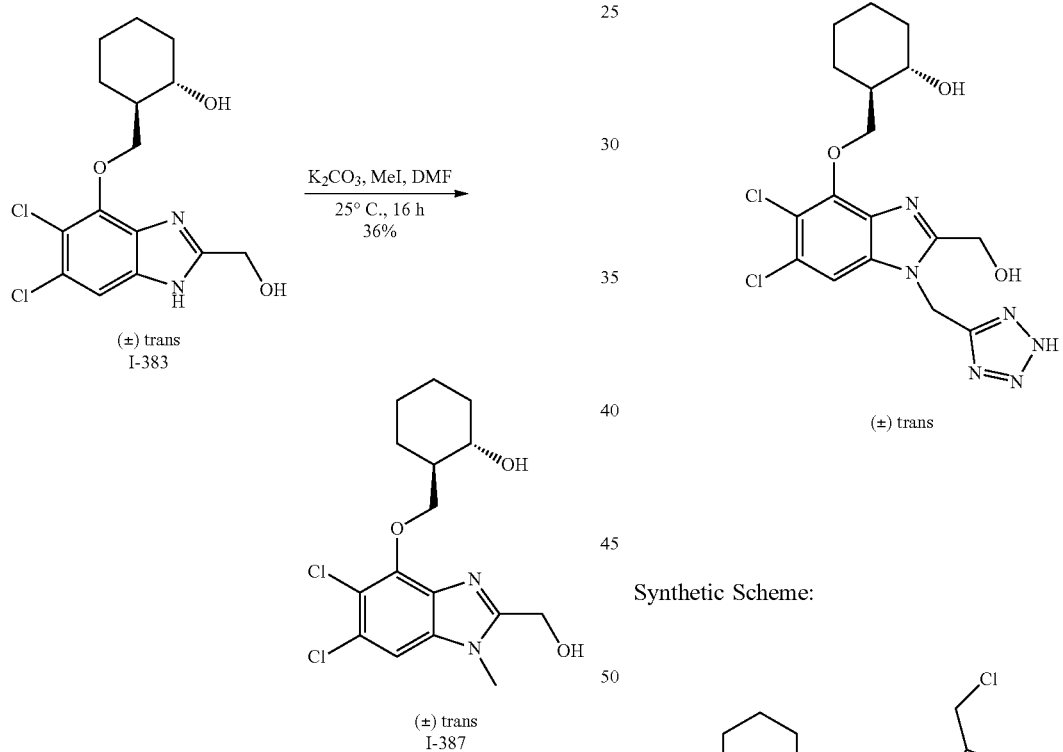

Procedures and Characterization:

Step 1: (+,−)-tras-2-((5,6-dichloro-2-(hydroxymethyl)-1-methyl-1H-benzo[d]imidazol-4-yloxy)methyl)cyclohexanol, I-387

A mixture of (+,−)-trans-2-((5,6-dichloro-2-(hydroxymethyl)-1H-benzo[d]imidazol-4-yloxy) methyl)cyclohexanol (100 mg, 0.29 mmol), MeI (83 mg, 0.58 mmol) and $K_2CO_3$ (120 mg, 0.87 mmol) in DMF (5 mL) was stirred for 16 h at 25° C. The reaction was quenched with water (10 mL) and extracted with ethyl acetate (20 mL). The organic layer was washed with water (50 mL×2), dried ($Na_2SO_4$), filtered and concentrated in vacuo, the crude product was purified by prep-HPLC (TFA) to afford (+,−)-trans-2-((5,6-dichloro-2-(hydroxymethyl)-1-methyl-1H-benzo[d]imidazol-4-yloxy) methyl)cyclohexanol I-387 (37 mg, 0.1 mmol, 35%) as a white solid. ESI-MS (EI+, m/z): 359.1 [M+H]⁻. ¹H NMR (500 MHz, MeOD) δ 7.69 (s, 1H), 4.98 (s, 2H), 4.58 (dd, J=9.5 Hz, J=5 Hz, 1H), 4.41 (dd, J=9.5 Hz, J=3 Hz, 1H), 3.92 (s, 3H), 3.73-3.72 (m, 1H), 2.09-2.01 (m, 2H), 1.85-1.78 (m, 2H), 1.76-1.72 (m, 1H)), 1.58-1.56 (m, 1H), 1.41-1.35 (m, 3H).

Example 204: (+,−)-trans-2-((1-((2H-tetrazol-5-yl)methyl)-5,6-dichloro-2-(hydroxymethyl)-1H-benzo[d]imidazol-4-yloxy)methyl)cyclohexanol, I-391

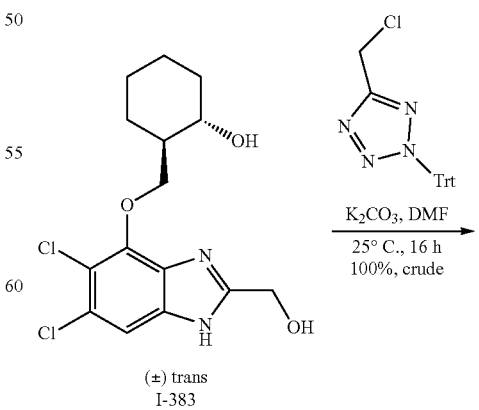

Synthetic Scheme:

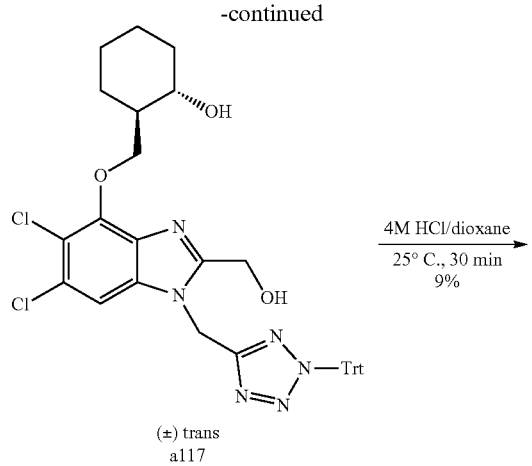

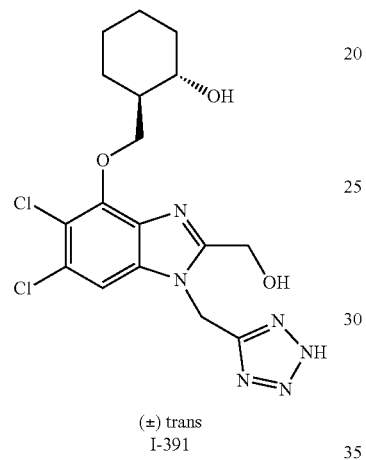

Procedures and Characterization:

Step 1: (+,−)-trans-2-((5,6-dichloro-2-(hydroxymethyl)-1-((2-trityl-2H-tetrazol-5-yl)methyl)-1H-benzo[d]imidazol-4-yloxy)methyl)cyclohexanol A mixture of (+,−)-trans-2-((5,6-dichloro-2-(hydroxymethyl)-1H-benzo[d]imidazol-4-yloxy) methyl)cyclohexanol (90 mg, 0.26 mmol), 5-(chloromethyl)-2-trityl-2H-tetrazole (113 mg, 0.31 mmol) and Cs$_2$CO$_3$ (171 mg, 0.52 mmol) in dry DMF (5 mL) was stirred for 16 h at 40° C. The reaction was quenched with water (10 mL) and extracted with ethyl acetate (20 mL). The organic layer was washed with water (50 mL×2), dried (Na$_2$SO$_4$), filtered and concentrated in vacuo to afford crude (+,−)-trans-2-((5,6-dichloro-2-(hydroxymethyl)-1-((2-trityl-2H-tetrazol-5-yl)methyl)-1H-benzo[d]imidazol-4-yloxy)methyl)cyclohexanol (175 mg, 0.26 mmol, 100%) as a brown solid. ESI-MS (EI+, m/z): 669.2 [M+H]$^+$.

Step 2: (+,−)-trans-2-((1-((2H-tetrazol-5-yl)methyl)-5,6-dichloro-2-(hydroxymethyl)-1H-benzo[d]imidazol-4-yloxy)methyl)cyclohexanol, I-391

A solution of (+,−)-trans-2-((5,6-dichloro-2-(hydroxymethyl)-1-((2-trityl-2H-tetrazol-5-yl)methyl)-1H-benzo[d]imidazol-4-yloxy)methyl)cyclohexanol (175 mg, 0.26 mmol) in 4 M HCl/dioxane (9 mL) was stirred for 30 min at 25° C. The reaction was diluted with water (20 mL) and neutralized with NaHCO$_3$ to pH 6. and extracted with ethyl acetate (50 mL). The organic layer was washed with water (20 mL×2), dried (Na$_2$SO$_4$), filtered and concentrated in vacuo, the crude product was purified by prep-HPLC (TFA) to afford (+,−)-trans-2-((1-((2H-tetrazol-5-yl)methyl)-5,6-dichloro-2-(hydroxymethyl)-1H-benzo[d]imidazol-4-yloxy) methyl) cyclohexanol I-391 as a white solid (10.2 mg, 0.13 mmol, 9%). ESI-MS (EI+, m/z): 237.1 [M+H]$^+$. $^1$H NMR (500 MHz, MeOD) δ 7.55 (s, 1H), 4.97 (s, 2H), 4.72 (dd, J=9.5 Hz, J=4.5 Hz, 1H), 4.56-4.54 (dd, J=9.5 Hz, J=3 Hz, 1H), 3.76-3.71 (m, 1H), 2.07-2.01 (m, 2H), 1.83-1.77 (m, 2H), 1.69-1.63 (m, 1H), 1.60-1.55 (m, 1H), 1.45-1.32 (m, 3H).

Example 205: 1-(5,6-dichloro-4-(cyclohexylmethoxy)-1H-benzo[d]imidazol-2-yl)ethane-1,2-diol, I-325

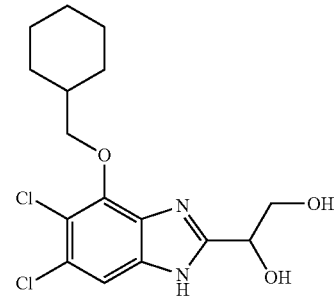

Synthetic Scheme:

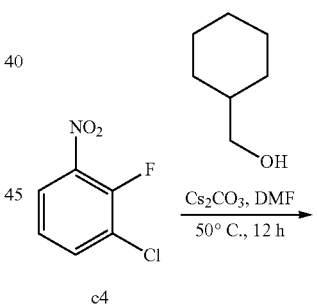

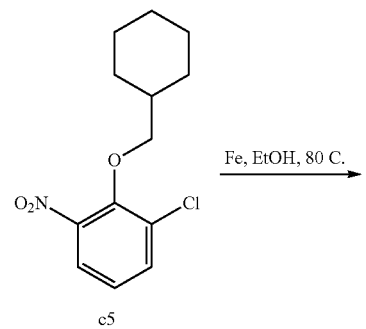

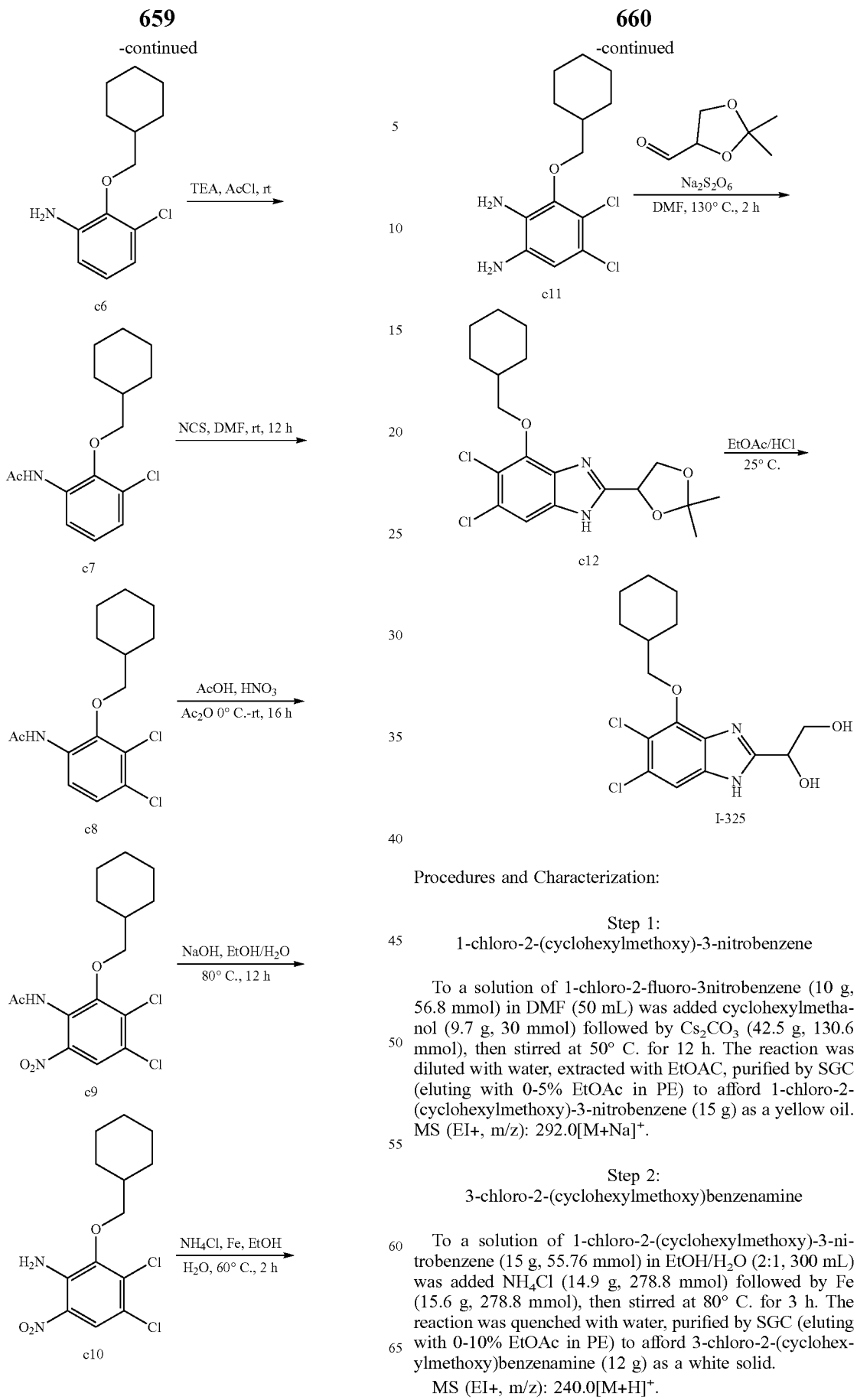

Procedures and Characterization:

Step 1:
1-chloro-2-(cyclohexylmethoxy)-3-nitrobenzene

To a solution of 1-chloro-2-fluoro-3nitrobenzene (10 g, 56.8 mmol) in DMF (50 mL) was added cyclohexylmethanol (9.7 g, 30 mmol) followed by $Cs_2CO_3$ (42.5 g, 130.6 mmol), then stirred at 50° C. for 12 h. The reaction was diluted with water, extracted with EtOAC, purified by SGC (eluting with 0-5% EtOAc in PE) to afford 1-chloro-2-(cyclohexylmethoxy)-3-nitrobenzene (15 g) as a yellow oil. MS (EI+, m/z): 292.0[M+Na]$^+$.

Step 2:
3-chloro-2-(cyclohexylmethoxy)benzenamine

To a solution of 1-chloro-2-(cyclohexylmethoxy)-3-nitrobenzene (15 g, 55.76 mmol) in EtOH/$H_2O$ (2:1, 300 mL) was added $NH_4Cl$ (14.9 g, 278.8 mmol) followed by Fe (15.6 g, 278.8 mmol), then stirred at 80° C. for 3 h. The reaction was quenched with water, purified by SGC (eluting with 0-10% EtOAc in PE) to afford 3-chloro-2-(cyclohexylmethoxy)benzenamine (12 g) as a white solid.
MS (EI+, m/z): 240.0[M+H]$^+$.

Step 3: N-(3-chloro-2-(cyclohexylmethoxy)phenyl)acetamide

To a solution of 3-chloro-2-(cyclohexylmethoxy)benzenamine (12 g, 50.2 mmol) in DCM (120 mL) was added TEA (15.2 g, 150.6 mmol) followed by AcCl (4.9 g, 100.4 mmol) at 0° C., then stirred for 12 h. The reaction was diluted with water, extracted with EtOAc, dried and purified by SGC (eluting with 0-5% EtOAc in PE) to afford N-(3-chloro-2-(cyclohexylmethoxy)phenyl)acetamide (7.2 g) as a white solid.
MS (EI+, m/z): 282.0[M+H]$^+$.

Step 4: N-(3,4-dichloro-2-(cyclohexylmethoxy)phenyl)acetamide

A solution of N-(3-chloro-2-(cyclohexylmethoxy)phenyl)acetamide (7.12 g, 25.33 mmol) and NCS (3.38 g, 25.33 mmol) in DMF (70 mL) was stirred at rt for 12 h. The reaction was purified by flash (eluting with 0-20% EtOAc in PE) to afford N-(3,4-dichloro-2-(cyclohexylmethoxy)phenyl)acetamide (6.9 g) as a white solid. MS (EI+, m/z): 316.0[M+H]$^+$.
$^1$H NMR (500 MHz, DMSO) δ 9.35 (s, 1H), 7.76 (d, J=9 Hz 1H), 7.25 (d, J=8.5 Hz, 1H), 3.69 (d, J=6.5 Hz, 2H), 2.09 (s, 3H), 1.87-1.64 (m, 6H), 1.87-1.64 (m, 6H), 1.29-1.15 (m, 5H),

Step 5: N-(3,4-dichloro-2-(cyclohexylmethoxy)-6-nitrophenyl)acetamide

To a solution of N-(3,4-dichloro-2-(cyclohexylmethoxy)phenyl)acetamide (2.4 g, 7.59 mmol) in AcOH (10 mL) was added a solution of HNO$_3$ in Ac$_2$O (30 mL/9 ml) at 0° C., then stirred for 16 h at rt. The reaction was diluted with water, extracted with DCM, dried and purified by prep-HPLC to afford N-(3,4-dichloro-2-(cyclohexylmethoxy)-6-nitrophenyl)acetamide (1.3 g) as pale solid. (two batches, recovery of SM 2.3 g.) MS (EI+, m/z): 361.0[M+H]$^+$

Step 6: 3,4-dichloro-2-(cyclohexylmethoxy)-6-nitrobenzenamine

A solution of N-(3,4-dichloro-2-(cyclohexylmethoxy)-6-nitrophenyl)acetamide (0.8 g, 2.22 mmol) and NaOH (450 mg, 11.1 mmol) in EtOH/H$_2$O (1:1, 16 mL) was stirred at 80° C. for 12 h. The reaction was purified by SGC (cluing with 0-50% EtOAc in PE) to afford 3,4-dichloro-2-(cyclohexylmethoxy)-6-nitrobenzenamine (0.65 g) as a yellow solid. MS (EI+, m/z): 19.0[M+H]$^+$.

Step 7: 4,5-dichloro-3-(cyclohexylmethoxy)benzene-1,2-diamine

A solution of 3,4-dichloro-2-(cyclohexylmethoxy)-6-nitrobenzenamine (0.6 g, 1.88 mmol), NH$_4$Cl (510 mg, 9.43 mmol) and Fe (528 mg, 9.43 mmol) in EtOH/H$_2$O (2.4:1, 17 mL) was stirred at 60° C. for 2 h. The reaction was diluted with water, extracted with EtOAc, purified by SGC (eluting with 0-30% EtOAc in PE) to afford 4,5-dichloro-3-(cyclohexylmethoxy)benzene-1,2-diamine (0.52 g) as a brown solid. MS (EI+, m/z): 289.0[M+H]$^+$.

Step 8: 5,6-dichloro-4-(cyclohexylmethoxy)-2-(2,2-dimethyl-1,3-dioxolan-4-yl)-1H-benzo[d]imidazole A mixture of 4,5-dichloro-3-(cyclohexylmethoxy)benzene-1,2-diamine (150 mg, 0.71 mmol), 2,2-dimethyl-1,3-dioxolane-4-carbaldehyde (76 mg, 0.71 mmol) and Na2S2O6 (135 mg, 0.71 mmol) in dry DMF (5 mL) was stirred for 16 h at 110° C. The reaction was quenched with water (10 mL) and extracted with ethyl acetate (20 mL). The organic layer was washed with water (5 mL×2), dried (Na$_2$SO$_4$), filtered and concentrated in vacuo, the crude product was purified by prep-HPLC (TFA) to 5,6-dichloro-4-(cyclohexylmethoxy)-2-(2,2-dimethyl-1,3-dioxolan-4-yl)-1H-benzo[d]imidazole (50 mg, 0.035 mmol, 27%) as a white solid. ESI-MS (EI+, m/z): 399.

Step 9: 1-(5,6-dichloro-4-(cyclohexylmethoxy)-1H-benzo[d]imidazol-2-yl)ethane-1,2-diol, I-325

A solution of 5,6-dichloro-4-(cyclohexylmethoxy)-2-(2,2-dimethyl-1,3-dioxolan-4-yl)-1H-benzo[d]imidazole (50 mg, 0.034 mmol) in 4 M HCl/dioxane (40 mL) was stirred for 4 h at 60° C. The reaction was diluted with water (40 mL) and neutralized with NaHCO$_3$ to pH 6. and extracted with ethyl acetate (200 mL). The organic layer was washed with water (50 mL×2), dried (Na$_2$SO$_4$), filtered and concentrated in vacuo, the crude product was purified by prep-HPLC (TFA) to afford 1-(5,6-dichloro-4-(cyclohexylmethoxy)-1H-benzo[d]imidazol-2-yl)ethane-1,2-diol I-325 as a white solid (20 mg, 0.0171 mmol, 50%). ESI-MS (EI+, m/z): 359.0 [M+H]$^+$. $^1$H NMR (500 MHz, DMSO) δ 12.53-12.63 (m, 1H), 7.29-7.32 (m, 1H), 5.88-5.89 (m, 1H), 4.47-4.92 (m, 4H), 3.81-3.82 (m, 2H), 1.72-1.87 (m, 6H), 1.72-1.87 (m, 6H), 1.20-1.25 (m, 5H).

Example 206: 6-chloro-5-(4-chlorobenzyloxy)-1H-benzo[d]imidazole-2-carboxylic acid, I-343

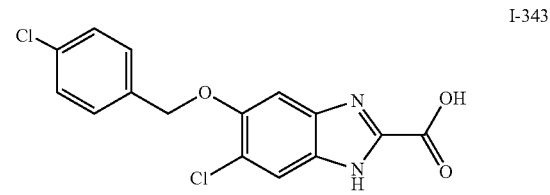 [SMILES: O=C(O)c1nc2cc(OCc3ccc(Cl)cc3)c(Cl)cc2[nH]1]

I-343

Synthetic Scheme:

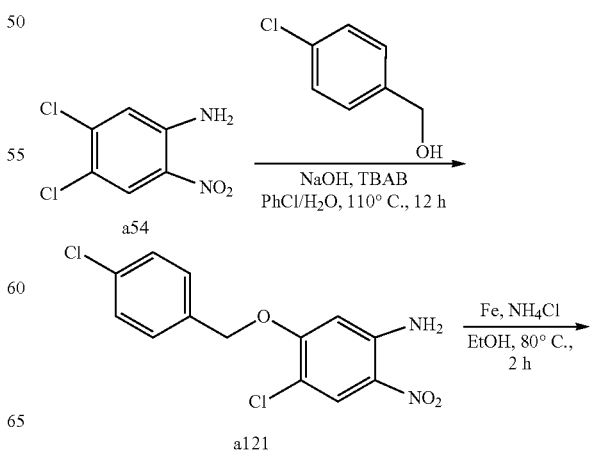

663
-continued

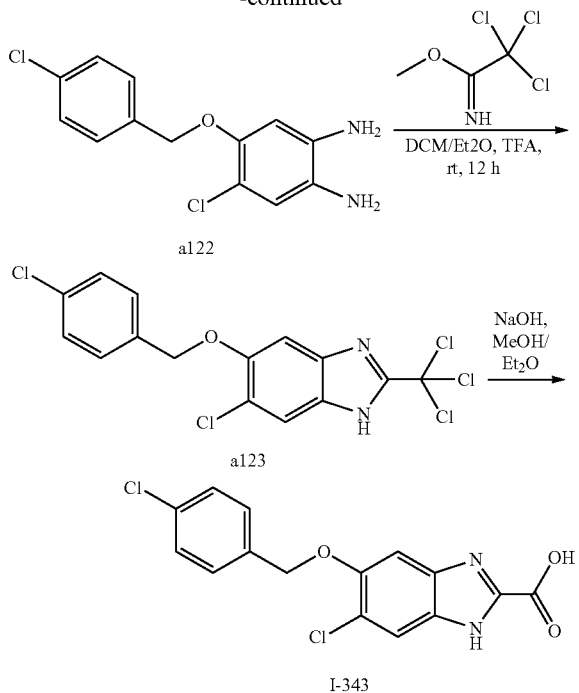

Procedures and Characterization:

Step 1:
4-chloro-5-(4-chlorobenzyloxy)-2-nitroaniline

A mixture of 4,5-dichloro-2-nitroaniline (200 mg, 0.80 mmol), (4-chlorophenyl)methanol (100 mg, 0.80 mmol), NaOH (100 mg, 2.39 mmol) and TBAB (20 mg, 0.08 mmol) in chlorobenzene/H$_2$O (5 mL/10 mL) was stirred at 110° C. for 12 h. It was diluted with EtOAc (100 ml) and water (100 ml) and filtered to give 4-chloro-5-(4-chlorobenzyloxy)-2-nitroaniline (100 mg) as a pale yellow solid.

Step 2: 3,4-dichloro-5-(4-chlorobenzyloxy)benzene-1,2-diamine

A mixture of 4-chloro-5-(4-chlorobenzyloxy)-2-nitroaniline (1.5 g, 5.0 mmol), Fe (13.0 g, 25 mmol) in EtOH (20.00 mL) and NH$_4$Cl (3 mL) was stirred at 80° C. for 2 h. It was extracted with EtOAc (100 ml), washed with water (100 ml*3), brine (100 ml*1), dried, filtered and concentrated to give 3,4-dichloro-5-(4-chlorobenzyloxy)benzene-1,2-diamine (1.3 g) as a pale yellow solid.

Step 3: 6-chloro-5-(4-chlorobenzyloxy)-2-(trichloromethyl)-1H-benzo[d]imidazole

To a solution of 4-chloro-5-(4-chlorobenzyloxy)benzene-1,2-diamine (282 mg, 1 mmol) in DCM (4 mL) and ethyl ether (1.6 mL) at 0° C. was added methyl 2,2,2-trichloroacetimidate (260 mg, 1.5 mmol) and TFA (1.6 mL). The resulting reaction mixture was stirred at 15° C. for 20 h. The reaction was quenched by adding ice, and white solid was formed, and then filtered. The solid was washed with excess DCM. The filtrate was concentrated in vacuo at 20° C. to give the residue (200 mg) as a tan gum. The residue was used directly in the next step. ESI-MS (EI+, m/z):

Step 4: 6-chloro-5-(4-chlorobenzyloxy)-1H-benzo[d]imidazole-2-carboxylic acid, I-343

To the solution of 6-chloro-5-(4-chlorobenzyloxy)-2-(trichloromethyl)-1H-benzo[d]imidazole (410 mg, 1 mmol) in THF (5 mL), H$_2$O (1 mL) was added Li OH (100 mg, 4.2 mmol). The resulting reaction mixture stirred at 15° C. for 8 h. The reaction was neutralized to pH=6~7, and then extracted with EtOAc. The organic phase was washed with brine, dried over sodium sulfate and concentrated to afford crude product. The crude product was purified by prep-HPLC (base column) to give 6-chloro-5-(4-chlorobenzyloxy)-1H-benzo[d]imidazole-2-carboxylic acid I-343 as a white solid (yield 8.3%). MS (EI–, m/z): 337, 339[M+H]$^+$.
$^1$H-NMR (DMSO-d6,400 MHz): $^1$H NMR (400 MHz, DMSO) δ 7.53 (m, 5H), 7.21 (s, 1H), 5.19 (s, 2H).

Example 207: 6,7-dichloro-5-(4-chlorobenzyloxy)-1H-benzo[d]imidazole-2-carboxylic acid, I-338

Synthetic Scheme:

Procedures and Characterization:

Step 1: 6,7-dichloro-5-(4-chlorobenzyloxy)-2-(trichloromethyl)-1H-benzo[d]imidazole The procedure for 6,7-dichloro-5-(4-chlorobenzyloxy)-2-(trichloromethyl)-1H-benzo[d]imidazole was the same as 6-chloro-5-(4-chlorobenzyloxy)-2-(trichloromethyl)-1H-benzo[d]imidazole (a123). ESI-MS (EI$^+$, m/z): 443

Step 2: 6,7-dichloro-5-(4-chlorobenzyloxy)-1H-benzo[d]imidazole-2-carboxylic acid The procedure for 6,7-dichloro-5-(4-chlorobenzyloxy)-1H-benzo[d]imidazole-2-carboxylic acid I-338 was the same as I-343. MS (EI–, m/z): 371,373 [M+H]$^+$.

$^1$H-NMR (DMSO-d6,400 MHz): $^1$H NMR (400 MHz, DMSO) δ 7.41 (d, J=8.0 Hz, 2H)), 7.38 (d, J=8.0 Hz, 2H)), 7.13 (s, 1H), 5.10 (s, 2H).

Example 208: 5,6-dichloro-4-(4-chlorobenzyloxy)-1H-benzo[d]imidazole-2-carboxylic acid, I-330

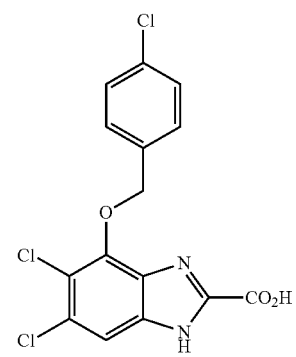

I-330

Synthetic Scheme:

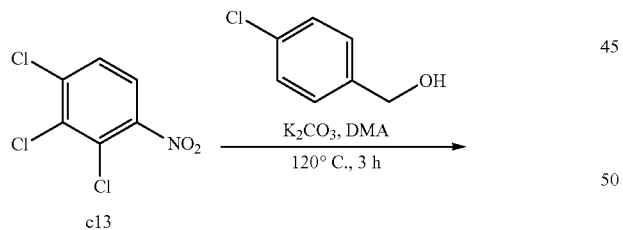

c13

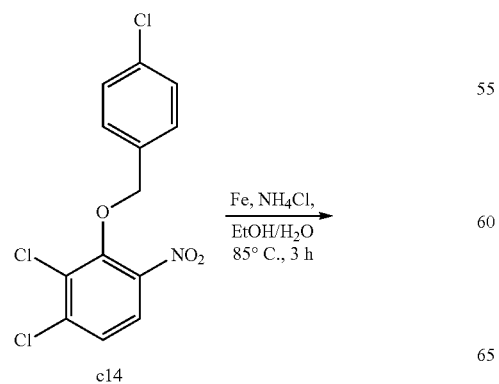

c14

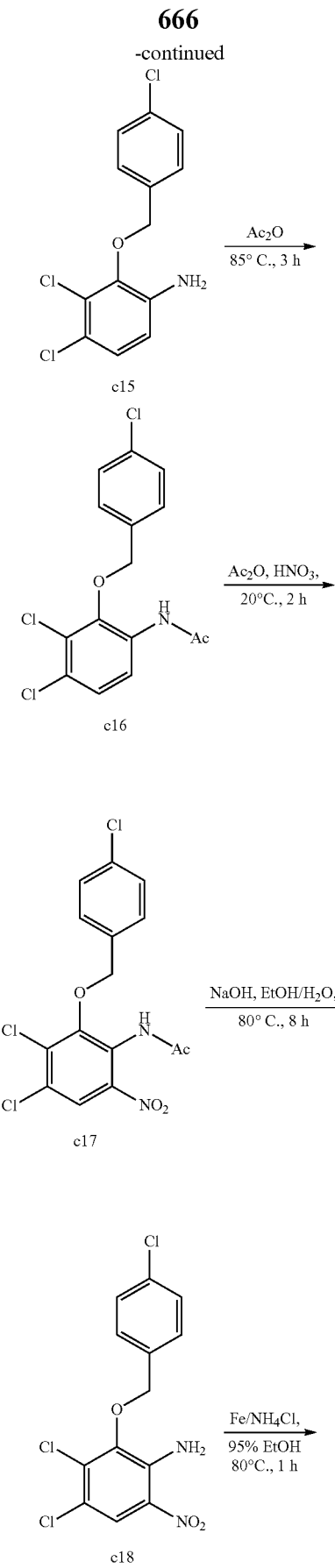

-continued

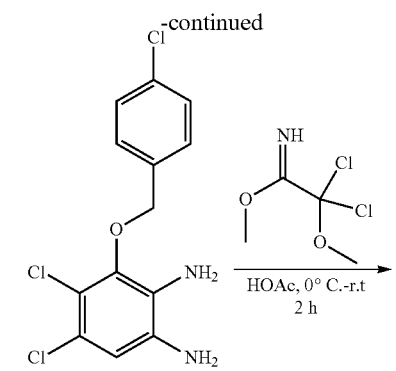

c19

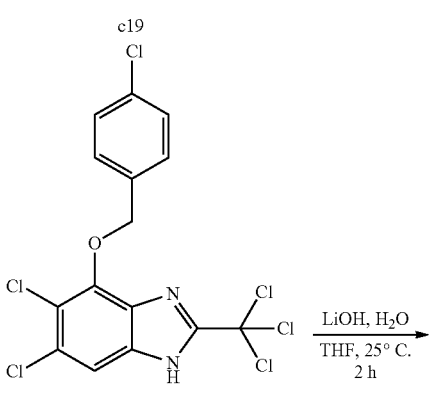

c20

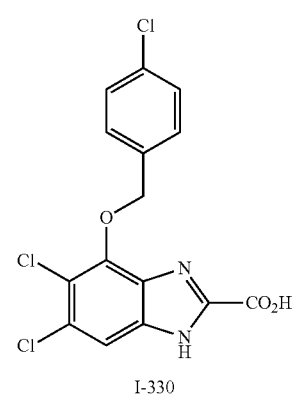

I-330

Procedures and Characterization:

Step 1:
1,2-dichloro-3-(4-chlorobenzyloxy)-4-nitrobenzene

A mixture of 1,2,3-trichloro-4-nitrobenzene (100 mg, 0.442 mmol), (4-chlorophenyl)methanol (126 mg, 0.884 mmol), $K_2CO_3$ (246 mg, 1.768 mmol) in DMA (3 mL) was kept stirring at 120° C. for 3 h. The mixture was cooled down to 5° C., poured into water (70 mL), extracted with EtOAc (50 mL×3). The organic layer was washed with water (30 mL×2), sat. NaCl (30 mL), then dried over $Na_2SO_4$ for 20 min, filtrated and concentrated by vacuo, the residue was purified by prep-HPLC to afford product 2,3-dichloro-1-(4-chlorobenzyloxy)-4-nitrobenzene (60 mg, 0.18 mmol, 42% yield) as a white solid, and product 1,2-dichloro-3-(4-chlorobenzyloxy)-4-nitrobenzene (19 mg, 0.06 mmol, 13.3% yield). $^1$H NMR (400 MHz, DMSO) of product 2,3-dichloro-1-(4-chlorobenzyloxy)-4-nitrobenzene δ 8.16 (d, J=9.3 Hz, 1H), 7.50 (s, 5H), 5.39 (s, 2H). $^1$H NMR (400 MHz, DMSO) of product 1,2-dichloro-3-(4-chlorobenzyloxy)-4-nitrobenzene δ 8.02 (d, J=9.0 Hz, 1H), 7.74 (d, J=9.0 Hz, 1H), 7.50 (s, 4H), 5.16 (s, 2H).

Step 2:
3,4-dichloro-2-(4-chlorobenzyloxy)benzenamine

To a solution of 1,2-dichloro-3-(4-chlorobenzyloxy)-4-nitrobenzene (4 g, 12 mmol) in a mix of ethanol (40 mL) and water (8 mL) was added Fe (6.4 g, 120 mmol) followed by ammonium chloride (6.4 g, 120 mmol) and stirred at 80° C. for 3 h. The solution was filtrated, then diluted with water (200 mL) and extracted with ethyl acetate (300 mL). The organic phase was washed with water (100 mL×2), and brine (100 mL), dried ($Na_2SO_4$), filtered and concentrated in vacuo, the crude product was purified by chromatography (silica, ethyl acetate/petroleum ether=1/5) to afford 3,4-dichloro-2-(4-chlorobenzyloxy)benzenamine (3.5 g, 11.56 mmol, 96%) as a white solid. ESI-MS (EI+, m/z): 301.96 $[M+H]^+$.

Step 3: N-(3,4-dichloro-2-(4-chlorobenzyloxy)phenyl)acetamide

A solution of 3,4-dichloro-2-(4-chlorobenzyloxy)benzenamine (3.5 g, 11.56 mmol) in acetic anhydride (35.00 mL) was stirred for 3 h at 85° C. The solution was diluted with water (200 mL) and extracted with ethyl acetate (100 mL). The organic phase was washed with water (100 mL×2), and brine (100 mL), dried ($Na_2SO_4$), filtered and concentrated in vacuo, the crude product was purified by chromatography (silica, ethyl acetate/petroleum ether=1/5) to afford N-(3,4-dichloro-2-(4-chlorobenzyloxy)phenyl)acetamide (2.6 g, 8 mmol, 70%) as a white solid. ESI-MS (EI+, m/z): 342.99 $[M+H]^+$.

Step 4: N-(3,4-dichloro-2-(4-chlorobenzyloxy)-6-nitrophenyl)acetamide

To a solution of N-(3,4-dichloro-2-(4-chlorobenzyloxy)phenyl)acetamide (2.6 g, 8 mmol) in acetic anhydride (35.00 mL) was added nitric acid (15.62 g, 248 mmol) dropwise at 0° C. and stirred for 2 h at 20° C. The solution was poured into ice-water (200 mL) and extracted with ethyl acetate (300 mL). The organic phase was washed with water (100 mL×2), and brine (100 mL), dried ($Na_2SO_4$), filtered and concentrated in vacuo, the crude product was purified by chromatography (silica, ethyl acetate/petroleum ether=1/5) to afford N-(3,4-dichloro-2-(4-chlorobenzyloxy)-6-nitrophenyl)acetamide (750 mg, 2 mmol, 25%) as a yellow solid. ESI-MS (EI+, m/z): 411 $[M+Na]^+$. H NMR (400 MHz, DMSO) δ 10.27 (s, 1H), 8.12 (s, 1H), 7.50 (q, J=8.4 Hz, 4H), 5.01 (s, 2H), 2.00 (s, 3H).

Step 5: 3,4-dichloro-2-(4-chlorobenzyloxy)-6-nitrobenzenamine

To a solution of N-(3,4-dichloro-2-(4-chlorobenzyloxy)-6-nitrophenyl)acetamide (750 mg, 2 mmol) in a mix of ethanol (10.00 mL) and water (10.00 mL) was added sodium hydroxide (320 mg, 8 mmol) and stirred for 8 h at 80° C. The solution was adjusted pH to 7, diluted with water (200 mL) and extracted with ethyl acetate (300 mL). The organic phase was washed with water (100 mL×2), and brine (100 mL), dried ($Na_2SO_4$), filtered and concentrated in vacuo, the crude product (250 mg, 0.72 mmol, 36%) was used directly for the next step.

Step 6: 4,5-dichloro-3-(4-chlorobenzyloxy)benzene-1,2-diamine

To a solution of 3,4-dichloro-2-(4-chlorobenzyloxy)-6-nitrobenzenamine (250 mg, 0.72 mmol) in a mix of ethanol (8 mL) and water (2 mL) was added Fe (403 mg, 7.2 mmol) followed by ammonium chloride (403 mg, 7.2 mmol) and stirred at 80° C. for 1 h. The solution was filtrated, then diluted with water (200 mL) and extracted with ethyl acetate (300 mL). The organic phase was washed with water (100 mL×2), and brine (100 mL), dried (Na$_2$SO$_4$), filtered and concentrated in vacuo, the crude product was used directly for the next step. ESI-MS (EI+, m/z): 316.97 [M+H]$^+$.

Step 7: 5,6-dichloro-2-(2-(4-nitrophenoxy)ethyl)-1H-benzo[d]imidazole

A solution of 5,6-dichloro-4-(4-chlorobenzyloxy)-2-(trichloromethyl)-1H-benzo[d]imidazole (200 mg, 1.14 mmol) in LiOH (2 ml, 20%) and THF (5 ml) was stirred at 25° C. for 2 h, concentrated in vacuo, the crude product was purified by prep-HPLC (TFA) to 5,6-dichloro-4-(4-chlorobenzyloxy)-1H-benzo[d]imidazole-2-carboxylic acid (14.5 mg, 0.039 mmol, 3.9%) as a white solid. ESI-MS (EI+, m/z): 371 [M+H]$^+$.

Step 8: 5,6-dichloro-4-(4-chlorobenzyloxy)-1H-benzo[d]imidazole-2-carboxylic acid, I-330

A solution of 4,5-dichloro-3-(4-chlorobenzyloxy)benzene-1,2-diamine (200 mg, 1.14 mmol) and 2,2,2-trichloroacetaldehyde (120 mg, 1.14 mmol) in HOAc (2 ml,) was stirred at 25° C. for 2 h, concentrated in vacuo, the crude product was purified by prep-HPLC (TFA) to 5,6-dichloro-4-(4-chlorobenzyloxy)-2-methyl-1H-benzo[d]imidazole I-330 (100 mg, 0.017 mmol, 40%) as a white solid. ESI-MS (EI+, m/z): 442.8 [M+H]$^+$. $^1$H NMR (500 MHz, DMSO) δ 7.56-7.58 (m, 2H), 7.43 (s, 1H), 7.34-7.36 (m, 2H), 5.76 (s, 2H).

Example 209: 5,6-dichloro-4-(cyclohexylmethoxy)-1H-benzo[d]imidazole-2-carboxylic acid, I-342

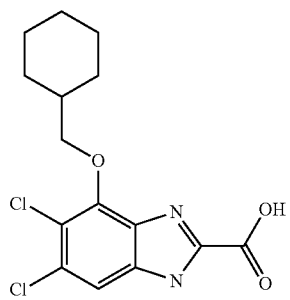

I-342

Synthetic Scheme:

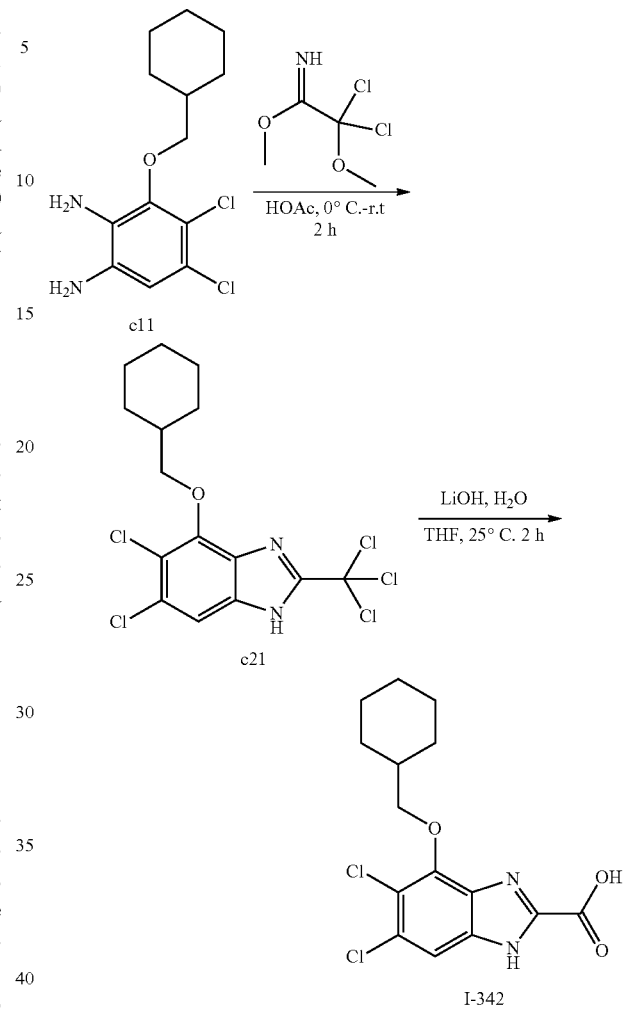

Procedures and Characterization:

Step 1: 5,6-dichloro-4-(cyclohexylmethoxy)-2-(trichloromethyl)-1H-benzo[d]imidazole A solution of 4,5-dichloro-3-(cyclohexylmethoxy)benzene-1,2-diamine (200 mg, 1.14 mmol) and 2,2,2-trichloroacetaldehyde (120 mg, 1.14 mmol) in HOAc (2 ml,) was stirred at 25° C. for 2 h, concentrated in vacuo, the crude product was purified by prep-HPLC (TFA) to 5,6-dichloro-4-(4-chlorobenzyloxy)-2-methyl-1H-benzo[d]imidazole (100 mg, 0.017 mmol, 40%) as a white solid.

Step 2: 5,6-dichloro-4-(cyclohexylmethoxy)-1H-benzo[d]imidazole-2-carboxylic acid, I-342

A solution of 5,6-dichloro-4-(4-chlorobenzyloxy)-2-(trichloromethyl)-1H-benzo[d]imidazole (200 mg, 1.14 mmol) in LiOH aqueous solution (2 ml, 20%) and THF (5 ml) was stirred at 25° C. for 2 h, concentrated in vacuo, the crude product was purified by prep-HPLC (TFA) to 5,6-dichloro-4-(cyclohexylmethoxy)-1H-benzo[d]imidazole-2-carboxylic acid I-342 (11.0 mg, 0.039 mmol, 3.9%) as a white solid. ESI-MS (EI+, m/z): 343 [M+H]$^+$. NMR (500 MHz, MeOD) δ 7.40 (s, 1H), 4.43-4.47 (m, 2H), 1.72-2.00 (m, 6H), 1.15-1.34 (m, 5H).

Example 210: 6,7-dichloro-5-(4-chlorobenzyloxy)-N-((1-methylpiperidin-4-yl)methyl)-1H-benzo[d]imidazole-2-carboxamide, I-337

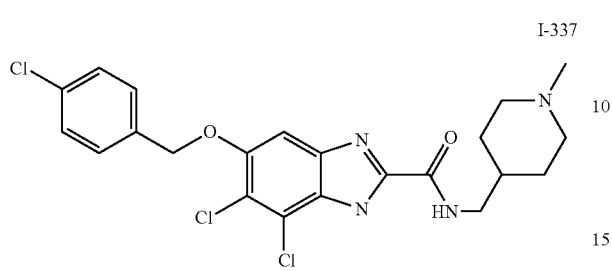

Example 211: 2-[5-chloro-6-[(4-chlorophenyl)methoxy]-1H-benzimidazol-2-yl]-1-(4-methylpiperazin-1-yl)ethanone, I-332

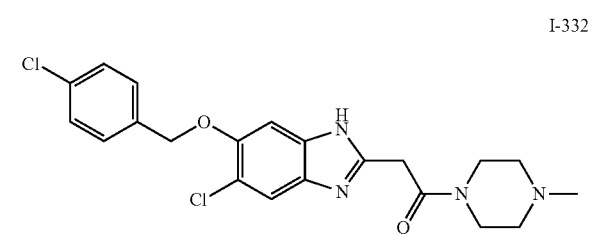 [SMILES: CN1CCN(C(=O)Cc2nc3cc(Cl)c(OCc4ccc(Cl)cc4)cc3[nH]2)CC1]

Synthetic Scheme:

Synthetic Scheme:

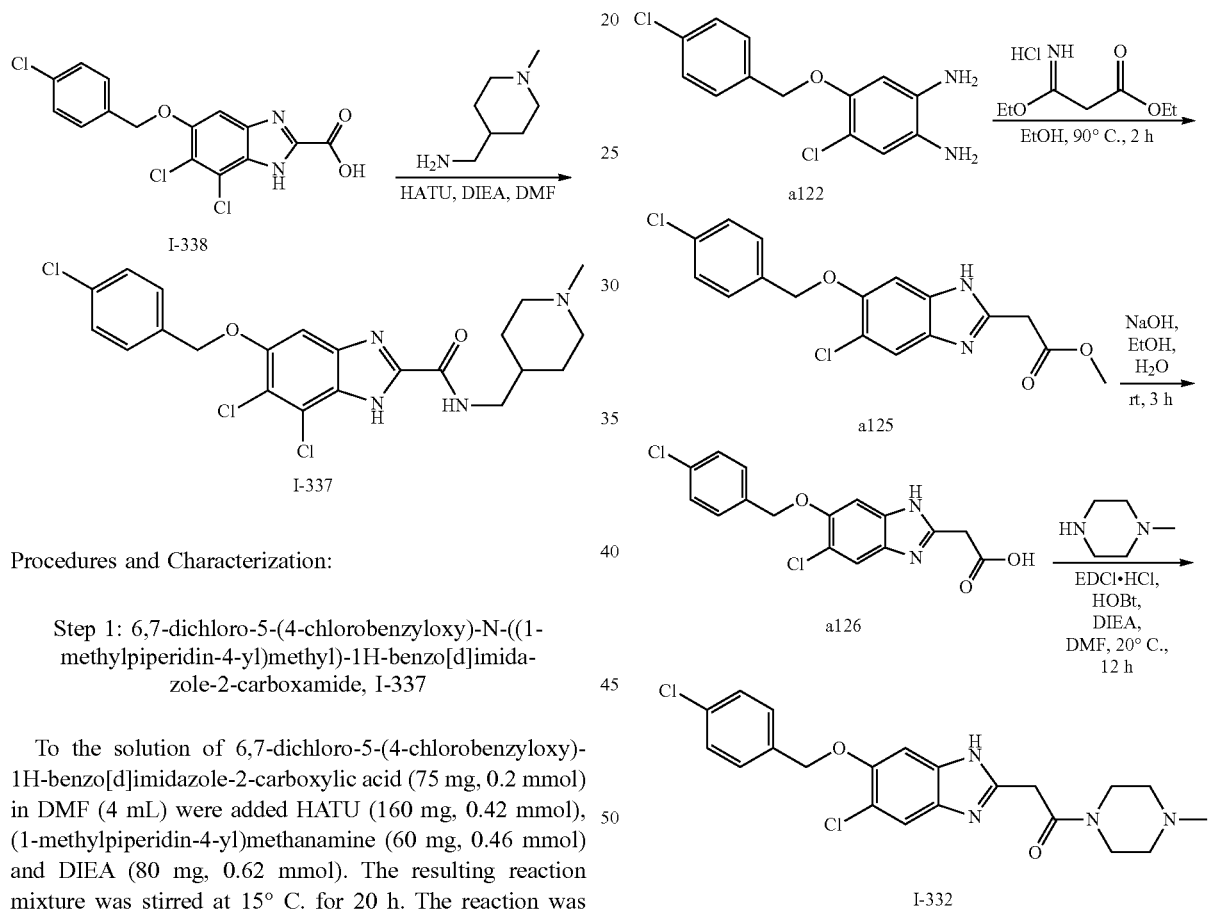

Procedures and Characterization:

Step 1: 6,7-dichloro-5-(4-chlorobenzyloxy)-N-((1-methylpiperidin-4-yl)methyl)-1H-benzo[d]imidazole-2-carboxamide, I-337

To the solution of 6,7-dichloro-5-(4-chlorobenzyloxy)-1H-benzo[d]imidazole-2-carboxylic acid (75 mg, 0.2 mmol) in DMF (4 mL) were added HATU (160 mg, 0.42 mmol), (1-methylpiperidin-4-yl)methanamine (60 mg, 0.46 mmol) and DIEA (80 mg, 0.62 mmol). The resulting reaction mixture was stirred at 15° C. for 20 h. The reaction was quenched by adding H$_2$O (10 ml), and then extracted with EtOAc (20 mL×2). The combined organics was concentrated in vacuo to afford the residue. The residue was purified by prep-HPLC (formic acid) to give 6,7-dichloro-5-(4-chlorobenzyloxy)-N-((1-methylpiperidin-4-yl)methyl)-1H-benzo[d]imidazole-2-carboxamide I-337 (8.9 mg, 10.2%) as a white solid. MS (EI−, m/z): 481,483 [M+H]⁻.

$^1$H-NMR (DMSO-d6,400 MHz): δ 13.55 (br s), 8.91 (t, J=7.2 Hz, 1H), 7.52 (m, 4H), 7.20 (s, 1H), 5.28 (s, 2H), 3.19 (t, J=6.0 Hz, 2H), 2.74 (d, J=10.8 Hz, 2H), 2.13 (s, 3H), 1.82 (t, J=11.2 Hz, 2H), 1.56 (m, 3H), 1.19 (m, 2H)

Procedures and Characterization:

Step 1: ethyl 2-(5-chloro-6-(4-chlorobenzyloxy)-1H-benzo[d]imidazol-2-yl)acetate A mixture of 4-chloro-5-(4-chlorobenzyloxy)benzene-1,2-diamine (200.00 mg, 0.71 mmol), ethyl 3-ethoxy-3-iminopropanoate hydrochloride (146 mg, 0.75 mmol) in EtOH (5 mL) was heated at for 12 h. The mixture was used for next step directly.

ESI-MS (EI⁺, m/z): 379[M+H]⁺.

Step 2: 2-[5-chloro-6-[(4-chlorophenyl)methoxy]-1H-benzimidazol-2-yl]-1-(4-methylpiperazin-1-yl)ethanone A mixture of ethyl 2-(5-chloro-6-(4-chlorobenzyloxy)-1H-benzo[d]imidazol-2-yl)acetate (200.00 mg, 0.71 mmol) and NaOH (170 mg, 2.1 mmol) in EtOH was stirred at rt overnight. The mixture was used for next step directly. ESI-MS (EI$^+$, m/z): 351[M+H]$^+$.

Step 3: 2-[5-chloro-6-[(4-chlorophenyl)methoxy]-1H-benzimidazol-2-yl]-1-(4-methylpiperazin-1-yl)ethanone, I-332

A mixture of 2-[5-chloro-6-[(4-chlorophenyl)methoxy]-1H-benzimidazol-2-yl]acetic acid (100.00 mg, 284.75 μmol), 1-methylpiperazine (34.22 mg, 341.70 μmol), EDCI.HCl (65.50 mg, 341.70 μmol), HOBt (46.17 mg, 341.70 μmol) was stirred at rt overnight. It was extracted with EtOAc (20 ml), washed with water (20 ml*3), brine (20 ml*1), dried, filtered and concentrated to give a crude. It was purified by prep-HPLC to give 2-[5-chloro-6-[(4-chlorophenyl)methoxy]-1H-benzimidazol-2-yl]-1-(4-methylpiperazin-1-yl)ethanone I-332 (13.10 mg, 30.23 μmol, 10.62% yield, 100% purity). ESI-MS (EI$^+$, m/z): 433[M+H]$^+$. $^1$H NMR (500 MHz, DMSO) δ 7.55 (s, 1H), 7.53 (m, 2H), 7.41 (m, 2H), 7.23 (s, 1H), 5.29 (s, 2H), 3.72 (m, 4H), 3.32 (s, 2H), 2.62 (m, 4H), 2.44 (s, 3H).

Example 212: (1-((1H-1,2,4-triazol-3-yl)methyl)-4-(2-chlorophenoxy)-1H-benzo[d]imidazol-2-yl)methanol, I-407

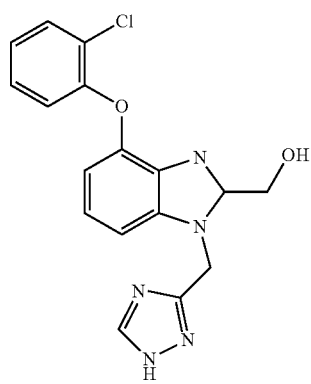

I-407

Synthetic Scheme:

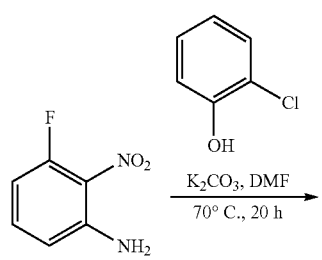

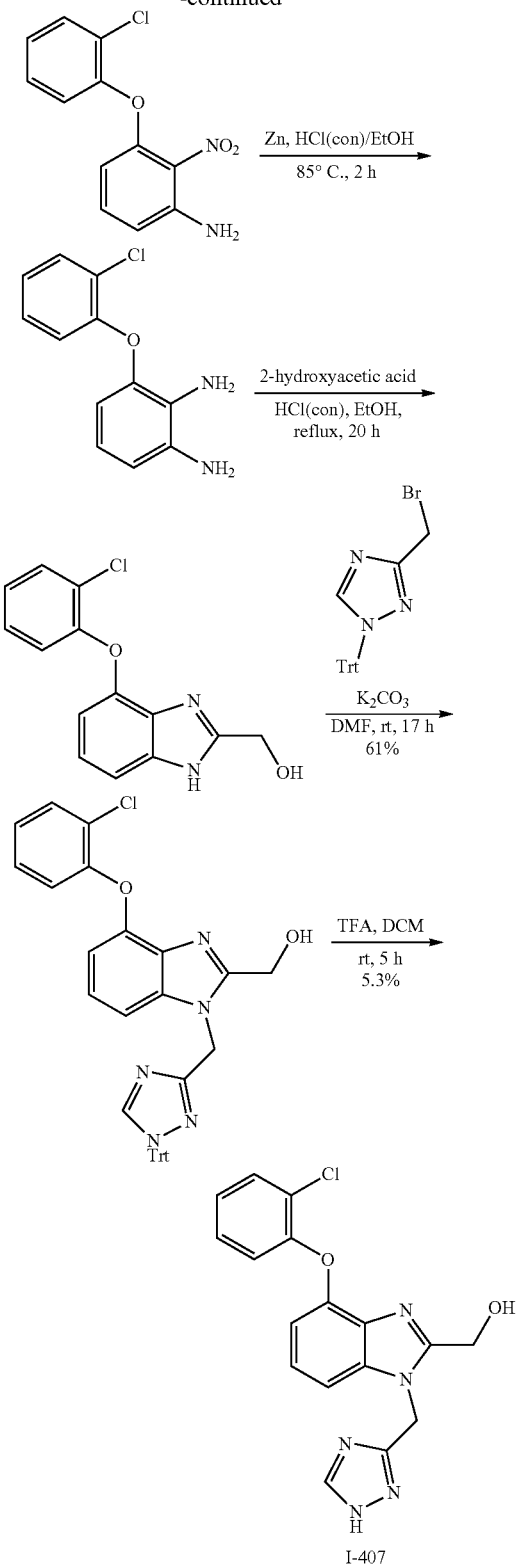

Procedures and Characterization:

Step 1: 3-(2-chlorophenoxy)-2-nitrobenzenamine 3-fluoro-2-nitrobenzenamine (1 g, 6.4 mmol) and 2-chlorophenol (0.9 g, 7.0 mmol) was dissolved in dry DMF (20 mL) and K₂CO₃ (1.8 g, 12.8 mmol) was added. The reaction mixture was stirred at 70° C. for 20 h. The mixture was extracted between EtOAc and brine. The combined organic layers were concentrated and purified by SGC (PE: EtOAc=0-35%) to give 3-(2-chlorophenoxy)-2-nitrobenzenamine (1.2 g, 4.5 mmol, 71%) as a yellow dope. ESI-MS (EI⁺, m/z): 265.2 [M+H]⁺.

Step 2: 3-(2-chlorophenoxy)benzene-1,2-diamine 3-(2-chlorophenoxy)-2-nitrobenzenamine (1.2 g, 4.5 mmol) and Zn (2 g, 30.7 mmol) in EtOH (20 mL) was added HCl (20 mL). The reaction mixture was stirred at 85° C. for 2.5 h. The mixture was used to next step as a yellow solution without purification. ESI-MS (EI⁻, m/z): 235.0 [M+H]⁺.

Step 3: (4-(2-chlorophenoxy)-1H-benzo[d]imidazol-2-yl)methanol

A solution of 3-(2-chlorophenoxy)benzene-1,2-diamine (crude from above) was added 2-hydroxyacetic acid (1.4 g, 18.0 mmol) and stirred at 100° C. for 25 h. The solution was adjust pH to 7-8 by 40% NaOH, concentrated and extracted between EtOAc and water. The combined organic layers were dried and concentrated to give (4-(2-chlorophenoxy)-1H-benzo[d]imidazol-2-yl)methanol (310 mg, 1.1 mmol, 25%) as a brown dope without further purification. ESI-MS (EI⁺, m/z): 275.0 [M+H]⁺.

Step 4: (4-(2-chlorophenoxy)-1-((1-trityl-1H-1,2,4-triazol-3-yl)methyl)-1H-benzo[d]imidazol-2-yl)methanol (4-(2-chlorophenoxy)-1H-benzo[d]imidazol-2-yl)methanol (310 mg, 1.1 mmol) and 3-(bromomethyl)-1-trityl-1H-1,2,4-triazole (540 mg, 1.4 mmol) was dissolved in dry DMF (4.0 mL) and K₂CO₃ (311 mg, 2.3 mmol) was added. The reaction mixture was stirred at rt for 17 h. The mixture was partitioned between EtOAc and brine. The combined organic layers were concentrated and purified by SGC (PE:EtOAc=0-100%) to give (4-(2-chlorophenoxy)-1-((1-trityl-1H-1,2,4-triazol-3-yl)methyl)-1H-benzo[d]imidazol-2-yl)methanol (110 mg, 0.18 mmol, 16%) as a yellow dope. ESI-MS (EI⁺, m/z): 598.2 [M+H]⁺.

Step 5: (1-((1H-1,2,4-triazol-3-yl)methyl)-4-(2-chlorophenoxy)-1H-benzo[d]imidazol-2-yl)methanol, I-407

(4-(2-chlorophenoxy)-1-((1-trityl-1H-1,2,4-triazol-3-yl)methyl)-1H-benzo[d]imidazol-2-yl)methanol (110 mg, 0.18 mmol) in DCM (4.00 mL) was added TFA (4 mL) and stirred at rt for 5 h. The mixture was purified prep-HPLC to give (1-((1H-1,2,4-triazol-3-yl)methyl)-4-(2-chlorophenoxy)-1H-benzo[d]imidazol-2-yl)methanol I-407 (3.5 mg, 5.3%) as a white solid. ESI-MS (EI+, m/z): 356.0 [M+H ¹H NMR (400 MHz, MeOD) δ 8.08 (s, 1H), 7.34 (ddd, J=12.3, 8.0, 1.1 Hz, 2H), 7.11 (td, J=7.8, 1.6 Hz, 1H), 7.06-6.99 (m, 2H), 6.75 (dd, J=8.1, 1.5 Hz, 1H), 6.40 (d, J=8.0 Hz, 1H), 5.85 (s, 2H), 4.82 (s, 2H).

Example 213: (6-chloro-5-phenethoxy-1H-benzo[d]imidazol-2-yl)methanol, I-483

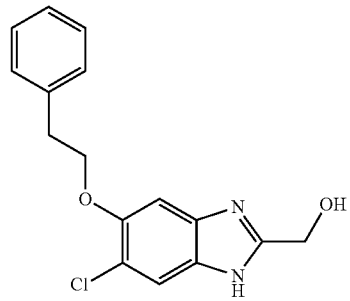

I-483

Synthetic Scheme:

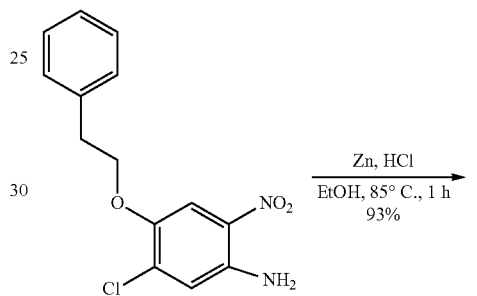

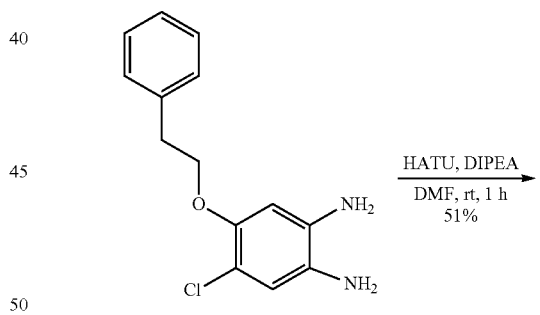

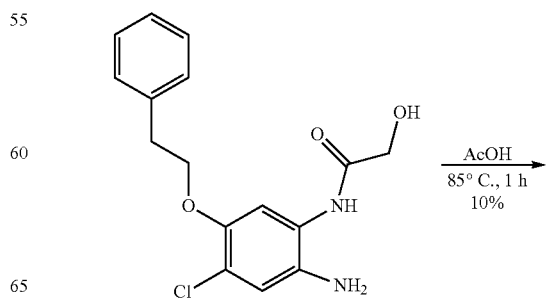

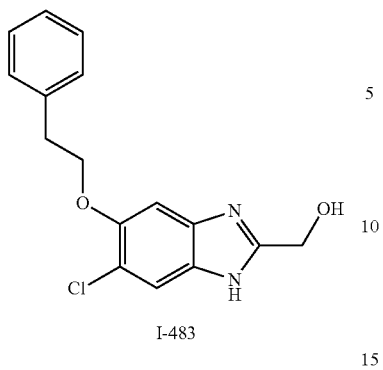

I-483

Procedures and Characterization:

Step 1: 4-chloro-5-phenethoxybenzene-1,2-diamine 5-chloro-2-nitro-4-phenethoxybenzenamine (2.2 g, 7.5 mmol) and Zn (4 g, 61.5 mmol) in EtOH (100 mL) was added HCl (6 mL). The reaction mixture was stirred at 85° C. for 1 h. The mixture was concentrated and extracted between EtOAc and H$_2$O. The combined organic layers were dried and concentrated to give crude 4-chloro-5-phenethoxybenzene-1,2-diamine (1.8 g, 93%) as a yellow solid. ESI-MS (EI$^+$, m/z): 263.0 [M+H]$^+$.

Step 2: N-(2-amino-4-chloro-5-phenethoxyphenyl)-2-hydroxyacetamide 4-chloro-5-phenethoxybenzene-1,2-diamine (crude 1.8 g, 6.7 mmol) in DMF (40 mL) was added 2-hydroxyacetic acid (0.76 g, 10.1 mmol), HATU (5.06 g, 13.4 mmol), DIPEA (1.73 g, 13.4 mmol) and stirred at rt for 1 h. The mixture was stirred and H$_2$O (1 L) was added. The solid was filtered and dried by vacuo to give N-(2-amino-4-chloro-5-phenethoxyphenyl)-2-hydroxyacetamide (1.1 g, 51%) as a yellow solid. ESI-MS (EI$^+$, m/z): 321.0 [M+H]$^+$.

Step 3: (6-chloro-5-phenethoxy-1H-benzo[d]imidazol-2-yl)methanol, I-483

N-(2-amino-4-chloro-5-phenethoxyphenyl)-2-hydroxyacetamide (1.1 g, 3.4 mmol) in AcOH (20 mL) was stirred at 85° C. for 1 h. The solution was concentrated and added H$_2$O (60 mL) and EtOAc (20 mL). The mixture was stirred for 1 h, filtered, collected the solid and dried to give (6-chloro-5-phenethoxy-1H-benzo[d]imidazol-2-yl)methanol I-483 (100 mg, 10%) as a white solid. ESI-MS (EI+, m/z): 303.0 [M+H]+. $^1$H NMR (400 MHz, DMSO) δ 12.31 (d, J=25.7 Hz, 1H), 7.63-7.03 (m, 7H), 5.69 (d, J=5.3 Hz, 1H), 4.64 (d, J=5.3 Hz, 2H), 4.23 (s, 2H), 3.08 (d, J=5.5 Hz, 2H).

Example 214: (6-chloro-5-(4-chlorobenzyloxy)-1H-benzo[d]imidazol-2-yl)methanol, I-486

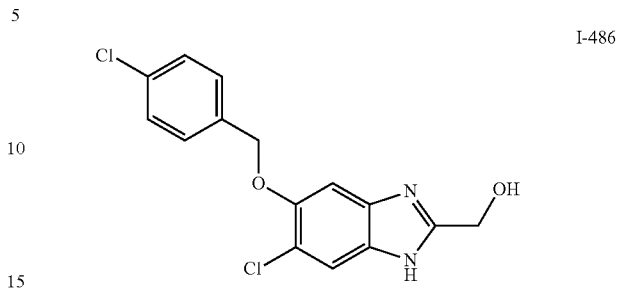

Synthetic Scheme:

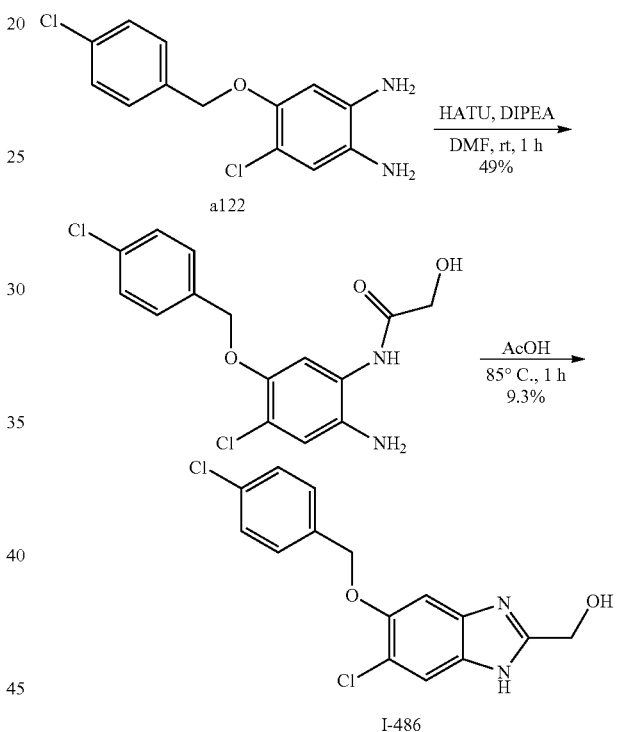

Procedures and Characterization:

Step 1: N-(2-amino-4-chloro-5-(4-chlorobenzyloxy)phenyl)-2-hydroxyacetamide 4-chloro-5-(4-chlorobenzyloxy)benzene-1,2-diamine (crude 2.7 g, 9.6 mmol) in DMF (60 mL) was added 2-hydroxyacetic acid (1.5 g, 19.2 mmol), HATU (7.3 g, 19.2 mmol), DIPEA (9.9 g, 76.8 mmol) and stirred at rt for 1 h. The mixture was stirred and H$_2$O (0.9 L) was added. The solid was filtered and dried by vacuo to give N-(2-amino-4-chloro-5-(4-chlorobenzyloxy)phenyl)-2-hydroxyacetamide (1.6 g, 49%) as a yellow solid. ESI-MS (EI$^+$, m/z): 341.0 [M+H]$^+$.

Step 2: (6-chloro-5-(4-chlorobenzyloxy)-1H-benzo[d]imidazol-2-yl)methanol, I-486

N-(2-amino-4-chloro-5-(4-chlorobenzyloxy)phenyl)-2-hydroxyacetamide (1.6 g, 4.7 mmol) in AcOH (20 mL) was stirred at 85° C. for 1 h. The solution was concentrated and added H₂O (50 mL) and EtOAc (50 mL). The mixture was stirred for 1 h, filtered, collected the solid and dried to give (6-chloro-5-(4-chlorobenzyloxy)-1H-benzo[d]imidazol-2-yl)methanol I-486 (140 mg, 9.3%) as a white solid. ESI-MS (EI+, m/z): 323.0 [M+H]+. ¹H NMR (500 MHz, DMSO) δ 12.47 (s, 1H), 7.75-7.39 (m, 5H), 7.25 (s, 1H), 5.79 (s, 1H), 5.21 (s, 2H), 4.64 (s, 2H).

Example 215: (1-((1H-1,2,4-triazol-3-yl)methyl)-4-(2-chlorophenoxy)-1H-benzo[d]imidazol-2-yl)methanol, I-482

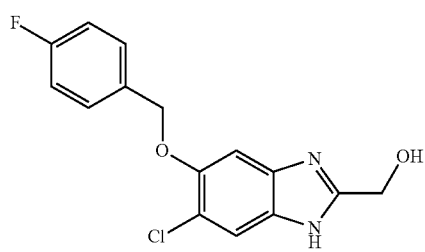

I-482

Synthetic Scheme:

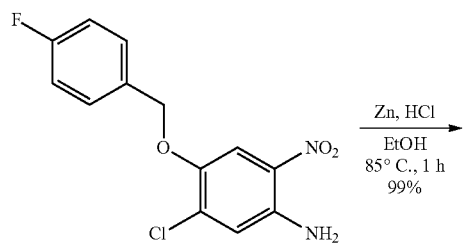

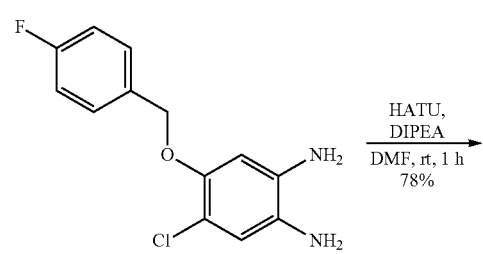

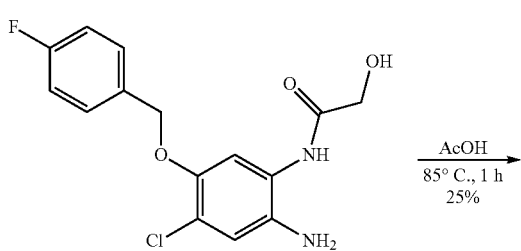

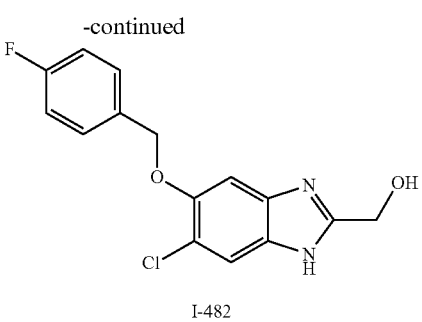

I-482

Procedures and Characterization:

Step 1: 4-chloro-5-(4-fluorobenzyloxy)benzene-1,2-diamine 5-chloro-4-(4-fluorobenzyloxy)-2-nitrobenzenamine (2 g, 6.7 mmol) and Zn (4 g, 61.5 mmol) in EtOH (100 mL) was added HCl (6 mL). The reaction mixture was stirred at 85° C. for 1 h. The mixture was concentrated and extracted between EtOAc and H₂O. The combined organic layers were dried and concentrated to give crude 4-chloro-5-(4-fluorobenzyloxy)benzene-1,2-diamine (1.9 g, 99%) as a yellow solid. ESI-MS (EI⁺, m/z): 267.0 [M+H]⁺.

Step 2: N-(2-amino-4-chloro-5-(4-fluorobenzyloxy)phenyl)-2-hydroxyacetamide 4-chloro-5-(4-fluorobenzyloxy)benzene-1,2-diamine (crude 1.9 g, 6.7 mmol) in DMF (40 mL) was added 2-hydroxyacetic acid (0.76 g, 10.1 mmol), HATU (5.06 g, 13.4 mmol), DIPEA (1.73 g, 13.4 mmol) and stirred at rt for 1 h. The mixture was stirred and H₂O (1 L) was added. The solid was filtered and dried by vacuo to give N-(2-amino-4-chloro-5-(4-fluorobenzyloxy)phenyl)-2-hydroxyacetamide (1.7 g, 78%) as a yellow solid. ESI-MS (EI⁺, m/z): 325.0 [M+H]⁺.

Step 3: (6-chloro-5-(4-fluorobenzyloxy)-1H-benzo[d]imidazol-2-yl)methanol, I-482

N-(2-amino-4-chloro-5-(4-fluorobenzyloxy)phenyl)-2-hydroxyacetamide (1.7 g, 5.2 mmol) in AcOH (20 mL) was stirred at 85° C. for 1 h. The solution was concentrated and added H₂O (60 mL) and EtOAc (20 mL). The mixture was stirred for 1 h, filtered, collected the solid and dried to give (6-chloro-5-(4-fluorobenzyloxy)-1H-benzo[d]imidazol-2-yl)methanol I-482 (410 mg, 25%) as a white solid. ESI-MS (EI⁺, m/z): 307.0 [M+H]⁺. ¹H NMR (400 MHz, DMSO) δ 12.35 (d, J=34.2 Hz, 1H), 7.65-7.44 (m, 3H), 7.39-7.15 (m, 3H), 5.80-5.62 (m, 1H), 5.19 (s, 2H), 4.64 (d, J=5.3 Hz, 2H).

Example 216: (6-chloro-5-(3-fluorobenzyloxy)-1H-benzo[d]imidazol-2-yl)methanol, I-484

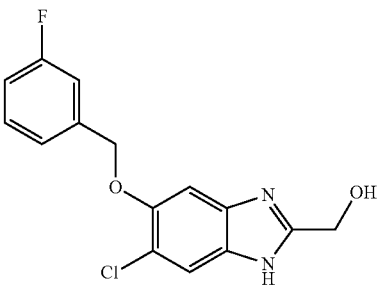

Synthetic Scheme:

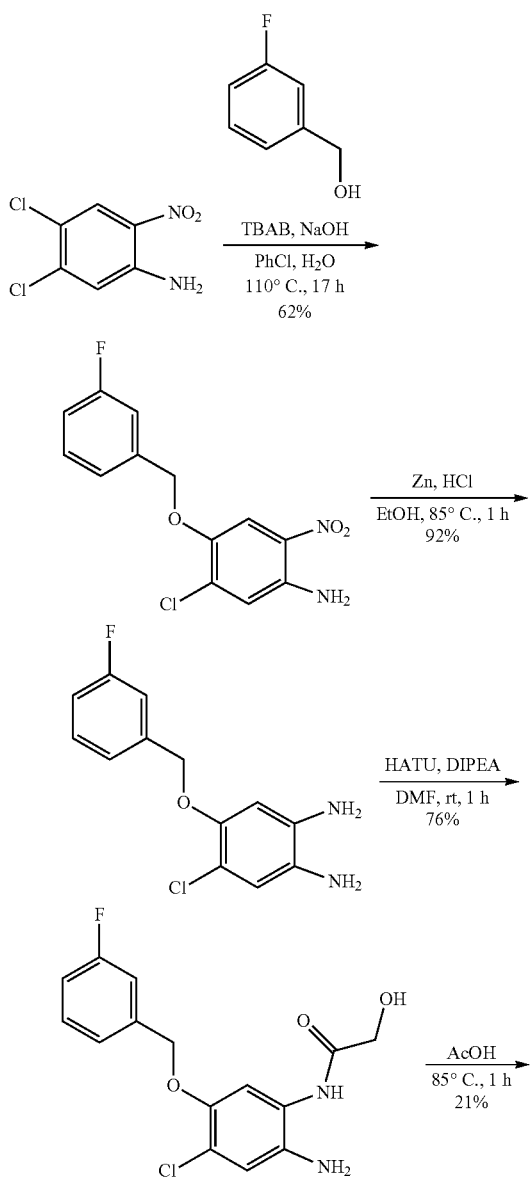

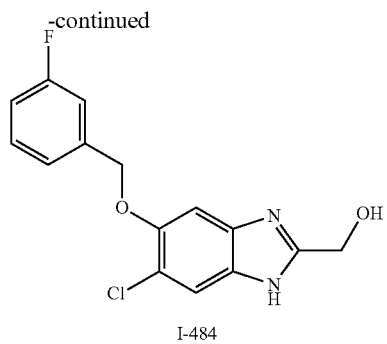

I-484

Procedures and Characterization:

Step 1:
5-chloro-4-(3-fluorobenzyloxy)-2-nitrobenzenamine

A mixture of (3-fluorophenyl)methanol (2.2 g, 17.4 mmol), 4,5-dichloro-2-nitrobenzenamine (3 g, 14.5 mmol), TBAB (340 mg, 1.02 mmol), NaOH (1.7 g, 43.5 mmol) in PhCl (13 mL) and H$_2$O (26 mL) was stirred at 110° C. for 17 h. The mixture was partitioned between EtOAc and brine. The combined organic layers were concentrated and purified by SGC (PE:EtOAc=3:1) to give 5-chloro-4-(3-fluorobenzyloxy)-2-nitrobenzenamine (2.7 g, 62%) as a yellow solid. ESI-MS (EI$^+$, m/z): 297.0 [M+H]$^-$.

Step 2:
4-chloro-5-(3-fluorobenzyloxy)benzene-1,2-diamine 5-chloro-4-(3-fluorobenzyloxy)-2-nitrobenzenamine (2.0 g, 6.7 mmol) and Zn (3.9 g, 60.8 mmol) in EtOH (58 mL) was added HCL (4 mL). The reaction mixture was stirred at 85° C. for 1 h. The mixture was concentrated and extracted between EtOAc and H$_2$O. The combined organic layers were dried and concentrated to give crude 4-chloro-5-(3-fluorobenzyloxy)benzene-1,2-diamine (1.8 g, 92%) as a brown oil. ESI-MS (EI$^+$, m/z): 267.0 [M+H]$^+$.

Step 3: N-(2-amino-4-chloro-5-(3-fluorobenzyloxy)phenyl)-2-hydroxyacetamide 4-chloro-5-(3-fluorobenzyloxy)benzene-1,2-diamine (crude 1.8 g, 6.7 mmol) in DMF (60 mL) was added 2-hydroxyacetic acid (0.68 g, 9.0 mmol), HATU (3.4 g, 9.0 mmol), DIPEA (3.0 g, 24.0 mmol) and stirred at rt for 1 h. The mixture was stirred and H$_2$O (1 L) was added. The solid was filtered and dried by vacuo to give N-(2-amino-4-chloro-5-(3-fluorobenzyloxy)phenyl)-2-hydroxyacetamide (1.5 g, 75%) as a yellow solid. ESI-MS (EI+, m/z): 325.1 [M+H]$^+$.

Step 4: (6-chloro-5-(3-fluorobenzyloxy)-1H-benzo[d]imidazol-2-yl)methanol, I-484

N-(2-amino-4-chloro-5-(3-fluorobenzyloxy)phenyl)-2-hydroxyacetamide (1.5 g, 4.5 mmol) in AcOH (20 mL) was stirred at 85° C. for 1 h. The solution was concentrated and added H$_2$O (50 mL) and EtOAc (50 mL). The mixture was stirred for 1 h, filtered, collected the solid and dried to give (6-chloro-5-(3-fluorobenzyloxy)-1H-benzo[d]imidazol-2-yl)methanol I-484 (300 mg, 21%) as a white solid. ESI-MS (EI+, m/z): 307.0 [M+H]+. $^1$H NMR (500 MHz, DMSO) δ 12.37 (s, 1H), 7.57 (s, 1H), 7.46 (dd, J=14.2, 7.8 Hz, 1H), 7.34 (t, J=8.4 Hz, 2H), 7.25 (s, 1H), 7.17 (t, J=8.5 Hz, 1H), 5.70 (t, J=5.6 Hz, 1H), 5.24 (s, 2H), 4.65 (d, J=5.6 Hz, 2H).

Example 217: (4-bromo-6-phenoxy-1H-benzo[d]imidazol-2-yl)methanol, I-428

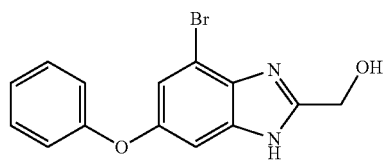

I-428

Synthetic Scheme:

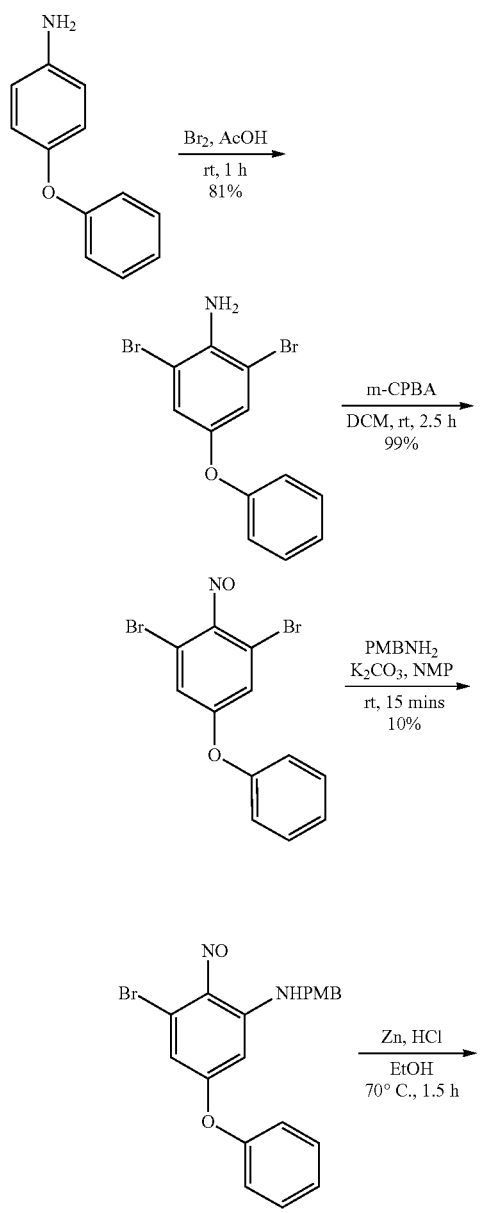

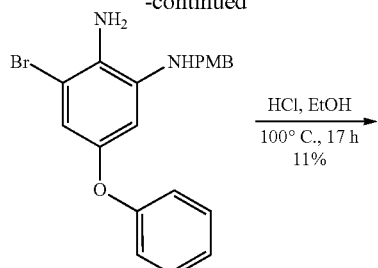

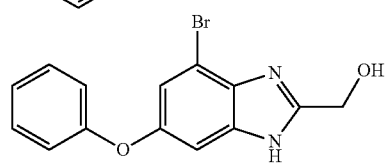

I-428

Procedures and Characterization:

Step 1: 2,6-dibromo-4-phenoxybenzenamine

A solution of 4-phenoxybenzenamine (8.0 g, 43.2 mmol) in AcOH (50 mL) was stirred and added Br2 (4.44 mL, 86.5 mmoL) at rt. The mixture was stirred at rt for 1 h, then, extracted between DCM and water. The organic layer was washed by aq.NaHCO$_3$, brine and concentrated to give crude residue. It was purified by SGC (PE:EtOAc=98:1) to give 2,6-dibromo-4-phenoxybenzenamine (12.0 g, 81%) as a dark solid. ESI-MS (EI$^+$, m/z): 344.0 [M+H]$^+$.

Step 2: 5-chloro-4-(3-fluorobenzyloxy)-2-nitrobenzenamine

A solution of 2,6-dibromo-4-phenoxybenzenamine (6.0 g, 17.5 mmol), m-CPBA (6.1 g, 35.0 mmol) in DCM (120 mL) was stirred at rt for 2.5 h. The mixture was extracted between DCM and aq. NaHCO$_3$. The combined organic layers were concentrated to give crude 1,3-dibromo-2-nitroso-5-phenoxybenzene (crude 6.7 g, 99%) as a yellow dope. ESI-MS (EI$^+$, m/z): 358.0 [M+H]$^+$.

Step 3: 3-bromo-N-(4-methoxybenzyl)-2-nitroso-5-phenoxybenzenamine 1,3-dibromo-2-nitroso-5-phenoxybenzene (crude 6.7 g, 17 mmol) in NMP (50 mL) was added (4-methoxyphenyl)methanamine (2.9 g, 21 mmol), K2CO3 (2.9 g, 21 mmol). The mixture was stirred at rt for 0.25 h. The mixture was partitioned between EtOAc and brine. The combined organic layers were concentrated and purified by SGC (PE:EtOAc=3:1) to give 3-bromo-N-(4-methoxybenzyl)-2-nitroso-5-phenoxybenzenamine (0.79 g, 10%) as a yellow solid. ESI-MS (EI$^+$, m/z): 413.0 [M+H]$^+$.

Step 4: 3-bromo-N1-(4-methoxybenzyl)-5-phenoxybenzene-1,2-diamine 3-bromo-N-(4-methoxybenzyl)-2-nitroso-5-phenoxybenzenamine (690 mg, 1.7 mmol) and Zn (0.6 g, 9.5 mmol) in EtOH (30 mL) was added HCl (0.7 mL). The reaction mixture was stirred at 70° C. for 1.5 h. The yellow solution contain 3-bromo-N1-(4-methoxybenzyl)-5-phenoxybenzene-1,2-diamine was used directly in the next step. ESI-MS (EI$^+$, m/z): 401.0 [M+H]$^+$.

Step 5: (4-bromo-6-phenoxy-1H-benzo[d]imidazol-2-yl)methanol, I-428

A mixture of 3-bromo-N1-(4-methoxybenzyl)-5-phenoxybenzene-1,2-diamine (15 mL crude solution, 0.8 mmol), 2-hydroxyacetic acid (300 mg, 3.9 mmol) in HCl (20 mL) and EtOH (15 mL) was stirred at 100° C. for 17 h. The solution was concentrated and partitioned between EtOAc and brine. The combined organic layers were concentrated and purified by prep-HPLC to give (4-bromo-6-phenoxy-1H-benzo[d]imidazol-2-yl)methanol I-428 (30 mg, 11%) as a white solid. ESI-MS (EI+, m/z): 321.0 [M+H]$^+$. $^1$H NMR (500 MHz, DMSO) δ 7.41 (t, J=7.9 Hz, 2H), 7.22 (d, J=1.8 Hz, 1H), 7.16 (t, J=7.4 Hz, 1H), 7.11 (d, J=2.0 Hz, 1H), 7.03 (d, J=7.9 Hz, 2H), 4.75 (s, 2H).

Example 218: 5,6-dichloro-2-(pyridin-4-yl)-1H-benzo[d]imidazole, I-378

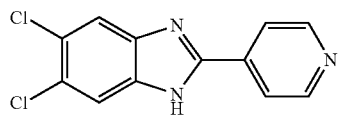

I-378

Synthetic Scheme:

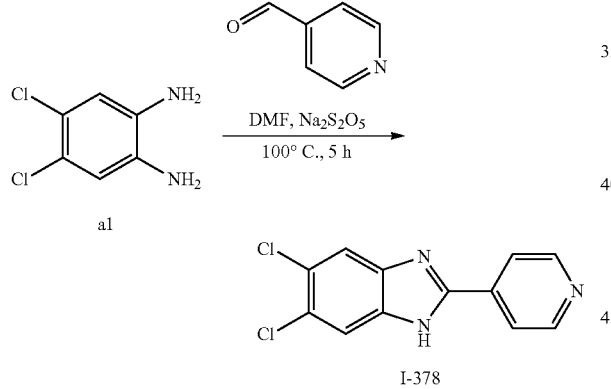

I-378

Procedures and Characterization:

Step 1: 5,6,7-trichloro-2-(pyridin-4-yl)-1H-benzo[d]imidazole, I-378

A mixture of 4,5-dichlorobenzene-1,2-diamine (176 mg, 1 mmol), isonicotinaldehyde (107, 1 mmol) and Na2S2O5 (190 mg, 1 mmol) in dry DMF (5 mL) was stirred for 16 h at 110° C. The reaction was quenched with water (10 mL) and extracted with ethyl acetate (20 mL). The organic layer was washed with water (5 mL×2), dried (Na$_2$SO$_4$), filtered and concentrated in vacuo, the crude product was purified by prep-HPLC (TFA) to 5,6-dichloro-2-(pyridin-4-yl)-1H-benzo[d]imidazole I-378 (22 mg, 0.083 mmol, 8.3%) as a white solid. ESI-MS (EI+, m/z): 264 [M+H]$^+$. $^1$H NMR (500 MHz, DMSO) δ 8.78-8.79 (m, 2H), 8.09-8.10 (in, 2H), 7.94 (s, 2H).

Example 219: 5,6-dichloro-2-(1H-pyrrolo[2,3-b]pyridin-4-yl)-1H-benzo[d]imidazole, I-359

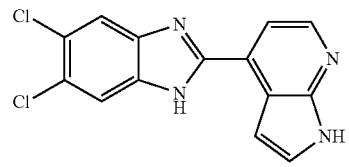

I-359

Synthetic Scheme:

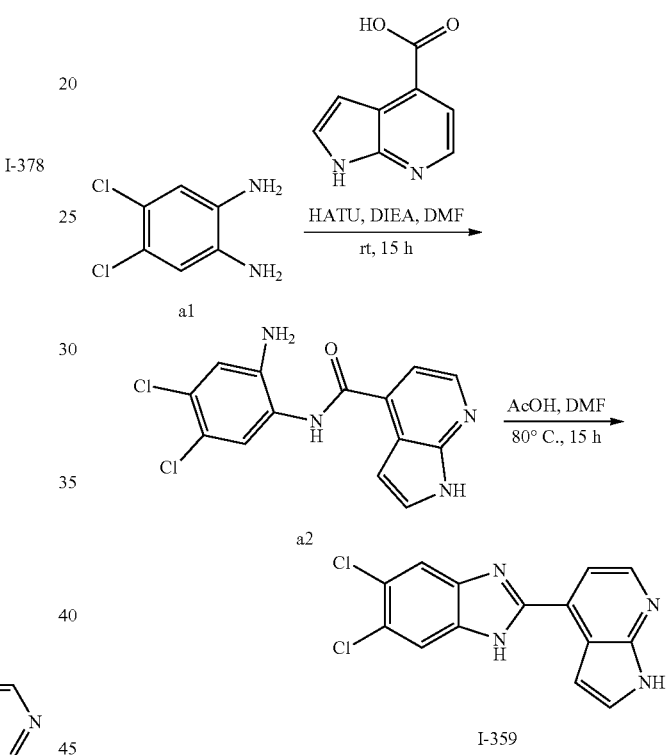

Procedures and Characterization:

Step 1: N-(2-amino-4,5-dichlorophenyl)-1H-pyrrolo[2,3-b]pyridine-4-carboxamide To a solution of 4,5-dichlorobenzene-1,2-diamine (200 mg, 1.13 mmol) and 1H-pyrrolo[2,3-b]pyridine-4-carboxylic acid (201 mg, 1.24 mmol) in DMF (10 mL) was added DIPEA (730 mg, 5.65 mmol) followed by HATU (645 mg, 1.69 mmol) and stirred at rt for 15 h. The solution was diluted with water (200 mL) and extracted with ethyl acetate (100 mL). The organic phase was washed with water (100 mL×2), and brine (100 mL), dried (Na$_2$SO$_4$), filtered and concentrated in vacuo, the crude product was used directly for the next step.

Step 2: 5,6-dichloro-2-(1H-pyrrolo[2,3-b]pyridin-4-yl)-1H-benzo[d]imidazole, I-359

To a solution of N-(2-amino-4,5-dichlorophenyl)-1H-pyrrolo[2,3-b]pyridine-4-carboxamide (240 mg, 0.75 mmol) in DMF (8.00 mL) was added AcOH (2.7 g, 45.2 mmol) dropwise and stirred for 15 h at 80° C. The solution was diluted with water (200 mL) and extracted with ethyl acetate (100 mL). The organic phase was washed with water (100 mL×2), and brine (100 mL), dried by $Na_2SO_4$, filtered and concentrated in vacuo, the crude product was purified by prep-HPLC to afford 5,6-dichloro-2-(1H-pyrrolo[2,3-b]pyridin-4-yl)-1H-benzo[d]imidazole I-359 as a white solid (23.7 mg, 0.08 mmol, 11%). ESI-MS (EI+, m/z): 303 [M+H]⁻. H NMR (500 MHz, DMSO) δ 11.99 (s, 1H), 8.42 (d, J=5.0 Hz, 1H), 7.95 (s, 2H), 7.77 (d, J=5.0 Hz, 1H), 7.69 (t, J=2.9 Hz, 1H), 7.34-7.26 (m, 1H).

Example 220: 4-(5,6-dichloro-1H-benzo[d]imidazol-2-yl)benzonitrile, I-370

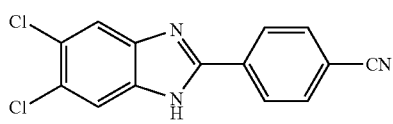

Synthetic Scheme:

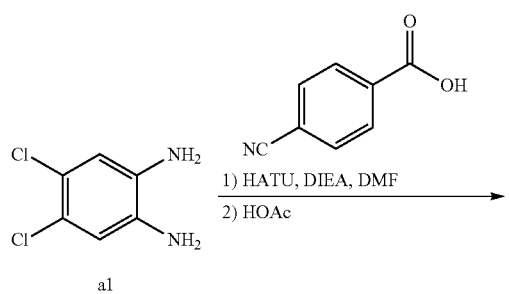

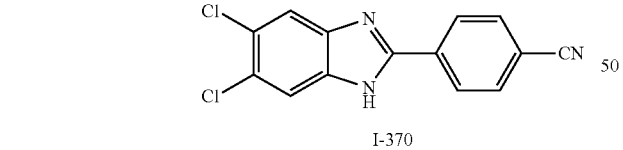

Procedures and Characterization:

Step 1: 4-(5,6-dichloro-1H-benzo[d]imidazol-2-yl)benzonitrile

The same procedure used to prepare I-359 afforded 4-(5,6-dichloro-1H-benzo[d]imidazol-2-yl)benzonitrile I-370 (100 mg). ESI-MS (ESI⁺, m/z): 288[M+H]⁺. ¹H-NMR (DMSO-d6,500 MHz): ¹H NMR (500 MHz, DMSO) δ 13.55 (d, J=6.0 Hz, 1H), 8.33 (d, J=8.0 Hz, 2H), 8.06 (d, J=8.0 Hz, 2H), 7.92 (m, 2H).

Example 221: methyl 4-(5,6-dichloro-1H-benzo[d]imidazol-2-yl)benzoate, I-363

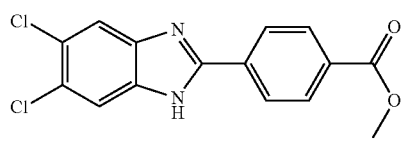

Synthetic Scheme:

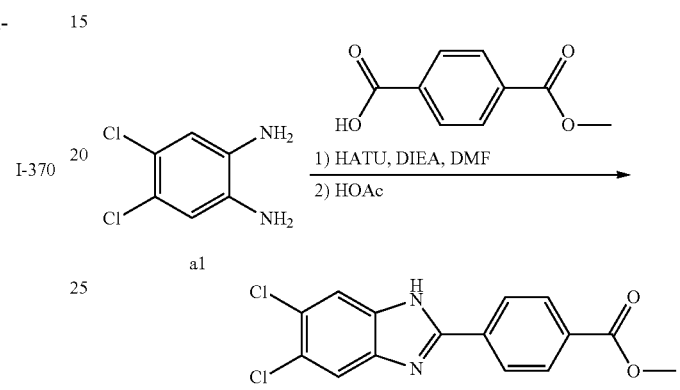

Procedures and Characterization:

Step 1: methyl 4-(5,6-dichloro-1H-benzo[d]imidazol-2-yl)benzoate

The same procedure used to prepare I-359 is to methyl 4-(5,6-dichloro-1H-benzo[d]imidazol-2-yl)benzoate I-363 (100 mg). ESI-MS (ESI⁺, m/z): 321[M+H]⁺.

¹H-NMR (DMSO-d6,500 MHz): SP-0015548-169-P1A-HI-DMSO-20151208-T225

¹H NMR (500 MHz, DMSO) δ 8.32 (d, J=8.5 Hz, 2H), 8.15 (d, J=8.5 Hz, 2H), 7.91 (bs, 2H), 3.90 (s, 3H).

Example 222: 4-(5,6-dichloro-1H-benzo[d]imidazol-2-yl)benzoic acid, I-364

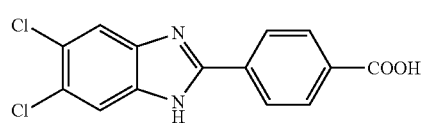

Synthetic Scheme:

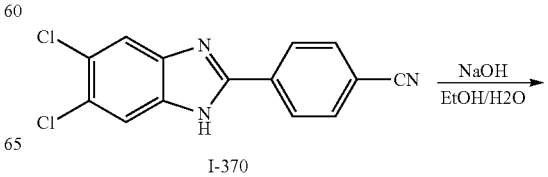

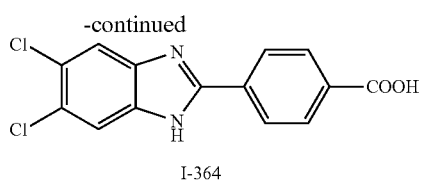

I-364

Procedures and Characterization:

Step 1: 4-(5,6-dichloro-1H-benzo[d]imidazol-2-yl)benzoic acid, I-364

To a stirred solution of 4-(5,6-dichloro-1H-benzo[d]imidazol-2-yl)benzonitrile (290 mg, 1.0 mmol, 1.0 eq.) in EtOH (2.0 mL) and H₂O (2.0 ml) at room temperature, was added NaOH (0.40 g, 10 mmol, 10.0 eq.) and the reaction mixture was stirred at refluxing for 12 h. 1N HCl (12 ml) was added to adjust pH=6 and the mixture was filtered to give a crude, which was purified by prep-HPLC to methyl 4-(5,6-dichloro-1H-benzo[d]imidazol-2-yl)benzoic acid I-364 (100 mg, 32 percent). ESI-MS (ESI⁺, m/z): 307[M+H]⁺.

¹H-NMR (DMSO-d6,500 MHz): SP-0015548-167-1-P1A-HI-DMSO-20151208-T225

¹H NMR (500 MHz, DMSO) δ 13.1 (bs, 11H), 8.29 (d, J=8.0 Hz, 2H), 8.12 (d, J=8.5 Hz, 2H), 7.91 (bs, 2H).

Example 223: 5,6-dichloro-2-(4-(4-methylpiperazin-1-yl)phenyl)-1H-benzo[d]imidazole, I-366

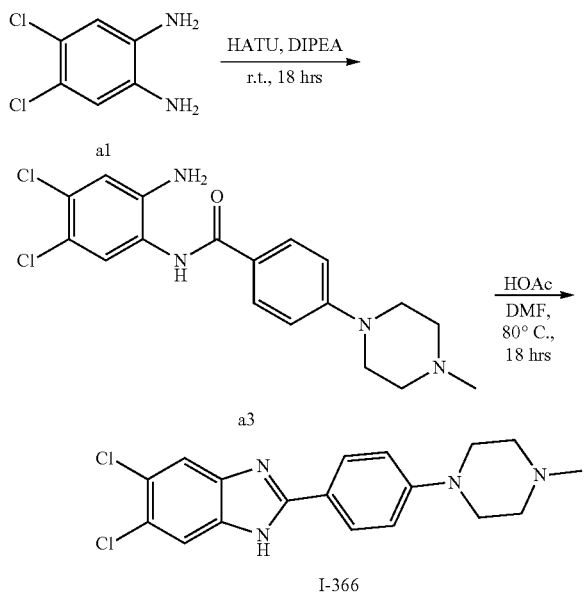

Procedures and Characterization:

Step 1: N-(2-amino-4,5-dichlorophenyl)-4-(4-methylpiperazin-1-yl)benzamide

The same procedure used to prepare a2 afforded N-(2-amino-4,5-dichlorophenyl)-4-(4-methylpiperazin-1-yl)benzamide as a white solid (110 mg, 0.29 mmol, 29%). ESI-MS (EI+, m/z): 379.0 [M+H]⁺.

Step 2: 5,6-dichloro-2-(4-(4-methylpiperazin-1-yl)phenyl)-1H-benzo[d]imidazole, I-366

The same procedure used to prepare I-359 afforded 5,6-dichloro-2-(4-(4-methylpiperazin-1-yl)phenyl)-1H-benzo[d]imidazole I-366 as a white solid (20 mg, 0.0171 mmol, 17%). ESI-MS (EI+, m/z): 361.0 [M+H]⁺. ¹H NMR (500 MHz, MeOD) δ 7.95-7.97 (m, 2H), 7.68 (s, 2H), 7.10-7.12 (m, 2H), 3.32-3.39 (m, 5H), 2.64-2.66 (m, 4H), 2.39 (s, 3H).

Example 224: 5,6,7-trichloro-2-(pyridin-4-yl)-1H-benzo[d]imidazole, I-353

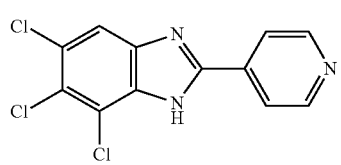

Synthetic Scheme:

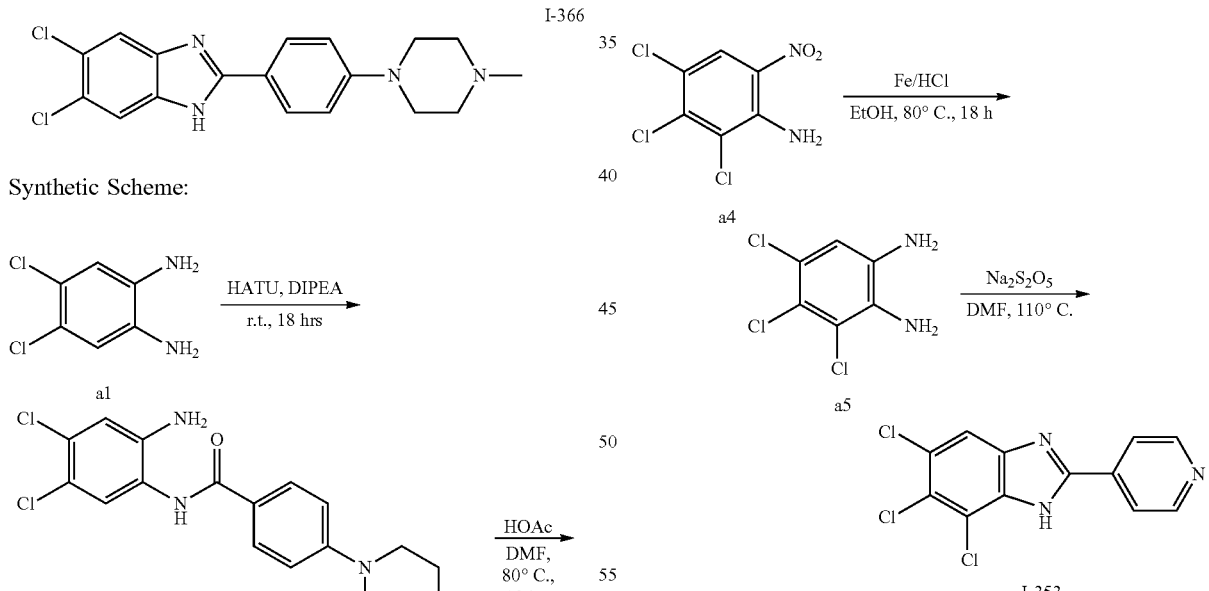

Procedures and Characterization:

Step 1: 4-(oxazol-5-yl)benzenamine

To a solution of 2,3,4-trichloro-6-nitrobenzenamine (400 mg, 1.67 mmol) in EtOH (5 mL) was added Fe (62 mg, 11 mmol) and HCl (2 mL, 6N) at 0° C. The reaction was stirred at 0° C. for 1 h and then at 25° C. for 16 h. The solution was diluted with DCM (20 mL) and neutralized with NaHCO₃ to pH=7 (10 mL×2), dried by Na₂SO₄, filtered and concentrated in vacuo, the crude product was purified by chromatography (silica, ethyl acetate/petroleum ether=1/1) to afford 4-(oxazol-5-yl)benzenamine (300 mg, 1.42 mmol, 85%) as a yellow solid. ESI-MS (EI+, m/z): 211 [M+H]⁺.

Step 2: 5,6,7-trichloro-2-(pyridin-4-yl)-1H-benzo[d]imidazole, I-353

A mixture of 4-(oxazol-5-yl)benzenamine (150 mg, 0.71 mmol), isonicotinaldehyde (76 mg, 0.71 mmol) and $Na_2S_2O_5$ (135 mg, 0.71 mmol) in dry DMF (5 mL) was stirred for 16 h at 110° C. The reaction was quenched with water (10 mL) and extracted with ethyl acetate (20 mL). The organic layer was washed with water (5 mL×2), dried by $Na_2SO_4$, filtered and concentrated in vacuo. The crude product was purified by prep-HPLC (TFA) to give 5,6,7-trichloro-2-(pyridin-4-yl)-1H-benzo[d]imidazole I-353 (10.6 mg, 0.035 mmol, 4.9%) as a white solid. ESI-MS (EI+, m/z): 297 [M+H]⁺. ¹H NMR (500 MHz, DMSO) δ 8.68-8.69 (m, 2H), 8.15-8.17 (m, 2H), 7.71 (s, 1H), Example 225: 6,7-dichloro-5-(4-chlorobenzyloxy)-2-(pyridin-4-yl)-1H-benzo[d]imidazole, I-354

I-354

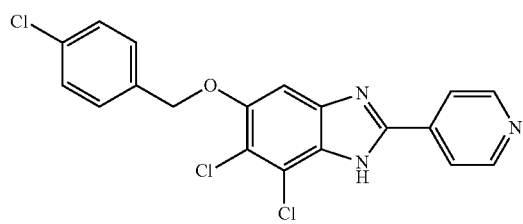

Synthetic Scheme:

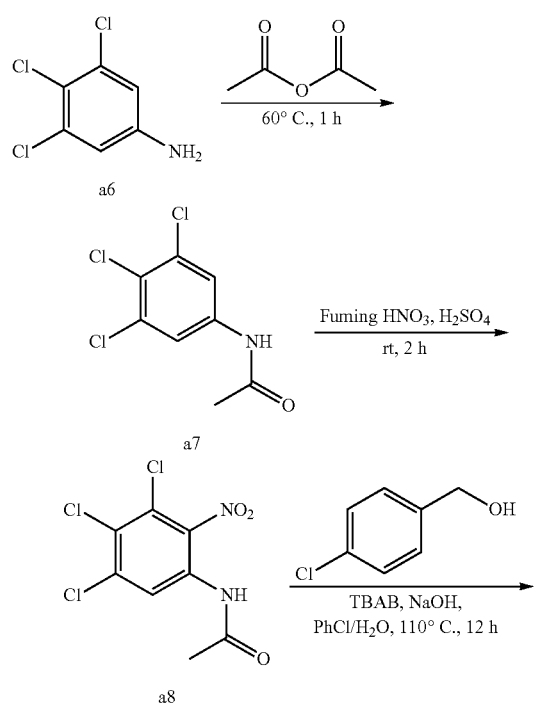

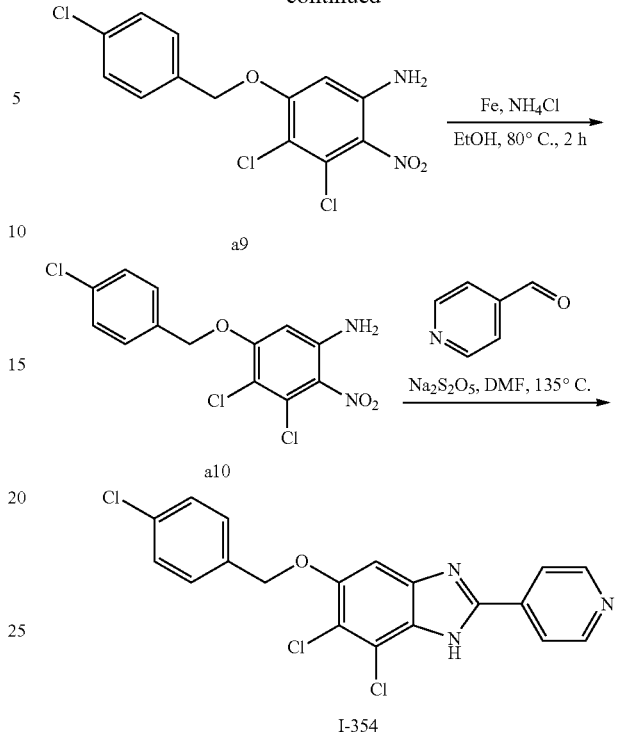

I-354

Procedures and Characterization:

Step 1: N-(3,4,5-trichlorophenyl)acetamide

A mixture of 3,4,5-trichloroaniline (277 mg, 2.0 mmol) in $Ac_2O$ (5 mL) was stirred at 60° C. for 1 h. It was diluted with Petroleum ether (100 ml) and filtered to give N-(3,4,5-trichlorophenyl)acetamide (300 mg) as a pale yellow solid.

Step 2: N-(3,4,5-trichloro-2-nitrophenyl)acetamide

To a mixture of N-(3,4,5-trichlorophenyl)acetamide (700 mg, 3.2 mmol) and $H_2SO_4$ (6 mL), fuming $HNO_3$ (3 mL) was added. The resulting reaction mixture was stirred at rt for 2 h. It was diluted with water (100 ml) and filtered to give N-(3,4,5-trichloro-2-nitrophenyl)acetamide (500 mg) as a pale yellow solid. MS (EI+, m/z): 283 [M+H]⁺.

Step 3: 3,4-dichloro-5-(4-chlorobenzyloxy)-2-nitroaniline

A mixture of N-(3,4,5-trichloro-2-nitrophenyl)acetamide (200 mg, 0.80 mmol), (4-chlorophenyl)methanol (100 mg, 0.80 mmol), NaOH (100 mg, 2.39 mmol) and TBAB (20 mg, 0.08 mmol) in chlorobenzene/1120 (5 mL/10 mL) was stirred at 110° C. for 12 h. It was diluted with EtOAc (100 ml) and water (100 ml) and filtered to give 3,4-dichloro-5-(4-chlorobenzyloxy)-2-nitroaniline (100 mg) as a pale yellow solid.

Step 4: 3,4-dichloro-5-(4-chlorobenzyloxy)benzene-1,2-diamine

A mixture of 3,4-dichloro-5-(4-chlorobenzyloxy)-2-nitroaniline (1.6 g, 5.0 mmol), Fe (13.0 g, 25 mmol) in EtOH (20.00 mL) and $NH_4Cl$ (3 mL) was stirred at 80° C. for 2 h. It was extracted with EtOAc (100 ml), washed with water (100 ml*3), brine (100 ml*1), dried, filtered and concentrated to give 3,4-dichloro-5-(4-chlorobenzyloxy)benzene-1,2-diamine (1.2 g) as a pale yellow solid.

Step 5: 6,7-dichloro-5-(4-chlorobenzyloxy)-2-(pyridin-4-yl)-1H-benzo[d]imidazole, I-354

A mixture of 3,4-dichloro-5-(4-chlorobenzyloxy)benzene-1,2-diamine (200 mg, 0.63 mmol), isonicotinaldehyde (68 mg, 0.76 mmol) and Na₂S2O5 (120 mg, 0.63 mmol) in DMF (2.00 mL) was stirred at 135° C. for 3 h. It was extracted with EtOAc (100 ml), washed with water (100 ml*3), brine (100 ml*1), dried, filtered and concentrated to give a crude. It was purified by prep-TLC to give 6,7-dichloro-5-(4-chlorobenzyloxy)-2-(pyridin-4-yl)-1H-benzo[d]imidazole I-354 (50 mg) as a pale yellow solid. MS (EI+, m/z): 404 [M−H]+. 1H-NMR (400 MHz, DMSO-d6): ¹H NMR (500 MHz, DMSO) δ 13.6 (s, 1H), 8.76 (m, 211), 8.08 (s, 2H), 7.53 (m, 4H), 7.32 (bs, 1H), 5.33 (s, 2H).

Example 226: 6-chloro-4-(4-chlorophenylthio)-2-(1H-pyrrolo[2,3-b]pyridin-3-yl)-1H-benzo[d]imidazole, I-339

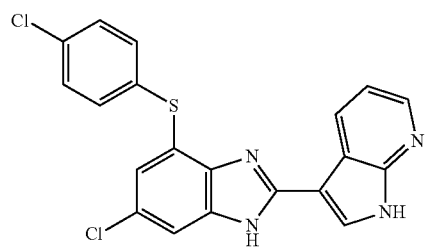

I-339

Synthetic Scheme:

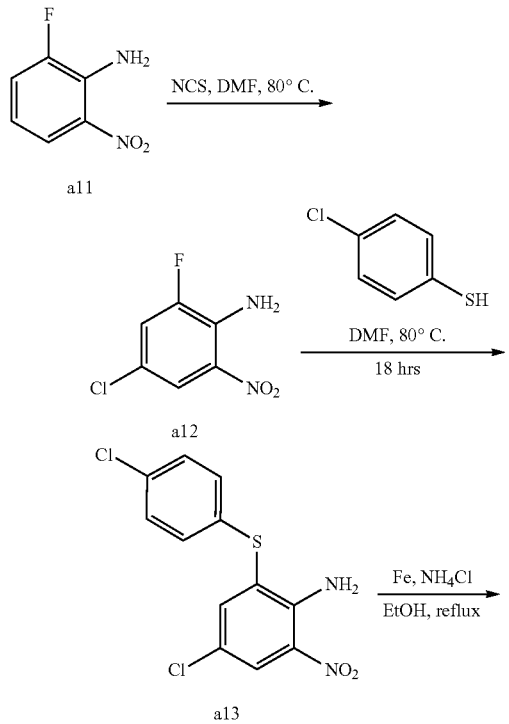

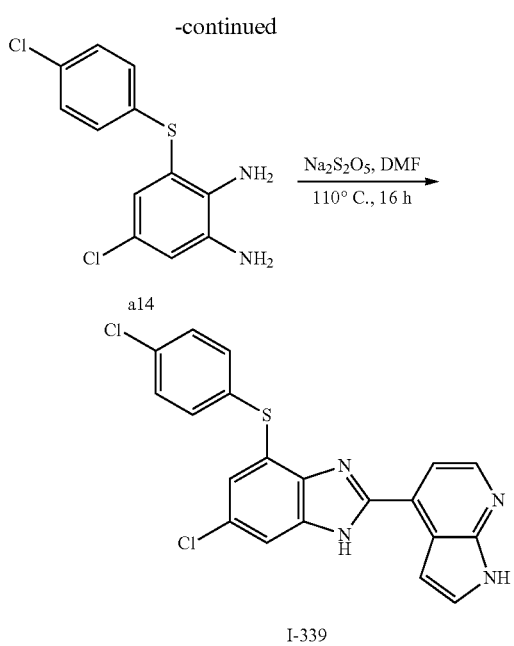

Procedures and Characterization:

Step 1: 4-chloro-2-fluoro-6-nitrobenzenamine

A mixture of 2-fluoro-6-nitrobenzenamine (3.2 g, 20 mmol), NCS (2.64 g, 20 mmol) in DMF (21 ml) was stirred for 16 h at 80° C. The reaction was quenched with water (30 mL) and extracted with ethyl acetate (100 mL). The organic layer was washed with water (500 mL×2), dried (Na₂SO₄), filtered and concentrated in vacuo, the crude product was purified by chromatography (silica, ethyl acetate/petroleum ether=1/1) to afford 4-chloro-2-fluoro-6-nitrobenzenamine (1.9 g, 10 mmol, 50%) as a light yellow solid ESI-MS (EI+, m/z): 191 [M+H]+.

Step 2: 4-chloro-2-(4-chlorophenylthio)-6-nitrobenzenamine

A mixture of 4-chloro-2-fluoro-6-nitrobenzenamine (1.9 g, 10 mmol), 4-chlorobenzenethiol (2.8 g, 20 mmol) in DMF (21 ml) was stirred for 16 h at 80° C. The reaction was quenched with water (30 mL) and extracted with ethyl acetate (100 mL). The organic layer was washed with water (500 mL×2), dried (Na₂SO₄), filtered and concentrated in vacuo, the crude product was purified by chromatography (silica, ethyl acetate/petroleum ether=1/1) to afford 4-chloro-2-(4-chlorophenylthio)-6-nitrobenzenamine (2.0 g, 6.3 mmol, 63%) as a light yellow solid ESI-MS (EI+, m/z): 315 [M+H]+.

Step 3: 5-chloro-3-(4-chlorophenylthio)benzene-1,2-diamine

A mixture of 4-chloro-2-(4-chlorophenylthio)-6-nitrobenzenamine (2.0 g, 6.3 mmol), Fe (3.3 g, 60 mmol) in EtOH (30 ml) was added HCl (20 ml, 2N), the solution was stirred for 18 h at 80° C. The reaction was quenched with water (20 mL) and NaHCO₃ (50 ml. 2N) and extracted with ethyl acetate (100 mL). The organic layer was washed with water (50 mL×2), dried (Na₂SO₄), filtered and concentrated in vacuo, the crude product was purified by chromatography (silica, ethyl acetate/petroleum ether=1/1) to afford 5-chloro-3-(4-chlorophenylthio)benzene-1,2-diamine (1.8 g, 6.3 mmol, 100%) as a light yellow solid ESI-MS (EI+, m/z): 285 [M+H]⁺.

Step 4: 4-chloro-2-(4-chlorophenylthio)-6-nitrobenzenamine, I-339

A mixture of 4-chloro-2-fluoro-6-nitrobenzenamine (150 mg, 1.0 mmol), 5-chloro-3-(4-chlorophenylthio)benzene-1,2-diamine (271 mg, 1.0 mmol) and Na₂S₂O₅ (135 mg, 1.0 mmol) in dry DMF (5 mL) was stirred for 16 h at 110° C. The reaction was quenched with water (10 mL) and extracted with ethyl acetate (20 mL). The organic layer was washed with water (5 mL×2), dried (Na₂SO₄), filtered and concentrated in vacuo, the crude product was purified by prep-HPLC (TFA) to 6-chloro-4-(4-chlorophenylthio)-2-(1H-pyrrolo[2,3-b]pyridin-3-yl)-1H-benzo[d]imidazole I-339 (11.7 mg, 0.035 mmol, 5.9%) as a white solid. ESI-MS (EI+, m/z): 411 [M+H]⁺. ¹H NMR (500 MHz, MeOD) δ 8.70-8.72 (m, 1H), 8.33-8.35 (m, 1H), 8.20 (m, 1H), 7.58 (s, 1H), 7.28-7.39 (m, 5H), 7.13 (s, 1H).

Example 227: 6-chloro-4-(4-chlorophenylthio)-2-(1H-pyrrolo[2,3-b]pyridin-4-yl)-1H-benzo[d]imidazole, I-326

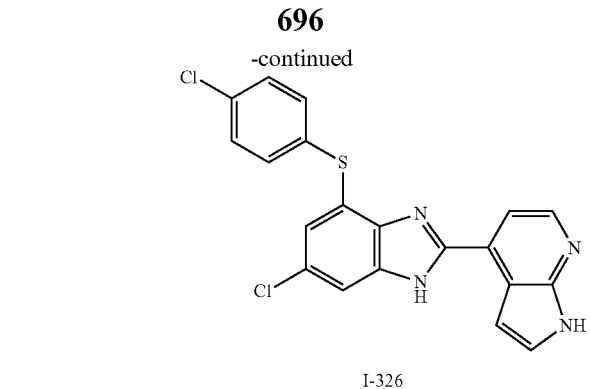

Procedures and Characterization:

Step 1: 6-chloro-4-(4-chlorophenylthio)-2-(1H-pyrrolo[2,3-b]pyridin-4-yl)-1H-benzo[d]imidazole The same procedure as the last step of I-339 afforded the crude product, which was purified by prep-HPLC (TFA) to 6-chloro-4-(4-chlorophenylthio)-2-(1H-pyrrolo[2,3-b]pyridin-3-yl)-1H-benzo[d]imidazole I-326 (8.0 mg, 0.035 mmol, 5.9%) as a white solid. ESI-MS (EI+, m/z): 411 [M+H]⁺. ¹H NMR (500 MHz, MeOD) δ 11.89 (s, 1H), 8.38-8.39 (m, 1H), 7.50-7.77 (m, 8H), 7.13 (m, 2H).

Example 228: 2-(1-(4-(2H-tetrazol-5-yl)benzyl)-5,6-dichloro-1H-benzo[d]imidazol-2-yl)oxazole, I-489

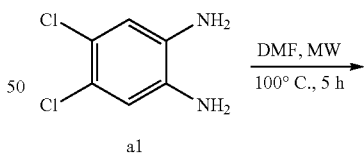

Synthetic Scheme:

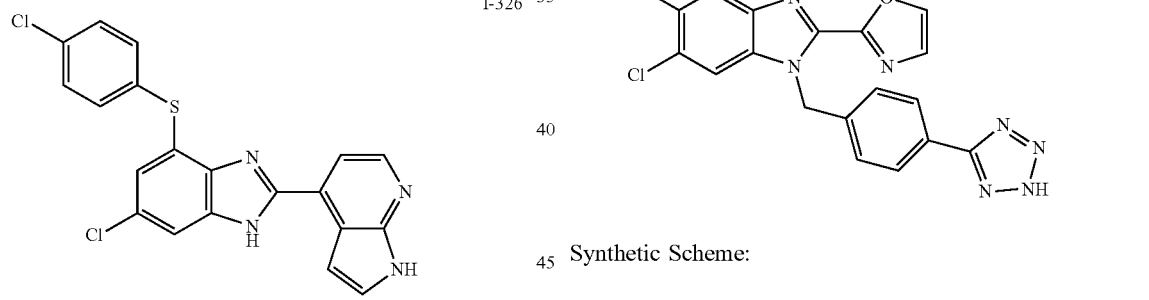

Synthetic Scheme:

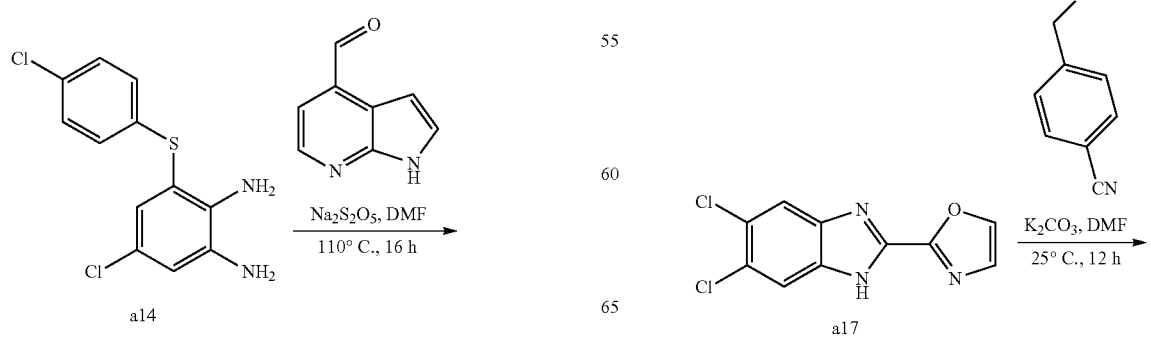

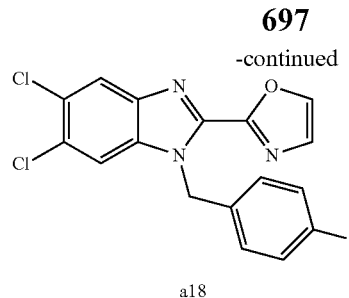

a18

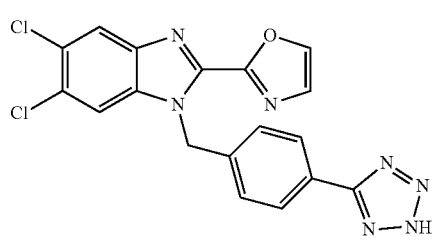

I-489

Procedures and Characterization:

Step 1: 2-(5,6-dichloro-1H-benzo[d]imidazol-2-yl)oxazole

A solution of 4,5-dichlorobenzene-1,2-diamine (179 mg, 1.01 mmol) and oxazole-2-carbaldehyde (0.19 g, 2.75 mmol) in DMF (6 mL) was microwave at 100° C. for 5 h. diluted with EtOAc and washed with water, dried and concentrated to give 2-(5,6-dichloro-1H-benzo[d]imidazol-2-yl)oxazole as a white solid. ESI-MS (EI+, m/z): 254 [M+H]$^+$.

Step 2: 4-((5,6-dichloro-2-(oxazol-2-yl)-1H-benzo[d]imidazol-1-yl)methyl)benzonitrile Using a similar procedure as step 3 of I-421, from 2-(5,6-dichloro-1H-benzo[d]imidazol-2-yl)oxazole (0.15 g, 0.593 mmol) and 4-(bromomethyl)benzonitrile (0.128 g, 0.652 mmol) to provide 4-((5,6-dichloro-2-(oxazol-2-yl)-1H-benzo[d]imidazol-1-yl)methyl)benzonitrile as a white solid. ESI-MS (EI+, m/z): 369 [M+H]$^+$.

Step 3: 2-(1-(4-(2H-tetrazol-5-yl)benzyl)-5,6-dichloro-1H-benzo[d]imidazol-2-yl)oxazole, I-489

4-((5,6-dichloro-2-(oxazol-2-yl)-1H-benzo[d]imidazol-1-yl)methyl)benzonitrile (90 mg, 0.245 mmol), sodium azide (95 mg, 1.467 mmol) and NH$_4$Cl (65 mg, 1.225 mmol) were dissolved in dry DMF (5.00 mL) and the mixture was stirred at 100° C. for 12 h. The mixture was purified by Prep-HPLC to give 2-(1-(4-(2H-tetrazol-5-yl)benzyl)-5,6-dichloro-1H-benzo[d]imidazol-2-yl)oxazole I-489 as a white solid. ESI-MS (EI+, m/z): 412 [M+H]+.

$^1$H NMR (500 MHz, DMSO) δ 8.46 (s, 1H), 8.15 (s, 1H), 8.09 (s, 1H), 7.96 (d, J=8 Hz, 2H), 7.59 (s, 1H), 7.37 (d, J=8 Hz, 2H), 6.19 (s, 2H).

Example 229: 2-(5-chloro-4-phenoxy-1H-benzo[d]imidazol-2-yl)oxazole, I-427

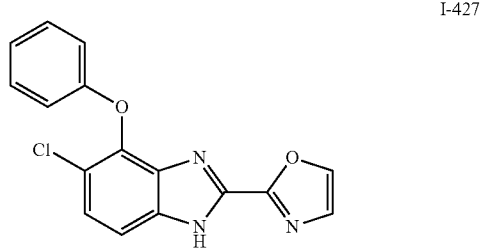 [SMILES: Clc1ccc2[nH]c(-c3ncco3)nc2c1Oc1ccccc1]

Synthetic Scheme:

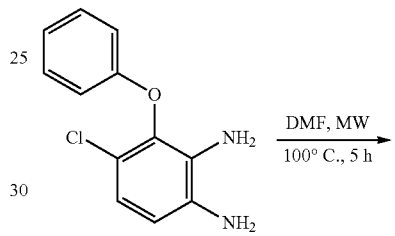

a19

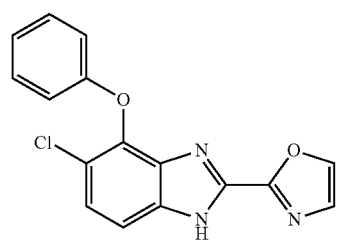

I-427

Procedures and Characterization:

Using a similar procedure as step 1 of I-489, from 4-chloro-3-phenoxybenzene-1,2-diamine (69 mg, 0.295 mmol) and oxazole-2-carbaldehyde (29 mg, 0.295 mmol) to provide 2-(5-chloro-4-phenoxy-1H-benzo[d]imidazol-2-yl)oxazole I-427 as a white solid. ESI-MS (EI+, m/z): 312 [M+H]$^+$. 1H NMR (500 MHz, DMSO) δ 8.38 (s, 1H), 7.55 (s, 1H) 7.49 (d, J=9.0 Hz, 2H), 7.30 (t, J=8.5 Hz, 2H), 7.04 (t, J=8.0 Hz, 1H), 6.85 (d, J=8.5 Hz, 2H).

Example 230: 2-(1-(4-(1H-tetrazol-5-yl)benzyl)-4-phenoxy-1H-benzo[d]imidazol-2-yl)oxazole, I-421

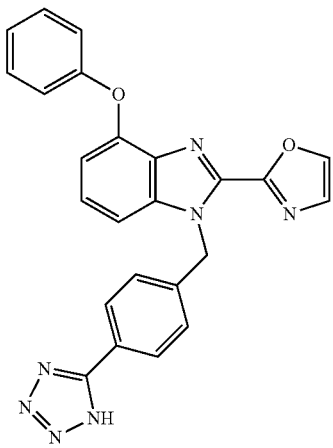

I-421

Synthetic Scheme:

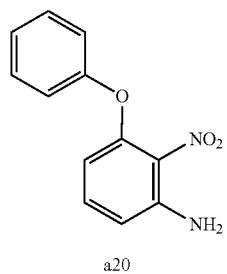

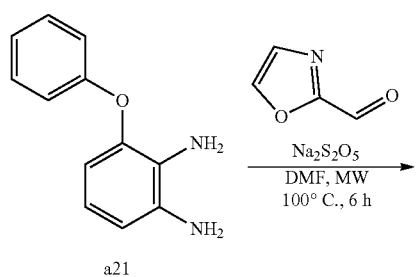

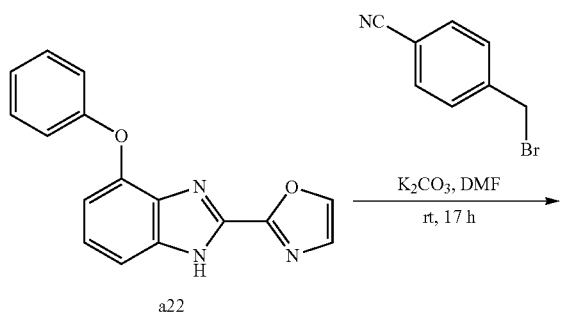

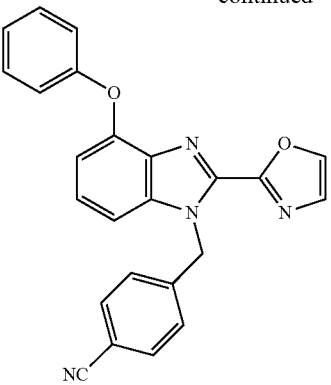

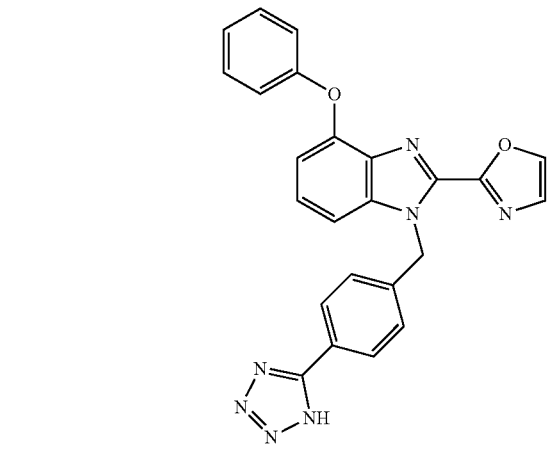

Procedures and Characterization:

Step 1: 3-phenoxybenzene-1,2-diamine 2-nitro-3-phenoxyaniline (2.0 g, 8.7 mmol) was dissolved in dry MeOH (50.00 mL) and SnCl$_2$ (8.2 g, 43.4 mmol) was added. The reaction mixture was refluxed for 24 h. The solvent was concentrated and the residue was extracted between EtOAc and aq. NaHCO$_3$. The combined organic layers were concentrated and purified by SGC (PE: EtOAc=5:1) to give 3-phenoxybenzene-1,2-diamine (1.1 g, 5.5 mmol, 65%) as a yellow oil. ESI-MS (EI$^+$, m/z): 201.3 [M+H]$^+$.

Step 2: 2-(4-phenoxy-1H-benzo[d]imidazol-2-yl) oxazole 3-phenoxybenzene-1,2-diamine (360 mg, 1.8 mmol), oxazole-2-carbaldehyde (175 mg, 1.8 mmol), Na$_2$S$_2$O$_5$ (342 mg, 1.8 mmol) were dissolved in dry DMF (7 mL). The mixture was stirred at 100° C. for 6 h in a microwave vial. The mixture was cooled to rt and extracted with EtOAc (20 mL). The organic layer was washed with brine, dried over MgSO$_4$, filtered and concentrated. The residue was purified by column chromatography (Petroleum ether/EtOAc=2) to give crude 2-(4-phenoxy-1H-benzo[d]imidazol-2-yl)oxazole (160 mg) as a yellow solid. ESI-MS (EI$^+$, m/z): 278.1 [M+H]$^+$.

Step 3: 4-((2-(oxazol-2-yl)-4-phenoxy-1H-benzo[d]imidazol-1-yl)methyl)benzonitrile 2-(4-phenoxy-1H-benzo[d]imidazol-2-yl)oxazole (530 mg, 1.9 mmol,) was dissolved in DMF (5 mL) then $K_2CO_3$ (525 mg, 3.8 mmol) and 4-(bromomethyl)benzonitrile (412 mg, 2.1 mmol) were added. The mixture was stirred at rt for 17 h. Then water (150 mL) was added and extracted with EtOAc (3 times). The organic layer was concentrated to give crude 4-((2-(oxazol-2-yl)-4-phenoxy-1H-benzo[d]imidazol-1-yl)methyl)benzonitrile (500 mg) as a yellow oil. ESI-MS (EI+, m/z): 393.2 [M+H]+.

Step 4: 2-(1-(4-(1H-tetrazol-5-yl)benzyl)-4-phenoxy-1H-benzo[d]imidazol-2-yl)oxazole, I-421

4-((2-(oxazol-2-yl)-4-phenoxy-1H-benzo[d]imidazol-1-yl)methyl)benzonitrile (530 mg, 1.35 mmol), $NaN_3$ (300 mg, 4.6 mmol), $NH_4Cl$ (361 mg, 6.75 mmol) were dissolved in dry DMF (5.00 mL) and the mixture was stirred at 100° C. for 17 h. The mixture was purified prep-HPLC to give 2-(1-(4-(1H-tetrazol-5-yl)benzyl)-4-phenoxy-1H-benzo[d]imidazol-2-yl)oxazole I-421 (19 mg) as a white solid. ESI-MS (EI+, m/z): 436.3 [M+H]+. 1H NMR (500 MHz, DMSO $d_6$) δ 8.41 (s, 1H), 7.97-7.95 (d, J=15 Hz, 2H), 7.57 (s, 1H), 7.45-7.38 (m, 5H), 7.33-7.30 (t, J=7.5 Hz, 1H), 7.17-7.14 (t, J=7 Hz, 1H), 7.08-7.07 (m, 2H), 6.83-6.81 (d, J=7.5 Hz, 1H), 6.20 (s, 2H).

Example 231: 2-(1-(4-(1H-tetrazol-5-yl)benzyl)-6-chloro-1H-benzo[d]imidazol-2-yl)oxazole, I-411

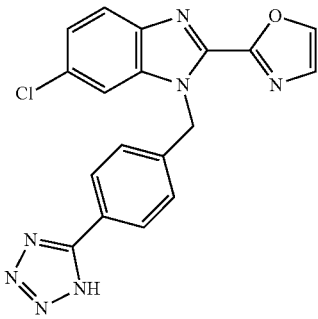

I-411

Synthetic Scheme:

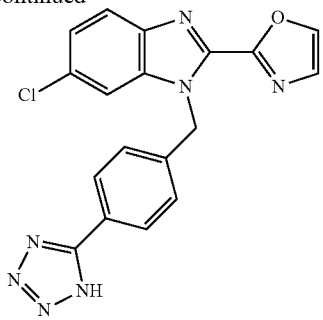

I-411

Procedures and Characterization:

Step 1: 2-(1-(4-(1H-tetrazol-5-yl) benzyl)-5-chloro-2,3-dihydro-1H-benzo[d]imidazol-2-yl) oxazole, I-411

A solution of 4-((5-chloro-2-(oxazol-2-yl)-2,3-dihydrobenzo[d]imidazol-1-yl)methyl) benzonitrile (170 mg, 0.5 mmol, 1 eq), $NaN_3$ (35 mg, 0.5 mmol, 1 eq), $NH_4Cl$ (30 mg, 0.5 mmol, 1 eq) in DMF (3 mL) was stirred at 100° C. for 17 h. Concentrated and purified by prep-HPLC to give 2-(1-(4-(1H-tetrazol-5-yl)benzyl)-5-chloro-2,3-dihydro-1H-benzo[d]imidazol-2-yl)oxazole I-411 (180 mg, 50%) as a yellow solid; 1H-NMR (500 MHz, $CDCl_3$): δ 8.45 (s, 1H), 7.84-8.01 (m, 4H), 7.58 (s, 1H), 7.36 (m, 3H), 6.2 (s, 2H).

Example 232 4-(1-(4-(2H-tetrazol-5-yl)benzyl)-5,6-dichloro-1H-benzo[d]imidazol-2-yl)-1,2,5-oxadiazol-3-amine, 1-490

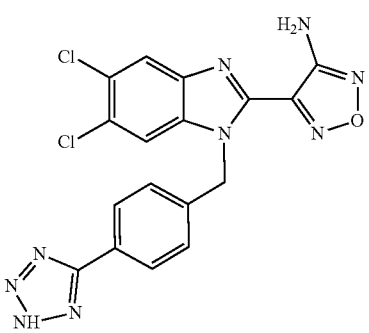

I-490

Synthetic Scheme:

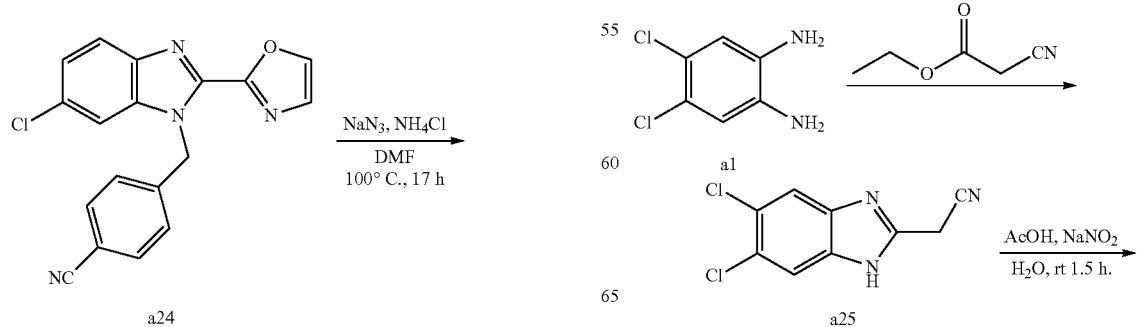

-continued

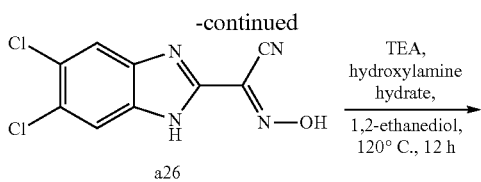

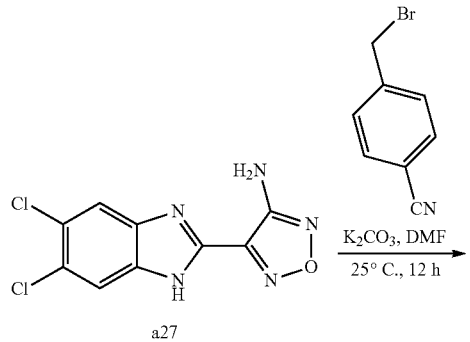

Procedures and Characterization:

Step 1: 2-(5,6-dichloro-1H-benzo[d]imidazol-2-yl)acetonitrile

The mixture of 4,5-dichlorobenzene-1,2-diamine (1.5 g, 8.47 mmol) and ethyl 2-cyanoacetate (4.8 g, 42.37 mmol) was heated to 185° C. and stirred for 1.5 h. The reaction was cooled down and purified by prep-HPLC to provide 2-(5,6-dichloro-1H-benzo[d]imidazol-2-yl)acetonitrile (0.242 g) as a white solid. ESI-MS (EI+, m/z): 226 [M+H]+.

Step 2: (E)-5,6-dichloro-N-hydroxy-1H-benzo[d]imidazole-2-carbimidoyl cyanide

To a solution of 2-(5,6-dichloro-1H-benzo[d]imidazol-2-yl)acetonitrile (0.55 g, 2.45 mmol) in AcOH (4 mL) was added a solution of NaNO$_2$ (0.19 g, 2.75 mmol) in H$_2$O (1 mL) at rt. Then stirred for 1.5 h. filtered and dried to give (E)-5,6-dichloro-N-hydroxy-1H-benzo[d]imidazole-2-carbimidoyl cyanide as a yellow solid. ESI-MS (EI+, m/z): 255 [M+H]$^+$.

Step 3:4-(5,6-dichloro-1H-benzo[d]imidazol-2-yl)-1,2,5-oxadiazol-3-amine

A solution of (E)-5,6-dichloro-N-hydroxy-1H-benzo[d] imidazole-2-carbimidoyl cyanide (0.64 g, 2.52 mmol) and TEA (1.3 g, 12.87 mmol), hydroxylamine hydrate (1.4 g, 25.93 mmol) in 1,2-ethanediol (10 mL) at 120° C. for 12 h. diluted with EtOAc, washed with water, dried and filtered, concentrated to give 4-(5,6-dichloro-1H-benzo[d]imidazol-2-yl)-1,2,5-oxadiazol-3-amine as a white solid. ESI-MS (EI+, m/z): 270 [M+H]$^+$.

Step 4: 4-((2-(4-amino-1,2,5-oxadiazol-3-yl)-5,6-dichloro-1H-benzo[d]imidazol-1-yl)methyl)benzonitrile Using a similar procedure as step 3 of I-421, from 4-(5,6-dichloro-1H-benzo[d]imidazol-2-yl)-1,2,5-oxadiazol-3-amine (0.1 g, 0.37 mmol) and 4-(bromomethyl)benzonitrile (80 mg, 0.41 mmol) to provide 4-((2-(4-amino-1,2,5-oxadiazol-3-yl)-5,6-dichloro-1H-benzo[d]imidazol-1-yl)methyl)benzonitrile as a white solid. ESI-MS (EI+, m/z): 385 [M+H]$^+$.

Step 5: 4-(1-(4-(2H-tetrazol-5-yl)benzyl)-5,6-dichloro-1H-benzo[d]imidazol-2-yl)-1,2,5-oxadiazol-3-amine, I-490

4-((2-(4-amino-1,2,5-oxadiazol-3-yl)-5,6-dichloro-1H-benzo[d]imidazol-1-yl)methyl)benzonitrile (0.15 g, 0.39 mmol), sodium azide (150 mg, 2.34 mmol) and NH$_4$Cl (104 mg, 1.95 mmol) were dissolved in dry DMF (5.00 mL) and the mixture was stirred at 100° C. for 12 h. The mixture was purified by Prep-HPLC to give 4-(1-(4-(2H-tetrazol-5-yl)benzyl)-5,6-dichloro-1H-benzo[d]imidazol-2-yl)-1,2,5-oxadiazol-3-amine I-490 as a white solid.

ESI-MS (EI+, m/z): 428 [M+H]$^+$.

$^1$H NMR (500 MHz, DMSO) δ 8.23 (d, J=11 Hz, 2H), 7.96 (d, J=9 Hz, 2H), 7.35 (d, J=8.0 Hz, 2H), 6.98 (s, 2H), 6.05 (s, 2H).

Example 233: 3-(1-(4-(2H-tetrazol-5-yl)benzyl)-5,6-dichloro-1H-benzo[d]imidazol-2-yl)-1,2,5-oxadiazole, I-474

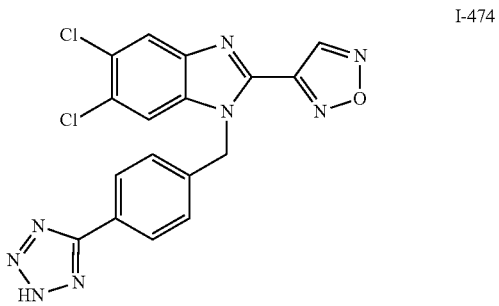 [SMILES: Clc1cc2nc(-c3cnon3)n(Cc3ccc(-c4nn[nH]n4)cc3)c2cc1Cl]

Synthetic Scheme:

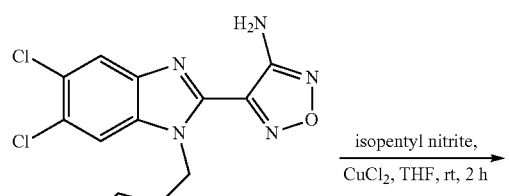

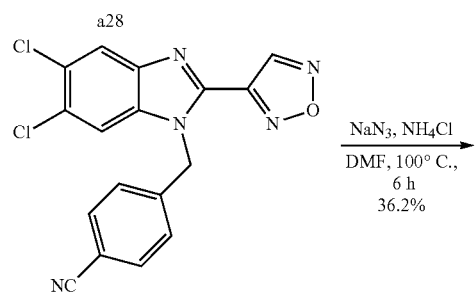

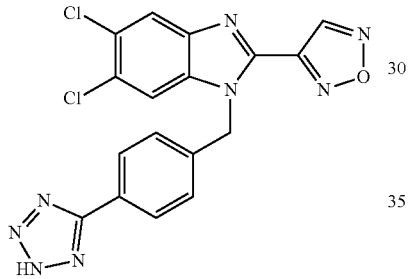

Procedures and Characterization:

Step 1: 4-((2-(4-amino-1,2,5-oxadiazol-3-yl)-5,6-dichloro-1H-benzo[d]imidazol-1-yl)methyl)benzonitrile A mixture of 4-((2-(4-amino-1,2,5-oxadiazol-3-yl)-5,6-dichloro-1H-benzo[d]imidazol-1-yl)methyl)benzonitrile (37 mg, 0.096 mmol) and isopentyl nitrite (101 mg, 0.863 mmol), CuCl$_2$ (6 mg, 0.045 mmol) in THF (6 mL). This mixture was stirred at rt for 2 h. The mixture was extracted with EtOAc/H$_2$O (50 mL/50 mL), the organic phase was dried over anhydrous Na$_2$SO$_4$, and concentrated in vacuo. The residue was purified by prep-HPLC to provide 3-(1-(4-(2H-tetrazol-5-yl)benzyl)-5,6-dichloro-1H-benzo[d]imidazol-2-yl)-1,2,5-oxadiazole as a yellow solid. ESI-MS (EI+, m/z): 370 [M+H]+.

Step 2: 3-(1-(4-(2H-tetrazol-5-yl)benzyl)-5,6-dichloro-1H-benzo[d]imidazol-2-yl)-1,2,5-oxadiazole 3-(1-(4-(2H-tetrazol-5-yl)benzyl)-5,6-dichloro-1H-benzo[d]imidazol-2-yl)-1,2,5-oxadiazole (15 mg, 0.041 mmol), sodium azide (16 mg, 0.243 mmol) and NH$_4$Cl (11 mg, 0.205 mmol) were dissolved in dry DMF (5.00 mL) and the mixture was stirred at 100° C. for 12 h. The mixture was purified by Prep-HPLC to give 3-(1-(4-(2H-tetrazol-5-yl)benzyl)-5,6-dichloro-1H-benzo[d]imidazol-2-yl)-1,2,5-oxadiazole I-474 as a white solid. ESI-MS (EI+, m/z): 413 [M+H]+ $^1$H NMR (500 MHz, DMSO) δ 8.23 (d, J=6 Hz, 2H), 7.97 (d, J=9 Hz, 2H), 7.35 (d, J=8 Hz, 2H), 6.98 (s, 2H), 6.05 (s, 2H).

Example 234: (1R,3S)-3-((5,6-dichloro-2-(pyridin-4-yl)-1H-benzo[d]imidazol-4-yloxy)methyl)cyclohexanol, I-324

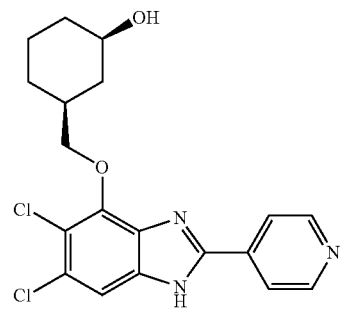

Synthetic Scheme:

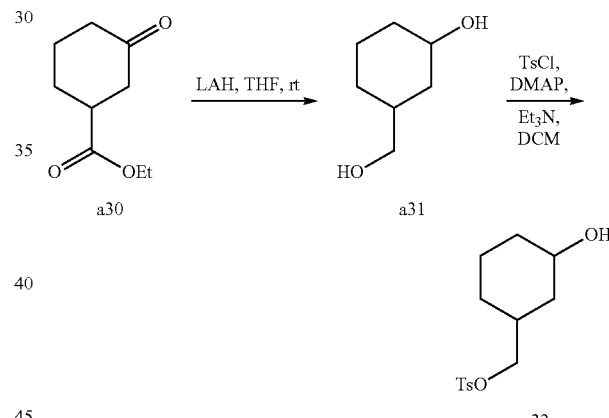

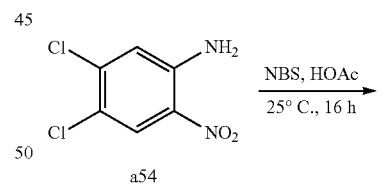

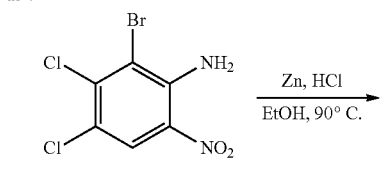

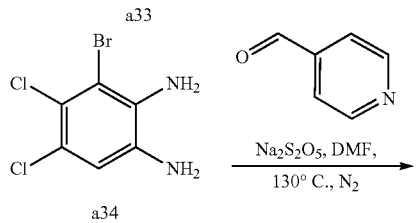

707
-continued

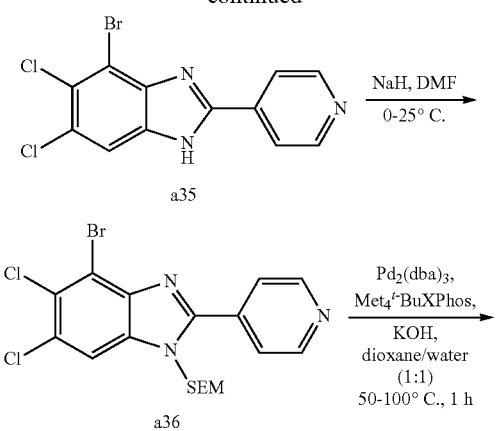

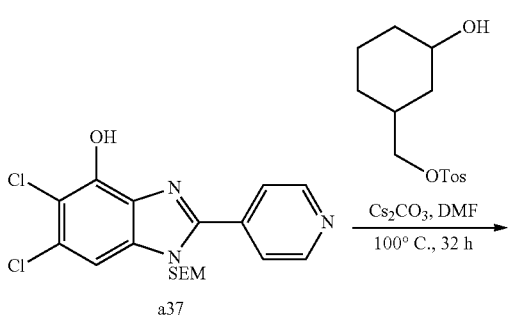

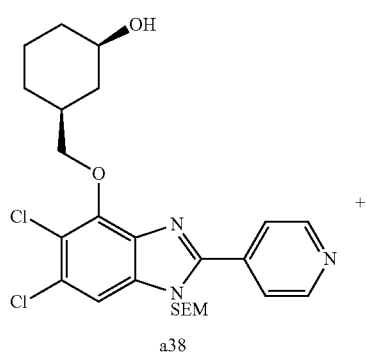

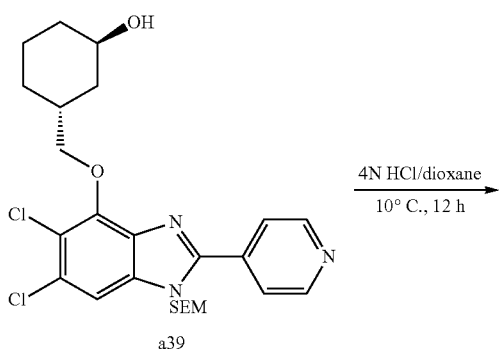

708
-continued

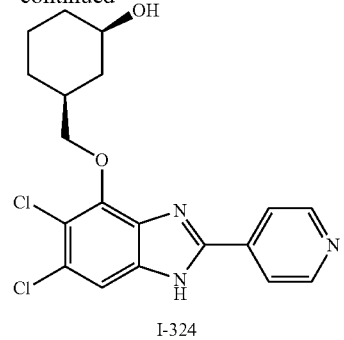

I-324

Procedures and Characterization:

Step 1: 3-(hydroxymethyl)cyclohexanol

To a solution of ethyl 3-oxocyclohexanecarboxylate (1.50 g, 8.81 mmol) in THF (15.00 mL) at 0° C. was added LiAlH$_4$ (1.34 g, 35.24 mmol) in portions. Then the reaction mixture was stirred at 20° C. for 12 h. Brine (20 mL) was added at 0° C. and the mixture was stirred for 30 min and filtered. The filtrate was concentrated to give 3-(hydroxymethyl)cyclohexanol (1.10 g, 8.45 mmol, 95.91% yield) (1.5 g, crude) as a pale yellow oil.

Step 2: [3-(hydroxymethyl)cyclohexyl] 4-methylbenzenesulfonate

A mixture of 3-(hydroxymethyl)cyclohexanol (1.50 g, 11.52 mmol), Tos-Cl (2.65 g, 13.82 mmol), NEt$_3$ (3.49 g, 34.56 mmol) and DMAP (140.76 mg, 1.15 mmol) in DCM (20.00 mL) was stirred at 10° C. for 12 h. The reaction mixture was purified by prep-TLC using DCM:MeOH=20:1 to give [3-(hydroxymethyl)cyclohexyl] 4-methylbenzenesulfonate (1.00 g, 3.52 mmol, 30.53% yield) as a pale yellow oil. MS (EI+, m/z): 307 [M+H]+.

Step 3: 2-Bromo-3,4-dichloro-6-nitroaniline

A mixture of 4,5-dichloro-2-nitrobenzenamine (17 g, 0.1 mol), NBS (17 g, 0.1 mol) and CH$_3$COOH (210 ml) was stirred for 16 h at 25° C. The reaction was quenched with water (100 mL) and extracted with ethyl acetate (1000 mL). The organic layer was washed with water (500 mL×2), dried (Na$_2$SO$_4$), filtered and concentrated in vacuo, the crude product was purified by chromatography (silica, ethyl acetate/petroleum ether=1/1) to afford 2-bromo-3,4-dichloro-6-nitrobenzenamine (20 g, 0.08 mmol, 80%) as a light yellow solid ESI-MS (EI+, m/z): 285 [M+H]$^+$.

Step 4: 3-Bromo-4,5-dichloro-1,2-phenylenediamine

2-Bromo-3,4-dichloro-6-nitroaniline (48.3 g, 168.9 mmol), Zn powder (30.0 g, 537.2 mmol) and ethanol (1 L) were combined and the resulting suspension was cooled to 0° C. Concentrated hydrochloric acid (37 percent, 193.0 mL, 2.36 mol) was then added. The resulting mixture was heated to reflux for 1 h, after which time it was allowed to cool to room temperature. The mixture was diluted with water (1.5 L) and the pH was adjusted to approximately 8 by the addition of sodium carbonate. The product was extracted with ethyl acetate (1 L), dried over magnesium sulfate, filtered and the solvents were removed under reduce pressure using a rotary evaporator. The product was crystallized from a methanol/water mixture to afford 3-Bromo-4,5-dichloro-1,2-phenylenediamine (34.21 g, yield=79%) as a brown solid.

MS (EI+, m/z): 254 [M+H]+.

Step 5: 4-bromo-5,6-dichloro-2-(pyridin-4-yl)-1H-benzo[d]imidazole

A mixture of 3-Bromo-4,5-dichloro-1,2-phenylenediamine (25.0 g, 100 mmol), isonicotinaldehyde (12.1 g, 113 mmol) and $Na_2S_2O_5$ (19.0 g, 100 mmol) in DMF (100.0 mL) was stirred at 130° C. for 3 h. It was extracted with EtOAc (100 ml), washed with water (100 ml*3), brine (100 ml*1), dried, filtered and concentrated to give a crude. It was purified to give 4-bromo-5,6-dichloro-2-(pyridin-4-yl)-1H-benzo[d]imidazole (12.5 g, 75% yield) as a pale yellow solid. MS (EI+, m/z): 343 [M+H]+.

Step 6: 2-[[4-bromo-5,6-dichloro-2-(4-pyridyl)benzimidazol-1-yl]methoxy]ethyl-trimethyl-silane To a stirred solution of 4-bromo-5,6-dichloro-2-(4-pyridyl)-1H-benzimidazole (5.00 g, 14.58 mmol) in DMF (30.00 mL) at 0° C., was added NaH (524.88 mg, 21.87 mmol) and the reaction mixture was stirred at 20° C. for 0.5 h. SEM-Cl (3.65 g, 21.87 mmol) in DMF (5 mL) was added dropwise. The reaction mixture was stirred at 20° C. for 12 h. The reaction mixture was extracted with EtOAc (100 ml), washed with water (100 ml*3), brine (100 ml*1), dried, filtered and concentrated to give the crude product. It was purified by column chromatography on silica gel with DCM:MeOH=50:1 to afford 2-[[4-bromo-5,6-dichloro-2-(4-pyridyl)benzimidazol-1-yl]methoxy]ethyl-trimethyl-silane (2.60 g, 5.49 mmol, 37.68% yield) 2-[[4-bromo-5,6-dichloro-2-(4-pyridyl)benzimidazol-1-yl]methoxy]ethyl-trimethyl-silane (2.60 g, 5.49 mmol, 37.68% yield). MS (EI+, m/z): 474 [M+H]+.

Step 7: 5,6-dichloro-2-(4-pyridyl)-1-(2-trimethylsilylethoxymethyl)benzimidazol-4-ol A mixture of 2-[[4-bromo-5,6-dichloro-2-(4-pyridyl)benzimidazol-1-yl]methoxy]ethyl-trimethyl-silane (2.60 g, 5.49 mmol), $Pd_2(dba)_3$ (2.46 g, 2.69 mmol), $Me_4$t-butylXPhos (2.45 g, 5.11 mmol) and KOH (2.19 g, 38.98 mmol) in dioxane (60.00 mL) and $H_2O$ (20.00 mL) was stirred in a oil bath previously heated to 50° C. And it was raised up to 100° C. and stirred for 1 h. It was extracted with EtOAc (100 ml), washed with water (100 ml*3), brine (100 ml*1), dried, filtered and concentrated to give a crude. It was purified by column chromatography on silica gel with DCM:MeOH=50:1 to afford 5,6-dichloro-2-(4-pyridyl)-1-(2-trimethylsilylethoxymethyl)benzimidazol-4-ol (600.00 mg, 1.46 mmol, 26.63% yield) as a light yellow solid. MS (EI+, m/z): 410 [M+H]+.

Step 8: (1R,3S)-3-((5,6-dichloro-2-(pyridin-4-yl)-1-((2-(trimethylsilyl)ethoxy)methyl)-1H-benzo[d]imidazol-4-yloxy)methyl)cyclohexanol and (1R,3R)—3-((5,6-dichloro-2-(pyridin-4-yl)-1-((2-(trimethylsilyl)ethoxy)methyl)-1H-benzo[d]imidazol-4-yloxy)methyl)cyclohexanol To a solution of 5,6-dichloro-2-(4-pyridyl)-1-(2-trimethylsilylethoxymethyl)benzimidazol-4-ol (600.00 mg, 1.46 mmol) and (3-hydroxycyclohexyl)methyl 4-methylbenzenesulfonate (498.22 mg, 1.75 mmol) in DMF (20.00 mL) was added $Cs_2CO_3$ (1.43 g, 4.38 mmol). Then it was stirred at 100° C. for 32 h. It was extracted with EtOAc (100 ml), washed with water (100 ml*3), brine (100 ml*1), dried, filtered and concentrated to give a crude. It was purified by prep-HPLC to 1R,3S)-3-((5,6-dichloro-2-(pyridin-4-yl)-1-((2-(trimethylsilyl)ethoxy)methyl)-1H-benzo[d]imidazol-4-yloxy)methyl)cyclohexanol (50 mg) as pale yellow solid and (1R,3R)—3-((5,6-dichloro-2-(pyridin-4-yl)-1-((2-(trimethylsilyl)ethoxy)methyl)-1H-benzo[d]imidazol-4-yloxy)methyl)cyclohexanol (20 mg) as pale yellow solid.

MS (EI+, m/z): 522[M+H]+.

Step 9: (1R,3S)-3-((5,6-dichloro-2-(pyridin-4-yl)-1H-benzo[d]imidazol-4-yloxy)methyl)cyclohexanol, I-324

A mixture of (1R,3S)-3-((5,6-dichloro-2-(pyridin-4-yl)-1-((2-(trimethylsilyl)ethoxy)methyl)-1H-benzo[d]imidazol-4-yloxy)methyl)cyclohexanol (50.00 mg, 95.69 µmol) and HCl/dioxane (956.86 µmol, 239.00 µL) in dioxane (2.00 mL) was stirred at 10° C. for 12 h. Then it was concentrated and purified by prep-HPLC to give (1R,3S)-3-((5,6-dichloro-2-(pyridin-4-yl)-1H-benzo[d]imidazol-4-yloxy)methyl)cyclohexanol 1-324 (11.40 mg, 29.06 µmol, 30.37% yield) as a pale yellow solid. MS (EI+, m/z): 392 [M–H]+.

1H-NMR (400 MHz, MeOD): $^1$H NMR (500 MHz, DMSO) δ 8.75 (m, 2H), 8.12 (m, 2H), 7.41 (s, 1H), 4.70 (m, 2H), 4.11 (m, 1H), 2.37 (m, 11H), 1.98 (m, 2H), 1.80 (m, 2H), 1.61 (m, 3H), 1.36 (m, 1H).

Example 235: (1R,3R)—3-((5,6-dichloro-2-(pyridin-4-yl)-1-((2-(trimethylsilyl)ethoxy)methyl)-1H-benzo[d]imidazol-4-yloxy)methyl)cyclohexanol, I-323

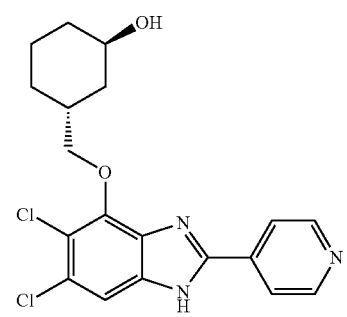

I-323

Synthetic Scheme:

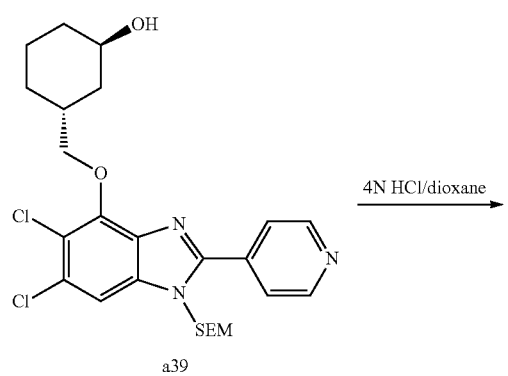

a39

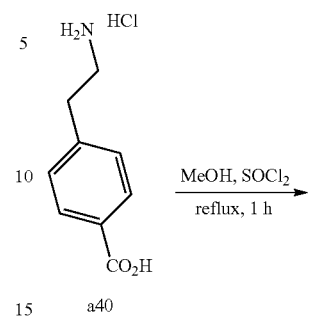

a40

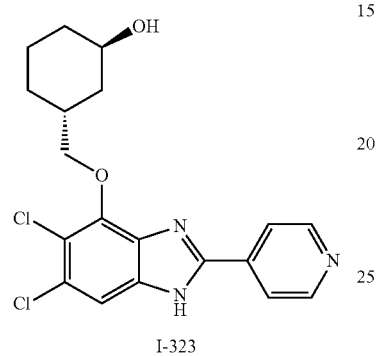

I-323

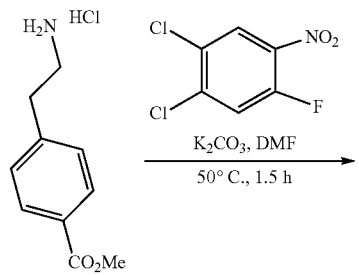

a41

Step 1: (1R,3R)—3-((5,6-dichloro-2-(pyridin-4-yl)-1-((2-(trimethylsilyl)ethoxy)methyl)-1H-benzo[d]imidazol-4-yloxy)methyl)cyclohexanol, I-323

The same procedure as I-324 using (1R,3R)—3-((5,6-dichloro-2-(pyridin-4-yl)-1-((2-(trimethylsilyl)ethoxy)methyl)-1H-benzo[d]imidazol-4-yloxy)methyl)cyclohexanol (20 mg, 38.3 μmol) to give (1R,3R)-3-((5,6-dichloro-2-(pyridin-4-yl)-1-((2-(trimethylsilyl)ethoxy)methyl)-1H-benzo[d]imidazol-4-yloxy)methyl)cyclohexanol I-323 (5.1 mg, 33% yield) as a pale yellow solid. MS (EI+, m/z): 392 [M−H]+.

1H-NMR (400 MHz, MeOD): $^1$H NMR (500 MHz, DMSO) δ 8.75 (m, 2H), 8.12 (m, 2H), 7.41 (s, 1H), 4.70 (m, 2H), 3.60 (m, 1H), 2.30 (m, 1H), 1.98 (m, 4H), 1.18 (m, 4H).

Example 236: 4-(2-(5,6-dichloro-2-(1H-pyrrolo[2,3-b]pyridin-4-yl)-1H-benzo[d]imidazol-1-yl)ethyl)benzoic acid, I-331

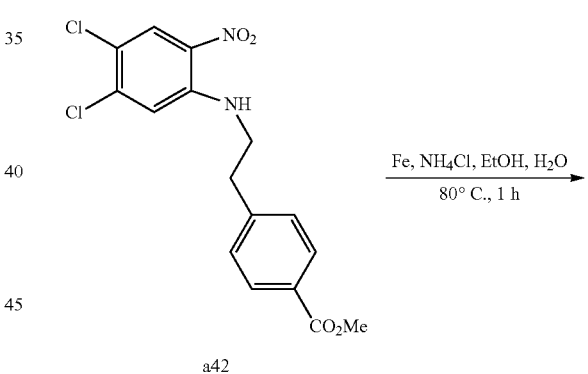

a42

I-331

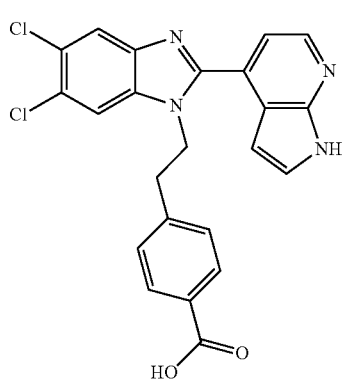

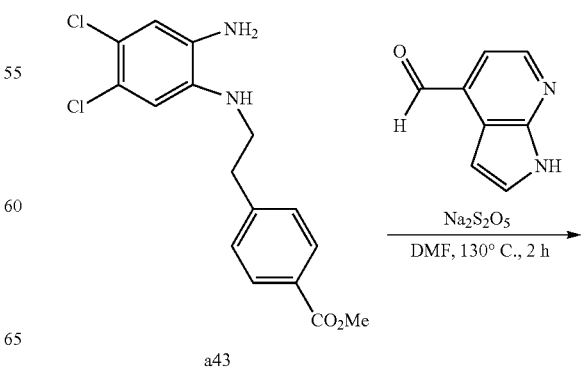

a43

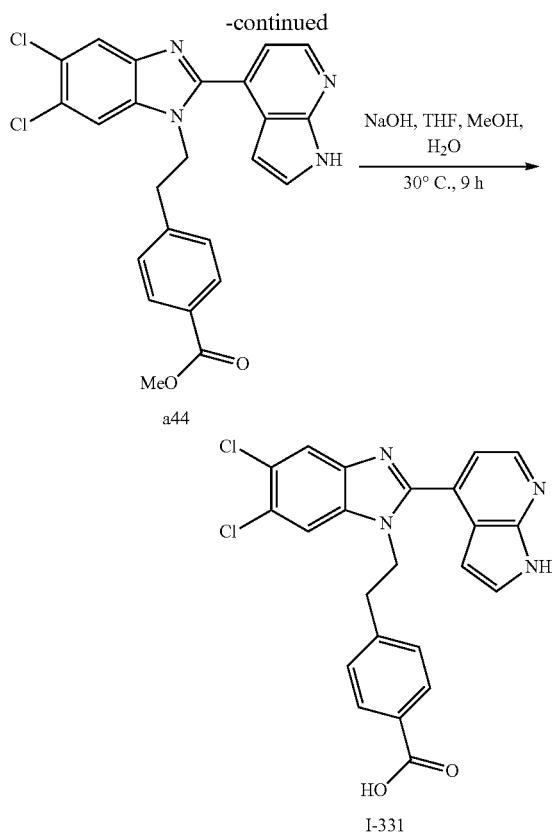

Procedures and Characterization:

Step 1: methyl 4-(2-aminoethyl)benzoate hydrochloride

To a solution of 4-(2-aminoethyl)benzoic acid hydrochloride (5.0 g, 24.8 mmol) in methanol (80 mL) was added dropwise thionyl chloride (3.6 mL, 49.6 mmol). The reaction was stirred for 1 h reflux. The reaction mixture was concentrated in vacuo to afford the desired methyl ester as a hydrochloride salt. The resulting salt was used without further purification. ESI-MS (EI+, m/z): 180.1 [M+H]+.

Step 2: methyl 4-(2-(4,5-dichloro-2-nitrophenylamino)ethyl)benzoate

To a solution of 880 mg (4.2 mmol) methyl 4-(2-aminoethyl)benzoate hydrochloride and 1730 mg (12.6 mmol) potassium carbonate in 15 mL DMF was added 990 mg (4.6 mmol) 1,2-dichloro-4-fluoro-5-nitrobenzene and the mixture was stirred for 1.5 h at 50° C. The reaction mixture was dissolved in EtOAc, the organic phase washed with water ten times, dried over sodium sulphate and evaporated. The crude product was used in the next reaction step without any further purification. ESI-MS (EI+, m/z): 369.0 [M+H]+.

Step 3: methyl 4-(2-(2-amino-4,5-dichlorophenylamino)ethyl)benzoate

To a solution methyl 4-(2-(4,5-dichloro-2-nitrophenylamino)ethyl)benzoate (736 mg, 2 mmol) in ethanol/water (30 mL/6 mL) was added $NH_4Cl$ (530 mg 10 mmol) and Fe (560 mg, 10 mmol). The mixture was stirred at 80° C. for 1 hour. After filtration, the filtrate extracted with ethyl acetate (100 mL×2), and dried over $Na_2SO_4$. Filtration and solvent evaporation led to crude Compound (800 mg, crude) as a red solid, which was used to next step without purified. ESI-MS (EI+, m/z): 339.0 [M+H]−.

Step 4: methyl 4-(2-(5,6-dichloro-2-(1H-pyrrolo[2,3-b]pyridin-4-yl)-1H-benzo[d]imidazol-1-yl)ethyl)benzoate A mixture of 338 mg (1.0 mmol) methyl 4-(2-(2-amino-4,5-dichlorophenylamino)ethyl)benzoate, 73 mg (0.5 mmol) 1H-pyrrolo[2,3-b]pyridine-4-carbaldehyde and 209 ng $Na_2S_2O_5$ (1.1 mmol) dissolved in 15 mL DMF was stirred at 130° C. for 2 h. The reaction mixture was dissolved in EtOAc, the org. phase washed with water for ten times, dried over sodium sulphate and evaporated. The crude product was purified by Prep-TLC with DCM:MeOH=10:1 to give the desired product. ESI-MS (EI+, m/z): 465.0 [M+H]+.

Step 5: 4-(2-(5,6-dichloro-2-(1H-pyrrolo[2,3-b]pyridin-4-yl)-1H-benzo[d]imidazol-1-yl)ethyl)benzoic acid, I-331

A mixture of 46 mg methyl 4-(2-(5,6-dichloro-2-(1H-pyrrolo[2,3-b]pyridin-4-yl)-1H-benzo[d]imidazol-1-yl)ethyl)benzoate (0.1 mmol), 20 mg NaOH (0.5 mmol), MeOH (4 ml), THF (4 ml) and $H_2O$ (1 ml) was stirred at room temperature for 9 h. Then diluted hydrochloric acid (6N) to make sure pH to about 5-6, and then many white solid appeared. Filtrated the mixture to give the white solid and sent it to prep-HPLC and afford the desired product I-331 (15 mg, 33%). ESI-MS (EI+, m/z): 451.0 [M+H]+. $^1$H NMR (500 MHz, MeOD) δ 8.25 (d, J=6.0 Hz, 1H), 7.95 (s, 1H), 7.90 (s, 1H), 7.58 (d, J=9.0 Hz, 2H), 7.50 (d, J=4.5 Hz, 1H), 6.95 (d, J=6.5 Hz, 1H), 6.64 (d, J=9.5 Hz, 2H), 6.36 (d, J=4.5 Hz, 1H), 4.74-4.71 (m, 2H), 3.01-2.98 (m, 2H).

Example 237: 4-(2-(5,6-dichloro-2-(1H-pyrrolo[2,3-b]pyridin-3-yl)-1H-benzo[d]imidazol-1-yl)ethyl)benzoic acid, I-335

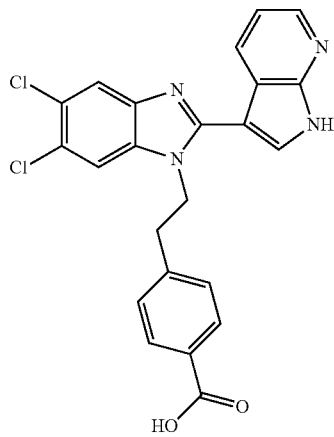

Synthetic Scheme:

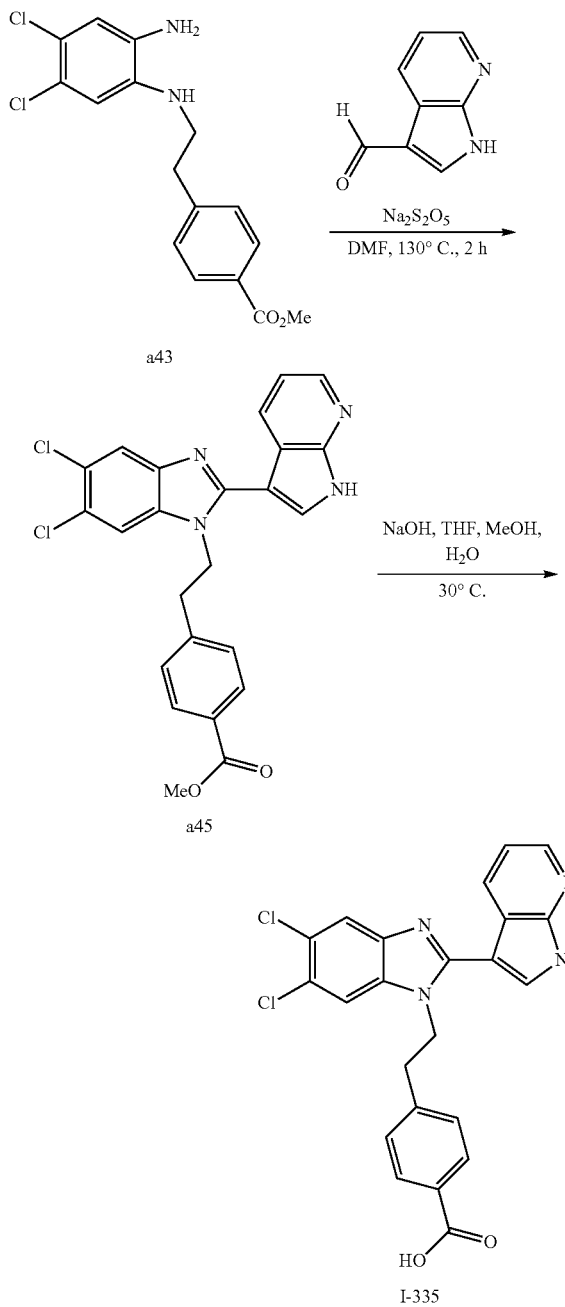

Procedures and Characterization:

Step 1: methyl 4-(2-(5,6-dichloro-2-(1H-pyrrolo[2,3-b]pyridin-3-yl)-1H-benzo[d]imidazol-1-yl)ethyl)benzoate A mixture of 169 mg (0.5 mmol), methyl 4-(2-(2-amino-4,5-dichlorophenylamino)ethyl)benzoate (146 mg, 0.25 mmol), 1H-pyrrolo[2,3-b]pyridine-3-carbaldehyde and Na$_2$S$_2$O$_5$ (105 mg, 0.55 mmol) dissolved in 7 mL DMF was stirred at 130° C. for 2 h. The reaction mixture was dissolved in EtOAc, the organic phase washed with water for ten times, dried over sodium sulphate and evaporated under high pressure. The crude product was purified by Prep-TLC with DCM:MeOH==12:1 to give the desired product. ESI-MS (EI+, m/z): 465.0 [M+H]$^+$.

Step 2: 4-(2-(5,6-dichloro-2-(1H-pyrrolo[2,3-b]pyridin-3-yl)-1H-benzo[d]imidazol-1-yl)ethyl)benzoic acid, I-335

A mixture of 46 mg methyl 4-(2-(5,6-dichloro-2-(1H-pyrrolo[2,3-b]pyridin-3-yl)-1H-benzo[d]imidazol-1-yl)ethyl)benzoate (0.1 mmol), 20 mg NaOH (0.5 mmol), MeOH (4 ml), THF (4 ml) and H$_2$O (1 ml) was stirred at room temperature for 9 h. Then diluted hydrochloric acid (6N) to make sure pH to about 5-6, and then a white solid appeared. Filtrated the mixture to give the white solid and sent it to prep-HPLC and afford the desired product I-335 (20 mg, 44%). ESI-MS (EI+, m/z): 451.0 [M+H]$^+$. $^1$H NMR (500 MHz, MeOD) δ 8.31-8.30 (m, 1H), 8.15-8.13 (m, 1H), 7.82 (d, J=7.0 Hz, 2H), 7.62-7.59 (m, 3H), 7.22-7.19 (m, 1H), 6.81 (d, J=10.5 Hz, 2H), 4.77-4.74 (m, 2H), 3.14-3.11 (m, 2H).

Examples 238: 2-(5,6-dichloro-2-(1H-pyrrolo[2,3-b]pyridin-3-yl)-1H-benzo[d]imidazol-1-yl)acetic acid, I-334

I-334

Synthetic Scheme:

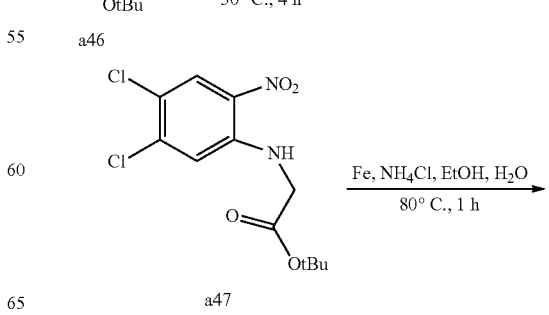

717
-continued

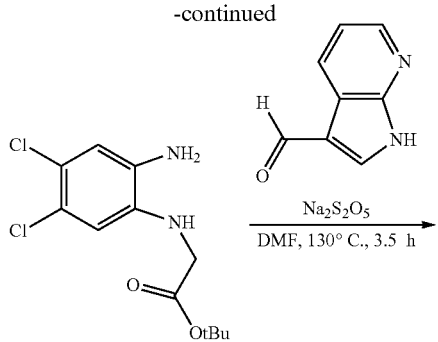

a48

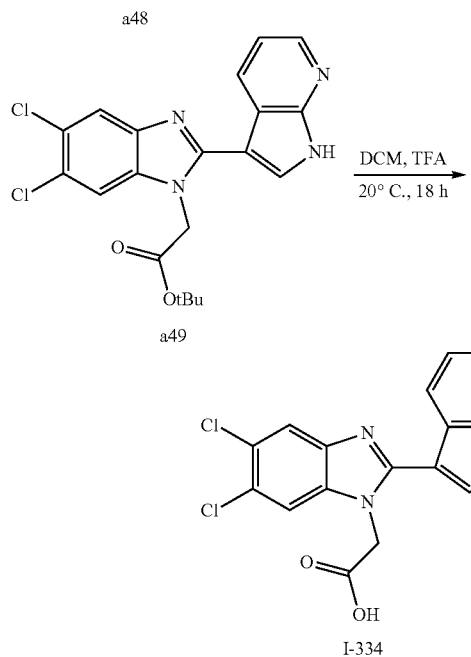

Procedures and Characterization:

Step 1: tert-butyl 2-(4,5-dichloro-2-nitrophenylamino)acetate

To a solution of 368 mg (2.2 mmol) tert-butyl 2-aminoacetate hydrochloride and 828 mg (12.6 mmol) potassium carbonate in 8 mL DMF was added 418 mg (2.0 mmol) 1,2-dichloro-4-fluoro-5-nitrobenzene and the mixture was stirred for 1.5 h at 50° C. The reaction mixture was dissolved in EtOAc, the org. phase washed with water ten times, dried over sodium sulphate and evaporated. The crude product was used in the next reaction step without any further purification. ESI-MS (EI+, m/z): 343.0 [M+Na]+.

Step 2: tert-butyl 2-(2-amino-4,5-dichlorophenylamino)acetate

To a solution tert-butyl 2-(4,5-dichloro-2-nitrophenylamino)acetate (480 mg, 1.5 mmol) in ethanol/water (25 mL/5 mL) was added NH$_4$Cl (398 mg 7.5 mmol) and Fe (420 mg, 7.5 mmol). The mixture was stirred at 80° C. for 1 hour. After filtration, the filtrate extracted with ethyl acetate (100 mL×2), and dried over Na$_2$SO$_4$. Filtration and solvent evaporation led to crude compound (500 mg, crude) as a red solid, which was used to next step without purified. ESI-MS (EI+, m/z): 313.0 [M+Na]+.

718

Step 3: tert-butyl 2-(5,6-dichloro-2-(1H-pyrrolo[2,3-b]pyridin-3-yl)-1H-benzo[d]imidazol-1-yl)acetate A mixture of 145 mg (0.5 mmol) tert-butyl 2-(2-amino-4,5-dichlorophenylamino)acetate, 146 mg (0.25 mmol) 1H-pyrrolo[2,3-b]pyridine-4-carbaldehyde and 105 mg Na$_2$S$_2$O$_5$ (0.55 mmol) dissolved in 7 mL DMF was stirred at 130° C. for 2 h. The reaction mixture was dissolved in EtOAc, the org. phase washed with water for ten times, dried over sodium sulphate and evaporated i. vac. The crude product was purified by prep-TLC with DCM:MeOH=15: to give the desired product. ESI-MS (EI+, m/z): 417.0 [M+H]+.

Step 4: 2-(5,6-dichloro-2-(1H-pyrrolo[2,3-b]pyridin-3-yl)-1H-benzo[d]imidazol-1-yl)acetic acid, I-334

A mixture of 62.4 mg tert-butyl 2-(5,6-dichloro-2-(1H-pyrrolo[2,3-b]pyridin-4-yl)-1H-benzo[d]imidazol-1-yl)acetate (0.15 mmol) and DCM (4 ml) was stirred at 0° C. Then dropwise added TFA (4 ml) slowly to make sure the temperature maintain 0° C. Then temperature to 15° C. for 18 h and concentrated to afford crude product and sent it to prep-HPLC and afford the desired product I-334 (15 mg, 27.8%). ESI-MS (EI+, m/z): 361.0 [M+H]+. $^1$H NMR (500 MHz, MeOD) δ 8.47 (d, J=9.0 Hz, 1H), 8.40 (d, J=5.0 Hz, 1H), 7.95 (s, 1H), 7.89 (s, 1H), 7.85 (s, 1H), 7.35-7.32 (m, 1H), 5.21 (s, 2H).

Example 239: 4-((5,6-dichloro-2-(pyridin-4-yl)-1H-benzo[d]imidazol-1-yl)methyl)benzoic acid, I-365

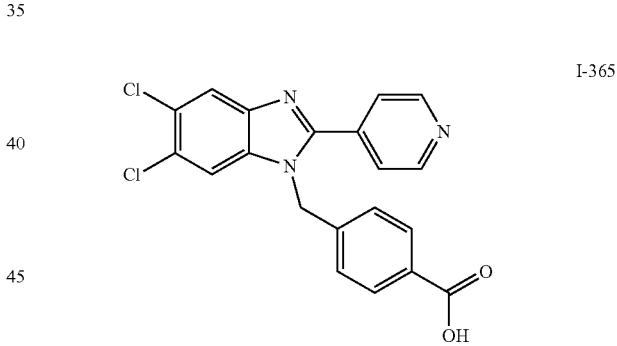

Synthetic Scheme:

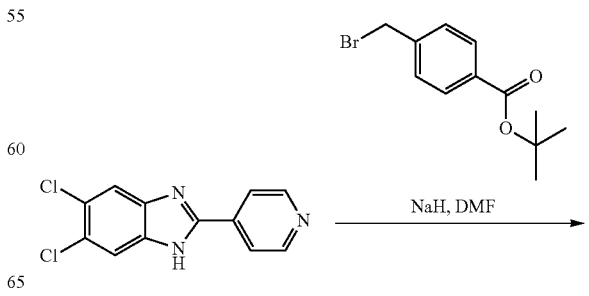

-continued

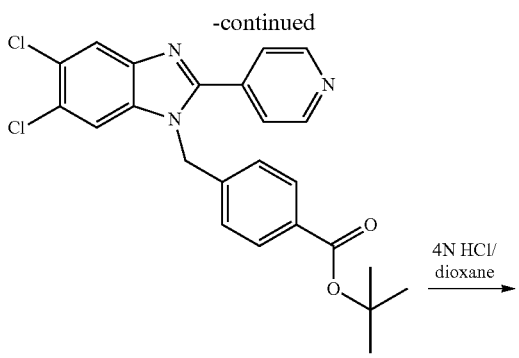

a50

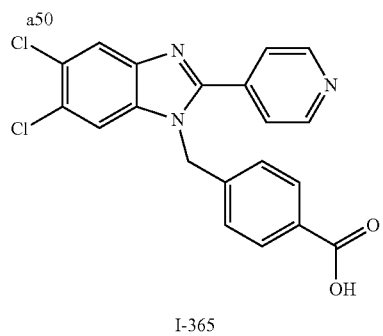

I-365

Procedures and Characterization:

Step 1: tert-butyl 4-((5,6-dichloro-2-(pyridin-4-yl)-1H-benzo[d]imidazol-1-yl)methyl)benzoate To a stirred solution of 5,6-dichloro-2-(pyridin-4-yl)-1H-benzo[d]imidazole (200 mg, 0.76 mmol, 1.0 eq.) in DMF (5.0 mL) at room temperature, was added NaH (38 mg, 0.92 mmol, 1.2 eq.) and the reaction mixture was stirred at rt for 0.5 h. tert-butyl 4-(bromomethyl)benzoate (232 mg, 0.836 mmol, 1.1 eq.) was added. The reaction mixture was stirred at rt for 12 h. Water (50 mL) was added, and the mixture was extracted into ethyl acetate (3×20 mL), and the combined organic extracts were dried over magnesium sulfate and concentrated in vacuo to give a crude which was purified by prep-HPLC to give tert-butyl 4-((5,6-dichloro-2-(pyridin-4-yl)-1H-benzo[d]imidazol-1-yl)methyl)benzoate (30.0 mg, 8.7 percent). ESI-MS (ESI⁺, m/z): 454[M+H]⁺. ¹H NMR (500 MHz, DMSO) δ 8.73 (d, J=5.5 Hz, 1H), 8.12 (s, 1H), 8.04 (s, 1H), 7.80 (d, J=8.0 Hz, 2H), 7.70 (d, J=6.5 Hz, 2H), 7.08 (d, J=8.0 Hz, 2H), 5.79 (s, 2H), 1.50 (s, 9H).

Step 2: 4-((5,6-dichloro-2-(pyridin-4-yl)-1H-benzo[d]imidazol-1-yl)methyl)benzoic acid, I-365

A solution of tert-butyl 4-((5,6-dichloro-2-(pyridin-4-yl)-1H-benzo[d]imidazol-1-yl)methyl)benzoate (50 mg, 0.76 mmol, 1.0 eq.) in 4N HCl (3 ml) and stirred at rt for 12 h. Then it was concentrated in vacuo to give a crude which was purified by prep-HPLC to give 4-((5,6-dichloro-2-(pyridin-4-yl)-1H-benzo[d]imidazol-1-yl)methyl)benzoic acid I-365 (23.9 mg, 55 percent).

ESI-MS (ESI⁺, m/z): 398[M+H]⁺.

¹H NMR (500 MHz, DMSO) δ 8.73 (d, J=6.5 Hz, 1H), 8.12 (s, 1H), 8.06 (s, 1H), 7.85 (d, J=8.5 Hz, 2H), 7.72 (d, J=6.0 Hz, 2H), 7.06 (d, J=8.0 Hz, 2H), 5.79 (s, 2H).

Example 240: 5-(benzyloxy)-6-chloro-1-ethyl-1H-benzo[d]imidazole, I-434

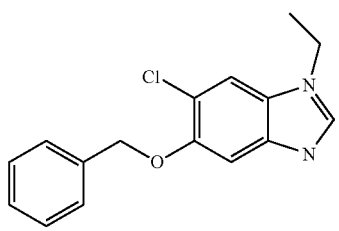

I-434

Synthetic Scheme:

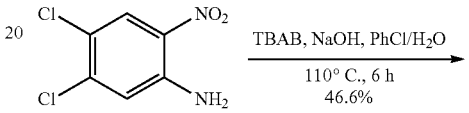

a54

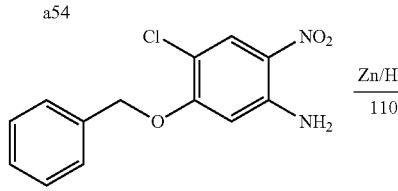

a55

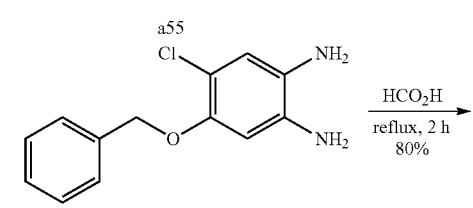

a56

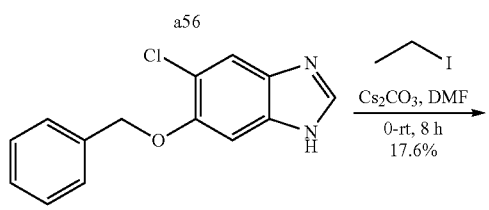

a57

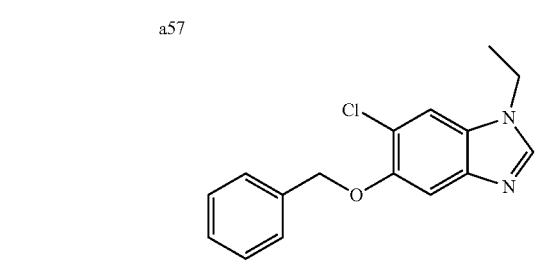

I-434

Procedures and Characterization:

Step 1: 5-(benzyloxy)-4-chloro-2-nitroaniline

The solution of 4,5-dichloro-2-nitroaniline (5.0 g, 24.2 mmol), phenylmethanol (3.1 g, 29.0 mmol), TBAB (562 mg, 1.7 mmol) and NaOH (2.9 g, 72.6 mmol) in chlorobenzene/H₂O (20 mL/40 mL) was stirred at 110° C. for 6 h, then diluted with EtOAc, washed with water, the organic layer was concentrated in vacuo, then diluted with PE, filtered and the solid was collected and used for next step without further purification.

Step 2: 4-(benzyloxy)-5-chlorobenzene-1,2-diamine

To a solution of 5-(benzyloxy)-4-chloro-2-nitroaniline (4.5 g, 16.2 mmol) in EtOH/Con. HCl (50 mL/6 mL) was added Zn (5.3 g, 80 mmol) in portions. The resultant solution was stirred at reflux for 2 h, then filtered and the filtrated was concentrated to next step.

Step 3: 6-(benzyloxy)-5-chloro-1H-benzo[d]imidazole

The solution of 4-(benzyloxy)-5-chlorobenzene-1,2-diamine (240 mg, 1.2 mmol) in formic acid (5.0 mL) was stirred at reflux for 2 h, then removed the solvent in vacuo to give a red solid and this crude was to next step directly.

Step 4: 5-(benzyloxy)-6-chloro-1-ethyl-1H-benzo[d]imidazole, I-434

To a solution of 6-(benzyloxy)-5-chloro-1H-benzo[d]imidazole (260 mg, 1.0 mmol), Cs$_2$CO$_3$ (975 mg, 3.0 mmol) in DMF (5.0 mL) was added iodoethane (312 mg, 2.0 mmol) at 0° C., the resultant solution was stirred at 0-rt for 8 h, then diluted with EtOAc, washed with water, brine. The crude was purified by SGC, then by chiral-HPLC to obtain 5-(benzyloxy)-6-chloro-1-ethyl-1H-benzo[d]imidazole I-434 as a white solid. ESI-MS (EI$^+$, m/z): 287.3 [M+H]$^-$.
$^1$H NMR (500 MHz, DMSO-d$_6$) δ 8.20 (d, J=12.4 Hz, 1H), 7.72 (s, 1H), 7.58-7.46 (m, 3H), 7.43 (dd, J=15.4, 8.1 Hz, 2H), 7.35 (t, J=7.3 Hz, 1H), 5.25 (d, J=12.8 Hz, 2H), 4.24 (p, J=7.3 Hz, 2H), 1.38 (t, J=7.2 Hz, 3H).

Example 241: 4-((6,7-dichloro-1,3-dihydrobenzo[d]oxazolo[3,4-a]imidazol-5-yloxy)methyl)cyclopentane-1,2-diol, I-373

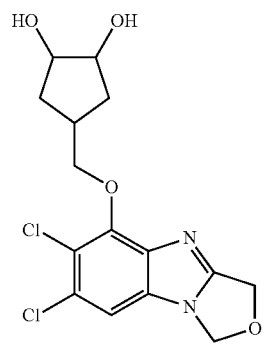

I-373

Synthetic Scheme:

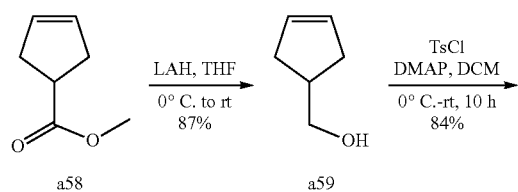

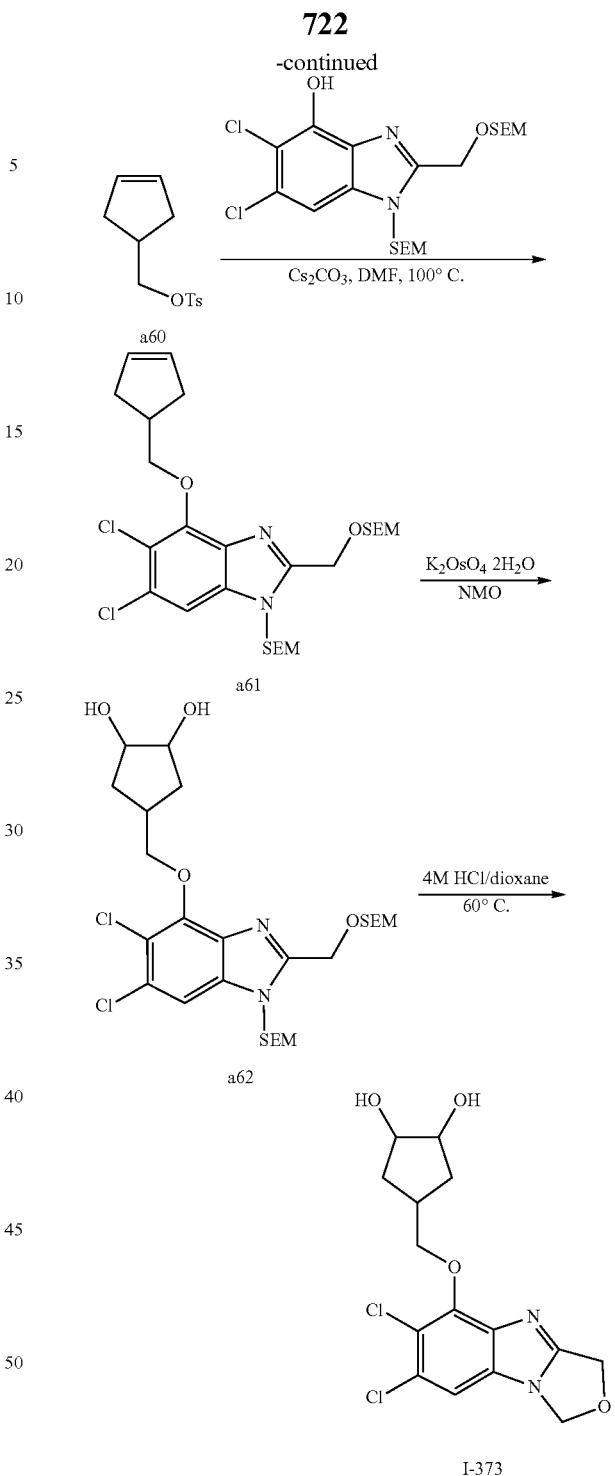

Procedures and Characterization:

Step 1: Cyclopent-3-enylmethanol

To a solution of methyl cyclopent-3-enecarboxylate (1 g, 8 mmol) in THF (10 mL) was added LAH (304 mg, 8 mmol) at 0° C. under N$_2$ atmosphere and stirred at rt for 20 h. The solution was extracted with ethyl acetate (100 mL). The organic phase was washed with water (100 mL×2), and brine (100 mL), dried (Na$_2$SO$_4$), filtered and concentrated in vacuo, the crude product was used purified by prep-HPLC to afford cyclopent-3-enylmethanol (0.68 g, 7 mmol, 87%) as colorless oil. H NMR (500 MHz, CDCl$_3$) δ 5.67 (s, 2H), 3.55 (d, J=4.7 Hz, 2H), 2.58-2.32 (m, 3H), 2.12 (td, J=8.3, 4.5 Hz, 2H), 1.74 (s, 1H).

Step 2: Cyclopent-3-enylmethyl 4-methylbenzenesulfonate

To a solution of cyclopent-3-enylmethanol (600 mg, 6.12 mmol) in DCM (12.00 mL) was added TEA (1.24 g, 12.24 mmol), DMAP (75 mg, 0.62 mmol) followed by TosCl (1.75 g, 9.18 mmol) at 0° C. under N$_2$ atmosphere and stirred for 10 h at rt. The solution was diluted with water (200 mL) and extracted with ethyl acetate (100 mL). The organic phase was washed with water (100 mL×2), and brine (100 mL), dried (Na$_2$SO$_4$), filtered and concentrated in vacuo, the crude product was purified by SGC to afford cyclopent-3-enylmethyl 4-methylbenzenesulfonate as a white solid (1.3 g, 5.14 mmol, 84%). ESI-MS (EI+, m/z): 275 [M+Na]$^+$. H NMR (500 MHz, CDCl$_3$) δ 7.79 (d, J=8.2 Hz, 2H), 7.35 (d, J=8.1 Hz, 2H), 5.64-5.54 (m, 2H), 3.92 (d, J=7.4 Hz, 2H), 2.60 (tt, J=7.4, 5.7 Hz, 1H), 2.48-2.41 (m, 5H), 2.03 (dd, J=15.1, 4.0 Hz, 2H).

Step 3: 5,6-dichloro-4-(cyclopent-3-enylmethoxy)-2-(((2-(trimethylsilyl)ethoxy)methoxy)methyl)-1-((2-(trimethylsilyl)ethoxy)methyl)-1H-benzo[d]imidazole To a solution of afford cyclopent-3-enylmethyl 4-methylbenzenesulfonate (320 mg, 1.27 mmol) in DMF (12.00 mL) was added Cs$_2$CO$_3$ (825 mg, 2.54 mmol under N$_2$ atmosphere and stirred for 20 h at 100° C. The solution was diluted with water (200 mL) and extracted with ethyl acetate (100 mL). The organic phase was washed with water (100 mL×2), and brine (100 mL), dried (Na$_2$SO$_4$), filtered and concentrated h vacuo, the crude product was purified by SGC to afford 5,6-dichloro-4-(cyclopent-3-enylmethoxy)-2-(((2-(trimethylsilyl)ethoxy)methoxy)methyl)-1-((2-(trimethylsilyl)ethoxy)methyl)-1H-benzo[d]imidazole (603 mg, 1.07 mmol, 84%). ESI-MS (EI+, m/z): 573 [M+H]$^+$.

Step 4: 4-((5,6-dichloro-2-(((2-(trimethylsilyl)ethoxy)methoxy)methyl)-1-((2-(trimethylsilyl)ethoxy)methyl)-1H-benzo[d]imidazol-4-yloxy)methyl)cyclopentane-1,2-diol To a solution of 6-dichloro-4-(cyclopent-3-enylmethoxy)-2-(((2-(trimethylsilyl) ethoxy)methoxy)methyl)-1-((2-(trimethylsilyl)ethoxy)methyl)-1H-benzo[d]imidazole (400 mg, 0.70 mmol) in acetone (16.00 mL) was added K$_2$OsO$_4$.2H$_2$O (258 mg, 0.70 mmol) and NMO (90 mg, 0.77 mmol) under N$_2$ atmosphere and stirred for 20 h at rt. The solution was treated with a solution of Na$_2$S$_2$O4 in water, filtered. The organic phase was washed with water (100 mL×2), and brine (100 mL), dried (Na$_2$SO$_4$), filtered and concentrated in vacuo, the crude product was used directly for the next step. ESI-MS (EI+, m/z): 607 [M+H]$^+$.

Step 5: 4-((6,7-dichloro-1,3-dihydrobenzo[d]oxazolo[3,4-a]imidazol-5-yloxy)methyl)cyclopentane-1,2-diol, I-373

A solution of 4-((5,6-dichloro-2-(((2-(trimethylsilyl) ethoxy)methoxy)methyl)-1-((2-(trimethylsilyl) ethoxy)methyl)-1H-benzo[d]imidazol-4-yloxy)methyl)cyclopentane-1,2-diol (100 mg, 0.17 mmol) in 4M HCl/dioxane (10.00 mL) was stirred for 20 h at 60° C. The solution was quenched with NaHCO$_3$, extracted with ethyl acetate. The organic phase was washed with water (100 mL×2), and brine (100 mL), dried (Na$_2$SO$_4$), filtered and concentrated in vacuo, the crude product was purified by prep-HPLC to afford I-373 as a white solid (12.4 mg, 0.04 mmol, 24%). ESI-MS (EI+, m/z): 359 [M+H]$^+$. $^1$H NMR (500 MHz, CDCl$_3$) δ 7.31 (s, 1H), 5.06 (s, 1H), 4.95 (s, 2H), 4.66 (s, 1H), 4.57 (d, J=4.2 Hz, 2H), 4.49 (s, 2H), 2.68 (dq, J=17.9, 6.0 Hz, 1H), 2.16 (dd, J=14.3, 6.0 Hz, 2H), 1.59 (d, J=11.5 Hz, 2H).

Example 242: Rheb Assays

Method 1 (Rheb-Dependent In Vitro Kinase Assay

To purify mTORC1, HEK-293E cells (ATCC #CRL-10852) stably expressing Flag-Raptor were serum-starved in DMEM (Fisher Scientific #MT10017CV) (no FBS) overnight. The next day, the cells were collected and lysed in the following lysis buffer: 0.4% CHAPS, 150 mM NaCl, 50 mM HEPES pH 7.4, protease inhibitor tab (Sigma #11873580001). Lysates were cleared by centrifugation at 4° C. and incubated with anti-FLAG M2 affinity agarose gel (Sigma #A2220) for 1 hour on nutator at 4° C. The beads were washed 3 times in wash buffer (0.1% CHAPS, 120 mM NaCl, 50 mM HEPES pH 7.4), and elution was performed in mTORC1 elution buffer (150 mM NaCl, 50 mM HEPES pH 7.4, 0.03% CHAPS, 375 ug/mL Flag peptide). The eluate was separated from the beads using a micro biospin column (BioRad #732-6204). The purified mTORC1 was stored at 4° C. for up to one week.

Human HA-GST-Rheb was purified from mammalian cells by first transfecting Freestyle 293-F suspension cells (ThermoFisher Scientific #R79007) grown in Freestyle 293 Expression Medium (ThermoFisher Scientific #12338018) with pRK5-HA-GST-Rheb DNA using polyeth-ylenimine (Polysciences, 23966-2). Five days after transfection, the cells were lysed in lysis buffer [150 mM NaCl, 50 mM HEPES pH 7.4, 1% Triton X-100, 5 mM MgCl$_2$, protease inhibitor tab (Sigma #11873580001)]. Lysates were cleared and incubated with glutathione agarose (Pierce #16100) for one hour at 4° C. HA-GST-Rheb was eluted from the glutathione agarose with elution buffer (150 mM NaCl, 50 mM Tris pH 8.0, 10 mM glutathione, 0.1% β-mercaptoethanol, 5 mM MgCl$_2$), concentrated, and stored at −80° C.

For the Rheb-dependent in vitro kinase assay, HA-GST-Rheb was first loaded with GTP-γ-S (Millipore #20-176) by incubating 600 ng/μL Rheb with 10 mM EDTA and 0.4 mM GTP-γ-S at 30° C. for 10 minutes. MgCl$_2$ was added to a final concentration of 20 mM to stop the reaction. This mixture was used at 20× in the kinase assay.

Loaded HA-GST-Rheb was then incubated with compound (final DMSO concentration 1%) for 30 minutes at room temperature. mTORC1, GFP-4E-BP1 substrate (Life Technologies #PV4759), and kinase assay buffer (HEPES pH 7.4, KCl, MgCl$_2$) were added to the Rheb-compound mixture and incubated at room temperature for 20 minutes. ATP was then added, and the kinase reaction proceeded at 30° C. for 45 min before being stopped by the addition of SDS-PAGE loading buffer for Westerns or 10 mM EDTA for the LanthaScreen readout. During the kinase reaction, the final concentration of reagents is as follows: Rheb—30 ng/μL, compound—variable, GTPγS—0.02 mM, EDTA—0.5 mM, MgCl2—1 mM, mTORC1—fixed volume of prep (molarity unknown), GFP-4E-BP1 substrate—15 ng/μL, ATP—0.5 mM. For LanthaScreen analysis (Thermo Fisher

PV4757), the manufacturer's instructions were followed and conditions were optimized for the amount of Rheb and mTORC1. The final concentration of reagents was as follows: 100 nM loaded HA-GST-Rheb, compound (variable), 0.5 mM EDTA, 10 mM $MgCl_2$, 25 mM HEPES pH 7.4, 50 mM KCl, mTORC1 (fixed volume—0.1 μL in 10 μL total volume), 0.4 μM GFP-4E-BP1 substrate, 0.5 mM ATP. Optimization is summarized in FIG. 1. Results were read on an EnVision reader (PerkinElmer) using 495ex/520em filters (Life Technologies, #PV00315). For Western analysis of kinase assay samples, blots were probed with a $^{T37/46}$p4E-BP1 antibody (Cell Signaling Technology, #2855).

Figure 2:
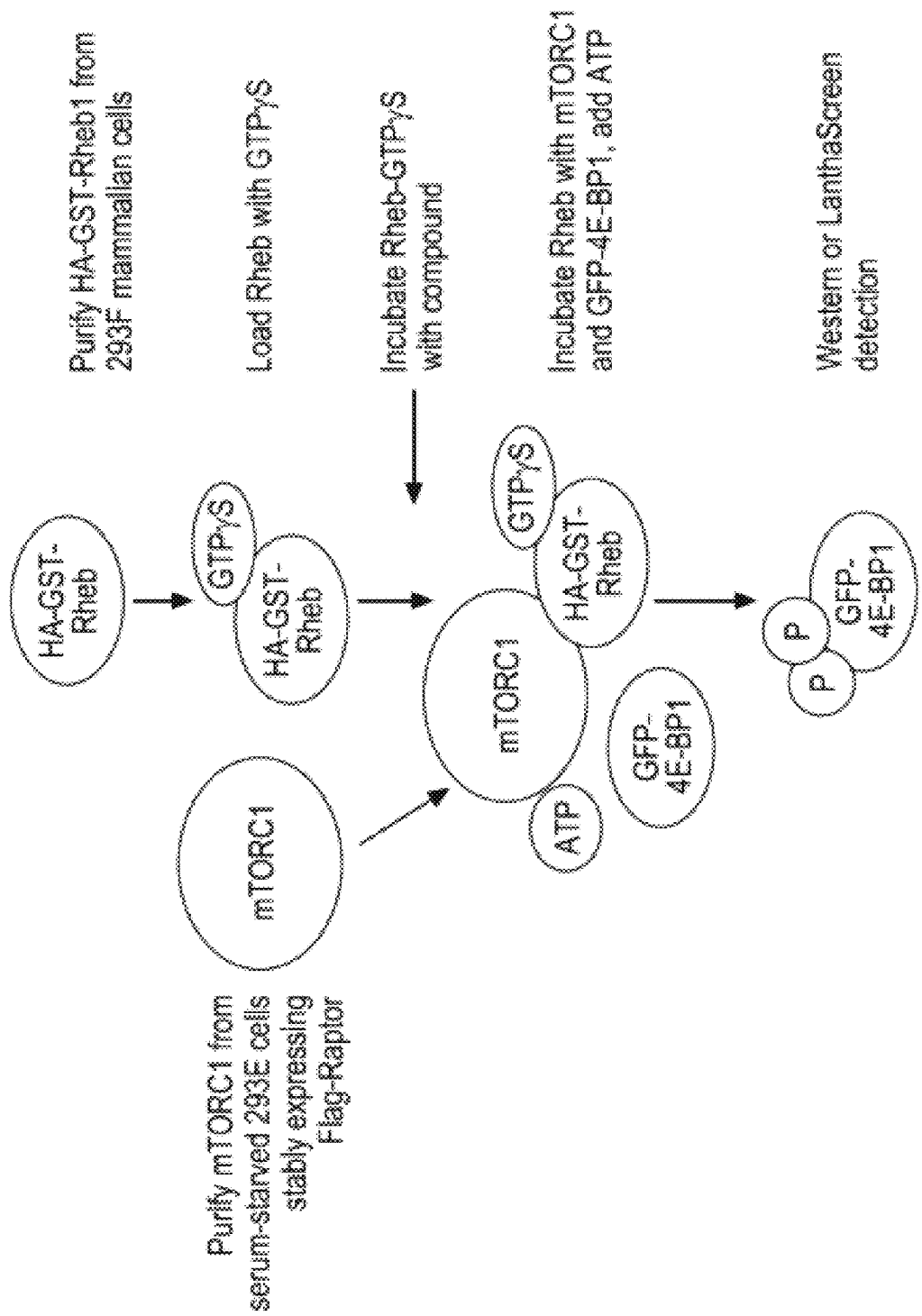
FIG. 2 shows a schematic of the Rheb-IVK protocol.

A schematic of the Rheb-IVK is depicted in FIG. 2.

Method 2 (Affinity Selection Mass Spectrometry

Protein: Rheb (19 KDa) in the following buffer: 20 mM Tris, pH 8.0, 200 mM NaCl, 2 mM DTT, 5 mM MgCl2 was prepared as under.

Human Rheb protein (I-169) was purified from BL21 (DE3) *E. coli* using a His-Smt-Rheb expression vector. The cell paste was lysed in lysis buffer (50 mM HEPES pH 7.5, 0.5 M NaCl, 5% Glycerol, 1% CHAPS, EDTA free protease inhibitor tablets, lysozyme to 1 mg/mL, benzonase 250U), sonicated, and purified on a HiTrap Ni Chelating Column (GE Healthcare) using the following buffer: 50 mM HEPES pH 7.5, 0.5 M NaCl, 5% Glycerol, and imidazole increasing in concentration from 5 mM to 500 mM. The His-Smt tag was cleaved using a Ulp1 enzyme and dialyzed into 50 mM HEPES pH 7.5, 0.5 M NaCl, 5% Glycerol. The resultant protein was again purified on a Ni Chelating column to remove the Ulp1 enzyme and His-Smt tag and then purified by size exclusion chromatography on a Sephacryl S-100 26/60 column into the following final buffer: 20 mM NaPhos pH 7.0, 100 mM NaCl, 5 mM MgCl2, 2 mM TCEP.
Concentrations: 60 μM Rheb, 180 μM GDP and 2 μM of each compound,
Ultrafiltration Filter (Sartorius, Germany) MW cutoff: 10 KDa
Screening Procedure:
  (a) Sample preparation: Prepare sample for each group in 1.5 mL microcentrifuge tube according to the experimental design, total volume 550 μL. In a standard ASMS experiment there are two groups: Protein plus (P+L+) and protein minus (P−L+).
  (b) Transfer 50 μL from the 550 μL to a vial as $R_0$ sample. Incubate the rest solution for 30 min at room temperature. Then transfer the 500 μL into an ultrafiltration filter tube and centrifuge at $12 \times 10^3$ rpm for ~10 min, leave about 50 μL solution (otherwise adjust this time).
  (c) Add incubation buffer to the ultrafiltration filter tube to about 500 μL. Stir gently and centrifuge mixtures as above, leave about 50 μL solution.
  (d) Repeat the step c. Transfer the remaining 50 μL upper layer solution to a new vial as $R^3$ sample.
Sample Extraction: Add 150 μL MeCN to denature the protein completely. Centrifuge at $12 \times 10^3$ rpm for 5 min. Transfer the supernatant into LC-MS auto sampler vials for LC-MS analysis (5 uL injection).

2.4 LC-MS Conditions

Waters Acquity UPLC system, Waters ACQUITY UPLC BEH C18 column (2.1×50 mm, 1.7 μM); Mobile phase A: 0.1% formic acid solution, B: MeCN; 0.3 mL/min, 5 μL injection, gradient elution (Table 5).

Waters Synapt G1 Q-TOF system, positive or negative ion scan modes; Capillary voltage: 3.0 kV; Method: MSE; Mass range: m/z=100-1000; Source temperature: 120° C.; Desolvation temperature: 400° C.; Collision voltage: 35 V; Sampling Cone: 35 V; Extraction Cone: 4.0 V; Cone Gas: 50 L/h; Desolvation Gas: 800 L/h.

TABLE 5

Gradient Elution Condition

| Time (min) | Mobile phase A (%) | Mobile phase B (%) |
|---|---|---|
| 0 | 98 | 2 |
| 1 | 98 | 2 |
| 7 | 10 | 90 |
| 8 | 10 | 90 |
| 10 | 98 | 2 |

Method 3 (Cell-Based ALPHALisa Assay)

Cells were plated on 96-well plates and treated for 120 min with compound before cell lysis. The AlphaLISA protocol was performed in 384-well plates as instructed by Perkin Elmer, and the plates were read on an EnVision plate reader. The maximum inhibition was defined by 1 M Torin-1 treatment, which abolishes $^{T189}$pS6K1 and $^{S473}$pAkt in both AlphaLISA and Western formats. Compounds with an $IC_{50}$ of less than 10 μM in the pS6K1 ALPHALisa assay are summarized in Table 7.

TABLE 6

Key Reagents/Supplies

| Reagents/materials | Vendor | Cat. No. |
|---|---|---|
| MCF-7 cells | ATCC | HTB-22 |
| DMEM | Invitrogen | 12430-054 |
| FBS | Invitrogen | 10099-141 |
| 0.25% Trypsin-EDTA | Invitrogen | 25200-072 |
| 384 well plate, tissue culture treated | Corning | CLS3701 |
| Corning 384 well storage plates | Corning | CLS3656 |
| Torin1 | Selleck | S2827 |
| Rapamycin | Selleck | S1039 |
| OptiPlate-384, White Opaque 384-well MicroPlate | PerkinElmer | 6007299 |
| AlphaLISA SureFire Ultra p-p70 S6 Kinase (Thr389) Assay Kit | PerkinElmer | ALSU-PP70-A10K |
| AlphaLISA SureFire Ultra AKT 1/2/3 (pS473) Assay Kit | PerkinElmer | ALSU-PAKT-B50K |

1. Seed MCF-7 cells in Corning 3701 plate and incubate for 20~24 hour. 12,000~16,000 cells will be seeded in 36 μL medium per well.
2. Change the culture medium with fresh medium and incubate for another 2 hours.
3. Add 12 μL (4×) compounds into the cell plate by HAMILTON. Final DMSO concentration is 0.5%. Incubate for 2 hours.
4. Aspirate 38 μL by HAMILTON, 10 μL rest per well.
5. Add 10 μL 2× lysis buffer using HAMILTON; total volume in wells is 20 μL. Allow cells to shake for 30 min. Cover plate by plastic foil and store plate at −80° C. up to analysis.
6. Thaw cell lysate at RT and transfer 10 ul lysate to assay plate (Optiplate-384).
7. Follow manufacturer's protocol for either AlphaLISA SureFire Ultra p-p70 S6 Kinase (Thr389) Assay Kit or AlphaLISA SureFire Ultra AKT 1/2/3 (pS473) Assay Kit:

a. Add 5 ul acceptor beads into assay plate and incubation for 2 hours
b. Add 5 ul donor beads and incubation for 2 hours
c. Count the plate by EnSpire or Envision 2105 Multi-mode Plate Reader
8. The maximum inhibition was defined by 1 μM Torin-1 treatment, which abolishes T389pS6K1 and S473pAkt in both AlphaLISA and Western formats.

TABLE 7

Compounds Active in the pS6K1 ALPHALisa Assay
Compound

I-120
I-30
I-79
I-102
I-142
I-141
I-106

Table 8 shows the inhibitory activity (IC$_{50}$) of selected compounds of this invention in the Rheb-dependent in vitro kinase assay (IVK) assay and the affinity (R3/R0) in the Affinity Selection Mass Spectrometry (ASMS) assay. The compound numbers correspond to the compound numbers in Tables 1 and 3. For the IVK assay, compounds having an activity designated as "A" provided inhibitory activity (IC$_{50}$) of <10 μM; compounds designated as "B" provided inhibitory activity (IC$_{50}$) of 10-100 μM; compounds designated as "C" provided inhibitory activity (IC$_{50}$) of 100-300 μM; compounds designated as "D" provided inhibitory activity (IC$_{50}$) 300-800 μM; compounds designated as "E" provided inhibitory activity (IC$_{50}$)>3 to >100 μM and compounds designated as "F" provided inhibitory activity (IC$_{50}$) >100 to >1000 μM. For the ASMS assay, compounds having an affinity designated as "A" provided an affinity (R3/R0) >100%; compounds designated as "B" provided an affinity (R3/R0) between 100% and 20% and compounds designated as "C" provided an affinity (R3/R0)<20%.

TABLE 8

Assay Data for Exemplary Compounds

| Compound Number | ASMS (R3/R0) | IVK IC$_{50}$ (μM) |
| --- | --- | --- |
| I-1 | B | A |
| I-2 | B | A |
| I-3 | B | B |
| I-4 | B | B |
| I-5 | B | A |
| I-6 | B | A |
| I-7 | B | A |
| I-8 | A | A |
| I-9 | A | A |
| I-10 | A | A |
| I-11 | B | E |
| I-12 | C | B |
| I-13 | B | F |
| I-14 | B | E |
| I-15 | B | A |
| I-16 | B | A |
| I-17 | B | A |
| I-18 | B | F |
| I-19 | B | A |
| I-20 | A | A |
| I-21 | C | F |
| I-22 | B | F |
| I-23 | B | F |
| I-24 | B | A |
| I-25 | B | A |
| I-26 | B | F |
| I-27 | B | F |
| I-28 | B | A |
| I-29 | A | A |
| I-30 | A | A |
| I-31 | A | F |
| I-32 | A | A |
| I-33 | A | A |
| I-34 | B | F |
| I-35 | A | A |
| I-36 | C | F |
| I-37 | C | F |
| I-38 | A | F |
| I-39 | B | F |
| I-40 | C | B |
| I-41 | C | C |
| I-42 | B | A |
| I-43 | A | F |
| I-44 | B | F |
| I-45 | A | A |
| I-46 | C | E |
| I-47 | B | B |
| I-48 | C | B |
| I-49 | B | A |
| I-50 | B | A |
| I-51 | B | A |
| I-52 | B | B |
| I-53 | B | F |
| I-54 | C | C |
| I-55 | C | B |
| I-56 | B | B |
| I-57 | A | F |
| I-58 | B | B |
| I-59 | C | F |
| I-60 | B | B |
| I-61 | C | F |
| I-62 | B | F |
| I-63 | A | F |
| I-64 | B | B |
| I-65 | B | A |
| I-66 | B | A |
| I-67 | C | B |
| I-68 | C | E |
| I-69 | C | B |
| I-70 | A | A |
| I-71 | B | A |
| I-72 | B | A |
| I-73 | A | A |
| I-74 | B | B |
| I-75 | B | A |
| I-76 | B | B |
| I-77 | B | A |
| I-78 | B | A |
| I-79 | B | A |
| I-80 | B | F |
| I-81 | B | B |
| I-82 | B | A |
| I-83 | B | F |
| I-84 | B | A |
| I-85 | B | B |
| I-86 | B | A |
| I-87 | B | B |
| I-88 | B | A |
| I-89 | A | F |
| I-90 | B | F |
| I-91 | B | B |
| I-92 | B | B |
| I-93 | A | A |
| I-94 | B | A |
| I-95 | B | B |
| I-96 | A | B |
| I-97 | B | F |
| I-98 | B | B |
| I-99 | B | F |
| I-100 | B | A |

TABLE 8-continued

Assay Data for Exemplary Compounds

| Compound Number | ASMS (R3/R0) | IVK IC$_{50}$ (μM) |
|---|---|---|
| I-101 | B | F |
| I-102 | B | A |
| I-103 | B | F |
| I-104 |   | F |
| I-105 | B | B |
| I-106 | B | A |
| I-107 | C | F |
| I-108 | B | C |
| I-109 | B | B |
| I-110 | C | F |
| I-111 | C | A |
| I-112 | C | A |
| I-113 | C | A |
| I-114 | B | F |
| I-115 | B | B |
| I-116 | B | A |
| I-117 | C | E |
| I-118 | B | A |
| I-119 | B | F |
| I-120 | B | A |
| I-121 | B | A |
| I-122 | B | A |
| I-123 | B | A |
| I-124 | B | A |
| I-125 | B | A |
| I-126 | B | B |
| I-127 | B | A |
| I-128 | A | A |
| I-129 | B | B |
| I-130 | B | A |
| I-131 | B | F |
| I-132 | B | F |
| I-133 | B | A |
| I-134 | B | B |
| I-135 | B | F |
| I-136 | A | F |
| I-137 | A | F |
| I-138 | B | C |
| I-139 | B | A |
| I-140 | B | B |
| I-141 | B | A |
| I-142 | A | A |
| I-143 | B | F |
| I-144 | B | F |
| I-145 | B | B |
| I-146 | B | A |
| I-147 | A | F |
| I-148 | B | B |
| I-149 | B | B |
| I-150 | C | F |
| I-151 | C | F |
| I-152 | B | B |
| I-153 | B | B |
| I-154 | A | A |
| I-155 | B | B |
| I-156 | B | B |
| I-157 | B | A |
| I-158 | B | B |
| I-159 | C | B |
| I-160 | C | F |
| I-161 | A | A |
| I-162 | B | C |
| I-163 | C | F |
| I-164 | B | B |
| I-165 | B | B |
| I-166 | B | F |
| I-167 | B | A |
| I-168 | C | F |
| I-169 | B | B |
| I-170 | B | B |
| I-171 | B | B |
| I-172 | B | B |
| I-173 | C | B |
| I-174 |   | F |
| I-175 | B | C |
| I-176 | B | B |
| I-177 | A | B |
| I-178 |   | F |
| I-179 |   | F |
| I-180 | B | B |
| I-181 |   | F |
| I-182 |   | F |
| I-183 |   | F |
| I-184 |   | F |
| I-185 | C | F |
| I-186 | B | B |
| I-187 | B | A |
| I-188 |   | F |
| I-189 |   | F |
| I-190 | B | B |
| I-191 |   | F |
| I-192 |   | F |
| I-193 |   | F |
| I-194 | C | B |
| I-195 |   | F |
| I-196 | B | B |
| I-197 |   | F |
| I-198 | B | B |
| I-199 |   | F |
| I-200 |   | F |
| I-201 | B | B |
| I-202 | B | B |
| I-203 |   | F |
| I-204 | C | B |
| I-205 |   | F |
| I-206 |   | F |
| I-207 | B | B |
| I-208 | B | B |
| I-209 | B | B |
| I-210 |   | F |
| I-211 |   | F |
| I-212 | B | E |
| I-213 |   | F |
| I-214 |   | F |
| I-215 | B | B |
| I-216 | B | B |
| I-217 |   | F |
| I-218 | B | B |
| I-219 |   | F |
| I-220 | A | A |
| I-221 |   | F |
| I-222 | B | F |
| I-223 |   | F |
| I-224 |   | F |
| I-225 |   | F |
| I-226 | C | F |
| I-227 |   | F |
| I-228 |   | F |
| I-229 |   | F |
| I-230 |   | F |
| I-231 |   | F |
| I-232 |   | F |
| I-233 |   | F |
| I-234 |   | E/F |
| I-235 | B | B |
| I-236 | B | B |
| I-237 | B | B |
| I-238 |   | F |
| I-239 | B | B |
| I-240 |   | F |
| I-241 | B | B |
| I-242 |   | F |
| I-243 | B | B |
| I-244 | B | B |
| I-245 |   | F |
| I-246 | C | B |
| I-247 | C | B |
| I-248 | C | B |
| I-249 | C | B |
| I-250 | B | B |

TABLE 8-continued

Assay Data for Exemplary Compounds

| Compound Number | ASMS (R3/R0) | IVK IC$_{50}$ (μM) |
|---|---|---|
| I-251 | C | B |
| I-252 | B | B |
| I-253 |   | F |
| I-254 | B | B |
| I-255 | B | B |
| I-256 | B | B |
| I-257 | C | B |
| I-258 |   | F |
| I-259 |   | F |
| I-260 |   | F |
| I-261 | C | B |
| I-262 |   | F |
| I-263 | C | B |
| I-264 |   | F |
| I-265 |   | F |
| I-266 |   | F |
| I-267 | C | E |
| I-268 |   | F |
| I-269 |   | F |
| I-270 |   | F |
| I-271 | C | E |
| I-272 |   | F |
| I-273 |   | F |
| I-274 |   | F |
| I-275 | C | C |
| I-276 |   | C |
| I-277 |   | D |
| I-278 |   | D |
| I-279 |   | F |
| I-280 |   | F |
| I-281 |   | F |
| I-282 | C | C |
| I-283 | C | C |
| I-284 |   | B |
| I-285 |   | F |
| I-286 |   | D |
| I-287 |   | F |
| I-288 | C | C |
| I-289 |   | F |
| I-290 | B | B |
| I-291 | C | B |
| I-292 |   | F |
| I-293 | C | C |
| I-294 |   | F |
| I-295 | C | F |
| I-296 | C | C |
| I-297 |   | D |
| I-298 |   | F |
| I-299 | C | F |
| I-320 | B | B |
| I-321 | C | F |
| I-322 | C | F |
| I-323 | B | E |
| I-324 | B | E |
| I-325 | B | B |
| I-326 | B | B |
| I-327 | C | F |
| I-328 | B | F |
| I-329 | A | B |
| I-330 | B | F |
| I-331 | B | B |
| I-332 | A | B |
| I-333 | A | B |
| I-334 | B | B |
| I-335 | B | C |
| I-336 | B | F |
| I-337 | B | E |
| I-338 | B | E |
| I-339 | B | E |
| I-340 | B | F |
| I-341 | B | F |
| I-342 | B | B |
| I-343 | A | B |
| I-344 | A | F |
| I-345 | B | F |
| I-346 | A | F |
| I-347 | B | F |
| I-348 | B | F |
| I-349 | B | F |
| I-350 | B | F |
| I-351 | A | F |
| I-352 | A | E |
| I-353 | A | E |
| I-354 | A | B |
| I-355 | B | F |
| I-356 | A | B |
| I-357 | A | F |
| I-358 | B | B |
| I-359 | A | B |
| I-360 | B | F |
| I-361 | B | C |
| I-362 | A | F |
| I-363 | A | B |
| I-364 | B | C |
| I-365 | C | B |
| I-366 | A | C |
| I-367 | B | F |
| I-368 | B | F |
| I-369 | C | B |
| I-370 | B | B |
| I-371 | B | B |
| I-372 | A | F |
| I-373 | C | B |
| I-374 | C | F |
| I-375 | A | A |
| I-376 | C | C |
| I-377 | B | F |
| I-378 | B | B |
| I-379 | C | F |
| I-380 | B | B |
| I-381 | C | F |
| I-382 | C | C |
| I-383 |   | B |
| I-384 |   | F |
| I-385 | C | F |
| I-386 | C | F |
| I-387 |   | C |
| I-388 | B | B |
| I-389 | C | F |
| I-390 | C | C |
| I-391 | C | B |
| I-392 |   | F |
| I-393 |   | F |
| I-394 | B | B |
| I-395 | A | A |
| I-396 | C | B |
| I-397 |   | F |
| I-398 |   | F |
| I-399 | C | B |
| I-400 |   | C |
| I-401 |   | F |
| I-402 |   | F |
| I-403 |   | C |
| I-404 |   | F |
| I-405 |   | F |
| I-406 |   | F |
| I-407 |   | F |
| I-408 |   | F |
| I-409 |   | F |
| I-410 |   | F |
| I-411 | C | B |
| I-412 |   | F |
| I-413 |   | F |
| I-414 |   | F |
| I-415 |   | F |
| I-416 |   | F |
| I-417 |   | F |
| I-418 |   | C |
| I-419 |   | F |
| I-420 |   | F |

TABLE 8-continued

Assay Data for Exemplary Compounds

| Compound Number | ASMS (R3/R0) | IVK IC$_{50}$ (µM) |
|---|---|---|
| I-421 | C | B |
| I-422 |   | F |
| I-423 |   | F |
| I-424 |   | F |
| I-425 | C | E |
| I-426 |   | F |
| I-427 |   | C |
| I-428 |   | F |
| I-429 |   | F |
| I-430 |   | F |
| I-431 |   | F |
| I-432 |   | F |
| I-433 |   | F |
| I-434 |   | C |
| I-435 |   | F |
| I-436 |   | F |
| I-437 | C | E |
| I-438 |   | F |
| I-439 | C | B |
| I-440 | C | B |
| I-441 |   | F |
| I-442 |   | F |
| I-443 |   | F |
| I-444 |   | F |
| I-445 |   | F |
| I-446 |   | F |
| I-447 |   | F |
| I-448 |   | F |
| I-449 |   | F |
| I-450 |   | F |
| I-451 |   | F |
| I-452 |   | F |
| I-453 |   | F |
| I-454 |   | F |
| I-455 |   | F |
| I-456 |   | F |
| I-457 |   | F |
| I-458 |   | F |
| I-459 |   | F |
| I-460 |   | F |
| I-461 |   | F |
| I-462 |   | F |
| I-463 |   | F |
| I-464 |   | F |
| I-465 |   | C |
| I-466 |   | F |
| I-467 |   | F |
| I-468 |   | F |
| I-469 |   | F |
| I-470 |   | F |
| I-471 |   | F |
| I-472 |   | F |
| I-473 |   | F |
| I-474 |   | D |
| I-475 |   | C |
| I-476 |   | F |
| I-477 |   | F |
| I-478 |   | D |
| I-479 |   | F |
| I-480 |   | F |
| I-481 | C | F |
| I-482 |   | C |
| I-483 |   | D |
| I-484 | B | C |
| I-485 |   | D |
| I-486 | A | F |
| I-487 |   | F |
| I-488 |   | F |
| I-489 | C | C |
| I-490 |   | B |
| I-491 |   | F |
| I-492 | C | F |
| I-493 | C | F |

General Methods and Materials for Cell-Based Assays

All cells used tested negative for mycoplasma. MCF7 (ATCC #HTB-22), TRI102, and PC3 (ATCC #CRL-1435 cells were grown in DMEM plus 10% FBS. Jurkat Clone E6-1 cells were grown in RPMI1640 plus 10% FBS. Antibodies used for probing included:

Anti $^{T389}$pS6K1 (Cell Signaling Technology #9234);
Anti $^{S473}$pAkt (Cell Signaling Technology #4060);
Anti 4E-BP1 (Cell Signaling Technology #9644);
Anti $^{T37/46}$p4E-BP1 (Cell Signaling Technology #2855);
Anti $^{T202/Y204}$pERK1/2 (Cell Signaling Technology #4370);
Anti tubulin (Sigma #T-5168); and
Anti $^{S240/244}$pS6 (Cell Signaling Technology #5364).

Torin-1 and rapamycin were obtained from LC Laboratories (#T-7887 and #R-5000, respectively). U0126 was obtained from Sigma Aldrich (#662005).

Western-based Signaling Assays. Cells were treated for either 90 min or 2-24 hrs as indicated before lysis, normalization and Western analysis. Cells were lysed in Triton lyssi buffer (1% Triton X-100, 50 mM HEPES pH 7.4, 100 mM NaCl, 2 mM EDTA, 10 mM β-glycerophosphate, 10 mM Na-pyrophosphate, and protease inhibitor).

Example A: Evaluation of [3] and Torin-1 in Rheb-IVK Western Blot Analysis

Figure 3:
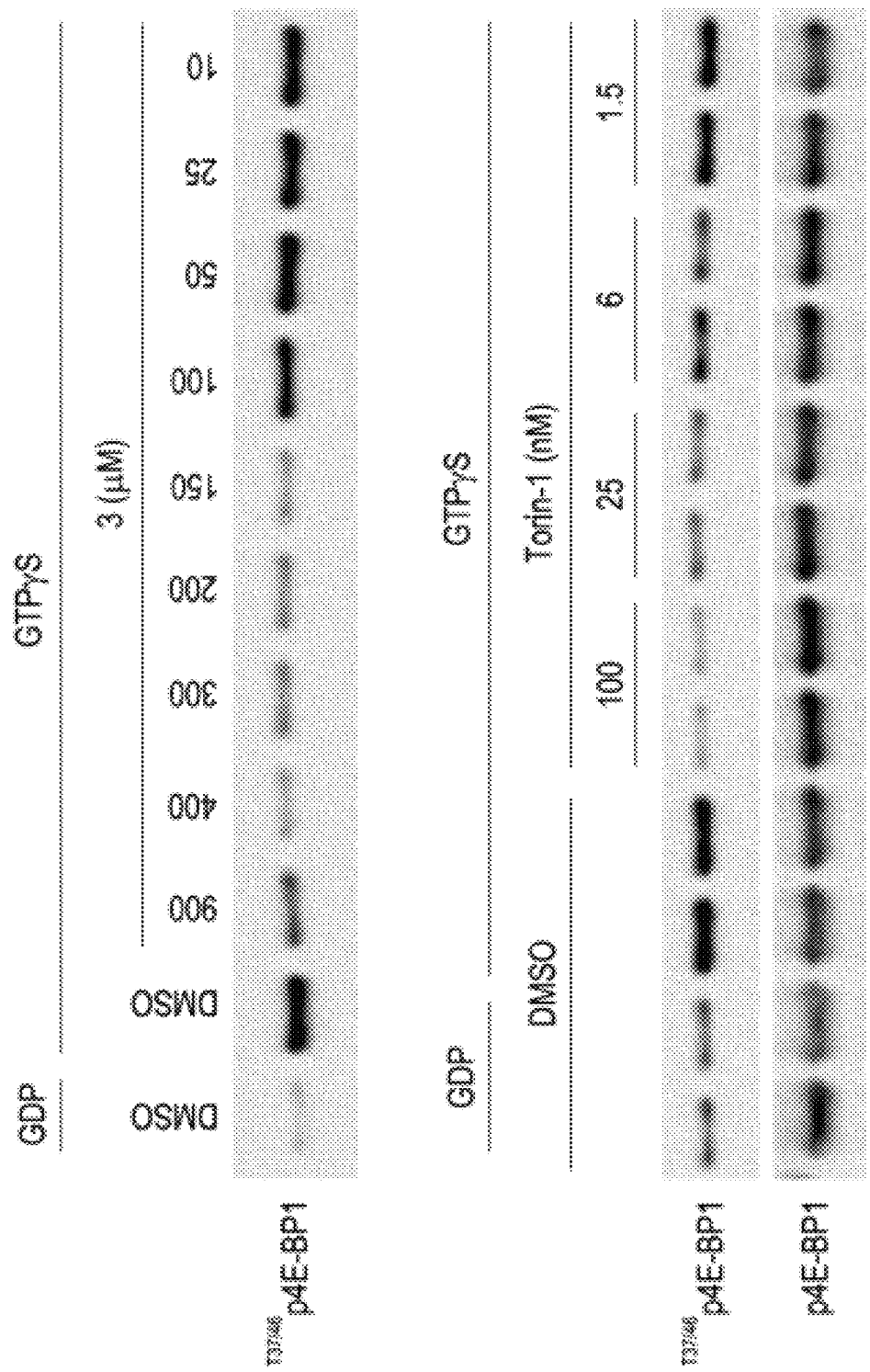
FIG. 3 shows the Western blot analysis of an Rheb-IVK experiment using indicated concentrations of I-293 ("[3]") and Torin-1. Anti 4E-BP1 and anti $^{T37/46}$p4E-BP1 antibodies were used for visualization.
Figure 4:
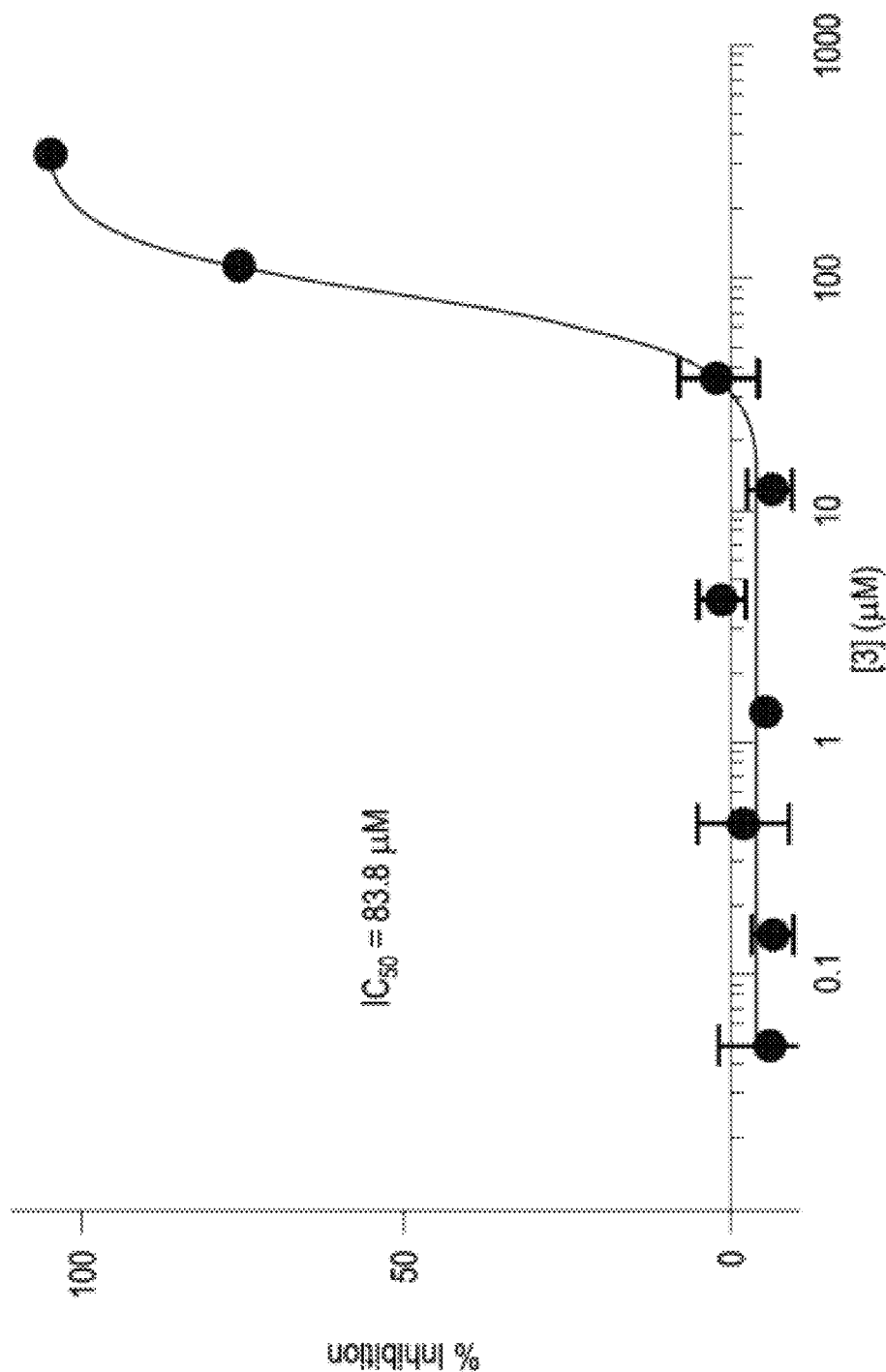
FIG. 4 shows the inhibitory activity of [3] in the Rheb-IVK utilizing a Terbium labeled $^{T46}$p4E-BP1 specific antibody.
Figure 5:
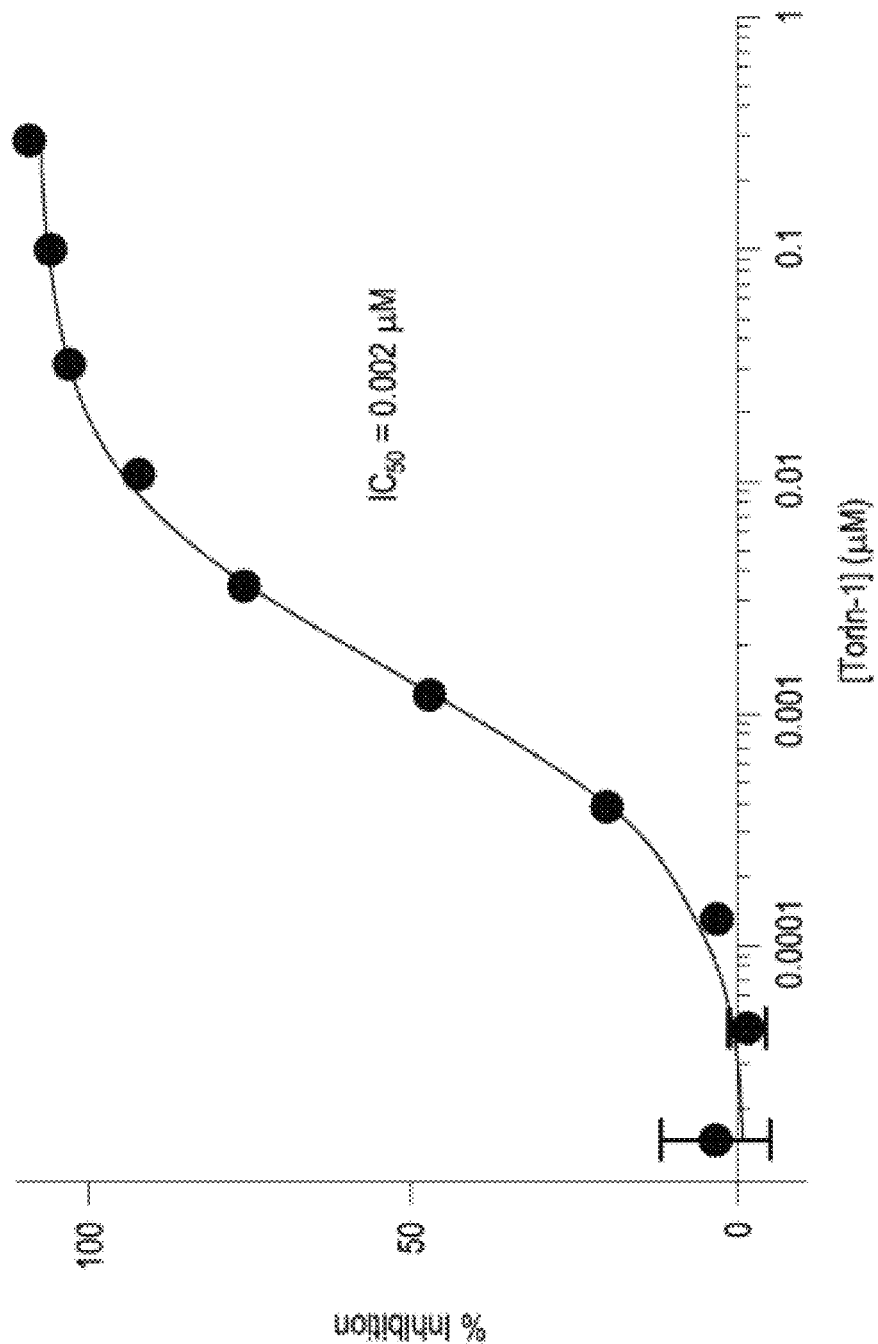
FIG. 5 shows the inhibitory activity of Torin-1 in the Rheb-IVK utilizing a Terbium labeled $^{T46}$p4E-BP1 specific antibody.
Figure 6:
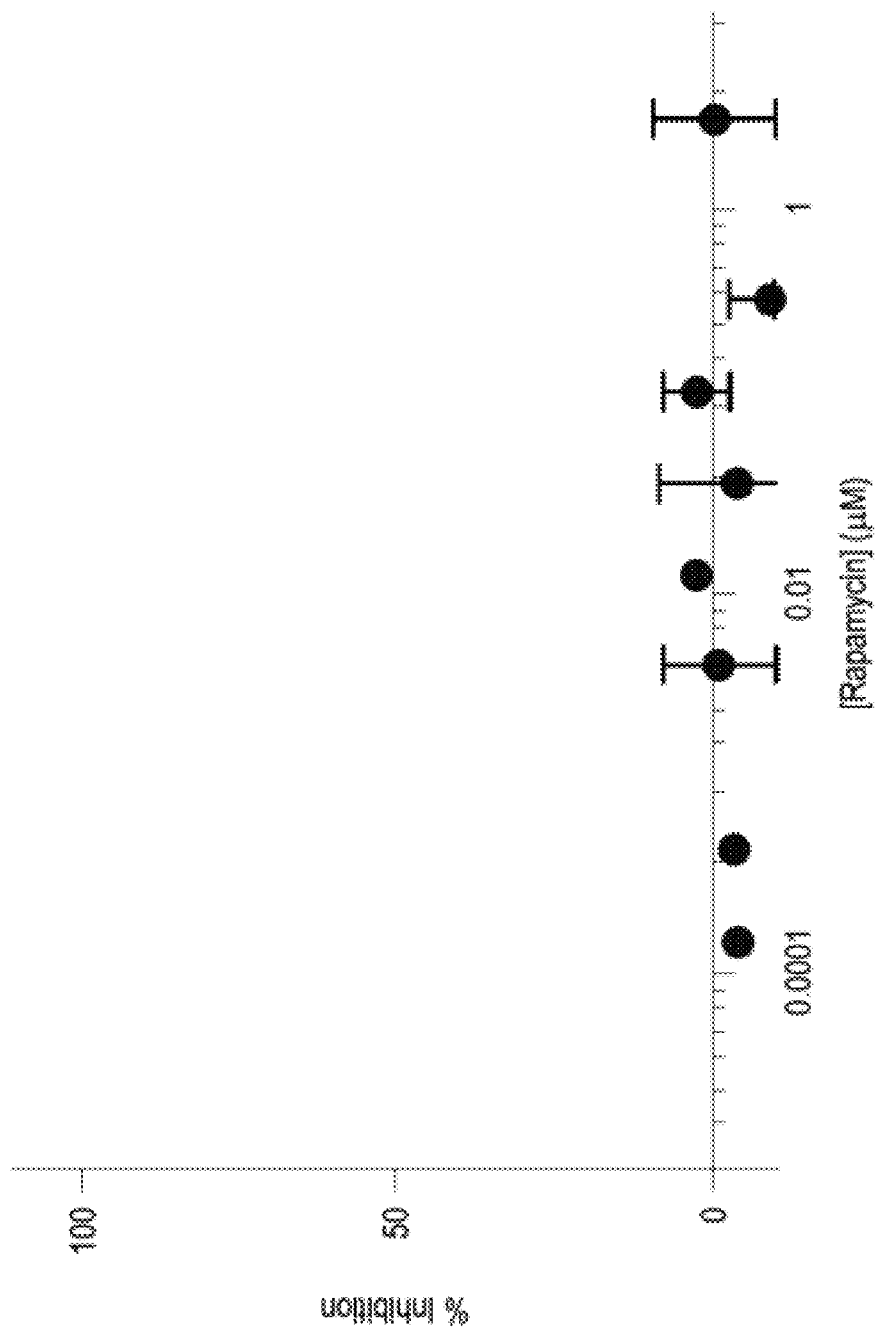
FIG. 6 shows the inhibitory activity of rapamycin in the Rheb-IVK utilizing a Terbium labeled $^{T46}$p4E-BP1 specific antibody.
Figure 7:
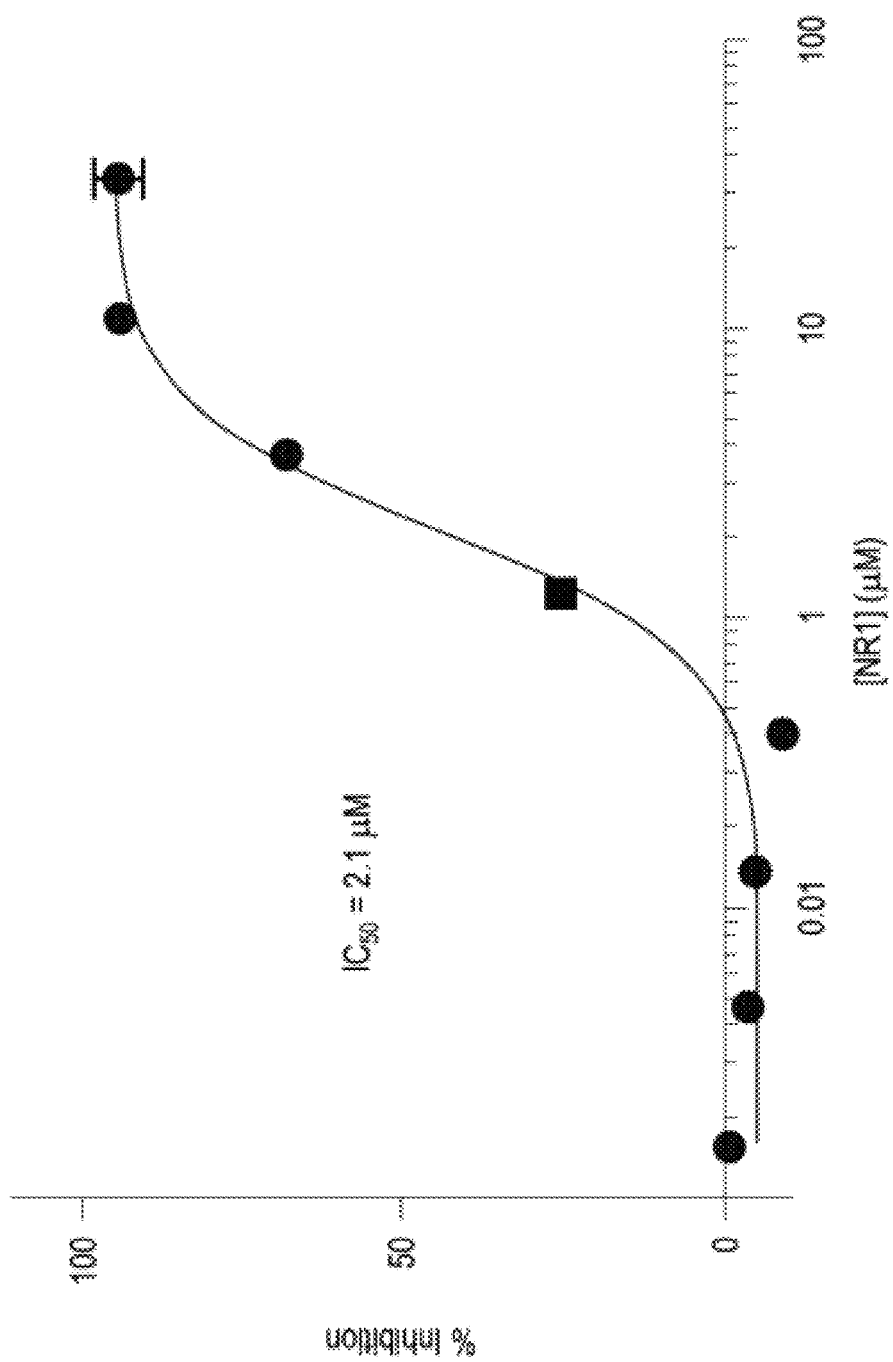
FIG. 7 shows the inhibitory activity of I-102 ("NR1") in the Rheb-IVK utilizing a Terbium labeled $^{T46}$p4E-BP1 specific antibody.

Varying concentrations of I-293 ("[3]") and Torin-1 (positive control) were tested using the Rheb-IVK as previously describe with DMSO serving as negative control. HA-GST-Rheb1 was charged with either GTPγS or GDP. The western blot variation was employed utilizing anti 4E-BP1 (Cell Signaling Technology #9644) and anti $^{T37/46}$p4E-BP1 (Cell Signaling Technology #2855) for visualization. Results indicated that GTP is required for Rheb activation of mTORC1 in vitro and [3] is capable of inhibiting mTORC1 activity in the Rheb-IVK. These results are summarized in FIG. 3.

Example B: Rheb-IVK Lantascreen Assay

[3], Torin-1, rapamycin (negative control), and I-102 ("NR1") were tested using the Rheb-IVK as described above. The LanthaScreen variation was employed utilizing a Terbium labeled $^{T46}$p4E-BP1 specific antibody and IC$_{50}$ curves were then generated. Torin-1 yielded an IC$_{50}$ of about 0.002 µM. [3] yielded an IC$_{50}$ of about 83.8 µM. NR1 yielded an IC$_{50}$ of about 2.1 µM. As expected, rapamycin did not inhibit the Rheb-IVK due to the absence of the accessory protein FKBP12 (the target of rapamycin). These results are summarized in FIGS. 4, 5, 6, and 7

Example C: IC$_{50}$ Determinations Using AlphaLISA Assay

Figure 8:
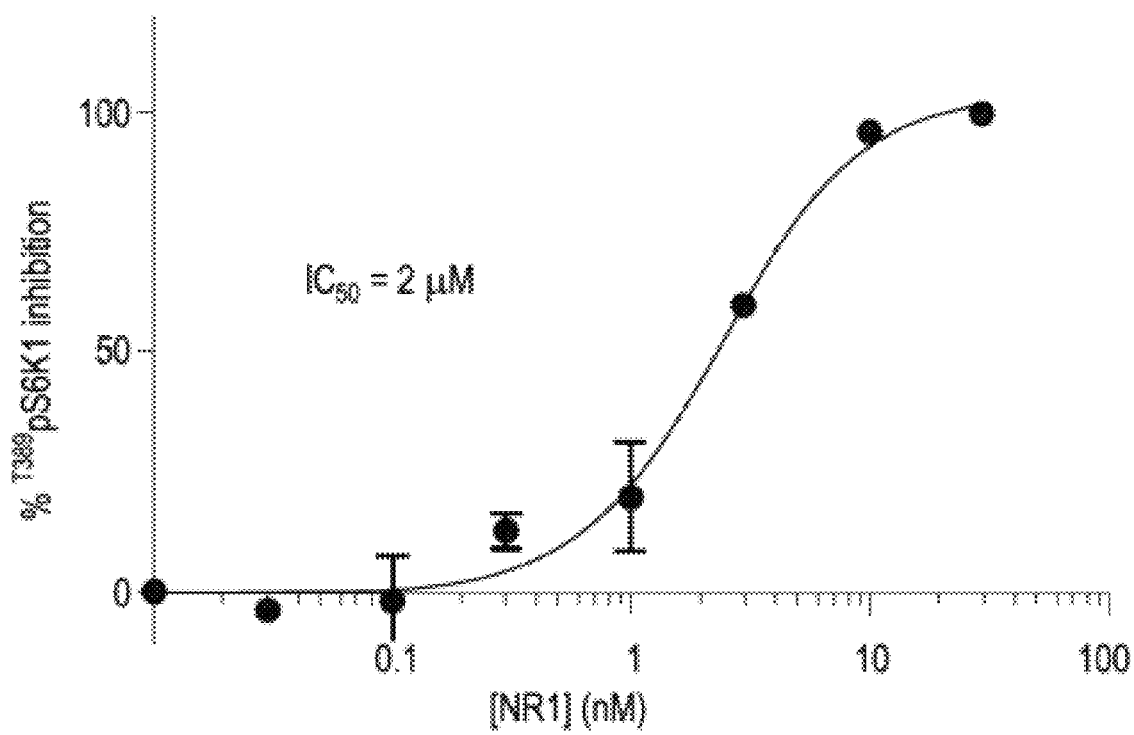
FIG. 8 shows the inhibitory activity of NR1 on pS6K1 and pAkt by AlphaLisa assay.
Figure 8:
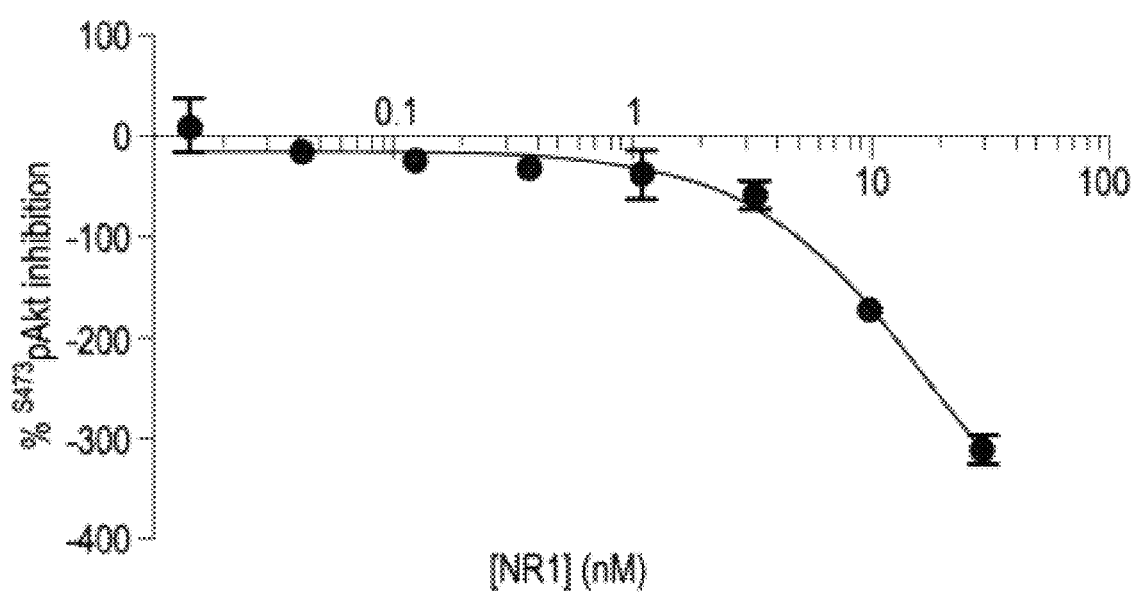
Figure 9:
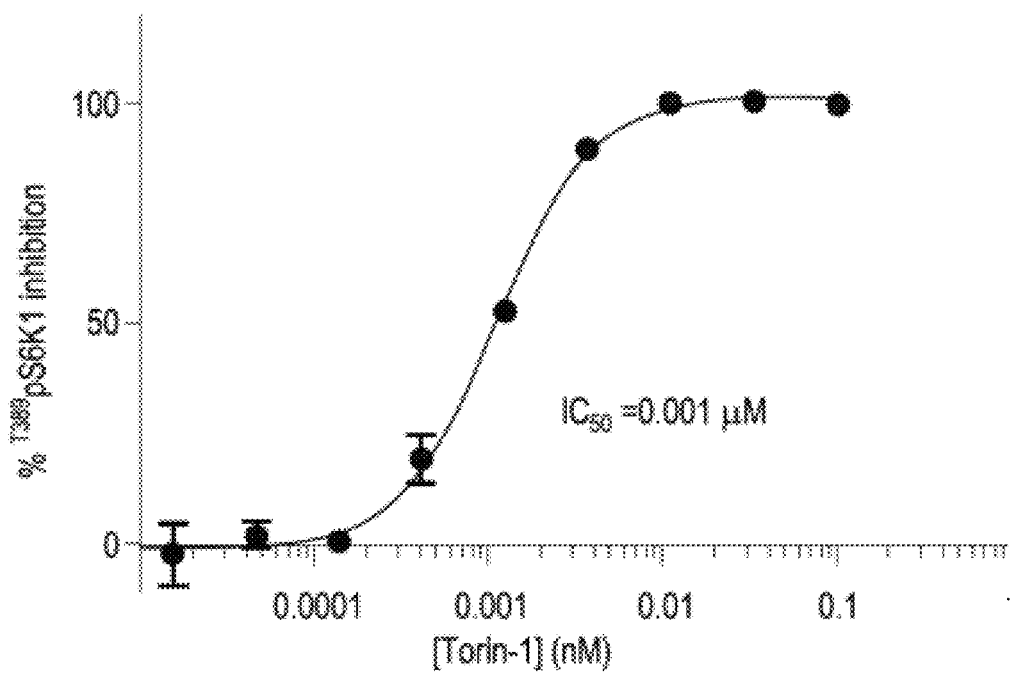
FIG. 9 shows the inhibitory activity of Torin-1 on pS6K1 and pAkt by AlphaLisa assay.
Figure 9:
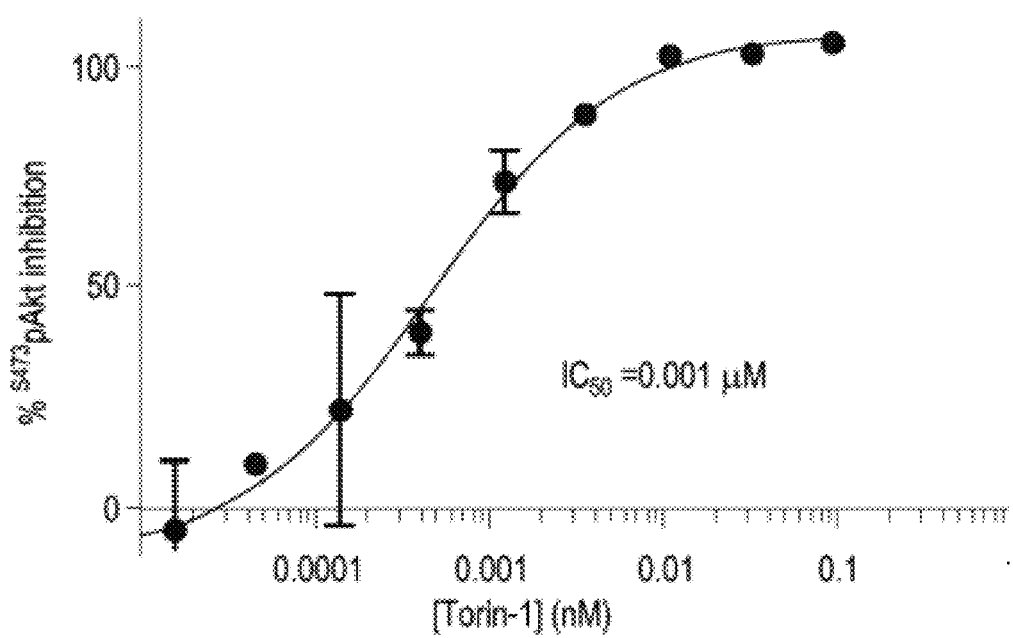

MCF-7 cells were treated with varying concentrations of I-102 ("NR1") and Torin-1. Percent inhibition of pS6K1 and pAkt was determined utilizing the AlphaLIZA method previously described. Torin-1 exhibits an IC$_{50}$ for pS6K1 of about 0.001 µM and an IC$_{50}$ for pAkt of about 0.005 µM. In comparison, NR1" did not inhibit pAKT and exhibited a pS6K1 IC$_{50}$ of about 2 µM. These results indicate that while Torin-1 is a duel mTORC1/2 inhibitor, NR1 is a selective mTORC1 inhibitor. The results for NR1 are summarized in FIG. 8. The results for Torin-1 are summarized in FIG. 9.

Example D: Rheb-Independent mTOR In Vitro Kinase Assay (Hot Spot

Figure 10:
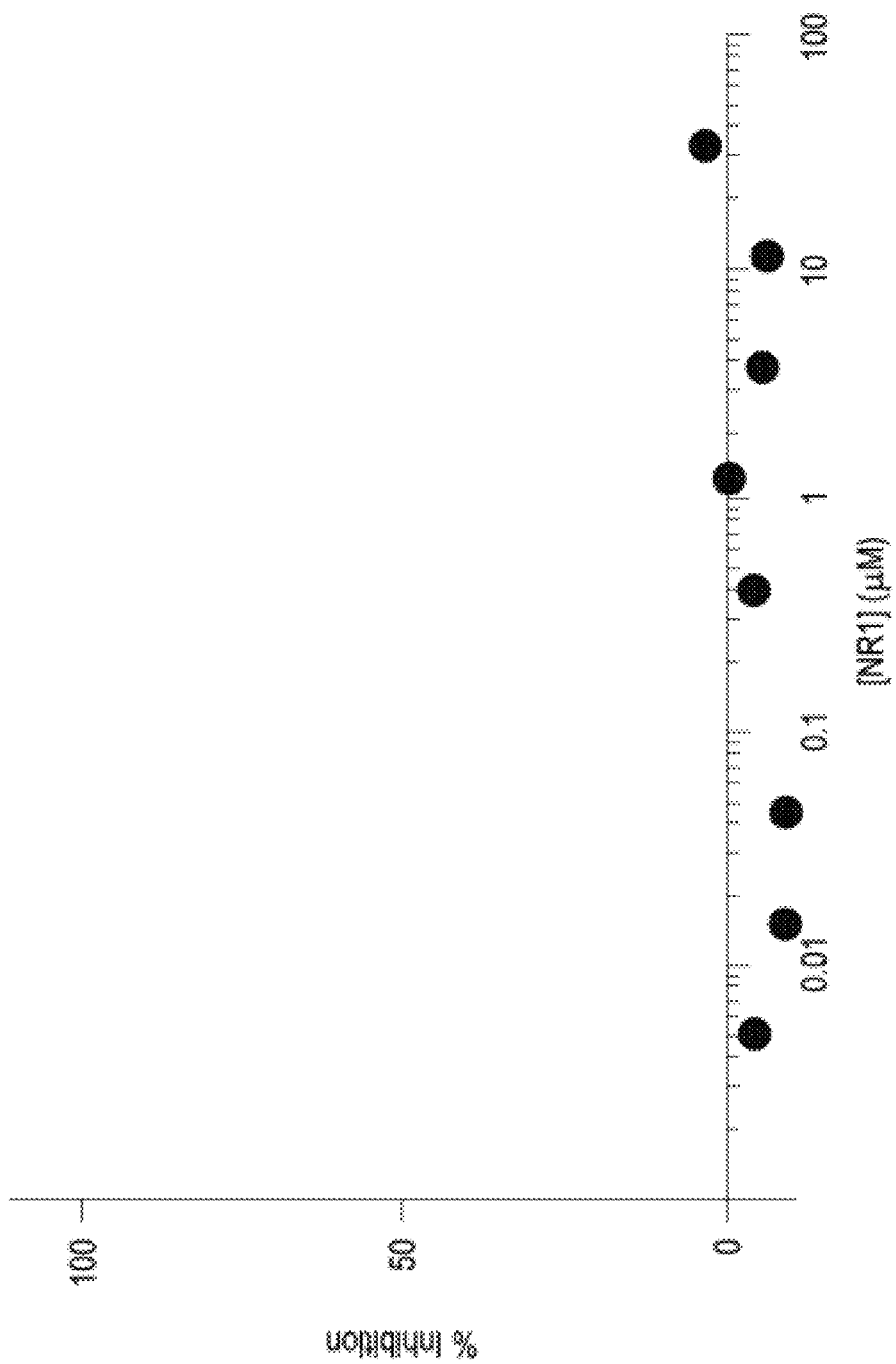
FIG. 10 shows the inhibitory activity of NR1 in the Rheb-independent mTOR kinase assay.
Figure 11:
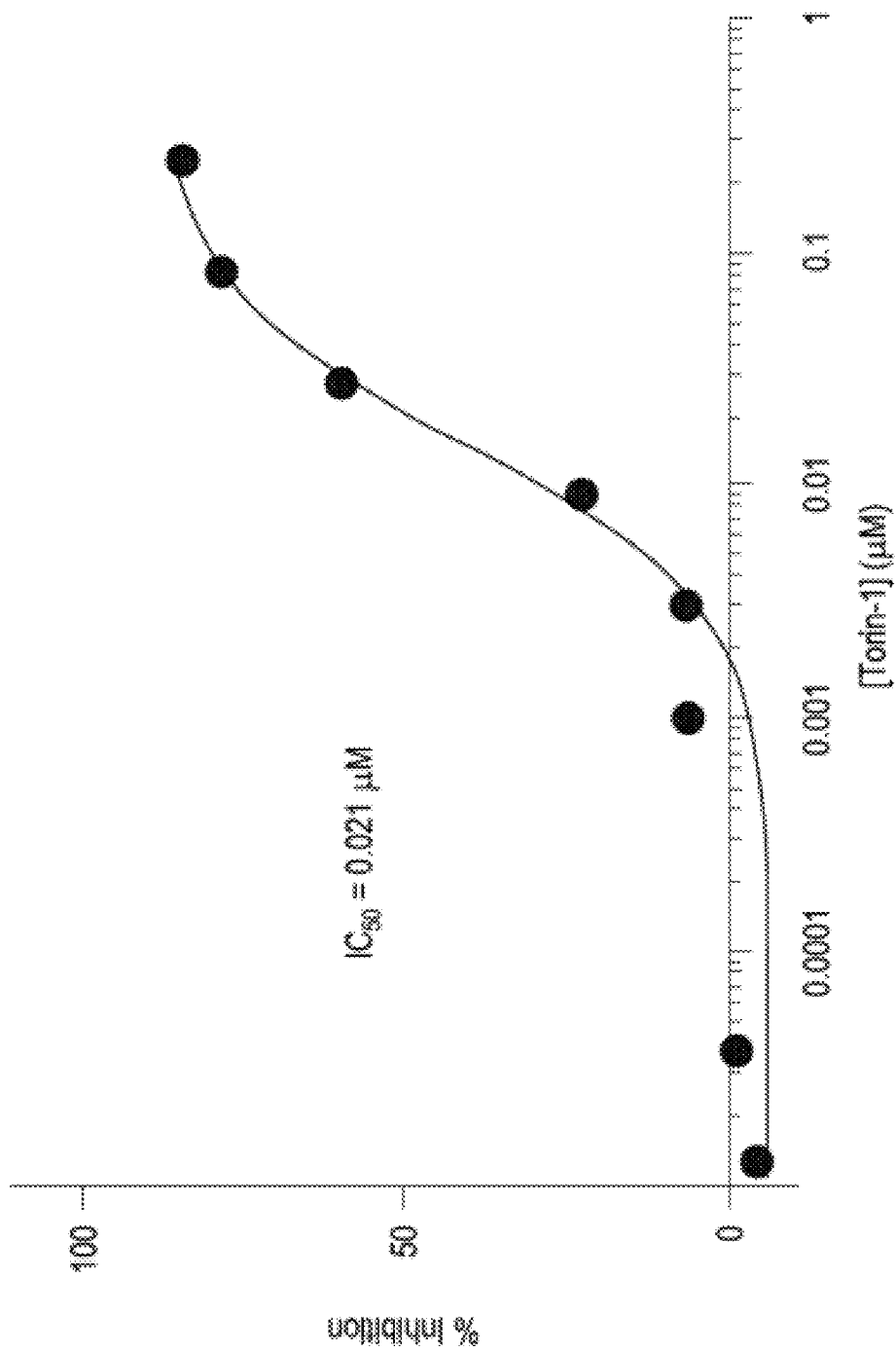
FIG. 11 shows the inhibitory activity of Torin-1 in the Rheb-independent mTOR kinase assay.

NR1 and Torin-1 were tested in the Rheb-independent direct mTOR kinase assay. N-terminal His-tagged human 4E-BP1 (Genbank Accession #NM_004095, 3 µM) was incubated with recombinant human mTOR (Genbank Accession #NP_004949.1, aa 1360-2549, N-terminal GST-tagged, expressed in insect cells) in reaction buffer (20 mM HEPES pH 7.5, 10 mM $MgCl_2$, 2 mM $MnCl_2$ 1 mM EGTA, 0.02% Brij35, 0.02 mg/mL BSA, 0.1 mM $Na_3VO_4$, 2 mM DTT, 2% DMSO). The compounds were added to the kinase reaction mixture by Acoustic technology (Echo550; nanoliter range) and incubated for 20 min at room temperature before the addition of 100 µM $^{33}$P-ATP. The reaction was incubated for 2 hrs at room temperature, and kinase activity was detected by a P81 filter-binding method. NR1 exhibited no inhibitory activity up to about 30 µM. In contrast, Torin-1 exhibited direct inhibition of mTOR with an $IC_{50}$ of 0.021 µM. These results indicated that NR1 does not directly inhibit mTOR kinase, independent of Rheb, and that NR1 is specific for Rheb. These results are summarized in FIGS. 10 and 11.

Example E: Insulin-Dependent Activating

Figure 12:
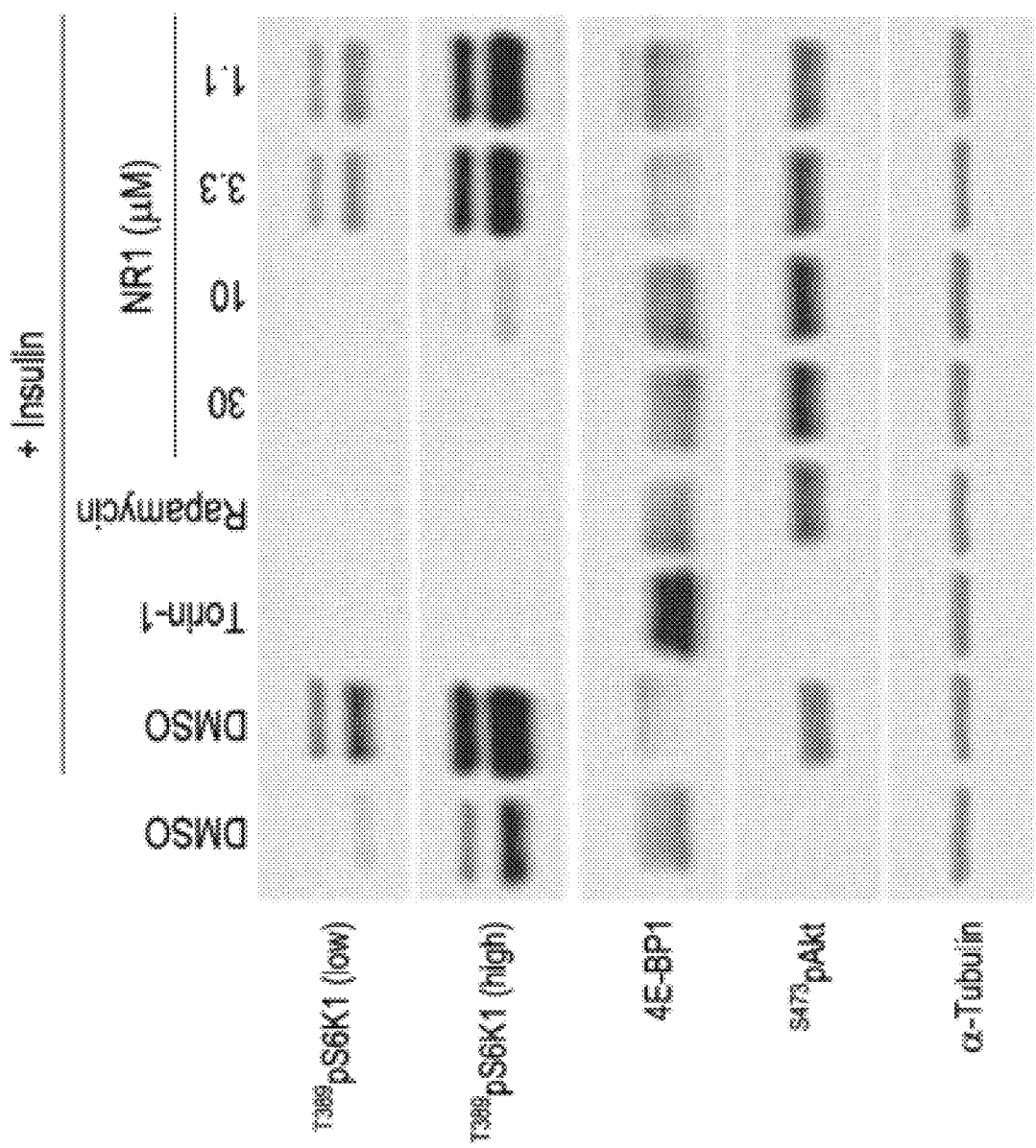
FIG. 12 shows the Western blot analysis of the insulin-dependent activity of Torin-1 (250 nM), rapamycin (100 nM), and NR1 (indicated concentrations) in MCF-7 cells. Anti $^{T389}$pS6K1, anti 4E-BP1, anti $^{S473}$pAkt, and anti-tubulin antibodies were used for visualization

To evaluate the effect of NV1 on the insulin-dependent signaling pathway, MCF-7 cells were serum starved to 16 hrs then treated with DMSO, Torin-1 (250 nM), Rapamycin (100 nM), or NR1 (30, 10, 3.3 and 1.1 µM) for ~90 min. Cells were then treated with 100 nM insulin, except for DMSO control. Thirty minutes later the cells were lysed in Triton lysis buffer (1% Triton X-100, 50 mM HEPES pH 7.4, 100 mM NaCl, 2 mM EDTA, 10 mM β-glycerophosphate, 10 mM Na-pyrophosphate, and protease inhibitor). Samples were normalized, separated by electrophoresis, transferred to membranes, and probed according to known methods. Antibodies used for visualization were: anti $^{T389}$pS6K1 (Cell Signaling Technology #9234), anti 4E-BP1 (Cell Signaling Technology #9644), anti $^{S473}$pAkt (Cell Signaling Technology #4060), and anti-tubulin (Sigma #T-5168). Results indicate that NR1 inhibited phosphorylation of $^{T389}$pS6K1 and increased the phosphorylation of $^{S473}$pAKT in a dose-dependent manner. These results are summarized in FIG. 12.

Example F: EDF-Dependent Activation

Figure 13:
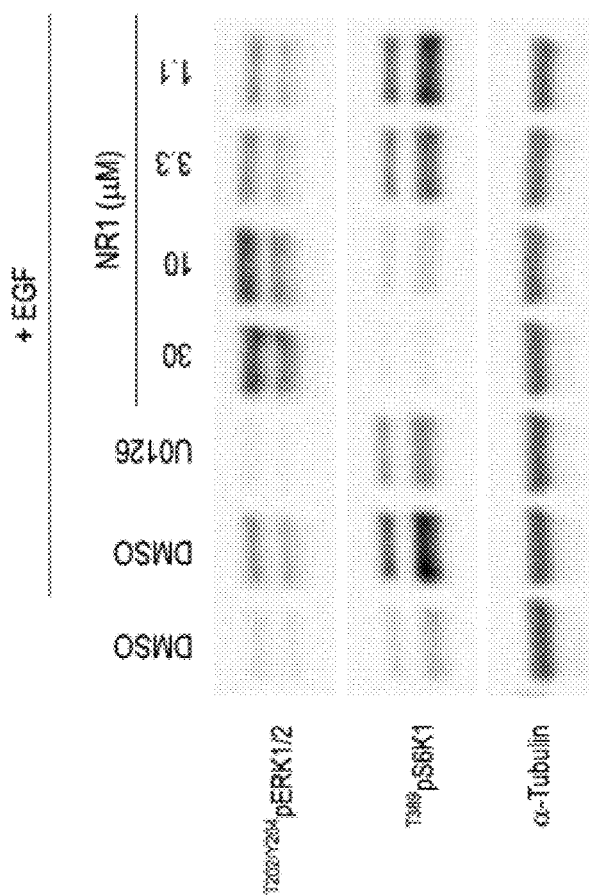
FIG. 13 shows the Western blot analysis of the EGF-dependent activity of Torin-1 (250 nM), rapamycin (100 nM), and NR1 (indicated concentrations) in MCF-7 cells. Anti $^{T202/Y204}$pERK1/2, anti $^{T389}$pS6K1, and anti-tubulin antibodies were used for visualization.

To evaluate the effect of NV1 on the Ras/ERK pathway, MCF-7 cells were serum starved to 16 hrs then treated with DMSO, U0126, or NR1 (30, 10, 3.3 and 1.1 µM) for ~90 min. Cells were then treated with 100 ng/mL EGF, except for DMSO control. Ten minutes later the cells were lysed in Triton lysis buffer (1% Triton X-100, 50 mM HEPES pH 7.4, 100 mM NaCl, 2 mM EDTA, 10 mM β-glycerophosphate, 10 mM Na-pyrophosphate, and protease inhibitor). Samples were normalized, separated by electrophoresis, transferred to membranes, and probed according to known methods. Antibodies used for visualization were: anti $^{T202/Y204}$pERK1/2 (Cell Signaling Technology #4370), anti $^{T389}$pS6K1 (Cell Signaling Technology #9234), and anti-tubulin (Sigma #T-5168). Results indicate that NR1 did not inhibit EGF-induced phosphorylation of $^{T202/Y204}$pERK1/2, indicating that Ras is not inhibited. These results are summarized in FIG. 13.

Example G: Related Small GTPase Selectivity

Figure 14:
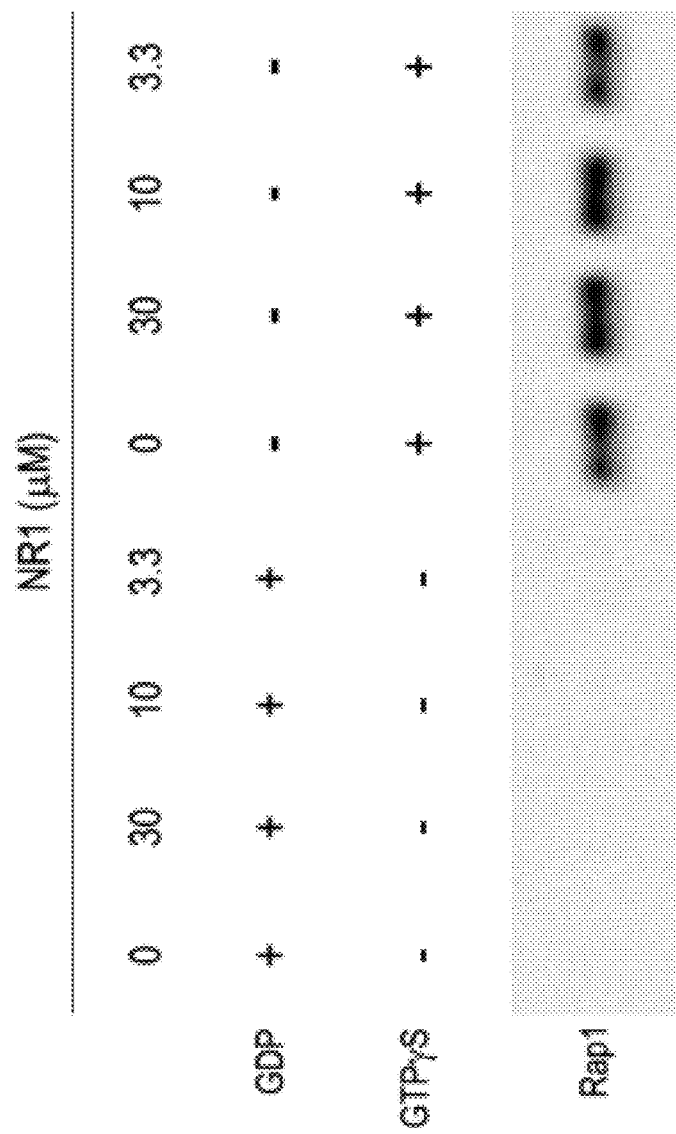
FIG. 14 shows the Western blot analysis of the Rap1 activity of NV1 in serum starved HEK-293 cells.

To evaluate the effect of NV1 on related small GTPases HEK-293 cells (ATCC #CRL3216) were serum-starved in DMEM (no FBS) overnight and lysed following the manufacturer's instructions (CDT #8818). Lysate was loaded with nucleotide (1 mM GDP or 0.1 mM GTPγS) and then incubated with NR1 (0, 30, 10, or 3.3 µM) and for 30 min at room temperature. Precipitation of Rap1 and immunoblot were performed as directed. Results indicate that NR1 did not affect Rap1 activity. These results are summarized in FIG. 14.

Example H: NR1 Treatment of a LAM Patient-Derived Cell Line

Figure 15:
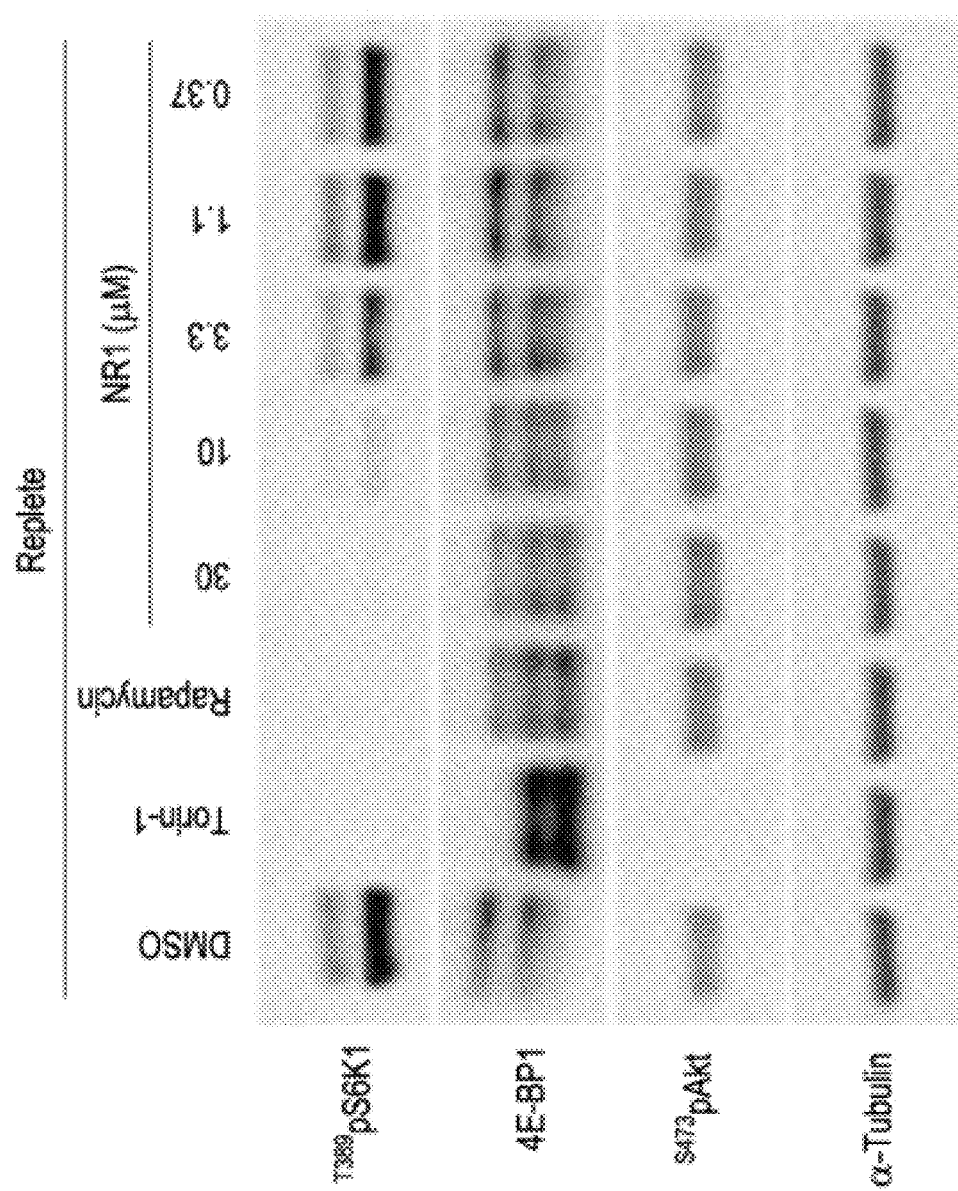
FIG. 15 shows the Western blot analysis of DMSO, Torin-1 (250 nM), rapamycin (100 nM), and NR1 (indicated concentrations) effect on mTORC1 signaling in patient derived TRI102 cells. Anti $^{T389}$pS6K1, anti 4E-BP1, anti $^{S473}$pAkt, and anti-tubulin antibodies were used for visualization.
Figure 15:
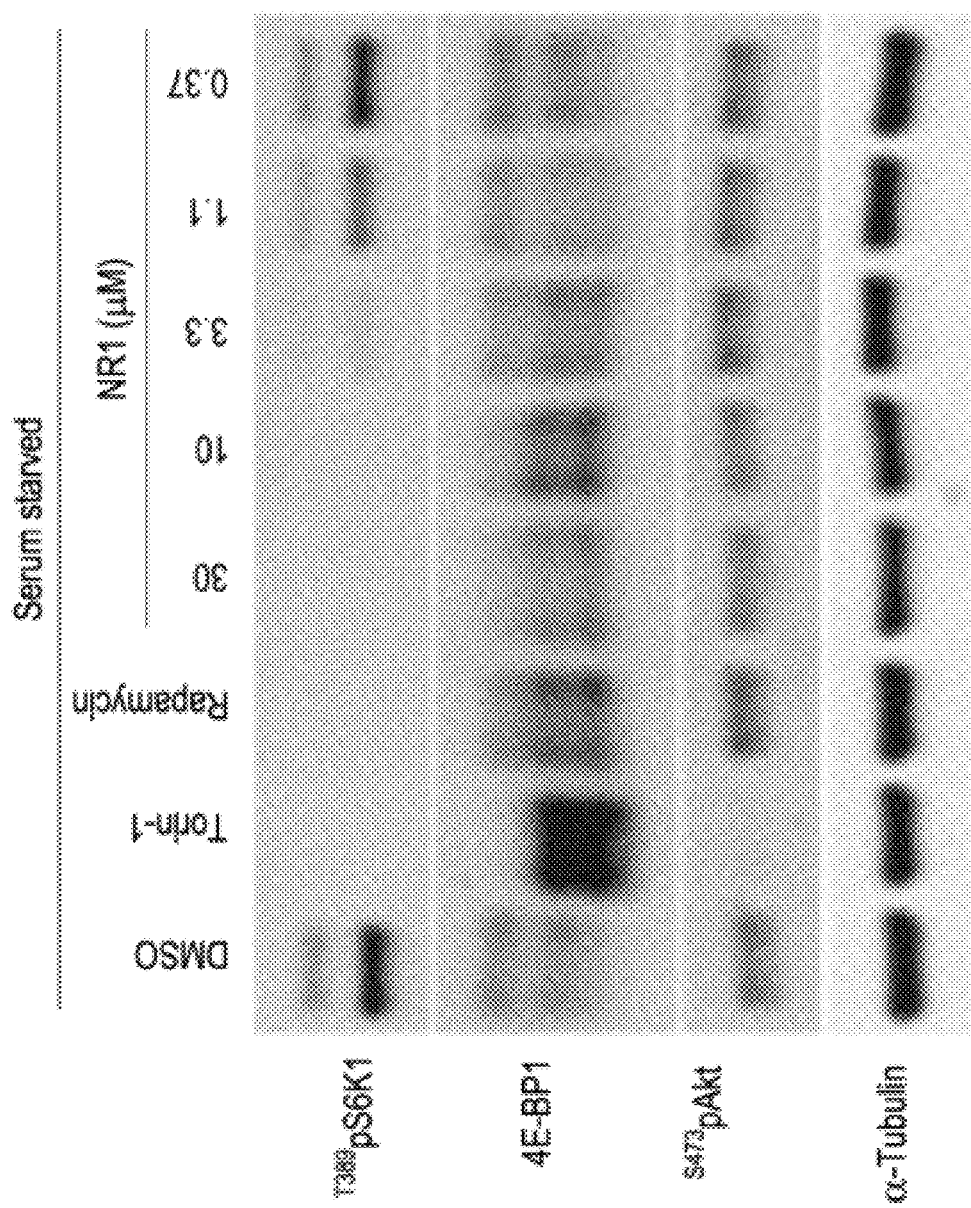

TRI102 cells (an immortalized angiomyolipoma cell line with hyperactive mTORC1 derived from a LAM patient) were treated for 90 min with NV1 (30, 10, 3.3 µl, or 0.37 µM), Torin-1 (250 nM), rapamycin (100 nM), or DMSO control under both replete and serum starved conditions. For replete condition, compounds were provided in DMEM plus 10% FBS. For serum starved conditions, cells were serum starved for 16 hrs and then treated with compounds. After 90 min cells in both the replete and serum starved conditions were lysed and analyzed by Western blot. Antibodies used for visualization were: anti $^{T389}$pS6K1 (Cell Signaling Technology #9234), anti 4E-BP1 (Cell Signaling Technology #9644), anti $^{S473}$pAkt (Cell Signaling Technology #4060), and anti-tubulin (Sigma #T-5168). Results indicate that NV1 selectively inhibits the mTORC1 signaling in a dose dependent manner in this growth factor insensitive cell line. These results are summarized in FIG. 15.

Example I: NR1 Treatment of Constitutively Active mTOR Mutants

Figure 16:
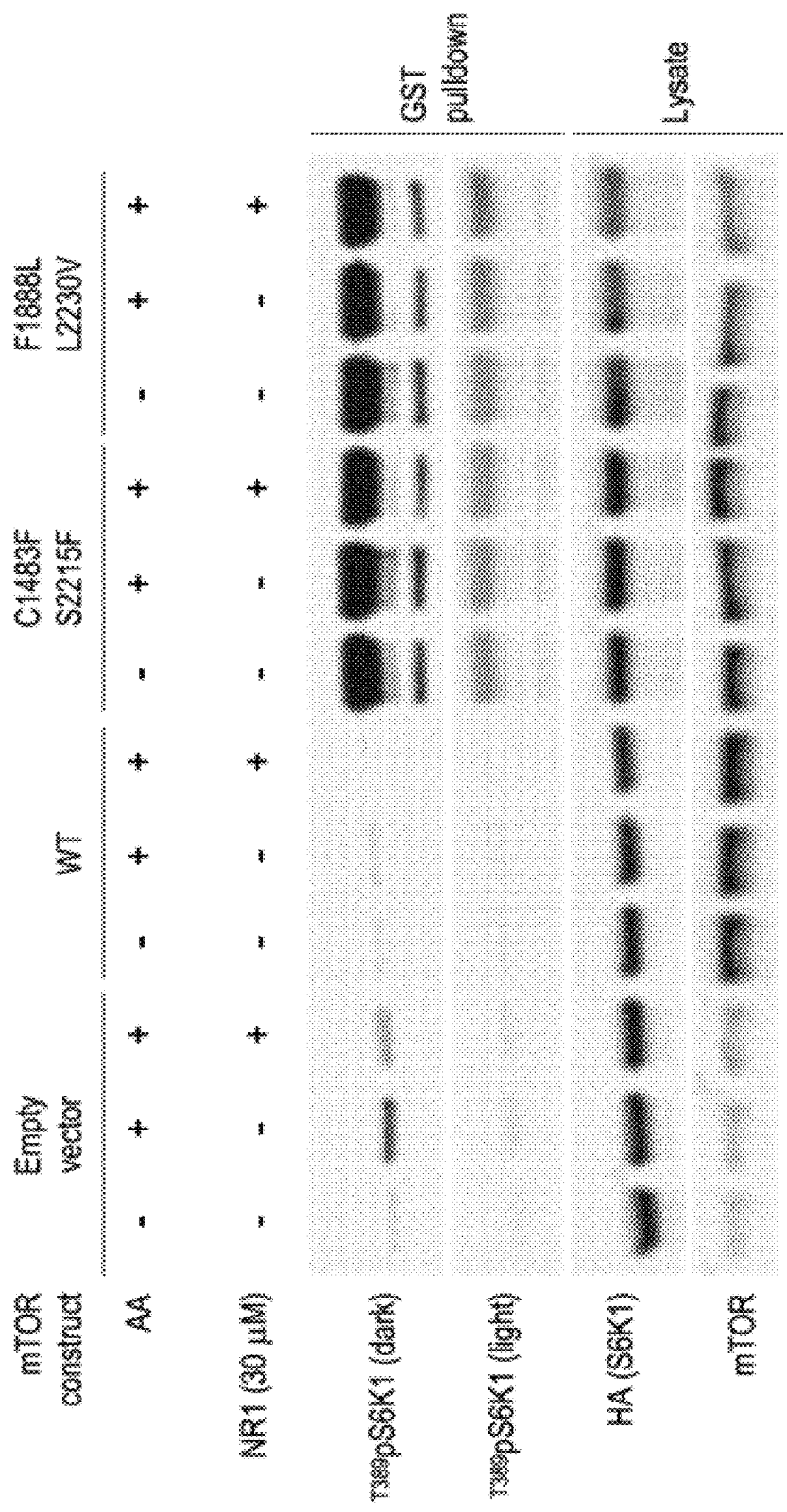
FIG. 16 shows the Western blot analysis of NR1 (30 µM) effect on HEK-293 cells transfected with constitutively active mTOR mutants. Anti $^{T389}$pS6K, anti HA-tag (S6K1) and anti-mTOR antibodies were used for visualization.

HEK-293 cells (ATCC #CRL-1573) were transiently co-transfected with pRK5-HA-GST-S6K1 and FLAG-tagged WT or mutant mTOR constructs using GeneJammer transfection reagent (Agilent #204132). Two days later, one set of cells were starved of all amino acids for 60 min in amino acid-free RPMI (MyBioSource #MBS6553421) with 5 mM glucose and 10% dialyzed FBS (Life Technologies #26400044). Another set of cells were treated with 30 µM NV1 for 90 min. After treatment, the cells were lysed in Triton X-100 lysis buffer, cleared, and normalized. Immunoprecipitation of S6K1 was performed using glutathione agarose (ThermoFisher #16100). The IPs and lysates were run on Western blots which were then probed for $^{T389}$pS6K1 (Cell Signaling Technology #9234S), HA-tag (Cell Signaling Technologies #3724), and mTOR (Cell Signaling Technology #2972). Results indicate that NV1 does not inhibit mTOR signaling in mTOR mutant cell lines. These results are summarized in FIG. 16.

Example J: Long-Term Treatment Vs. Rapamycin

Figure 17:
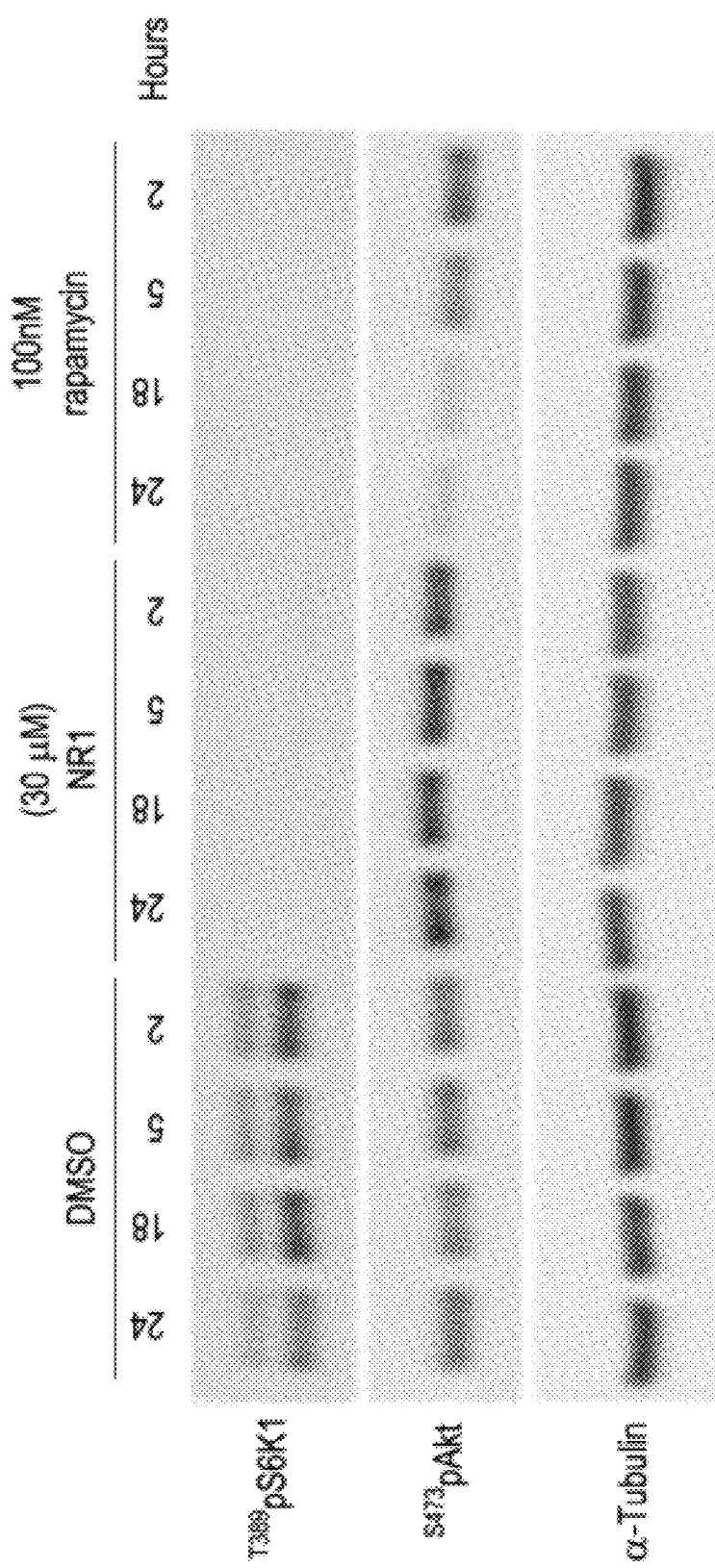
FIG. 17 shows the effect of chronic treatment with NR1 (30 µM) and rapamycin (100 nM) on mTORC1 selective inhibition in PC3 cells. Anti $^{T389}$pS6K1, anti $^{S473}$pAkt, and anti-tubulin antibodies were used for visualization.

PC3 cells (ATCC #CRL-1435) were treated with DMSO, NR1 (30 µM), and rapamycin (100 nM) under replete conditions for 2, 5, 18, or 24 hrs. Cells were then lysed and Western blot analyses. Antibodies used for visualization were: $^{T389}$pS6K1 (Cell Signaling Technology #9234S), anti $^{S473}$pAkt (Cell Signaling Technology #4060), and anti-tubulin (Sigma #T-5168). Results indicate that while rapamycin inhibits mTORC2 signaling with chronic exposure, NR1 maintains selectivity for mTORC1 for at least 24 hrs. These results are summarized in FIG. 17.

Example K: Jurkat Cell Size Analysis

Figure 18:
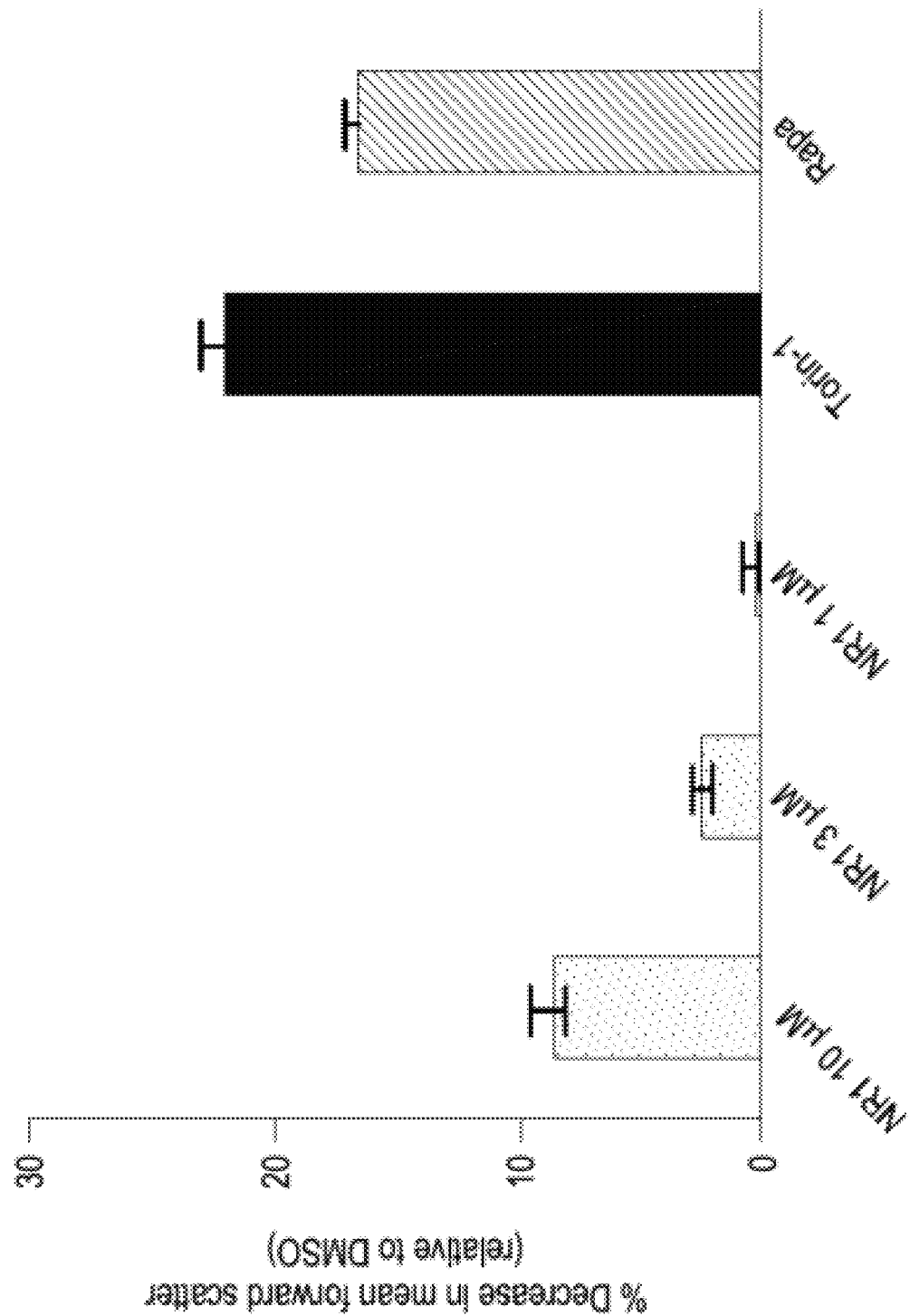
FIG. 18 shows the effect of NR1 (indicated concentrations), Torin-1 (250 nM), and rapamycin (100 nM) on the size of Jurkat Clone E-61 cells.

Jurkat Clone E-61 cells were plated in 96-well plates concurrent with NR1 (10, 3, or 1 M), Torin-1 (250 nM), and Rapamycin (100 nM). The cells were incubated at 37° C. and 5% $CO_2$ for 48 hrs. PI stain (Invitrogen #727949) was added at a final concentration of 1 μg/mL and cells were incubated for 15 min at room temperature. FACS analysis was performed with at least 10,000 events collected for each sample. Viable cells (PI minus) were counted for FSC and SSC, and cell size (as measured by FSC) relative to the DMSO control was calculated. NR1 reduced the size of Jurkat cells in a dose-dependent manner similar to Torin-1 and rapamycin. These results are summarized in FIG. 18.

Example L: Protein Synthesis

Figure 19:
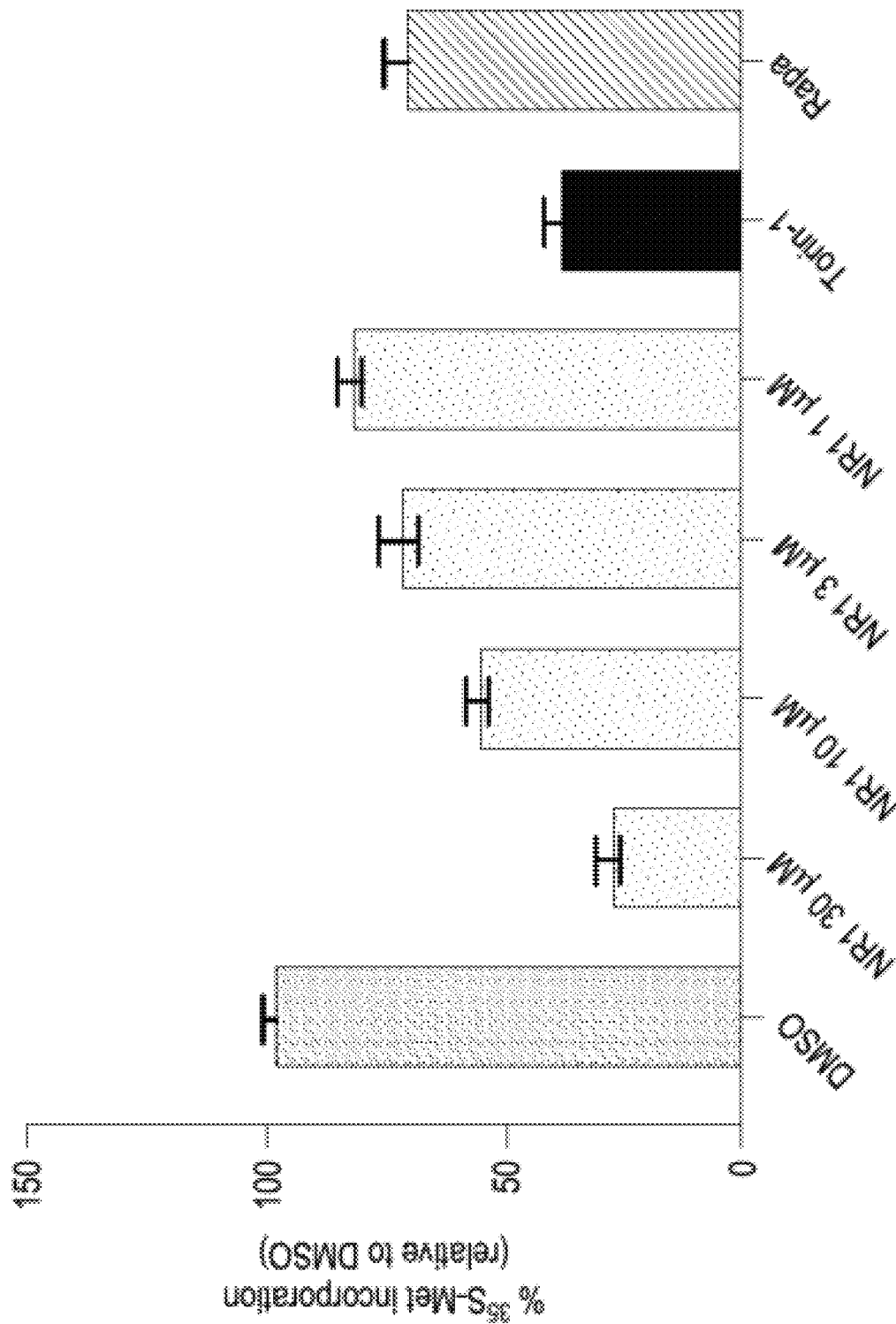
FIG. 19 effect of NR1 (indicated concentrations), Torin-1 (250 nM), and rapamycin (100 nM) on protein synthesis in MCF-7 cells.

MCF-7 cells were incubated with compounds in MEM plus 10% dialyzed FBS for 2.5 hrs and then incubated in labeling mix (compounds (DMSO control, NR1 (30, 10, 3, or 1 μM), Torin-1 (250 nM), or rapamycin (100 nM)), Met- and Cys-free media, 10% dialyzed FBS, and $^{35}S$ protein labeling mix) for 30 min. Cells were lysed, proteins were precipitated, and resuspended pellets were read on a Microbeta 2. Results indicate that NR1 could reduce protein synthesis (measured by $^{35}S$ incorporation) in a dose dependent manner similar to Torin-1 and rapamycin. These results are summarized in FIG. 19.

Example M: Pharmacokinetics

These studies were conducted in accordance with the requirements for the human care and use of animals set forth in the Animal Welfare Act, the IACUC Guide for the Case and Use of Laboratory Animals, applicable Shanghai and state laws, and regulations and policies of Shanghai ChemPartner Ltd. The animals were not randomized, and the studies were not blinded.

Figure 20:
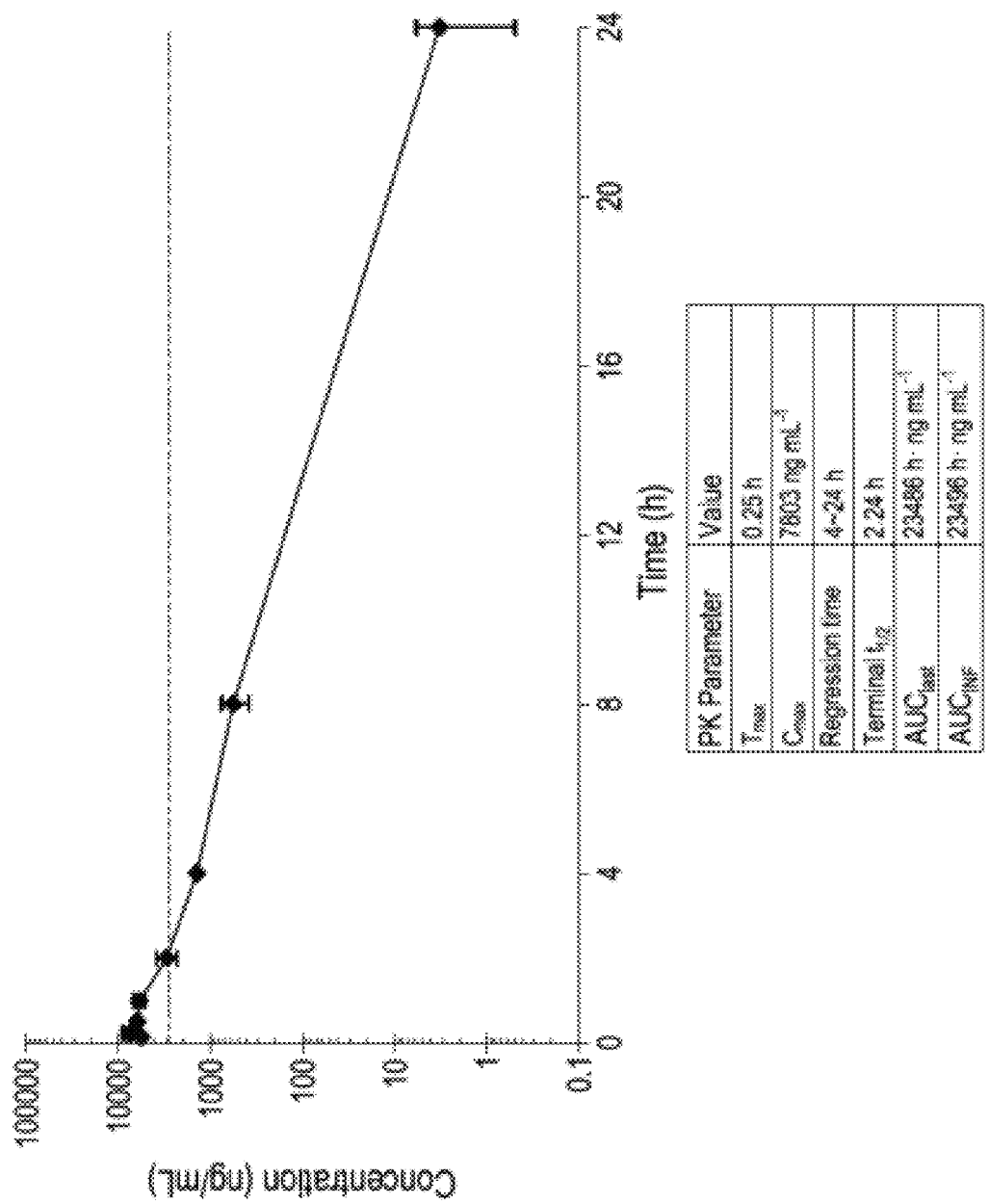
FIG. 20 shows the pharmacokinetic parameters of NR1 in C57BL/6 mice following single i.p injection at 30 mg/kg.

Male C57BL/6 mice (5 per treatment group; 6-7 weeks old) were fasted for food overnight for 16 hrs. Injections (i.p.) of compound dissolved in MC Tween (0.5% methylcellulose and 0.1% Tween-80 in water) were given, and the mice were allowed to feed again ad libitum until sacrificed (2 hrs). The animals were euthanized with $CO_2$. Compound levels in the plasma of treated mice were measured by LC-MS/MS and compared to a standard curve of compound diluted into mouse plasma. A plasma concentration of over 5 μM was attained and sustained for 2 hrs after i.p. dosing of 30 mg/kg. Results are summarized in FIG. 20.

Example N: Pharmacodynamics

These studies were conducted in accordance with the requirements for the human care and use of animals set forth in the Animal Welfare Act, the IACUC Guide for the Case and Use of Laboratory Animals, applicable Shanghai and state laws, and regulations and policies of Shanghai ChemPartner Ltd. The animals were not randomized, and the studies were not blinded.

Figure 21:
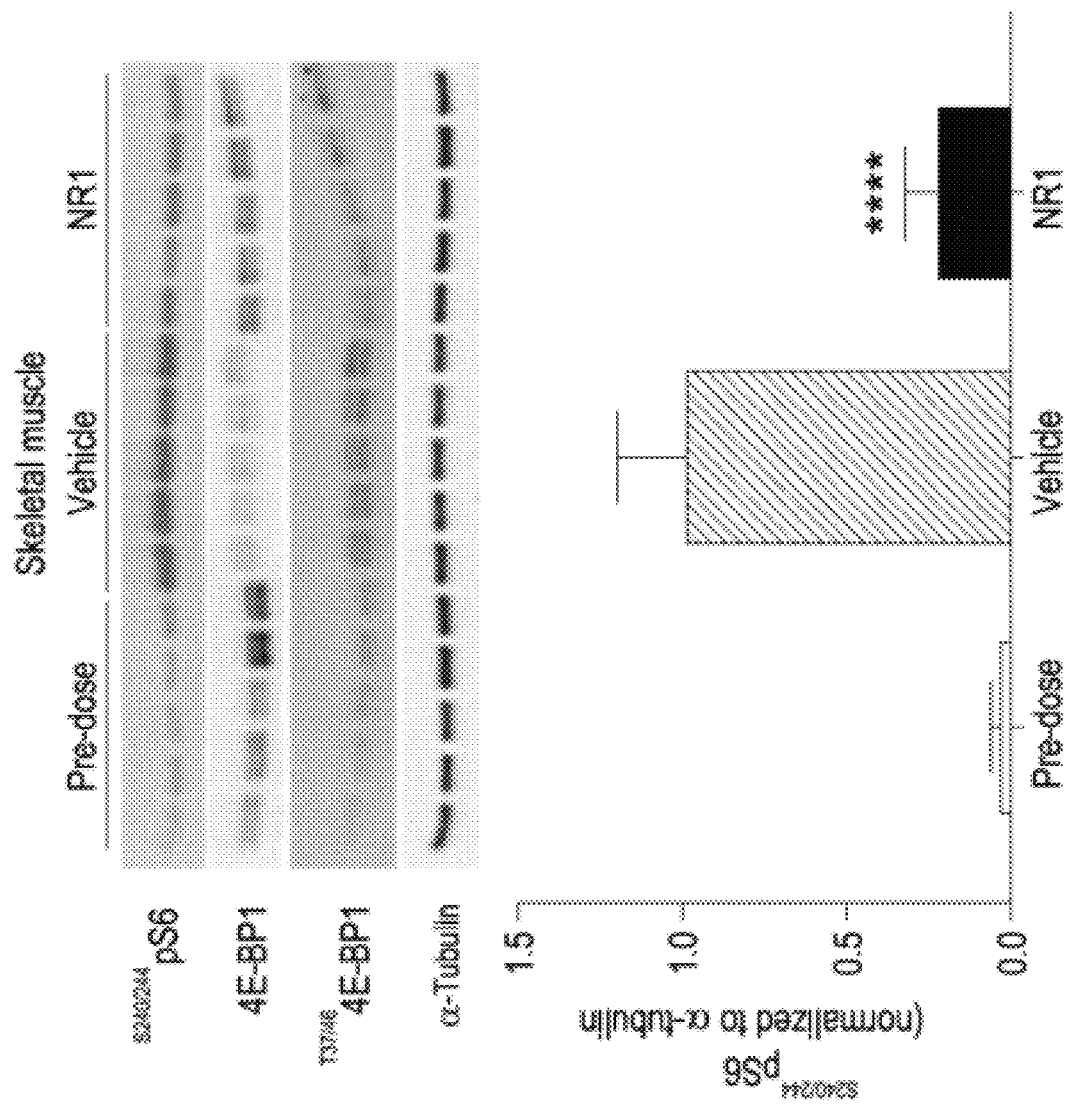
FIG. 21 shows the effect of NV1 on mTORC1 activity in skeletal muscle of C57BL/6 mice 2 hrs after single i.p injection at 30 mg/kg.
Figure 22:
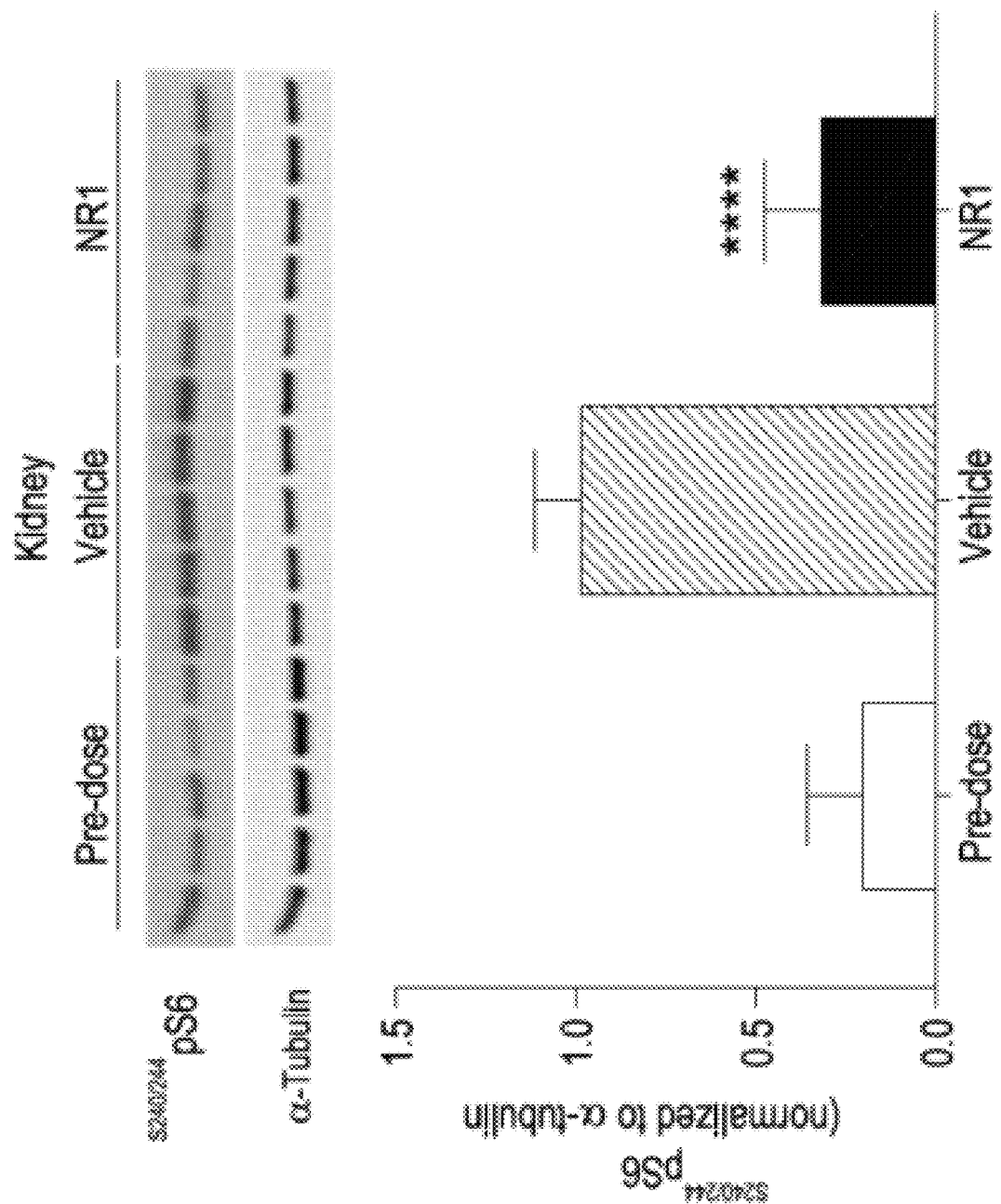
FIG. 22 shows the effect of NV1 on mTORC1 activity in kidney tissue of C57BL/6 mice 2 hrs after single i.p injection at 30 mg/kg.

Male C57BL/6 mice (5 per treatment group; 6-7 weeks old) were fasted for food overnight for 16 hrs. Injections (i.p.) of compound dissolved in MC Tween (0.5% methylcellulose and 0.1% Tween-80 in water) were given, and the mice were allowed to feed again ad libitum until sacrificed (2 hrs). The animals were euthanized with $CO_2$. Mouse tissues were harvested after euthanizing and immediately frozen at −80° C. The tissues were then homogenized in Triton lysis buffer using a FastPrep-24 homogenizer (MP Biomedicals) and a steel bead (Qiagen #69989). Homogenates were processed for Western blotting as described above. Antibodies used for visualization were: anti $^{S240/244}$pS6 (Cell Signaling Technology #5364); anti $^{T37/46}$p4E-BP1 (Cell Signaling Technology #2855); and anti-tubulin (Sigma #T-5168). Results indicate that NR1 treated animals had significantly reduced mTORC1 activity in both kidney and skeletal muscle (gastrocnemius) compared to vehicle-treated mice. Results for muscle tissue are summarized in FIG. 21. Results for kidney tissue are summarized in FIG. 22.

In some embodiments, the present invention provides a compound other than a compound set forth in Table 4.

5. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit Rheb, in a biological sample or in a patient. In certain embodiments, the amount of compound in compositions of this

We claim:

1. A compound of Formula I-b:

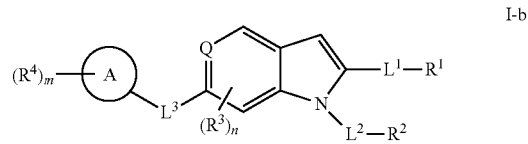

I-b or a pharmaceutically acceptable salt thereof, wherein:
Q is CH, $CR^3$, or N;
$L^1$ is a covalent bond or a $C_{1-6}$ bivalent hydrocarbon chain wherein one, two, or three methylene units of the chain are optionally and independently replaced by -$Cy^1$-, —N(R)—, —O—, —C(O)—, —OC(O)—, —C(O)O—, —C(O)N(R)—, —N(R)C(O)—, —S(O)—, or —S(O)$_2$—;
each R is independently hydrogen, or an optionally substituted group selected from $C_{1-6}$ aliphatic, a 3-8 membered saturated or partially unsaturated monocyclic carbocyclic ring, phenyl, 4-7 membered saturated or partially unsaturated heterocyclic ring having 1-2 heteroatoms independently selected from nitrogen, oxygen, or sulfur, or 5-6 membered heteroaryl ring having 1-4 heteroatoms independently selected from nitrogen, oxygen, or sulfur, or:
  two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, or sulfur;
each -$Cy^1$- is independently an optionally substituted bivalent ring selected from phenylene, 3-7 membered saturated or partially unsaturated carbocyclylene, 4-7 membered saturated or partially unsaturated heterocyclylene having 1-2 heteroatoms independently selected from nitrogen, oxygen, or sulfur, or 5-6 membered heteroarylene having 1-4 heteroatoms independently selected from nitrogen, oxygen, or sulfur;
$R^1$ is hydrogen, halogen, —CN, —$NO_2$ or an optionally substituted group selected from $C_{1-6}$ aliphatic, a 3-8 membered saturated or partially unsaturated monocyclic carbocyclic ring, phenyl, a 4-7 membered saturated or partially unsaturated heterocyclic ring having 1-2 heteroatoms independently selected from nitrogen, oxygen, or sulfur, or a 5-6 membered heteroaryl ring having 1-4 heteroatoms independently selected from nitrogen, oxygen, or sulfur;

$L^2$ is a covalent bond or a $C_{1-6}$ bivalent hydrocarbon chain wherein one, two, or three methylene units of the chain are optionally and independently replaced by -Cy²-, —C(O)—, —CH(R)—, —N(R)—, —C(O)N(R)—, —N(R)C(O)—, —O—, —C(O)O—, —OC(O)—, or —S(O)₂—;

each -Cy²- is independently an optionally substituted bivalent ring selected from phenylene, 4-7 membered saturated or partially unsaturated heterocyclylene having 1-2 heteroatoms independently selected from nitrogen, oxygen, or sulfur, or 5-6 membered heteroarylene having 1-4 heteroatoms independently selected from nitrogen, oxygen, or sulfur;

$R^2$ is halogen, —CN, —NO₂ or an optionally substituted group selected from $C_{2-6}$ aliphatic, a 3-8 membered saturated or partially unsaturated monocyclic carbocyclic ring, phenyl, a 4-7 membered saturated or partially unsaturated heterocyclic ring having 1-2 heteroatoms independently selected from nitrogen, oxygen, or sulfur, or a 5-6 membered heteroaryl ring having 1-4 heteroatoms independently selected from nitrogen, oxygen, or sulfur;

$L^3$ is —S—,;

Ring A is phenyl, wherein Ring A is substituted with m occurrences of $R^4$;

each $R^3$ is independently an optionally substituted $C_{1-6}$ aliphatic, phenyl, halogen, —CN, —SR, or two $R^3$ groups are optionally taken together to form a 5-8 membered partially unsaturated or aryl fused ring having 0-2 heteroatoms independently selected from nitrogen, oxygen, or sulfur;

n is 0, 1, 2, or 3;

each $R^4$ is independently an optionally substituted $C_{1-6}$ aliphatic, halogen, or —OR; and m is 0, 1, 2, 3, 4, or 5.

2. The compound according to claim 1, wherein $L^1$ is a covalent bond or a $C_{1-6}$ bivalent hydrocarbon chain wherein one, two, or three methylene units of the chain are optionally and independently replaced by -Cy¹-, —N(R)—, —O—, —C(O)—, —OC(O)—, —C(O)O—, —C(O)N(R)—, —N(R)C(O)—, or —S(O)—.

3. The compound according to claim 1, wherein $R^1$ is hydrogen, or an optionally substituted group selected from $C_{1-6}$ aliphatic, phenyl, a 4-7 membered saturated or partially unsaturated heterocyclic ring having 1-2 heteroatoms independently selected from nitrogen, oxygen, or sulfur, or a 5-6 membered heteroaryl ring having 1-4 heteroatoms independently selected from nitrogen, B oxygen, or sulfur.

4. The compound according to claim 1, wherein $L^2$ is a covalent bond or a $C_{1-6}$ bivalent hydrocarbon chain wherein one, two, or three methylene units of the chain are optionally and independently replaced by -Cy²-, —C(O)—, —CH(R)—, —N(R)—, —C(O)N(R)—, —N(R)C(O)—, —O—, —C(O)O—, or —S(O)₂—.

5. The compound according to claim 1, wherein $R^2$ is halogen, —CN, or an optionally substituted group selected from $C_{2-6}$ aliphatic, a 3-8 membered saturated or partially unsaturated monocyclic carbocyclic ring, phenyl, a 4-7 membered saturated or partially unsaturated heterocyclic ring having 1-2 heteroatoms independently selected from nitrogen, oxygen, or sulfur, or a 5-6 membered heteroaryl ring having 1-4 heteroatoms independently selected from nitrogen, oxygen, or sulfur.

6. The compound according to claim 1, wherein the compound is selected from any one of the following:

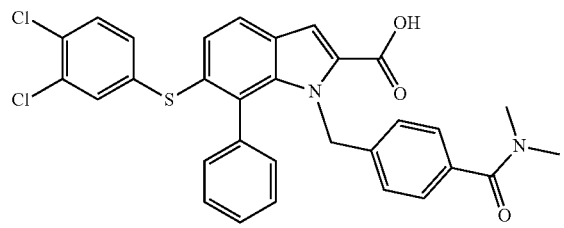

I-1

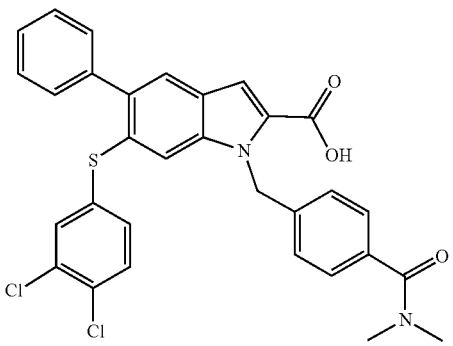

I-2

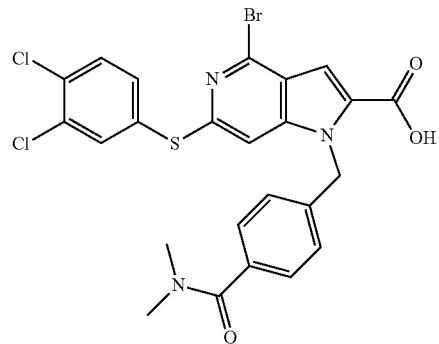

I-3

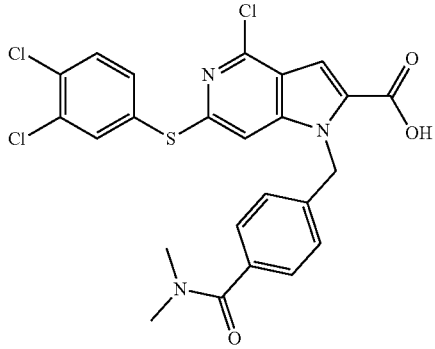

I-4

I-5
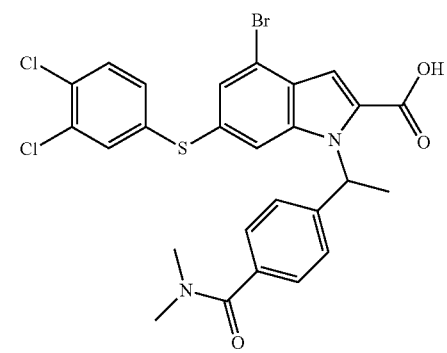
I-6
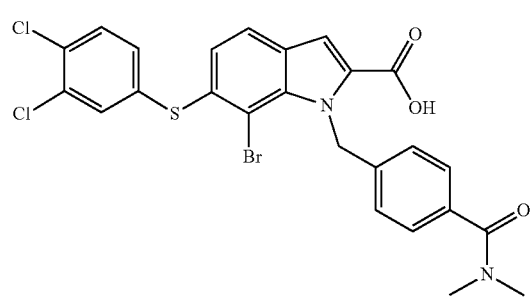
I-7
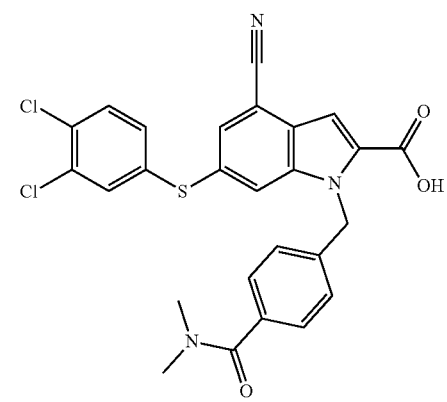
I-8
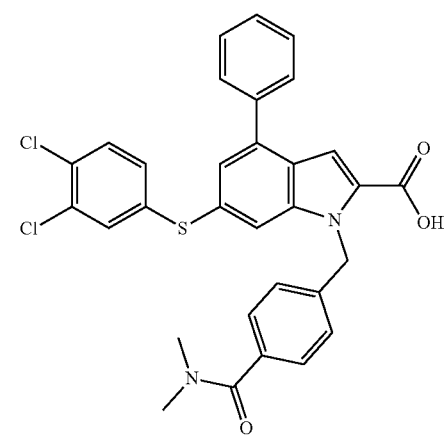
I-9
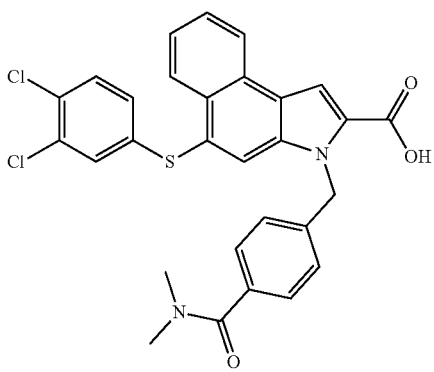
I-10
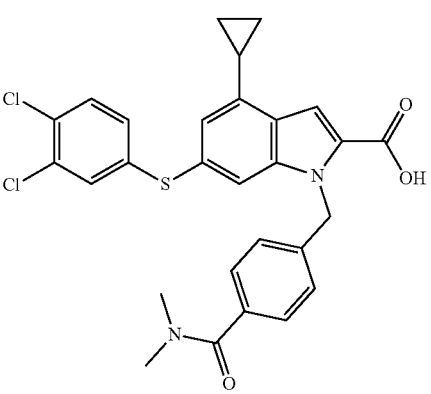
I-13
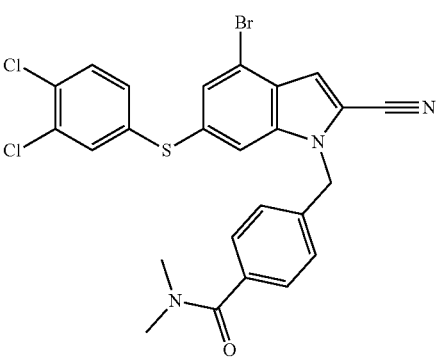
I-14
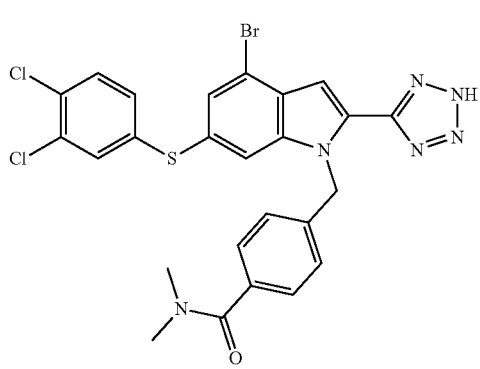

-continued
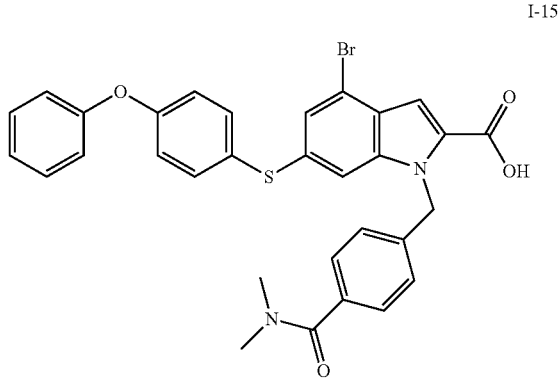
I-15
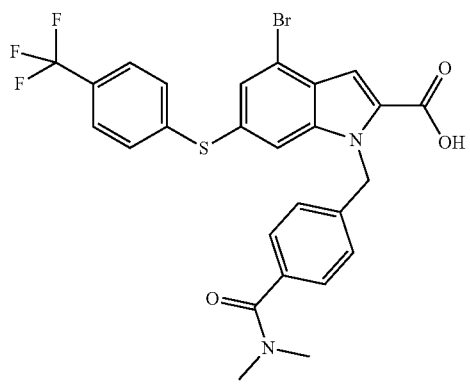
I-22
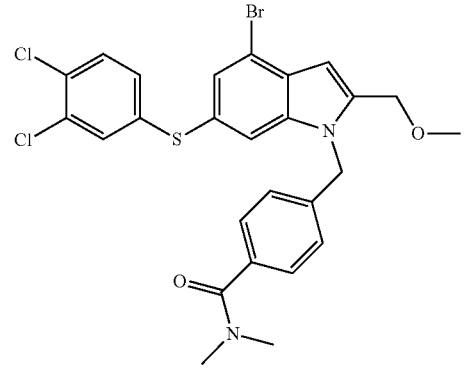
I-34
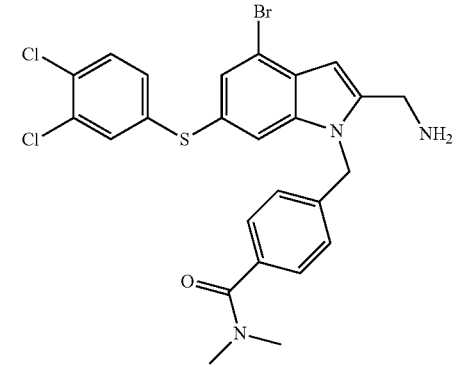
I-37
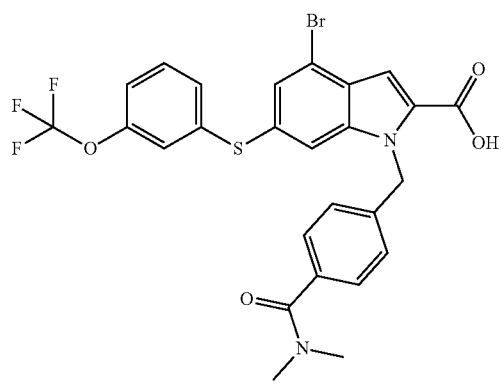
I-20
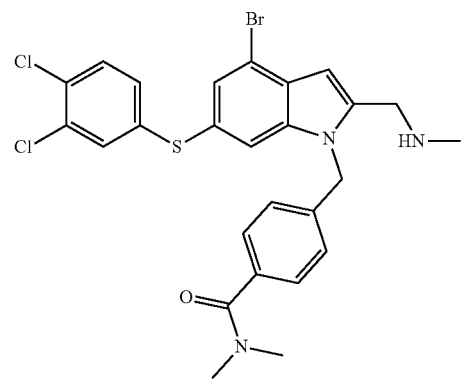
I-38

I-39
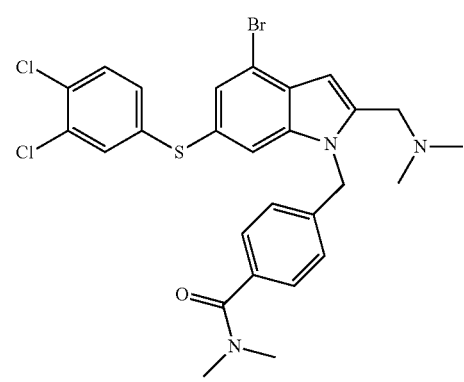
I-42
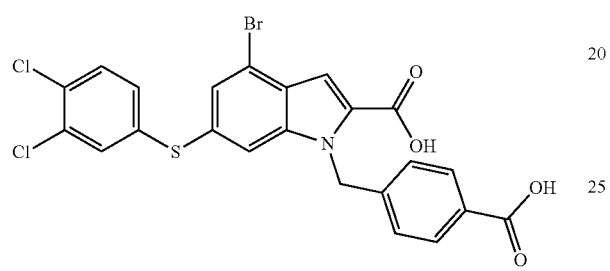
I-43
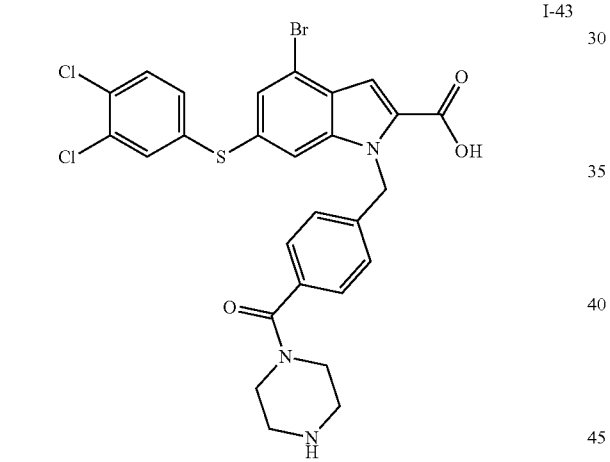
I-44
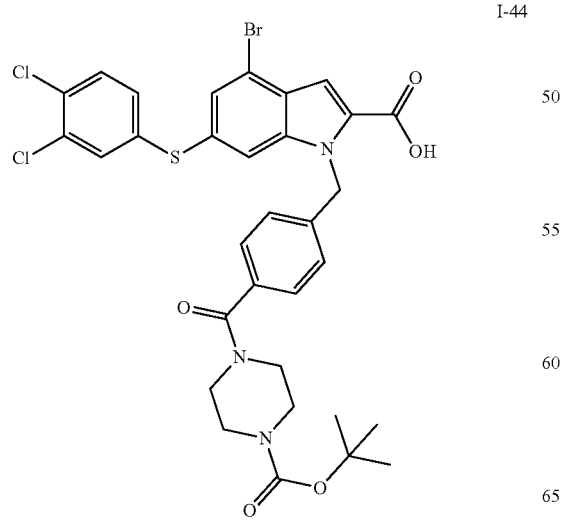
I-50
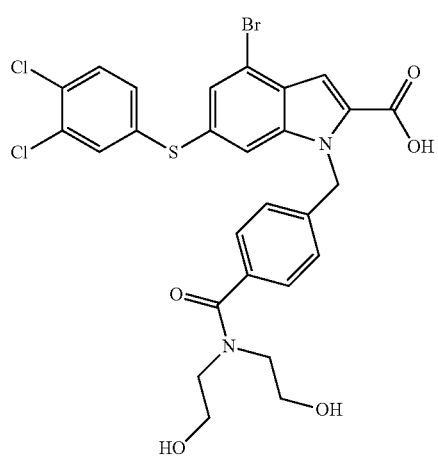
I-51
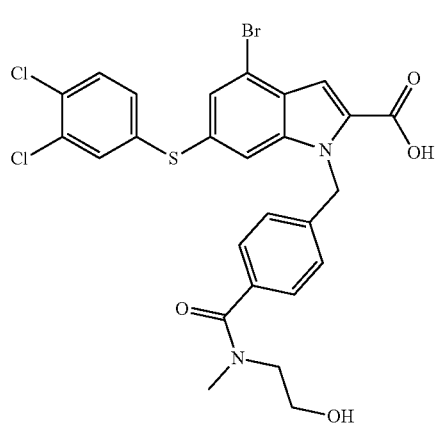
I-52
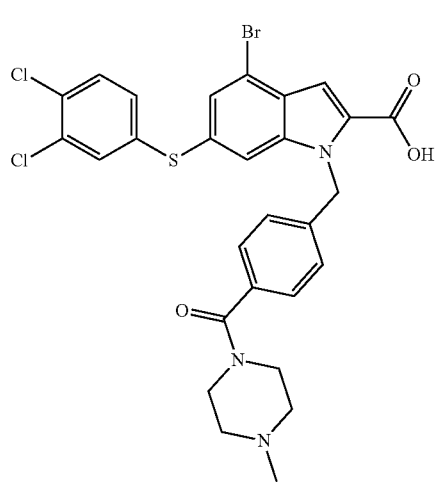

I-75
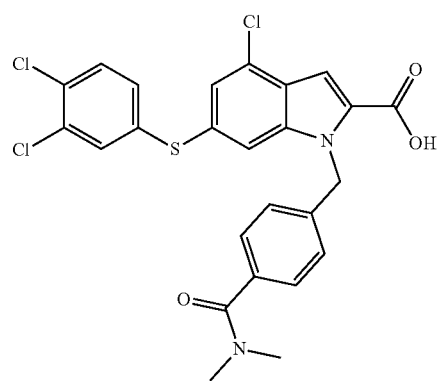
I-95
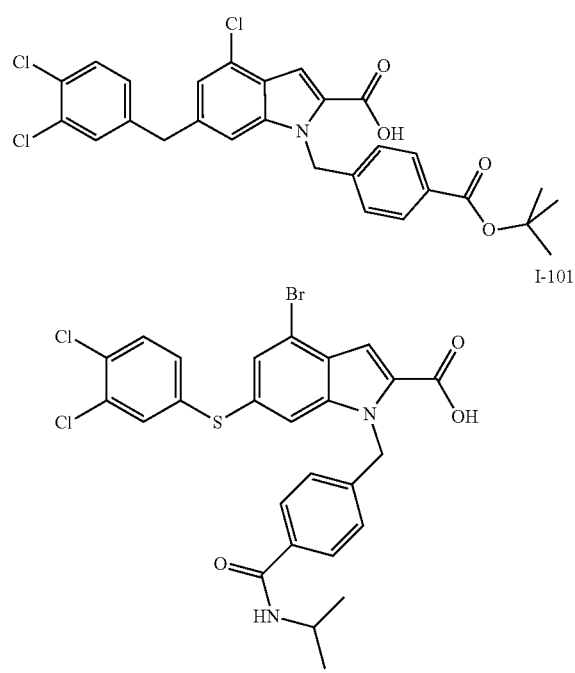
I-101
I-102
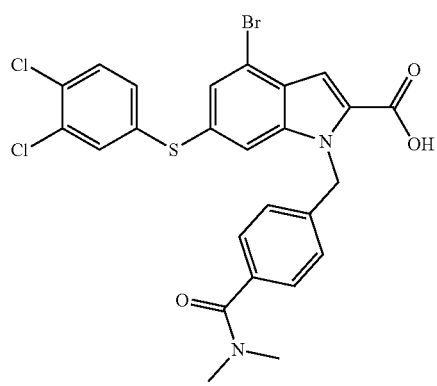
I-109
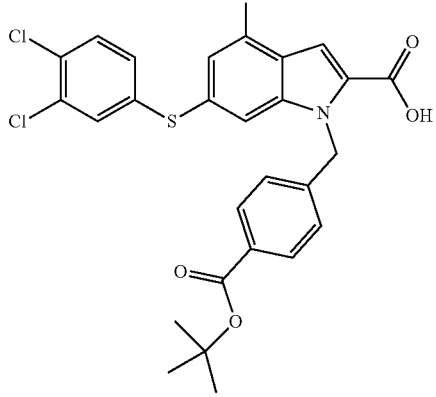
I-110
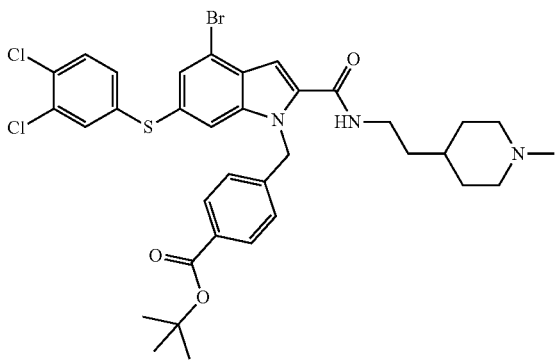
I-185
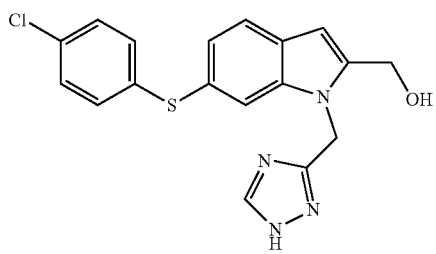
or a pharmaceutically acceptable salt thereof.
7. A pharmaceutical composition comprising a compound according to claim 1, or a pharmaceutically acceptable salt thereof, and a pharmaceutically acceptable adjuvant, carrier or vehicle.
* * * * *